US012281122B1

United States Patent
Chatterjee et al.

(10) Patent No.: US 12,281,122 B1
(45) Date of Patent: Apr. 22, 2025

(54) PI3K INHIBITORS

(71) Applicant: Cogent Biosciences, Inc., Waltham, MA (US)

(72) Inventors: Payal Chatterjee, Boulder, CO (US); Mark J. Chicarelli, Boulder, CO (US); Michael L. Conner, Boulder, CO (US); John Fischer, Boulder, CO (US); Jennifer Fulton, Boulder, CO (US); Ravi Kumar Jalluri, Boulder, CO (US); Hailey J. Knox, Boulder, CO (US); Vijay Kumar, Boulder, CO (US); Bradley J. Newhouse, Boulder, CO (US); Martha E. Rodriguez, Boulder, CO (US); Leah J. Salituro, Boulder, CO (US); Aaron C. Smith, Boulder, CO (US); Lee M. Stunkard, Boulder, CO (US); Yeyun Zhou, Boulder, CO (US); Paul R. Carlson, Boulder, CO (US); Scott W. Niman, Boulder, CO (US); Patrick J. Sutter, Boulder, CO (US); John I. Trujillo, Boulder, CO (US); Logan E. Vine, Boulder, CO (US); Brooklynn Venteicher, Boulder, CO (US)

(73) Assignee: COGENT BIOSCIENCES, INC., Waltham, MA (US)

( * ) Notice: Subject to any disclaimer, the term of this patent is extended or adjusted under 35 U.S.C. 154(b) by 0 days.

(21) Appl. No.: 18/794,551

(22) Filed: Aug. 5, 2024

Related U.S. Application Data

(63) Continuation of application No. PCT/US2024/039889, filed on Jul. 26, 2024.

(60) Provisional application No. 63/516,375, filed on Jul. 28, 2023.

(51) Int. Cl.
| | | |
|---|---|---|
| *C07D 487/08* | (2006.01) | |
| *A61K 31/517* | (2006.01) | |
| *C07D 401/14* | (2006.01) | |
| *C07D 413/14* | (2006.01) | |
| *C07D 471/04* | (2006.01) | |
| *C07D 471/08* | (2006.01) | |
| *C07D 487/04* | (2006.01) | |

(52) U.S. Cl.
CPC .......... *C07D 487/08* (2013.01); *A61K 31/517* (2013.01); *C07D 401/14* (2013.01); *C07D 413/14* (2013.01); *C07D 471/04* (2013.01); *C07D 471/08* (2013.01); *C07D 487/04* (2013.01)

(58) Field of Classification Search
CPC .. C07D 487/08; C07D 401/14; C07D 413/14; C07D 471/04; C07D 471/08; C07D 487/04; A61K 31/517
See application file for complete search history.

(56) References Cited

U.S. PATENT DOCUMENTS

| | | |
|---|---|---|
| 9,155,739 B2 | 10/2015 | Chern et al. |
| 10,005,739 B2 | 6/2018 | Murata et al. |
| 2020/0407344 A1 | 12/2020 | Barbour et al. |
| 2023/0108594 A1 | 4/2023 | Sperry et al. |

FOREIGN PATENT DOCUMENTS

| | | |
|---|---|---|
| WO | WO-2014080290 A2 | 5/2014 |
| WO | WO-2023060262 A1 | 4/2023 |
| WO | WO-2023078401 A1 | 5/2023 |
| WO | WO-2023081209 A1 | 5/2023 |
| WO | WO-2023159155 A1 | 8/2023 |
| WO | WO-2023192416 A1 | 10/2023 |
| WO | WO-2023207881 A1 | 11/2023 |
| WO | WO-2023239710 A1 | 12/2023 |
| WO | WO-2024000401 A1 | 1/2024 |
| WO | WO-2024008122 A1 | 1/2024 |
| WO | WO-2024026424 A1 | 2/2024 |
| WO | WO-2024051778 A1 | 3/2024 |
| WO | WO-2024064024 A1 | 3/2024 |
| WO | WO-2024081345 A1 | 4/2024 |

(Continued)

OTHER PUBLICATIONS

International Search Report and Written Opinion mailed Dec. 12, 2024 in Application No. PCT/US2024/039889 (11 pages).

*Primary Examiner* — Sarah Pihonak
*Assistant Examiner* — Padmaja S Rao
(74) *Attorney, Agent, or Firm* — Goodwin Procter LLP

(57) ABSTRACT

A compound having the following structure of Formula (I):

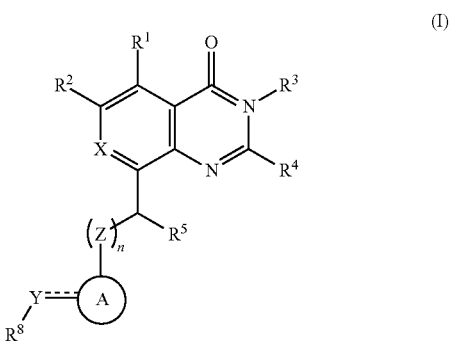

or a stereoisomer of the compound, tautomer of the compound, pharmaceutically acceptable salt thereof, wherein $R^1$, $R^2$, $R^3$, $R^4$, $R^5$, $R^8$, A, X, Z, and Y are as defined herein. Pharmaceutical composition comprising the compounds, and their use in methods of treating diseases are also described.

30 Claims, No Drawings

(56) References Cited

FOREIGN PATENT DOCUMENTS

| WO | WO-2024081904 A1 | 4/2024 |
|----|------------------|--------|
| WO | WO-2024086789 A2 | 4/2024 |
| WO | WO-2024099437 A1 | 5/2024 |

PI3K INHIBITORS

RELATED APPLICATIONS

This application is a continuation of International Patent Application No. PCT/US2024/039889, filed on Jul. 26, 2024, which claims the benefit of, and priority to, U.S. Provisional Patent Application 63/516,375, filed Jul. 28, 2023, the contents of which are hereby incorporated by reference in their entirety for all purposes.

TECHNICAL FIELD

The disclosure relates to compounds that act as phosphatidylinositol 3-kinase (PI3-kinase or PI3K) inhibitors. The disclosure also provides compounds of Formula (I) and pharmaceutically acceptable salts thereof and uses of the compounds for the treatment of abnormal cell growth, such as cancer, in a subject.

BACKGROUND

The PI3K signaling pathway plays a role in physiological processes that drive tumor progression including metabolism, cell growth and proliferation. However, the development of therapeutic PI3K pathway inhibitors has faced challenges including poor drug tolerance and drug resistance. There remains a need to identify potent PI3K inhibitors for the treatment of patients with cancer or other proliferative diseases or conditions driven by PI3K alterations, including alterations of the phosphatidylinositol 3-kinase catalytic alpha subunit (PI 3-kinase CA or PIK3CA).

BRIEF SUMMARY

In brief, the present disclosure provides compounds, including stereoisomers, tautomers, or pharmaceutically acceptable salts thereof, which can be used alone or in combination with other therapeutic agents.

In one embodiment, a compound having a structure of Formula (I) is provided:

(I)

or a stereoisomer of the compound, tautomer of the compound, pharmaceutically acceptable salt thereof, wherein $R^1$, $R^2$, $R^3$, $R^4$, $R^5$, $R^8$, A, X, Z, and Y are as defined herein.

Pharmaceutical compositions comprising one or more of the foregoing compounds of Formula (I), (IA)-(IC), (IA-1)-(IA-3), (IB-1)-(IB-3), (IA-a)-(IA-1), (IB-a)-(IB-b), or (II) or of Table 1 and an additional therapeutic agent are also provided.

In other embodiments, methods of treatment by administering the foregoing compounds of Formula (I), (IA)-(IC), (IA-1)-(IA-3), (IB-1)-(IB-3), (IA-a)-(IA-1), (IB-a)-(IB-b), or (II) or of Table 1 or the pharmaceutical compositions comprising a compound of Formula (I), (IA)-(IC), (IA-1)-(IA-3), (IB-1)-(IB-3), (IA-a)-(IA-1), (IB-a)-(IB-b), or (II) or of Table 1 to a subject in need thereof to treat a disease are provided.

Various aspects and embodiments now will be described more fully hereinafter. Such aspects and embodiments may take many different forms, and the exemplary ones disclosed herein should not be construed as limiting; rather, these embodiments are provided so that this disclosure will be thorough and complete, and will fully convey its scope to those skilled in the art.

DETAILED DESCRIPTION

I. Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Where a range of values is provided, it is intended that each intervening value between the upper and lower limit of that range and any other stated or intervening value in that stated range is encompassed within the disclosure. For example, if a range of 1 μM to 8 μM is stated, it is intended that 2 μM, 3 μM, 4 μM, 5 μM, 6 μM, and 7 μM are also explicitly disclosed, as well as the range of non-integer values greater than or equal to 1 μM and the range of non-integer values less than or equal to 8 μM.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The term "about," particularly in reference to a given quantity, is meant to encompass deviations of plus or minus five percent.

The compositions of the present disclosure can comprise, consist essentially of, or consist of, the components disclosed.

All percentages, parts and ratios are based upon the total weight of the compositions and all measurements made are at about 25° C., unless otherwise specified.

As used in the specification and appended claims, unless specified to the contrary, the following terms have the meaning indicated:

"Amino" refers to the —$NH_2$, —NHR, or —$NR_2$ radical,
"Cyano" refers to the —CN radical,
"Hydroxyl" refers to the —OH radical,
"Imino" refers to the =NH or =NR substituent,
"Nitro" refers to the —$NO_2$ radical,
"Oxo" refers to the =O substituent,
"Thio" refers to the =S substituent,
"Trifluoromethyl" refers to the —$CF_3$ radical,
Hydrazido or hydrazino refers to N—N substituent, wherein each R of "amino" or "imino" is a compatible substituent as described in this disclosure and wherein an R group is chiral, isomers are contemplated and included herein.

"Alkyl" refers to a linear, saturated, acyclic, monovalent hydrocarbon radical or branched, saturated, acyclic, monovalent hydrocarbon radical, having from one to twelve carbon atoms, preferably one to eight carbon atoms or one to six carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), 3-methylhexyl, 2-methylhexyl and the like. An optionally substituted alkyl radical is an alkyl radical that is optionally substituted, valence permitting, by one, two, three, four, or five substituents independently selected from the group consisting of halo, cyano, nitro, aryl, cycloalkyl, heterocyclyl, heteroaryl, oxo, trimethylsilyl, —OR', —OC(O)R', —N(R')$_2$, C(O)R", —C(O)OR', —C(O)N(R')$_2$, —N(R')C(O)OR''', N(R')C(O)R''', —N(R')S(O)$_t$R''' (where t is 1 or 2), —S(O)$_t$OR''' (where t is 1 or 2), —S(O)$_p$R''' (where p is 0, 1, or 2) and —S(O)$_t$N(R')$_2$ (where t is 1 or 2), where each R' is independently hydrogen, alkyl, haloalkyl, cycloalkyl, cycloalkylalkyl, aryl, aralkyl, heterocyclyl, or heteroaryl; each R" is independently hydrogen, cycloalkyl, aryl, heterocyclyl, or heteroaryl; and each R''' is independently alkyl, haloalkyl, cycloalkyl, aryl, heterocyclyl, or heteroaryl.

"Alkylene" refers to a divalent radical of an alkyl group.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl").

"Alkenylene" refers to a divalent radical of an alkenyl group.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl").

"Alkynylene" refers to a divalent radical of an alkynyl group.

"Alkylalcohol" refers to an alkyl group substituted with an alcohol (—OH) group.

"Alkoxy" refers to a radical of the formula —OR$_a$ where R$_a$ is an alkyl radical as defined above containing one to twelve carbon atoms. The alkyl part of the optionally substituted alkoxy radical is optionally substituted as defined above for an alkyl radical.

"Alkoxyalkyl" refers to a radical of the formula —R$_a$—O—R$_b$ where R$_a$ is alkylene and R$_b$ is alkyl as defined above. Alkyl and alkylene parts of the optionally substituted alkoxyalkyl radical are optionally substituted as defined above for an alkyl radical and alkylene chain, respectively.

"Aralkyl" refers to a radical of the formula —R$_a$—R$_b$, where R$_a$ is alkylene and R$_b$ is aryl as described herein. Alkylene and aryl portions of optionally substituted aralkyl are optionally substituted as described herein for alkylene and aryl, respectively.

"Aryl" refers to an aromatic monocyclic or multicyclic hydrocarbon ring system radical containing from 6 to 18 carbon atoms, where the multicyclic aryl ring system is a bicyclic, tricyclic, or tetracyclic ring system. Aryl radicals include, but are not limited to, groups such as fluorenyl, phenyl and naphthyl. An optionally substituted aryl is an aryl radical that is optionally substituted by one, two, three, four, or five substituents independently selected from the group consisting of alkyl, alkenyl, alkynyl, halo, haloalkyl, haloalkenyl, cyano, nitro, aryl, heteroaryl, heteroarylalkyl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2), and —R"—S(O)$_t$N(R')$_2$ (where t is 1 or 2), where each R' is independently hydrogen, alkyl, haloalkyl, cycloalkyl, aryl, heterocyclyl, or heteroaryl; each R" is independently a direct bond or a linear or branched alkylene or alkenylene chain; and each R''' is independently alkyl, haloalkyl, cycloalkyl, cycloalkylalkyl, aryl, heterocyclyl, or heteroaryl.

"Arylene" refers to a divalent radical of an aryl group.

"Carbocyclyl" refers to a radical of a monocyclic or multicyclic hydrocarbon ring system containing from 3 to 15 ring carbon atoms ("$C_{3-15}$ carbocyclyl") and zero heteroatoms in the ring system. A multicyclic ring system is a bicyclic, tricyclic, or tetracyclic ring system. A bicyclic, tricyclic, or tetracyclic carbocyclyl is a fused, spiro, and/or bridged ring system. Carbocyclyl includes ring systems that are saturated, partially unsaturated (non-aromatic), or aromatic. Exemplary carbocyclyl radicals include, but are not limited to, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), phenyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), naphthyl ($C_{10}$), and the like. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

"Arylalkoxy" refers to a group of formula —O—R, where R is aralkyl. An optionally substituted arylalkoxy is an arylalkoxy that is optionally substituted as described herein for aralkyl. In some embodiments, arylalkoxy is benzyloxy.

"Cycloalkyl" refers to a stable non-aromatic monocyclic or polycyclic hydrocarbon radical having from three to fifteen carbon atoms, preferably having from three to ten carbon atoms, and which is saturated or unsaturated, and which attaches to the rest of the molecule by a single bond. A polycyclic hydrocarbon radical is bicyclic, tricyclic, or tetracyclic ring system. An unsaturated cycloalkyl contains one, two, or three carbon-carbon double bonds and/or one carbon-carbon triple bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, and the like. An optionally substituted cycloalkyl is a cycloalkyl radical that is optionally substituted by one, two, three, four, or five substituents independently selected from the group consisting of alkyl, alkenyl, halo, haloalkyl, haloalkenyl, cyano, nitro, oxo, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR''', —R"—N(R')C(O)R''', —R"—N(R')S(O)$_t$R''' (where t is 1 or 2), —R"—S(O)$_t$OR''' (where t is 1 or 2), —R"—S(O)$_p$R''' (where p is 0, 1, or 2) and —R"—S(O)$_t$N(R')$_2$ (where t is 1 or 2) where each R' is independently hydrogen, alkyl, haloalkyl, cycloalkyl, aryl, heterocyclyl, or heteroaryl; each R" is independently a direct bond or a linear or branched alkylene or alkenylene chain; and each R''' is independently alkyl, haloalkyl, cycloalkyl, cycloalkylalkyl, aryl, aralkyl, heterocyclyl, or heteroaryl.

"Deuterated compounds" are compounds where one or more hydrogen atoms have been replaced with a deuterium atom. Deuterated drugs may be derivatives of an active compound. Deuterated drugs may be prodrugs. Deuteration may alter the physical properties, metabolic properties, activity or safety of a drug.

"Deuteroalkyl" refers to an alkyl group where 1 or more hydrogen atoms of an alkyl are replaced with deuterium.

"Derivatives" are related chemical species that can be derived from a similar compound via chemical reactions. They may encompass slight chemical modifications, substitution of atoms with deuterated atoms, substitution of atoms with stable or radioactive isotopes or other modifications that imbue a compound with desirable properties.

"Fused" refers to any ring system described herein which is fused to an existing ring structure in the compounds of the invention. When the fused ring system is a heterocyclyl or a heteroaryl, any carbon atom on the existing ring structure which becomes part of the fused ring system may be replaced with a nitrogen atom.

"Halo" refers to the halogen substituents: bromo, chloro, fluoro, and iodo.

"Haloalkyl" refers to an alkyl radical, as defined above, that is further substituted by one or more halogen substituents. The number of halo substituents included in haloalkyl is from one and up to the total number of the hydrogen atoms available for replacement with the halo substituents (e.g., perfluoroalkyl). Non-limiting examples of haloalkyl include trifluoromethyl, difluoromethyl, trichloromethyl, 2,2,2-trifluoroethyl, 1-fluoromethyl, 2-fluoroethyl, 3-bromo 2-fluoropropyl, 1-bromomethyl, 2-bromoethyl and the like. For an optionally substituted haloalkyl, the hydrogen atoms bonded to the carbon atoms of the alkyl part of the haloalkyl radical may be optionally replaced with substituents as defined above for an optionally substituted alkyl.

"Haloalkenyl" refers to an alkenyl radical, as defined above, that is further substituted by one or more halo substituents. The number of halo substituents included in haloalkenyl is from one and up to the total number of the hydrogen atoms available for replacement with the halo substituents (e.g., perfluoroalkenyl). Non-limiting examples of haloalkenyl include 2,2-difluoroethenyl, 3-chloroprop-1-enyl, and the like. For an optionally substituted haloalkenyl, the hydrogen atoms bonded to the carbon atoms of the alkenyl part of the haloalkenyl radical may be optionally replaced with substituents as defined above for an optionally substituted alkenyl group.

"Haloalkynyl" refers to an alkynyl radical, as defined above, that is further substituted by one or more halo substituents. The number of halo substituents included in haloalkynyl is from one and up to the total number of the hydrogen atoms available for replacement with the halo substituents (e.g., perfluoroalkynyl). Non-limiting examples of haloalkynyl include 3-chloroprop-1-ynyl and the like. The alkynyl part of the haloalkynyl radical may be additionally optionally substituted as defined above for an alkynyl group.

"Heteroalkyl" refers to a non-cyclic stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Exemplary heteroalkyl groups include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, and —O—$CH_2$—$CH_3$. Up to two or three heteroatoms may be consecutive, such as, for example, —$CH_2$—NH—$OCH_3$ and —$CH_2$—O—Si($CH_3$)$_3$.

"Heteroalkylene" refers to a divalent radical of a heteroalkyl.

"Heteroarylalkyl" refers to a radical of the formula —$R_a$—$R_b$, where $R_a$ is alkylene and $R_b$ is heteroaryl as described herein. Alkylene and heteroaryl portions of optionally substituted heteroarylalkyl are optionally substituted as described herein for alkylene and heteroaryl, respectively.

"Heterocyclyl" refers to a stable 3- to 18-membered nonaromatic ring system radical having the carbon count of two to twelve and containing a total of one to six heteroatoms independently selected from the group consisting of nitrogen, oxygen, phosphorus, and sulfur. A heterocyclyl radical is a monocyclic, bicyclic, tricyclic, or tetracyclic ring system. A bicyclic, tricyclic, or tetracyclic heterocyclyl is a fused, spiro, and/or bridged ring system. The heterocyclyl radical may be saturated or unsaturated. Heterocyclyl includes ring systems wherein the heterocyclyl ring is fused with one or more aryl or heteroaryl groups, wherein the point of attachment is on the heterocyclyl ring. An unsaturated heterocyclyl contains one, two, or three carbon-carbon double bonds and/or one carbon-carbon triple bond. An optionally substituted heterocyclyl is a heterocyclyl radical that is optionally substituted by one, two, three, four, or five substituents independently selected from the group consisting of alkyl, alkenyl, halo, haloalkyl, haloalkenyl, cyano, oxo, thioxo, nitro, aryl, aralkyl, cycloalkyl, heterocyclyl-, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2), and —R"—S(O)$_t$N(R')$_2$ (where t is 1 or 2), where each R' is independently hydrogen, alkyl, alkenyl, haloalkyl, cycloalkyl, aryl, heterocyclyl, or heteroaryl; each R" is independently a direct bond or a linear or branched alkylene or alkenylene chain; and each R'" is independently alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom); the nitrogen atom may be optionally quaternized (when the substituent is alkyl, alkenyl, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2), and —R"—S(O)$_t$N(R')$_2$ (where t is 1 or 2), where R" is a linear or branched alkylene or alkenylene chain, and R' and R'" are as defined above). Examples of optionally substituted heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2oxopyrrolidinyl, oxazolidinyl-, piperidinyl, piperazinyl, 4piperidonyl, pyrrolidinyl, pyrazolidinyl, thiazolidinyl, tetrahydrofuryl, trithianyl, tetrahydropyranyl, thiomorpholinyl, thiamorpholinyl, 1-xo-thiomorpholinyl, and 1,1-ioxo-thiomorpholinyl.

"Heterocyclylene" refers to a heterocyclyl in which one hydrogen atom is replaced with a valency. An optionally substituted heterocyclylene is optionally substituted as described herein for heterocyclyl.

"Heteroaryl" refers to a 5- to 18-membered ring system radical containing at least one aromatic ring, having the carbon count of one to seventeen carbon atoms, and containing a total of one to ten heteroatoms independently selected from the group consisting of nitrogen, oxygen, and sulfur. The heteroaryl radical is a monocyclic, bicyclic, tricyclic, or tetracyclic ring system. The bicyclic, tricyclic, or tetracyclic heteroaryl radical is a fused and/or bridged ring system. "Heteroaryl" also includes ring systems wherein the heteroaryl ring is fused with one or more aryl groups wherein the point of attachment is either on the aryl or heteroaryl ring. An optionally substituted heteroaryl is a heteroaryl radical that is optionally substituted by one, two, three, four, or five substituents independently selected from the group consisting of alkyl, alkenyl, alkoxy, halo, haloalkyl, haloalkenyl, cyano, oxo, thioxo, nitro, oxo, aryl, aralkyl, cycloalkyl, heterocyclyl, heteroaryl, or heteroarylalkyl-, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2), and —R"—S(O)$_t$N(R')$_2$ (where t is 1 or 2), where each R' is independently hydrogen, alkyl, alkenyl, haloalkyl, cycloalkyl, aryl, heterocyclyl, or heteroaryl; each R" is independently a direct bond or a linear or branched alkylene or alkenylene chain; and each R'" is alkyl, alkenyl, haloalkyl, cycloalkyl, aryl, heterocyclyl, or heteroaryl. The nitrogen, carbon, or sulfur atoms in the heterocyclyl radical may be optionally oxidized (when the substituent is oxo and is present on the heteroatom), provided that at least one ring in heteroaryl remains aromatic; the nitrogen atom may be optionally quaternized (when the substituent is alkyl, alkenyl, aryl, aralkyl, cycloalkyl, heterocyclyl, heteroaryl, —R"—OR', —R"—OC(O)—R', —R"—N(R')$_2$, —R"—C(O)R', —R"—C(O)OR', —R"—C(O)N(R')$_2$, —R"—N(R')C(O)OR'", —R"—N(R')C(O)R'", —R"—N(R')S(O)$_t$R'" (where t is 1 or 2), —R"—S(O)$_t$OR'" (where t is 1 or 2), —R"—S(O)$_p$R'" (where p is 0, 1, or 2), and —R"—S(O)$_t$N(R')$_2$ (where t is 1 or 2), where R" is a linear or branched alkylene or alkenylene chain, and R' and R'" are as defined above), provided that at least one ring in heteroaryl remains aromatic. Examples of optionally substituted heteroaryl radicals include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo-[1,2a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl-, 2oxoazepinyl, oxazolyl, oxiranyl-, 1-phenyl-1Hpyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl- (i.e., thienyl).

"Heteroarylene" is a divalent radical of a heteroaryl group.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in animals (e.g., mammals), and more particularly, in humans.

"Prodrugs" are compounds that after administration are metabolized or otherwise chemically transformed into an active moiety. Prodrugs may be derivatives of an active compound. Prodrugs may or may not be active prior to conversion into an active form in vivo.

The term "treating" is used herein, for instance, in reference, for example, to methods of treating inflammatory diseases or to a gastrointestinal disease, and generally includes the administration of a compound or composition which reduces the frequency of, or delays the onset of, symptoms of a medical condition (e.g., autoimmune disease, inflammatory disorder, gastrointestinal disorder) in a subject relative to a subject not receiving the compound or composition. This can include reversing, reducing, or arresting the symptoms, clinical signs, and underlying pathology of a condition in a manner to improve or stabilize a subject's condition (e.g., regression of symptoms of an autoimmune or inflammatory disease such as improvement in the MAYO score in the treatment of ulcerative colitis).

The embodiments disclosed herein encompass all pharmaceutically acceptable compounds of the compound of Formula (I), (IA)-(IC), (IA-1)-(IA-3), (IB-1)-(IB-3), (IA-a)-(IA-1), (IB-a)-(IB-b), or (II) or of Table 1 being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula (I), (IA)-(IC), (IA-1)-(IA-3), (IB-1)-(IB-3), (IA-a)-(IA-1), (IB-a)-(IB-b), or (II) or of Table 1, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of Formula (I), (IA)-(IC), (IA-1)-(IA-3), (IB-1)-(IB-3), (IA-a)-(IA-1), (IB-a)-(IB-b), or (II) or of Table 1 can generally be prepared by conventional techniques known to those skilled in the art or by processes analogous to those described in the Preparations and Examples as set out below using an appropriate isotopically-labeled reagent in place of the non-labeled reagent previously employed.

The embodiments disclosed herein encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid (TFA), undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, tris(hydroxymethyl)aminomethane, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the disclosure and a medium generally accepted in the art for the delivery of the biologically active compound to mammals, e.g., humans. Such a medium includes all pharmaceutically acceptable carriers, diluents and excipients thereof.

"Effective amount" or "therapeutically effective amount" refers to that amount of a compound of the disclosure which, when administered to a mammal, preferably a human, is sufficient to effect treatment in the mammal, preferably a human. The amount of a compound which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. The present disclosure also contemplates "diastereomers", which refers to non-mirror image of non-identical stereoisomers. Diastereomers occur when two or more stereoisomers of a compound have different configurations at one or more of the equivalent stereocenters and are not mirror images of each other.

A "tautomer" refers to a proton shift from one atom of a molecule to another atom of the same molecule. The present disclosure includes tautomers of any said compounds.

"Abnormal cell growth", as used herein, unless otherwise indicated, means cell growth that is independent of normal regulatory mechanisms (e.g., loss of contact inhibition). Abnormal cell growth may be benign (not cancerous) or malignant (cancerous).

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

II. Compounds

The compounds described herein are PI3K inhibitors. In one embodiment, a compound having a structure of Formula (I), or a stereoisomer, tautomer of the compound, or a pharmaceutically acceptable salt thereof is provided:

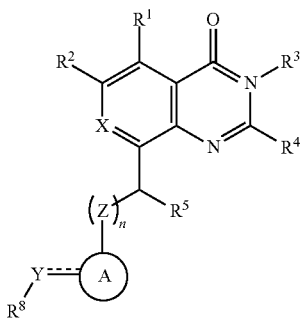

(I)

wherein X is $CR^7$ or N; Z is $CHR^6$, $NR^6$, or O; n is an integer between 0 and 1; $R^1$, $R^2$, and $R^7$ are, each independently, a hydrogen, halo, $C_1$-$C_3$ alkyl, $C_1$-$C_3$ heteroalkyl, $C_3$-$C_7$ cycloalkyl; $R^3$ is a hydrogen, $C_1$-$C_3$ alkyl, $C_1$-$C_3$ heteroalkyl, $C_3$-$C_7$ cycloalkyl, 4-6 membered heterocyclyl, aryl, or heteroaryl; $R^5$ and $R^6$ are, each independently, hydrogen, $C_1$-$C_3$ alkyl, or $C_1$-$C_3$ heteroalkyl; $R^4$ is —C≡$CR^9$, —$NR^9R^{10}$, —$OR^9$, $C_1$-$C_6$ heteroalkyl, 3-12 membered carbocyclyl, 3-12 membered heterocyclyl, or 5-10 membered heteroaryl, wherein the $C_1$-$C_6$ heteroalkyl, 3-12 membered carbocyclyl, 3-12 membered heterocyclyl, or 5-10 membered heteroaryl is optionally substituted; $R^9$ and $R^{10}$ are, each independently, a hydrogen, $C_1$-$C_6$ alkyl, $C_3$-$C_7$ cycloalkyl, 3-7 membered heterocyclyl, or 5-10 membered heteroaryl, wherein the $C_1$-$C_6$ alkyl, $C_3$-$C_7$ cycloalkyl, 3-7 membered heterocyclyl, or 5-10 membered heteroaryl is optionally substituted; A is phenylene, 5-10 membered heteroarylene, phenylene fused to 5-6 membered heteroarylene, or 3-12 membered heterocyclylene, each of which is optionally substituted; Y is —$SO_2NHC(=O)$—, —$C(=O)NHSO_2$—, —$SO_2$—, or O; === is a single bond when Y is —$SO_2NHC(=O)$—, —$C(=O)NHSO_2$—, or —$SO_2$— or a double bond when Y is O; and $R^8$ is hydrogen, halo, —$OR^{11a}$, —$NR^{11a}R^{11b}$, $C_3$-$C_7$ cycloalkyl, 3-6 membered heterocyclyl, $C_1$-$C_4$ alkyl, $C_1$-$C_4$ haloalkyl, aryl, heteroaryl, or absent, and $R^{11a}$ and $R^{11b}$ are, each independently, a hydrogen, $C_1$-$C_3$ alkyl, $C_3$-$C_7$ cycloalkyl, $C_3$-$C_7$ heterocyclyl, aryl, or heteroaryl, wherein when Y is —$SO_2$, $R^8$ is $NR^{11a}R^{11b}$, and $R^{11a}$ and $R^{11b}$ are each independently hydrogen or $C_1$-$C_3$ alkyl, A is not phenylene; and when Y is O, the compound has the following structure:

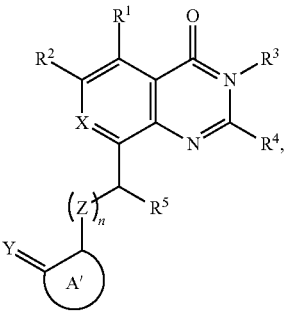

wherein A' is an unsaturated 5-6 membered heterocyclylene. The points of attachment of Y and Z to A' are on adjacent atoms of A'. For Example, non-limiting examples of A' include

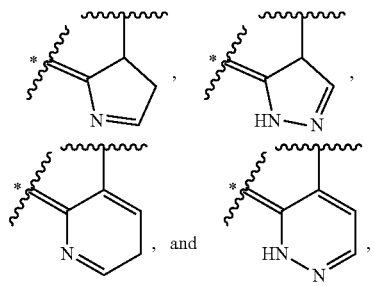

wherein * indicates the point of attachment to Y.

In some embodiments, n in an integer of 0. In some embodiments, n in an integer of 1.

In some embodiments, the compound has one of the following structures of Formula (IA)-(IB):

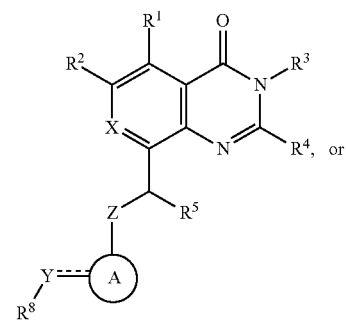, or

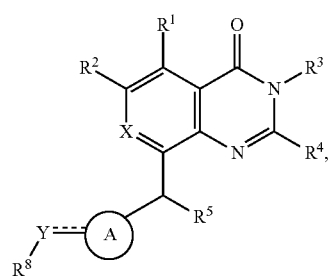

or a stereoisomer, tautomer of the compound, or a salt thereof. In some embodiments, the compound is

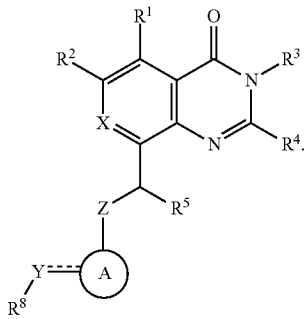

In some embodiments, the compound is

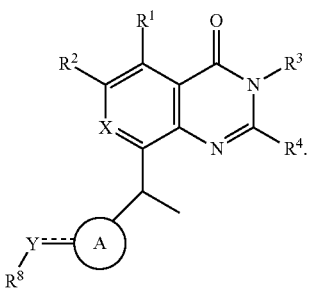

In one embodiment, A is phenylene, 5-10 membered heteroarylene, or 3-12 membered heterocyclylene, each of which is optionally substituted. In some embodiments, A is optionally substituted phenylene. In some embodiments, A is optionally substituted 5-10 membered heteroarylene. In some embodiments, A is optionally substituted 3-12 membered heterocyclylene.

In some embodiments, A is optionally substituted with 1-3 $R^A$, wherein $R^A$ is, each independently, hydrogen, halo, cyano, $C_1$-$C_3$ alkyl, $C_1$-$C_3$ heteroalkyl, $C_3$-$C_7$ cycloalkyl, —$OR^{11a}$, or —$NR^{11a}R^{11b}$. In some embodiments, A is not substituted. In some embodiments, A is substituted with 1 $R^A$. In some embodiments, A is substituted with 2 $R^A$. In some embodiments, A is substituted with 3 $R^A$. In some embodiments, $R^A$ is, each independently, hydrogen, —CN, —Br, —Cl, —F, —CH, —$CH_2CH_3$, cyclopropyl, —$OCH_3$, —$NHCH_3$, —$NHCH_2CH_3$, —$CF_3$, —$CH_2CF_3$, or —$CF_2H$.

In some embodiments, A is optionally substituted phenylene. In some embodiments, A is phenylene optionally substituted with 1, 2, or 3 $R^A$. In some embodiments, A has the following structure:

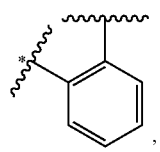

which is optionally substituted with 1, 2, or 3 $R^A$, wherein * indicates the point of attachment to Y.

In some embodiments, the 5-10 membered heteroarylene of A is pyrrolylene, imidazolylene, pyrazolylene, triazolylene, pyridinylene, diazinylene, triazinylene, thiazolylnee, isothiazolylene, oxazolylene, or isoxazolylene, each of which is optionally substituted. In some embodiments, the 5-10 membered heteroarylene of A is optionally substituted with 1, 2, or 3 $R^A$. In some embodiments, the 5-10 membered heteroarylene of A has one of the following structures:

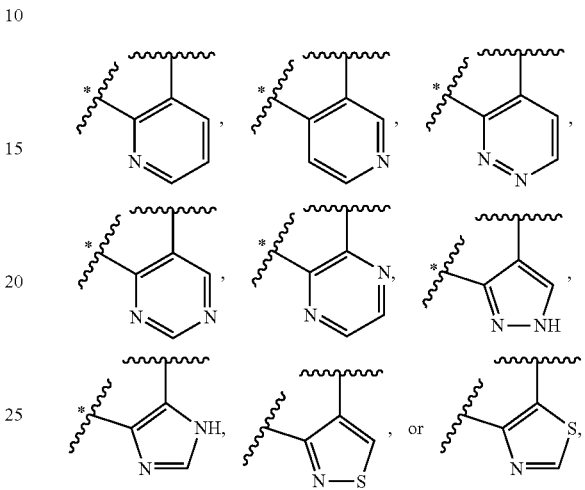

each optionally substituted with 1, 2, or 3 $R^A$, wherein * indicates the point of attachment to Y. In some embodiments, the 5-10 membered heteroarylene of A is

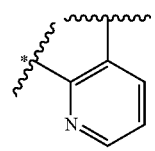

optionally substituted with 1, 2, or 3 $R^A$. In some embodiments, the 5-10 membered heteroarylene of A is

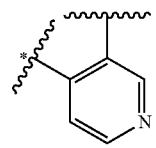 [SMILES: *c1ccncc1*]

optionally substituted with 1, 2, or 3 $R^A$. In some embodiments, the 5-10 membered heteroarylene of A is

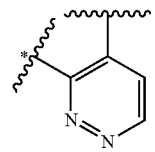 [SMILES: *c1ccnnc1*]

optionally substituted with 1, 2, or 3 $R^A$. In some embodiments, the 5-6 membered heteroarylene of A is

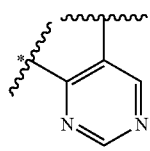 [SMILES: *c1cncnc1*]

optionally substituted with 1, 2, or 3 $R^A$. In some embodiments, the 5-10 membered heteroarylene of A is

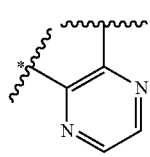 [SMILES: *c1nccnc1*]

optionally substituted with 1, 2, or 3 $R^A$. In some embodiments, the 5-10 membered heteroarylene of A is

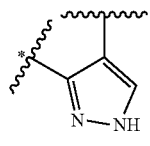

optionally substituted with 1, 2, or 3 $R^A$. In some embodiments, the 5-10 membered heteroarylene of A is

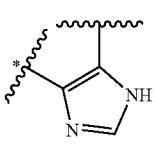

optionally substituted with 1, 2, or 3 $R^A$. In some embodiments, the 5-10 membered heteroarylene of A is

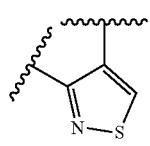

optionally substituted with 1, 2, or 3 $R^A$.

In some embodiments, the 3-12 membered heterocyclylene of A is unsaturated 5-6 membered heterocyclylene. In some embodiments, the unsaturated 5-6 membered heterocyclylene of A is 1,2-dihydropyridinylene, 1,4-dihydropyridinylene, 2,3-dihydropyridinylene, 2,5-dihydropyridinylene, 1,2-dihydropyridazinylene, or 1,4-dihydropyridazinylene, each of which is optionally substituted. In some embodiments, the unsaturated 5-6 membered heterocyclylene of A is optionally substituted with 1, 2, or 3 $R^A$. In some embodiments, the unsaturated 5-6 membered heterocycle of A has one of the following structures:

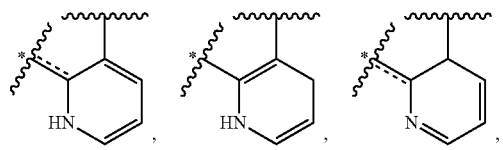

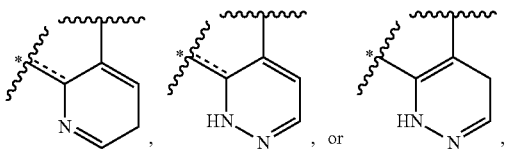

each optionally substituted with 1, 2, or 3 $R^A$, wherein * indicates the point of attachment to Y. In some embodiments, the unsaturated 5-6 membered heterocyclylene of A is

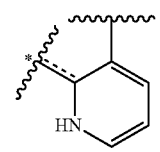

optionally substituted with 1, 2, or 3 $R^A$. In some embodiments, the unsaturated 5-6 membered heterocyclylene of A is

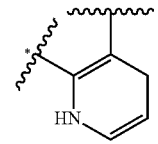 [SMILES: *C1=C(*)NC=CC1]

optionally substituted with 1, 2, or 3 $R^A$. In some embodiments, the unsaturated 5-6 membered heterocyclylene of A is

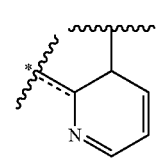

optionally substituted with 1, 2, or 3 $R^A$. In some embodiments, the unsaturated 5-6 membered heterocyclylene of A is

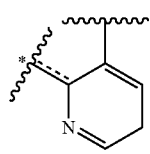

optionally substituted with 1, 2, or 3 $R^A$. In some embodiments, the unsaturated 5-6 membered heterocyclylene of A is

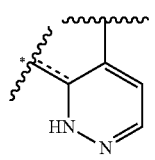

optionally substituted with 1, 2, or 3 $R^A$. In some embodiments, the unsaturated 5-6 membered heterocyclylene of A is

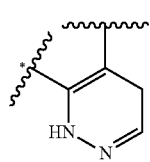

optionally substituted with 1, 2, or 3 $R^A$.

In some embodiments, the 3-12 membered heterocyclylene of A comprises a 5 membered heterocycle and a 6 membered aryl. In some embodiments, the 3-12 membered heterocyclylene of A comprises a 5 membered heterocycle and a 6 membered heteroaryl.

In some other embodiments, the 5-10 membered heteroarylene of A comprises a 5 membered heteroaryl and a 6 membered aryl. In some embodiments, the 5-10 membered heteroarylene of A comprises a 5 membered heteroaryl and a 6 membered heteroaryl.

In some embodiments, the 5-10 membered heteroarylene of A is benzimidazolylene, indazolylene, imidazopyridinylene, or pyrazolopyridinylene, each of which is optionally substituted. In some embodiments, the 5-10 membered heteroarylene of A is optionally substituted with 1, 2, or 3 $R^A$. In some embodiments, the 5-10 membered heteroarylene of A has one of the following structures:

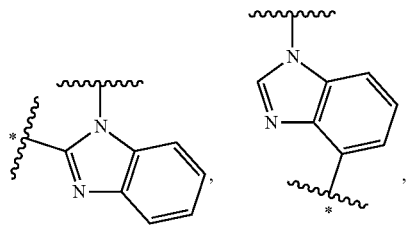

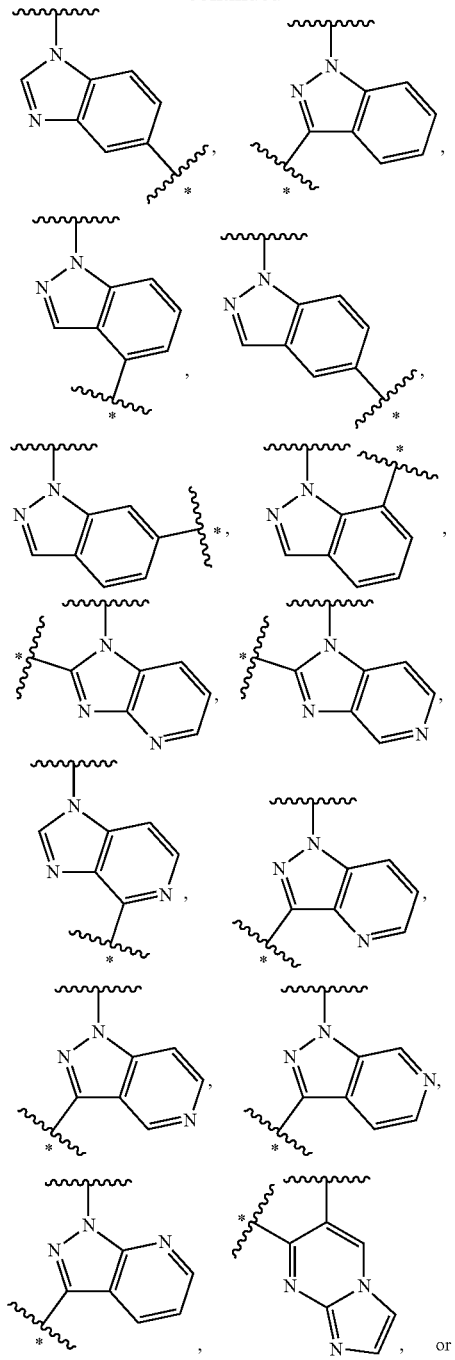

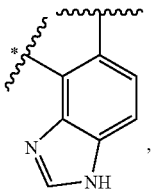

each optionally substituted with 1, 2, or 3 $R^A$, wherein * indicates the point of attachment to Y. In some embodiments, the 5-10 membered heteroarylene of A is

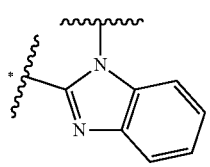 [SMILES: *c1nc2ccccc2n1*]

optionally substituted with 1, 2, or 3 $R^A$. In some embodiments, the 5-10 membered heteroarylene of A is

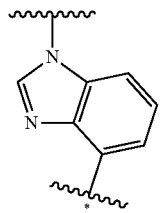

optionally substituted with 1, 2, or 3 $R^A$. In some embodiments, the 5-10 membered heteroarylene of A is

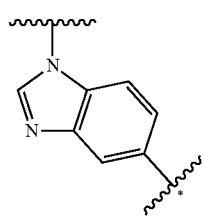 [SMILES: *c1ccc2c(c1)ncn2*]

optionally substituted with 1, 2, or 3 $R^A$. In some embodiments, the 5-10 membered heteroarylene of A is

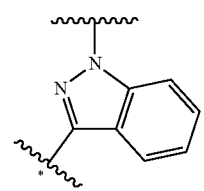 [SMILES: *c1nn(*)c2ccccc12]

optionally substituted with 1, 2, or 3 $R^A$. In some embodiments, the 5-10 membered heteroarylene of A is

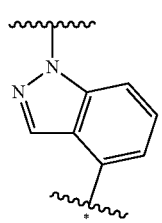

optionally substituted with 1, 2, or 3 $R^A$. In some embodiments, the 5-10 membered heteroarylene of A is

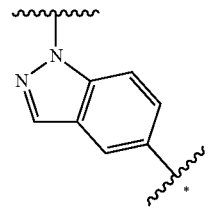 [SMILES: *c1ccc2c(cnn2*)c1]

optionally substituted with 1, 2, or 3 $R^A$. In some embodiments, the 5-10 membered heteroarylene of A is

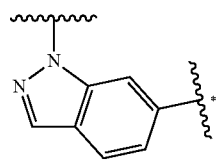 [SMILES: *c1ccc2cnn(*)c2c1]

optionally substituted with 1, 2, or 3 $R^A$. In some embodiments, the 5-10 membered heteroarylene of A is

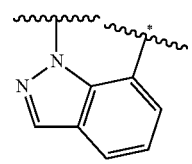 [SMILES: *c1cccc2cnn(*)c12]

optionally substituted with 1, 2, or 3 $R^A$. In some embodiments, the 5-10 membered heteroarylene of A is

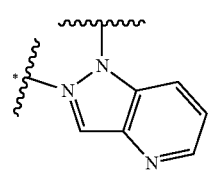

optionally substituted with 1, 2, or 3 $R^A$. In some embodiments, the 5-10 membered heteroarylene of A is

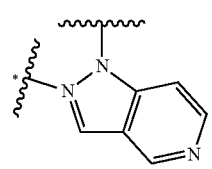

optionally substituted with 1, 2, or 3 $R^A$. In some embodiments, the 5-10 membered heteroarylene of A is

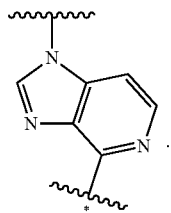 [SMILES: *c1nccc2c1ncn2* ; "."]

In some embodiments, the heterobicyclic of A is

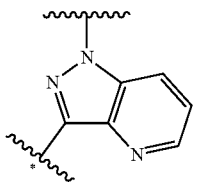 [SMILES: *c1nn(*)c2cccnc12]

optionally substituted with 1, 2, or 3 $R^A$. In some embodiments, the 5-10 membered heteroarylene of A is

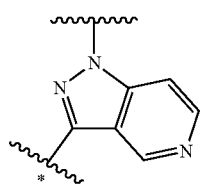 [SMILES: *c1nn(*)c2ccncc12]

optionally substituted with 1, 2, or 3 $R^A$. In some embodiments, the 5-10 membered heteroarylene of A is

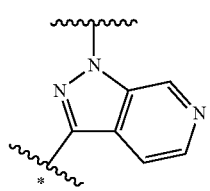 [SMILES: *c1nn(*)c2cnccc12]

optionally substituted with 1, 2, or 3 $R^A$. In some embodiments, the 5-10 membered heteroarylene of A is

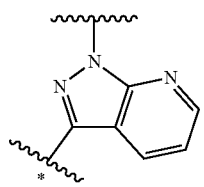 [SMILES: *c1nn(*)c2ncccc12]

optionally substituted with 1, 2, or 3 $R^A$. In some embodiments, the heterobicyclic of A is

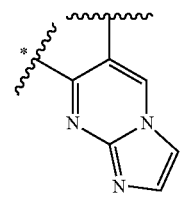

optionally substituted with 1, 2, or 3 $R^A$. In some embodiments, the 5-10 membered heteroarylene of A is

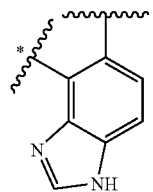 [SMILES: *c1ccc2[nH]cnc2c1*]

optionally substituted with 1, 2, or 3 $R^A$.

In some embodiments, the compound has one of the following structures of Formula (IA-a)-(IA-1) and (IB-a)-(IB-b):

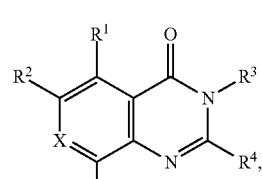
(IA-a)

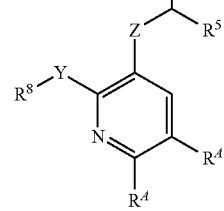

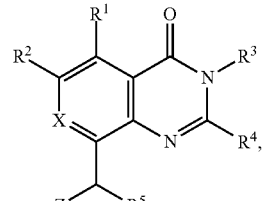
(IA-b)

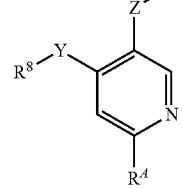

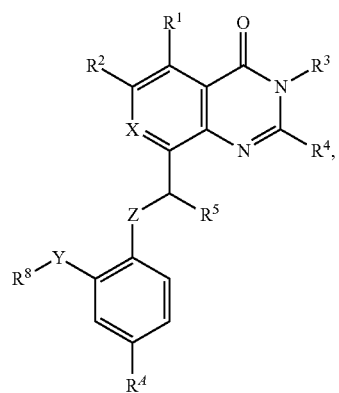
(IA-c)
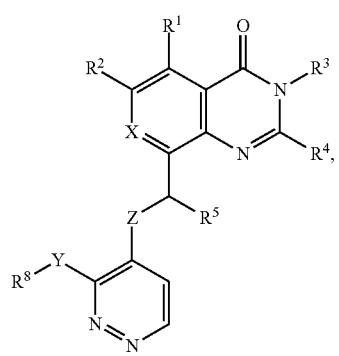
(IA-d)
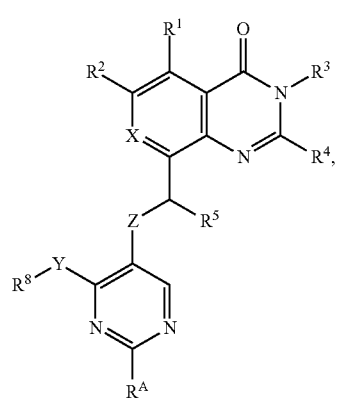
(IA-e)
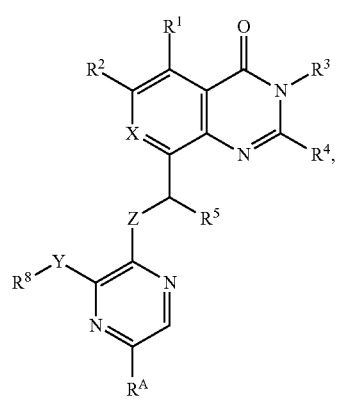
(IA-f)
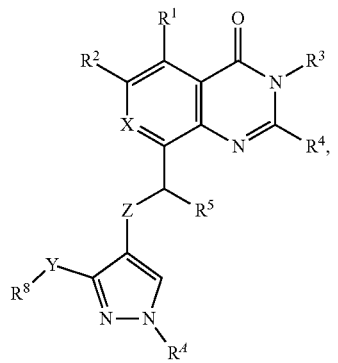
(IA-g)
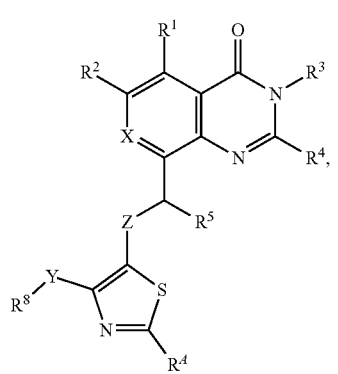
(IA-h)
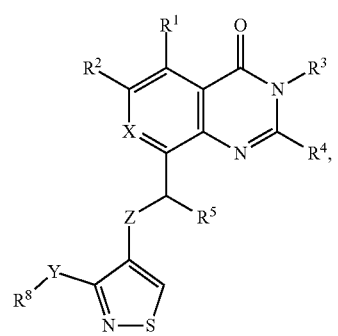
(IA-i)
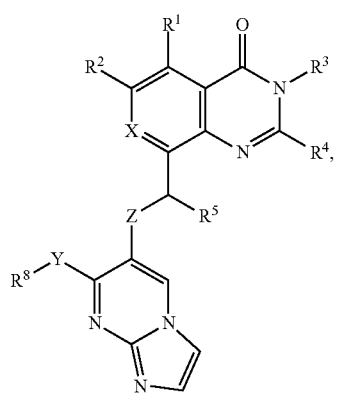
(IA-j)

-continued

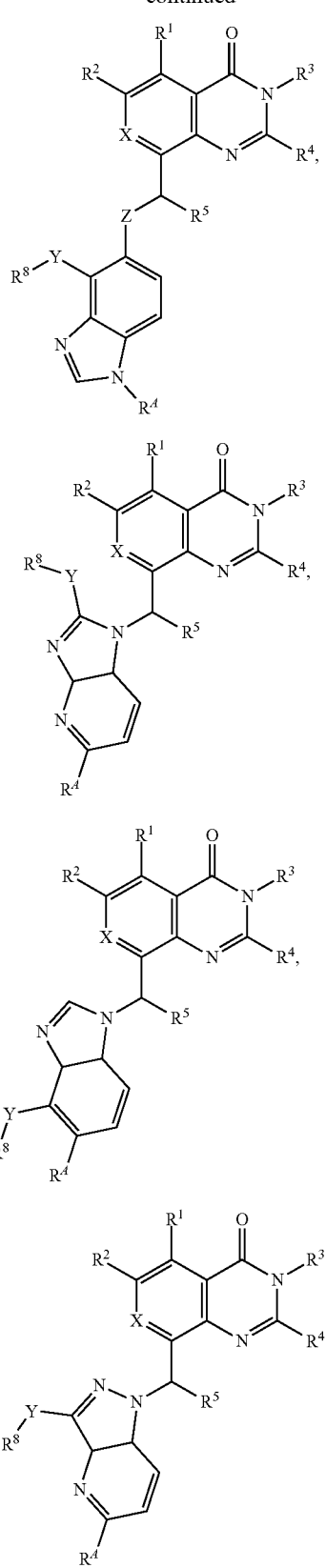

or a stereoisomer, tautomer of the compound, or a salt thereof.

In some embodiments, the compound has one of the following structure of Formula (IA-a) or a stereoisomer, tautomer of the compound, or a salt thereof:

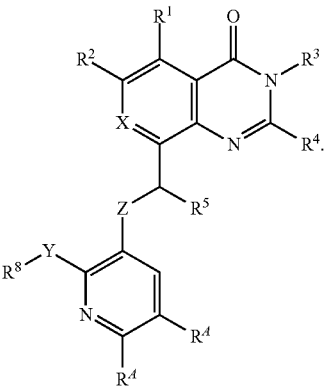

(IA-a) In some embodiments, Y is

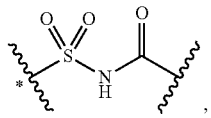 [SMILES: *C(=O)NS(*)(=O)=O]

wherein * indicates a bond to $R^8$. In some embodiments, Y is

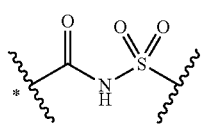

wherein * indicates a bond to $R^8$. In some embodiments, Y is

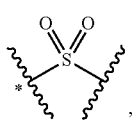 [SMILES: *S(*)(=O)=O]

wherein * indicates a bond to $R^8$. In some embodiments, Y is O and $R^8$ is absent.

In some embodiments, the compound has one of the following structures of Formula (IA-1)-(IA-3), (IB-1)-(IB-3), and (IC):

(IA-1)
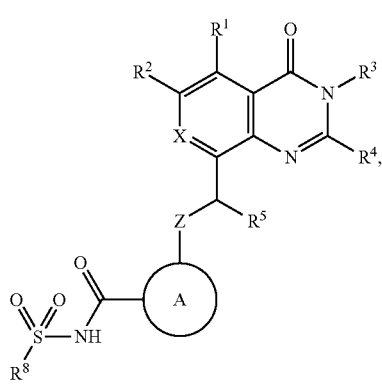
(IA-2)
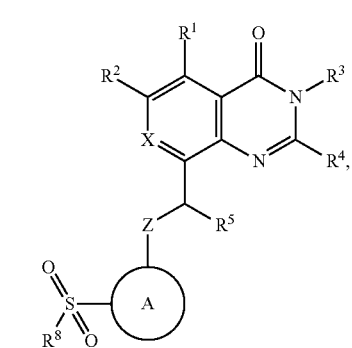
(IA-3)
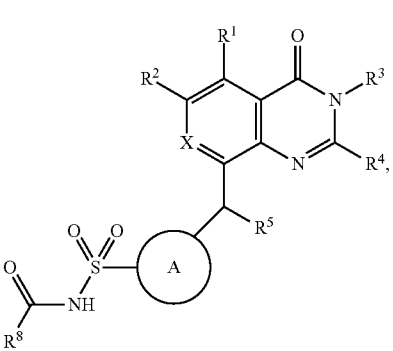
(IB-1)
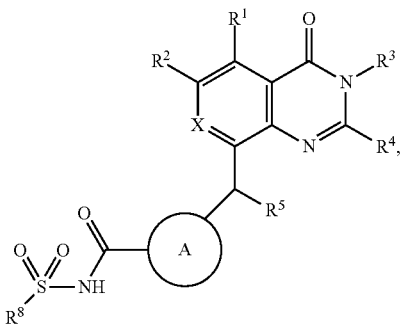
(IB-2)
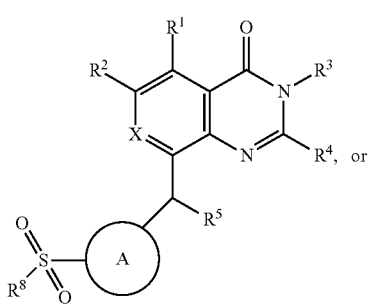
(IB-3)
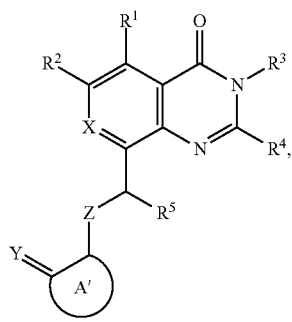
(IC)
or a stereoisomer, tautomer of the compound, or a salt thereof. In some embodiments, the compound is
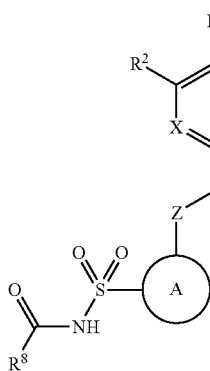

In some embodiments, the compound is

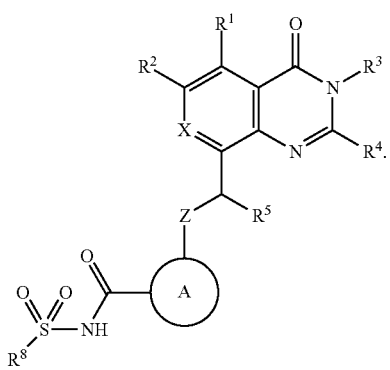

In some embodiments, the compound is

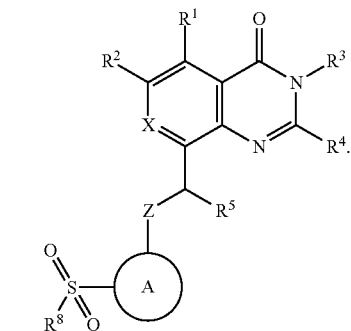

In some embodiments, the compound is

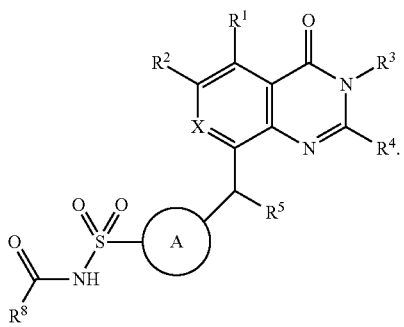

In some embodiments, the compound is

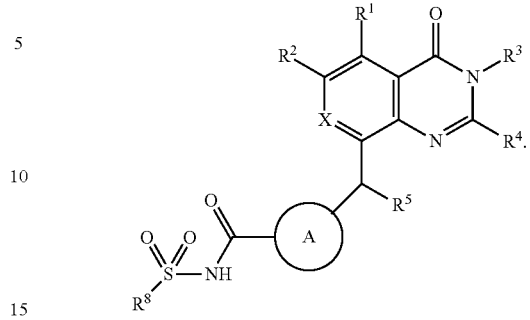

In some embodiments, the compound is

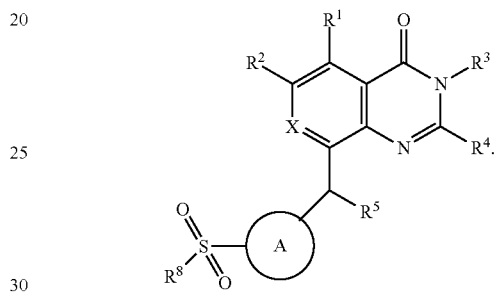

In some embodiments, the compound is

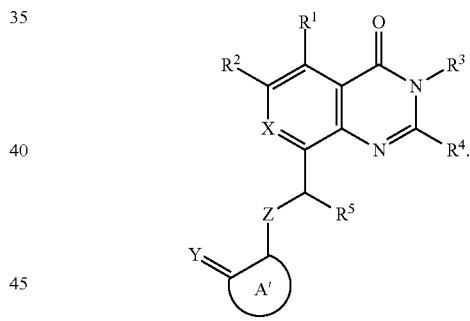

In some embodiments, $R^1$, $R^2$, and $R^7$ are, each independently, a hydrogen, halo, $C_1$ alkyl, $C_1$ heteroalkyl, or 3-5 membered cycloalkyl. In some other embodiments, $R^1$, $R^2$, and $R^7$ are, each independently, —H, —F, —CH$_3$, or cyclopropyl. In some embodiments, $R^1$ is —H, $R^2$ is —CH$_3$, and $R^7$ is —H. In some embodiments, $R^1$ is —H, $R^2$ is —F, and $R^7$ is —H. In some embodiments, $R^1$ is —F, $R^2$ is —F, and $R^7$ is —H. In some embodiments, $R^1$ is —H, $R^2$ is —H, and $R^7$ is —H. In some embodiments, $R^1$ is —CH$_3$ or —CH$_2$CH$_3$, $R^2$ is —H, and $R^7$ is —H.

In some embodiments, the 4-6 membered heterocyclyl of $R^3$ has 1-3 nitrogen atoms. In some embodiments, the 4-6 membered heterocyclyl of $R^3$ has 1-2 oxygen atoms. In some embodiments, the 4-6 membered heterocyclyl of $R^3$ has 1 oxygen atom. In some embodiments, the 4-6 membered heterocyclyl of $R^3$ has 2 oxygen atoms. In some embodiments, the 4-6 membered heterocyclyl of $R^3$ has 3 oxygen atoms.

In some embodiments, the 4-6 membered heterocyclyl of $R^3$ is oxetanyl, azetidinyl, dioxetanyl, pyrrolidinyl, tetrahydrofuranyl, imidazolidinyl, pyrazolidinyl, oxazolidinyl, isoxazolidinyl, dioxolanyl, triazolyl, furazanyl, oxadiazolyl, piperidinyl, oxanyl, diazinanyl, morpholinyl, dioxanyl, triazinanyl, or trioxanyl. In some embodiments, the 4-6 membered heterocyclyl of $R^3$ is oxetanyl. In some embodiments, the 4-6 membered heterocyclyl of $R^3$ is azetidinyl. In some embodiments, the 4-6 membered heterocyclyl of $R^3$ is dioxetanyl. In some embodiments, the 4-6 membered heterocyclyl of $R^3$ is pyrrolidinyl. In some embodiments, the 4-6 membered heterocyclyl of $R^3$ is tetrahydrofuranyl. In some embodiments, the 4-6 membered heterocyclyl of $R^3$ is imidazolidinyl. In some embodiments, the 4-6 membered heterocyclyl of $R^3$ is pyrazolidinyl. In some embodiments, the 4-6 membered heterocyclyl of $R^3$ is oxazolidinyl. In some embodiments, the 4-6 membered heterocyclyl of $R^3$ is isoxazolidinyl. In some embodiments, the 4-6 membered heterocyclyl of $R^3$ is dioxolanyl. In some embodiments, the 4-6 membered heterocyclyl of $R^3$ is triazolyl. In some embodiments, the 4-6 membered heterocyclyl of $R^3$ is furazanyl. In some embodiments, the 4-6 membered heterocyclyl of $R^3$ is oxadiazolyl. In some embodiments, the 4-6 membered heterocyclyl of $R^3$ is piperidinyl. In some embodiments, the 4-6 membered heterocyclyl of $R^3$ is oxanyl. In some embodiments, the 4-6 membered heterocyclyl of $R^3$ is diazinanyl. In some embodiments, the 4-6 membered heterocyclyl of $R^3$ is morpholinyl. In some embodiments, the 4-6 membered heterocyclyl of $R^3$ is dioxanyl. In some embodiments, the 4-6 membered heterocyclyl of $R^3$ is triazinanyl. In some embodiments, the 4-6 membered heterocyclyl of $R^3$ is trioxanyl.

In some embodiments, $R^3$ is a hydrogen, $C_1$-$C_2$ alkyl, $C_1$-$C_2$ heteroalkyl, cyclopropyl, or a 4 membered heterocyclyl. In some certain embodiments, $R^3$ is —H, —$CH_3$, $CH_2CH_3$,

or

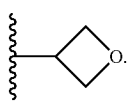

In some embodiments, $R^3$ is —H. In some embodiments, $R^3$ is —$CH_3$. In some embodiments, $R^3$ is —$CH_2CH_3$. In some embodiments, $R^3$ is

In some embodiments, $R^3$ is

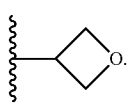 [SMILES: *C1COC1]

In some embodiments, $R^5$ and $R^6$ are, each independently, a hydrogen, $C_1$-$C_2$ alkyl, or $C_1$-$C_2$ heteroalkyl. In some certain embodiments, $R^5$ and $R^6$ are, each independently, —H, —$CH_3$, —$CH_2OH$, or —$CH_2CH_3$. In some embodiments, $R^5$ is —$CH_3$. In some embodiments, $R^5$ is —$CH_2OH$. In some embodiments, $R^3$ is —H, —$CH_3$, or

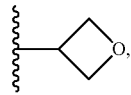

$R^5$ is —$CH_3$, and $R^6$ is —H.

In some embodiments, the 3-12 membered carbocyclyl, 3-12 membered heterocyclyl, or 5-10 membered heteroaryl of $R^4$ is optionally substituted with 1, 2, 3, or 4 $R^X$. In some embodiments, wherein $R^X$ is, each independently, hydrogen, halo, oxo, cyano, $C_1$-$C_6$ alkyl, $C_1$-$C_6$ heteroalkyl, —C(O)$R^{11a}$, —$OR^{11a}$, —$NR^{11a}R^{11b}$, $C_3$-$C_{12}$ cycloalkyl, 3-12 membered heterocyclyl, 5-10 membered heteroaryl, —($C_1$-$C_6$ alkylene)-G, or —($C_1$-$C_6$ heteroalkylene)-G, wherein the $C_1$-$C_6$ alkyl or $C_1$-$C_6$ heteroalkyl is optionally substituted with one or more deuterium, halo, or hydroxyl, and the $C_3$-$C_2$ cycloalkyl, 3-12 membered heterocyclyl, or 5-10 membered heteroaryl is optionally substituted with one or more $R^Y$; or 2 $R^X$, together with the atoms to which they are attached, form a $C_3$-$C_7$ carbocyclyl, $^3$-7 membered heterocyclyl, phenyl, or 5-6 membered heteroaryl, wherein the $C_3$-$C_7$ carbocyclyl, 3-7 membered heterocyclyl, phenyl, or 5-6 membered heteroaryl is optionally substituted with one or more $R^Y$; G is $C_3$-$C_7$ cycloalkyl, 3-7 membered heterocyclyl, or 5-10 membered heteroaryl, wherein the $C_3$-$C_7$ cycloalkyl, 3-7 membered heterocyclyl, or 5-10 membered heteroaryl is optionally substituted with one or more $R^Y$. In some embodiments, $R^Y$ is, each independently, halo, oxo, cyano, $C_1$-$C_6$ alkyl, $C_1$-$C_6$ heteroalkyl, —C(O)$R^{11a}$, —$OR^{11a}$, —$NR^{11a}R^{11b}$, —$NR^{11a}C(O)R^{11b}$, $C_3$-$C_7$ cycloalkyl, 3-12 membered heterocyclyl, or 5-10 membered heteroaryl, wherein the $C_1$-$C_6$ alkyl or $C_1$-$C_6$ heteroalkyl is optionally substituted with one or more deuterium, halo, or cyano, and the $C_3$-$C_7$ cycloalkyl, 3-12 membered heterocyclyl, or 5-10 membered heteroaryl is optionally substituted with one or more $C_1$-$C_6$ alkyl.

In some embodiments, $R^4$ is $C_1$-$C_4$ heteroalkyl. In some embodiments, $R^4$ is $C_1$-$C_4$ alkylamine, monosubstituted alkylamine, or disubstituted alkylamine. In some certain embodiments, $R^4$ is N-methyl alkylamine or N,N-dimethyl alkylamine. In some embodiments, $R^4$ is N-methyl alkylamine. In some embodiments, $R^4$ is N,N-dimethyl alkylamine.

In some embodiments, the 3-12 membered carbocyclyl of $R^4$ is optionally substituted aryl. In some embodiments, the 3-12 membered carbocyclyl of $R^4$ is optionally substituted with 1, 2, 3, or 4 $R^X$. In some embodiments, the 3-12 membered carbocyclyl of $R^4$ phenyl optionally substituted with 1, 2, 3, or 4 $R^X$. In some embodiments, $R^4$ has one of the following structures:

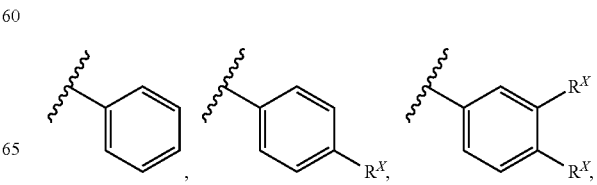

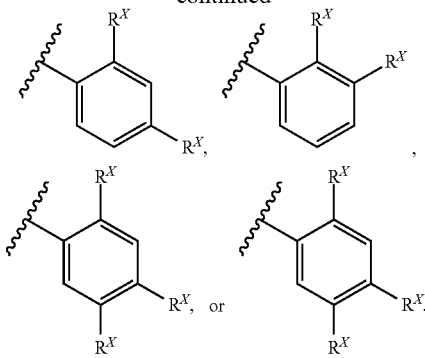

In some embodiments, the 3-12 membered carbocyclyl of $R^4$ is optionally substituted $C_3$-$C_{12}$ cycloalkyl. In some embodiments, the 3-12 membered carbocyclyl of $R^4$ is optionally substituted with 1, 2, 3, or 4 $R^X$. In some embodiments, the $C_3$-$C_2$ cycloalkyl of $R^4$ is a cyclopronayl or cyclohexanyl, each of which is optionally substituted with 1, 2, 3, or 4 $R^X$. In some embodiments, $R^4$ has one of the following structures:

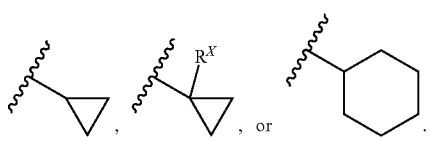

In some embodiments, the 3-12 membered heterocyclyl or 5-10 membered heteroaryl of $R^4$ has 1-4 nitrogen atoms. In some embodiments, the 3-12 membered heterocyclyl or 5-10 membered heteroaryl of $R^4$ has 1 nitrogen atom. In some embodiments, the 3-12 membered heterocyclyl or 5-10 membered heteroaryl of $R^4$ has 2 nitrogen atoms. In some embodiments, the 3-12 membered heterocyclyl or 5-10 membered heteroaryl of $R^4$ has 3 nitrogen atoms. In some embodiments, the 3-12 membered heterocyclyl or 5-10 membered heteroaryl of $R^4$ has 4 nitrogen atoms.

In some embodiments, the 3-12 membered heterocyclyl or 5-10 membered heteroaryl of $R^4$ has 1-3 nitrogen atoms and 1 sulfur or 1 oxygen atom. In some other embodiments, the 3-12 membered heterocyclyl or 5-10 membered heteroaryl of $R^4$ has 1-2 oxygen atoms.

In some embodiments, the 3-12 membered heterocyclyl or 5-10 membered heteroaryl of $R^4$ is monocyclic or bicyclic. In some embodiments, $R^4$ is a saturated mono-heterocyclyl or mono-heteroaryl. In some embodiments, the saturated mono-heterocyclyl or mono-heteroaryl of $R^4$ is azetidinyl, pyrrolidinyl, piperidinyl, piperazinyl, 1,4-diazinanyl, morpholinyl, oxazepanyl, azapanyl, diazepanyl, or azocanyl, each of which is optionally substituted with 1, 2, 3, or 4 $R^X$.

In some embodiments, $R^4$ is optionally substituted saturated mono-heterocyclyl. In some embodiments, the saturated mono-heterocyclyl of $R^4$ has one of the following structures:

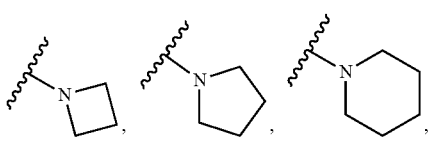

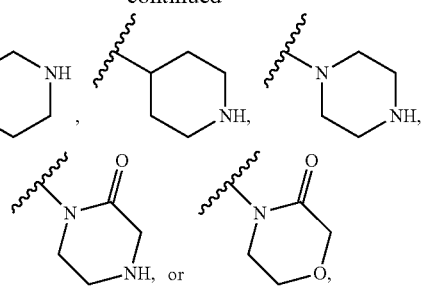

each optionally substituted with 1, 2, 3, or 4 $R^X$. In some embodiments, the saturated mono-heterocyclyl of $R^4$ is

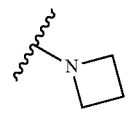

optionally substituted with 1, 2, 3, or 4 $R^X$. In some embodiments, the saturated mono-heterocyclyl of $R^4$ is

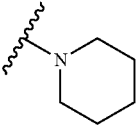

optionally substituted with 1, 2, 3, or 4 $R^X$. In some embodiments, the saturated mono-heterocyclyl of $R^4$ is

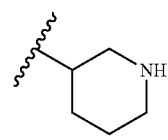

optionally substituted with 1, 2, 3, or 4 $R^X$. In some embodiments, the saturated mono-heterocyclyl of $R^4$ is

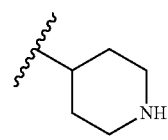

optionally substituted with 1, 2, 3, or 4 $R^X$. In some embodiments, the saturated mono-heterocyclyl of $R^4$ is optionally substituted with 1, 2, 3, or 4 $R^X$. In some embodiments, the saturated mono-heterocyclyl of $R^4$ is

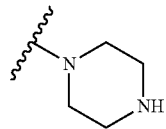

optionally substituted with 1, 2, 3, or 4 $R^X$. In some embodiments, the saturated mono-heterocyclyl of $R^4$ is

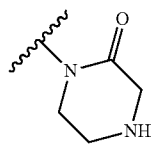 [SMILES: *N1CCNCC1=O]

optionally substituted with 1, 2, 3, or 4 $R^X$. In some embodiments, the saturated mono-heterocyclyl of $R^4$ is

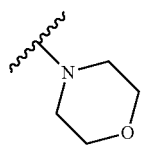 [SMILES: *N1CCOCC1]

optionally substituted with 1, 2, 3, or 4 $R^X$. In some embodiments, $R^4$ has one of the following structures:

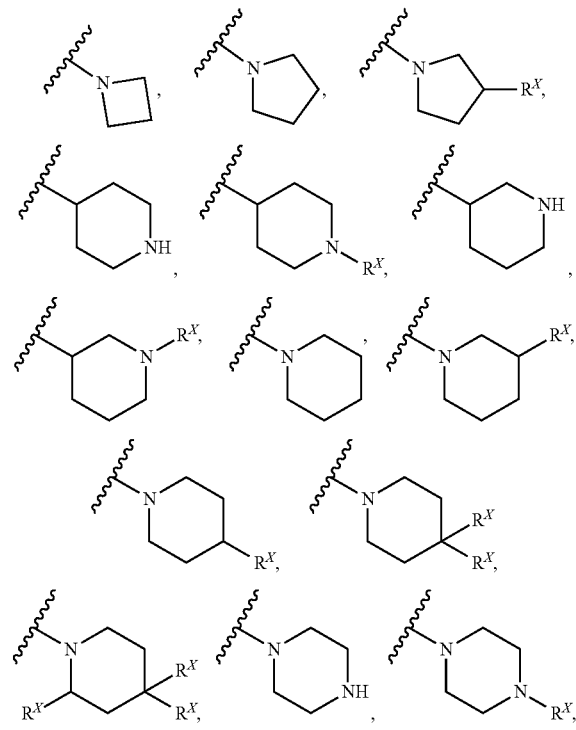

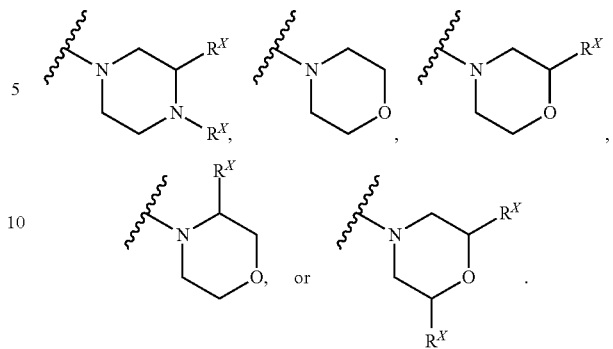

In some embodiments, $R^4$ is optionally substituted unsaturated mono-heterocyclyl or mono-heteroaryl. In some embodiments, the unsaturated mono-heterocyclyl or mono-heteroaryl of $R^4$ is azirinyl, azetyl, oxetyl, thietyl, pyrrolyl, furanyl, thiophenyl, imidazolyl, pyrazolyl, oxazolyl, isoxazolyl, pyrimidinyl, pyridazinyl, pyrazinyl, oxadiazolyl, thiadiazolyl, tetrazolyl, thiazolyl, isothiazolyl, triazolyl, pyridinyl, pyranyl, thiopyranyl, diazinyl, oxazinyl, triazinyl, or pyridonyl, each of which is optionally substituted with 1, 2, 3, 4 $R^X$. In some certain embodiments, the unsaturated mono-heterocyclyl or mono-heteroaryl of $R^4$ has one of the following structures:

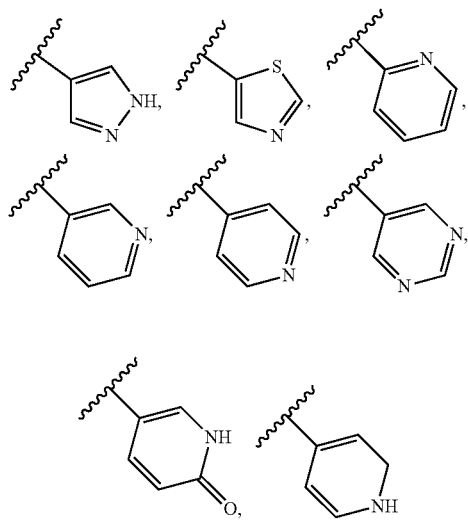

each optionally substituted with 1, 2, 3, or 4 $R^X$. In some embodiments, the unsaturated mono-heterocyclyl or mono-heteroaryl of $R^4$ is

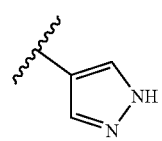 [SMILES: *c1cn[nH]c1]

optionally substituted with 1, 2, 3, or 4 $R^X$. In some embodiments, the unsaturated mono-heterocyclyl or mono-heteroaryl of $R^4$

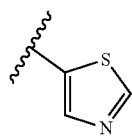

optionally substituted with 1, 2, 3, or 4 $R^X$. In some embodiments, the unsaturated mono-heterocyclyl or mono-heteroaryl of $R^4$ is

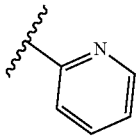 [SMILES: *c1ccccn1]

optionally substituted with 1, 2, 3, or 4 $R^X$. In some embodiments, the unsaturated mono-heterocyclyl or mono-heteroaryl of $R^4$ is

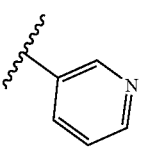 [SMILES: *c1cccnc1]

optionally substituted with 1, 2, 3, or 4 $R^X$. In some embodiments, the unsaturated mono-heterocyclyl or mono-heteroaryl of $R^4$ is

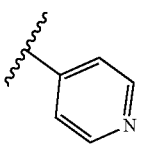 [SMILES: *c1ccncc1]

optionally substituted with 1, 2, 3, or 4 $R^X$. In some embodiments, the unsaturated mono-heterocyclyl or mono-heteroaryl of $R^4$ is

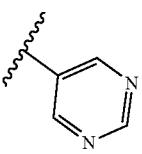

optionally substituted with 1, 2, 3, or 4 $R^X$. In some embodiments, the unsaturated mono-heterocyclyl or mono-heteroaryl of $R^4$ is

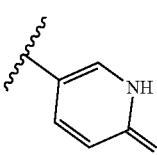

optionally substituted with 1, 2, 3, or 4 $R^X$. In some embodiments, the unsaturated mono-heterocyclyl or mono-heteroaryl of $R^4$ is

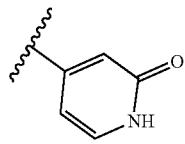 [SMILES: *c1cc[nH]c(=O)c1]

optionally substituted with 1, 2, 3, or 4 $R^X$. In some embodiments, $R^4$ has one of the following structures:

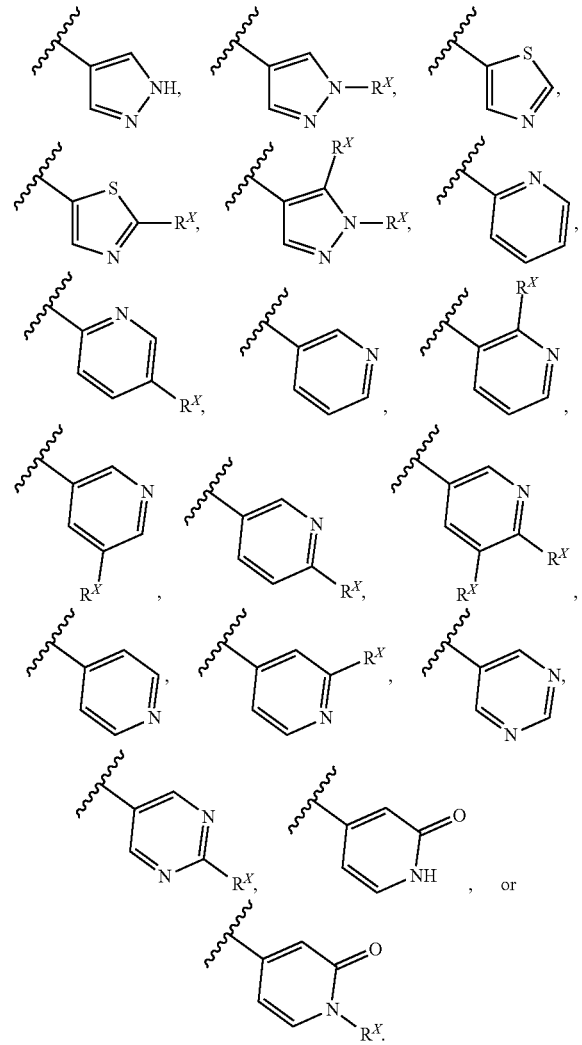

In some embodiments, $R^4$ is a fused bicyclic heterocyclyl or heteroaryl, a spiro bicyclic heterocyclyl or heteroaryl, or a bridged bicyclic heterocyclyl or heteroaryl, each of which is optionally substituted. In some embodiments, the fused bicyclic heterocyclyl or heteroaryl of $R^4$ is 4,5,6,7-tetrahydro-[1,2,3]triazolo[1,5-a]pyrazinyl, 4,5,6,7-tetrahydro-2H-pyrazolo[4,3-c]pyridinyl, 5,6,7,8-tetrahydro-[1,2,4]triazolo[4,3-a]pyrazinyl, 4,5,6,7-tetrahydro-3H-[1,2,3]triazolo[4,5-c]pyridinyl, 5,6,7,8-tetrahydroimidazo[1,5-a]pyrazinyl, 5,6,7,8-tetrahydro-[1,2,4]triazolo[1,5-a]pyrazinyl, 4,5,6,7- tetrahydro-3H-imidazo[4,5-c]pyridinyl, 1,2,3,4-tetrahydro-2,7-naphthyridinyl, 3-azabicyclo[3.1.0]hexanyl, 2H-pyrazolo[3,4-b]pyridinyl, octahydropyrrolo[3,4-c]pyrrolyl, 1H-benzo[d]imidazolyl, 1,2,3,4-tetrahydroisoquinolinyl, 3,4-dihydroquinolin-2(1H)-onyl, benzo[d]thiazolyl, imidazo[1,2-a]pyridinyl, isoxazolo[5,4-b]pyridinyl, octahydropyrrolo[1,2-a]pyrazinyl, 1H-indole, benzo[d]oxazolyl, pyrazolo[1,5-a]pyridinyl, isoindolinyl, 1,4,5,6-tetrahydropyrrolo[3,4-c]pyrazolyl, [1,2,4]triazolo[1,5-a]pyridinyl, 1H-indazolyl, 2H-indazolyl, 1,4,5,6-tetrahydropyrrolo[3,4-c]pyrazolyl, 6,7-dihydro-5H-pyrrolo[3,4-d]pyrimidinyl, 5,6,7,8-tetrahydro-1,7-naphthyridinyl, 6,7-dihydro-5H-pyrrolo[3,4-b]pyridinyl, 2H-benzo[d][1,2,3]triazolyl, 2H-pyrazolo[3,4-c]pyridinyl, 2l-pyrazolo[4,3-b]pyridinyl, isoindolin-1-onyl, 3,4-dihydroisoquinolin-1(2H)-onyl, octahydrocyclopenta[c]pyrrolyl, 6,7-dihydro-5H-pyrrolo[3,4-b]pyrazinyl, 4,5,6,7-tetrahydropyrazolo[1,5-a]pyrazinyl, 4,5,6,7-tetrahydro-1H-pyrazolo[4,3-c]pyridinyl, 4,5,6,7-tetrahydro-2H-pyrazolo[3,4-c]pyridinyl, 4,5,6,7-tetrahydroisoxazolo[4,3-c]pyridinyl, 4,5,6,7-tetrahydroisoxazolo[4,5-c]pyridinyl, each of which is optionally substituted with 1, 2, 3, or 4 $R^X$. In some embodiments, the fused bicyclic heterocyclyl or heteroaryl of $R^4$ has one of the following structures:

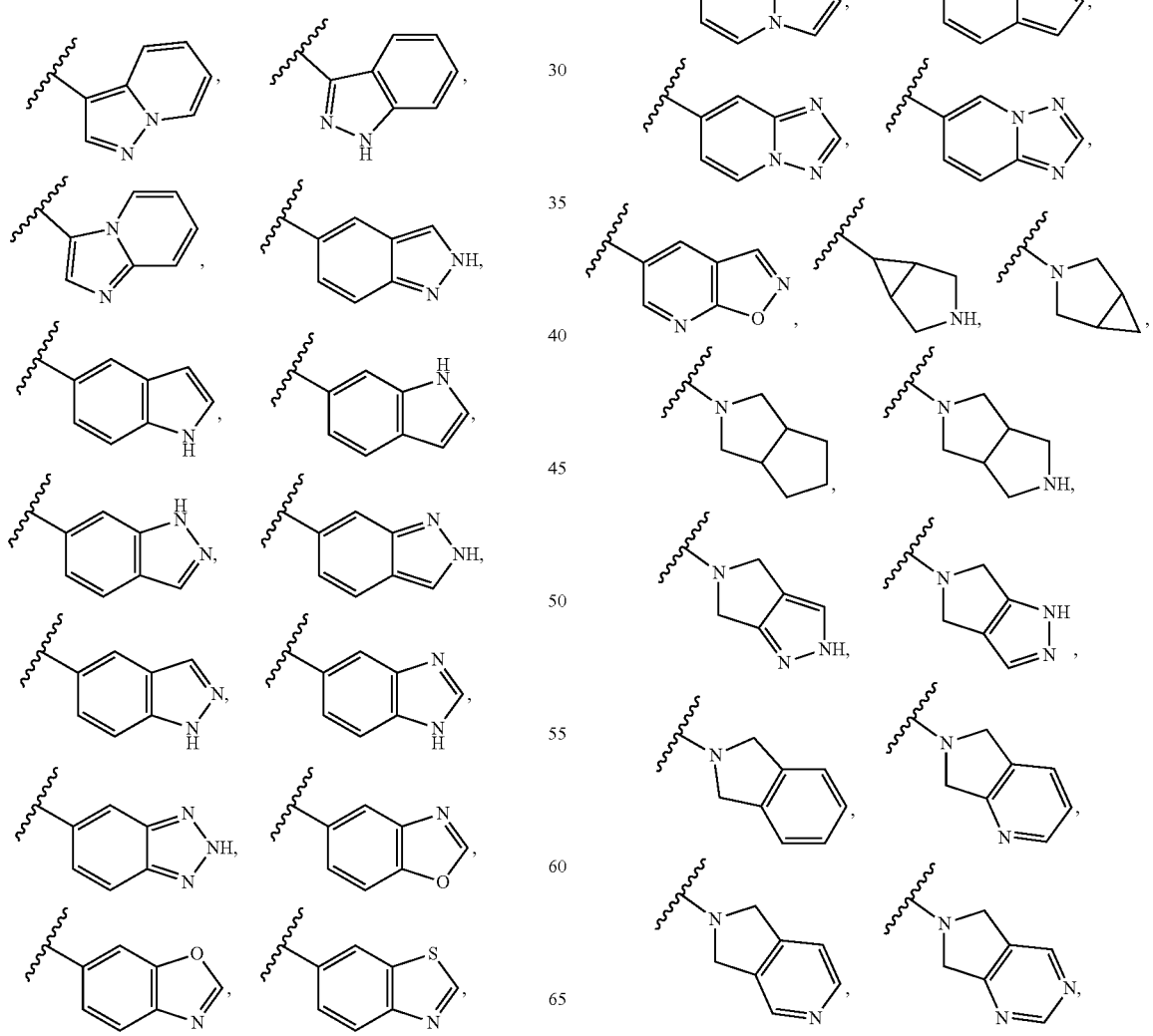

-continued

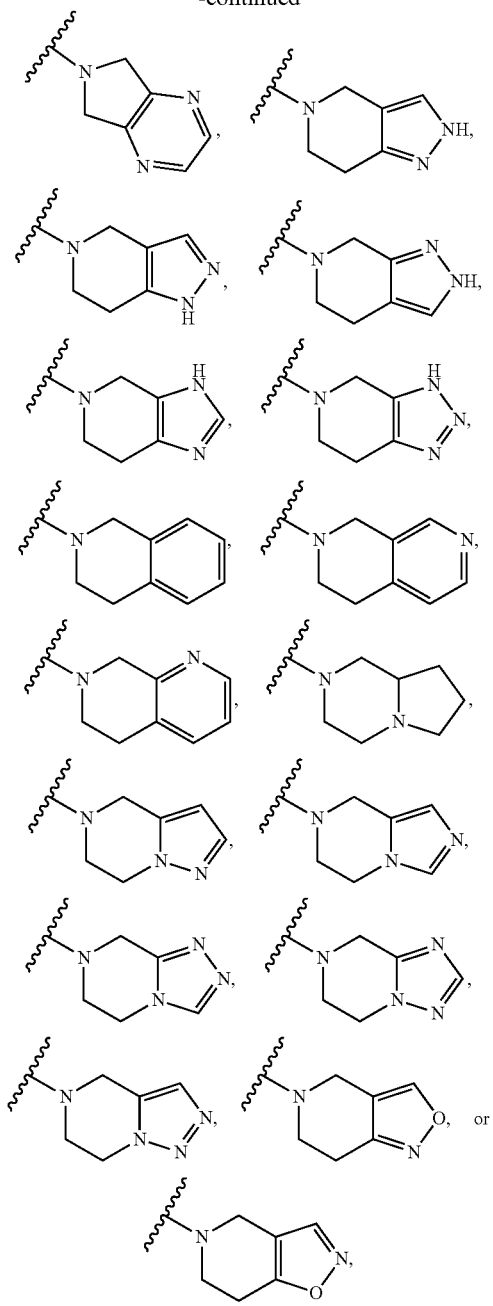

each optionally substituted with 1, 2, 3, or 4 $R^X$. In some embodiments, the fused bicyclic heterocyclyl or heteroaryl of $R^4$ is

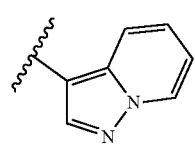 [SMILES: *c1cnn2ccccc12]

optionally substituted with 1, 2, 3, or 4 $R^X$. In some embodiments, the fused bicyclic heterocyclyl or heteroaryl of $R^4$ is

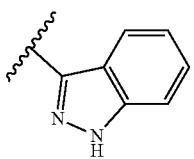 [SMILES: *c1n[nH]c2ccccc12]

optionally substituted with 1, 2, 3, or 4 $R^X$. In some embodiments, the fused bicyclic heterocyclyl or heteroaryl of $R^4$ is

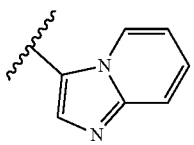 [SMILES: *c1cnc2ccccn12]

optionally substituted with 1, 2, 3, or 4 $R^X$. In some embodiments, the fused bicyclic heterocyclyl or heteroaryl of $R^4$ is

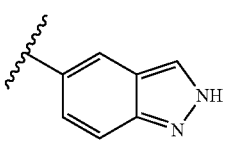 [SMILES: *c1ccc2n[nH]cc2c1]

optionally substituted with 1, 2, 3, or 4 $R^X$. In some embodiments, the fused bicyclic heterocyclyl or heteroaryl of $R^4$ is

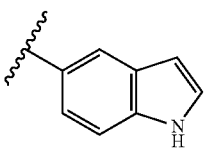 [SMILES: *c1ccc2[nH]ccc2c1]

optionally substituted with 1, 2, 3, or 4 $R^X$. In some embodiments, the fused bicyclic heterocyclyl or heteroaryl of $R^4$ is

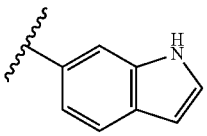 [SMILES: *c1ccc2cc[nH]c2c1]

optionally substituted with 1, 2, 3, or 4 $R^X$. In some embodiments, the fused bicyclic heterocyclyl or heteroaryl of $R^4$ is

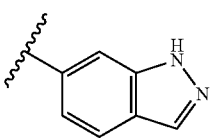 [SMILES: *c1ccc2cn[nH]c2c1]

optionally substituted with 1, 2, 3, or 4 $R^X$. In some embodiments, the fused bicyclic heterocyclyl or heteroaryl of $R^4$ is

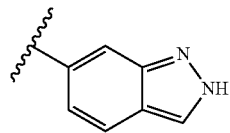 [SMILES: *c1ccc2c[nH]nc2c1]

optionally substituted with 1, 2, 3, or 4 $R^X$. In some embodiments, the fused bicyclic heterocyclyl or heteroaryl of $R^4$ is

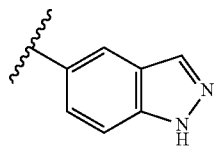 [SMILES: *c1ccc2[nH]ncc2c1]

optionally substituted with 1, 2, 3, or 4 $R^X$. In some embodiments, the fused bicyclic heterocyclyl or heteroaryl of $R^4$ is

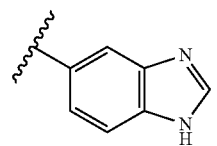 [SMILES: *c1ccc2[nH]cnc2c1]

optionally substituted with 1, 2, 3, or 4 $R^X$. In some embodiments, the fused bicyclic heterocyclyl or heteroaryl of $R^4$ is

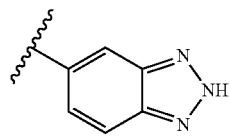 [SMILES: *c1ccc2n[nH]nc2c1]

optionally substituted with 1, 2, 3, or 4 $R^X$. In some embodiments, the fused bicyclic heterocyclyl or heteroaryl of $R^4$ is

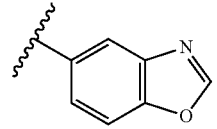 [SMILES: *c1ccc2ocnc2c1]

optionally substituted with 1, 2, 3, or 4 $R^X$. In some embodiments, the fused bicyclic heterocyclyl or heteroaryl of $R^4$ is

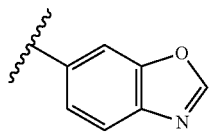 [SMILES: *c1ccc2ncoc2c1]

optionally substituted with 1, 2, 3, or 4 $R^X$. In some embodiments, the fused bicyclic heterocyclyl or heteroaryl of $R^4$ is

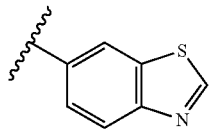 [SMILES: *c1ccc2ncsc2c1]

optionally substituted with 1, 2, 3, or 4 $R^X$. In some embodiments, the fused bicyclic heterocyclyl or heteroaryl of $R^4$ is

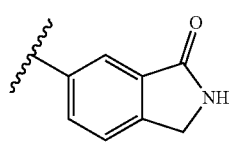 [SMILES: *c1ccc2c(c1)C(=O)NC2]

optionally substituted with 1, 2, 3, or 4 $R^X$. In some embodiments, the fused bicyclic heterocyclyl or heteroaryl of $R^4$ is

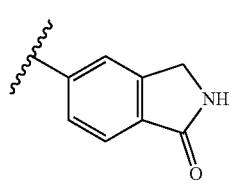 [SMILES: *c1ccc2c(c1)CNC2=O]

optionally substituted with 1, 2, 3, or 4 $R^X$. In some embodiments, the fused bicyclic heterocyclyl or heteroaryl of $R^4$ is

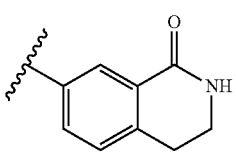 [SMILES: *c1ccc2c(c1)C(=O)NCC2]

optionally substituted with 1, 2, 3, or 4 $R^X$. In some embodiments, the fused bicyclic heterocyclyl or heteroaryl of $R^4$ is

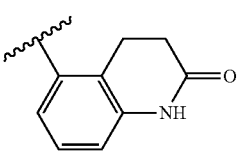 [SMILES: *c1cccc2c1CCC(=O)N2]

optionally substituted with 1, 2, 3, or 4 $R^X$. In some embodiments, the fused bicyclic heterocyclyl or heteroaryl of $R^4$ is

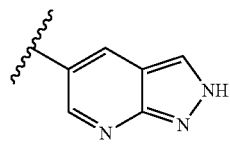 [SMILES: *c1cnc2n[nH]cc2c1]

optionally substituted with 1, 2, 3, or 4 $R^X$. In some embodiments, the fused bicyclic heterocyclyl or heteroaryl of $R^4$ is

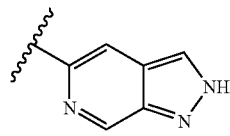 [SMILES: *c1cc2c[nH]nc2cn1]

optionally substituted with 1, 2, 3, or 4 $R^X$. In some embodiments, the fused bicyclic heterocyclyl or heteroaryl of $R^4$ is

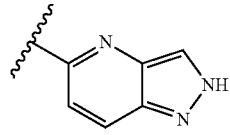 [SMILES: *c1ccc2n[nH]cc2n1]

optionally substituted with 1, 2, 3, or 4 $R^X$. In some embodiments, the fused bicyclic heterocyclyl or heteroaryl of $R^4$ is

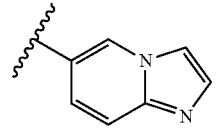 [SMILES: *c1ccc2nccn2c1]

optionally substituted with 1, 2, 3, or 4 $R^X$. In some embodiments, the fused bicyclic heterocyclyl or heteroaryl of $R^4$ is

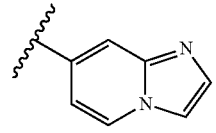 [SMILES: *c1ccn2ccnc2c1]

optionally substituted with 1, 2, 3, or 4 $R^X$. In some embodiments, the fused bicyclic heterocyclyl or heteroaryl of $R^4$ is

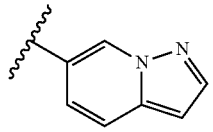 [SMILES: *c1ccc2ccnn2c1]

optionally substituted with 1, 2, 3, or 4 $R^X$. In some embodiments, the f fused bicyclic heterocyclyl or heteroaryl of $R^4$ is

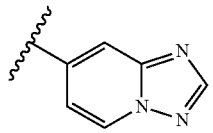 [SMILES: *c1ccn2ncnc2c1]

optionally substituted with 1, 2, 3, or 4 $R^X$. In some embodiments, the fused bicyclic heterocyclyl or heteroaryl of $R^4$ is

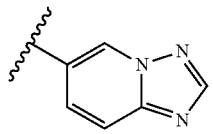 [SMILES: *c1ccc2ncnn2c1]

optionally substituted with 1, 2, 3, or 4 $R^X$. In some embodiments, the fused bicyclic heterocyclyl or heteroaryl of $R^4$ is

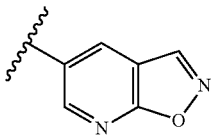

optionally substituted with 1, 2, 3, or 4 $R^X$. In some embodiments, the fused bicyclic heterocyclyl or heteroaryl of $R^4$ is

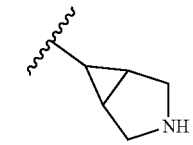 [SMILES: *C1C2CNCC12]

optionally substituted with 1, 2, 3, or 4 $R^X$. In some embodiments, the fused bicyclic heterocyclyl or heteroaryl of $R^4$ is

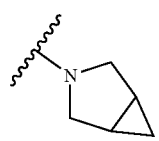 [SMILES: *N1CC2CC2C1]

optionally substituted with 1, 2, 3, or 4 $R^X$. In some embodiments, the fused bicyclic heterocyclyl or heteroaryl of $R^4$ is

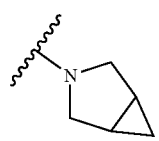 [SMILES: *N1CC2CC2C1]

optionally substituted with 1, 2, 3, or 4 $R^X$. In some embodiments, the fused bicyclic heterocyclyl or heteroaryl of $R^4$ is

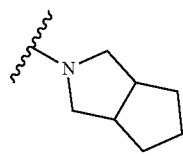 [SMILES: *N1CC2CCCC2C1]

optionally substituted with 1, 2, 3, or 4 $R^X$. In some embodiments, the fused bicyclic heterocyclyl or heteroaryl of $R^4$ is

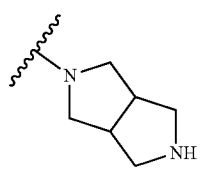 [SMILES: *N1CC2CNCC2C1]

optionally substituted with 1, 2, 3, or 4 $R^X$. In some embodiments, the fused bicyclic heterocyclyl or heteroaryl of $R^4$ is

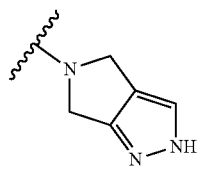 [SMILES: *N1Cc2c[nH]nc2C1]

optionally substituted with 1, 2, 3, or 4 $R^X$. In some embodiments, the fused bicyclic heterocyclyl or heteroaryl of $R^4$ is

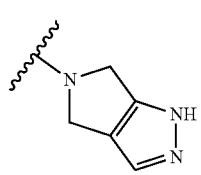 [SMILES: *N1Cc2cn[nH]c2C1]

optionally substituted with 1, 2, 3, or 4 $R^X$. In some embodiments, the fused bicyclic heterocyclyl or heteroaryl of $R^4$ is

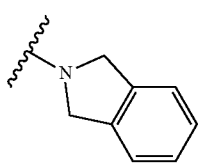 [SMILES: *N1Cc2ccccc2C1]

optionally substituted with 1, 2, 3, or 4 $R^X$. In some embodiments, the fused bicyclic heterocyclyl or heteroaryl of $R^4$ is

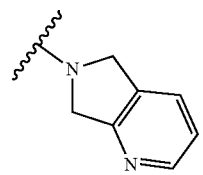 [SMILES: *N1Cc2cccnc2C1]

optionally substituted with 1, 2, 3, or 4 $R^X$. In some embodiments, the fused bicyclic heterocyclyl or heteroaryl of $R^4$ is optionally substituted with 1, 2, 3, or 4 $R^X$. In some embodiments, the fused bicyclic heterocyclyl or heteroaryl of $R^4$ is optionally substituted with 1, 2, 3, or 4 $R^X$. In some embodiments, the fused bicyclic heterocyclyl or heteroaryl of $R^4$ is optionally substituted with 1, 2, 3, or 4 $R^X$. In some embodiments, the fused bicyclic heterocyclyl or heteroaryl of $R^4$ is

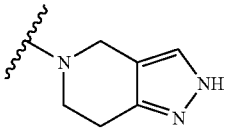 [SMILES: *N1CCc2n[nH]cc2C1]

optionally substituted with 1, 2, 3, or 4 $R^X$. In some embodiments, the fused bicyclic heterocyclyl or heteroaryl of $R^4$ is

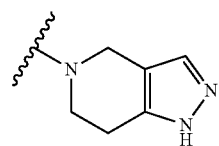 [SMILES: *N1CCc2[nH]ncc2C1]

optionally substituted with 1, 2, 3, or 4 $R^X$. In some embodiments, the fused bicyclic heterocyclyl or heteroaryl of $R^4$ is

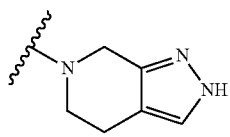 [SMILES: *N1CCc2c[nH]nc2C1]

optionally substituted with 1, 2, 3, or 4 $R^X$. In some embodiments, the fused bicyclic heterocyclyl or heteroaryl of $R^4$ is

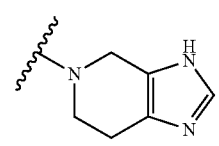 [SMILES: *N1CCc2nc[nH]c2C1]

optionally substituted with 1, 2, 3, or 4 $R^X$. In some embodiments, the fused bicyclic heterocyclyl or heteroaryl of $R^4$ is

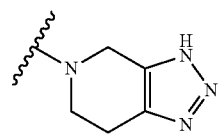 [SMILES: *N1CCc2nn[nH]c2C1]

optionally substituted with 1, 2, 3, or 4 $R^X$. In some embodiments, the fused bicyclic heterocyclyl or heteroaryl of $R^4$ is

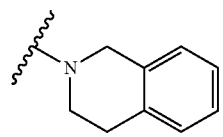 [SMILES: *N1CCc2ccccc2C1]

optionally substituted with 1, 2, 3, or 4 $R^X$. In some embodiments, the fused bicyclic heterocyclyl or heteroaryl of $R^4$ is

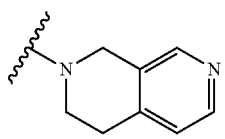 [SMILES: *N1CCc2ccncc2C1]

optionally substituted with 1, 2, 3, or 4 $R^X$. In some embodiments, the fused bicyclic heterocyclyl or heteroaryl of $R^4$ is

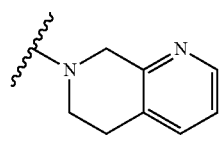 [SMILES: *N1CCc2cccnc2C1]

optionally substituted with 1, 2, 3, or 4 $R^X$. In some embodiments, the fused bicyclic heterocyclyl or heteroaryl of $R^4$ is

[Image of bicyclic structure with pyrrolidine fused to piperazine]

optionally substituted with 1, 2, 3, or 4 $R^X$. In some embodiments, the fused bicyclic heterocyclyl or heteroaryl of $R^4$ is

[Image of pyrazolo-piperazine structure]

optionally substituted with 1, 2, 3, or 4 $R^X$. In some embodiments, the fused bicyclic heterocyclyl or heteroaryl of $R^4$ is

[Image of imidazo-piperazine structure]

optionally substituted with 1, 2, 3, or 4 $R^X$. In some embodiments, the fused bicyclic heterocyclyl or heteroaryl of $R^4$ is

[Image of triazolo-piperazine structure]

optionally substituted with 1, 2, 3, or 4 $R^X$. In some embodiments, the fused bicyclic heterocyclyl or heteroaryl of $R^4$ is

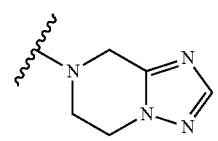 [SMILES: *N1CCn2ncnc2C1]

optionally substituted with 1, 2, 3, or 4 $R^X$. In some embodiments, the fused bicyclic heterocyclyl or heteroaryl of $R^4$ is

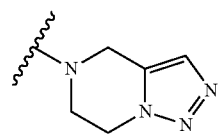 [SMILES: *N1CCn2nncc2C1]
optionally substituted with 1, 2, 3, or 4 $R^X$. In some embodiments, the fused bicyclic heterocyclyl or heteroaryl of $R^4$ is
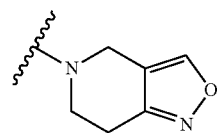 [SMILES: *N1CCc2nocc2C1]
optionally substituted with 1, 2, 3, or 4 $R^X$. In some embodiments, the fused bicyclic heterocyclyl or heteroaryl of $R^4$ is
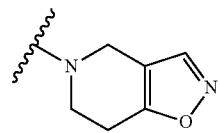 [SMILES: *N1CCc2oncc2C1]
optionally substituted with 1, 2, 3, or 4 $R^Y$. In some embodiments, $R^4$ has one of the following structures:
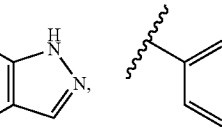
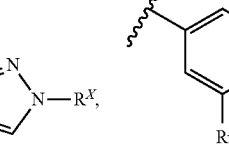
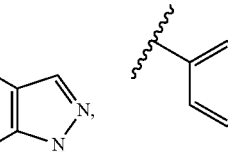
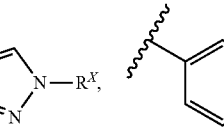
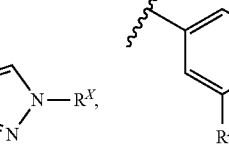
-continued
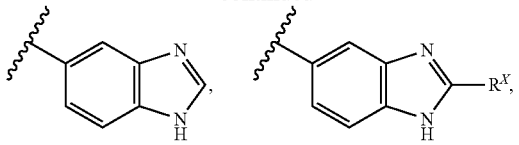
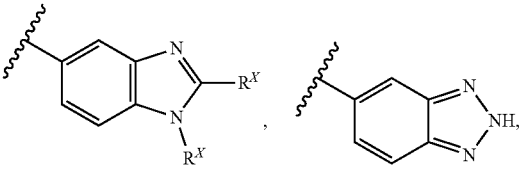
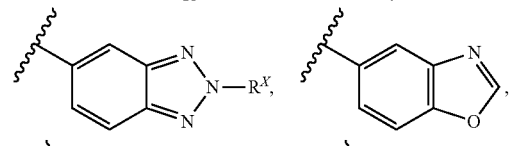
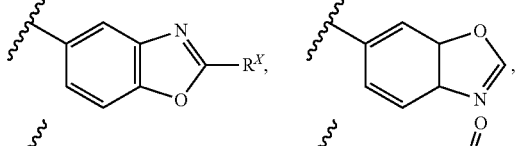
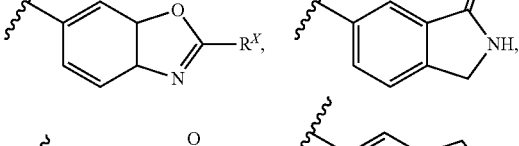
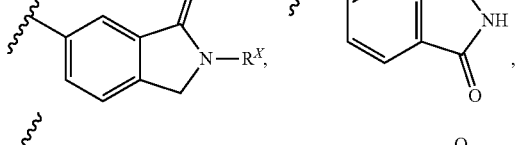
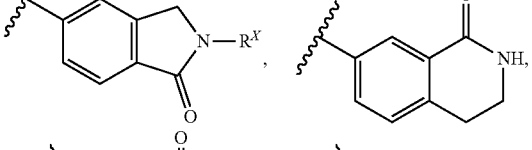
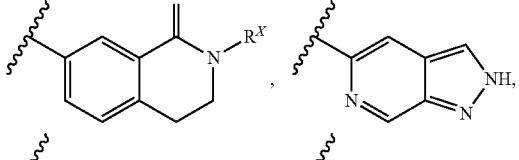
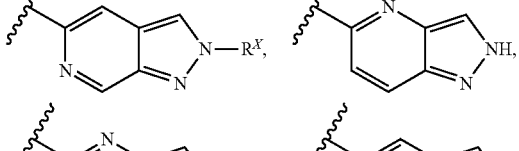
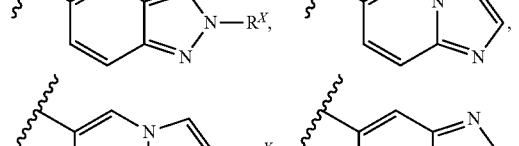
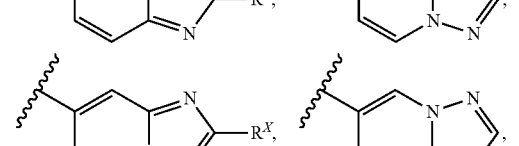
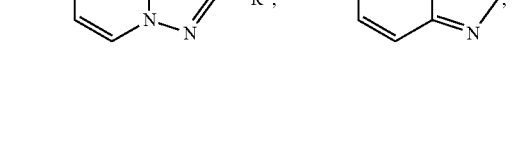

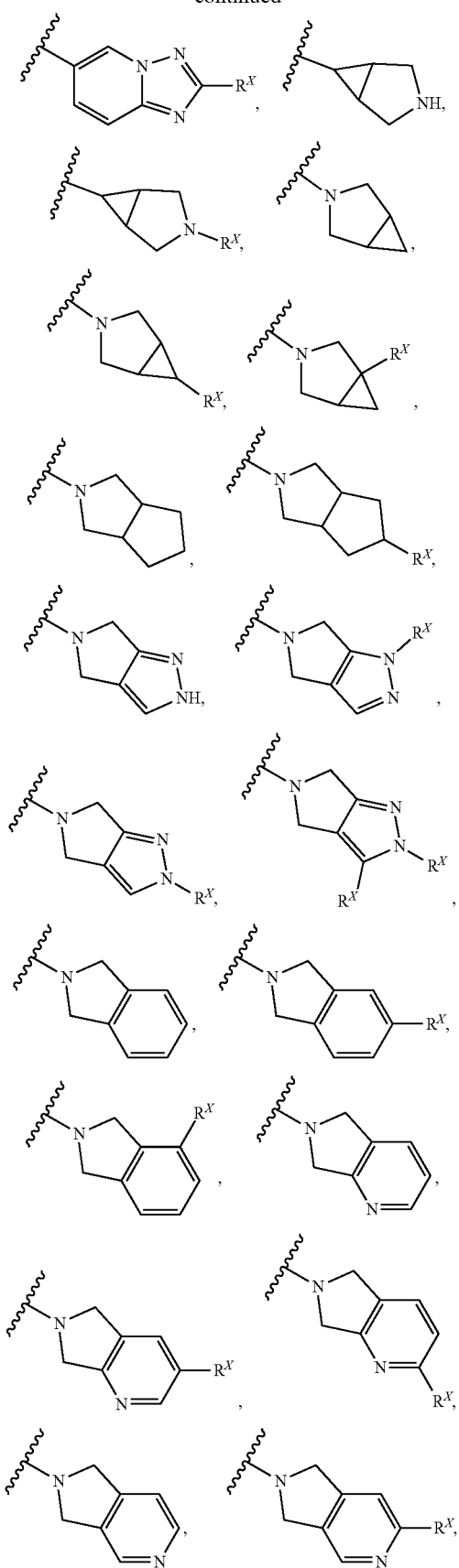
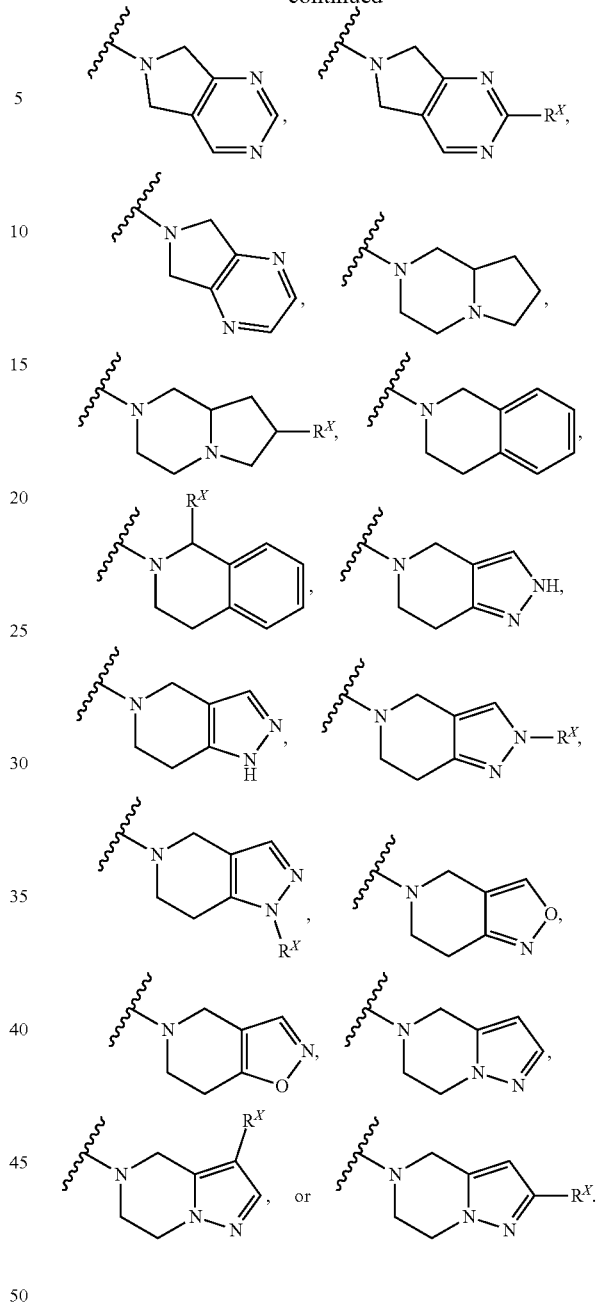

In some embodiments, $R^4$ is optionally substituted bridged bicyclic heterocyclyl or heteroaryl. In some embodiments, the bridged heterocyclyl or heteroaryl of $R^4$ is 3-azabicyclo[3.1.1]heptanyl, 7-azabicyclo[2.2.1]heptanyl, 2-oxa-5-azabicyclo[2.2.1]heptanyl, 3,8-diazabicyclo[3.2.1]octanyl, 2,5-diazabicyclo[2.2.2]octanyl, 8-azabicyclo[3.2.1]octanyl, 3,6-diazabicyclo[3.1.1]heptanyl, (1 S,4S)-2-oxa-5-azabicyclo[2.2.1]heptanyl, (1R,4R)-2-oxa-5-azabicyclo[2.2.1]heptanyl, 2-azabicyclo[2.2.1]heptanyl, or 2,5-diazabicyclo[2.2.1]heptanyl, each of which is optionally substituted with 1, 2, 3, or 4 $R^X$. In some embodiments, the bridged heterocyclyl or heteroaryl of $R^4$ has one of the following structures:

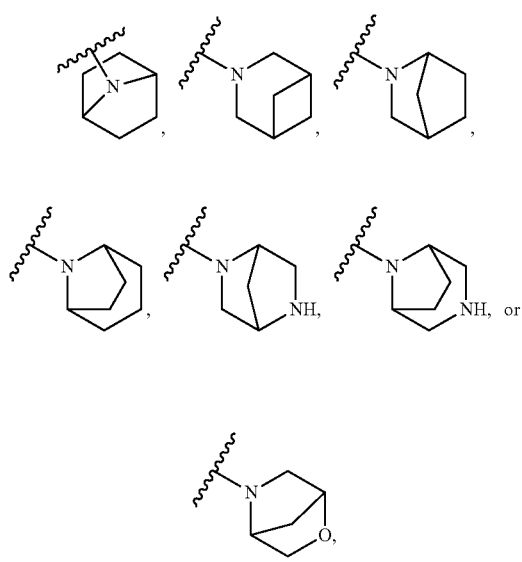

each of which substituted with 1, 2, 3, or 4 $R^X$. In some embodiments, the bridged heterocyclyl or heteroaryl of $R^4$ is

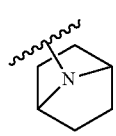

optionally substituted with 1, 2, 3, or 4 $R^X$. In some embodiments, the bridged heterocyclyl or heteroaryl of $R^4$ is

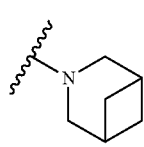 [SMILES: *N1CC2CC(C2)C1]

optionally substituted with 1, 2, 3, or 4 $R^X$. In some embodiments, the bridged heterocyclyl or heteroaryl of $R^4$ is

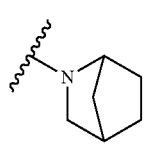 [SMILES: *N1CC2CCC1C2]

optionally substituted with 1, 2, 3, or 4 $R^X$. In some embodiments, the bridged heterocyclyl or heteroaryl of $R^4$ is

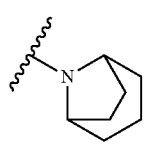 [SMILES: *N1C2CCCC1CC2]

optionally substituted with 1, 2, 3, or 4 $R^X$. In some embodiments, the bridged heterocyclyl or heteroaryl of $R^4$ is

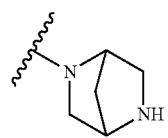

optionally substituted with 1, 2, 3, or 4 $R^X$. In some embodiments, the bridged heterocyclyl or heteroaryl of $R^4$ is

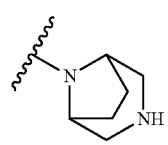

optionally substituted with 1, 2, 3, or 4 $R^X$. In some embodiments, the bridged heterocyclyl or heteroaryl of $R^4$ is

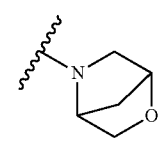

optionally substituted with 1, 2, 3, or 4 $R^X$. In some certain embodiments, $R^4$ has one of the following structures:

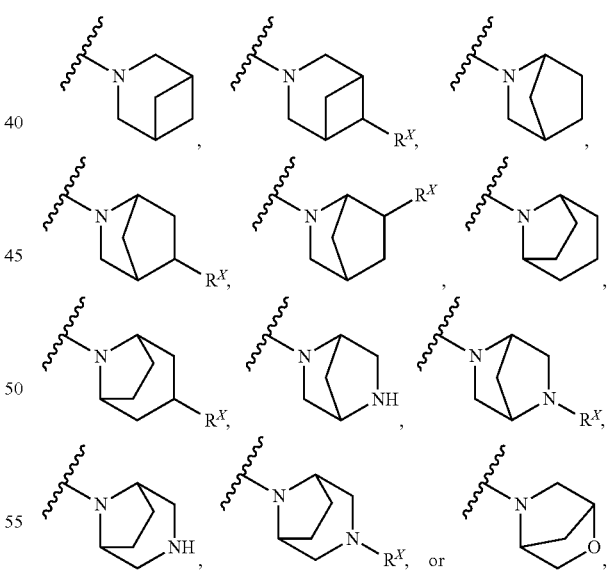

In some embodiments, $R^4$ is optionally substituted spiro bicyclic heterocyclyl or heteroaryl. In some embodiments, the spiro bicyclic heterocyclyl or heteroaryl of $R^4$ is 6-azaspiro[2.5]octanyl, 1-oxa-7-azaspiro[4.4]nonanyl, 2-oxa-8-azaspiro[4.5]decanyl, 2,6-diazaspiro[3.3]heptanyl, 1,6-diazaspiro[3.3]heptanyl, 2-azaspiro[3.3]heptanyl, 1,6-diazaspiro[3.4]octanyl, 2,6-diazaspiro[3.4]octanyl, 2,7-diazaspiro[3.5]nonanyl, 2,8-diazaspiro[4.5]decanyl, 8-oxa-2-azaspiro[4.5]decanyl, 3,9-diazaspiro[5.5]undecanyl, 4,8- diazaspiro[2.5]octanyl, 5,9-diazaspiro[3.5]honanyl, 6,10-diazaspiro[4.5]decanyl, 1,5-diazaspiro[5.5]undecanyl, 2,7-diazaspiro[4.4]nonanyl, 2,7-diazaspiro[4.5]decanyl, 3-azaspiro[5.5]undecanyl, 1-oxa-9λ²-azaspiro[5.5]undecanyl, 3-oxa-9λ²-azaspiro[5.5]undecanyl, 8-oxa-3-azaspiro[5.6]dodecanyl, 2,8λ²-diazaspiro[4.5]decanyl, or 3λ²,9-diazaspiro[5.5]undecanyl, each of which is optionally substituted with 1, 2, 3, or 4 R$^X$.

In some embodiments, the spiro bicyclic heterocyclyl or heteroaryl of R$^4$ has one of the following structures:

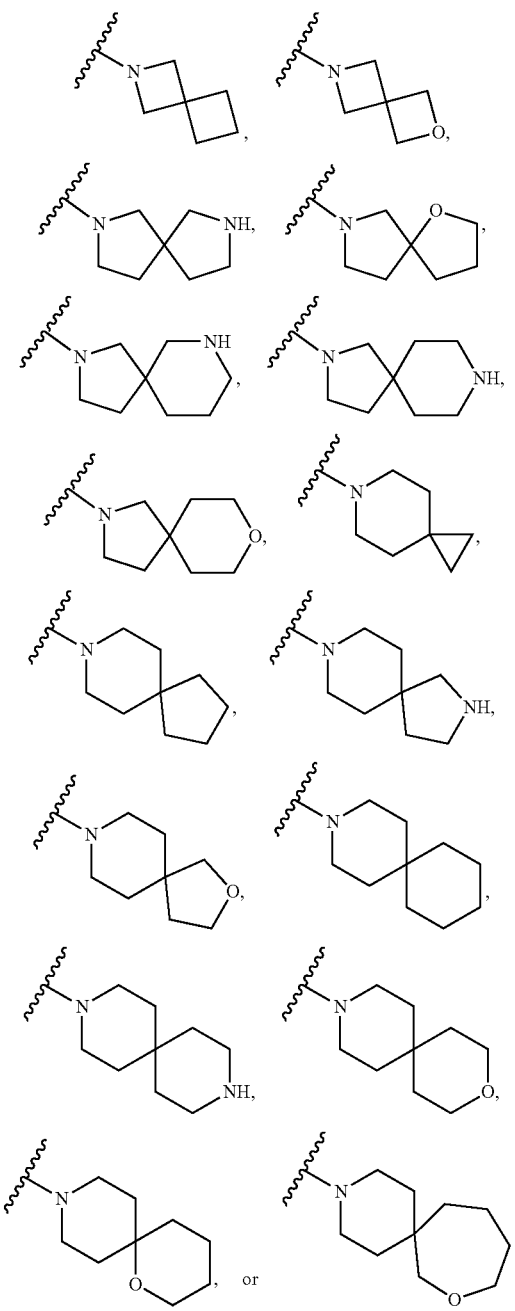

each optionally substituted with 1, 2, 3, or 4 R$^X$. In some embodiments, the spiro bicyclic heterocyclyl or heteroaryl of R$^4$ is

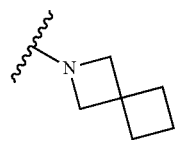 [SMILES: *N1CC2(CCC2)C1]

optionally substituted with 1, 2, 3, or 4 R$^X$. In some embodiments, the spiro bicyclic heterocyclyl or heteroaryl of R$^4$ is

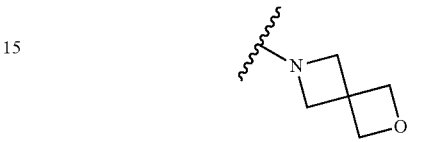

optionally substituted with 1, 2, 3, or 4 R$^X$. In some embodiments, the spiro bicyclic heterocyclyl or heteroaryl of R$^4$ is

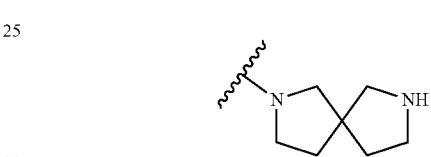

optionally substituted with 1, 2, 3, or 4 R$^X$. In some embodiments, the spiro bicyclic heterocyclyl or heteroaryl of R$^4$ is

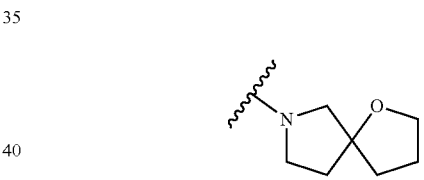

optionally substituted with 1, 2, 3, or 4 R$^X$. In some embodiments, the spiro bicyclic heterocyclyl or heteroaryl of R$^4$ is

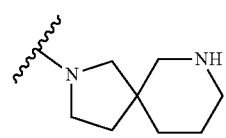 [SMILES: *N1CCC2(CCCNC2)C1]

optionally substituted with 1, 2, 3, or 4 R$^X$. In some embodiments, the spiro heterobicyclic of R$^4$ is

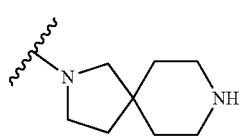 [SMILES: *N1CCC2(CCNCC2)C1]

optionally substituted with 1, 2, 3, or 4 R$^X$. In some embodiments, the spiro bicyclic heterocyclyl or heteroaryl of R$^4$ is

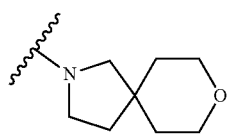 [SMILES: *N1CCC2(CCOCC2)C1]

optionally substituted with 1, 2, 3, or 4 $R^X$. In some embodiments, the spiro heterobicyclic of $R^4$ is

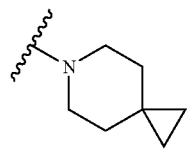 [SMILES: *N1CCC2(CC1)CC2]

optionally substituted with 1, 2, 3, or 4 $R^X$. In some embodiments, the spiro bicyclic heterocyclyl or heteroaryl of $R^4$ is

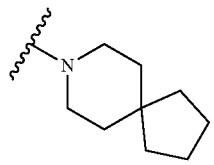 [SMILES: *N1CCC2(CCCC2)CC1]

optionally substituted with 1, 2, 3, or 4 $R^X$. In some embodiments, the spiro heterobicyclic of $R^4$ is

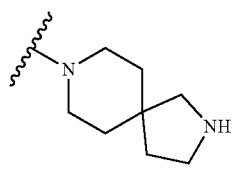 [SMILES: *N1CCC2(CCNC2)CC1]

optionally substituted with 1, 2, 3, or 4 $R^X$. In some embodiments, the spiro bicyclic heterocyclyl or heteroaryl of $R^4$ is

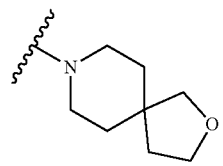 [SMILES: *N1CCC2(CCOC2)CC1]

optionally substituted with 1, 2, 3, or 4 $R^X$. In some embodiments, the spiro heterobicyclic of $R^4$ is

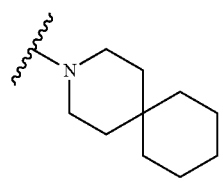 [SMILES: *N1CCC2(CCCCC2)CC1]

optionally substituted with 1, 2, 3, or 4 $R^X$. In some embodiments, the spiro bicyclic heterocyclyl or heteroaryl of $R^4$ is

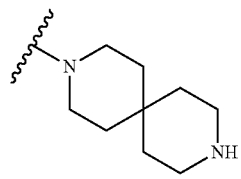 [SMILES: *N1CCC2(CCNCC2)CC1]

optionally substituted with 1, 2, 3, or 4 $R^X$. In some embodiments, the spiro heterobicyclic of $R^4$ is

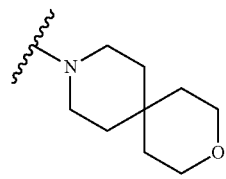 [SMILES: *N1CCC2(CCOCC2)CC1]

optionally substituted with 1, 2, 3, or 4 $R^X$. In some embodiments, the spiro bicyclic heterocyclyl or heteroaryl of $R^4$ is

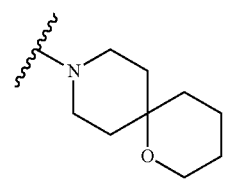 [SMILES: *N1CCC2(CCCCO2)CC1]

optionally substituted with 1, 2, 3, or 4 $R^X$. In some embodiments, the spiro heterobicyclic of $R^4$ is

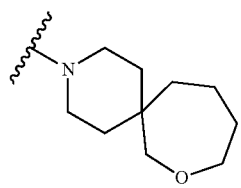 [SMILES: *N1CCC2(CCCCOC2)CC1]

optionally substituted with 1, 2, 3, or 4 $R^X$. In some embodiments, $R^4$ has one of the following structures:

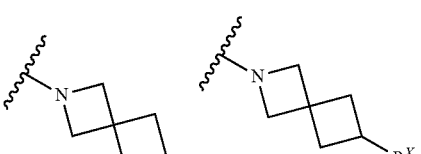
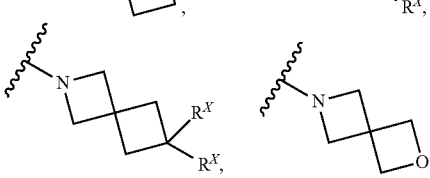

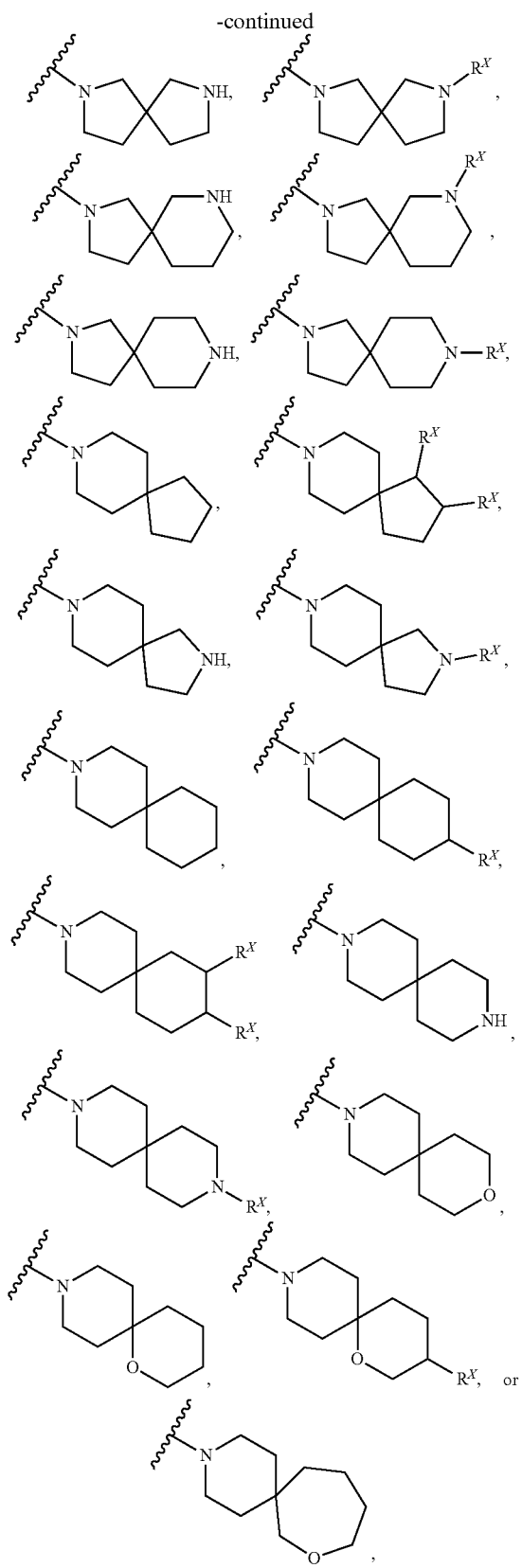

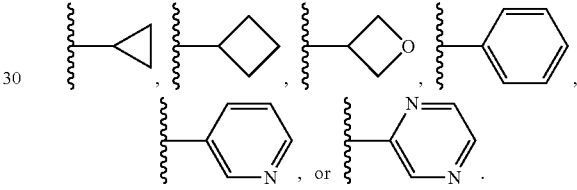

—CH₂C(CH₃)₂OH, —CH₂CH₂OCH₃, —C(O)CH₃, —OH, —OCH₃, —NH₂, —N(CH₃)₂, cyclopropyl, cyclobutyl, cyclohexyl, bicyclo[1.1.1]pentanyl, oxetanyl, piperidinyl, 3-azabicyclo[3.2.1]octanyl, tetrahydropyranyl, morpholinyl, piperazinyl, 3,8-diazabicyclo[3.2.1]octanyl, pyridin-2(1H)-onyl, diazinyl, pyrazolyl, triazolyl, tetrazolyl, oxazolyl, isoxazolyl, dihydrothiazolyl, oxadiazolyl, thiazolyl, thiadiazolyl, phenyl, pyridinyl, pyrazinyl, pyrimidinyl, pyridazinyl, 1H-indazolyl, 1H-pyrazolo[3,4-c]pyridinyl, pyrazolo[3,4-c]pyridinyl, pyrazolo[1,5-a]pyridinyl, 1H-pyrazolo[1,5-b]pyridazine, pyrazolo[1,5-a]pyrimidinyl, 5,6-dihydro-4H-pyrrolo[1,2-b]pyrazole, 2,3-dihydropyrazolo[5,1-b]oxazolyl, tetrahydropyranyl, —O-piperidinyl, —O—pyrazolyl, —O-phenyl, —O-pyridinyl, —O-pyrimidinyl, —O-pyrazinyl, —O-pyridazinyl, —NH— phenyl, —NH-pyrimidinyl, —N(CH₃)-pyrimidinyl, —NH-pyrazolyl, —CH₂-cyclopropyl, —CH₂— oxetanyl, —CH₂-phenyl, —O—CH₂-pyrazolyl, —O—CH₂-piperidinyl, or —O(CH₂)₂-morpholinyl, wherein each ring is optionally substituted with 1-3 R^Y.

In some embodiments, R' is, each independently, —H, —F, —Cl, —CN, —CH₃, —CH₂CH₃, —CH(CH₃)₂, —CD₃, —CHF₂, —CF₃, —CH₂CHF₂, —CH₂CF₃, —CH₂CN, —CH₂CH₂OCH₃, —OCH₃, —C(O)CH₃, —OH, =O, —NH₂, —N(CH₃)₂, —NHC(O)CH₃,

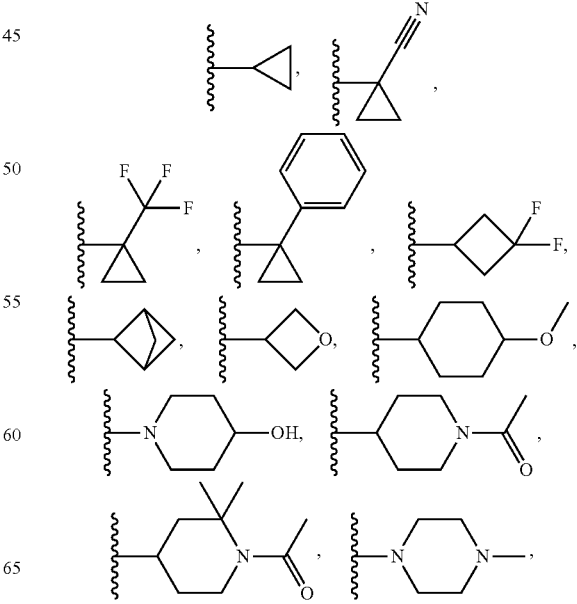

In some embodiments, R^X is, each independently, —H, —F, —Cl, —CN, —CH₃, —CD₃, —CHF₂, —CF₃, —CH₂CF₃, —CH₂CHF₂, —CH(CH₃)CF₃, —C(CH₃)₂CN, —C(CH₃)₂OH, —CH₂CH₂OH, —CH₂C(CH₃)₂OH, —CH₂CH₂OCH₃, —C(O)CH₃, —OH, —OCH₃, —NH₂, —N(CH₃)₂, In some embodiments, R^X is, each independently, —H, —F, —Cl, —CN, —CH₃, —CD₃, —CHF₂, —CF₃, —CH₂CF₃, —CH₂CHF₂, —CH(CH₃)CF₃, —CH₂CH₂OH,

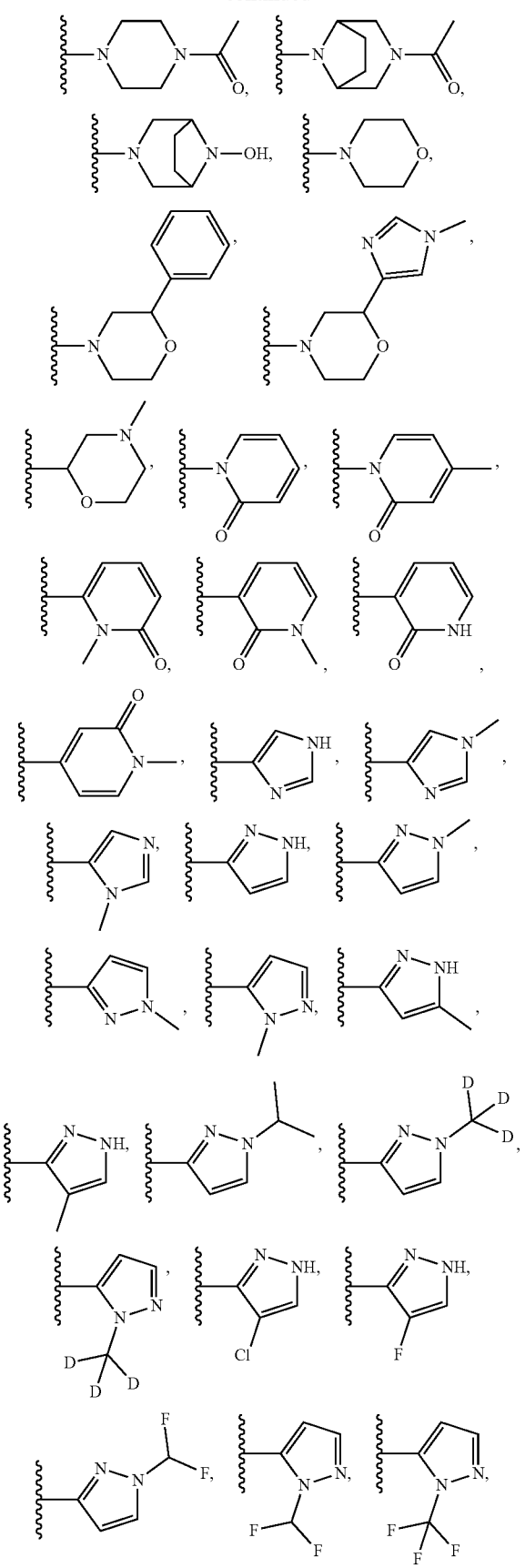
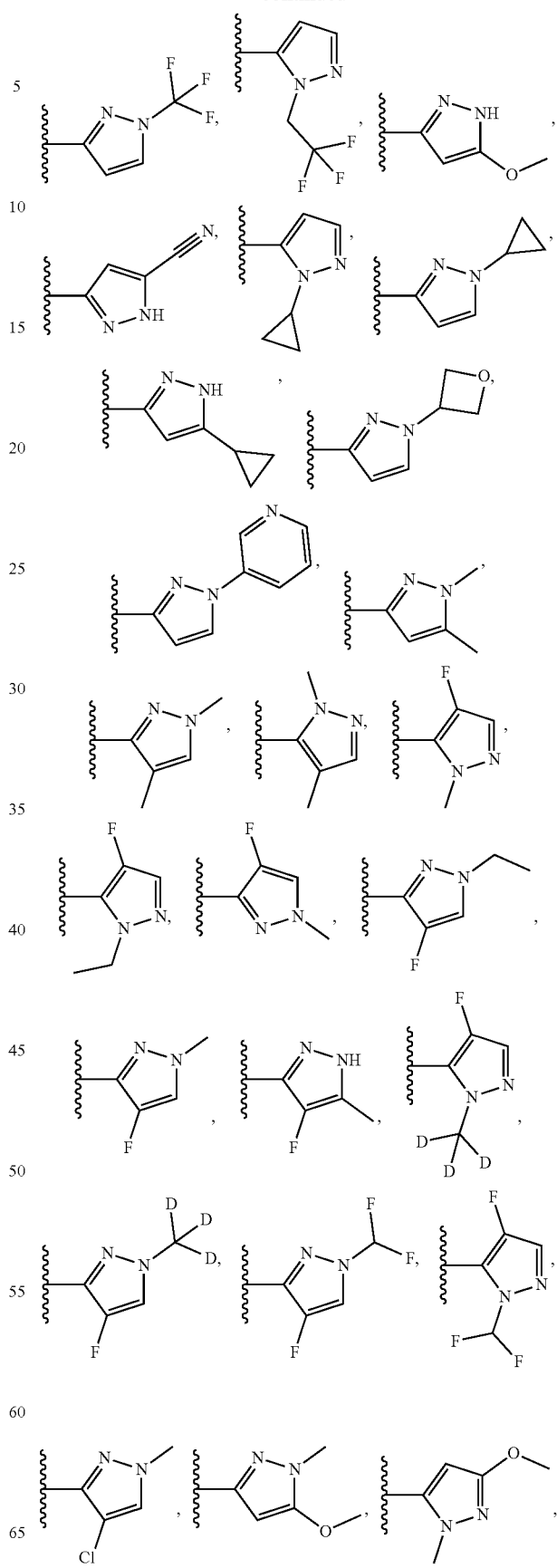

-continued
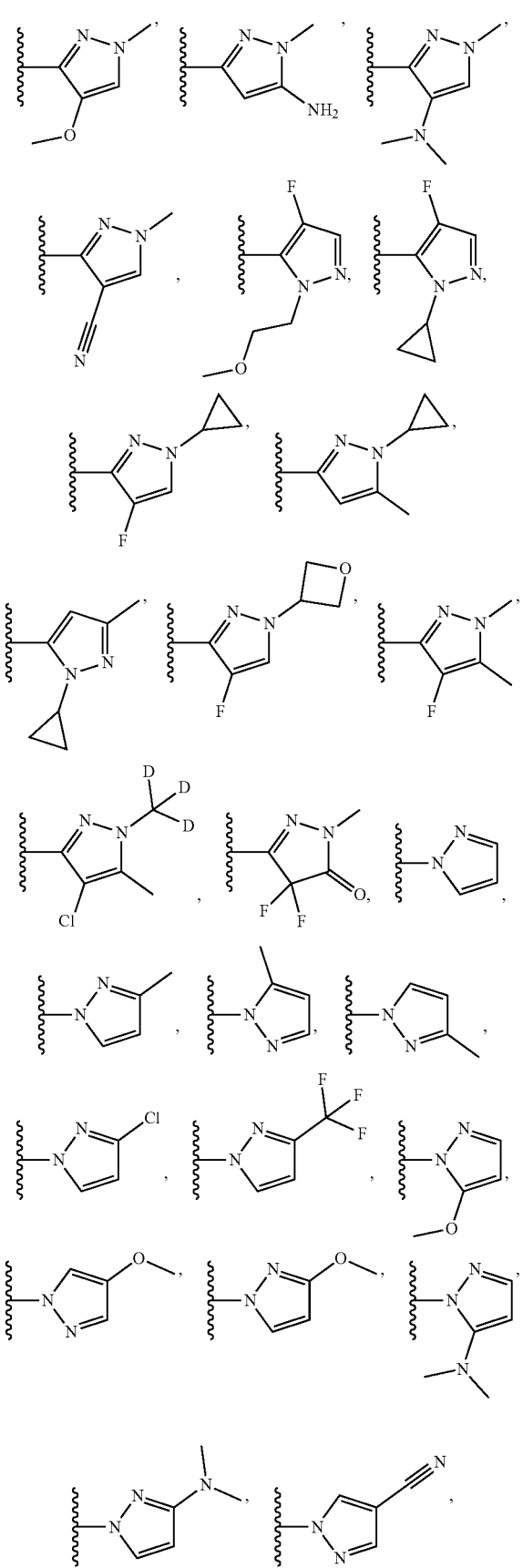
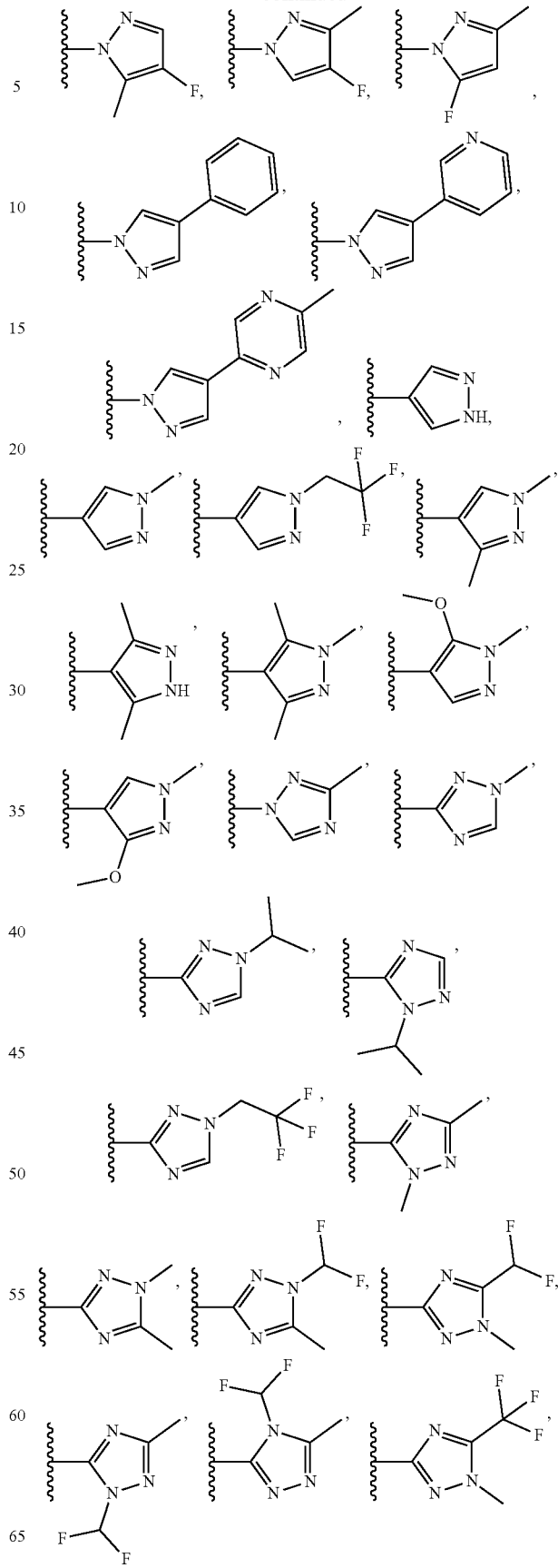

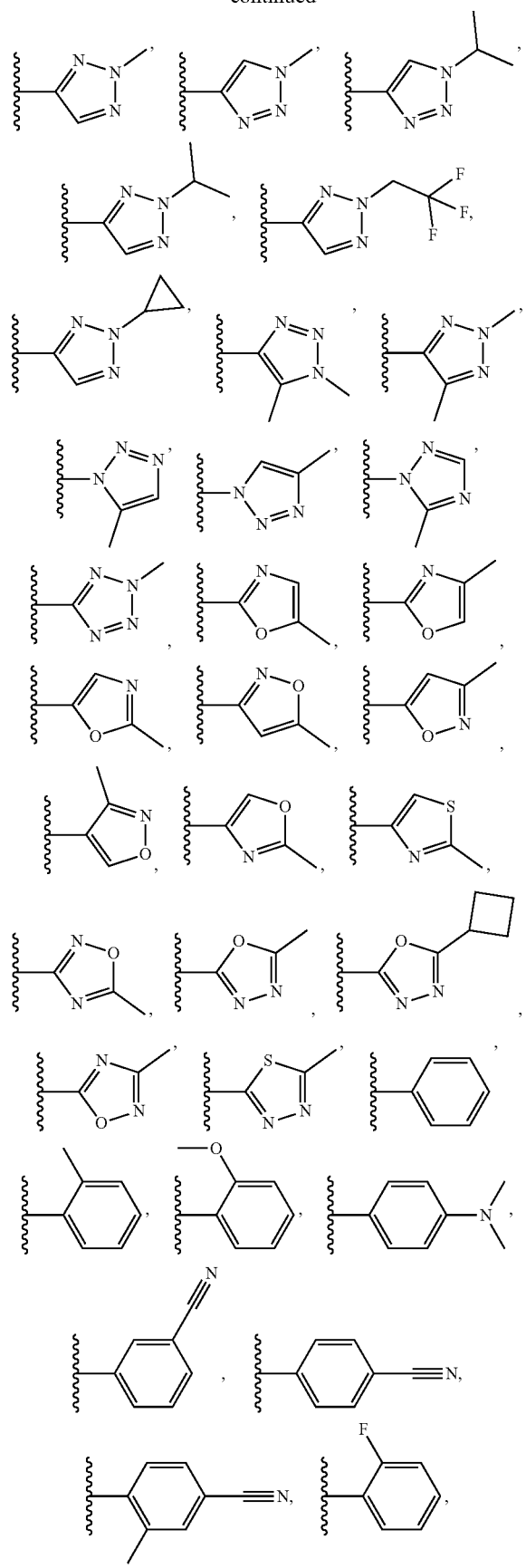
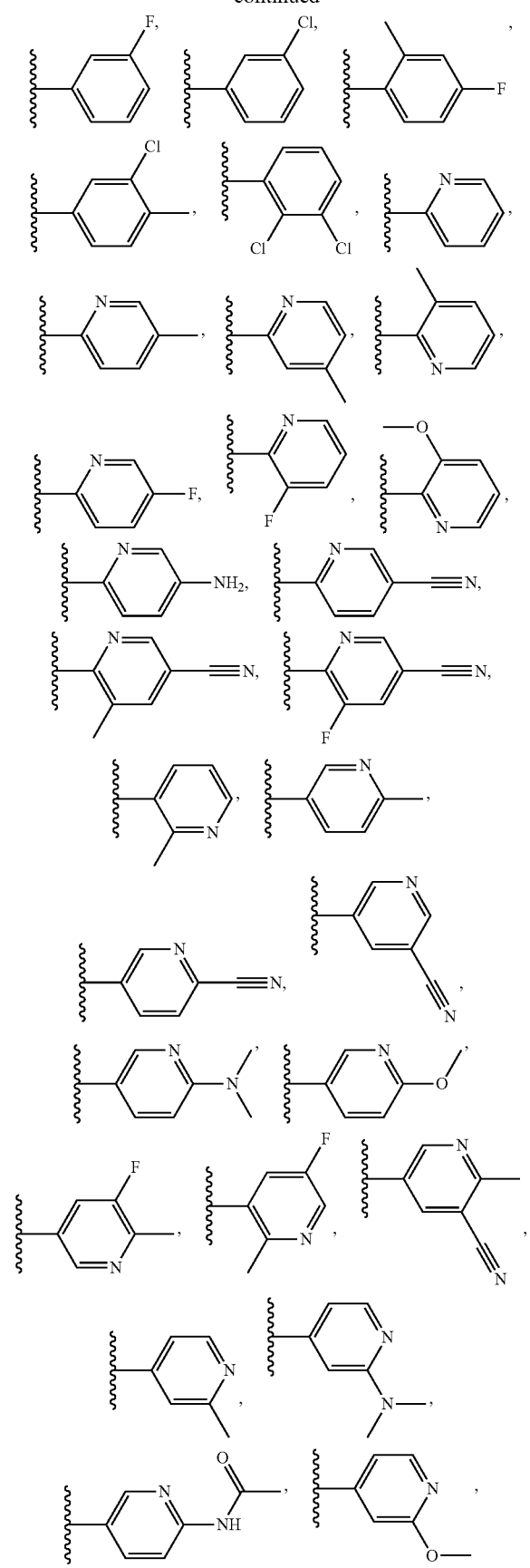

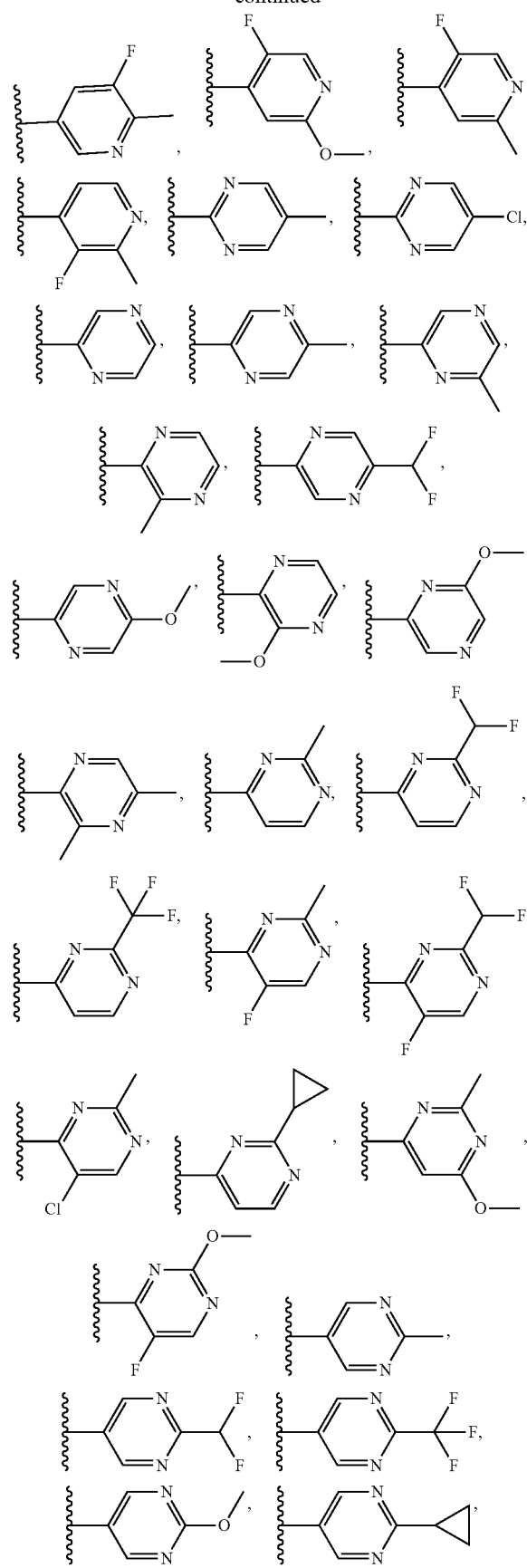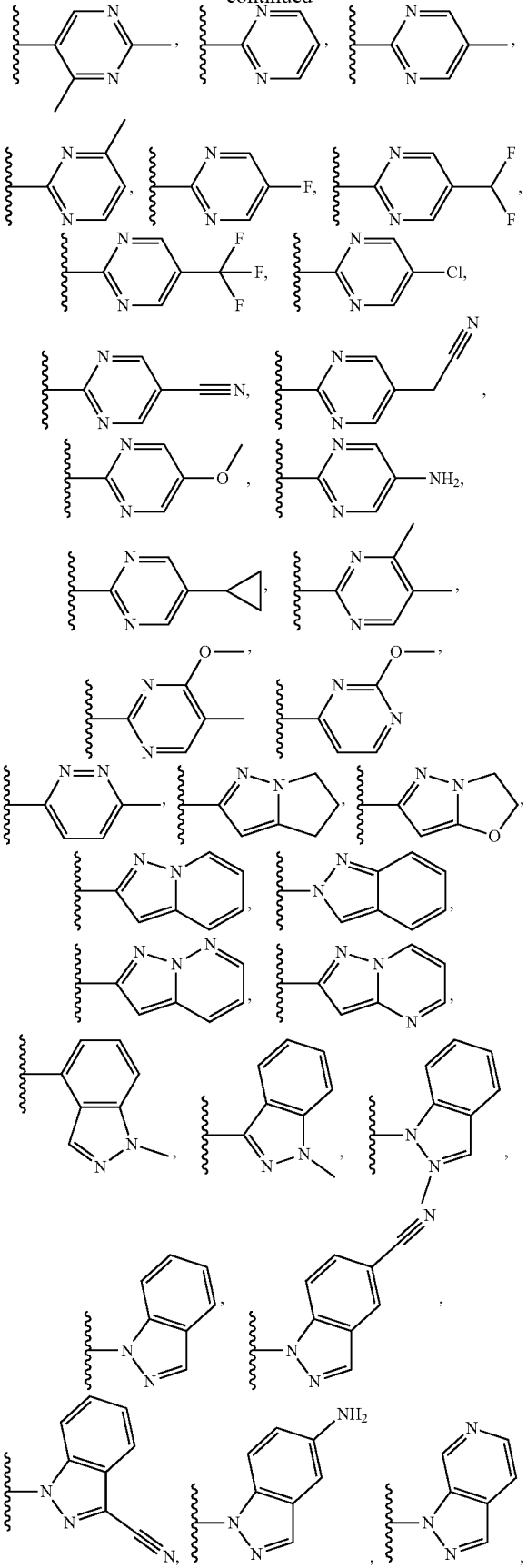

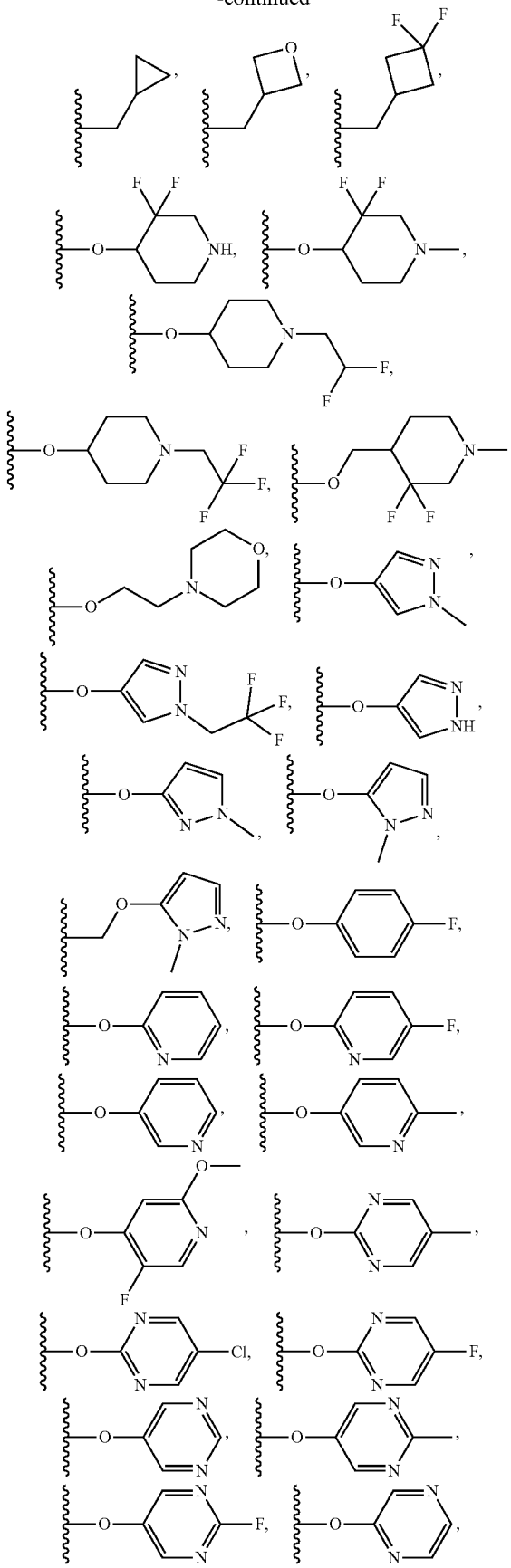
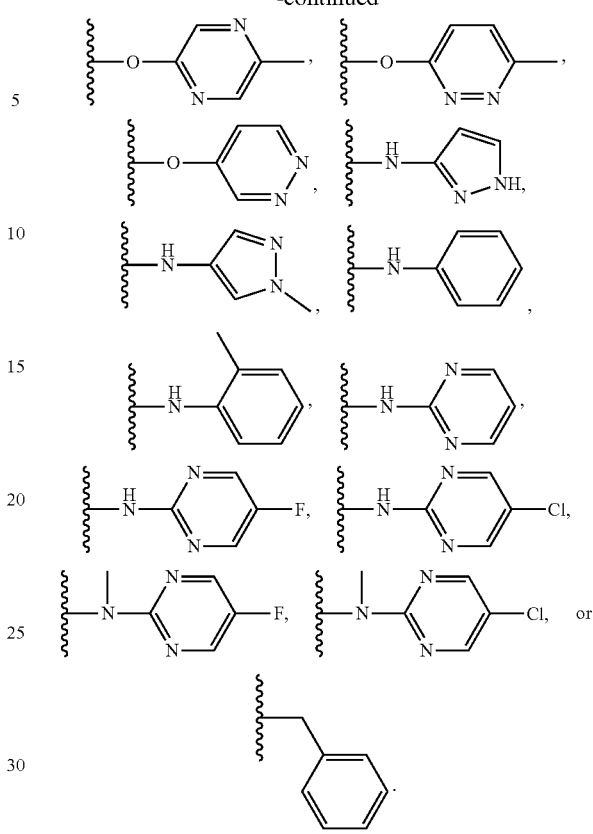

In some embodiments, $R^9$ and $R^{10}$ are, each independently, H, $C_1$-$C_3$ alkyl, $C_1$-$C_3$ alkylene-$C_3$-$C_7$ cycloalkyl, $C_3$-$C_7$ cycloalkyl, 3-7 membered heterocyclyl, or 5-6 membered heteroaryl, wherein the $C_1$-$C_3$ alkyl is optionally substituted with one or more halo, hydroxyl. $C_3$-$C_7$ cycloalkyl, aryl, or 5-6 membered heteroaryl, and wherein the $C_1$-$C_3$ alkylene-$C_3$-$C_7$ cycloalkyl, $C_3$-$C_7$ cycloalkyl, 3-7 membered heterocyclyl, aryl, or 5-6 membered heteroaryl is optionally substituted. In some embodiments, the $C_3$-$C_7$ cycloalkyl of $R^9$ and $R^{10}$ are, each independently, cyclobutyl, cyclopentyl, cyclohexyl, cycloheptyl, or bicyclo[1.1.1]pentanyl. In some embodiments, the $C_3$-$C_7$ heterocyclyl of $R^9$ and $R^{10}$ are, each independently, tetrahydropyranyl, tetrahydrofuranyl, or oxetanyl, each of which is optionally substituted with one or more halo or $C_1$-$C_3$ alkyl. In some embodiments, $R^9$ and $R^{10}$ are, each independently, H, —$CH_3$, —$C(CH_3)_3$, —$CH_2CF_3$, —$CH_2CH_2OH$,

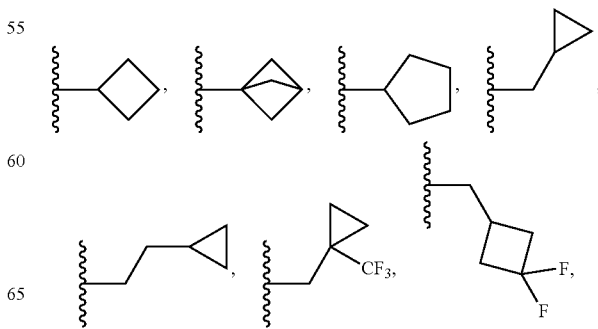

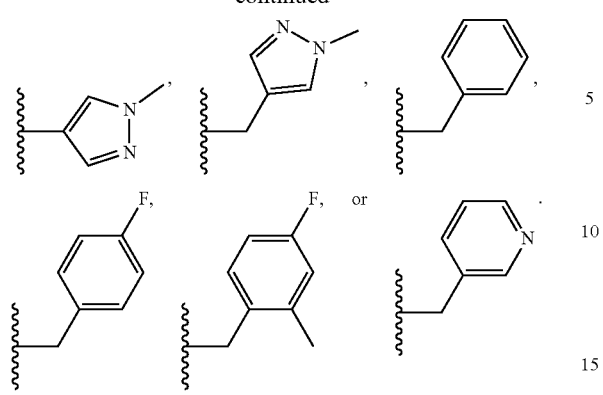
In some embodiments, R⁴ has one of the following structures:
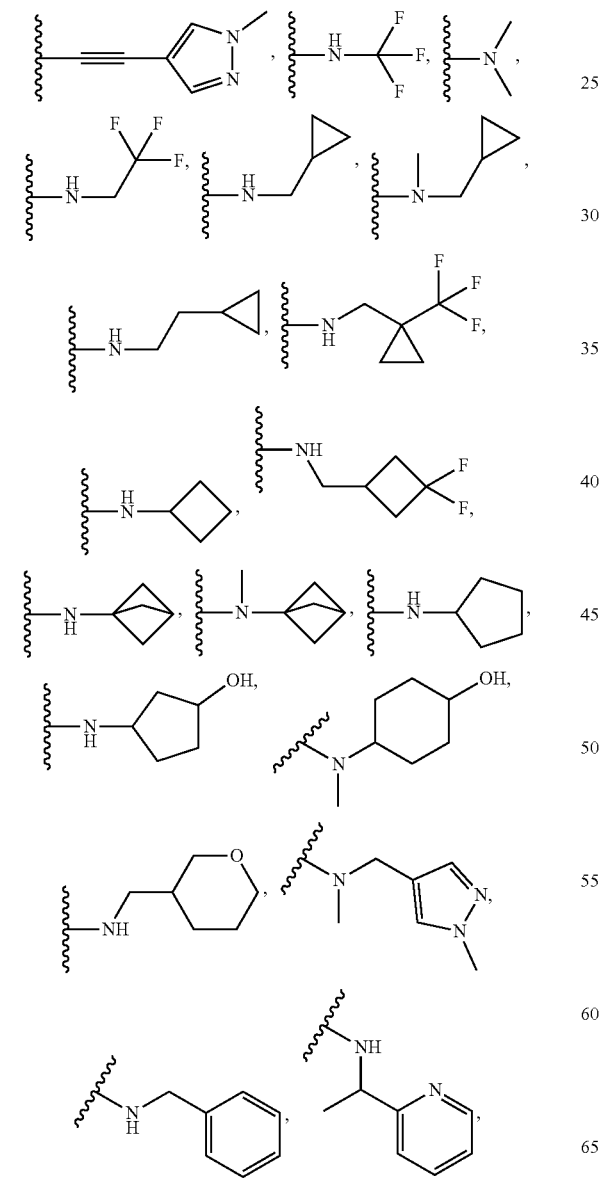
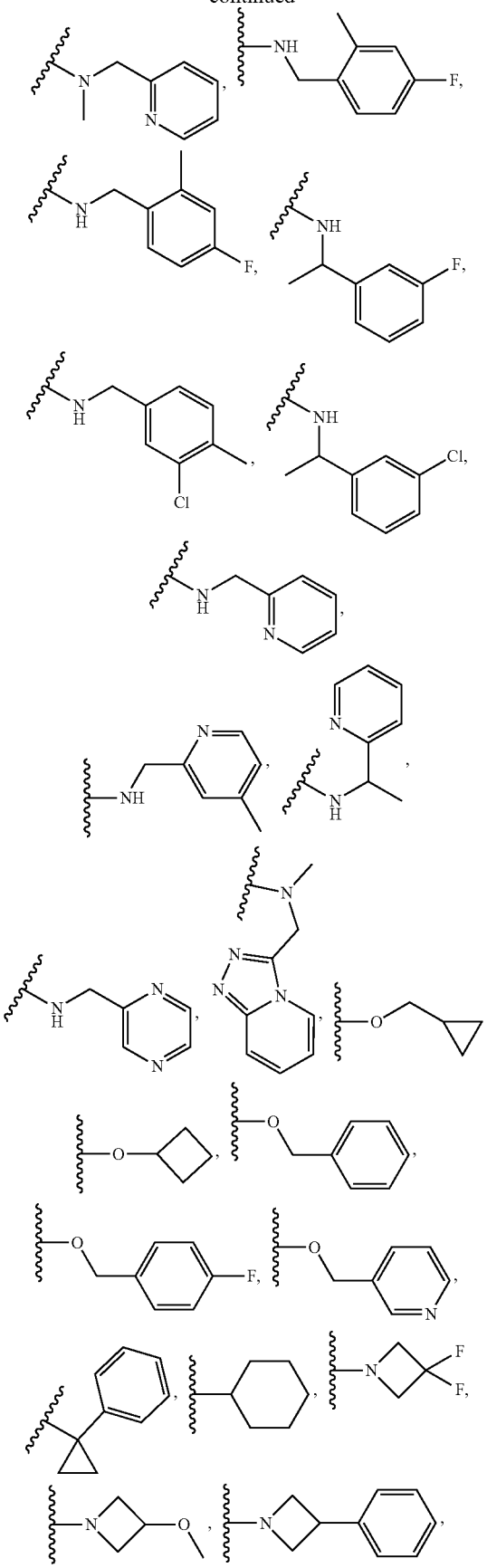

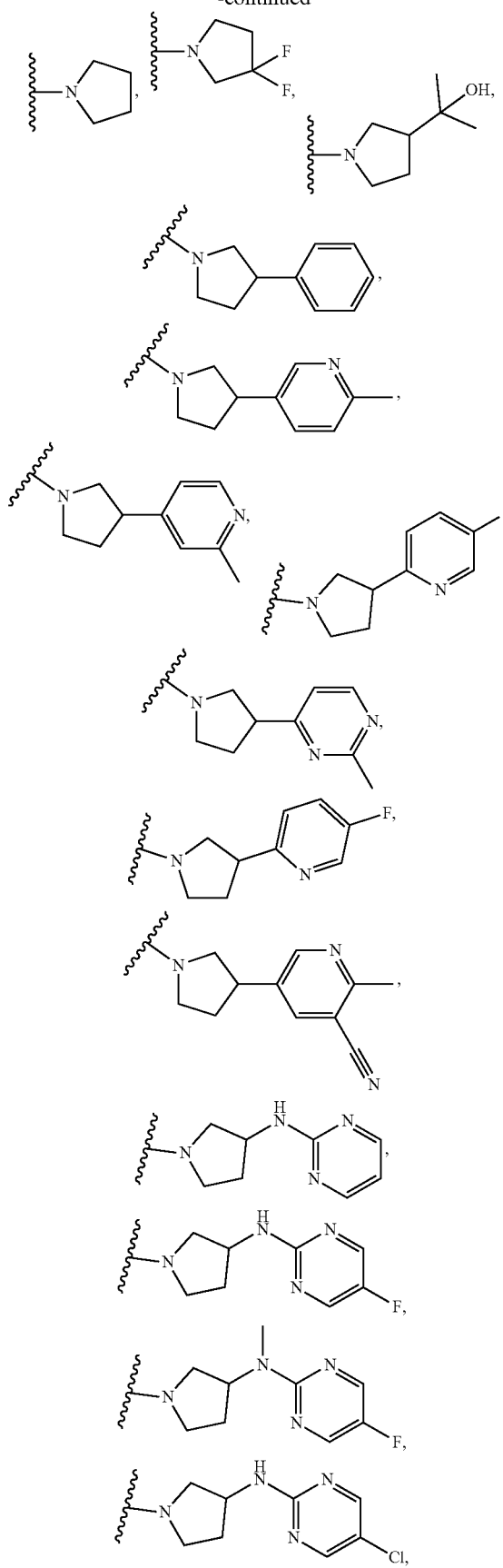
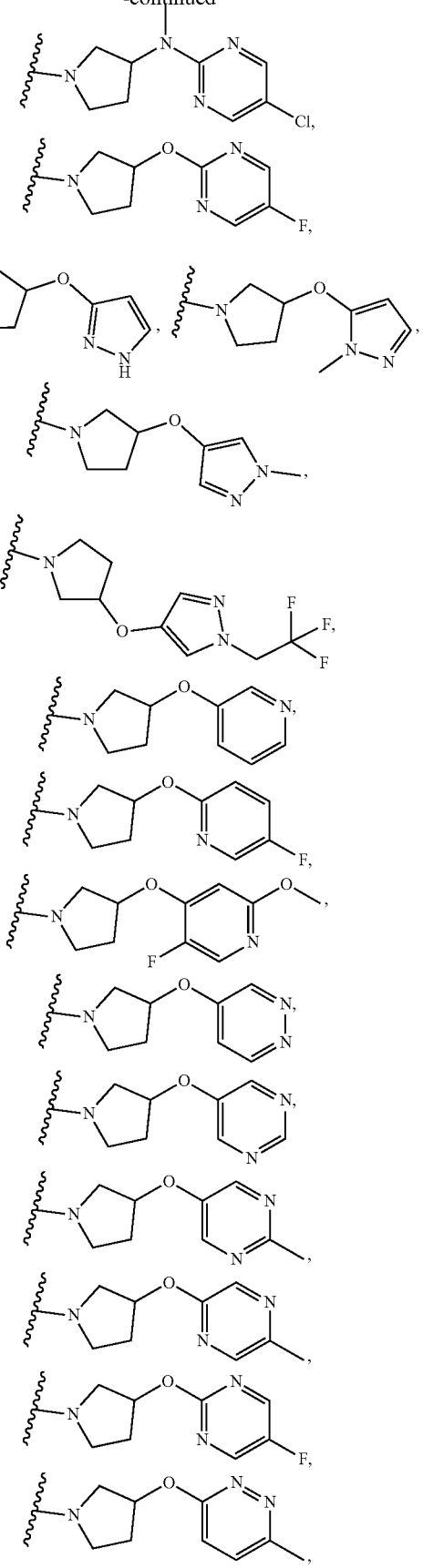

-continued
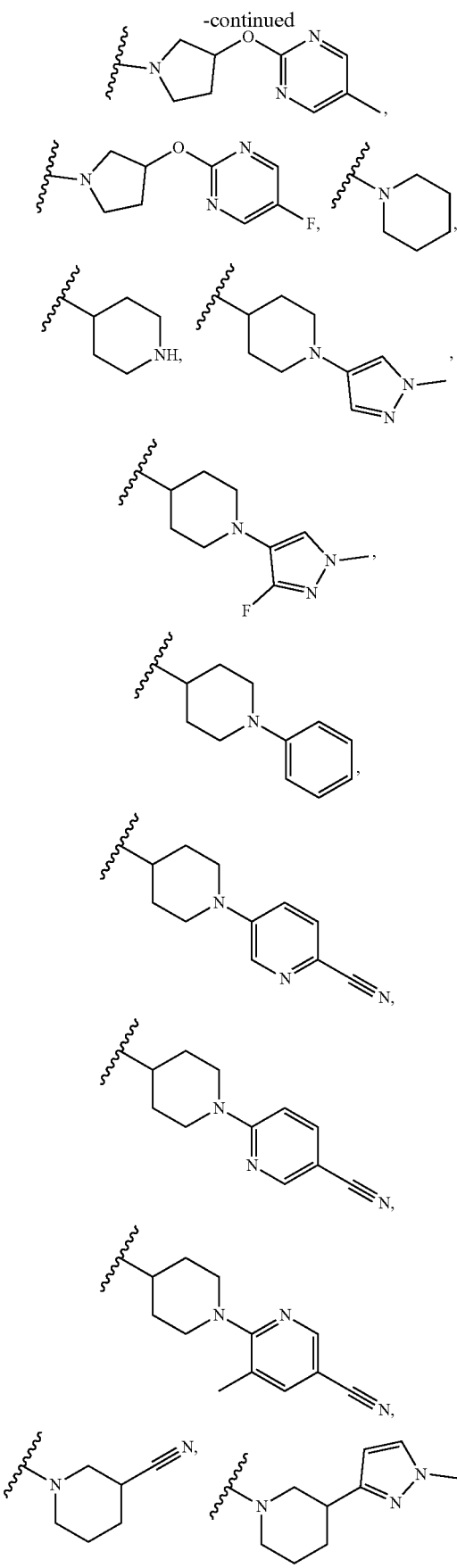
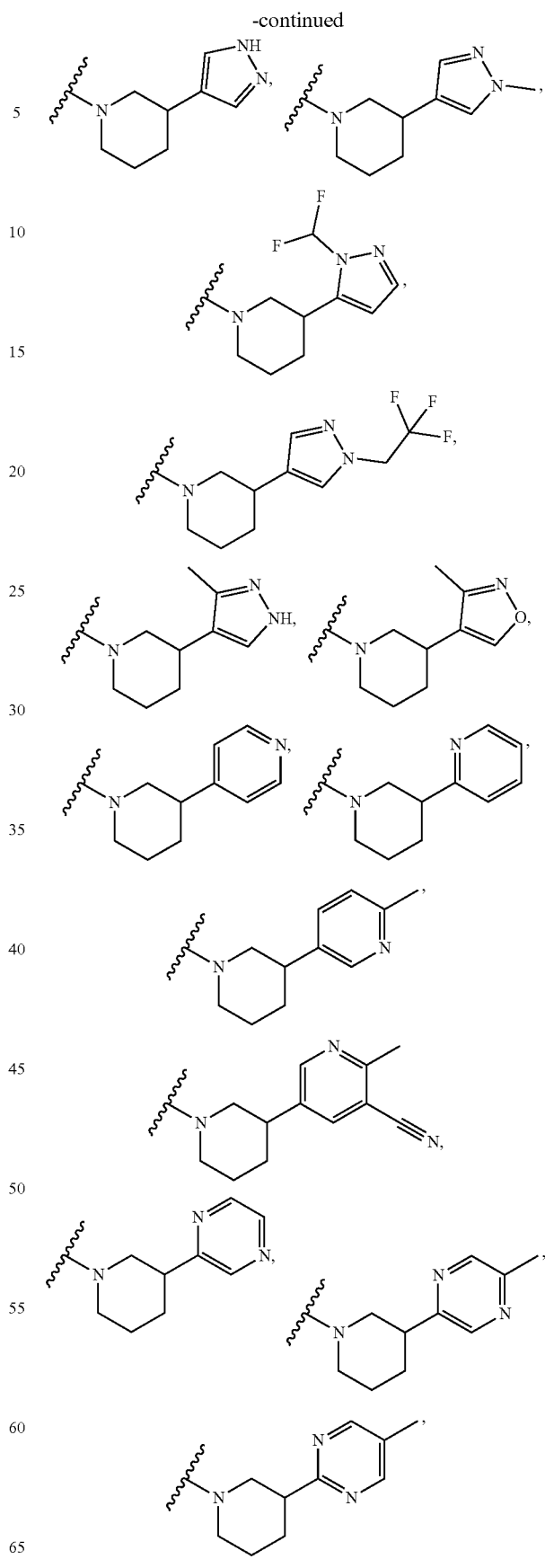

-continued
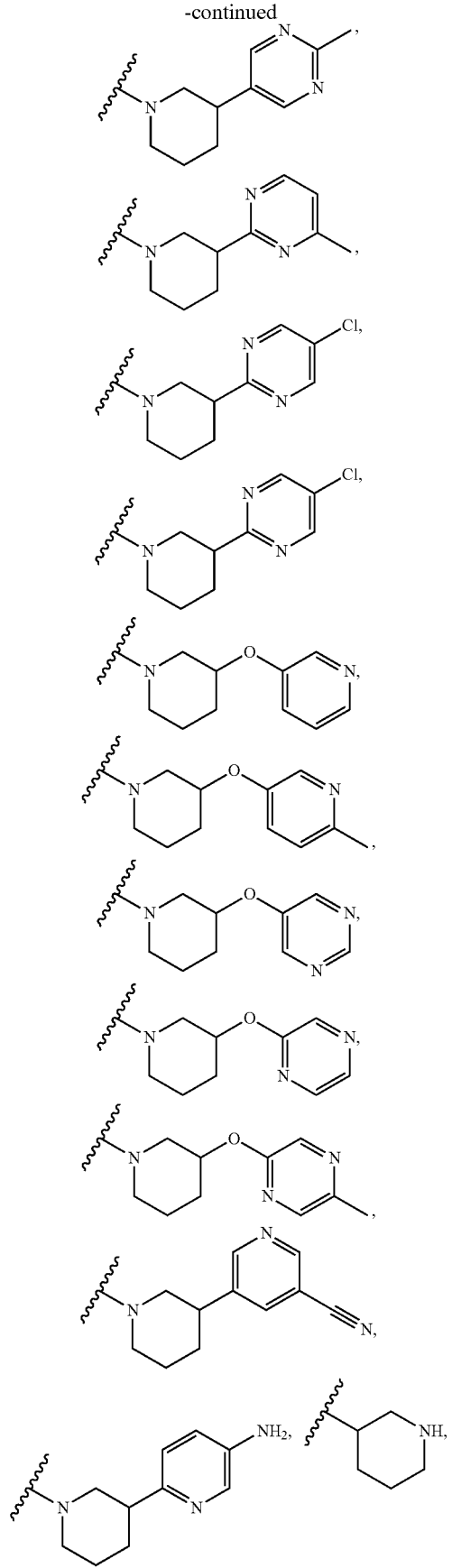
-continued
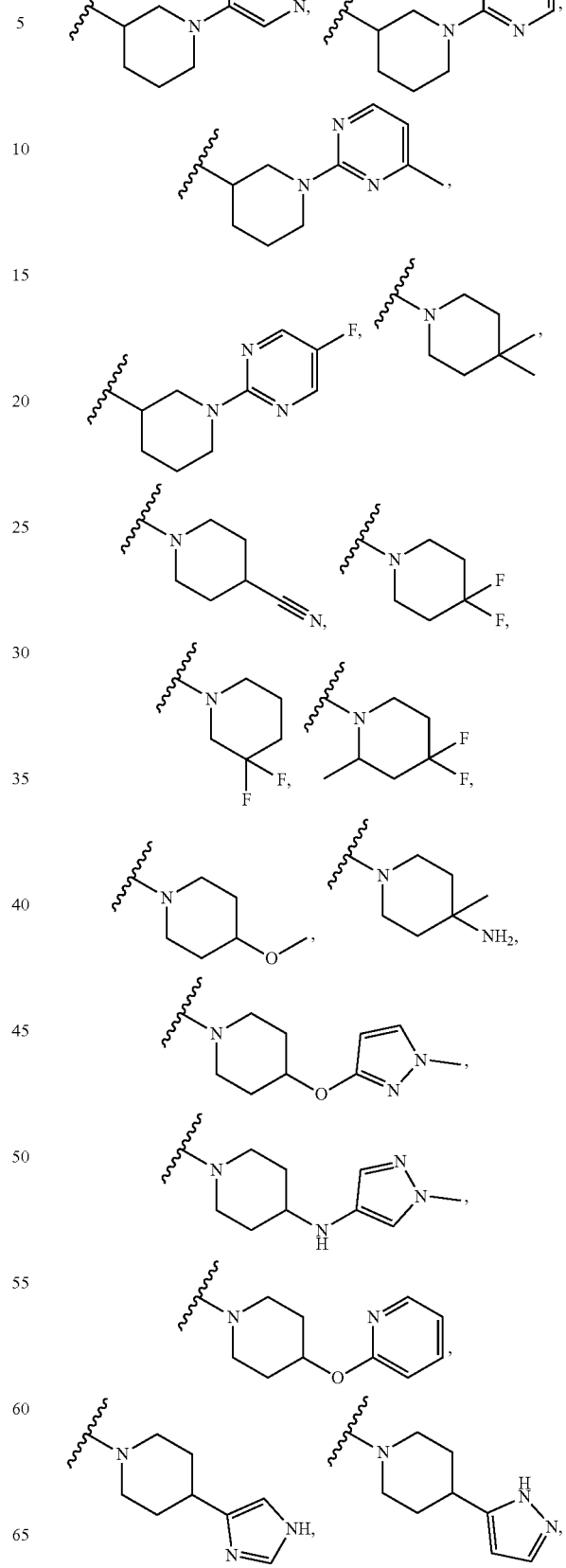

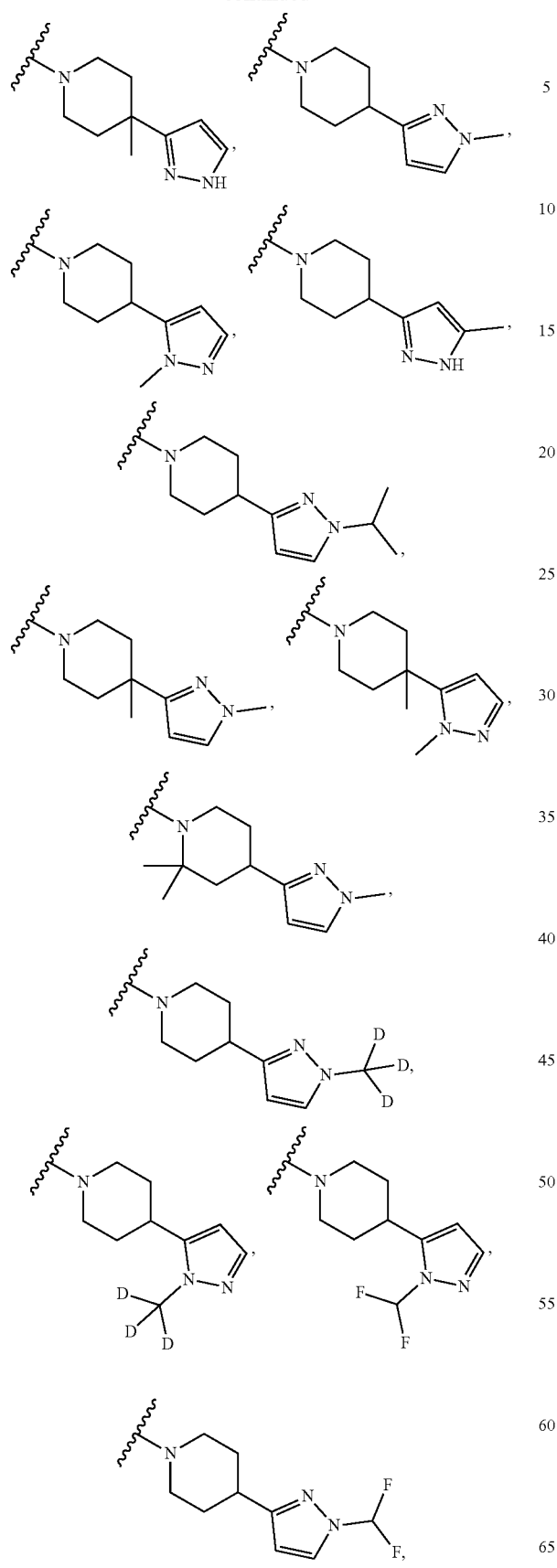
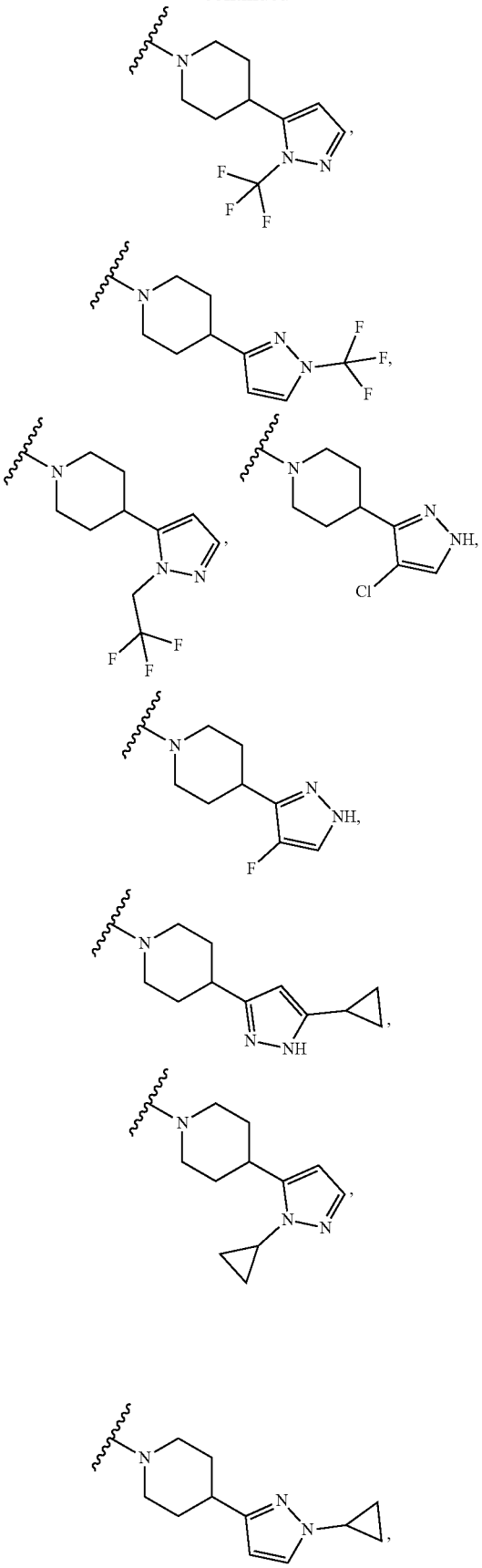

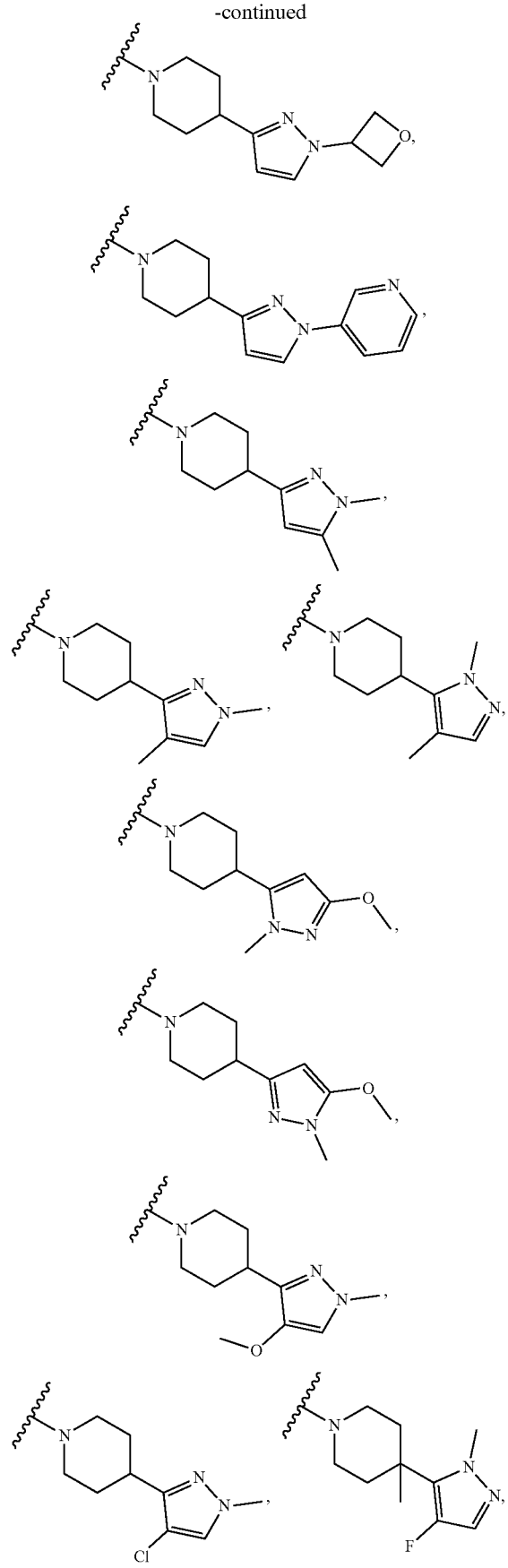
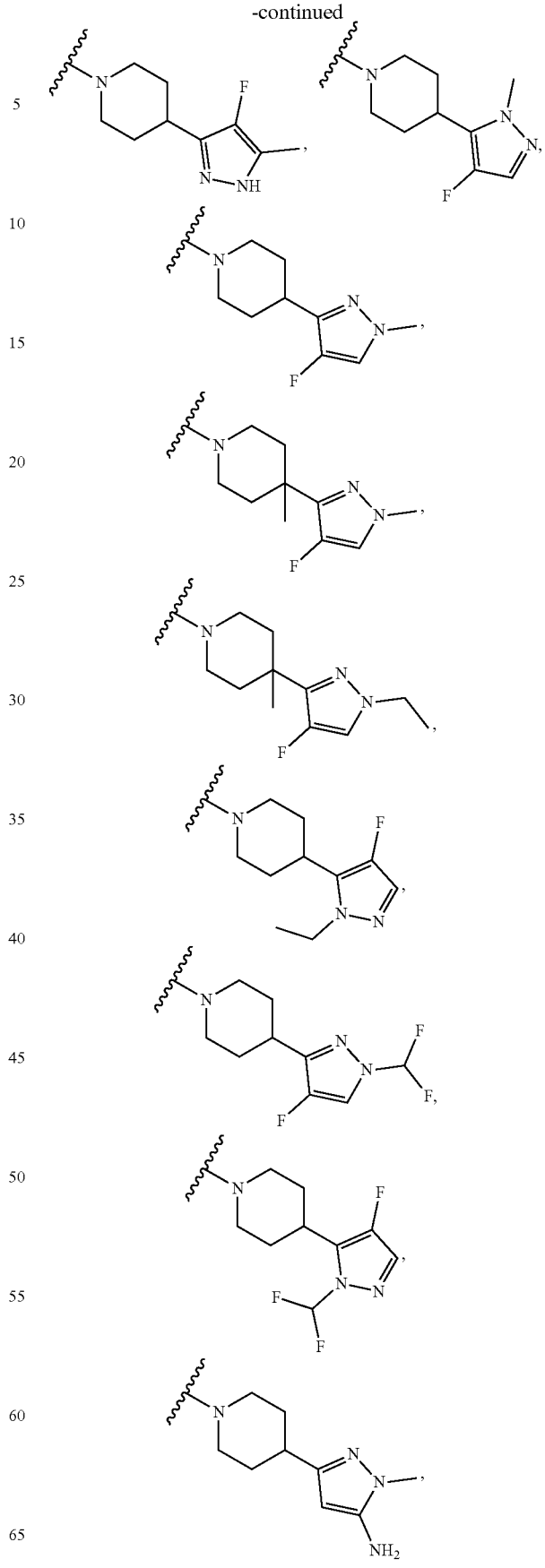

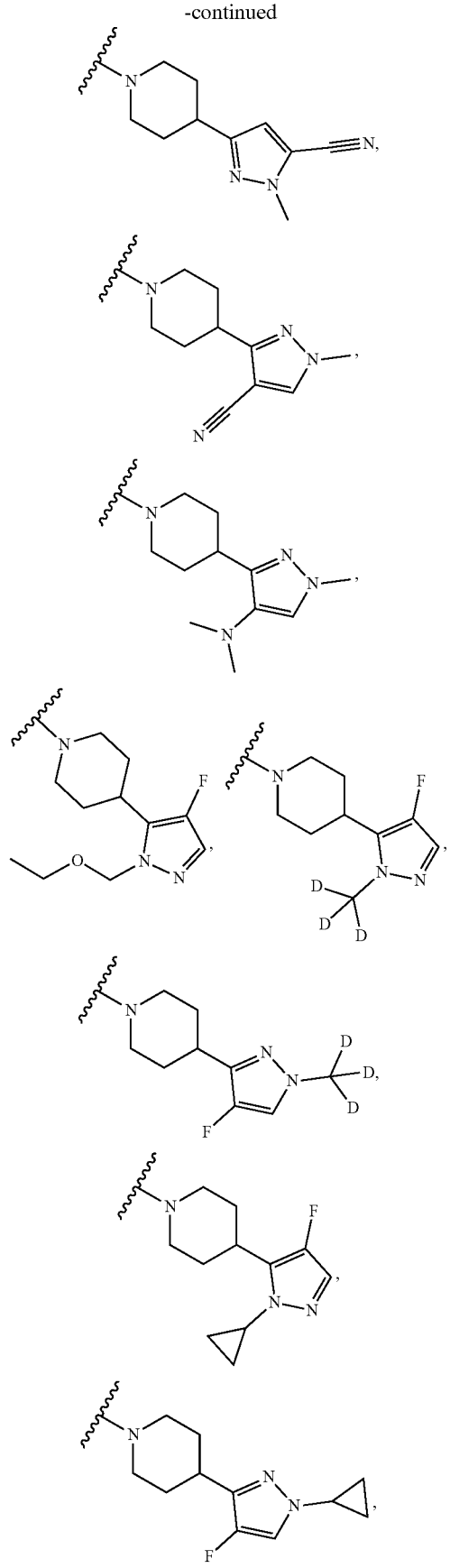
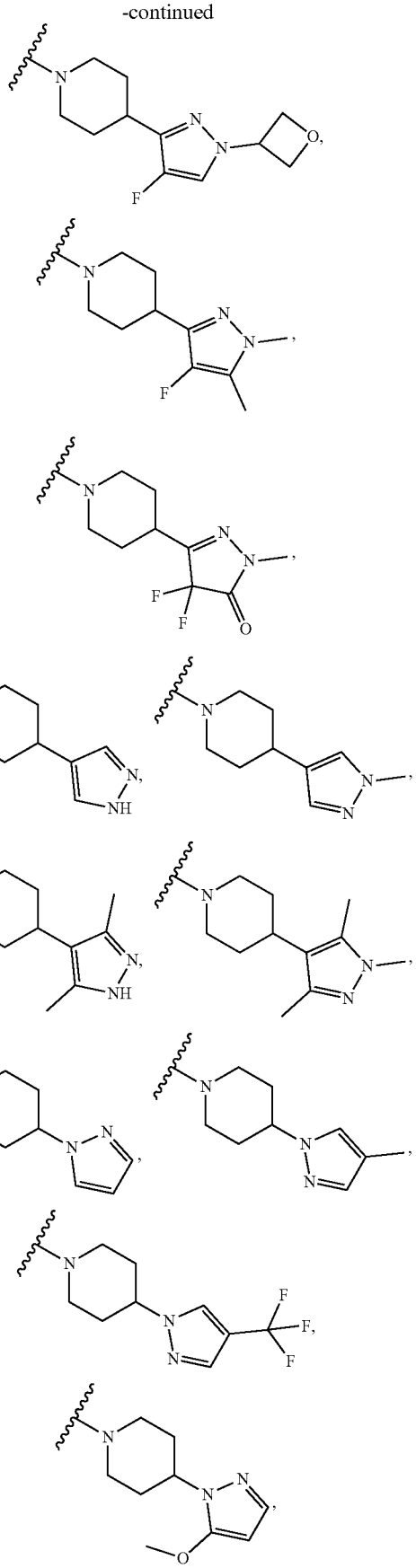

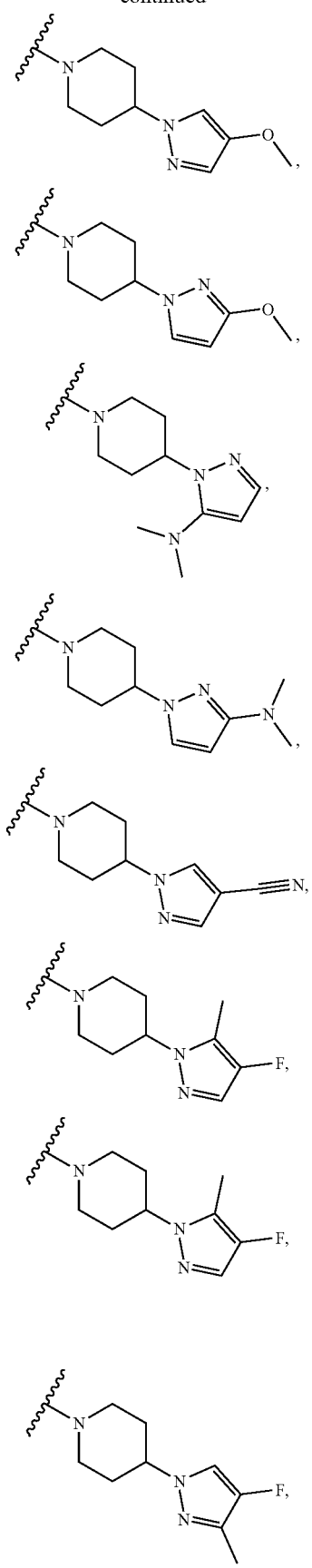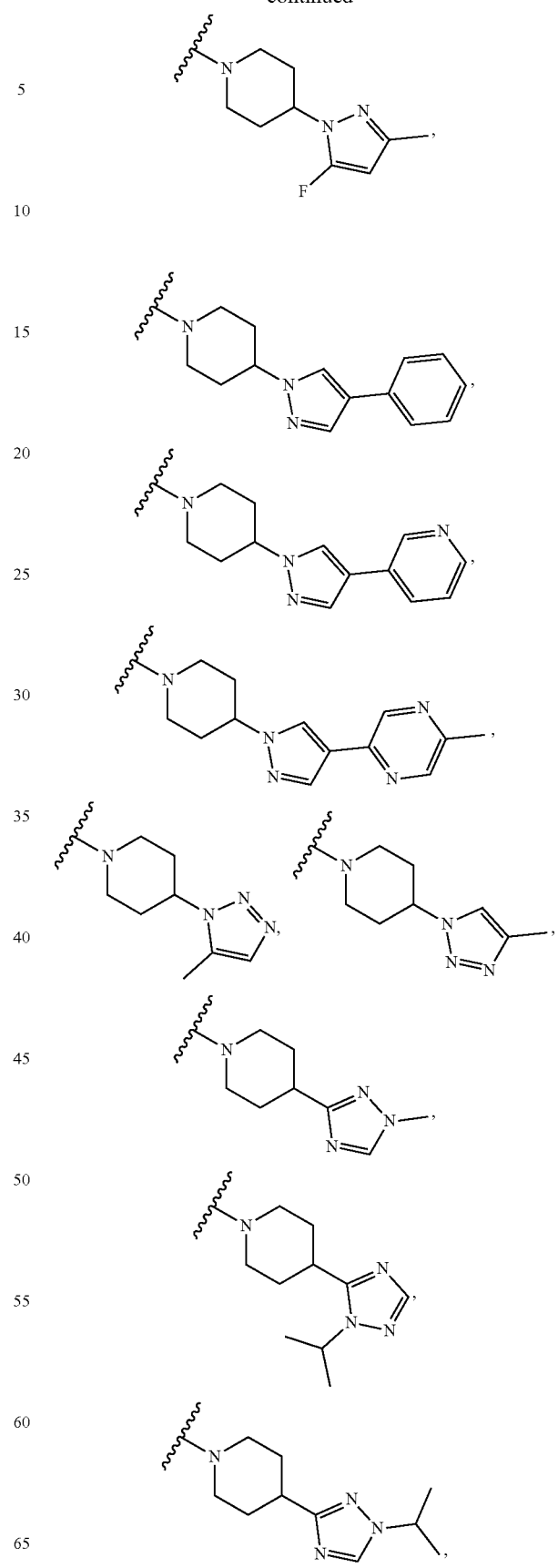

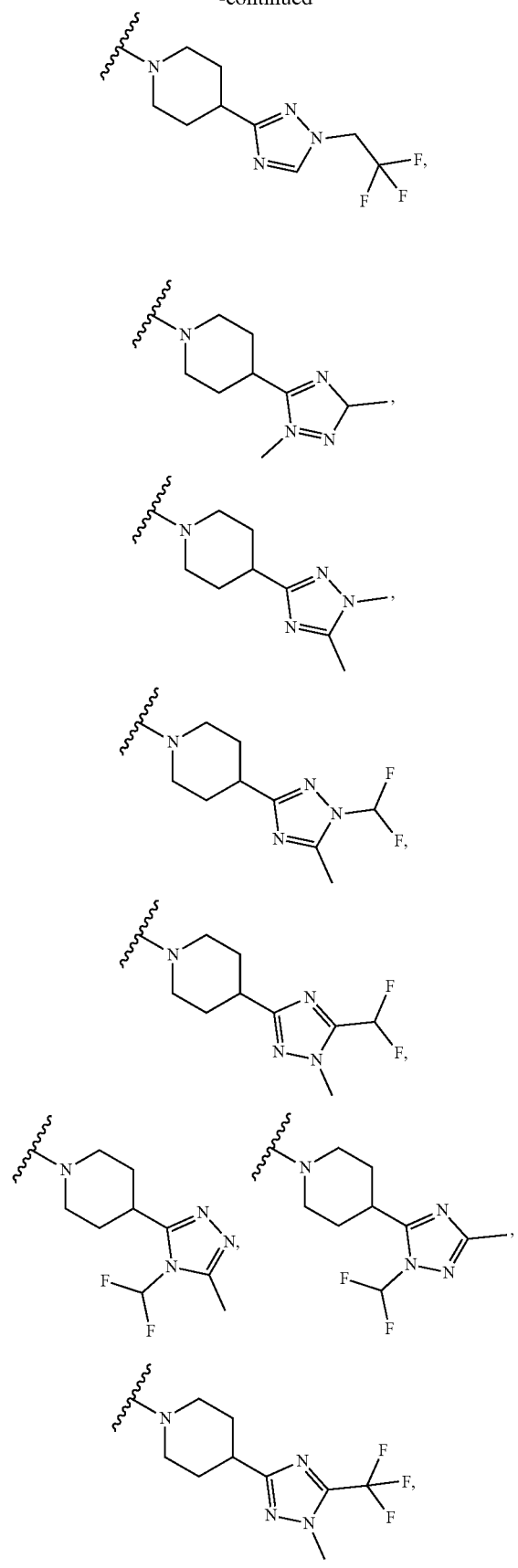
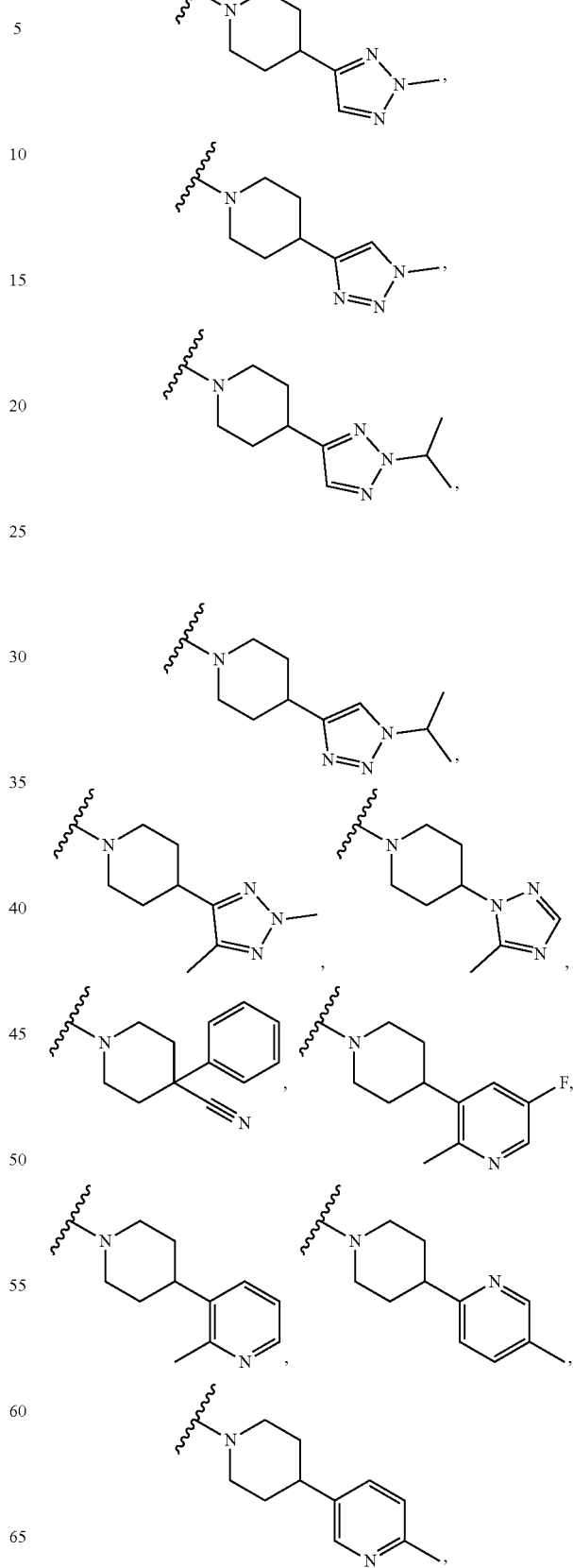

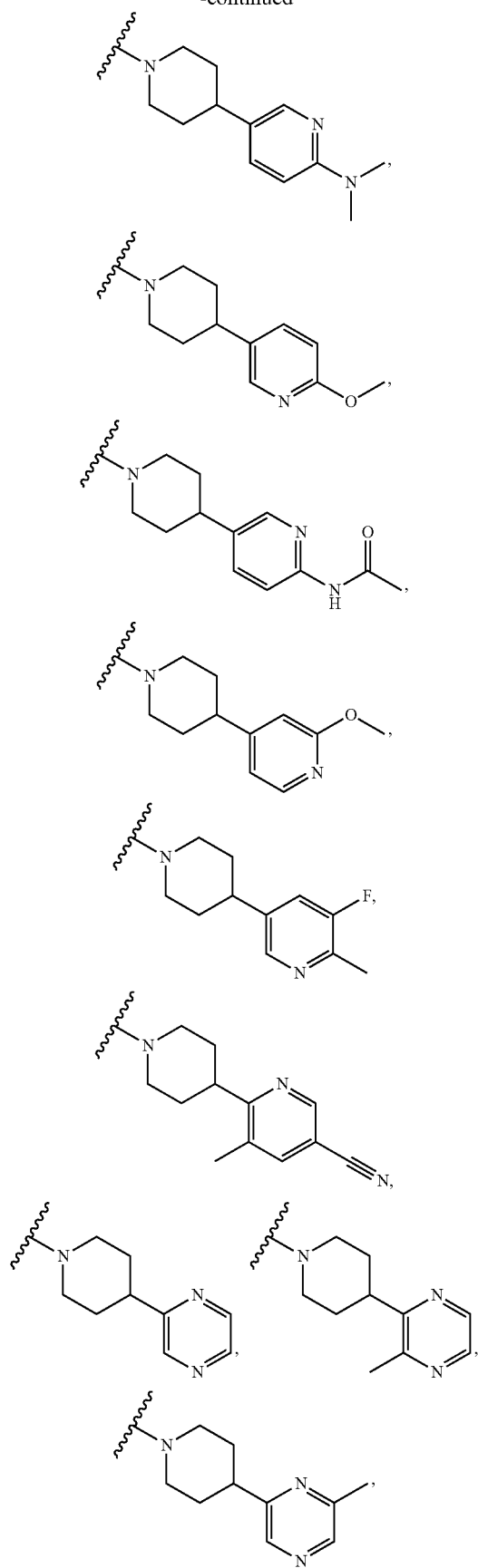
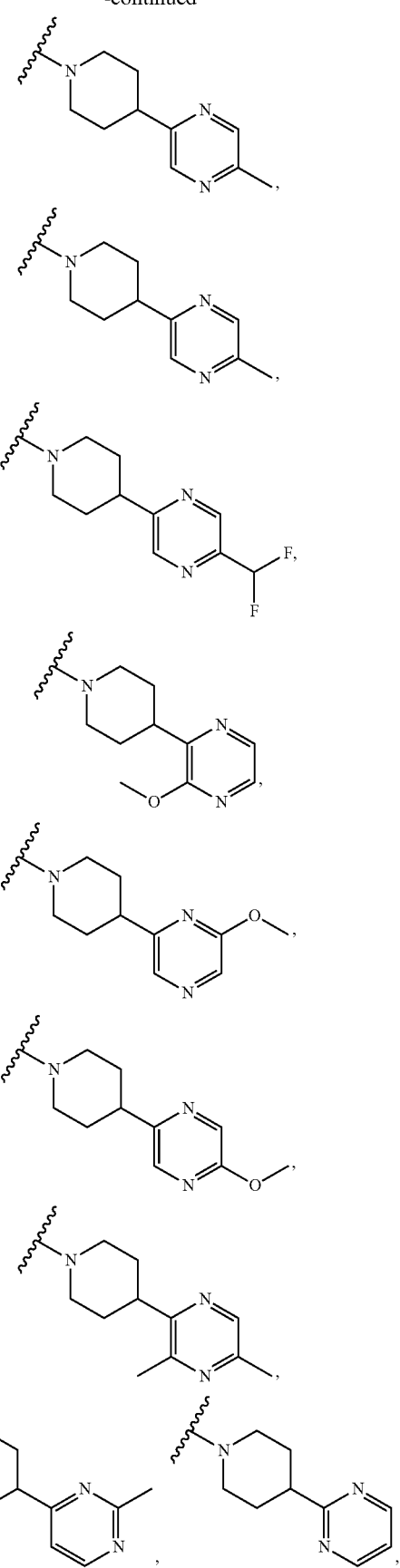

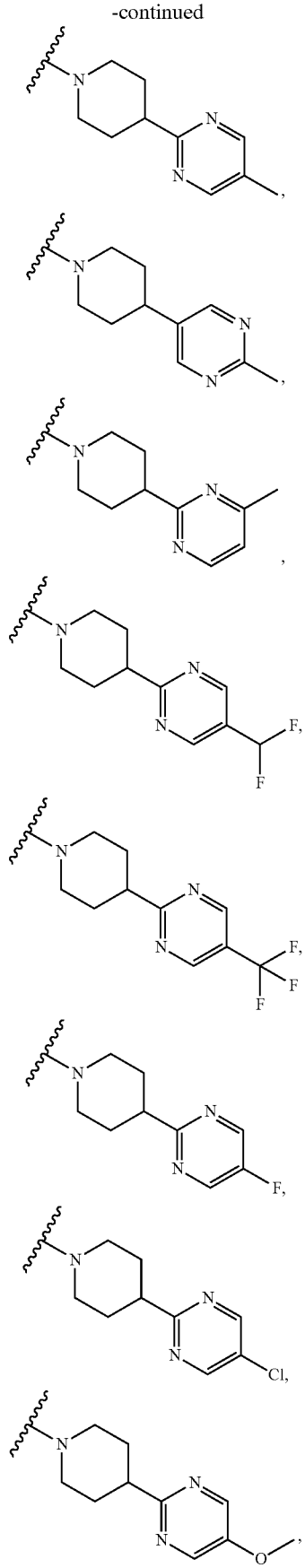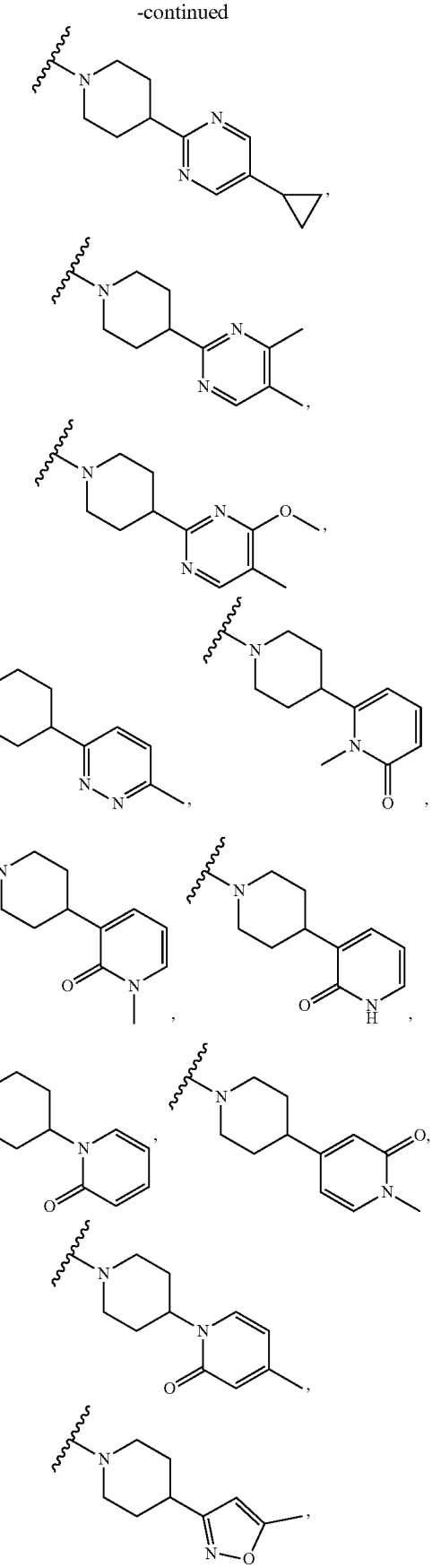

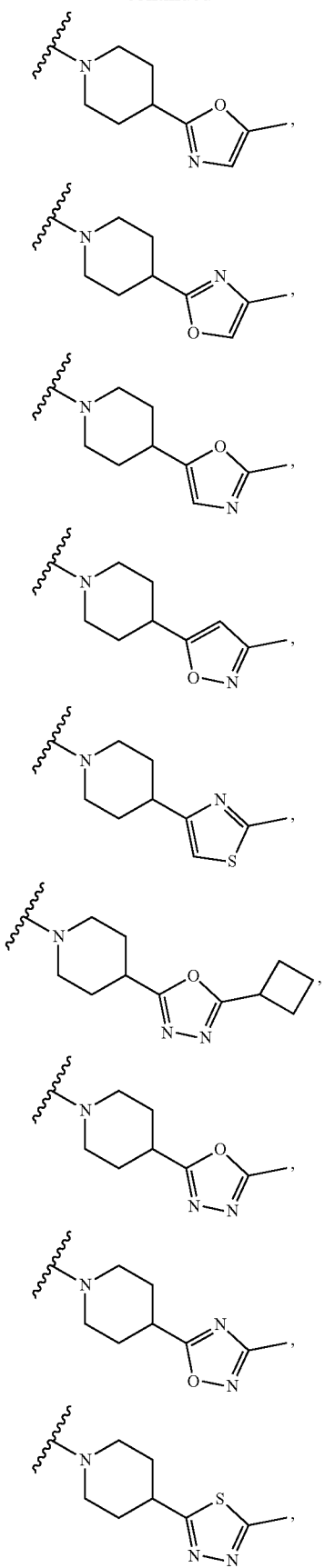
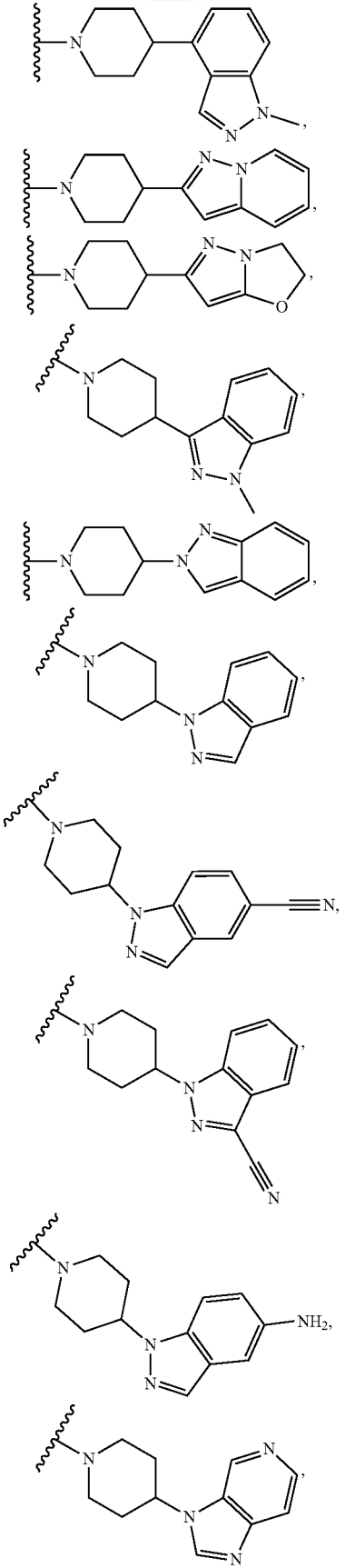

97
-continued
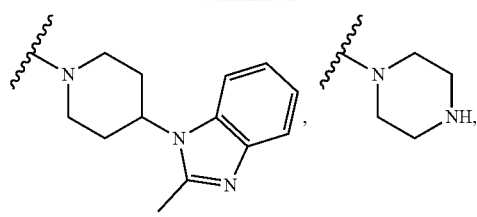
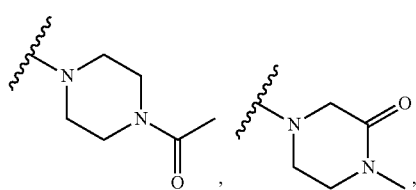
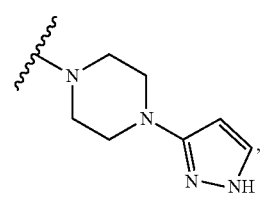
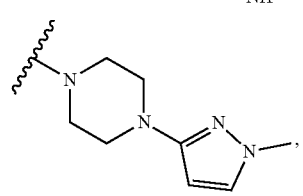
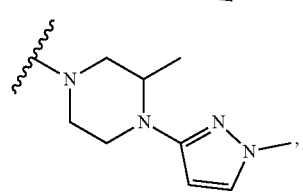
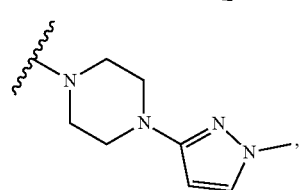
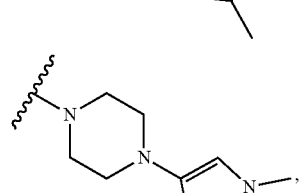
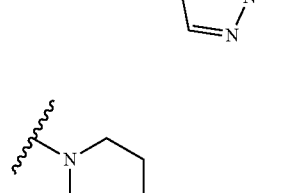
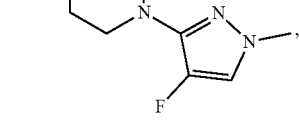
98
-continued
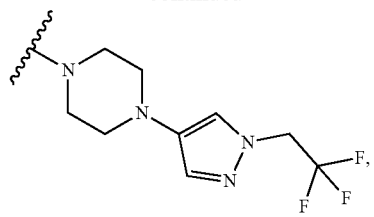
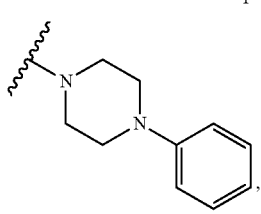
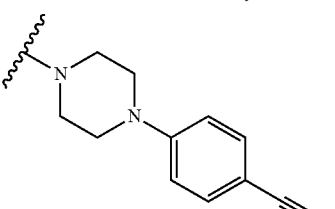
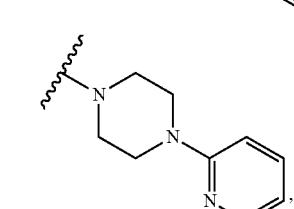
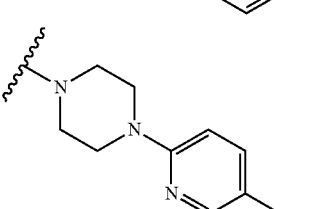
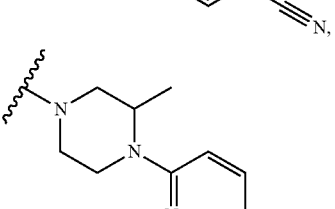
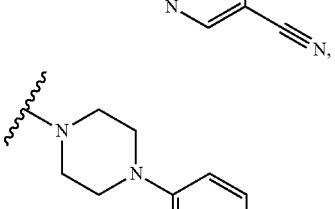
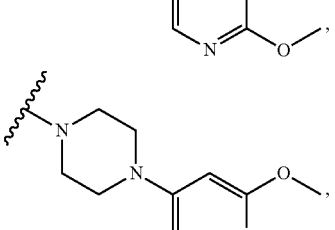

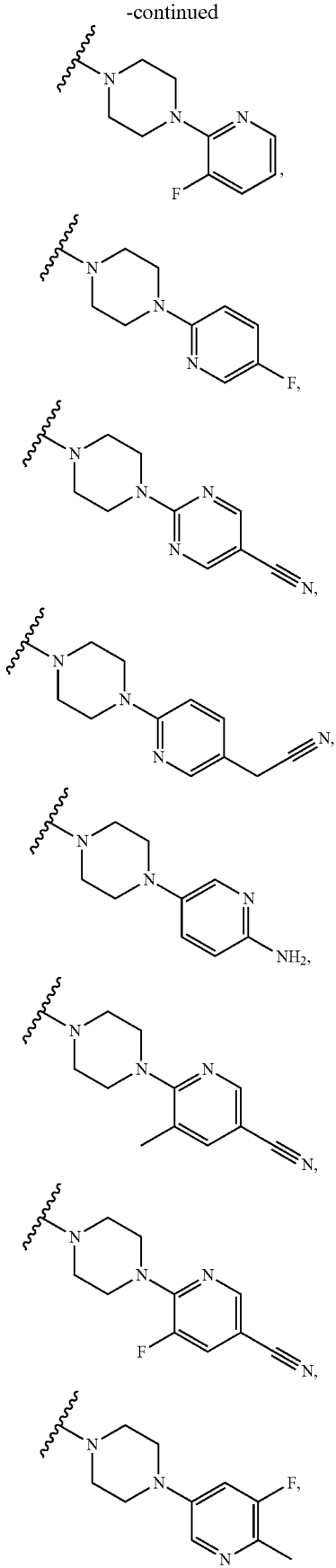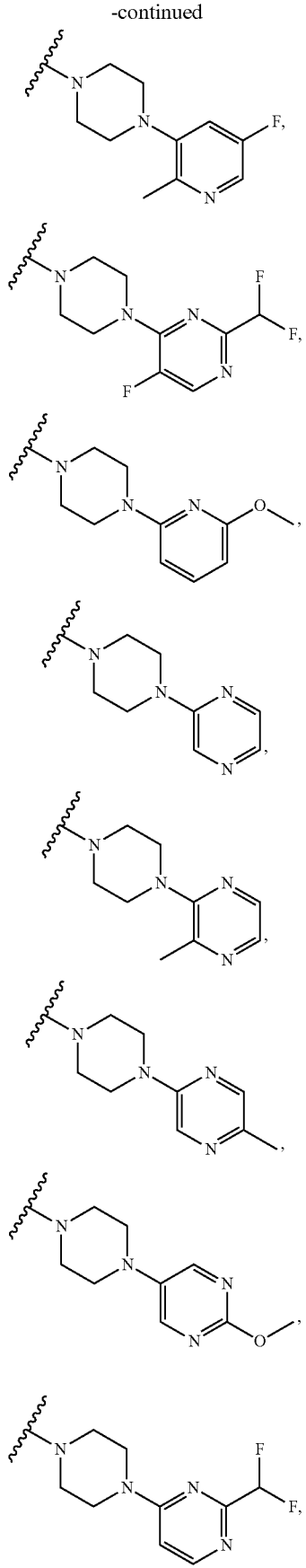

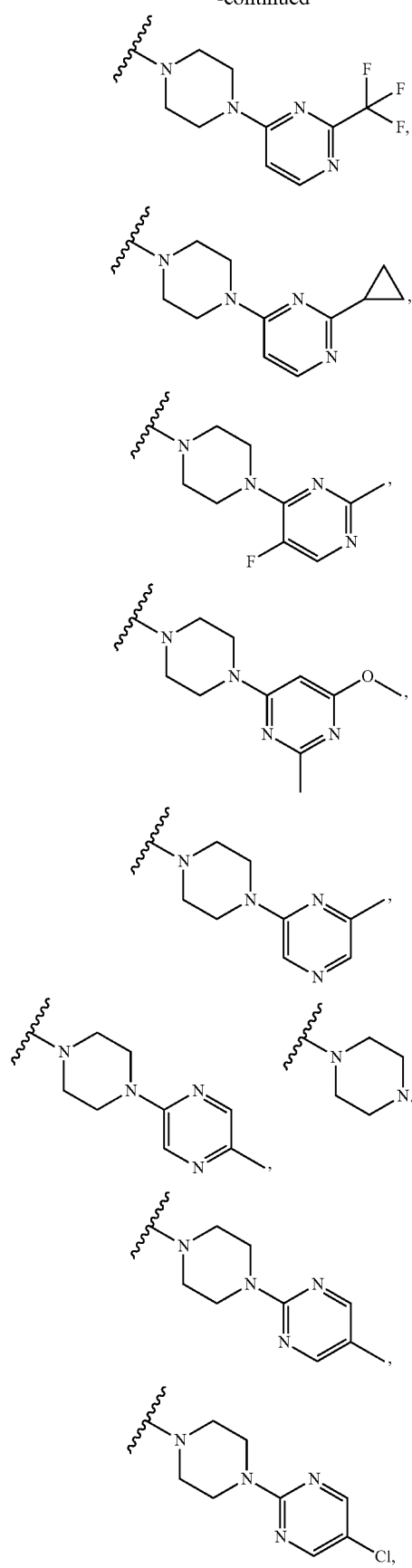
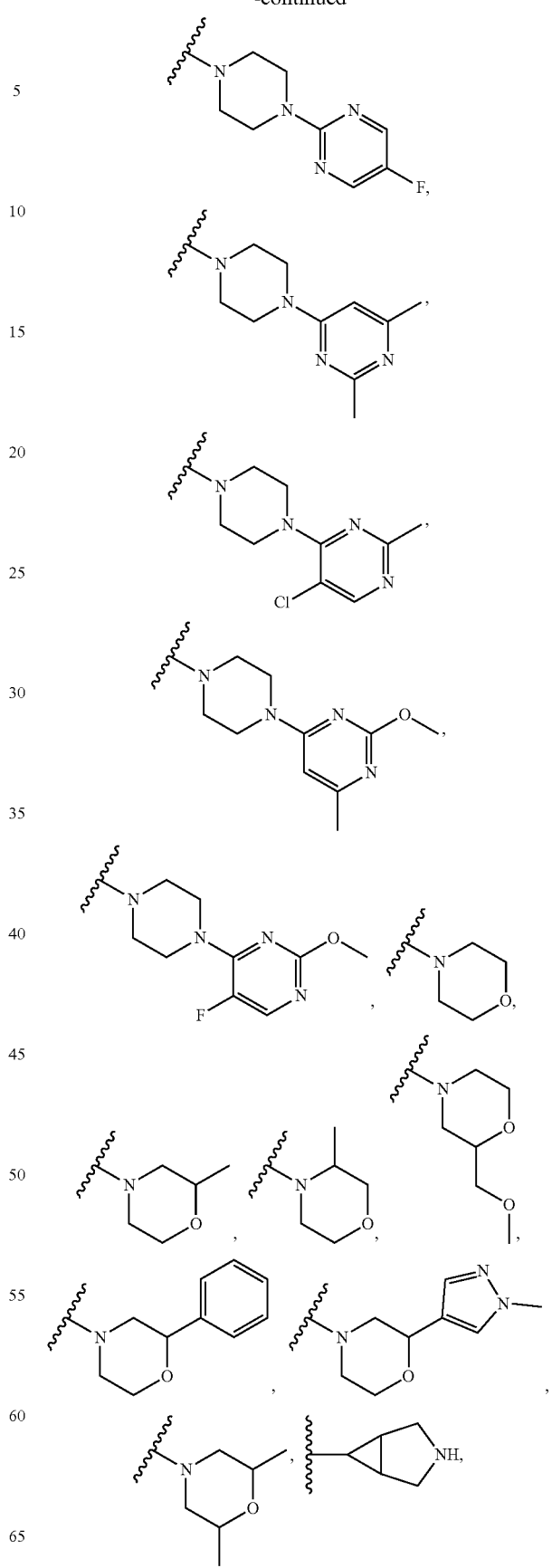

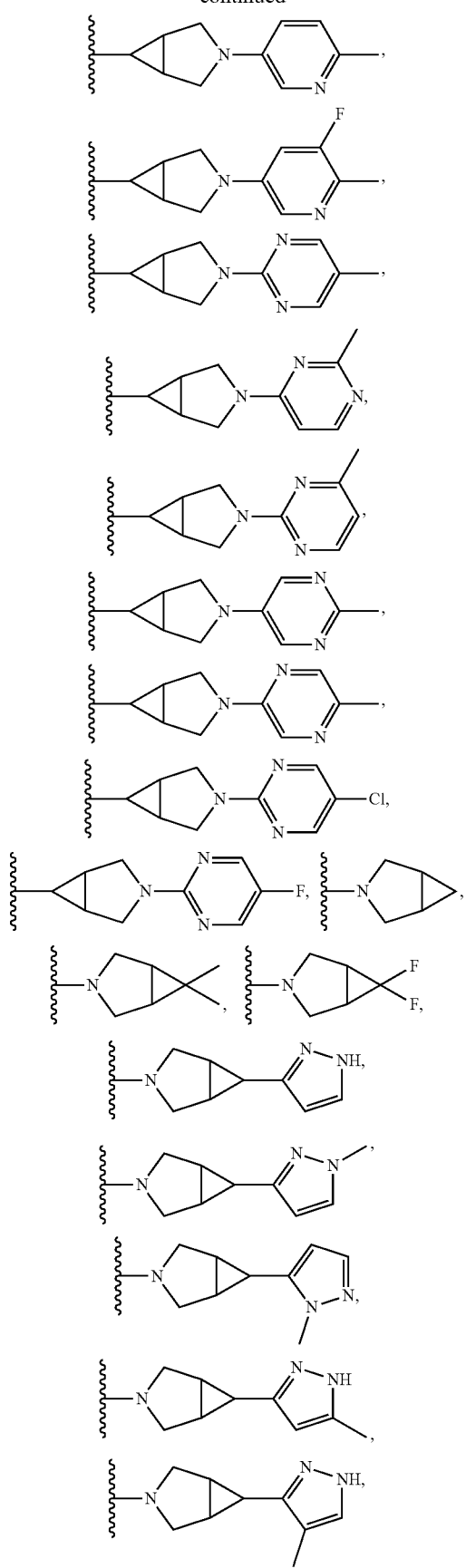
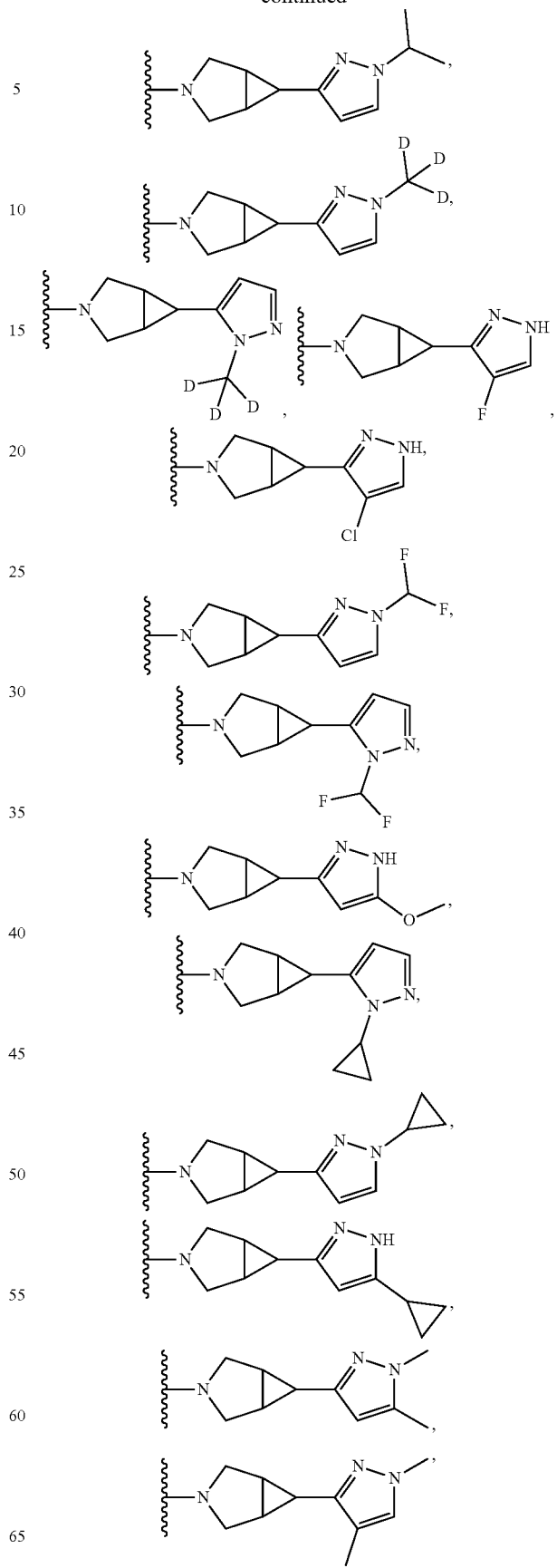

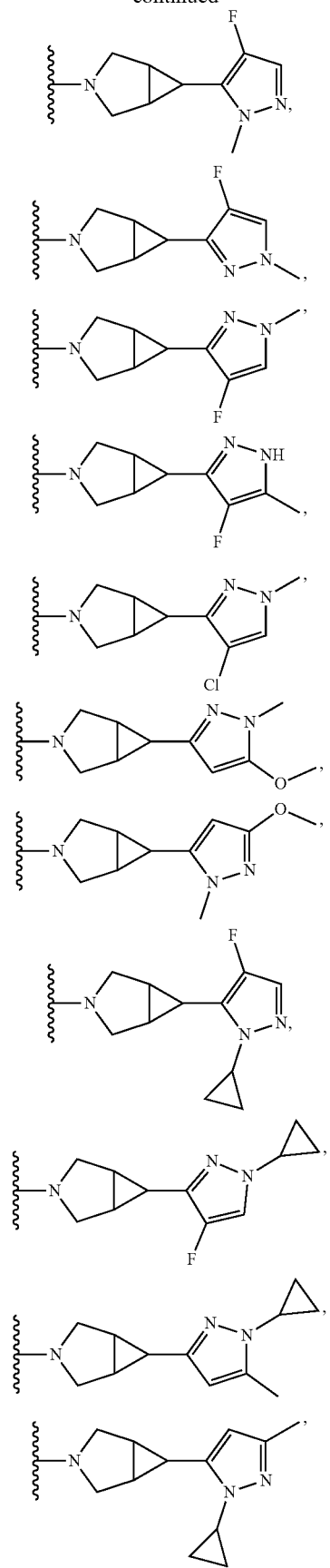
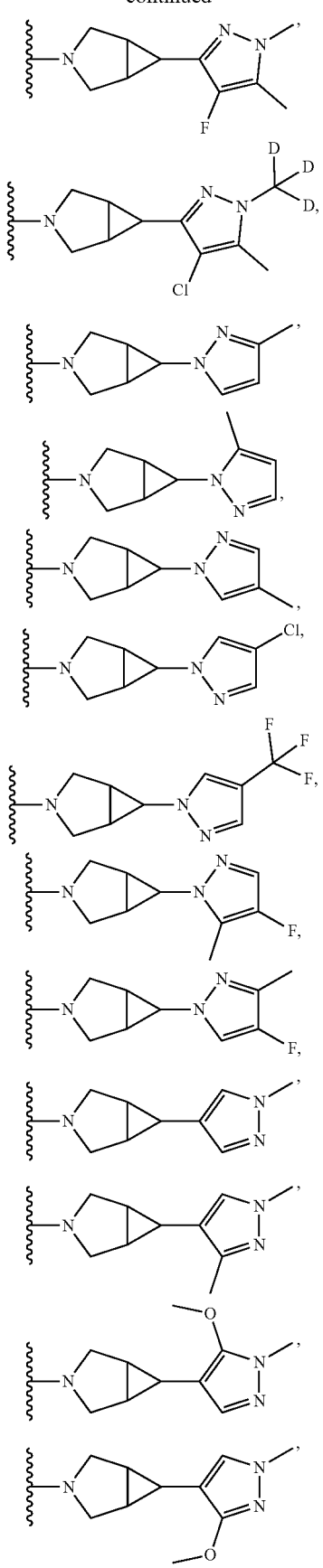

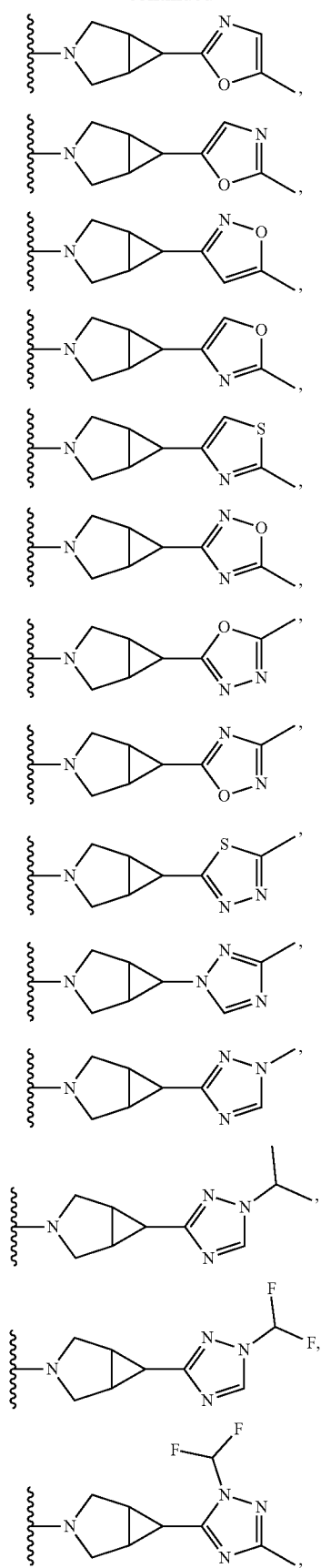
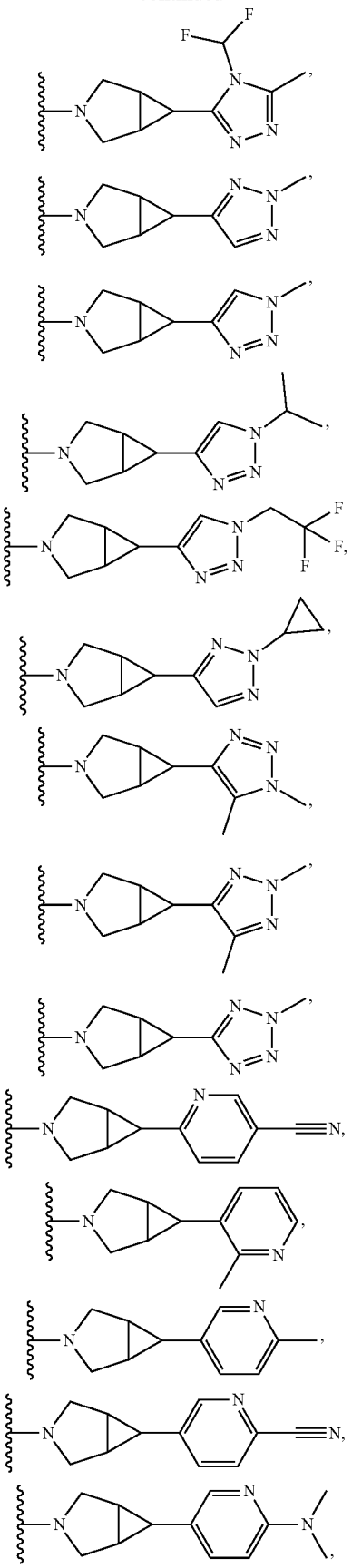

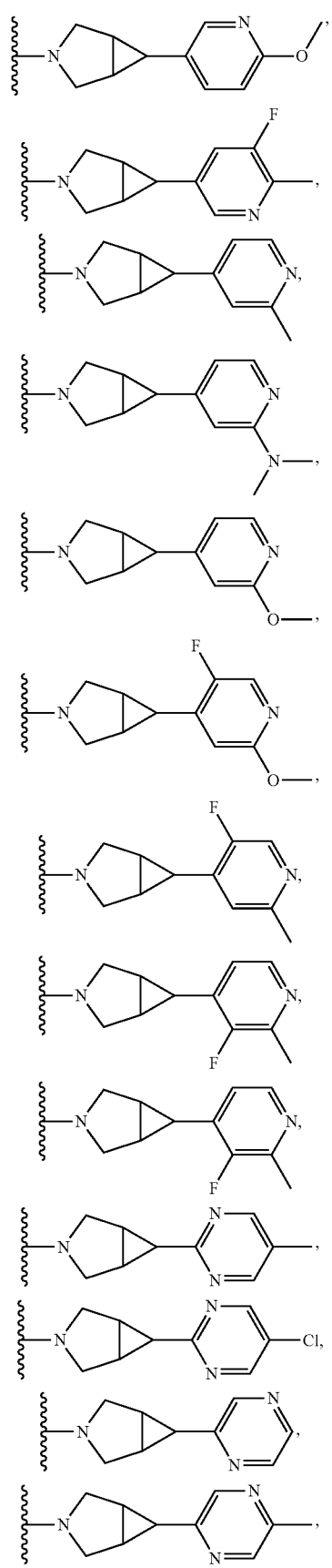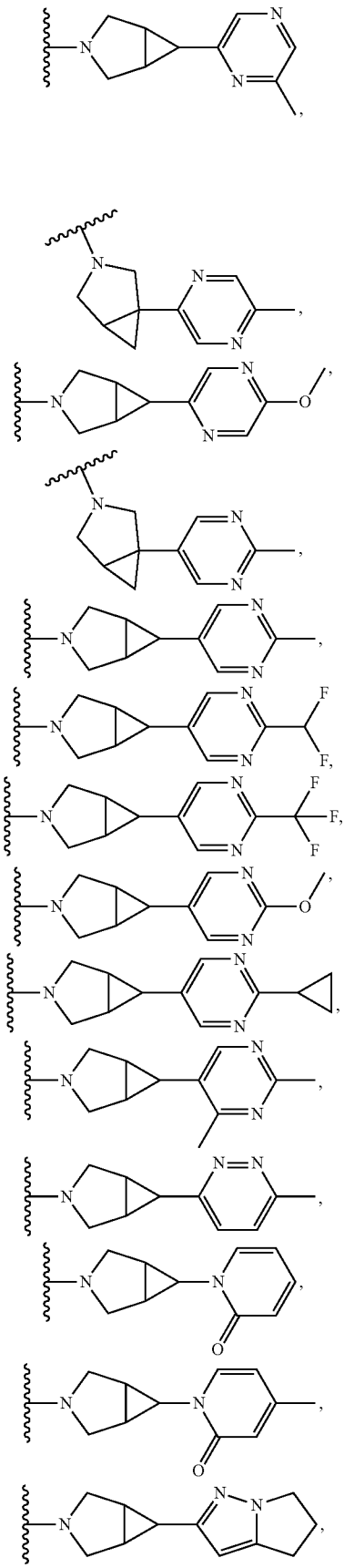

111
-continued
112
-continued
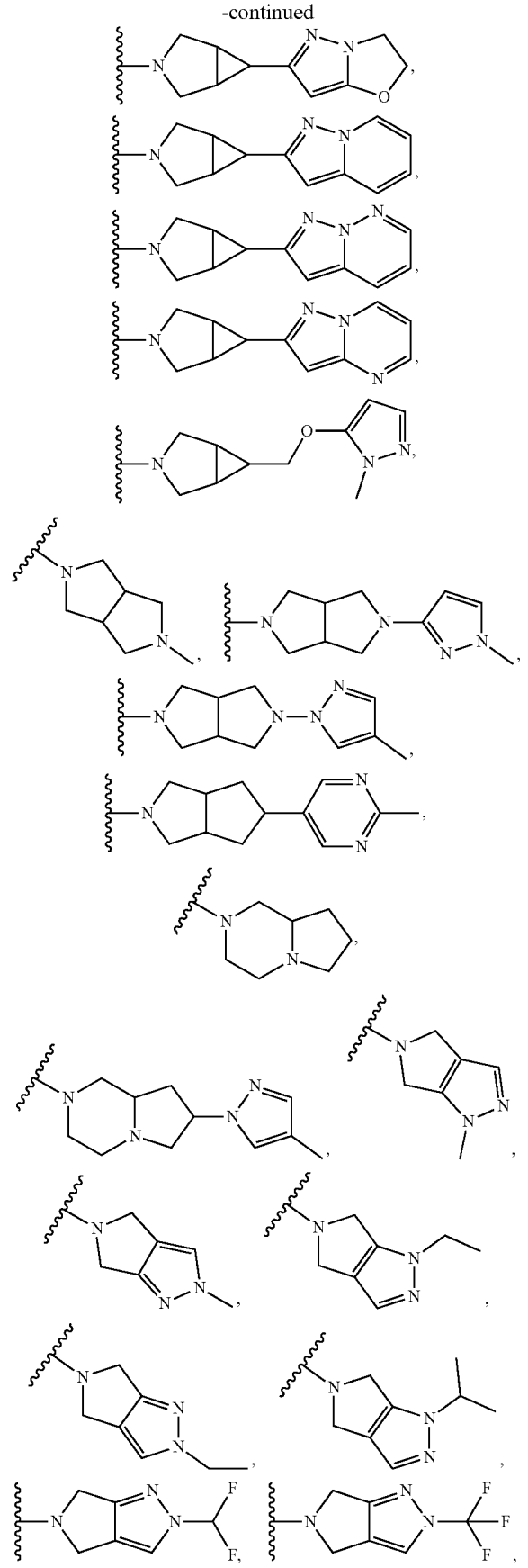
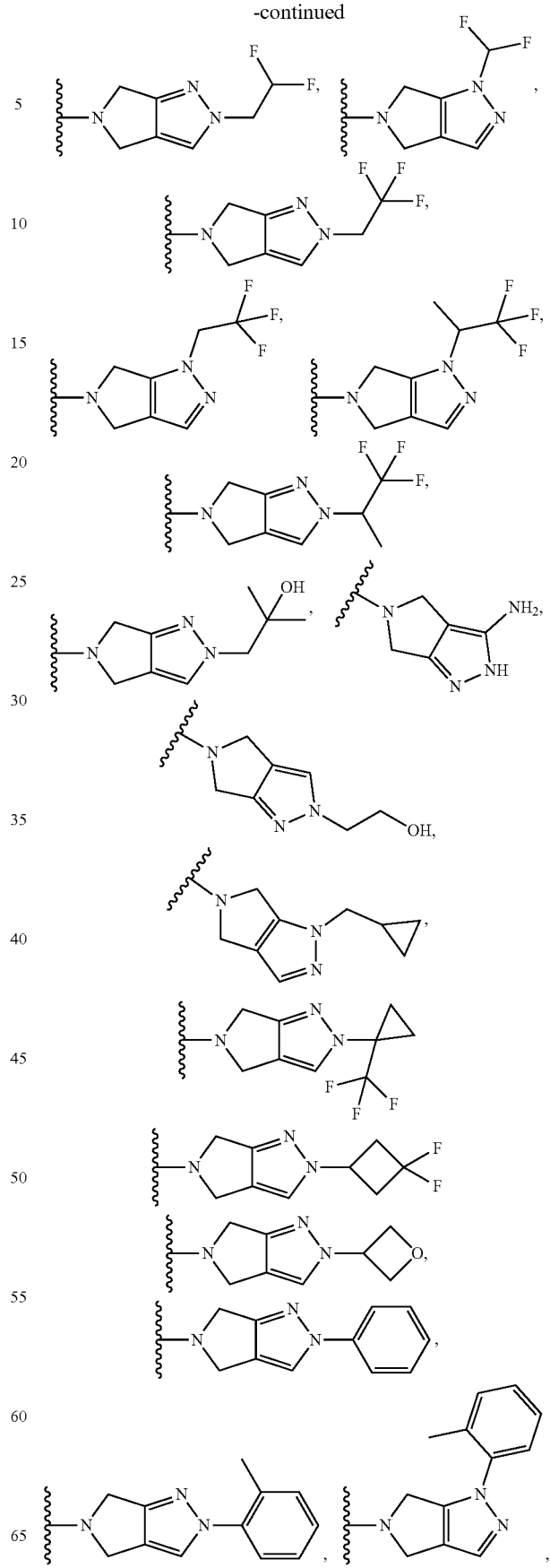

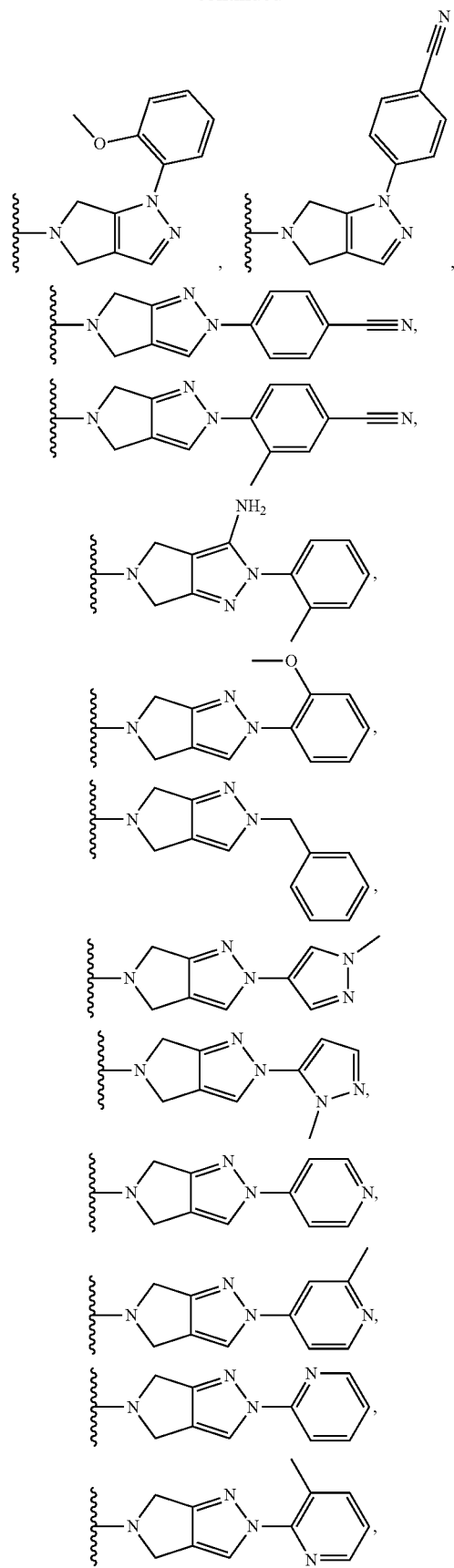
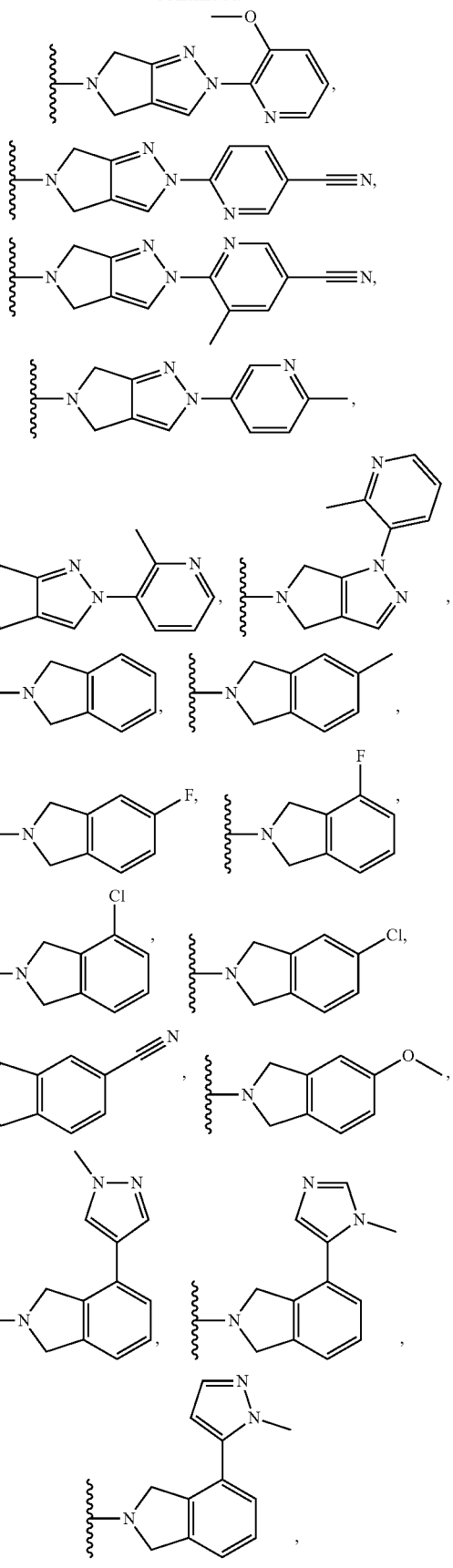

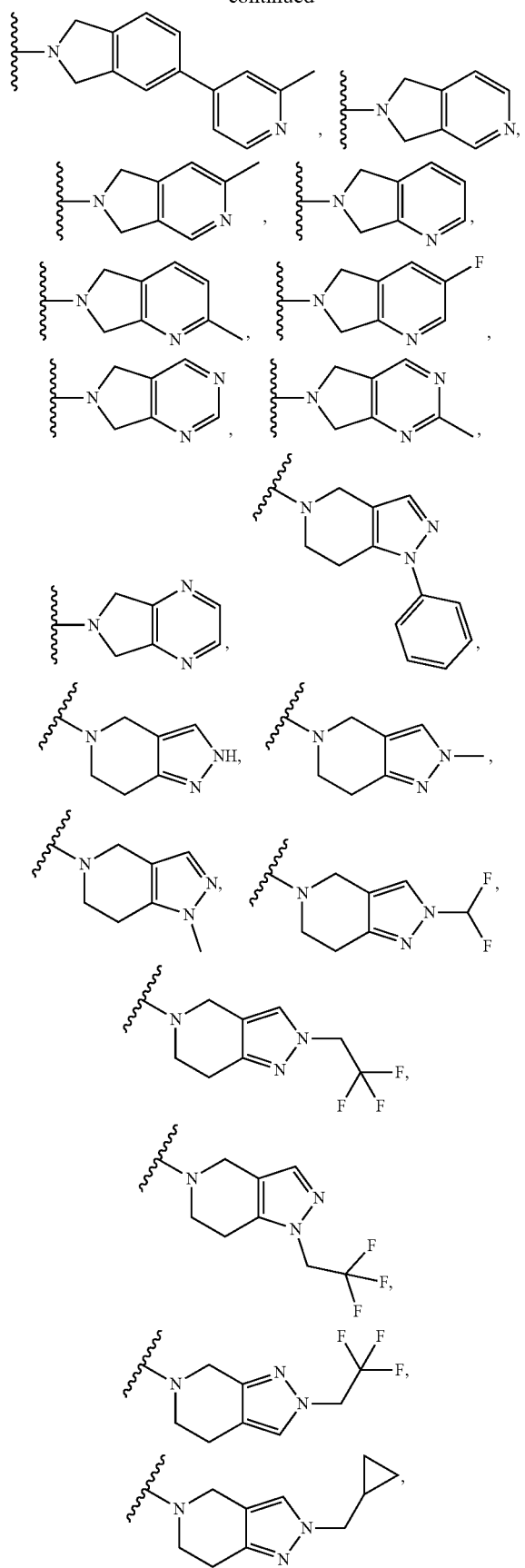
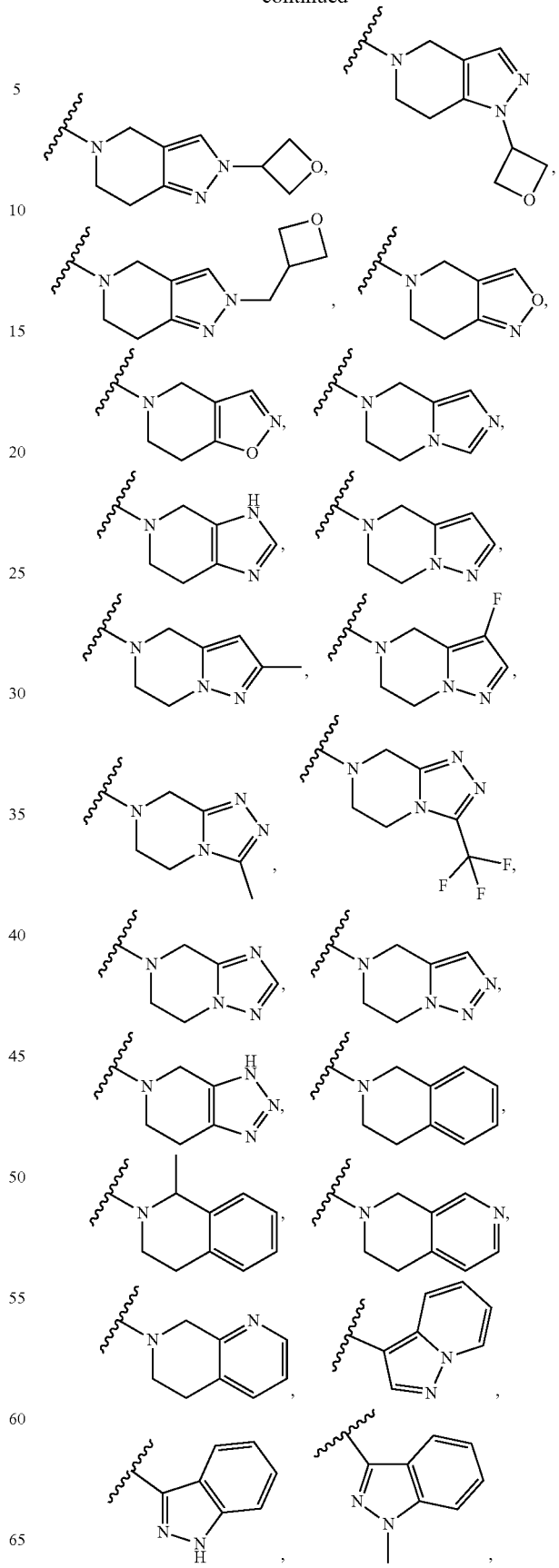

117
-continued
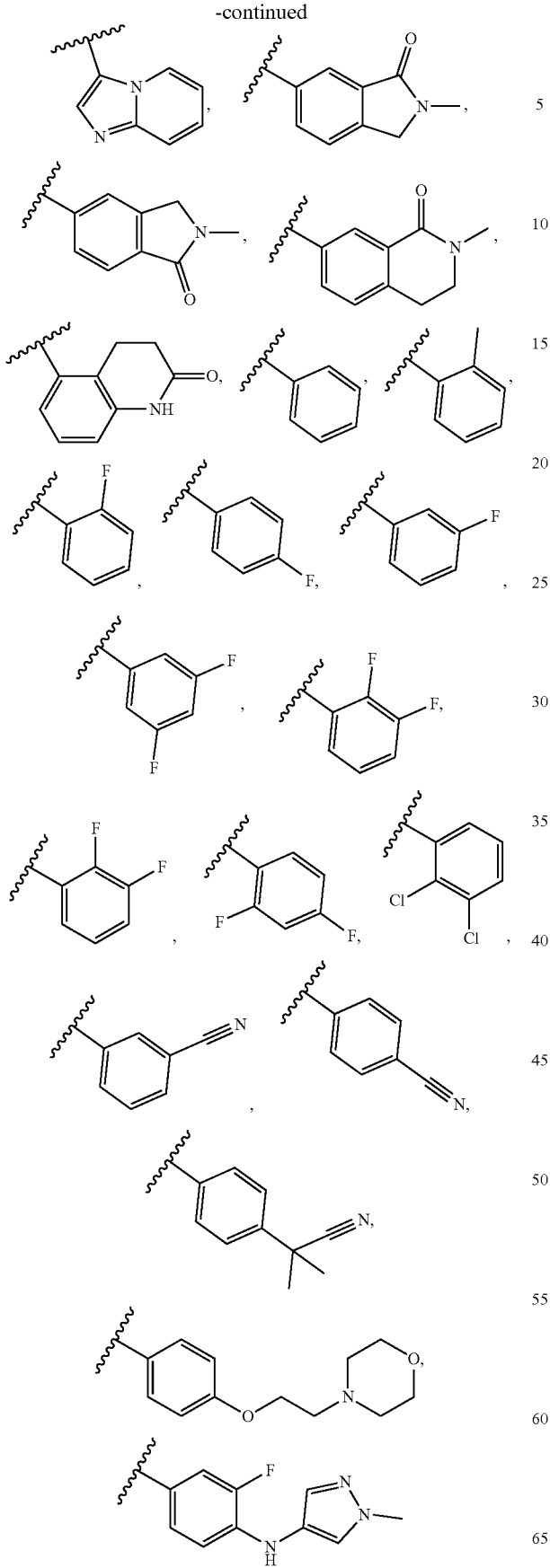
118
-continued
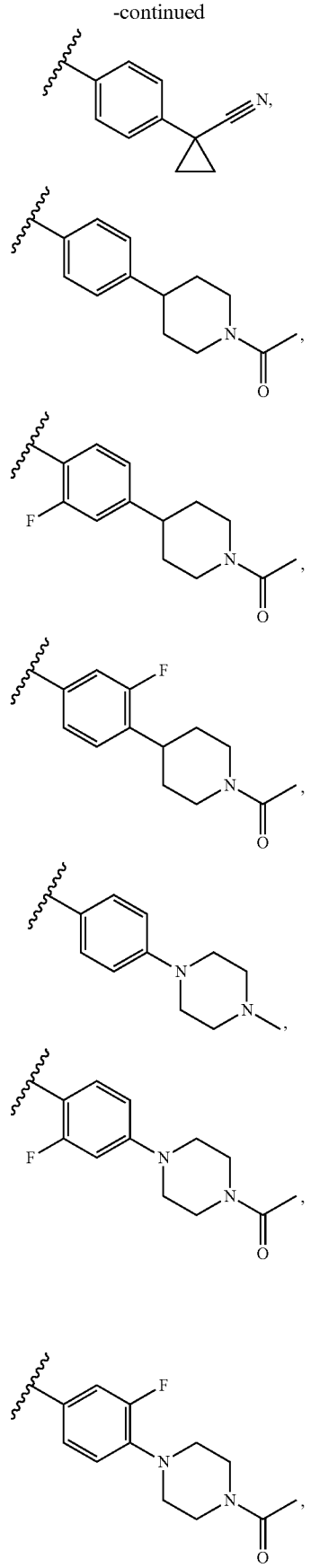

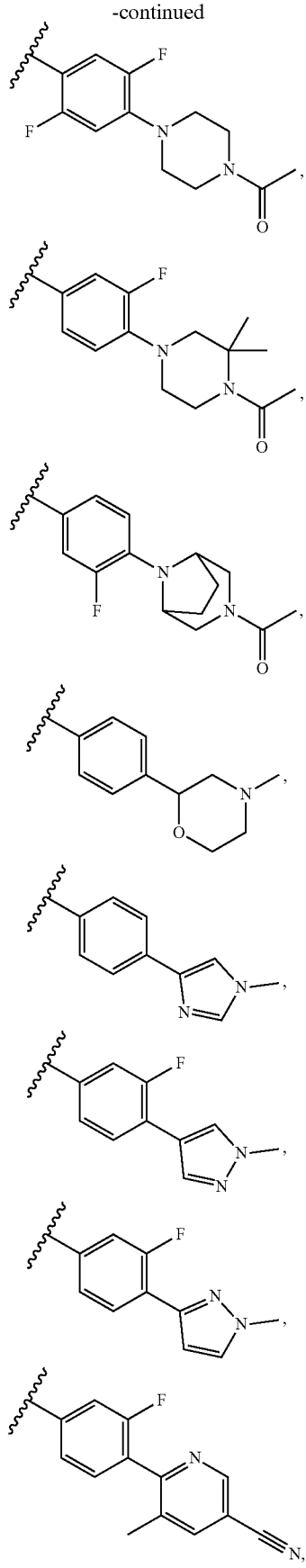
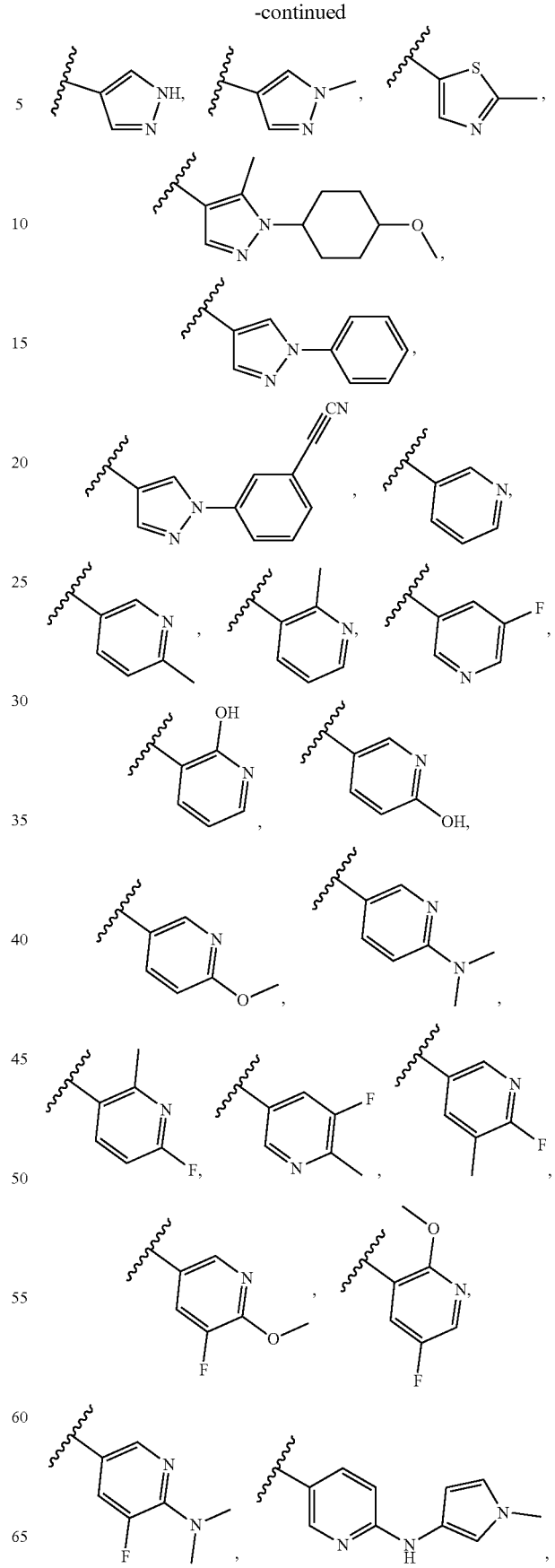

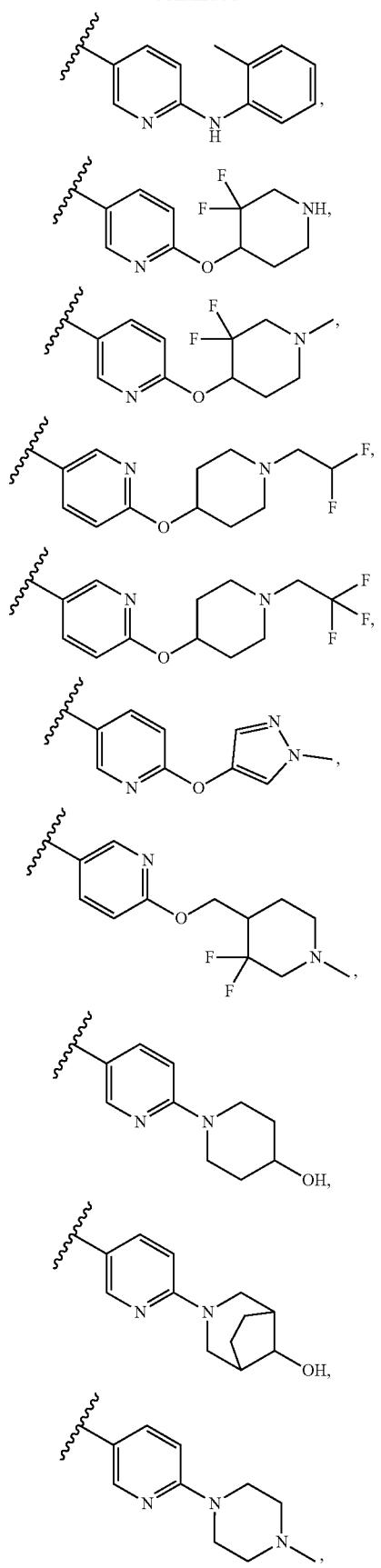
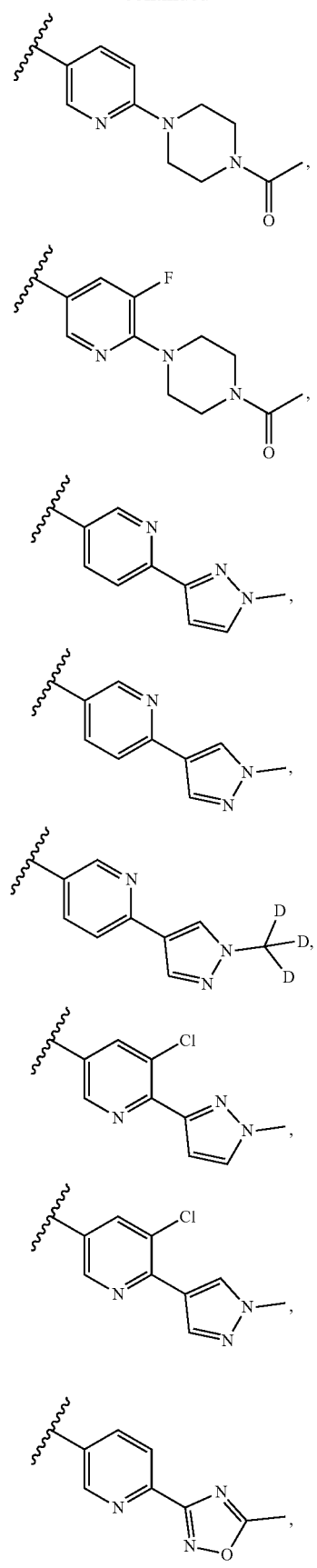

123
-continued
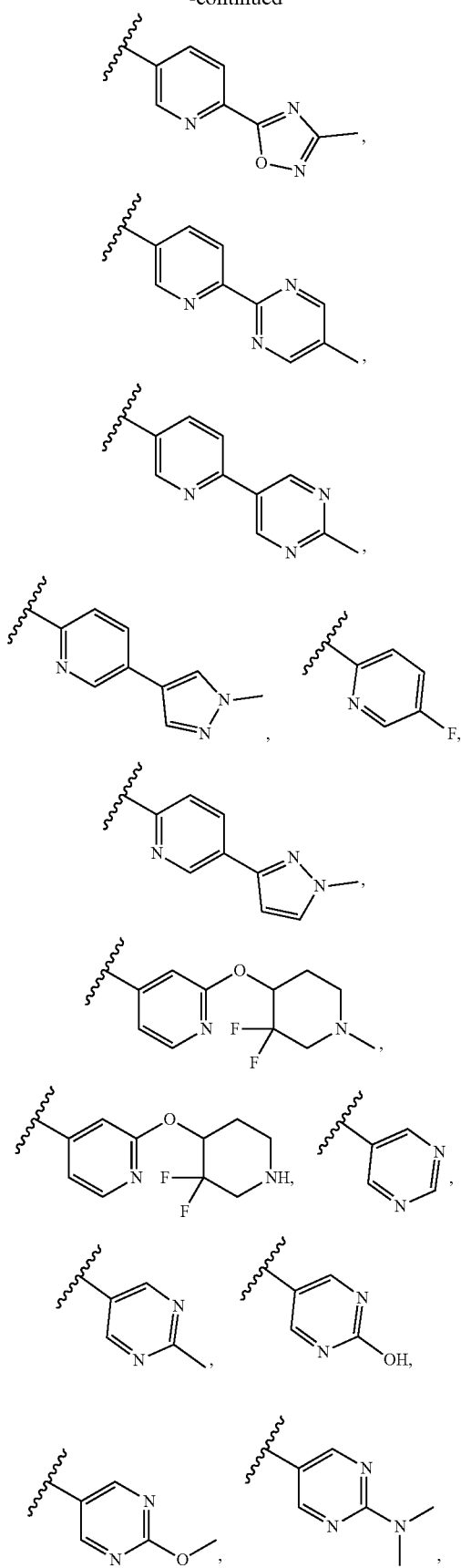
124
-continued
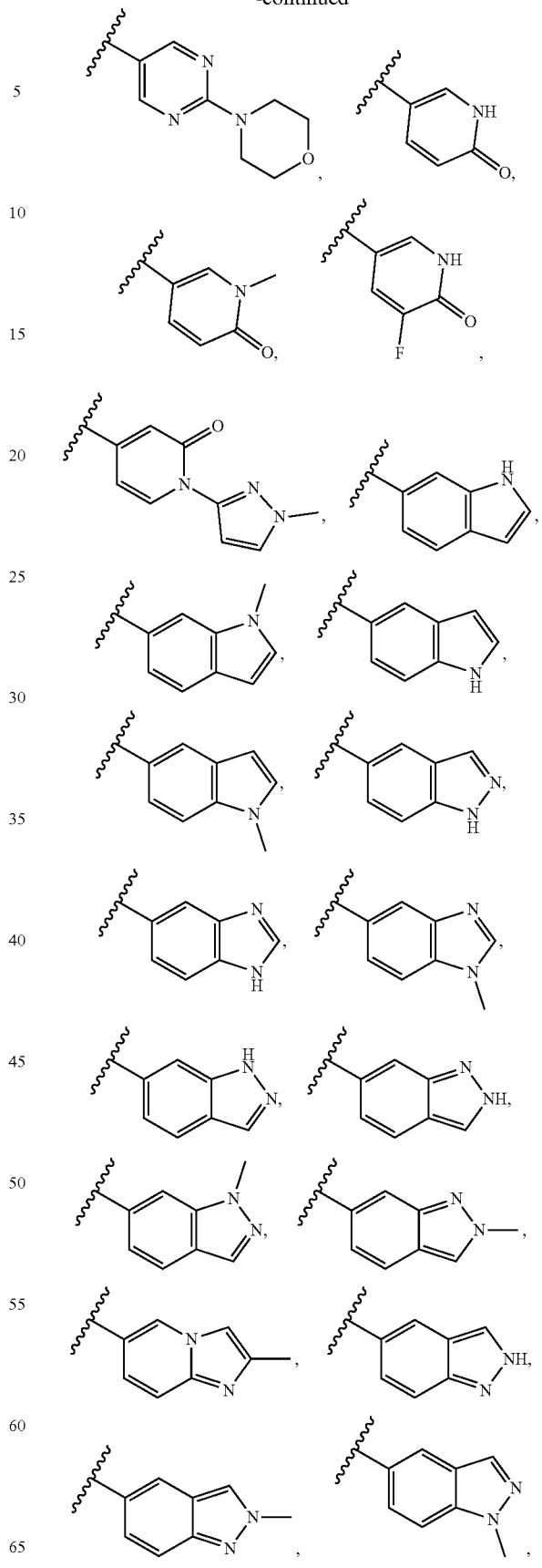

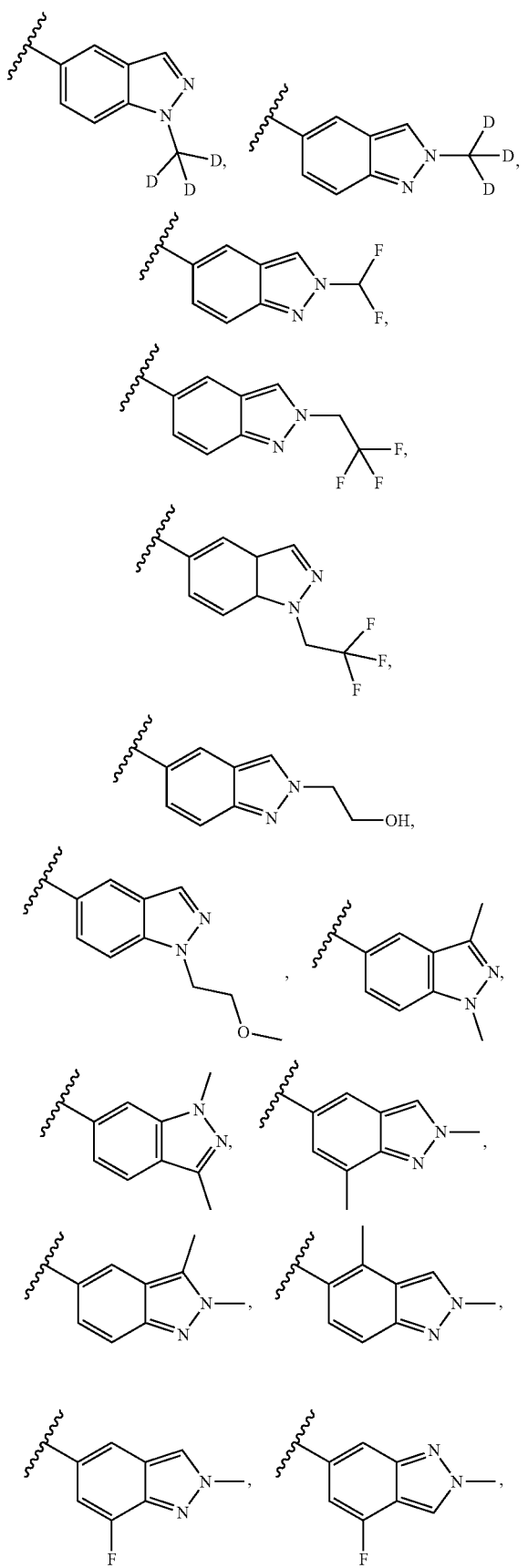
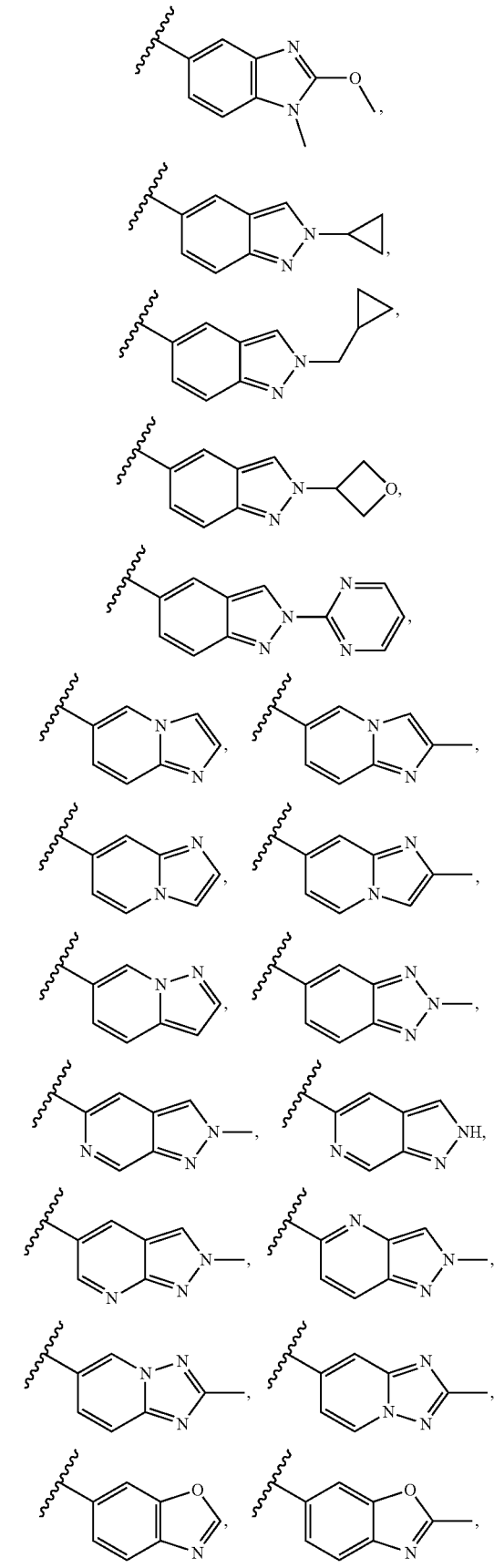

127
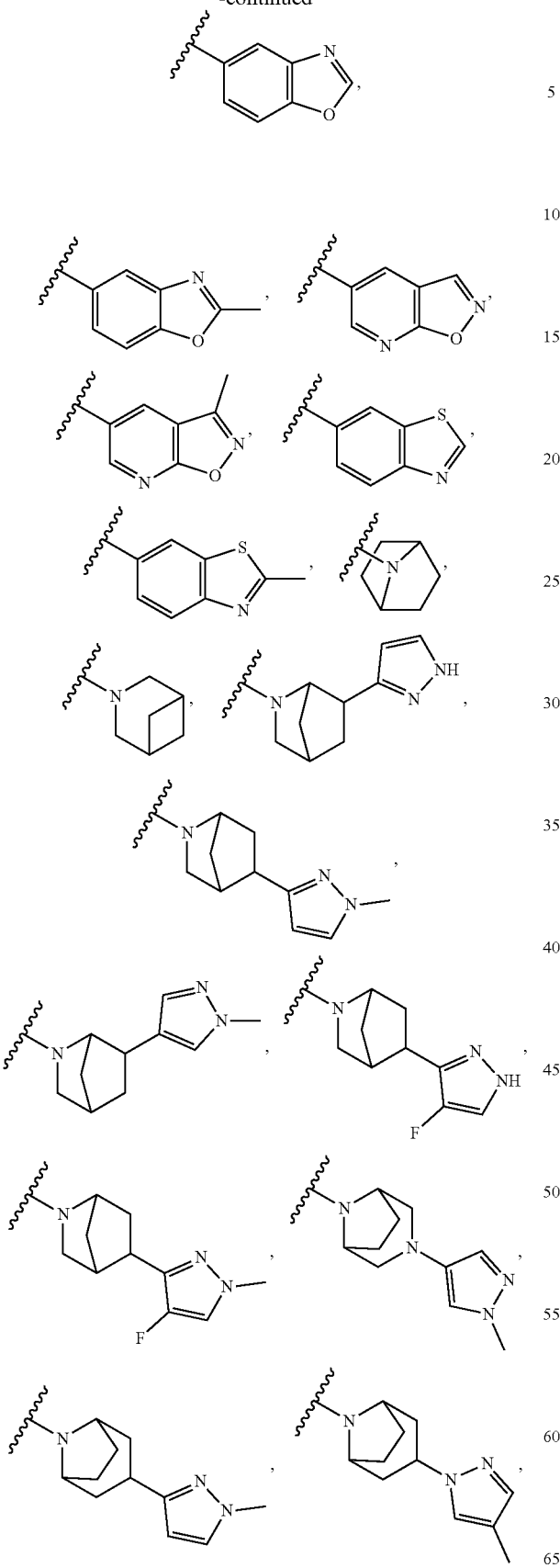
128
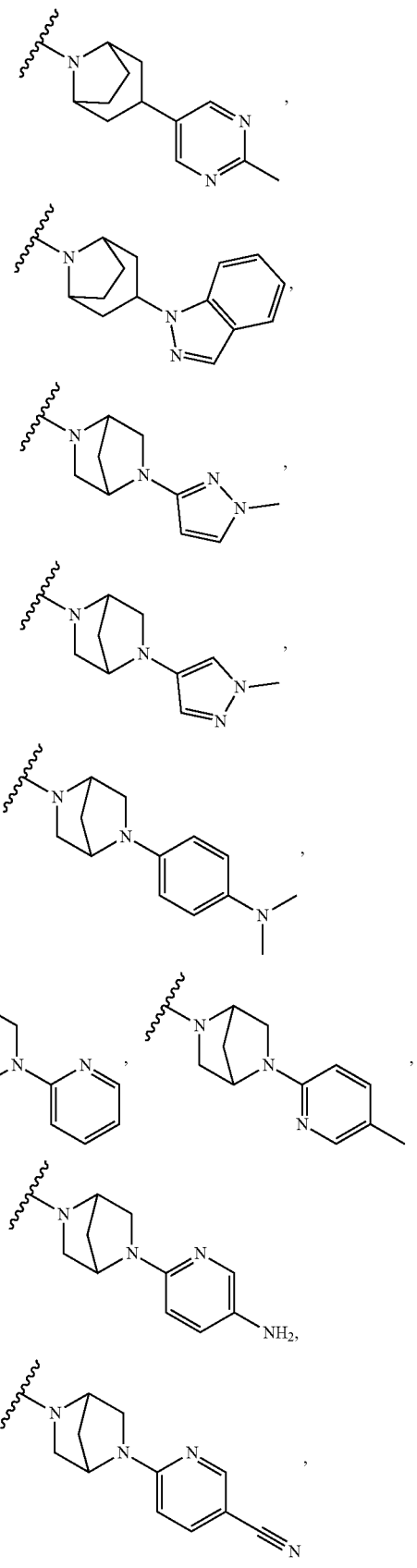

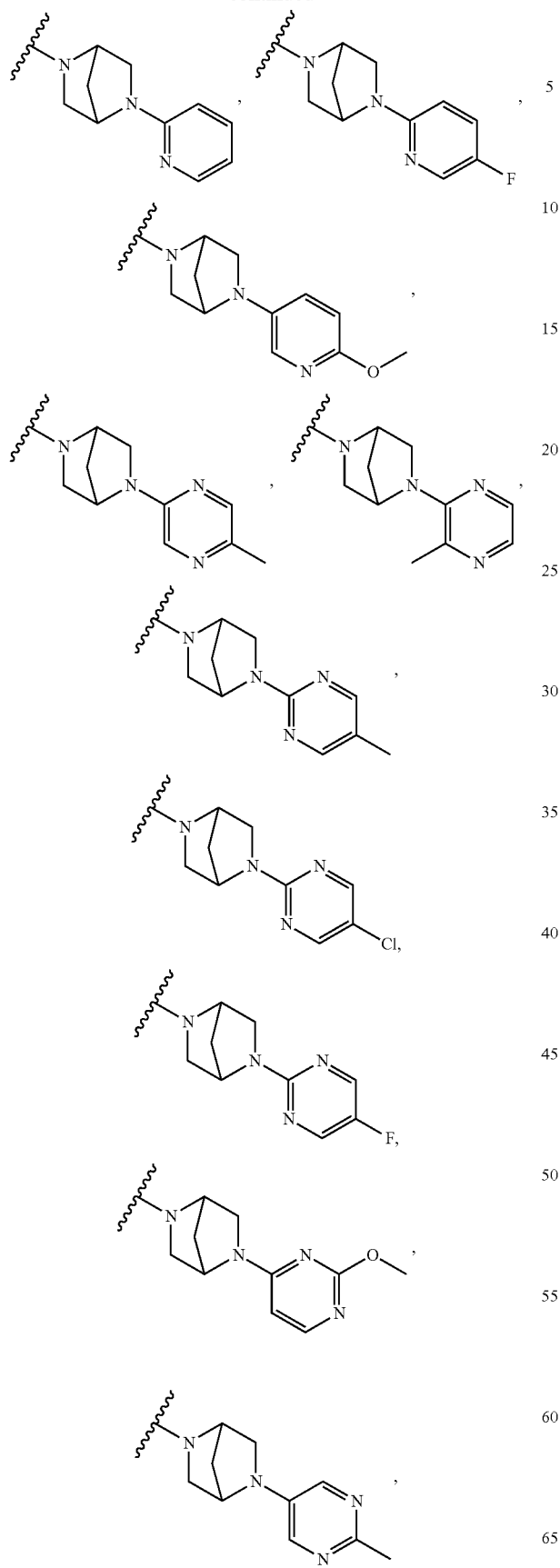
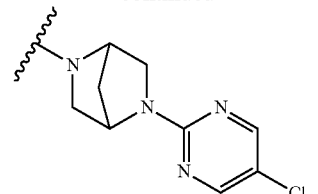
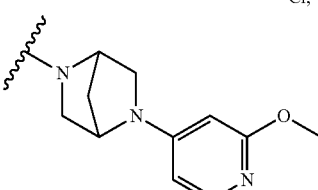
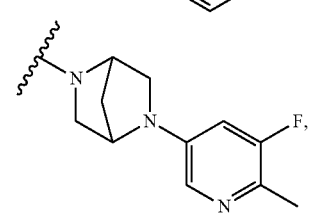
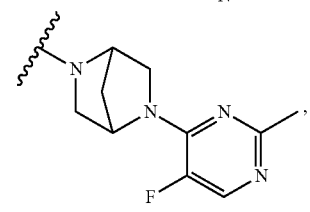
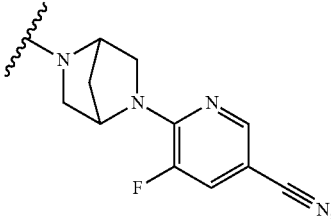
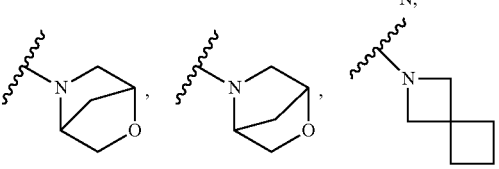
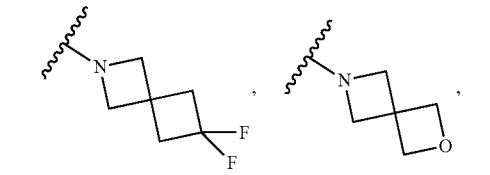
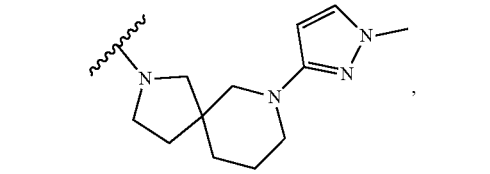
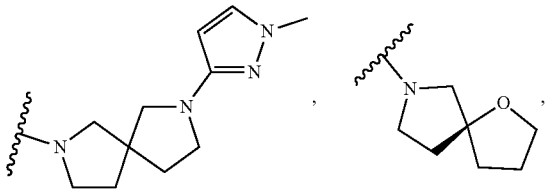

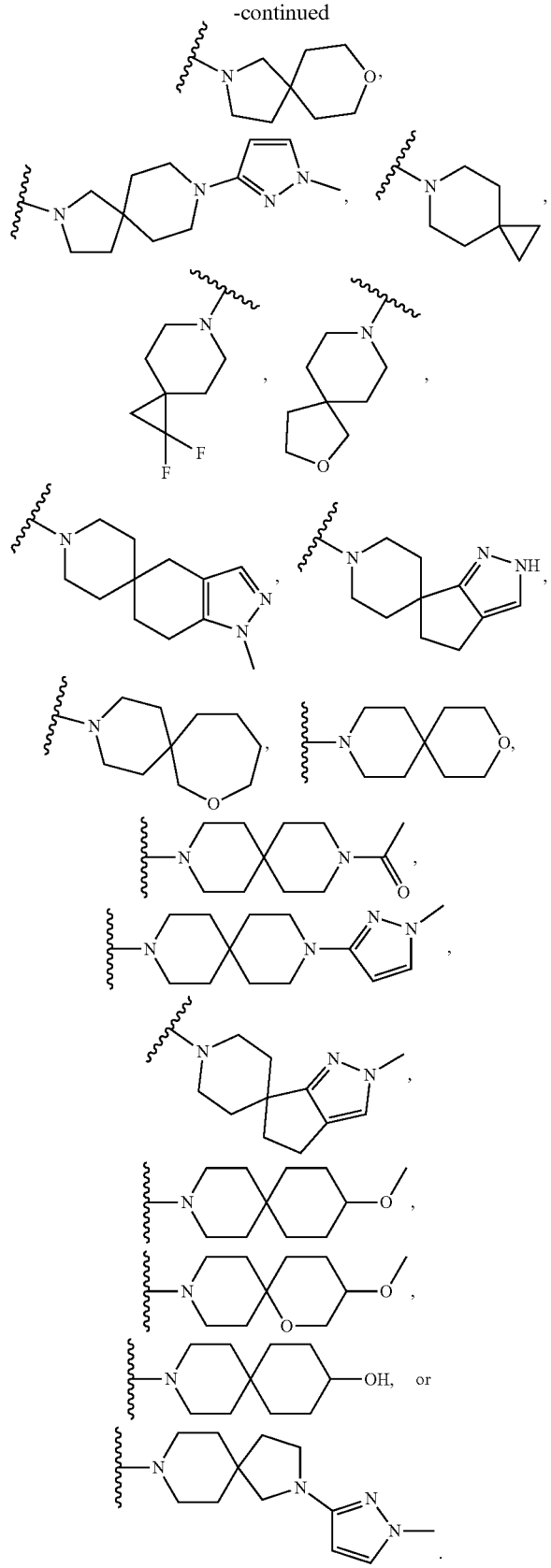

In some embodiments, $R^8$ is hydrogen, halo, —$OR^{11a}$, —$NR^{11a}R^{11b}$, $C_3$-$C_6$ cycloalkyl, $C_1$-$C_3$ haloalkyl, or absent.

In some embodiments, $R^8$ in Formula (IA)-(IB) is, each independently, —H, halo, —$OR^1a$, —$NR^{11a}R^{11b}$, $C_3$-$C_6$ cycloalkyl, 4-6 membered heterocyclyl, heteroaryl, or $C_1$-$C_3$ haloalkyl. In some certain embodiments, $R^8$ in Formula (IA)-(IB) is, each independently, —H, —F, —$N(CH_3)_2$, —$NHCH_3$, —$OCH_3$, $C_3$-cycloalkyl, 4-6 membered heterocyclyl, heteroaryl, —$CF_2H$, or —$CF_3$. In some embodiments, the heteroaryl or $R^8$ in Formula (IA)-(IB) is further substituted with $C_1$-$C_4$ alkyl.

In some embodiments, the $C_1$-$C_3$ alkyl of $R^{11a}$ or $R^{11b}$ is further substituted with a 4-6 membered heterocyclyl. In some other embodiment, the $C_1$-$C_3$ alkyl of $R^{11a}$ or $R^{11b}$ is further substituted with a 5 membered heterocyclyl. For example, the 5 membered heterocyclyl is tetrahydrofuran or pyrrolidine. In some certain embodiments, the $C_1$-$C_3$ alkyl of $R^{11a}$ or $R^{11b}$ substituted with a 5 membered heterocyclyl is

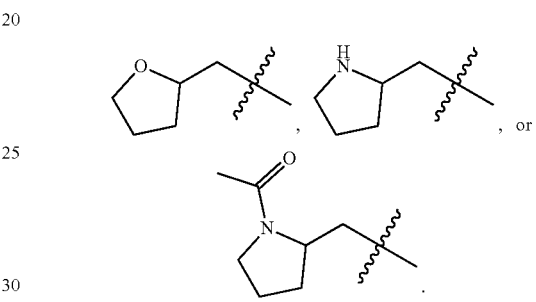

In some embodiments, X is $CR^7$ and $R^7$ is H.

In some embodiments, the compound has the following structure of Formula (II):

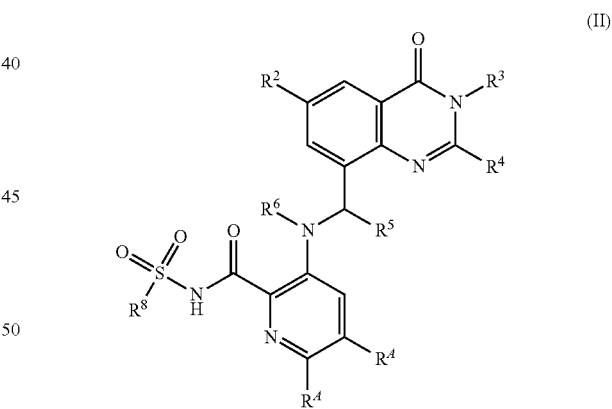

or a stereoisomer of the compound, tautomer of the compound, or a salt thereof, wherein: $R^2$ is $C_1$-$C_3$ alkyl; $R^3$ is $C_1$-$C_3$ alkyl; $R^5$ and $R^6$ are, each independently, hydrogen or $C_1$-$C_3$ alkyl; $R^4$ is 3-12 membered heterocyclyl or 5-10 membered heteroaryl, wherein the 3-12 membered heterocyclyl or 5-10 membered heteroaryl is optionally substituted with $C_1$-$C_6$ alkyl, $C_1$-$C_6$ haloalkyl, or 5-10 membered heteroaryl optionally substituted with 1, 2, 3, or 4 substituents each independently selected from the group consisting of $C_1$-$C_6$ alkyl, $C_1$-$C_6$ haloalkyl, $C_1$-$C_6$ alkoxy, halo, —CN, and $C_3$-$C_7$ cycloalkyl; $R^8$ is $C_1$-$C_4$ alkyl; and each R A is independently hydrogen or halo.

In some embodiments, $R^2$ is —CH$_3$.
In some embodiments, $R^3$ is —CH$_3$.
In some embodiments, $R^5$ is —CH$_3$, and $R^6$ is hydrogen.
In some embodiments, $R^8$ is —CH$_3$.
In some embodiments, each $R^A$ is independently hydrogen or chloro.
In some embodiments, $R^4$ is 6-9 membered heterocyclyl substituted with 5-9 membered heteroaryl or $C_1$-$C_3$ haloalkyl, wherein the 5-9 membered heteroaryl is optionally substituted with 1 or 2 substituents each independently selected from the group consisting of $C_1$-$C_3$ alkyl, $C_1$-$C_3$ haloalkyl, $C_1$-$C_3$ alkoxy, halo, —CN, and $C_3$-$C_6$ cycloalkyl. In some embodiments, the 6-9 membered heterocyclyl is piperazinyl, piperidine, 8-azabicyclo[3.2.1]octanyl, 2,5-diazabicyclo[2.2.1]heptanyl, 3-azabicyclo[3.1.0]hexanyl, 2,4,5,6-tetrahydropyrrolo[3,4-c]pyrazolyl, or 4,5,6,7-tetrahydro-2H-pyrazolo[4,3-c]pyridinyl. In some embodiments, the 6-9 membered heterocyclyl has one of the following structures:

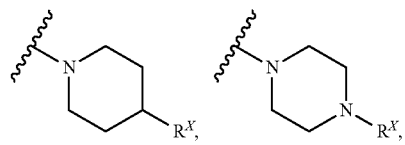

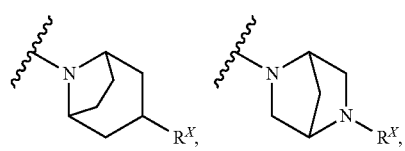

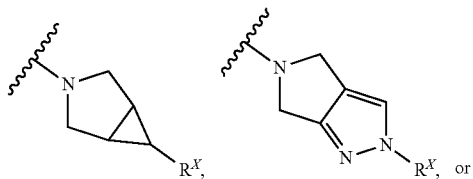

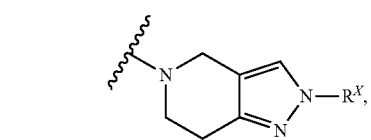

wherein $R^X$ is the $C_1$-$C_6$ alkyl, $C_1$-$C_6$ haloalkyl, or 5-10 membered heteroaryl. In some embodiments, the 5-9 membered heteroaryl is pyrazolyl, pyridinyl, pyrimidinyl, pyrazinyl, pyrazolo[1,5-a]pyridinyl, or pyrazolo[1,5-b]pyridazinyl. In some embodiments, the 5-9 membered heterocyclyl has one of the following structures:

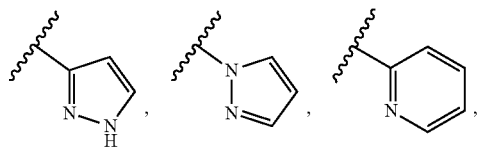

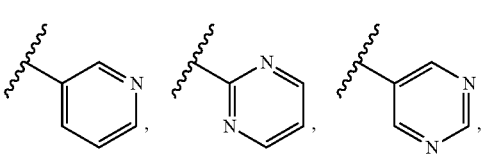

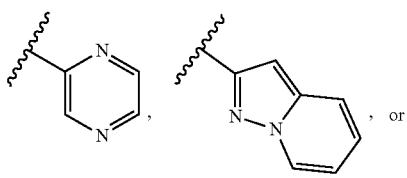

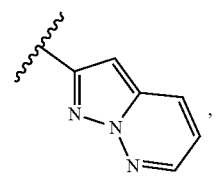

each optionally substituted with 1 or 2 substituents each independently selected from the group consisting of —CH$_3$, —CHF$_2$, —CH$_2$CF$_3$, —OCH$_3$, —F, —CN, and cyclopropyl.

In some embodiments, $R^4$ is 9 membered fused bicyclic heteroaryl substituted with $C_1$-$C_3$haloalkyl. In some embodiments, $R^4$ is benzo[d]oxazolyl or indazolyl. In some embodiments, $R^4$ has one of the following structures:

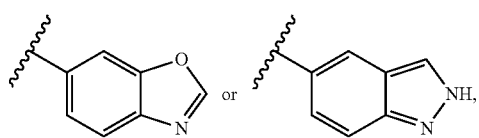 [SMILES: *c1ccc2ncoc2c1 ; *c1ccc2n[nH]cc2c1]

each optionally substituted with $C_1$-$C_3$ haloalkyl.

In one embodiment, the compound has one of the following structures shown in Table 1 below.

TABLE 1
List of Compounds
| Cpd. ID | Chemical structure |
|---|---|
| 1 | 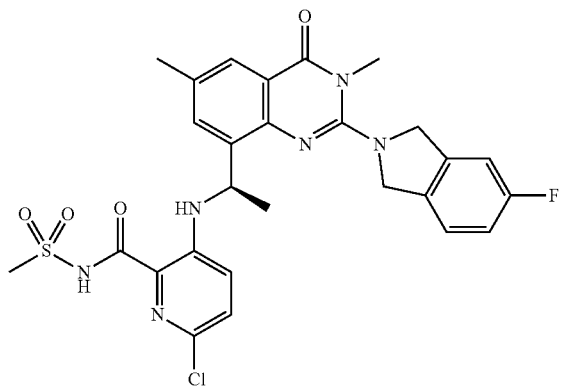 |
| 2 | 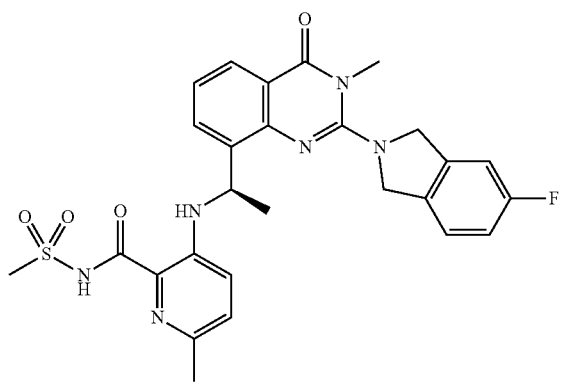 [SMILES: Cc1ccc(N[C@H](C)c2cccc3c(=O)n(C)c(N4Cc5ccc(F)cc5C4)nc23)c(C(=O)NS(C)(=O)=O)n1] |
| 3 | 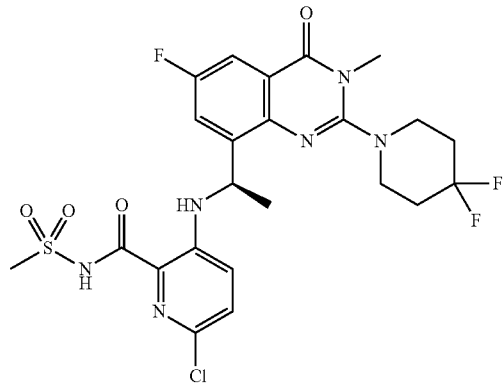 |
| 4 | 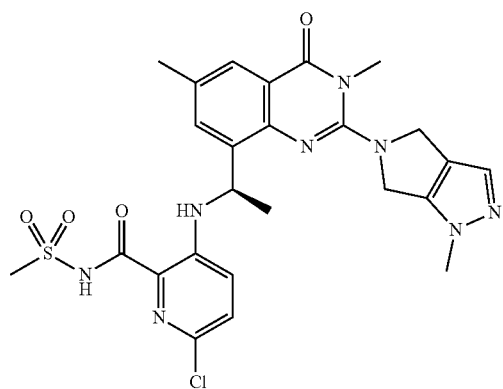 [SMILES: Cc1cc([C@@H](C)Nc2ccc(Cl)nc2C(=O)NS(C)(=O)=O)c2nc(N3Cc4cnn(C)c4C3)n(C)c(=O)c2c1] |

TABLE 1-continued
List of Compounds
| Cpd. ID | Chemical structure |
|---|---|
| 5 | 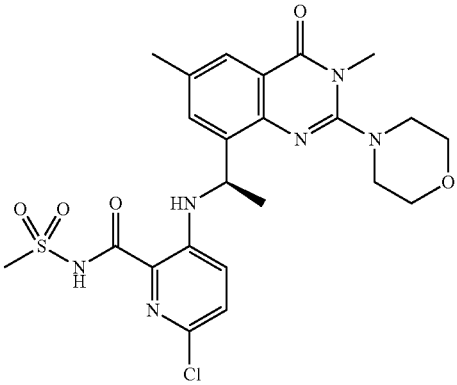 [SMILES: Cc1cc([C@@H](C)Nc2ccc(Cl)nc2C(=O)NS(C)(=O)=O)c2nc(N3CCOCC3)n(C)c(=O)c2c1] |
| 6 | 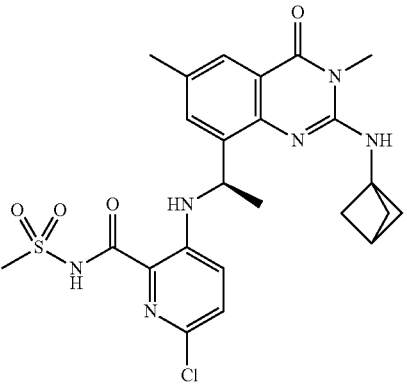 [SMILES: Cc1cc([C@@H](C)Nc2ccc(Cl)nc2C(=O)NS(C)(=O)=O)c2nc(NC34CC(C3)C4)n(C)c(=O)c2c1] |
| 7 | 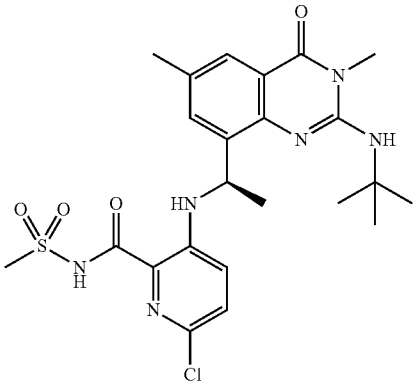 [SMILES: Cc1cc([C@@H](C)Nc2ccc(Cl)nc2C(=O)NS(C)(=O)=O)c2nc(NC(C)(C)C)n(C)c(=O)c2c1] |
| 8 | 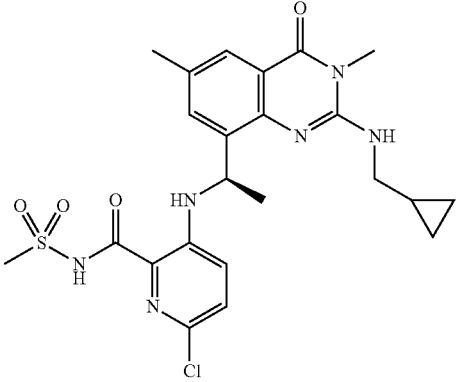 [SMILES: Cc1cc([C@@H](C)Nc2ccc(Cl)nc2C(=O)NS(C)(=O)=O)c2nc(NCC3CC3)n(C)c(=O)c2c1] |

TABLE 1-continued
List of Compounds
| Cpd. ID | Chemical structure |
|---|---|
| 9 | 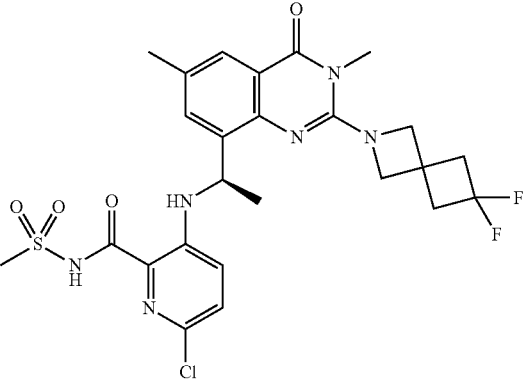 [SMILES: Cc1cc([C@@H](C)Nc2ccc(Cl)nc2C(=O)NS(C)(=O)=O)c2nc(N3CC4(C3)CC(F)(F)C4)n(C)c(=O)c2c1] |
| 10 | 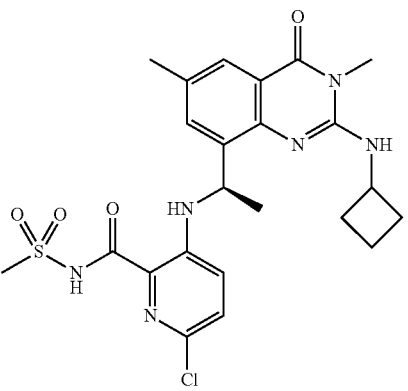 [SMILES: Cc1cc([C@@H](C)Nc2ccc(Cl)nc2C(=O)NS(C)(=O)=O)c2nc(NC3CCC3)n(C)c(=O)c2c1] |
| 11 | 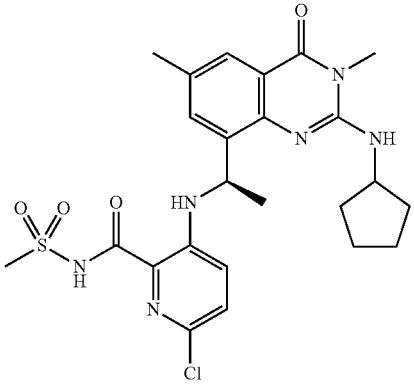 [SMILES: Cc1cc([C@@H](C)Nc2ccc(Cl)nc2C(=O)NS(C)(=O)=O)c2nc(NC3CCCC3)n(C)c(=O)c2c1] |
| 12 | 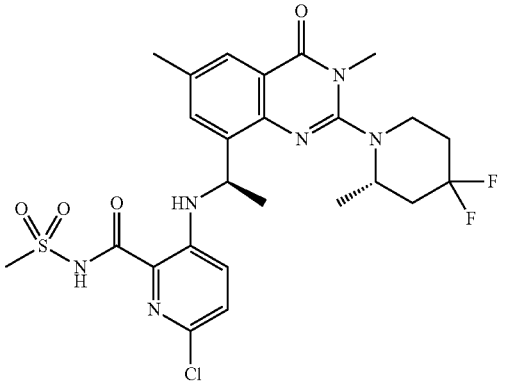 [SMILES: Cc1cc([C@@H](C)Nc2ccc(Cl)nc2C(=O)NS(C)(=O)=O)c2nc(N3CCC(F)(F)C[C@@H]3C)n(C)c(=O)c2c1] |

TABLE 1-continued

List of Compounds

| Cpd. ID | Chemical structure |
|---|---|
| 13 | 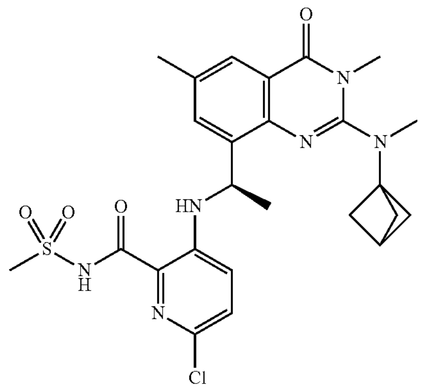 |
| 14 | 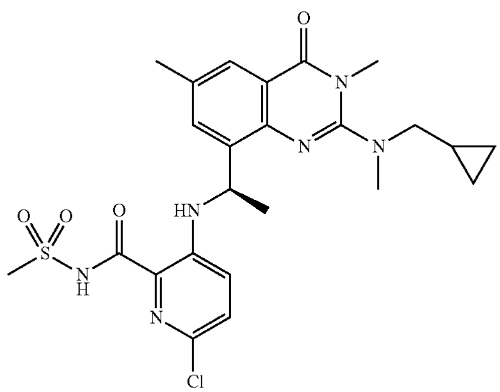 [SMILES: Cc1cc([C@@H](C)Nc2ccc(Cl)nc2C(=O)NS(C)(=O)=O)c2nc(N(C)CC3CC3)n(C)c(=O)c2c1] |
| 15 | 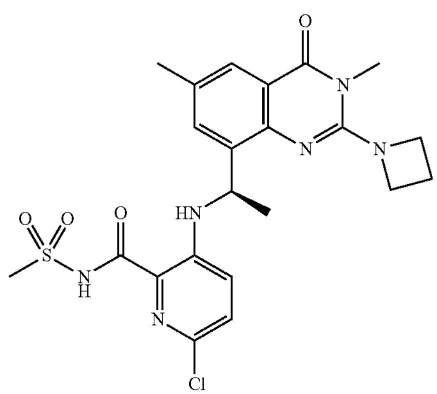 [SMILES: Cc1cc([C@@H](C)Nc2ccc(Cl)nc2C(=O)NS(C)(=O)=O)c2nc(N3CCC3)n(C)c(=O)c2c1] |
| 16 | 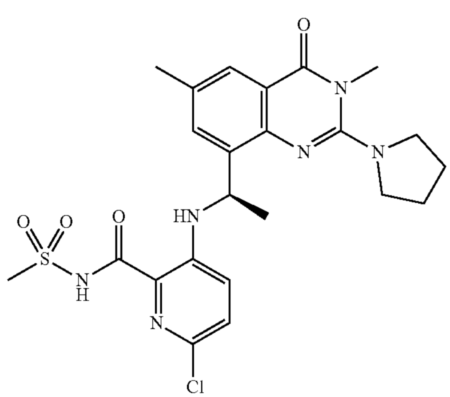 [SMILES: Cc1cc([C@@H](C)Nc2ccc(Cl)nc2C(=O)NS(C)(=O)=O)c2nc(N3CCCC3)n(C)c(=O)c2c1] |

TABLE 1-continued
List of Compounds
| Cpd. ID | Chemical structure |
|---|---|
| 17 | 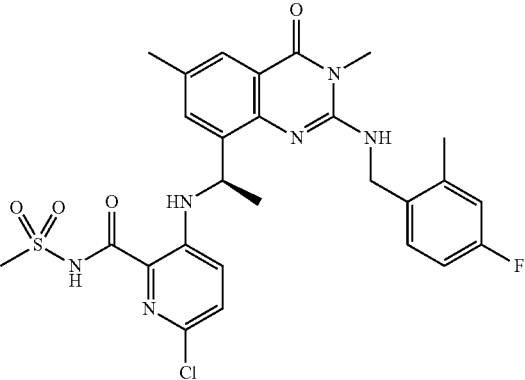 [SMILES: Cc1cc([C@@H](C)Nc2ccc(Cl)nc2C(=O)NS(C)(=O)=O)c2nc(NCc3ccc(F)cc3C)n(C)c(=O)c2c1] |
| 18 | 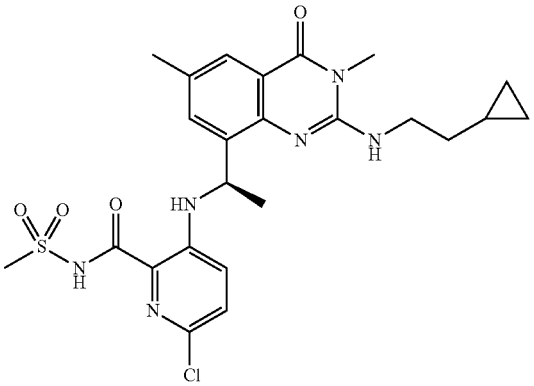 [SMILES: Cc1cc([C@@H](C)Nc2ccc(Cl)nc2C(=O)NS(C)(=O)=O)c2nc(NCCC3CC3)n(C)c(=O)c2c1] |
| 19 | 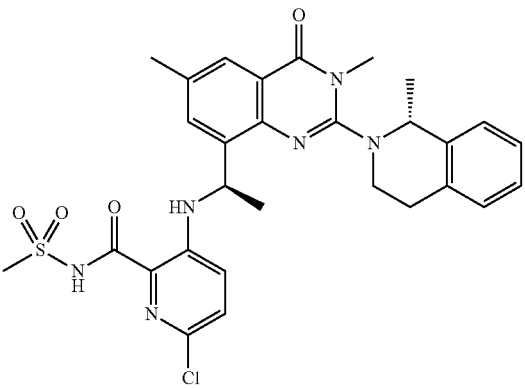 [SMILES: Cc1cc([C@@H](C)Nc2ccc(Cl)nc2C(=O)NS(C)(=O)=O)c2nc(N3CCc4ccccc4[C@H]3C)n(C)c(=O)c2c1] |
| 20 | 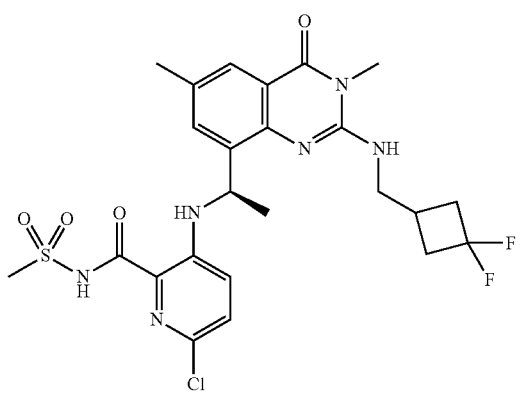 [SMILES: Cc1cc([C@@H](C)Nc2ccc(Cl)nc2C(=O)NS(C)(=O)=O)c2nc(NCC3CC(F)(F)C3)n(C)c(=O)c2c1] |

TABLE 1-continued

| Cpd. ID | Chemical structure |
|---|---|
| 21 | 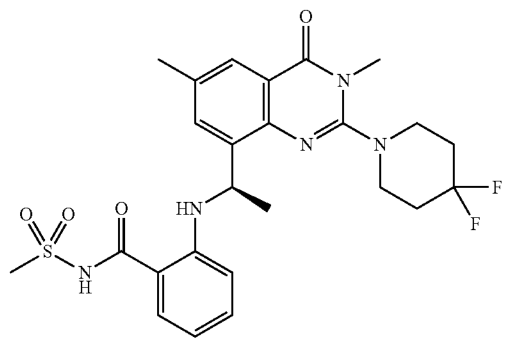 [SMILES: Cc1cc([C@@H](C)Nc2ccccc2C(=O)NS(C)(=O)=O)c2nc(N3CCC(F)(F)CC3)n(C)c(=O)c2c1] |
| 22 | 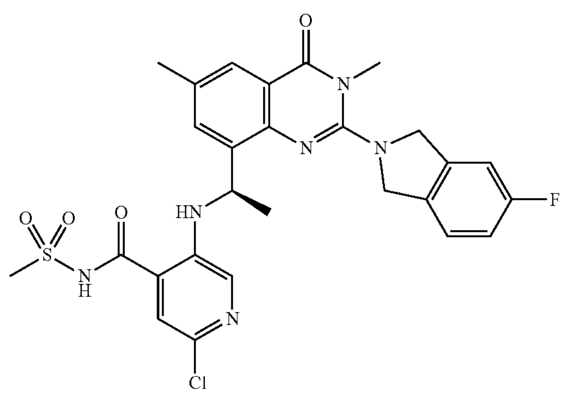 [SMILES: Cc1cc([C@@H](C)Nc2cnc(Cl)cc2C(=O)NS(C)(=O)=O)c2nc(N3Cc4ccc(F)cc4C3)n(C)c(=O)c2c1] |
| 23 | 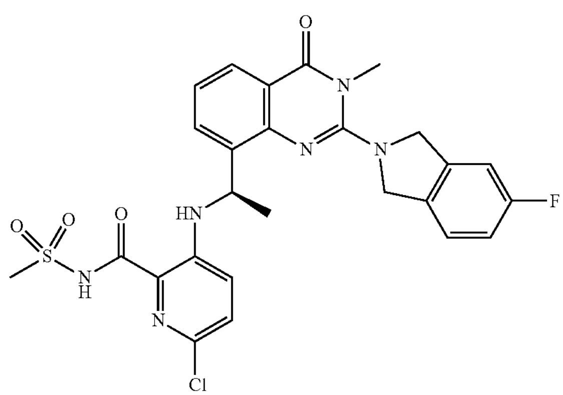 [SMILES: C[C@@H](Nc1ccc(Cl)nc1C(=O)NS(C)(=O)=O)c1cccc2c(=O)n(C)c(N3Cc4ccc(F)cc4C3)nc12] |
| 24 | 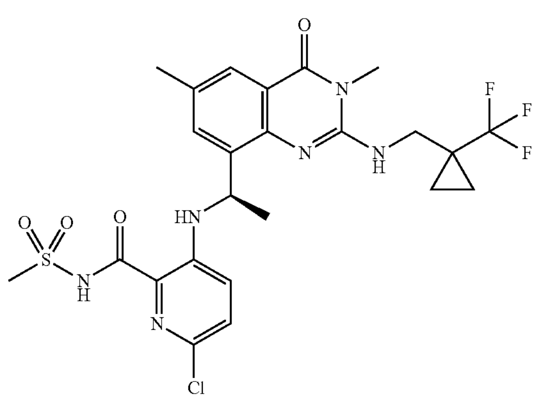 [SMILES: Cc1cc([C@@H](C)Nc2ccc(Cl)nc2C(=O)NS(C)(=O)=O)c2nc(NCC3(C(F)(F)F)CC3)n(C)c(=O)c2c1] |

TABLE 1-continued
List of Compounds
| Cpd. ID | Chemical structure |
|---|---|
| 25 | 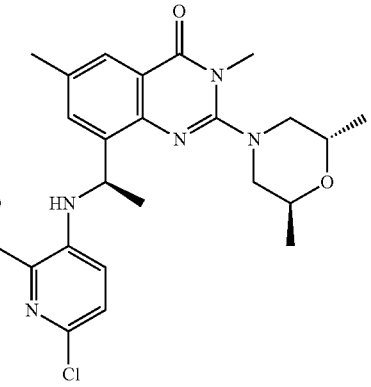 |
| 26 | 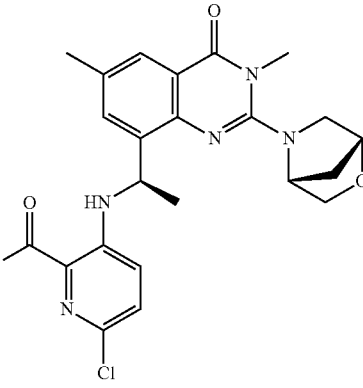 |
| 27 | 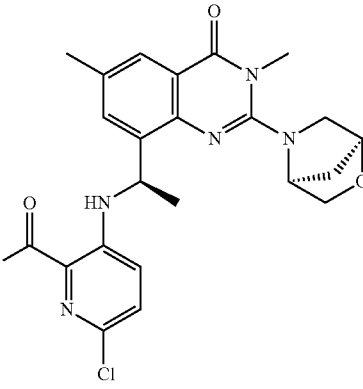 |
| 28 | 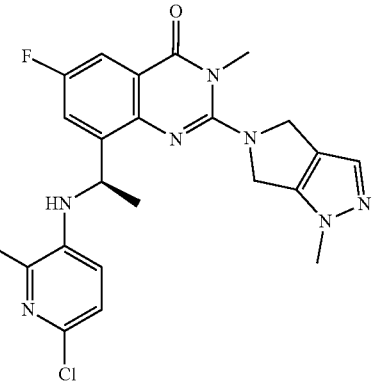 |

TABLE 1-continued
List of Compounds
| Cpd. ID | Chemical structure |
|---|---|
| 29 | 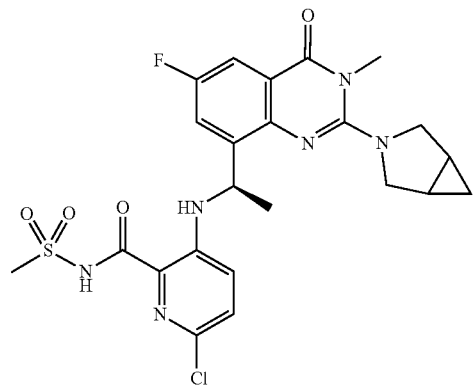 [SMILES: C[C@@H](Nc1ccc(Cl)nc1C(=O)NS(C)(=O)=O)c1cc(F)cc2c(=O)n(C)c(N3CC4CC4C3)nc12] |
| 30 | 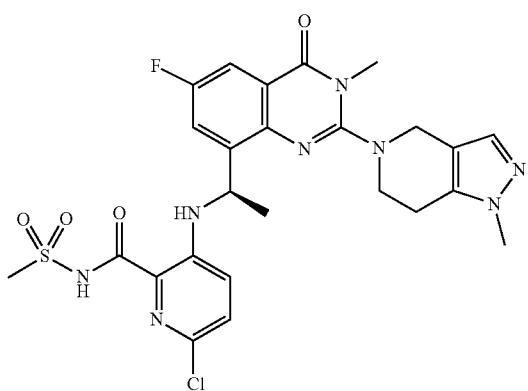 [SMILES: C[C@@H](Nc1ccc(Cl)nc1C(=O)NS(C)(=O)=O)c1cc(F)cc2c(=O)n(C)c(N3CCc4c(cnn4C)C3)nc12] |
| 31 | 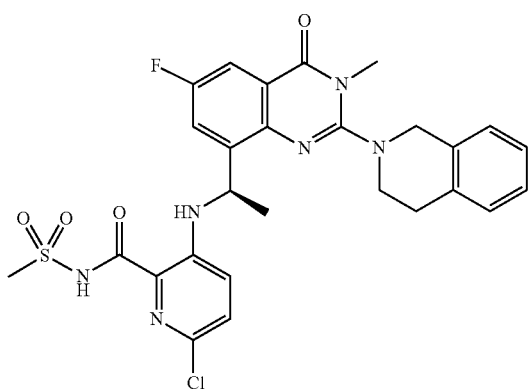 [SMILES: C[C@@H](Nc1ccc(Cl)nc1C(=O)NS(C)(=O)=O)c1cc(F)cc2c(=O)n(C)c(N3CCc4ccccc4C3)nc12] |

TABLE 1-continued

| Cpd. ID | Chemical structure |
|---|---|
| 32 | 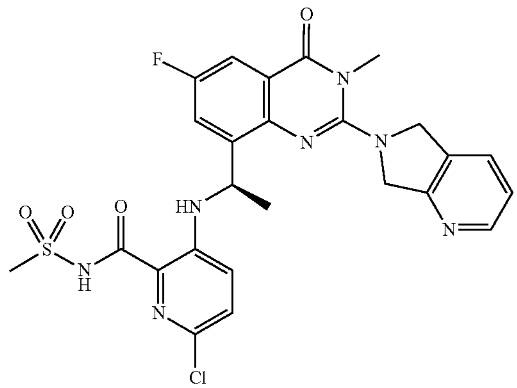 [SMILES: C[C@@H](Nc1ccc(Cl)nc1C(=O)NS(C)(=O)=O)c1cc(F)cc2c(=O)n(C)c(N3Cc4cccnc4C3)nc12] |
| 33 | 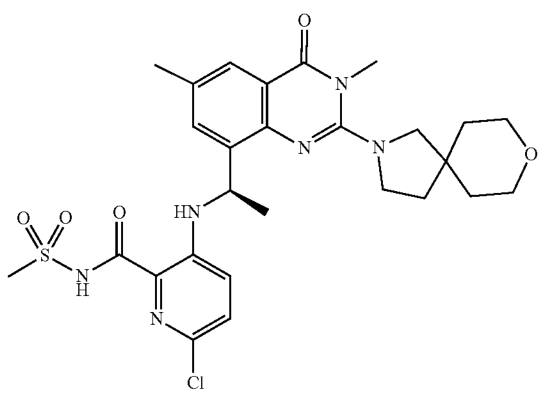 [SMILES: Cc1cc([C@@H](C)Nc2ccc(Cl)nc2C(=O)NS(C)(=O)=O)c2nc(N3CCC4(CCOCC4)C3)n(C)c(=O)c2c1] |
| 34 | 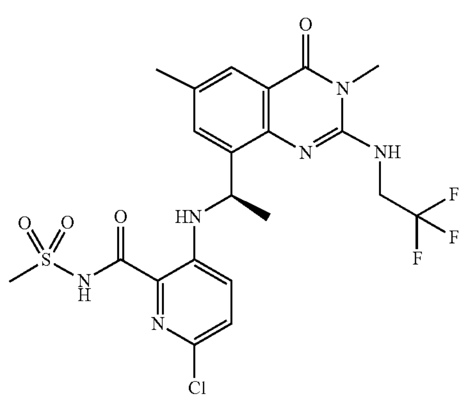 [SMILES: Cc1cc([C@@H](C)Nc2ccc(Cl)nc2C(=O)NS(C)(=O)=O)c2nc(NCC(F)(F)F)n(C)c(=O)c2c1] |

TABLE 1-continued
| | List of Compounds |
|---|---|
| Cpd. ID | Chemical structure |
| 35 | 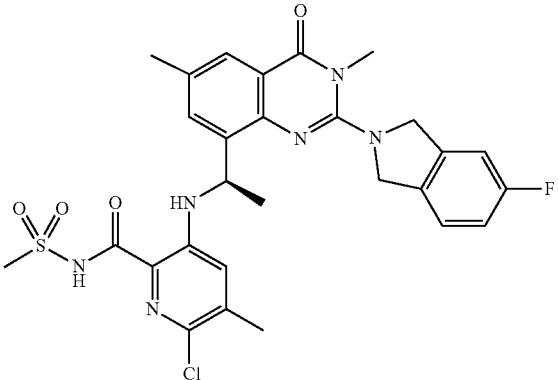 [SMILES: Cc1cc([C@@H](C)Nc2cc(C)c(Cl)nc2C(=O)NS(C)(=O)=O)c2nc(N3Cc4ccc(F)cc4C3)n(C)c(=O)c2c1] |
| 36 | 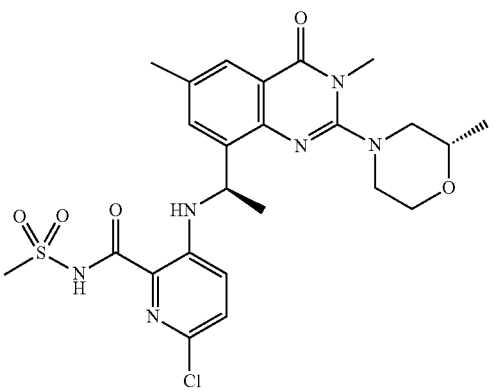 |
| 37 | 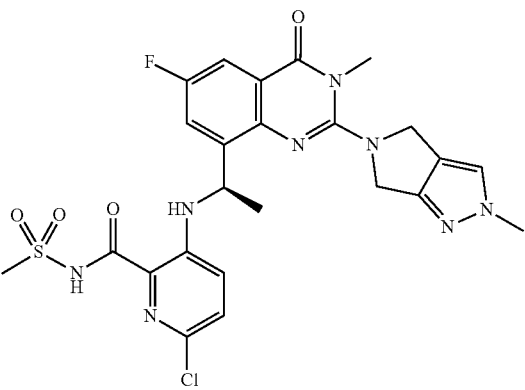 |

TABLE 1-continued
| | List of Compounds |
|---|---|
| Cpd. ID | Chemical structure |
| 38 | 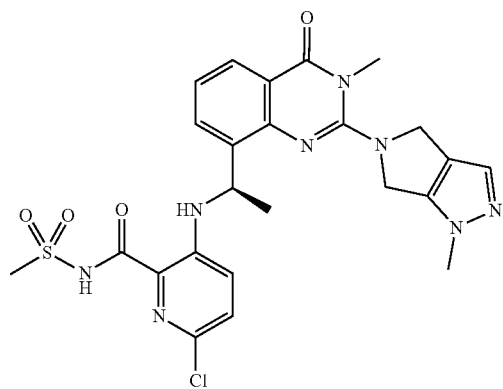 |
| 39 | 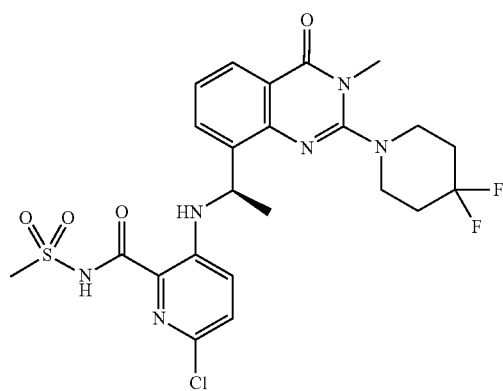 [SMILES: C[C@@H](Nc1ccc(Cl)nc1C(=O)NS(C)(=O)=O)c1cccc2c(=O)n(C)c(N3CCC(F)(F)CC3)nc12] |
| 40 | 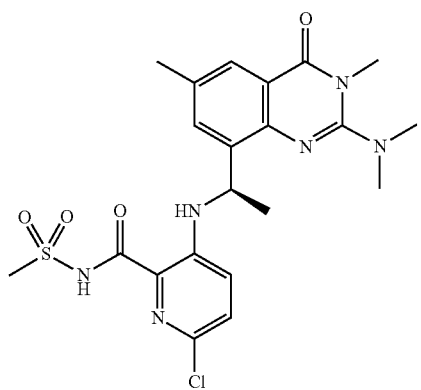 |

TABLE 1-continued

List of Compounds

| Cpd. ID | Chemical structure |
|---|---|
| 41 | 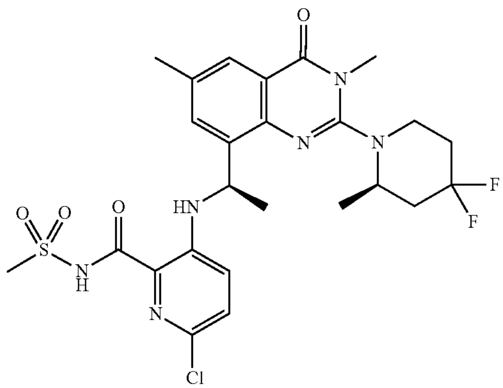 [SMILES: Cc1cc([C@@H](C)Nc2ccc(Cl)nc2C(=O)NS(C)(=O)=O)c2nc(N3CCC(F)(F)C[C@H]3C)n(C)c(=O)c2c1] |
| 42 | 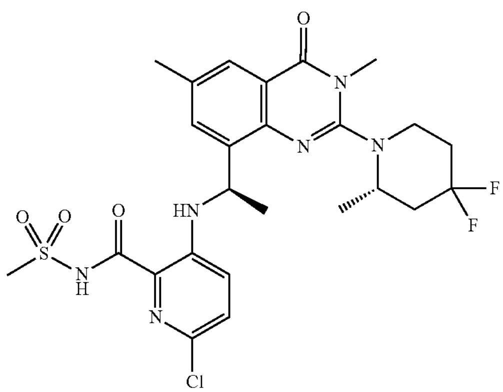 [SMILES: Cc1cc([C@@H](C)Nc2ccc(Cl)nc2C(=O)NS(C)(=O)=O)c2nc(N3CCC(F)(F)C[C@@H]3C)n(C)c(=O)c2c1] |
| 43 | 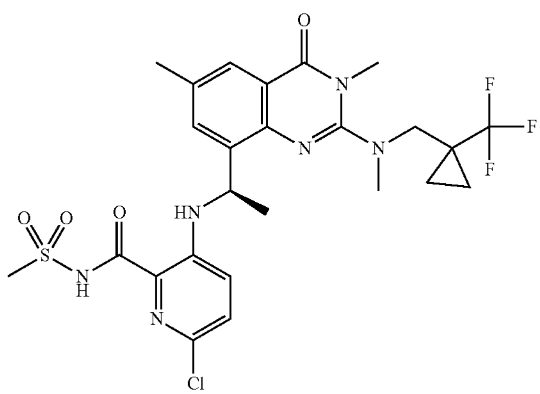 [SMILES: Cc1cc([C@@H](C)Nc2ccc(Cl)nc2C(=O)NS(C)(=O)=O)c2nc(N(C)CC3(C(F)(F)F)CC3)n(C)c(=O)c2c1] |
| 44 | 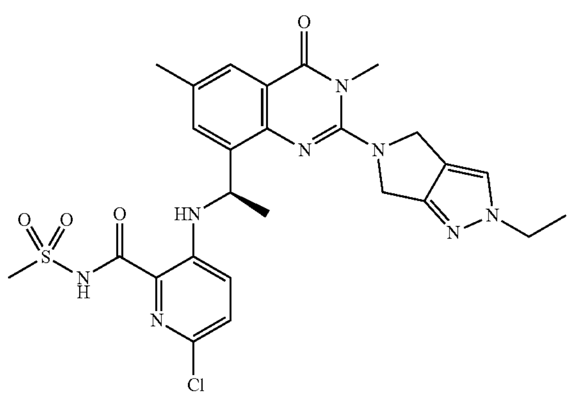 [SMILES: CCn1cc2c(n1)CN(c1nc3c([C@@H](C)Nc4ccc(Cl)nc4C(=O)NS(C)(=O)=O)cc(C)cc3c(=O)n1C)C2] |

TABLE 1-continued

List of Compounds

| Cpd. ID | Chemical structure |
|---------|--------------------|
| 45 | 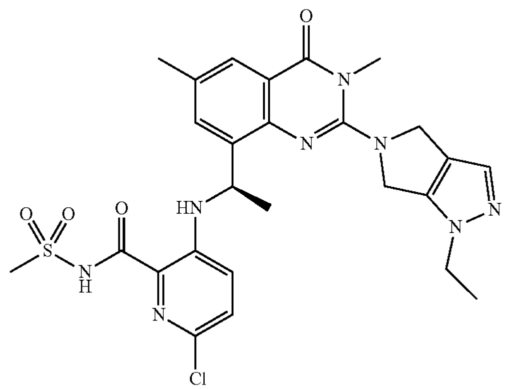 [SMILES: CCn1ncc2c1CN(c1nc3c([C@@H](C)Nc4ccc(Cl)nc4C(=O)NS(C)(=O)=O)cc(C)cc3c(=O)n1C)C2] |
| 46 | 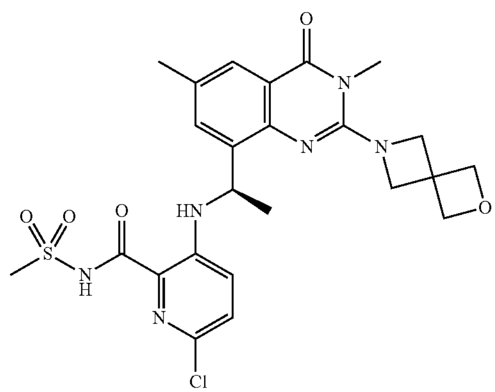 [SMILES: Cc1cc([C@@H](C)Nc2ccc(Cl)nc2C(=O)NS(C)(=O)=O)c2nc(N3CC4(COC4)C3)n(C)c(=O)c2c1] |
| 47 | 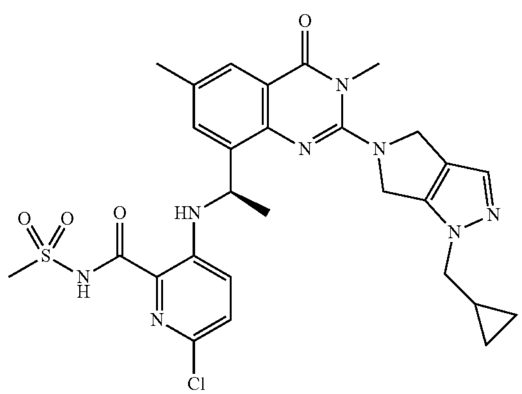 [SMILES: Cc1cc([C@@H](C)Nc2ccc(Cl)nc2C(=O)NS(C)(=O)=O)c2nc(N3Cc4cnn(CC5CC5)c4C3)n(C)c(=O)c2c1] |
| 48 | 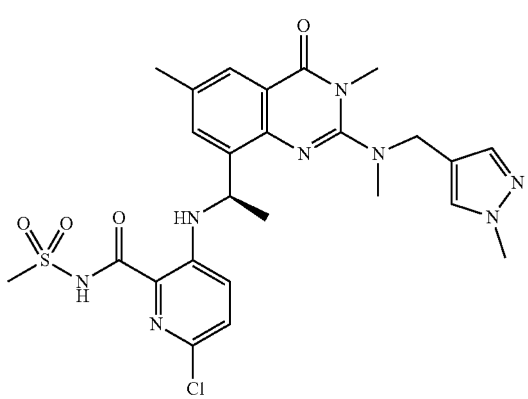 [SMILES: Cc1cc([C@@H](C)Nc2ccc(Cl)nc2C(=O)NS(C)(=O)=O)c2nc(N(C)Cc3cnn(C)c3)n(C)c(=O)c2c1] |

TABLE 1-continued
List of Compounds
| Cpd. ID | Chemical structure |
|---|---|
| 49 | 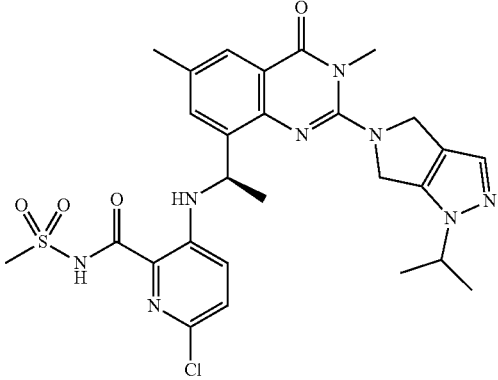 [SMILES: Cc1cc([C@@H](C)Nc2ccc(Cl)nc2C(=O)NS(C)(=O)=O)c2nc(N3Cc4cnn(C(C)C)c4C3)n(C)c(=O)c2c1] |
| 50 | 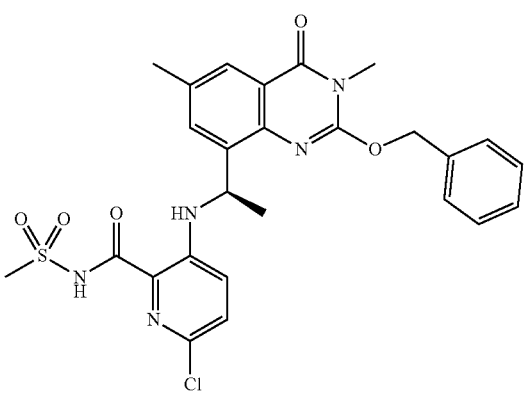 [SMILES: Cc1cc([C@@H](C)Nc2ccc(Cl)nc2C(=O)NS(C)(=O)=O)c2nc(OCc3ccccc3)n(C)c(=O)c2c1] |
| 51 | 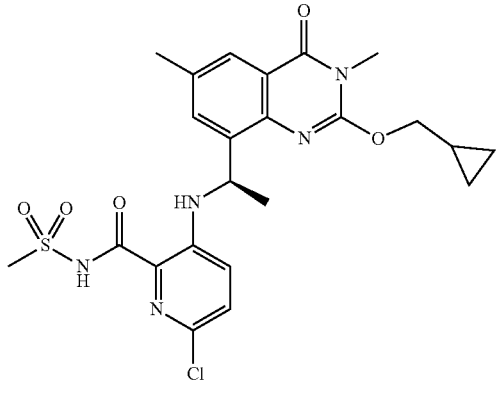 [SMILES: Cc1cc([C@@H](C)Nc2ccc(Cl)nc2C(=O)NS(C)(=O)=O)c2nc(OCC3CC3)n(C)c(=O)c2c1] |
| 52 | 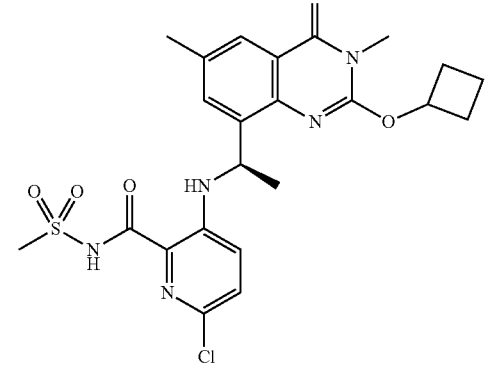 |

TABLE 1-continued

List of Compounds

| Cpd. ID | Chemical structure |
|---|---|
| 53 | 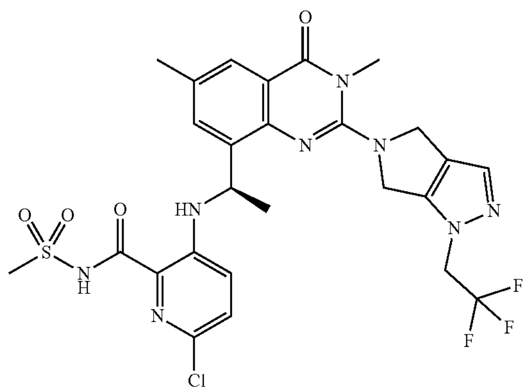 [SMILES: Cc1cc([C@@H](C)Nc2ccc(Cl)nc2C(=O)NS(C)(=O)=O)c2nc(N3Cc4cnn(CC(F)(F)F)c4C3)n(C)c(=O)c2c1] |
| 54 | 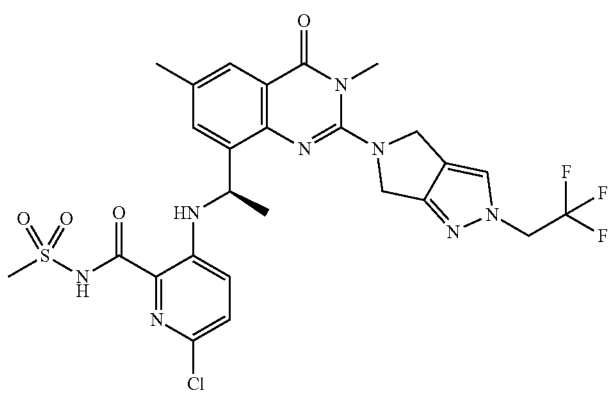 [SMILES: Cc1cc([C@@H](C)Nc2ccc(Cl)nc2C(=O)NS(C)(=O)=O)c2nc(N3Cc4cn(CC(F)(F)F)nc4C3)n(C)c(=O)c2c1] |
| 55 | 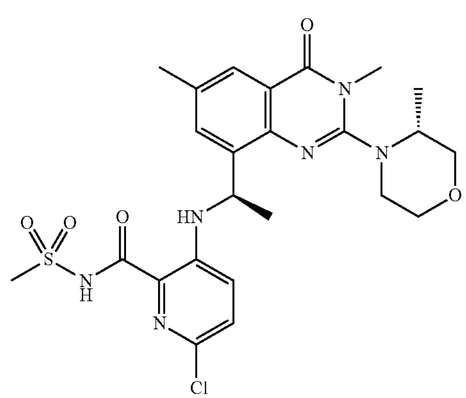 [SMILES: Cc1cc([C@@H](C)Nc2ccc(Cl)nc2C(=O)NS(C)(=O)=O)c2nc(N3CCOC[C@H]3C)n(C)c(=O)c2c1] |
| 56 | 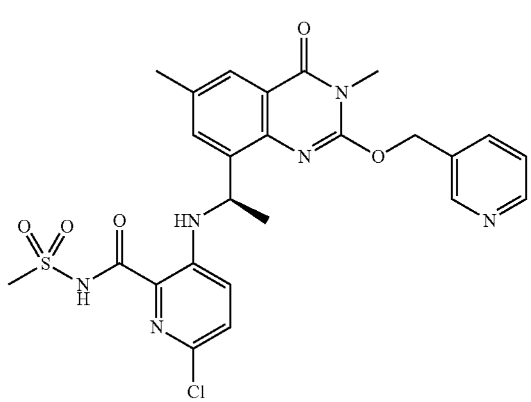 [SMILES: Cc1cc([C@@H](C)Nc2ccc(Cl)nc2C(=O)NS(C)(=O)=O)c2nc(OCc3cccnc3)n(C)c(=O)c2c1] |

TABLE 1-continued
List of Compounds
| Cpd. ID | Chemical structure |
|---|---|
| 57 | 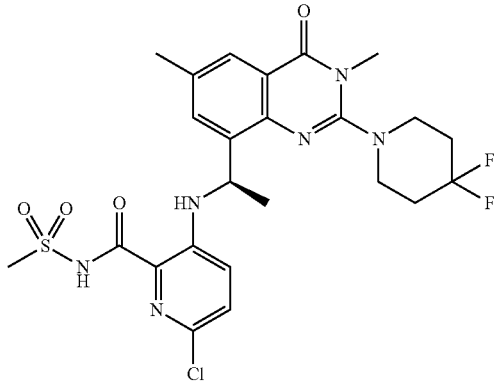 [SMILES: Cc1cc([C@@H](C)Nc2ccc(Cl)nc2C(=O)NS(C)(=O)=O)c2nc(N3CCC(F)(F)CC3)n(C)c(=O)c2c1] |
| 58 | 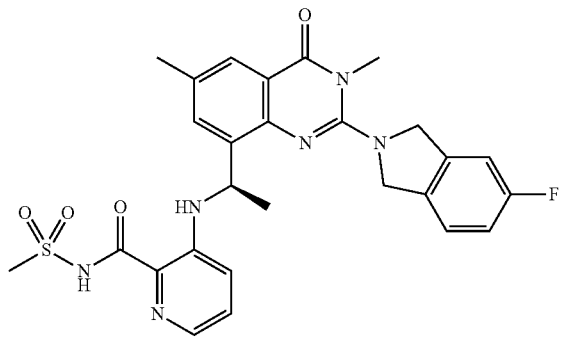 [SMILES: Cc1cc([C@@H](C)Nc2cccnc2C(=O)NS(C)(=O)=O)c2nc(N3Cc4ccc(F)cc4C3)n(C)c(=O)c2c1] |
| 59 | 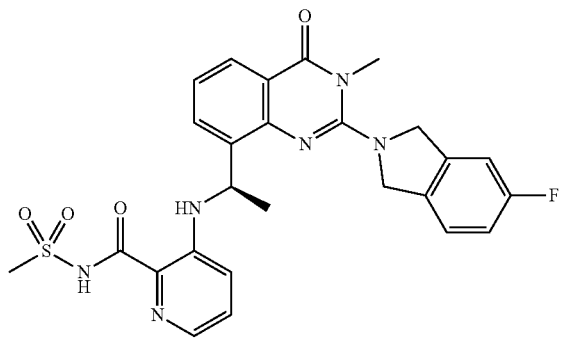 [SMILES: C[C@@H](Nc1cccnc1C(=O)NS(C)(=O)=O)c1cccc2c(=O)n(C)c(N3Cc4ccc(F)cc4C3)nc12] |
| 60 | 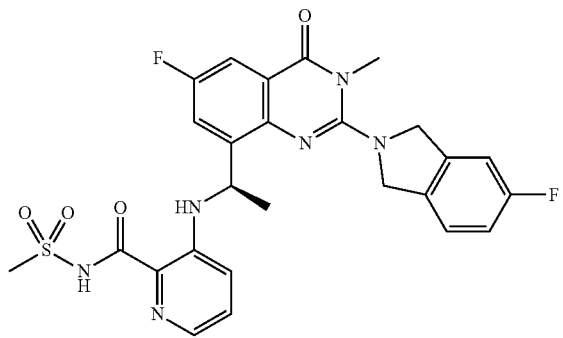 [SMILES: C[C@@H](Nc1cccnc1C(=O)NS(C)(=O)=O)c1cc(F)cc2c(=O)n(C)c(N3Cc4ccc(F)cc4C3)nc12] |

TABLE 1-continued

List of Compounds

| Cpd. ID | Chemical structure |
|---|---|
| 61 | 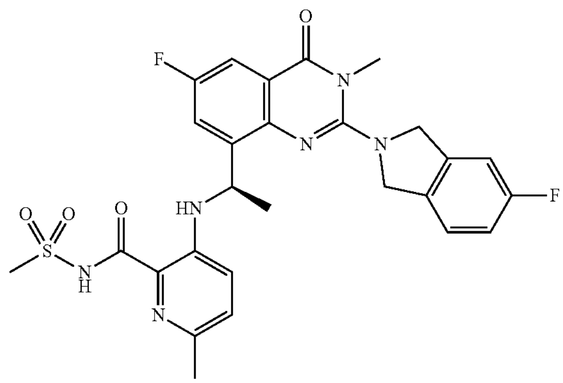 [SMILES: Cc1ccc(N[C@H](C)c2cc(F)cc3c(=O)n(C)c(N4Cc5ccc(F)cc5C4)nc23)c(C(=O)NS(C)(=O)=O)n1] |
| 62 | 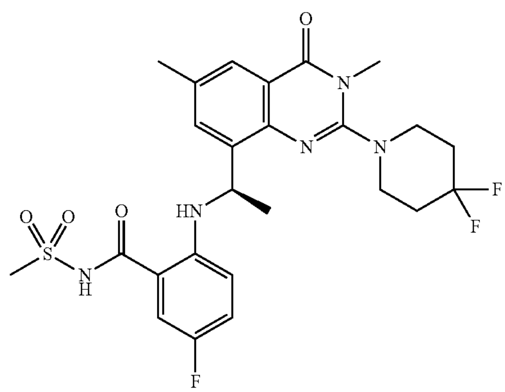 [SMILES: Cc1cc([C@@H](C)Nc2ccc(F)cc2C(=O)NS(C)(=O)=O)c2nc(N3CCC(F)(F)CC3)n(C)c(=O)c2c1] |
| 63 | 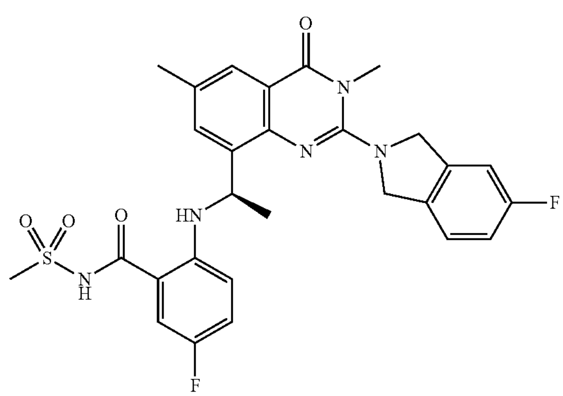 [SMILES: Cc1cc([C@@H](C)Nc2ccc(F)cc2C(=O)NS(C)(=O)=O)c2nc(N3Cc4ccc(F)cc4C3)n(C)c(=O)c2c1] |
| 64 | 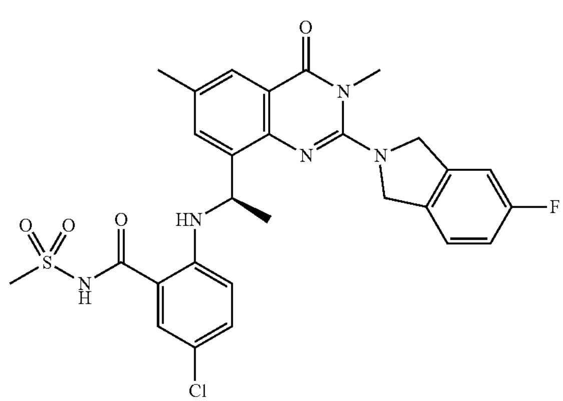 |

TABLE 1-continued

List of Compounds

| Cpd. ID | Chemical structure |
|---------|--------------------|
| 65 | 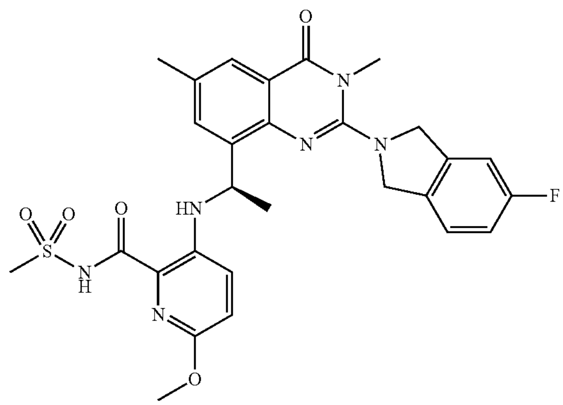 [SMILES: COc1ccc(N[C@H](C)c2cc(C)cc3c(=O)n(C)c(N4Cc5ccc(F)cc5C4)nc23)c(C(=O)NS(C)(=O)=O)n1] |
| 66 | 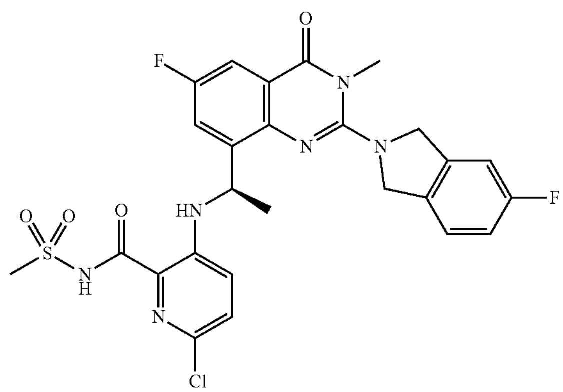 [SMILES: C[C@@H](Nc1ccc(Cl)nc1C(=O)NS(C)(=O)=O)c1cc(F)cc2c(=O)n(C)c(N3Cc4ccc(F)cc4C3)nc12] |
| 67 | 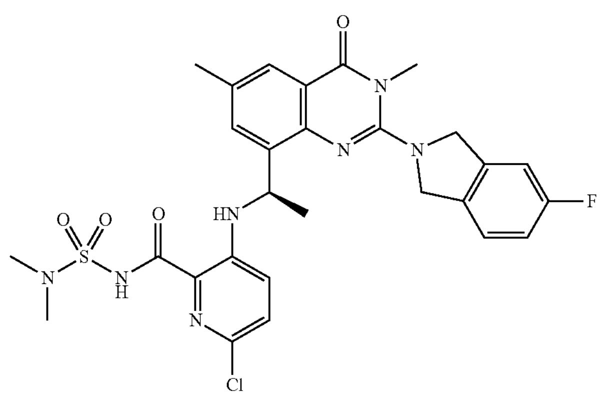 [SMILES: Cc1cc([C@@H](C)Nc2ccc(Cl)nc2C(=O)NS(=O)(=O)N(C)C)c2nc(N3Cc4ccc(F)cc4C3)n(C)c(=O)c2c1] |
| 68 | 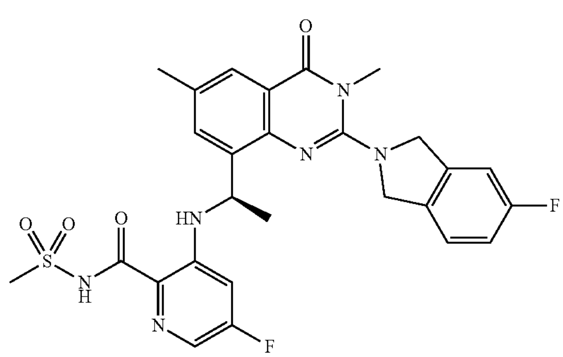 [SMILES: Cc1cc([C@@H](C)Nc2cc(F)cnc2C(=O)NS(C)(=O)=O)c2nc(N3Cc4ccc(F)cc4C3)n(C)c(=O)c2c1] |

TABLE 1-continued

List of Compounds

| Cpd. ID | Chemical structure |
|---|---|
| 69 | 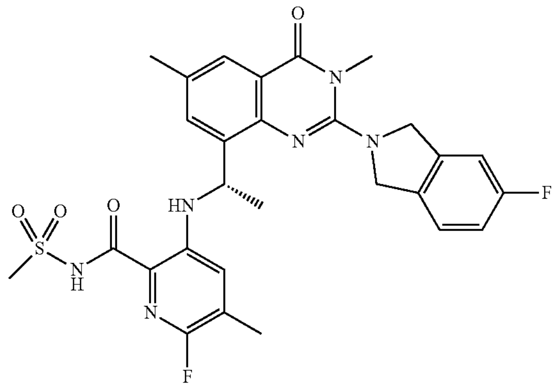 [SMILES: Cc1cc([C@H](C)Nc2cc(C)c(F)nc2C(=O)NS(C)(=O)=O)c2nc(N3Cc4ccc(F)cc4C3)n(C)c(=O)c2c1] |
| 70 | 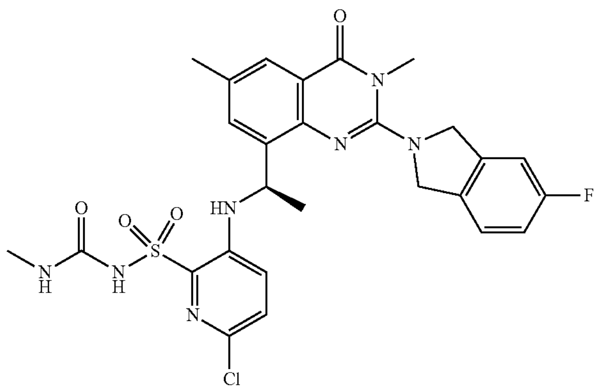 [SMILES: CNC(=O)NS(=O)(=O)c1nc(Cl)ccc1N[C@H](C)c1cc(C)cc2c(=O)n(C)c(N3Cc4ccc(F)cc4C3)nc12] |
| 71 | 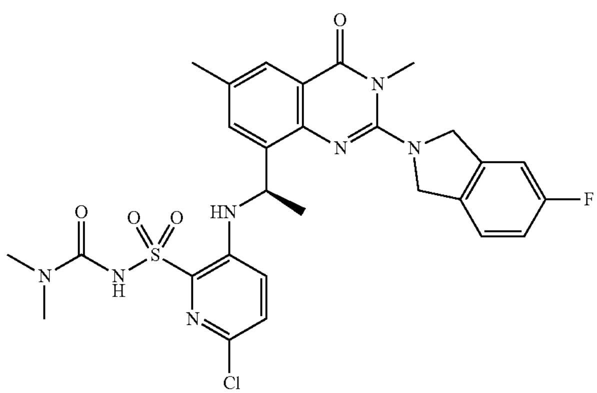 [SMILES: Cc1cc([C@@H](C)Nc2ccc(Cl)nc2S(=O)(=O)NC(=O)N(C)C)c2nc(N3Cc4ccc(F)cc4C3)n(C)c(=O)c2c1] |
| 72 | 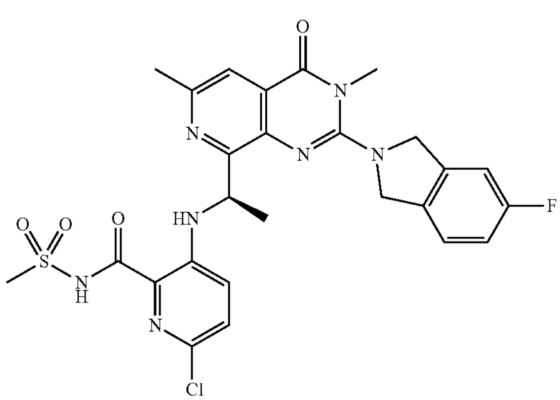 [SMILES: Cc1cc2c(=O)n(C)c(N3Cc4ccc(F)cc4C3)nc2c([C@@H](C)Nc2ccc(Cl)nc2C(=O)NS(C)(=O)=O)n1] |

TABLE 1-continued

List of Compounds

| Cpd. ID | Chemical structure |
|---------|--------------------|
| 73 | 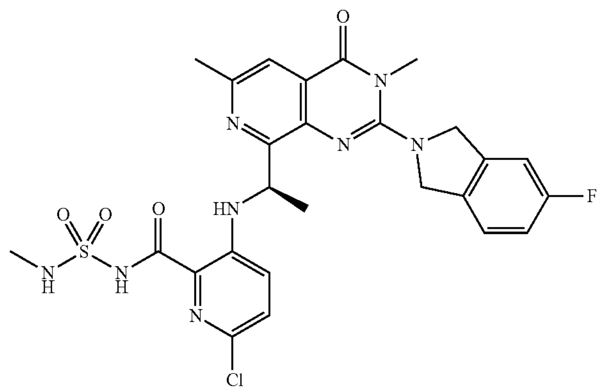 |
| 74 | 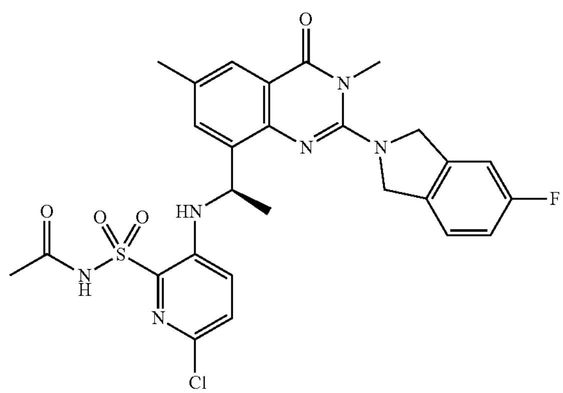 [SMILES: CC(=O)NS(=O)(=O)c1nc(Cl)ccc1N[C@H](C)c1cc(C)cc2c(=O)n(C)c(N3Cc4ccc(F)cc4C3)nc12] |
| 75 | 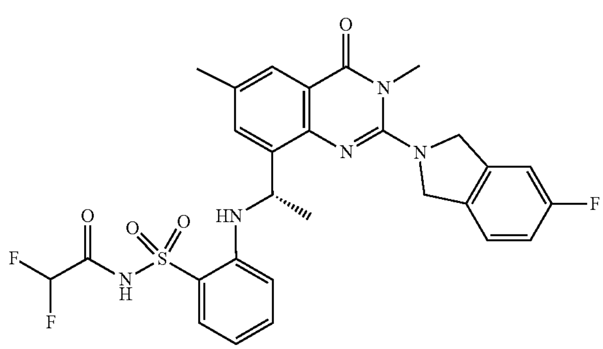 [SMILES: Cc1cc([C@H](C)Nc2ccccc2S(=O)(=O)NC(=O)C(F)F)c2nc(N3Cc4ccc(F)cc4C3)n(C)c(=O)c2c1] |
| 76 | 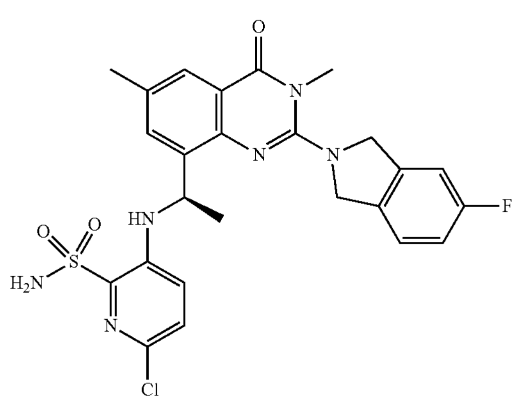 [SMILES: Cc1cc([C@@H](C)Nc2ccc(Cl)nc2S(N)(=O)=O)c2nc(N3Cc4ccc(F)cc4C3)n(C)c(=O)c2c1] |

TABLE 1-continued
List of Compounds
| Cpd. ID | Chemical structure |
|---|---|
| 77 | 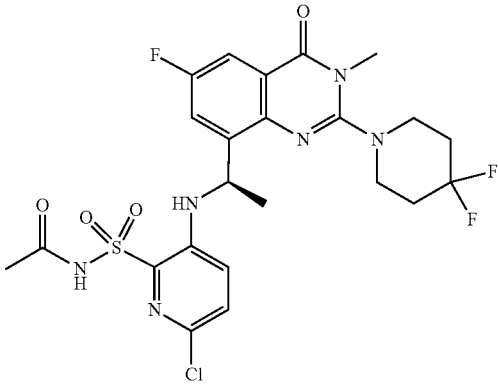 |
| 78 | 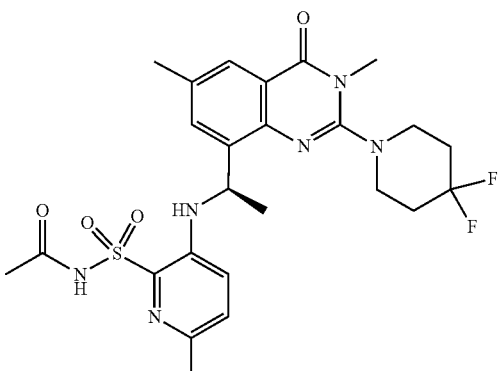 |
| 79 | 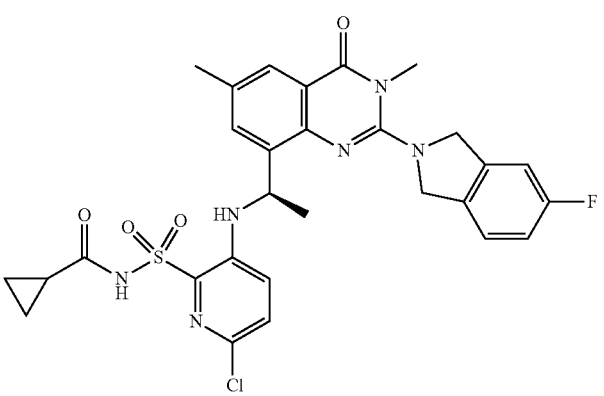 [SMILES: Cc1cc([C@@H](C)Nc2ccc(Cl)nc2S(=O)(=O)NC(=O)C2CC2)c2nc(N3Cc4ccc(F)cc4C3)n(C)c(=O)c2c1] |
| 80 | 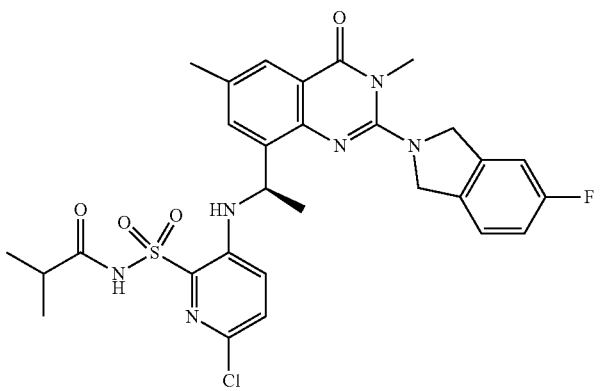 [SMILES: Cc1cc([C@@H](C)Nc2ccc(Cl)nc2S(=O)(=O)NC(=O)C(C)C)c2nc(N3Cc4ccc(F)cc4C3)n(C)c(=O)c2c1] |

TABLE 1-continued
List of Compounds
| Cpd. ID | Chemical structure |
|---|---|
| 81 | 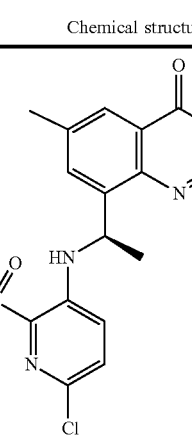 |
| 82 | 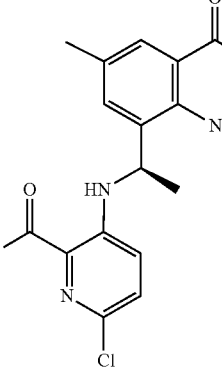 |
| 83 | 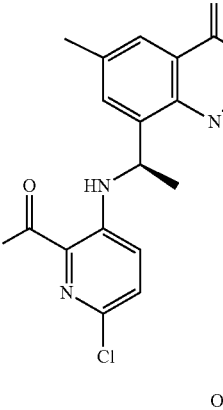 |
| 84 | 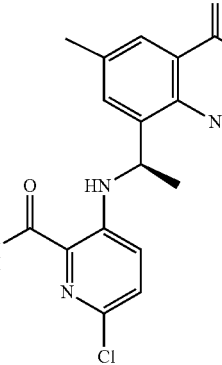 |

TABLE 1-continued
List of Compounds
| Cpd. ID | Chemical structure |
|---|---|
| 85 | 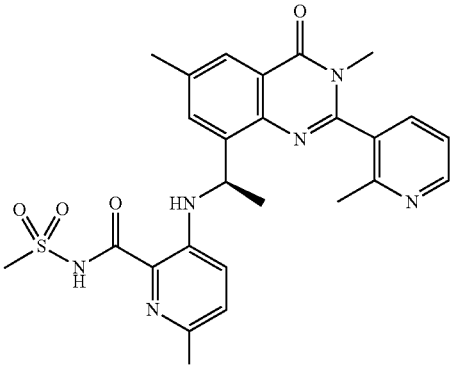 |
| 86 | 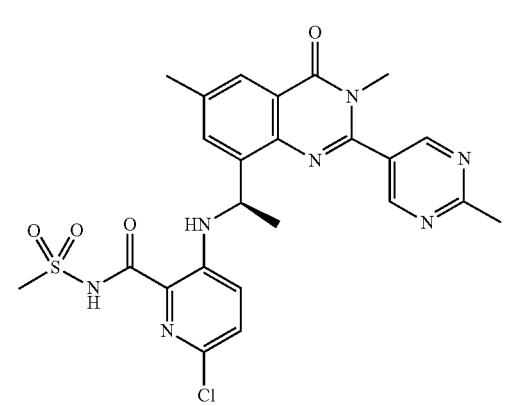 |
| 87 | 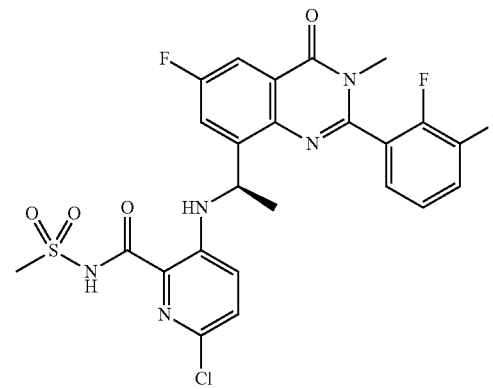 |
| 88 | 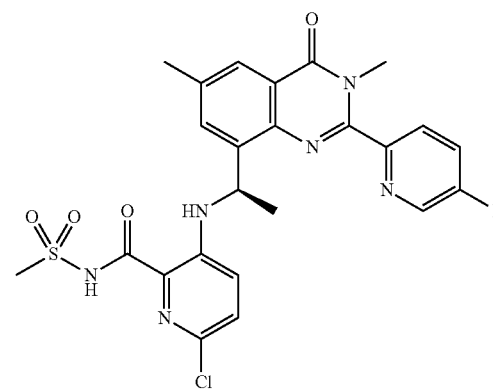 |

TABLE 1-continued
List of Compounds
| Cpd. ID | Chemical structure |
|---|---|
| 89 | 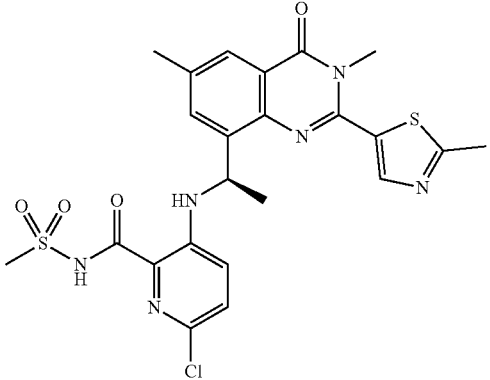 |
| 90 | 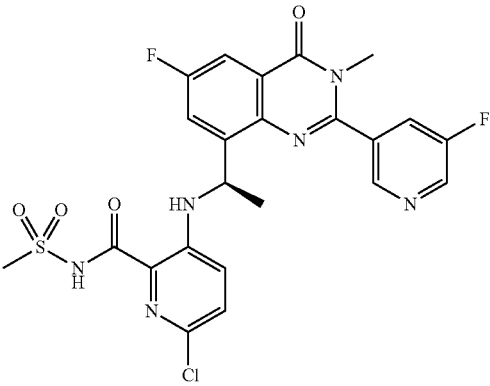 [SMILES: Cc1cc([C@@H](C)Nc2ccc(Cl)nc2C(=O)NS(C)(=O)=O)c2nc(-c3cncc(F)c3)n(C)c(=O)c2c1] |
| 91 | 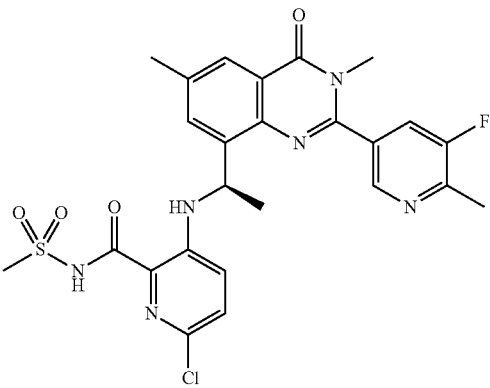 |
| 92 | 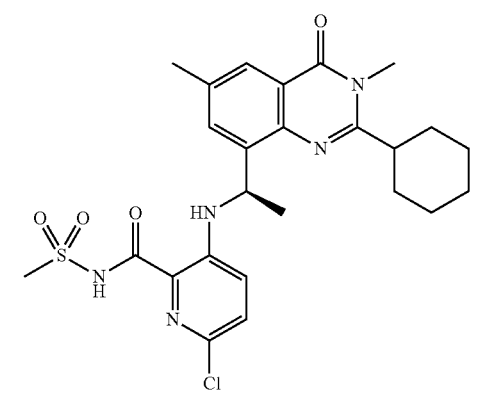 [SMILES: Cc1cc([C@@H](C)Nc2ccc(Cl)nc2C(=O)NS(C)(=O)=O)c2nc(C3CCCCC3)n(C)c(=O)c2c1] |

TABLE 1-continued
| Cpd. ID | Chemical structure |
|---|---|
| 93 | 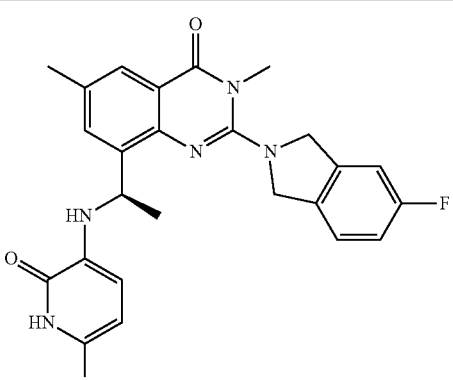 |
| 94 | 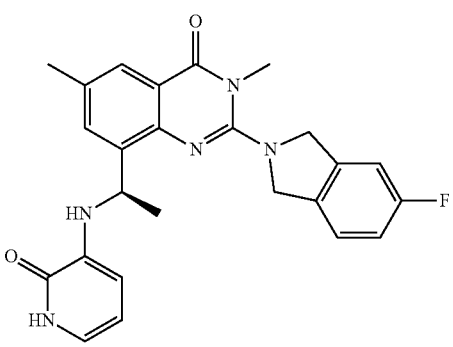 [SMILES: Cc1cc([C@@H](C)Nc2ccc[nH]c2=O)c2nc(N3Cc4ccc(F)cc4C3)n(C)c(=O)c2c1] |
| 95 | 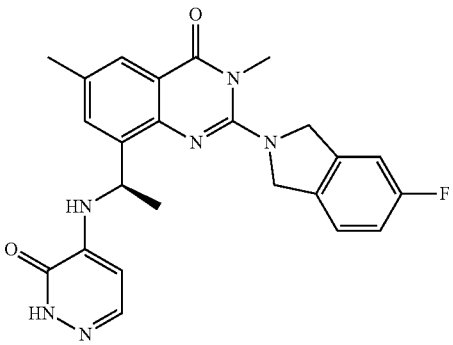 [SMILES: Cc1cc([C@@H](C)Nc2ccn[nH]c2=O)c2nc(N3Cc4ccc(F)cc4C3)n(C)c(=O)c2c1] |
| 96 | 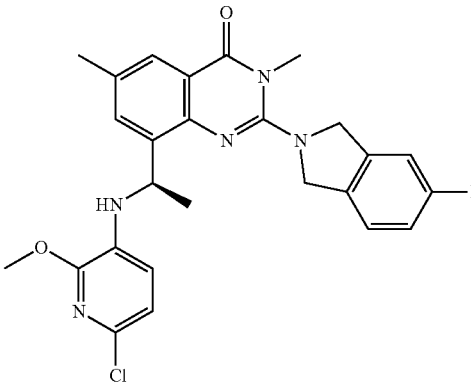 |

TABLE 1-continued

| Cpd. ID | Chemical structure |
|---|---|
| 97 | 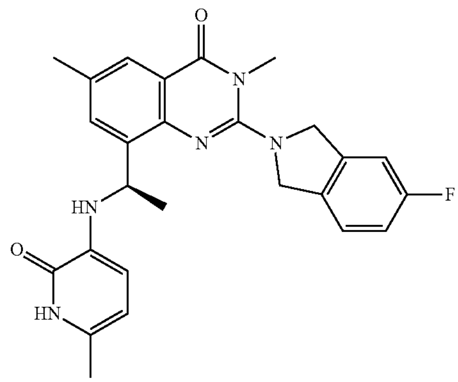 [SMILES: Cc1cc([C@@H](C)Nc2ccc(C)[nH]c2=O)c2nc(N3Cc4ccc(F)cc4C3)n(C)c(=O)c2c1] |
| 98 | 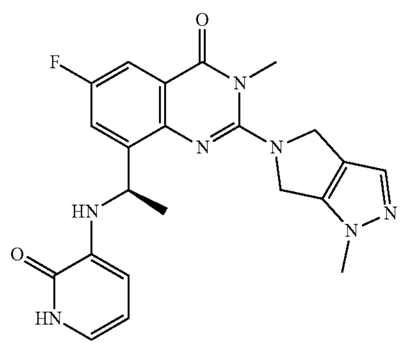 [SMILES: C[C@@H](Nc1ccc[nH]c1=O)c1cc(F)cc2c(=O)n(C)c(N3Cc4cnn(C)c4C3)nc12] |
| 99 | 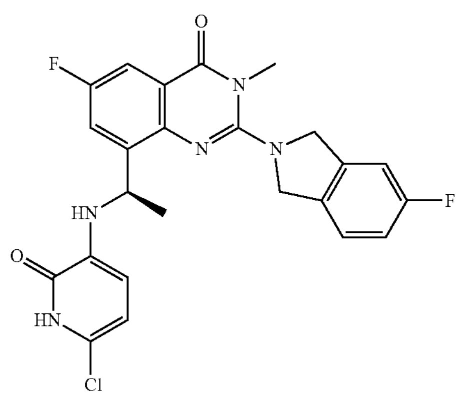 [SMILES: C[C@@H](Nc1ccc(Cl)[nH]c1=O)c1cc(F)cc2c(=O)n(C)c(N3Cc4ccc(F)cc4C3)nc12] |
| 100 | 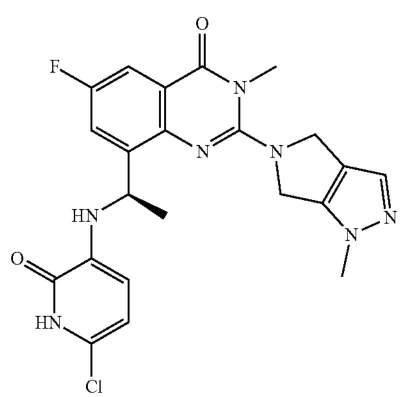 [SMILES: C[C@@H](Nc1ccc(Cl)[nH]c1=O)c1cc(F)cc2c(=O)n(C)c(N3Cc4cnn(C)c4C3)nc12] |

TABLE 1-continued
| Cpd. ID | Chemical structure |
|---|---|
| 101 | 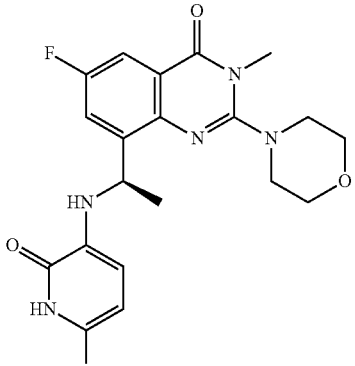 |
| 102 | 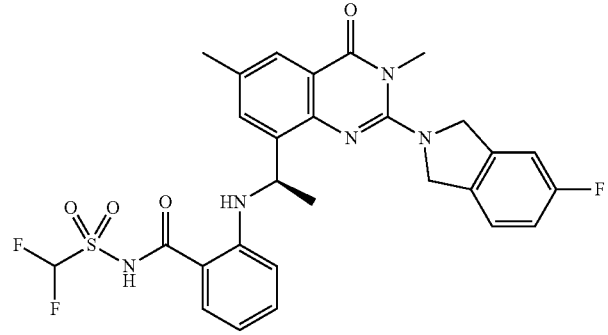 [SMILES: Cc1cc([C@@H](C)Nc2ccccc2C(=O)NS(=O)(=O)C(F)F)c2nc(N3Cc4ccc(F)cc4C3)n(C)c(=O)c2c1] |
| 103 | 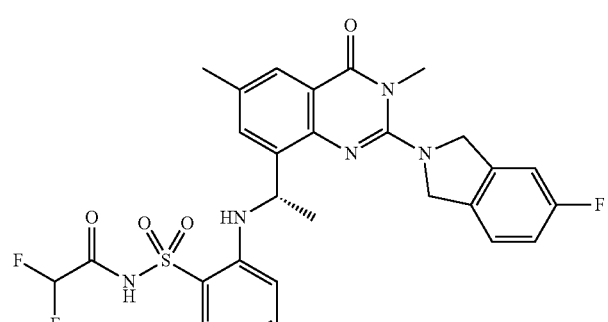 |
| 104 | 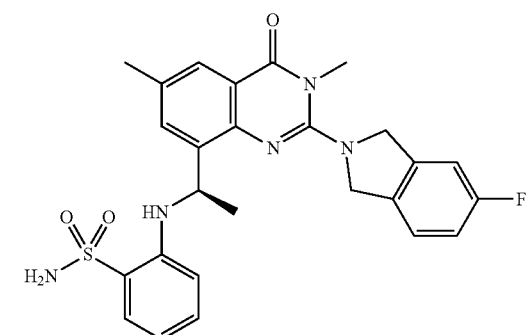 |

TABLE 1-continued

| Cpd. ID | Chemical structure |
|---|---|
| 105 | 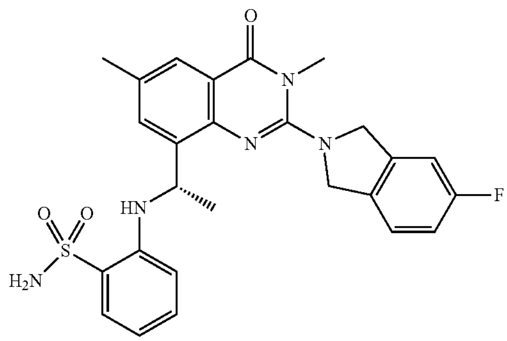 [SMILES: Cc1cc([C@H](C)Nc2ccccc2S(N)(=O)=O)c2nc(N3Cc4ccc(F)cc4C3)n(C)c(=O)c2c1] |
| 106 | 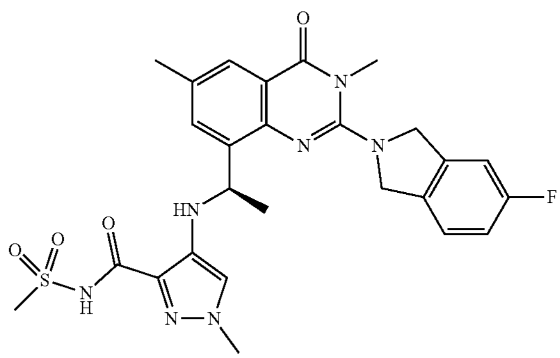 [SMILES: Cc1cc([C@@H](C)Nc2cn(C)nc2C(=O)NS(C)(=O)=O)c2nc(N3Cc4ccc(F)cc4C3)n(C)c(=O)c2c1] |
| 107 | 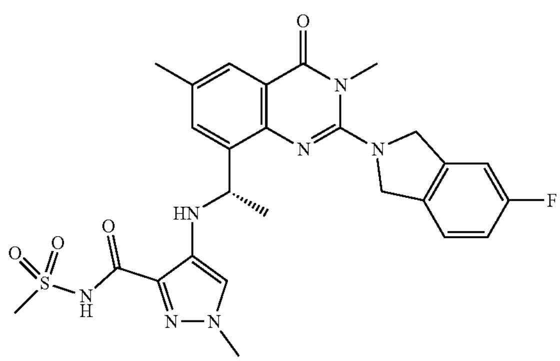 [SMILES: Cc1cc([C@H](C)Nc2cn(C)nc2C(=O)NS(C)(=O)=O)c2nc(N3Cc4ccc(F)cc4C3)n(C)c(=O)c2c1] |
| 108 | 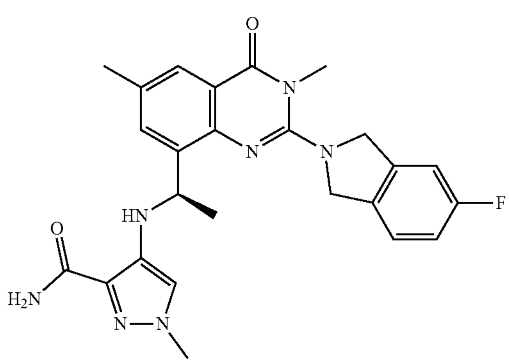 [SMILES: Cc1cc([C@@H](C)Nc2cn(C)nc2C(N)=O)c2nc(N3Cc4ccc(F)cc4C3)n(C)c(=O)c2c1] |

TABLE 1-continued

| Cpd. ID | Chemical structure |
|---|---|
| 109 | 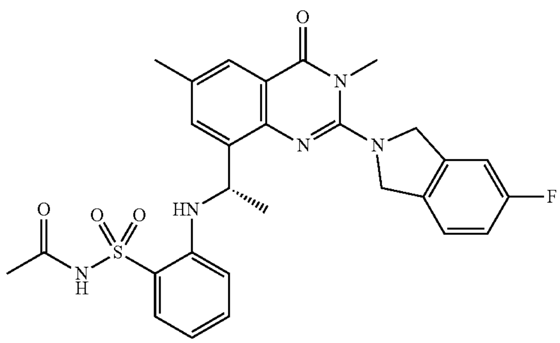 [SMILES: CC(=O)NS(=O)(=O)c1ccccc1N[C@@H](C)c1cc(C)cc2c(=O)n(C)c(N3Cc4ccc(F)cc4C3)nc12] |
| 110 | 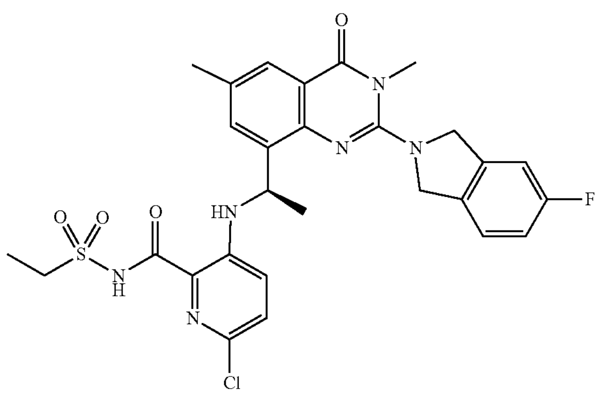 [SMILES: CCS(=O)(=O)NC(=O)c1nc(Cl)ccc1N[C@H](C)c1cc(C)cc2c(=O)n(C)c(N3Cc4ccc(F)cc4C3)nc12] |
| 111 | 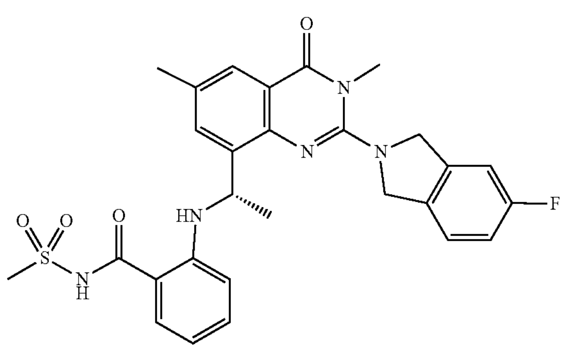 [SMILES: Cc1cc([C@H](C)Nc2ccccc2C(=O)NS(C)(=O)=O)c2nc(N3Cc4ccc(F)cc4C3)n(C)c(=O)c2c1] |
| 112 | 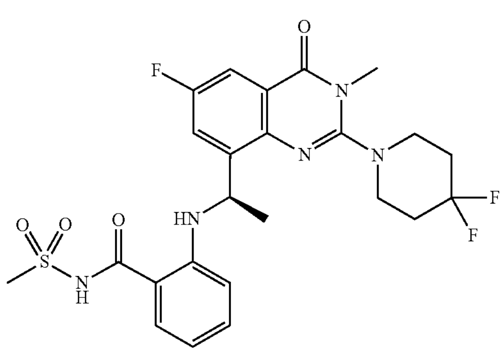 [SMILES: C[C@@H](Nc1ccccc1C(=O)NS(C)(=O)=O)c1cc(F)cc2c(=O)n(C)c(N3CCC(F)(F)CC3)nc12] |

TABLE 1-continued
List of Compounds
| Cpd. ID | Chemical structure |
|---|---|
| 113 | 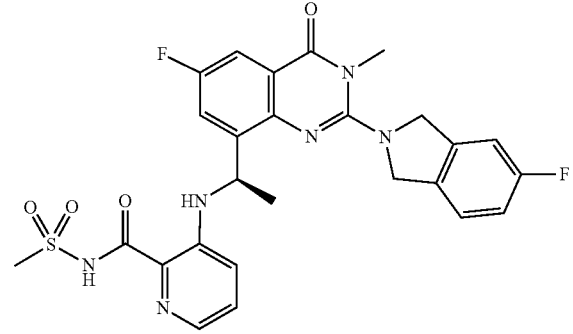 [SMILES: C[C@@H](Nc1cccnc1C(=O)NS(C)(=O)=O)c1cc(F)cc2c(=O)n(C)c(N3Cc4ccc(F)cc4C3)nc12] |
| 114 | 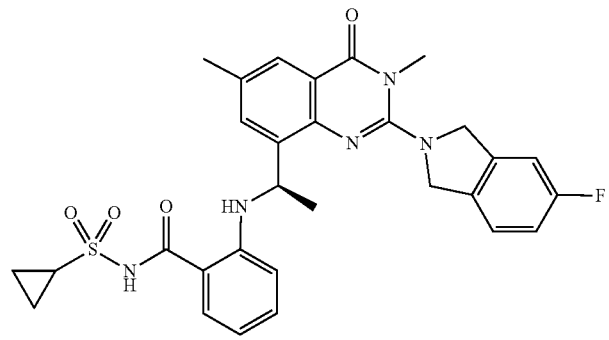 [SMILES: Cc1cc([C@@H](C)Nc2ccccc2C(=O)NS(=O)(=O)C2CC2)c2nc(N3Cc4ccc(F)cc4C3)n(C)c(=O)c2c1] |
| 115 | 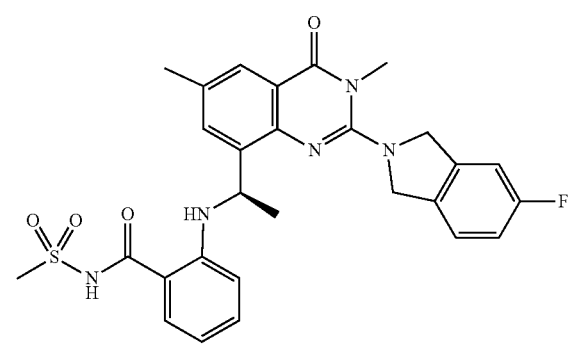 [SMILES: Cc1cc([C@@H](C)Nc2ccccc2C(=O)NS(C)(=O)=O)c2nc(N3Cc4ccc(F)cc4C3)n(C)c(=O)c2c1] |
| 116 | 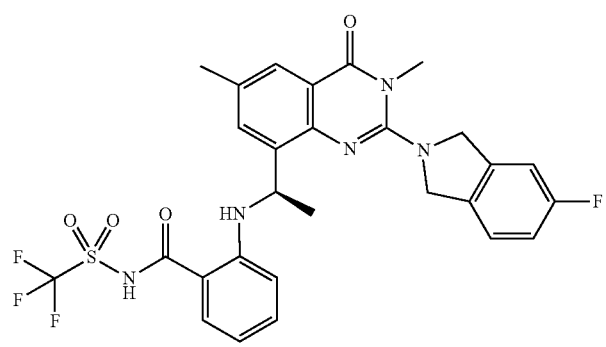 [SMILES: Cc1cc([C@@H](C)Nc2ccccc2C(=O)NS(=O)(=O)C(F)(F)F)c2nc(N3Cc4ccc(F)cc4C3)n(C)c(=O)c2c1] |

TABLE 1-continued

| Cpd. ID | Chemical structure |
|---|---|
| 117 | 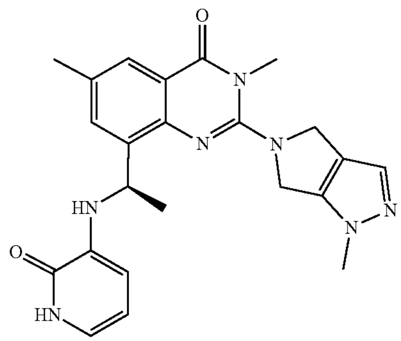 [SMILES: Cc1cc([C@@H](C)Nc2ccc[nH]c2=O)c2nc(N3Cc4cnn(C)c4C3)n(C)c(=O)c2c1] |
| 118 | 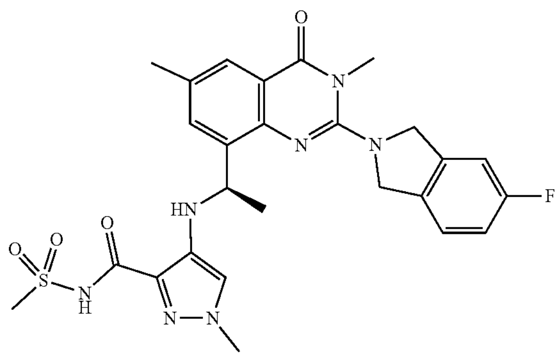 [SMILES: Cc1cc([C@@H](C)Nc2cn(C)nc2C(=O)NS(C)(=O)=O)c2nc(N3Cc4ccc(F)cc4C3)n(C)c(=O)c2c1] |
| 119 | 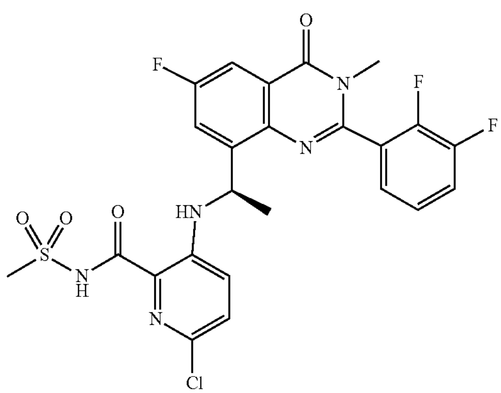 [SMILES: C[C@@H](Nc1ccc(Cl)nc1C(=O)NS(C)(=O)=O)c1cc(F)cc2c(=O)n(C)c(-c3cccc(F)c3F)nc12] |
| 120 | 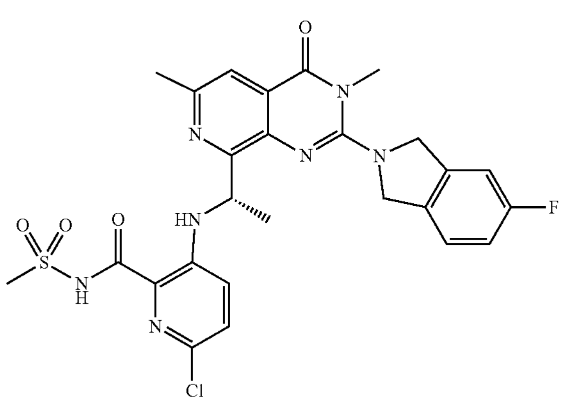 [SMILES: Cc1cc2c(=O)n(C)c(N3Cc4ccc(F)cc4C3)nc2c([C@H](C)Nc2ccc(Cl)nc2C(=O)NS(C)(=O)=O)n1] |

TABLE 1-continued

List of Compounds

| Cpd. ID | Chemical structure |
|---|---|
| 121 | 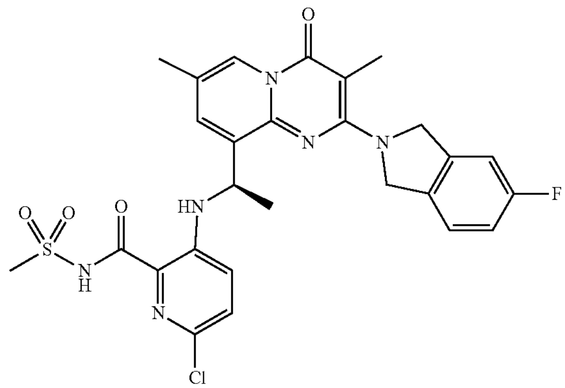 [SMILES: Cc1cc([C@@H](C)Nc2ccc(Cl)nc2C(=O)NS(C)(=O)=O)c2nc(N3Cc4ccc(F)cc4C3)c(C)c(=O)n2c1] |
| 122 | 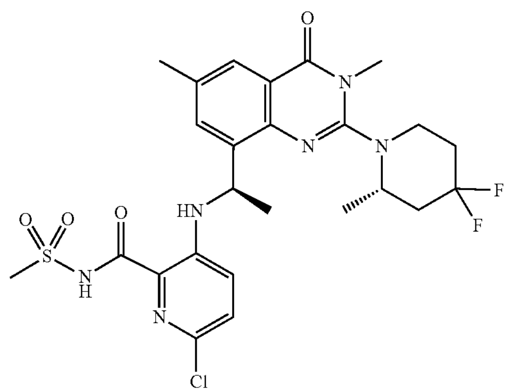 [SMILES: Cc1cc([C@@H](C)Nc2ccc(Cl)nc2C(=O)NS(C)(=O)=O)c2nc(N3CCC(F)(F)C[C@@H]3C)n(C)c(=O)c2c1] |
| 123 | 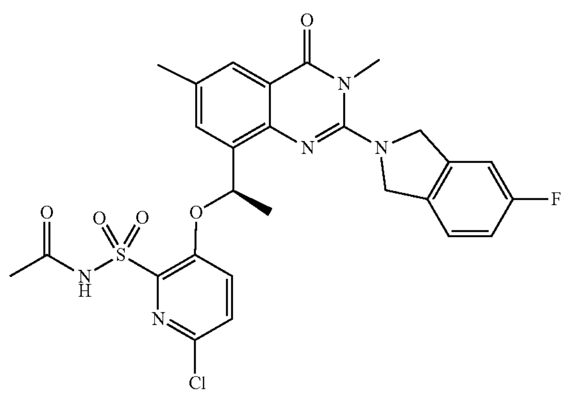 [SMILES: CC(=O)NS(=O)(=O)c1nc(Cl)ccc1O[C@H](C)c1cc(C)cc2c(=O)n(C)c(N3Cc4ccc(F)cc4C3)nc12] |
| 124 | 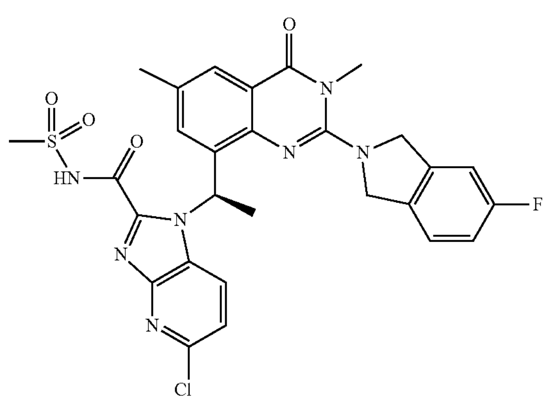 [SMILES: Cc1cc([C@@H](C)n2c(C(=O)NS(C)(=O)=O)nc3nc(Cl)ccc32)c2nc(N3Cc4ccc(F)cc4C3)n(C)c(=O)c2c1] |

TABLE 1-continued

List of Compounds

| Cpd. ID | Chemical structure |
|---|---|
| 125 | 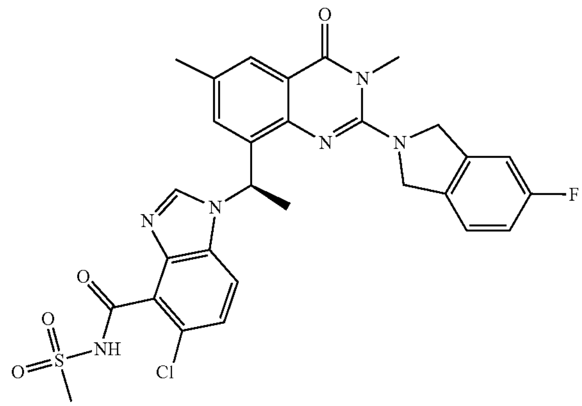 [SMILES: Cc1cc([C@@H](C)n2cnc3c(C(=O)NS(C)(=O)=O)c(Cl)ccc32)c2nc(N3Cc4ccc(F)cc4C3)n(C)c(=O)c2c1] |
| 126 | 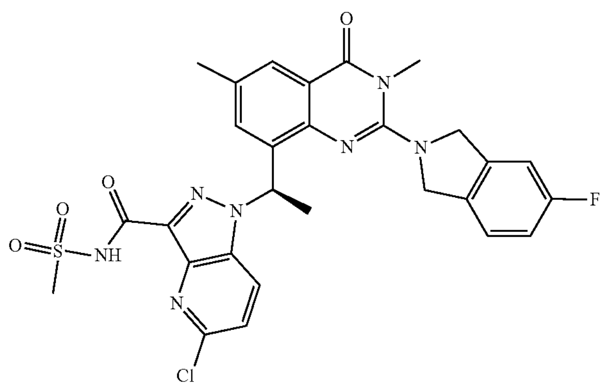 [SMILES: Cc1cc([C@@H](C)n2nc(C(=O)NS(C)(=O)=O)c3nc(Cl)ccc32)c2nc(N3Cc4ccc(F)cc4C3)n(C)c(=O)c2c1] |
| 127 | 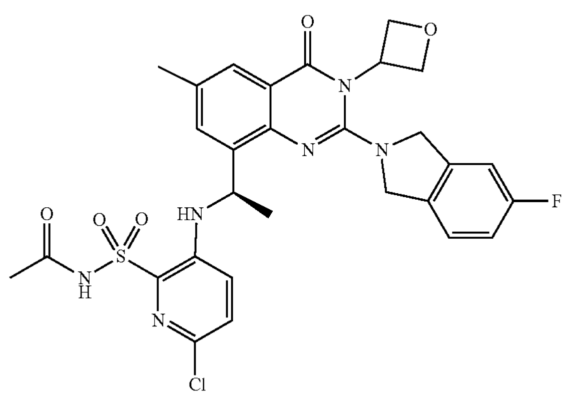 [SMILES: CC(=O)NS(=O)(=O)c1nc(Cl)ccc1N[C@H](C)c1cc(C)cc2c(=O)n(C3COC3)c(N3Cc4ccc(F)cc4C3)nc12] |
| 128 | 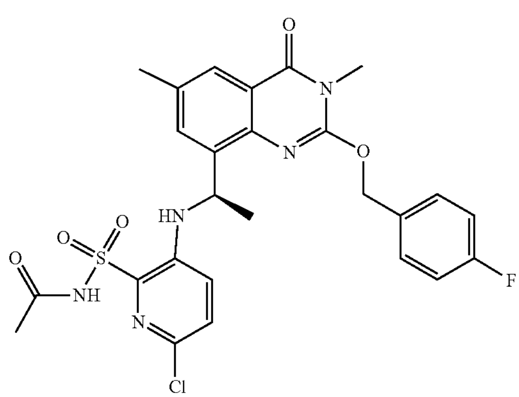 [SMILES: CC(=O)NS(=O)(=O)c1nc(Cl)ccc1N[C@H](C)c1cc(C)cc2c(=O)n(C)c(OCc3ccc(F)cc3)nc12] |

TABLE 1-continued
List of Compounds
| Cpd. ID | Chemical structure |
|---------|--------------------|
| 129 | 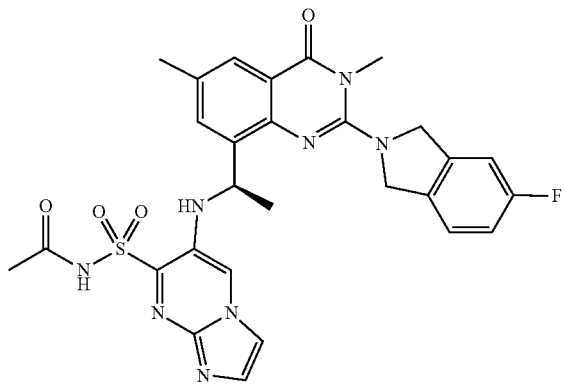 [SMILES: CC(=O)NS(=O)(=O)c1nc2nccn2cc1N[C@H](C)c1cc(C)cc2c(=O)n(C)c(N3Cc4ccc(F)cc4C3)nc12] |
| 130 | 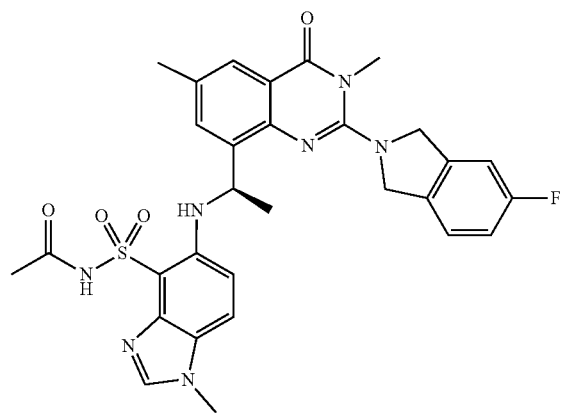 [SMILES: CC(=O)NS(=O)(=O)c1c(N[C@H](C)c2cc(C)cc3c(=O)n(C)c(N4Cc5ccc(F)cc5C4)nc23)ccc2c1ncn2C] |
| 131 | 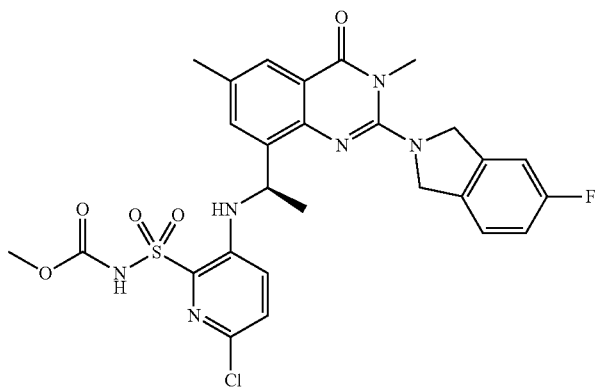 [SMILES: COC(=O)NS(=O)(=O)c1nc(Cl)ccc1N[C@H](C)c1cc(C)cc2c(=O)n(C)c(N3Cc4ccc(F)cc4C3)nc12] |

TABLE 1-continued

List of Compounds

| Cpd. ID | Chemical structure |
|---|---|
| 132 | 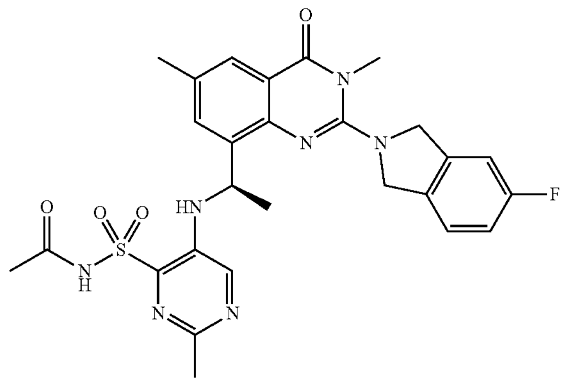 [SMILES: CC(=O)NS(=O)(=O)c1nc(C)ncc1N[C@H](C)c1cc(C)cc2c(=O)n(C)c(N3Cc4ccc(F)cc4C3)nc12] |
| 133 | 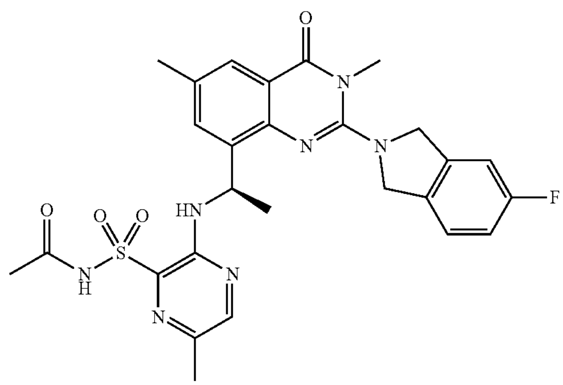 [SMILES: CC(=O)NS(=O)(=O)c1nc(C)cnc1N[C@H](C)c1cc(C)cc2c(=O)n(C)c(N3Cc4ccc(F)cc4C3)nc12] |
| 134 | 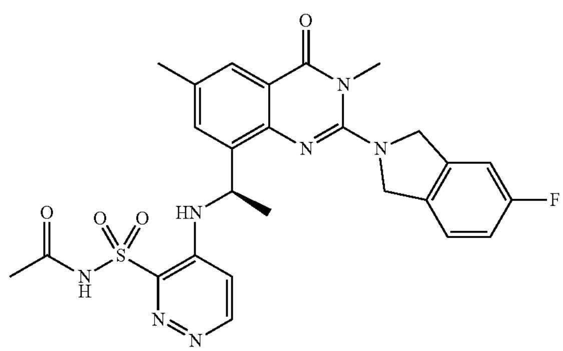 [SMILES: CC(=O)NS(=O)(=O)c1nnccc1N[C@H](C)c1cc(C)cc2c(=O)n(C)c(N3Cc4ccc(F)cc4C3)nc12] |
| 135 | 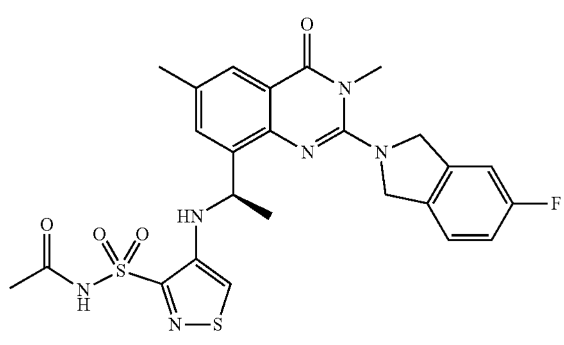 [SMILES: CC(=O)NS(=O)(=O)c1nscc1N[C@H](C)c1cc(C)cc2c(=O)n(C)c(N3Cc4ccc(F)cc4C3)nc12] |

TABLE 1-continued

List of Compounds

| Cpd. ID | Chemical structure |
|---|---|
| 136 | 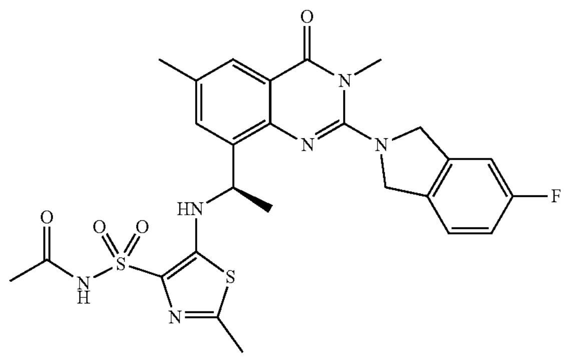 [SMILES: CC(=O)NS(=O)(=O)c1nc(C)sc1N[C@H](C)c1cc(C)cc2c(=O)n(C)c(N3Cc4ccc(F)cc4C3)nc12] |
| 137 | 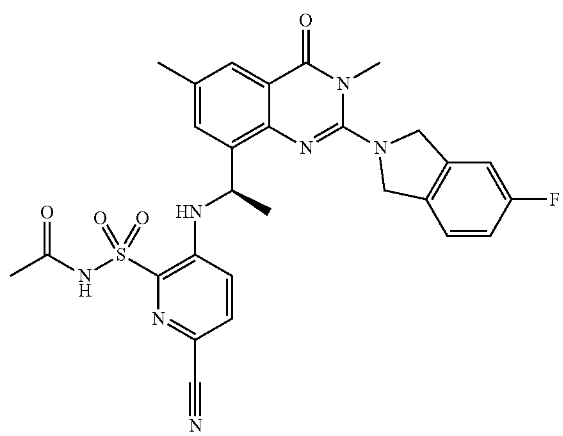 [SMILES: CC(=O)NS(=O)(=O)c1nc(C#N)ccc1N[C@H](C)c1cc(C)cc2c(=O)n(C)c(N3Cc4ccc(F)cc4C3)nc12] |
| 138 | 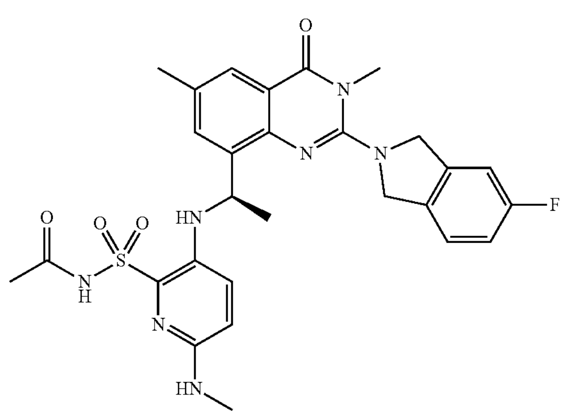 [SMILES: COc1ccc(N[C@H](C)c2cc(C)cc3c(=O)n(C)c(N4Cc5ccc(F)cc5C4)nc23)c(S(=O)(=O)NC(C)=O)n1] |

TABLE 1-continued
| List of Compounds | |
|---|---|
| Cpd. ID | Chemical structure |
| 139 | 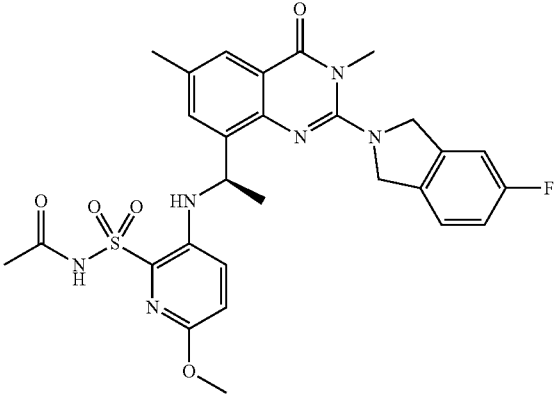 |
| 140 | 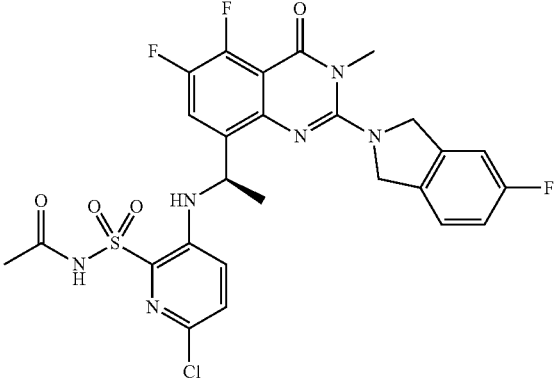 [SMILES: CC(=O)NS(=O)(=O)c1nc(Cl)ccc1N[C@H](C)c1cc(F)c(F)c2c(=O)n(C)c(N3Cc4ccc(F)cc4C3)nc12] |
| 141 | 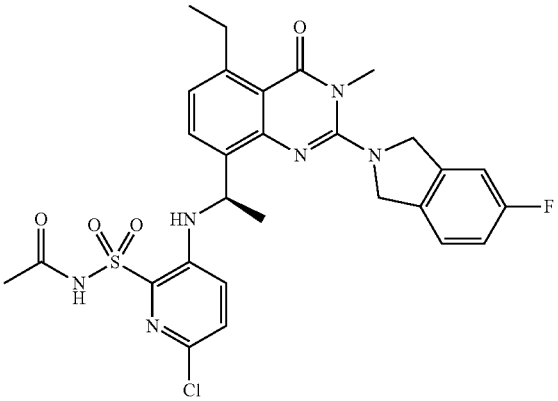 [SMILES: CCc1ccc([C@@H](C)Nc2ccc(Cl)nc2S(=O)(=O)NC(C)=O)c2nc(N3Cc4ccc(F)cc4C3)n(C)c(=O)c12] |

TABLE 1-continued

List of Compounds

| Cpd. ID | Chemical structure |
|---|---|
| 142 | 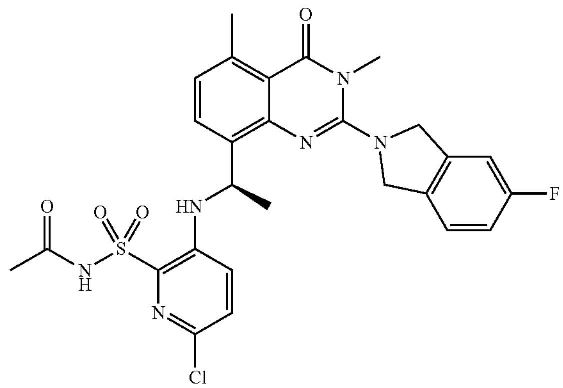 [SMILES: CC(=O)NS(=O)(=O)c1nc(Cl)ccc1N[C@H](C)c1ccc(C)c2c(=O)n(C)c(N3Cc4ccc(F)cc4C3)nc12] |
| 143 | 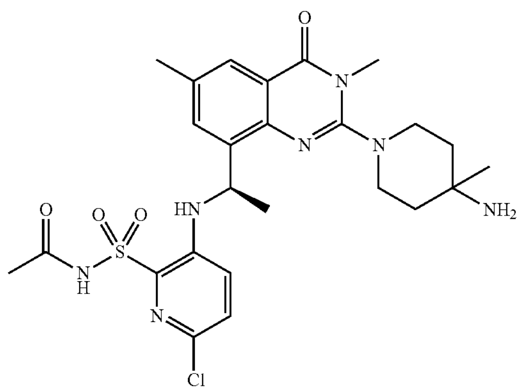 [SMILES: CC(=O)NS(=O)(=O)c1nc(Cl)ccc1N[C@H](C)c1cc(C)cc2c(=O)n(C)c(N3CCC(C)(N)CC3)nc12] |
| 144 | 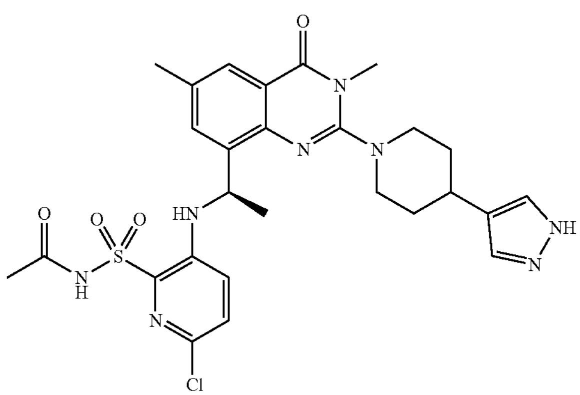 [SMILES: CC(=O)NS(=O)(=O)c1nc(Cl)ccc1N[C@H](C)c1cc(C)cc2c(=O)n(C)c(N3CCC(c4cn[nH]c4)CC3)nc12] |
| 145 | 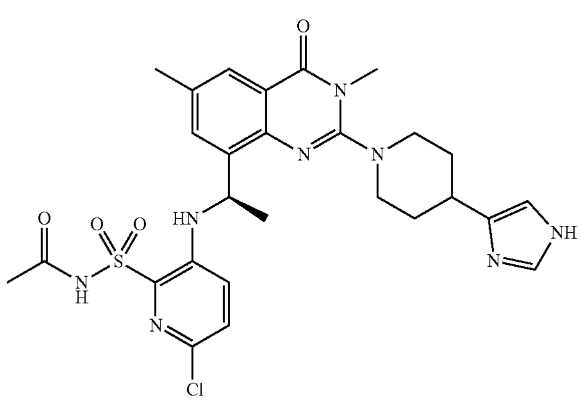 [SMILES: CC(=O)NS(=O)(=O)c1nc(Cl)ccc1N[C@H](C)c1cc(C)cc2c(=O)n(C)c(N3CCC(c4c[nH]cn4)CC3)nc12] |

TABLE 1-continued

List of Compounds

| Cpd. ID | Chemical structure |
|---|---|
| 146 | 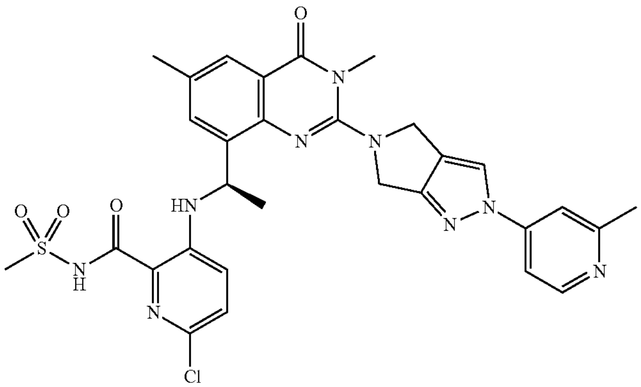 |
| 147 | 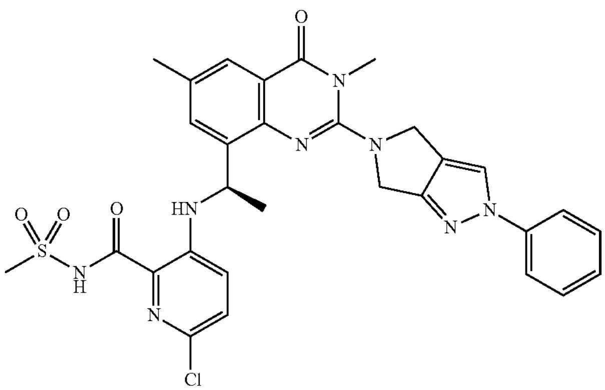 [SMILES: Cc1cc([C@@H](C)Nc2ccc(Cl)nc2C(=O)NS(C)(=O)=O)c2nc(N3Cc4cn(-c5ccccc5)nc4C3)n(C)c(=O)c2c1] |
| 148 | 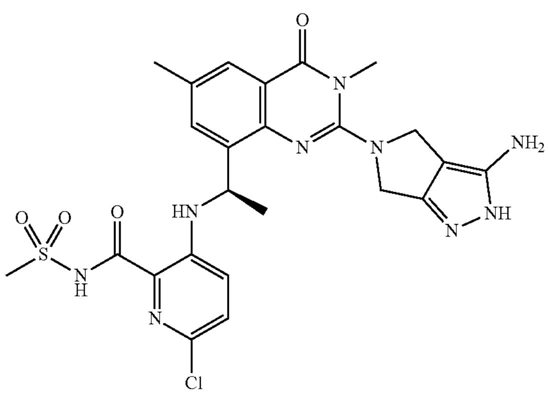 [SMILES: Cc1cc([C@@H](C)Nc2ccc(Cl)nc2C(=O)NS(C)(=O)=O)c2nc(N3Cc4n[nH]c(N)c4C3)n(C)c(=O)c2c1] |
| 149 | 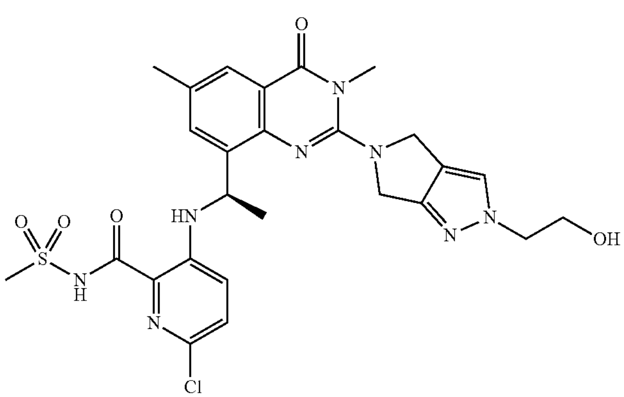 [SMILES: Cc1cc([C@@H](C)Nc2ccc(Cl)nc2C(=O)NS(C)(=O)=O)c2nc(N3Cc4cn(CCO)nc4C3)n(C)c(=O)c2c1] |

TABLE 1-continued

List of Compounds

| Cpd. ID | Chemical structure |
|---|---|
| 150 | 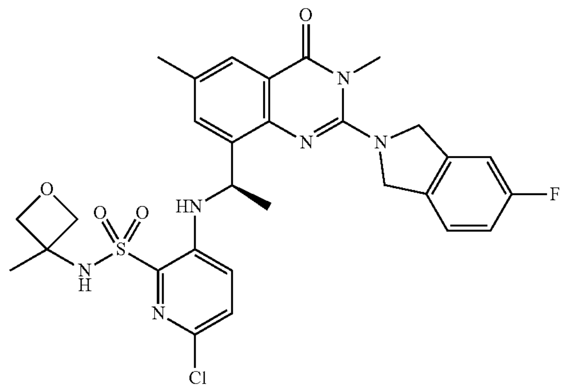 [SMILES: Cc1cc([C@@H](C)Nc2ccc(Cl)nc2S(=O)(=O)NC2(C)COC2)c2nc(N3Cc4ccc(F)cc4C3)n(C)c(=O)c2c1] |
| 151 | 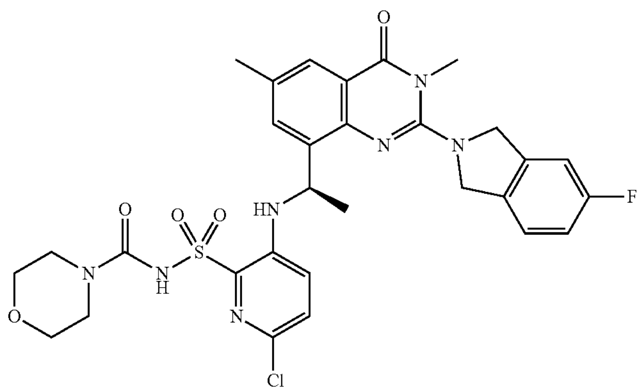 [SMILES: Cc1cc([C@@H](C)Nc2ccc(Cl)nc2S(=O)(=O)NC(=O)N2CCOCC2)c2nc(N3Cc4ccc(F)cc4C3)n(C)c(=O)c2c1] |
| 152 | 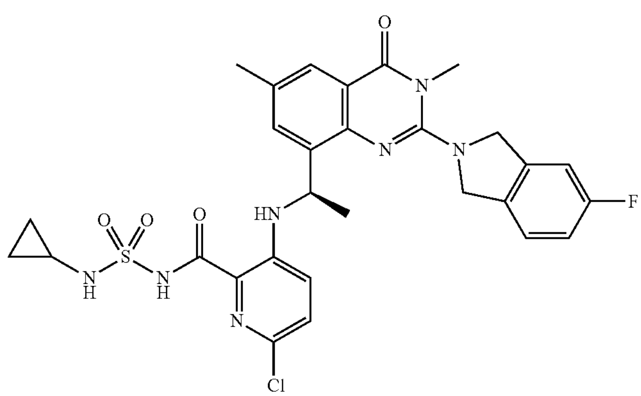 [SMILES: Cc1cc([C@@H](C)Nc2ccc(Cl)nc2C(=O)NS(=O)(=O)NC2CC2)c2nc(N3Cc4ccc(F)cc4C3)n(C)c(=O)c2c1] |
| 153 | 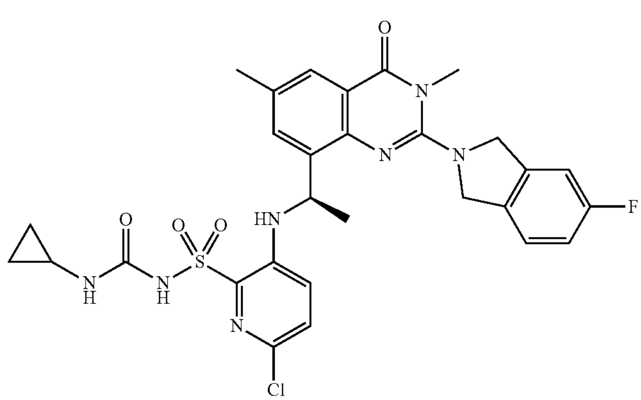 [SMILES: Cc1cc([C@@H](C)Nc2ccc(Cl)nc2S(=O)(=O)NC(=O)NC2CC2)c2nc(N3Cc4ccc(F)cc4C3)n(C)c(=O)c2c1] |

TABLE 1-continued

List of Compounds

| Cpd. ID | Chemical structure |
|---|---|
| 154 | 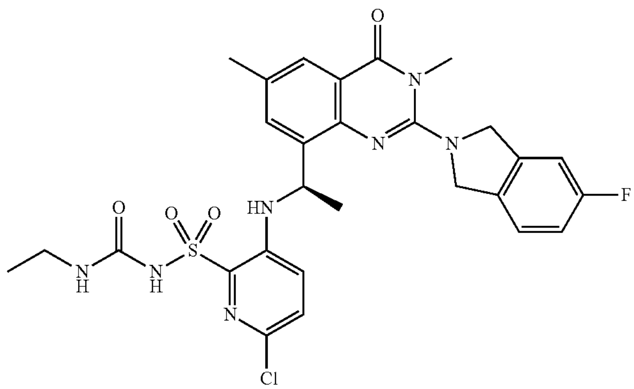 [SMILES: CCNC(=O)NS(=O)(=O)c1nc(Cl)ccc1N[C@H](C)c1cc(C)cc2c(=O)n(C)c(N3Cc4ccc(F)cc4C3)nc12] |
| 155 | 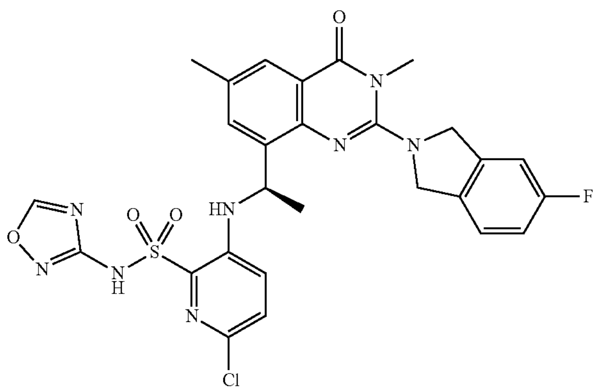 [SMILES: Cc1cc([C@@H](C)Nc2ccc(Cl)nc2S(=O)(=O)Nc2ncon2)c2nc(N3Cc4ccc(F)cc4C3)n(C)c(=O)c2c1] |
| 156 | 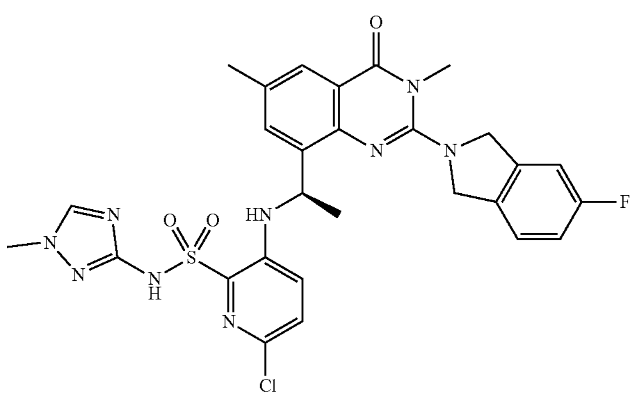 [SMILES: Cc1cc([C@@H](C)Nc2ccc(Cl)nc2S(=O)(=O)Nc2ncn(C)n2)c2nc(N3Cc4ccc(F)cc4C3)n(C)c(=O)c2c1] |
| 157 | 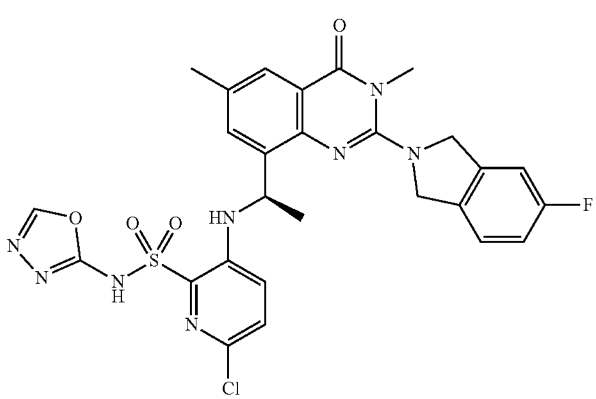 [SMILES: Cc1cc([C@@H](C)Nc2ccc(Cl)nc2S(=O)(=O)Nc2nnco2)c2nc(N3Cc4ccc(F)cc4C3)n(C)c(=O)c2c1] |

TABLE 1-continued

List of Compounds

| Cpd. ID | Chemical structure |
|---------|-------------------|
| 158 | 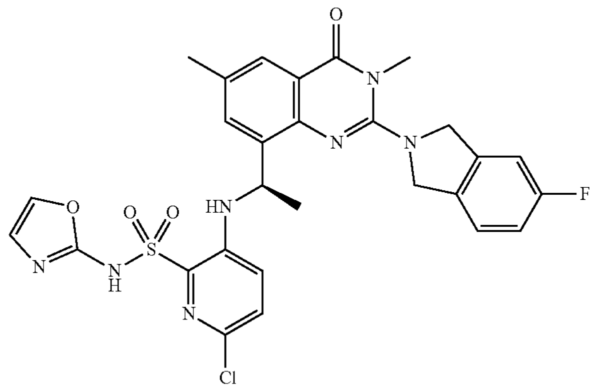 [SMILES: Cc1cc([C@@H](C)Nc2ccc(Cl)nc2S(=O)(=O)Nc2ncco2)c2nc(N3Cc4ccc(F)cc4C3)n(C)c(=O)c2c1] |
| 159 | 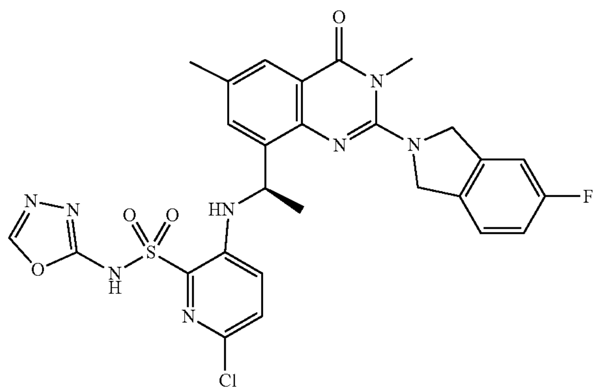 [SMILES: Cc1cc([C@@H](C)Nc2ccc(Cl)nc2S(=O)(=O)Nc2nnco2)c2nc(N3Cc4ccc(F)cc4C3)n(C)c(=O)c2c1] |
| 160 | 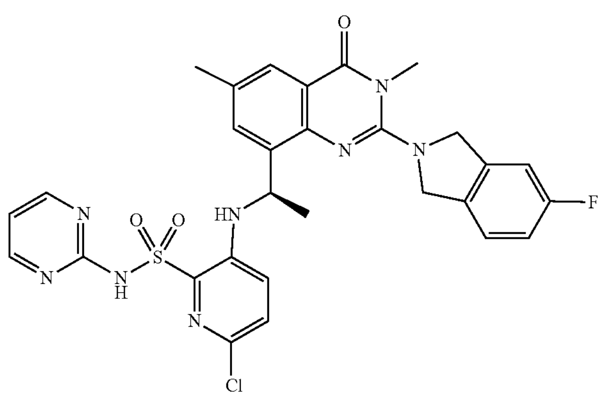 [SMILES: Cc1cc([C@@H](C)Nc2ccc(Cl)nc2S(=O)(=O)Nc2ncccn2)c2nc(N3Cc4ccc(F)cc4C3)n(C)c(=O)c2c1] |
| 161 | 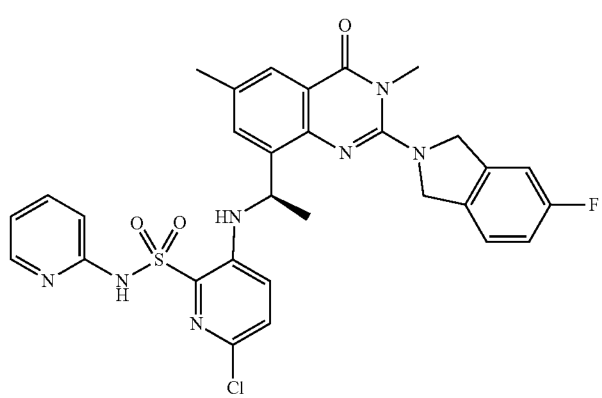 [SMILES: Cc1cc([C@@H](C)Nc2ccc(Cl)nc2S(=O)(=O)Nc2ccccn2)c2nc(N3Cc4ccc(F)cc4C3)n(C)c(=O)c2c1] |

TABLE 1-continued
List of Compounds
| Cpd. ID | Chemical structure |
|---|---|
| 162 | 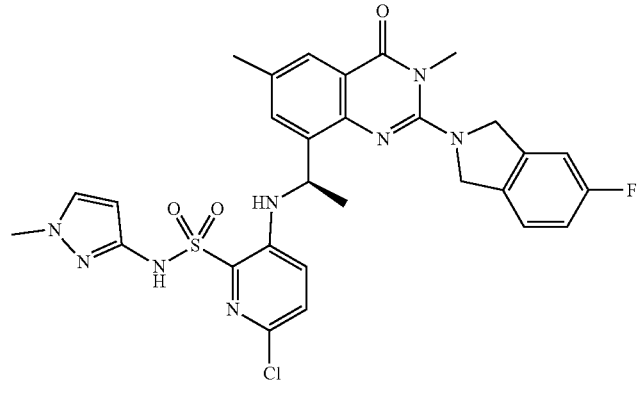 [SMILES: Cc1cc([C@@H](C)Nc2ccc(Cl)nc2S(=O)(=O)Nc2ccn(C)n2)c2nc(N3Cc4ccc(F)cc4C3)n(C)c(=O)c2c1] |
| 163 | 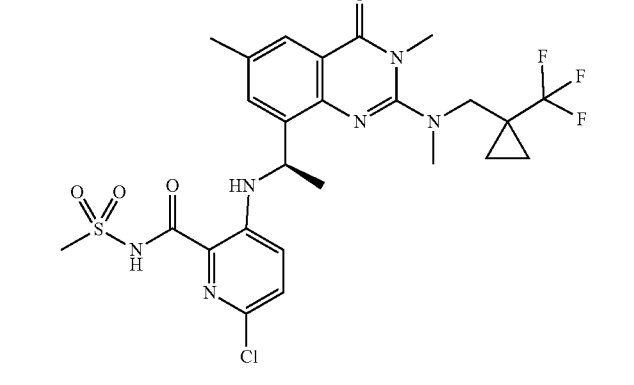 |
| 164 | 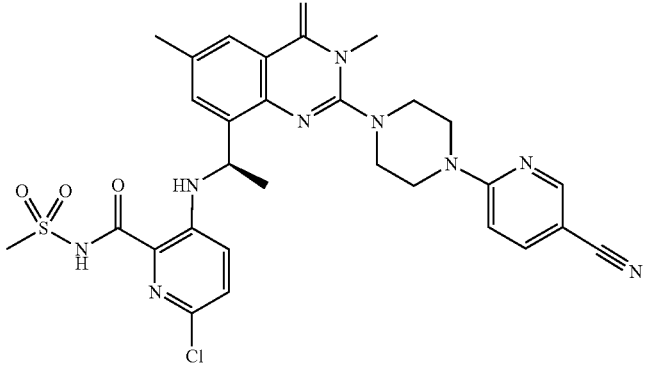 |
| 165 | 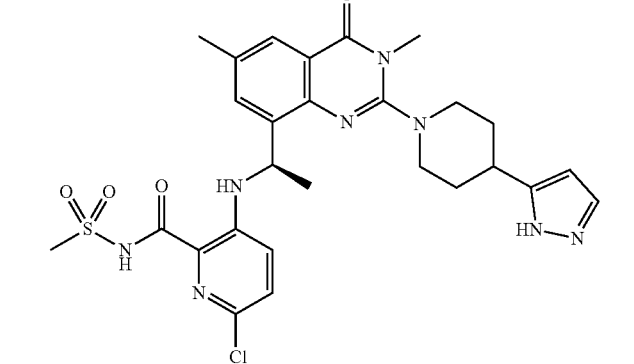 |

TABLE 1-continued
List of Compounds
| Cpd. ID | Chemical structure |
|---|---|
| 166 | 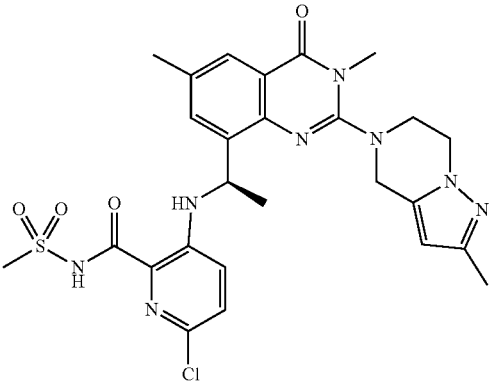 |
| 167 | 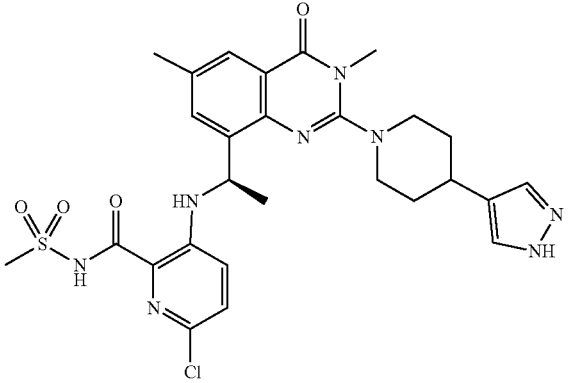 [SMILES: Cc1cc([C@@H](C)Nc2ccc(Cl)nc2C(=O)NS(C)(=O)=O)c2nc(N3CCC(c4cn[nH]c4)CC3)n(C)c(=O)c2c1] |
| 168 | 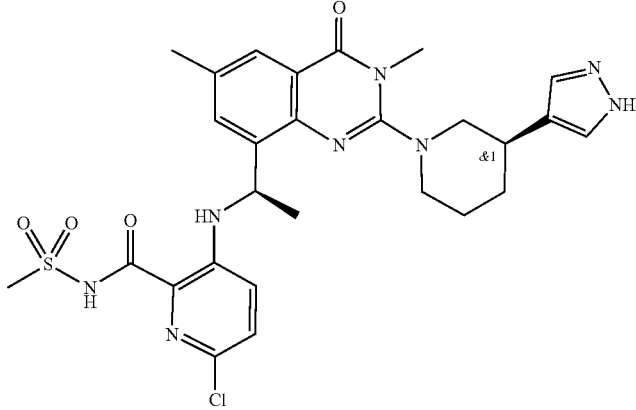 [SMILES: Cc1cc([C@@H](C)Nc2ccc(Cl)nc2C(=O)NS(C)(=O)=O)c2nc(N3CCC[C@H](c4cn[nH]c4)C3)n(C)c(=O)c2c1] |

TABLE 1-continued

List of Compounds

| Cpd. ID | Chemical structure |
|---|---|
| 169 | 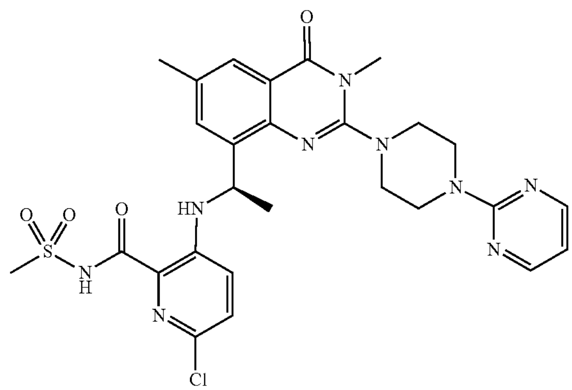 [SMILES: Cc1cc([C@@H](C)Nc2ccc(Cl)nc2C(=O)NS(C)(=O)=O)c2nc(N3CCN(c4ncccn4)CC3)n(C)c(=O)c2c1] |
| 170 | 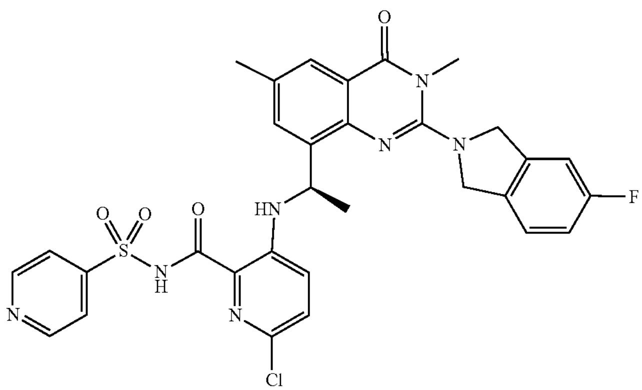 [SMILES: Cc1cc([C@@H](C)Nc2ccc(Cl)nc2C(=O)NS(=O)(=O)c2ccncc2)c2nc(N3Cc4ccc(F)cc4C3)n(C)c(=O)c2c1] |
| 171 | 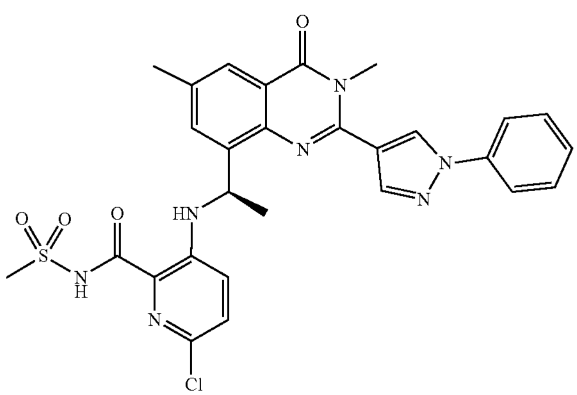 [SMILES: Cc1cc([C@@H](C)Nc2ccc(Cl)nc2C(=O)NS(C)(=O)=O)c2nc(-c3cnn(-c4ccccc4)c3)n(C)c(=O)c2c1] |
| 172 | 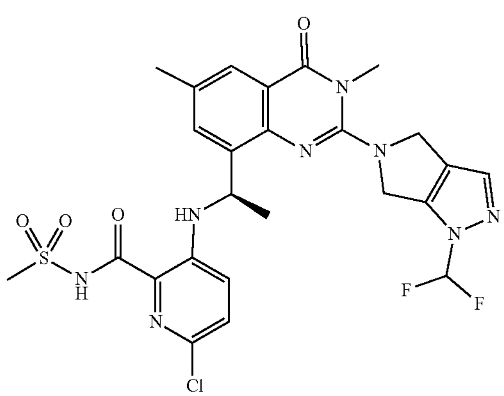 [SMILES: Cc1cc([C@@H](C)Nc2ccc(Cl)nc2C(=O)NS(C)(=O)=O)c2nc(N3Cc4cnn(C(F)F)c4C3)n(C)c(=O)c2c1] |

TABLE 1-continued
List of Compounds
| Cpd. ID | Chemical structure |
|---|---|
| 173 | 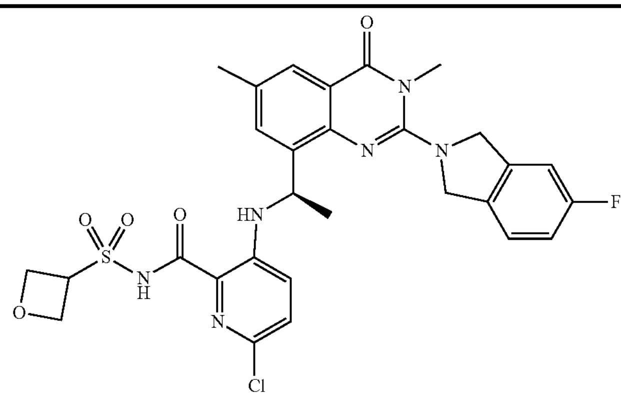 |
| 174 | 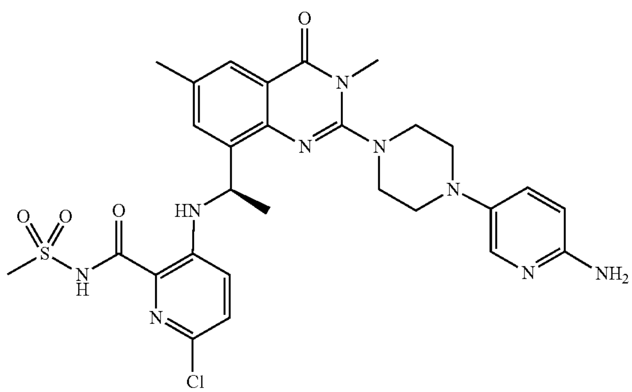 [SMILES: Cc1cc([C@@H](C)Nc2ccc(Cl)nc2C(=O)NS(C)(=O)=O)c2nc(N3CCN(c4ccc(N)nc4)CC3)n(C)c(=O)c2c1] |
| 175 | 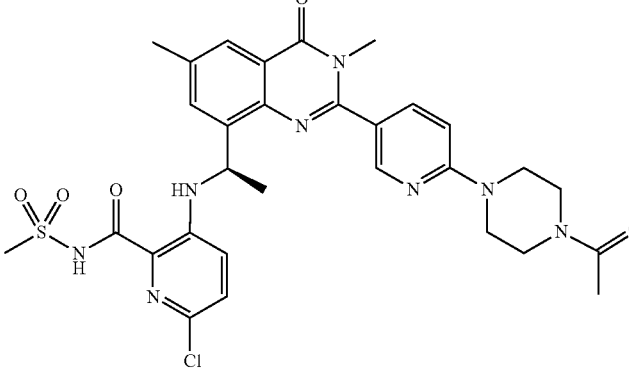 |
| 176 | 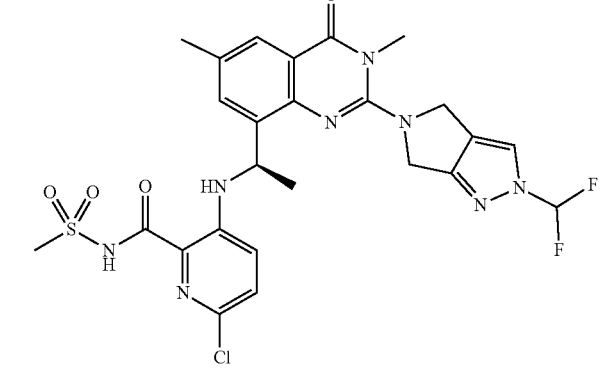 |

TABLE 1-continued
List of Compounds
| Cpd. ID | Chemical structure |
| --- | --- |
| 177 | 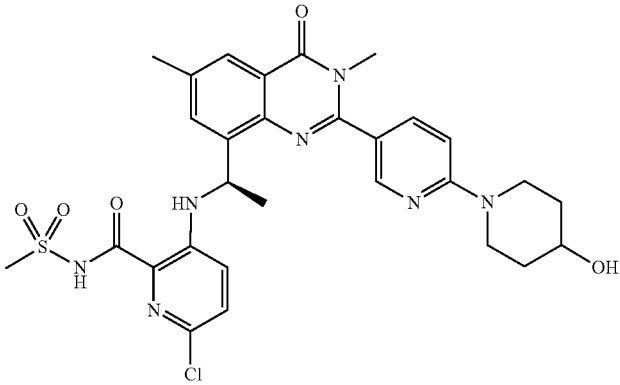 [SMILES: Cc1cc([C@@H](C)Nc2ccc(Cl)nc2C(=O)NS(C)(=O)=O)c2nc(-c3ccc(N4CCC(O)CC4)nc3)n(C)c(=O)c2c1] |
| 178 | 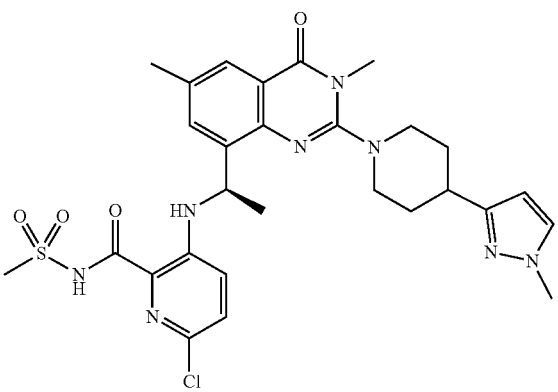 [SMILES: Cc1cc([C@@H](C)Nc2ccc(Cl)nc2C(=O)NS(C)(=O)=O)c2nc(N3CCC(c4ccn(C)n4)CC3)n(C)c(=O)c2c1] |
| 179 | 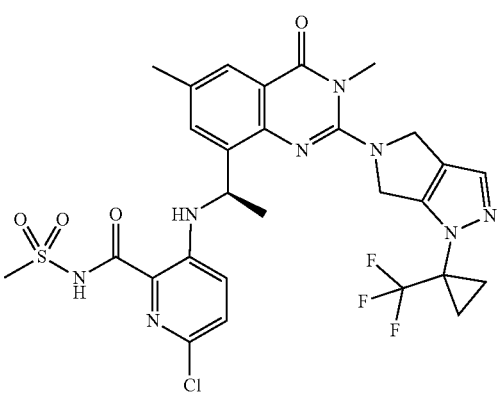 [SMILES: Cc1cc([C@@H](C)Nc2ccc(Cl)nc2C(=O)NS(C)(=O)=O)c2nc(N3Cc4cnn(C5(C(F)(F)F)CC5)c4C3)n(C)c(=O)c2c1] |
| 180 | 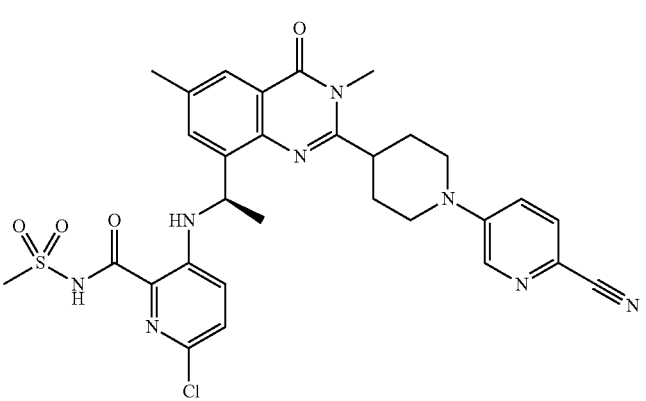 [SMILES: Cc1cc([C@@H](C)Nc2ccc(Cl)nc2C(=O)NS(C)(=O)=O)c2nc(C3CCN(c4ccc(C#N)nc4)CC3)n(C)c(=O)c2c1] |

TABLE 1-continued

List of Compounds

| Cpd. ID | Chemical structure |
|---|---|
| 181 | 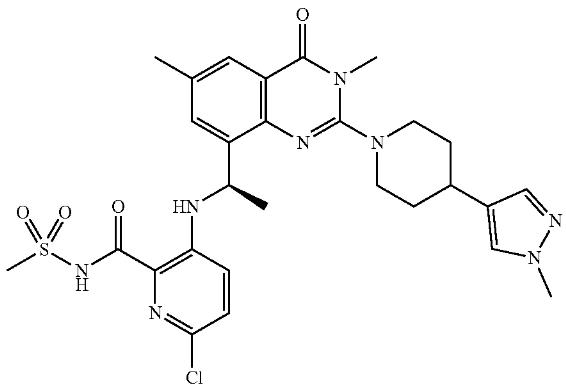 [SMILES: Cc1cc([C@@H](C)Nc2ccc(Cl)nc2C(=O)NS(C)(=O)=O)c2nc(N3CCC(c4cnn(C)c4)CC3)n(C)c(=O)c2c1] |
| 182 | 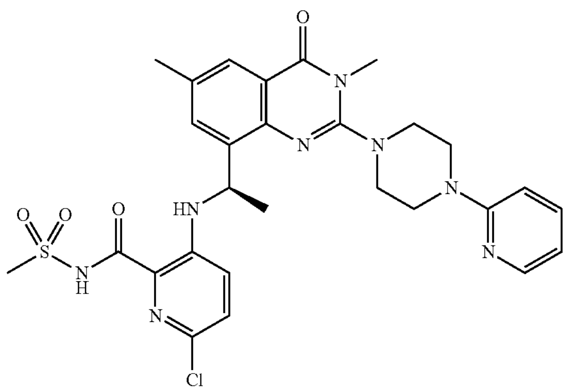 [SMILES: Cc1cc([C@@H](C)Nc2ccc(Cl)nc2C(=O)NS(C)(=O)=O)c2nc(N3CCN(c4ccccn4)CC3)n(C)c(=O)c2c1] |
| 183 | 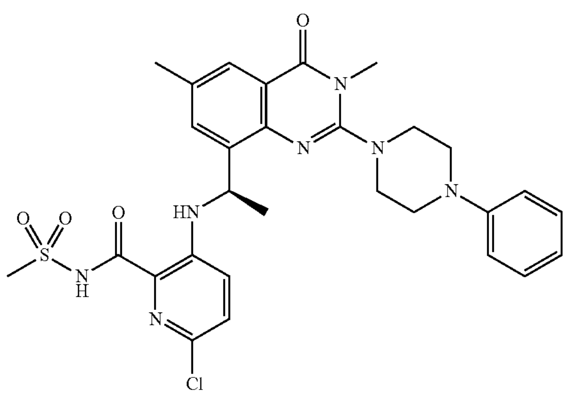 [SMILES: Cc1cc([C@@H](C)Nc2ccc(Cl)nc2C(=O)NS(C)(=O)=O)c2nc(N3CCN(c4ccccc4)CC3)n(C)c(=O)c2c1] |
| 184 | 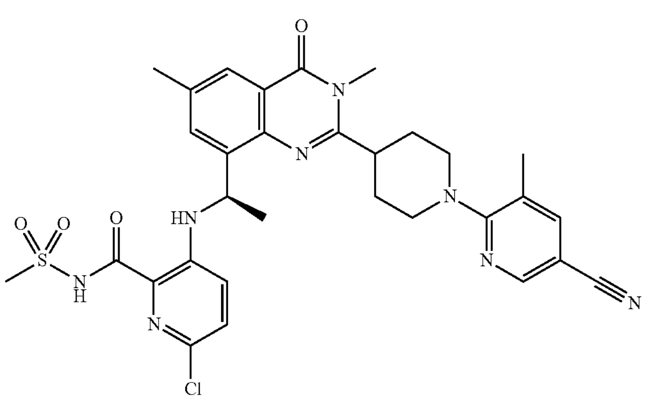 [SMILES: Cc1cc([C@@H](C)Nc2ccc(Cl)nc2C(=O)NS(C)(=O)=O)c2nc(C3CCN(c4ncc(C#N)cc4C)CC3)n(C)c(=O)c2c1] |

TABLE 1-continued
List of Compounds
| Cpd. ID | Chemical structure |
|---|---|
| 185 | 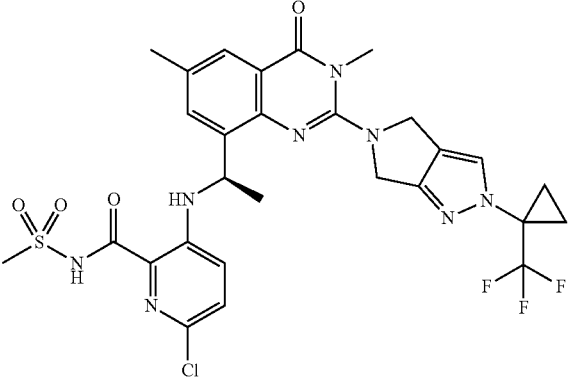 [SMILES: Cc1cc([C@@H](C)Nc2ccc(Cl)nc2C(=O)NS(C)(=O)=O)c2nc(N3Cc4cn(C5(C(F)(F)F)CC5)nc4C3)n(C)c(=O)c2c1] |
| 186 | 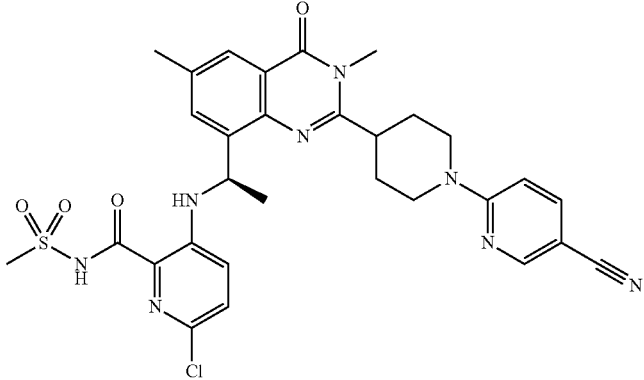 [SMILES: Cc1cc([C@@H](C)Nc2ccc(Cl)nc2C(=O)NS(C)(=O)=O)c2nc(C3CCN(c4ccc(C#N)cn4)CC3)n(C)c(=O)c2c1] |
| 187 | 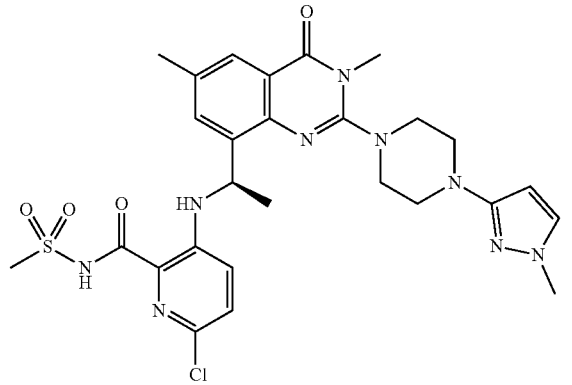 [SMILES: Cc1cc([C@@H](C)Nc2ccc(Cl)nc2C(=O)NS(C)(=O)=O)c2nc(N3CCN(c4ccn(C)n4)CC3)n(C)c(=O)c2c1] |
| 188 | 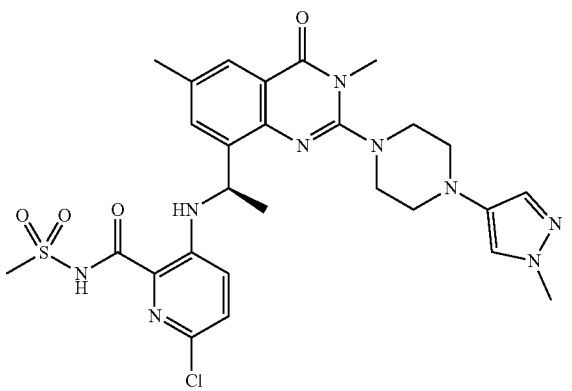 [SMILES: Cc1cc([C@@H](C)Nc2ccc(Cl)nc2C(=O)NS(C)(=O)=O)c2nc(N3CCN(c4cnn(C)c4)CC3)n(C)c(=O)c2c1] |

TABLE 1-continued

List of Compounds

| Cpd. ID | Chemical structure |
|---|---|
| 189 | 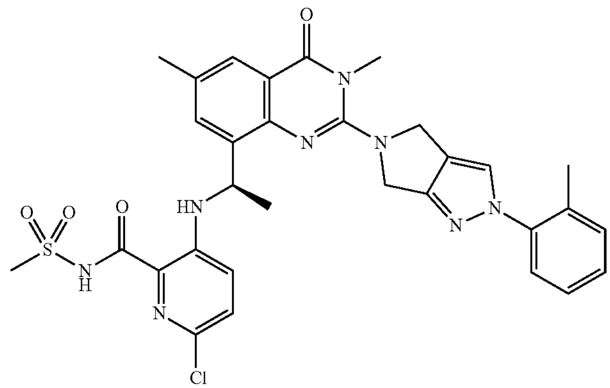 [SMILES: Cc1cc([C@@H](C)Nc2ccc(Cl)nc2C(=O)NS(C)(=O)=O)c2nc(N3Cc4cn(-c5ccccc5C)nc4C3)n(C)c(=O)c2c1] |
| 190 | 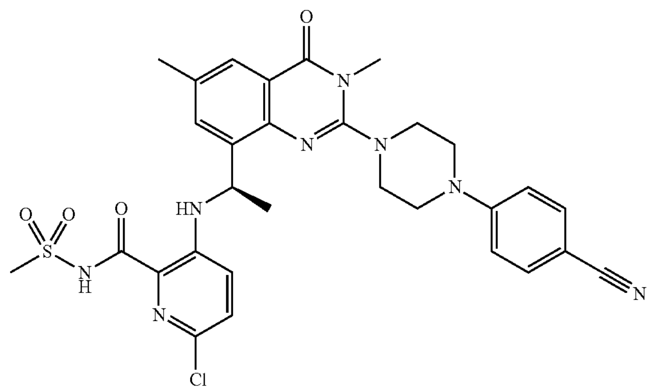 [SMILES: Cc1cc([C@@H](C)Nc2ccc(Cl)nc2C(=O)NS(C)(=O)=O)c2nc(N3CCN(c4ccc(C#N)cc4)CC3)n(C)c(=O)c2c1] |
| 191 | 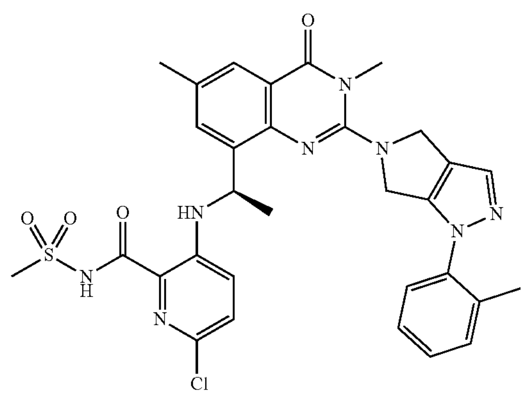 |
| 192 | 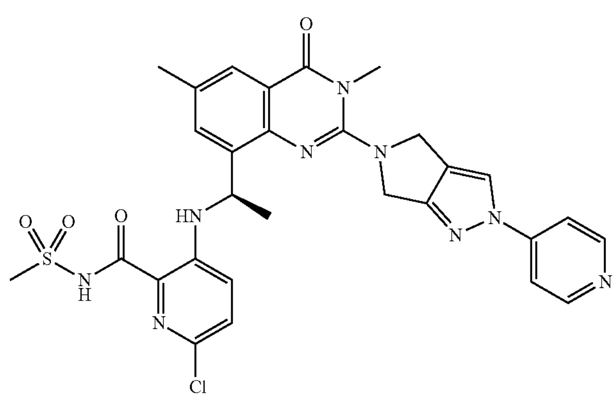 [SMILES: Cc1cc([C@@H](C)Nc2ccc(Cl)nc2C(=O)NS(C)(=O)=O)c2nc(N3Cc4cn(-c5ccncc5)nc4C3)n(C)c(=O)c2c1] |

TABLE 1-continued
List of Compounds
| Cpd. ID | Chemical structure |
|---|---|
| 193 | 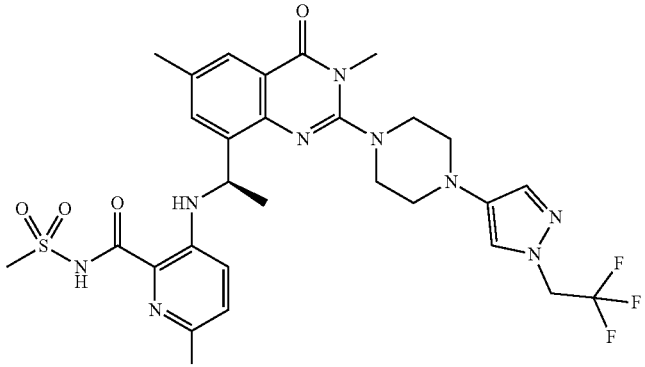 |
| 194 | 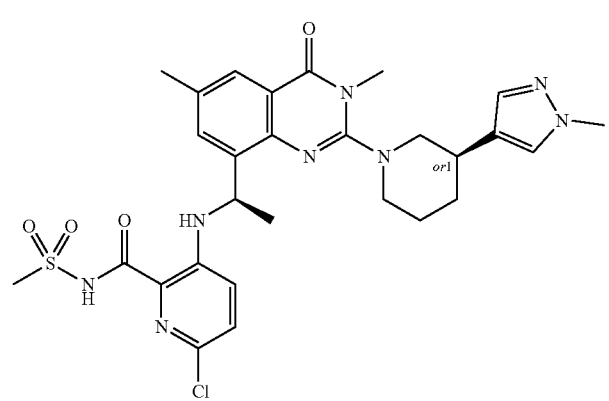 |
| 195 | 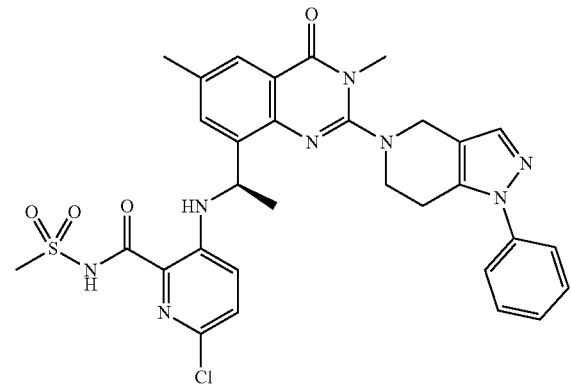 [SMILES: Cc1cc([C@@H](C)Nc2ccc(Cl)nc2C(=O)NS(C)(=O)=O)c2nc(N3CCc4c(cnn4-c4ccccc4)C3)n(C)c(=O)c2c1] |
| 196 | 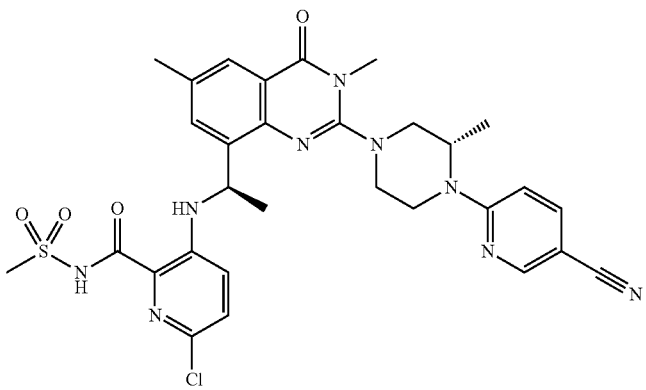 [SMILES: Cc1cc([C@@H](C)Nc2ccc(Cl)nc2C(=O)NS(C)(=O)=O)c2nc(N3CCN(c4ccc(C#N)cn4)[C@@H](C)C3)n(C)c(=O)c2c1] |

TABLE 1-continued

List of Compounds

| Cpd. ID | Chemical structure |
|---|---|
| 197 | 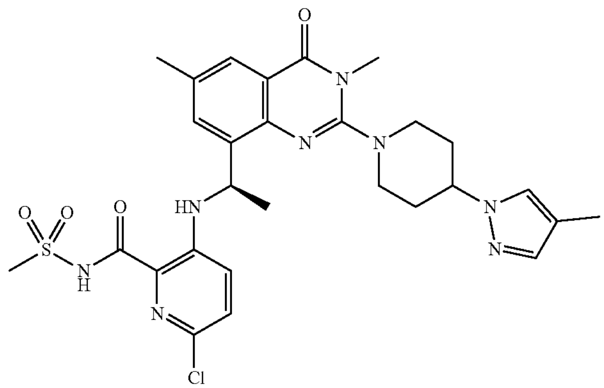 |
| 198 | 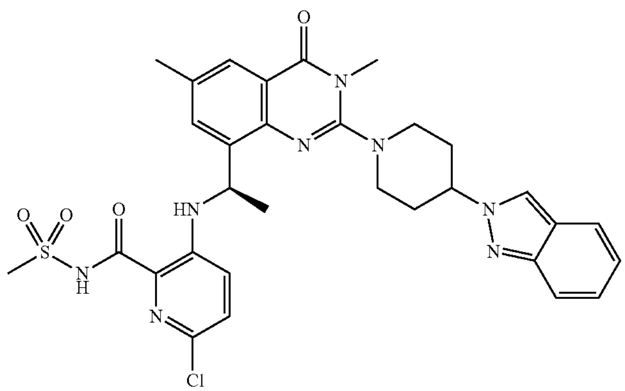 [SMILES: Cc1cc([C@@H](C)Nc2ccc(Cl)nc2C(=O)NS(C)(=O)=O)c2nc(N3CCC(n4cc5ccccc5n4)CC3)n(C)c(=O)c2c1] |
| 199 | 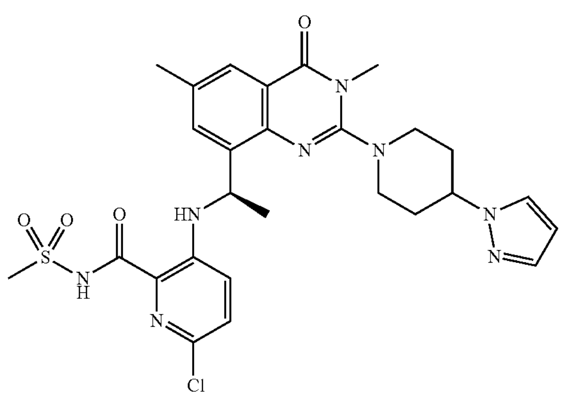 [SMILES: Cc1cc([C@@H](C)Nc2ccc(Cl)nc2C(=O)NS(C)(=O)=O)c2nc(N3CCC(n4cccn4)CC3)n(C)c(=O)c2c1] |
| 200 | 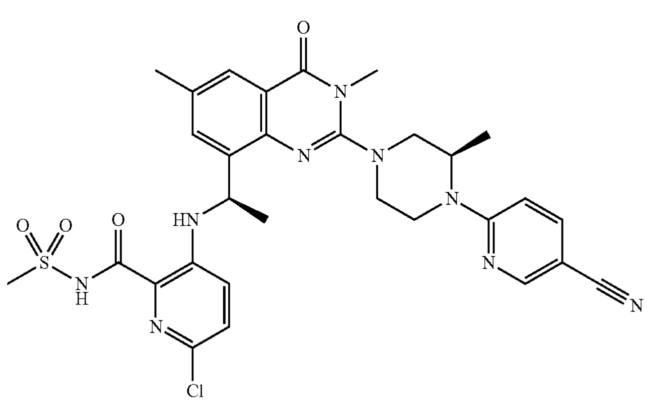 [SMILES: Cc1cc([C@@H](C)Nc2ccc(Cl)nc2C(=O)NS(C)(=O)=O)c2nc(N3CCN(c4ccc(C#N)cn4)[C@H](C)C3)n(C)c(=O)c2c1] |

TABLE 1-continued

List of Compounds

| Cpd. ID | Chemical structure |
|---|---|
| 201 | 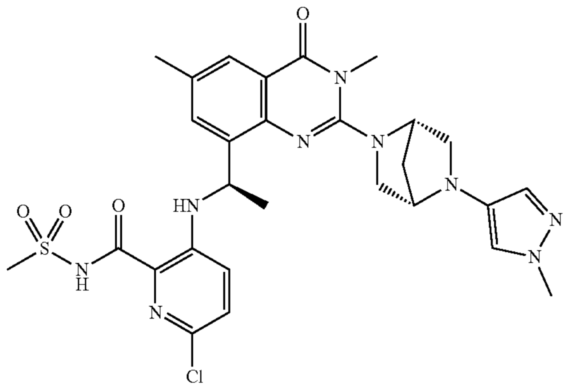 [SMILES: Cc1cc([C@@H](C)Nc2ccc(Cl)nc2C(=O)NS(C)(=O)=O)c2nc(N3C[C@@H]4C[C@H]3CN4c3cnn(C)c3)n(C)c(=O)c2c1] |
| 202 | 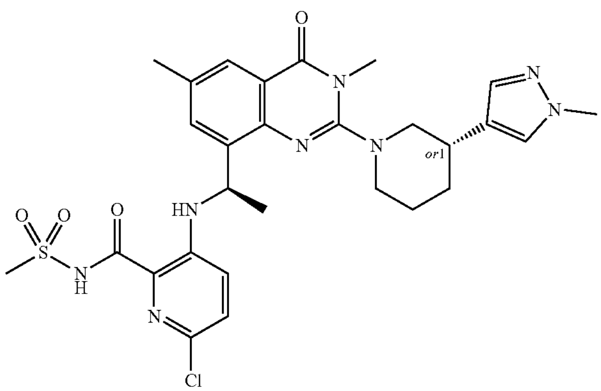 |
| 203 | 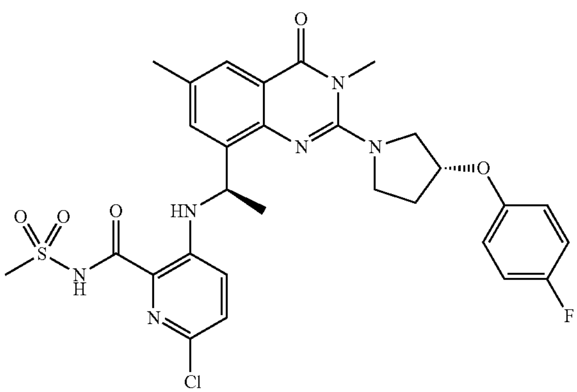 [SMILES: Cc1cc([C@@H](C)Nc2ccc(Cl)nc2C(=O)NS(C)(=O)=O)c2nc(N3CC[C@@H](Oc4ccc(F)cc4)C3)n(C)c(=O)c2c1] |
| 204 | 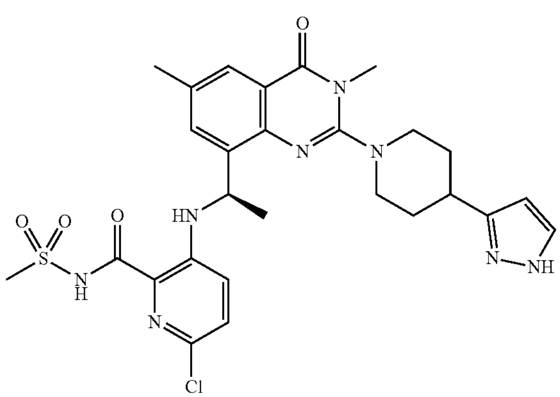 |

TABLE 1-continued

List of Compounds

| Cpd. ID | Chemical structure |
|---------|--------------------|
| 205 | 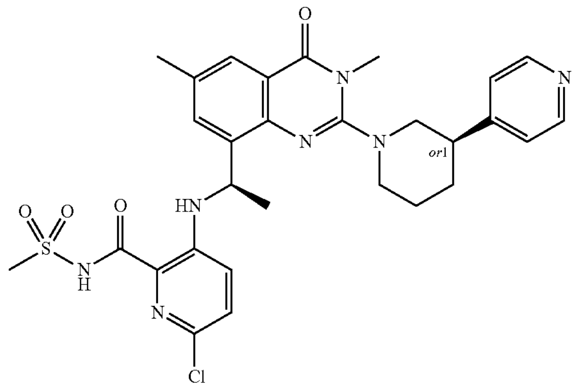 [SMILES: Cc1cc([C@@H](C)Nc2ccc(Cl)nc2C(=O)NS(C)(=O)=O)c2nc(N3CCC[C@H](c4ccncc4)C3)n(C)c(=O)c2c1] |
| 206 | 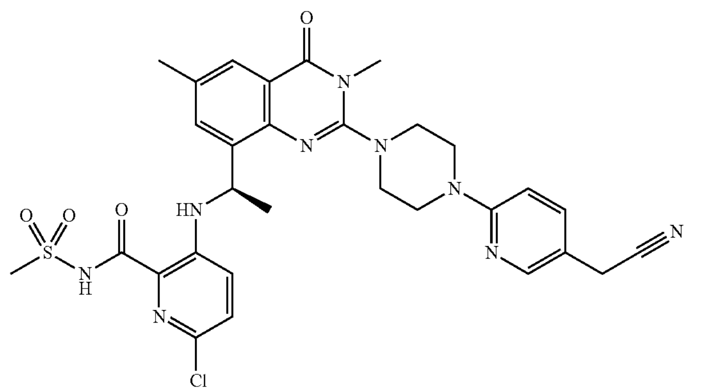 [SMILES: Cc1cc([C@@H](C)Nc2ccc(Cl)nc2C(=O)NS(C)(=O)=O)c2nc(N3CCN(c4ccc(CC#N)cn4)CC3)n(C)c(=O)c2c1] |
| 207 | 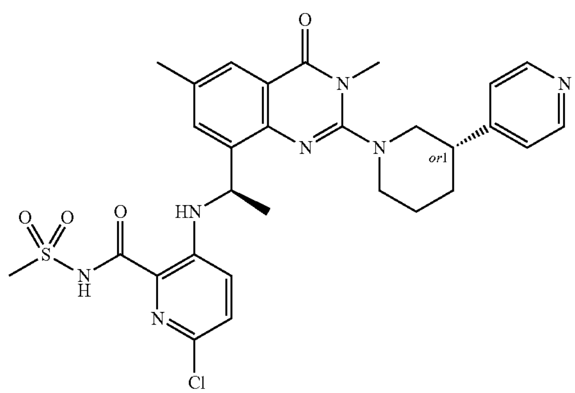 [SMILES: Cc1cc([C@@H](C)Nc2ccc(Cl)nc2C(=O)NS(C)(=O)=O)c2nc(N3CCC[C@@H](c4ccncc4)C3)n(C)c(=O)c2c1] |
| 208 | 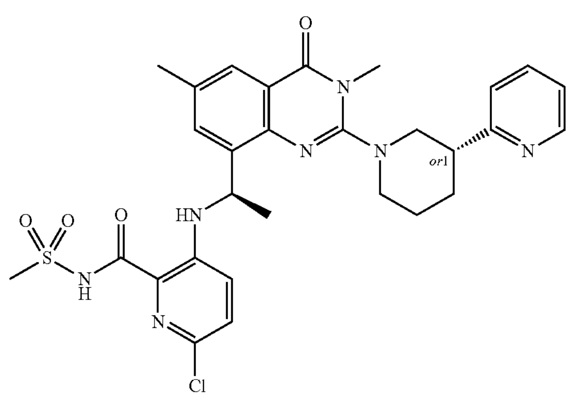 [SMILES: Cc1cc([C@@H](C)Nc2ccc(Cl)nc2C(=O)NS(C)(=O)=O)c2nc(N3CCC[C@@H](c4ccccn4)C3)n(C)c(=O)c2c1] |

TABLE 1-continued

List of Compounds

| Cpd. ID | Chemical structure |
|---|---|
| 209 | 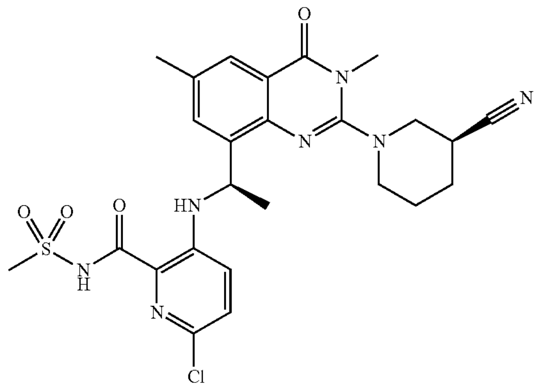 [SMILES: Cc1cc([C@@H](C)Nc2ccc(Cl)nc2C(=O)NS(C)(=O)=O)c2nc(N3CCC[C@H](C#N)C3)n(C)c(=O)c2c1] |
| 210 | 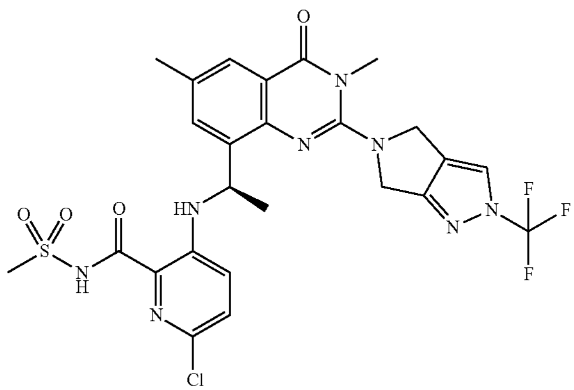 [SMILES: Cc1cc([C@@H](C)Nc2ccc(Cl)nc2C(=O)NS(C)(=O)=O)c2nc(N3Cc4cn(C(F)(F)F)nc4C3)n(C)c(=O)c2c1] |
| 211 | 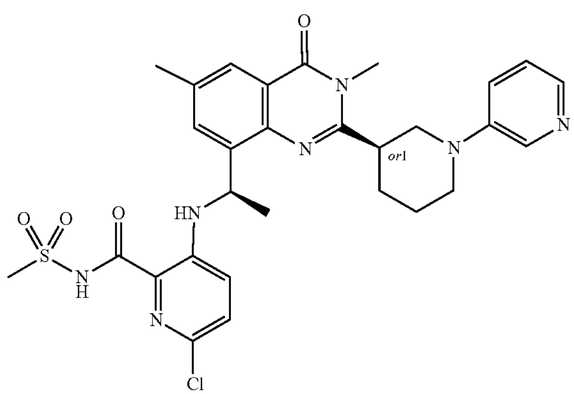 [SMILES: Cc1cc([C@@H](C)Nc2ccc(Cl)nc2C(=O)NS(C)(=O)=O)c2nc([C@@H]3CCCN(c4cccnc4)C3)n(C)c(=O)c2c1] |
| 212 | 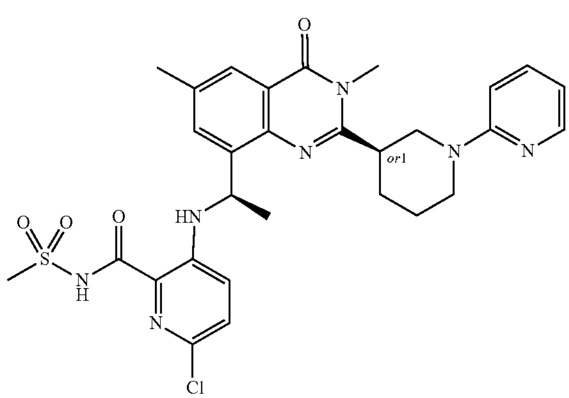 [SMILES: Cc1cc([C@@H](C)Nc2ccc(Cl)nc2C(=O)NS(C)(=O)=O)c2nc([C@@H]3CCCN(c4ccccn4)C3)n(C)c(=O)c2c1] |

TABLE 1-continued

List of Compounds

| Cpd. ID | Chemical structure |
|---|---|
| 213 | 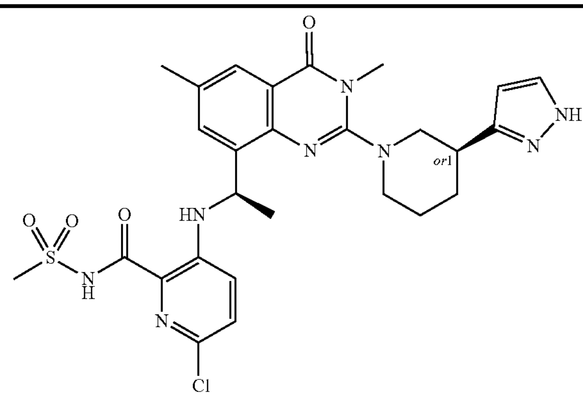 |
| 214 | 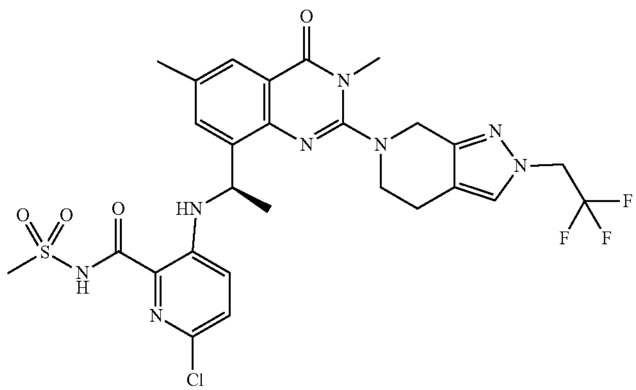 [SMILES: Cc1cc([C@@H](C)Nc2ccc(Cl)nc2C(=O)NS(C)(=O)=O)c2nc(N3CCc4cn(CC(F)(F)F)nc4C3)n(C)c(=O)c2c1] |
| 215 | 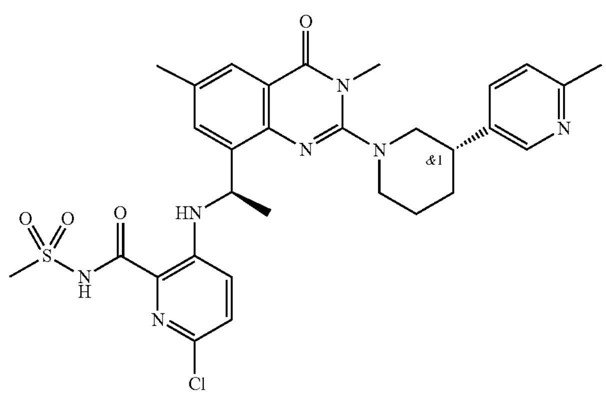 |
| 216 | 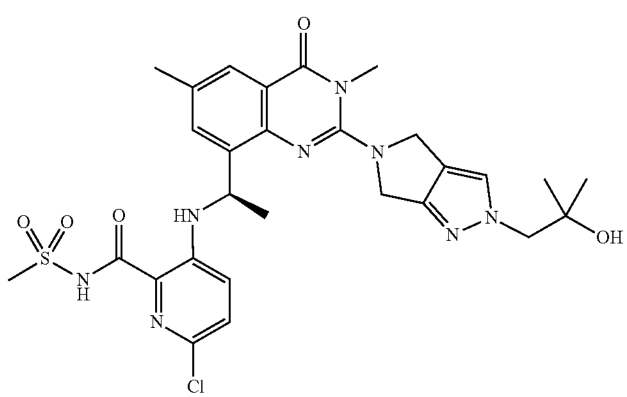 [SMILES: Cc1cc([C@@H](C)Nc2ccc(Cl)nc2C(=O)NS(C)(=O)=O)c2nc(N3Cc4cn(CC(C)(C)O)nc4C3)n(C)c(=O)c2c1] |

TABLE 1-continued
List of Compounds
| Cpd. ID | Chemical structure |
|---|---|
| 217 | 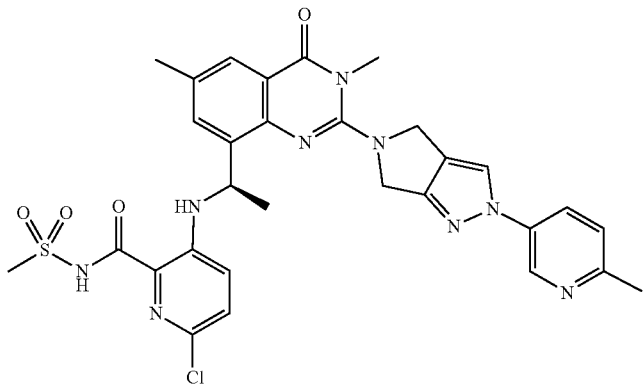 |
| 218 | 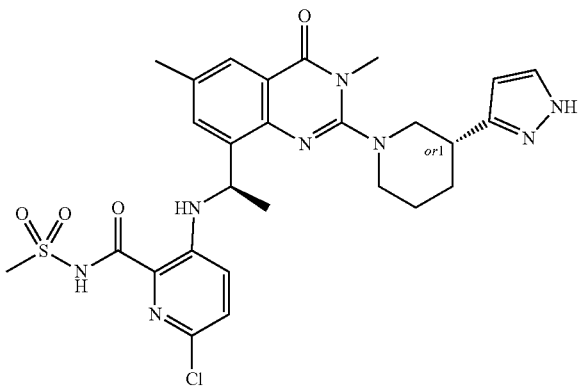 [SMILES: Cc1cc([C@@H](C)Nc2ccc(Cl)nc2C(=O)NS(C)(=O)=O)c2nc(N3CCC[C@@H](c4cc[nH]n4)C3)n(C)c(=O)c2c1] |
| 219 | 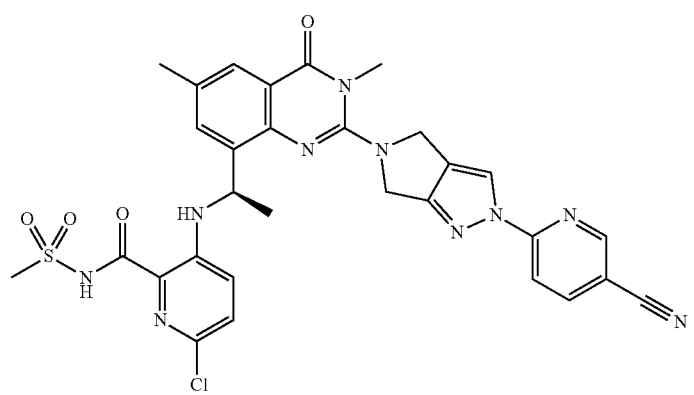 [SMILES: Cc1cc([C@@H](C)Nc2ccc(Cl)nc2C(=O)NS(C)(=O)=O)c2nc(N3Cc4cn(-c5ccc(C#N)cn5)nc4C3)n(C)c(=O)c2c1] |
| 220 | 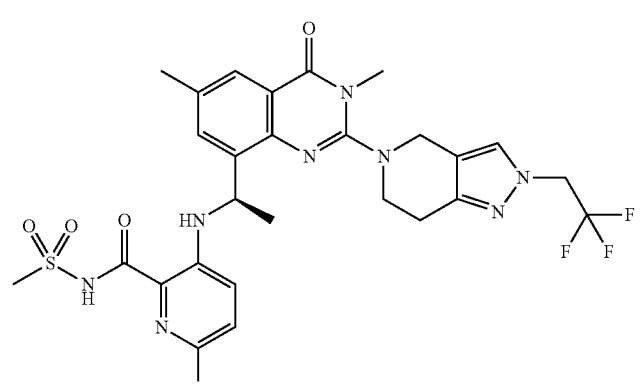 |

TABLE 1-continued

List of Compounds

| Cpd. ID | Chemical structure |
|---|---|
| 221 | 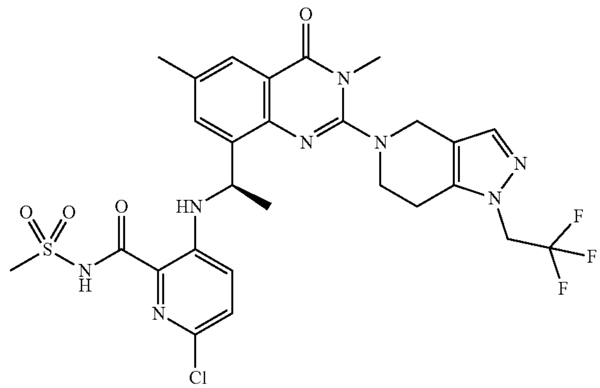 [SMILES: Cc1cc([C@@H](C)Nc2ccc(Cl)nc2C(=O)NS(C)(=O)=O)c2nc(N3CCc4c(cnn4CC(F)(F)F)C3)n(C)c(=O)c2c1] |
| 222 | 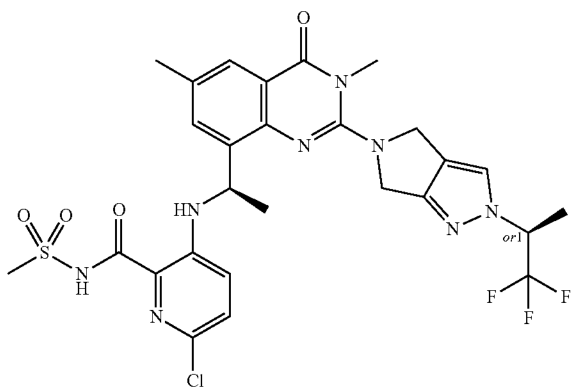 [SMILES: Cc1cc([C@@H](C)Nc2ccc(Cl)nc2C(=O)NS(C)(=O)=O)c2nc(N3Cc4cn([C@@H](C)C(F)(F)F)nc4C3)n(C)c(=O)c2c1] |
| 223 | 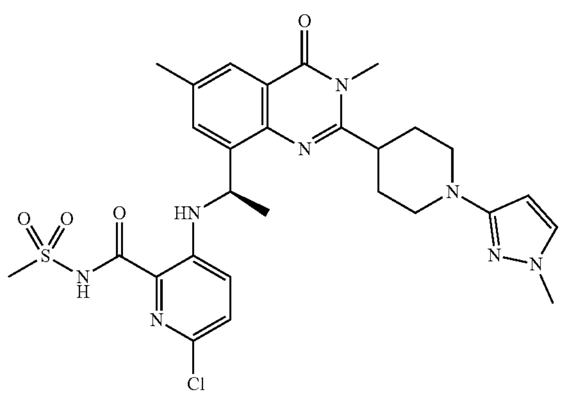 |
| 224 | 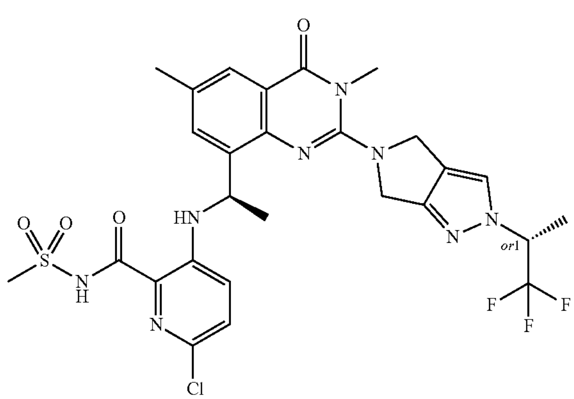 [SMILES: Cc1cc([C@@H](C)Nc2ccc(Cl)nc2C(=O)NS(C)(=O)=O)c2nc(N3Cc4cn([C@H](C)C(F)(F)F)nc4C3)n(C)c(=O)c2c1] |

TABLE 1-continued
List of Compounds
| Cpd. ID | Chemical structure |
|---|---|
| 225 | 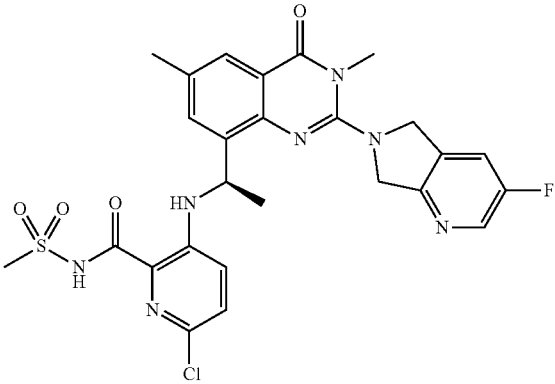 [SMILES: Cc1cc([C@@H](C)Nc2ccc(Cl)nc2C(=O)NS(C)(=O)=O)c2nc(N3Cc4cc(F)cnc4C3)n(C)c(=O)c2c1] |
| 226 | 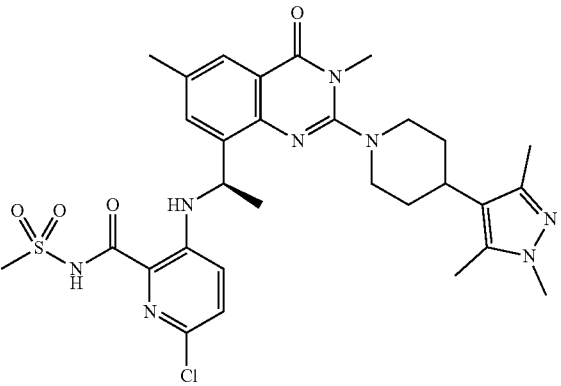 [SMILES: Cc1cc([C@@H](C)Nc2ccc(Cl)nc2C(=O)NS(C)(=O)=O)c2nc(N3CCC(c4c(C)nn(C)c4C)CC3)n(C)c(=O)c2c1] |
| 227 | 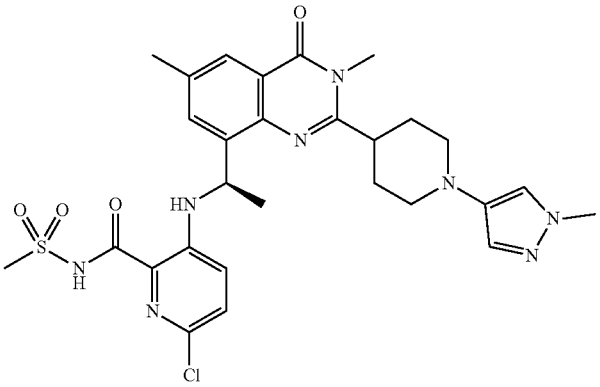 |
| 228 | 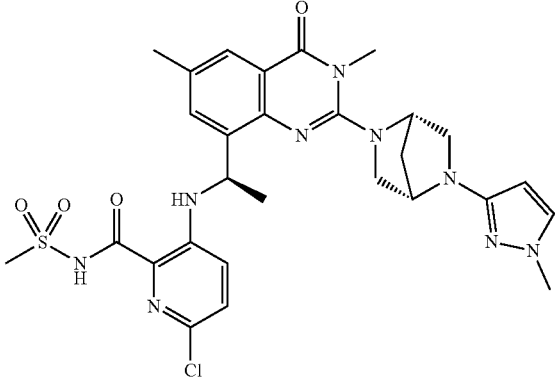 [SMILES: Cc1cc([C@@H](C)Nc2ccc(Cl)nc2C(=O)NS(C)(=O)=O)c2nc(N3C[C@@H]4C[C@H]3CN4c3ccn(C)n3)n(C)c(=O)c2c1] |

TABLE 1-continued

List of Compounds

| Cpd. ID | Chemical structure |
|---|---|
| 229 | 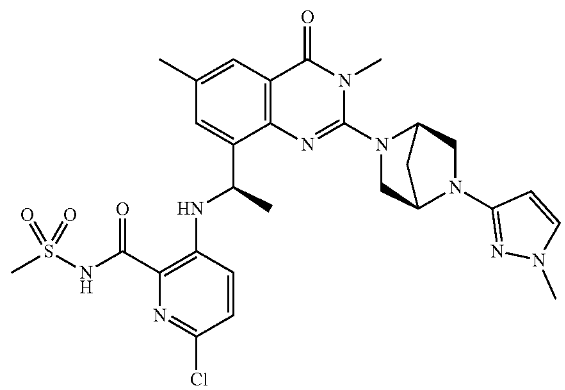 [SMILES: Cc1cc([C@@H](C)Nc2ccc(Cl)nc2C(=O)NS(C)(=O)=O)c2nc(N3C[C@H]4C[C@@H]3CN4c3ccn(C)n3)n(C)c(=O)c2c1] |
| 230 | 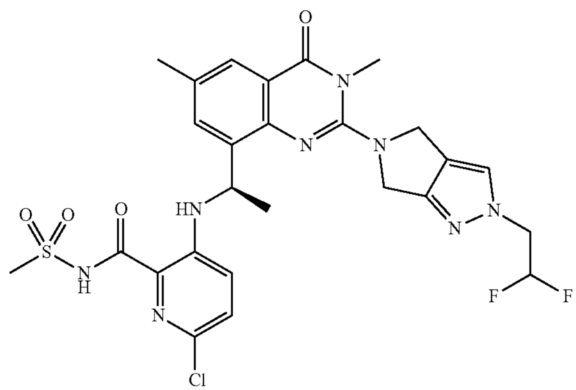 [SMILES: Cc1cc([C@@H](C)Nc2ccc(Cl)nc2C(=O)NS(C)(=O)=O)c2nc(N3Cc4cn(CC(F)F)nc4C3)n(C)c(=O)c2c1] |
| 231 | 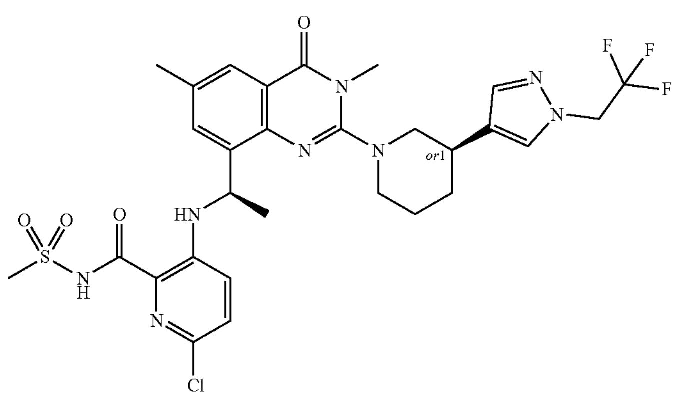 |
| 232 | 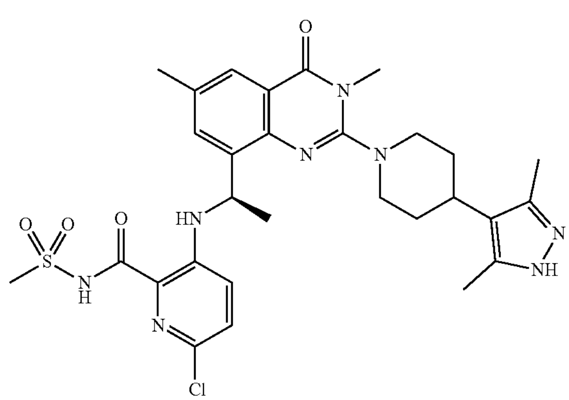 [SMILES: Cc1cc([C@@H](C)Nc2ccc(Cl)nc2C(=O)NS(C)(=O)=O)c2nc(N3CCC(c4c(C)n[nH]c4C)CC3)n(C)c(=O)c2c1] |

TABLE 1-continued

List of Compounds

| Cpd. ID | Chemical structure |
|---|---|
| 233 | 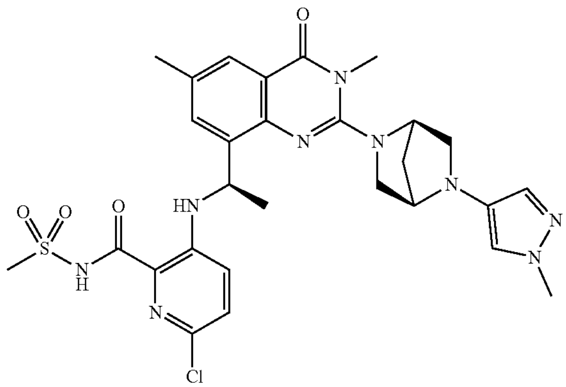 [SMILES: Cc1cc([C@@H](C)Nc2ccc(Cl)nc2C(=O)NS(C)(=O)=O)c2nc(N3C[C@H]4C[C@@H]3CN4c3cnn(C)c3)n(C)c(=O)c2c1] |
| 234 | 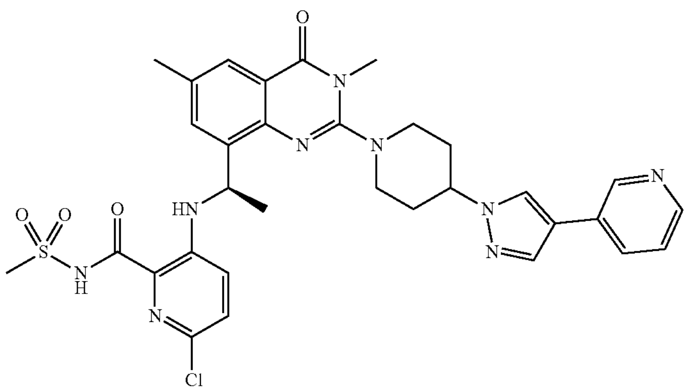 [SMILES: Cc1cc([C@@H](C)Nc2ccc(Cl)nc2C(=O)NS(C)(=O)=O)c2nc(N3CCC(n4cc(-c5ccccc5)cn4)CC3)n(C)c(=O)c2c1] |
| 235 | 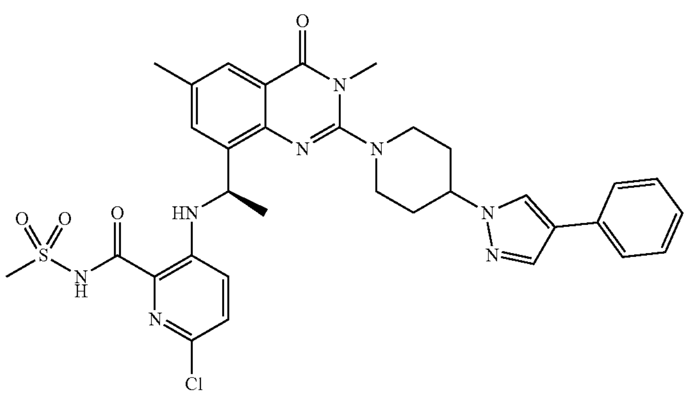 |
| 236 | 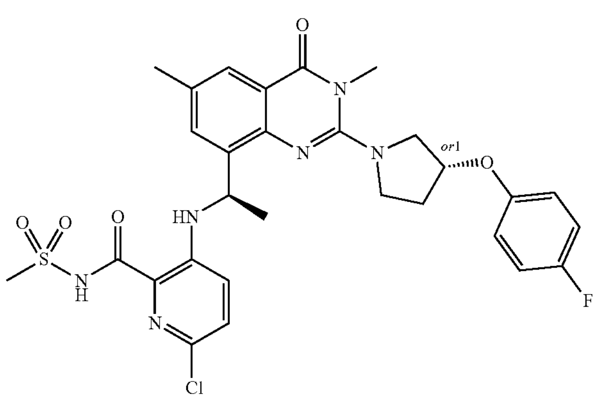 [SMILES: Cc1cc([C@@H](C)Nc2ccc(Cl)nc2C(=O)NS(C)(=O)=O)c2nc(N3CC[C@@H](Oc4ccc(F)cc4)C3)n(C)c(=O)c2c1] |

TABLE 1-continued

List of Compounds

| Cpd. ID | Chemical structure |
|---|---|
| 237 | 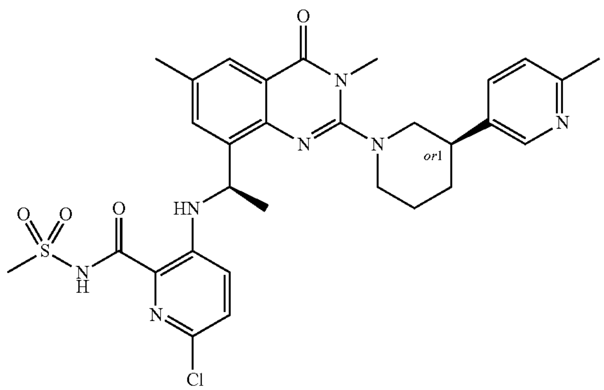 |
| 238 | 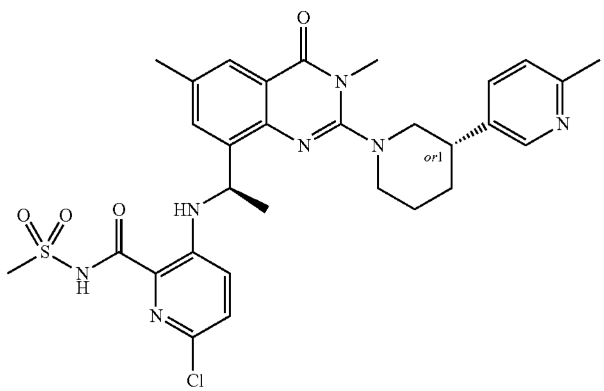 |
| 239 | 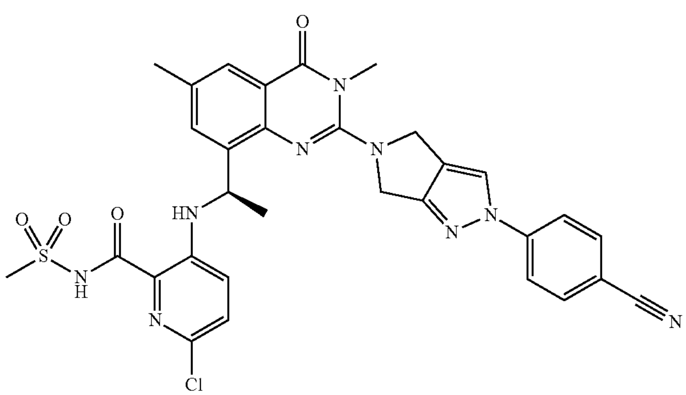 [SMILES: Cc1cc([C@@H](C)Nc2ccc(Cl)nc2C(=O)NS(C)(=O)=O)c2nc(N3Cc4cn(-c5ccc(C#N)cc5)nc4C3)n(C)c(=O)c2c1] |
| 240 | 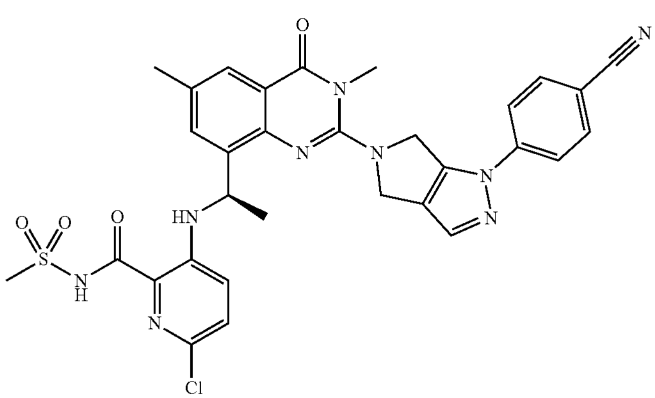 [SMILES: Cc1cc([C@@H](C)Nc2ccc(Cl)nc2C(=O)NS(C)(=O)=O)c2nc(N3Cc4cnn(-c5ccc(C#N)cc5)c4C3)n(C)c(=O)c2c1] |

TABLE 1-continued

List of Compounds

| Cpd. ID | Chemical structure |
|---|---|
| 241 | 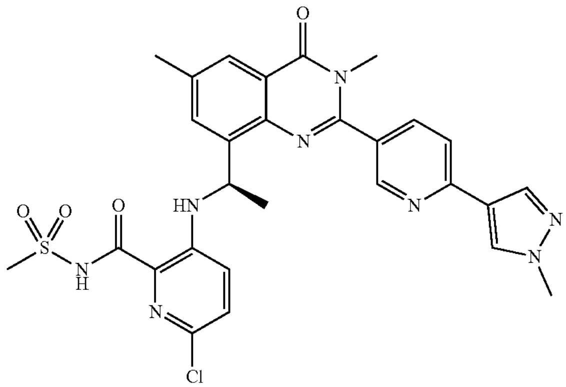 [SMILES: Cc1cc([C@@H](C)Nc2ccc(Cl)nc2C(=O)NS(C)(=O)=O)c2nc(-c3ccc(-c4cnn(C)c4)nc3)n(C)c(=O)c2c1] |
| 242 | 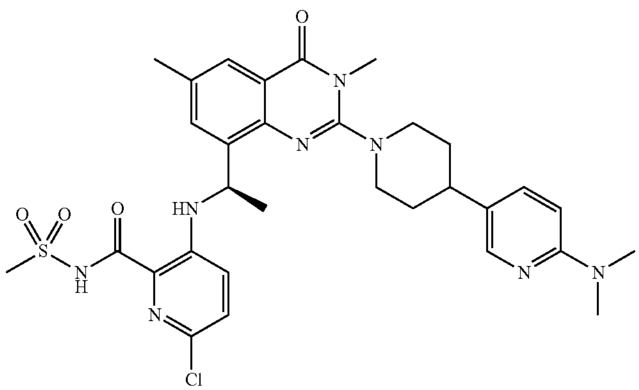 |
| 243 | 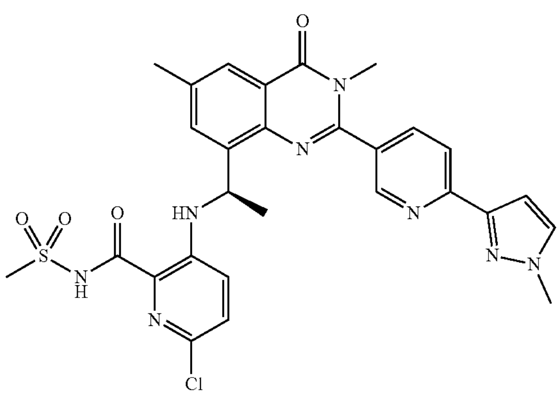 [SMILES: Cc1cc([C@@H](C)Nc2ccc(Cl)nc2C(=O)NS(C)(=O)=O)c2nc(-c3ccc(-c4ccn(C)n4)nc3)n(C)c(=O)c2c1] |
| 244 | 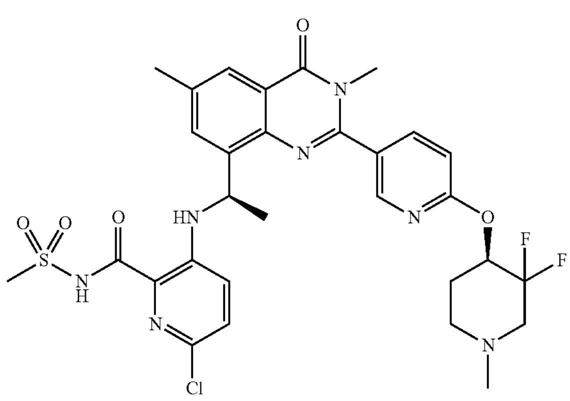 [SMILES: Cc1cc([C@@H](C)Nc2ccc(Cl)nc2C(=O)NS(C)(=O)=O)c2nc(-c3ccc(O[C@@H]4CCN(C)CC4(F)F)nc3)n(C)c(=O)c2c1] |

TABLE 1-continued
List of Compounds
| Cpd. ID | Chemical structure |
|---|---|
| 245 | 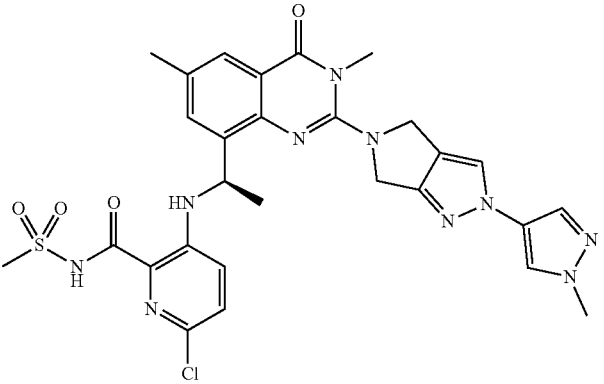 [SMILES: Cc1cc([C@@H](C)Nc2ccc(Cl)nc2C(=O)NS(C)(=O)=O)c2nc(N3Cc4cn(-c5cnn(C)c5)nc4C3)n(C)c(=O)c2c1] |
| 246 | 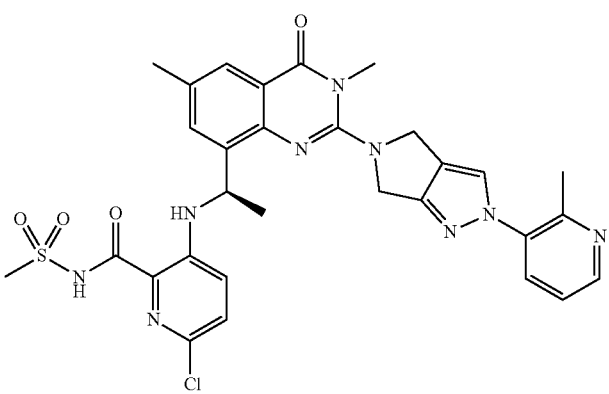 [SMILES: Cc1cc([C@@H](C)Nc2ccc(Cl)nc2C(=O)NS(C)(=O)=O)c2nc(N3Cc4cn(-c5cccnc5C)nc4C3)n(C)c(=O)c2c1] |
| 247 | 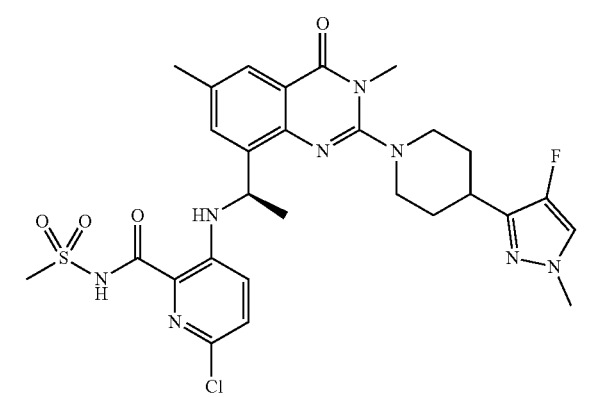 [SMILES: Cc1cc([C@@H](C)Nc2ccc(Cl)nc2C(=O)NS(C)(=O)=O)c2nc(N3CCC(c4nn(C)cc4F)CC3)n(C)c(=O)c2c1] |
| 248 | 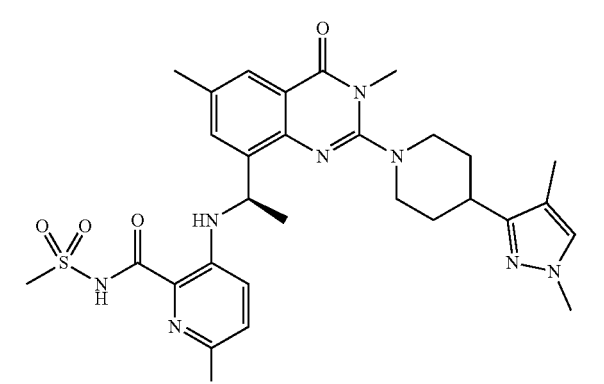 |

TABLE 1-continued

List of Compounds

| Cpd. ID | Chemical structure |
|---|---|
| 249 | 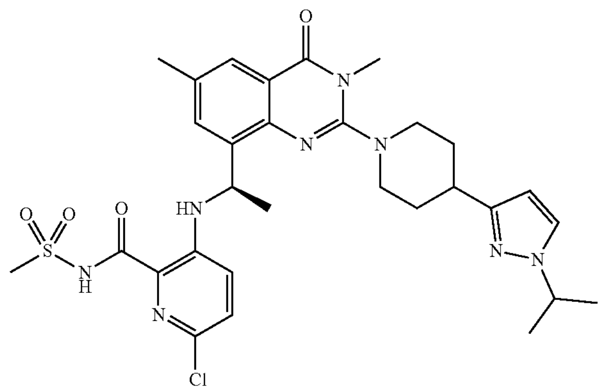 [SMILES: Cc1cc([C@@H](C)Nc2ccc(Cl)nc2C(=O)NS(C)(=O)=O)c2nc(N3CCC(c4ccn(C(C)C)n4)CC3)n(C)c(=O)c2c1] |
| 250 | 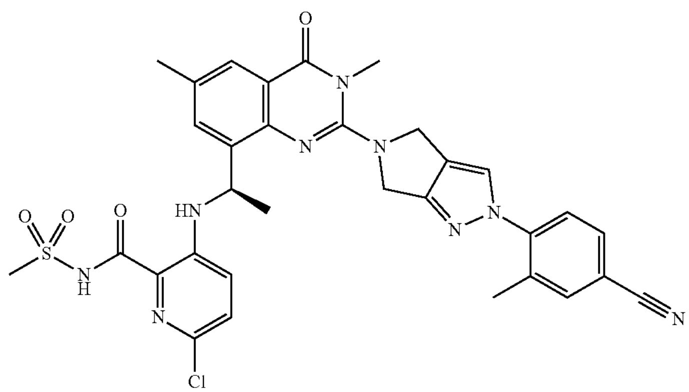 [SMILES: Cc1cc([C@@H](C)Nc2ccc(Cl)nc2C(=O)NS(C)(=O)=O)c2nc(N3Cc4cn(-c5ccc(C#N)cc5C)nc4C3)n(C)c(=O)c2c1] |
| 251 | 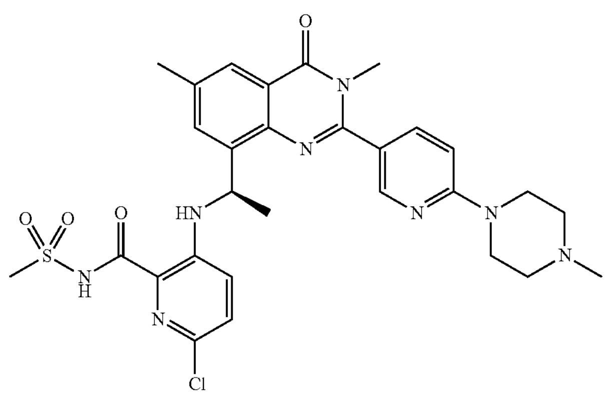 |
| 252 | 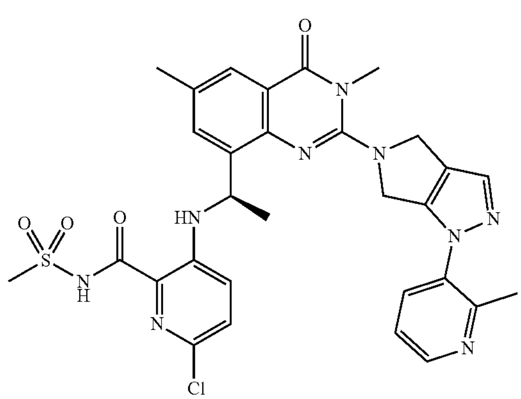 |

TABLE 1-continued

List of Compounds

| Cpd. ID | Chemical structure |
| --- | --- |
| 253 | 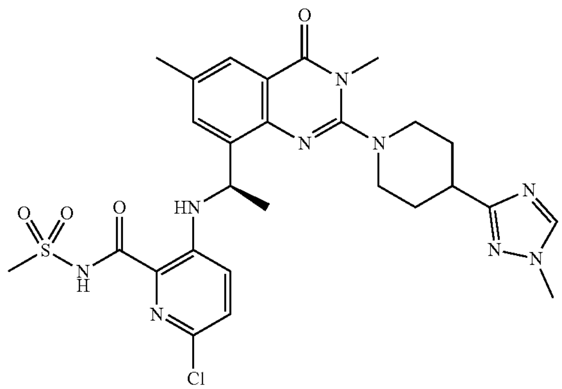 [SMILES: Cc1cc([C@@H](C)Nc2ccc(Cl)nc2C(=O)NS(C)(=O)=O)c2nc(N3CCC(c4ncn(C)n4)CC3)n(C)c(=O)c2c1] |
| 254 | 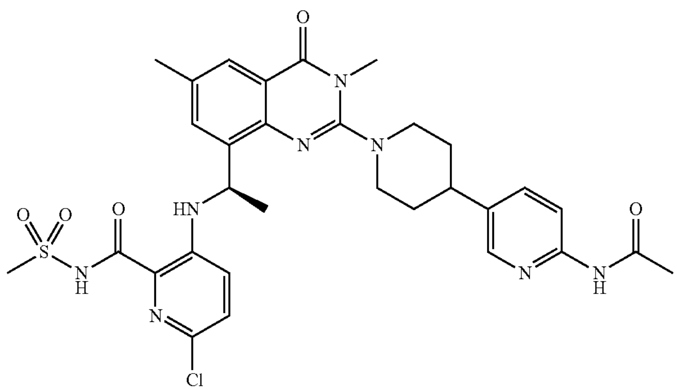 [SMILES: CC(=O)Nc1ccc(C2CCN(c3nc4c([C@@H](C)Nc5ccc(Cl)nc5C(=O)NS(C)(=O)=O)cc(C)cc4c(=O)n3C)CC2)cn1] |
| 255 | 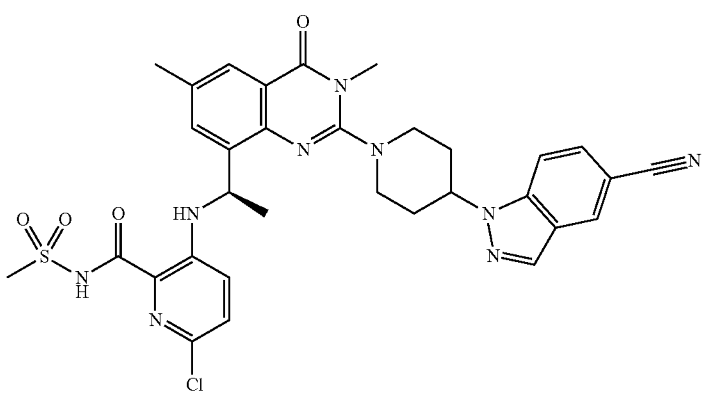 [SMILES: Cc1cc([C@@H](C)Nc2ccc(Cl)nc2C(=O)NS(C)(=O)=O)c2nc(N3CCC(n4ncc5cc(C#N)ccc54)CC3)n(C)c(=O)c2c1] |
| 256 | 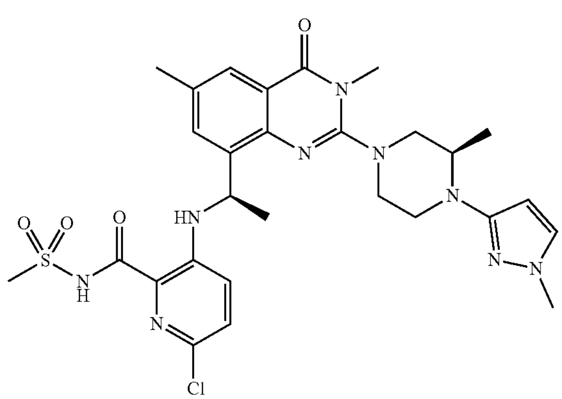 [SMILES: Cc1cc([C@@H](C)Nc2ccc(Cl)nc2C(=O)NS(C)(=O)=O)c2nc(N3CCN(c4ccn(C)n4)[C@H](C)C3)n(C)c(=O)c2c1] |

TABLE 1-continued
List of Compounds
| Cpd. ID | Chemical structure |
|---|---|
| 257 | 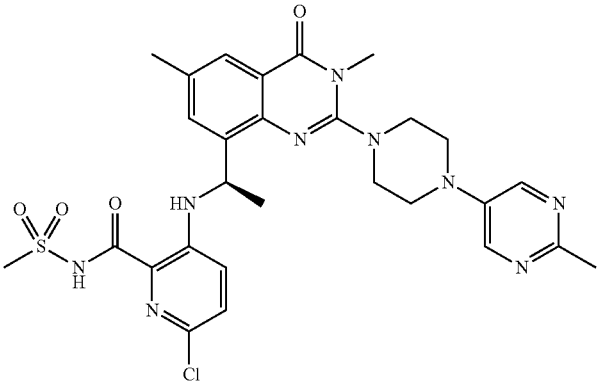 |
| 258 | 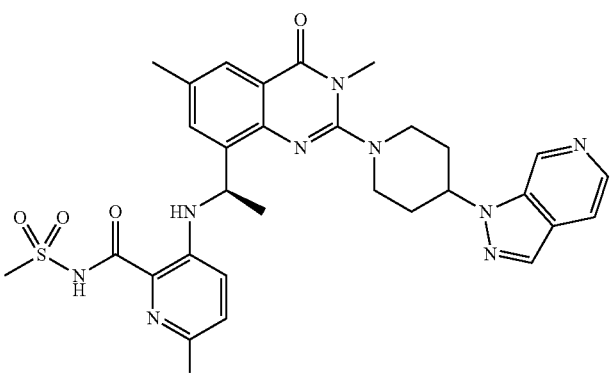 |
| 259 | 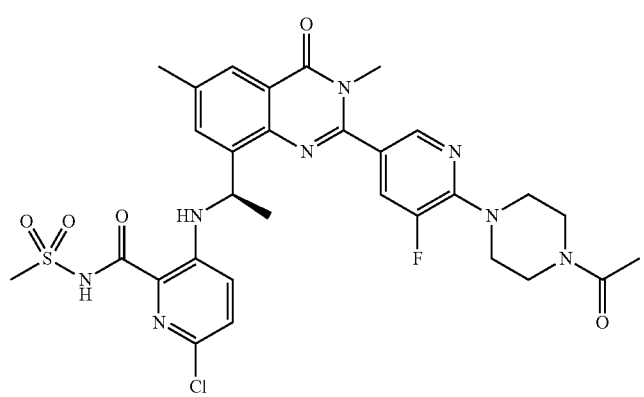 |
| 260 | 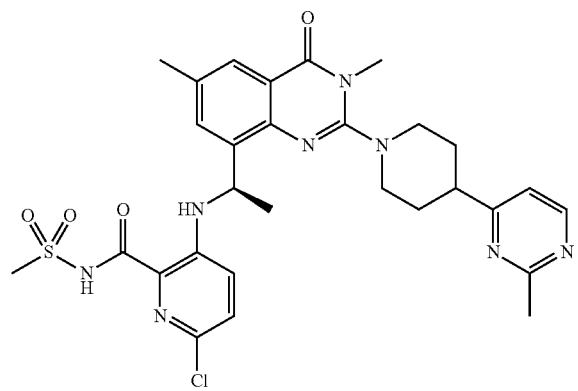 [SMILES: Cc1cc([C@@H](C)Nc2ccc(Cl)nc2C(=O)NS(C)(=O)=O)c2nc(N3CCC(c4ccnc(C)n4)CC3)n(C)c(=O)c2c1] |

TABLE 1-continued
| Cpd. ID | Chemical structure |
|---|---|
| 261 | 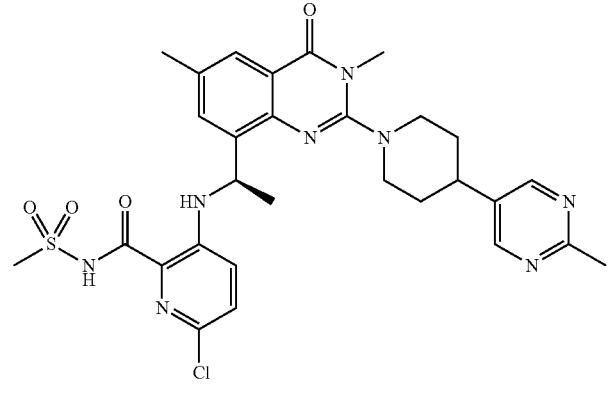 |
| 262 | 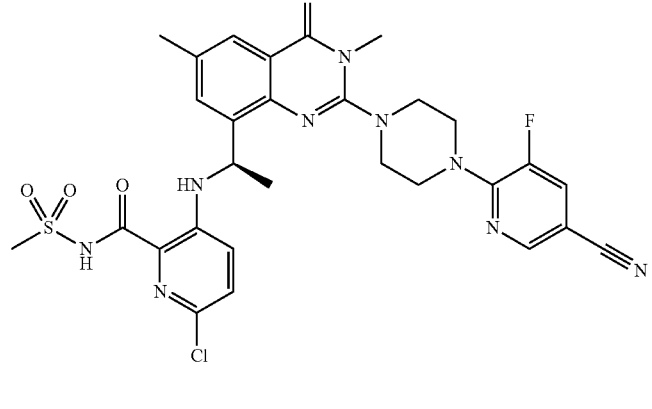 |
| 263 | 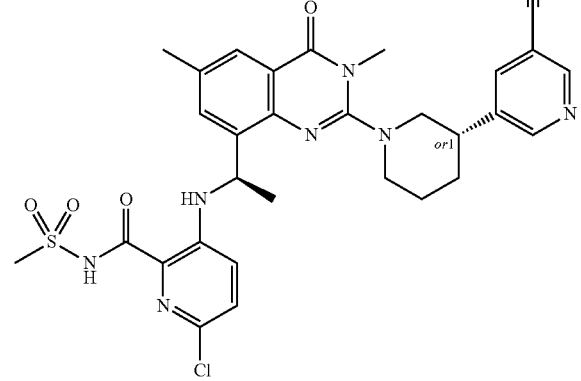 |

TABLE 1-continued

List of Compounds

| Cpd. ID | Chemical structure |
|---|---|
| 264 | 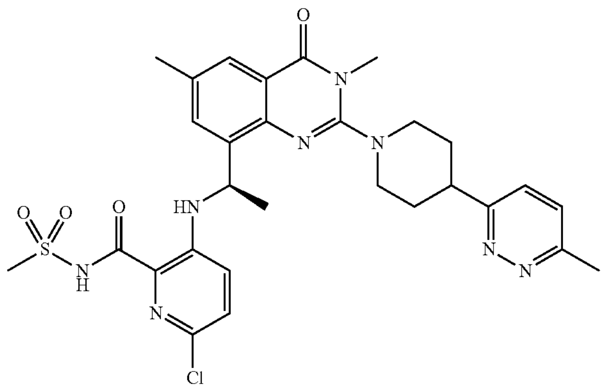 |
| 265 | 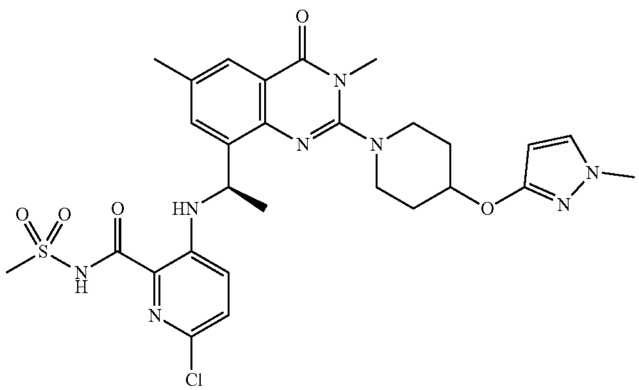 |
| 266 | 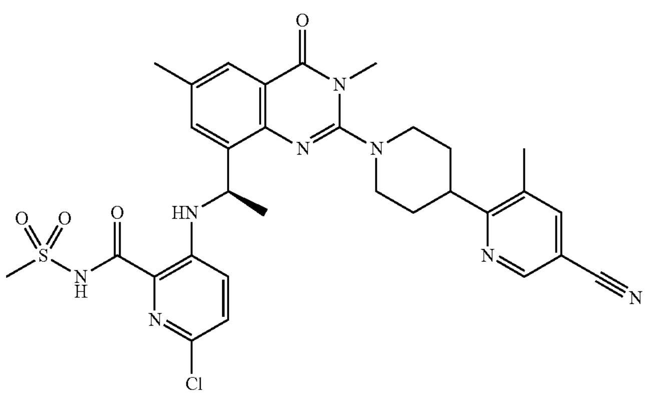 [SMILES: Cc1cc([C@@H](C)Nc2ccc(Cl)nc2C(=O)NS(C)(=O)=O)c2nc(N3CCC(c4ncc(C#N)cc4C)CC3)n(C)c(=O)c2c1] |
| 267 | 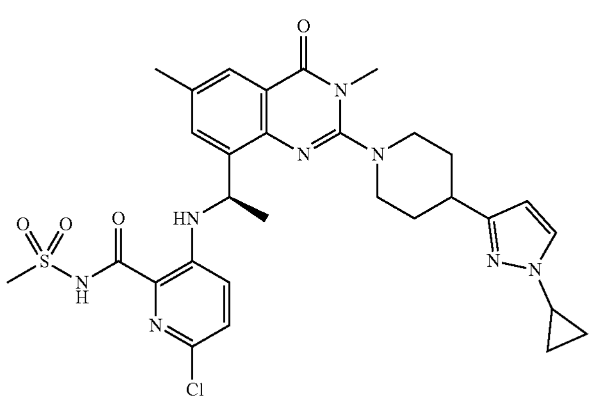 [SMILES: Cc1cc([C@@H](C)Nc2ccc(Cl)nc2C(=O)NS(C)(=O)=O)c2nc(N3CCC(c4ccn(C5CC5)n4)CC3)n(C)c(=O)c2c1] |

TABLE 1-continued
List of Compounds
| Cpd. ID | Chemical structure |
|---|---|
| 268 | 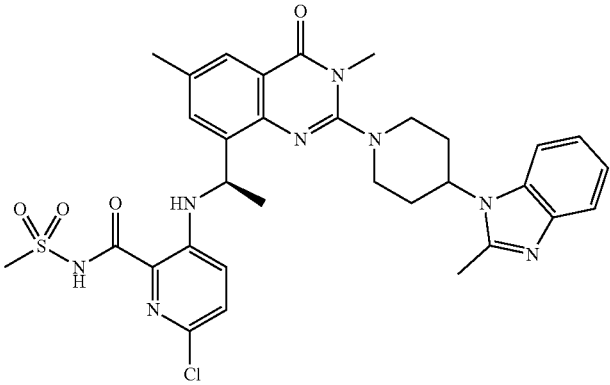 [SMILES: Cc1cc([C@@H](C)Nc2ccc(Cl)nc2C(=O)NS(C)(=O)=O)c2nc(N3CCC(n4c(C)nc5ccccc54)CC3)n(C)c(=O)c2c1] |
| 269 | 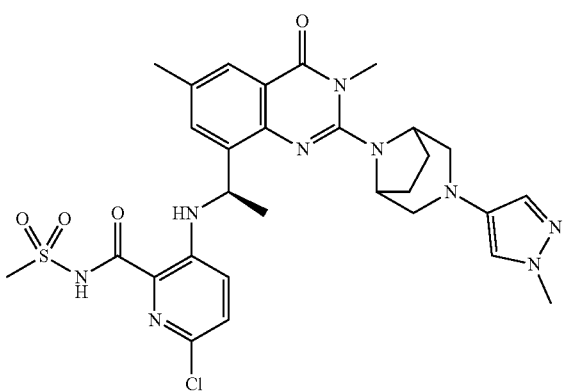 [SMILES: Cc1cc([C@@H](C)Nc2ccc(Cl)nc2C(=O)NS(C)(=O)=O)c2nc(N3C4CCC3CN(c3cnn(C)c3)C4)n(C)c(=O)c2c1] |
| 270 | 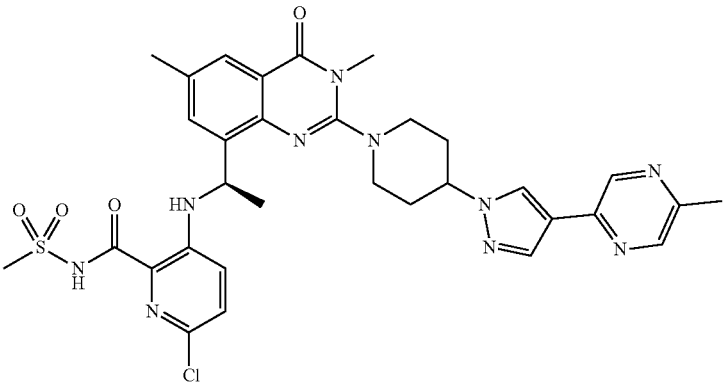 |
| 271 | 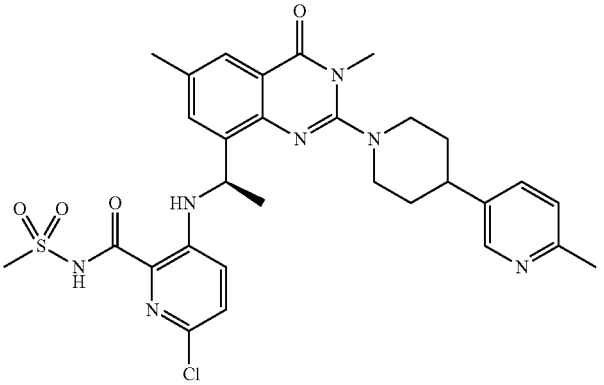 |

TABLE 1-continued

List of Compounds

| Cpd. ID | Chemical structure |
|---|---|
| 272 | 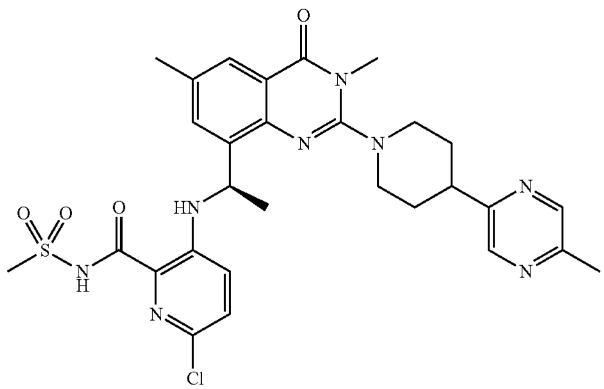 |
| 273 | 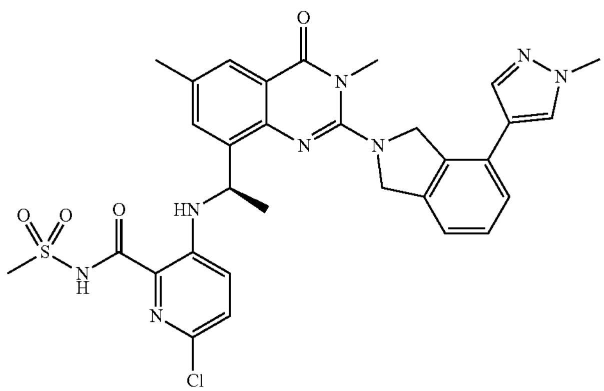 |
| 274 | 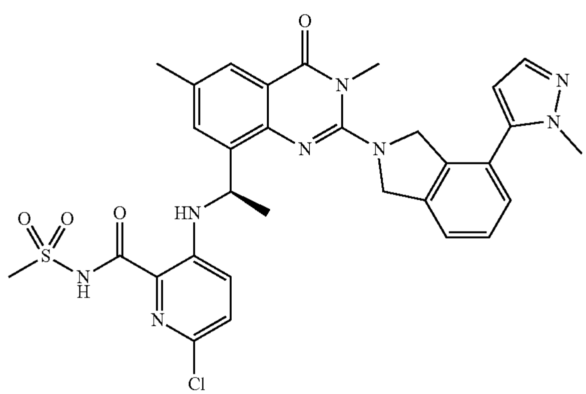 |
| 275 | 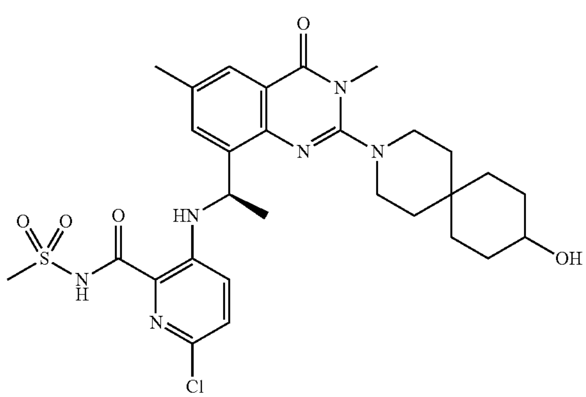 [SMILES: Cc1cc([C@@H](C)Nc2ccc(Cl)nc2C(=O)NS(C)(=O)=O)c2nc(N3CCC4(CCC(O)CC4)CC3)n(C)c(=O)c2c1] |

TABLE 1-continued
List of Compounds
| Cpd. ID | Chemical structure |
|---|---|
| 276 | 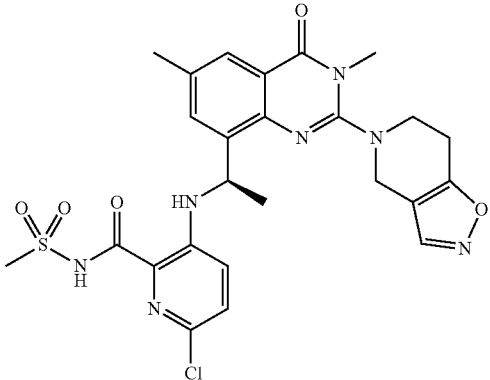 [SMILES: Cc1cc([C@@H](C)Nc2ccc(Cl)nc2C(=O)NS(C)(=O)=O)c2nc(N3CCc4oncc4C3)n(C)c(=O)c2c1] |
| 277 | 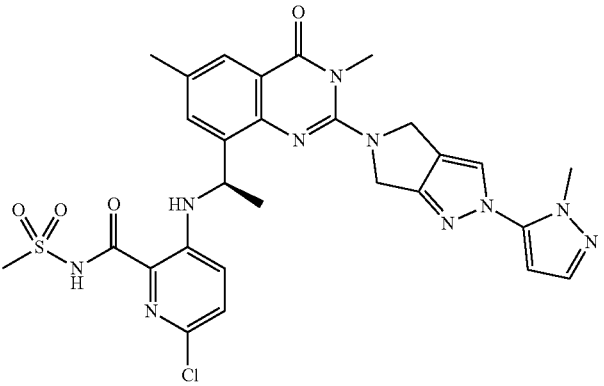 [SMILES: Cc1cc([C@@H](C)Nc2ccc(Cl)nc2C(=O)NS(C)(=O)=O)c2nc(N3Cc4cn(-c5ccnn5C)nc4C3)n(C)c(=O)c2c1] |
| 278 | 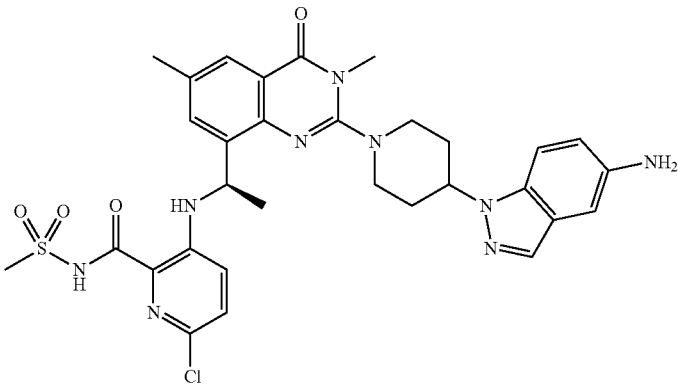 [SMILES: Cc1cc([C@@H](C)Nc2ccc(Cl)nc2C(=O)NS(C)(=O)=O)c2nc(N3CCC(n4ncc5cc(N)ccc54)CC3)n(C)c(=O)c2c1] |
| 279 | 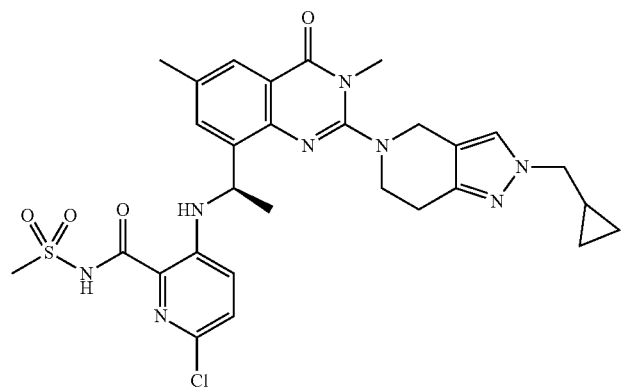 [SMILES: Cc1cc([C@@H](C)Nc2ccc(Cl)nc2C(=O)NS(C)(=O)=O)c2nc(N3CCc4nn(CC5CC5)cc4C3)n(C)c(=O)c2c1] |

TABLE 1-continued

List of Compounds

| Cpd. ID | Chemical structure |
|---|---|
| 280 | 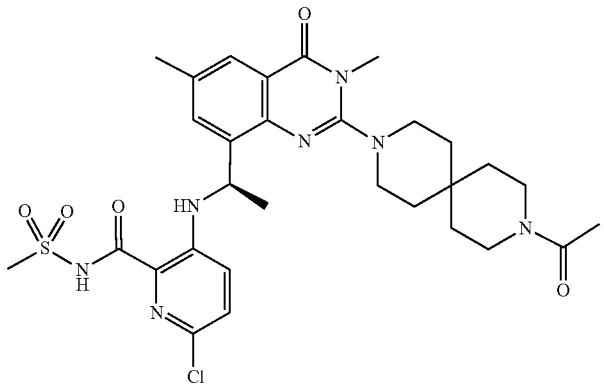 [SMILES: CC(=O)N1CCC2(CC1)CCN(c1nc3c([C@@H](C)Nc4ccc(Cl)nc4C(=O)NS(C)(=O)=O)cc(C)cc3c(=O)n1C)CC2] |
| 281 | 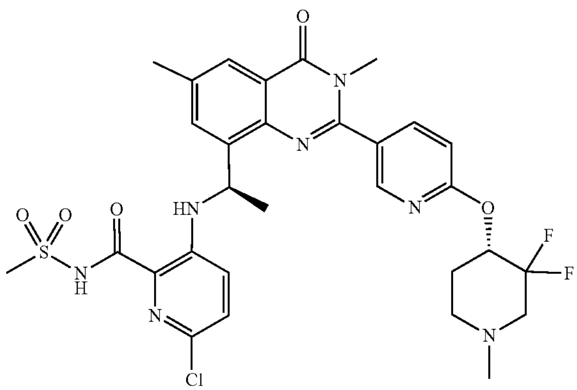 [SMILES: Cc1cc([C@@H](C)Nc2ccc(Cl)nc2C(=O)NS(C)(=O)=O)c2nc(-c3ccc(O[C@H]4CCN(C)CC4(F)F)nc3)n(C)c(=O)c2c1] |
| 282 | 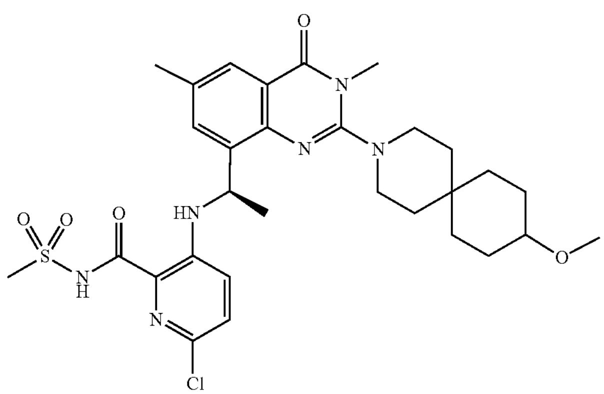 |
| 283 | 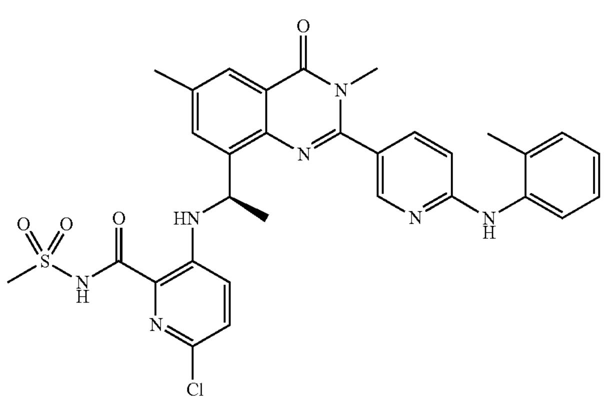 [SMILES: Cc1cc([C@@H](C)Nc2ccc(Cl)nc2C(=O)NS(C)(=O)=O)c2nc(-c3ccc(Nc4ccccc4C)nc3)n(C)c(=O)c2c1] |

TABLE 1-continued

List of Compounds

| Cpd. ID | Chemical structure |
|---|---|
| 284 | 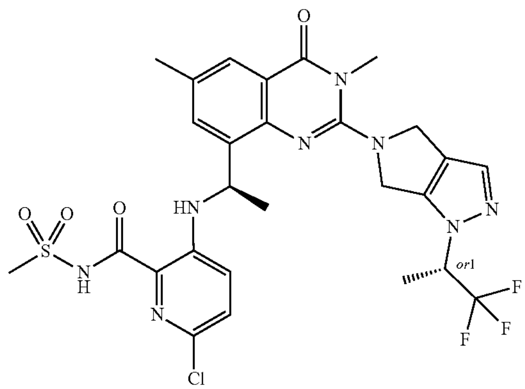 [SMILES: Cc1cc([C@@H](C)Nc2ccc(Cl)nc2C(=O)NS(C)(=O)=O)c2nc(N3Cc4cnn([C@@H](C)C(F)(F)F)c4C3)n(C)c(=O)c2c1] |
| 285 | 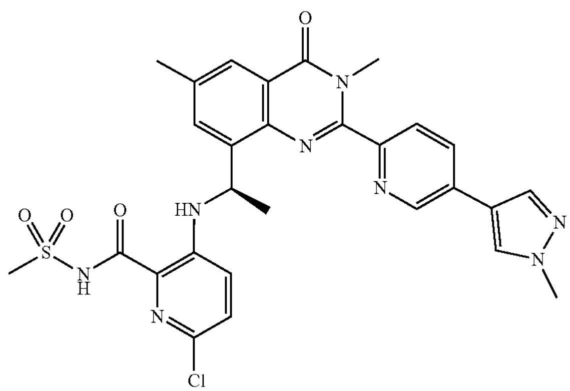 [SMILES: Cc1cc([C@@H](C)Nc2ccc(Cl)nc2C(=O)NS(C)(=O)=O)c2nc(-c3ccc(-c4cnn(C)c4)cn3)n(C)c(=O)c2c1] |
| 286 | 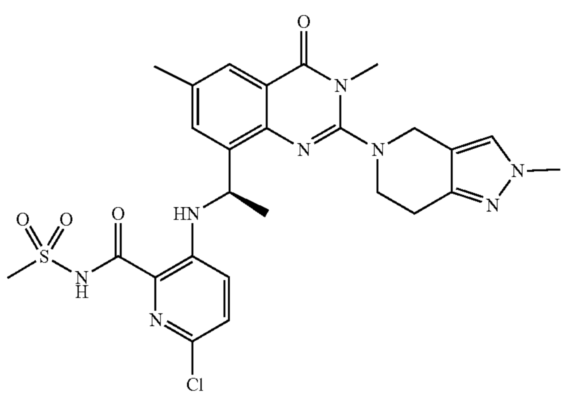 |
| 287 | 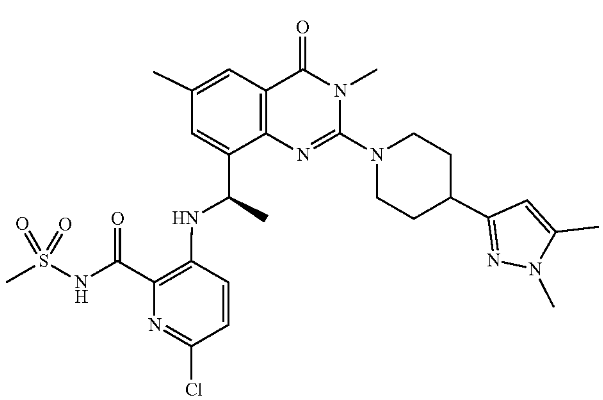 |

TABLE 1-continued
List of Compounds
| Cpd. ID | Chemical structure |
|---|---|
| 288 | 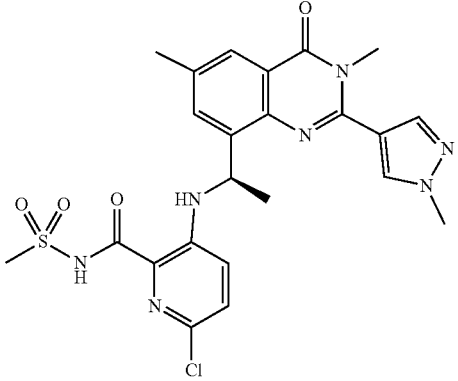 [SMILES: Cc1cc([C@@H](C)Nc2ccc(Cl)nc2C(=O)NS(C)(=O)=O)c2nc(-c3cnn(C)c3)n(C)c(=O)c2c1] |
| 289 | 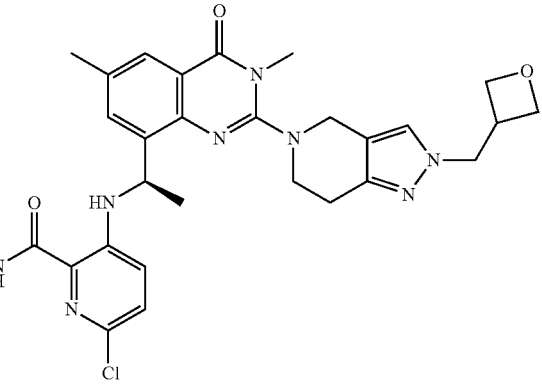 |
| 290 | 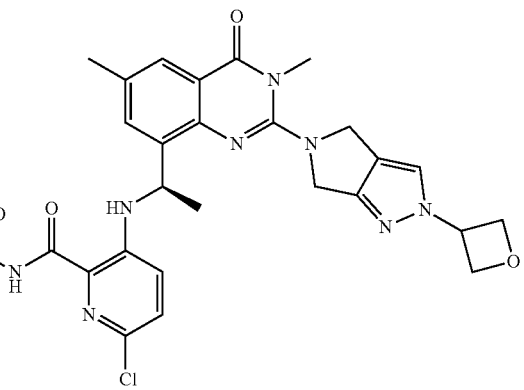 |
| 291 | 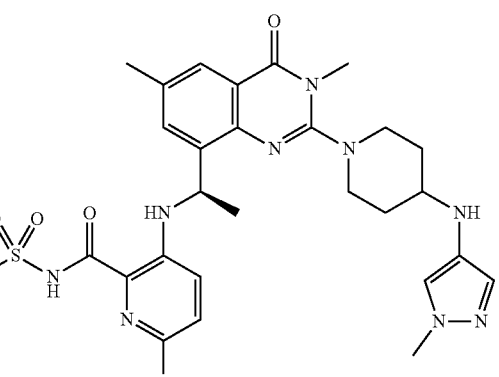 |

TABLE 1-continued

List of Compounds

| Cpd. ID | Chemical structure |
|---------|--------------------|
| 292 | 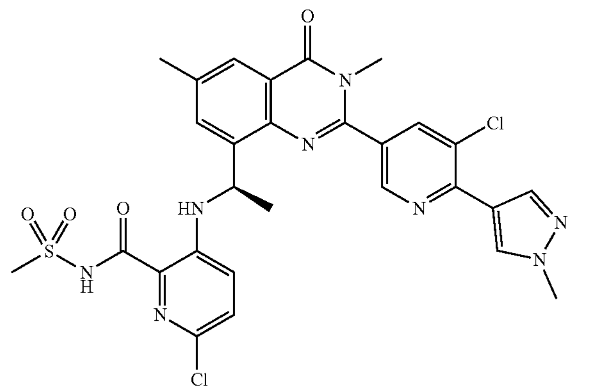 [SMILES: Cc1cc([C@@H](C)Nc2ccc(Cl)nc2C(=O)NS(C)(=O)=O)c2nc(-c3cnc(-c4cnn(C)c4)c(Cl)c3)n(C)c(=O)c2c1] |
| 293 | 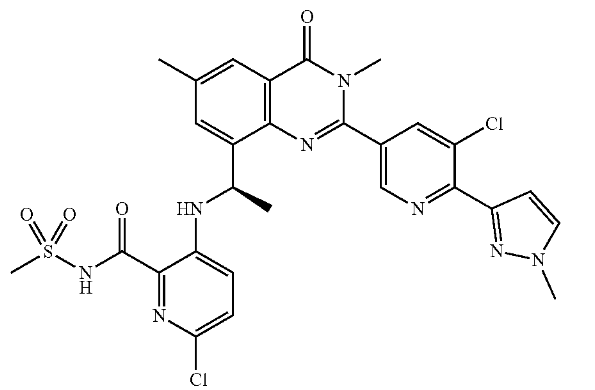 [SMILES: Cc1cc([C@@H](C)Nc2ccc(Cl)nc2C(=O)NS(C)(=O)=O)c2nc(-c3cnc(-c4ccn(C)n4)c(Cl)c3)n(C)c(=O)c2c1] |
| 294 | 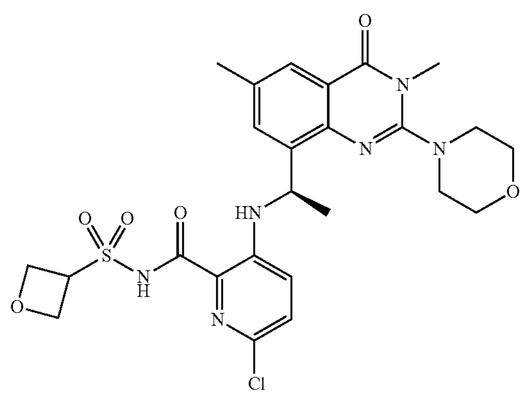 [SMILES: Cc1cc([C@@H](C)Nc2ccc(Cl)nc2C(=O)NS(=O)(=O)C2COC2)c2nc(N3CCOCC3)n(C)c(=O)c2c1] |
| 295 | 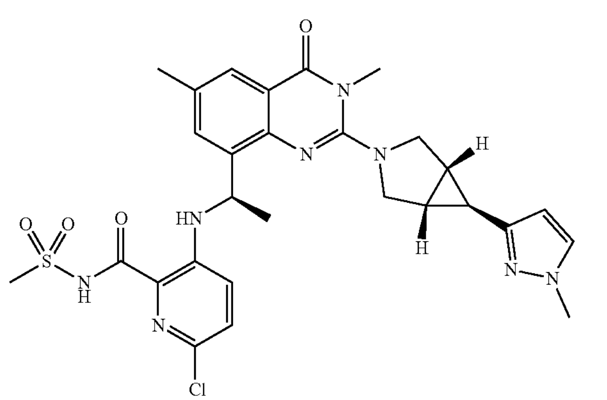 [SMILES: Cc1cc([C@@H](C)Nc2ccc(Cl)nc2C(=O)NS(C)(=O)=O)c2nc(N3C[C@@H]4[C@H](C3)[C@H]4c3ccn(C)n3)n(C)c(=O)c2c1] |

TABLE 1-continued
List of Compounds
| Cpd. ID | Chemical structure |
|---|---|
| 296 | 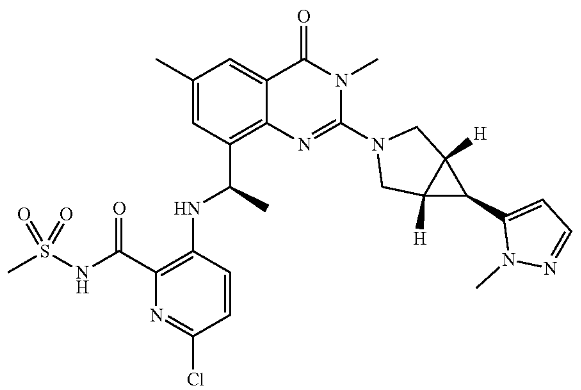 [SMILES: Cc1cc([C@@H](C)Nc2ccc(Cl)nc2C(=O)NS(C)(=O)=O)c2nc(N3C[C@@H]4[C@H](C3)[C@H]4c3ccnn3C)n(C)c(=O)c2c1] |
| 297 | 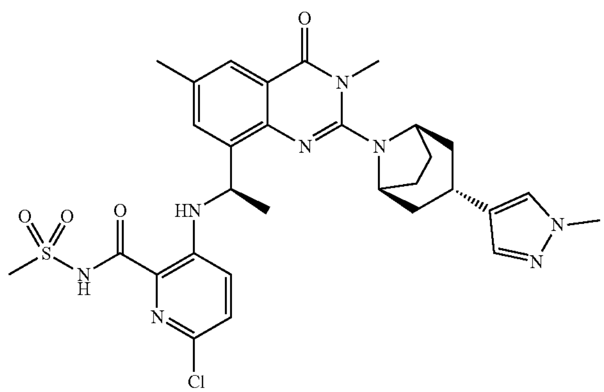 |
| 298 | 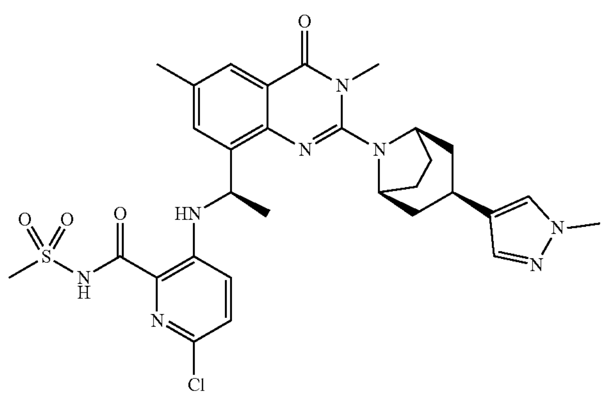 |
| 299 | 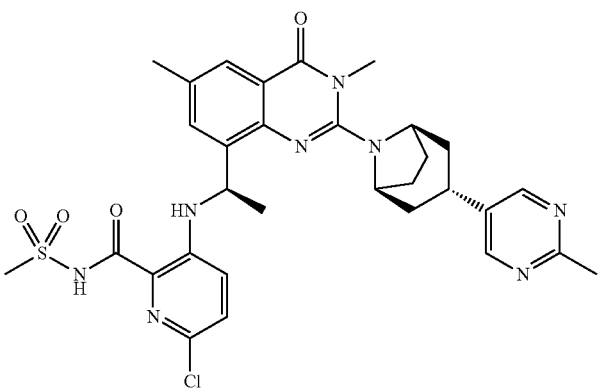 |

TABLE 1-continued

List of Compounds

| Cpd. ID | Chemical structure |
|---|---|
| 300 | 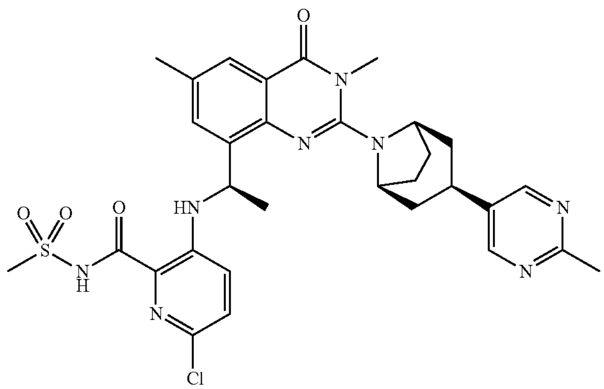 |
| 301 | 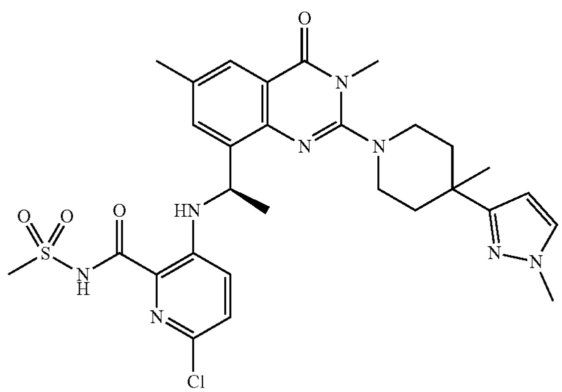 [SMILES: Cc1cc([C@@H](C)Nc2ccc(Cl)nc2C(=O)NS(C)(=O)=O)c2nc(N3CCC(C)(c4ccn(C)n4)CC3)n(C)c(=O)c2c1] |
| 302 | 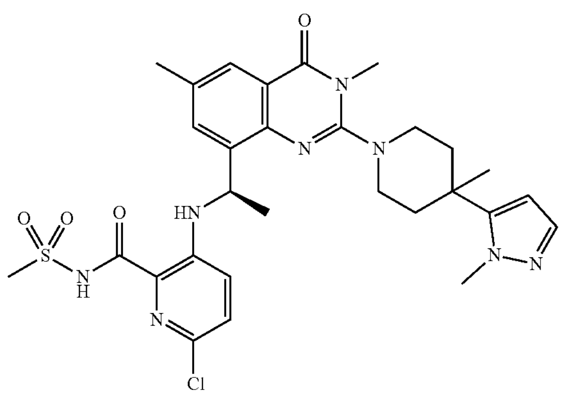 [SMILES: Cc1cc([C@@H](C)Nc2ccc(Cl)nc2C(=O)NS(C)(=O)=O)c2nc(N3CCC(C)(c4ccnn4C)CC3)n(C)c(=O)c2c1] |
| 303 | 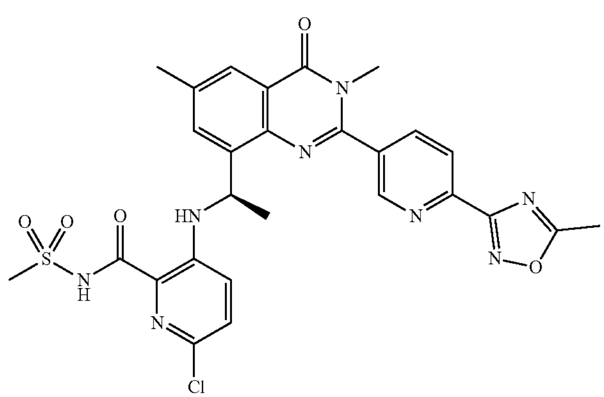 |

TABLE 1-continued

List of Compounds

| Cpd. ID | Chemical structure |
|---|---|
| 304 | 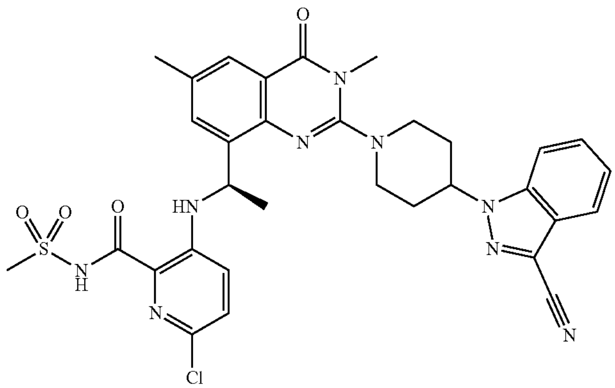 [SMILES: Cc1cc([C@@H](C)Nc2ccc(Cl)nc2C(=O)NS(C)(=O)=O)c2nc(N3CCC(n4nc(C#N)c5ccccc54)CC3)n(C)c(=O)c2c1] |
| 305 | 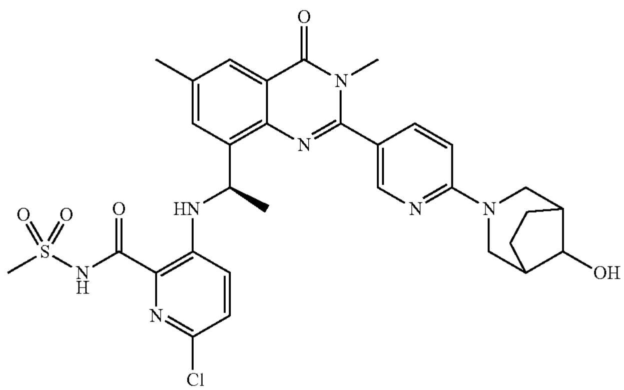 [SMILES: Cc1cc([C@@H](C)Nc2ccc(Cl)nc2C(=O)NS(C)(=O)=O)c2nc(-c3ccc(N4CC5CCC(C4)C5O)nc3)n(C)c(=O)c2c1] |
| 306 | 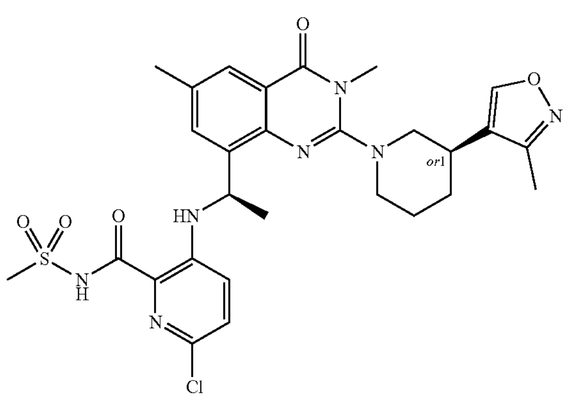 [SMILES: Cc1cc([C@@H](C)Nc2ccc(Cl)nc2C(=O)NS(C)(=O)=O)c2nc(N3CCC[C@H](c4conc4C)C3)n(C)c(=O)c2c1] |
| 307 | 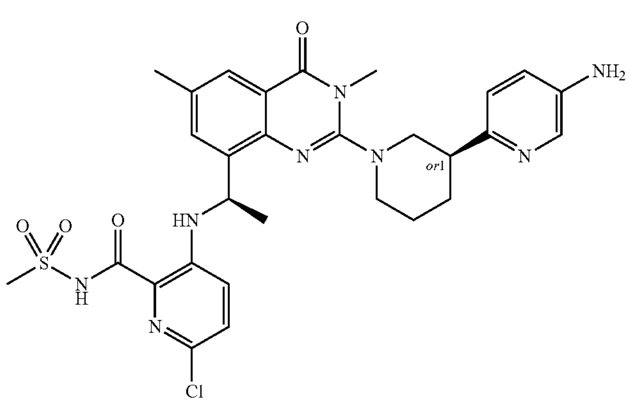 [SMILES: Cc1cc([C@@H](C)Nc2ccc(Cl)nc2C(=O)NS(C)(=O)=O)c2nc(N3CCC[C@H](c4ccc(N)cn4)C3)n(C)c(=O)c2c1] |

TABLE 1-continued
List of Compounds
| Cpd. ID | Chemical structure |
|---------|--------------------|
| 308 | 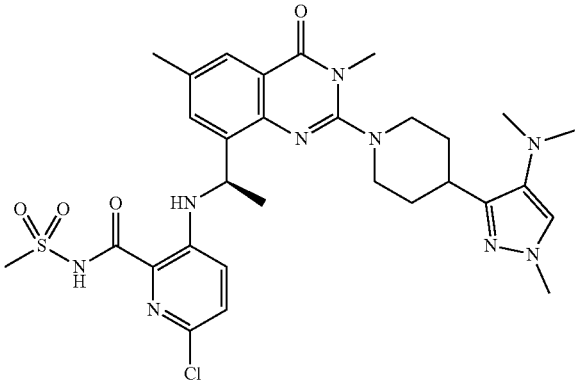 |
| 309 | 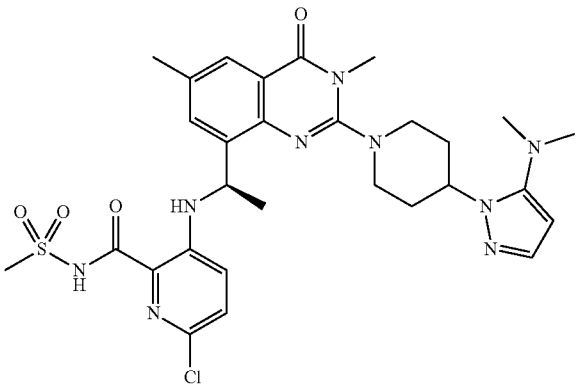 |
| 310 | 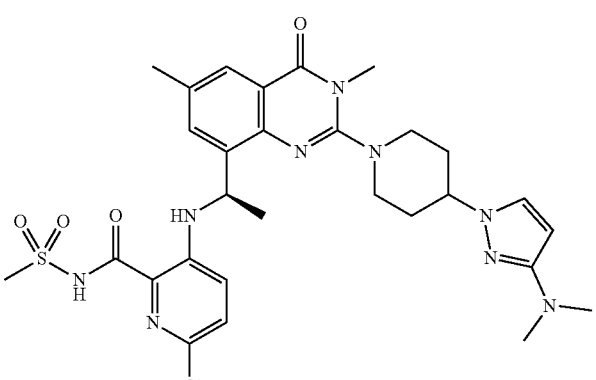 |
| 311 | 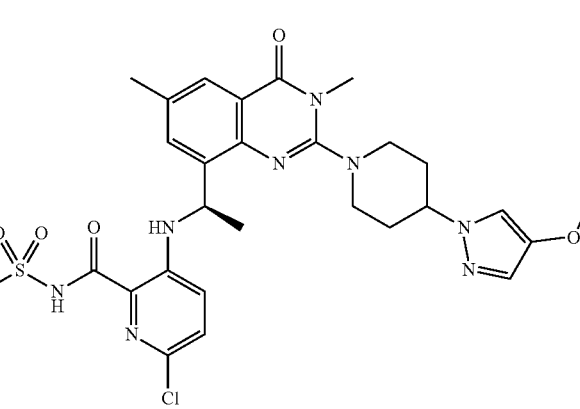 |

TABLE 1-continued

List of Compounds

| Cpd. ID | Chemical structure |
|---|---|
| 312 | 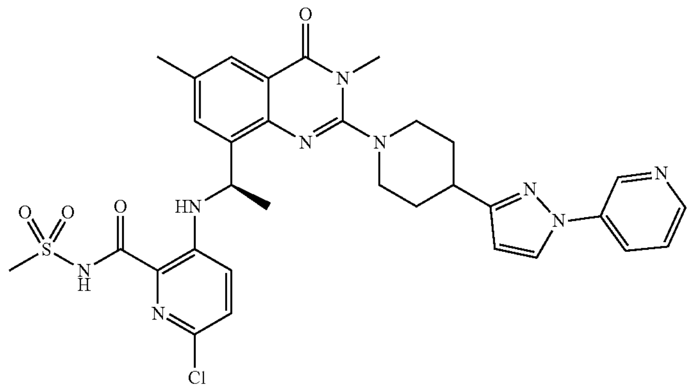 [SMILES: Cc1cc([C@@H](C)Nc2ccc(Cl)nc2C(=O)NS(C)(=O)=O)c2nc(N3CCC(c4ccn(-c5cccnc5)n4)CC3)n(C)c(=O)c2c1] |
| 313 | 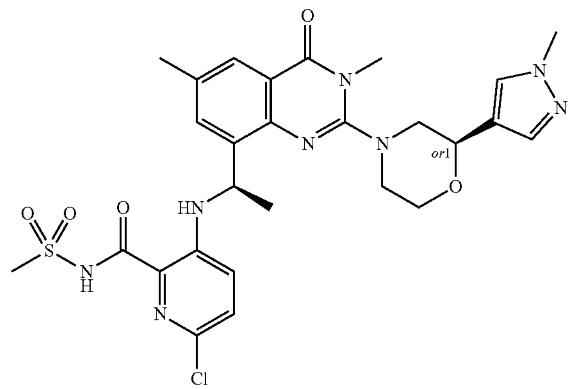 [SMILES: Cc1cc([C@@H](C)Nc2ccc(Cl)nc2C(=O)NS(C)(=O)=O)c2nc(N3CCO[C@H](c4cnn(C)c4)C3)n(C)c(=O)c2c1] |
| 314 | 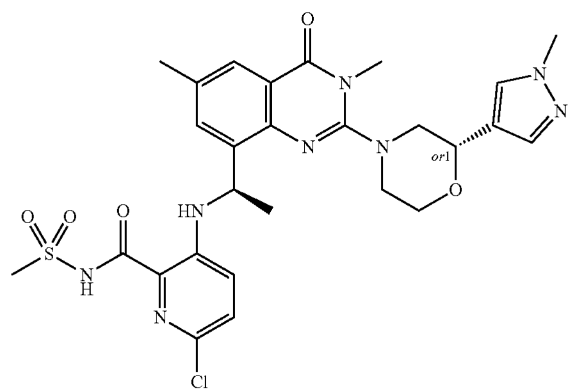 [SMILES: Cc1cc([C@@H](C)Nc2ccc(Cl)nc2C(=O)NS(C)(=O)=O)c2nc(N3CCO[C@@H](c4cnn(C)c4)C3)n(C)c(=O)c2c1] |
| 315 | 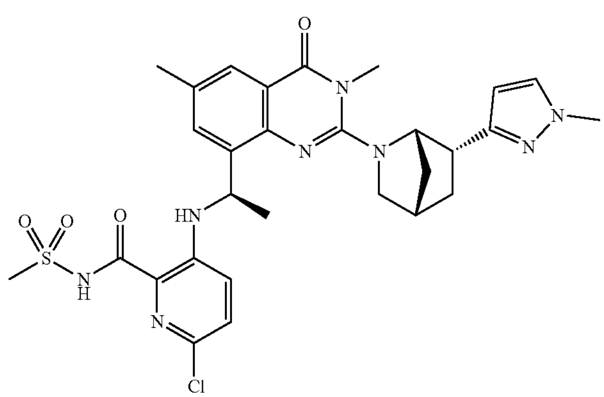 |

TABLE 1-continued
List of Compounds
| Cpd. ID | Chemical structure |
|---|---|
| 316 | 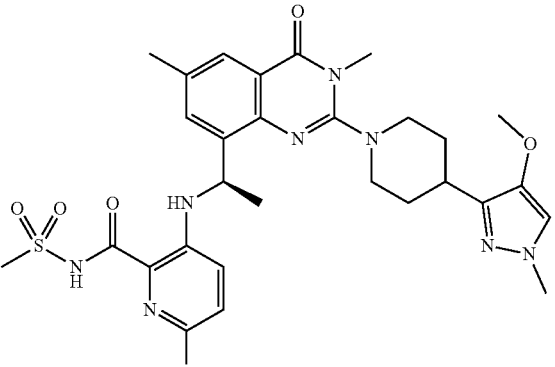 |
| 317 | 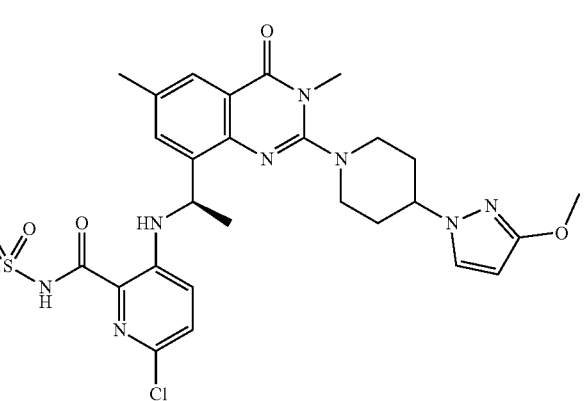 |
| 318 | 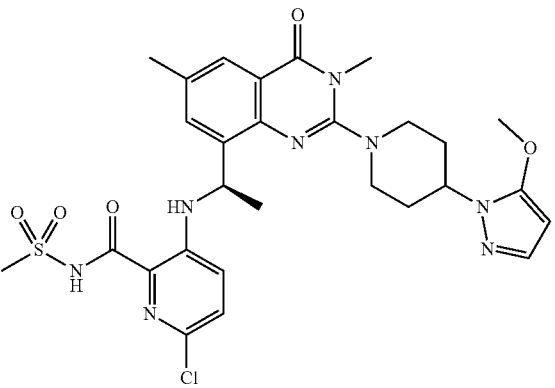 [SMILES: COc1ccnn1C1CCN(c2nc3c([C@@H](C)Nc4ccc(Cl)nc4C(=O)NS(C)(=O)=O)cc(C)cc3c(=O)n2C)CC1] |
| 319 | 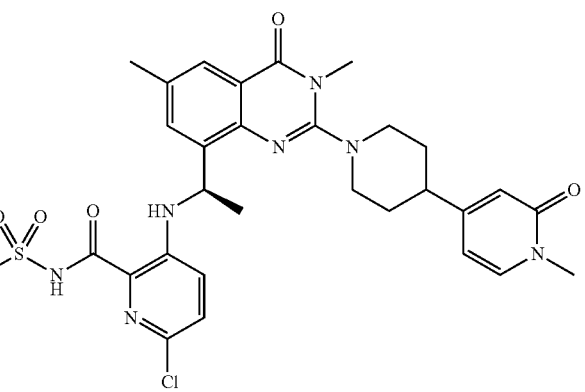 |

TABLE 1-continued
List of Compounds
| Cpd. ID | Chemical structure |
|---|---|
| 320 | 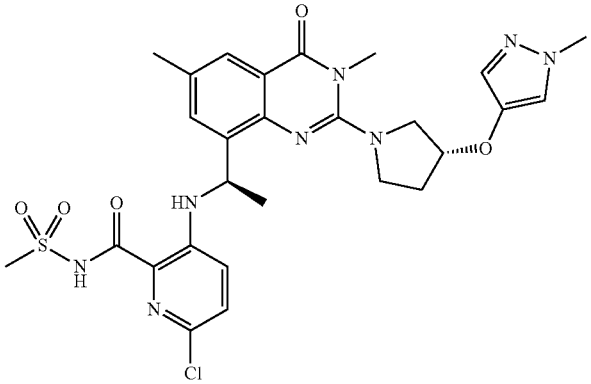 |
| 321 | 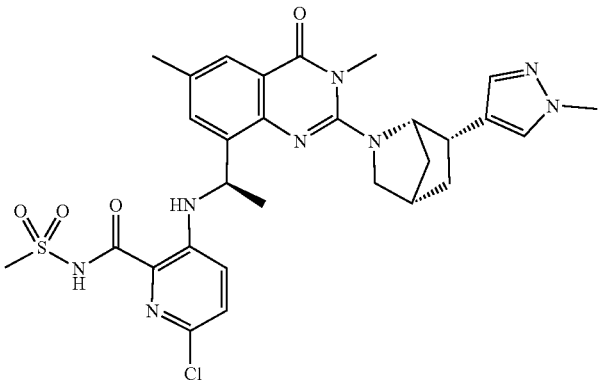 |
| 322 | 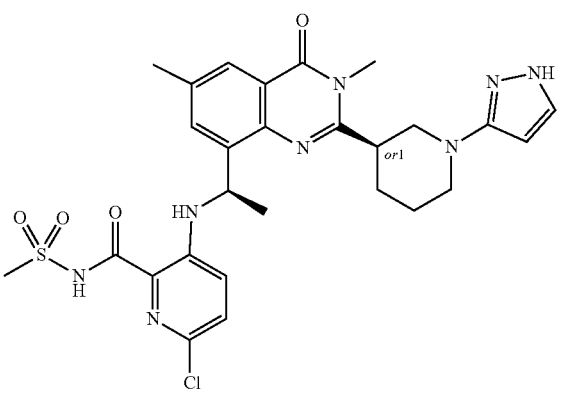 [SMILES: Cc1cc([C@@H](C)Nc2ccc(Cl)nc2C(=O)NS(C)(=O)=O)c2nc([C@@H]3CCCN(c4cc[nH]n4)C3)n(C)c(=O)c2c1] |
| 323 | 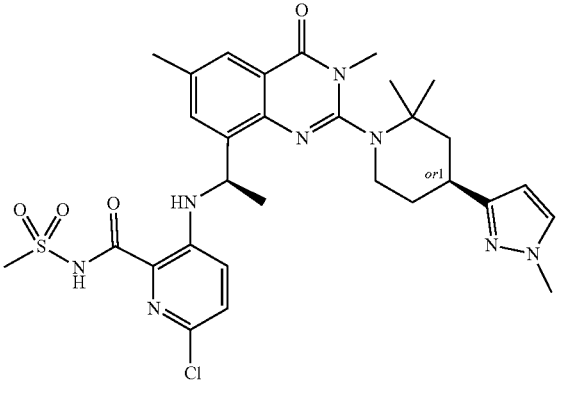 [SMILES: Cc1cc([C@@H](C)Nc2ccc(Cl)nc2C(=O)NS(C)(=O)=O)c2nc(N3CC[C@H](c4ccn(C)n4)CC3(C)C)n(C)c(=O)c2c1] |

TABLE 1-continued

List of Compounds

| Cpd. ID | Chemical structure |
|---|---|
| 324 | 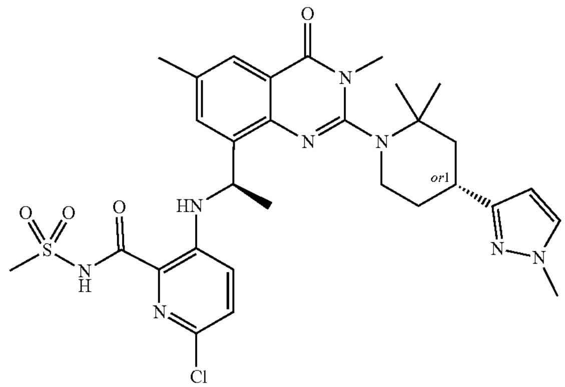 [SMILES: Cc1cc([C@@H](C)Nc2ccc(Cl)nc2C(=O)NS(C)(=O)=O)c2nc(N3CC[C@@H](c4ccn(C)n4)CC3(C)C)n(C)c(=O)c2c1] |
| 325 | 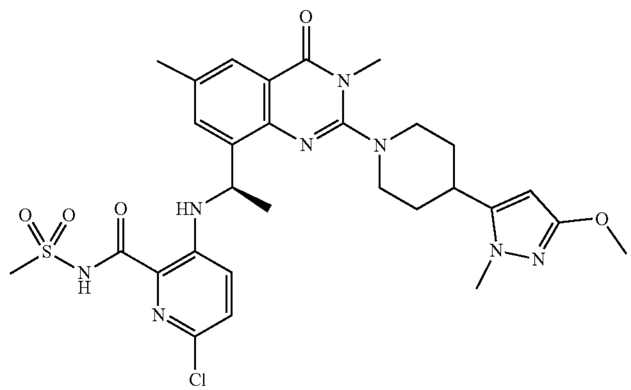 |
| 326 | 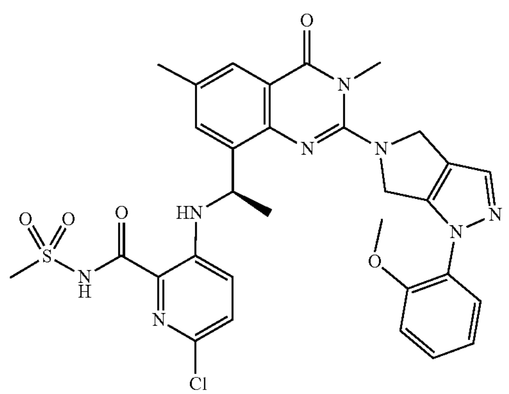 [SMILES: COc1ccccc1-n1ncc2c1CN(c1nc3c([C@@H](C)Nc4ccc(Cl)nc4C(=O)NS(C)(=O)=O)cc(C)cc3c(=O)n1C)C2] |
| 327 | 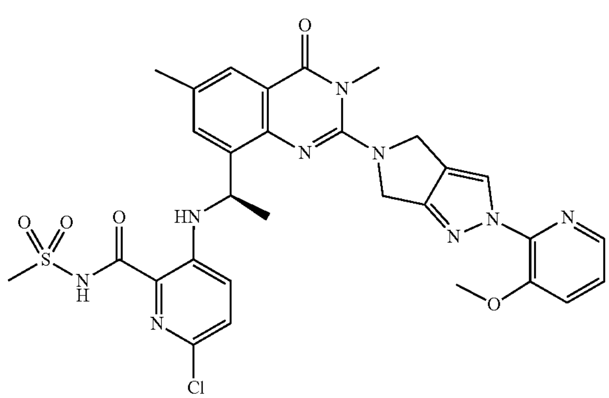 [SMILES: COc1cccnc1-n1cc2c(n1)CN(c1nc3c([C@@H](C)Nc4ccc(Cl)nc4C(=O)NS(C)(=O)=O)cc(C)cc3c(=O)n1C)C2] |

TABLE 1-continued

List of Compounds

| Cpd. ID | Chemical structure |
|---|---|
| 328 | 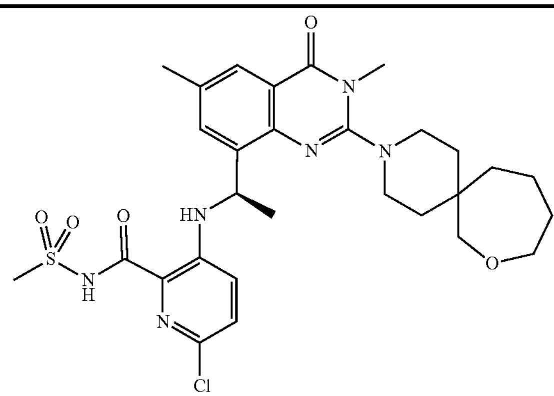 |
| 329 | 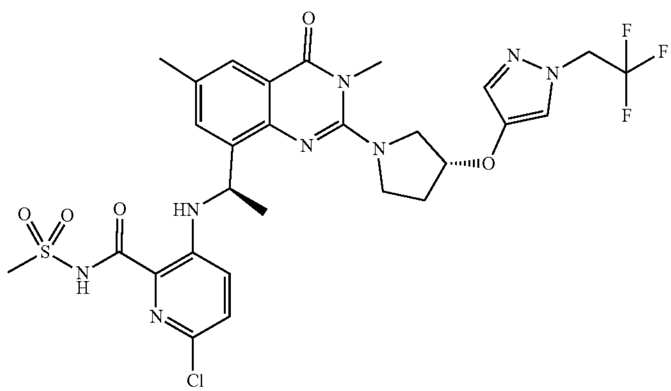 [SMILES: Cc1cc([C@@H](C)Nc2ccc(Cl)nc2C(=O)NS(C)(=O)=O)c2nc(N3CC[C@@H](Oc4cnn(CC(F)(F)F)c4)C3)n(C)c(=O)c2c1] |
| 330 | 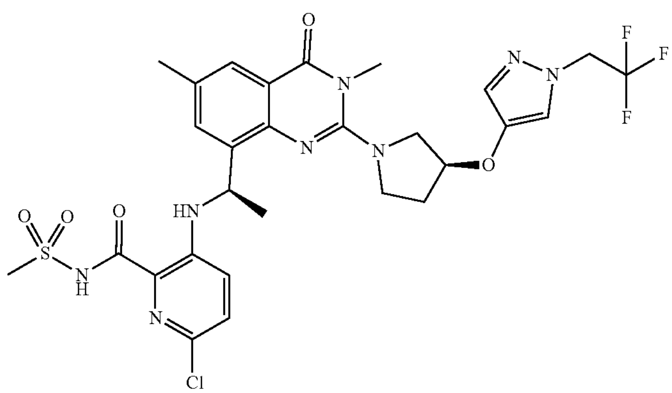 [SMILES: Cc1cc([C@@H](C)Nc2ccc(Cl)nc2C(=O)NS(C)(=O)=O)c2nc(N3CC[C@H](Oc4cnn(CC(F)(F)F)c4)C3)n(C)c(=O)c2c1] |
| 331 | 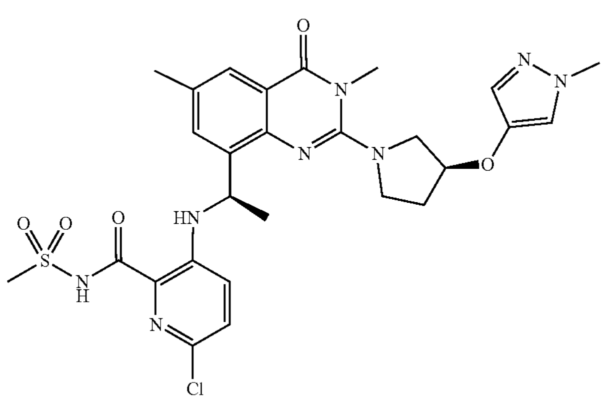 |

TABLE 1-continued
List of Compounds
| Cpd. ID | Chemical structure |
|---|---|
| 332 | 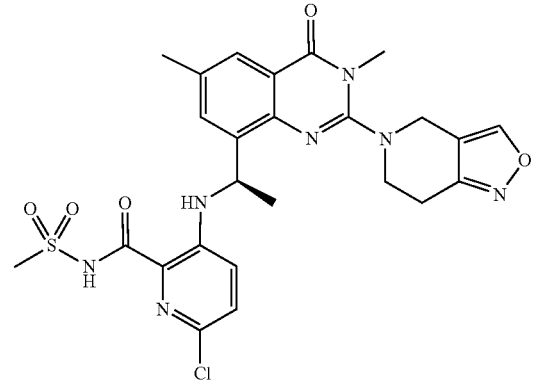 [SMILES: Cc1cc([C@@H](C)Nc2ccc(Cl)nc2C(=O)NS(C)(=O)=O)c2nc(N3CCc4nocc4C3)n(C)c(=O)c2c1] |
| 333 | 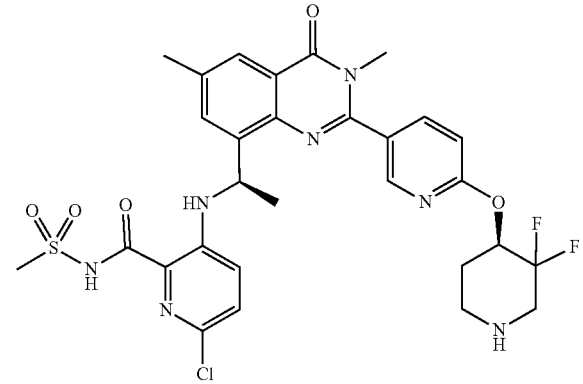 [SMILES: Cc1cc([C@@H](C)Nc2ccc(Cl)nc2C(=O)NS(C)(=O)=O)c2nc(-c3ccc(O[C@@H]4CCNCC4(F)F)nc3)n(C)c(=O)c2c1] |
| 334 | 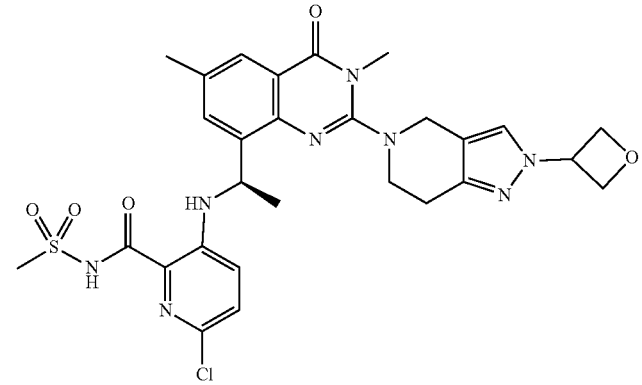 [SMILES: Cc1cc([C@@H](C)Nc2ccc(Cl)nc2C(=O)NS(C)(=O)=O)c2nc(N3CCc4nn(C5COC5)cc4C3)n(C)c(=O)c2c1] |
| 335 | 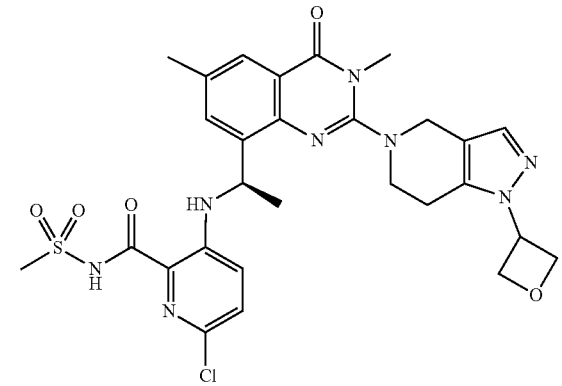 [SMILES: Cc1cc([C@@H](C)Nc2ccc(Cl)nc2C(=O)NS(C)(=O)=O)c2nc(N3CCc4c(cnn4C4COC4)C3)n(C)c(=O)c2c1] |

TABLE 1-continued

List of Compounds

| Cpd. ID | Chemical structure |
|---|---|
| 336 | 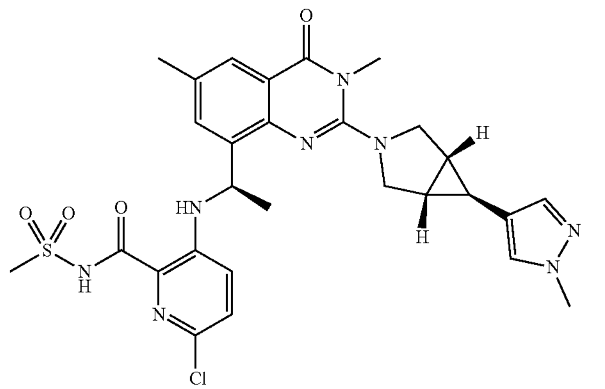 [SMILES: Cc1cc([C@@H](C)Nc2ccc(Cl)nc2C(=O)NS(C)(=O)=O)c2nc(N3C[C@@H]4[C@H](C3)[C@H]4c3cnn(C)c3)n(C)c(=O)c2c1] |
| 337 | 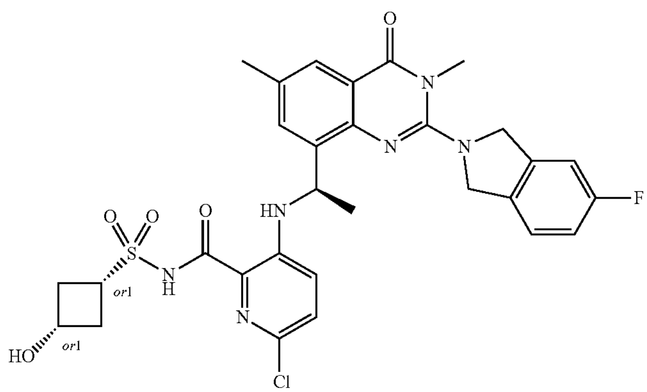 [SMILES: Cc1cc([C@@H](C)Nc2ccc(Cl)nc2C(=O)NS(=O)(=O)[C@H]2C[C@@H](O)C2)c2nc(N3Cc4ccc(F)cc4C3)n(C)c(=O)c2c1] |
| 338 | 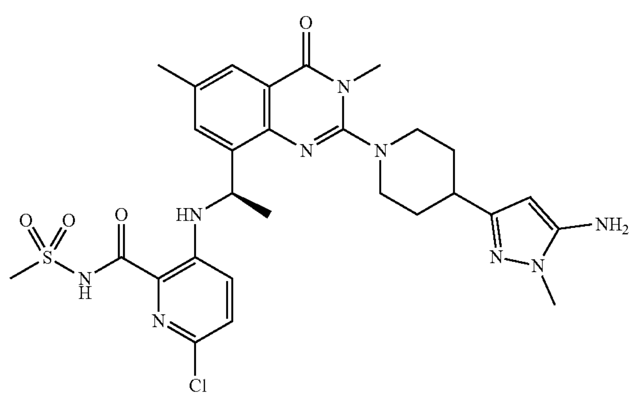 [SMILES: Cc1cc([C@@H](C)Nc2ccc(Cl)nc2C(=O)NS(C)(=O)=O)c2nc(N3CCC(c4cc(N)n(C)n4)CC3)n(C)c(=O)c2c1] |
| 339 | 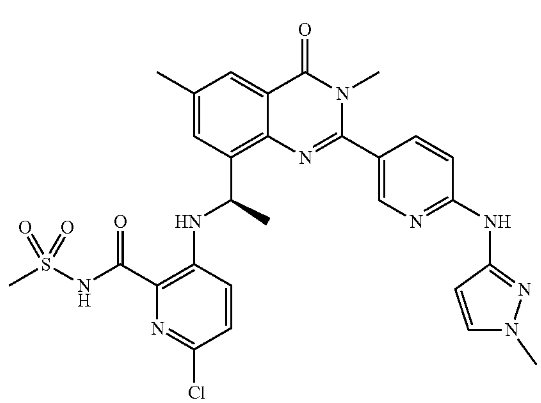 |

TABLE 1-continued
List of Compounds
| Cpd. ID | Chemical structure |
|---|---|
| 340 | 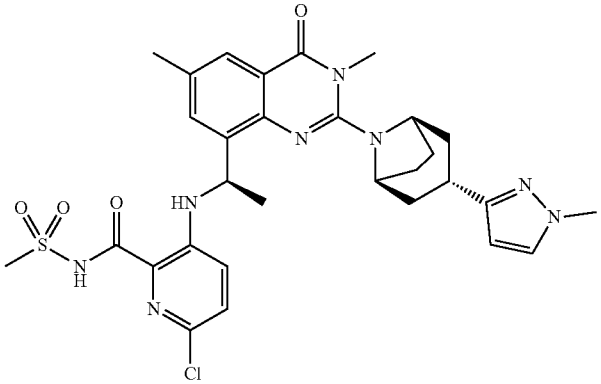 |
| 341 | 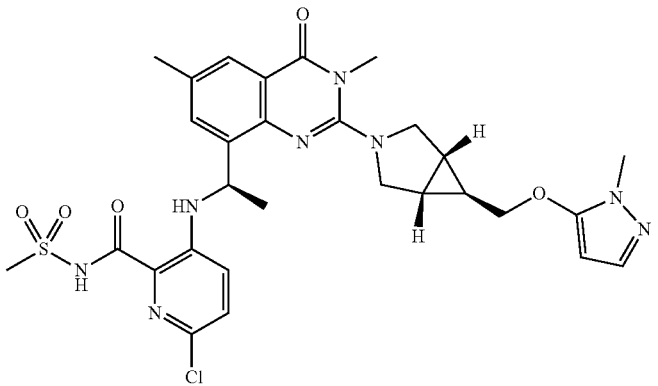 [SMILES: Cc1cc([C@@H](C)Nc2ccc(Cl)nc2C(=O)NS(C)(=O)=O)c2nc(N3C[C@@H]4[C@@H](COc5ccnn5C)[C@@H]4C3)n(C)c(=O)c2c1] |
| 342 | 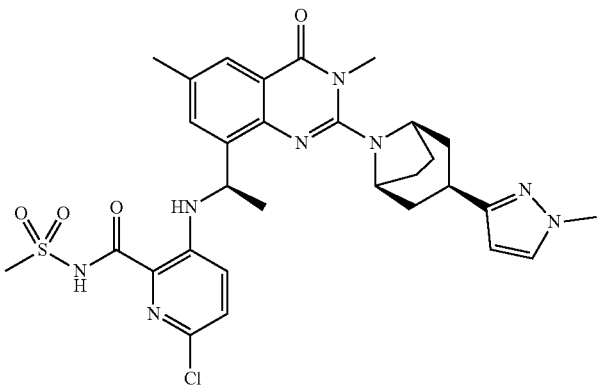 |
| 343 | 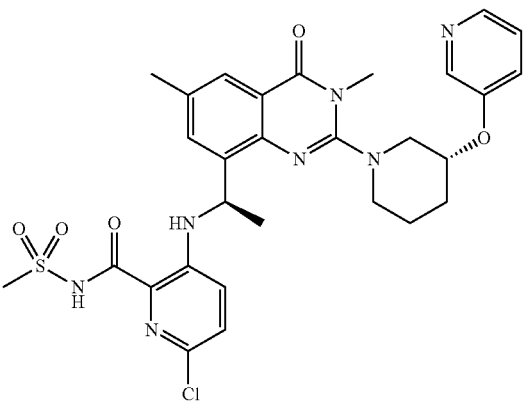 [SMILES: Cc1cc([C@@H](C)Nc2ccc(Cl)nc2C(=O)NS(C)(=O)=O)c2nc(N3CCC[C@@H](Oc4cccnc4)C3)n(C)c(=O)c2c1] |

TABLE 1-continued
List of Compounds
| Cpd. ID | Chemical structure |
|---|---|
| 344 | 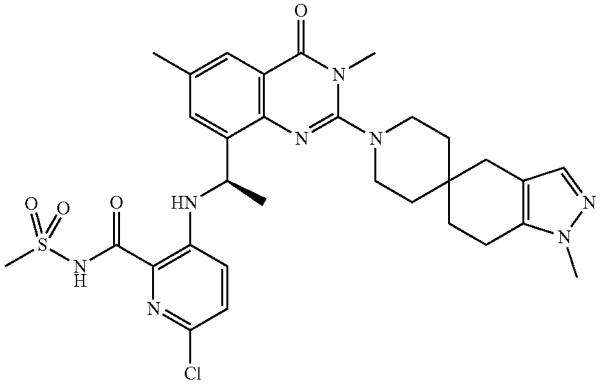 [SMILES: Cc1cc([C@@H](C)Nc2ccc(Cl)nc2C(=O)NS(C)(=O)=O)c2nc(N3CCC4(CCc5c(cnn5C)C4)CC3)n(C)c(=O)c2c1] |
| 345 | 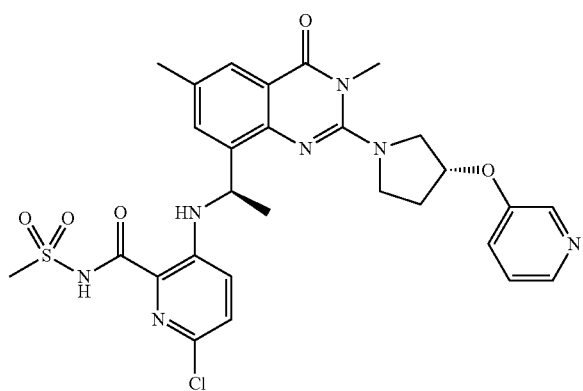 [SMILES: Cc1cc([C@@H](C)Nc2ccc(Cl)nc2C(=O)NS(C)(=O)=O)c2nc(N3CC[C@@H](Oc4cccnc4)C3)n(C)c(=O)c2c1] |
| 346 | 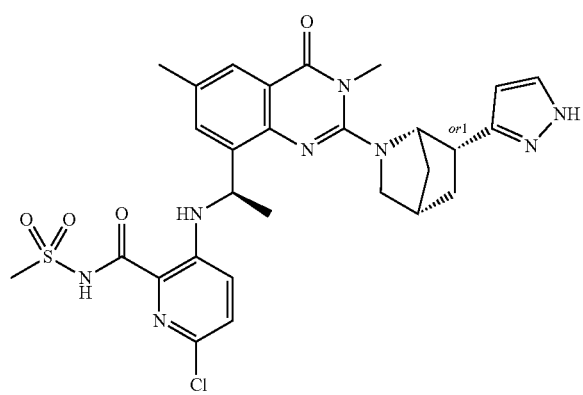 [SMILES: Cc1cc([C@@H](C)Nc2ccc(Cl)nc2C(=O)NS(C)(=O)=O)c2nc(N3C[C@H]4C[C@@H](c5cc[nH]n5)[C@@H]3C4)n(C)c(=O)c2c1] |
| 347 | 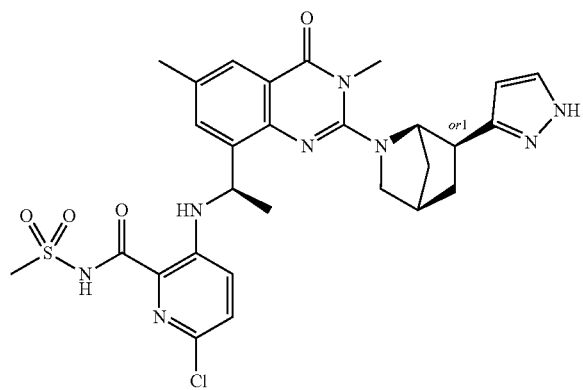 [SMILES: Cc1cc([C@@H](C)Nc2ccc(Cl)nc2C(=O)NS(C)(=O)=O)c2nc(N3C[C@@H]4C[C@H](c5cc[nH]n5)[C@H]3C4)n(C)c(=O)c2c1] |

TABLE 1-continued

List of Compounds

| Cpd. ID | Chemical structure |
|---------|--------------------|
| 348 | 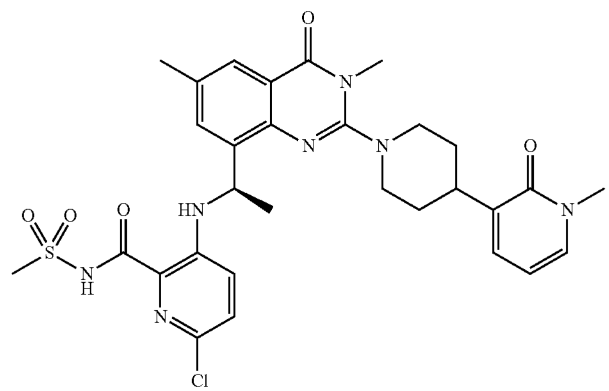 |
| 349 | 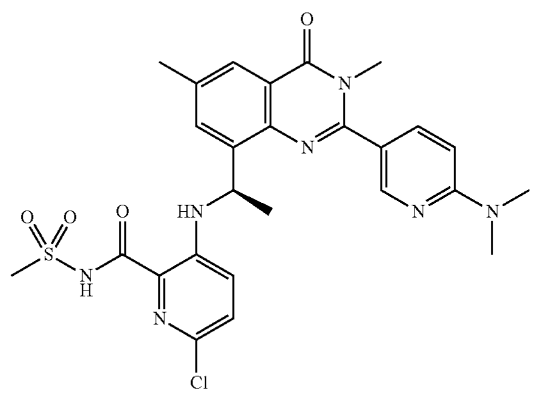 |
| 350 | 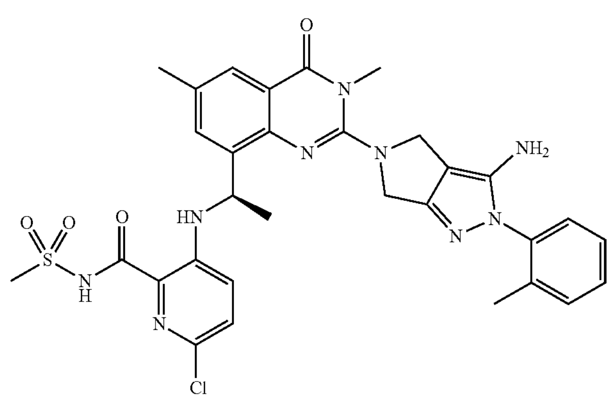 [SMILES: Cc1cc([C@@H](C)Nc2ccc(Cl)nc2C(=O)NS(C)(=O)=O)c2nc(N3Cc4nn(-c5ccccc5C)c(N)c4C3)n(C)c(=O)c2c1] |
| 351 | 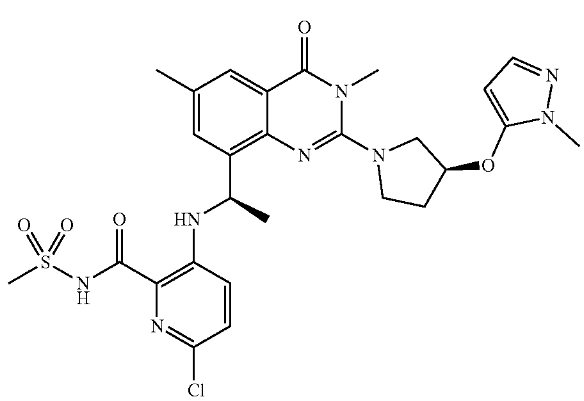 |

TABLE 1-continued

List of Compounds

| Cpd. ID | Chemical structure |
| --- | --- |
| 352 | 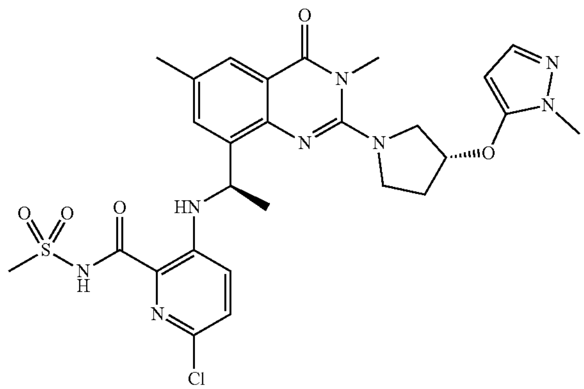 |
| 353 | 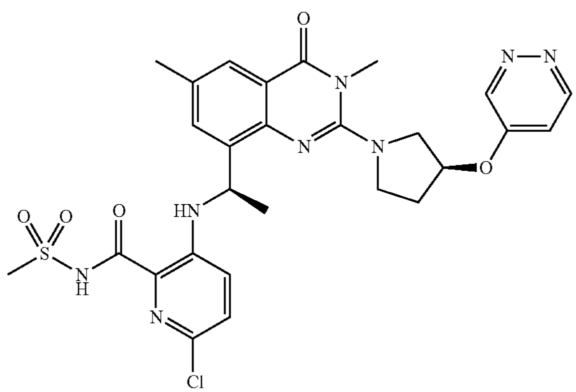 [SMILES: Cc1cc([C@@H](C)Nc2ccc(Cl)nc2C(=O)NS(C)(=O)=O)c2nc(N3CC[C@H](Oc4ccnnc4)C3)n(C)c(=O)c2c1] |
| 354 | 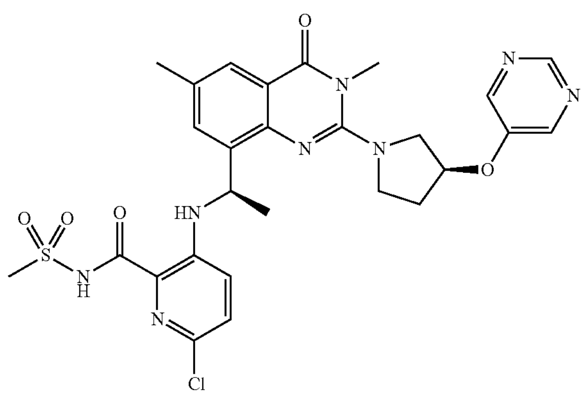 [SMILES: Cc1cc([C@@H](C)Nc2ccc(Cl)nc2C(=O)NS(C)(=O)=O)c2nc(N3CC[C@H](Oc4cncnc4)C3)n(C)c(=O)c2c1] |
| 355 | 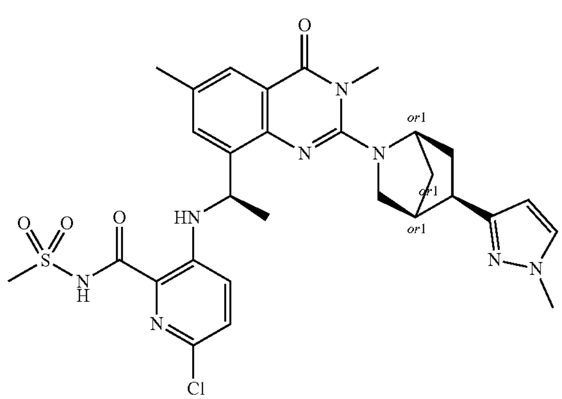 [SMILES: Cc1cc([C@@H](C)Nc2ccc(Cl)nc2C(=O)NS(C)(=O)=O)c2nc(N3C[C@H]4C[C@@H]3C[C@H]4c3ccn(C)n3)n(C)c(=O)c2c1] |

TABLE 1-continued

List of Compounds

| Cpd. ID | Chemical structure |
|---|---|
| 356 | 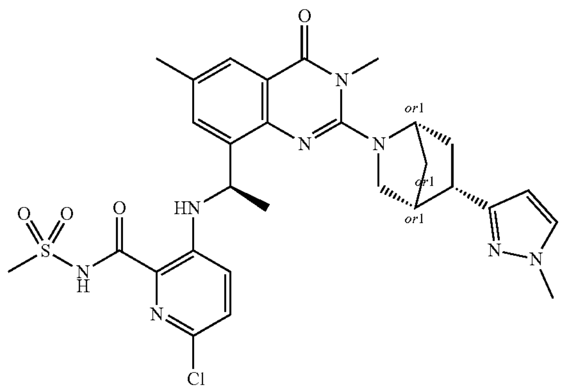 [SMILES: Cc1cc([C@@H](C)Nc2ccc(Cl)nc2C(=O)NS(C)(=O)=O)c2nc(N3C[C@@H]4C[C@H]3C[C@@H]4c3ccn(C)n3)n(C)c(=O)c2c1] |
| 357 | 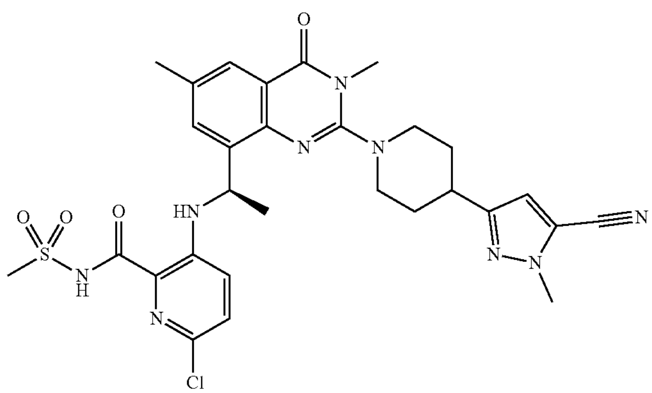 [SMILES: Cc1cc([C@@H](C)Nc2ccc(Cl)nc2C(=O)NS(C)(=O)=O)c2nc(N3CCC(c4cc(C#N)n(C)n4)CC3)n(C)c(=O)c2c1] |
| 358 | 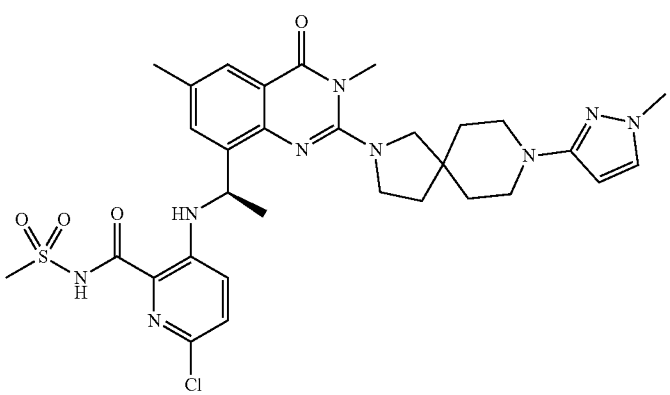 |
| 359 | 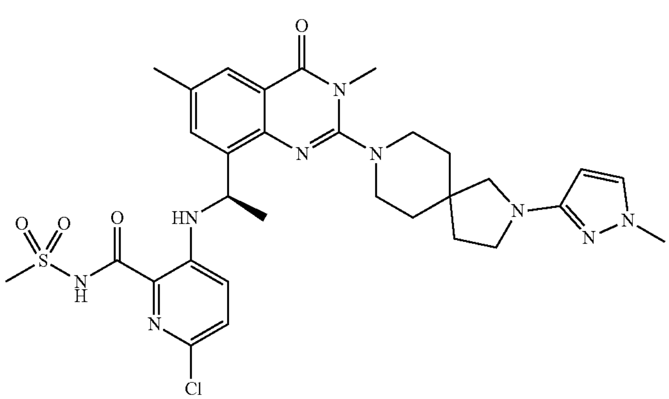 |

TABLE 1-continued
| Cpd. ID | Chemical structure |
|---|---|
| 360 | 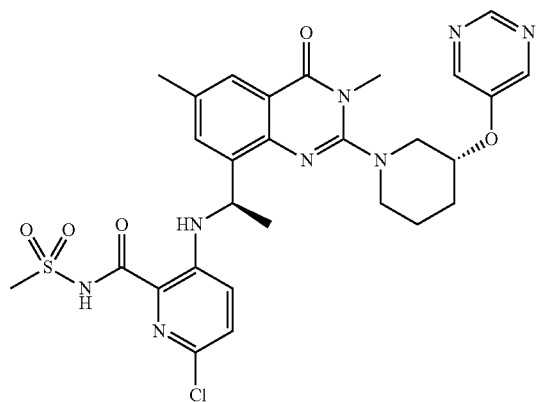 [SMILES: Cc1cc([C@@H](C)Nc2ccc(Cl)nc2C(=O)NS(C)(=O)=O)c2nc(N3CCC[C@@H](Oc4cncnc4)C3)n(C)c(=O)c2c1] |
| 361 | 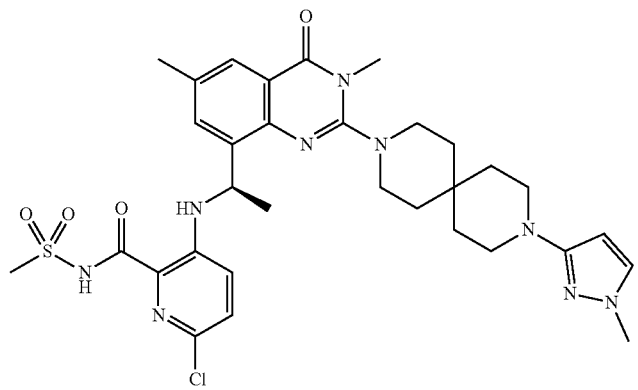 [SMILES: Cc1cc([C@@H](C)Nc2ccc(Cl)nc2C(=O)NS(C)(=O)=O)c2nc(N3CCC4(CCN(c5ccn(C)n5)CC4)CC3)n(C)c(=O)c2c1] |
| 362 | 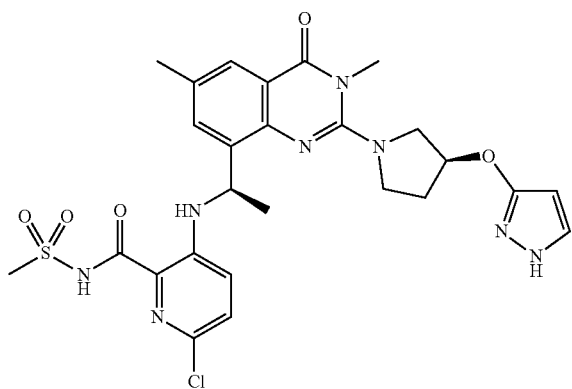 [SMILES: Cc1cc([C@@H](C)Nc2ccc(Cl)nc2C(=O)NS(C)(=O)=O)c2nc(N3CC[C@H](Oc4cc[nH]n4)C3)n(C)c(=O)c2c1] |

TABLE 1-continued

List of Compounds

| Cpd. ID | Chemical structure |
|---|---|
| 363 | 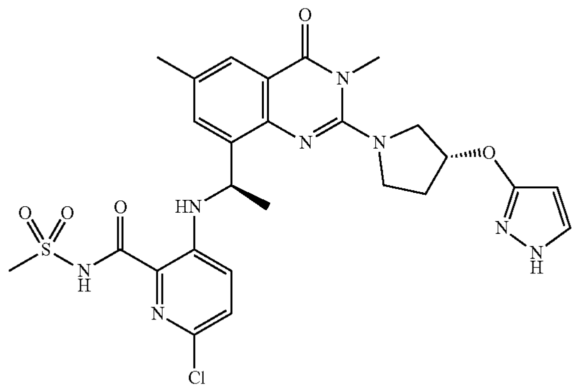 [SMILES: Cc1cc([C@@H](C)Nc2ccc(Cl)nc2C(=O)NS(C)(=O)=O)c2nc(N3CC[C@@H](Oc4cc[nH]n4)C3)n(C)c(=O)c2c1] |
| 364 | 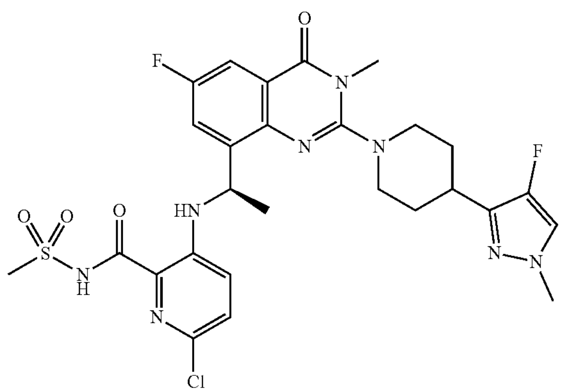 [SMILES: C[C@@H](Nc1ccc(Cl)nc1C(=O)NS(C)(=O)=O)c1cc(F)cc2c(=O)n(C)c(N3CCC(c4nn(C)cc4F)CC3)nc12] |
| 365 | 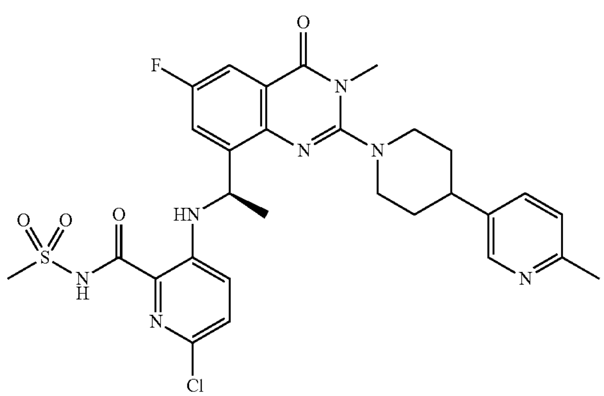 |
| 366 | 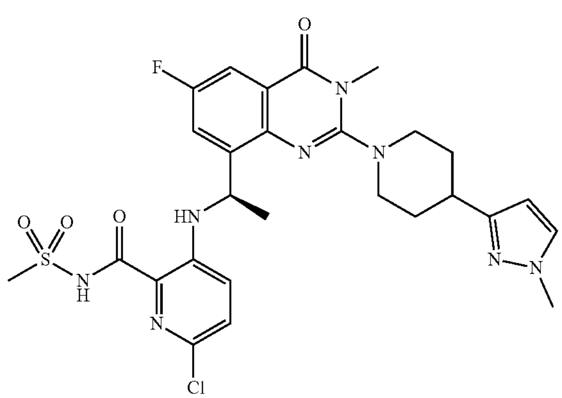 [SMILES: C[C@@H](Nc1ccc(Cl)nc1C(=O)NS(C)(=O)=O)c1cc(F)cc2c(=O)n(C)c(N3CCC(c4ccn(C)n4)CC3)nc12] |

TABLE 1-continued
| List of Compounds | |
|---|---|
| Cpd. ID | Chemical structure |
| 367 | 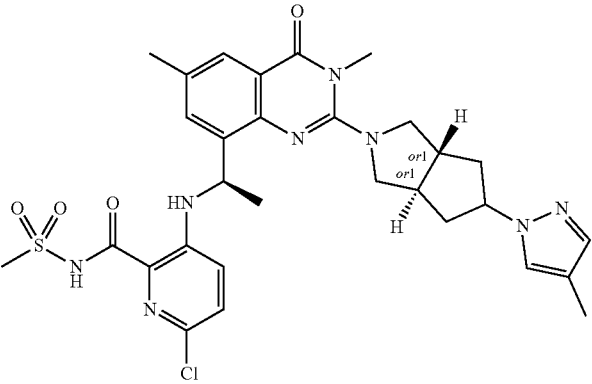 [SMILES: Cc1cc([C@@H](C)Nc2ccc(Cl)nc2C(=O)NS(C)(=O)=O)c2nc(N3C[C@@H]4CC(n5cc(C)cn5)C[C@H]4C3)n(C)c(=O)c2c1] |
| 368 | 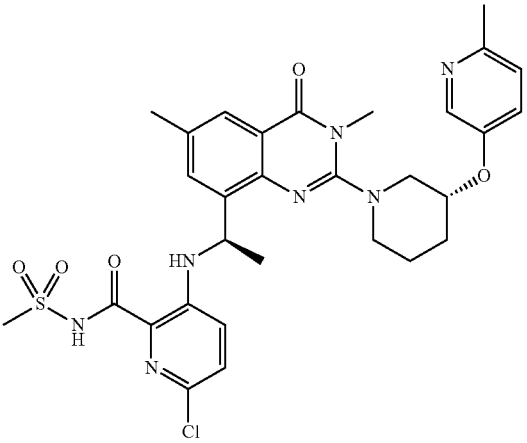 [SMILES: Cc1cc([C@@H](C)Nc2ccc(Cl)nc2C(=O)NS(C)(=O)=O)c2nc(N3CCC[C@@H](Oc4ccc(C)nc4)C3)n(C)c(=O)c2c1] |
| 369 | 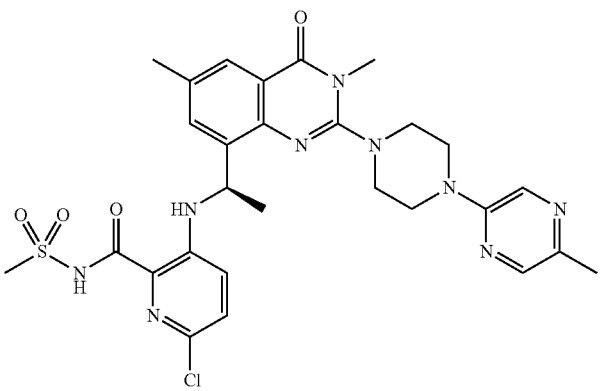 |

TABLE 1-continued
List of Compounds
| Cpd. ID | Chemical structure |
|---|---|
| 370 | 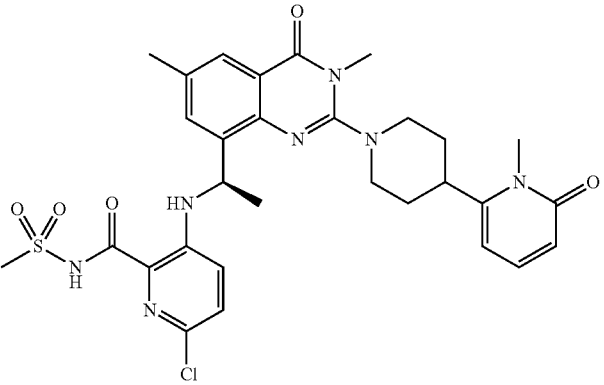 [SMILES: Cc1cc([C@@H](C)Nc2ccc(Cl)nc2C(=O)NS(C)(=O)=O)c2nc(N3CCC(c4cccc(=O)n4C)CC3)n(C)c(=O)c2c1] |
| 371 | 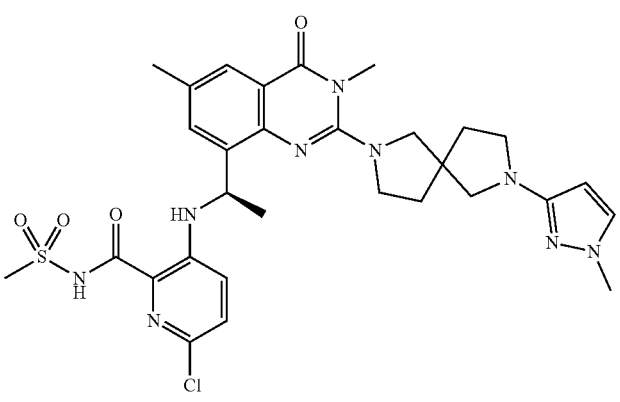 [SMILES: Cc1cc([C@@H](C)Nc2ccc(Cl)nc2C(=O)NS(C)(=O)=O)c2nc(N3CCC4(CCN(c5ccn(C)n5)C4)C3)n(C)c(=O)c2c1] |
| 372 | 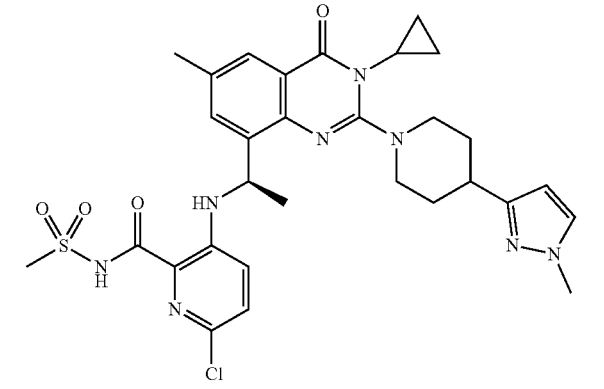 [SMILES: Cc1cc([C@@H](C)Nc2ccc(Cl)nc2C(=O)NS(C)(=O)=O)c2nc(N3CCC(c4ccn(C)n4)CC3)n(C3CC3)c(=O)c2c1] |
| 373 | 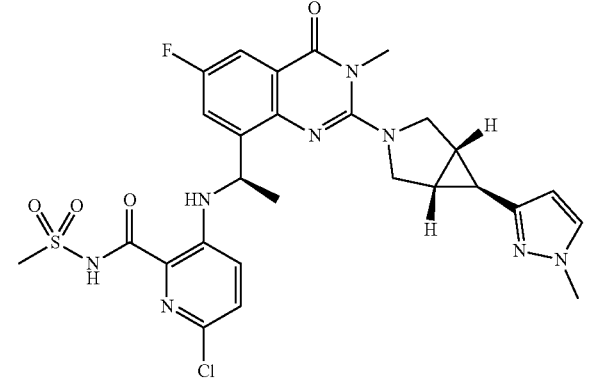 [SMILES: C[C@@H](Nc1ccc(Cl)nc1C(=O)NS(C)(=O)=O)c1cc(F)cc2c(=O)n(C)c(N3C[C@@H]4[C@H](C3)[C@H]4c3ccn(C)n3)nc12] |

TABLE 1-continued

List of Compounds

| Cpd. ID | Chemical structure |
|---|---|
| 374 | 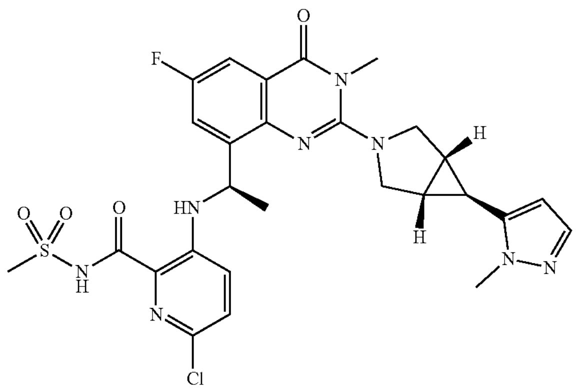 [SMILES: C[C@@H](Nc1ccc(Cl)nc1C(=O)NS(C)(=O)=O)c1cc(F)cc2c(=O)n(C)c(N3C[C@@H]4[C@H](C3)[C@H]4c3ccnn3C)nc12] |
| 375 | 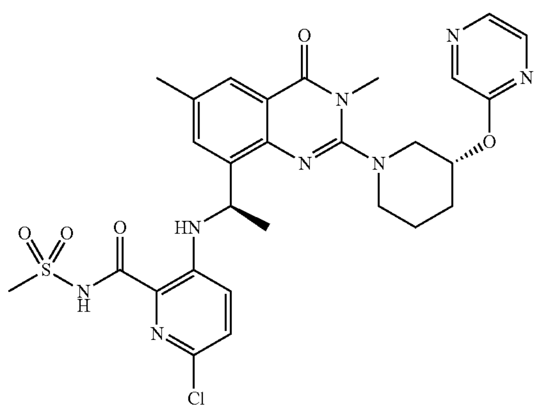 [SMILES: Cc1cc([C@@H](C)Nc2ccc(Cl)nc2C(=O)NS(C)(=O)=O)c2nc(N3CCC[C@@H](Oc4cnccn4)C3)n(C)c(=O)c2c1] |
| 376 | 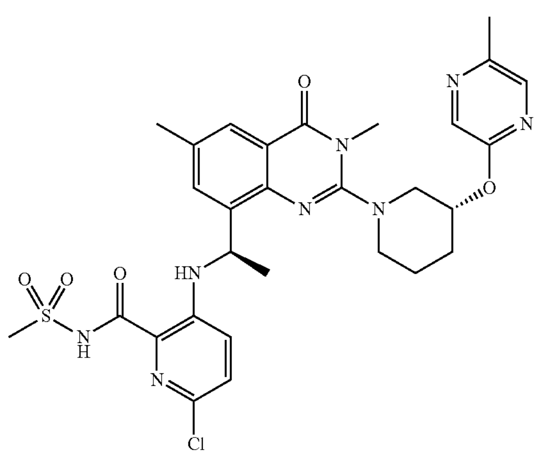 [SMILES: Cc1cc([C@@H](C)Nc2ccc(Cl)nc2C(=O)NS(C)(=O)=O)c2nc(N3CCC[C@@H](Oc4cnc(C)cn4)C3)n(C)c(=O)c2c1] |

TABLE 1-continued
List of Compounds
| Cpd. ID | Chemical structure |
|---|---|
| 377 | 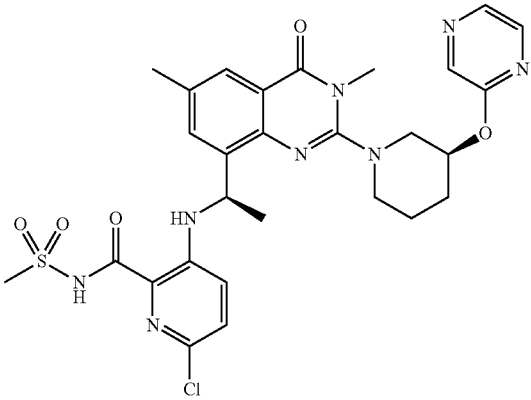 [SMILES: Cc1cc([C@@H](C)Nc2ccc(Cl)nc2C(=O)NS(C)(=O)=O)c2nc(N3CCC[C@H](Oc4cnccn4)C3)n(C)c(=O)c2c1] |
| 378 | 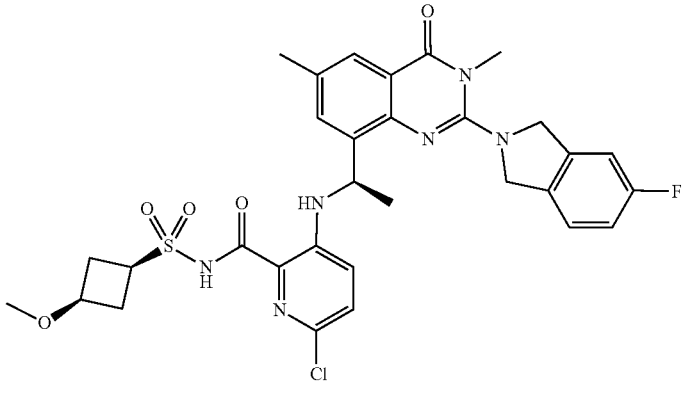 [SMILES: CO[C@H]1C[C@@H](S(=O)(=O)NC(=O)c2nc(Cl)ccc2N[C@H](C)c2cc(C)cc3c(=O)n(C)c(N4Cc5ccc(F)cc5C4)nc23)C1] |
| 379 | 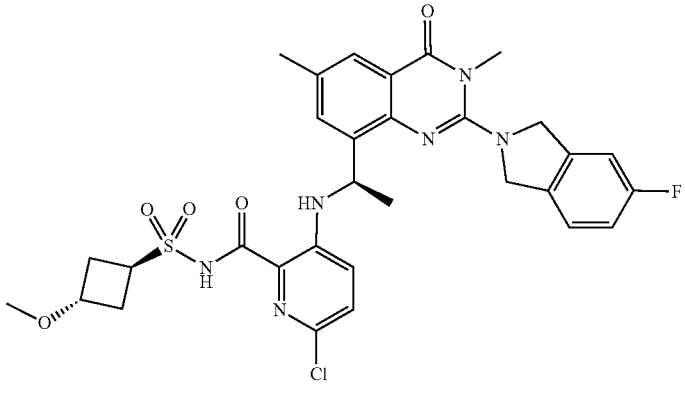 [SMILES: CO[C@H]1C[C@H](S(=O)(=O)NC(=O)c2nc(Cl)ccc2N[C@H](C)c2cc(C)cc3c(=O)n(C)c(N4Cc5ccc(F)cc5C4)nc23)C1] |
| 380 | 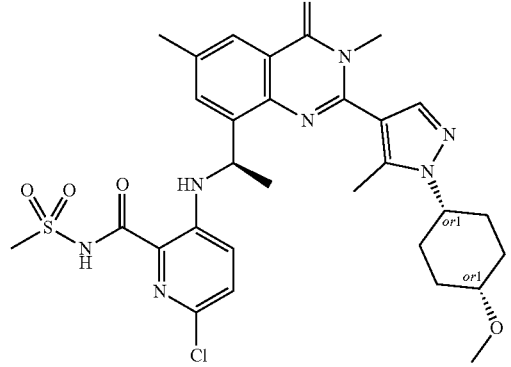 |

TABLE 1-continued

List of Compounds

| Cpd. ID | Chemical structure |
|---|---|
| 381 | 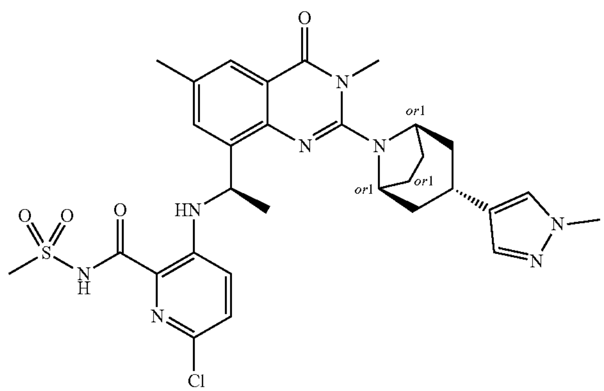 |
| 382 | 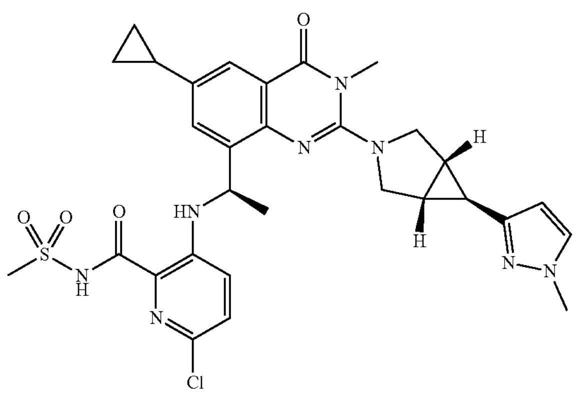 [SMILES: C[C@@H](Nc1ccc(Cl)nc1C(=O)NS(C)(=O)=O)c1cc(C2CC2)cc2c(=O)n(C)c(N3C[C@@H]4[C@H](C3)[C@H]4c3ccn(C)n3)nc12] |
| 383 | 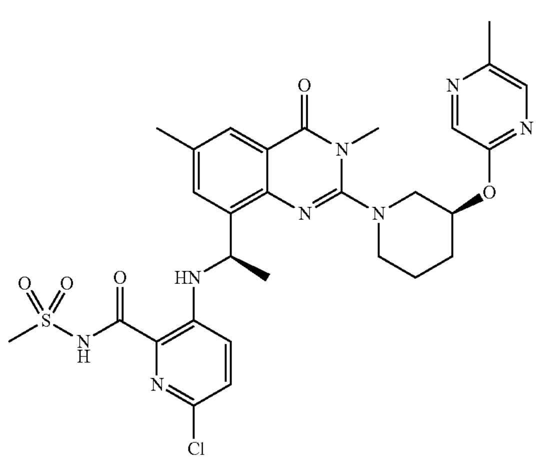 [SMILES: Cc1cc([C@@H](C)Nc2ccc(Cl)nc2C(=O)NS(C)(=O)=O)c2nc(N3CCC[C@H](Oc4cnc(C)cn4)C3)n(C)c(=O)c2c1] |

TABLE 1-continued
List of Compounds
| Cpd. ID | Chemical structure |
|---|---|
| 384 | 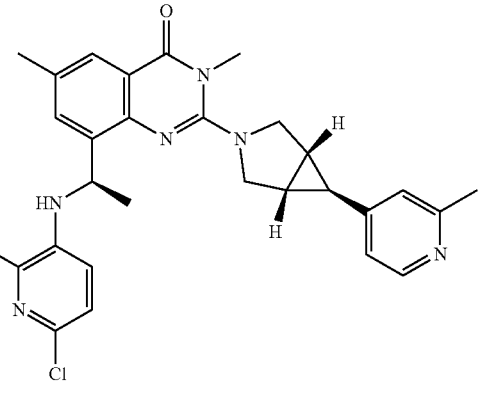 |
| 385 | 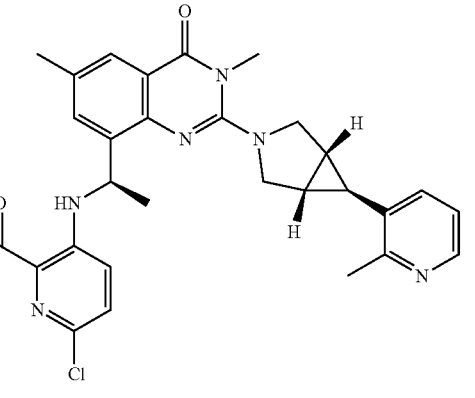 |
| 386 | 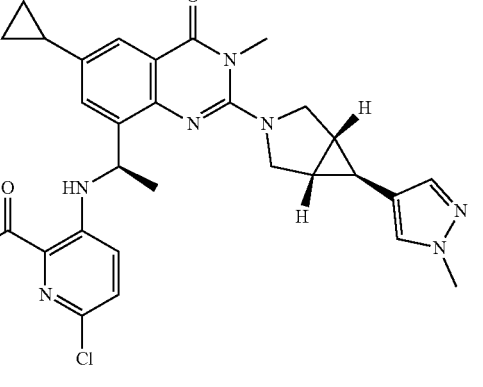 |
| 387 | 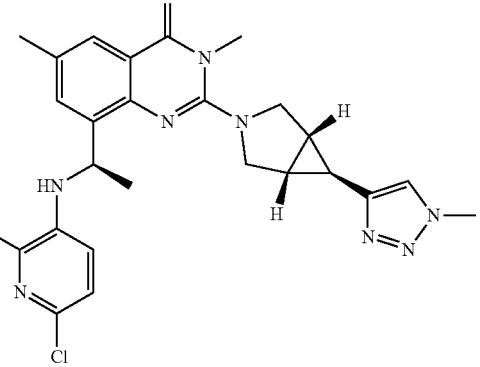 |

TABLE 1-continued

List of Compounds

| Cpd. ID | Chemical structure |
|---------|--------------------|
| 388 | 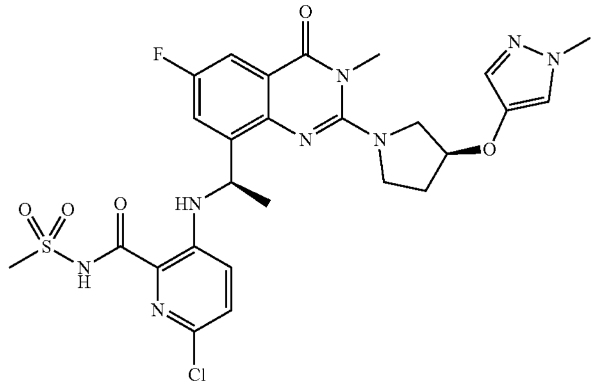 |
| 389 | 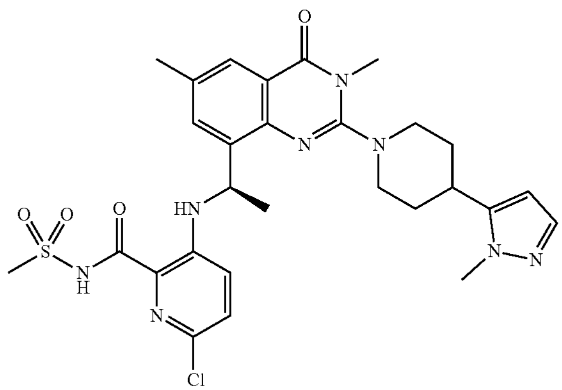 [SMILES: Cc1cc([C@@H](C)Nc2ccc(Cl)nc2C(=O)NS(C)(=O)=O)c2nc(N3CCC(c4ccnn4C)CC3)n(C)c(=O)c2c1] |
| 390 | 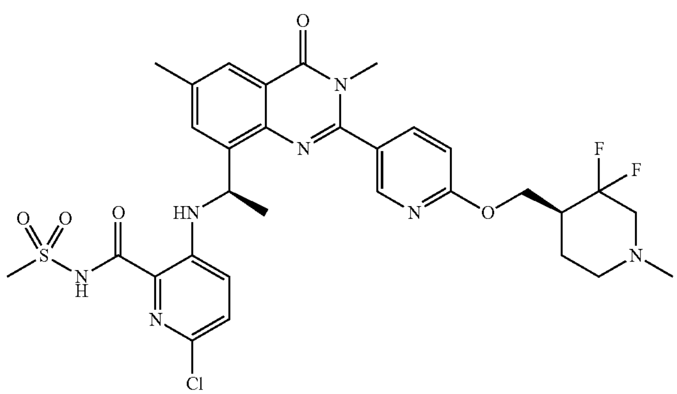 |
| 391 | 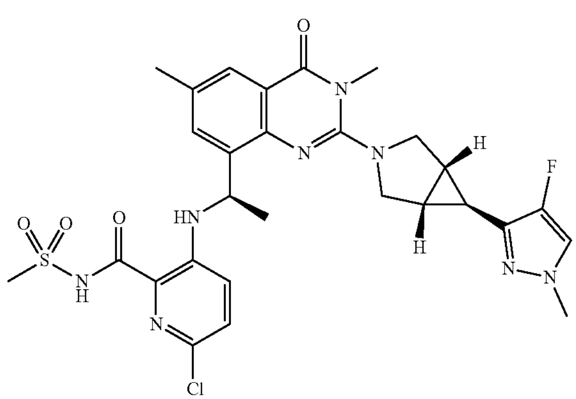 [SMILES: Cc1cc([C@@H](C)Nc2ccc(Cl)nc2C(=O)NS(C)(=O)=O)c2nc(N3C[C@@H]4[C@H](C3)[C@H]4c3nn(C)cc3F)n(C)c(=O)c2c1] |

TABLE 1-continued

List of Compounds

| Cpd. ID | Chemical structure |
|---|---|
| 392 | 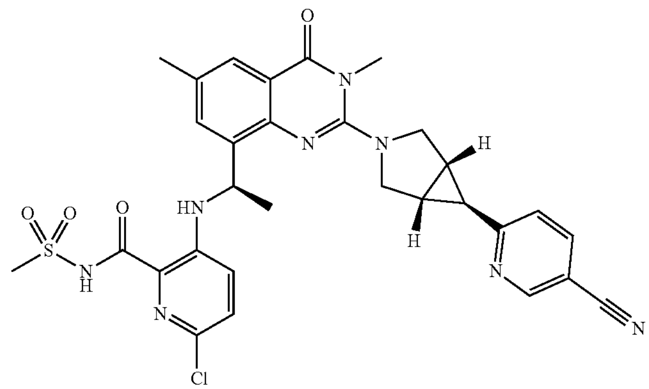 [SMILES: Cc1cc([C@@H](C)Nc2ccc(Cl)nc2C(=O)NS(C)(=O)=O)c2nc(N3C[C@@H]4[C@H](C3)[C@H]4c3ccc(C#N)cn3)n(C)c(=O)c2c1] |
| 393 | 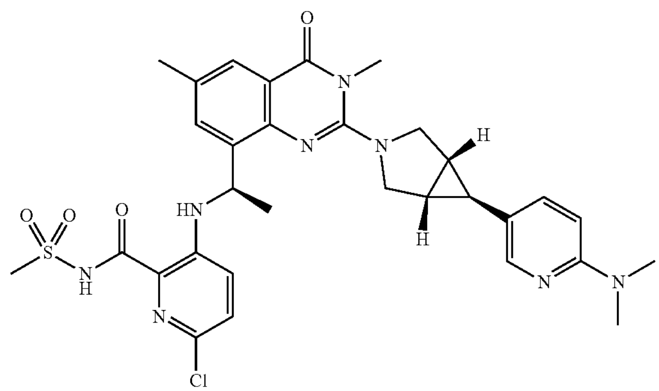 |
| 394 | 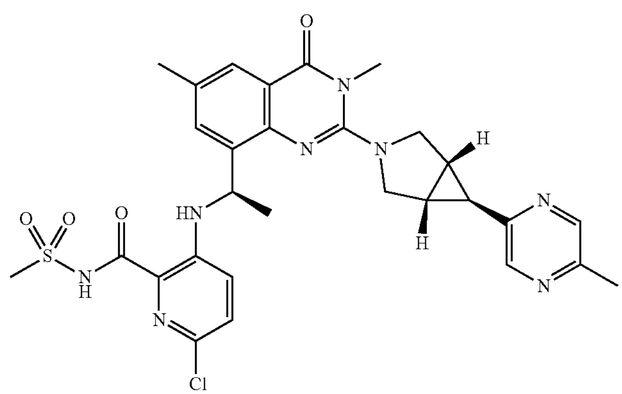 |
| 395 | 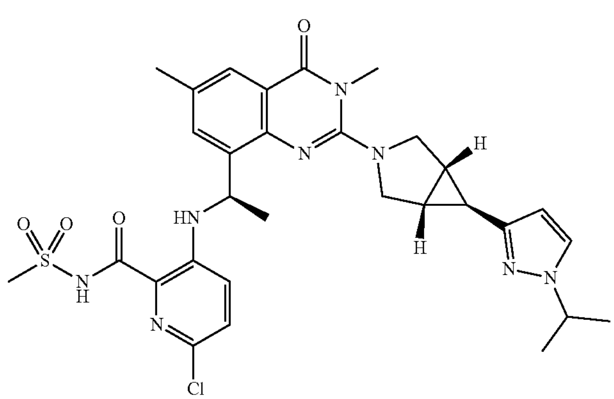 [SMILES: Cc1cc([C@@H](C)Nc2ccc(Cl)nc2C(=O)NS(C)(=O)=O)c2nc(N3C[C@@H]4[C@H](C3)[C@H]4c3ccn(C(C)C)n3)n(C)c(=O)c2c1] |

TABLE 1-continued

List of Compounds

| Cpd. ID | Chemical structure |
|---|---|
| 396 | 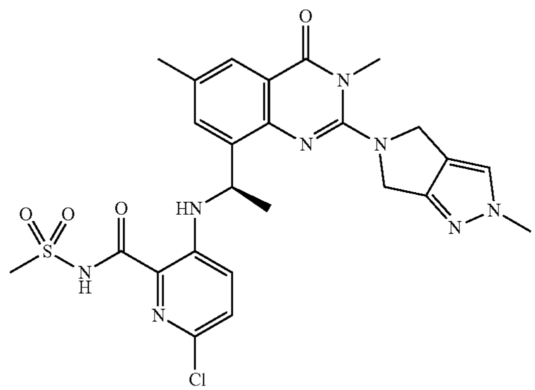 |
| 397 | 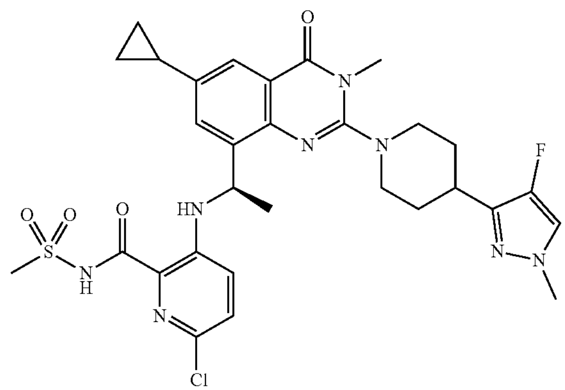 [SMILES: C[C@@H](Nc1ccc(Cl)nc1C(=O)NS(C)(=O)=O)c1cc(C2CC2)cc2c(=O)n(C)c(N3CCC(c4nn(C)cc4F)CC3)nc12] |
| 398 | 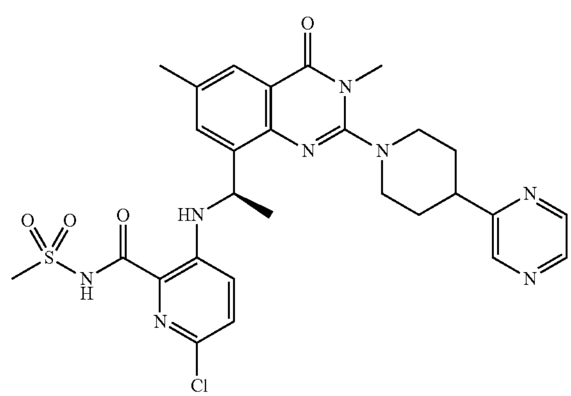 [SMILES: Cc1cc([C@@H](C)Nc2ccc(Cl)nc2C(=O)NS(C)(=O)=O)c2nc(N3CCC(c4cnccn4)CC3)n(C)c(=O)c2c1] |
| 399 | 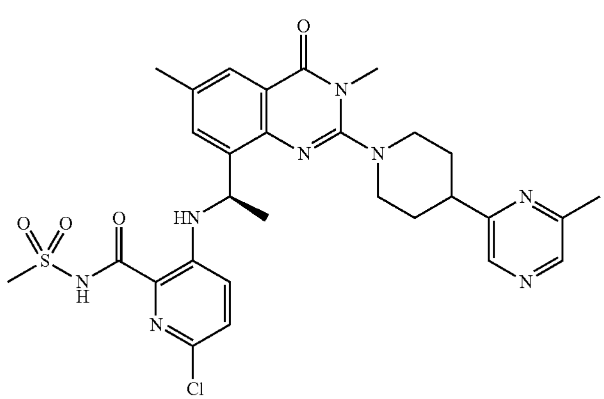 |

TABLE 1-continued

List of Compounds

| Cpd. ID | Chemical structure |
|---|---|
| 400 | 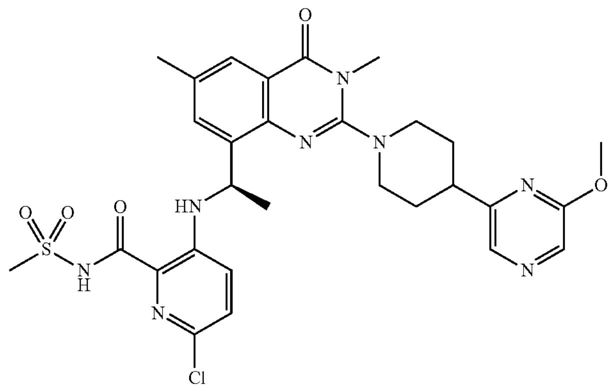 |
| 401 | 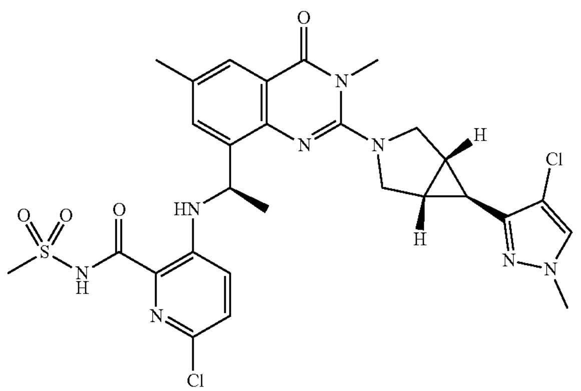 |
| 402 | 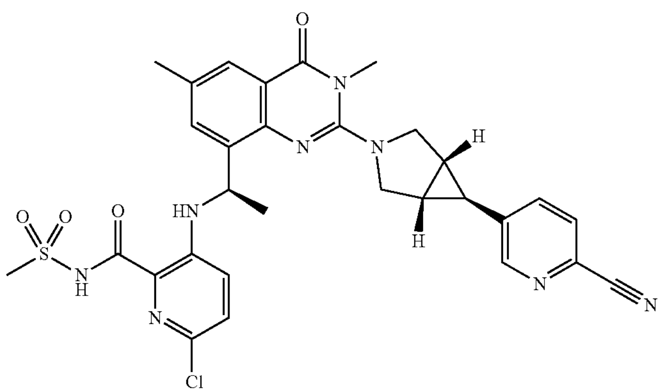 [SMILES: Cc1cc([C@@H](C)Nc2ccc(Cl)nc2C(=O)NS(C)(=O)=O)c2nc(N3C[C@@H]4[C@H](C3)[C@H]4c3ccc(C#N)nc3)n(C)c(=O)c2c1] |
| 403 | 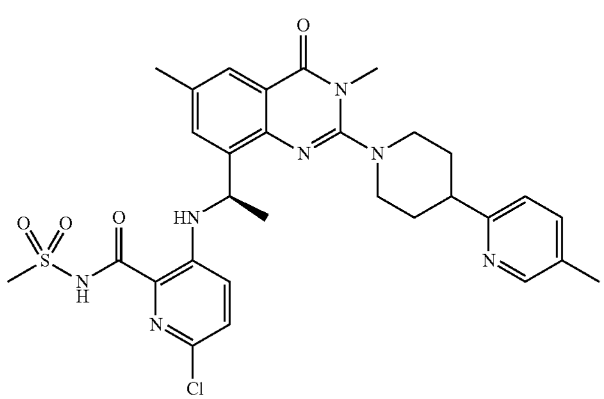 |

TABLE 1-continued

List of Compounds

| Cpd. ID | Chemical structure |
|---|---|
| 404 | 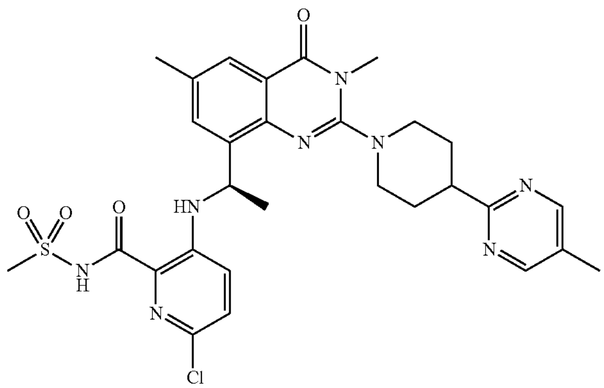 |
| 405 | 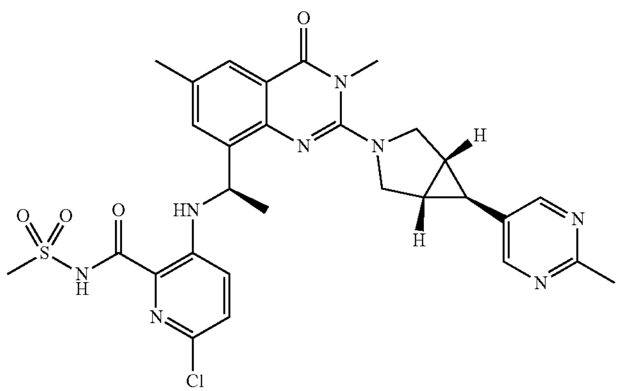 |
| 406 | 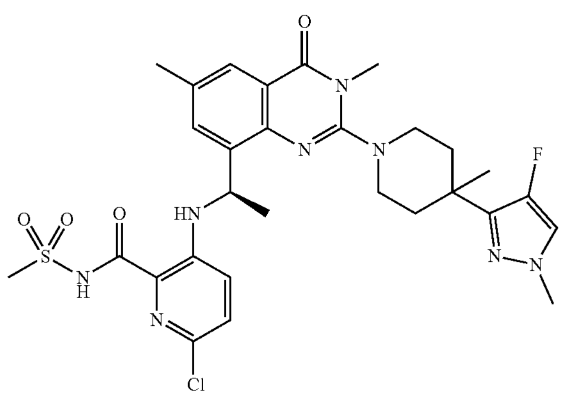 [SMILES: Cc1cc([C@@H](C)Nc2ccc(Cl)nc2C(=O)NS(C)(=O)=O)c2nc(N3CCC(C)(c4nn(C)cc4F)CC3)n(C)c(=O)c2c1] |
| 407 | 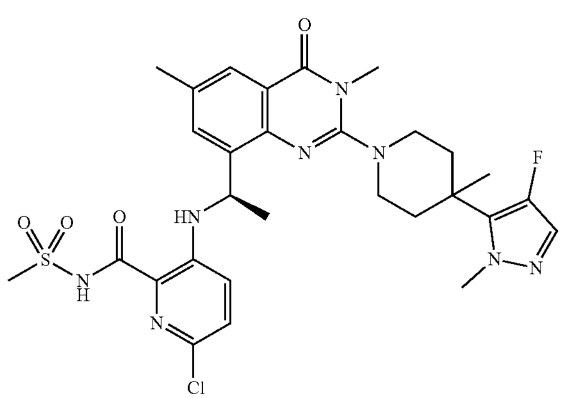 [SMILES: Cc1cc([C@@H](C)Nc2ccc(Cl)nc2C(=O)NS(C)(=O)=O)c2nc(N3CCC(C)(c4c(F)cnn4C)CC3)n(C)c(=O)c2c1] |

TABLE 1-continued

List of Compounds

| Cpd. ID | Chemical structure |
|---|---|
| 408 | 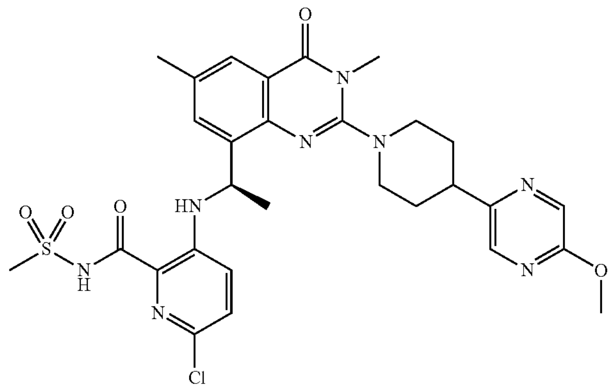 |
| 409 | 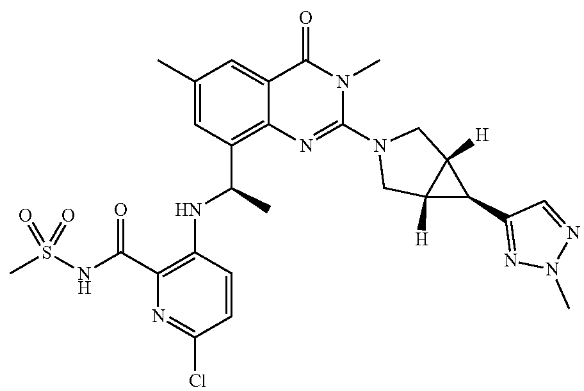 |
| 410 | 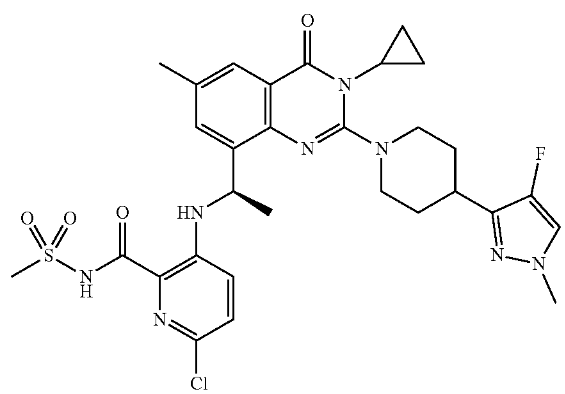 |
| 411 | 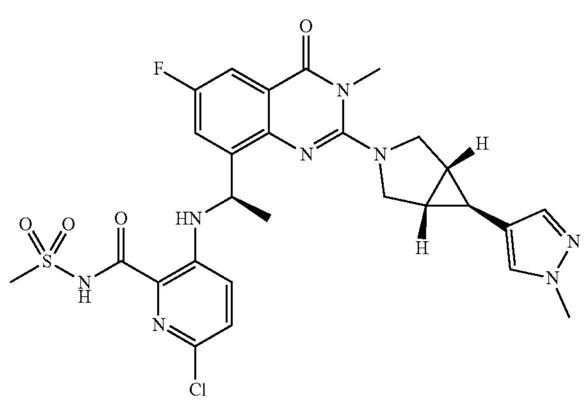 |

TABLE 1-continued
List of Compounds
| Cpd. ID | Chemical structure |
|---|---|
| 412 | 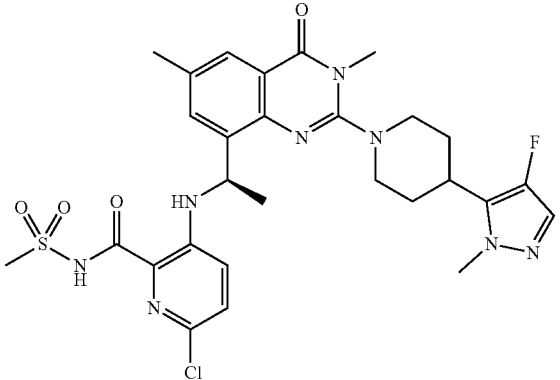 |
| 413 | 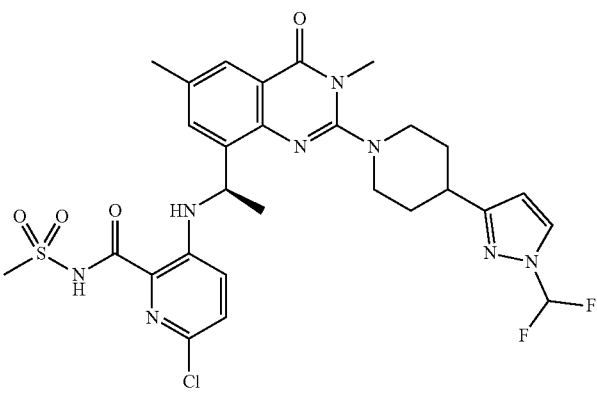 [SMILES: Cc1cc([C@@H](C)Nc2ccc(Cl)nc2C(=O)NS(C)(=O)=O)c2nc(N3CCC(c4ccn(C(F)F)n4)CC3)n(C)c(=O)c2c1] |
| 414 | 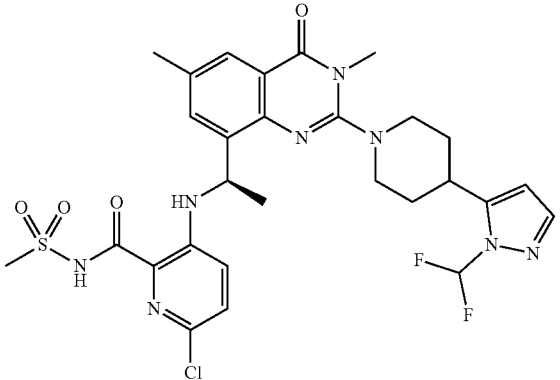 [SMILES: Cc1cc([C@@H](C)Nc2ccc(Cl)nc2C(=O)NS(C)(=O)=O)c2nc(N3CCC(c4ccnn4C(F)F)CC3)n(C)c(=O)c2c1] |
| 415 | 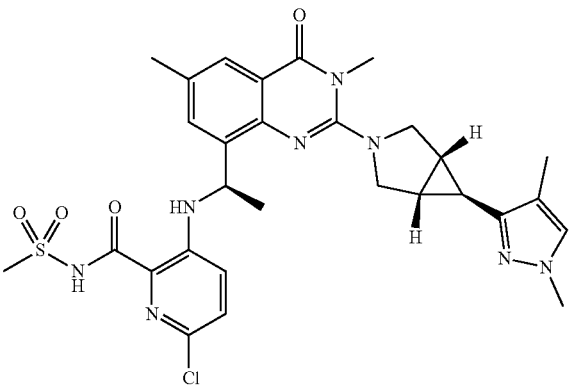 |

TABLE 1-continued

List of Compounds

| Cpd. ID | Chemical structure |
|---|---|
| 416 | 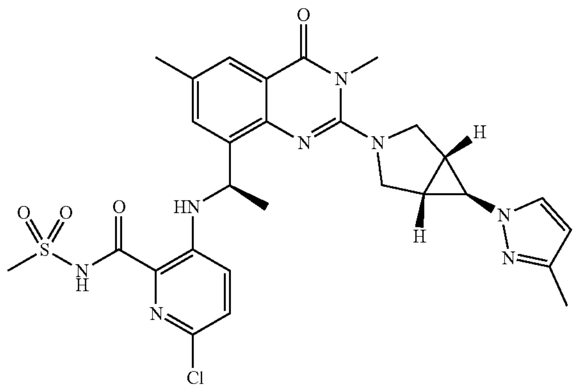 [SMILES: Cc1cc([C@@H](C)Nc2ccc(Cl)nc2C(=O)NS(C)(=O)=O)c2nc(N3C[C@@H]4[C@H](C3)[C@H]4n3ccc(C)n3)n(C)c(=O)c2c1] |
| 417 | 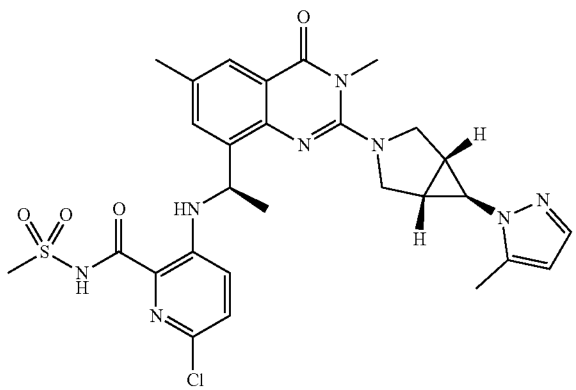 [SMILES: Cc1cc([C@@H](C)Nc2ccc(Cl)nc2C(=O)NS(C)(=O)=O)c2nc(N3C[C@@H]4[C@H](C3)[C@H]4n3nccc3C)n(C)c(=O)c2c1] |
| 418 | 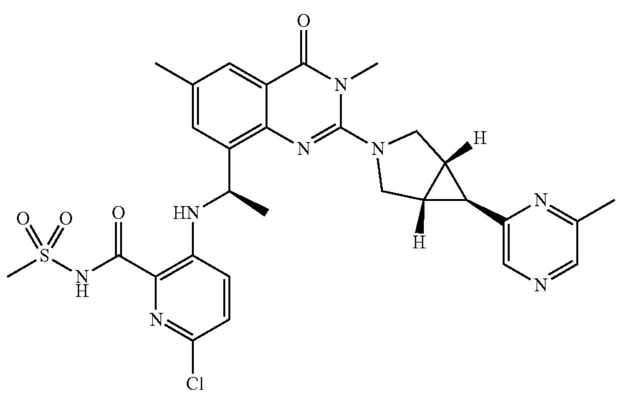 |
| 419 | 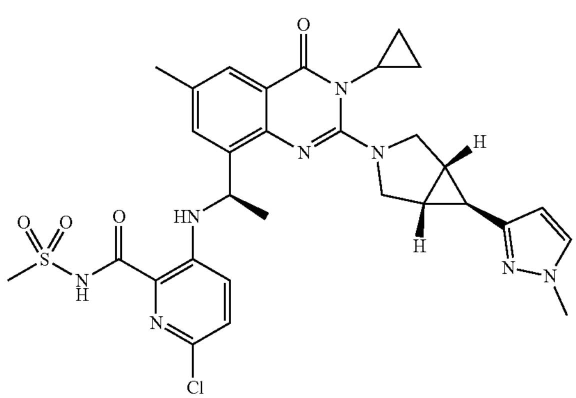 [SMILES: Cc1cc([C@@H](C)Nc2ccc(Cl)nc2C(=O)NS(C)(=O)=O)c2nc(N3C[C@@H]4[C@H](C3)[C@H]4c3ccn(C)n3)n(C3CC3)c(=O)c2c1] |

TABLE 1-continued

List of Compounds

| Cpd. ID | Chemical structure |
|---|---|
| 420 | 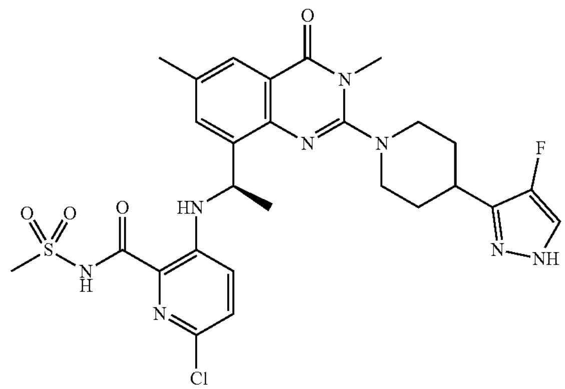 [SMILES: Cc1cc([C@@H](C)Nc2ccc(Cl)nc2C(=O)NS(C)(=O)=O)c2nc(N3CCC(c4n[nH]cc4F)CC3)n(C)c(=O)c2c1] |
| 421 | 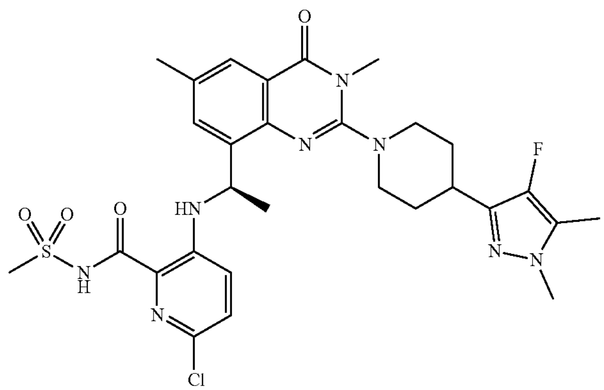 |
| 422 | 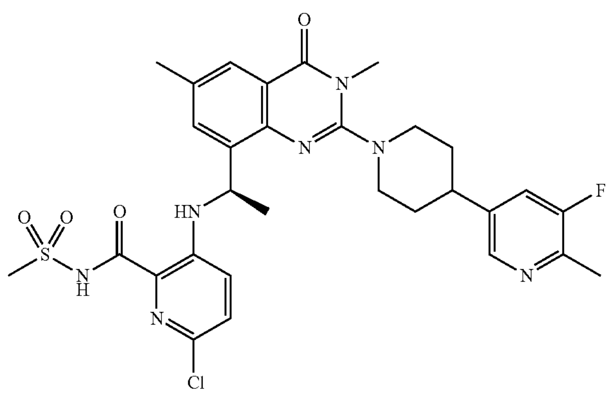 |
| 423 | 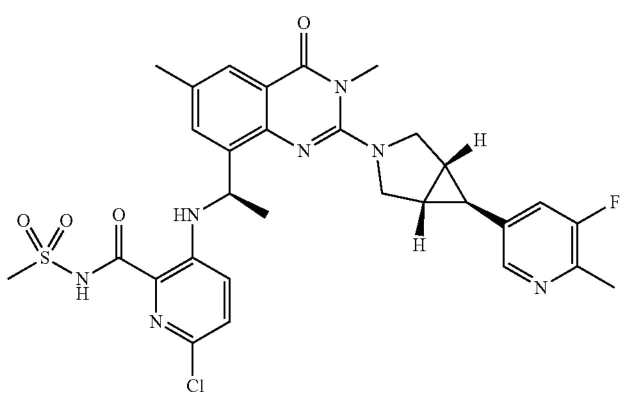 [SMILES: Cc1cc([C@@H](C)Nc2ccc(Cl)nc2C(=O)NS(C)(=O)=O)c2nc(N3C[C@@H]4[C@H](C3)[C@H]4c3cnc(C)c(F)c3)n(C)c(=O)c2c1] |

TABLE 1-continued
List of Compounds
| Cpd. ID | Chemical structure |
|---|---|
| 424 | 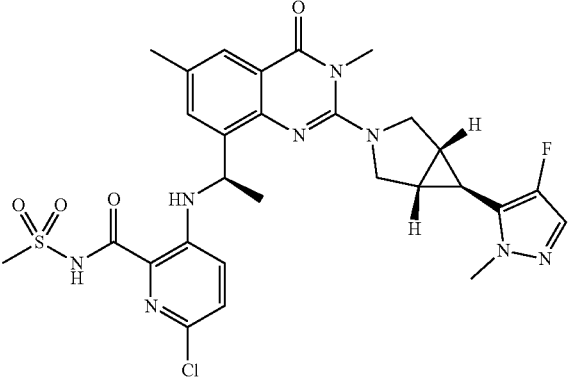 [SMILES: Cc1cc([C@@H](C)Nc2ccc(Cl)nc2C(=O)NS(C)(=O)=O)c2nc(N3C[C@@H]4[C@H](C3)[C@H]4c3c(F)cnn3C)n(C)c(=O)c2c1] |
| 425 | 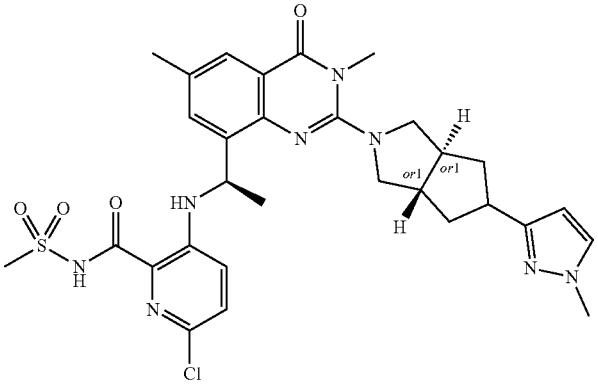 [SMILES: Cc1cc([C@@H](C)Nc2ccc(Cl)nc2C(=O)NS(C)(=O)=O)c2nc(N3C[C@H]4CC(c5ccn(C)n5)C[C@@H]4C3)n(C)c(=O)c2c1] |
| 426 | 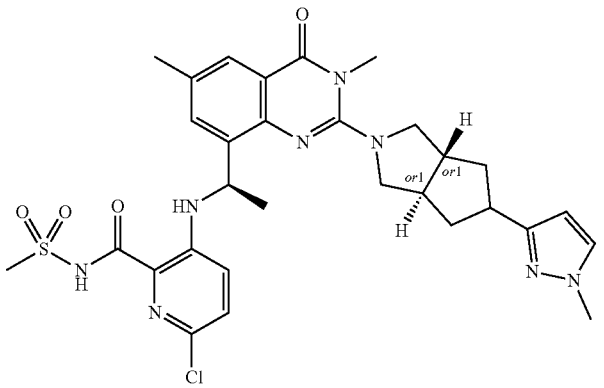 [SMILES: Cc1cc([C@@H](C)Nc2ccc(Cl)nc2C(=O)NS(C)(=O)=O)c2nc(N3C[C@@H]4CC(c5ccn(C)n5)C[C@H]4C3)n(C)c(=O)c2c1] |
| 427 | 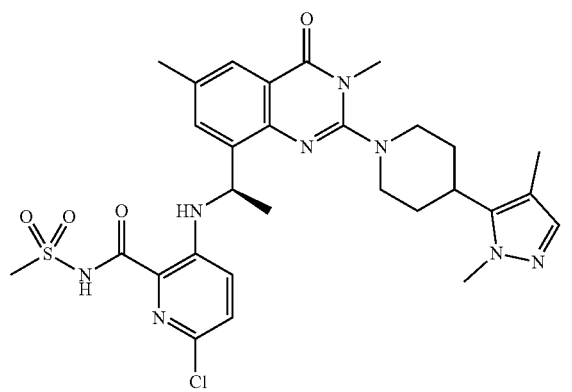 |

TABLE 1-continued

List of Compounds

| Cpd. ID | Chemical structure |
|---|---|
| 428 | 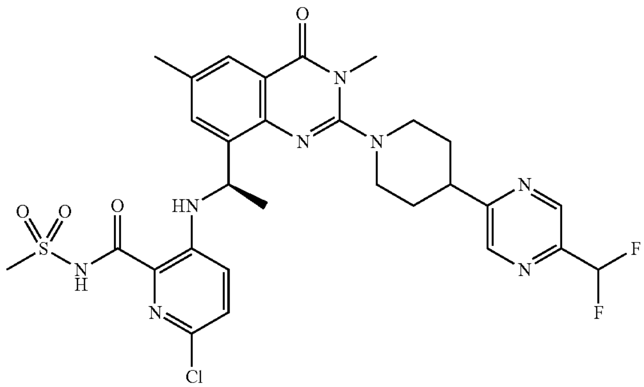 [SMILES: Cc1cc([C@@H](C)Nc2ccc(Cl)nc2C(=O)NS(C)(=O)=O)c2nc(N3CCC(c4cnc(C(F)F)cn4)CC3)n(C)c(=O)c2c1] |
| 429 | 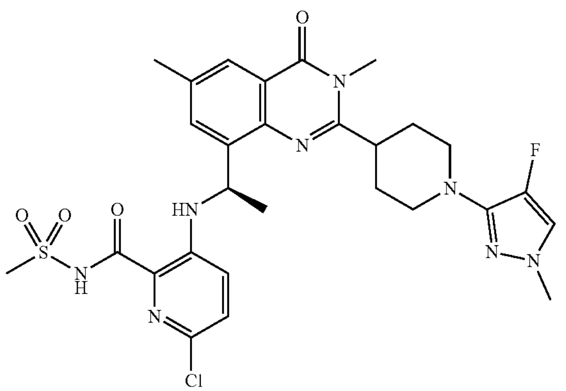 |
| 430 | 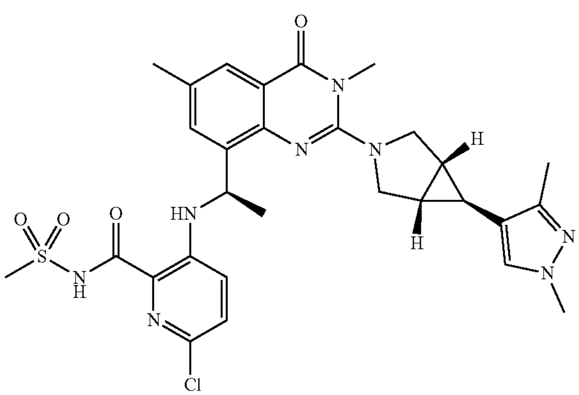 [SMILES: Cc1cc([C@@H](C)Nc2ccc(Cl)nc2C(=O)NS(C)(=O)=O)c2nc(N3C[C@@H]4[C@H](C3)[C@H]4c3cn(C)nc3C)n(C)c(=O)c2c1] |
| 431 | 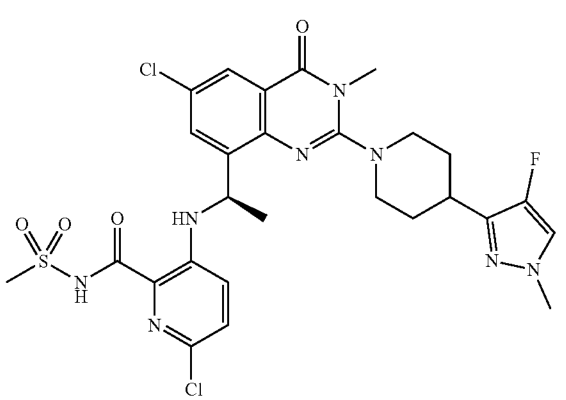 |

TABLE 1-continued

List of Compounds

| Cpd. ID | Chemical structure |
|---|---|
| 432 | 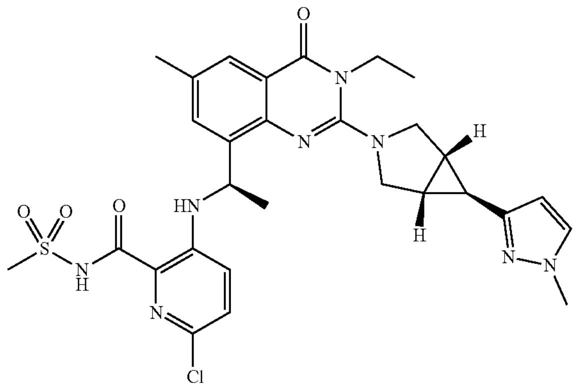 [SMILES: CCn1c(N2C[C@@H]3[C@H](C2)[C@H]3c2ccn(C)n2)nc2c([C@@H](C)Nc3ccc(Cl)nc3C(=O)NS(C)(=O)=O)cc(C)cc2c1=O] |
| 433 | 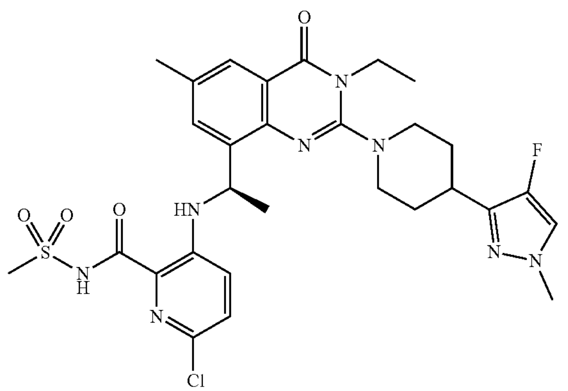 [SMILES: CCn1c(N2CCC(c3nn(C)cc3F)CC2)nc2c([C@@H](C)Nc3ccc(Cl)nc3C(=O)NS(C)(=O)=O)cc(C)cc2c1=O] |
| 434 | 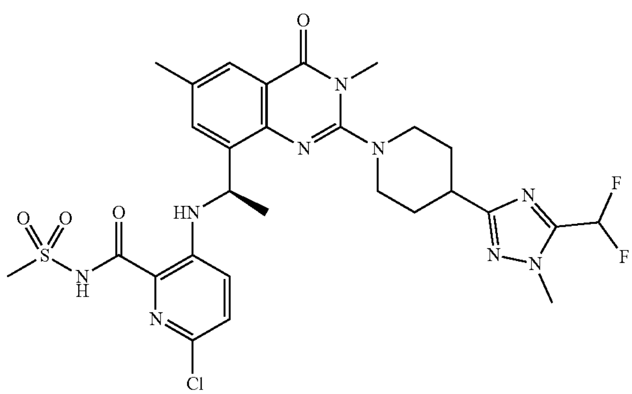 [SMILES: Cc1cc([C@@H](C)Nc2ccc(Cl)nc2C(=O)NS(C)(=O)=O)c2nc(N3CCC(c4nc(C(F)F)n(C)n4)CC3)n(C)c(=O)c2c1] |
| 435 | 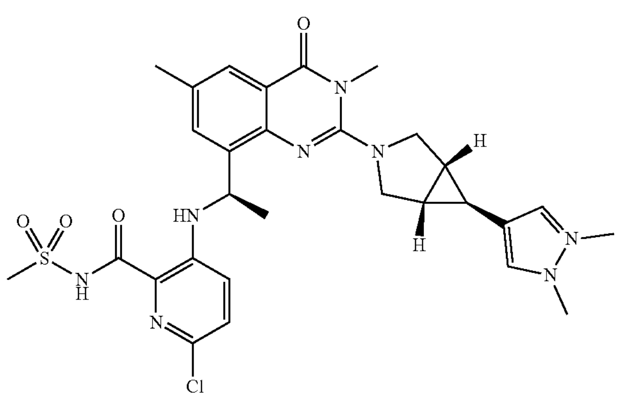 |

TABLE 1-continued

List of Compounds

| Cpd. ID | Chemical structure |
|---------|--------------------|
| 436 | 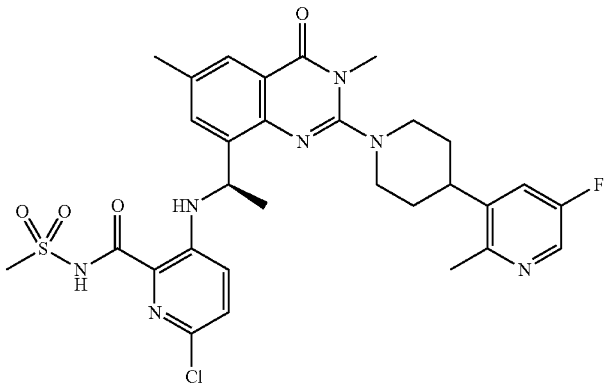 [SMILES: Cc1cc([C@@H](C)Nc2ccc(Cl)nc2C(=O)NS(C)(=O)=O)c2nc(N3CCC(c4cc(F)cnc4C)CC3)n(C)c(=O)c2c1] |
| 437 | 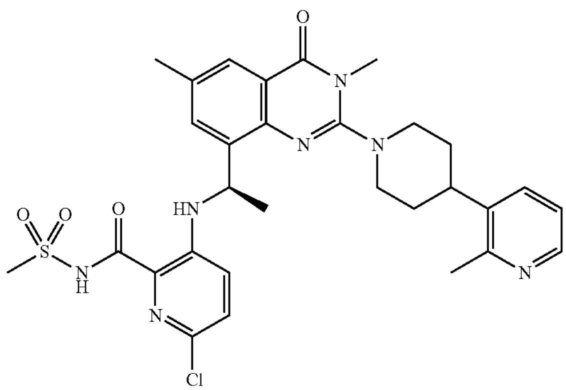 [SMILES: Cc1cc([C@@H](C)Nc2ccc(Cl)nc2C(=O)NS(C)(=O)=O)c2nc(N3CCC(c4cccnc4C)CC3)n(C)c(=O)c2c1] |
| 438 | 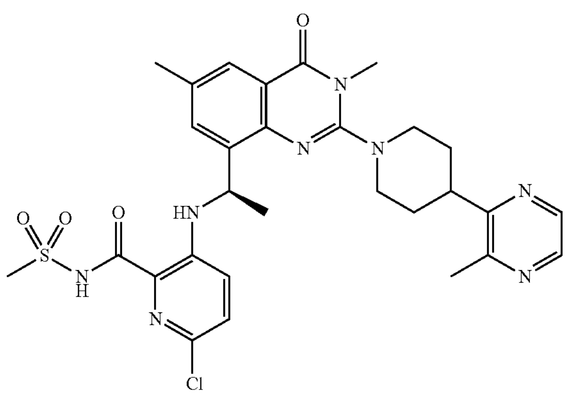 [SMILES: Cc1cc([C@@H](C)Nc2ccc(Cl)nc2C(=O)NS(C)(=O)=O)c2nc(N3CCC(c4nccnc4C)CC3)n(C)c(=O)c2c1] |
| 439 | 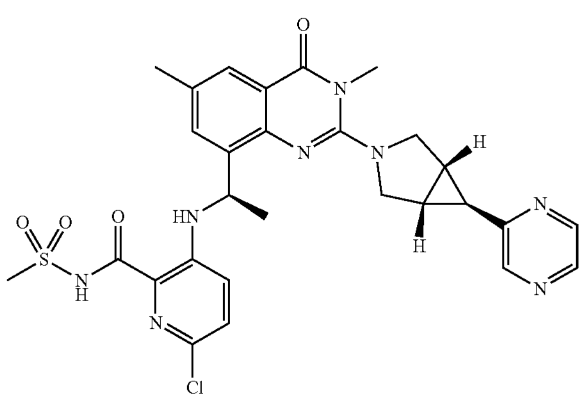 [SMILES: Cc1cc([C@@H](C)Nc2ccc(Cl)nc2C(=O)NS(C)(=O)=O)c2nc(N3C[C@@H]4[C@H](C3)[C@H]4c3cnccn3)n(C)c(=O)c2c1] |

TABLE 1-continued

List of Compounds

| Cpd. ID | Chemical structure |
|---|---|
| 440 | 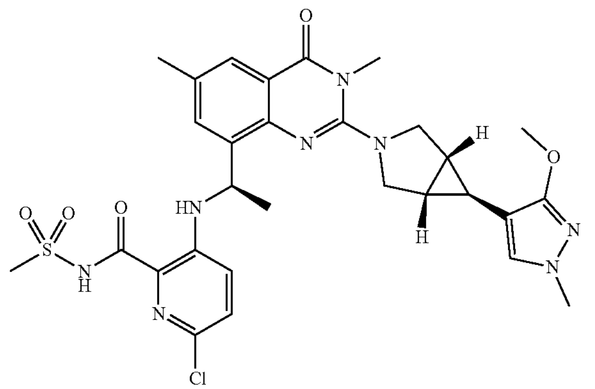 [SMILES: COc1nn(C)cc1[C@H]1[C@@H]2CN(c3nc4c([C@@H](C)Nc5ccc(Cl)nc5C(=O)NS(C)(=O)=O)cc(C)cc4c(=O)n3C)C[C@@H]21] |
| 441 | 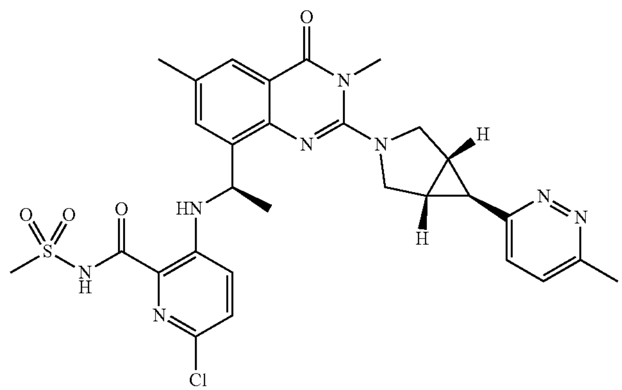 |
| 442 | 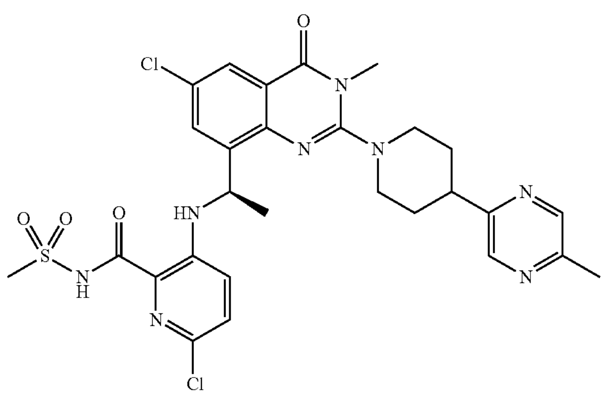 |
| 443 | 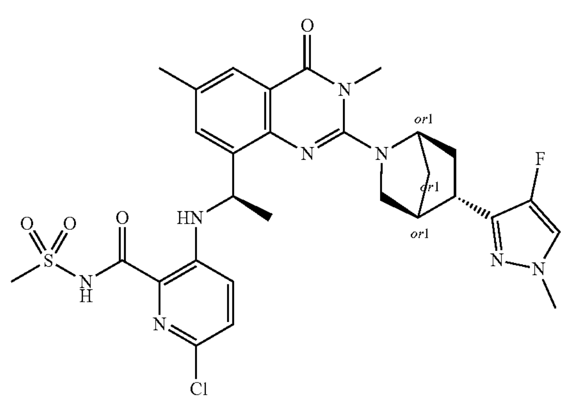 [SMILES: Cc1cc([C@@H](C)Nc2ccc(Cl)nc2C(=O)NS(C)(=O)=O)c2nc(N3C[C@H]4C[C@@H]3C[C@@H]4c3nn(C)cc3F)n(C)c(=O)c2c1] |

TABLE 1-continued
List of Compounds
| Cpd. ID | Chemical structure |
|---|---|
| 444 | 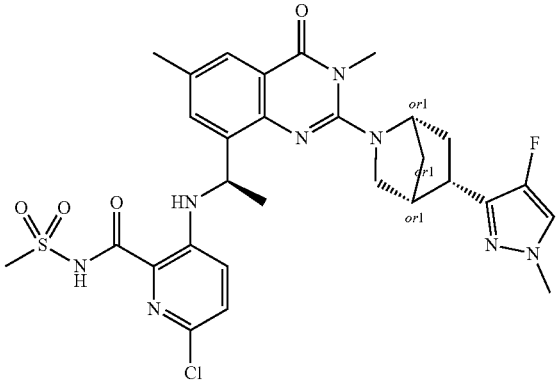 [SMILES: Cc1cc([C@@H](C)Nc2ccc(Cl)nc2C(=O)NS(C)(=O)=O)c2nc(N3C[C@@H]4C[C@H]3C[C@@H]4c3nn(C)cc3F)n(C)c(=O)c2c1] |
| 445 | 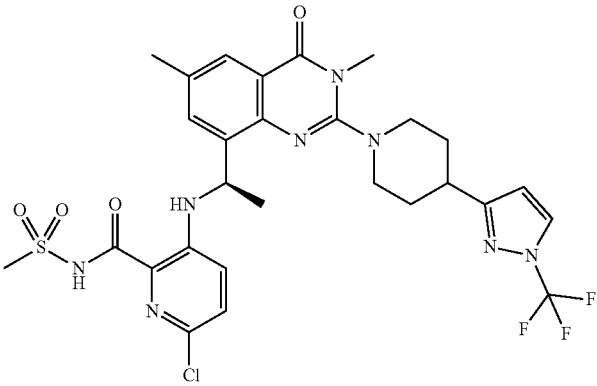 [SMILES: Cc1cc([C@@H](C)Nc2ccc(Cl)nc2C(=O)NS(C)(=O)=O)c2nc(N3CCC(c4ccn(C(F)(F)F)n4)CC3)n(C)c(=O)c2c1] |
| 446 | 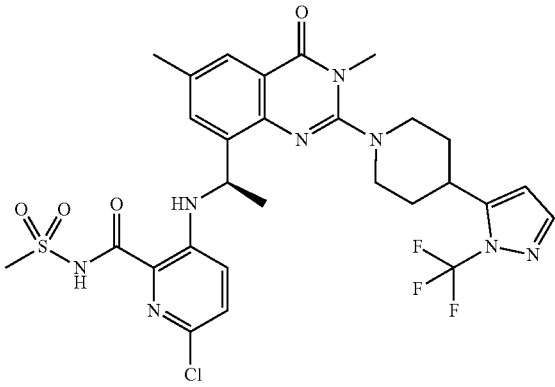 [SMILES: Cc1cc([C@@H](C)Nc2ccc(Cl)nc2C(=O)NS(C)(=O)=O)c2nc(N3CCC(c4ccnn4C(F)(F)F)CC3)n(C)c(=O)c2c1] |
| 447 | 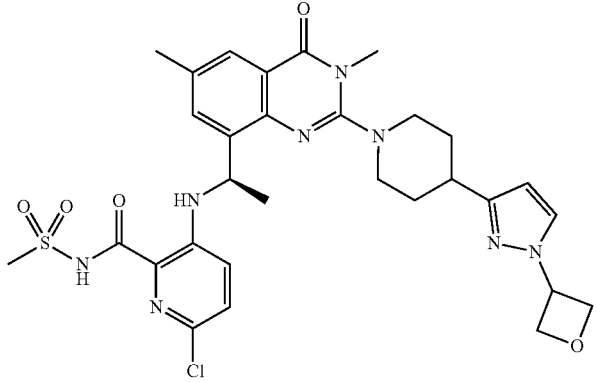 [SMILES: Cc1cc([C@@H](C)Nc2ccc(Cl)nc2C(=O)NS(C)(=O)=O)c2nc(N3CCC(c4ccn(C5COC5)n4)CC3)n(C)c(=O)c2c1] |

TABLE 1-continued

List of Compounds

| Cpd. ID | Chemical structure |
|---|---|
| 448 | 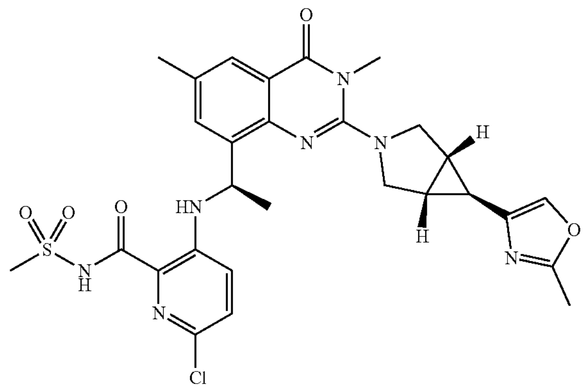 [SMILES: Cc1cc([C@@H](C)Nc2ccc(Cl)nc2C(=O)NS(C)(=O)=O)c2nc(N3C[C@@H]4[C@H](C3)[C@H]4c3coc(C)n3)n(C)c(=O)c2c1] |
| 449 | 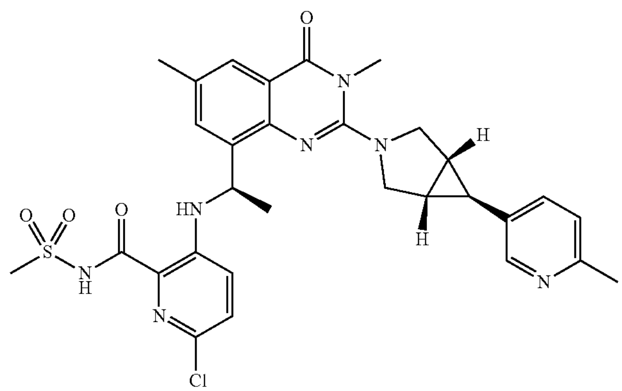 |
| 450 | 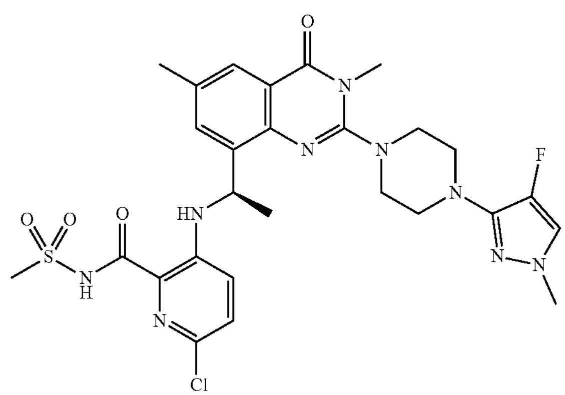 |
| 451 | 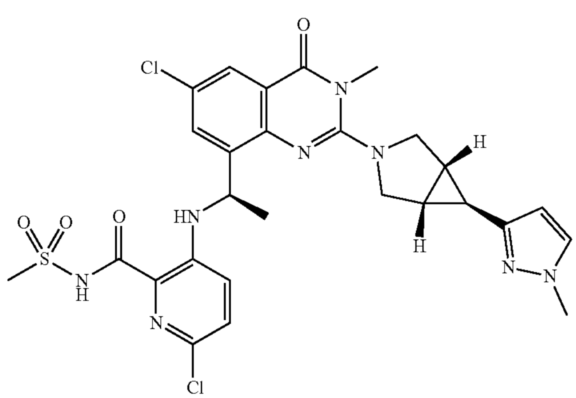 [SMILES: C[C@@H](Nc1ccc(Cl)nc1C(=O)NS(C)(=O)=O)c1cc(Cl)cc2c(=O)n(C)c(N3C[C@@H]4[C@H](C3)[C@H]4c3ccn(C)n3)nc12] |

TABLE 1-continued

List of Compounds

| Cpd. ID | Chemical structure |
|---|---|
| 452 | 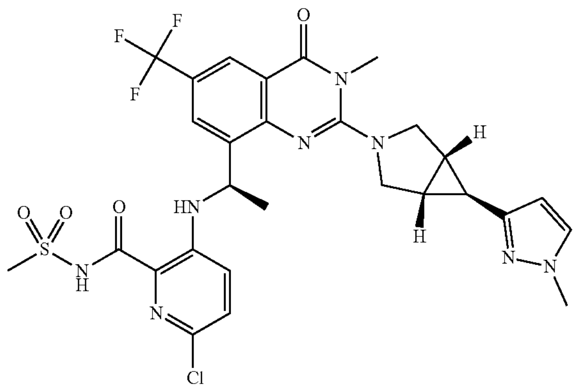 [SMILES: C[C@@H](Nc1ccc(Cl)nc1C(=O)NS(C)(=O)=O)c1cc(C(F)(F)F)cc2c(=O)n(C)c(N3C[C@@H]4[C@H](C3)[C@H]4c3ccn(C)n3)nc12] |
| 453 | 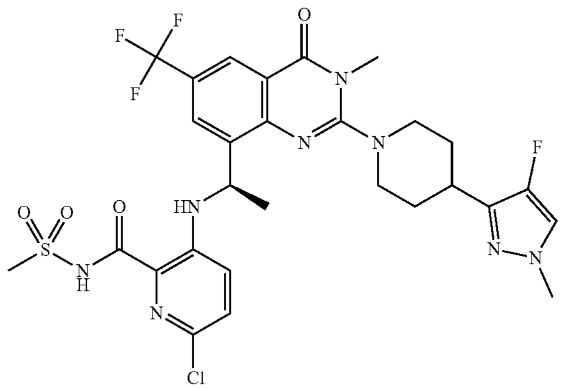 [SMILES: C[C@@H](Nc1ccc(Cl)nc1C(=O)NS(C)(=O)=O)c1cc(C(F)(F)F)cc2c(=O)n(C)c(N3CCC(c4nn(C)cc4F)CC3)nc12] |
| 454 | 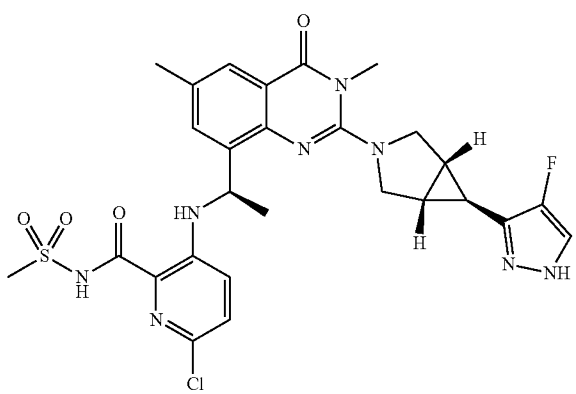 |
| 455 | 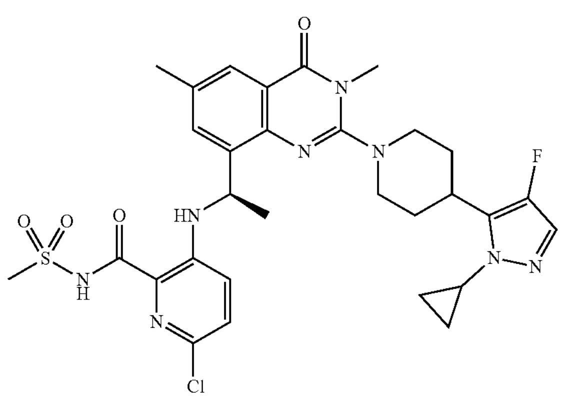 [SMILES: Cc1cc([C@@H](C)Nc2ccc(Cl)nc2C(=O)NS(C)(=O)=O)c2nc(N3CCC(c4c(F)cnn4C4CC4)CC3)n(C)c(=O)c2c1] |

TABLE 1-continued
List of Compounds
| Cpd. ID | Chemical structure |
|---|---|
| 456 | 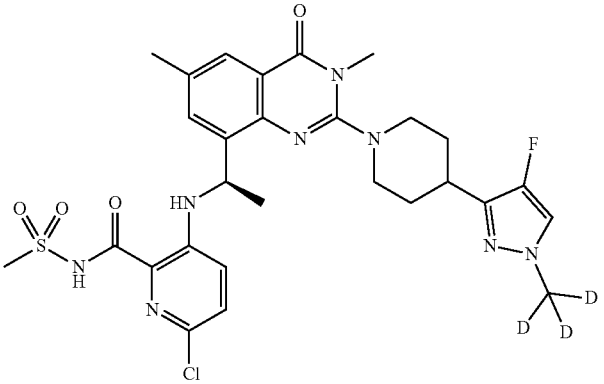 [SMILES: [2H]C([2H])([2H])n1cc(F)c(C2CCN(c3nc4c([C@@H](C)Nc5ccc(Cl)nc5C(=O)NS(C)(=O)=O)cc(C)cc4c(=O)n3C)CC2)n1] |
| 457 | 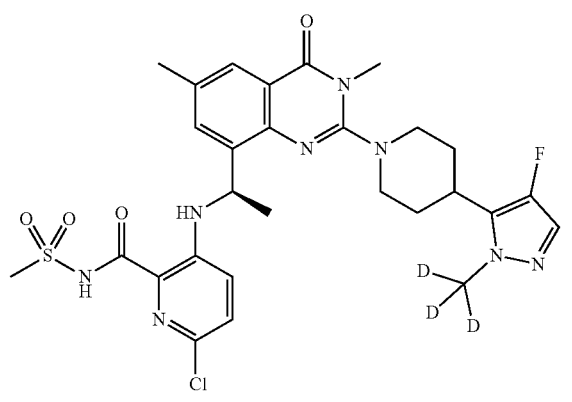 [SMILES: [2H]C([2H])([2H])n1ncc(F)c1C1CCN(c2nc3c([C@@H](C)Nc4ccc(Cl)nc4C(=O)NS(C)(=O)=O)cc(C)cc3c(=O)n2C)CC1] |
| 458 | 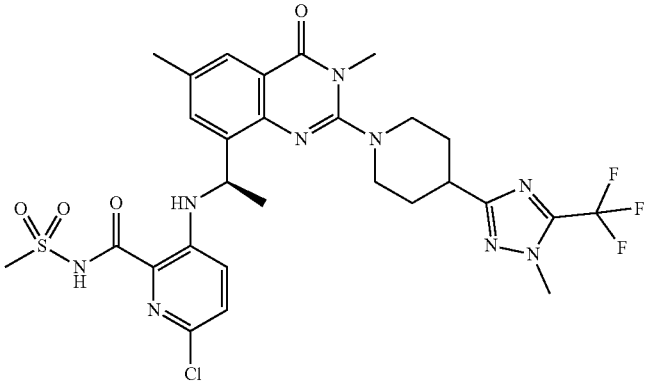 [SMILES: Cc1cc([C@@H](C)Nc2ccc(Cl)nc2C(=O)NS(C)(=O)=O)c2nc(N3CCC(c4nc(C(F)(F)F)n(C)n4)CC3)n(C)c(=O)c2c1] |
| 459 | 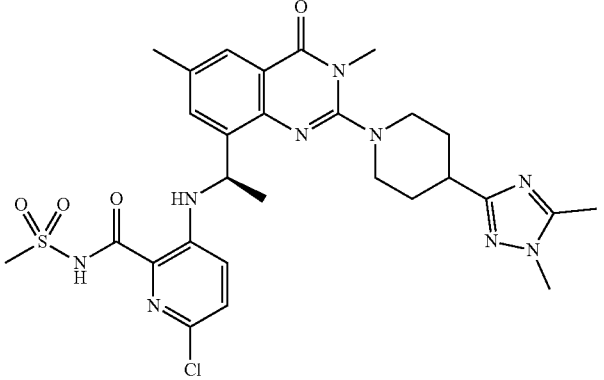 |

TABLE 1-continued

List of Compounds

| Cpd. ID | Chemical structure |
|---|---|
| 460 | 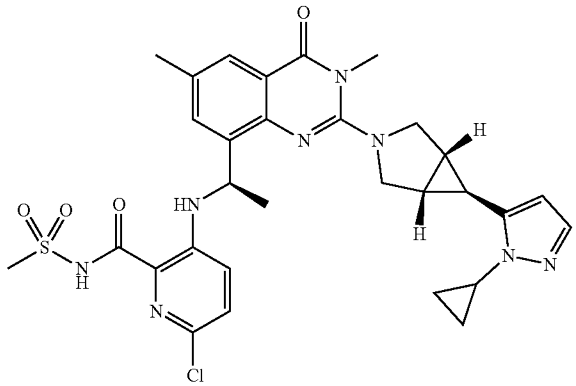 [SMILES: Cc1cc([C@@H](C)Nc2ccc(Cl)nc2C(=O)NS(C)(=O)=O)c2nc(N3C[C@@H]4[C@H](C3)[C@H]4c3ccnn3C3CC3)n(C)c(=O)c2c1] |
| 461 | 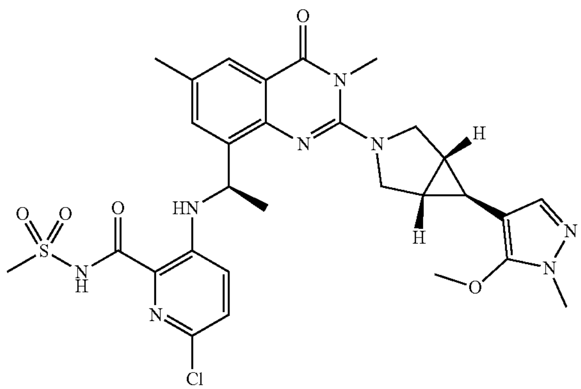 [SMILES: COc1c([C@H]2[C@@H]3CN(c4nc5c([C@@H](C)Nc6ccc(Cl)nc6C(=O)NS(C)(=O)=O)cc(C)cc5c(=O)n4C)C[C@@H]32)cnn1C] |
| 462 | 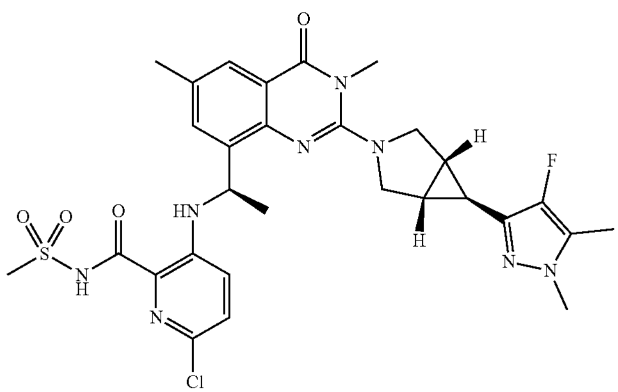 |
| 463 | 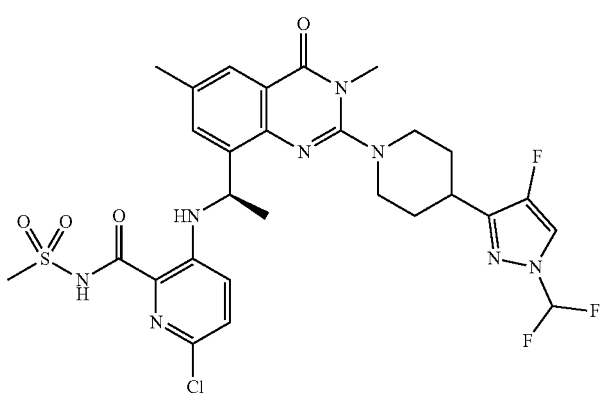 [SMILES: Cc1cc([C@@H](C)Nc2ccc(Cl)nc2C(=O)NS(C)(=O)=O)c2nc(N3CCC(c4nn(C(F)F)cc4F)CC3)n(C)c(=O)c2c1] |

TABLE 1-continued
List of Compounds
| Cpd. ID | Chemical structure |
|---|---|
| 464 | 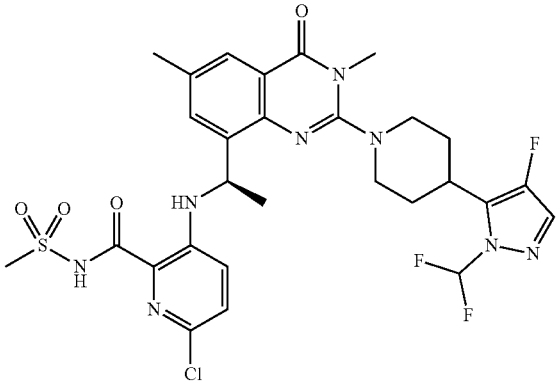 [SMILES: Cc1cc([C@@H](C)Nc2ccc(Cl)nc2C(=O)NS(C)(=O)=O)c2nc(N3CCC(c4c(F)cnn4C(F)F)CC3)n(C)c(=O)c2c1] |
| 465 | 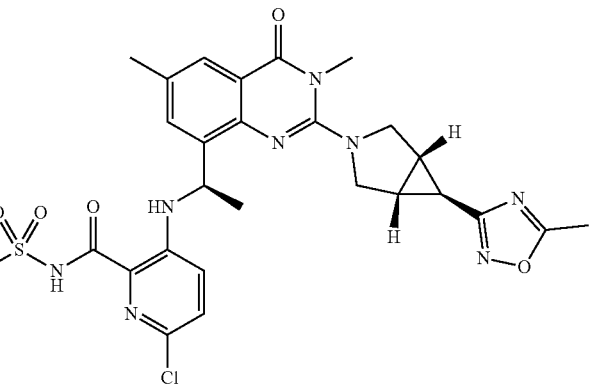 |
| 466 | 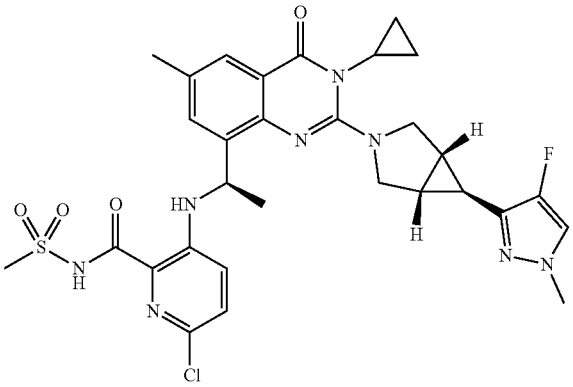 [SMILES: Cc1cc([C@@H](C)Nc2ccc(Cl)nc2C(=O)NS(C)(=O)=O)c2nc(N3C[C@@H]4[C@H](C3)[C@H]4c3nn(C)cc3F)n(C3CC3)c(=O)c2c1] |
| 467 | 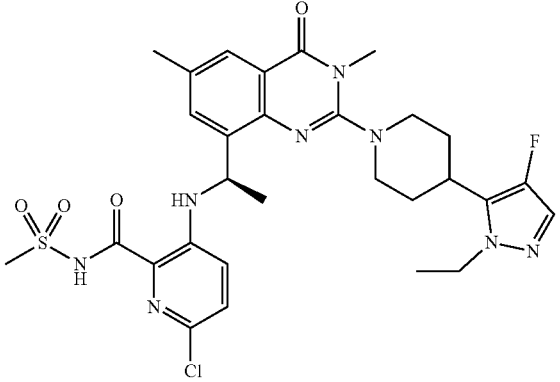 |

TABLE 1-continued

List of Compounds

| Cpd. ID | Chemical structure |
|---|---|
| 468 | 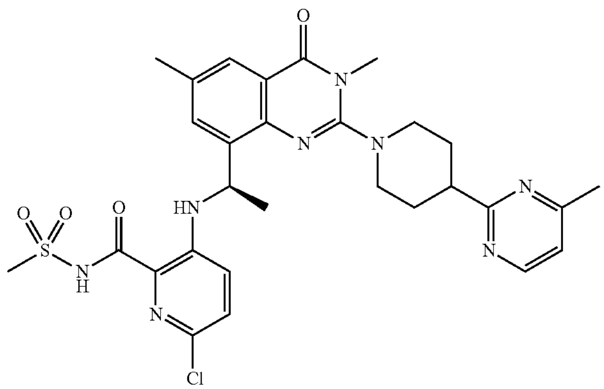 |
| 469 | 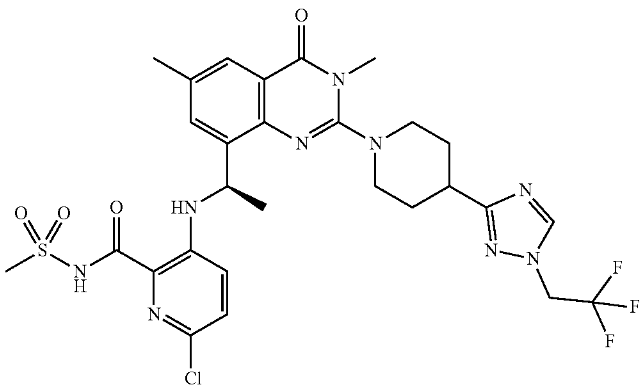 [SMILES: Cc1cc([C@@H](C)Nc2ccc(Cl)nc2C(=O)NS(C)(=O)=O)c2nc(N3CCC(c4ncn(CC(F)(F)F)n4)CC3)n(C)c(=O)c2c1] |
| 470 | 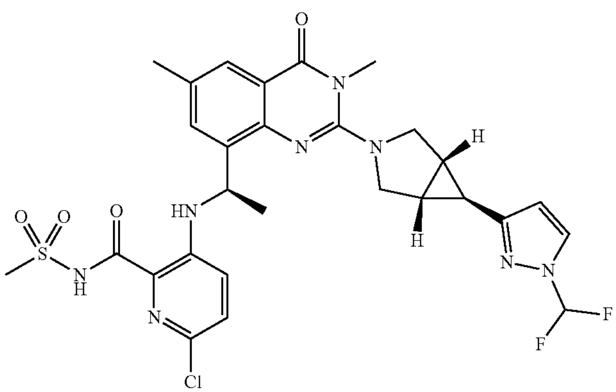 [SMILES: Cc1cc([C@@H](C)Nc2ccc(Cl)nc2C(=O)NS(C)(=O)=O)c2nc(N3C[C@@H]4[C@H](C3)[C@H]4c3ccn(C(F)F)n3)n(C)c(=O)c2c1] |
| 471 | 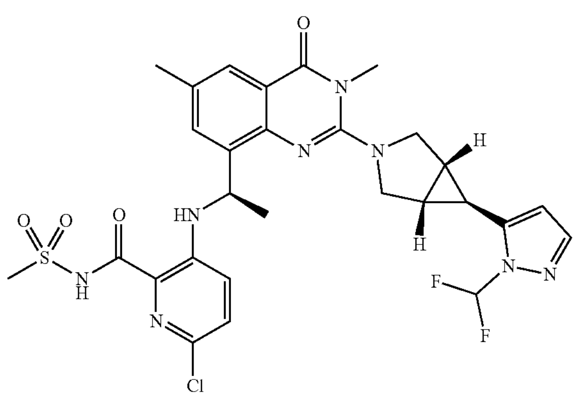 [SMILES: Cc1cc([C@@H](C)Nc2ccc(Cl)nc2C(=O)NS(C)(=O)=O)c2nc(N3C[C@@H]4[C@H](C3)[C@H]4c3ccnn3C(F)F)n(C)c(=O)c2c1] |

TABLE 1-continued
List of Compounds
| Cpd. ID | Chemical structure |
|---|---|
| 472 | 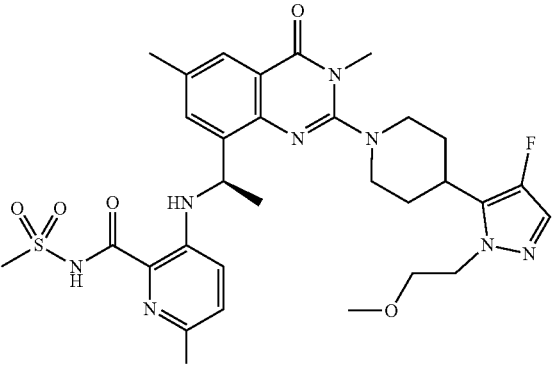 |
| 473 | 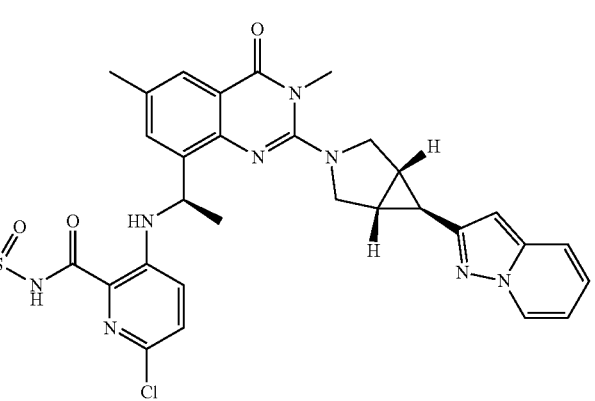 |
| 474 | 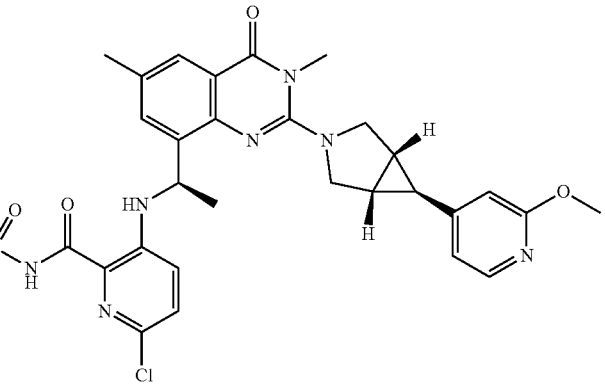 |
| 475 | 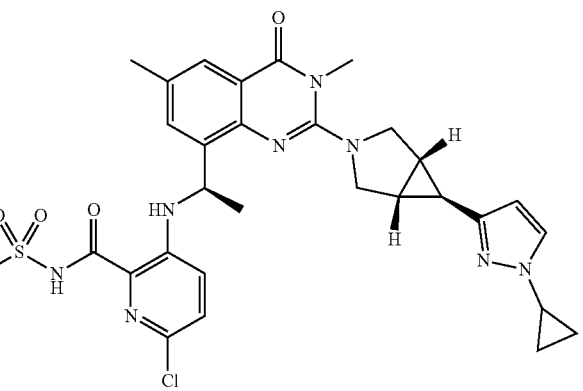 |

TABLE 1-continued

List of Compounds

| Cpd. ID | Chemical structure |
|---|---|
| 476 | 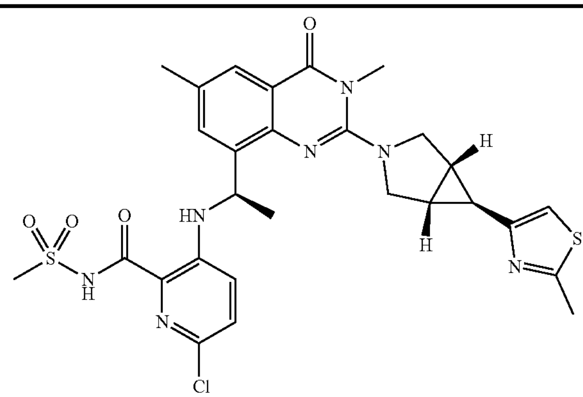 |
| 477 | 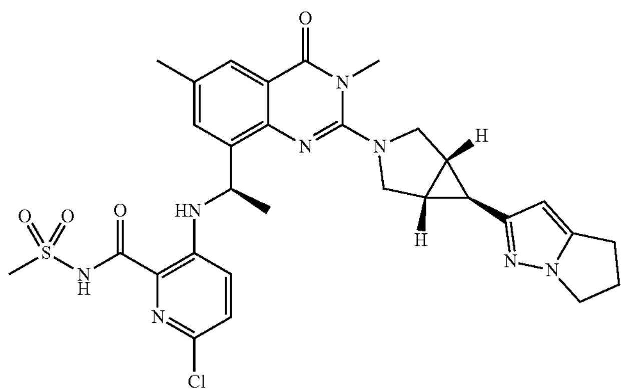 [SMILES: Cc1cc([C@@H](C)Nc2ccc(Cl)nc2C(=O)NS(C)(=O)=O)c2nc(N3C[C@@H]4[C@H](C3)[C@H]4c3cc4n(n3)CCC4)n(C)c(=O)c2c1] |
| 478 | 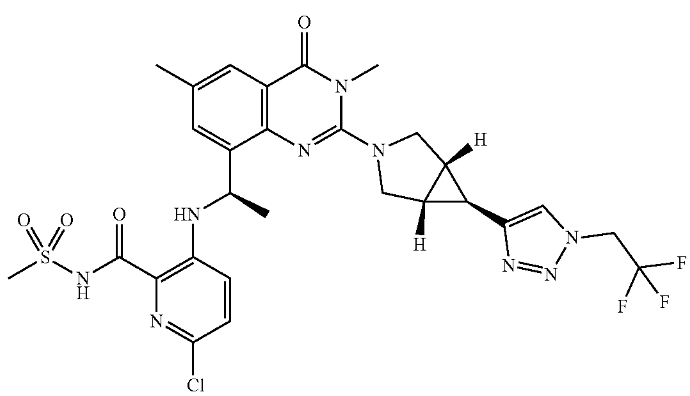 [SMILES: Cc1cc([C@@H](C)Nc2ccc(Cl)nc2C(=O)NS(C)(=O)=O)c2nc(N3C[C@@H]4[C@H](C3)[C@H]4c3cn(CC(F)(F)F)nn3)n(C)c(=O)c2c1] |
| 479 | 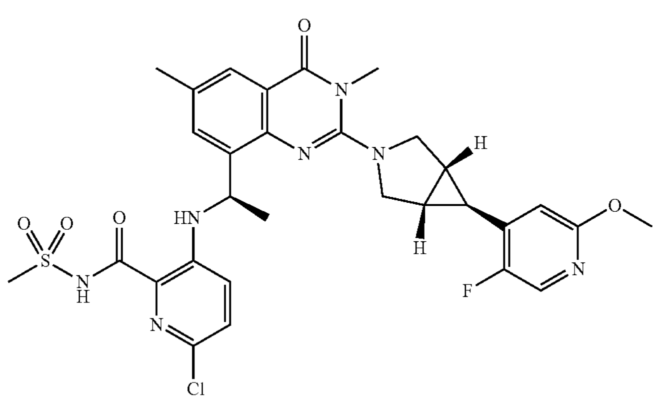 |

TABLE 1-continued

List of Compounds

| Cpd. ID | Chemical structure |
|---|---|
| 480 | 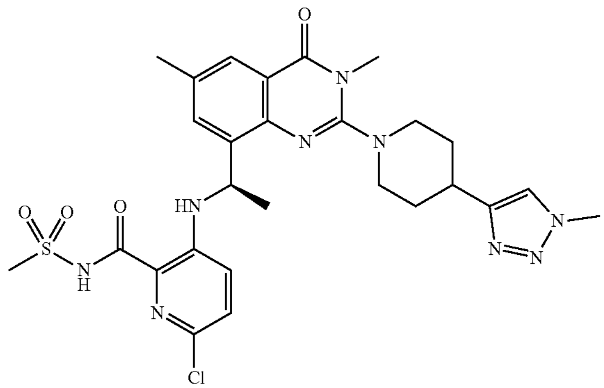 |
| 481 | 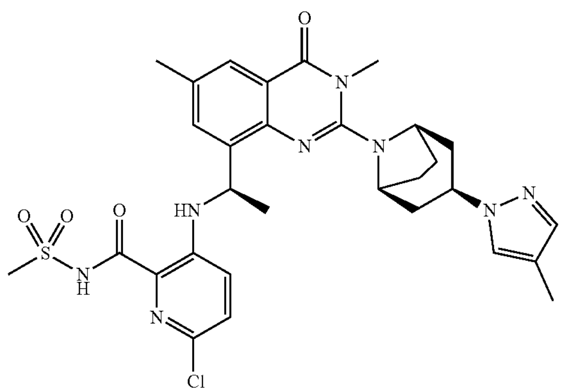 [SMILES: Cc1cc([C@@H](C)Nc2ccc(Cl)nc2C(=O)NS(C)(=O)=O)c2nc(N3[C@@H]4CC[C@H]3C[C@H](n3cc(C)cn3)C4)n(C)c(=O)c2c1] |
| 482 | 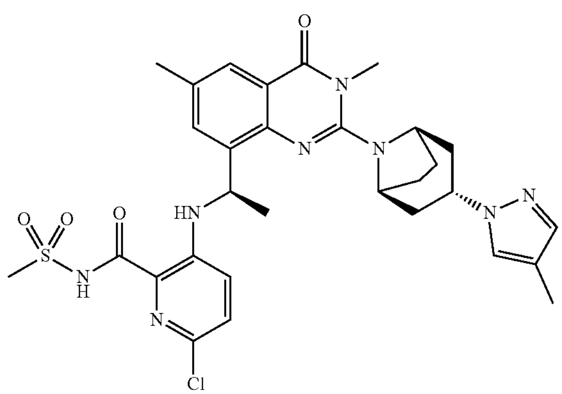 [SMILES: Cc1cc([C@@H](C)Nc2ccc(Cl)nc2C(=O)NS(C)(=O)=O)c2nc(N3[C@@H]4CC[C@H]3C[C@@H](n3cc(C)cn3)C4)n(C)c(=O)c2c1] |
| 483 | 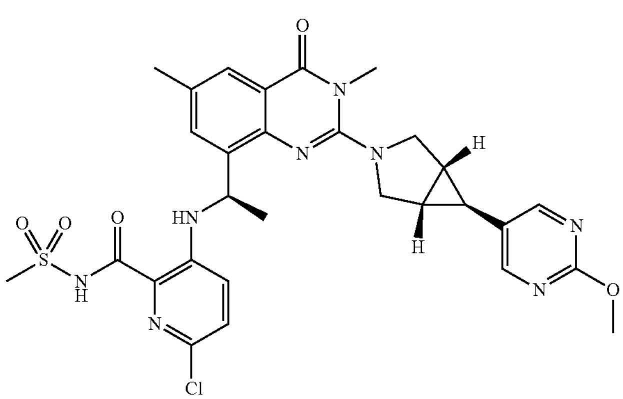 |

TABLE 1-continued

List of Compounds

| Cpd. ID | Chemical structure |
|---|---|
| 484 | 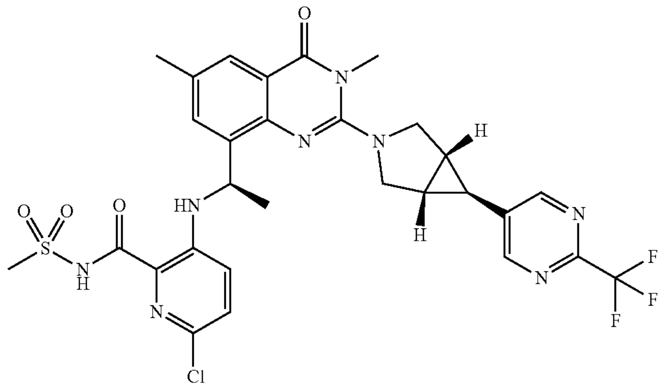 [SMILES: Cc1cc([C@@H](C)Nc2ccc(Cl)nc2C(=O)NS(C)(=O)=O)c2nc(N3C[C@@H]4[C@H](C3)[C@H]4c3cnc(C(F)(F)F)nc3)n(C)c(=O)c2c1] |
| 485 | 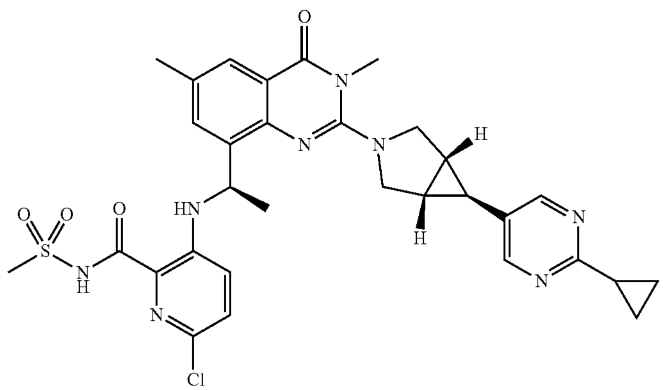 [SMILES: Cc1cc([C@@H](C)Nc2ccc(Cl)nc2C(=O)NS(C)(=O)=O)c2nc(N3C[C@@H]4[C@H](C3)[C@H]4c3cnc(C4CC4)nc3)n(C)c(=O)c2c1] |
| 486 | 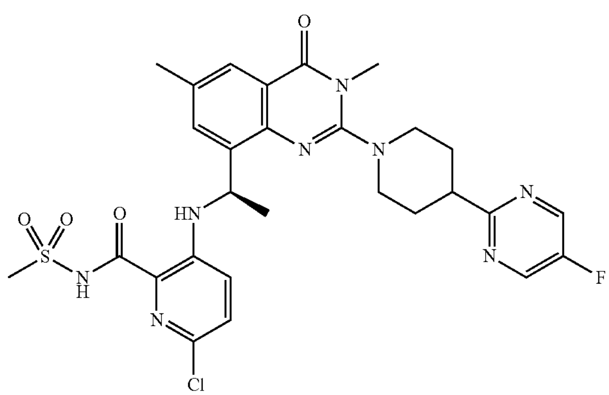 [SMILES: Cc1cc([C@@H](C)Nc2ccc(Cl)nc2C(=O)NS(C)(=O)=O)c2nc(N3CCC(c4ncc(F)cn4)CC3)n(C)c(=O)c2c1] |
| 487 | 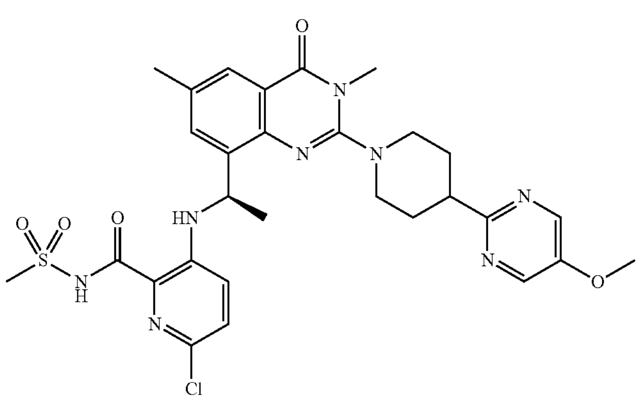 |

TABLE 1-continued
List of Compounds
| Cpd. ID | Chemical structure |
|---|---|
| 488 | 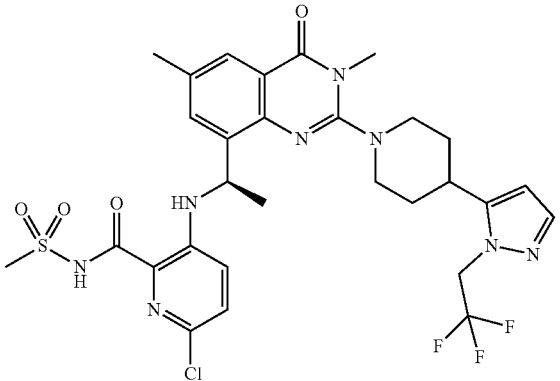 [SMILES: Cc1cc([C@@H](C)Nc2ccc(Cl)nc2C(=O)NS(C)(=O)=O)c2nc(N3CCC(c4ccnn4CC(F)(F)F)CC3)n(C)c(=O)c2c1] |
| 489 | 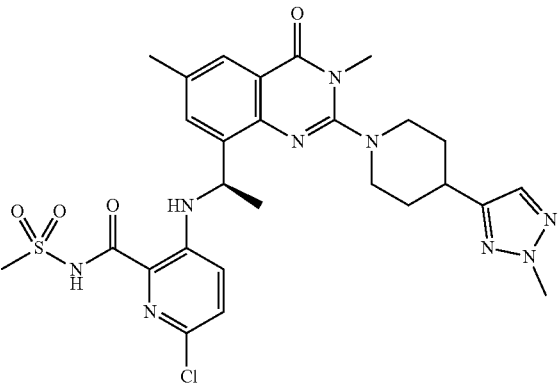 |
| 490 | 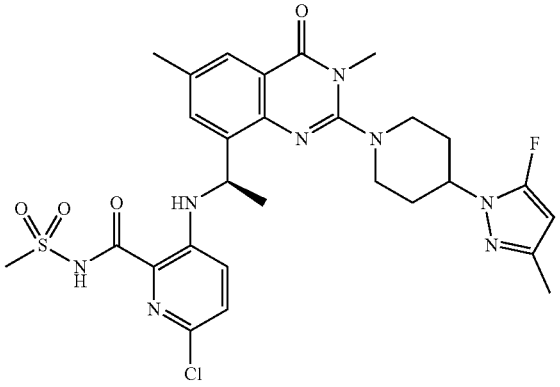 [SMILES: Cc1cc([C@@H](C)Nc2ccc(Cl)nc2C(=O)NS(C)(=O)=O)c2nc(N3CCC(n4nc(C)cc4F)CC3)n(C)c(=O)c2c1] |
| 491 | 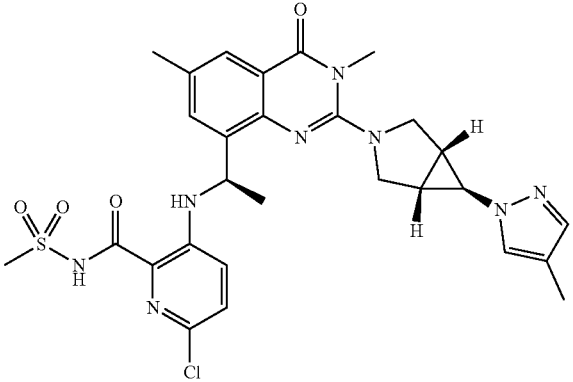 [SMILES: Cc1cc([C@@H](C)Nc2ccc(Cl)nc2C(=O)NS(C)(=O)=O)c2nc(N3C[C@@H]4[C@H](C3)[C@H]4n3cc(C)cn3)n(C)c(=O)c2c1] |

TABLE 1-continued

List of Compounds

| Cpd. ID | Chemical structure |
|---|---|
| 492 | 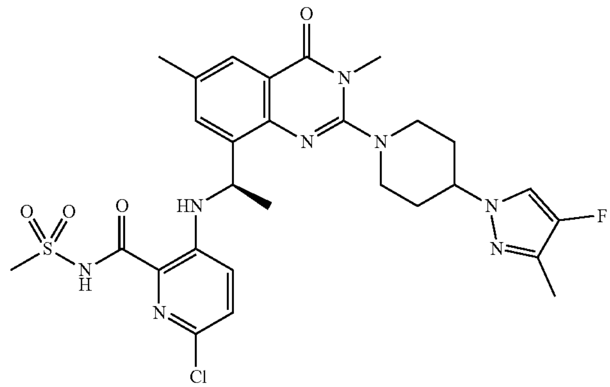 [SMILES: Cc1cc([C@@H](C)Nc2ccc(Cl)nc2C(=O)NS(C)(=O)=O)c2nc(N3CCC(n4cc(F)c(C)n4)CC3)n(C)c(=O)c2c1] |
| 493 | 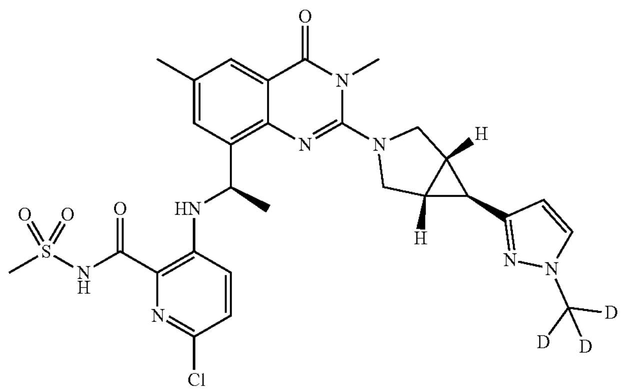 [SMILES: [2H]C([2H])([2H])n1ccc([C@H]2[C@@H]3CN(c4nc5c([C@@H](C)Nc6ccc(Cl)nc6C(=O)NS(C)(=O)=O)cc(C)cc5c(=O)n4C)C[C@@H]32)n1] |
| 494 | 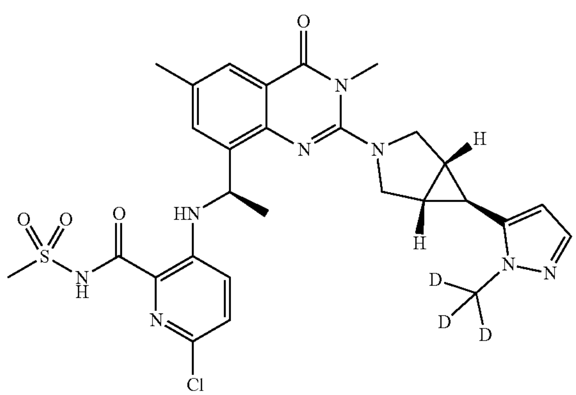 [SMILES: [2H]C([2H])([2H])n1nccc1[C@H]1[C@@H]2CN(c3nc4c([C@@H](C)Nc5ccc(Cl)nc5C(=O)NS(C)(=O)=O)cc(C)cc4c(=O)n3C)C[C@@H]21] |
| 495 | 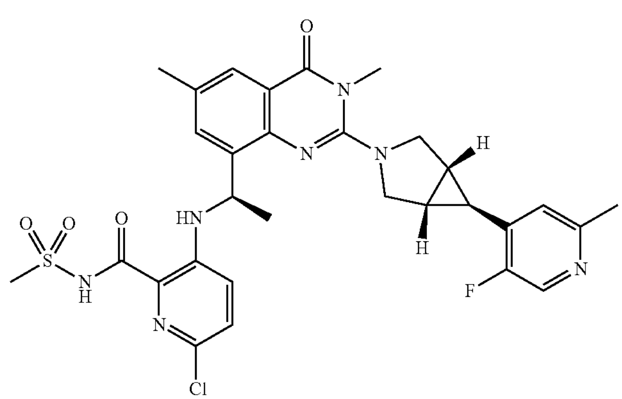 |

TABLE 1-continued

List of Compounds

| Cpd. ID | Chemical structure |
|---------|---------------------|
| 496 | 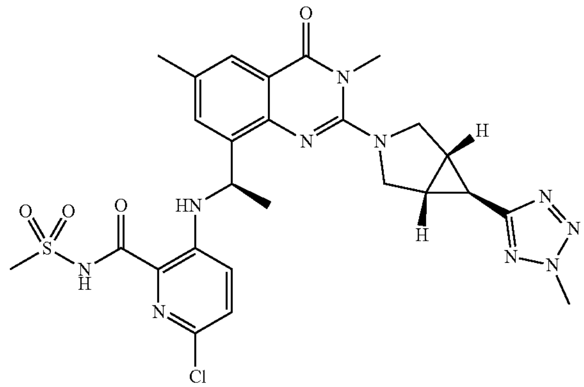 [SMILES: Cc1cc([C@@H](C)Nc2ccc(Cl)nc2C(=O)NS(C)(=O)=O)c2nc(N3C[C@@H]4[C@H](C3)[C@H]4c3nnn(C)n3)n(C)c(=O)c2c1] |
| 497 | 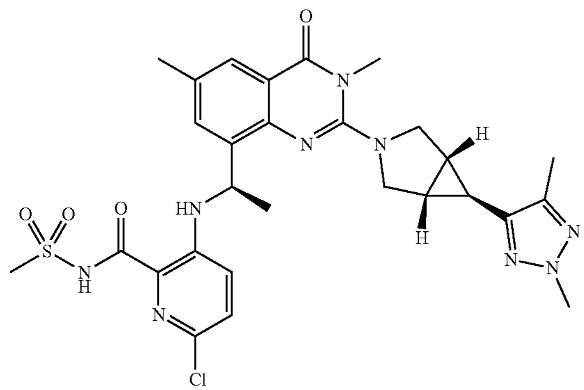 [SMILES: Cc1cc([C@@H](C)Nc2ccc(Cl)nc2C(=O)NS(C)(=O)=O)c2nc(N3C[C@@H]4[C@H](C3)[C@H]4c3nn(C)nc3C)n(C)c(=O)c2c1] |
| 498 | 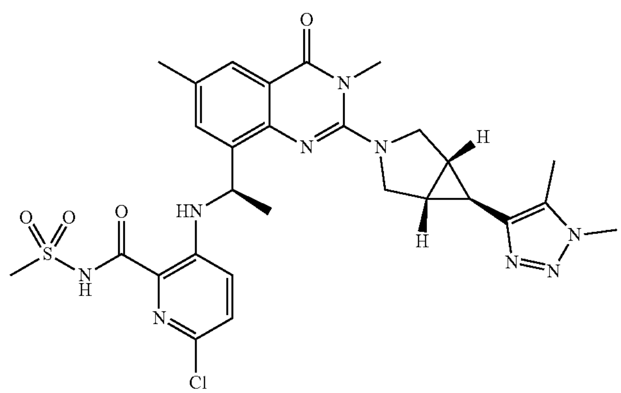 |
| 499 | 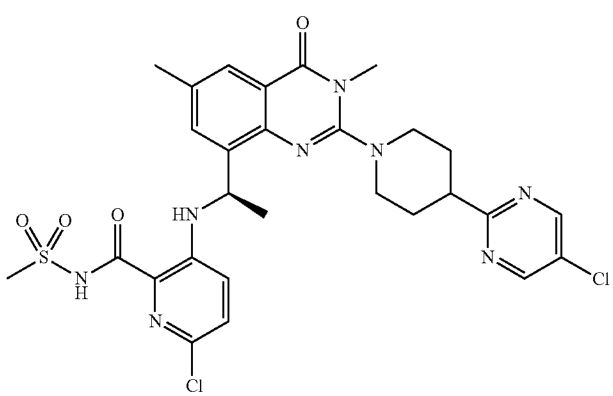 [SMILES: Cc1cc([C@@H](C)Nc2ccc(Cl)nc2C(=O)NS(C)(=O)=O)c2nc(N3CCC(c4ncc(Cl)cn4)CC3)n(C)c(=O)c2c1] |

TABLE 1-continued

List of Compounds

| Cpd. ID | Chemical structure |
|---|---|
| 500 | 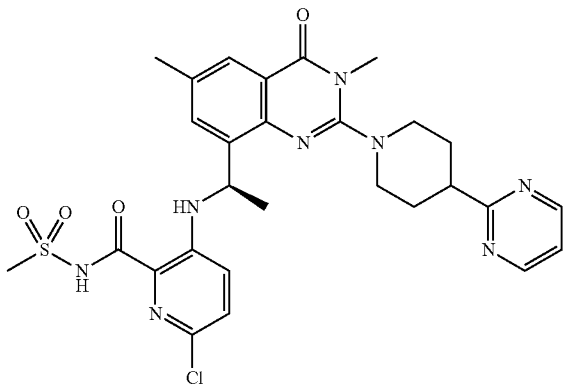 [SMILES: Cc1cc([C@@H](C)Nc2ccc(Cl)nc2C(=O)NS(C)(=O)=O)c2nc(N3CCC(c4ncccn4)CC3)n(C)c(=O)c2c1] |
| 501 | 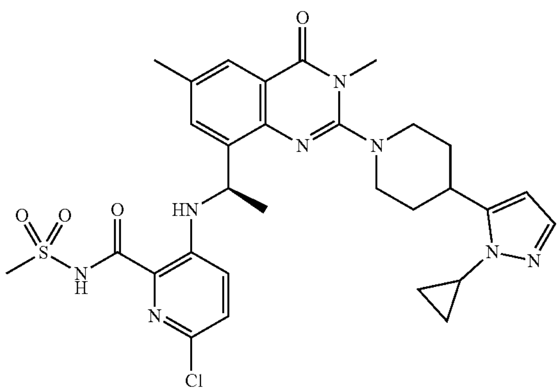 [SMILES: Cc1cc([C@@H](C)Nc2ccc(Cl)nc2C(=O)NS(C)(=O)=O)c2nc(N3CCC(c4ccnn4C4CC4)CC3)n(C)c(=O)c2c1] |
| 502 | 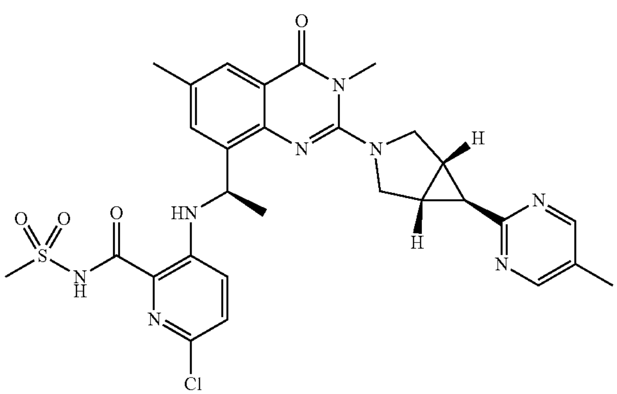 |
| 503 | 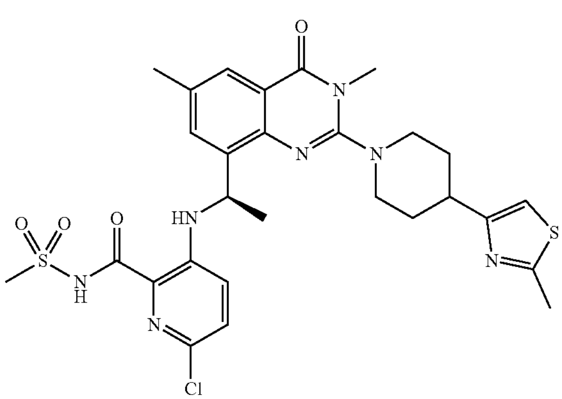 [SMILES: Cc1cc([C@@H](C)Nc2ccc(Cl)nc2C(=O)NS(C)(=O)=O)c2nc(N3CCC(c4csc(C)n4)CC3)n(C)c(=O)c2c1] |

TABLE 1-continued
List of Compounds
| Cpd. ID | Chemical structure |
|---|---|
| 504 | 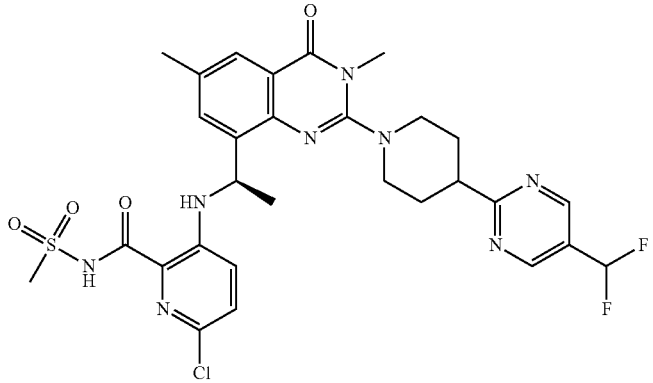 [SMILES: Cc1cc([C@@H](C)Nc2ccc(Cl)nc2C(=O)NS(C)(=O)=O)c2nc(N3CCC(c4ncc(C(F)F)cn4)CC3)n(C)c(=O)c2c1] |
| 505 | 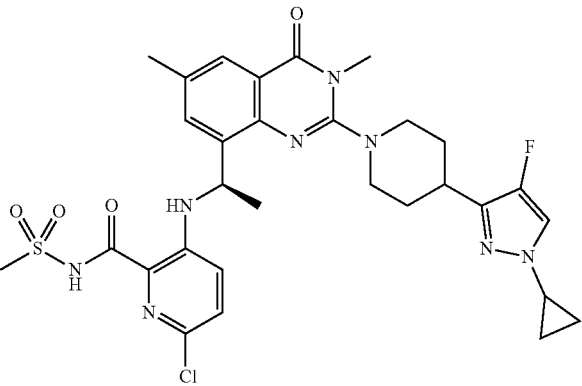 [SMILES: Cc1cc([C@@H](C)Nc2ccc(Cl)nc2C(=O)NS(C)(=O)=O)c2nc(N3CCC(c4nn(C5CC5)cc4F)CC3)n(C)c(=O)c2c1] |
| 506 | 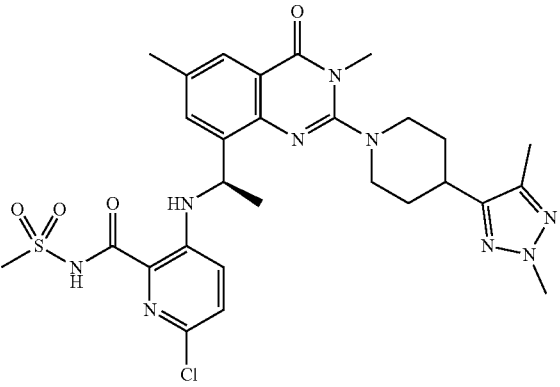 [SMILES: Cc1cc([C@@H](C)Nc2ccc(Cl)nc2C(=O)NS(C)(=O)=O)c2nc(N3CCC(c4nn(C)nc4C)CC3)n(C)c(=O)c2c1] |
| 507 | 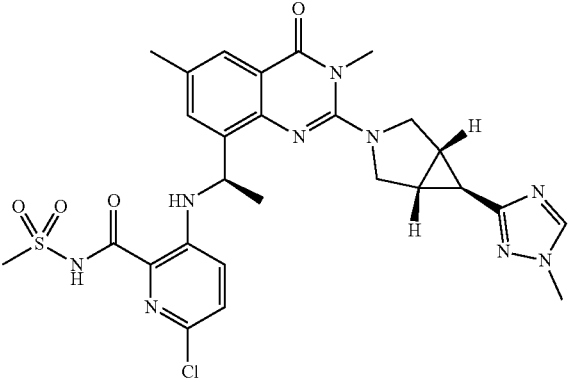 [SMILES: Cc1cc([C@@H](C)Nc2ccc(Cl)nc2C(=O)NS(C)(=O)=O)c2nc(N3C[C@@H]4[C@H](C3)[C@H]4c3ncn(C)n3)n(C)c(=O)c2c1] |

TABLE 1-continued

List of Compounds

| Cpd. ID | Chemical structure |
|---------|--------------------|
| 508 | 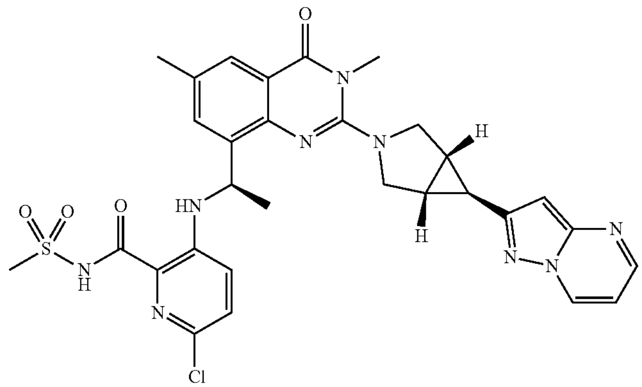 |
| 509 | 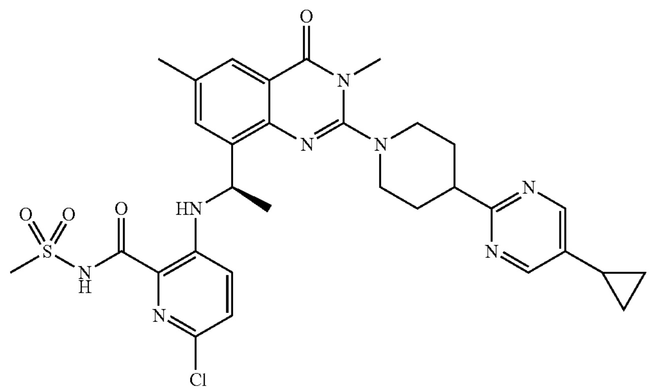 [SMILES: Cc1cc([C@@H](C)Nc2ccc(Cl)nc2C(=O)NS(C)(=O)=O)c2nc(N3CCC(c4ncc(C5CC5)cn4)CC3)n(C)c(=O)c2c1] |
| 510 | 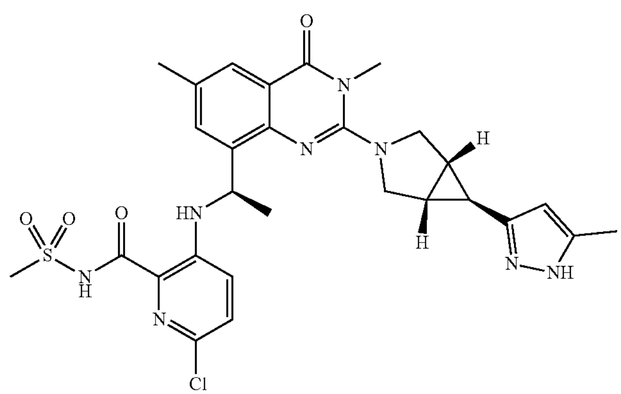 |
| 511 | 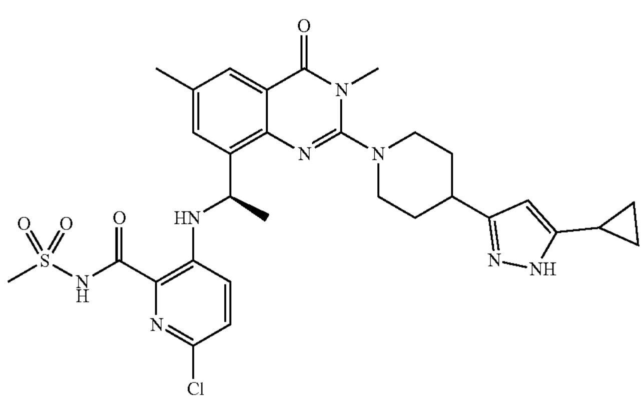 [SMILES: Cc1cc([C@@H](C)Nc2ccc(Cl)nc2C(=O)NS(C)(=O)=O)c2nc(N3CCC(c4cc(C5CC5)[nH]n4)CC3)n(C)c(=O)c2c1] |

TABLE 1-continued

List of Compounds

| Cpd. ID | Chemical structure |
|---|---|
| 512 | 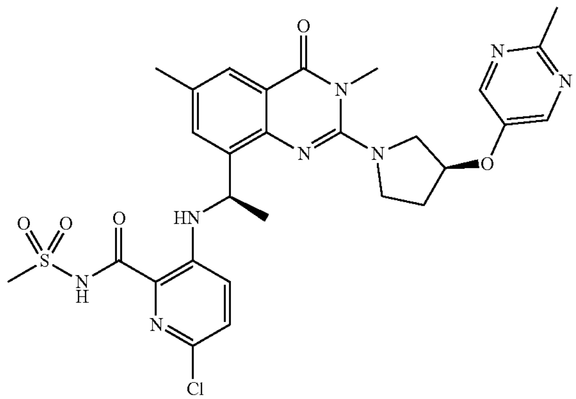 [SMILES: Cc1cc([C@@H](C)Nc2ccc(Cl)nc2C(=O)NS(C)(=O)=O)c2nc(N3CC[C@H](Oc4cnc(C)nc4)C3)n(C)c(=O)c2c1] |
| 513 | 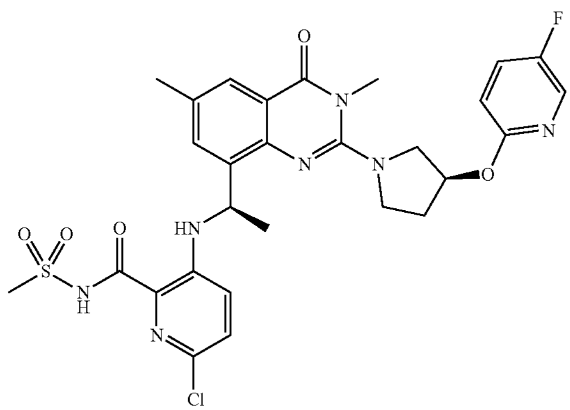 [SMILES: Cc1cc([C@@H](C)Nc2ccc(Cl)nc2C(=O)NS(C)(=O)=O)c2nc(N3CC[C@H](Oc4ccc(F)cn4)C3)n(C)c(=O)c2c1] |
| 514 | 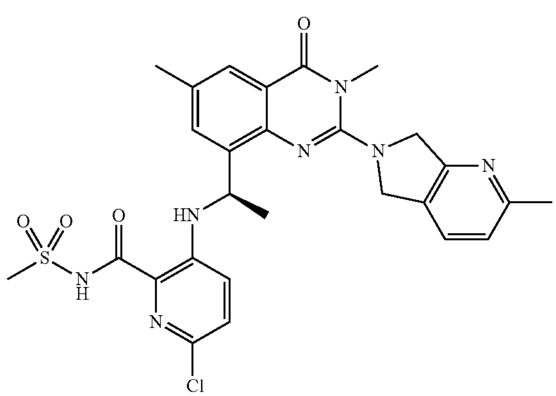 |

TABLE 1-continued

List of Compounds

| Cpd. ID | Chemical structure |
|---------|--------------------|
| 515 | 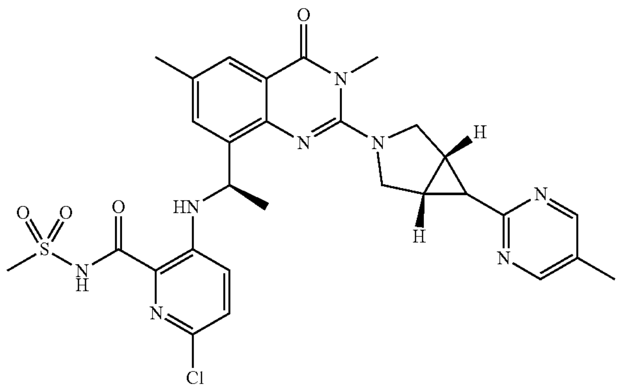 |
| 516 | 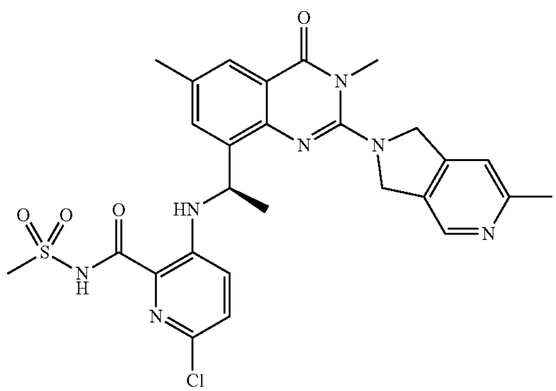 |
| 517 | 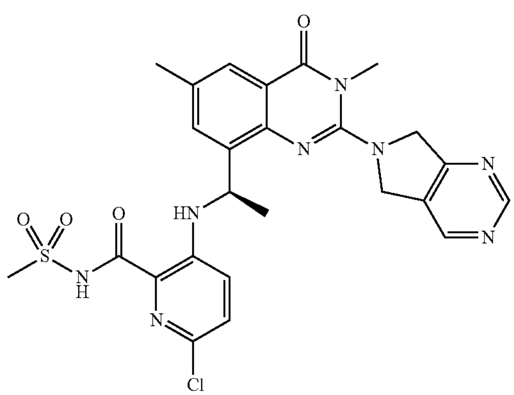 [SMILES: Cc1cc([C@@H](C)Nc2ccc(Cl)nc2C(=O)NS(C)(=O)=O)c2nc(N3Cc4cncnc4C3)n(C)c(=O)c2c1] |
| 518 | 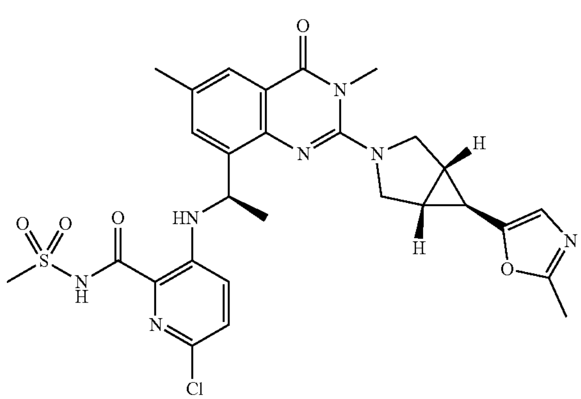 [SMILES: Cc1cc([C@@H](C)Nc2ccc(Cl)nc2C(=O)NS(C)(=O)=O)c2nc(N3C[C@@H]4[C@H](C3)[C@H]4c3cnc(C)o3)n(C)c(=O)c2c1] |

TABLE 1-continued

List of Compounds

| Cpd. ID | Chemical structure |
|---|---|
| 519 | 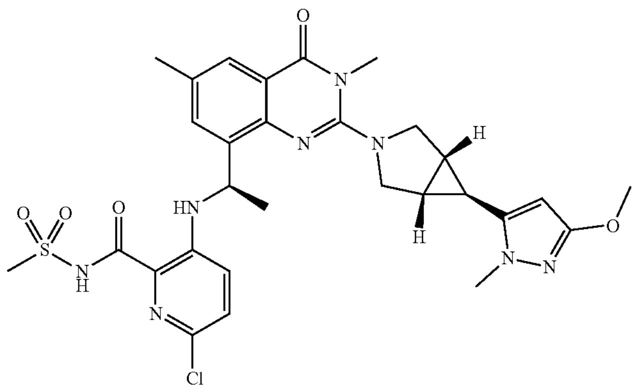 |
| 520 | 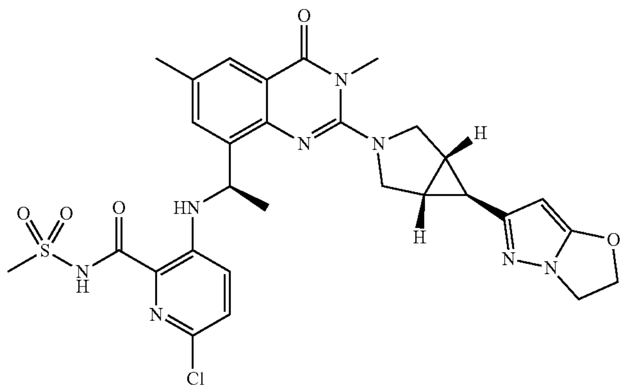 |
| 521 | 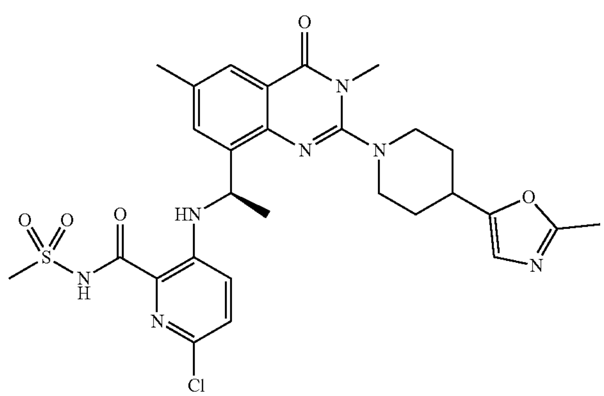 |
| 522 | 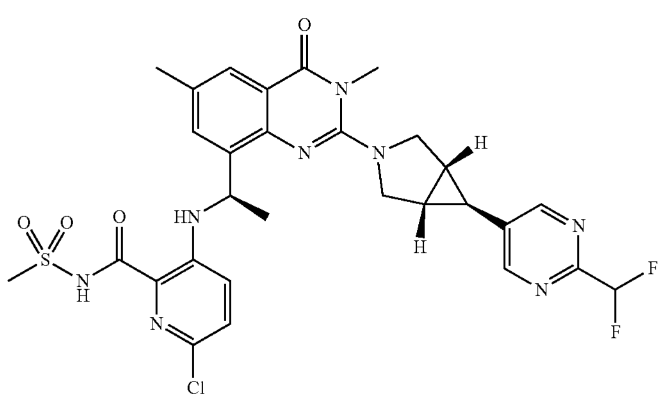 [SMILES: Cc1cc([C@@H](C)Nc2ccc(Cl)nc2C(=O)NS(C)(=O)=O)c2nc(N3C[C@@H]4[C@H](C3)[C@H]4c3cnc(C(F)F)nc3)n(C)c(=O)c2c1] |

TABLE 1-continued

List of Compounds

| Cpd. ID | Chemical structure |
|---|---|
| 523 | 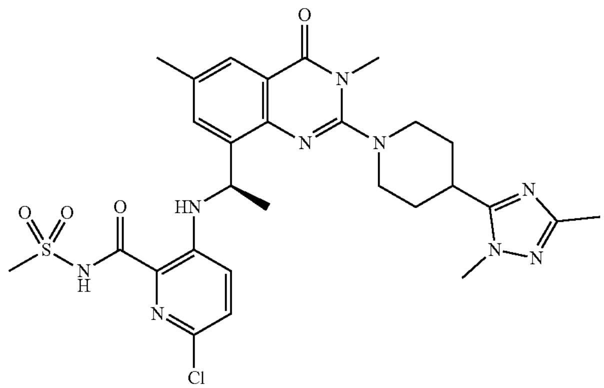 |
| 524 | 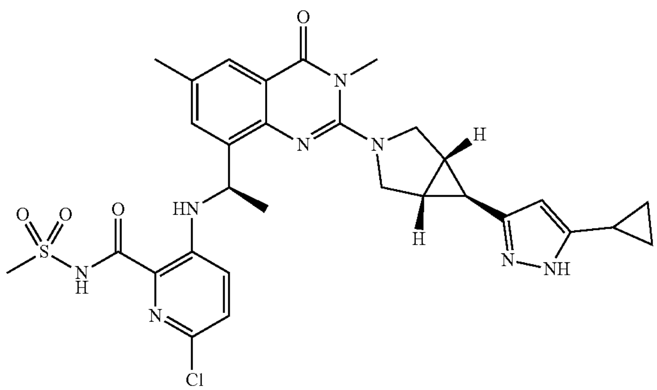 [SMILES: Cc1cc([C@@H](C)Nc2ccc(Cl)nc2C(=O)NS(C)(=O)=O)c2nc(N3C[C@@H]4[C@H](C3)[C@H]4c3cc(C4CC4)[nH]n3)n(C)c(=O)c2c1] |
| 525 | 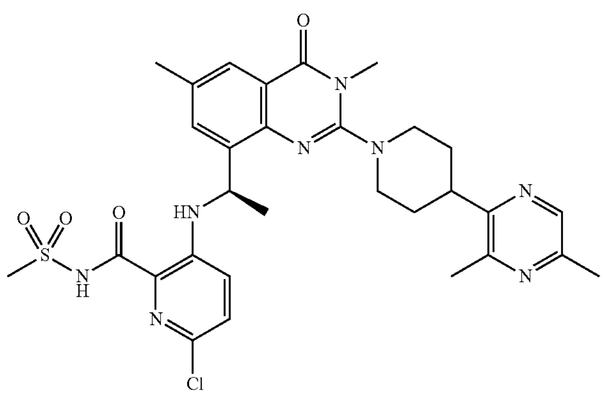 |
| 526 | 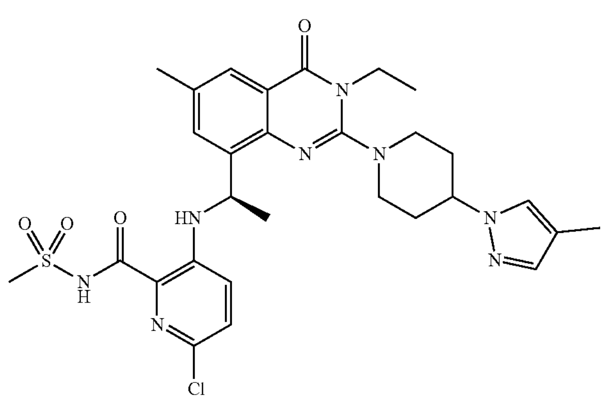 |

TABLE 1-continued

List of Compounds

| Cpd. ID | Chemical structure |
|---|---|
| 527 | 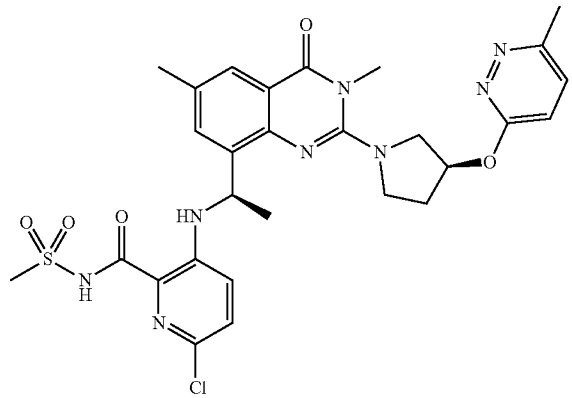 [SMILES: Cc1cc([C@@H](C)Nc2ccc(Cl)nc2C(=O)NS(C)(=O)=O)c2nc(N3CC[C@H](Oc4ccc(C)nn4)C3)n(C)c(=O)c2c1] |
| 528 | 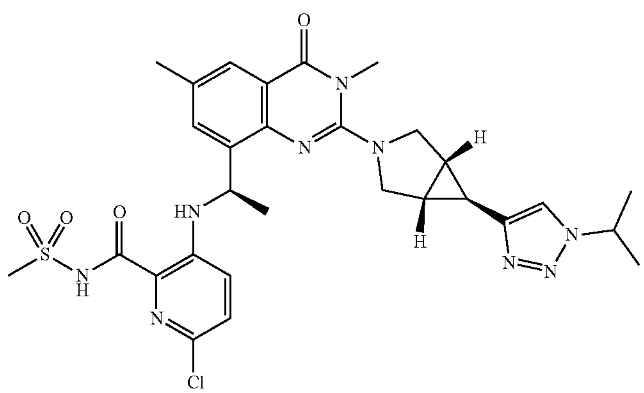 [SMILES: Cc1cc([C@@H](C)Nc2ccc(Cl)nc2C(=O)NS(C)(=O)=O)c2nc(N3C[C@@H]4[C@H](C3)[C@H]4c3cn(C(C)C)nn3)n(C)c(=O)c2c1] |
| 529 | 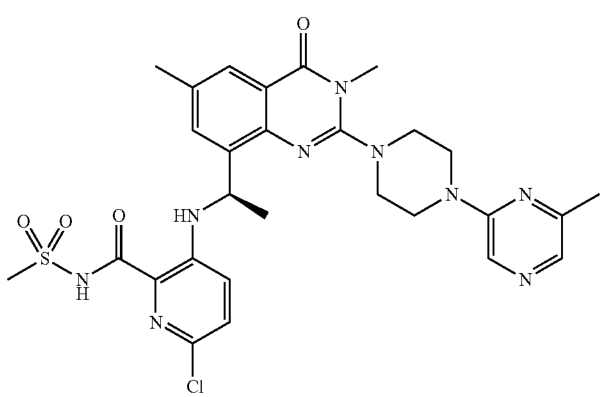 |
| 530 | 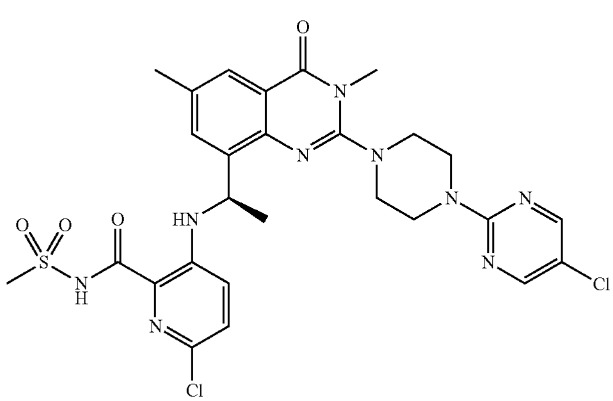 [SMILES: Cc1cc([C@@H](C)Nc2ccc(Cl)nc2C(=O)NS(C)(=O)=O)c2nc(N3CCN(c4ncc(Cl)cn4)CC3)n(C)c(=O)c2c1] |

TABLE 1-continued

List of Compounds

| Cpd. ID | Chemical structure |
|---|---|
| 531 | 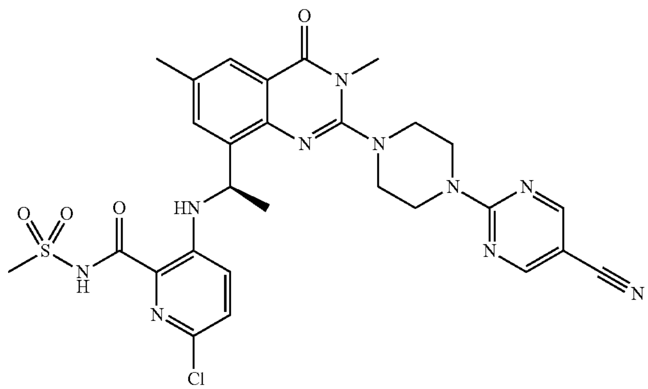 [SMILES: Cc1cc([C@@H](C)Nc2ccc(Cl)nc2C(=O)NS(C)(=O)=O)c2nc(N3CCN(c4ncc(C#N)cn4)CC3)n(C)c(=O)c2c1] |
| 532 | 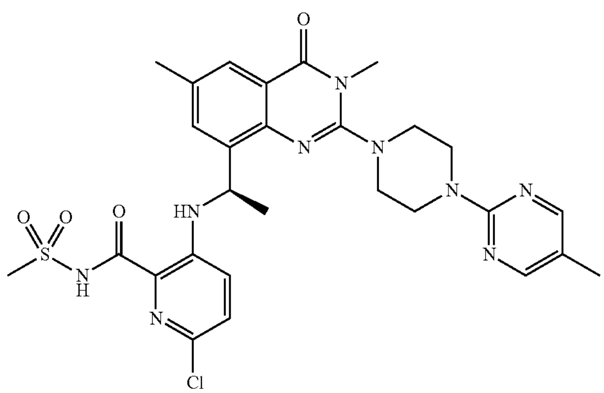 |
| 533 | 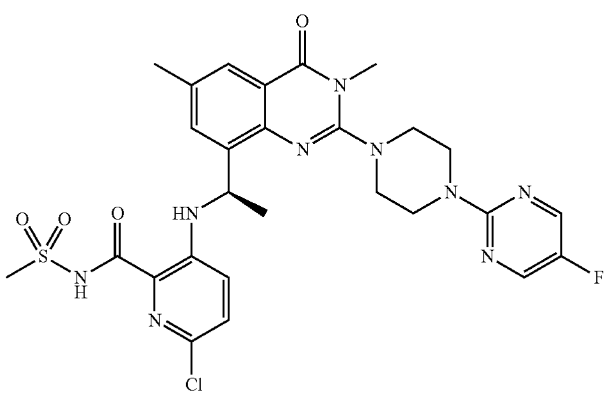 |
| 534 | 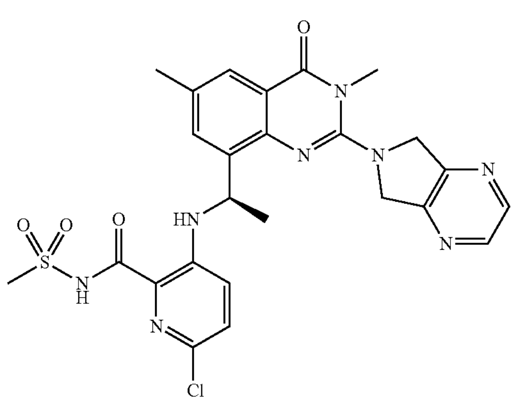 [SMILES: Cc1cc([C@@H](C)Nc2ccc(Cl)nc2C(=O)NS(C)(=O)=O)c2nc(N3Cc4nccnc4C3)n(C)c(=O)c2c1] |

TABLE 1-continued

| List of Compounds | |
|---|---|
| Cpd. ID | Chemical structure |

535

536

537

TABLE 1-continued

List of Compounds

| Cpd. ID | Chemical structure |
|---|---|
| 538 | 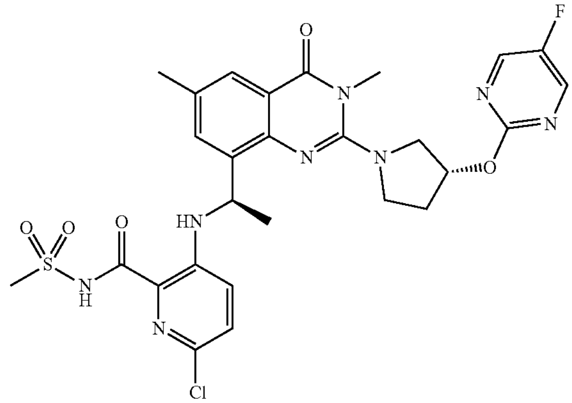 [SMILES: Cc1cc([C@@H](C)Nc2ccc(Cl)nc2C(=O)NS(C)(=O)=O)c2nc(N3CC[C@@H](Oc4ncc(F)cn4)C3)n(C)c(=O)c2c1] |
| 539 | 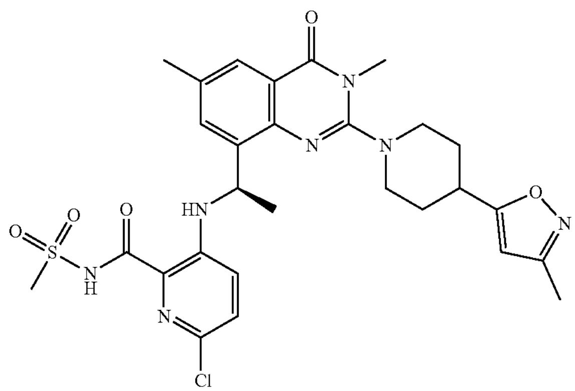 [SMILES: Cc1cc([C@@H](C)Nc2ccc(Cl)nc2C(=O)NS(C)(=O)=O)c2nc(N3CCC(c4cc(C)no4)CC3)n(C)c(=O)c2c1] |
| 540 | 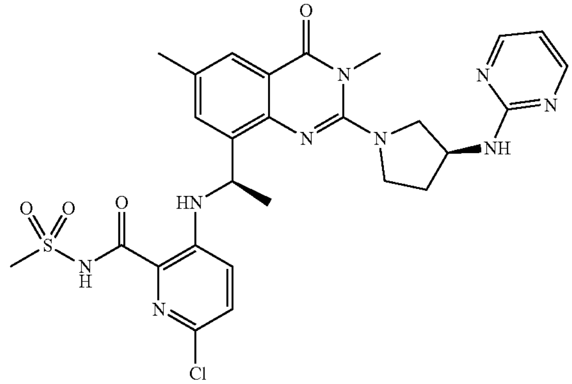 [SMILES: Cc1cc([C@@H](C)Nc2ccc(Cl)nc2C(=O)NS(C)(=O)=O)c2nc(N3CC[C@H](Nc4ncccn4)C3)n(C)c(=O)c2c1] |
| 541 | 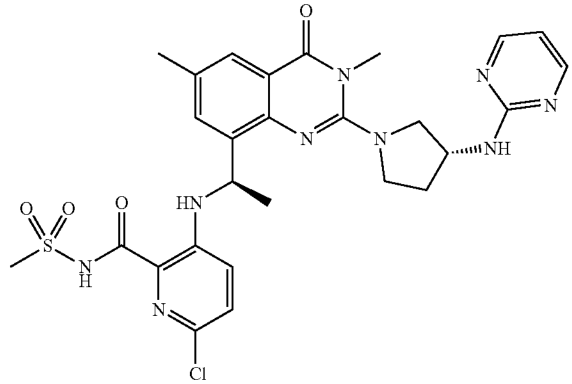 [SMILES: Cc1cc([C@@H](C)Nc2ccc(Cl)nc2C(=O)NS(C)(=O)=O)c2nc(N3CC[C@@H](Nc4ncccn4)C3)n(C)c(=O)c2c1] |

TABLE 1-continued

List of Compounds

| Cpd. ID | Chemical structure |
|---|---|
| 542 | 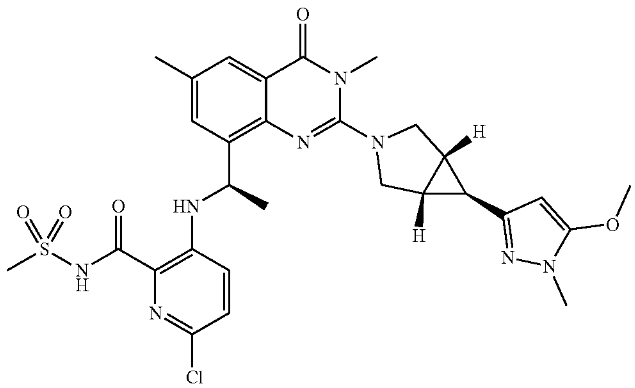 |
| 543 | 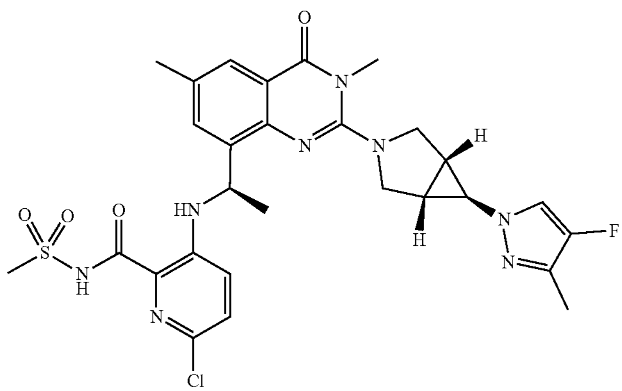 [SMILES: Cc1cc([C@@H](C)Nc2ccc(Cl)nc2C(=O)NS(C)(=O)=O)c2nc(N3C[C@@H]4[C@H](C3)[C@H]4n3cc(F)c(C)n3)n(C)c(=O)c2c1] |
| 544 | 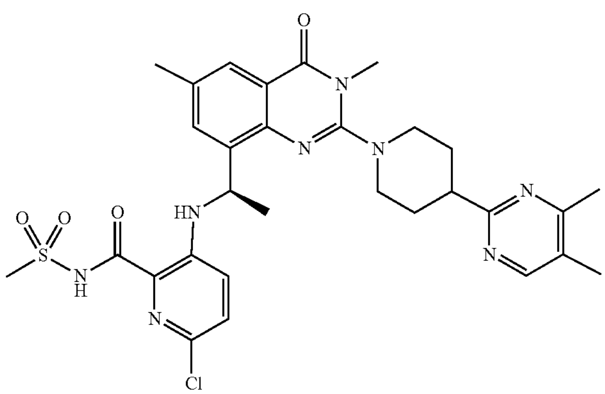 |
| 545 | 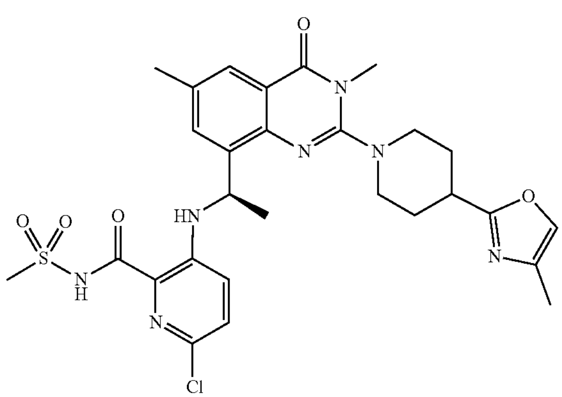 [SMILES: Cc1cc([C@@H](C)Nc2ccc(Cl)nc2C(=O)NS(C)(=O)=O)c2nc(N3CCC(c4nc(C)co4)CC3)n(C)c(=O)c2c1] |

TABLE 1-continued

List of Compounds

| Cpd. ID | Chemical structure |
|---------|--------------------|
| 546 | 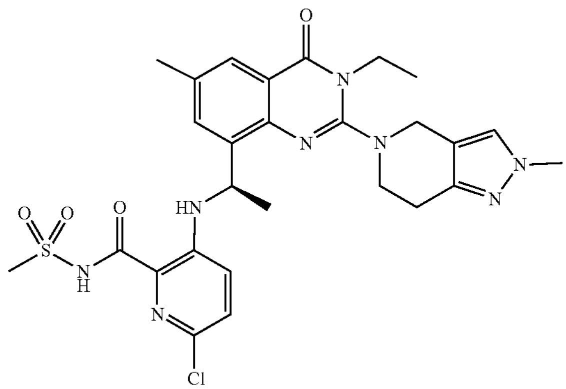 |
| 547 | 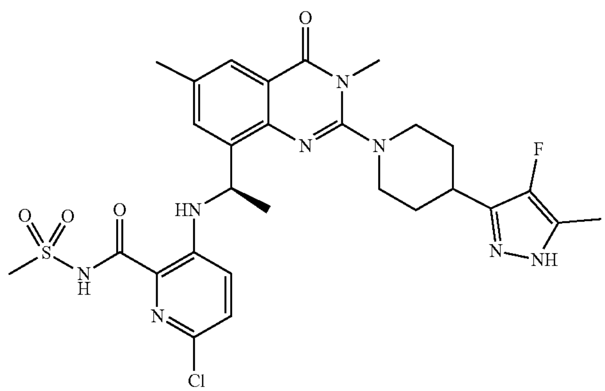 |
| 548 | 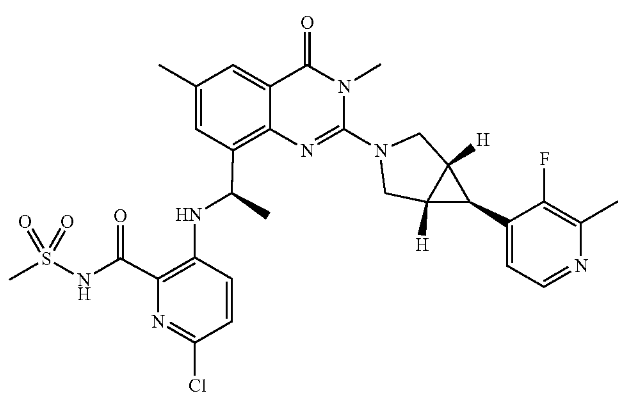 |
| 549 | 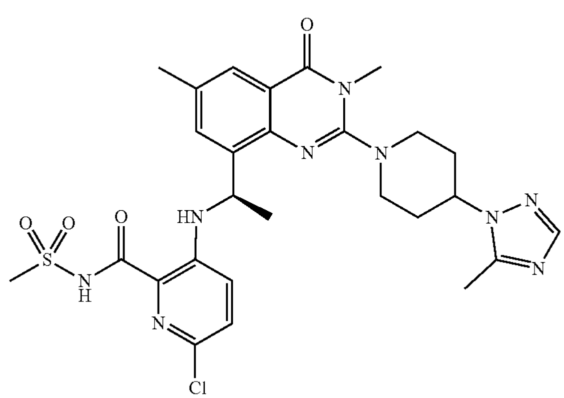 [SMILES: Cc1cc([C@@H](C)Nc2ccc(Cl)nc2C(=O)NS(C)(=O)=O)c2nc(N3CCC(n4ncnc4C)CC3)n(C)c(=O)c2c1] |

TABLE 1-continued
List of Compounds
| Cpd. ID | Chemical structure |
|---|---|
| 550 | 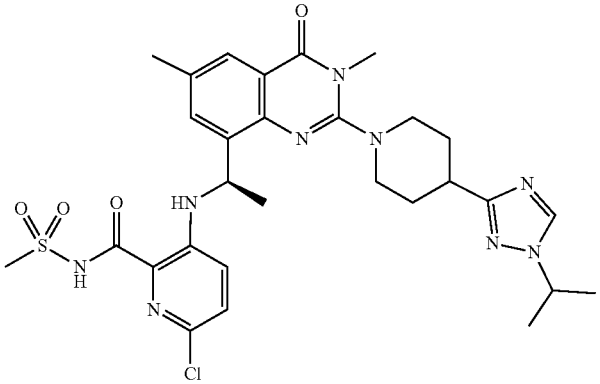 [SMILES: Cc1cc([C@@H](C)Nc2ccc(Cl)nc2C(=O)NS(C)(=O)=O)c2nc(N3CCC(c4ncn(C(C)C)n4)CC3)n(C)c(=O)c2c1] |
| 551 | 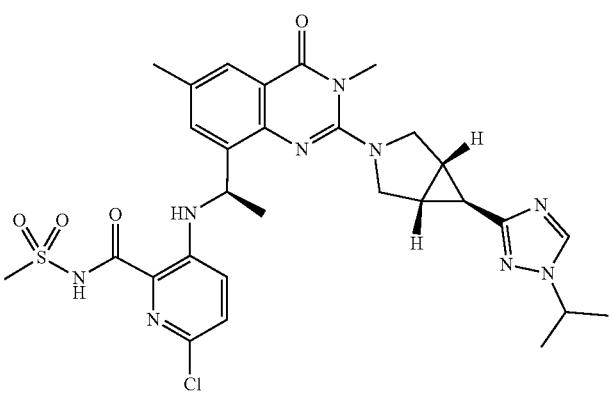 [SMILES: Cc1cc([C@@H](C)Nc2ccc(Cl)nc2C(=O)NS(C)(=O)=O)c2nc(N3C[C@@H]4[C@H](C3)[C@H]4c3ncn(C(C)C)n3)n(C)c(=O)c2c1] |
| 552 | 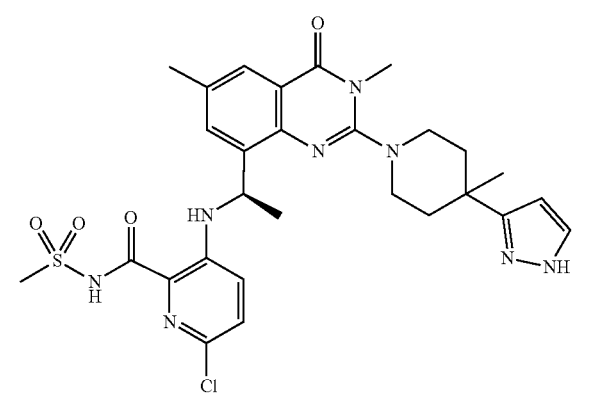 [SMILES: Cc1cc([C@@H](C)Nc2ccc(Cl)nc2C(=O)NS(C)(=O)=O)c2nc(N3CCC(C)(c4cc[nH]n4)CC3)n(C)c(=O)c2c1] |
| 553 | 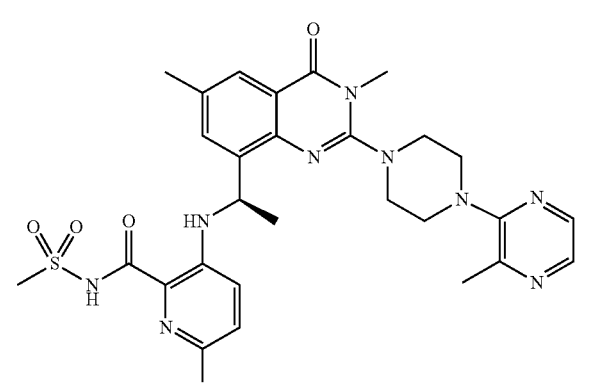 |

TABLE 1-continued

List of Compounds

| Cpd. ID | Chemical structure |
|---|---|
| 554 | 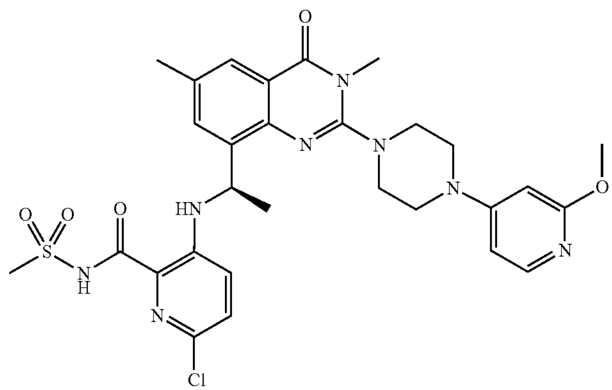 |
| 555 | 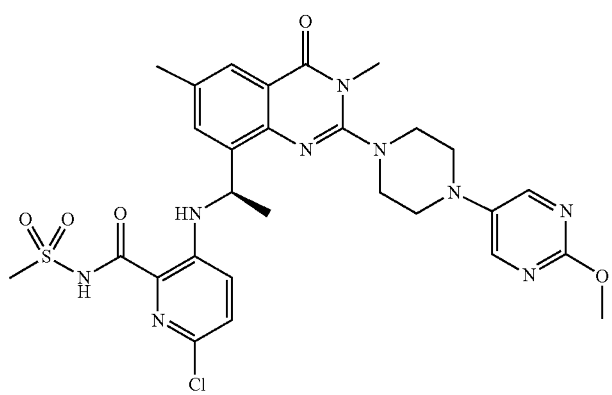 |
| 556 | 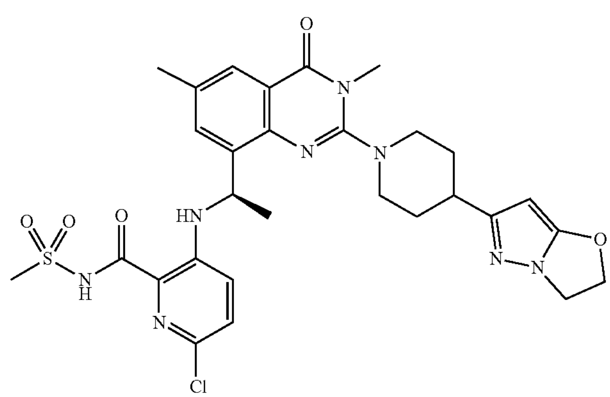 [SMILES: Cc1cc([C@@H](C)Nc2ccc(Cl)nc2C(=O)NS(C)(=O)=O)c2nc(N3CCC(c4cc5n(n4)CCO5)CC3)n(C)c(=O)c2c1] |
| 557 | 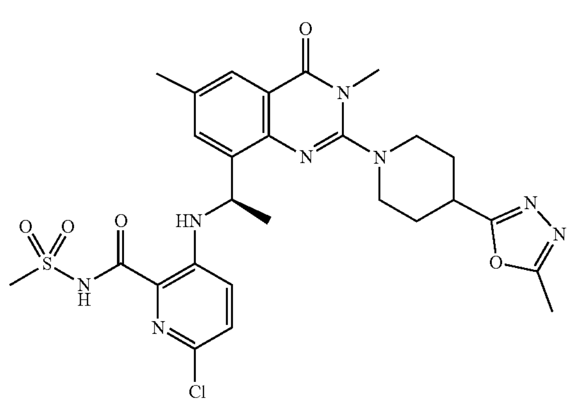 |

TABLE 1-continued
List of Compounds
| Cpd. ID | Chemical structure |
|---|---|
| 558 | 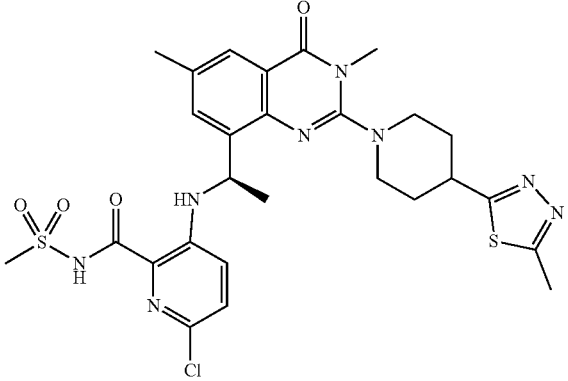 [SMILES: Cc1cc([C@@H](C)Nc2ccc(Cl)nc2C(=O)NS(C)(=O)=O)c2nc(N3CCC(c4nnc(C)s4)CC3)n(C)c(=O)c2c1] |
| 559 | 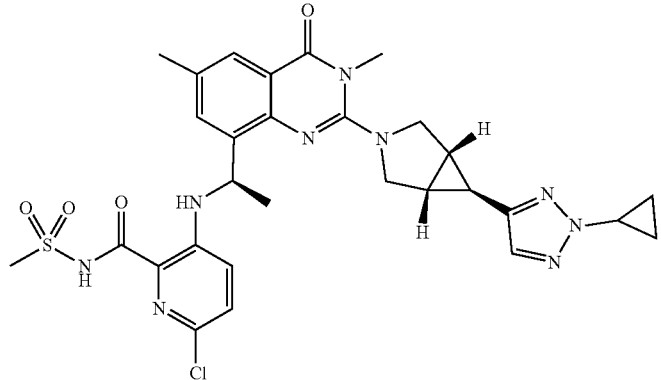 [SMILES: Cc1cc([C@@H](C)Nc2ccc(Cl)nc2C(=O)NS(C)(=O)=O)c2nc(N3C[C@@H]4[C@H](C3)[C@H]4c3cnn(C4CC4)n3)n(C)c(=O)c2c1] |
| 560 | 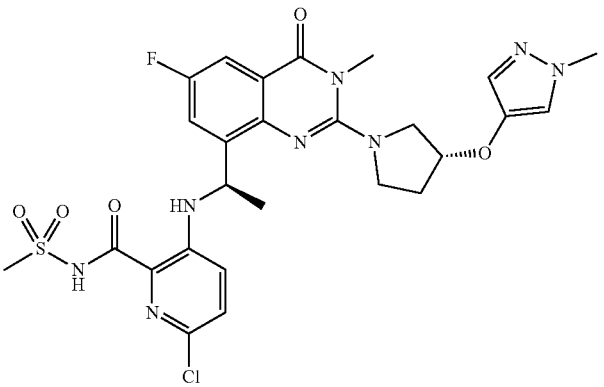 |
| 561 | 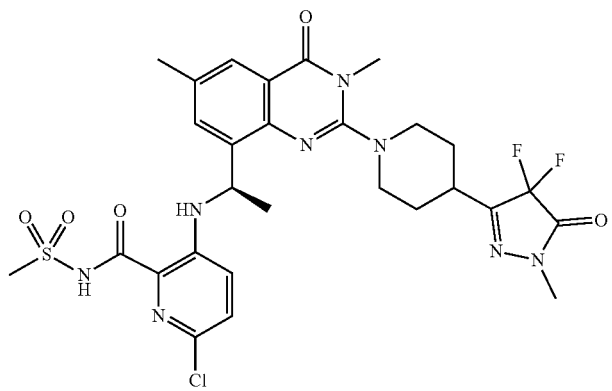 [SMILES: Cc1cc([C@@H](C)Nc2ccc(Cl)nc2C(=O)NS(C)(=O)=O)c2nc(N3CCC(C4=NN(C)C(=O)C4(F)F)CC3)n(C)c(=O)c2c1] |

TABLE 1-continued

List of Compounds

| Cpd. ID | Chemical structure |
|---|---|
| 562 | 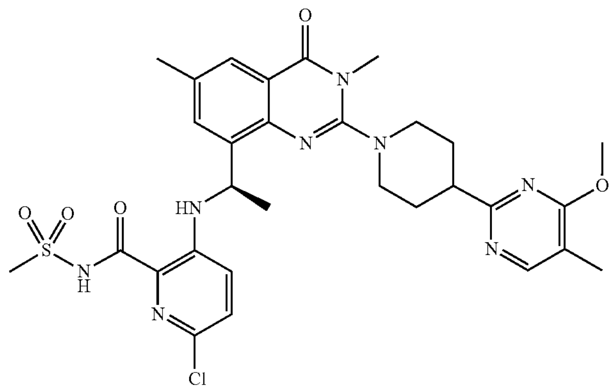 |
| 563 | 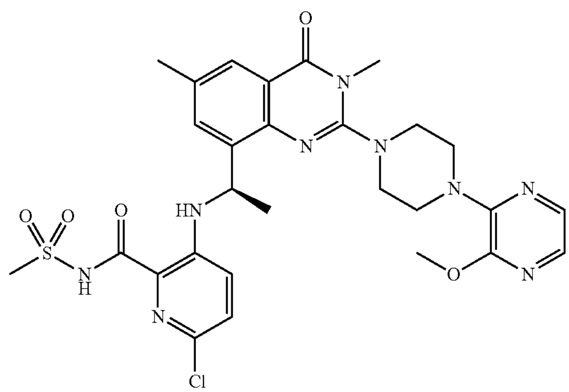 |
| 564 | 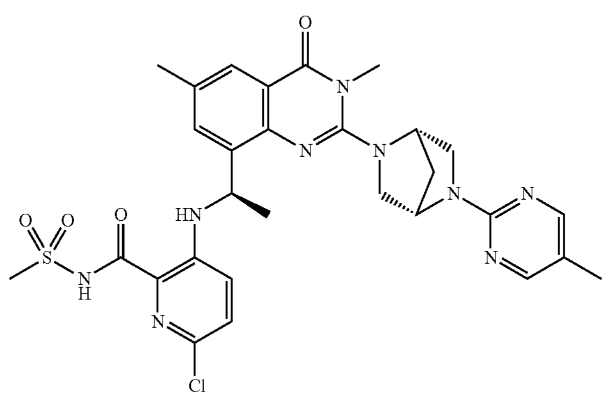 |
| 565 | 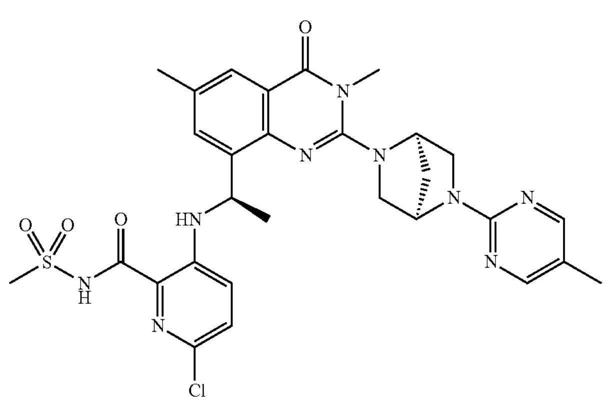 |

TABLE 1-continued
List of Compounds
| Cpd. ID | Chemical structure |
|---|---|
| 566 | 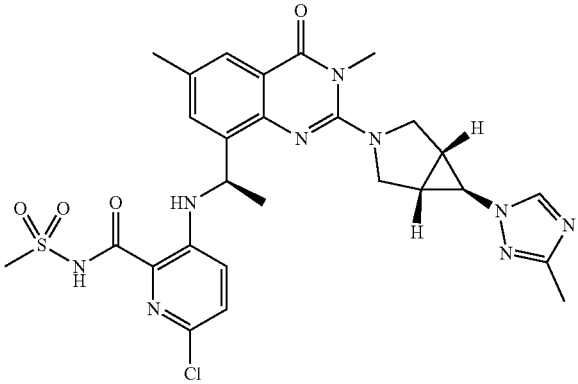 [SMILES: Cc1cc([C@@H](C)Nc2ccc(Cl)nc2C(=O)NS(C)(=O)=O)c2nc(N3C[C@@H]4[C@H](C3)[C@H]4n3cnc(C)n3)n(C)c(=O)c2c1] |
| 567 | 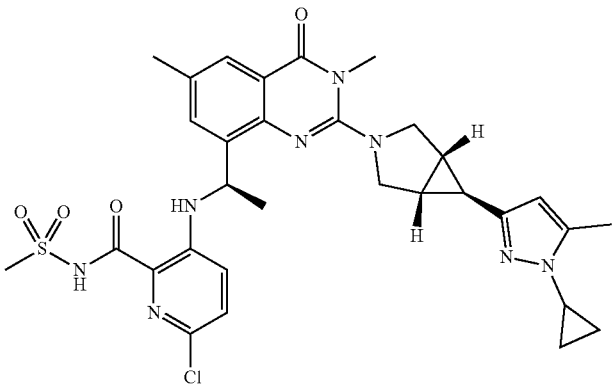 |
| 568 | 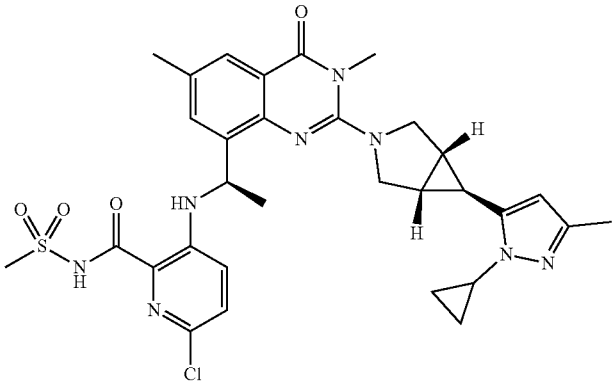 |
| 569 | 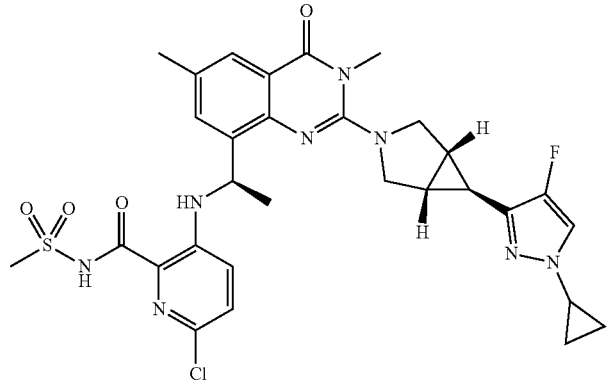 [SMILES: Cc1cc([C@@H](C)Nc2ccc(Cl)nc2C(=O)NS(C)(=O)=O)c2nc(N3C[C@@H]4[C@H](C3)[C@H]4c3nn(C4CC4)cc3F)n(C)c(=O)c2c1] |

TABLE 1-continued

List of Compounds

| Cpd. ID | Chemical structure |
|---|---|
| 570 | 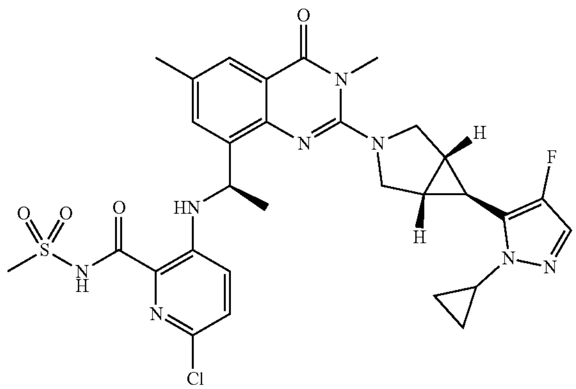 [SMILES: Cc1cc([C@@H](C)Nc2ccc(Cl)nc2C(=O)NS(C)(=O)=O)c2nc(N3C[C@@H]4[C@H](C3)[C@H]4c3c(F)cnn3C3CC3)n(C)c(=O)c2c1] |
| 571 | 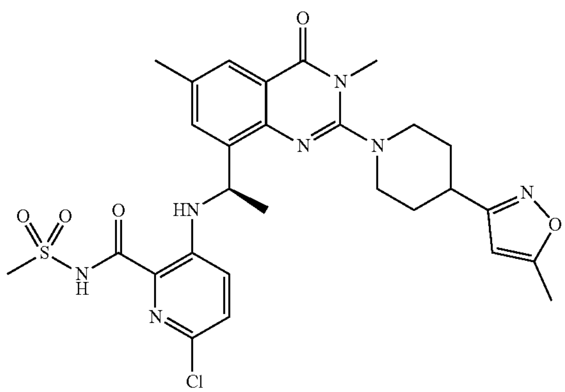 [SMILES: Cc1cc([C@@H](C)Nc2ccc(Cl)nc2C(=O)NS(C)(=O)=O)c2nc(N3CCC(c4cc(C)on4)CC3)n(C)c(=O)c2c1] |
| 572 | 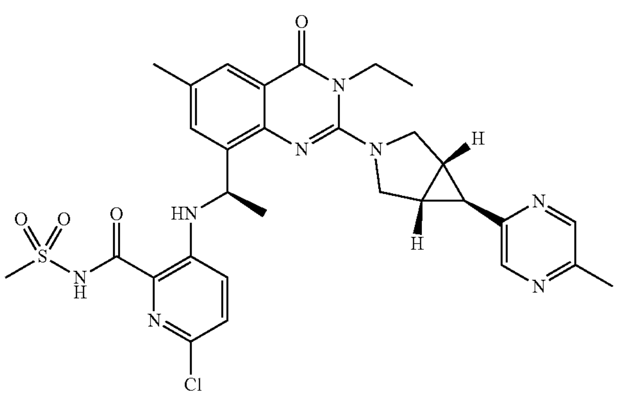 |
| 573 | 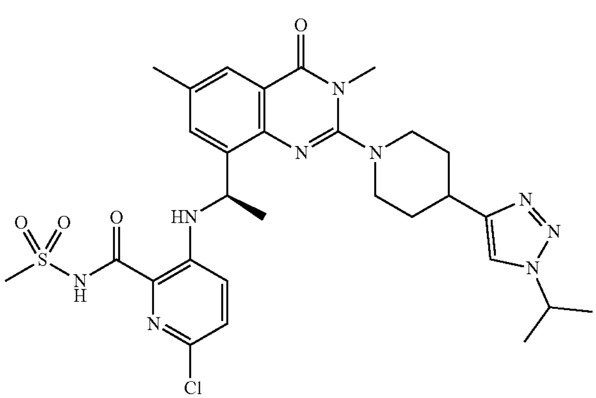 [SMILES: Cc1cc([C@@H](C)Nc2ccc(Cl)nc2C(=O)NS(C)(=O)=O)c2nc(N3CCC(c4cn(C(C)C)nn4)CC3)n(C)c(=O)c2c1] |

TABLE 1-continued
List of Compounds
| Cpd. ID | Chemical structure |
|---|---|
| 574 | 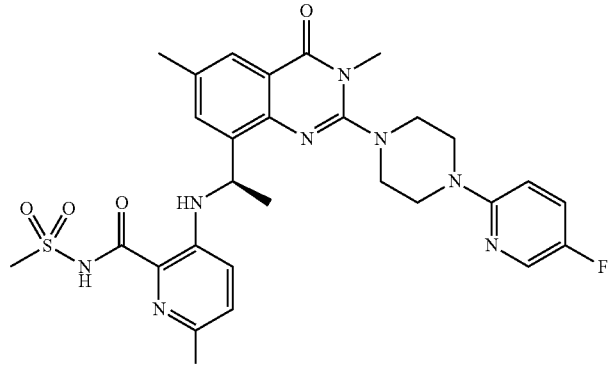 |
| 575 | 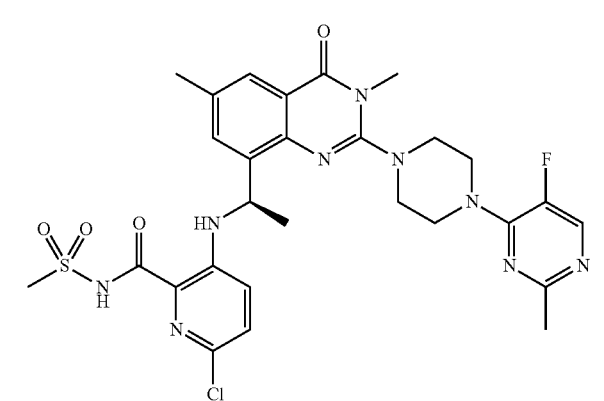 |
| 576 | 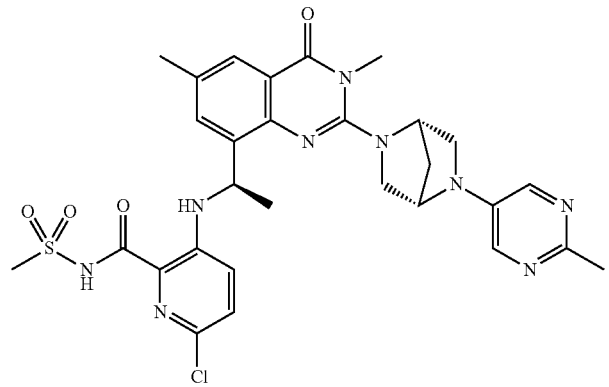 |
| 577 | 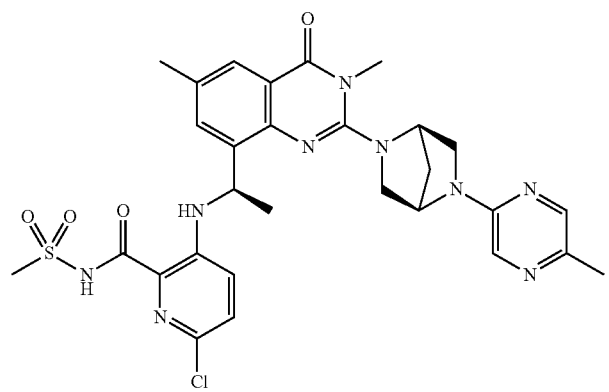 |

TABLE 1-continued

List of Compounds

| Cpd. ID | Chemical structure |
|---------|--------------------|
| 578 | 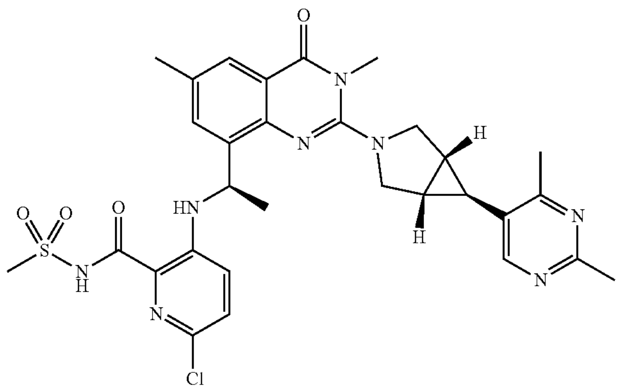 |
| 579 | 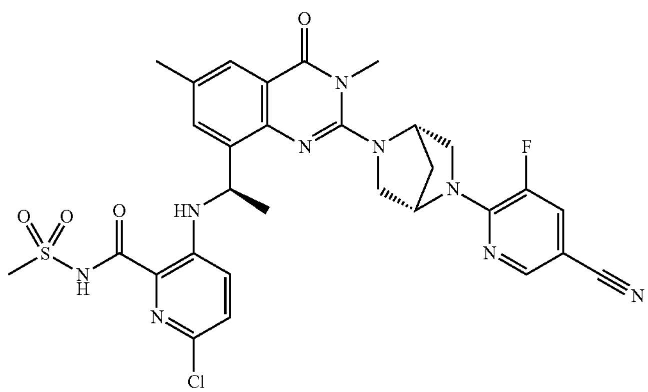 [SMILES: Cc1cc([C@@H](C)Nc2ccc(Cl)nc2C(=O)NS(C)(=O)=O)c2nc(N3C[C@@H]4C[C@H]3CN4c3ncc(C#N)cc3F)n(C)c(=O)c2c1] |
| 580 | 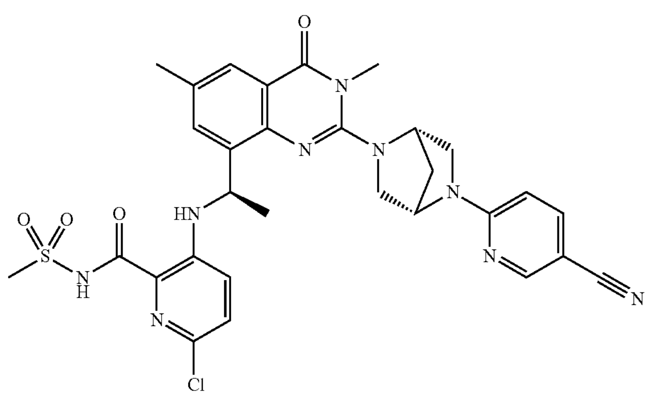 [SMILES: Cc1cc([C@@H](C)Nc2ccc(Cl)nc2C(=O)NS(C)(=O)=O)c2nc(N3C[C@@H]4C[C@H]3CN4c3ccc(C#N)cn3)n(C)c(=O)c2c1] |
| 581 | 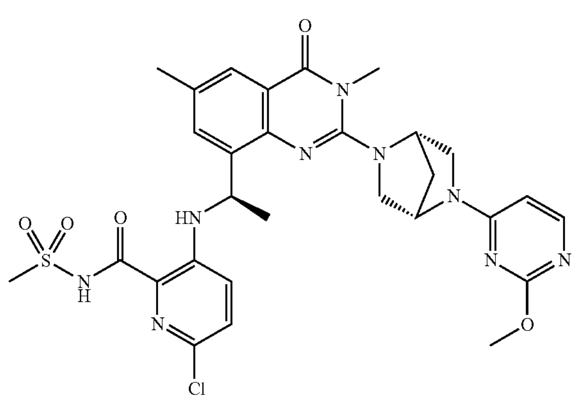 |

TABLE 1-continued

List of Compounds

| Cpd. ID | Chemical structure |
|---|---|
| 582 | 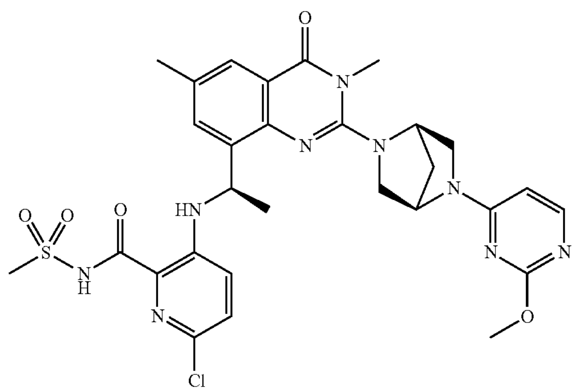 [SMILES: COc1nccc(N2C[C@H]3C[C@@H]2CN3c2nc3c([C@@H](C)Nc4ccc(Cl)nc4C(=O)NS(C)(=O)=O)cc(C)cc3c(=O)n2C)n1] |
| 583 | 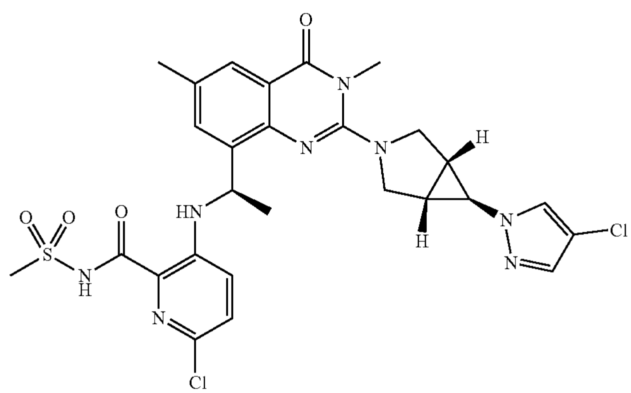 [SMILES: Cc1cc([C@@H](C)Nc2ccc(Cl)nc2C(=O)NS(C)(=O)=O)c2nc(N3C[C@@H]4[C@H](C3)[C@H]4n3cc(Cl)cn3)n(C)c(=O)c2c1] |
| 584 | 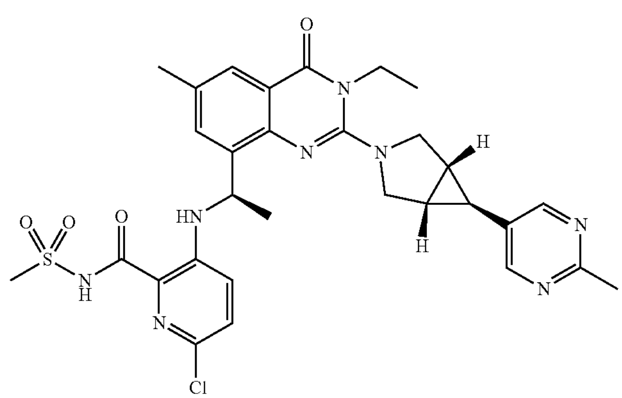 |
| 585 | 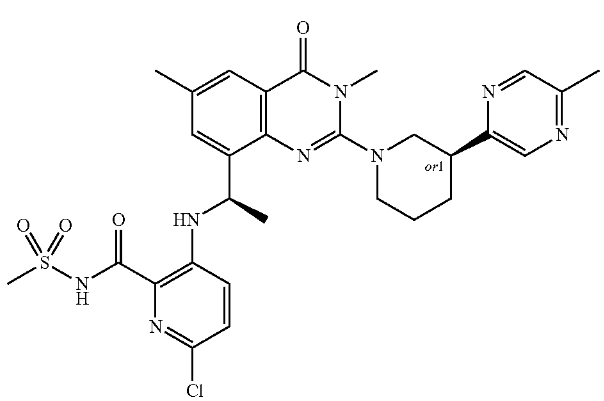 |

TABLE 1-continued

List of Compounds

| Cpd. ID | Chemical structure |
|---------|--------------------|
| 586 | 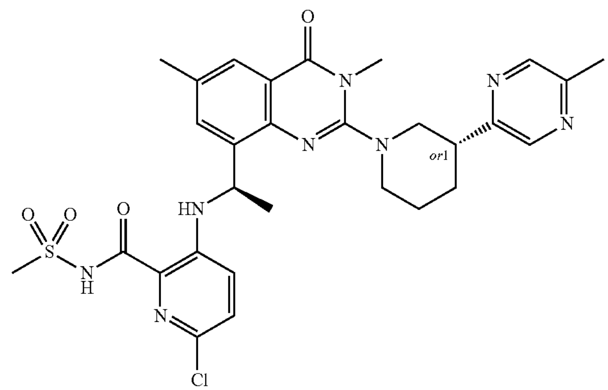 |
| 587 | 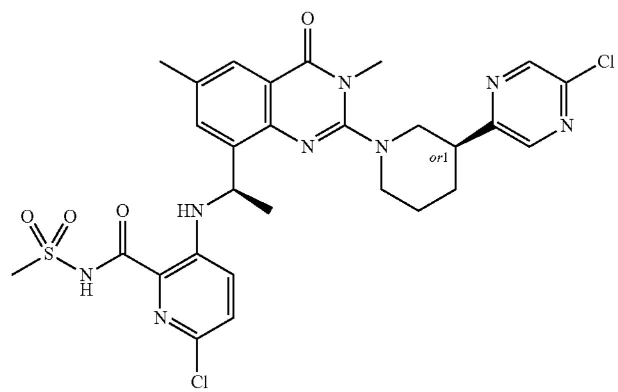 [SMILES: Cc1cc([C@@H](C)Nc2ccc(Cl)nc2C(=O)NS(C)(=O)=O)c2nc(N3CCC[C@H](c4cnc(Cl)cn4)C3)n(C)c(=O)c2c1] |
| 588 | 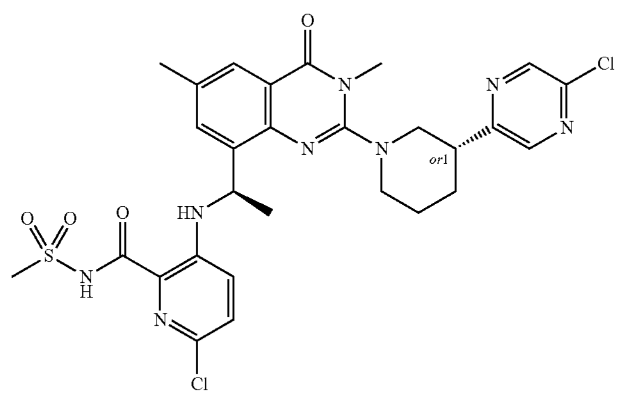 [SMILES: Cc1cc([C@@H](C)Nc2ccc(Cl)nc2C(=O)NS(C)(=O)=O)c2nc(N3CCC[C@@H](c4cnc(Cl)cn4)C3)n(C)c(=O)c2c1] |
| 589 | 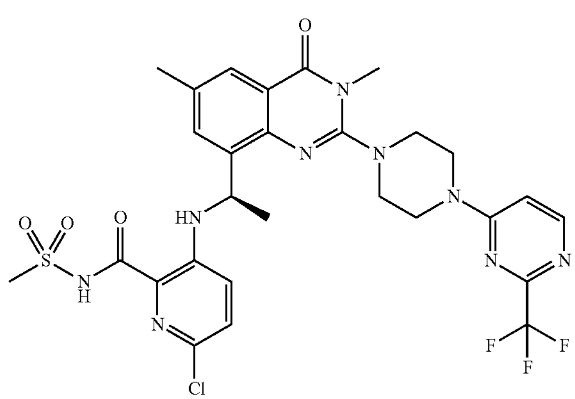 [SMILES: Cc1cc([C@@H](C)Nc2ccc(Cl)nc2C(=O)NS(C)(=O)=O)c2nc(N3CCN(c4ccnc(C(F)(F)F)n4)CC3)n(C)c(=O)c2c1] |

TABLE 1-continued

List of Compounds

| Cpd. ID | Chemical structure |
|---------|---------------------|
| 590 | 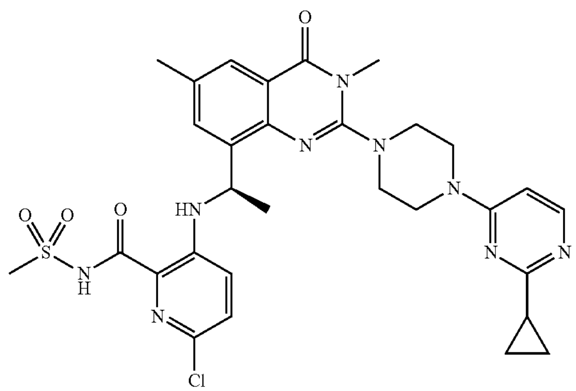 [SMILES: Cc1cc([C@@H](C)Nc2ccc(Cl)nc2C(=O)NS(C)(=O)=O)c2nc(N3CCN(c4ccnc(C5CC5)n4)CC3)n(C)c(=O)c2c1] |
| 591 | 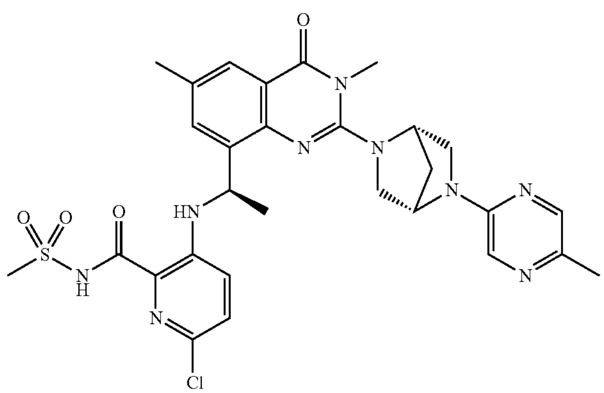 |
| 592 | 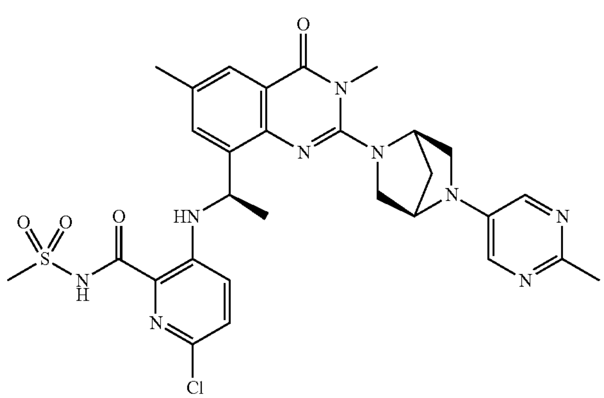 |
| 593 | 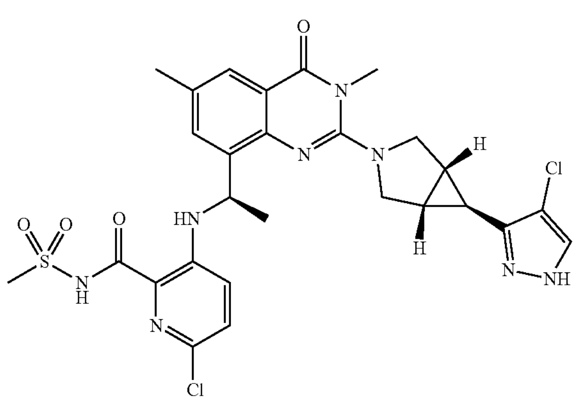 |

TABLE 1-continued

List of Compounds

| Cpd. ID | Chemical structure |
|---|---|
| 594 | 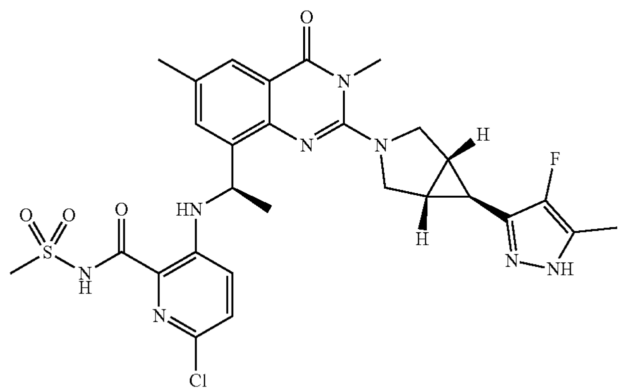 |
| 595 | 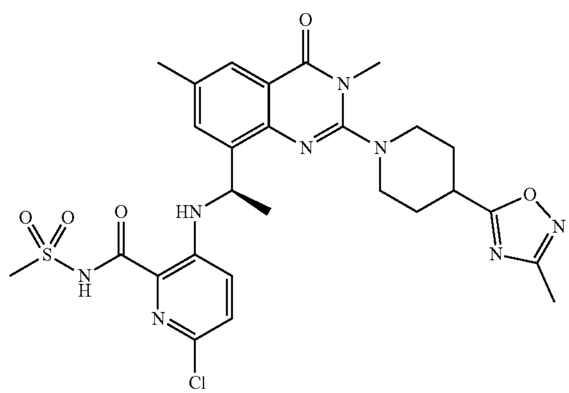 [SMILES: Cc1cc([C@@H](C)Nc2ccc(Cl)nc2C(=O)NS(C)(=O)=O)c2nc(N3CCC(c4nc(C)no4)CC3)n(C)c(=O)c2c1] |
| 596 | 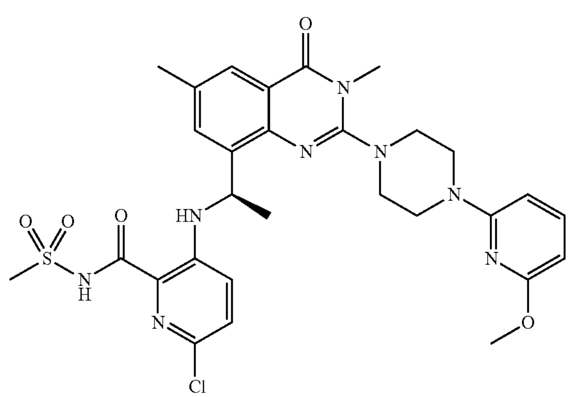 [SMILES: COc1cccc(N2CCN(c3nc4c([C@@H](C)Nc5ccc(Cl)nc5C(=O)NS(C)(=O)=O)cc(C)cc4c(=O)n3C)CC2)n1] |
| 597 | 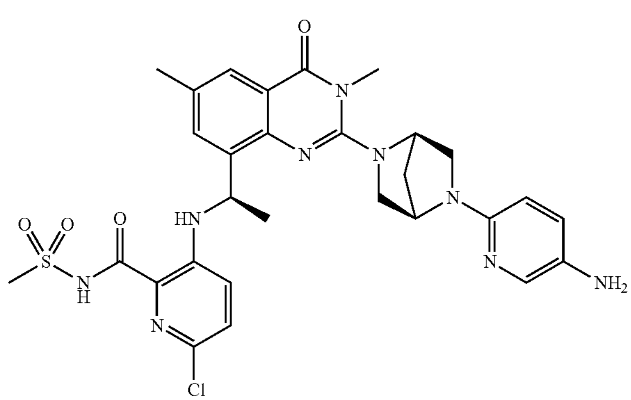 [SMILES: Cc1cc([C@@H](C)Nc2ccc(Cl)nc2C(=O)NS(C)(=O)=O)c2nc(N3C[C@H]4C[C@@H]3CN4c3ccc(N)cn3)n(C)c(=O)c2c1] |

TABLE 1-continued

List of Compounds

| Cpd. ID | Chemical structure |
|---------|--------------------|
| 598 | 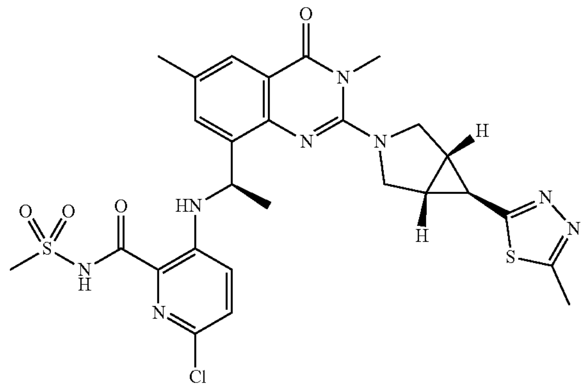 [SMILES: Cc1cc([C@@H](C)Nc2ccc(Cl)nc2C(=O)NS(C)(=O)=O)c2nc(N3C[C@@H]4[C@H](C3)[C@H]4c3nnc(C)s3)n(C)c(=O)c2c1] |
| 599 | 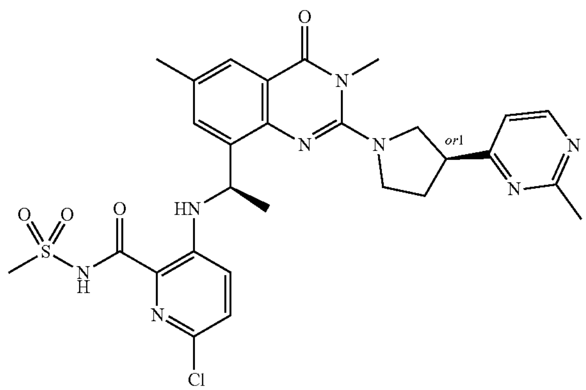 |
| 600 | 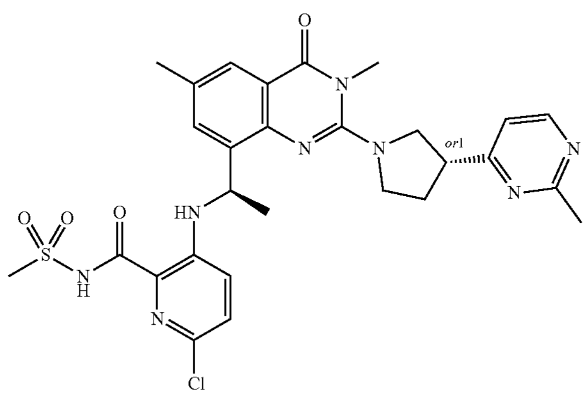 |
| 601 | 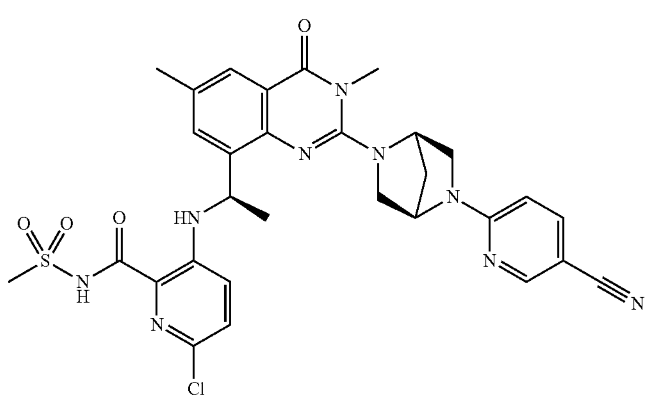 [SMILES: Cc1cc([C@@H](C)Nc2ccc(Cl)nc2C(=O)NS(C)(=O)=O)c2nc(N3C[C@H]4C[C@@H]3CN4c3ccc(C#N)cn3)n(C)c(=O)c2c1] |

TABLE 1-continued

List of Compounds

| Cpd. ID | Chemical structure |
|---|---|
| 602 | 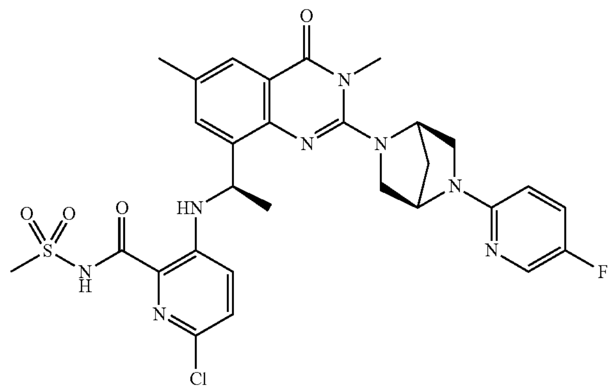 [SMILES: Cc1cc([C@@H](C)Nc2ccc(Cl)nc2C(=O)NS(C)(=O)=O)c2nc(N3C[C@H]4C[C@@H]3CN4c3ccc(F)cn3)n(C)c(=O)c2c1] |
| 603 | 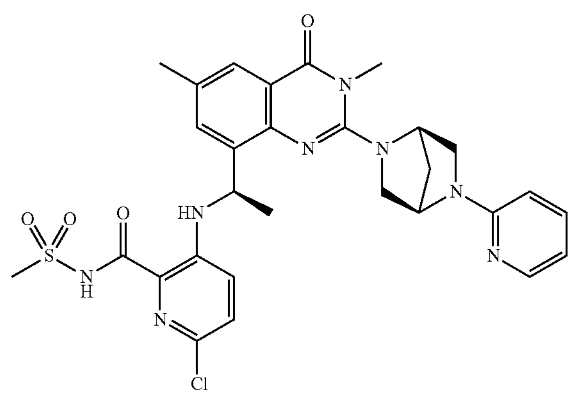 [SMILES: Cc1cc([C@@H](C)Nc2ccc(Cl)nc2C(=O)NS(C)(=O)=O)c2nc(N3C[C@H]4C[C@@H]3CN4c3ccccn3)n(C)c(=O)c2c1] |
| 604 | 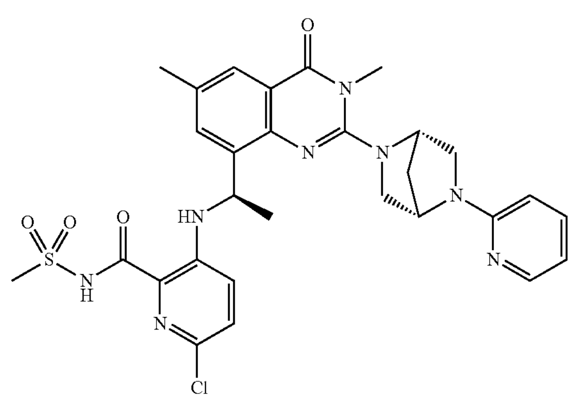 [SMILES: Cc1cc([C@@H](C)Nc2ccc(Cl)nc2C(=O)NS(C)(=O)=O)c2nc(N3C[C@@H]4C[C@H]3CN4c3ccccn3)n(C)c(=O)c2c1] |
| 605 | 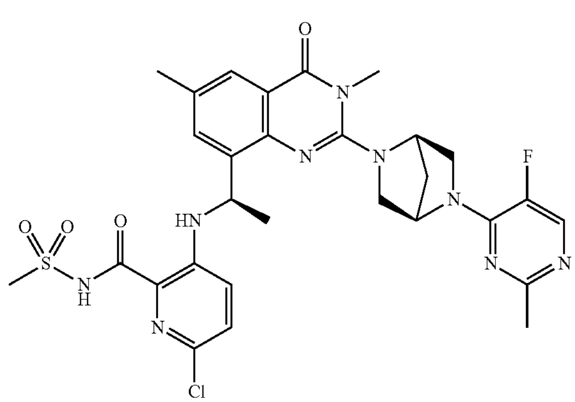 [SMILES: Cc1cc([C@@H](C)Nc2ccc(Cl)nc2C(=O)NS(C)(=O)=O)c2nc(N3C[C@H]4C[C@@H]3CN4c3nc(C)ncc3F)n(C)c(=O)c2c1] |

TABLE 1-continued

List of Compounds

| Cpd. ID | Chemical structure |
|---------|--------------------|
| 606 | 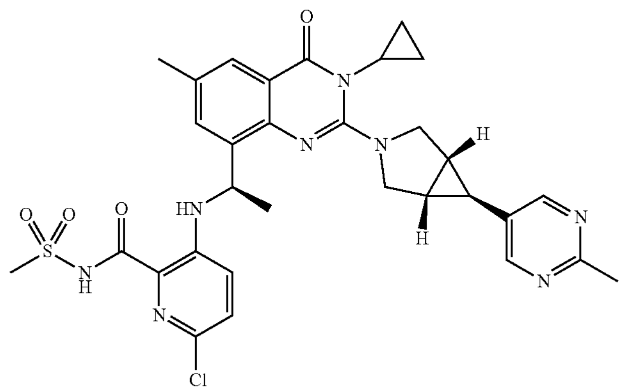 |
| 607 | 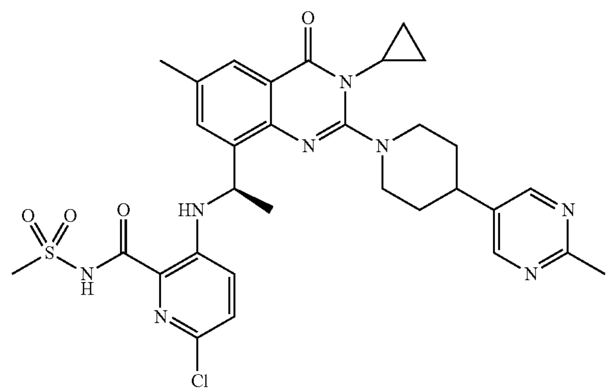 |
| 608 | 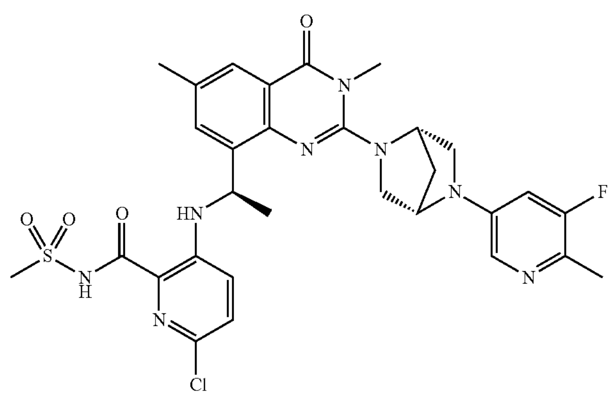 |
| 609 | 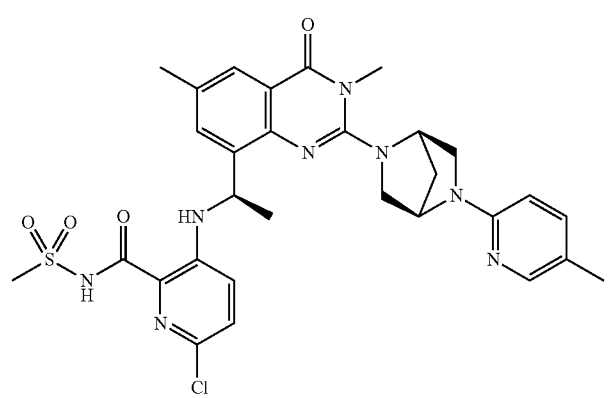 |

TABLE 1-continued
| List of Compounds | |
|---|---|
| Cpd. ID | Chemical structure |
| 610 | 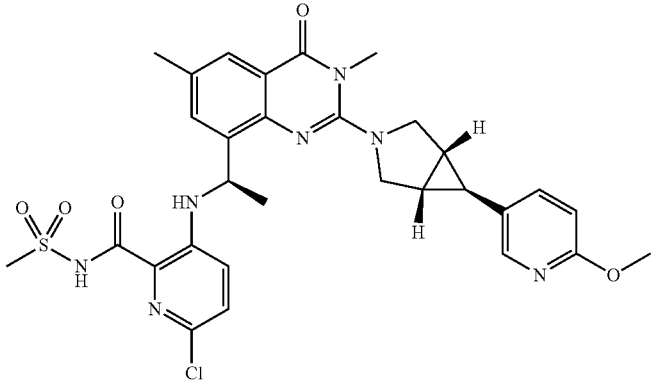 |
| 611 | 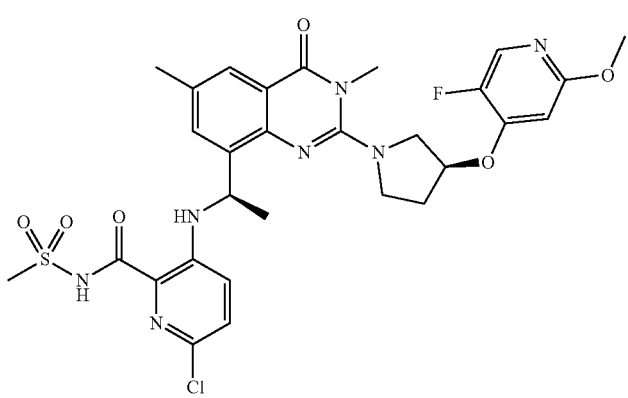 |
| 612 | 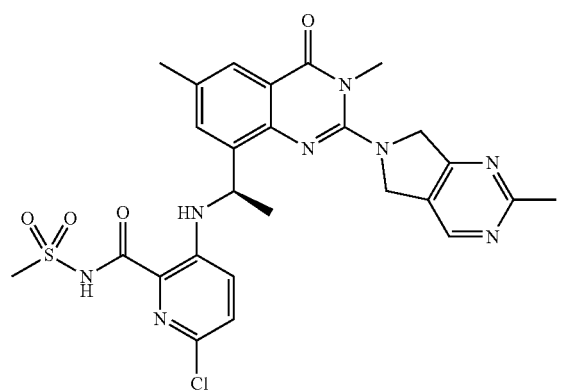 |

TABLE 1-continued

List of Compounds

| Cpd. ID | Chemical structure |
|---|---|
| 613 | 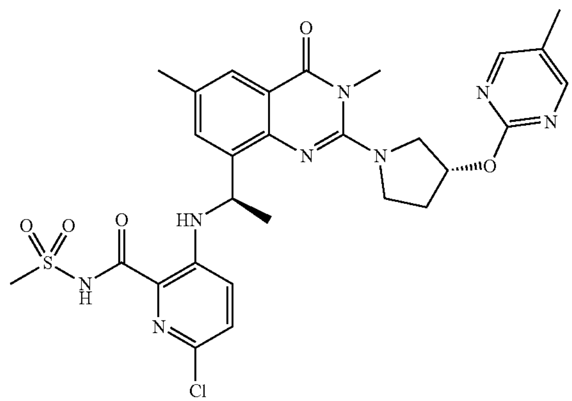 [SMILES: Cc1cnc(O[C@@H]2CCN(c3nc4c([C@@H](C)Nc5ccc(Cl)nc5C(=O)NS(C)(=O)=O)cc(C)cc4c(=O)n3C)C2)nc1] |
| 614 | 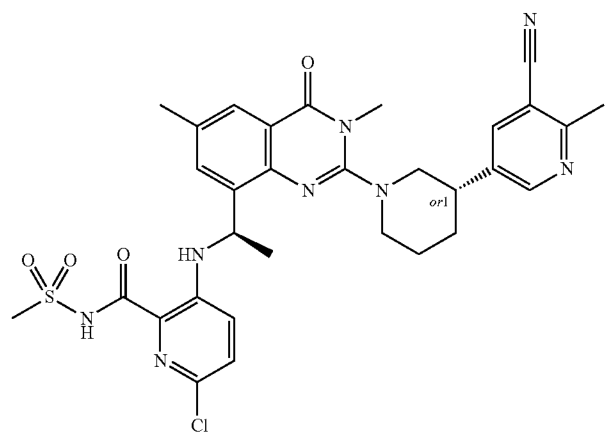 |
| 615 | 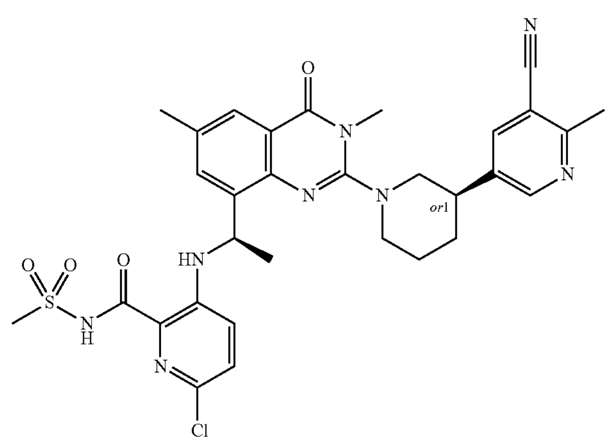 |

TABLE 1-continued
List of Compounds
| Cpd. ID | Chemical structure |
|---|---|
| 616 | 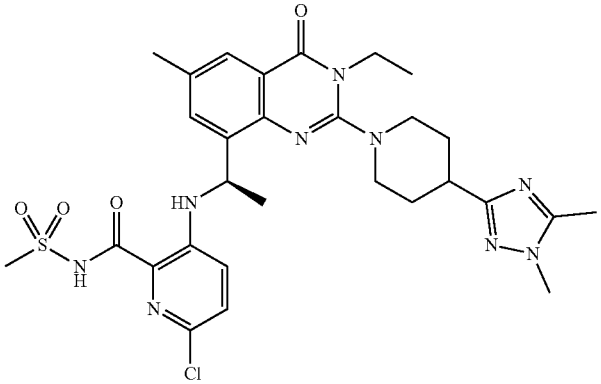 |
| 617 | 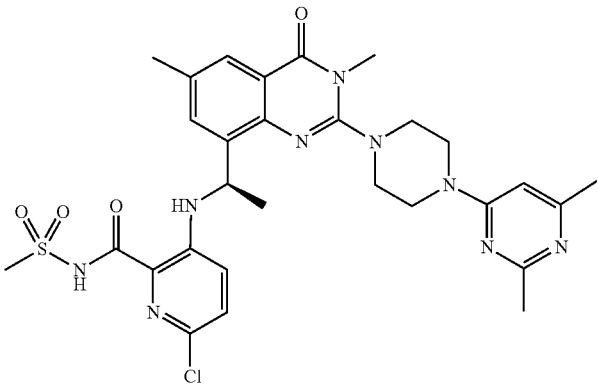 |
| 618 | 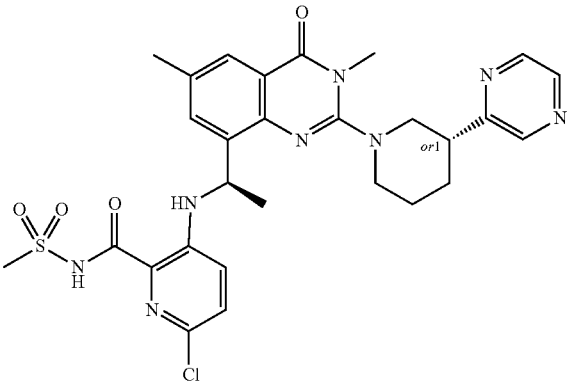 [SMILES: Cc1cc([C@@H](C)Nc2ccc(Cl)nc2C(=O)NS(C)(=O)=O)c2nc(N3CCC[C@@H](c4cnccn4)C3)n(C)c(=O)c2c1] |
| 619 | 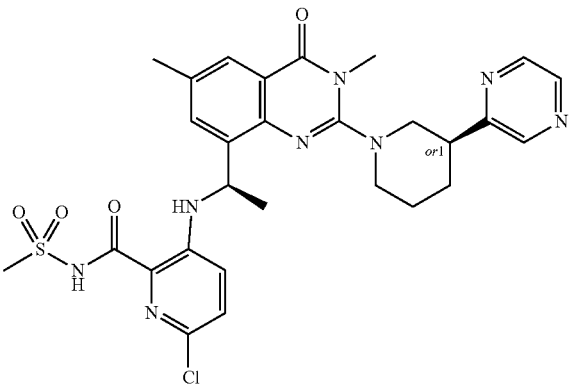 [SMILES: Cc1cc([C@@H](C)Nc2ccc(Cl)nc2C(=O)NS(C)(=O)=O)c2nc(N3CCC[C@H](c4cnccn4)C3)n(C)c(=O)c2c1] |

TABLE 1-continued

List of Compounds

| Cpd. ID | Chemical structure |
|---|---|
| 620 | 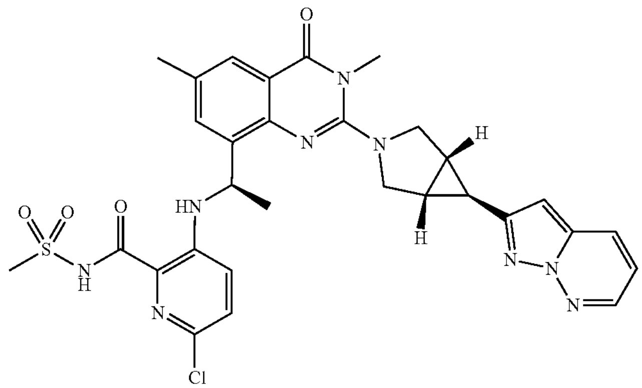 [SMILES: Cc1cc([C@@H](C)Nc2ccc(Cl)nc2C(=O)NS(C)(=O)=O)c2nc(N3C[C@@H]4[C@H](C3)[C@H]4c3cc4cccnn4n3)n(C)c(=O)c2c1] |
| 621 | 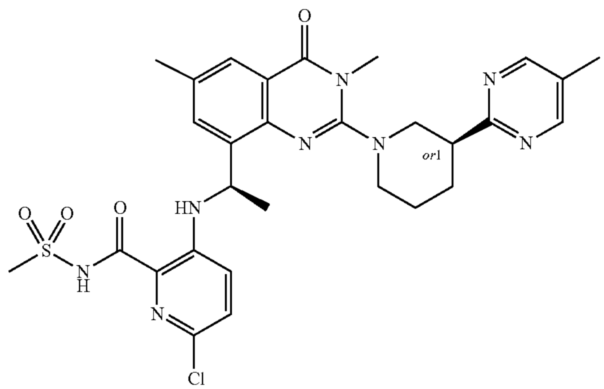 |
| 622 | 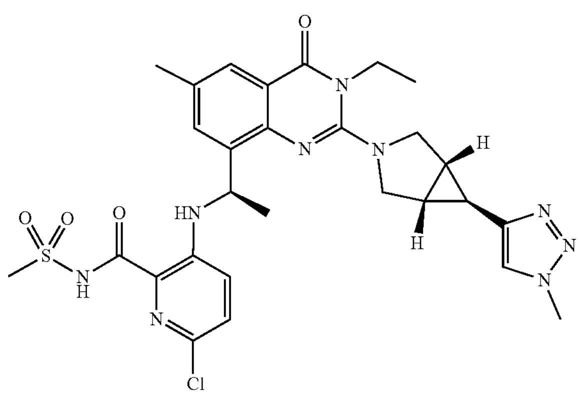 [SMILES: CCn1c(N2C[C@@H]3[C@H](C2)[C@H]3c2cn(C)nn2)nc2c([C@@H](C)Nc3ccc(Cl)nc3C(=O)NS(C)(=O)=O)cc(C)cc2c1=O] |
| 623 | 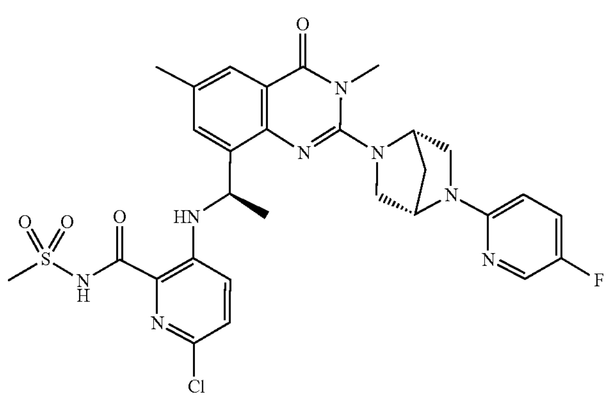 [SMILES: Cc1cc([C@@H](C)Nc2ccc(Cl)nc2C(=O)NS(C)(=O)=O)c2nc(N3C[C@@H]4C[C@H]3CN4c3ccc(F)cn3)n(C)c(=O)c2c1] |

TABLE 1-continued

List of Compounds

| Cpd. ID | Chemical structure |
|---|---|
| 624 | 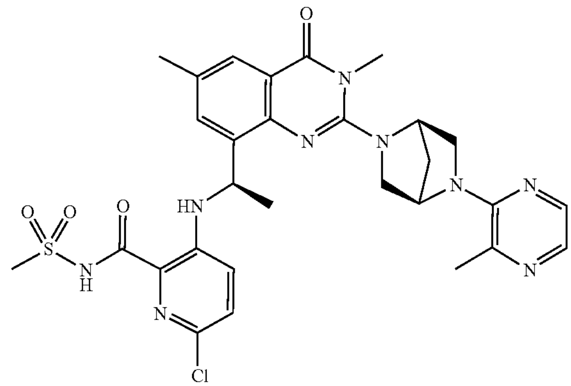 [SMILES: Cc1cc([C@@H](C)Nc2ccc(Cl)nc2C(=O)NS(C)(=O)=O)c2nc(N3C[C@H]4C[C@@H]3CN4c3nccnc3C)n(C)c(=O)c2c1] |
| 625 | 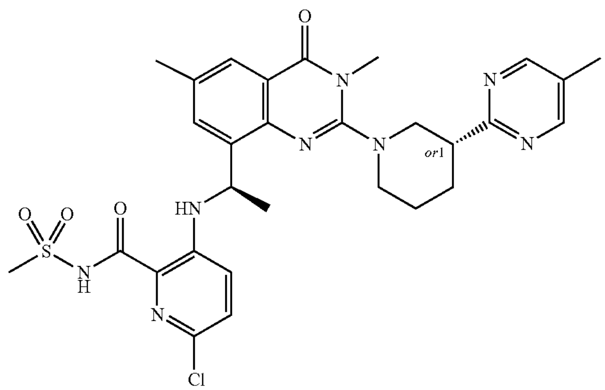 |
| 626 | 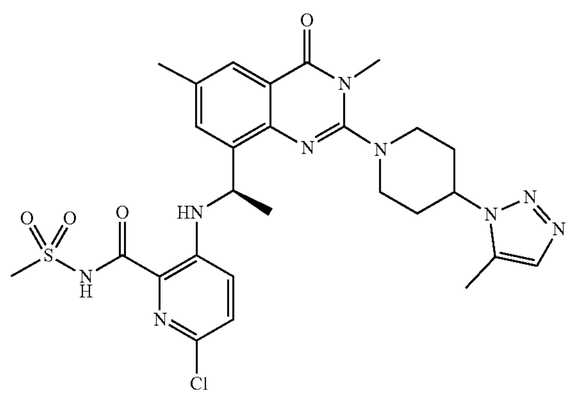 [SMILES: Cc1cc([C@@H](C)Nc2ccc(Cl)nc2C(=O)NS(C)(=O)=O)c2nc(N3CCC(n4nncc4C)CC3)n(C)c(=O)c2c1] |
| 627 | 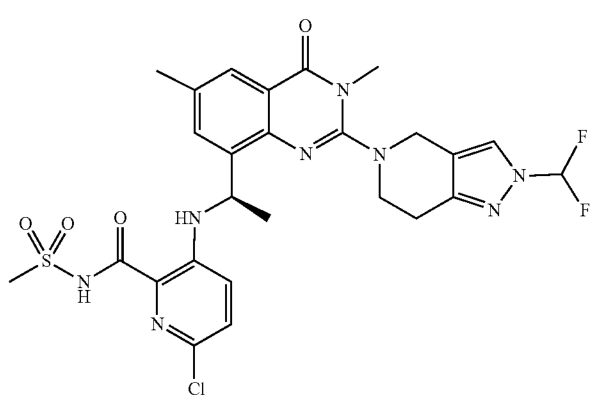 [SMILES: Cc1cc([C@@H](C)Nc2ccc(Cl)nc2C(=O)NS(C)(=O)=O)c2nc(N3CCc4nn(C(F)F)cc4C3)n(C)c(=O)c2c1] |

TABLE 1-continued

List of Compounds

| Cpd. ID | Chemical structure |
|---|---|
| 628 | 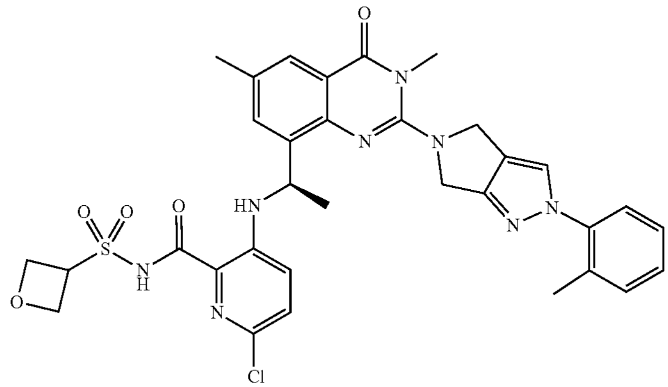 [SMILES: Cc1cc([C@@H](C)Nc2ccc(Cl)nc2C(=O)NS(=O)(=O)C2COC2)c2nc(N3Cc4cn(-c5ccccc5C)nc4C3)n(C)c(=O)c2c1] |
| 629 | 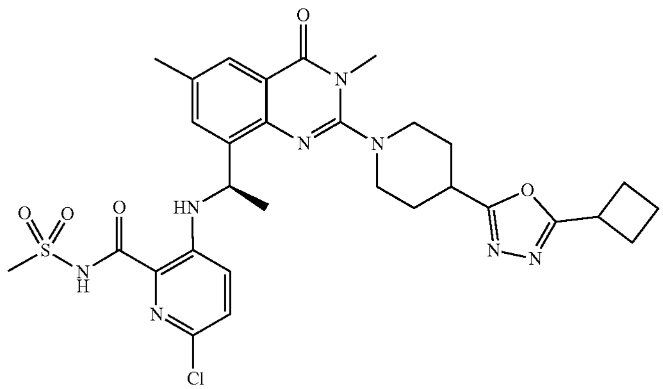 [SMILES: Cc1cc([C@@H](C)Nc2ccc(Cl)nc2C(=O)NS(C)(=O)=O)c2nc(N3CCC(c4nnc(C5CCC5)o4)CC3)n(C)c(=O)c2c1] |
| 630 | 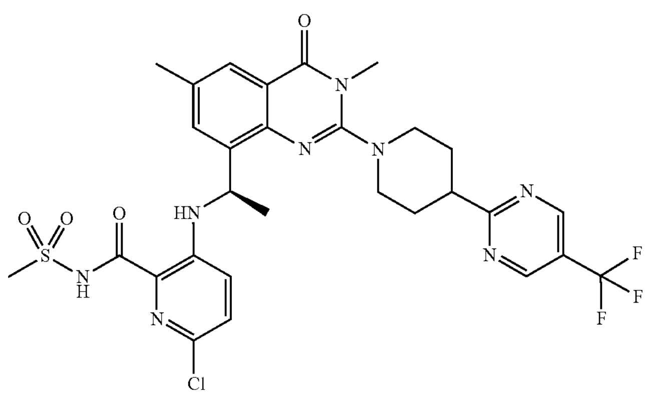 [SMILES: Cc1cc([C@@H](C)Nc2ccc(Cl)nc2C(=O)NS(C)(=O)=O)c2nc(N3CCC(c4ncc(C(F)(F)F)cn4)CC3)n(C)c(=O)c2c1] |
| 631 | 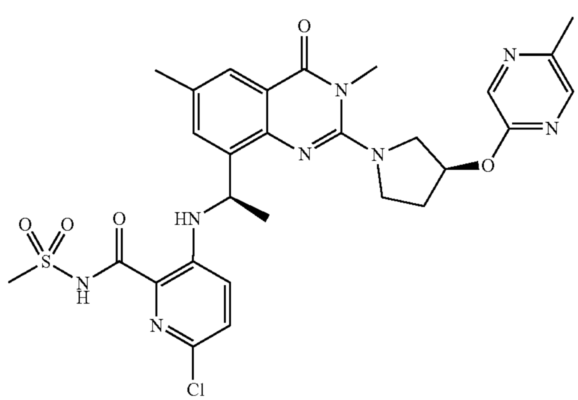 [SMILES: Cc1cc([C@@H](C)Nc2ccc(Cl)nc2C(=O)NS(C)(=O)=O)c2nc(N3CC[C@H](Oc4cnc(C)cn4)C3)n(C)c(=O)c2c1] |

TABLE 1-continued

List of Compounds

| Cpd. ID | Chemical structure |
|---|---|
| 632 | 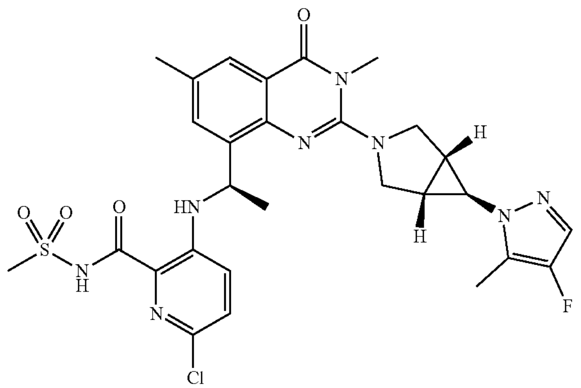 [SMILES: Cc1cc([C@@H](C)Nc2ccc(Cl)nc2C(=O)NS(C)(=O)=O)c2nc(N3C[C@@H]4[C@H](C3)[C@H]4n3ncc(F)c3C)n(C)c(=O)c2c1] |
| 633 | 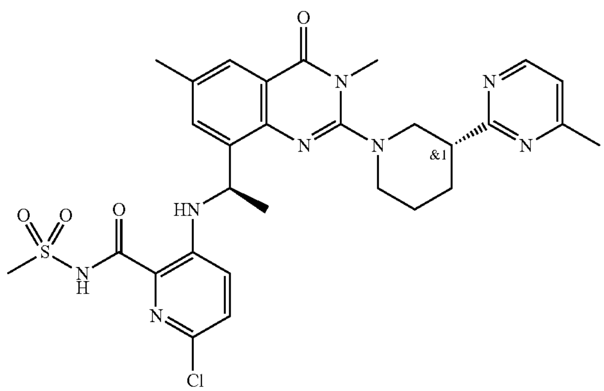 |
| 634 | 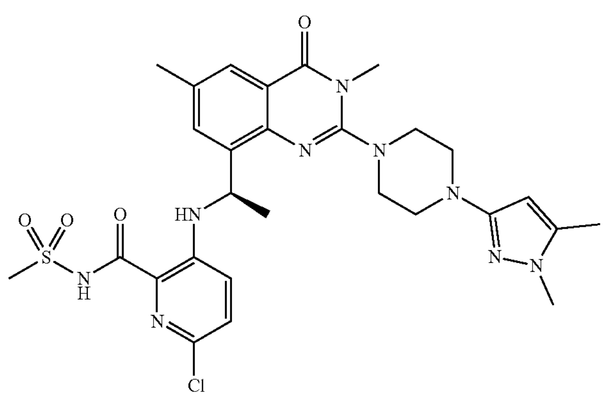 |
| 635 | 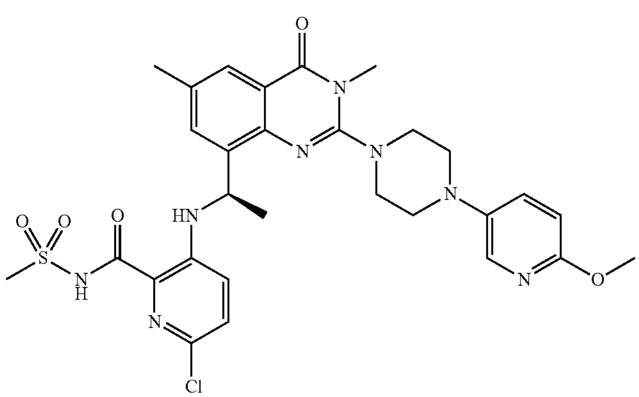 |

TABLE 1-continued

List of Compounds

| Cpd. ID | Chemical structure |
|---|---|
| 636 | 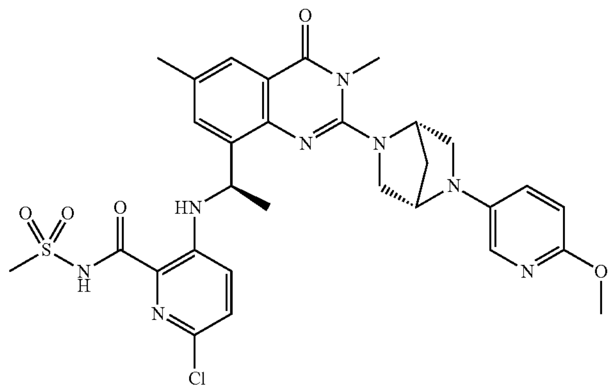 |
| 637 | 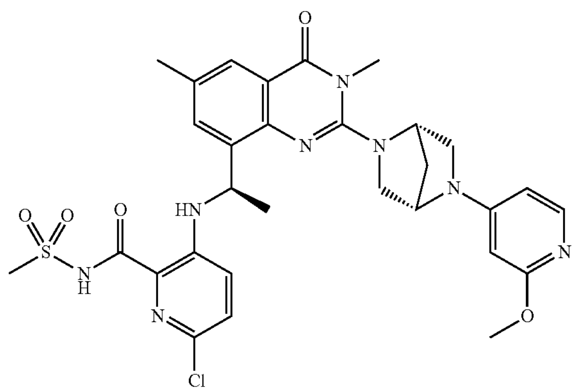 [SMILES: COc1cc(N2C[C@@H]3C[C@H]2CN3c2nc3c([C@@H](C)Nc4ccc(Cl)nc4C(=O)NS(C)(=O)=O)cc(C)cc3c(=O)n2C)ccn1] |
| 638 | 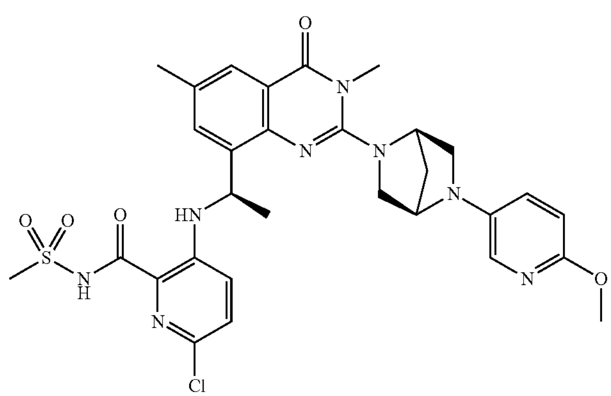 |
| 639 | 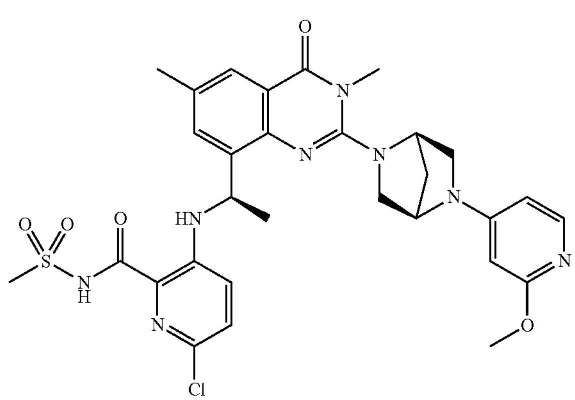 [SMILES: COc1cc(N2C[C@H]3C[C@@H]2CN3c2nc3c([C@@H](C)Nc4ccc(Cl)nc4C(=O)NS(C)(=O)=O)cc(C)cc3c(=O)n2C)ccn1] |

TABLE 1-continued
List of Compounds
| Cpd. ID | Chemical structure |
|---|---|
| 640 | 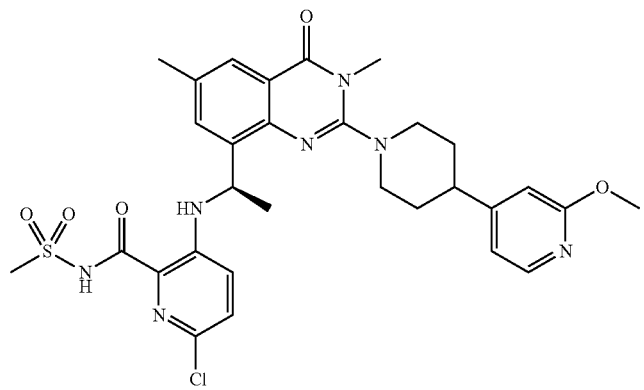 |
| 641 | 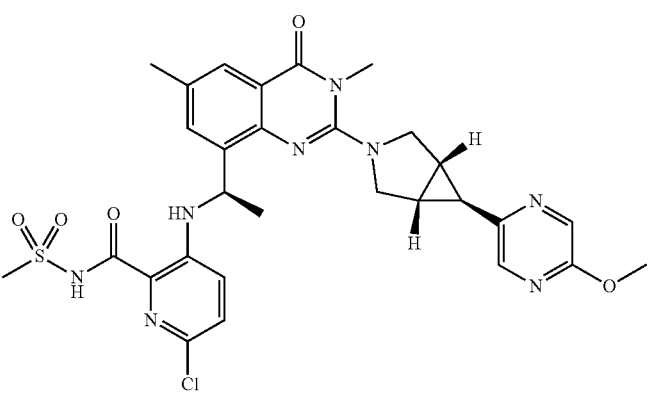 |
| 642 | 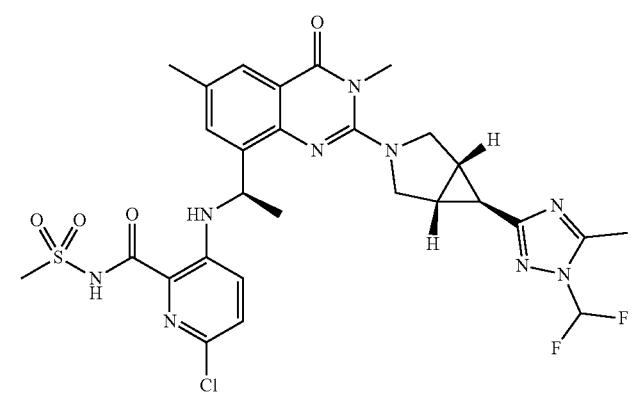 |
| 643 | 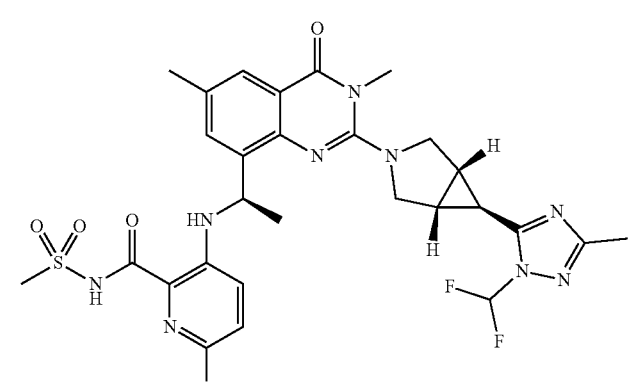 |

TABLE 1-continued
List of Compounds
| Cpd. ID | Chemical structure |
|---|---|
| 644 | 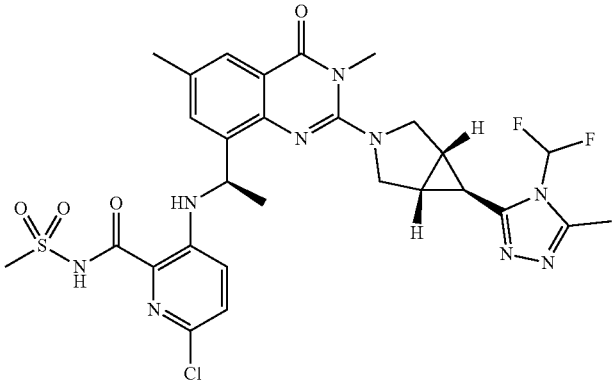 |
| 645 | 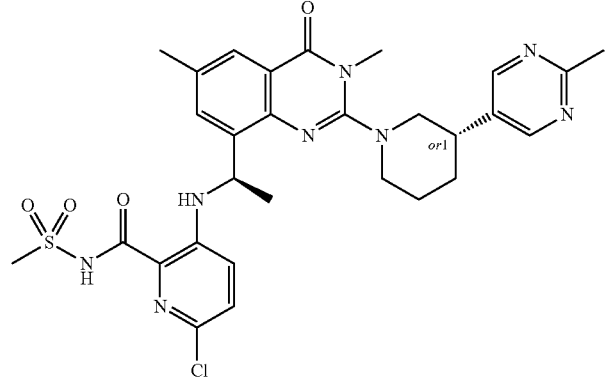 |
| 646 | 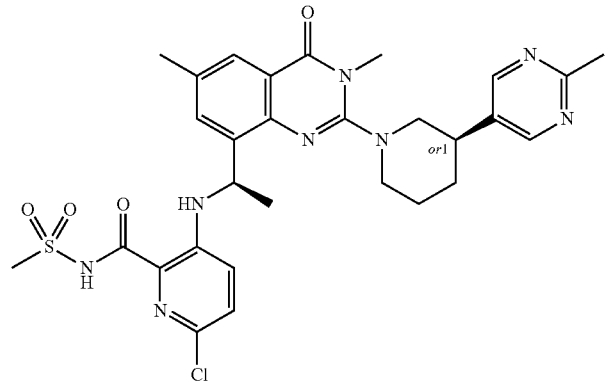 |
| 647 | 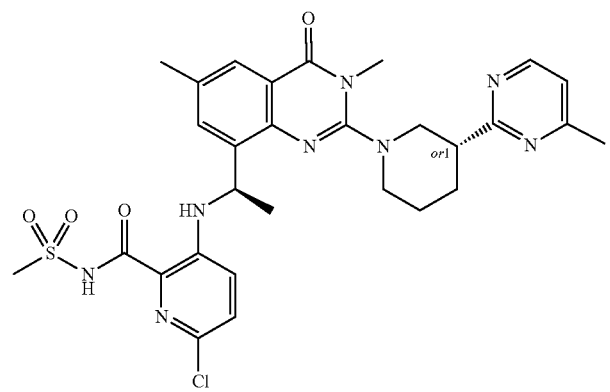 |

TABLE 1-continued

List of Compounds

| Cpd. ID | Chemical structure |
|---|---|
| 648 | 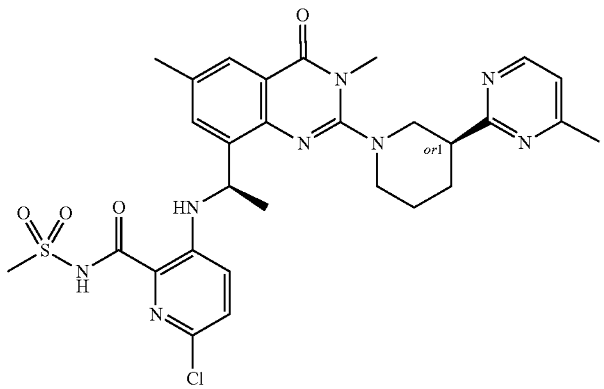 |
| 649 | 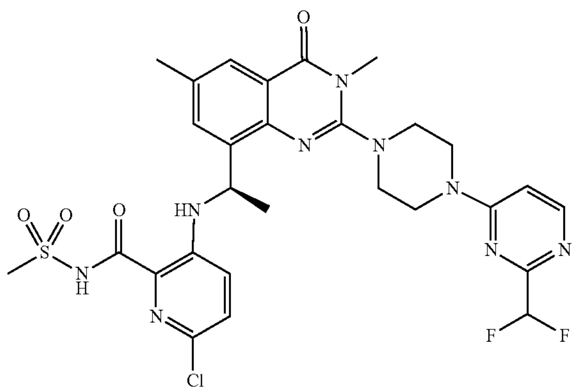 [SMILES: Cc1cc([C@@H](C)Nc2ccc(Cl)nc2C(=O)NS(C)(=O)=O)c2nc(N3CCN(c4ccnc(C(F)F)n4)CC3)n(C)c(=O)c2c1] |
| 650 | 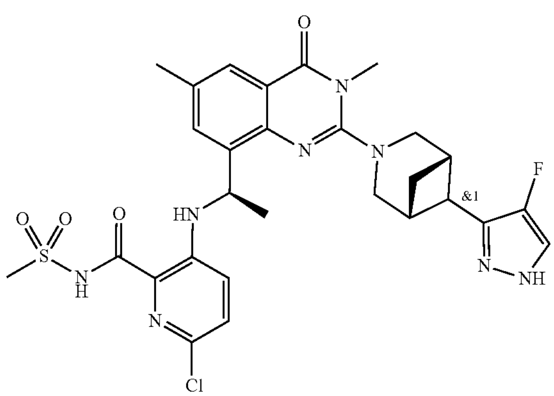 [SMILES: Cc1cc([C@@H](C)Nc2ccc(Cl)nc2C(=O)NS(C)(=O)=O)c2nc(N3C[C@H]4C[C@@H](C3)C4c3n[nH]cc3F)n(C)c(=O)c2c1] |
| 651 | 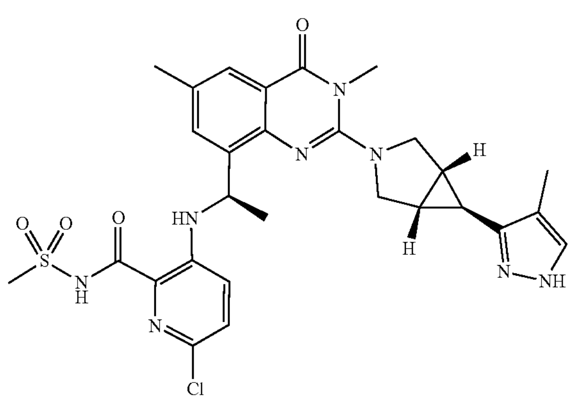 [SMILES: Cc1cc([C@@H](C)Nc2ccc(Cl)nc2C(=O)NS(C)(=O)=O)c2nc(N3C[C@@H]4[C@H](C3)[C@H]4c3n[nH]cc3C)n(C)c(=O)c2c1] |

TABLE 1-continued

List of Compounds

| Cpd. ID | Chemical structure |
|---------|-------------------|
| 652 | 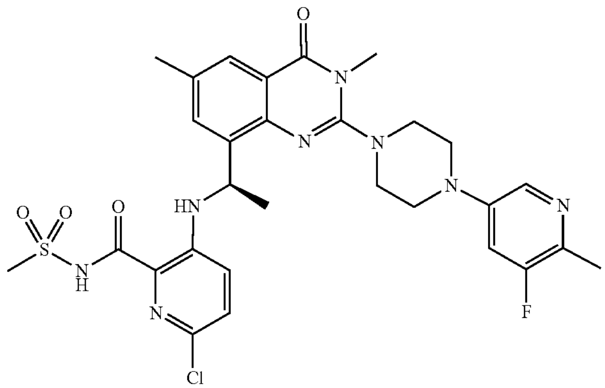 |
| 653 | 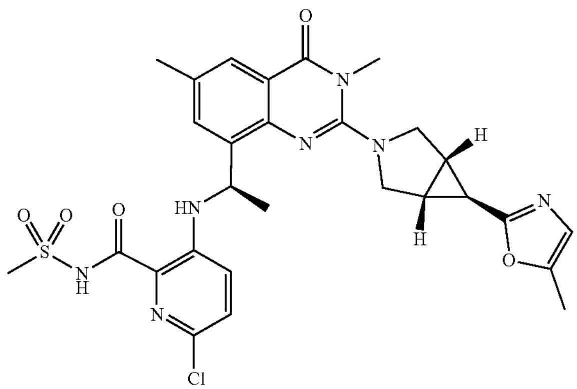 [SMILES: Cc1cc([C@@H](C)Nc2ccc(Cl)nc2C(=O)NS(C)(=O)=O)c2nc(N3C[C@@H]4[C@H](C3)[C@H]4c3ncc(C)o3)n(C)c(=O)c2c1] |
| 654 | 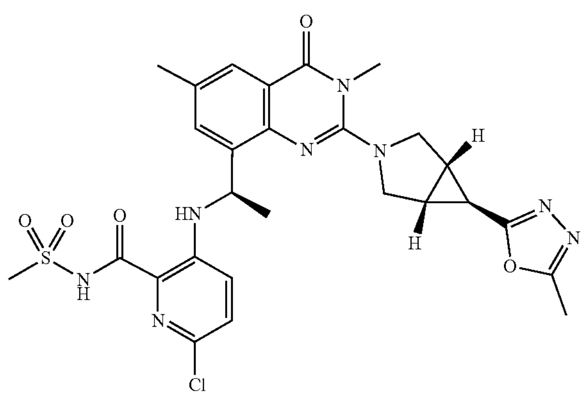 [SMILES: Cc1cc([C@@H](C)Nc2ccc(Cl)nc2C(=O)NS(C)(=O)=O)c2nc(N3C[C@@H]4[C@H](C3)[C@H]4c3nnc(C)o3)n(C)c(=O)c2c1] |
| 655 | 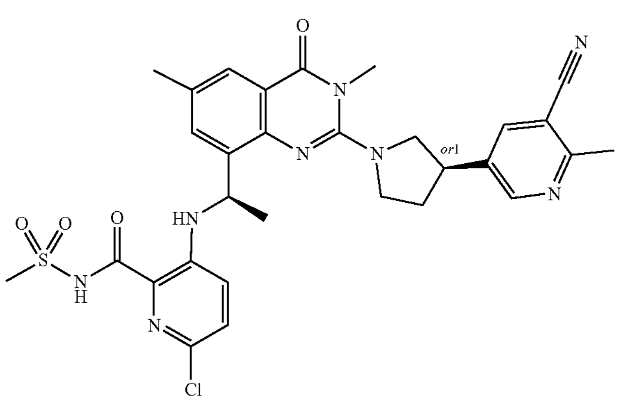 |

TABLE 1-continued
List of Compounds
| Cpd. ID | Chemical structure |
|---|---|
| 656 | 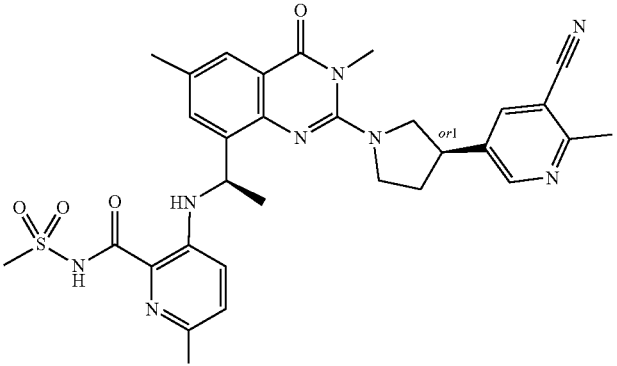 |
| 657 | 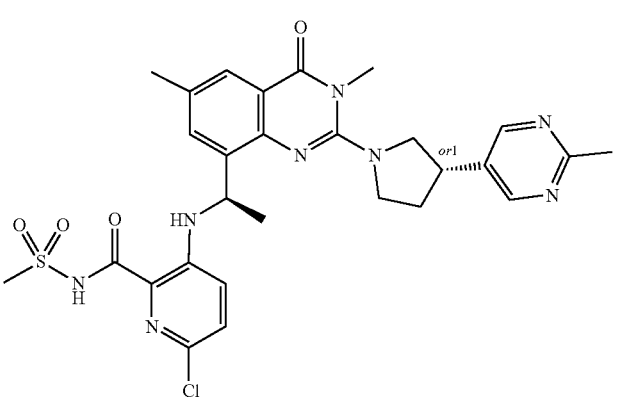 |
| 658 | 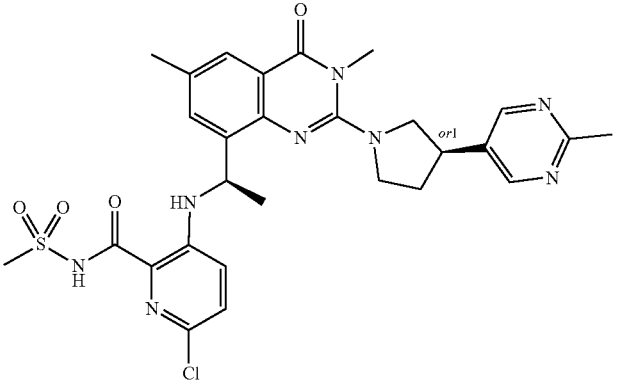 |
| 659 | 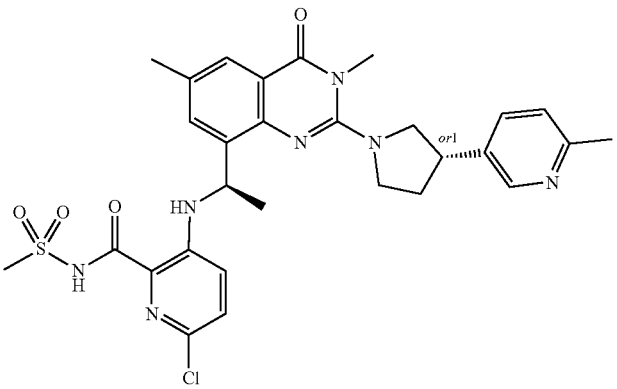 |

TABLE 1-continued

List of Compounds

| Cpd. ID | Chemical structure |
|---|---|
| 660 | 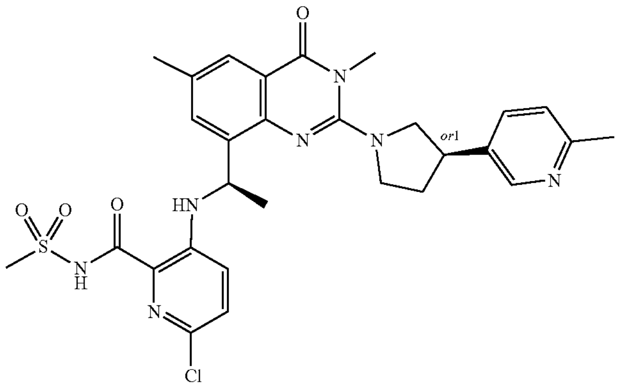 |
| 661 | 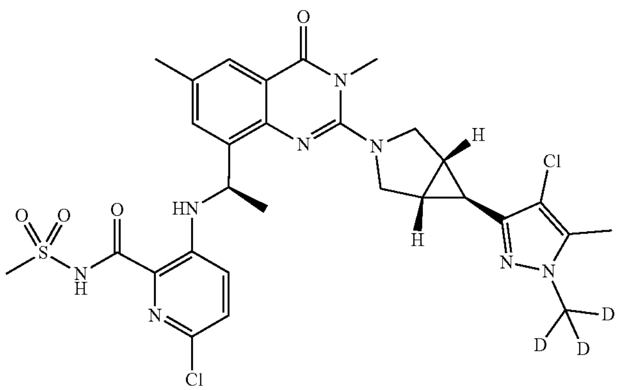 |
| 662 | 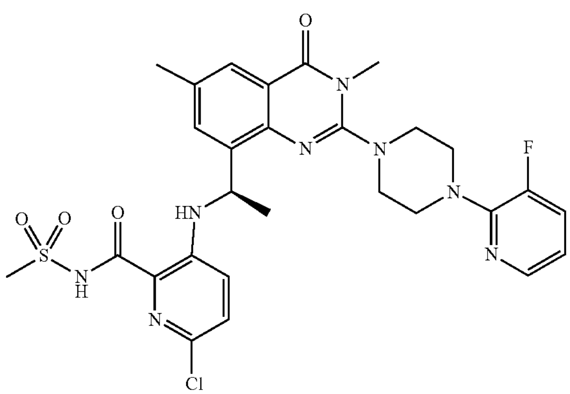 [SMILES: Cc1cc([C@@H](C)Nc2ccc(Cl)nc2C(=O)NS(C)(=O)=O)c2nc(N3CCN(c4ncccc4F)CC3)n(C)c(=O)c2c1] |
| 663 | 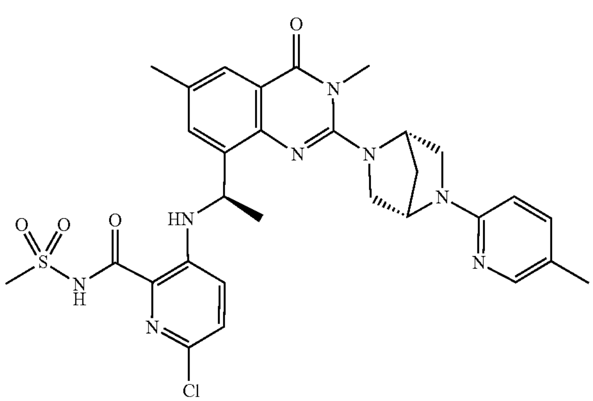 |

TABLE 1-continued

List of Compounds

| Cpd. ID | Chemical structure |
|---------|--------------------|
| 664 | 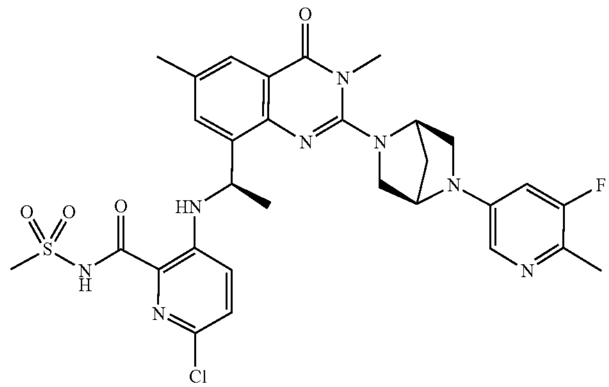 |
| 665 | 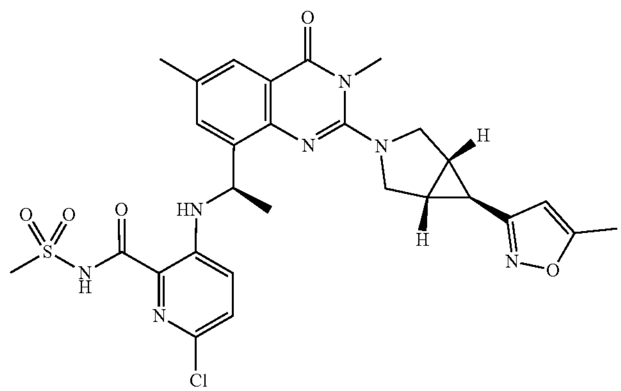 |
| 666 | 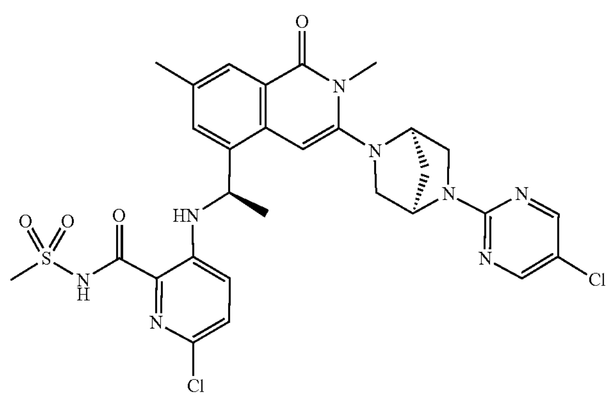 [SMILES: Cc1cc([C@@H](C)Nc2ccc(Cl)nc2C(=O)NS(C)(=O)=O)c2cc(N3C[C@H]4C[C@@H]3CN4c3ncc(Cl)cn3)n(C)c(=O)c2c1] |
| 667 | 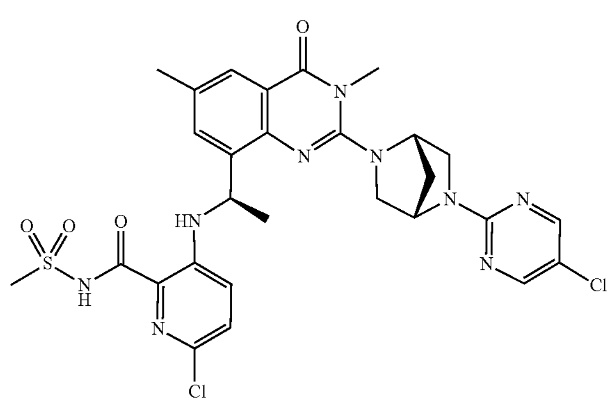 [SMILES: Cc1cc([C@@H](C)Nc2ccc(Cl)nc2C(=O)NS(C)(=O)=O)c2nc(N3C[C@@H]4C[C@H]3CN4c3ncc(Cl)cn3)n(C)c(=O)c2c1] |

TABLE 1-continued

List of Compounds

| Cpd. ID | Chemical structure |
|---|---|
| 668 | 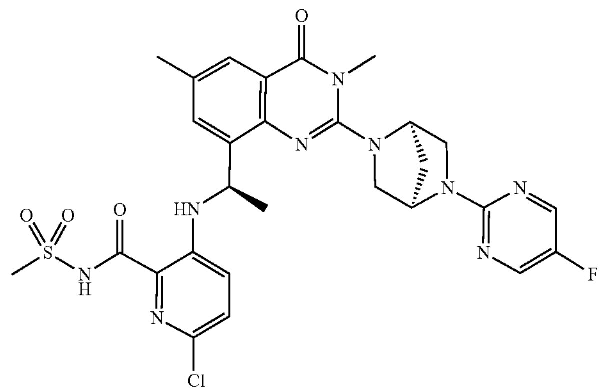 [SMILES: Cc1cc([C@@H](C)Nc2ccc(Cl)nc2C(=O)NS(C)(=O)=O)c2nc(N3C[C@H]4C[C@@H]3CN4c3ncc(F)cn3)n(C)c(=O)c2c1] |
| 669 | 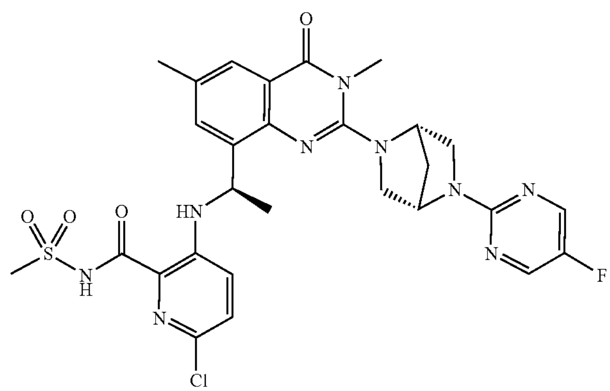 [SMILES: Cc1cc([C@@H](C)Nc2ccc(Cl)nc2C(=O)NS(C)(=O)=O)c2nc(N3C[C@@H]4C[C@H]3CN4c3ncc(F)cn3)n(C)c(=O)c2c1] |
| 670 | 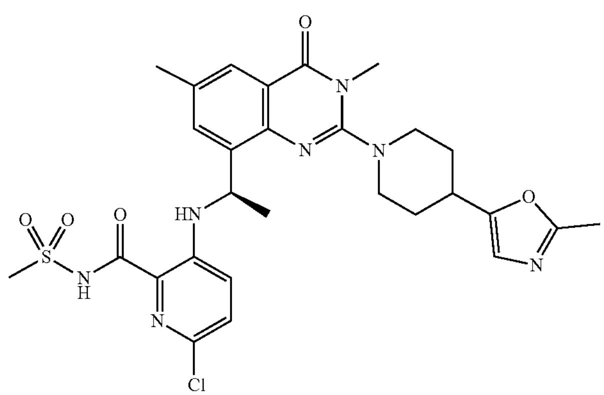 |
| 671 | 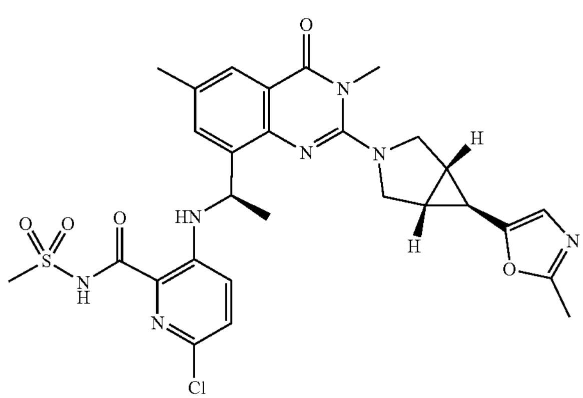 [SMILES: Cc1cc([C@@H](C)Nc2ccc(Cl)nc2C(=O)NS(C)(=O)=O)c2nc(N3C[C@@H]4[C@H](C3)[C@H]4c3cnc(C)o3)n(C)c(=O)c2c1] |

TABLE 1-continued
List of Compounds
| Cpd. ID | Chemical structure |
|---|---|
| 672 | 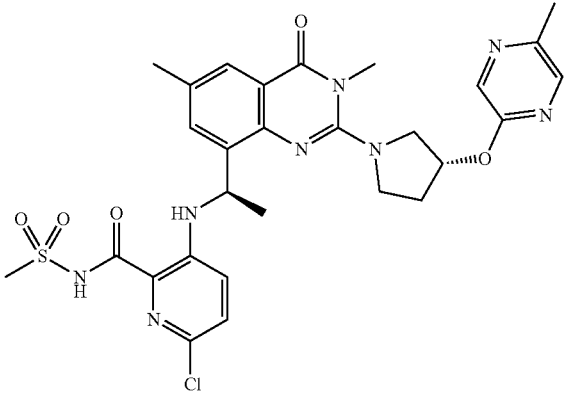 [SMILES: Cc1cc([C@@H](C)Nc2ccc(Cl)nc2C(=O)NS(C)(=O)=O)c2nc(N3CC[C@@H](Oc4cnc(C)cn4)C3)n(C)c(=O)c2c1] |
| 673 | 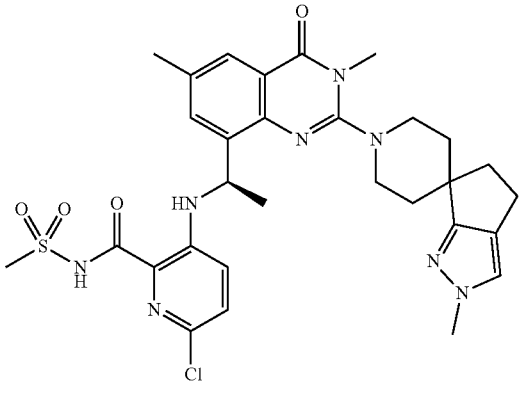 [SMILES: Cc1cc([C@@H](C)Nc2ccc(Cl)nc2C(=O)NS(C)(=O)=O)c2nc(N3CCC4(CCc5cn(C)nc54)CC3)n(C)c(=O)c2c1] |
| 674 | 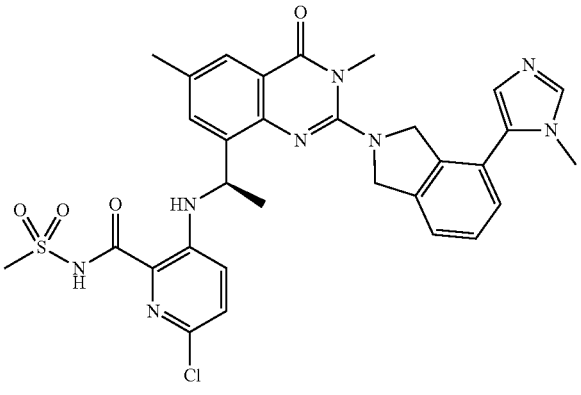 |
| 675 | 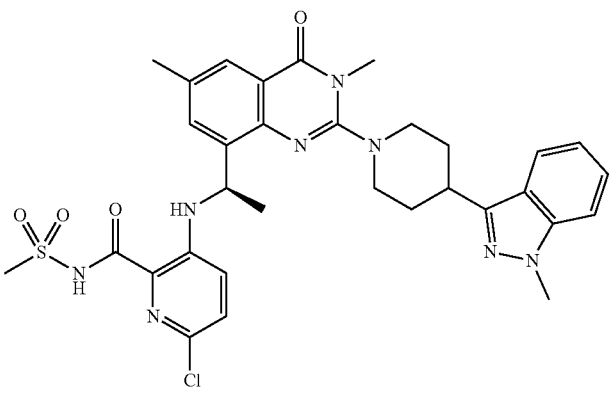 [SMILES: Cc1cc([C@@H](C)Nc2ccc(Cl)nc2C(=O)NS(C)(=O)=O)c2nc(N3CCC(c4nn(C)c5ccccc45)CC3)n(C)c(=O)c2c1] |

TABLE 1-continued

List of Compounds

| Cpd. ID | Chemical structure |
|---|---|
| 676 | 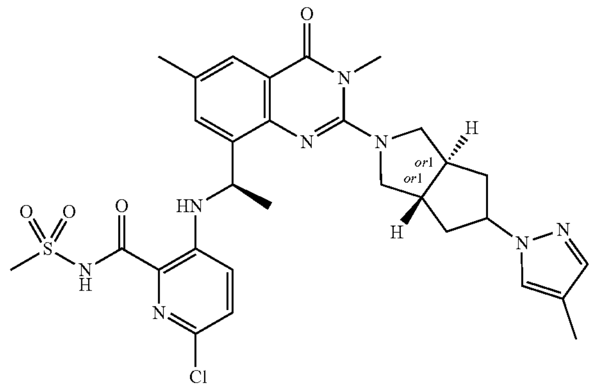 [SMILES: Cc1cc([C@@H](C)Nc2ccc(Cl)nc2C(=O)NS(C)(=O)=O)c2nc(N3C[C@H]4CC(n5cc(C)cn5)C[C@@H]4C3)n(C)c(=O)c2c1] |
| 677 | 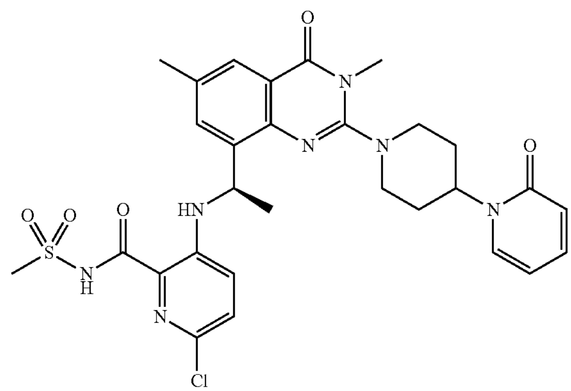 [SMILES: Cc1cc([C@@H](C)Nc2ccc(Cl)nc2C(=O)NS(C)(=O)=O)c2nc(N3CCC(n4ccccc4=O)CC3)n(C)c(=O)c2c1] |
| 678 | 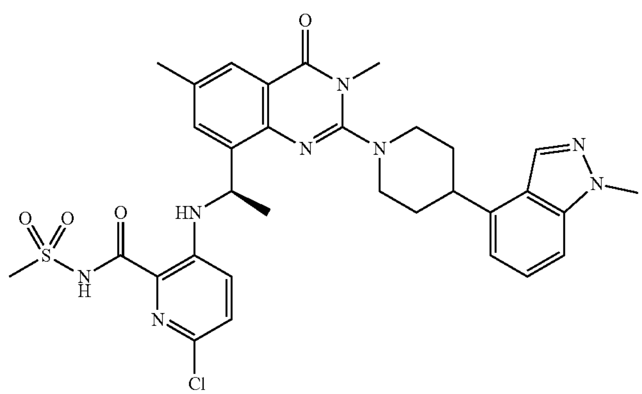 |
| 679 | 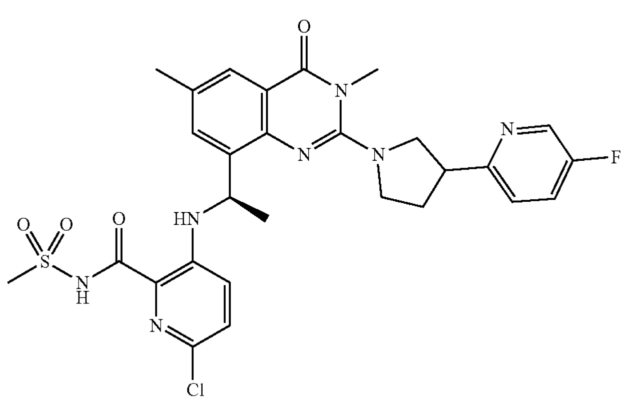 [SMILES: Cc1cc([C@@H](C)Nc2ccc(Cl)nc2C(=O)NS(C)(=O)=O)c2nc(N3CCC(c4ccc(F)cn4)C3)n(C)c(=O)c2c1] |

TABLE 1-continued

List of Compounds

| Cpd. ID | Chemical structure |
|---------|--------------------|
| 680 | 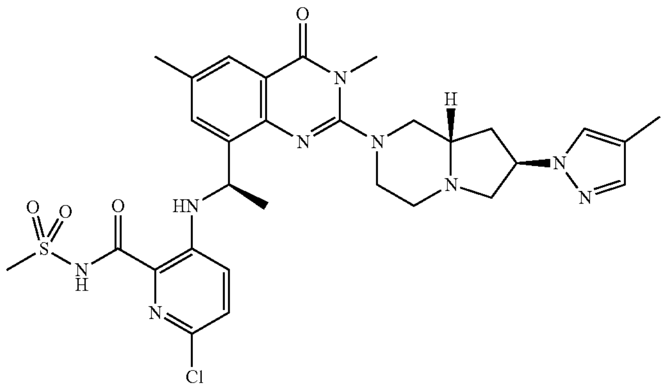 |
| 681 | 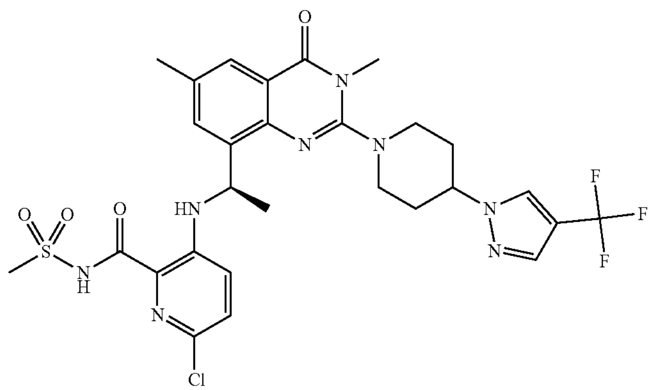 [SMILES: Cc1cc([C@@H](C)Nc2ccc(Cl)nc2C(=O)NS(C)(=O)=O)c2nc(N3CCC(n4cc(C(F)(F)F)cn4)CC3)n(C)c(=O)c2c1] |
| 682 | 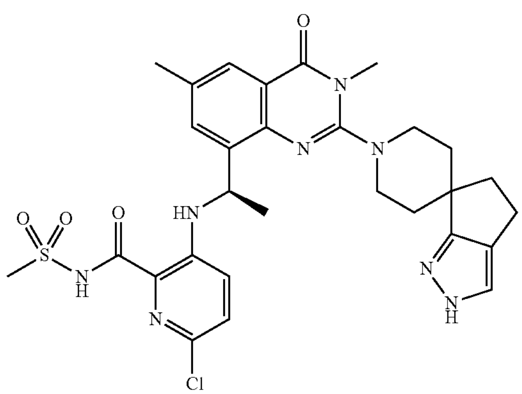 [SMILES: Cc1cc([C@@H](C)Nc2ccc(Cl)nc2C(=O)NS(C)(=O)=O)c2nc(N3CCC4(CCc5c[nH]nc54)CC3)n(C)c(=O)c2c1] |
| 683 | 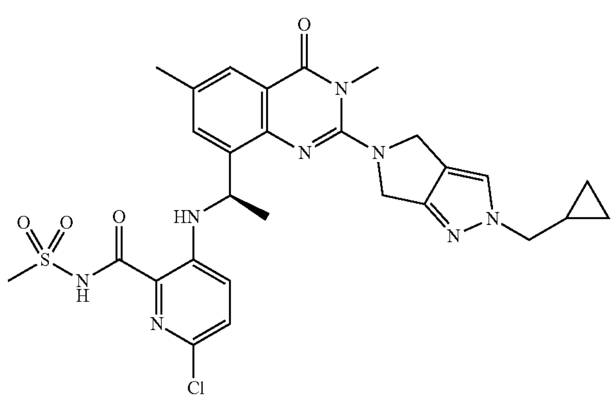 [SMILES: Cc1cc([C@@H](C)Nc2ccc(Cl)nc2C(=O)NS(C)(=O)=O)c2nc(N3Cc4cn(CC5CC5)nc4C3)n(C)c(=O)c2c1] |

TABLE 1-continued

List of Compounds

| Cpd. ID | Chemical structure |
|---|---|
| 684 | 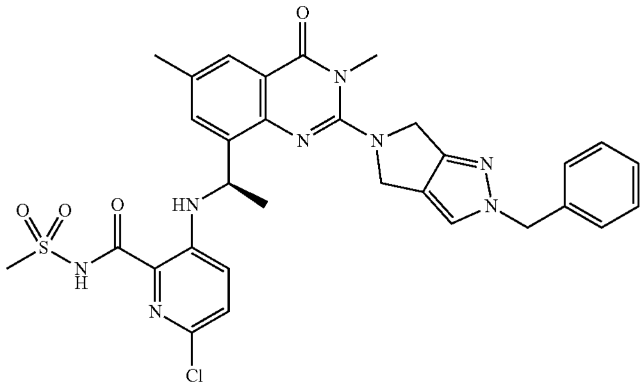 [SMILES: Cc1cc([C@@H](C)Nc2ccc(Cl)nc2C(=O)NS(C)(=O)=O)c2nc(N3Cc4cn(Cc5ccccc5)nc4C3)n(C)c(=O)c2c1] |
| 685 | 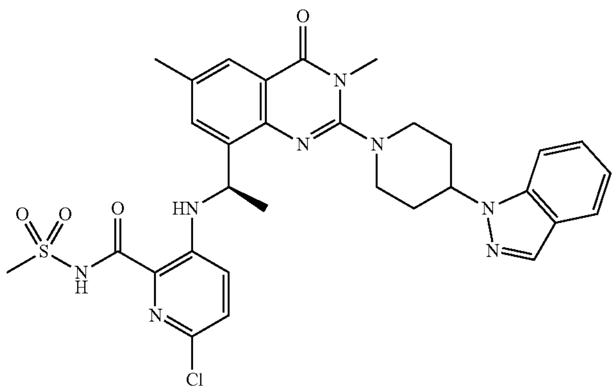 [SMILES: Cc1cc([C@@H](C)Nc2ccc(Cl)nc2C(=O)NS(C)(=O)=O)c2nc(N3CCC(n4ncc5ccccc54)CC3)n(C)c(=O)c2c1] |
| 686 | 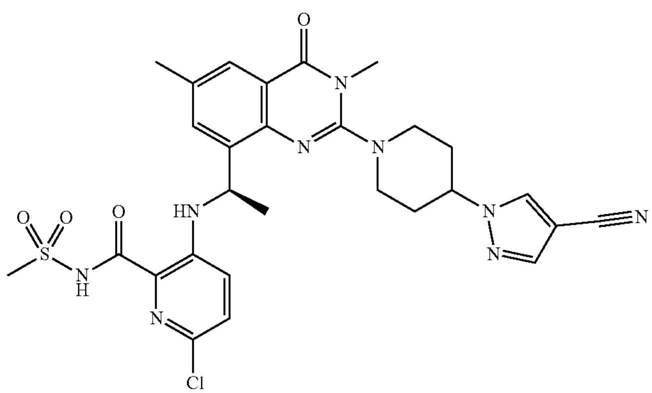 [SMILES: Cc1cc([C@@H](C)Nc2ccc(Cl)nc2C(=O)NS(C)(=O)=O)c2nc(N3CCC(n4cc(C#N)cn4)CC3)n(C)c(=O)c2c1] |
| 687 | 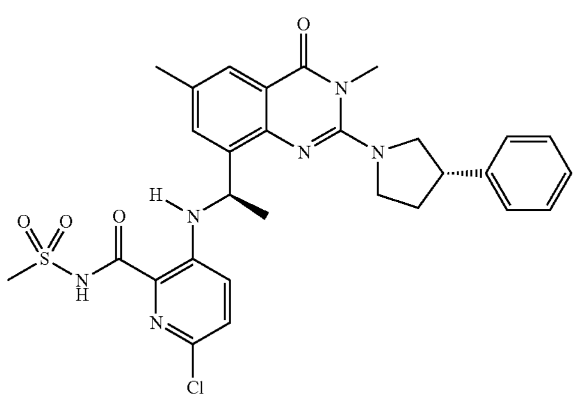 [SMILES: Cc1cc([C@@H](C)Nc2ccc(Cl)nc2C(=O)NS(C)(=O)=O)c2nc(N3CC[C@@H](c4ccccc4)C3)n(C)c(=O)c2c1] |

TABLE 1-continued
List of Compounds
| Cpd. ID | Chemical structure |
|---|---|
| 688 | 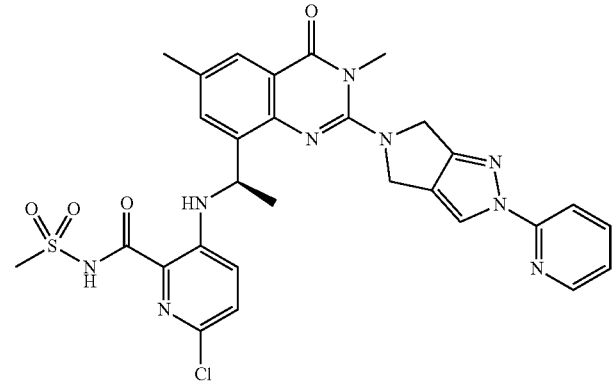 [SMILES: Cc1cc([C@@H](C)Nc2ccc(Cl)nc2C(=O)NS(C)(=O)=O)c2nc(N3Cc4cn(-c5ccccn5)nc4C3)n(C)c(=O)c2c1] |
| 689 | 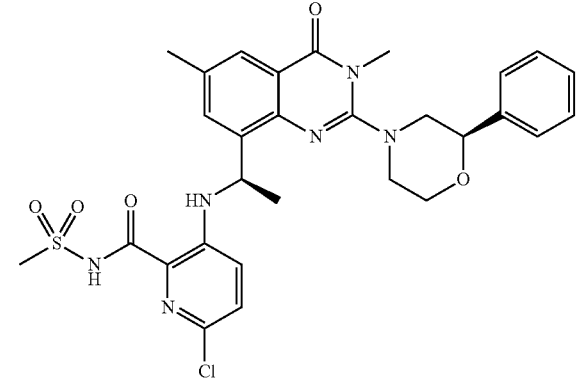 [SMILES: Cc1cc([C@@H](C)Nc2ccc(Cl)nc2C(=O)NS(C)(=O)=O)c2nc(N3CCO[C@H](c4ccccc4)C3)n(C)c(=O)c2c1] |
| 690 | 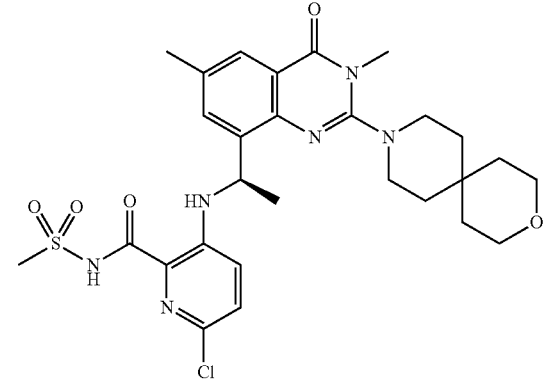 [SMILES: Cc1cc([C@@H](C)Nc2ccc(Cl)nc2C(=O)NS(C)(=O)=O)c2nc(N3CCC4(CCOCC4)CC3)n(C)c(=O)c2c1] |
| 691 | 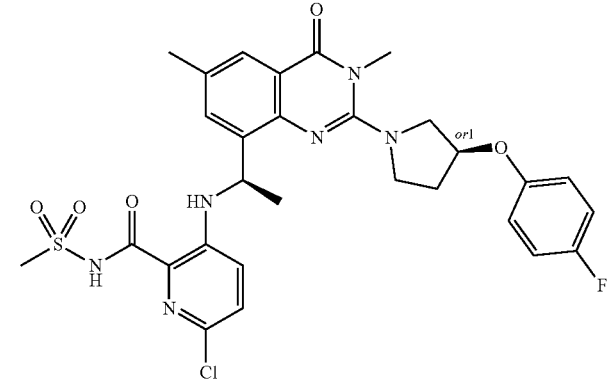 [SMILES: Cc1cc([C@@H](C)Nc2ccc(Cl)nc2C(=O)NS(C)(=O)=O)c2nc(N3CC[C@H](Oc4ccc(F)cc4)C3)n(C)c(=O)c2c1] |

TABLE 1-continued

List of Compounds

| Cpd. ID | Chemical structure |
|---|---|
| 692 | 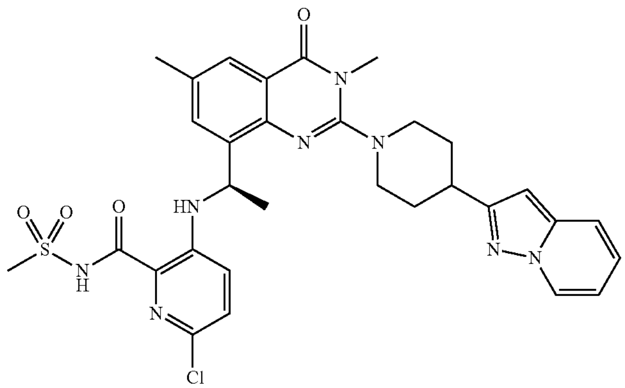 [SMILES: Cc1cc([C@@H](C)Nc2ccc(Cl)nc2C(=O)NS(C)(=O)=O)c2nc(N3CCC(c4cc5ccccn5n4)CC3)n(C)c(=O)c2c1] |
| 693 | 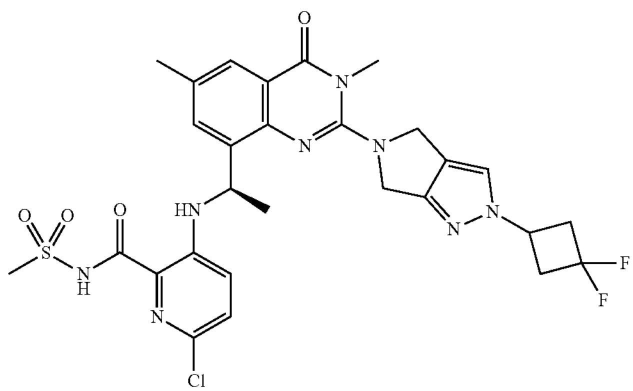 [SMILES: Cc1cc([C@@H](C)Nc2ccc(Cl)nc2C(=O)NS(C)(=O)=O)c2nc(N3Cc4cn(C5CC(F)(F)C5)nc4C3)n(C)c(=O)c2c1] |
| 694 | 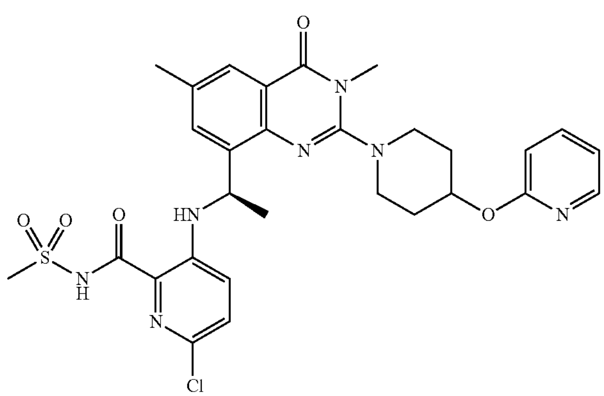 [SMILES: Cc1cc([C@@H](C)Nc2ccc(Cl)nc2C(=O)NS(C)(=O)=O)c2nc(N3CCC(Oc4ccccn4)CC3)n(C)c(=O)c2c1] |
| 695 | 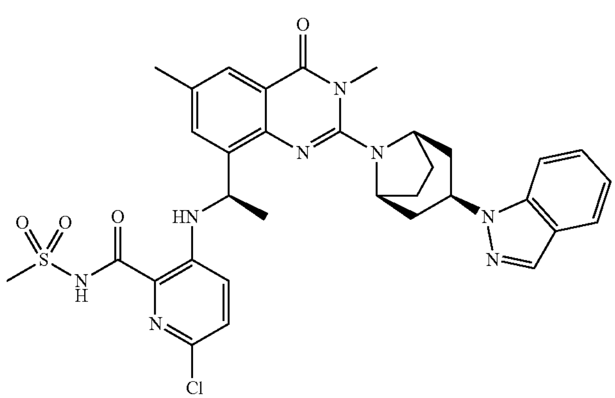 [SMILES: Cc1cc([C@@H](C)Nc2ccc(Cl)nc2C(=O)NS(C)(=O)=O)c2nc(N3[C@@H]4CC[C@H]3C[C@H](n3ncc5ccccc53)C4)n(C)c(=O)c2c1] |

TABLE 1-continued
List of Compounds
| Cpd. ID | Chemical structure |
|---|---|
| 696 | 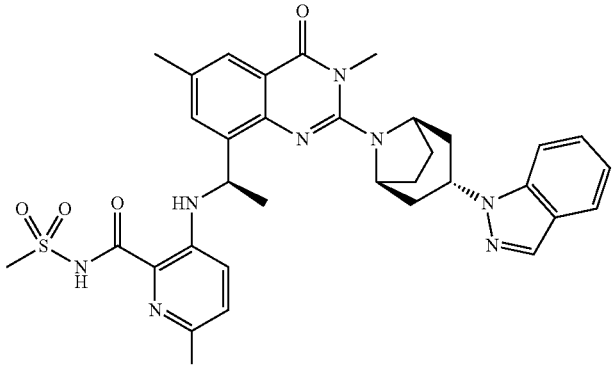 |
| 697 | 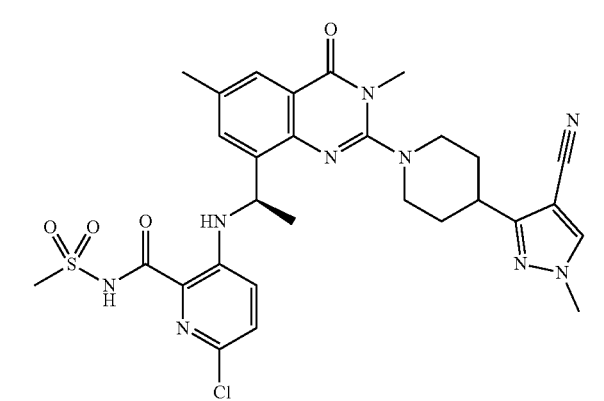 [SMILES: Cc1cc([C@@H](C)Nc2ccc(Cl)nc2C(=O)NS(C)(=O)=O)c2nc(N3CCC(c4nn(C)cc4C#N)CC3)n(C)c(=O)c2c1] |
| 698 | 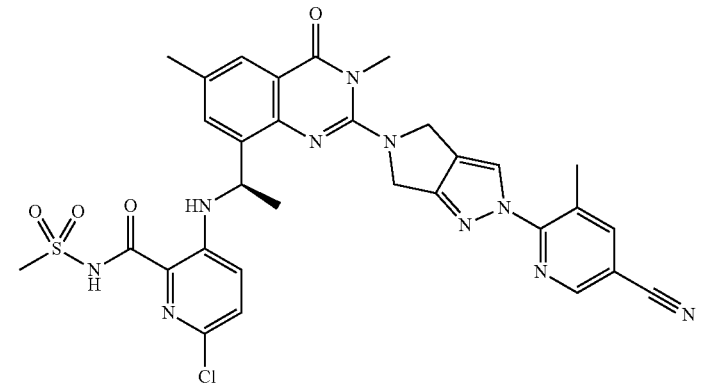 [SMILES: Cc1cc([C@@H](C)Nc2ccc(Cl)nc2C(=O)NS(C)(=O)=O)c2nc(N3Cc4cn(-c5ncc(C#N)cc5C)nc4C3)n(C)c(=O)c2c1] |
| 699 | 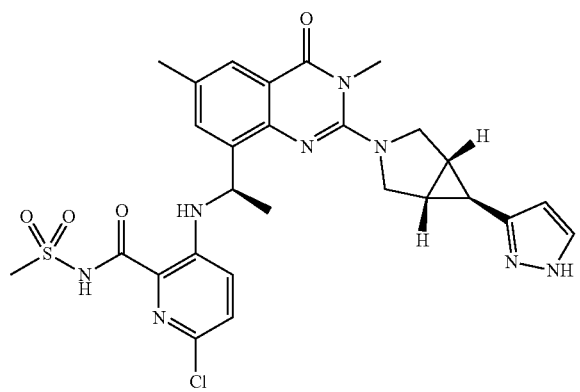 [SMILES: Cc1cc([C@@H](C)Nc2ccc(Cl)nc2C(=O)NS(C)(=O)=O)c2nc(N3C[C@@H]4[C@H](C3)[C@H]4c3cc[nH]n3)n(C)c(=O)c2c1] |

TABLE 1-continued

List of Compounds

| Cpd. ID | Chemical structure |
|---|---|
| 700 | 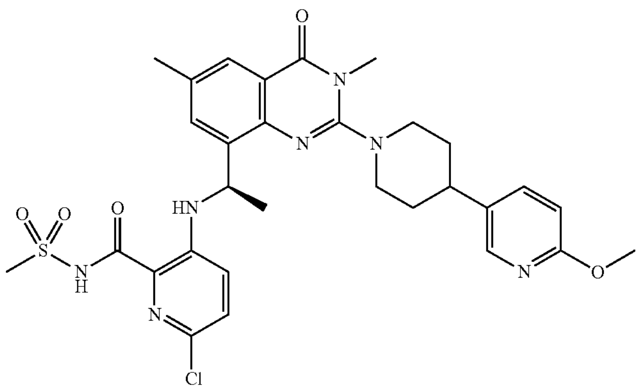 |
| 701 | 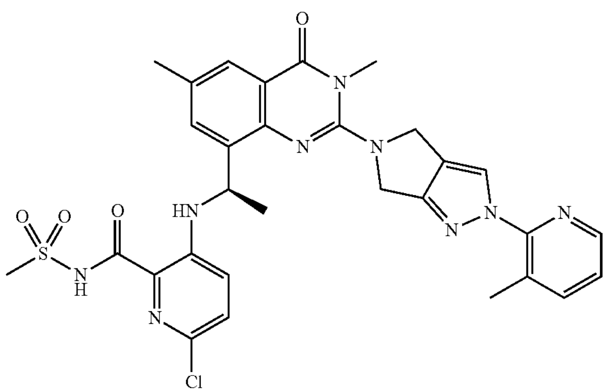 [SMILES: Cc1cc([C@@H](C)Nc2ccc(Cl)nc2C(=O)NS(C)(=O)=O)c2nc(N3Cc4cn(-c5ncccc5C)nc4C3)n(C)c(=O)c2c1] |
| 702 | 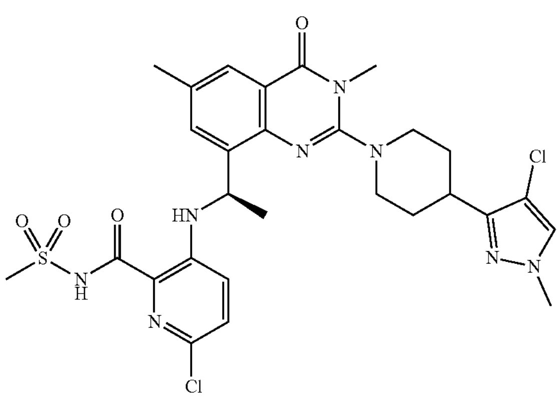 |
| 703 | 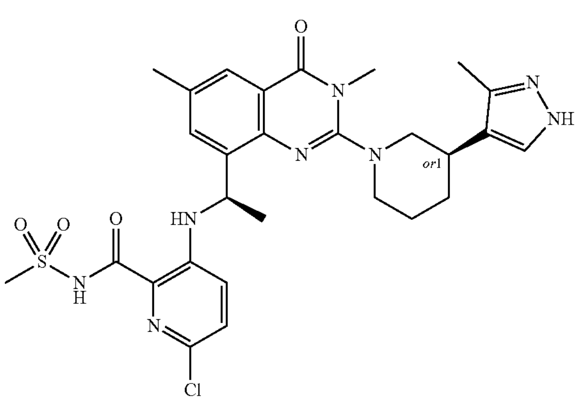 [SMILES: Cc1cc([C@@H](C)Nc2ccc(Cl)nc2C(=O)NS(C)(=O)=O)c2nc(N3CCC[C@H](c4c[nH]nc4C)C3)n(C)c(=O)c2c1] |

TABLE 1-continued
List of Compounds
| Cpd. ID | Chemical structure |
|---|---|
| 704 | 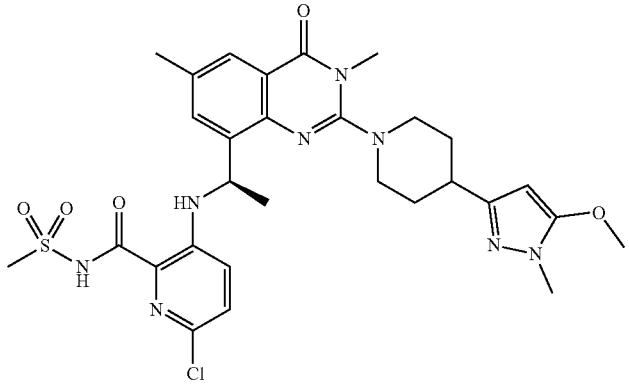 |
| 705 | 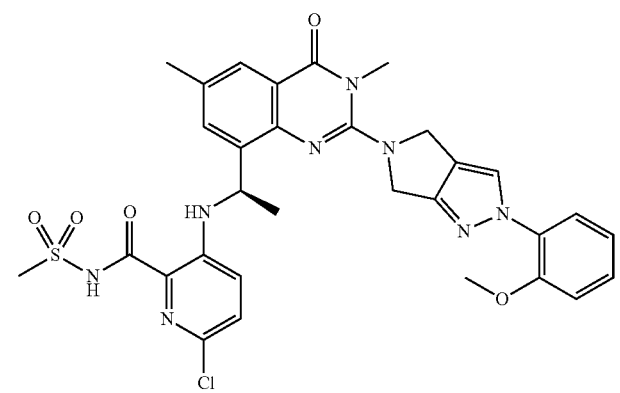 [SMILES: COc1ccccc1-n1cc2c(n1)CN(c1nc3c([C@@H](C)Nc4ccc(Cl)nc4C(=O)NS(C)(=O)=O)cc(C)cc3c(=O)n1C)C2] |
| 706 | 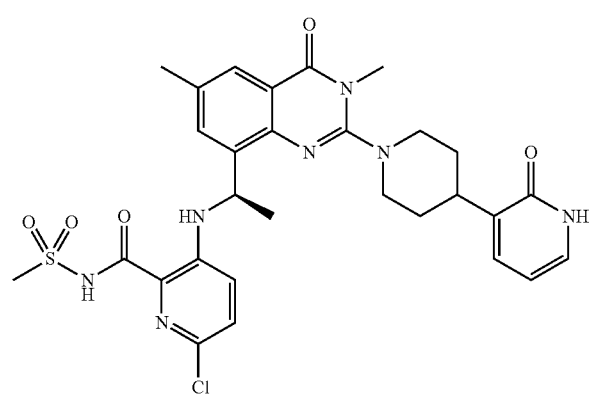 [SMILES: Cc1cc([C@@H](C)Nc2ccc(Cl)nc2C(=O)NS(C)(=O)=O)c2nc(N3CCC(c4ccc[nH]c4=O)CC3)n(C)c(=O)c2c1] |
| 707 | 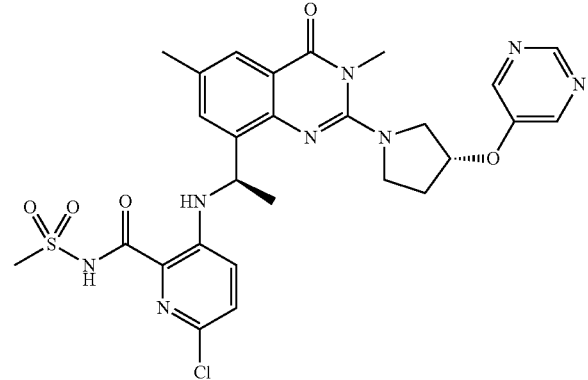 [SMILES: Cc1cc([C@@H](C)Nc2ccc(Cl)nc2C(=O)NS(C)(=O)=O)c2nc(N3CC[C@@H](Oc4cncnc4)C3)n(C)c(=O)c2c1] |

TABLE 1-continued

List of Compounds

| Cpd. ID | Chemical structure |
|---|---|
| 708 | 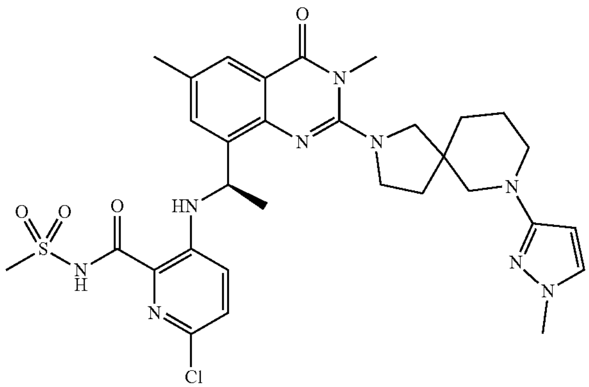 [SMILES: Cc1cc([C@@H](C)Nc2ccc(Cl)nc2C(=O)NS(C)(=O)=O)c2nc(N3CCC4(CCCN(c5ccn(C)n5)C4)C3)n(C)c(=O)c2c1] |
| 709 | 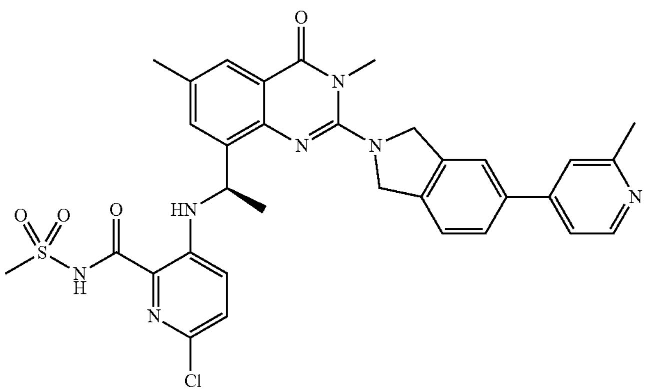 [SMILES: Cc1cc([C@@H](C)Nc2ccc(Cl)nc2C(=O)NS(C)(=O)=O)c2nc(N3Cc4ccc(-c5ccnc(C)c5)cc4C3)n(C)c(=O)c2c1] |
| 710 | 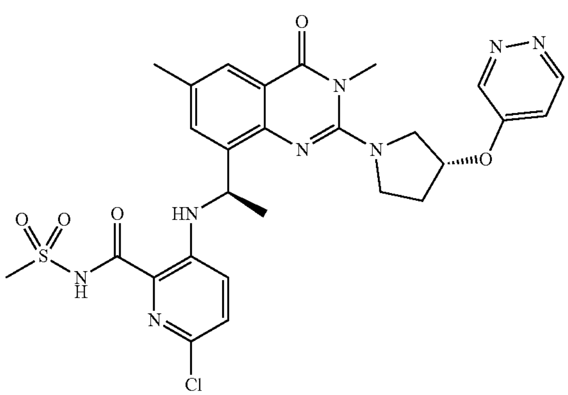 [SMILES: Cc1cc([C@@H](C)Nc2ccc(Cl)nc2C(=O)NS(C)(=O)=O)c2nc(N3CC[C@@H](Oc4ccnnc4)C3)n(C)c(=O)c2c1] |
| 711 | 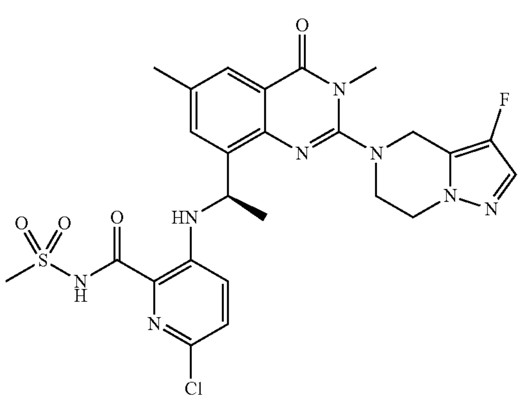 [SMILES: Cc1cc([C@@H](C)Nc2ccc(Cl)nc2C(=O)NS(C)(=O)=O)c2nc(N3CCn4ncc(F)c4C3)n(C)c(=O)c2c1] |

TABLE 1-continued

List of Compounds

| Cpd. ID | Chemical structure |
|---|---|
| 712 | 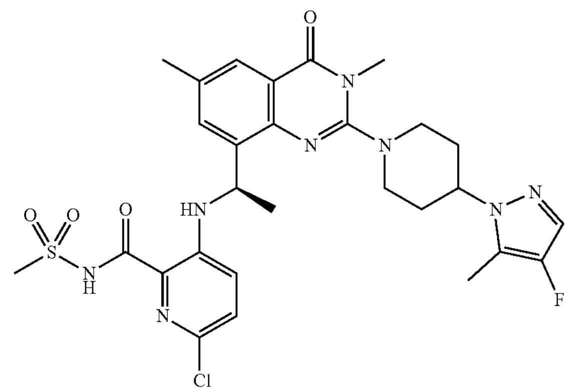 [SMILES: Cc1cc([C@@H](C)Nc2ccc(Cl)nc2C(=O)NS(C)(=O)=O)c2nc(N3CCC(n4ncc(F)c4C)CC3)n(C)c(=O)c2c1] |
| 713 | 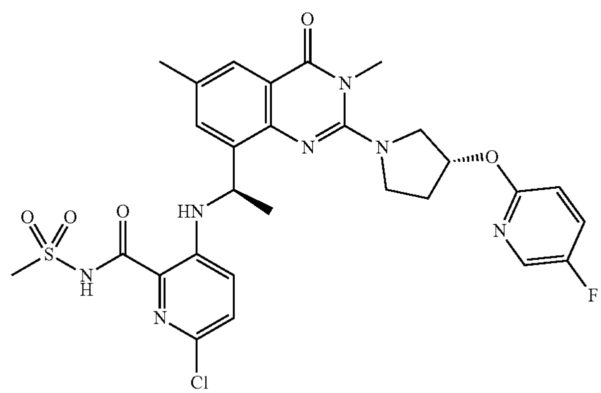 [SMILES: Cc1cc([C@@H](C)Nc2ccc(Cl)nc2C(=O)NS(C)(=O)=O)c2nc(N3CC[C@@H](Oc4ccc(F)cn4)C3)n(C)c(=O)c2c1] |
| 714 | 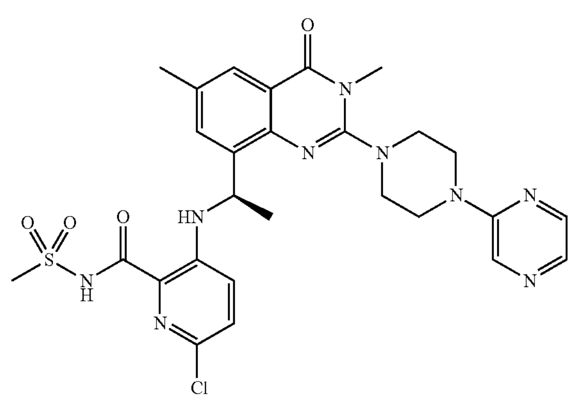 [SMILES: Cc1cc([C@@H](C)Nc2ccc(Cl)nc2C(=O)NS(C)(=O)=O)c2nc(N3CCN(c4cnccn4)CC3)n(C)c(=O)c2c1] |
| 715 | 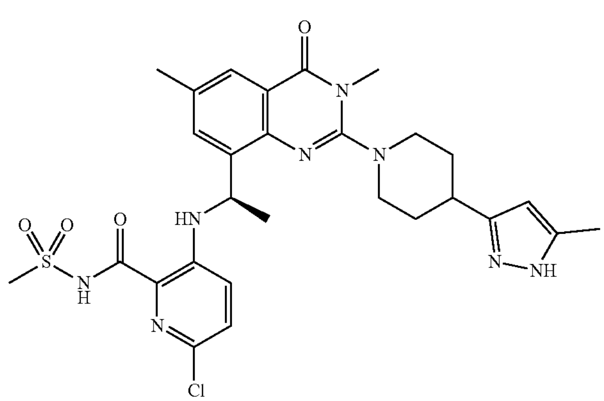 |

TABLE 1-continued

List of Compounds

| Cpd. ID | Chemical structure |
|---|---|
| 716 | 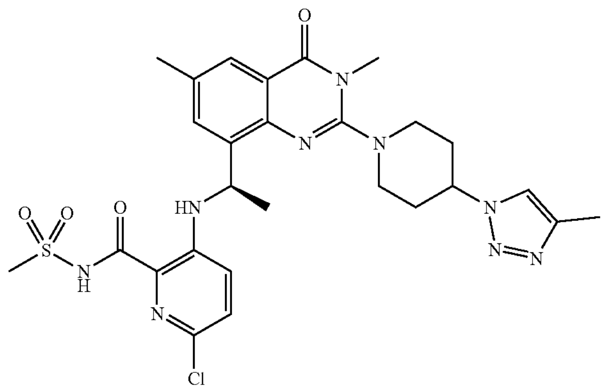 |
| 717 | 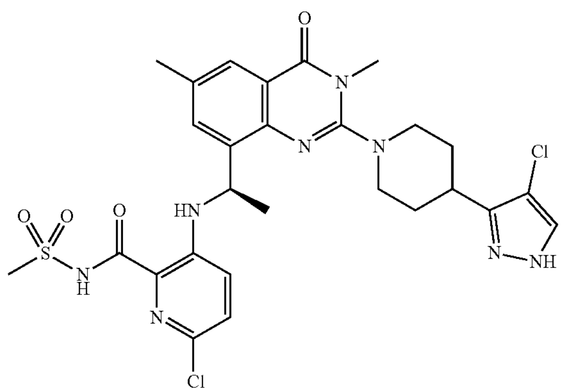 |
| 718 | 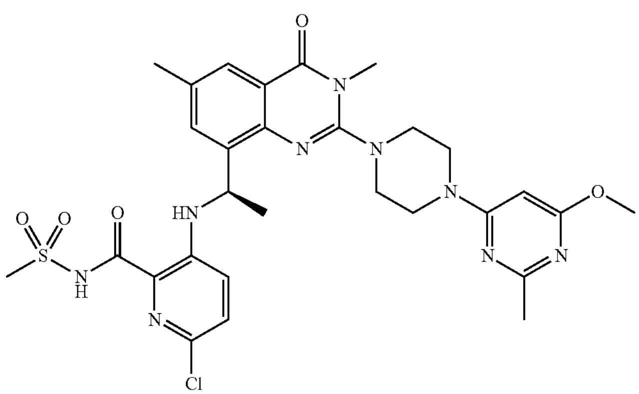 |
| 719 | 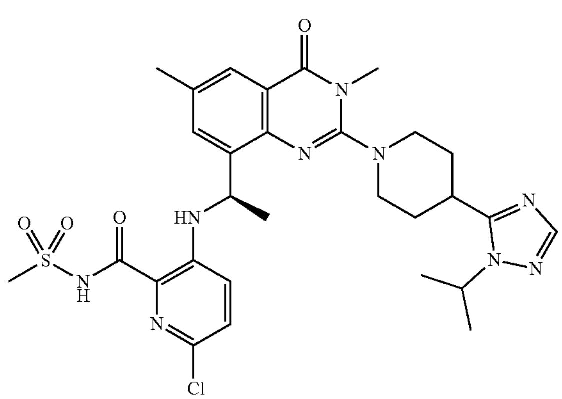 [SMILES: Cc1cc([C@@H](C)Nc2ccc(Cl)nc2C(=O)NS(C)(=O)=O)c2nc(N3CCC(c4ncnn4C(C)C)CC3)n(C)c(=O)c2c1] |

TABLE 1-continued
List of Compounds
| Cpd. ID | Chemical structure |
|---|---|
| 720 | 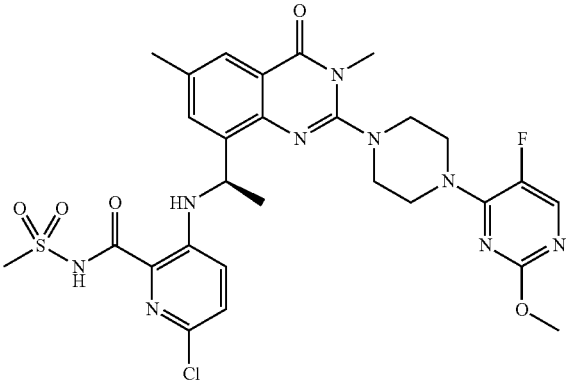 |
| 721 | 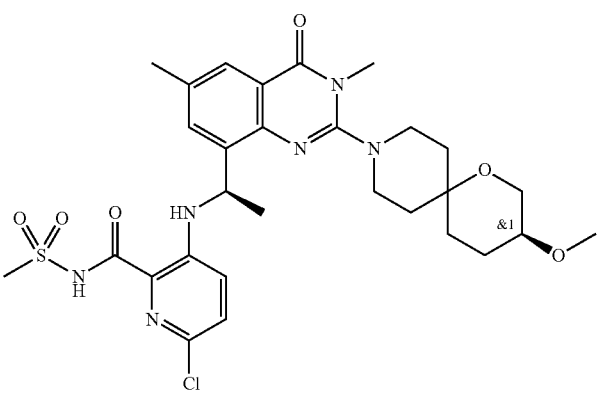 |
| 722 | 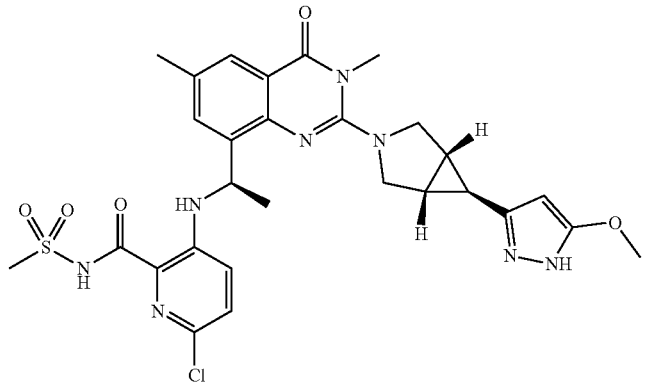 |
| 723 | 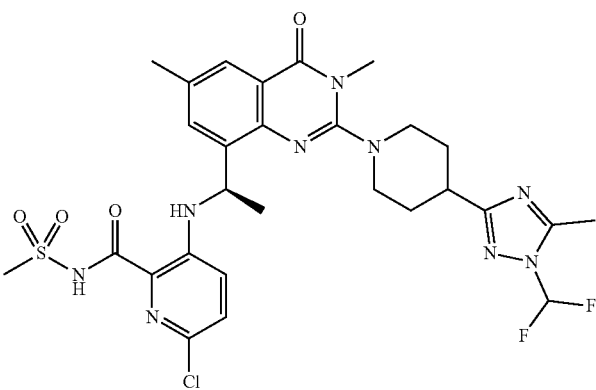 |

TABLE 1-continued
List of Compounds
| Cpd. ID | Chemical structure |
|---|---|
| 724 | 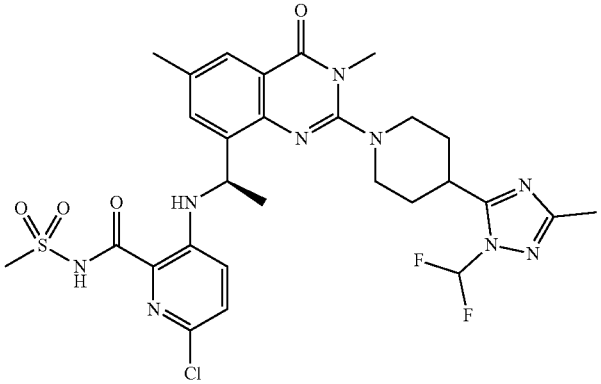 |
| 725 | 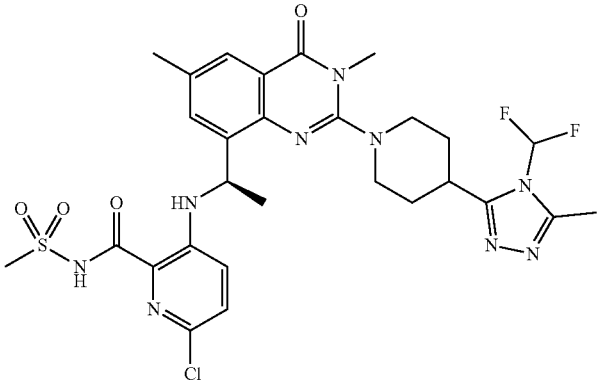 |
| 726 | 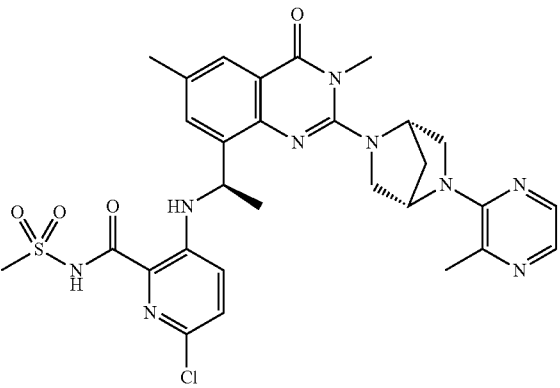 [SMILES: Cc1cc([C@@H](C)Nc2ccc(Cl)nc2C(=O)NS(C)(=O)=O)c2nc(N3C[C@@H]4C[C@H]3CN4c3nccnc3C)n(C)c(=O)c2c1] |
| 727 | 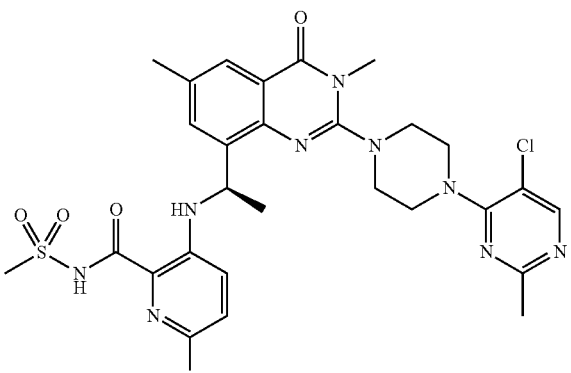 |

TABLE 1-continued

List of Compounds

| Cpd. ID | Chemical structure |
|---|---|
| 728 | 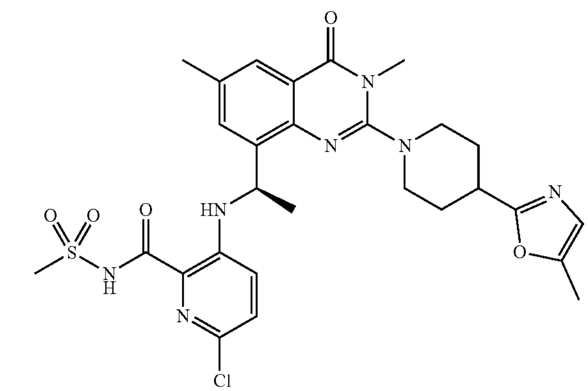 [SMILES: Cc1cc([C@@H](C)Nc2ccc(Cl)nc2C(=O)NS(C)(=O)=O)c2nc(N3CCC(c4ncc(C)o4)CC3)n(C)c(=O)c2c1] |
| 729 | 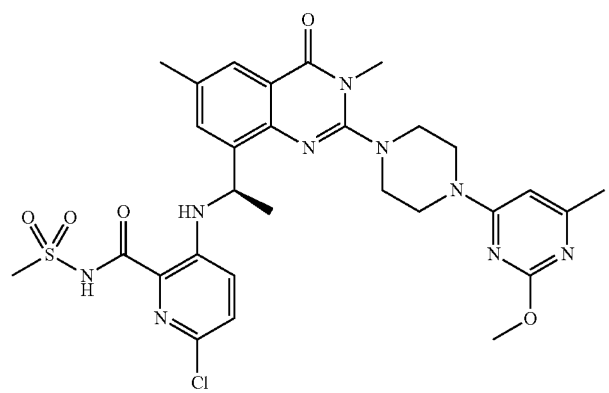 |
| 730 | 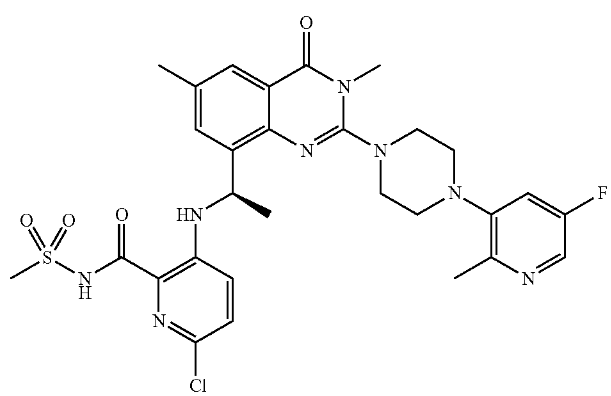 [SMILES: Cc1cc([C@@H](C)Nc2ccc(Cl)nc2C(=O)NS(C)(=O)=O)c2nc(N3CCN(c4cc(F)cnc4C)CC3)n(C)c(=O)c2c1] |
| 731 | 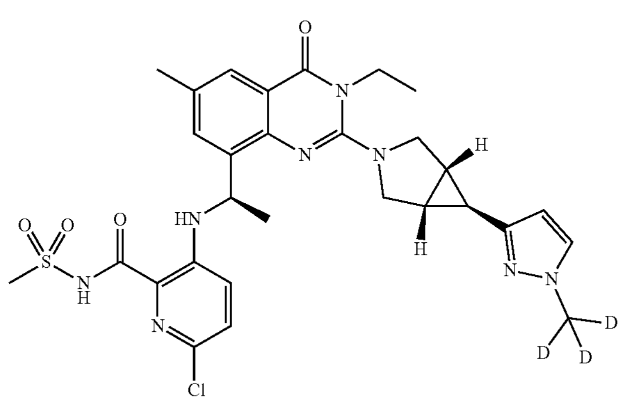 [SMILES: [2H]C([2H])([2H])n1ccc([C@H]2[C@@H]3CN(c4nc5c([C@@H](C)Nc6ccc(Cl)nc6C(=O)NS(C)(=O)=O)cc(C)cc5c(=O)n4CC)C[C@@H]32)n1] |

TABLE 1-continued

List of Compounds

| Cpd. ID | Chemical structure |
|---|---|
| 732 | 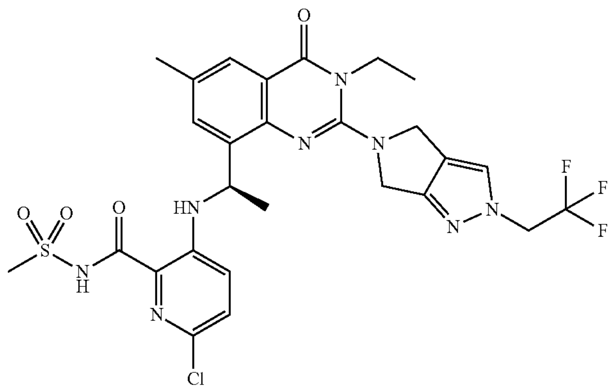 [SMILES: CCn1c(N2Cc3cn(CC(F)(F)F)nc3C2)nc2c([C@@H](C)Nc3ccc(Cl)nc3C(=O)NS(C)(=O)=O)cc(C)cc2c1=O] |
| 733 | 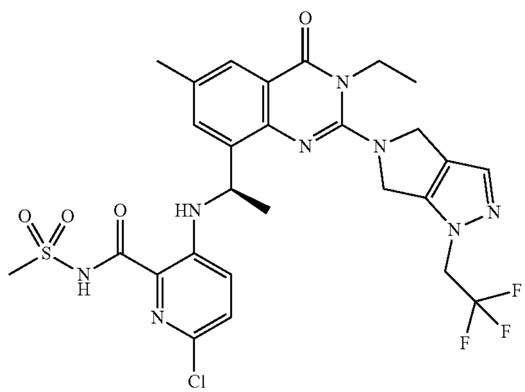 [SMILES: CCn1c(N2Cc3cnn(CC(F)(F)F)c3C2)nc2c([C@@H](C)Nc3ccc(Cl)nc3C(=O)NS(C)(=O)=O)cc(C)cc2c1=O] |
| 734 | 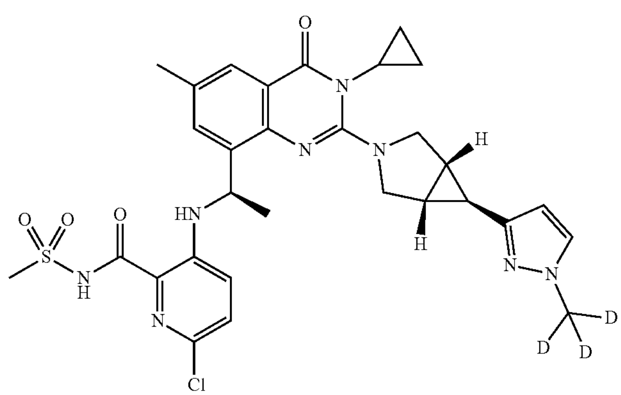 [SMILES: [2H]C([2H])([2H])n1ccc([C@H]2[C@@H]3CN(c4nc5c([C@@H](C)Nc6ccc(Cl)nc6C(=O)NS(C)(=O)=O)cc(C)cc5c(=O)n4C4CC4)C[C@@H]32)n1] |
| 735 | 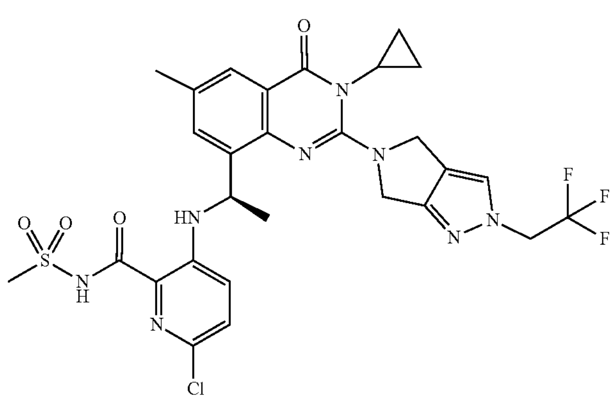 [SMILES: Cc1cc([C@@H](C)Nc2ccc(Cl)nc2C(=O)NS(C)(=O)=O)c2nc(N3Cc4cn(CC(F)(F)F)nc4C3)n(C3CC3)c(=O)c2c1] |

TABLE 1-continued
| List of Compounds | |
|---|---|
| Cpd. ID | Chemical structure |
| 736 | 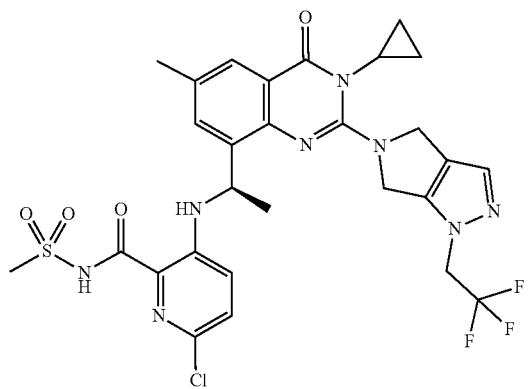 [SMILES: Cc1cc([C@@H](C)Nc2ccc(Cl)nc2C(=O)NS(C)(=O)=O)c2nc(N3Cc4cnn(CC(F)(F)F)c4C3)n(C3CC3)c(=O)c2c1] |
| 737 | 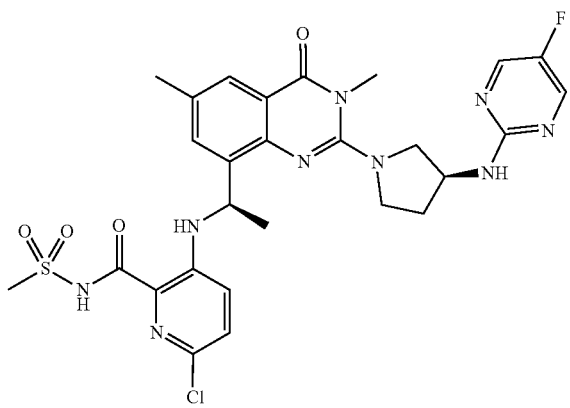 [SMILES: Cc1cc([C@@H](C)Nc2ccc(Cl)nc2C(=O)NS(C)(=O)=O)c2nc(N3CC[C@H](Nc4ncc(F)cn4)C3)n(C)c(=O)c2c1] |
| 738 | 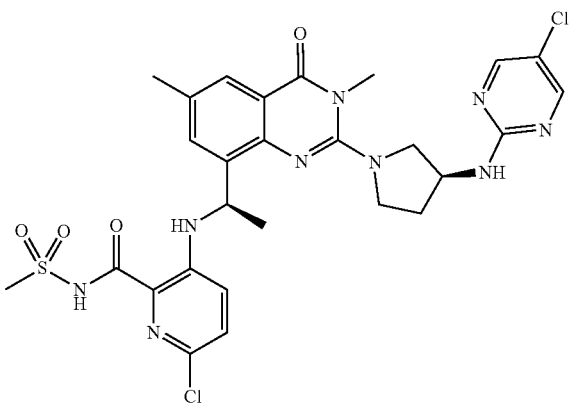 [SMILES: Cc1cc([C@@H](C)Nc2ccc(Cl)nc2C(=O)NS(C)(=O)=O)c2nc(N3CC[C@H](Nc4ncc(Cl)cn4)C3)n(C)c(=O)c2c1] |

TABLE 1-continued
| List of Compounds | |
|---|---|
| Cpd. ID | Chemical structure |
| 739 | 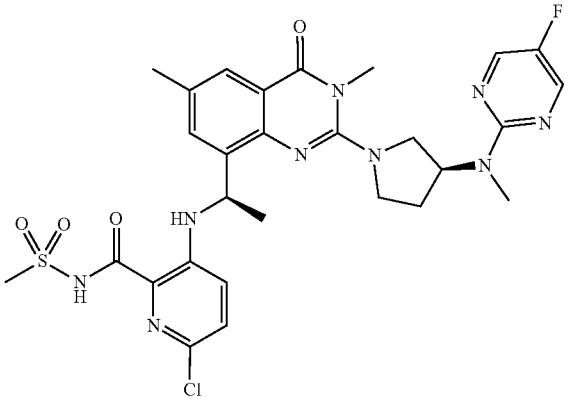 [SMILES: Cc1cc([C@@H](C)Nc2ccc(Cl)nc2C(=O)NS(C)(=O)=O)c2nc(N3CC[C@H](N(C)c4ncc(F)cn4)C3)n(C)c(=O)c2c1] |
| 740 | 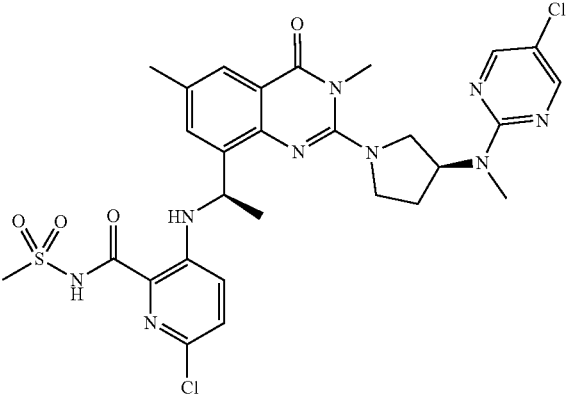 [SMILES: Cc1cc([C@@H](C)Nc2ccc(Cl)nc2C(=O)NS(C)(=O)=O)c2nc(N3CC[C@H](N(C)c4ncc(Cl)cn4)C3)n(C)c(=O)c2c1] |
| 741 | 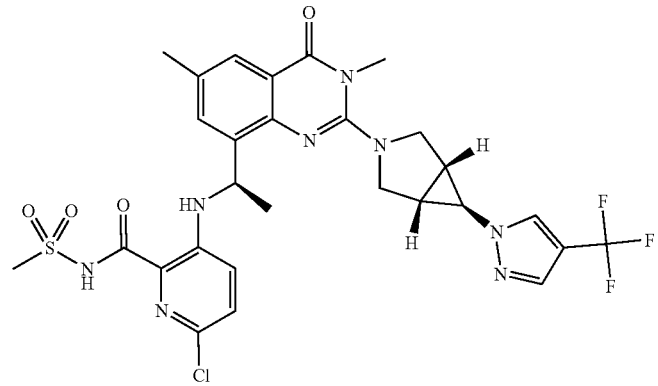 [SMILES: Cc1cc([C@@H](C)Nc2ccc(Cl)nc2C(=O)NS(C)(=O)=O)c2nc(N3C[C@@H]4[C@H](C3)[C@H]4n3cc(C(F)(F)F)cn3)n(C)c(=O)c2c1] |

TABLE 1-continued
List of Compounds
| Cpd. ID | Chemical structure |
|---|---|
| 742 | 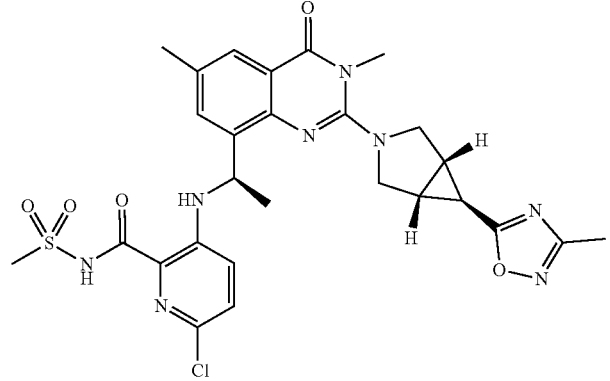 |
| 743 | 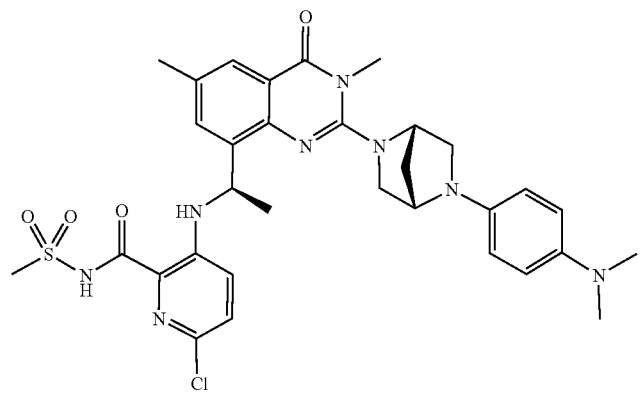 |
| 744 | 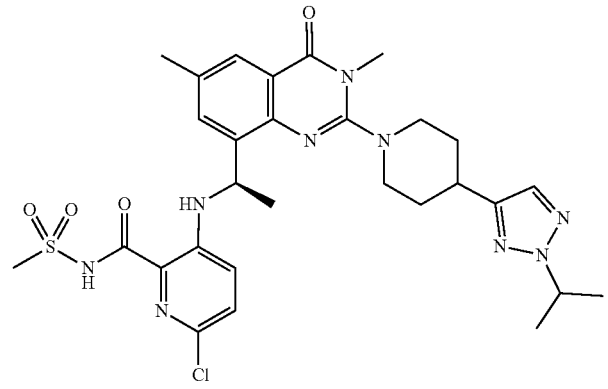 [SMILES: Cc1cc([C@@H](C)Nc2ccc(Cl)nc2C(=O)NS(C)(=O)=O)c2nc(N3CCC(c4cnn(C(C)C)n4)CC3)n(C)c(=O)c2c1] |
| 745 | 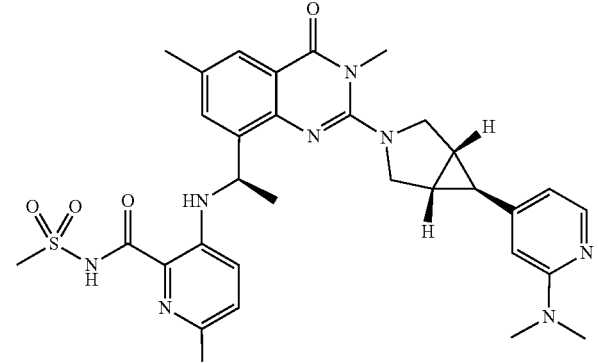 |

TABLE 1-continued

List of Compounds

| Cpd. ID | Chemical structure |
|---|---|
| 746 | 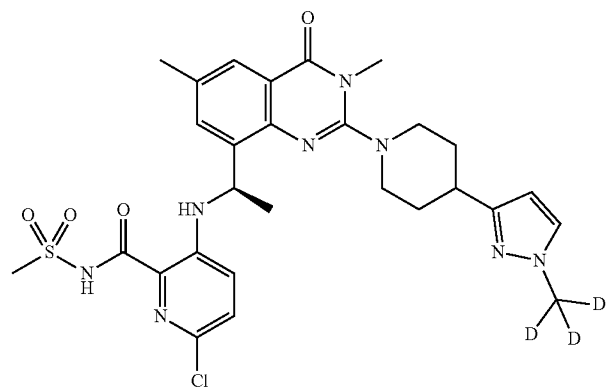 [SMILES: [2H]C([2H])([2H])n1ccc(C2CCN(c3nc4c([C@@H](C)Nc5ccc(Cl)nc5C(=O)NS(C)(=O)=O)cc(C)cc4c(=O)n3C)CC2)n1] |
| 747 | 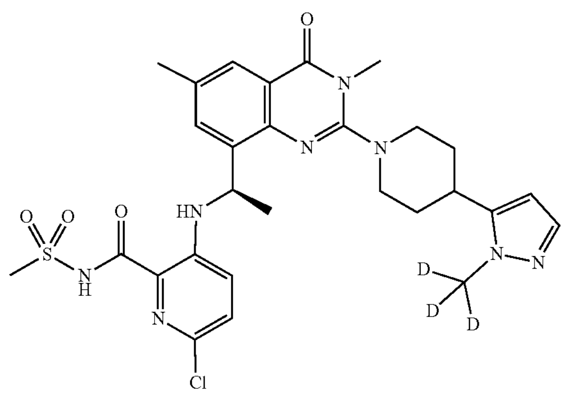 [SMILES: [2H]C([2H])([2H])n1nccc1C1CCN(c2nc3c([C@@H](C)Nc4ccc(Cl)nc4C(=O)NS(C)(=O)=O)cc(C)cc3c(=O)n2C)CC1] |
| 748 | 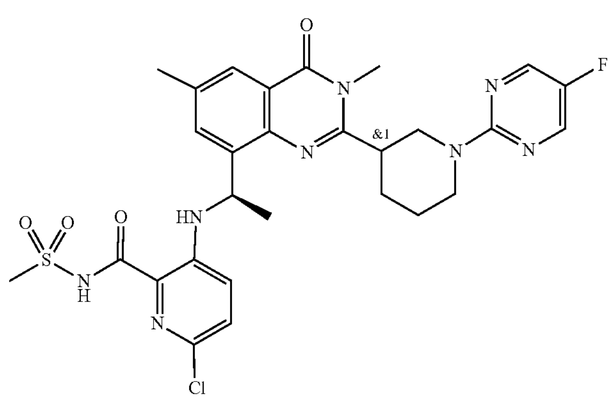 [SMILES: Cc1cc([C@@H](C)Nc2ccc(Cl)nc2C(=O)NS(C)(=O)=O)c2nc(C3CCCN(c4ncc(F)cn4)C3)n(C)c(=O)c2c1] |
| 749 | 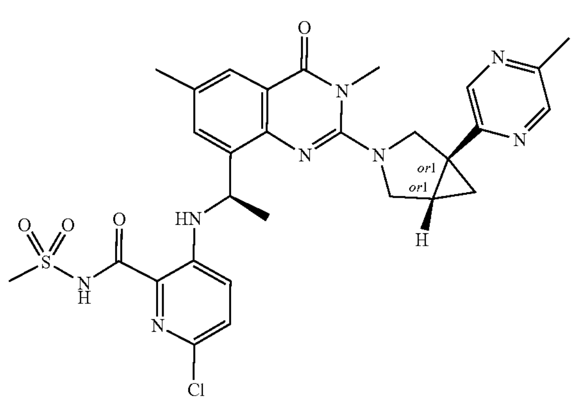 |

TABLE 1-continued

List of Compounds

| Cpd. ID | Chemical structure |
|---|---|
| 750 | 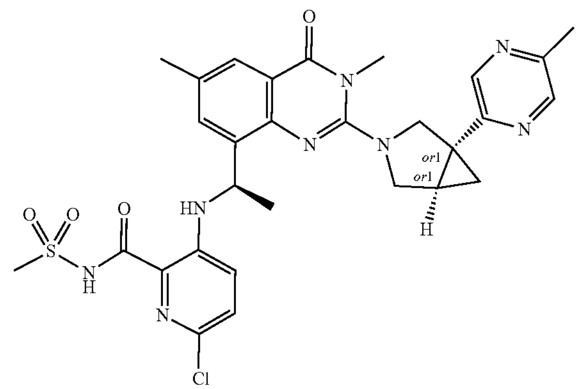 |
| 751 | 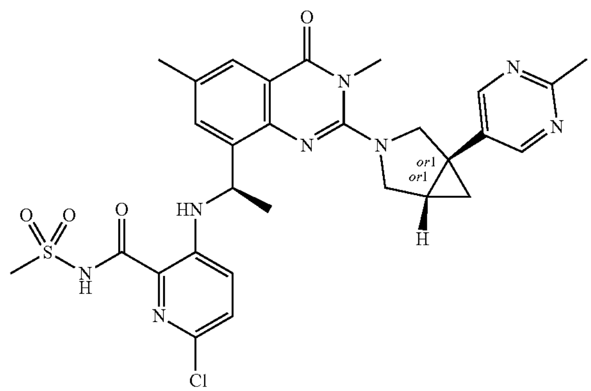 |
| 752 | 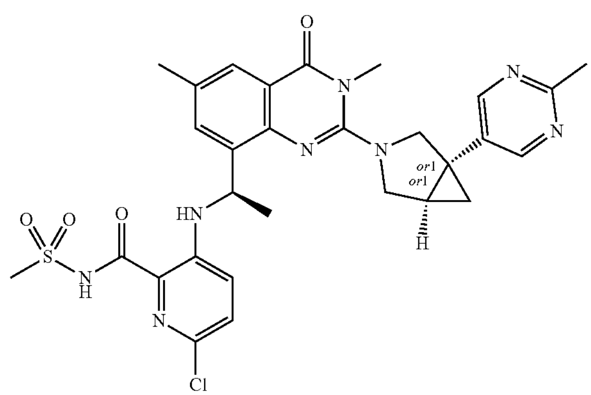 |
| 753 | 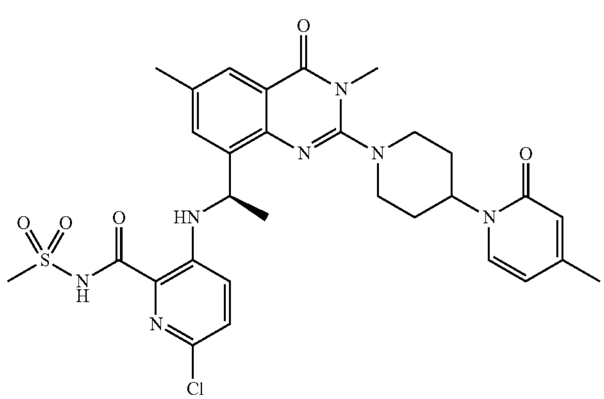 |

TABLE 1-continued

List of Compounds

| Cpd. ID | Chemical structure |
|---|---|
| 754 | 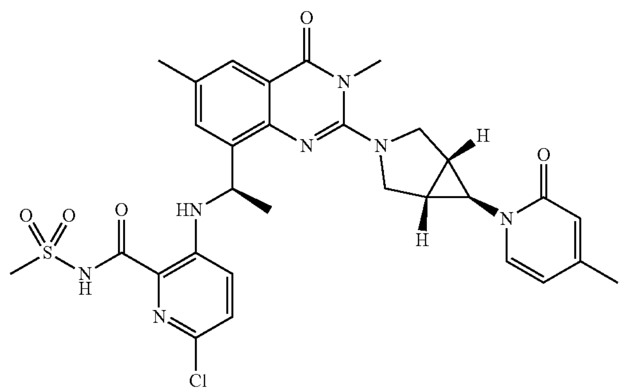 |
| 755 | 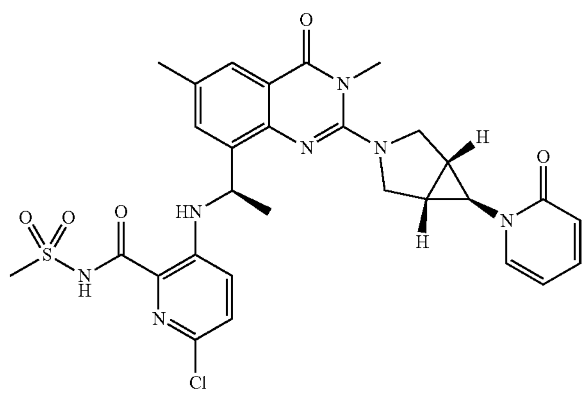 [SMILES: Cc1cc([C@@H](C)Nc2ccc(Cl)nc2C(=O)NS(C)(=O)=O)c2nc(N3C[C@@H]4[C@H](C3)[C@H]4n3ccccc3=O)n(C)c(=O)c2c1] |
| 756 | 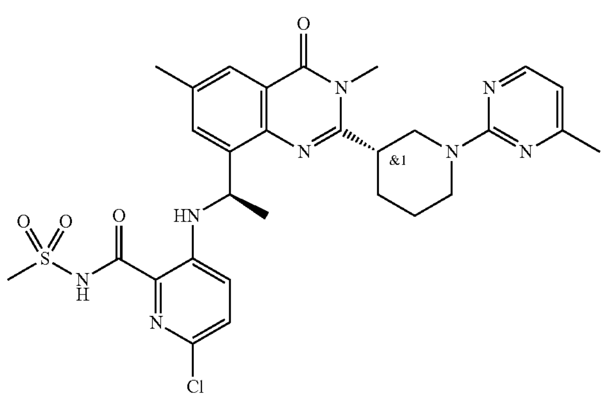 |
| 757 | 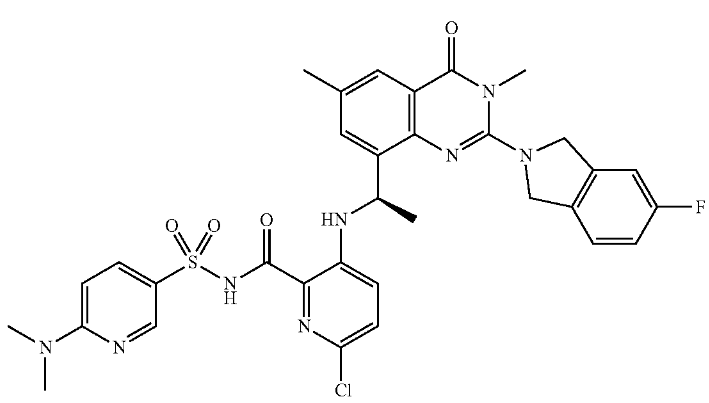 [SMILES: Cc1cc([C@@H](C)Nc2ccc(Cl)nc2C(=O)NS(=O)(=O)c2ccc(N(C)C)nc2)c2nc(N3Cc4ccc(F)cc4C3)n(C)c(=O)c2c1] |

TABLE 1-continued

List of Compounds

| Cpd. ID | Chemical structure |
|---|---|
| 758 | 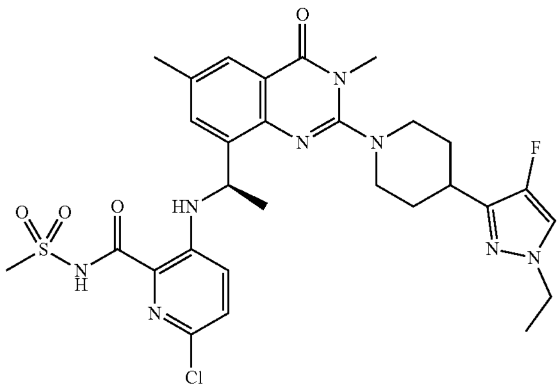 [SMILES: CCn1cc(F)c(C2CCN(c3nc4c([C@@H](C)Nc5ccc(Cl)nc5C(=O)NS(C)(=O)=O)cc(C)cc4c(=O)n3C)CC2)n1] |
| 759 | 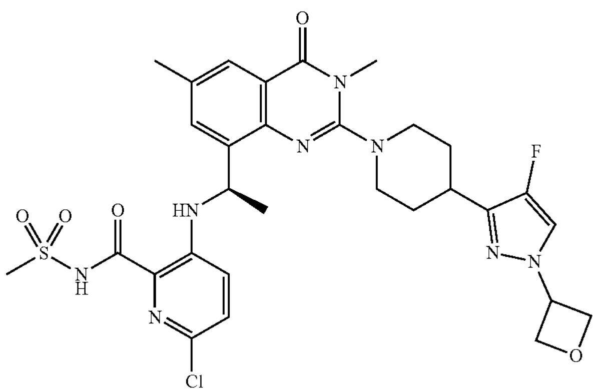 [SMILES: Cc1cc([C@@H](C)Nc2ccc(Cl)nc2C(=O)NS(C)(=O)=O)c2nc(N3CCC(c4nn(C5COC5)cc4F)CC3)n(C)c(=O)c2c1] |
| 760 | 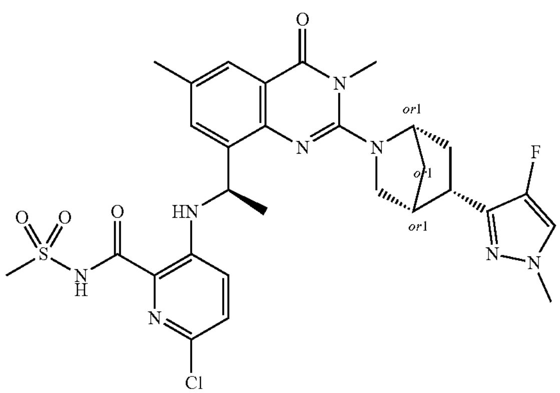 [SMILES: Cc1cc([C@@H](C)Nc2ccc(Cl)nc2C(=O)NS(C)(=O)=O)c2nc(N3C[C@@H]4C[C@H]3C[C@@H]4c3nn(C)cc3F)n(C)c(=O)c2c1] |
| 761 | 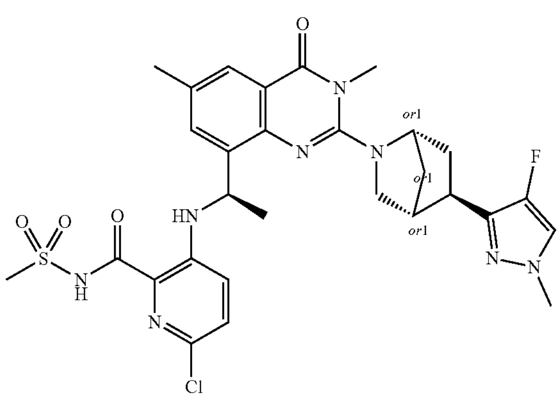 [SMILES: Cc1cc([C@@H](C)Nc2ccc(Cl)nc2C(=O)NS(C)(=O)=O)c2nc(N3C[C@@H]4C[C@H]3C[C@H]4c3nn(C)cc3F)n(C)c(=O)c2c1] |

TABLE 1-continued

List of Compounds

| Cpd. ID | Chemical structure |
|---------|--------------------|
| 762 | 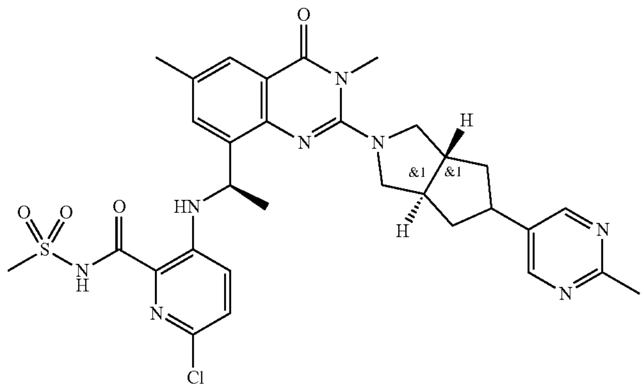 |
| 763 | 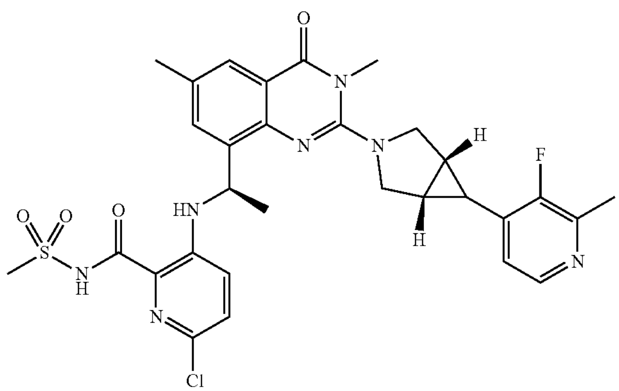 |
| 764 | 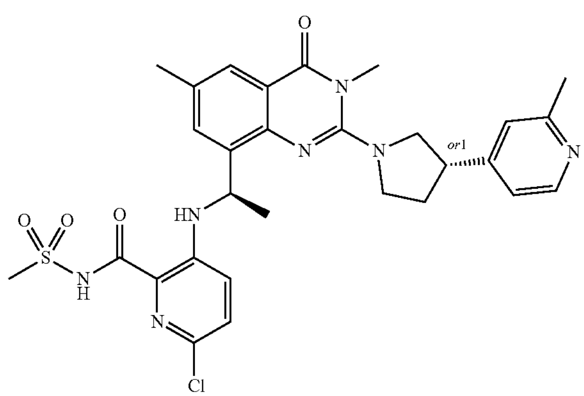 [SMILES: Cc1cc([C@@H](C)Nc2ccc(Cl)nc2C(=O)NS(C)(=O)=O)c2nc(N3CC[C@@H](c4ccnc(C)c4)C3)n(C)c(=O)c2c1] |
| 765 | 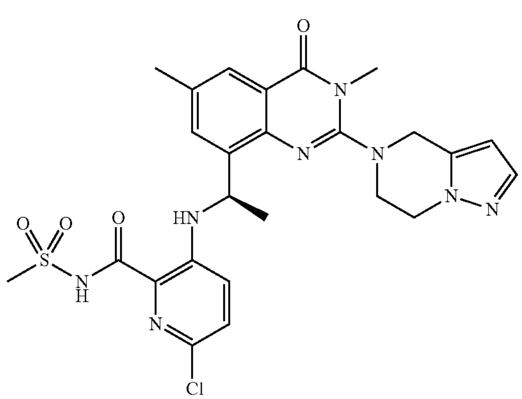 [SMILES: Cc1cc([C@@H](C)Nc2ccc(Cl)nc2C(=O)NS(C)(=O)=O)c2nc(N3CCn4nccc4C3)n(C)c(=O)c2c1] |

TABLE 1-continued
List of Compounds
| Cpd. ID | Chemical structure |
|---|---|
| 766 | 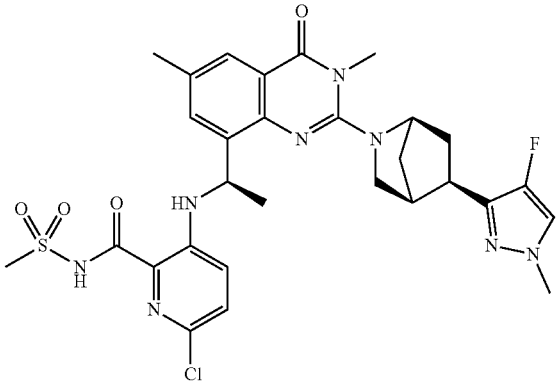 [SMILES: Cc1cc([C@@H](C)Nc2ccc(Cl)nc2C(=O)NS(C)(=O)=O)c2nc(N3C[C@H]4C[C@@H]3C[C@H]4c3nn(C)cc3F)n(C)c(=O)c2c1] |
| 767 | 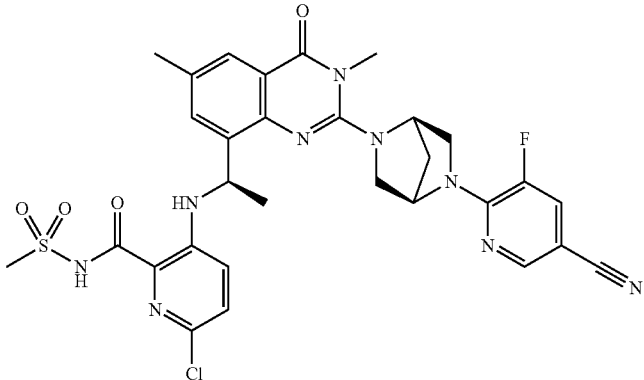 [SMILES: Cc1cc([C@@H](C)Nc2ccc(Cl)nc2C(=O)NS(C)(=O)=O)c2nc(N3C[C@H]4C[C@@H]3CN4c3ncc(C#N)cc3F)n(C)c(=O)c2c1] |
| 768 | 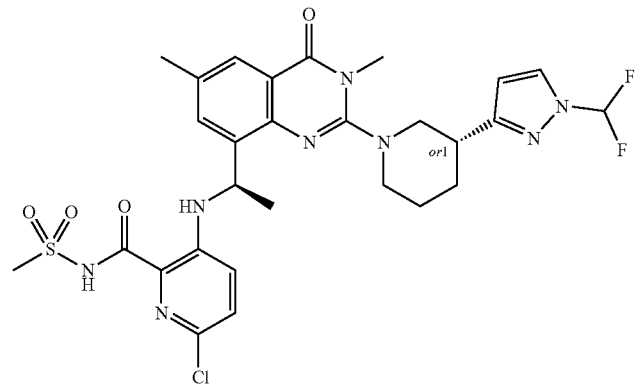 [SMILES: Cc1cc([C@@H](C)Nc2ccc(Cl)nc2C(=O)NS(C)(=O)=O)c2nc(N3CCC[C@@H](c4ccn(C(F)F)n4)C3)n(C)c(=O)c2c1] |
| 769 | 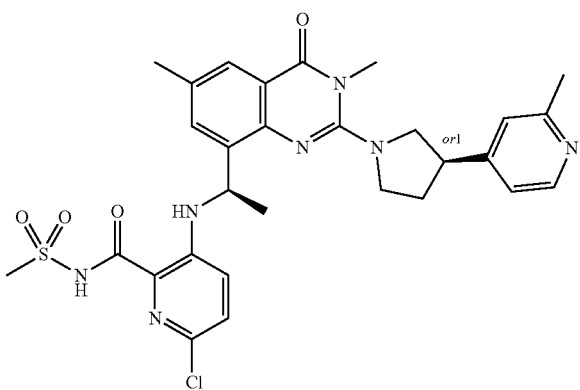 [SMILES: Cc1cc([C@@H](C)Nc2ccc(Cl)nc2C(=O)NS(C)(=O)=O)c2nc(N3CC[C@H](c4ccnc(C)c4)C3)n(C)c(=O)c2c1] |

TABLE 1-continued

List of Compounds

| Cpd. ID | Chemical structure |
|---|---|
| 770 | 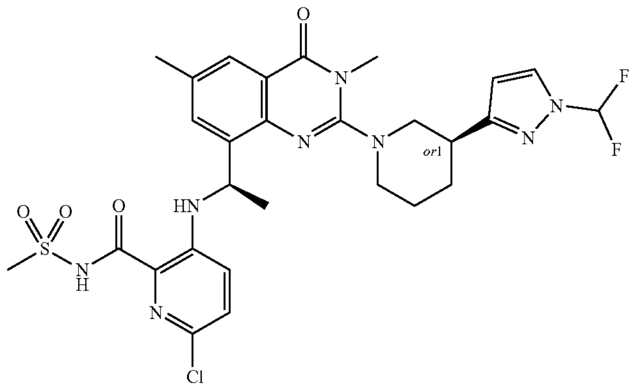 [SMILES: Cc1cc([C@@H](C)Nc2ccc(Cl)nc2C(=O)NS(C)(=O)=O)c2nc(N3CCC[C@H](c4ccn(C(F)F)n4)C3)n(C)c(=O)c2c1] |
| 771 | 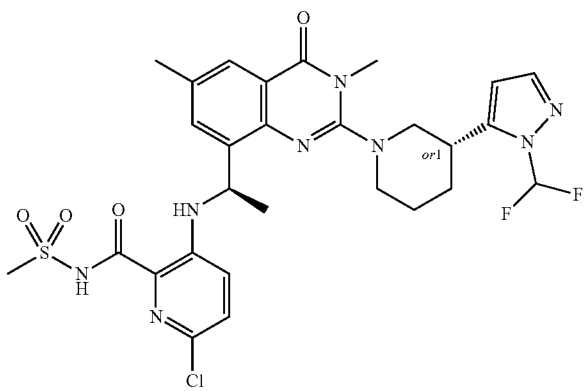 [SMILES: Cc1cc([C@@H](C)Nc2ccc(Cl)nc2C(=O)NS(C)(=O)=O)c2nc(N3CCC[C@@H](c4ccnn4C(F)F)C3)n(C)c(=O)c2c1] |
| 772 | 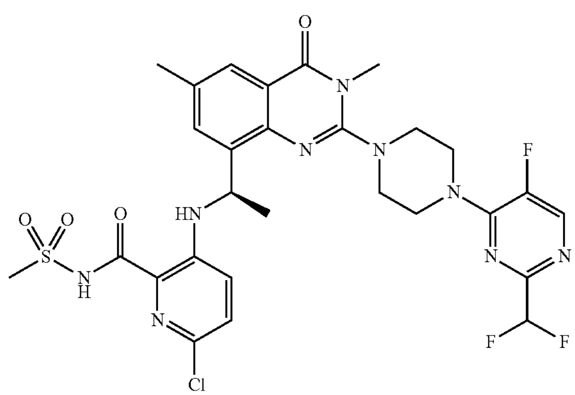 [SMILES: Cc1cc([C@@H](C)Nc2ccc(Cl)nc2C(=O)NS(C)(=O)=O)c2nc(N3CCN(c4nc(C(F)F)ncc4F)CC3)n(C)c(=O)c2c1] |
| 773 | 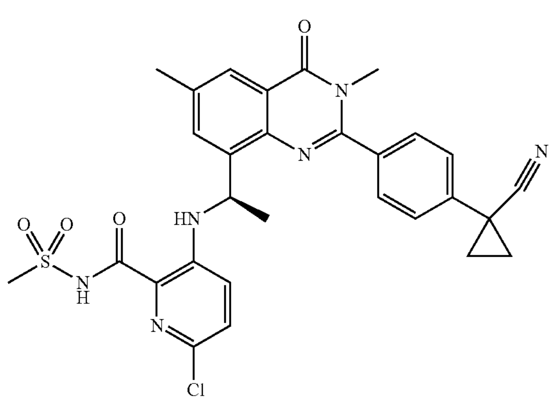 [SMILES: Cc1cc([C@@H](C)Nc2ccc(Cl)nc2C(=O)NS(C)(=O)=O)c2nc(-c3ccc(C4(C#N)CC4)cc3)n(C)c(=O)c2c1] |

TABLE 1-continued

List of Compounds

| Cpd. ID | Chemical structure |
|---|---|
| 774 | 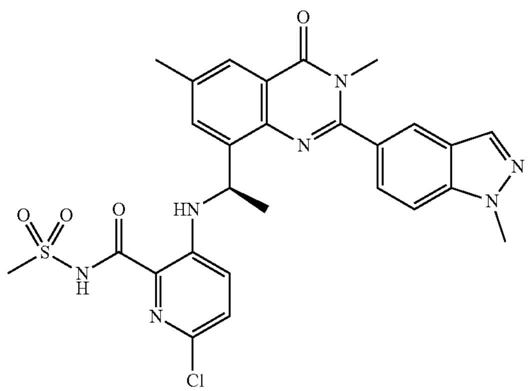 [SMILES: Cc1cc([C@@H](C)Nc2ccc(Cl)nc2C(=O)NS(C)(=O)=O)c2nc(-c3ccc4c(cnn4C)c3)n(C)c(=O)c2c1] |
| 775 | 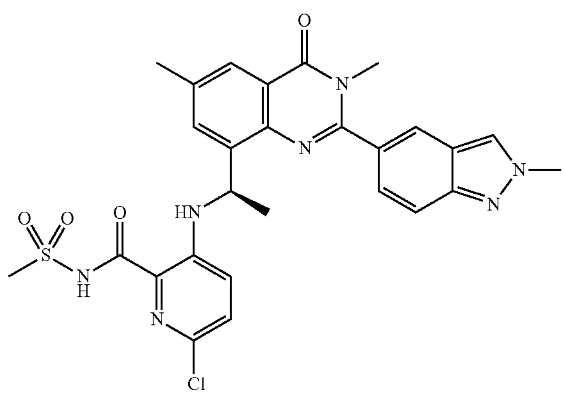 |
| 776 | 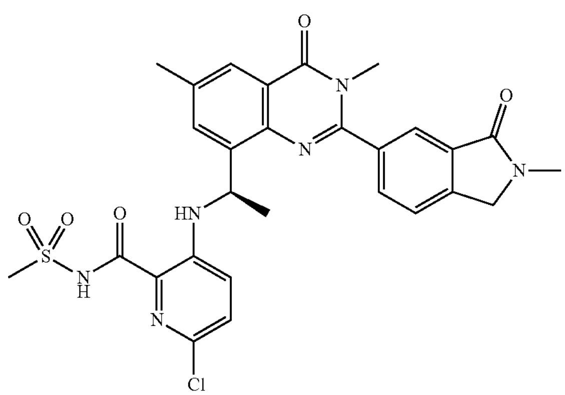 |
| 777 | 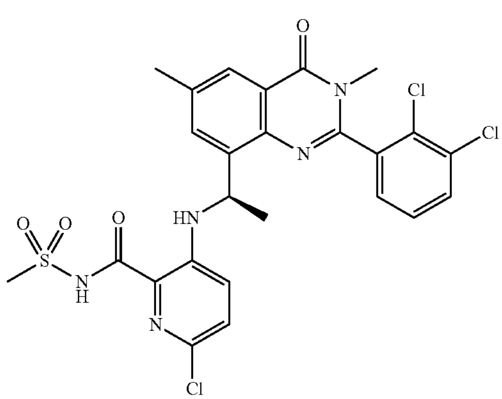 [SMILES: Cc1cc([C@@H](C)Nc2ccc(Cl)nc2C(=O)NS(C)(=O)=O)c2nc(-c3cccc(Cl)c3Cl)n(C)c(=O)c2c1] |

TABLE 1-continued

List of Compounds

| Cpd. ID | Chemical structure |
|---|---|
| 778 | 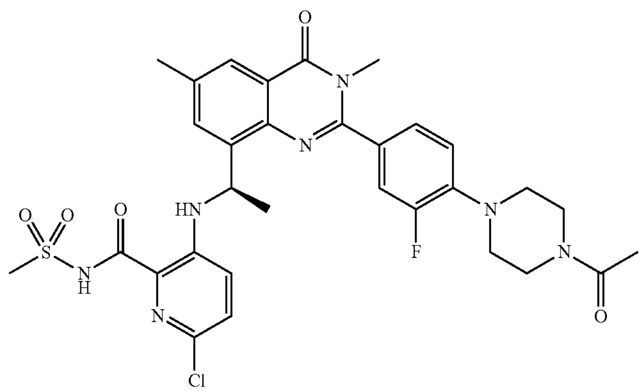 |
| 779 | 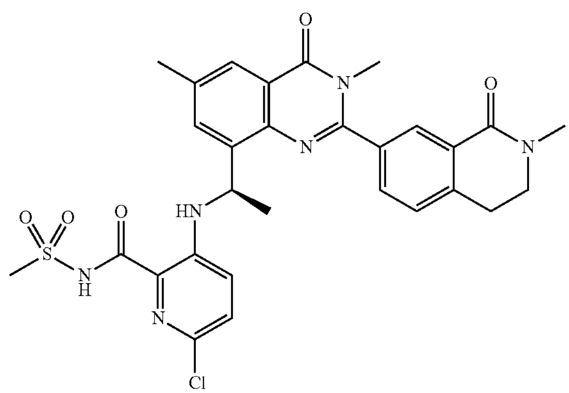 |
| 780 | 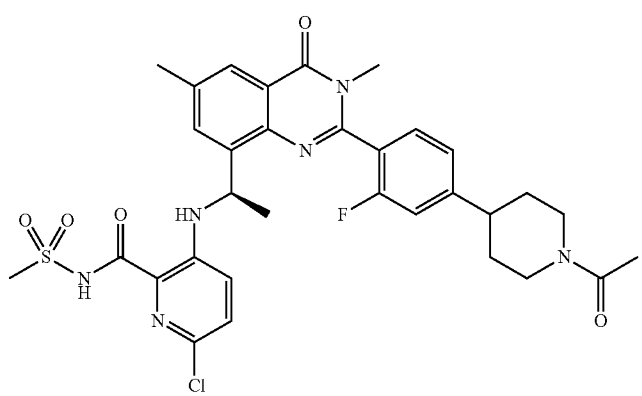 |
| 781 | 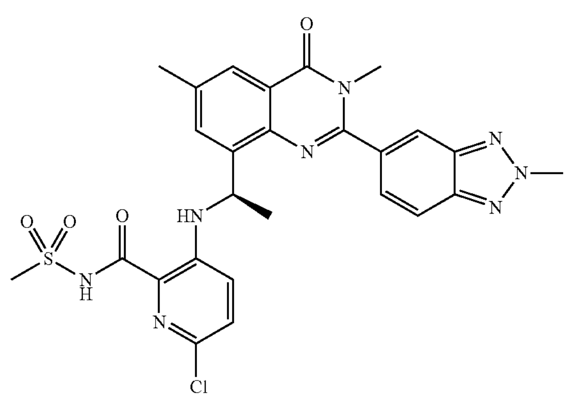 |

TABLE 1-continued
List of Compounds
| Cpd. ID | Chemical structure |
|---|---|
| 782 | 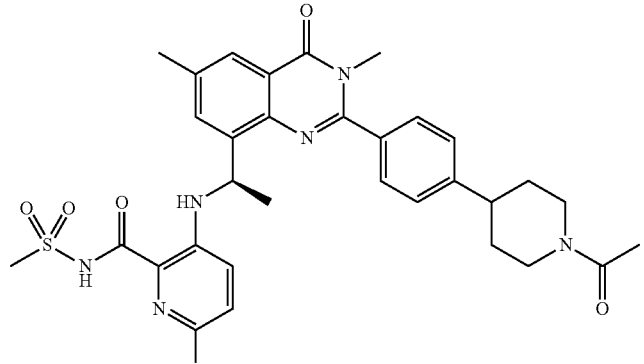 |
| 783 | 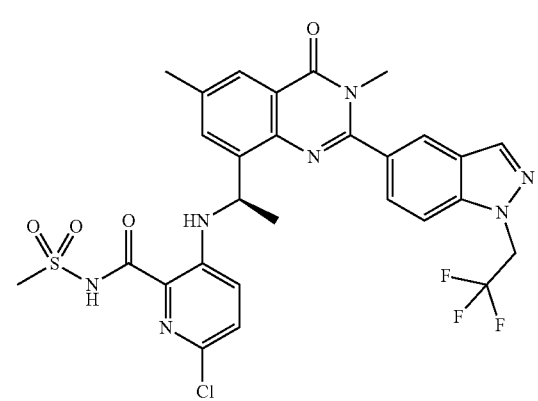 [SMILES: Cc1cc([C@@H](C)Nc2ccc(Cl)nc2C(=O)NS(C)(=O)=O)c2nc(-c3ccc4c(cnn4CC(F)(F)F)c3)n(C)c(=O)c2c1] |
| 784 | 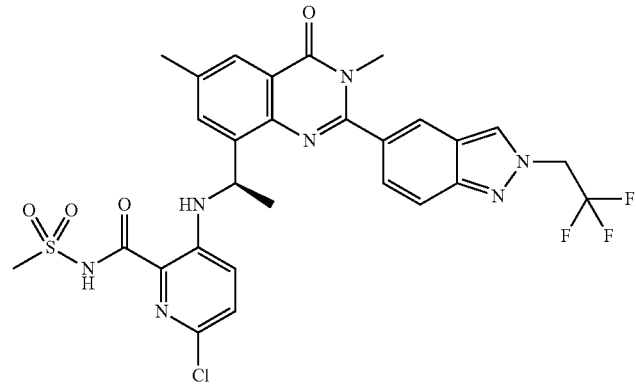 [SMILES: Cc1cc([C@@H](C)Nc2ccc(Cl)nc2C(=O)NS(C)(=O)=O)c2nc(-c3ccc4nn(CC(F)(F)F)cc4c3)n(C)c(=O)c2c1] |
| 785 | 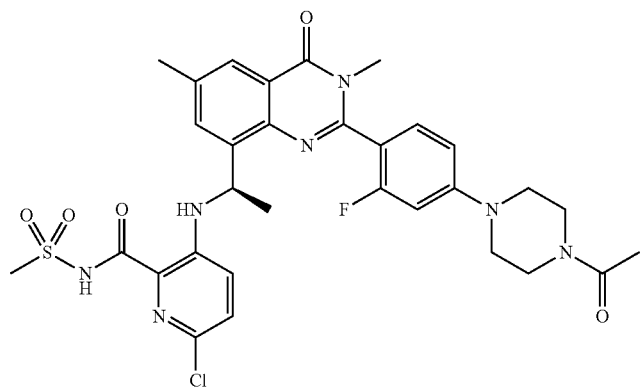 |

TABLE 1-continued

| Cpd. ID | Chemical structure |
|---|---|
| 786 | 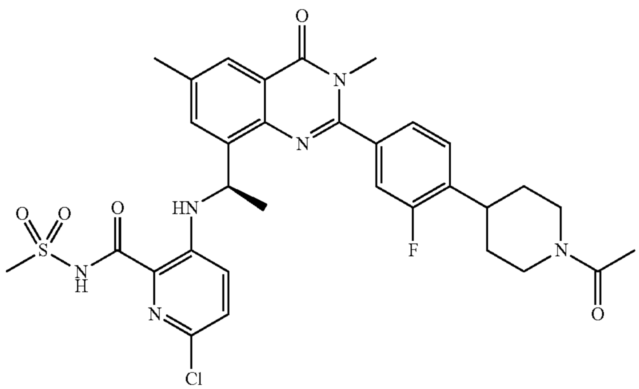 |
| 787 | 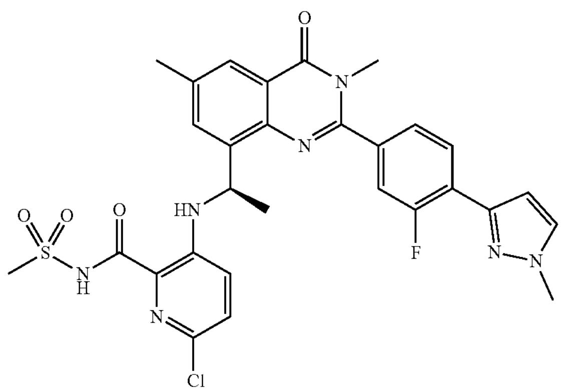 [SMILES: Cc1cc([C@@H](C)Nc2ccc(Cl)nc2C(=O)NS(C)(=O)=O)c2nc(-c3ccc(-c4ccn(C)n4)c(F)c3)n(C)c(=O)c2c1] |
| 788 | 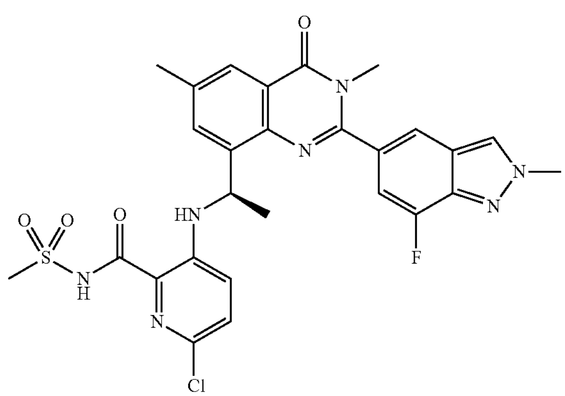 |
| 789 | 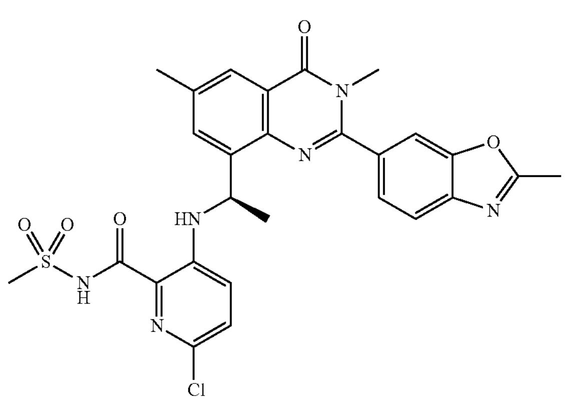 |

TABLE 1-continued

List of Compounds

| Cpd. ID | Chemical structure |
|---|---|
| 790 | 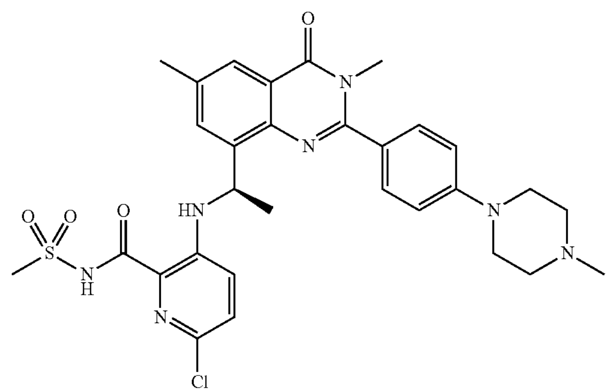 |
| 791 | 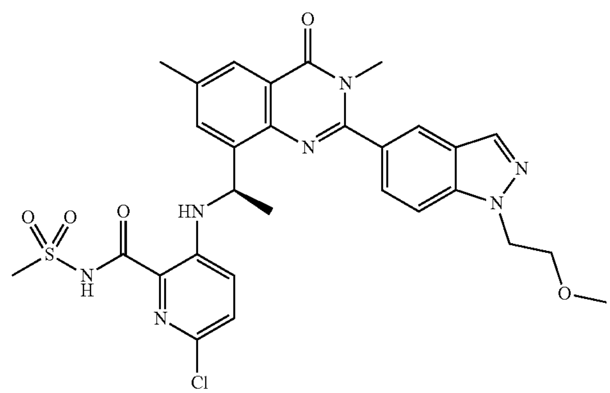 |
| 792 | 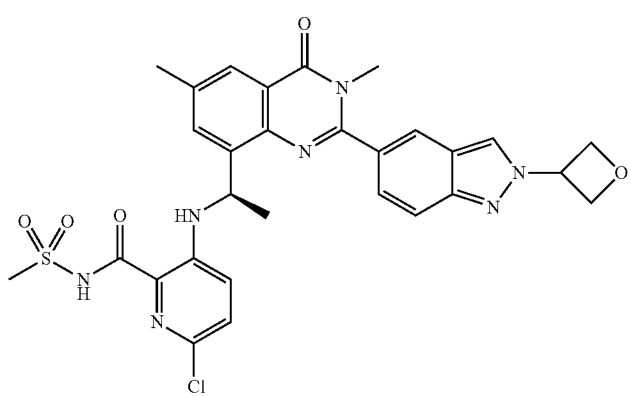 [SMILES: Cc1cc([C@@H](C)Nc2ccc(Cl)nc2C(=O)NS(C)(=O)=O)c2nc(-c3ccc4nn(C5COC5)cc4c3)n(C)c(=O)c2c1] |
| 793 | 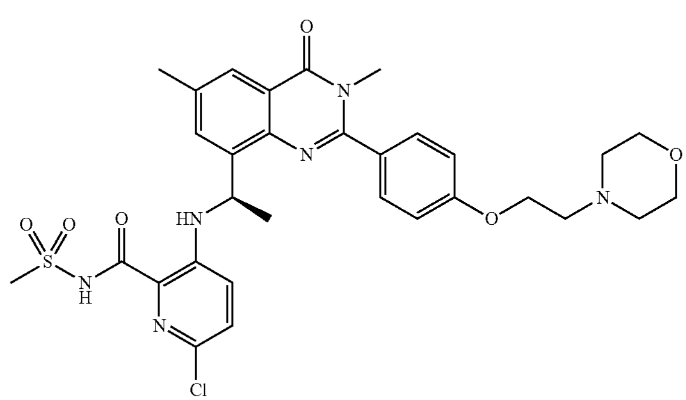 [SMILES: Cc1cc([C@@H](C)Nc2ccc(Cl)nc2C(=O)NS(C)(=O)=O)c2nc(-c3ccc(OCCN4CCOCC4)cc3)n(C)c(=O)c2c1] |

TABLE 1-continued

List of Compounds

| Cpd. ID | Chemical structure |
|---|---|
| 794 | 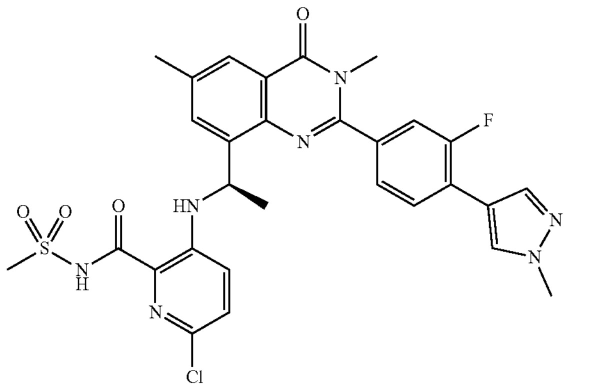 [SMILES: Cc1cc([C@@H](C)Nc2ccc(Cl)nc2C(=O)NS(C)(=O)=O)c2nc(-c3ccc(-c4cnn(C)c4)c(F)c3)n(C)c(=O)c2c1] |
| 795 | 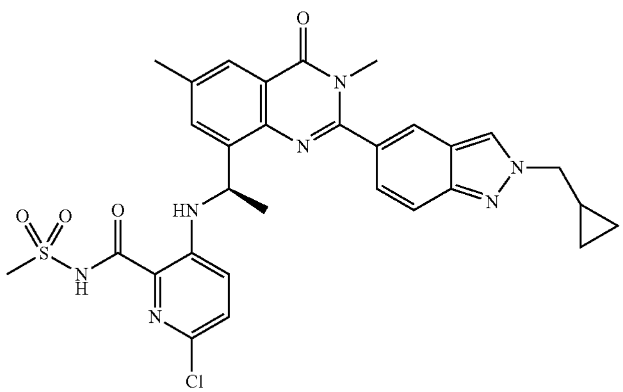 [SMILES: Cc1cc([C@@H](C)Nc2ccc(Cl)nc2C(=O)NS(C)(=O)=O)c2nc(-c3ccc4nn(CC5CC5)cc4c3)n(C)c(=O)c2c1] |
| 796 | 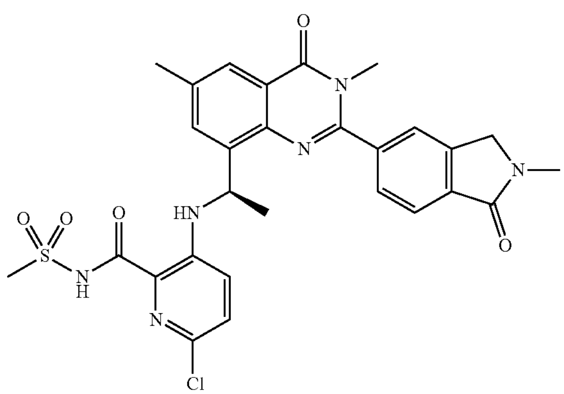 |
| 797 | 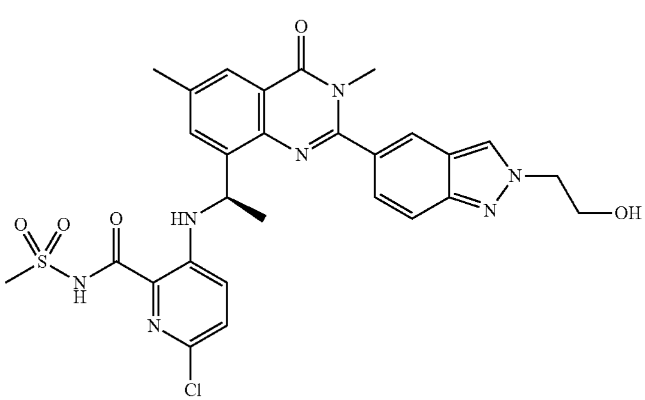 [SMILES: Cc1cc([C@@H](C)Nc2ccc(Cl)nc2C(=O)NS(C)(=O)=O)c2nc(-c3ccc4nn(CCO)cc4c3)n(C)c(=O)c2c1] |

TABLE 1-continued

List of Compounds

| Cpd. ID | Chemical structure |
|---|---|
| 798 | 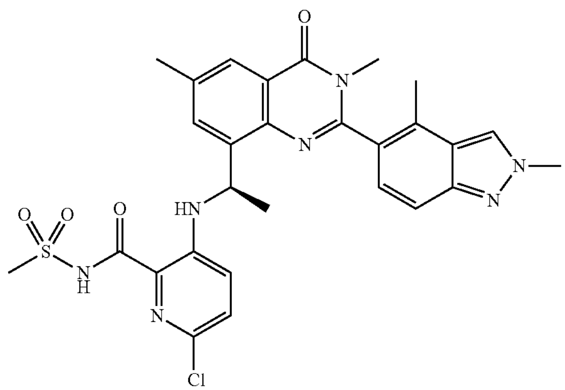 |
| 799 | 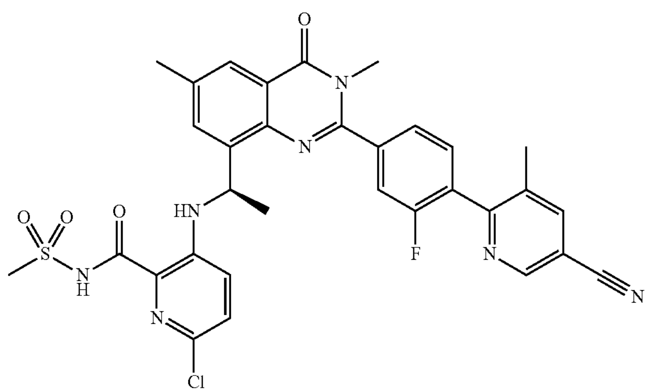 [SMILES: Cc1cc([C@@H](C)Nc2ccc(Cl)nc2C(=O)NS(C)(=O)=O)c2nc(-c3ccc(-c4ncc(C#N)cc4C)c(F)c3)n(C)c(=O)c2c1] |
| 800 | 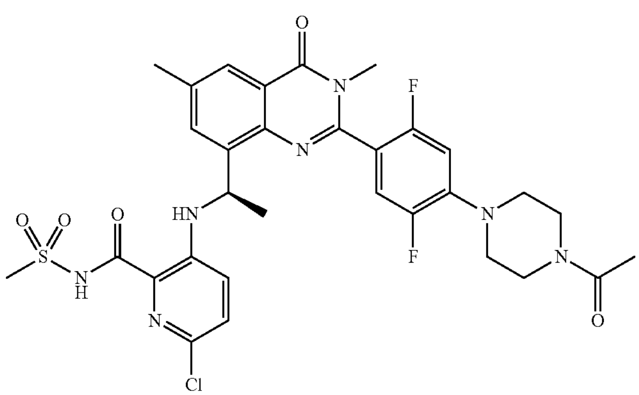 [SMILES: CC(=O)N1CCN(c2cc(F)c(-c3nc4c([C@@H](C)Nc5ccc(Cl)nc5C(=O)NS(C)(=O)=O)cc(C)cc4c(=O)n3C)cc2F)CC1] |
| 801 | 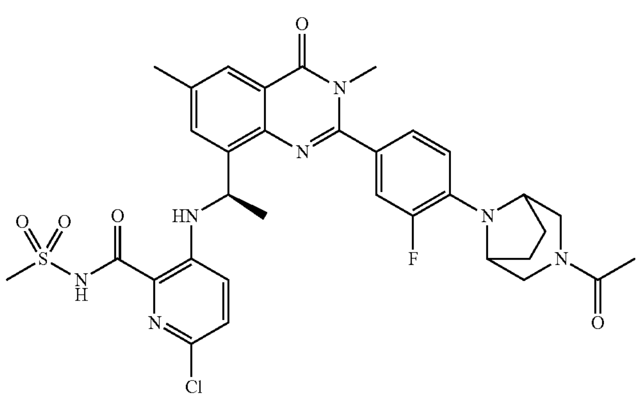 [SMILES: CC(=O)N1CC2CCC(C1)N2c1ccc(-c2nc3c([C@@H](C)Nc4ccc(Cl)nc4C(=O)NS(C)(=O)=O)cc(C)cc3c(=O)n2C)cc1F] |

TABLE 1-continued

List of Compounds

| Cpd. ID | Chemical structure |
|---|---|
| 802 | 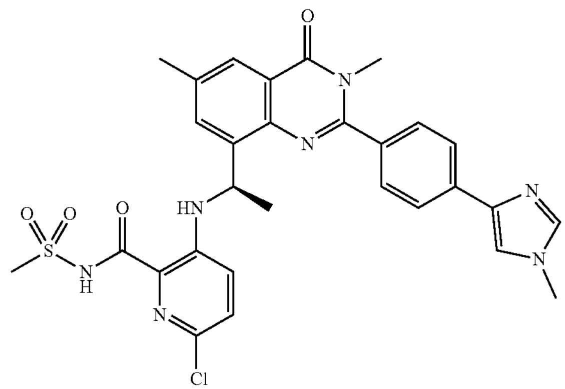 [SMILES: Cc1cc([C@@H](C)Nc2ccc(Cl)nc2C(=O)NS(C)(=O)=O)c2nc(-c3ccc(-c4cn(C)cn4)cc3)n(C)c(=O)c2c1] |
| 803 | 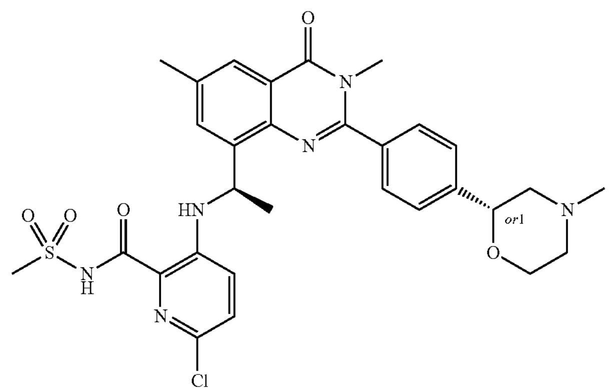 |
| 804 | 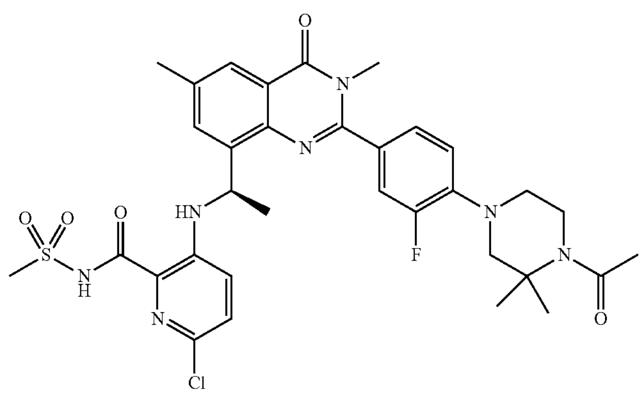 [SMILES: CC(=O)N1CCN(c2ccc(-c3nc4c([C@@H](C)Nc5ccc(Cl)nc5C(=O)NS(C)(=O)=O)cc(C)cc4c(=O)n3C)cc2F)CC1(C)C] |
| 805 | 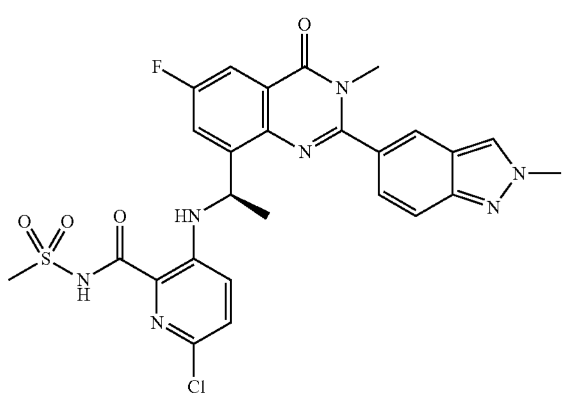 |

TABLE 1-continued

List of Compounds

| Cpd. ID | Chemical structure |
|---|---|
| 806 | 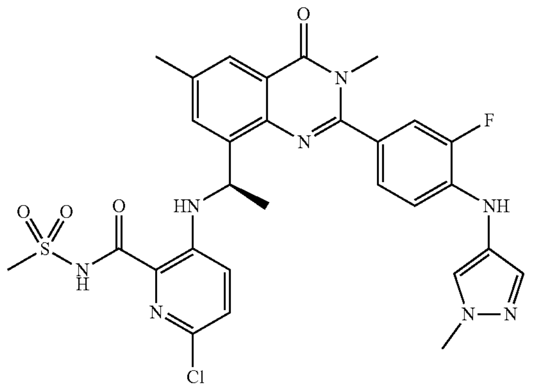 [SMILES: Cc1cc([C@@H](C)Nc2ccc(Cl)nc2C(=O)NS(C)(=O)=O)c2nc(-c3ccc(Nc4cnn(C)c4)c(F)c3)n(C)c(=O)c2c1] |
| 807 | 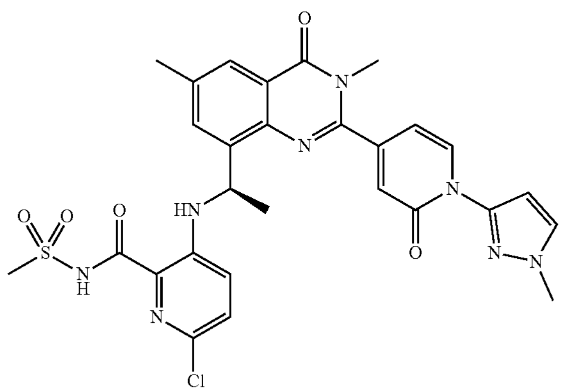 [SMILES: Cc1cc([C@@H](C)Nc2ccc(Cl)nc2C(=O)NS(C)(=O)=O)c2nc(-c3ccn(-c4ccn(C)n4)c(=O)c3)n(C)c(=O)c2c1] |
| 808 | 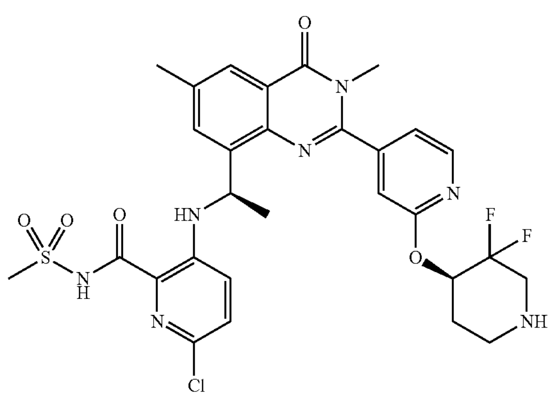 [SMILES: Cc1cc([C@@H](C)Nc2ccc(Cl)nc2C(=O)NS(C)(=O)=O)c2nc(-c3ccnc(O[C@@H]4CCNCC4(F)F)c3)n(C)c(=O)c2c1] |
| 809 | 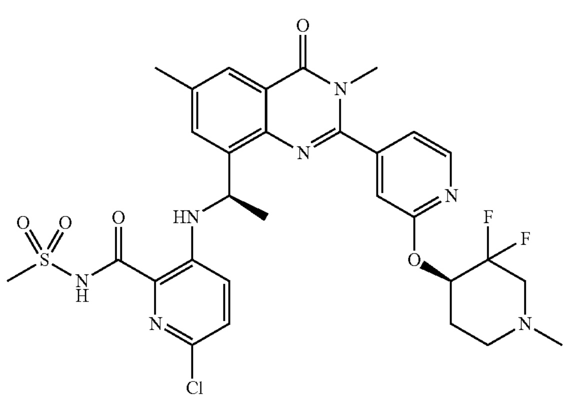 |

TABLE 1-continued

List of Compounds

| Cpd. ID | Chemical structure |
|---|---|
| 810 | 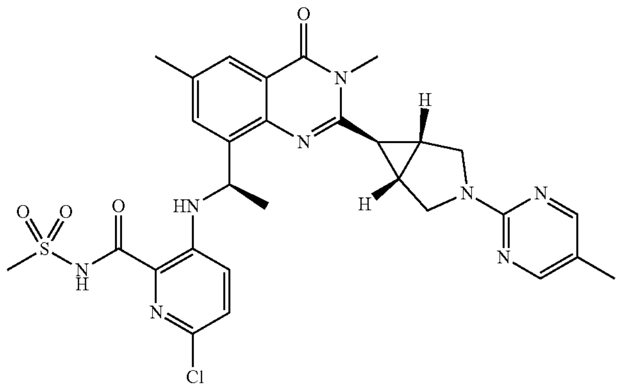 |
| 811 | 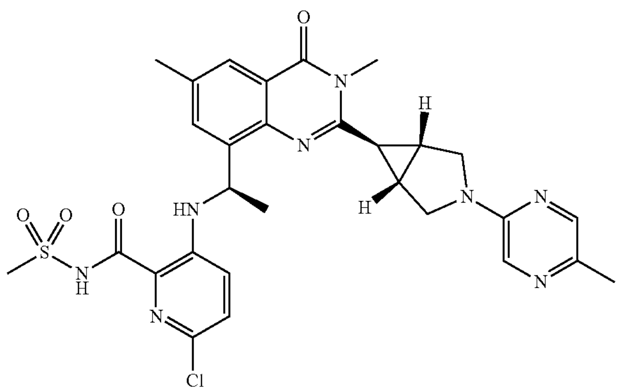 |
| 812 | 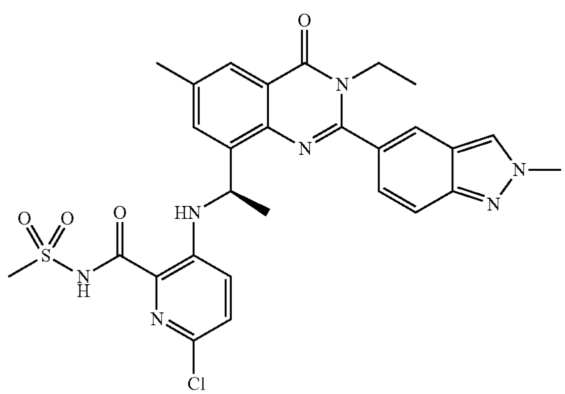 |
| 813 | 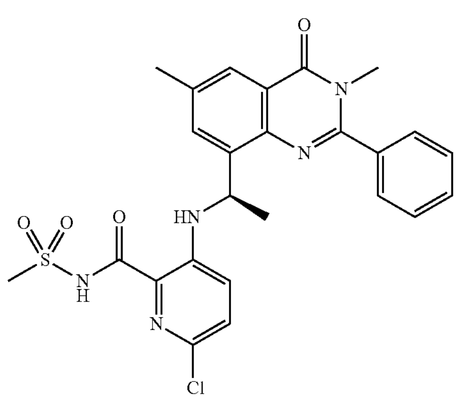 [SMILES: Cc1cc([C@@H](C)Nc2ccc(Cl)nc2C(=O)NS(C)(=O)=O)c2nc(-c3ccccc3)n(C)c(=O)c2c1] |

TABLE 1-continued

List of Compounds

| Cpd. ID | Chemical structure |
|---------|--------------------|
| 814 | 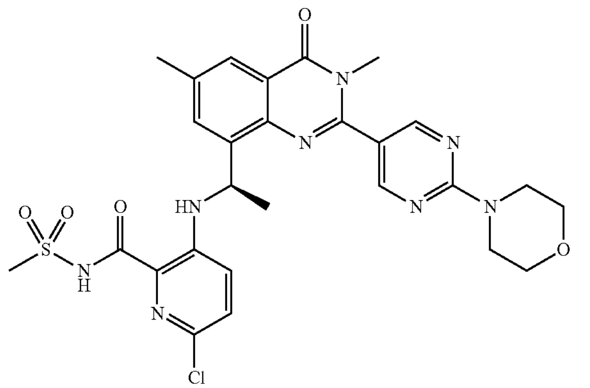 [SMILES: Cc1cc([C@@H](C)Nc2ccc(Cl)nc2C(=O)NS(C)(=O)=O)c2nc(-c3cnc(N4CCOCC4)nc3)n(C)c(=O)c2c1] |
| 815 | 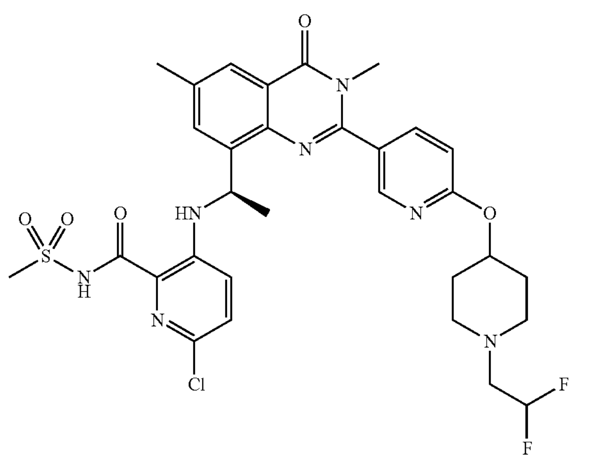 [SMILES: Cc1cc([C@@H](C)Nc2ccc(Cl)nc2C(=O)NS(C)(=O)=O)c2nc(-c3ccc(OC4CCN(CC(F)F)CC4)nc3)n(C)c(=O)c2c1] |
| 816 | 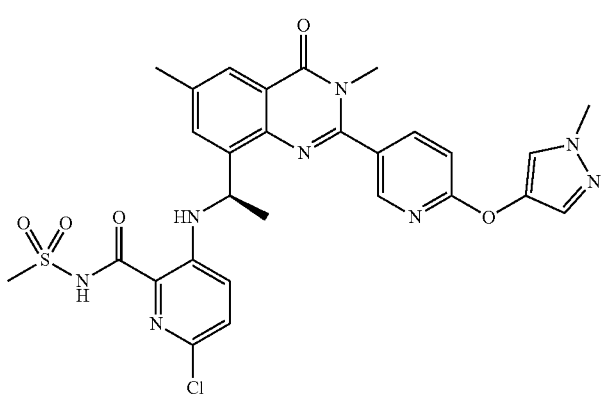 |

TABLE 1-continued

List of Compounds

| Cpd. ID | Chemical structure |
|---|---|
| 817 | 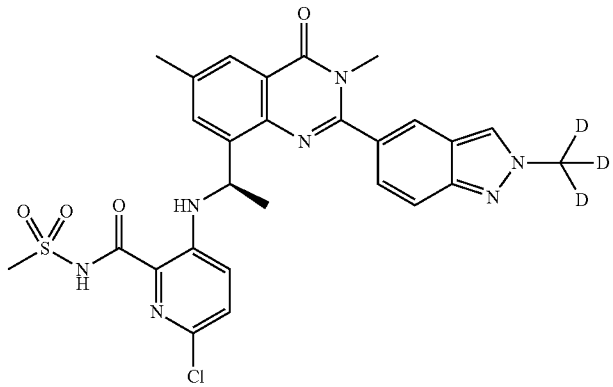 [SMILES: [2H]C([2H])([2H])n1cc2cc(-c3nc4c([C@@H](C)Nc5ccc(Cl)nc5C(=O)NS(C)(=O)=O)cc(C)cc4c(=O)n3C)ccc2n1] |
| 818 | 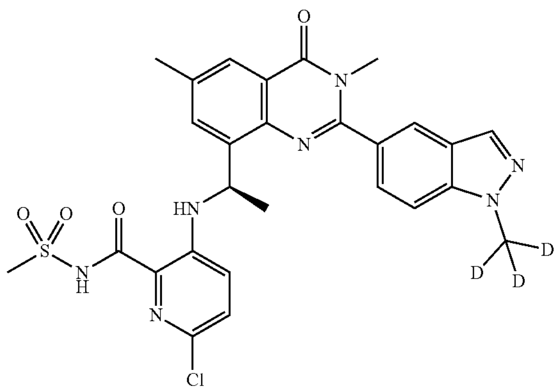 [SMILES: [2H]C([2H])([2H])n1ncc2cc(-c3nc4c([C@@H](C)Nc5ccc(Cl)nc5C(=O)NS(C)(=O)=O)cc(C)cc4c(=O)n3C)ccc21] |
| 819 | 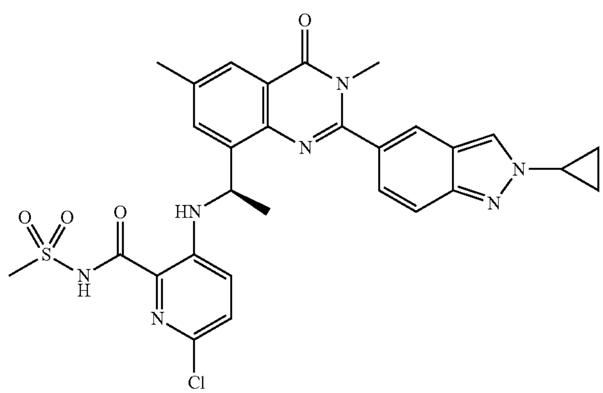 [SMILES: Cc1cc([C@@H](C)Nc2ccc(Cl)nc2C(=O)NS(C)(=O)=O)c2nc(-c3ccc4nn(C5CC5)cc4c3)n(C)c(=O)c2c1] |
| 820 | 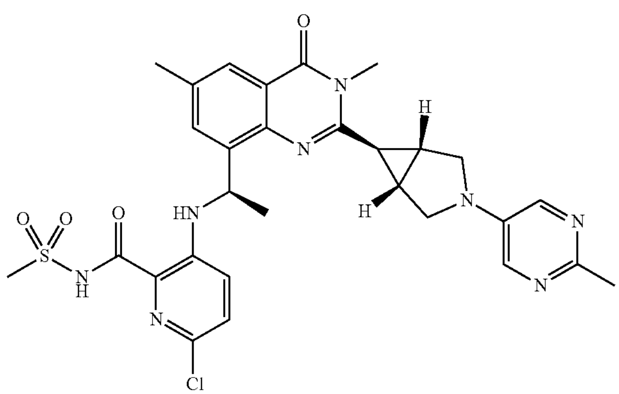 |

TABLE 1-continued

List of Compounds

| Cpd. ID | Chemical structure |
|---|---|
| 821 | 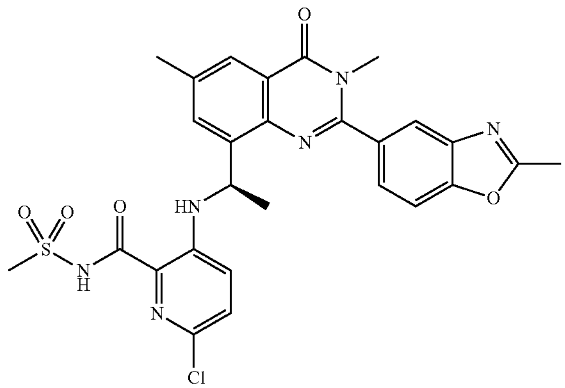 |
| 822 | 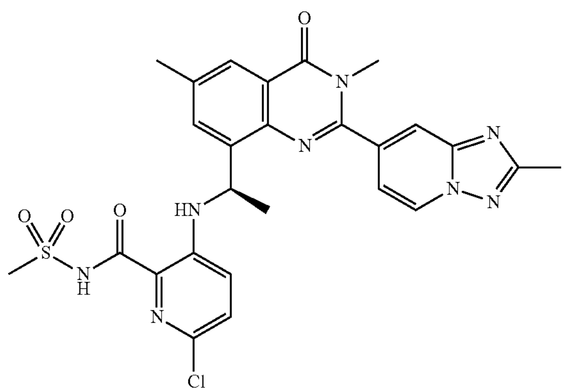 |
| 823 | 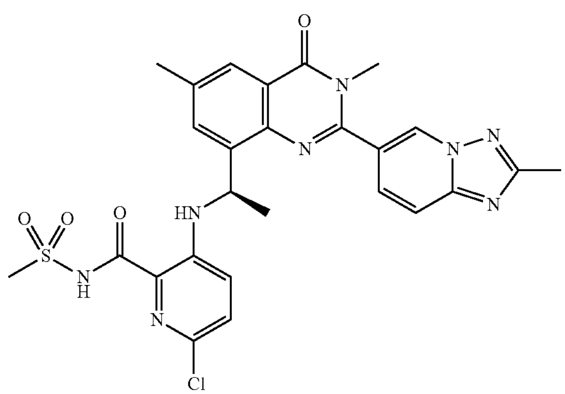 |
| 824 | 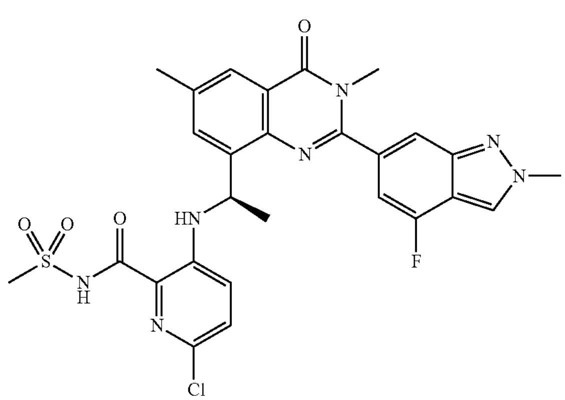 |

TABLE 1-continued

List of Compounds

| Cpd. ID | Chemical structure |
|---|---|
| 825 | 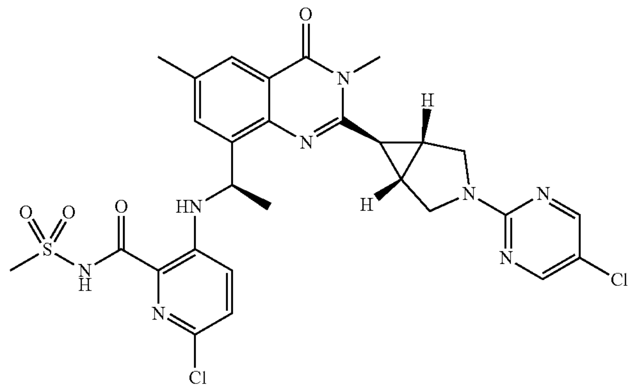 [SMILES: Cc1cc([C@@H](C)Nc2ccc(Cl)nc2C(=O)NS(C)(=O)=O)c2nc([C@H]3[C@@H]4CN(c5ncc(Cl)cn5)C[C@@H]43)n(C)c(=O)c2c1] |
| 826 | 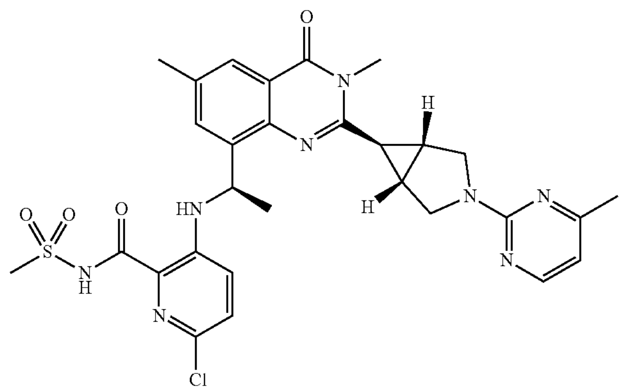 |
| 827 | 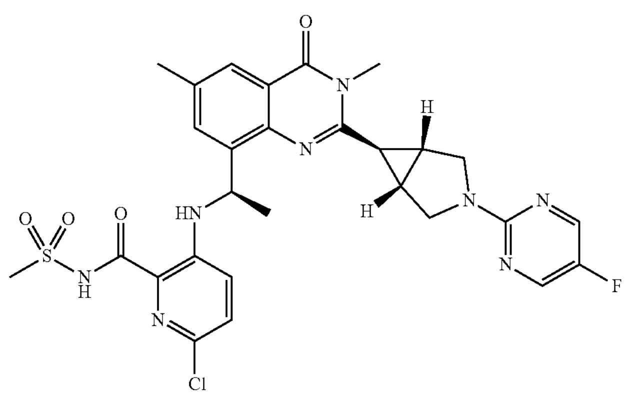 [SMILES: Cc1cc([C@@H](C)Nc2ccc(Cl)nc2C(=O)NS(C)(=O)=O)c2nc([C@H]3[C@@H]4CN(c5ncc(F)cn5)C[C@@H]43)n(C)c(=O)c2c1] |
| 828 | 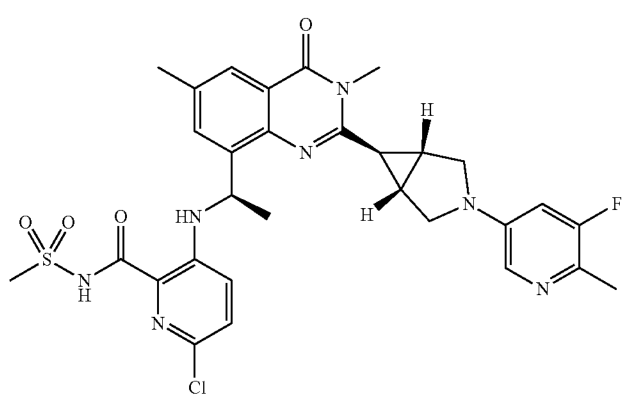 |

TABLE 1-continued
List of Compounds
| Cpd. ID | Chemical structure |
|---|---|
| 829 | 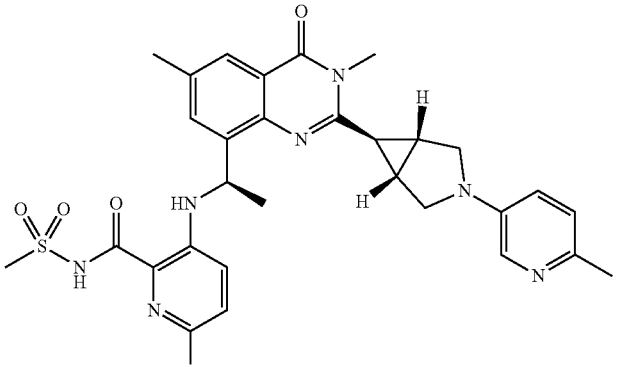 |
| 830 | 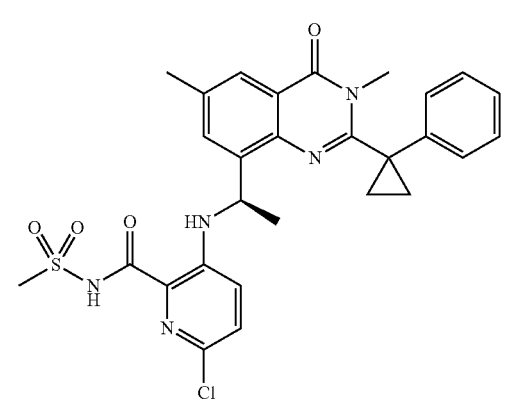 [SMILES: Cc1cc([C@@H](C)Nc2ccc(Cl)nc2C(=O)NS(C)(=O)=O)c2nc(C3(c4ccccc4)CC3)n(C)c(=O)c2c1] |
| 831 | 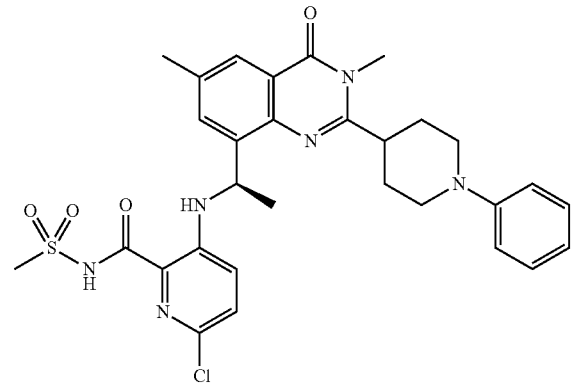 [SMILES: Cc1cc([C@@H](C)Nc2ccc(Cl)nc2C(=O)NS(C)(=O)=O)c2nc(C3CCN(c4ccccc4)CC3)n(C)c(=O)c2c1] |
| 832 | 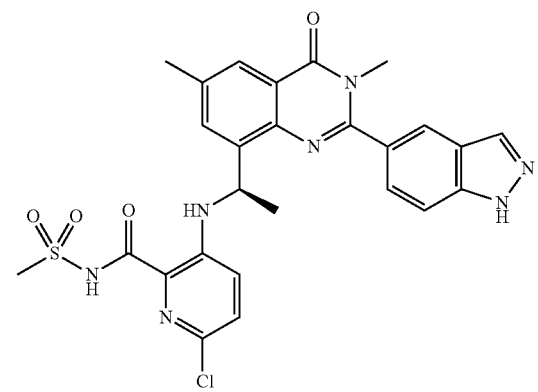 [SMILES: Cc1cc([C@@H](C)Nc2ccc(Cl)nc2C(=O)NS(C)(=O)=O)c2nc(-c3ccc4[nH]ncc4c3)n(C)c(=O)c2c1] |

TABLE 1-continued
List of Compounds
| Cpd. ID | Chemical structure |
|---|---|
| 833 | 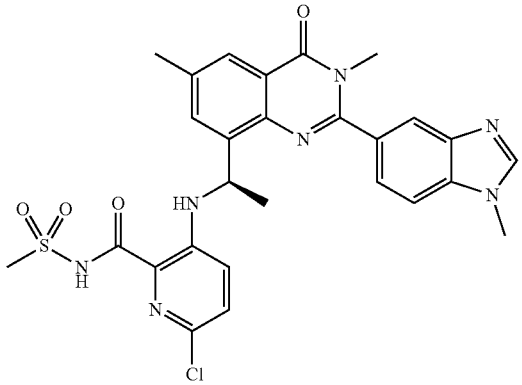 [SMILES: Cc1cc([C@@H](C)Nc2ccc(Cl)nc2C(=O)NS(C)(=O)=O)c2nc(-c3ccc4c(c3)ncn4C)n(C)c(=O)c2c1] |
| 834 | 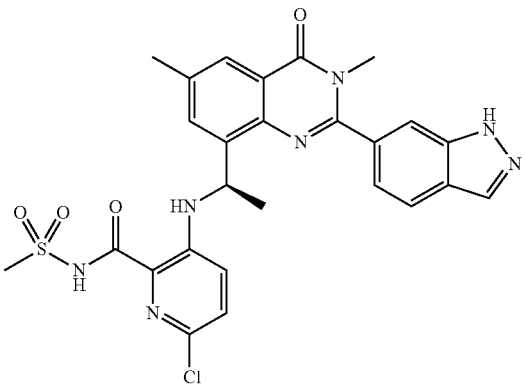 [SMILES: Cc1cc([C@@H](C)Nc2ccc(Cl)nc2C(=O)NS(C)(=O)=O)c2nc(-c3ccc4cn[nH]c4c3)n(C)c(=O)c2c1] |
| 835 | 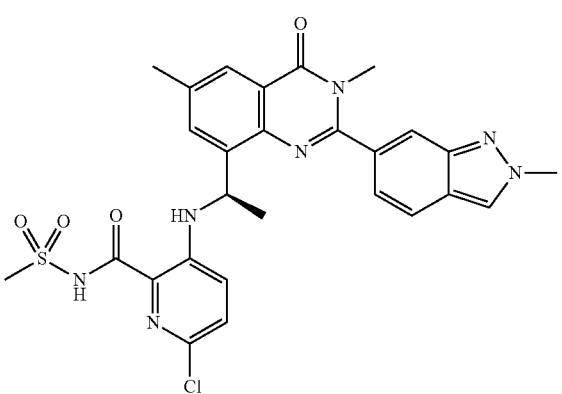 |
| 836 | 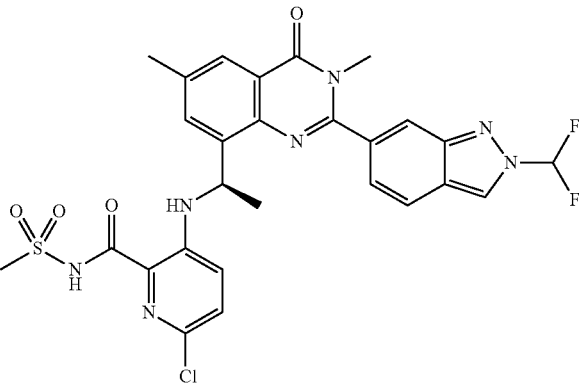 |

TABLE 1-continued

List of Compounds

| Cpd. ID | Chemical structure |
|---|---|
| 837 | 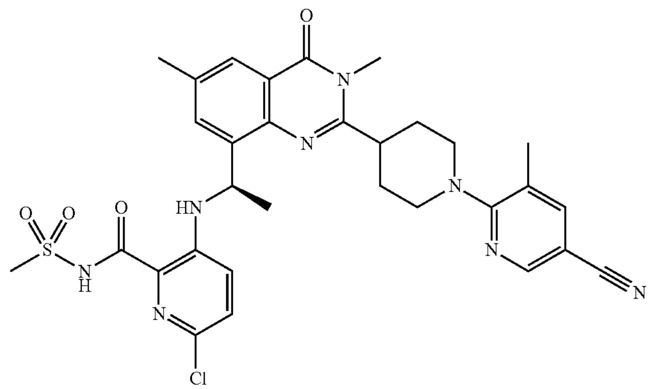 [SMILES: Cc1cc([C@@H](C)Nc2ccc(Cl)nc2C(=O)NS(C)(=O)=O)c2nc(C3CCN(c4ncc(C#N)cc4C)CC3)n(C)c(=O)c2c1] |
| 838 | 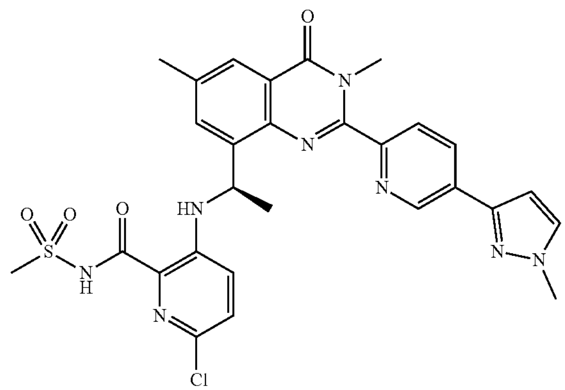 [SMILES: Cc1cc([C@@H](C)Nc2ccc(Cl)nc2C(=O)NS(C)(=O)=O)c2nc(-c3ccc(-c4ccn(C)n4)cn3)n(C)c(=O)c2c1] |
| 839 | 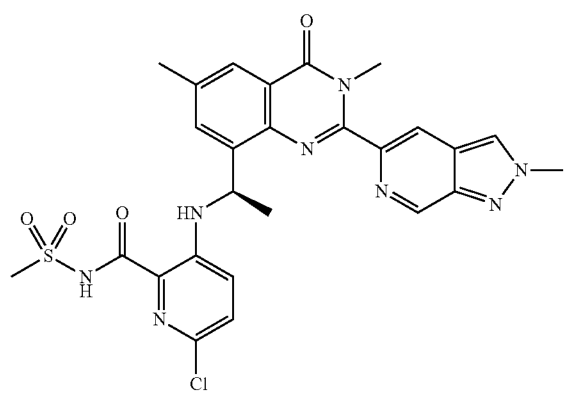 |
| 840 | 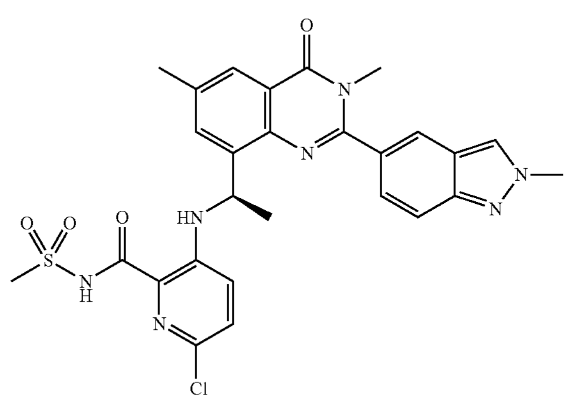 |

TABLE 1-continued

List of Compounds

| Cpd. ID | Chemical structure |
|---|---|
| 841 | 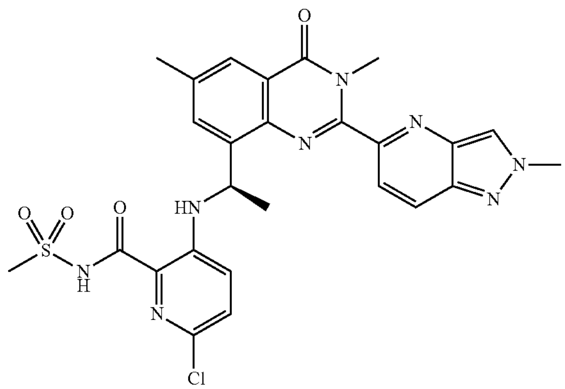 |
| 842 | 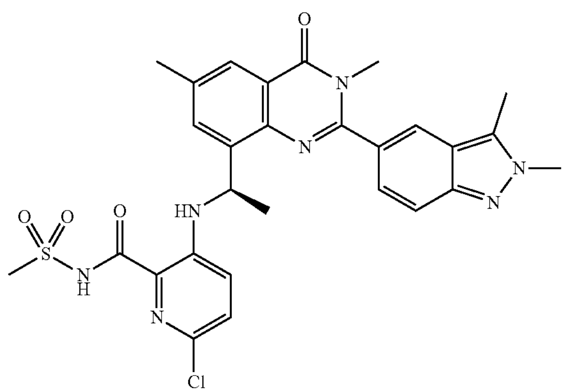 |
| 843 | 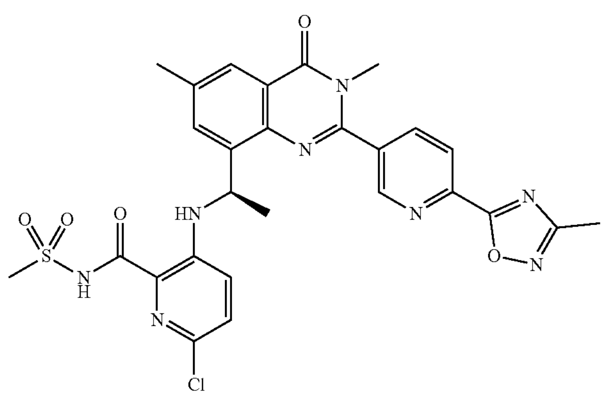 |
| 844 | 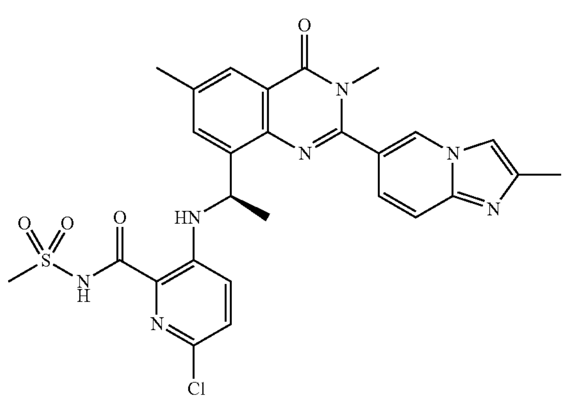 |

TABLE 1-continued
List of Compounds
| Cpd. ID | Chemical structure |
|---|---|
| 845 | 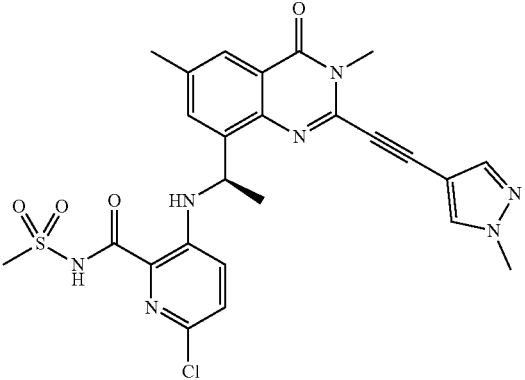 [SMILES: Cc1cc([C@@H](C)Nc2ccc(Cl)nc2C(=O)NS(C)(=O)=O)c2nc(C#Cc3cnn(C)c3)n(C)c(=O)c2c1] |
| 846 | 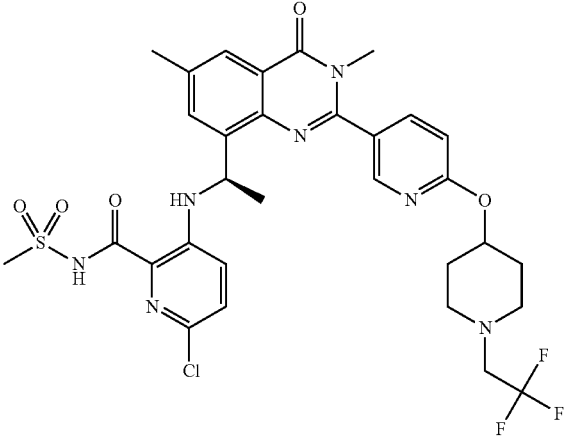 [SMILES: Cc1cc([C@@H](C)Nc2ccc(Cl)nc2C(=O)NS(C)(=O)=O)c2nc(-c3ccc(OC4CCN(CC(F)(F)F)CC4)nc3)n(C)c(=O)c2c1] |
| 847 | 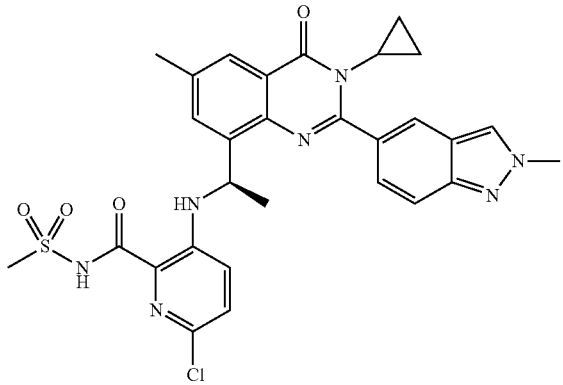 |

TABLE 1-continued

List of Compounds

| Cpd. ID | Chemical structure |
|---|---|
| 848 | 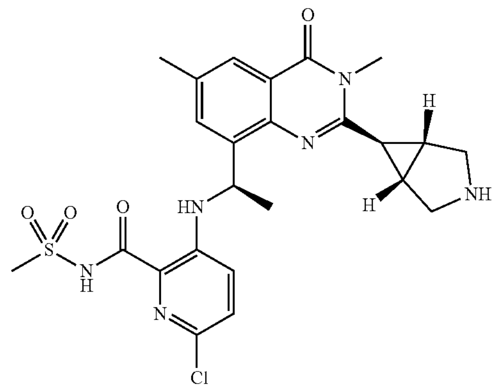 [SMILES: Cc1cc([C@@H](C)Nc2ccc(Cl)nc2C(=O)NS(C)(=O)=O)c2nc([C@H]3[C@@H]4CNC[C@@H]43)n(C)c(=O)c2c1] |
| 849 | 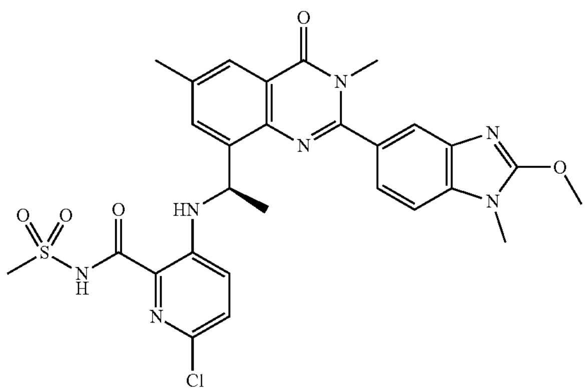 |
| 850 | 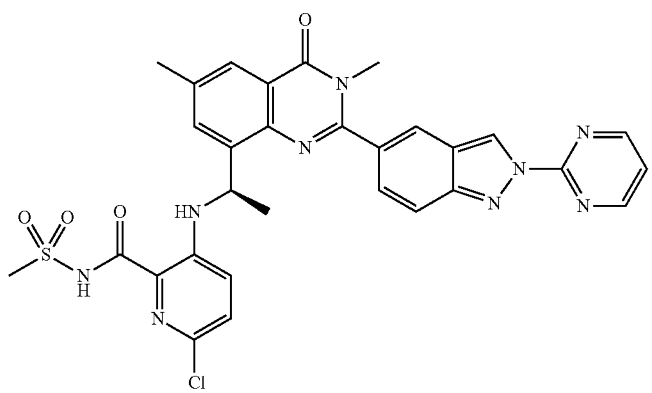 [SMILES: Cc1cc([C@@H](C)Nc2ccc(Cl)nc2C(=O)NS(C)(=O)=O)c2nc(-c3ccc4nn(-c5ncccn5)cc4c3)n(C)c(=O)c2c1] |
| 851 | 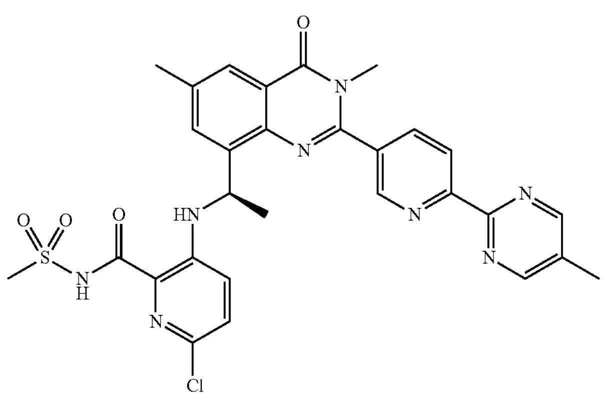 |

TABLE 1-continued

List of Compounds

| Cpd. ID | Chemical structure |
|---------|--------------------|
| 852 | 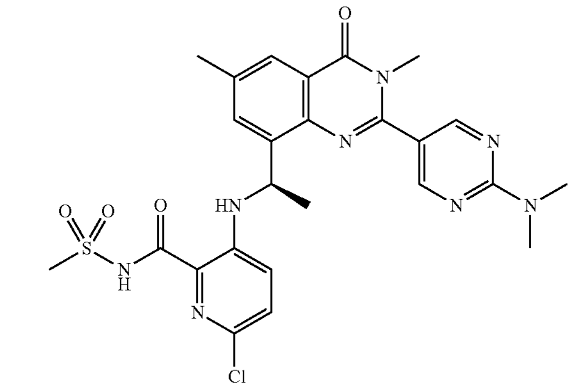 |
| 853 | 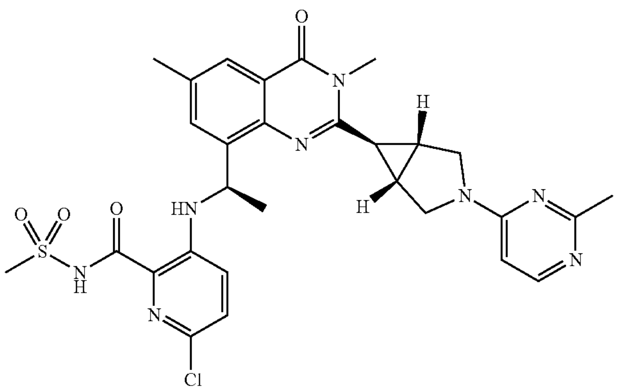 |
| 854 | 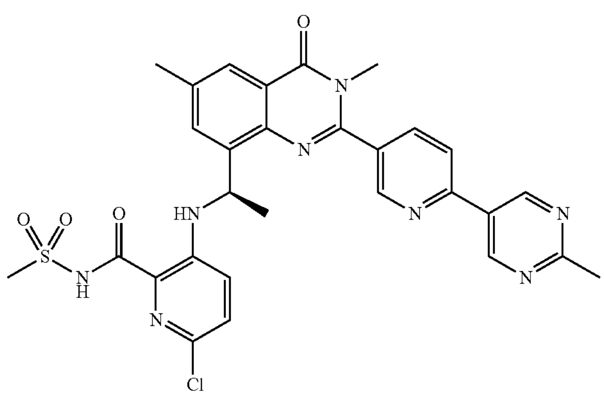 |
| 855 | 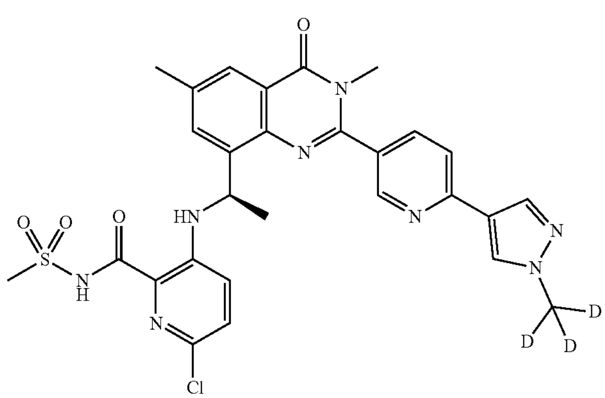 [SMILES: [2H]C([2H])([2H])n1cc(-c2ccc(-c3nc4c([C@@H](C)Nc5ccc(Cl)nc5C(=O)NS(C)(=O)=O)cc(C)cc4c(=O)n3C)cn2)cn1] |

TABLE 1-continued

List of Compounds

| Cpd. ID | Chemical structure |
|---|---|
| 856 | [chemical structure] |

As can be appreciated, the compounds described herein enable the development of new therapies for disease without the need for exotic chemistry or specialized reagents or manufacturing techniques.

III. Pharmaceutical Compositions

Other embodiments are directed to pharmaceutical compositions. In an embodiment, the pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such additional therapeutic agents are described herein below.

Suitable routes of administration include, but are not limited to, oral, intravenous, rectal, aerosol, parenteral, ophthalmic, pulmonary, transmucosal, transdermal, vaginal, optical, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the compound is delivered in a targeted drug delivery system, for example, in a liposome coated with an organ specific antibody, or the compound can be conjugated to an antibody. In such embodiments, the liposomes are targeted to and taken up selectively by the organ. In yet other embodiments, the compound as described herein is provided in the form of a rapid release formulation, in the form of an extended-release formulation, or in the form of an intermediate release formulation. In yet other embodiments, the compound described herein is administered topically.

In treatment methods according to embodiments of the disclosure, an effective amount of at least one compound of Formula (I), (IA)-(IC), (IA-1)-(IA-3), (IB-1)-(IB-3), (IA-a)-(IA-1), (IB-a)-(IB-b), or (II) or of Table 1 is administered to a subject suffering from or diagnosed as having such a disease, disorder, or medical condition. Effective amounts or doses may be ascertained by methods such as modeling, dose escalation studies or clinical trials, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician.

The compounds according to the disclosure are effective over a wide dosage range. For example, in the treatment of adult humans, dosages from about 0.001 to 0.1 mg, 0.01 to 0.1 mg, 0.5 to 5 mg, 0.5 to 10 mg, 0.01 to 10 mg, 0.1 to 10 mg, 10 to 5000 mg, 100 to 5000 mg, 1000 mg to 4000 mg per day, or 1000 to 3000 mg per day are examples of dosages that are used in some embodiments. The exact dosage will depend upon the route of administration, the form in which the compound is administered, the subject to be treated, the body weight of the subject to be treated, and the preference and experience of the attending physician.

In some embodiments, compounds of the disclosure are administered in a single dose. In an embodiment, the single dose is administered orally. In another embodiment, the single dose is administered by injection. However, other routes are used as appropriate. In some embodiments, compounds of the disclosure are administered in multiple doses. In some embodiments, dosing is about once, twice, three times, four times, five times, six times, or more than six times per day. In other embodiments, dosing is about once a month, once every two weeks, once a week, or once every other day. In another embodiment compounds of the disclosure and another agent (e.g., an additional anti-cancer agent) are administered together about once per day to about 6 times per day. In another embodiment the administration of compounds of the disclosure and an agent continues for less than about 7 days. In yet another embodiment the administration continues for more than about 6, 10, 14, 28 days, two months, six months, or one year. In some cases, continuous dosing is achieved and maintained as long as necessary.

Administration of compounds of the disclosure may continue as long as necessary. In some embodiments, compounds of the disclosure are administered for more than 1, 2, 3, 4, 5, 6, 7, 14, or 28 days. In some embodiments, compounds of the disclosure are administered for less than 28, 14, 7, 6, 5, 4, 3, 2, or 1 day. In some embodiments, compounds of the disclosure are administered chronically on an ongoing basis, e.g., for the treatment of chronic effects.

In some embodiments, the compounds of the disclosure are administered in individual dosage forms. It is known in the art that due to intersubject variability in compound pharmacokinetics, individualization of dosing regimen is necessary for optimal therapy.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the disclosed compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising one or more compounds of Formula (I), (IA)-(IC), (IA-1)-(IA-3), (IB-1)-(IB-3), (IA-a)-(IA-1), (IB-a)-(IB-b), or (11) or of Table 1, and a pharmaceutically acceptable carrier. Also provided herein are pharmaceutical compositions comprising one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 and pharmaceutically acceptable diluent(s), excipient(s), and carrier(s). In certain embodiments, the compounds described are administered as pharmaceutical compositions in which one or more compounds selected from compounds of Formula (I), (IA)-(IC), (IA-1)-(IA-3), (IB-1)-(IB-3), (IA-a)-(IA-1), (IB-a)-(IB-b), or (11) or of Table 1 are mixed with other active ingredients, as in combination therapy. Encompassed herein are all combinations of actives set forth in the combination therapies section below and throughout this disclosure. In specific embodiments, the pharmaceutical compositions include one or more compounds of Formula (I), (IA)-(IC), (IA-1)-(IA-3), (IB-1)-(IB-3), (IA-a)-(IA-1), (IB-a)-(IB-b), or (II) or of Table 1.

A pharmaceutical composition, as used herein, refers to a mixture of one or more compounds selected from compounds of Formula (I), (IA)-(TC), (IA-1)-(IA-3), (IB-1)-(IB-3), (IA-a)-(IA-1), (IB-a)-(IB-b), or (II) or of Table 1 with other chemical components, such as carriers, stabilizers, diluents, dispersing agents, suspending agents, thickening agents, and/or excipients. In certain embodiments, the pharmaceutical composition facilitates administration of the compound to an organism. In some embodiments, therapeutically effective amounts of one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 are formulated in aqueous solutions. In specific embodiments, the aqueous solution is selected from, by way of example only, a physiologically compatible buffer, such as Hank's solution, Ringer's solution, or physiological saline buffer. In other embodiments, one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross linked croscarmellose sodium, polyvinylpyrrolidone, agar, or alginic acid or a pharmaceutically acceptable salt thereof such as sodium alginate.

In one embodiment, the oral dosage forms, such as a pill, capsule or tablet, comprises one or more suitable layers or coatings. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push fit capsules made of gelatin, as well as soft, sealed capsules made of gelatin and a plasticizer, such as glycerol or sorbitol. In specific embodiments, push fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds described herein are formulated for parental injection, including formulations suitable for bolus injection or continuous infusion. In specific embodiments, formulations for injection are presented in unit dosage form (e.g., in ampoules) or in multi dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water soluble form. In additional embodiments, suspensions of one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions include at least one pharmaceutically acceptable carrier, diluent or excipient, and one or more compounds selected from compounds of Formula (I), (IA)-(IC), (IA-1)-(IA-3), (IB-1)-(IB-3), (IC), (IA-a)-(IA-1), (IB-a)-(IB-b), or (11) or of Table 1 as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, pharmaceutically acceptable salts for regulating the osmotic pressure, buffers, and/or other therapeutically valuable substances.

Methods for the preparation of compositions comprising the compounds described herein include formulating the compound(s) with one or more inert, pharmaceutically acceptable excipients or carriers to form a solid, semi-solid or liquid composition. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, ointments, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical compositions comprising one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 illustratively takes the form of a liquid where the agents are present in solution, in suspension or both. Typically when the composition is administered as a suspension, a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, aqueous suspensions contain one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally, include solubilizing agents to aid in the solubility of one or more compounds selected from compounds of Formula (I), (IA)-(IC), (IA-1)-(IA-3), (IB-1)-(IB-3), (IA-a)-(IA-1), (IB-a)-(IB-b), or (11) or of Table 1 The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Compositions also, optionally, include one or more pharmaceutically acceptable salts in an amount required to bring osmolality of the composition into an acceptable range. Such pharmaceutically acceptable salts include those having sodium, potassium or ammonium cations and chloride, citrate, ascorbate, borate, phosphate, bicarbonate, sulfate, thiosulfate or bisulfite anions; suitable pharmaceutically acceptable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Compositions may include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Compositions may include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained release system, such as semipermeable matrices of solid hydrophobic polymers containing the therapeutic agent. Various sustained release materials are useful herein. In some embodiments, sustained release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 provided in the pharmaceutical compositions is greater than 90%, 80%, 75%, 70%, 65%, 60%, 55%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v. In another embodiment, the amount of a compound selected from compounds of (1), (IA)-(IC), (IA-1)-(IA-3), (IB-1)-(IB-3), (IA-a)-(IA-1), (IB-a)-(IB-b), or (11) or of Table 1 in the pharmaceutical compositions is an amount between about any two of the values recited in the preceding sentence, for example, between about 2-70 w/w %, 3.5-80 w/w %, 1-30 w/w %, etc.

In some embodiments, the concentration of one or more compounds selected from compounds of Formula (I), (IA)-(IC), (IA-1)-(IA-3), (IB-1)-(IB-3), (IA-a)-(IA-1), (IB-a)-(IB-b), or (II) or of Table 1 provided in the pharmaceutical compositions of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the amount the one or more compounds selected from compounds of Formula (I), (IA)-(IC), (IA-1)-(IA-3), (IB-1)-(IB-3), (IA-a)-(IA-1), (IB-a)-(B-b), or (II) or of Table 1 provided in the pharmaceutical compositions of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds selected from compounds of Formula (I), (IA)-(IC), (IA-1)-(IA-3), (IB-1)-(IIB-3), (IA-a)-(IA-1), (IB-a)-(IB-b), or (II) or of Table 1 provided in the pharmaceutical compositions of the present disclosure is in the range of 0.0001-10 g, 0.0005-9 g, 0.001-8 g, 0.005-7 g, 0.01-6 g, 0.05-5 g, 0.1-4 g, 0.5-4 g, or 1-3 g.

Packaging materials for use in packaging pharmaceutical compositions described herein include those found in, e.g., U.S. Pat. Nos. 5,323,907, 5,052,558 and 5,033,252.

Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container (s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Alternatively, the pack or dispenser device is accompanied by instructions for administration, or the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

As mentioned above, the compounds and compositions of the disclosure will find utility in a broad range of diseases and conditions mediated by protein kinases, including diseases and conditions mediated by kinase. Such diseases may include by way of example and not limitation, cancers such as lung cancer, NSCLC (non-small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colon-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In some embodiments, a pharmaceutical composition has a compound described above and a pharmaceutically acceptable carrier including, for example, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In one embodiment, a pharmaceutical composition comprising the compound of Formula (I), (IA)-(IC), (IA-1)-(IA-3), (IB-1)-(IB-3), (IA-a)-(IA-1), (IB-a)-(IB-b), or (II) or of Table 1 and an additional therapeutic agent is disclosed.

In one embodiment, the compound of (I), (IA)-(IC), (IA-1)-(IA-3), (IB-1)-(IB-3), (IA-a)-(IA-1), (IB-a)-(IB-b), or (11) or of Table 1 or the pharmaceutical composition comprising the compound of Formula (I), (IA)-(IC), (IA-1)-(IA-3), (IB-1)-(IB-3), (IA-a)-(IA-1), (IB-a)-(IB-b), or (II) or of Table 1 and an additional therapeutic agent for use in treating a disease associated with mutations in phosphatidylinositol 3-kinase (PI 3-kinase or PI3K) or phosphatidylinositol 3-kinase catalytic alpha subunit (PI 3-kinase CA or PIK3CA) is disclosed.

In one embodiment, a method of treating a disease associated with mutations in PI3K or PIK3CA, comprises administering the compound of Formula (I), (IA)-(IC), (IA-1)-(IA-3), (IB-1)-(IB-3), (IA-a)-(IA-1), (IB-a)-(IB-b), or (II) or of Table 1 or the pharmaceutical composition comprising the compound of Formula (I), (IA)-(IC), (IA-1)-(IA-3), (IB-1)-(IB-3), (IA-a)-(IA-1), (IB-a)-(IB-b), or (II) or of Table 1 to a subject in need thereof. In one embodiment, the subject is an animal. In some embodiments, the subject is a human. In some embodiments, the disease associated with mutations in PI3K or PIK3CA is a cancer. For example, the cancer associated with mutations in PI3K or PIK3CA includes lung, glioma, esophageal, liver, stomach, uterine, cervical, biliary tract, skin, head and neck, salivary gland, breast, pancreatic, colorectal, renal, bladder, or prostate cancer. In some embodiments, the cancer associated with mutations in PI3K or PIK3CA is lung cancer. In some embodiments, the cancer associated with mutations in PI3K or PIK3CA is glioma cancer. In some embodiments, the cancer associated with mutations in PI3K or PIK3CA is esophageal cancer. In some embodiments, the cancer associated with mutations in PI3K or PIK3CA is liver cancer. In some embodiments, the cancer associated with mutations in PI3K or PIK3CA is stomach cancer. In some embodiments, the cancer associated with mutations in PI3K or PIK3CA is uterine cancer. In some embodiments, the cancer associated with mutations in PI3K or PIK3CA is cervical cancer. In some embodiments, the cancer associated with mutations in PI3K or PIK3CA is biliary tract cancer. In some embodiments, the cancer associated with mutations in PI3K or PIK3CA is skin cancer. In some embodiments, the cancer associated with mutations in PI3K or PIK3CA is head and neck cancer. In some embodiments, the cancer associated with mutations in PI3K or PIK3CA is salivary gland cancer. In some embodiments, the cancer associated with mutations in PI3K or PIK3CA is breast cancer. In some embodiments, the cancer associated with mutations in PI3K or PIK3CA is pancreatic cancer. In some embodiments, the cancer associated with mutations in PI3K or PIK3CA is colorectal cancer. In some embodiments, the cancer associated with mutations in PI3K or PIK3CA is renal cancer. In some embodiments, the cancer associated with mutations in PI3K or PIK3CA is bladder cancer. In some embodiments, the cancer associated with mutations in PI3K or PIK3CA is prostate cancer. In some certain embodiments, the cancer is non-small cell lung cancer.

In one embodiment, the compound of Formula (I), (IA)-(IC), (IA-1)-(IA-3), (IB-1)-(IB-3), (IA-a)-(IA-1), (IB-a)-(IB-b), or (II) or of Table 1 or the pharmaceutical composition comprising the compound of Formula (I), (IA)-(IC), (IA-1)-(IA-3), (IB-1)-(IB-3), (IA-a)-(IA-1), (IB-a)-(IB-b), or (II) or of Table 1 for use in treating a disease associated with mutations in PI3K or PIK3CA, wherein the mutation is on H1047. In some certain embodiments, the mutation is H1047R, H1047L, or H1047Y. In some embodiments, the mutation is H1047R. In some embodiments, the mutation is H1047L. In some embodiments, the mutation is H1047Y.

IV. Methods of Preparation

Preparation methods for the above compounds and compositions are described herein below and/or known in the art.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention. In some embodiments, for example, a phosphate bearing compound of (1), (IA)-(IC), (IA-1)-(IA-3), (IB-1I)-(IB-3), (IA-a)-(IA-1), (IB-a)-(B-b), or (II) or of Table 1 is a prodrug and the structure of such example is described in the disclosure.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The schemes below provide a general description of some of the methodologies used to prepare the compounds described within this disclosure. The methods described may be performed on compounds that are a single enantiomer, enantioenriched, racemic, mixtures of diastereomers, or possible stereochemistries. In some cases, mixtures of stereoisomers can be purified into single enantiomers at any point in the syntheses, including at the end, by using chromatographic separations, crystallizations, or other methods known in literature.

In the schemes below, the variables A, $R^1$, $R^2$, $R^3$, $R^4$, $R^5$, $R^8$, X, Z, and Y are consistent with those already described in the above claims. Additionally, the variables $LG^1$, $LG^2$, $LG^3$, $LG^4$, $LG^5$, $LG^6$, $LG^7$, $PG^1$, $R^{12}$ are described below.

Scheme 1

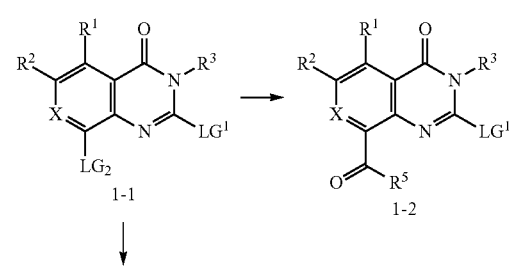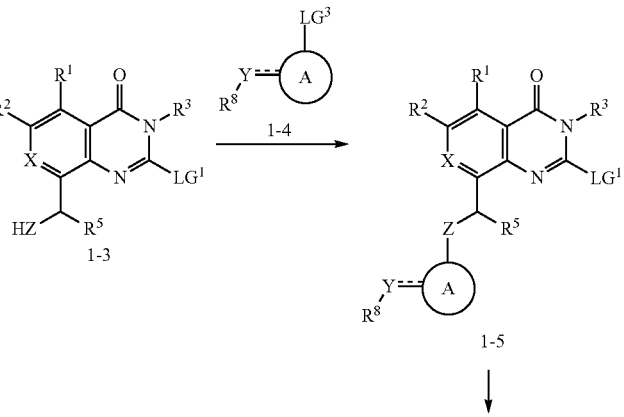

-continued

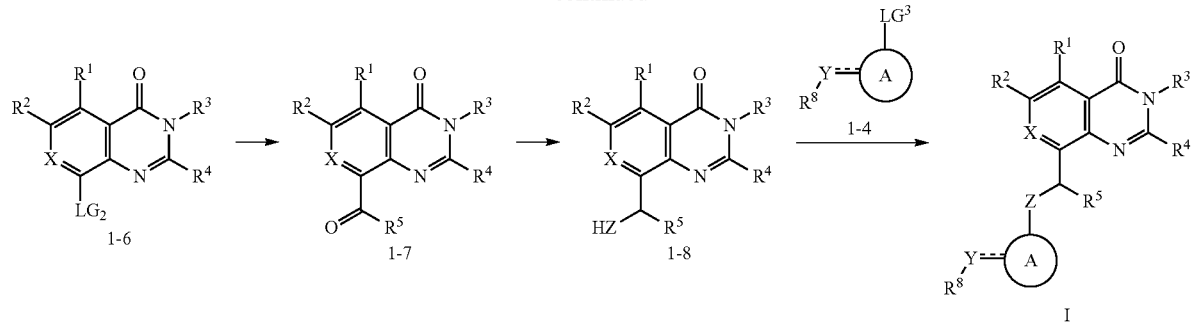

Scheme 1 describes the synthesis of compounds of formula I. Compounds of formula 1-1 (where $LG^1$ and $LG^2$ are each a differentiated leaving group such as a halide (e.g. F, Cl, Br, I), OH, OMs, OTf, S-alkyl, $SO_2$-alkyl, or others and which can be synthesized as described in Scheme 2 or other methods described in literature) can be converted into compounds 1-2 by reacting with metalated (or metalloid) acyl groups or masked acyl groups (such as tributyl(1-ethoxyvinyl) stannane or others) that can be unmasked to reveal a ketone. Alternatively, Compounds 1-1 can be reacted with a metalating reagent such as magnesium, isopropylmagnesium chloride-lithium chloride, n-butyl lithium, or others and treated with an acyl equivalent such as an ester, ketone (to provide an alcohol that could then be oxidized to a ketone using any variety of common reagents), amides such as N-methoxy-N-methylacetamide, or a variety of other electrophilic sources of acyl groups to provide compounds 1-2. Compounds 1-2 could be converted to compounds 1-3 (when Z is nitrogen) either by using standard reductive amination conditions, converting to imines with reagents such as sulfinamides (such as Ellman's tert-butanesulfinamide auxiliary), alkyl-, aryl-, or heteroaryl-amines followed by reduction with a variety of reducing agents such as sodium borohydride or others and subsequent removal of any common protecting groups that may have been installed during the process. Stereochemical outcomes of the reduction would be analogous to others found in literature (for example reducing a chiral N-sulfinyl imine would follow the stereochemical outcomes found in Ellman, et al, J. Org. Chem. 2007, 72, 2, 626-629). Alternatively, compounds 1-2 can be converted into compounds 1-3 (when Z is oxygen) using a reducing agent such as sodium borohydride, DIBAL, Red-Al, $LiAlH_4$, metal-catalysts in the presence of hydrogen, or many other conditions to form alcohols. Compounds 1-3 can be converted to compounds 1-5 by reacting with compounds 1-4 (where $LG^3$ is a leaving group such as a halide, OMs, OTf, $SO_2$Alkyl, or other common leaving group on aromatic or heteroaromatic rings) via a variety of methods including metal-catalyzed cross-coupling reaction utilizing a variety of metal catalysts (e.g. Pd, Cu, or others) and ligands with bases or using nucleophilic aromatic substitution ($S_NAr$) reactions with a variety of organic or inorganic bases such as triethylamine, sodium-, potassium-, or cesium carbonate, and many others. Compounds 1-5 can be converted into I by employing reagents such as BOP, PyBOP, or other coupling agents (when $LG^1$ is OH and $R^4$ is $NR^9R^{10}$ or $OR^9$), by employing $S_NAr$ or activation and metal catalyzed conditions analogous to those described for the conversion of 1-3 to 1-5 (when $R^4$ is $NR^9R^{10}$ or $OR^9$), or by Suzuki coupling (when $R^4$ is an aromatic or heteroaromatic ring and $LG^1$ is a halide, OMs, OTf, or other leaving groups appropriate for cross-coupling) with a variety of metal and ligand combinations such as $Pd(dppf)Cl_2$, palladium tetrakis(triphenylphosphine), or many others in the presence of a base such as potassium phosphate, sodium carbonate, or many others. Alternatively, the reactions in the sequence can be re-ordered such that 1-1 is converted into 1-6 in an analogous manner to the described conversion of 1-5 to I. Compounds 1-6 can be converted to 1-7 in an analogous manner to the described conversion of 1-1 to 1-2. Compounds 1-7 can be converted to 1-8 in an analogous manner to the described conversion of 1-2 to 1-3. Compounds 1-8 can be converted to I in an analogous manner to the described conversion of 1-3 to 1-5.

Scheme 2

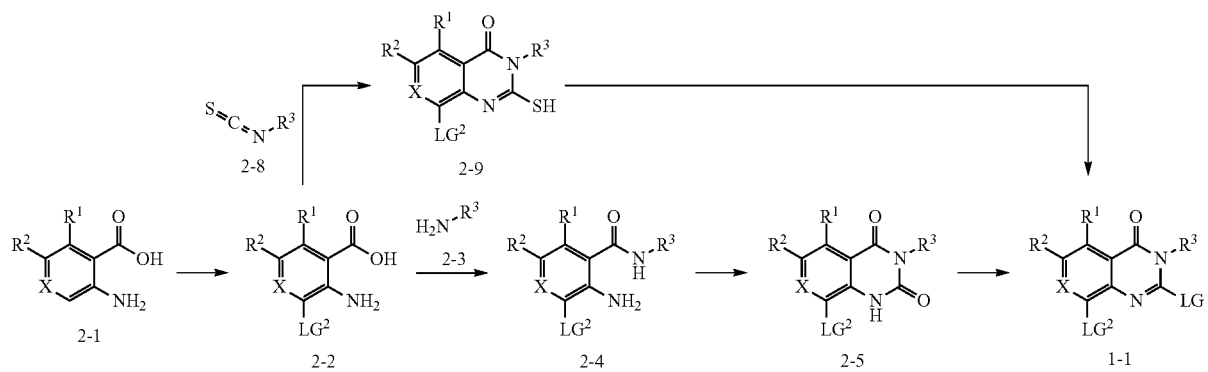

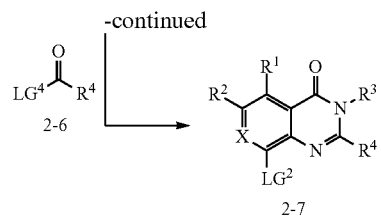

Compounds 1-1 can be synthesized as described in Scheme 2. Compounds 2-1 (which can be purchased or synthesized according to methods described in literature) can be converted to compounds 2-2 through an electrophilic aromatic substitution reaction with reagents such as iodine, bromine, N-halosuccinimides, dichlorodimethylhydantoin, or other similar reagents. Compounds 2-2 can be reacted with amines 2-3 and an amidation reagent such as HATU, CDI, T3P, or many others or by using a reagent such as POCl$_3$, oxalyl chloride, or the like to provide compounds 2-4. Compounds 2-4 can be converted to compounds 2-5 by using an activated carbonyl source such as phosgene, triphosgene, or others. Compounds 2-5 can be converted into compounds 1-1 by using a reagent that turns OH into LG$^1$ such as POCl$_3$, oxalyl chloride, Vilsmeier reagent, mesyl- or p-tosylchloride, triflic anhydride, or many others. Alternatively, compounds 2-4 can converted into compounds 2-7 (a sub-type of compounds 1-6 where R$^4$ is aryl, bicycloaryl, heteroaryl, alkyl, cycloalkyl, cycloheteroalkyl or others previously described) by using compounds 2-6 (where LG$^4$ is any leaving group compatible with a condensation reaction such as OH, O-alkyl or O-aryl, halogen, S-alkyl or S-aryl, NH$_2$, H when an additional oxidant is used, or many other leaving groups described in literature) and conditions such as heat, basic conditions such as sodium methoxide, ethoxide, acidic conditions such as HCl solutions, tosic acid, or many other conditions. Alternatively, compounds 2-2 can be converted to compounds 2-9 (a sub-type of compounds 1-6 where R$^4$ is SH) by reaction with compounds 2-8 in the presence of a variety of organic bases such as trimethylamine, triethylamine, or many others in the presence of heat. 2-9 can be converted to 1-1 via reaction with a variety of alkylating reagents such as MeI, EtI, and the like under basic conditions such as potassium-, sodium-, or cesium carbonate and subsequent oxidation via oxidizing reagents such as mCPBA, oxone, or many others.

Scheme 3

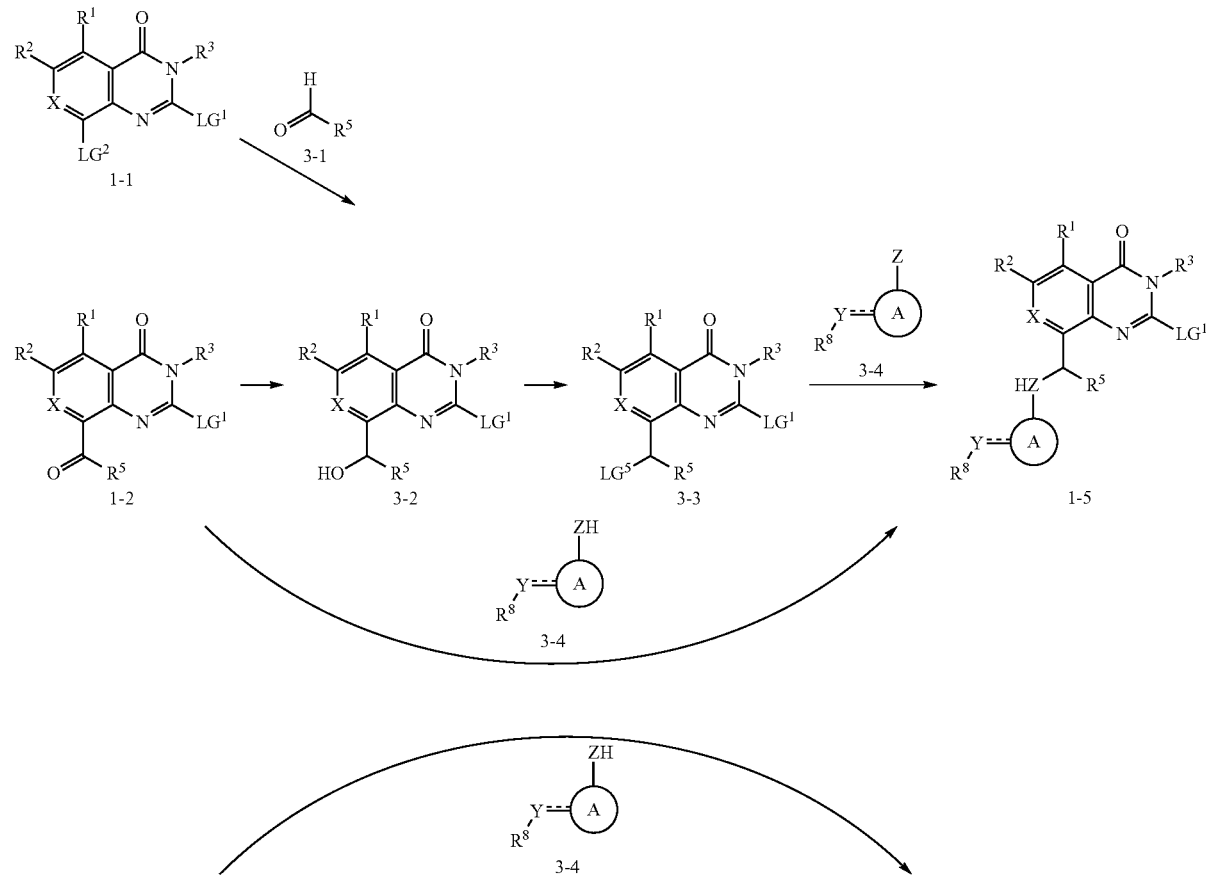

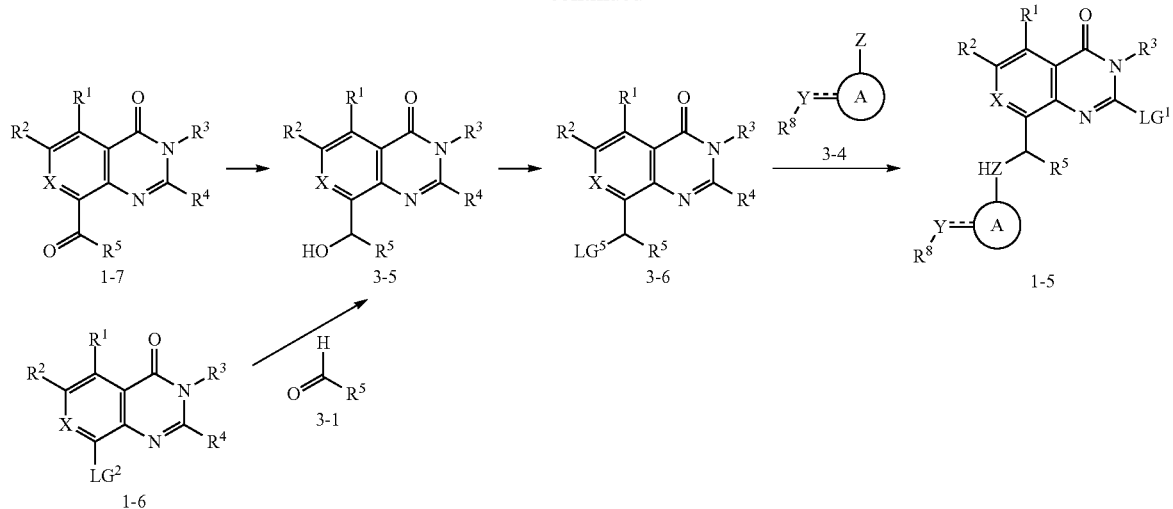

Alternatively, compounds of formula I can be synthesized as shown in Scheme 3. Compounds 1-1 can be metalated in an analogous manner to the described conversion of 1-1 to 1-2 (Scheme 1) and treated with an aldehyde 3-1 to provide compounds 3-2 (a sub-type of compounds 1-3 where Z is oxygen). Alternatively, the ketone of compounds 1-2 can converted to compound 3-2 by using a reducing agent such as sodium- or lithium borohydride, lithium aluminum hydride, diisobutylaluminum hydride or one of many other hydride sources or reducing agents demonstrated to reduce ketones. Compounds 3-2 can be converted into compounds 3-3 (where LG⁵ is a halide such as Cl, Br, or I, or an activated leaving group such as OMs, OTs, OTf, or sometimes OH) by activating the OH into a leaving group using reagents such as phosphorus oxychloride, phosphorus tribromide, triphenylphosphine with iodine, mesylchloride, p-tosylchloride, triflic anhydride, or many other reagents that can convert OH into a leaving group appropriate for nucleophilic substitution. Compounds 3-3 can be reacted with compounds 3-4 (when Z is oxygen or nitrogen) to form compounds 1-5 by stirring in a variety of solvents such as DMF, dichloromethane, THF, acetonitrile, or others in the absence or in the presence of an organic or inorganic base such as triethylamine, diisopropylethylamine, potassium- or sodium carbonate or bicarbonate, or many other bases. Compounds 1-5 can be converted to compounds I as described in Scheme 1. Alternatively, compounds 1-6 or 1-7 can be converted into compounds I using an analogous sequence as described for the conversion of 1-1 or 1-2 into compounds 1-5 as described in Scheme 3. Alternatively, compounds 1-2 can be directly converted into compounds 1-5 using compounds 3-4 (when Z is nitrogen) under reductive amination conditions analogous to those described previously for the conversion of compounds 1-2 to compounds 1-3 (Scheme 1).

Scheme 4

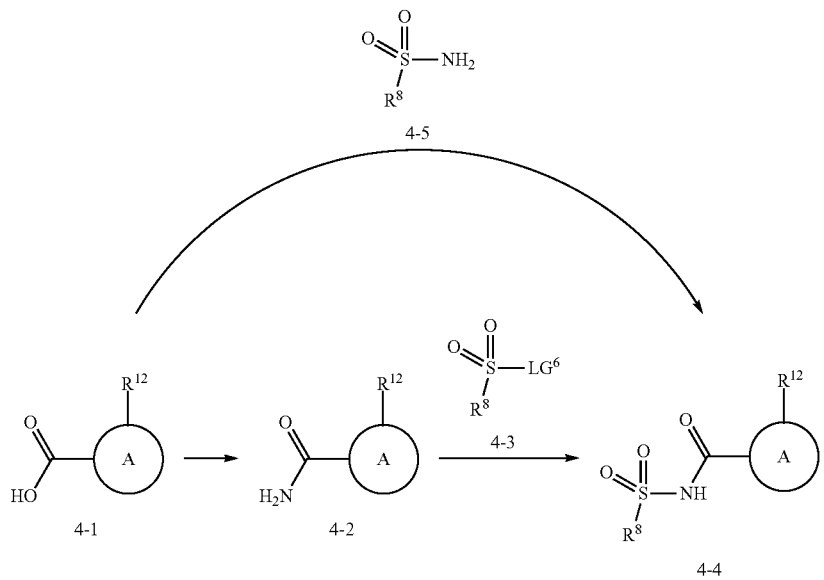

Compounds 4-4 (a subtype of compounds I or 1-5 when $R^{12}$ is defined as the rest of the molecule of compounds I or 1-5 (attached at Z); or a subtype of compounds 1-4 when $R^{12}$ is $LG^3$; or a subtype of compounds 3-4 when $R^{12}$ is ZH) can be synthesized as shown in Scheme 4. Compounds 4-1 (which can be purchased or synthesized using analogous methods described in literature) can be converted into compounds 4-2 using a variety of amidation conditions using a reagent such as ammonia, ammonia in a solvent such as methanol, ammonium chloride, ammonium hydroxide, or other source of ammonia and a coupling reagent such as CDI, T3P, HATU, HOBT, phosphorus oxychloride, oxalyl chloride, Mukaiyama reagent or any other reagents that facilitate amidation. Compounds 4-2 can be reacted with compounds 4-3 (where $LG^6$ is a halide such as F or Cl, imidazole, O-alkyl, or another leaving group compatible with sulfonyl functional groups) in the absence or presence of an organic or inorganic base such as triethylamine, DMAP, imidazole, pyridine, potassium- or sodium carbonate or bicarbonate, or any other bases that are compatible with a sulfonylation reaction to form compounds 4-4. Alternatively, compounds 4-1 can be converted directly into compounds 4-4 by reacting with compounds 4-5 using amidation coupling conditions such as those described for the conversion of 4-1 into 4-2 (but using 4-5 instead of an ammonia source).

Scheme 5

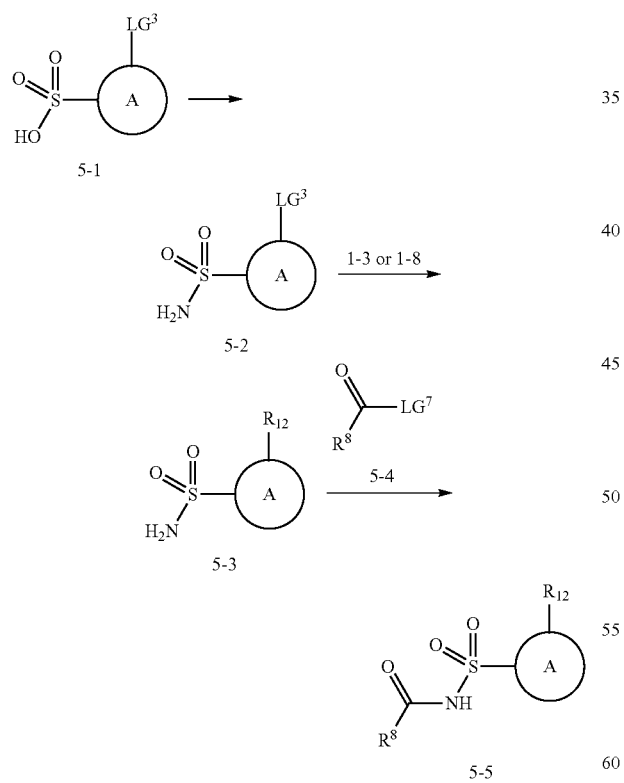

Compounds 5-5 (a subtype of compounds I or 1-5 when $R^{12}$ is defined as the rest of the molecule of compounds I or 1-5 (attached at Z) and Y is acyl sulfonamide as shown; or a subtype of compounds 1-4 when $R^{12}$ is $LG^3$; or a subtype of compounds 3-4 when $R^{12}$ is ZH) can be synthesized as described in Scheme 5. Compounds 5-1 (which can be purchased or synthesized using analogous methods described in literature) can be converted into compounds 5-2 using a variety of amidation conditions using a reagent such as ammonia, ammonia in a solvent such as methanol, ammonium chloride, ammonium hydroxide, or other source of ammonia and a coupling reagent such as sulfuryl chloride or others. Compounds 5-2 can be reacted with compounds 1-3 or 1-8 in the presence of an organic base such as triethylamine, DMAP, DIPEA or other base compatible with $S_NAr$ reactions under heating conditions to provide compounds 5-3. Compounds 5-3 can be reacted with compounds 5-4 (where $LG^7$ is a halide such as Cl, imidazole, O-alkyl, or another leaving group compatible with acylation chemistry in the absence or presence of an organic or inorganic base such as triethylamine, DIPEA, DMAP, imidazole, pyridine, potassium- or sodium carbonate or bicarbonate, or any other bases that are compatible with an acylation reaction to form compounds 5-5. Alternatively, compounds 5-3 can be reacted with compounds 5-4 (when $LG^7$ is OH) using amidation conditions similar to those described for the transformation of compounds 4-1 into 4-4 (Scheme 4) to provide compounds 5-5.

Scheme 6

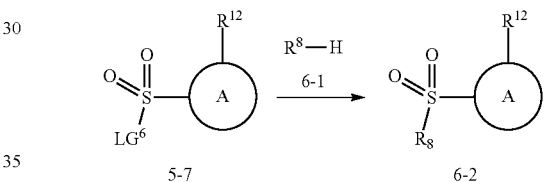

Compounds 6-2 (a subtype of compounds I or 1-5 when $R^{12}$ is defined as the rest of the molecule of compounds I or 1-5 (attached at Z); or a subtype of compounds 1-4 when $R^{12}$ is $LG^3$; or a subtype of compounds 3-4 when $R^{12}$ is ZH; and where $R^8$ is a primary or secondary amine containing fragment as previously described) can be synthesized as described in Scheme 6. Compounds 5-7 (which can be purchased or synthesized using analogous methods described in literature) can be converted into compounds 6-2 by reacting with amines 6-1 in an analogous manner to the conversion of compounds 4-3 to 4-4.

Scheme 7

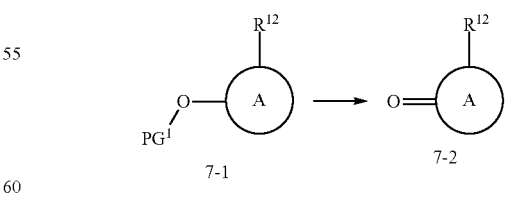

Compounds 7-2 (a subtype of compounds I or 1-5 when $R^{12}$ is defined as the rest of the molecule of compounds I or 1-5 (attached at Z); or a subtype of compounds 1-4 when $R^{12}$ is $LG^3$; or a subtype of compounds 3-4 when $R^{12}$ is ZH; and Y is O as shown) can be synthesized as described in Scheme 7. Compound 7-1 (which can be purchased or synthesized using analogous methods as described in literature and where PG$^1$ can be any number of oxygen protecting groups such as methyl, SEM, silyl protecting groups, carbamates, esters, or many others) can be converted to compounds 7-2 via deprotection reagents such as BBr$_3$, HBr, NaSMe, HCl, NaOMe, TBAF, and many others.

V. List of Exemplary Embodiments

The invention is further described by the following non-limiting exemplary embodiments:

Embodiment 1. A compound having the following structure of Formula (I):

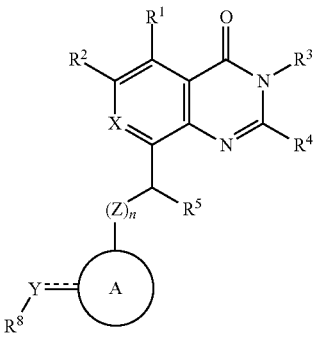

(I)

or a stereoisomer of the compound, tautomer of the compound, or a salt thereof, wherein:

X is CR$^7$ or N;

Z is CHR$^6$, NR$^6$, or O;

n is an integer between 0 and 1;

R$^1$, R$^2$, and R$^7$ are, each independently, a hydrogen, halo, C$_1$-C$_3$ alkyl. C$_1$-C$_3$ heteroalkyl, 3-7 membered cycloalkyl;

R$^3$ is a hydrogen, C$_1$-C$_3$ alkyl. C$_1$-C$_3$ heteroalkyl, C$_3$-C$_7$ cycloalkyl, 4-6 membered heterocycloalkyl, aryl, or heteroaryl;

R$^5$ and R$^6$ are, each independently, a hydrogen, C$_1$-C$_3$ alkyl, or C$_1$-C$_3$ heteroalkyl;

R$^4$ is —NR$^9$R$^{10}$, —OR$^9$, C$_1$-C$_6$ heteroalkyl, 3-12 membered cyclic, or 3-12 membered heterocyclic;

R$^9$ and R$^{10}$ are, each independently, a hydrogen, C$_1$-C$_6$ alkyl, C$_3$-C$_7$ cycloalkyl, C$_3$-C$_7$ heterocycloalkyl;

A is a 5-6 membered aryl, 5-6 membered heteroaryl, heterobicyclic, or unsaturated 5-6 membered heterocycle;

Y is —SO$_2$NHC(=O)—, —C(=O)NHSO$_2$—, —SO$_2$—, or O;

=== is a single bond when Y is —SO$_2$NHC(=O)—, —C(=O)NHSO$_2$—, or —SO$_2$— or a double bond when Y is O; and R$^8$ is a hydrogen, halo, —OR$^{11a}$, —NR$^{11a}$R$^{11b}$, C$_3$-C$_7$ cycloalkyl, 3-6 membered heterocycloalkyl, C$_1$-C$_4$ alkyl, C$_1$-C$_4$ haloalkyl, aryl, heteroaryl, or absent, wherein R$^{11a}$ and R$^{11b}$ are, each independently, a hydrogen, C$_1$-C$_3$ alkyl, C$_3$-C$_7$ cycloalkyl, C$_3$-C$_7$ heterocycloalkyl, aryl, or heteroaryl.

Embodiment 2. The compound of embodiment 1, wherein the compound has one of the following structures of Formula (IA)-(IB):

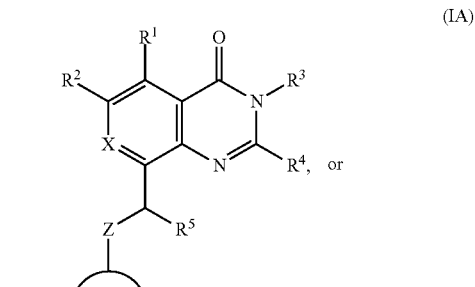

(IA)

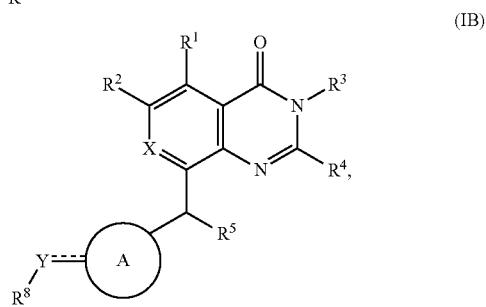

(IB)

or a stereoisomer, tautomer of the compound, or a salt thereof.

Embodiment 3. The compound of any one of embodiments 1-2, wherein the 5-6 membered aryl of A is a phenyl.

Embodiment 4. The compound of any one of embodiments 1-2, wherein the 5-6 membered heteroaryl of A is a pyrrole, imidazole, pyrazole, triazole, pyridine, diazine, triazine, thiazole, isothiazole, oxazole, or isoxazole.

Embodiment 5. The compound of embodiment 4, wherein the 5-6 membered heteroaryl of A has one of the following structures:

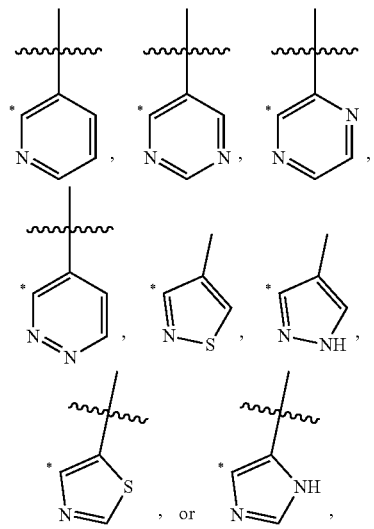

wherein * indicates a bond to Y.

Embodiment 6. The compound of any one of embodiments 1-2, wherein the unsaturated, 5-6 membered heterocycle of A is 1,2-dihydropyridine, 1,4-dihydropyridine, 2,3-dihyydropyridine, 2,5-dihydropyridine, 1,2-dihydropyridazine, or 1,4-dihydropyridazine.

Embodiment 7. The compound of embodiment 6, wherein the unsaturated 5-6 membered heterocycle of A has one of the following structures:

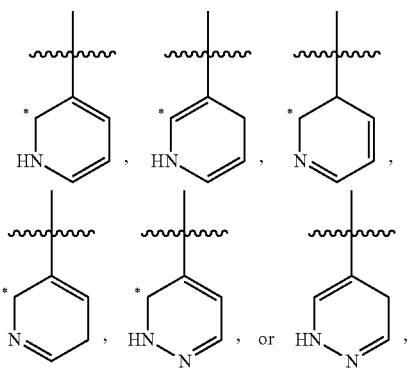

wherein * indicates a bond to Y.

Embodiment 8. The compound of any one of embodiments 1-2, wherein the heterobicyclic of A comprises a 5 membered heterocycle and a 6 membered aryl or a 5 membered heterocycle and a 6 membered heteroaryl.

Embodiment 9. The compound of any one of embodiments 1-2, wherein the heterobicyclic of A comprises a 5 membered heteroaryl and a 6 membered aryl or a 5 membered heteroaryl and a 6 membered heteroaryl.

Embodiment 10. The compound of compound of any one of embodiments 1-2, wherein the heterobicyclic of A is benzimidazole, indazole, imidazopyridine, or pyrazolopyridine.

Embodiment 11. The compound of embodiment 10, wherein the heterobicyclic of A has one of the following structures:

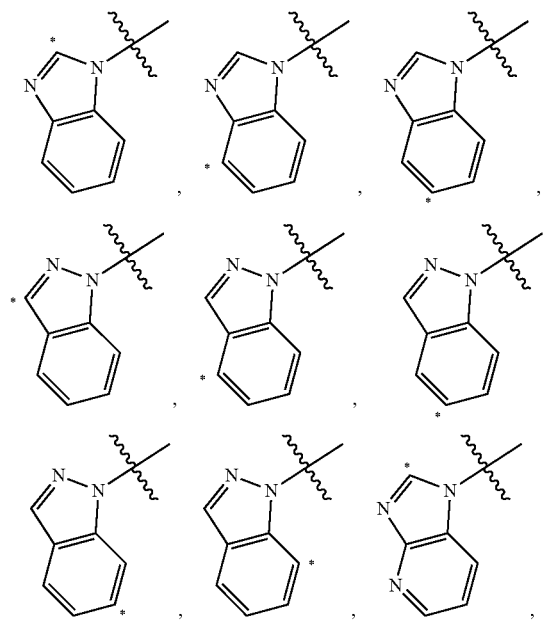

-continued

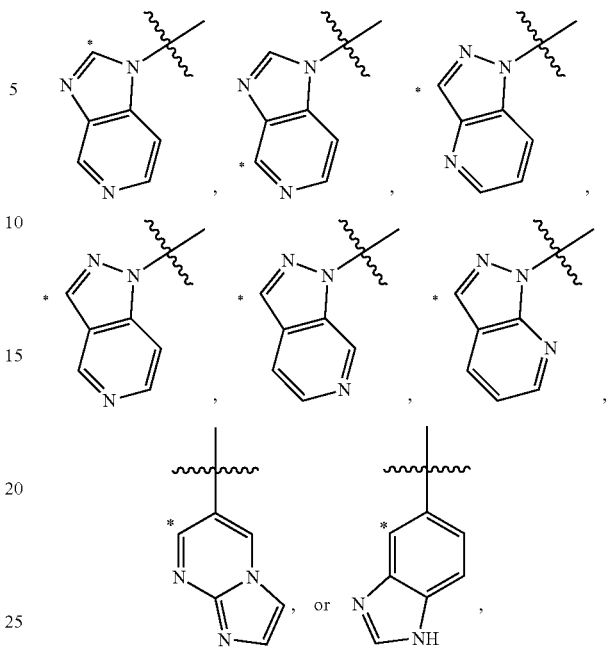

wherein * indicates a bond to Y.

Embodiment 12. The compound of any one of embodiments 1-11, wherein the 5-6 membered aryl, 5-6 membered heteroaryl, heterobicyclic, or unsaturated 5-6 membered heterocycle of A is further substituted with cyano, halo, $C_1$-$C_3$ alkyl, $C_1$-$C_3$ heteroalkyl, or 3-7 membered cycloalkyl.

Embodiment 13. The compound of embodiment 12, wherein the 5-6 membered aryl, 5-6 membered heteroaryl, heterobicyclic, or unsaturated 5-6 membered heterocycle of A is further substituted with —CN, —Br, —Cl, —F, —CH$_3$, —CH$_2$CH$_3$, cyclopropyl, —OCH$_3$, —NHCH$_3$, —NHCH$_2$CH$_3$, —CF$_3$, —CH$_2$CF$_3$, or —CF$_2$H.

Embodiment 14. The compound of embodiment 13, wherein the 5-6 membered aryl, 5-6 membered heteroaryl, heterobicyclic, or unsaturated 5-6 membered heterocycle of A is mono-, di-, or tri-substituted.

Embodiment 15. The compound of any one of embodiments 1-14, wherein Y is

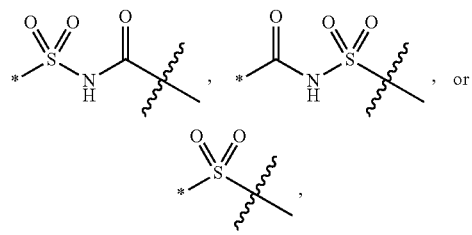

wherein * indicates a bond to R$^8$.

Embodiment 16. The compound of any one of embodiments 1-15, wherein Y is O and R$^8$ is absent.

Embodiment 17. The compound of any one of embodiments 1-16, wherein the compound has one of the following structures of Formula (IA-1)-(IC):

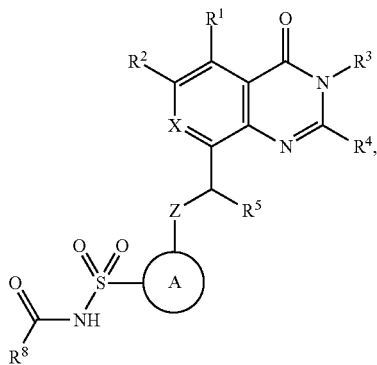
(IA-1)

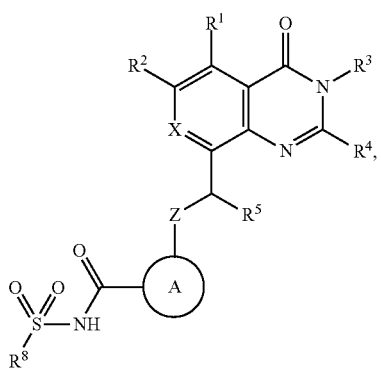
(IA-2)

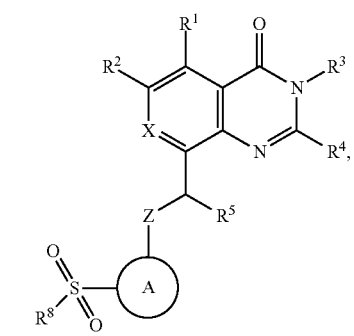
(IA-3)

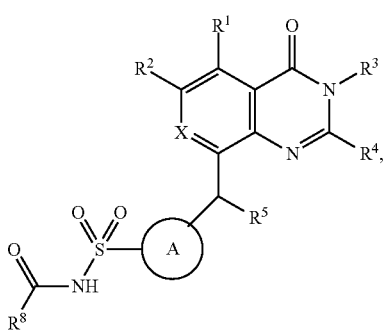
(IB-1)

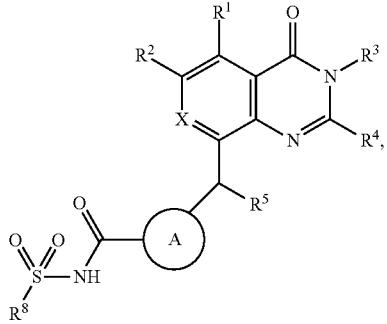
(IB-2)

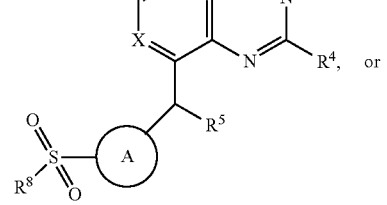
(IB-3)

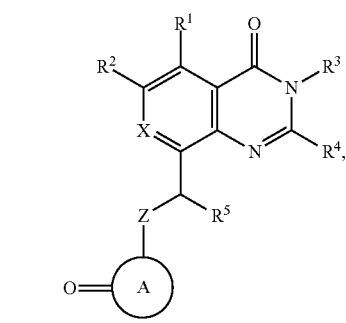
(IC)

or a stereoisomer, tautomer of the compound, or a salt thereof.

Embodiment 18. The compound of any one of embodiments 1-17, wherein $R^1$, $R^2$, and $R^7$ are, each independently, a hydrogen, halo, $C_1$ alkyl, $C_1$ heteroalkyl, or 3-5 membered cycloalkyl.

Embodiment 19. The compound of any one of embodiments 1-18, wherein $R^1$, $R^2$, and $R^7$ are, each independently, —H, —F, —CH$_3$, or cyclopropyl.

Embodiment 20. The compound of any one of embodiments 1-19, wherein $R^1$ is —H, R is —CH$_3$, and $R^7$ is —H.

Embodiment 21. The compound of any one of embodiments 1-19, wherein $R^1$ is —H, $R^2$ is —F, and $R^7$ is —H.

Embodiment 22. The compound of any one of embodiments 1-19, wherein $R^1$ is —F, $R^2$ is —F, and $R^7$ is —H.

Embodiment 23. The compound of any one of embodiments 1-19, wherein $R^1$ is —H, $R^2$ is —H, and $R^7$ is —H.

Embodiment 24. The compound of any one of embodiments 1-19, wherein $R^1$ is —CH$_3$ or —CH$_2$CH$_3$, $R^2$ is —H, and $R^7$ is —H.

Embodiment 25. The compound of any one of embodiments 1-24, wherein the 4-6 membered heterocycloalkyl of $R^3$ has 1-3 nitrogen atoms.

Embodiment 26. The compound of any one of embodiments 1-25, wherein the 4-6 membered heterocycloalkyl of $R^3$ has 1-2 oxygen atoms.

Embodiment 27. The compound of any one of embodiments 1-26, wherein the 4-6 membered heterocycloalkyl of $R^3$ is oxetane, azetidine, dioxetane, pyrrolidine, tetrahydrofuran, imidazolidine, pyrazolidine, oxazolidine, isoxazolidine, dioxolane, triazole, furazan, oxadiazole, piperidine, oxane, diazinane, morpholine, dioxane, triazinane, or trioxane.

Embodiment 28. The compound of any one of embodiments 1-27, wherein $R^3$ is a hydrogen, $C_1$-$C_2$ alkyl, $C_1$-$C_2$ heteroalkyl, or a 4 membered heterocycloalkyl.

Embodiment 29. The compound of any one of embodiments 1-28, wherein $R^3$ is —H, —$CH_3$, —$CH_2CH_3$, or

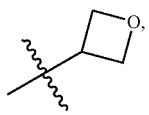 [SMILES: *C1COC1]

Embodiment 30. The compound of any one of embodiments 1-29, wherein $R^5$ and $R^6$ are, each independently, a hydrogen, $C_1$-$C_2$ alkyl, or $C_1$-$C_2$ heteroalkyl.

Embodiment 31. The compound of any one of embodiments 1-30, wherein $R^1$ and $R^6$ are, each independently, —H, —$CH_3$, —$CH_2OH$, or —$CH_2CH_3$.

Embodiment 32. The compound of any one of embodiments 1-31, wherein $R^5$ is —$CH_2OH$.

Embodiment 33. The compound of any one of embodiments 1-32, wherein $R^3$ is —H, —$CH_3$, or

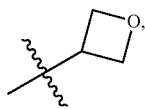 [SMILES: *C1COC1]

$R^5$ is —$CH_3$, and $R^6$ is —H.

Embodiment 34. The compound of any one of embodiments 1-33, wherein $R^4$ is $C_1$-$C_4$ heteroalkyl.

Embodiment 35. The compound of any one of embodiments 1-34, wherein $R^4$ is $C_1$-$C_4$ alkylamine, monosubstituted alkylamine, or disubstituted alkylamine.

Embodiment 36. The compound of embodiment 35, wherein $R^4$ is N-methyl alkylamine or N,N-dimethyl alkylamine.

Embodiment 37. The compound of any one of embodiments 1-33, wherein the 3-12 membered cyclic of $R^4$ is an aryl.

Embodiment 38. The compound of embodiment 37, wherein the 3-12 membered cyclic of $R^4$ is a phenyl.

Embodiment 39. The compound of any one of embodiments 1-33, wherein the 3-12 membered cyclic of $R^4$ is a cyclohexanyl.

Embodiment 40. The compound of any one of embodiments 1-33, wherein the 3-12 membered heterocyclic of $R^4$ has 1-4 nitrogen atoms.

Embodiment 41. The compound of embodiment 40, wherein the 3-12 membered heterocyclic of $R^4$ has 1-3 nitrogen atoms and 1 sulfur or 1 oxygen atom.

Embodiment 42. The compound of any one of embodiments 1-33, wherein the 3-12 membered heterocyclic of $R^4$ has 1-2 oxygen atoms.

Embodiment 43. The compound of any one of embodiments 1-33, wherein the 3-12 membered heterocyclic of $R^4$ is monocyclic or bicyclic.

Embodiment 44. The compound of embodiment 43, wherein $R^4$ is a saturated mono-heterocyclic.

Embodiment 45. The compound of embodiment 44, wherein the saturated mono-heterocyclic of $R^4$ is azetidine, pyrrolidine, piperidine, 1,4-diazinane, morpholine, oxazepane, azapane, diazepane, or azocane.

Embodiment 46. The compound of embodiment 44, wherein the saturated mono-heterocyclic of $R^4$ has one of the following structures:

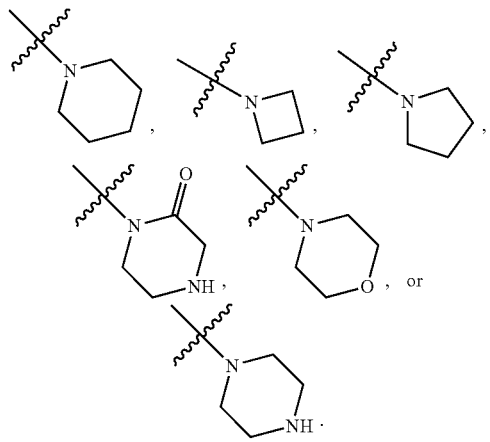

Embodiment 47. The compound of embodiment 43, wherein $R^4$ is an unsaturated mono-heterocyclic.

Embodiment 48. The compound of embodiment 47, wherein the unsaturated mono-heterocyclic of $R^4$ is azirine, azete, oxete, thiete, pyrrole, furan, thiophene, imidazole, pyrazole, oxazole, isoxazole, pyrimidine, pyridazine, pyrazine, oxadiazole, thiadiazole, tetrazole, thiazole, isothiazole, triazole, pyridine, pyran, thiopyran, diazine, oxazine, or triazine.

Embodiment 49. The compound of embodiment 43, wherein the unsaturated mono-heterocyclic of $R^4$ has one of the following structures:

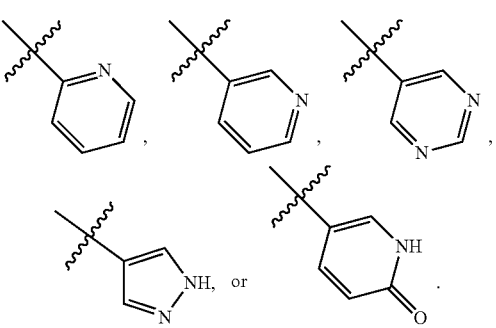

Embodiment 50. The compound of embodiment 43, wherein the bicyclic of $R^4$ is a fused heterobicyclic, a spiro heterobicyclic, or a bridged heterobicyclic.

Embodiment 51. The compound of embodiment 50, wherein the fused heterobicyclic of $R^4$ is 4,5,6,7-tetrahydro-[1,2,3]triazolo[1,5-a]pyrazine, 4,5,6,7-tetrahydro-2H-pyrazolo[4,3-c]pyridine, 5,6,7,8-tetrahydro-[1,2,4]triazolo[4,3-a]pyrazine, 4,5,6,7-tetrahydro-3H-[1,2,3]triazolo[4,5-c]pyridine, 5,6,7,8-tetrahydroimidazo[1,5-a]pyrazine, 5,6,7,8-tetrahydro-[1,2,4]triazolo[1,5-a]pyrazine, 4,5,6,7-tetrahydro-3H-imidazo[4,5-c]pyridine, 1,2,3,4-tetrahydro-2,7-naphthyridine, 3-azabicyclo[3.1.0]hexane, 2H-pyrazolo[3,4-b]pyridine, octahydropyrrolo[3,4-c]pyrrole, 1H-benzo[d]imidazole, 1,2,3,4-tetrahydroisoquinoline, 3,4- dihydroquinolin-2(11-1)-one, benzo[d]thiazole, imidazo[1,2-a]pyridine, isoxazolo[5,4-b]pyridine, octahydropyrrolo[1,2-a]pyrazine, 11-indole, benzo[d]oxazole, pyrazolo[1,5-a]pyridine, isoindoline, 1,4,5,6-tetrahydropyrrolo[3,4-c]pyrazole, [1,2,4]triazolo[1,5-a]pyridine, 1H-indazole, 2H-indazole, 1,4,5,6-tetrahydropyrrolo[3,4-c]pyrazole, 6,7-dihydro-5H-pyrrolo[3,4-d]pyrimidine, 5,6,7,8-tetrahydro-1,7-naphthyridine, or 6,7-dihydro-5-H-pyrrolo[3,4-b]pyridine.

Embodiment 52. The compound of embodiment 50, wherein the fused heterobicyclic of $R^4$ has one of the following structures:

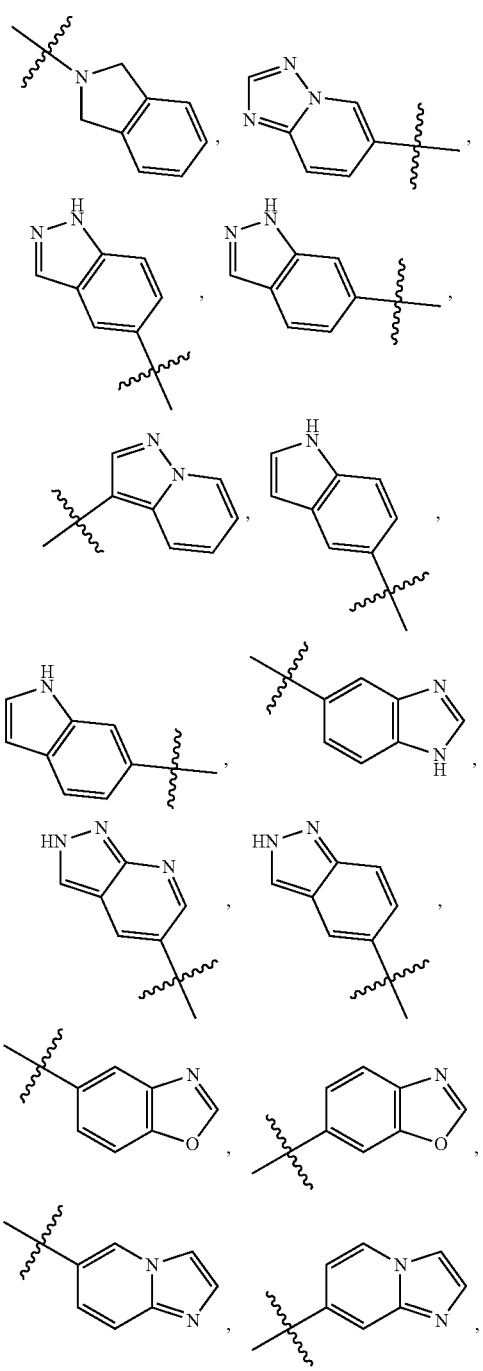

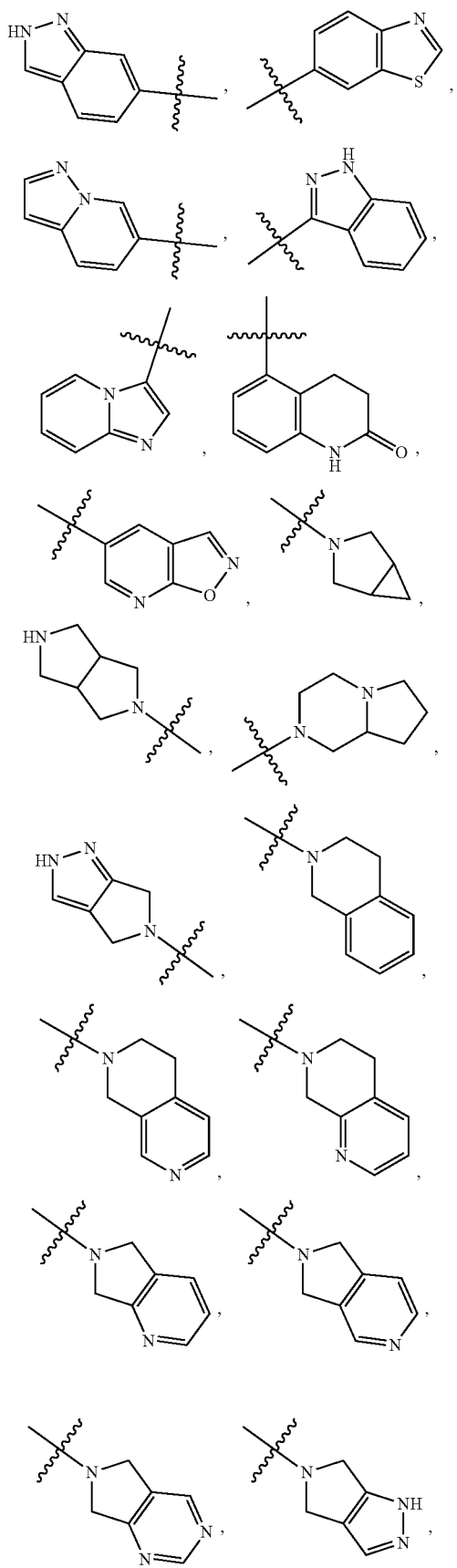

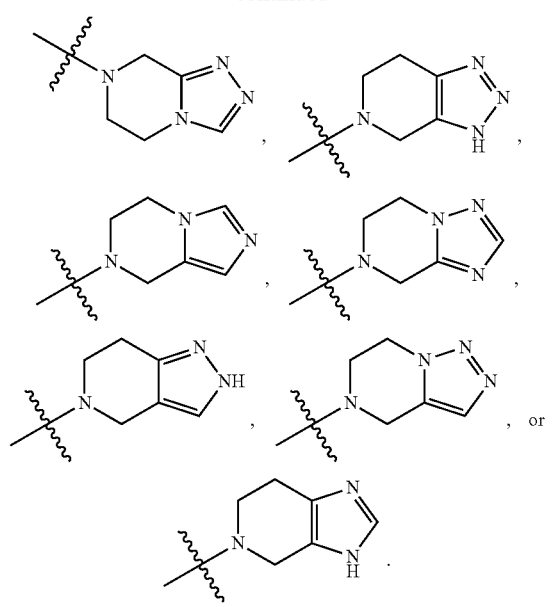

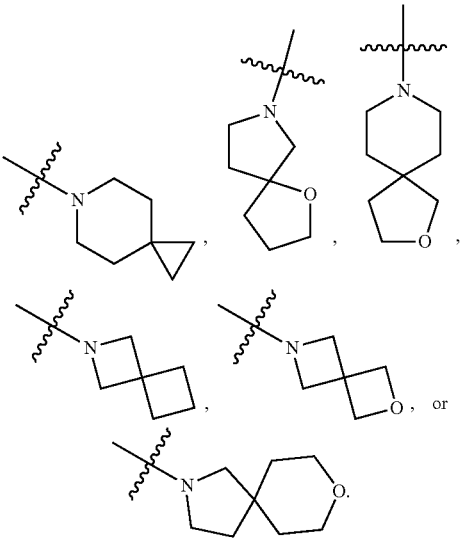

Embodiment 53. The compound of embodiment 50, wherein the bridged heterobicyclic of $R^4$ is 3-azabicyclo[3.1.1]heptane, 7-azabicyclo[2.2.1]heptane, 2-oxa-5-azabicyclo[2.2.1]heptane, 3,8-diazabicyclo[3.2.1]octane, 2,5-diazabicyclo[2.2.2]octane, 8-azabicyclo[3.2.1]octane, 3,6-diazabicyclo[3.1.1]heptane, (1S,4S)-2-oxa-5-azabicyclo[2.2.1]heptane, or (1R,4R)-2-oxa-5-azabicyclo[2.2.1]heptane.

Embodiment 54. The compound of embodiment 50, wherein the bridged heterobicyclic of $R^4$ has one of the following structures:

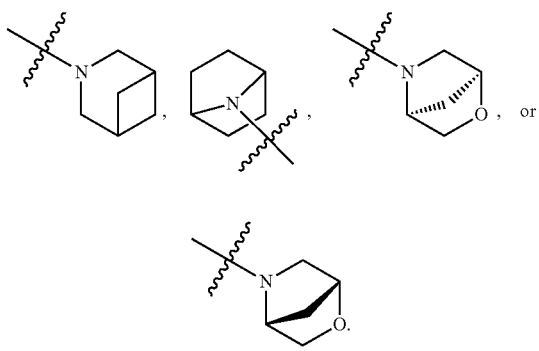

Embodiment 55. The compound of embodiment 50, wherein the spiro heterobicyclic of $R^4$ is 6-azaspiro[2.5]octane, 1-oxa-7-azaspiro[4.4]nonane, 2-oxa-8-azaspiro[4.5]decane, 2,6-diazaspiro[3.3]heptane, 1,6-diazaspiro[3.3]heptane, 2-azaspiro[3.3]heptane, 1,6-diazaspiro[3.4]octane, 2,6-diazaspiro[3.4]octane, 2,7-diazaspiro[3.5]nonane, 2,8-diazaspiro[4.5]decane, 8-oxa-2-azaspiro[4.5]decane, 3,9-diazaspiro[5.5]undecane, 4,8-diazaspiro[2.5]octane, 5,9-diazaspiro[3.5]honane, 6,10-diazaspiro[4.5]decane, or 1,5-diazaspiro[5.5]undecane.

Embodiment 56. The compound of embodiment 50, wherein the spiro heterobicyclic of $R^4$ has one of the following structures:

Embodiment 57. The compound of any one of embodiments 1-56, wherein the $C_1$-$C_6$ heteroalkyl, 3-12 membered cyclic, or 3-12 membered heterocyclic of $R^4$ is further substituted with a halo, —$NH_2$, —OH, —CN, —C(=O)$CH_3$, $C_1$-$C_6$ alkyl, $C_1$-$C_4$ alkyl-CN, $C_1$-$C_4$ alkyl-OH, $C_3$ cycloalkyl, $C_3$ cycloalkyl-CN, bicyclo[1.1.1]pentane, $C_1$-$C_6$ heteroalkyl, aryl, or heteroaryl.

Embodiment 58. The compound of any one of embodiments 1-57, wherein the $C_1$-$C_6$ heteroalkyl, 3-12 membered cyclic, aryl, or 3-12 membered heterocyclic of $R^4$ is further substituted with —$NH_2$, —F, —Cl, —$CH_3$, —$CF_3$, —OH, —CN, —C(=O)$CH_3$, —$(CH_2)_2$OH, —$OCH_3$, —$N(CH_3)_2$, cyclopropyl, pyridinyl, phenyl, diazinyl, tetrahydropyranyl, cyclohexanoyl,

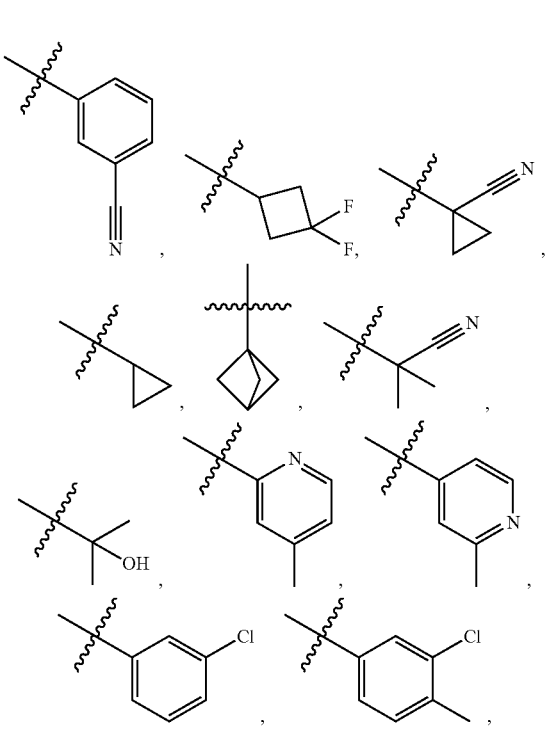

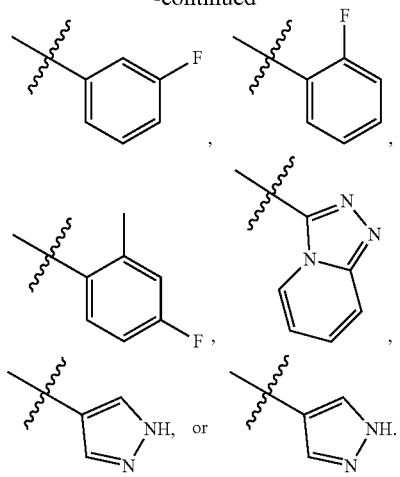

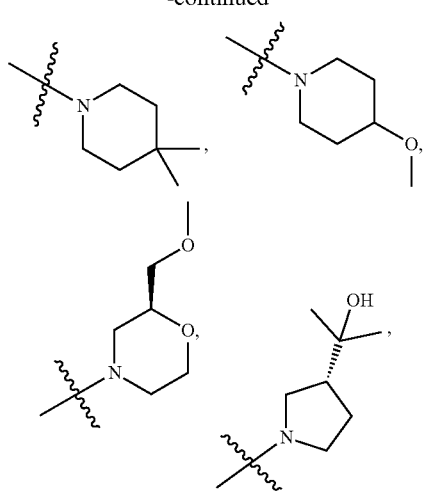

Embodiment 59. The compound of any one of embodiments 1-58, wherein $R^9$ and $R^{10}$ are, each independently, H, $C_1$-$C_3$ alkyl, $C_3$-$C_7$ cycloalkyl, or $C_3$-$C_7$ heterocycloalkyl.

Embodiment 60. The compound of any one of embodiments 1-59, wherein the $C_3$-$C_7$ cycloalkyl of $R^9$ and $R^{10}$ are, each independently, cyclobutane, cyclopentane, cyclohexane, cycloheptane, or bicyclo[1.1.1]pentane.

Embodiment 61. The compound of any one of embodiments 1-59, wherein the $C_3$-$C_7$ heterocycloalkyl of $R^9$ and $R^{10}$ are, each independently, tetrahydropyrane, tetrahydrofuran, or oxetane.

Embodiment 62. The compound of any one of embodiments 1-59, wherein the $C_1$-$C_3$ alkyl of $R^9$ and $R^{10}$ is further substituted with an aryl or a benzyl.

Embodiment 63. The compound of any one of embodiments 1-62, wherein $C_1$-$C_6$ heteroalkyl, 3-12 membered cyclic, aryl, or 3-12 membered heterocyclic of $R^4$ is mono-, di-, or tri-substituted.

Embodiment 64. The compound of any one of embodiments 1-63, wherein $R^4$ has one of the following structures:

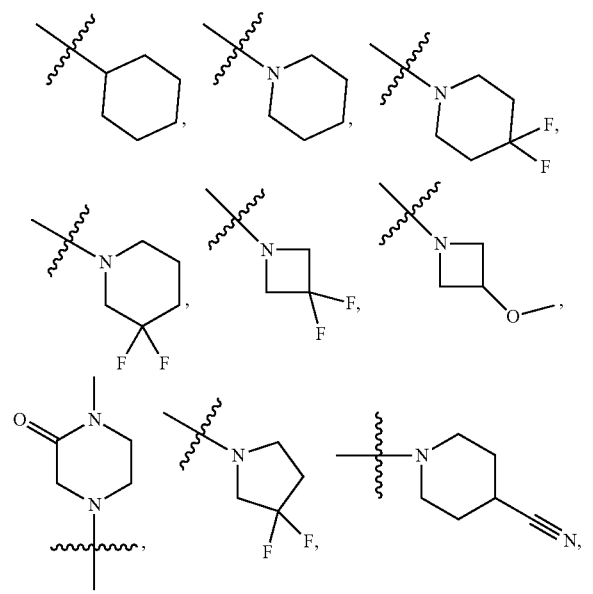

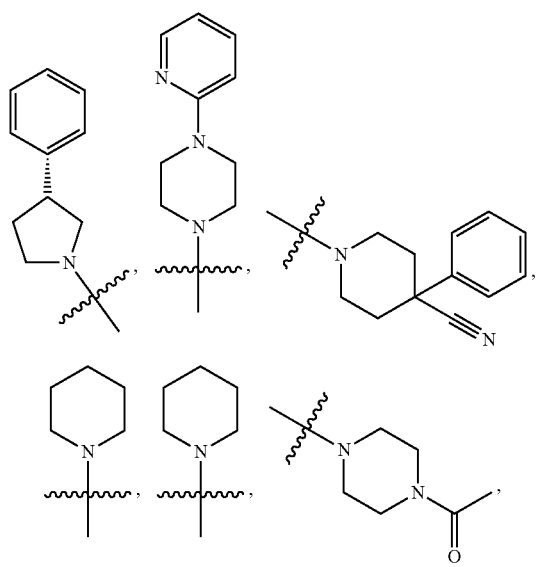

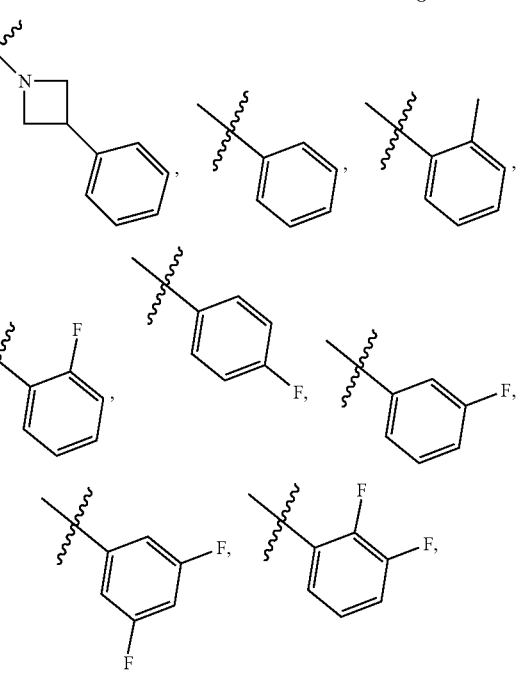

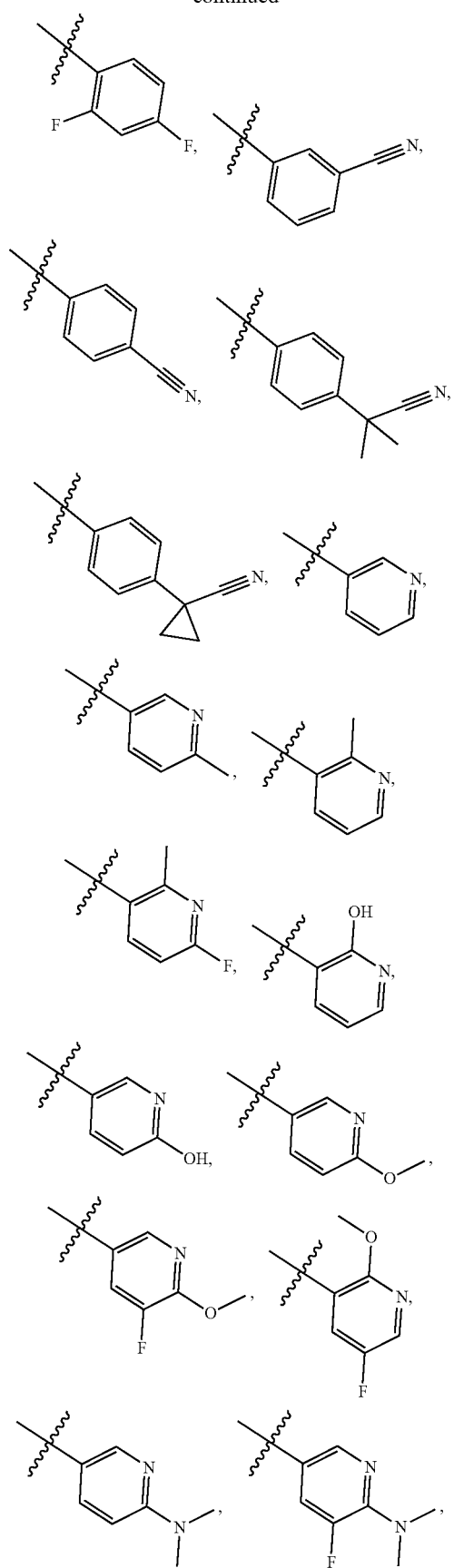
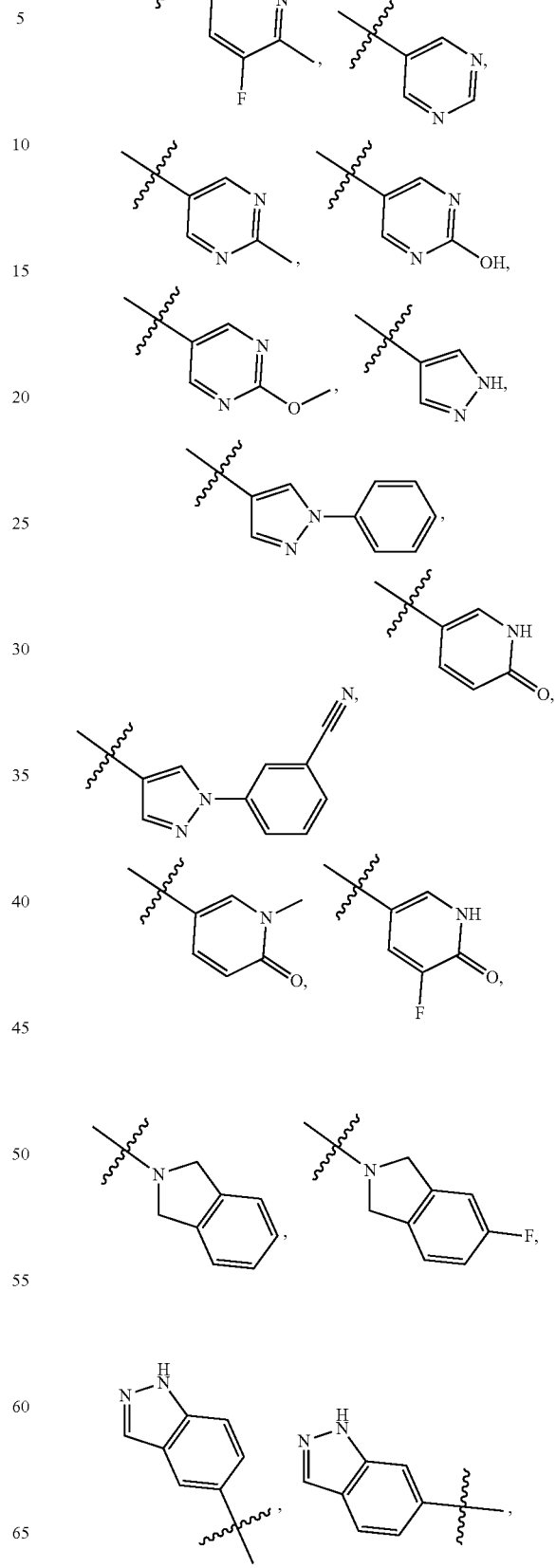

609
-continued
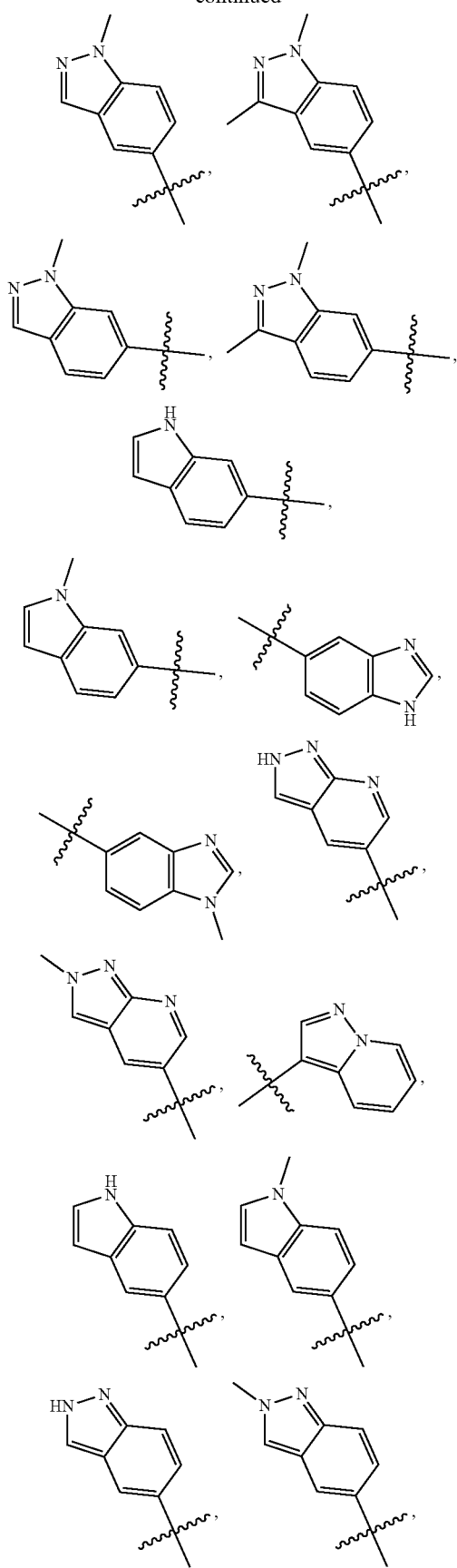
610
-continued
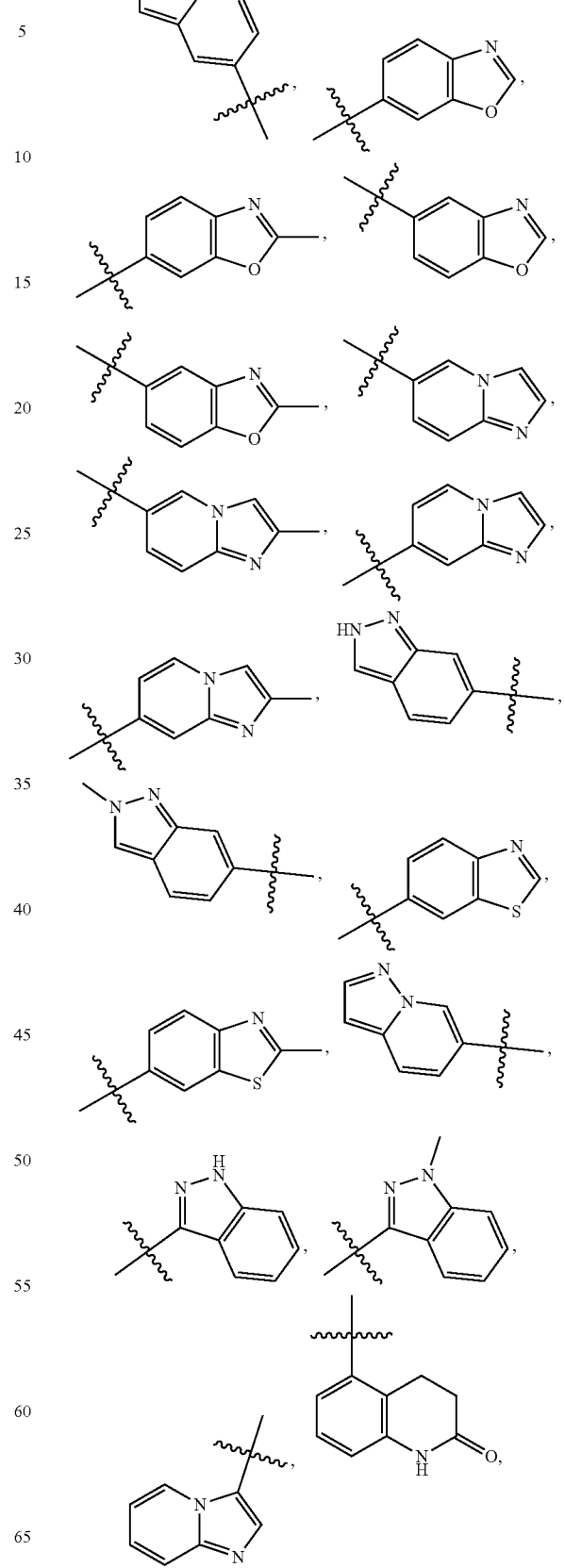

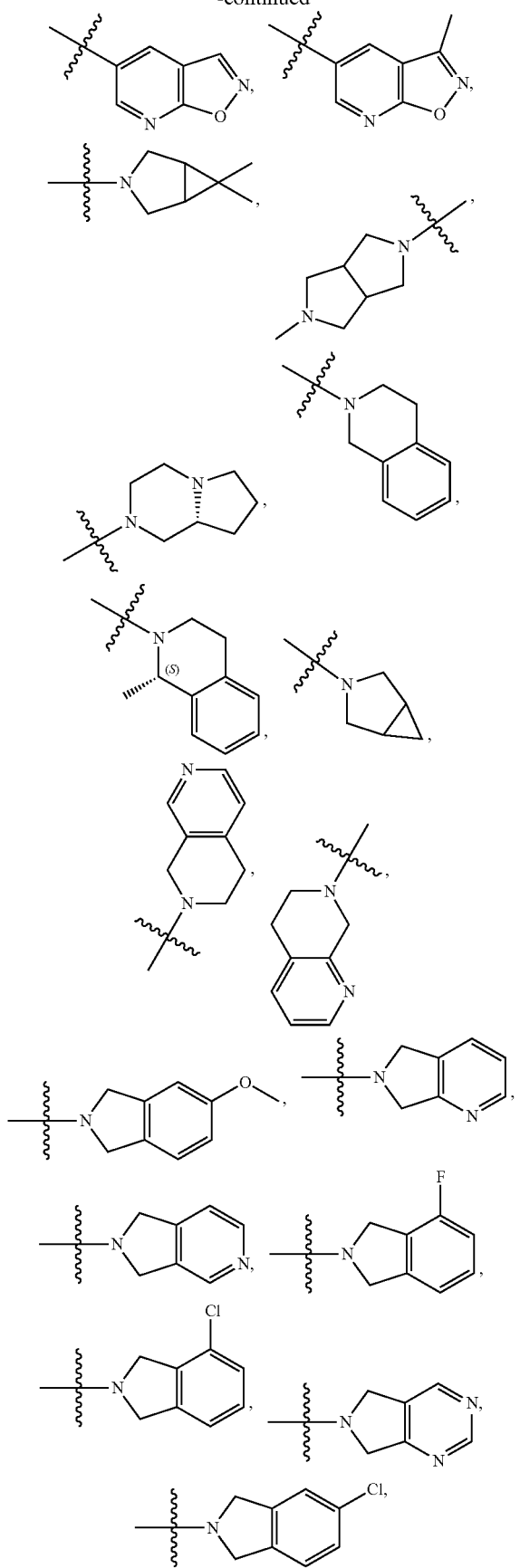
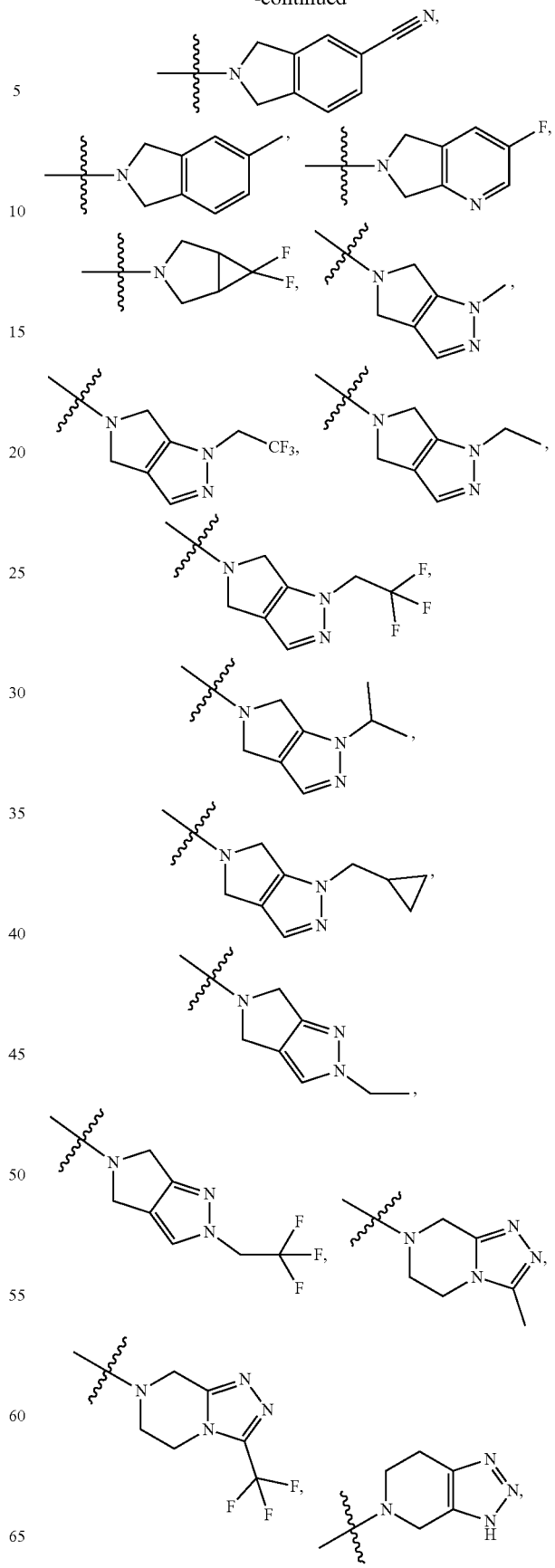

613
-continued
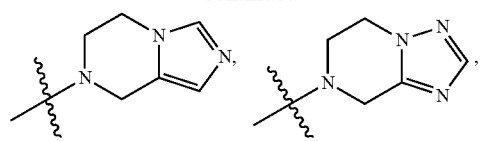
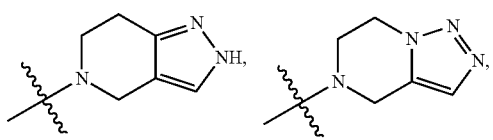
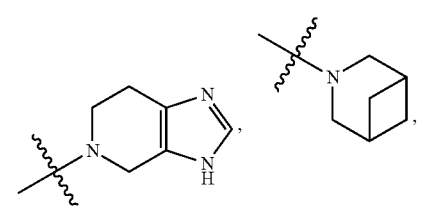
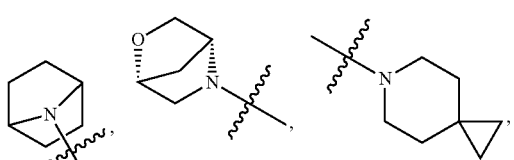
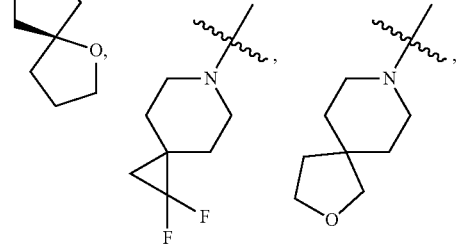
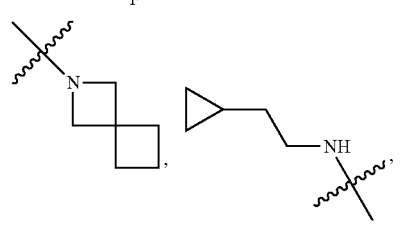
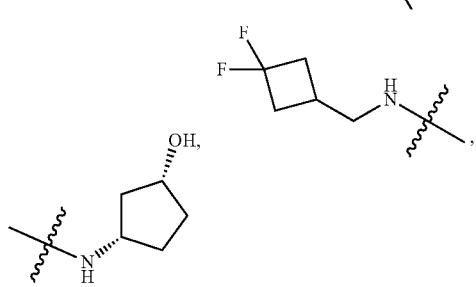
614
-continued
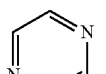
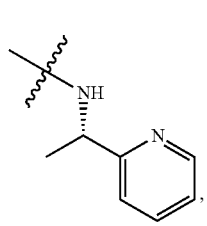
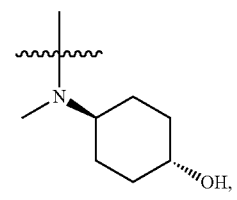
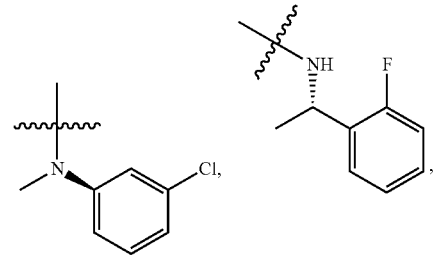
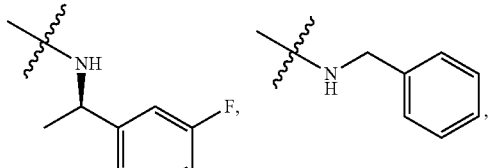
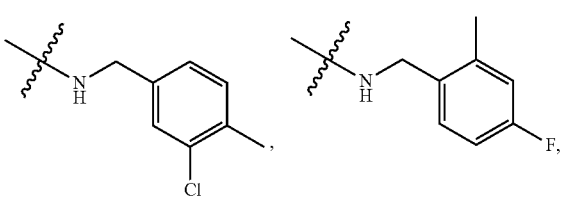
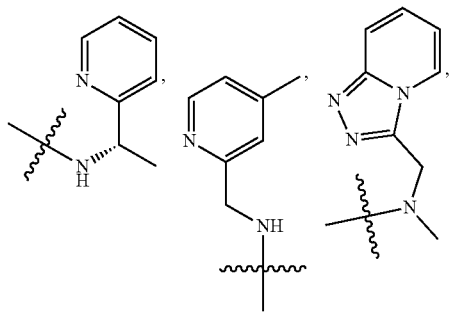
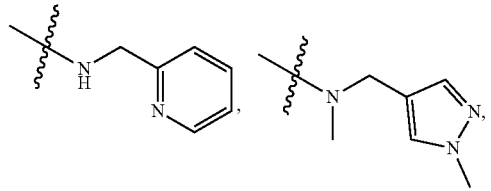

615
-continued
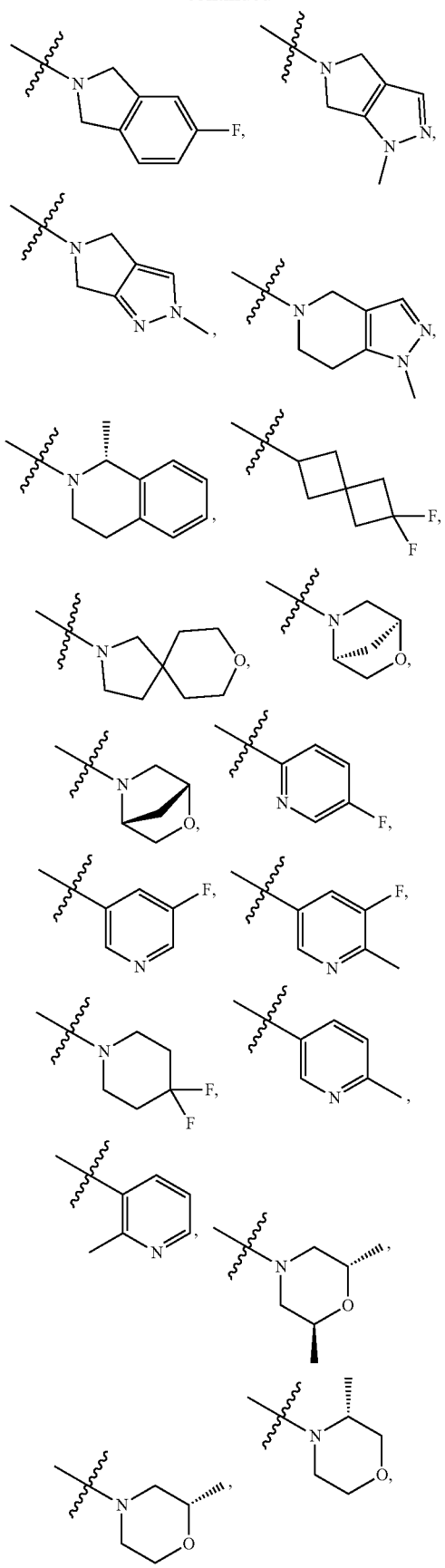
616
-continued
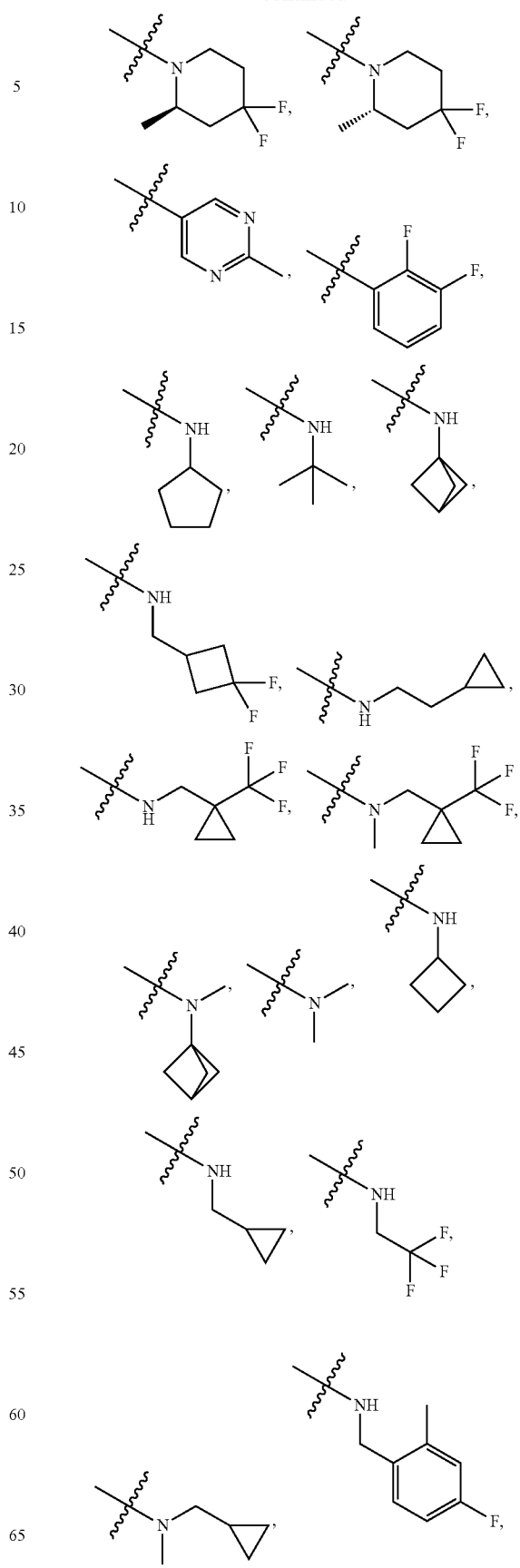

-continued

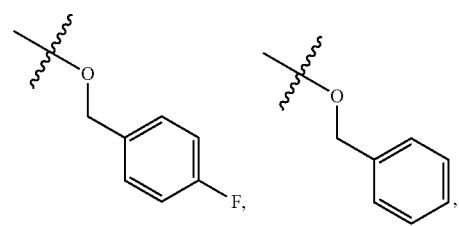

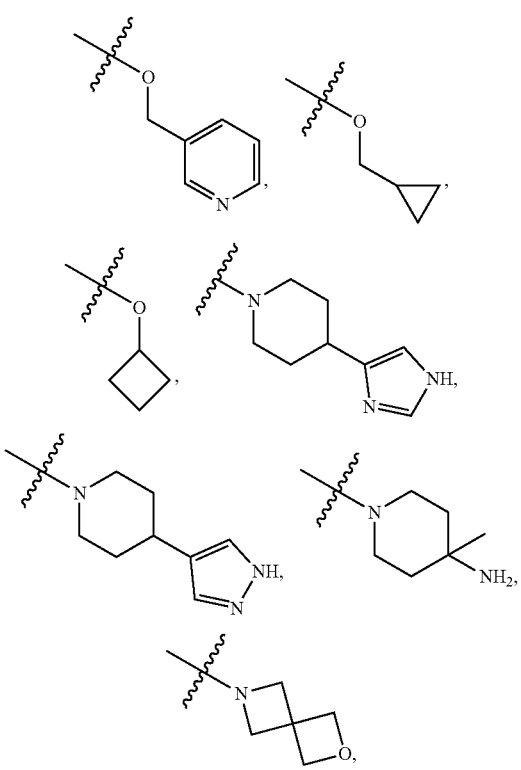

-continued

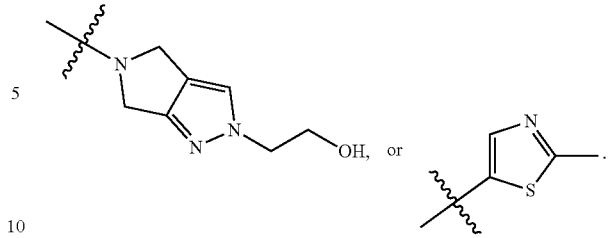

Embodiment 65. The compound of any one of embodiments 1-64, wherein $R^8$ is hydrogen, halo, —$OR^{11a}$, —$NR^{11a}R^{11b}$, $C_3$-$C_6$ cycloalkyl, $C_1$-$C_3$ haloalkyl, or absent.

Embodiment 66. The compound of any one of embodiments 1-65, wherein $R^8$ in Formula (IA)-(IB) is, each independently, —H, halo, —$OR^{11a}$, —$NR^{11a}R^{11b}$, $C_3$-$C_6$ cycloalkyl, 4-6 membered heterocycloalkyl, heteroaryl, or $C_1$-$C_3$ haloalkyl.

Embodiment 67. The compound of any one of embodiments 1-66, wherein $R^8$ in Formula (IA)-(IB) is, each independently, —H, —F, —$N(CH_3)_2$, —$NHCH_3$, —$OCH_3$, $C_3$-cycloalkyl, 4-6 membered heterocycloalkyl, heteroaryl, —$CF_2$-1, or —$CF_3$.

Embodiment 68. The compound of embodiment 67, wherein the heteroaryl or $R^8$ in Formula (IA)-(II) is further substituted with $C_1$-$C_4$ alkyl.

Embodiment 69. The compound of any one of embodiments 1-64, wherein the $C_1$-$C_3$ alkyl of $R^{11a}$ or $R^{11b}$ is further substituted with a 4-6 membered heterocycloalkyl.

Embodiment 70. The compound of embodiment 69, wherein the $C_1$-$C_3$ alkyl of $R^{11a}$ or $R^{11b}$ is further substituted with a 5 membered heterocycloalkyl.

Embodiment 71. The compound of embodiment 70, wherein the 5 membered heterocycloalkyl is a tetrahydrofuran or pyrrolidine.

Embodiment 72. The compound of embodiment 71, wherein the $C_1$-$C_3$ alkyl of $R^{11a}$ or $R^{11b}$ substituted with a 5 membered heterocycloalkyl is

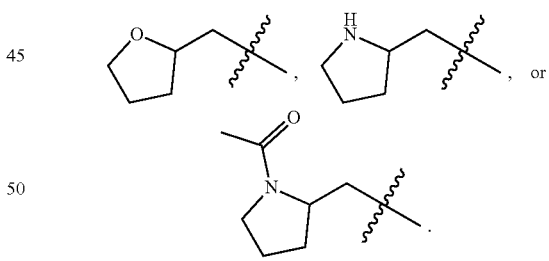

Embodiment 73. The compound of any one of embodiments 1-72, wherein X is $CR^7$ and $R^7$ is H.

Embodiment 74. The compound of embodiment 1, wherein the compound has one of the structures selected from Compound Nos. 1-163 of Table 1.

Embodiment 75. A pharmaceutical composition comprising the compound of embodiment 1 and a therapeutic agent.

Embodiment 76. The compound of any one of embodiments 1-74 or the pharmaceutical composition of embodiment 75 for use in treating a disease associated with mutations in phosphoinositide 3-kinase (PI 3-kinase or PI3K) or phosphatidylinositol 3-kinase catalytic alpha subunit (PI 3-kinase CA or PIK3CA).

Embodiment 77. The compound of any one of embodiments 1-74 or the pharmaceutical composition of embodiment 75 for use, wherein the mutation is on H1047.

Embodiment 78. The compound of any one of embodiments 1-74 or the pharmaceutical composition of embodiment 75 for use, wherein the mutation is H1047R, H1047L, or H1047Y.

Embodiment 79. The compound of any one of embodiments 1-74 or the pharmaceutical composition of embodiment 75 for use, wherein the mutation is H1047R.

Embodiment 80. A method of treating a disease associated with mutations in PI3K, comprising: administering the compound of any one of embodiments 1-74 or the pharmaceutical composition of embodiment 75 to a subject in need thereof.

Embodiment 81. The method of embodiment 80, wherein the subject is an animal.

Embodiment 82. The method of any one of embodiments 80-81, wherein the subject is a human.

Embodiment 83. The method of any one of embodiments 80-82, wherein the disease associated with mutations in PI3K is a cancer.

Embodiment 84. The method of any one of embodiments 80-83, wherein the cancer is lung, glioma, esophageal, liver, stomach, uterine, cervical, biliary tract, skin, head and neck, salivary gland, breast, pancreatic, colorectal, renal, bladder, or prostate cancer.

EXAMPLES

The following section describes abbreviations used in the examples and includes examples for making intermediate compounds (Examples 1-3) and examples for making compounds 1-108 (Examples 4-10).

I. Abbreviations

ACN: Acetonitrile
Aq.: Aqueous
$BBr_3$: Boron tribromide
$Cs_2CO_3$: Cesium Carbonate
DavePhos: 2-Dicyclohexylphosphino-2'-(N,N-dimethylamino)biphenyl
DBU: 1,8-Diazabicyclo[5.4.0]undec-7-ene
DCM: Dichloromethane
DIPEA: N,N-Diisopropylethylamine
DMA: N,N-Dimethylacetamide
DMF: N,N-Dimethylformamide
DMSO: Dimethyl sulfoxide
EDC: 1-(3-Dimethylaminopropyl)-3-ethylcarbodiimide
EtOAc: Ethyl acetate
$Et_3N$: Triethylamine
H: hour(s)
HATU: 2-(3H-[1,2,3]triazolo[4,5-b]pyridin-3-yl)-1,1,3,3-tetramethylisouronium hexafluorophosphate(V)
HCl: Hydrochloric acid
$H_2O$: Water
HPLC: High-performance liquid chromatography
IPA: Isopropyl alcohol
$K_2CO_3$: Potassium carbonate
KOAc: Potassium acetate
KOH: Potassium hydroxide
LCMS: Liquid chromatography mass spectrometry
MeCN: Acetonitrile
MeI: Methyl iodide
MeOH: Methanol
$MgSO_4$: Magnesium sulfate
Ms: Methanesulfonyl
MOA: Mode of analysis
$NaBH_4$: Sodium borohydride
$NaHCO_3$: Sodium bicarbonate
NaOH: Sodium hydroxide
$Na_2SO_4$: Sodium sulfate
Pd/C: Palladium on activated carbon
$PdCl_2(PPh_3)_2$: Palladium(II)bis(triphenylphosphine)dichloride
$Pd_2(dba)_3$: Tris(dibenzylideneacetone)dipalladium(0)
PhMe: Toluene
$POCl_3$: Phosphorus oxychloride
$PPh_3$: Triphenylphosphine
Pt/C: Platinum on activated carbon
Qt: Quantity
Quant: Quantitative
RT: Room temperature
Sat.: Saturated
$SOCl_2$: Thionyl chloride
SPhos: 2-dicyclohexylphosphino-2,6-dimethoxy-1,1-biphenyl
Tf: Trifluoromethanesulfonyl
TLC: Thin layer chromatography
TFA: 2,2,2-Trifluoroacetic acid
THF: Tetrahydrofuran
$Ti(OiPr)_4$: Titanium tetraisopropoxide
Ts: p-Toluenesulfonyl

II. LCMS Methods

The following section describes analytical methods to provide LCMS data for making intermediate and final disclosed herein.

TABLE E1

| LCMS Method A: | |
| --- | --- |
| Instrument: | AQUITY H-Class with PDA detector and SQD |
| Column | C18, 50*2.1 mm, 1.6 µm |
| Mobile Phase | (A) 0.1% Formic acid in Milli Q water (pH = 2.70) |
| | (B) 0.1% Formic acid in water:Acetonitrile (10:90) |
| Column Temperature | 35° C. |
| Auto sampler Temperature | 5° C. |
| Run Time: | 4 min |

| Gradient table for AQUITY with PDA detector and SQD | | | |
| --- | --- | --- | --- |
| TIME (Minute) | (%)A | (%)B | Flow (ml/min) |
| 0.00 | 97 | 03 | 0.8 |
| 0.20 | 97 | 03 | 0.8 |

TABLE E1-continued

| 2.70 | 02 | 98 | 0.8 |
| 3.00 | 00 | 100 | 1.0 |
| 3.50 | 00 | 100 | 1.0 |
| 3.51 | 97 | 03 | 0.8 |
| 4.00 | 97 | 03 | 0.8 |

TABLE E2

LCMS Method B:

| Instrument | AQUITY with PDA detector and SQD Performance |
|---|---|
| Column | X-bridge C18, 50*2.1 mm, 2.5 μm |
| Mobile Phase | A. 2 mM Ammonium Acetate + 0.1% Formic acid in Milli-Q water (B) 0.1% Formic acid in Acetonitrile |
| Column Temperature | Ambient |
| Auto sampler Temperature | 15° C. |
| Run Time | 4 min |

Gradient table for AQUITY with PDA detector and SQD Performance

| TIME (Minute) | (%)A | (%)B | Flow (ml/min) |
|---|---|---|---|
| 0.00 | 95 | 5 | 0.55 |
| 0.40 | 95 | 5 | 0.55 |
| 0.80 | 65 | 35 | 0.55 |
| 1.20 | 45 | 55 | 0.55 |
| 2.50 | 0 | 100 | 0.55 |
| 3.30 | 0 | 100 | 0.55 |
| 3.31 | 95 | 5 | 0.55 |
| 4.00 | 95 | 5 | 0.55 |

TABLE E3

LCMS Method C:

| Instrument | Agilent 1290 Infinity II with PDA and Infinity MSD |
|---|---|
| Column | InfinityLab Poroshell 120 EC-C18 |
| Mobile Phase | (A) Water with 0.1% Formic Acid (B) Acetonitrile with 0.1% Formic Acid |
| Column Temperature | 30.0° C. |
| Auto sampler Temperature | Ambient |
| Run Time | 4.5 min |
| Post Time | 0.5 min |

Gradient table for 05 to 95 4 min Formic Method

| TIME (Minute) | A (%) | B (%) | Flow Rate (ml/min) |
|---|---|---|---|
| 0.0 | 95.0 | 5.0 | 1.0 |
| 0.1 | 95.0 | 5.0 | 1.0 |
| 4.0 | 5.0 | 95.0 | 1.0 |
| 4.5 | 95.0 | 5.0 | 1.0 |

Example 1

5-fluoroisoindoline

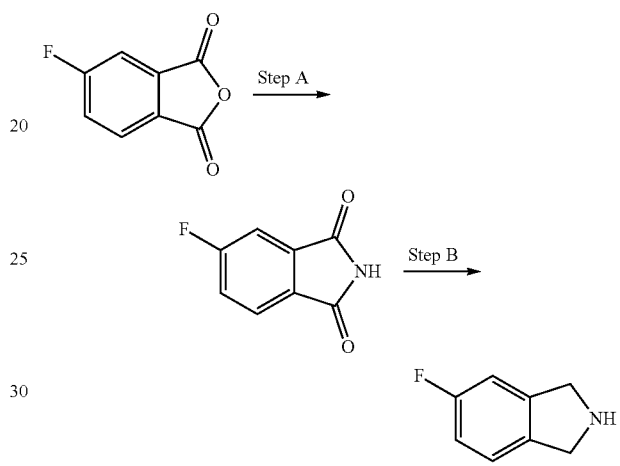

Step A: To a stirred solution of 5-fluoroisobenzofuran-1,3-dione (200 g, 1.20 mol) in Toluene (2.00 L) was added urea (126 g, 2.09 mol) portion-wise at room temperature. The reaction mixture was stirred at 110° C. for 16 h. After completion of the reaction as indicated by TLC (using 50% EtOAc in Hexane as a mobile phase), the reaction mixture was cooled to room temperature and poured into ice cold water (1.00 L) and extracted with EtOAc (3×1.00 L) then the organic layer was separated and concentrated under reduced pressure to afford 5-fluoroisoindoline-1,3-dione as an off white solid (150 g, 75%). $^1$H NMR (DMSO-$d_6$, 400 MHz): δ 11.45 (s, 1H), 7.89-7.86 (m, 1H), 7.68-7.60 (m, 2H).

Step B: To a stirred solution of 5-fluoroisoindoline-1,3-dione (150 g, 908 mmol) in THF (1.00 L) were added 1M BH$_3$·THF in THF (6.00 L, 40 v) at −5° C. dropwise. The reaction mixture was stirred at 80° C. for 16 h. After completion of the reaction as indicated by TLC (using 50% EtOAc in Hexane as a mobile phase), the reaction mixture was cooled to 0° C. and MeOH (1.50 L) was added slowly and directly concentrated under reduced pressure. After concentration, the residue was collected and dissolved in 1,4-dioxane (825 mL) and stirred the reaction mixture. 4M HCl in Dioxane (825 mL) was added at 0° C. and stirred for 2 h. After completion of the reaction as indicated by TLC (using 50% EtOAc in Hexane as a mobile phase), the reaction mixture was directly concentrated under vacuum to afford crude product. The crude product was triturated by Diethyl ether (1.00 L) to afford 5-fluoroisoindoline as an off white solid (120 g, 96%). $^1$H NMR (DMSO-$d_6$, 400 MHz): δ 10.14 (bs, 1H), 7.45-7.42 (m, 1H), 7.28 (dd, J=8.8, 2.0 Hz, 1H), 7.21 (dt, J=9.2, 2.4 Hz, 1H), 4.49 (s, 2H), 4.45 (s, 2H).

Example 2

Methyl 6-chloro-3-fluoropicolinate

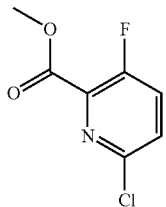

To a stirred solution of 6-chloro-3-fluoropicolinic acid (20.0 g, 114 mmol) in MeOH (200 mL) was added $SOCl_2$ (40.0 mL) at room temperature. The reaction mixture was stirred at room temperature for 3 h. After completion of the reaction as indicated by TLC (using 100% EtOAc as a mobile phase), the reaction solvent was removed in vacuo to afford crude compound. The crude compound was purified by trituration with pentane to afford methyl 6-chloro-3-fluoropicolinate as a green solid (21.0 g, 97%). LCMS: MS (ES+) $C_7H_5ClFNO_2$ requires: 189.0, found: 190.0 $[M+H]^+$. $^1H$ NMR (DMSO-$d_6$, 400 MHz): δ 8.04 (t, J=9.2 Hz, 1H), 7.87 (dd, J=3.2, 8.8 Hz, 1H), 3.90 (s, 3H).

Example 3

6-chloro-3-fluoropyridine-2-sulfonamide

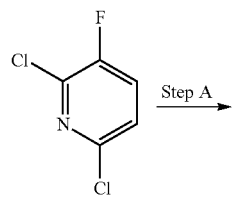
Step A →

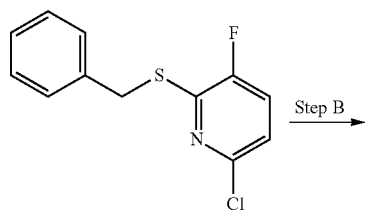
Step B →

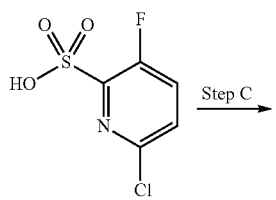
Step C →

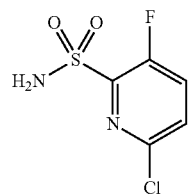

Step A: To a stirred solution of a 2,6-dichloro-3-fluoropyridine (20.0 g, 121 mmol) and phenylmethanethiol (12.0 g, 97.0 mmol) in 1,4-Dioxane (200 mL) was added DIPEA (31.0 g, 242 mmol). The resulting mixture was purged with nitrogen for 10 min, followed by the addition of $Pd_2(dba)_3$ (5.50 g, 6.06 mmol) and Xantphos (7.0 g, 12.1 mmol). The resulting mixture was stirred at 100° C. for 16 h. After completion of the reaction as indicated by TLC (using 100% hexane as a mobile phase), the reaction mixture was diluted by water (500 mL) and extracted using ethyl acetate (3×200 mL), the combined organic layer was dried over $Na_2SO_4$ and concentrated under reduced pressure. The crude product was purified by normal phase column chromatography (silica gel, 230-400 mesh, 2% EtOAc/Hexane) to afford 2-(benzylthio)-6-chloro-3-fluoropyridine as a colorless liquid (14.0 g, 46%). LCMS: MS (ES+) $C_{12}H_9ClFNS$ requires: 253.0, found: 254.1 $[M+H]^+$. $^1H$ NMR (DMSO-$d_6$, 400 MHz): δ 7.74 (t, J=8.8 Hz, 1H), 7.44 (d, J=7.2 Hz, 2H), 7.35-7.30 (m, 3H), 7.27-7.23 (m, 1H), 4.44 (s, 2H).

Step B: To a stirred solution of 2-(benzylthio)-6-chloro-3-fluoropyridine (5.00 g, 19.7 mmol) in DCM (50.0 mL) was added sulfuryl chloride (10.6 g, 78.8 mmol) at 0° C. followed by the addition of AcOH (2.00 mL, 0.40 V) and water (0.50 mL, 0.10 V). The reaction mixture was stirred at RT for 6 h. After completion of the reaction as indicated by TLC (using 20% EtOAc in Hexane as a mobile phase), the reaction mixture was concentrated under reduced pressure to get semi-solid material which was diluted with water (100 mL) and extracted with EtOAc (3×100 mL). The combined organic layer was dried over $Na_2SO_4$ and the solvent was removed in vacuo. The crude product was triturated using n-pentane (50 mL) to afford 6-chloro-3-fluoropyridine-2-sulfonic acid as a pale-yellow liquid (4.00 g, 96%). $^1H$ NMR (DMSO-$d_6$, 400 MHz): δ 14.46 (s, 1H), 7.79 (t, J=8.4 Hz, 1H), 7.56 (dd, J=8.4, 3.2 Hz, 1H), Step C: To a stirred 0° C. solution of 6-chloro-3-fluoropyridine-2-sulfonic acid (4.00 g, 18.9 mmol) in thionyl chloride (40.0 mL, 10.0 V) was DMF (0.14 mL, 1.89 mmol) dropwise. The reaction mixture was stirred at 70° C. for 16 h. After completion of the reaction as indicated by TLC (using 10% EtOAc in Hexane as a mobile phase), the reaction mixture was concentrated under a vacuum to get liquid material which was cooled to 0° C. temperature in THF (40 mL, 10 V) followed by the dropwise addition of $NH_4OH$ (20 mL, 5.0 V). The reaction mixture was stirred at RT for 16 h. After completion of the reaction as indicated by TLC (using 20% EtOAc in Hexane as a mobile phase), the reaction mixture was concentrated under a vacuum to get solid material that was diluted with water (50 mL) and extracted with 10% MeOH in DCM (3×70 mL). The combined organic layer was dried over $Na_2SO_4$ and the solvent was removed in vacuo to afford 6-chloro-3-fluoropyridine-2-sulfonamide as a light-brown solid (1.40 g, 35%). LCMS: MS (ES+) $C_5H_4ClFN_2O_2S$ requires: 210.0, found: 211.0 $[M+H]^+$. $^1H$ NMR (DMSO-$d_6$, 400 MHz): δ 8.13 (t, J=8.8 Hz, 1H), 7.99 (br s, 2H), 7.91 (dd, J=8.8, 3.2 Hz, 1H).

Example 4
Route A: Compound 1 (R)-6-chloro-3-((1-(2-(5-fluoroisoindolin-2-yl)-3,6-dimethyl-4-oxo-3,4-dihydroquinazolin-8-yl)ethyl)amino)-N-(methylsulfonyl)picolinamide
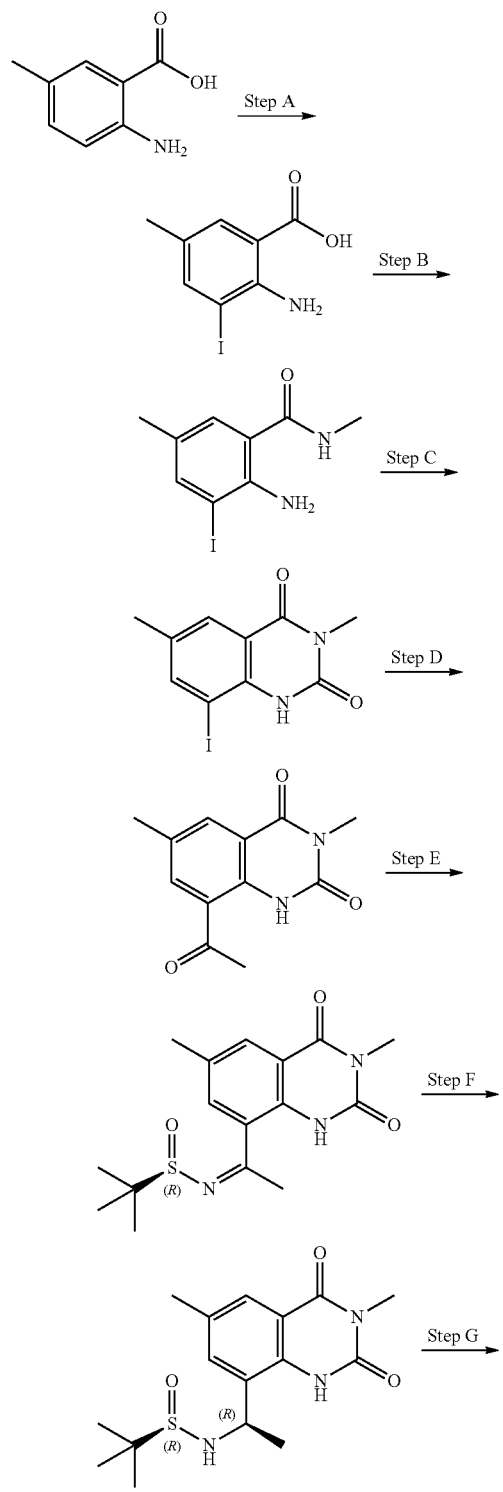
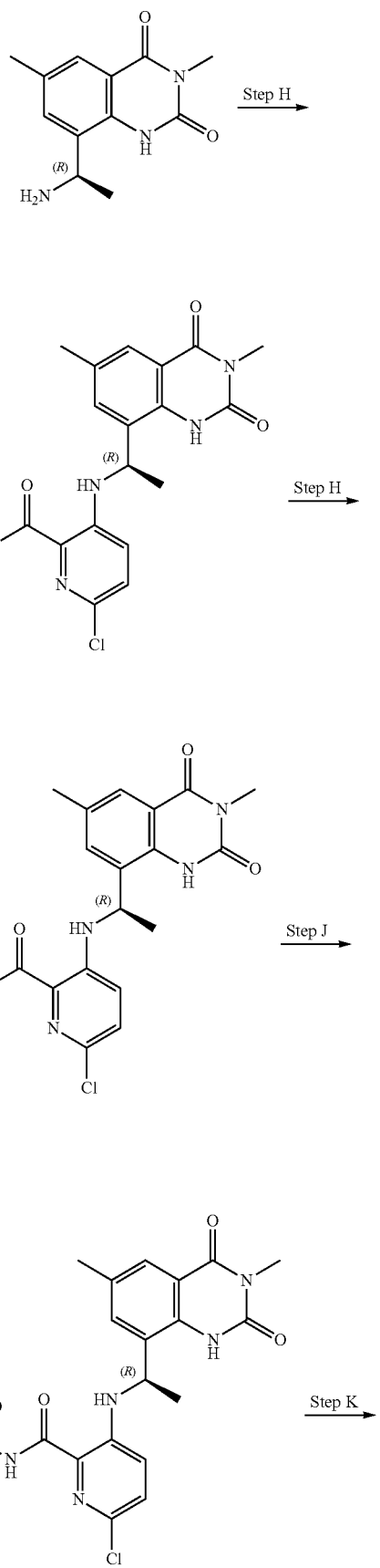

-continued

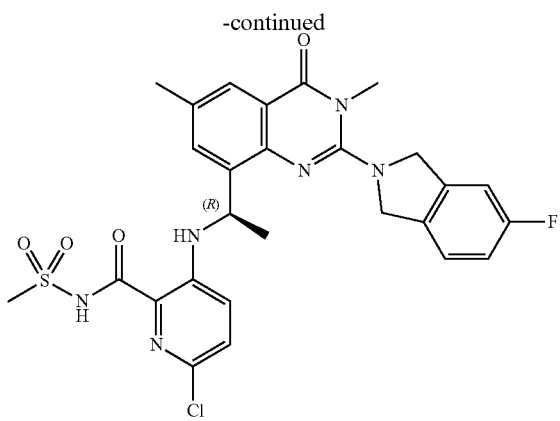

Step A: To a stirred solution of 2-amino-5-methylbenzoic acid (500 g, 3.30 mol) in Aq. 6% HCl (18 v) solution was prepared in 20 L three neck round bottom flask at RT and stirred at 50° C. To this solution was added 1 M iodine monochloride in acetic acid (1.07 kg in 6.61 L AcOH, 6.61 mol) dropwise at 50° C. The resulting mixture was stirred at 50° C. for 30 min. After completion of the reaction as indicated by TLC (using 10% MeOH:DCM as a mobile phase), the reaction mixture was cooled to RT and $Na_2S_2O_5$ (522 g, 3.30 mol) added. The reaction mixture was neutralized with aq. KOH solution to pH=~7 and stirred at RT for 30 min to obtain solid material. The resulting solid material was filtered through a Buchner funnel and the filter cake washed with water (100 mL). The solid was dissolved in ethyl acetate, dried over sodium sulfate, and concentrated under reduced pressure to afford 2-amino-3-iodo-5-methylbenzoic acid as dark yellow solid (720 g, 76%). LCMS: 2.157 min, 210.0 nm, MS (ES+) $C_8H_{81}NO_2$ requires: 277.1, found: 277.9 [M+H]$^+$. $^1$H NMR (DMSO-$d_6$, 400 MHz): δ 12.85 (bs, 1H), 7.70 (s, 1H), 7.61 (s, 1H), 6.54 (bs, 2H), 2.14 (s, 3H).

Step B: To a stirred solution of 2-amino-3-iodo-5-methylbenzoic acid (620 g, 2.24 mol) in DMF (6.20 L) was added HATU (1.28 kg, 2.69 mol), and $Et_3N$ (930 mL, 6.71 mol). The resulting solution was stirred for 10-15 min at RT. $MeNH_2$ (1.34 L, 2.69 mol, 2M in THF) was added dropwise into the reaction mixture and stirred at RT for 1 h. After completion of the reaction as indicated by TLC (using 10% MeOH:DCM as a mobile phase), the resulting reaction mixture was poured into ice-cold water (10.0 L) to obtain a precipitate which was filtered through a Buchner funnel. The solid material was collected, dissolved in DCM, dried over sodium sulfate, and concentrated under reduced pressure to afford 2-amino-3-iodo-N,5-dimethylbenzamide as an off-white solid (545 g, 84%). LCMS: MS (ES+) $C_9H_{11}IN_2O$ requires: 290.0, found: 290.9 [M+H]$^+$. $^1$H NMR (DMSO-$d_6$, 400 MHz): δ 8.34 (d, J=4.0 Hz, 1H), 7.58 (d, J=1.2 Hz, 1H), 7.33 (d, J=1.2 Hz, 1H), 6.16 (s, 2H), 2.73 (d, J=4.4 Hz, 3H), 2.15 (s, 3H).

Step C: To a cooled 0° C. solution of triphosgene (557 g, 1.88 mol) in DCM (10.9 L) was added 2-amino-3-iodo-N,5-dimethylbenzamide (545 g, 1.88 mol). $Et_3N$ (260 mL, 1.88 mol) was added to the resulting solution. After complete addition, the cooling bath was removed, and the reaction stirred for 1 h at RT. After completion of the reaction as indicated by TLC (using 50% EtOAc: Hexane as a mobile phase), the resulting reaction mixture was neutralized with sat $NaHCO_3$ solution to pH: 6-7 and then filtered through a bed of celite. The organic layer was separated, dried over sodium sulfate, and concentrated under reduced pressure to afford 8-iodo-3,6-dimethylquinazoline-2,4(1H,3H)-dione as an off-white solid (400 g, 67.36%). LCMS: MS (ES+) $C_{10}H_{91}N_2O_2$ requires: 316.0, found: 317.0 [M+H]$^+$. $^1$H NMR (DMSO-$d_6$, 400 MHz): δ 9.79 (s, 1H), 8.01 (d, J=1.2 Hz, 1H), 7.78 (dd, J=0.8, 2.0 Hz, 1H), 3.25 (s, 3H), 2.31 (s, 3H).

Step D: To a stirred solution of 8-iodo-3,6-dimethylquinazoline-2,4(1H,3H)-dione (250 g, 791 mmol) in 1,4-Dioxane (1.25 L) at room temperature. The reaction mixture was purged with Nitrogen for 15 minutes. After 15 min, the tributyl (1-ethoxyvinyl) stannane (428 g, 1.19 mol) and $PdCl_2(PPh_3)_2$ (55.4 g, 79.1 mmol) were added into reaction at the same temperature. The reaction mixture was stirred at 110° C. for 16 h. After completion of the reaction as indicated by TLC (using 50% EtOAc in Hexane as a mobile phase), the reaction mixture was cooled to room temperature. 2N HCl (200 mL) was added and stirred reaction mixture at room temperature for 30 min. After completion of the reaction as indicated by TLC (using 50% EtOAc in Hexane as a mobile phase). The reaction mixture was neutralized with Aq. $NaHCO_3$ solution, filtered through a pad of celite and washed with DCM (2.00 L). The filtrate was concentrated under reduced pressure to afford crude product. The crude material was purified by trituration using ethyl acetate and pentane to afford 8-acetyl-3,6-dimethylquinazoline-2,4(1H,3H)-dione as a brown solid (150 g, 82%). LCMS: MS (ES+) $C_{12}H_{12}N_2O_3$ requires: 232.1, found: 233.1 [M+H]$^+$. $^1$H NMR (DMSO-$d_6$, 400 MHz): δ 11.26 (s, 1H), 8.27 (d, J=1.6 Hz, 1H), 8.03 (s, 1H), 3.25 (s, 3H), 2.70 (s, 3H), 2.42 (s, 3H).

Step E: To a stirred solution of 8-acetyl-3,6-dimethylquinazoline-2,4(1H,3H)-dione (100 g, 431 mmol) in Toluene (2.00 L) were added (R)-(+)-tert-Butylsulfinamide (130 g, 1.08 mol) and Ti(i-Pro)$_4$ (535 mL, 1.81 mol) at room temperature. The reaction mixture was stirred at 130° C. using dean-stark apparatus for 9 h. After completion of the reaction as indicated by TLC (using 50% EtOAc in Hexane as a mobile phase), the reaction mixture was cooled to room temperature. The reaction mixture was poured into water (1.00 L), filtered through a pad of celite, and washed with DCM (2.00 L). The organic layer was separated, dried over anhydrous $Na_2SO_4$ and concentrated under reduced pressure to afford (R,Z)—N-(1-(3,6-dimethyl-2,4-dioxo-1,2,3,4-tetrahydroquinazolin-8-yl)ethylidene)-2-methylpropane-2-sulfinamide as a brown solid (70 g, Quantitative). The crude material was used as such in the next reaction without further purification. LCMS: MS (ES+) $C_{16}H_{21}N_3O_3S$ requires: 335.1, found: 336.1 [M+H]$^+$.

Step F: To a stirred solution of (R)—N-(1-(3,6-dimethyl-2,4-dioxo-1,2,3,4-tetrahydroquinazolin-8-yl)ethylidene)-2-methylpropane-2-sulfinamide (70.0 g, 209 mmol, 1.00 equiv) in MeOH (700 mL) and DCM (700 ml) at −78° C. was added CeCl$_3$·7H$_2$O (69.9 g, 188 mmol). NaBH$_4$ (15.7 g, 417 mmol) was added portion-wise into the reaction and maintained the reaction at −78° C. for 6 h. After completion of the reaction as indicated by TLC (using 50% EtOAc in Hexane as a mobile phase), the reaction mixture was poured into water (1.00 mL), filtered through celite, and washed with DCM (2.00 mL). The organic layer was separated from the filtrate, dried over $Na_2SO_4$ and concentrated under reduced pressure to afford crude material. The crude was purified by column chromatography (Neutral alumina, 1% MeOH in DCM) to afford (R)—N—((R)-1-(3,6-dimethyl-2,4-dioxo-1,2,3,4-tetrahydroquinazolin-8-yl)ethyl)-2-methylpropane-2-sulfinamide as a pale-yellow solid (40 g, 57%). LCMS: MS (ES−) $C_{16}H_{23}N_3O_3S$ requires: 337.2, found:

336.4 [M−H]⁺. ¹H NMR (DMSO-d₆, 400 MHz): δ 10.53 (s, 1H), 7.71 (s, 1H), 7.64 (d, J=2.0 Hz, 1H), 5.77 (s, 1H), 4.95-4.92 (m, 1H), 3.27 (s, 3H), 2.35 (s, 3H), 1.40 (d, J=6.8 Hz, 3H), 1.10 (s, 9H).

Step G: To a stirred solution of (R)—N—((R)-1-(3,6-dimethyl-2,4-dioxo-1,2,3,4-tetrahydroquinazolin-8-yl)ethyl)-2-methylpropane-2-sulfinamide (40.0 g, 119 mmol) in DCM (400 ml) at 0° C. was added dropwise addition of 4M HCl in Dioxane (400 mL, 10 v). The resulting reaction mixture was stirred at room temperature for 16 h. After completion of the reaction as indicated by TLC (using 5% MeOH in DCM as a mobile phase), the reaction mixture was concentrated under reduced pressure to get crude. The crude was quenched with sat. NaHCO₃ solution and extracted with DCM. The combined organic layer was dried over Na₂SO₄ and concentrated under reduced pressure to afford (R)-8-(1-aminoethyl)-3,6-dimethylquinazoline-2,4(1H,3H)-dione as a pale-yellow solid (11.0 g, 40%). LCMS: MS (ES+) $C_{12}H_{15}N_3O_2$ requires: 233.1, found: 234.2 [M+H]⁺. HPLC: 98.51%, 3.88 min, 254 nm. Chiral HPLC: 99.76%, 4.31 min, 225 nm. ¹H NMR (DMSO-d₆, 400 MHz): δ 7.62 (t, J=0.8 Hz, 1H), 7.36 (d, J=2.0 Hz, 1H), 5.91 (bs, 3H), 4.39-4.34 (m, 1H), 3.24 (s, 3H), 2.31 (s, 3H), 1.32 (d, J=6.8 Hz, 3H).

Step H: To a stirred solution of (R)-8-(1-aminoethyl)-3,6-dimethylquinazoline-2,4(1H,3H)-dione (4.00 g, 17.2 mmol) in DMSO (5.00 mL) at room temperature was added methyl 6-chloro-3-fluoropicolinate (4.80 g, 25.8 mmol) and reaction mixture was stirred for 5 min. To this reaction mixture DIPEA (11.9 mL, 68.7 mmol) was added dropwise at RT and the reaction was heated at 120° C. for 16 h. After completion of the reaction as indicated by TLC (using 50% EtOAc in Hexane as a mobile phase), the reaction mixture was diluted by water (40.0 mL) and extracted with EtOAc (3×30.0 mL). The combined organic layer was dried over Na₂SO₄ and the solvent was removed in vacuo to afford crude. The crude was purified by column chromatography (silica gel, 230-400 mesh, 40% EtOAc/Hexane) to afford methyl (R)-6-chloro-3-((1-(3,6-dimethyl-2,4-dioxo-1,2,3,4-tetrahydroquinazolin-8-yl)ethyl)amino)picolinate as a yellow solid (1.40 g, 20%). LCMS: MS (ES+) $C_{19}H_{19}ClN_4O_4$ requires: 402.8, found: 403.2 [M+H]⁺. ¹H NMR (DMSO-d₆, 400 MHz): δ 10.97 (s, 1H), 8.11 (d, J=6.0 Hz, 1H), 7.71 (d, J=1.2 Hz, 1H), 7.42-7.39 (m, 2H), 6.91 (d, J=8.8 Hz, 1H), 5.29-5.25 (m, 1H), 3.90 (s, 3H), 3.29 (s, 3H), 2.27 (s, 3H), 1.46 (d, J=6.4 Hz, 3H).

Step I: To a stirred solution of methyl (R)-6-chloro-3-((1-(3,6-dimethyl-2,4-dioxo-1,2,3,4-tetrahydroquinazolin-8-yl)ethyl)amino)picolinate (1.40 g, 3.47 mmol) in THF (7.00 mL):MeOH (7.00 mL) at 0° C. 2N NaOH in H₂O (7.00 mL) was added at 0° C. and allowed to stir at RT for 30 min and heated the reaction at 60° C. for 3 h. After completion of the reaction as indicated by TLC (using 10% MeOH in DCM as a mobile phase), the reaction mixture was concentrated under a vacuum to obtain the crude. The crude was diluted with water and acidified using saturated solution of citric acid up to pH 5 to obtain precipitates and filtered out the precipitates dried in vacuo to afford (R)-6-chloro-3-((1-(3,6-dimethyl-2,4-dioxo-1,2,3,4-tetrahydroquinazolin-8-yl)ethyl)amino)picolinic acid as a white solid (1.20 g, 89%). LCMS: MS (ES+) $C_{18}H_{17}ClN_4O_4$ requires: 388.8, found: 389.3 [M+H]⁺. ¹H NMR (DMSO-d₆, 400 MHz): δ 10.96 (s, 1H), 8.69 (bs, 1H), 7.70 (d, J=1.2 Hz, 1H), 7.40 (d, J=1.6 Hz, 1H), 7.29 (d, J=8.8 Hz, 1H), 6.81 (d, J=8.8 Hz, 1H), 5.22-5.21 (m, 1H), 3.29 (s, 3H), 2.26 (s, 3H), 1.43 (d, J=6.4 Hz, 3H).

Step J: To a stirred solution of methanesulfonamide (0.94 g, 9.87 mmol) in DCM (320 mL, 10 v) at room temperature was added DMAP (1.20 g, 9.87 mmol). The (R)-6-chloro-3-((1-(3,6-dimethyl-2,4-dioxo-1,2,3,4-tetrahydroquinazolin-8-yl)ethyl)amino)picolinic acid (3.20 g, 8.23 mmol) and EDC·HCl (1.89 g, 9.87 mmol) were added at room temperature. The reaction mixture was stirred at RT for 16 h. After completion of the reaction as indicated by TLC (using 5% MeOH in DCM as a mobile phase), the reaction mixture was diluted with water (2×30.0 mL) and extracted with DCM (3×40.0 mL). The combined organic layer was dried over Na₂SO₄ and the solvent was removed in vacuo to afford crude. The crude was purified by column chromatography (silica gel, 230-400 mesh, 2.5% DCM/MeOH) to afford (R)-6-chloro-3-((1-(3,6-dimethyl-2,4-dioxo-1,2,3,4-tetrahydroquinazolin-8-yl)ethyl)amino)-N-(methylsulfonyl)picolinamide as an off white solid (1.4 g, 36.51%). LCMS: MS (ES+) $C_{19}H_{20}ClN_5O_5S$ requires: 465.9, found: 483.5 [M+NH₄]⁺. HPLC: 7.646 min, 99.53%, 254 nm. Chiral HPLC: 4.207 min, 260.0 nm. ¹H NMR (DMSO-d₆, 400 MHz): δ 11.26 (s, 1H), 10.97 (s, 1H), 8.36 (d, J=6.0 Hz, 1H), 7.71 (s, 1H), 7.46 (s, 1H), 7.44 (s, 1H), 6.94 (d, J=9.2 Hz, 1H), 5.29-5.26 (m, 1H), 3.44 (s, 3H), 3.30 (s, 3H), 2.27 (s, 3H), 1.48 (d, J=6.4 Hz, 3H).

Step K: To a stirred solution of (R)-6-chloro-3-((1-(3,6-dimethyl-2,4-dioxo-1,2,3,4-tetrahydroquinazolin-8-yl)ethyl)amino)-N-(methylsulfonyl)picolinamide (0.11 g, 0.24 mmol) in DMF (1.10 mL, 10 v) were added 5-fluoroisoindoline hydrochloride (81.0 mg, 0.47 mmol), BOP (0.21 g, 0.47 mmol) and DBU (0.17 mL, 1.18 mmol) at room temperature under nitrogen atmosphere. The resulting reaction mixture was stirred at room temperature for 2 h. After completion of the reaction as indicated by TLC (using 10% MeOH:DCM as a mobile phase), the resulting reaction mixture was diluted with cold water (6.5 mL) and extracted with EtOAc (2×10 mL). The combined organic layer was washed with brine solution, dried over Na₂SO₄, filtered, and concentrated under reduced pressure to afford crude product. The crude product was purified by flash column chromatography (C18 silica, 70% ACN in 0.1% FA in water) to afford (R)-6-chloro-3-((1-(2-(5-fluoroisoindolin-2-yl)-3,6-dimethyl-4-oxo-3,4-dihydroquinazolin-8-yl)ethyl)amino)-N-(methylsulfonyl)picolinamide as a pale-yellow solid (35 mg, 25%). LCMS: MS (ES+) $C_{27}H_{26}ClFN_6O_4S$ requires: 584.2, found: 585.3 [M+H]⁺. HPLC: 10.036 min, 99.70%, 210.0 nm. Chiral HPLC: 13.322 min, 270.0 nm. ¹H NMR (DMSO-d6, 400 MHz): δ 8.95 (bs, 1H), 7.71 (s, 1H), 7.49 (s, 1H), 7.41 (dd, J=8.4, 5.2 Hz, 1H), 7.25 (d, J=9.2 Hz, 2H), 7.17-7.12 (m, 1H), 7.00 (bs, 1H), 5.40-5.37 (m, 1H), 5.11-5.03 (m, 2H), 5.03-4.95 (m, 2H), 3.59 (s, 3H), 3.12 (bs, 3H), 2.32 (s, 3H), 1.60 (d, J=5.6 Hz, 3H).

TABLE E4 compound list prepared according to Route A in Example 4

| Cpd. ID | Structure | Name | LCMS |
|---|---|---|---|
| 2 | 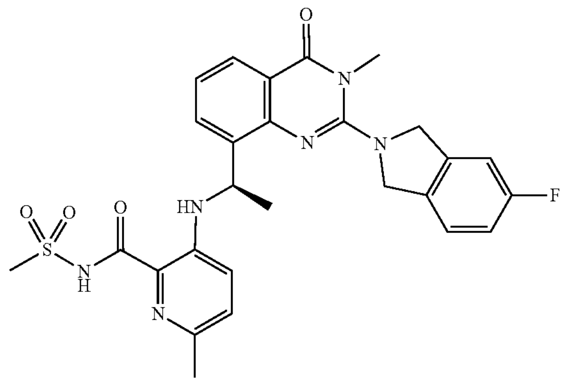 [SMILES: Cc1ccc(N[C@H](C)c2cccc3c(=O)n(C)c(N4Cc5ccc(F)cc5C4)nc23)c(C(=O)NS(C)(=O)=O)n1] | (R)-3-((1-(2-(5-fluoroisoindolin-2-yl)-3-methyl-4-oxo-3,4-dihydroquinazolin-8-yl)ethyl)amino)-6-methyl-N-(methylsulfonyl)picolinamide | 2.40 min, 275 nm, MS (ES+)[a] $C_{27}H_{27}FN_6O_4S$ requires: 550.1, found: 551.4 [M + H]+. |
| 3 | 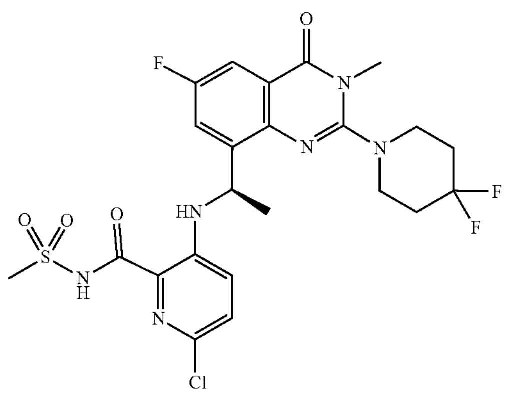 [SMILES: C[C@@H](Nc1ccc(Cl)nc1C(=O)NS(C)(=O)=O)c1cc(F)cc2c(=O)n(C)c(N3CCC(F)(F)CC3)nc12] | (R)-6-chloro-3-((1-(2-(4,4-difluoropiperidin-1-yl)-6-fluoro-3-methyl-4-oxo-3,4-dihydroquinazolin-8-yl)ethyl)amino)-N-(methylsulfonyl)picolinamide | 2.69 min, 254 nm, MS (ES+)[a] $C_{23}H_{24}ClF_3N_6O_4S$ requires: 572.1, found: 573.3 [M + H]+ |
| 4 | 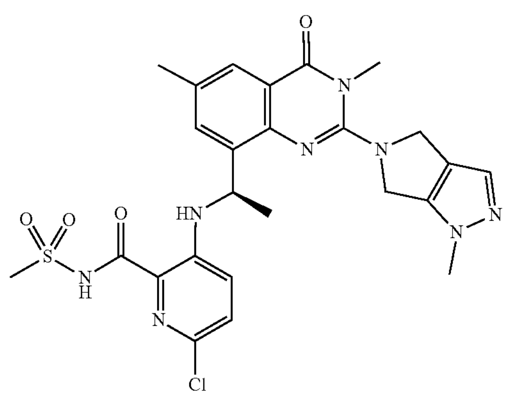 [SMILES: Cc1cc([C@@H](C)Nc2ccc(Cl)nc2C(=O)NS(C)(=O)=O)c2nc(N3Cc4cnn(C)c4C3)n(C)c(=O)c2c1] | (R)-6-chloro-3-((1-(3,6-dimethyl-2-(1-methyl-4,6-dihydropyrrolo[3,4-c]pyrazol-5(1H)-yl)-4-oxo-3,4-dihydroquinazolin-8-yl)ethyl)amino)-N-(methylsulfonyl)picolinamide | 2.41 min, 254 nm, MS (ES+)[b] $C_{25}H_{27}ClN_8O_4S$ requires: 570.2, found: 571.3 [M + H]+ |
| 5 | 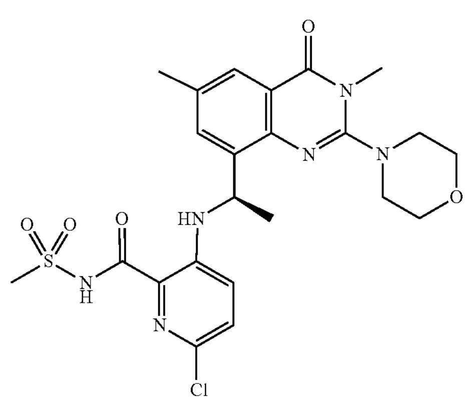 [SMILES: Cc1cc([C@@H](C)Nc2ccc(Cl)nc2C(=O)NS(C)(=O)=O)c2nc(N3CCOCC3)n(C)c(=O)c2c1] | (R)-6-chloro-3-((1-(3,6-dimethyl-2-morpholino-4-oxo-3,4-dihydroquinazolin-8-yl)ethyl)amino)-N-(methylsulfonyl)picolinamide | 2.42 min, 254 nm, MS (ES+)[a] $C_{23}H_{27}ClN_6O_5S$ requires: 534.2, found: 535.4 [M + H]+ |

TABLE E4-continued compound list prepared according to Route A in Example 4

| Cpd. ID | Structure | Name | LCMS |
|---|---|---|---|
| 6 | 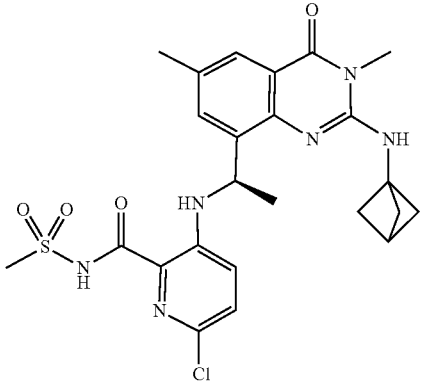 [SMILES: Cc1cc([C@@H](C)Nc2ccc(Cl)nc2C(=O)NS(C)(=O)=O)c2nc(NC34CC(C3)C4)n(C)c(=O)c2c1] | (R)-3-((1-(2-(bicyclo[1.1.1]pentan-1-ylamino)-3,6-dimethyl-4-oxo-3,4-dihydroquinazolin-8-yl)ethyl)amino)-6-chloro-N-(methylsulfonyl)picolinamide | 2.63 min, 254 nm, MS (ES+)$^a$ $C_{24}H_{27}ClN_6O_4S$ requires: 530.1, found: 531.5 [M + H]$^+$ |
| 7 | 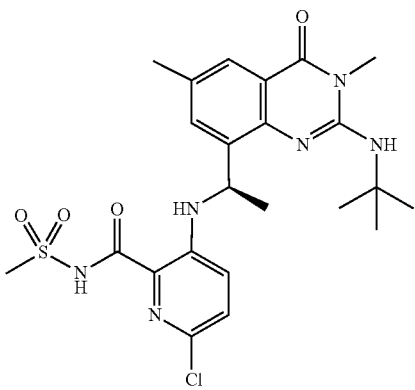 [SMILES: Cc1cc([C@@H](C)Nc2ccc(Cl)nc2C(=O)NS(C)(=O)=O)c2nc(NC(C)(C)C)n(C)c(=O)c2c1] | (R)-3-((1-(2-(tert-butylamino)-3,6-dimethyl-4-oxo-3,4-dihydroquinazolin-8-yl)ethyl)amino)-6-chloro-N-(methylsulfonyl)picolinamide | 2.67 min, 254 nm, MS (ES+)$^a$ $C_{23}H_{29}ClN_6O_4S$ requires: 520.1, found: 521.3 [M + H]$^+$ |
| 8 | 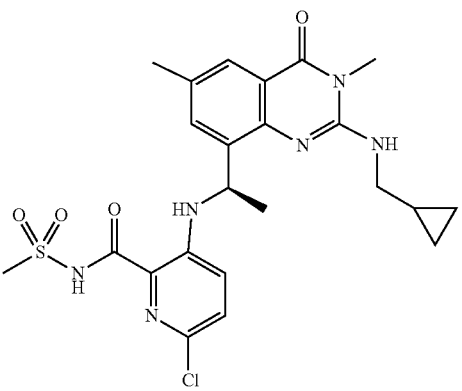 [SMILES: Cc1cc([C@@H](C)Nc2ccc(Cl)nc2C(=O)NS(C)(=O)=O)c2nc(NCC3CC3)n(C)c(=O)c2c1] | (R)-6-chloro-3-((1-(2-((cyclopropylmethyl)amino)-3,6-dimethyl-4-oxo-3,4-dihydroquinazolin-8-yl)ethyl)amino)-N-(methylsulfonyl)picolinamide | 2.57 min, 254 nm, MS (ES+)$^a$ $C_{23}H_{27}ClN_6O_4S$ requires: 518.1, found: 519.5, [M + H]$^+$ |

TABLE E4-continued compound list prepared according to Route A in Example 4

| Cpd. ID | Structure | Name | LCMS |
|---|---|---|---|
| 9 | 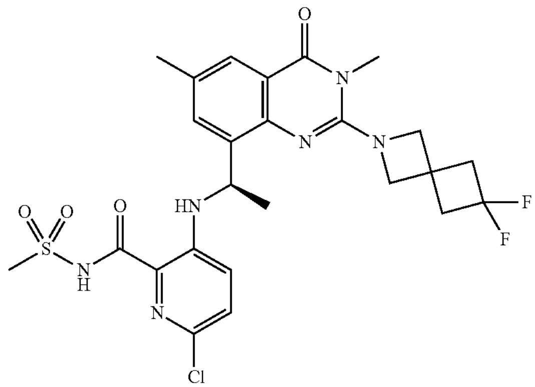 [SMILES: Cc1cc([C@@H](C)Nc2ccc(Cl)nc2C(=O)NS(C)(=O)=O)c2nc(N3CC4(C3)CC(F)(F)C4)n(C)c(=O)c2c1] | (R)-6-chloro-3-((1-(2-(6,6-difluoro-2-azaspiro[3.3]heptan-2-yl)-3,6-dimethyl-4-oxo-3,4-dihydroquinazolin-8-yl)ethyl)amino)-N-(methylsulfonyl)picolinamide | 2.67 min, 254 nm, MS (ES+)$^a$ $C_{25}H_{27}ClF_2N_6O_4S$ requires: 580.1, found: 581.4 [M + H]$^+$ |
| 10 | 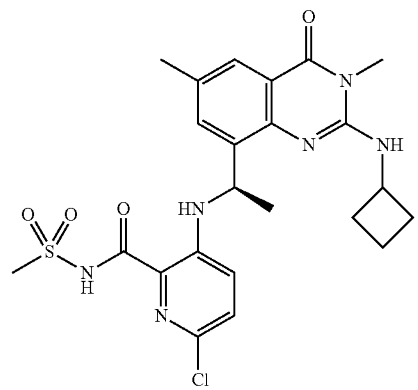 [SMILES: Cc1cc([C@@H](C)Nc2ccc(Cl)nc2C(=O)NS(C)(=O)=O)c2nc(NC3CCC3)n(C)c(=O)c2c1] | (R)-6-chloro-3-((1-(2-(cyclobutylamino)-3,6-dimethyl-4-oxo-3,4-dihydroquinazolin-8-yl)ethyl)amino)-N-(methylsulfonyl)picolinamide | 2.63 min, 270 nm, MS (ES+)$^b$ $C_{23}H_{27}ClN_6O_4S$ requires: 518.1, found: 519.3 [M + H]$^+$ |
| 11 | 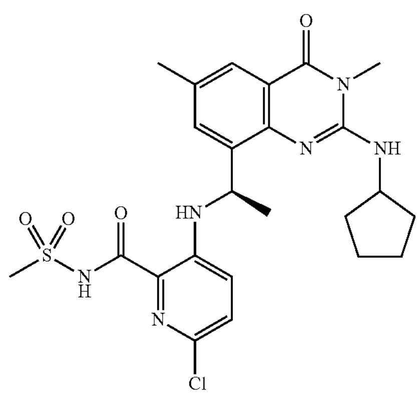 [SMILES: Cc1cc([C@@H](C)Nc2ccc(Cl)nc2C(=O)NS(C)(=O)=O)c2nc(NC3CCCC3)n(C)c(=O)c2c1] | (R)-6-chloro-3-((1-(2-(cyclopentylamino)-3,6-dimethyl-4-oxo-3,4-dihydroquinazolin-8-yl)ethyl)amino)-N-(methylsulfonyl)picolinamide | 2.75 min, 254 nm, MS (ES+)$^a$ $C_{24}H_{29}ClN_6O_4S$ requires: 532.1, found: 533.3 [M + H]$^+$ |
| 12 | 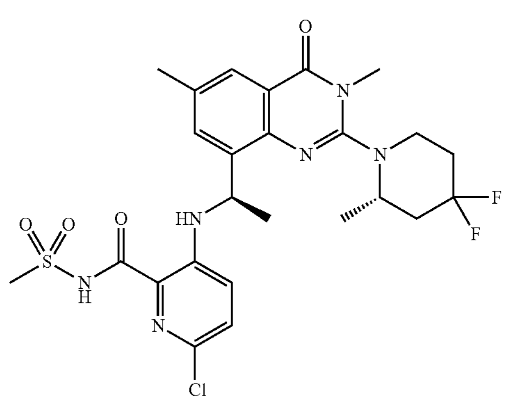 | 6-chloro-3-(((R)-1-(2-((S)-4,4-difluoro-2-methylpiperidin-1-yl)-3,6-dimethyl-4-oxo-3,4-dihydroquinazolin-8-yl)ethyl)amino)-N-(methylsulfonyl)picolinamide AND 6-chloro-3-(((R)-1-(2-((R)-4,4-difluoro-2-methylpiperidin-1-yl)-3,6-dimethyl-4-oxo-3,4-dihydroquinazolin-8-yl)ethyl)amino)-N-(methylsulfonyl)picolinamide | 2.73 min, 254 nm, MS (ES+)$^a$ $C_{25}H_{29}ClF_2N_6O_4S$ requires: 582.1, found: 583.3 [M + H]$^+$ |

TABLE E4-continued compound list prepared according to Route A in Example 4

| Cpd. ID | Structure | Name | LCMS |
|---|---|---|---|
| | | | |
| 13 | 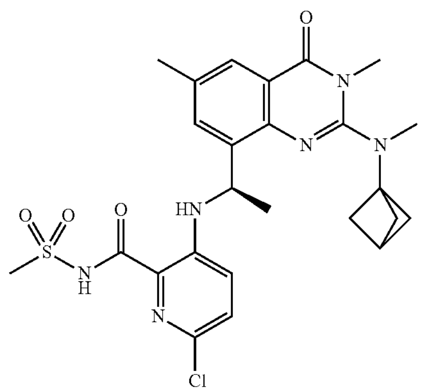 | (R)-3-((1-(2-(bicyclo[1.1.1]pentan-1-yl(methyl)amino)-3,6-dimethyl-4-oxo-3,4-dihydroquinazolin-8-yl)ethyl)amino)-6-chloro-N-(methylsulfonyl)picolinamide | 2.88 min, 254 nm, MS (ES+)$^a$ C$_{25}$H$_{29}$ClN$_6$O$_4$S requires: 544.1, found: 545.4 [M + H]$^+$ |
| 14 | 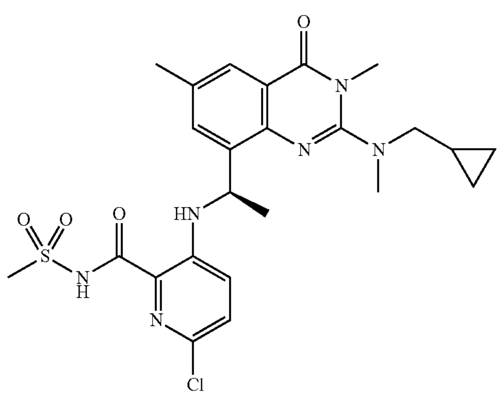 [SMILES: Cc1cc([C@@H](C)Nc2ccc(Cl)nc2C(=O)NS(C)(=O)=O)c2nc(N(C)CC3CC3)n(C)c(=O)c2c1] | (R)-6-chloro-3-((1-(2-((cyclopropylmethyl)(methyl)amino)-3,6-dimethyl-4-oxo-3,4-dihydroquinazolin-8-yl)ethyl)amino)-N-(methylsulfonyl)picolinamide | 2.80 min, 254 nm, MS (ES+)$^a$ C$_{24}$H$_{29}$ClN$_6$O$_4$S requires: 532.1, found: 533.4 [M + H]$^+$ |
| 15 | 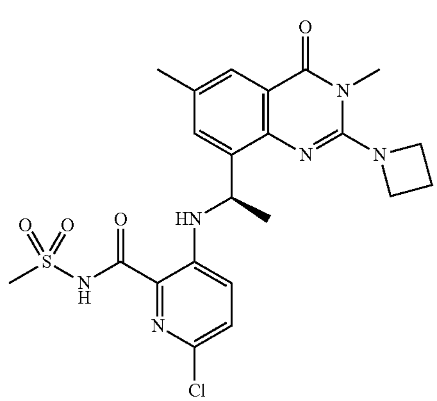 [SMILES: Cc1cc([C@@H](C)Nc2ccc(Cl)nc2C(=O)NS(C)(=O)=O)c2nc(N3CCC3)n(C)c(=O)c2c1] | (R)-3-((1-(pyrrolidin-1-yl)-3,6-dimethyl-4-oxo-3,4-dihydroquinazolin-8-yl)ethyl)amino)-6-chloro-N-(methylsulfonyl)picolinamide | 2.53 min, 254 nm, MS (ES+)$^a$ C$_{22}$H$_{25}$ClN$_6$O$_4$S requires: 504.1, found: 505.3 [M + H]$^+$ |

TABLE E4-continued compound list prepared according to Route A in Example 4

| Cpd. ID | Structure | Name | LCMS |
|---|---|---|---|
| 16 | 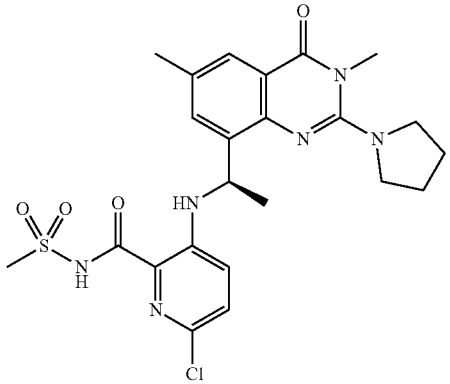 [SMILES: Cc1cc([C@@H](C)Nc2ccc(Cl)nc2C(=O)NS(C)(=O)=O)c2nc(N3CCCC3)n(C)c(=O)c2c1] | (R)-6-chloro-3-((1-(3,6-dimethyl-4-oxo-pyrrolidin-1-yl)-3,4-dihydroquinazolin-8-yl)ethyl)amino)-N-(methylsulfonyl)picolinamide | 2.70 min, 254 nm, MS (ES+)$^a$ $C_{23}H_{27}ClN_6O_4S$ requires: 518.2, found: 519.3 $[M + H]^+$ |
| 17 | 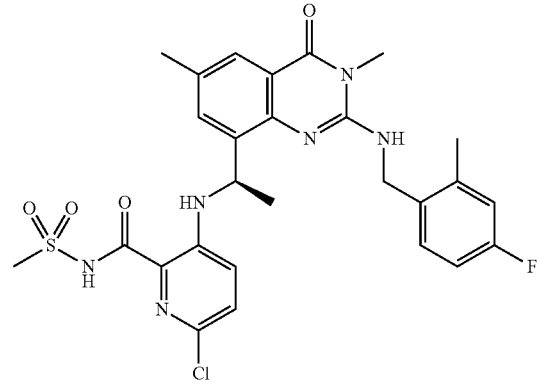 [SMILES: Cc1cc([C@@H](C)Nc2ccc(Cl)nc2C(=O)NS(C)(=O)=O)c2nc(NCc3ccc(F)cc3C)n(C)c(=O)c2c1] | (R)-6-chloro-3-((1-(2-((4-fluoro-2-methylbenzyl)amino)-3,6-dimethyl-4-oxo-3,4-dihydroquinazolin-8-yl)ethyl)amino)-N-(methylsulfonyl)picolinamide | 2.68 min, 254 nm, MS (ES+)$^a$ $C_{27}H_{28}ClFN_6O_4S$ requires: 586.2, found: 587.5 $[M + H]^+$ |
| 18 | 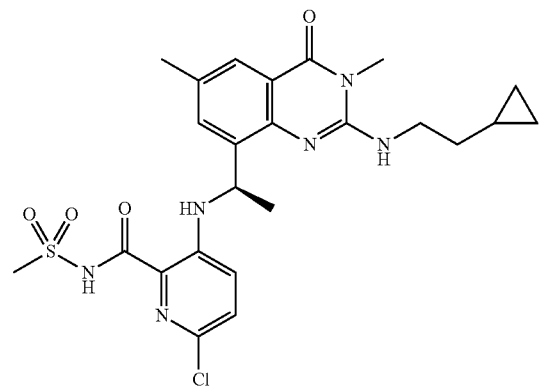 [SMILES: Cc1cc([C@@H](C)Nc2ccc(Cl)nc2C(=O)NS(C)(=O)=O)c2nc(NCCC3CC3)n(C)c(=O)c2c1] | (R)-6-chloro-3-((1-(2-((2-cyclopropylethyl)amino)-3,6-dimethyl-4-oxo-3,4-dihydroquinazolin-8-yl)ethyl)amino)-N-(methylsulfonyl)picolinamide | 2.41 min, 254 nm, MS (ES+)$^a$ $C_{24}H_{29}ClN_6O_4S$ requires: 532.2, found: 533.2 $[M + H]^+$ |

TABLE E4-continued compound list prepared according to Route A in Example 4

| Cpd. ID | Structure | Name | LCMS |
|---|---|---|---|
| 19 | 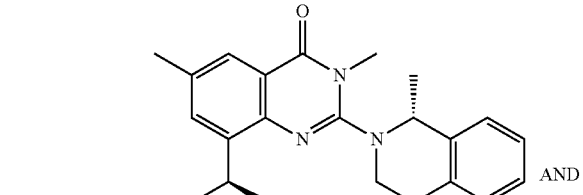 AND 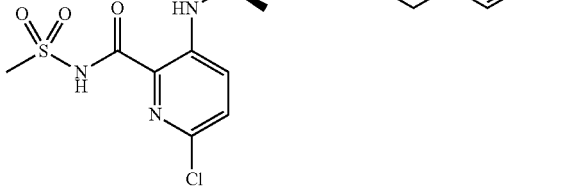 | 6-chloro-3-(((R)-1-(3,6-dimethyl-2-((R)-1-methyl-3,4-dihydroisoquinolin-2(1H)-yl)-4-oxo-3,4-dihydroquinazolin-8-yl)ethyl)amino)-N-(methylsulfonyl) picolinamide AND 6-chloro-3-(((R)-1-(3,6-dimethyl-2-((S)-1-methyl-3,4-dihydroisoquinolin-2(1H)-yl)-4-oxo-3,4-dihydroquinazolin-8-yl)ethyl)amino)-N-(methylsulfonyl) picolinamide | 2.70 min, 270 nm, MS (ES+)$^a$ $C_{29}H_{31}ClN_6O_4S$ requires: 594.1, found: 595.5 $[M + H]^+$ |
| 20 | 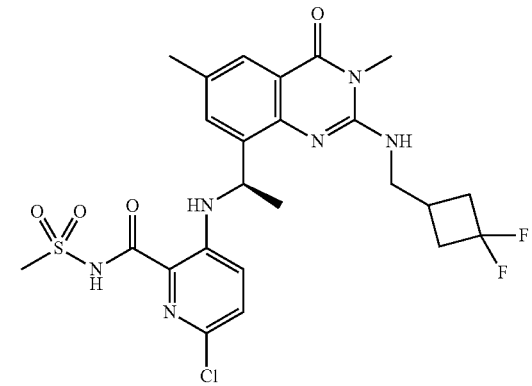 | (R)-6-chloro-3-((1-(2-(((3,3-difluorocyclobutyl)methyl)amino)-3,6-dimethyl-4-oxo-3,4-dihydroquinazolin-8-yl)ethyl)amino)-N-(methylsulfonyl) picolinamide | 2.46 min, 254 nm, MS (ES+)$^a$ $C_{24}H_{27}ClF_2N_6O_4S$ requires: 568.1, found: 568.7 $[M + H]^+$ |
| 21 | 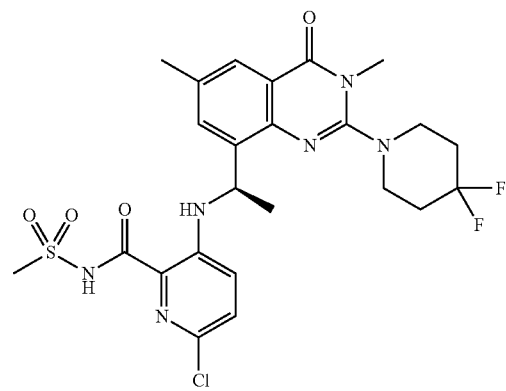 | (R)-2-chloro-5-((1-(2-(5-fluoroisoindolin-2-yl)-3,6-dimethyl-4-oxo-3,4-dihydroquinazolin-8-yl)ethyl)amino)-N-(methylsulfonyl) isonicotinamide | 2.55 min, 254 nm, MS (ES+)$^b$ $C_{24}H_{27}ClF_2N_6O_4S$ requires: 568.2, found: 568.7 $[M]^+$ |

TABLE E4-continued compound list prepared according to Route A in Example 4

| Cpd. ID | Structure | Name | LCMS |
|---|---|---|---|
| 22 | 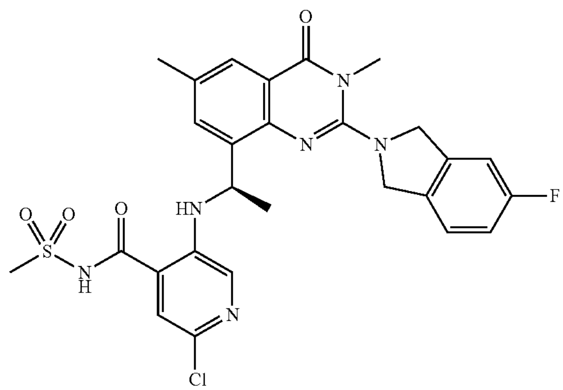 | (R)-2-chloro-5-((1-(2-(5-fluoroisoindolin-2-yl)-3,6-dimethyl-4-oxo-3,4-dihydroquinazolin-8-yl)ethyl)amino)-N-(methylsulfonyl)isonicotinamide | 2.64 min, 210 nm, MS (ES+)$^a$ $C_{26}H_{23}ClF_2N_6O_4S$ requires: 588.1, found: 588.8 [M + H]$^+$ |
| 23 | 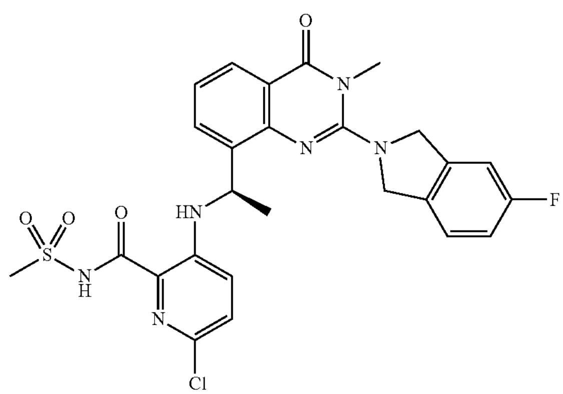 [SMILES: C[C@@H](Nc1ccc(Cl)nc1C(=O)NS(C)(=O)=O)c1cccc2c(=O)n(C)c(N3Cc4ccc(F)cc4C3)nc12] | (R)-6-chloro-3-((1-(2-(5-fluoroisoindolin-2-yl)-3-methyl-4-oxo-3,4-dihydroquinazolin-8-yl)ethyl)amino)-N-(methylsulfonyl)picolinamide | 2.50 min, 270 nm, MS (ES+)$^b$ $C_{26}H_{24}ClFN_6O_4S$ requires: 570.1, found: 570.7 [M + H]$^+$ |
| 24 | 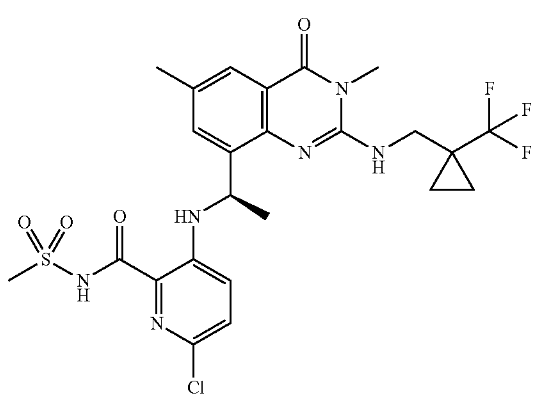 [SMILES: Cc1cc([C@@H](C)Nc2ccc(Cl)nc2C(=O)NS(C)(=O)=O)c2nc(NCC3(C(F)(F)F)CC3)n(C)c(=O)c2c1] | (R)-6-chloro-3-((1-(3,6-dimethyl-4-oxo-2-(((1-(trifluoromethyl)cyclopropyl)methyl)amino)-3,4-dihydroquinazolin-8-yl)ethyl)amino)-N-(methylsulfonyl)picolinamide | 2.48 min, 230 nm, MS (ES+)$^b$ $C_{24}H_{26}ClF_3N_6O_4S$ requires: 586.1, found: 587.2 [M + H]$^+$ |

TABLE E4-continued compound list prepared according to Route A in Example 4

| Cpd. ID | Structure | Name | LCMS |
|---|---|---|---|
| 25 | 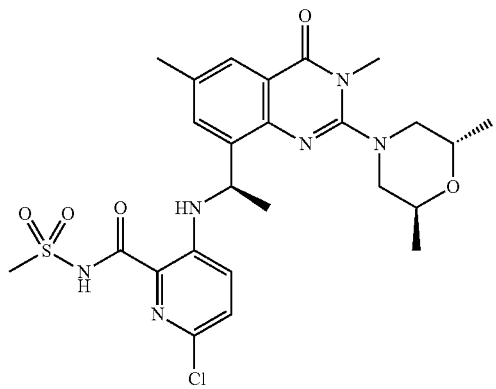 | 6-chloro-3-(((R)-1-(2-((2S,6S)-2,6-dimethylmorpholino)-3,6-dimethyl-4-oxo-3,4-dihydroquinazolin-8-yl)ethyl)amino)-N-(methylsulfonyl)picolinamide | 2.40 min, 270 nm, MS (ES+)[b] $C_{25}H_{31}ClN_6O_5S$ requires: 562.1, found: 562.8 $[M + H]^+$ |
| 26 | 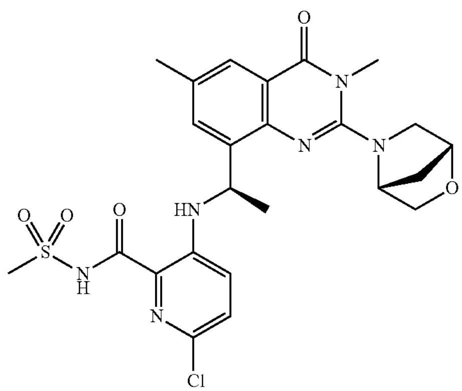 [SMILES: Cc1cc([C@@H](C)Nc2ccc(Cl)nc2C(=O)NS(C)(=O)=O)c2nc(N3C[C@H]4C[C@@H]3CO4)n(C)c(=O)c2c1] | 3-(((R)-1-(2-((1R,4R)-2-oxa-5-azabicyclo[2.2.1]heptan-5-yl)-3,6-dimethyl-4-oxo-3,4-dihydroquinazolin-8-yl)ethyl)amino)-6-chloro-N-(methylsulfonyl)picolinamide | 2.20 min, 254 nm, MS (ES+)[b] $C_{24}H_{27}ClN_6O_5S$ requires: 546.1, found: 547.2 $[M + H]^+$ |
| 27 | 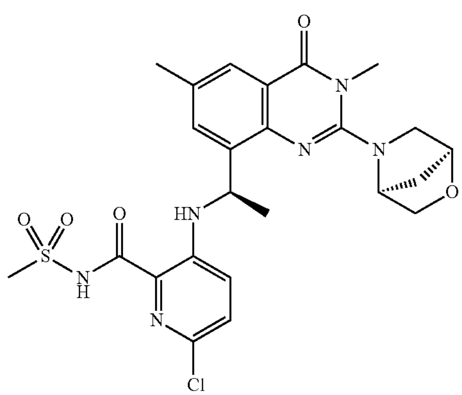 [SMILES: Cc1cc([C@@H](C)Nc2ccc(Cl)nc2C(=O)NS(C)(=O)=O)c2nc(N3C[C@@H]4C[C@H]3CO4)n(C)c(=O)c2c1] | 3-(((R)-1-(2-((1S,4S)-2-oxa-5-azabicyclo[2.2.1]heptan-5-yl)-3,6-dimethyl-4-oxo-3,4-dihydroquinazolin-8-yl)ethyl)amino)-6-chloro-N-(methylsulfonyl)picolinamide | 2.29 min, 254 nm, MS (ES+)[b] $C_{24}H_{27}ClN_6O_5S$ requires: 546.1, found: 546.7 $[M + H]^+$ |
| 28 | 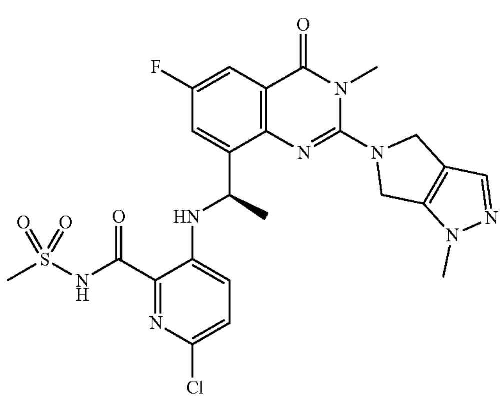 [SMILES: C[C@@H](Nc1ccc(Cl)nc1C(=O)NS(C)(=O)=O)c1cc(F)cc2c(=O)n(C)c(N3Cc4cnn(C)c4C3)nc12] | (R)-6-chloro-3-((1-(6-fluoro-3-methyl-2-(1-methyl-4,6-dihydropyrrolo[3,4-c]pyrazol-5(1H)-yl)-4-oxo-3,4-dihydroquinazolin-8-yl)ethyl)amino)-N-(methylsulfonyl)picolinamide | 2.23 min, 254 nm, MS (ES+)[b] $C_{24}H_{24}ClFN_8O_4S$ requires: 574.1, found: 574.7 $[M + H]^+$ |

TABLE E4-continued compound list prepared according to Route A in Example 4

| Cpd. ID | Structure | Name | LCMS |
|---|---|---|---|
| 29 | 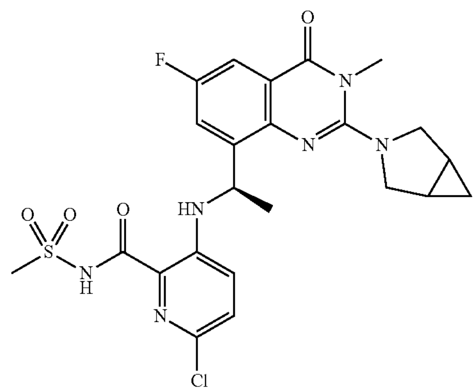 [SMILES: C[C@@H](Nc1ccc(Cl)nc1C(=O)NS(C)(=O)=O)c1cc(F)cc2c(=O)n(C)c(N3CC4CC4C3)nc12] | 3-(((1R)-1-(2-(3-azabicyclo[3.1.0]hexan-3-yl)-6-fluoro-3-methyl-4-oxo-3,4-dihydroquinazolin-8-yl)ethyl)amino)-6-chloro-N-(methylsulfonyl)picolinamide | 2.48 min, 254 nm, MS (ES+)[b] $C_{23}H_{24}ClFN_6O_4S$ requires: 534.1, found: 534.6 $[M + H]^+$ |
| 30 | 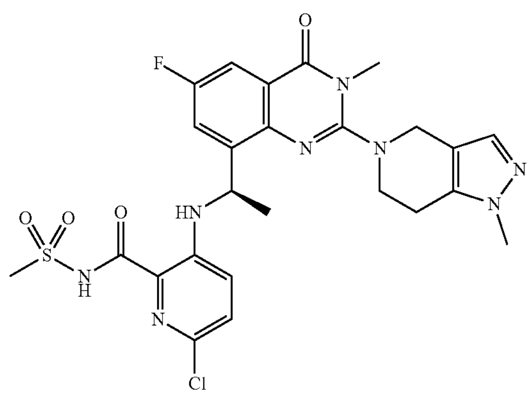 [SMILES: C[C@@H](Nc1ccc(Cl)nc1C(=O)NS(C)(=O)=O)c1cc(F)cc2c(=O)n(C)c(N3CCc4c(cnn4C)C3)nc12] | (R)-6-chloro-3-((1-(6-fluoro-3-methyl-2-(1-methyl-1,4,6,7-tetrahydro-5H-pyrazolo[4,3-c]pyridin-5-yl)-4-oxo-3,4-dihydroquinazolin-8-yl)ethyl)amino)-N-(methylsulfonyl)picolinamide | 2.26 min, 254 nm, MS (ES+)[b] $C_{25}H_{26}ClFN_8O_4S$ requires: 588.1, found: 588.9 $[M + H]^+$ |
| 31 | 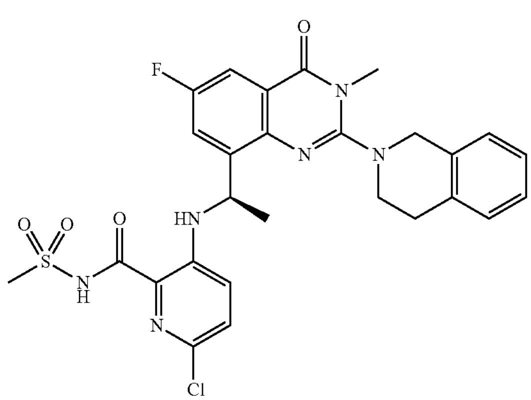 [SMILES: C[C@@H](Nc1ccc(Cl)nc1C(=O)NS(C)(=O)=O)c1cc(F)cc2c(=O)n(C)c(N3CCc4ccccc4C3)nc12] | (R)-6-chloro-3-((1-(2-(3,4-dihydroisoquinolin-2(1H)-yl)-6-fluoro-3-methyl-4-oxo-3,4-dihydroquinazolin-8-yl)ethyl)amino)-N-(methylsulfonyl)picolinamide | 2.77 min, 254 nm, MS (ES+)[b] $C_{27}H_{26}ClFN_6O_4S$ requires: 584.1, found: 584.9 $[M + H]^+$ |

TABLE E4-continued compound list prepared according to Route A in Example 4

| Cpd. ID | Structure | Name | LCMS |
|---|---|---|---|
| 32 | 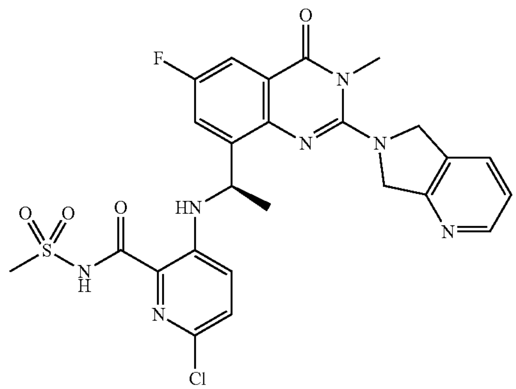 [SMILES: C[C@@H](Nc1ccc(Cl)nc1C(=O)NS(C)(=O)=O)c1cc(F)cc2c(=O)n(C)c(N3Cc4cccnc4C3)nc12] | (R)-6-chloro-3-((1-(2-(5,7-dihydro-6H-pyrrolo[3,4-b]pyridin-6-yl)-6-fluoro-3-methyl-4-oxo-3,4-dihydroquinazolin-8-yl)ethyl)amino)-N-(methylsulfonyl)picolinamide | 2.28 min, 254 nm, MS (ES+)[b] $C_{25}H_{23}ClFN_7O_4S$ requires: 571.1, found: 571.7 $[M + H]^+$ |
| 33 | 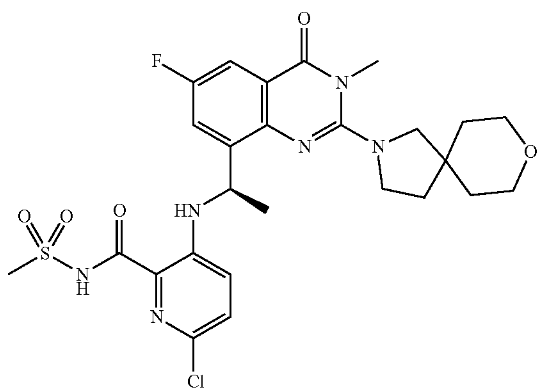 | (R)-6-chloro-3-((1-(3,6-dimethyl-4-oxo-2-(8-oxa-2-azaspiro[4.5]decan-2-yl)-3,4-dihydroquinazolin-8-yl)ethyl)amino)-N-(methylsulfonyl)picolinamide | 2.46 min, 254 nm, MS (ES+)[b] $C_{27}H_{33}ClN_6O_5S$ requires: 588.1, found: 588.7 $[M + H]^+$ |
| 34 | 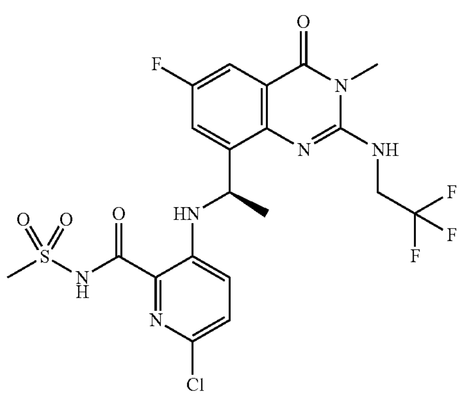 | (R)-6-chloro-3-((1-(3,6-dimethyl-4-oxo-2-((2,2,2-trifluoroethyl)amino)-3,4-dihydroquinazolin-8-yl)ethyl)amino)-N-(methylsulfonyl)picolinamide | 2.24 min, 270 nm, MS (ES+)[b] $C_{21}H_{22}ClF_3N_6O_4S$ requires: 546.1, found: 547.2 $[M + H]^+$ |
| 35 | 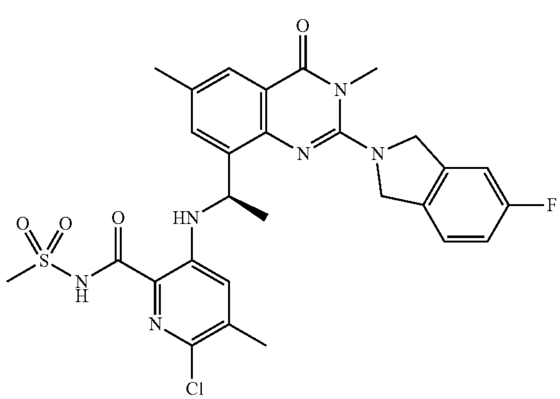 [SMILES: Cc1cc([C@@H](C)Nc2cc(C)c(Cl)nc2C(=O)NS(C)(=O)=O)c2nc(N3Cc4ccc(F)cc4C3)n(C)c(=O)c2c1] | (R)-6-chloro-3-((1-(2-(5-fluoroisoindolin-2-yl)-3,6-dimethyl-4-oxo-3,4-dihydroquinazolin-8-yl)ethyl)amino)-5-methyl-N-(methylsulfonyl)picolinamide | 2.66 min, 254 nm, MS (ES+)[b] $C_{28}H_{28}ClFN_6O_4S$ requires: 598.1, found: 599.3 $[M + H]^+$ |

TABLE E4-continued compound list prepared according to Route A in Example 4

| Cpd. ID | Structure | Name | LCMS |
|---|---|---|---|
| 36 | 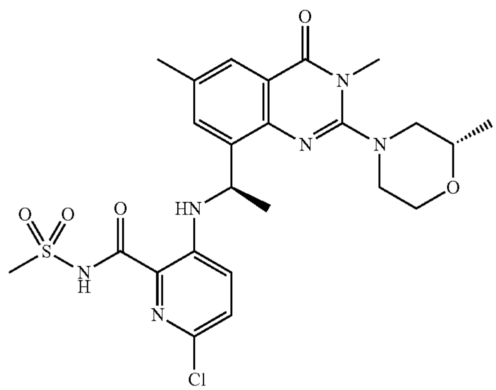 | 6-chloro-3-(((R)-1-(3,6-dimethyl-2-((S)-2-methylmorpholino)-4-oxo-3,4-dihydroquinazolin-8-yl)ethyl)amino)-N-(methylsulfonyl)picolinamide | 2.26 min, 254 nm, MS (ES+)[b] $C_{24}H_{29}ClN_6O_5S$ requires: 548.1, found: 549.3 [M + H]+ |
| 37 | 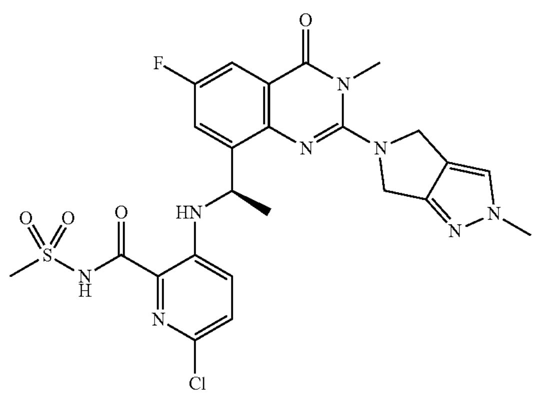 | (R)-6-chloro-3-((1-(6-fluoro-3-methyl-2-(2-methyl-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.24 min, 254. nm, MS (ES+)[b] $C_{24}H_{24}ClFN_8O_4S$ requires: 574.1, found: 575.3 [M + H]+ |
| 38 | 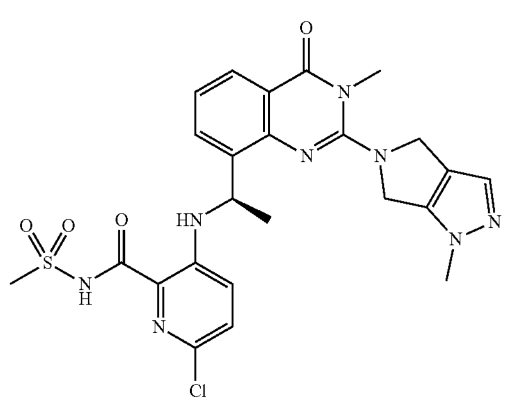 [SMILES: C[C@@H](Nc1ccc(Cl)nc1C(=O)NS(C)(=O)=O)c1cccc2c(=O)n(C)c(N3Cc4cnn(C)c4C3)nc12] | (R)-6-chloro-3-((1-(3-methyl-2-(1-methyl-4,6-dihydropyrrolo[3,4-c]pyrazol-5(1H)-yl)-4-oxo-3,4-dihydroquinazolin-8-yl)ethyl)amino)-N-(methylsulfonyl)picolinamide | 2.17 min, 254 nm, MS (ES+)[b] $C_{24}H_{25}ClN_8O_4S$ requires: 556.1, found: 557.3 [M + H]+ |

TABLE E4-continued compound list prepared according to Route A in Example 4

| Cpd. ID | Structure | Name | LCMS |
|---|---|---|---|
| 39 | 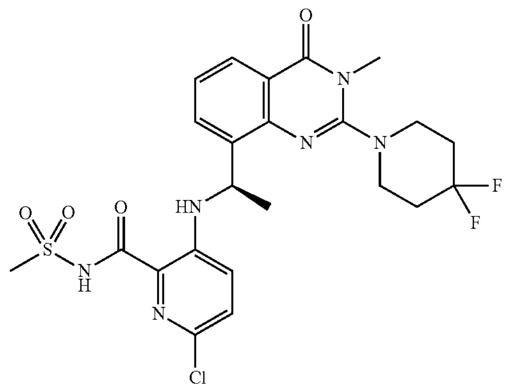 [SMILES: C[C@@H](Nc1ccc(Cl)nc1C(=O)NS(C)(=O)=O)c1cccc2c(=O)n(C)c(N3CCC(F)(F)CC3)nc12] | (R)-6-chloro-3-((1-(2-(4,4-difluoropiperidin-1-yl)-3-methyl-4-oxo-3,4-dihydroquinazolin-8-yl)ethyl)amino)-N-(methylsulfonyl)picolinamide | 2.45 min, 270 nm, MS (ES+)[b] $C_{23}H_{25}ClF_2N_6O_4S$ requires: 554.1, found: 555.3 $[M + H]^+$ |
| 40 | 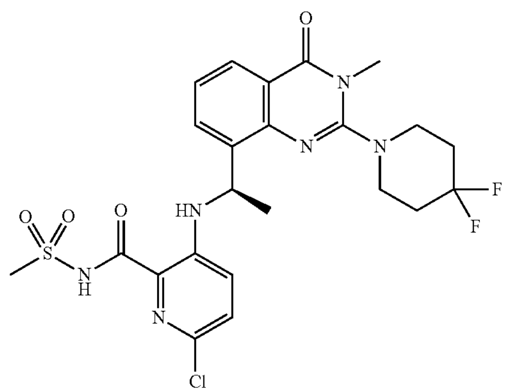 | (R)-6-chloro-3-((1-(2-(dimethylamino)-3,6-dimethyl-4-oxo-3,4-dihydroquinazolin-8-yl)ethyl)amino)-N-(methylsulfonyl)picolinamide | 2.38 min, 270 nm, MS (ES+)[b] $C_{21}H_{25}ClN_6O_4S$ requires: 492.1, found: 492.6 $[M + H]^+$ |
| 41 | 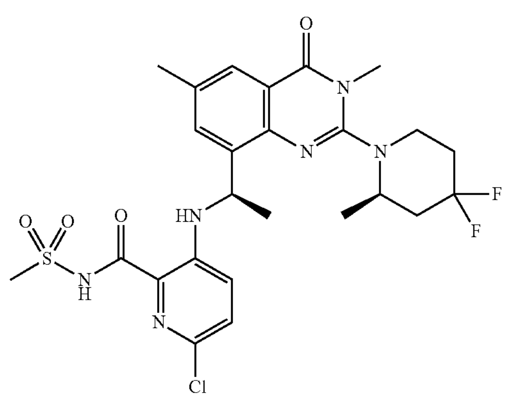 [SMILES: Cc1cc([C@@H](C)Nc2ccc(Cl)nc2C(=O)NS(C)(=O)=O)c2nc(N3CCC(F)(F)C[C@H]3C)n(C)c(=O)c2c1] | 6-chloro-3-(((R)-1-(2-((R*)-4,4-difluoro-2-methylpiperidin-1-yl)-3,6-dimethyl-4-oxo-3,4-dihydroquinazolin-8-yl)ethyl)amino)-N-(methylsulfonyl)picolinamide | 2.59 min, 254 nm, MS (ES+)[b] $C_{25}H_{29}ClF_2N_6O_4S$ requires: 582.1, found: 583.4 $[M + H]^+$ |
| 42 | 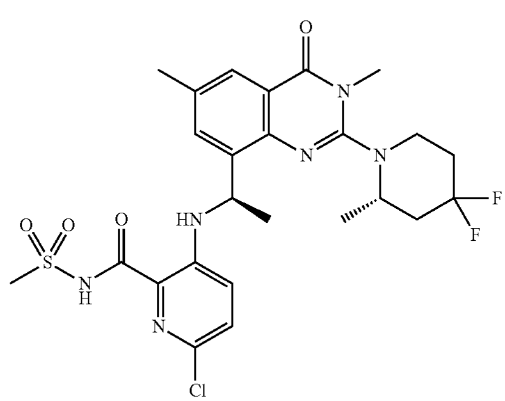 [SMILES: Cc1cc([C@@H](C)Nc2ccc(Cl)nc2C(=O)NS(C)(=O)=O)c2nc(N3CCC(F)(F)C[C@@H]3C)n(C)c(=O)c2c1] | 6-chloro-3-(((R)-1-(2-((R*)-4,4-difluoro-2-methylpiperidin-1-yl)-3,6-dimethyl-4-oxo-3,4-dihydroquinazolin-8-yl)ethyl)amino)-N-(methylsulfonyl)picolinamide | 2.59 min, 270 nm, MS (ES+)[b] $C_{25}H_{29}ClF_2N_6O_4S$ requires: 582.1, found: 583.7 $[M + H]^+$ |

TABLE E4-continued compound list prepared according to Route A in Example 4

| Cpd. ID | Structure | Name | LCMS |
|---|---|---|---|
| 43 | 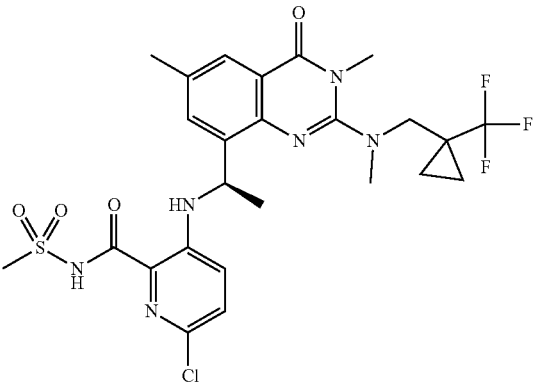 [SMILES: Cc1cc([C@@H](C)Nc2ccc(Cl)nc2C(=O)NS(C)(=O)=O)c2nc(N(C)CC3(C(F)(F)F)CC3)n(C)c(=O)c2c1] | (R)-6-chloro-3-((1-(3,6-dimethyl-2-(methyl((1-(trifluoromethyl)cyclopropyl)methyl)amino)-4-oxo-3,4-dihydroquinazolin-8-yl)ethyl)amino)-N-(methylsulfonyl)picolinamide | 2.69 min, 270 nm, MS (ES+)[b] $C_{25}H_{28}ClF_3N_6O_4S$ requires: 600.1, found: 601.5 $[M + H]^+$ |
| 44 | 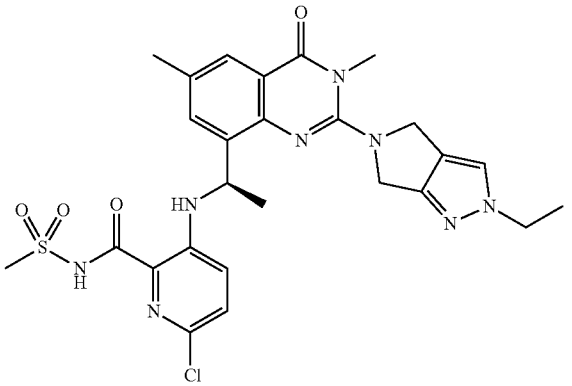 [SMILES: CCn1cc2c(n1)CN(c1nc3c([C@@H](C)Nc4ccc(Cl)nc4C(=O)NS(C)(=O)=O)cc(C)cc3c(=O)n1C)C2] | (R)-6-chloro-3-((1-(2-(2-ethyl-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.34 min, 254 nm, MS (ES+)[b] $C_{26}H_{29}ClN_8O_4S$ requires: 584.1, found: 585.6 $[M + H]^+$ |
| 45 | 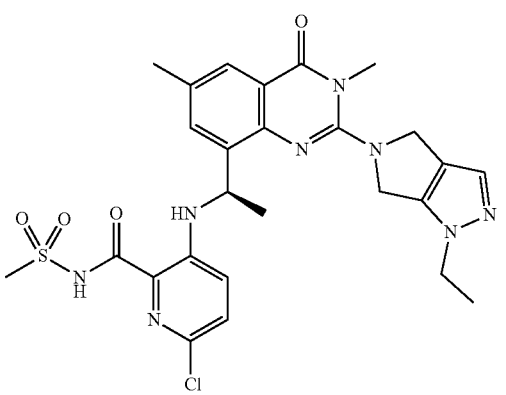 [SMILES: CCn1ncc2c1CN(c1nc3c([C@@H](C)Nc4ccc(Cl)nc4C(=O)NS(C)(=O)=O)cc(C)cc3c(=O)n1C)C2] | (R)-6-chloro-3-((1-(2-(1-ethyl-4,6-dihydropyrrolo[3,4-c]pyrazol-5(1H)-yl)-3,6-dimethyl-4-oxo-3,4-dihydroquinazolin-8-yl)ethyl)amino)-N-(methylsulfonyl)picolinamide | 2.29 min, 254 nm, MS (ES+)[b] $C_{26}H_{29}ClN_8O_4S$ requires: 584.1, found: 585.5 $[M + H]^+$ |

TABLE E4-continued compound list prepared according to Route A in Example 4

| Cpd. ID | Structure | Name | LCMS |
|---|---|---|---|
| 46 | 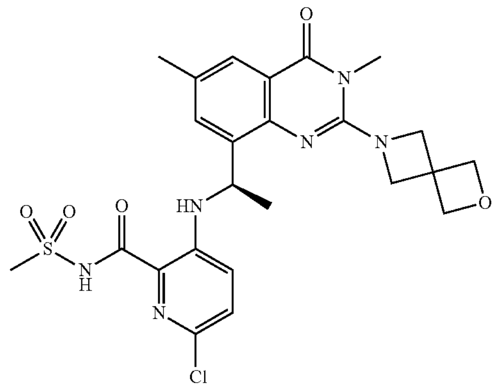 [SMILES: Cc1cc([C@@H](C)Nc2ccc(Cl)nc2C(=O)NS(C)(=O)=O)c2nc(N3CC4(COC4)C3)n(C)c(=O)c2c1] | (R)-6-chloro-3-((1-(3,6-dimethyl-4-oxo-2-(2-oxa-6-azaspiro[3.3]heptan-6-yl)-3,4-dihydroquinazolin-8-yl)ethyl)amino)-N-(methylsulfonyl)picolinamide | 2.23 min, 210 nm, MS (ES+)[b] $C_{24}H_{27}ClN_6O_5S$ requires: 546.1, found: 547.3 $[M + H]^+$ |
| 47 | 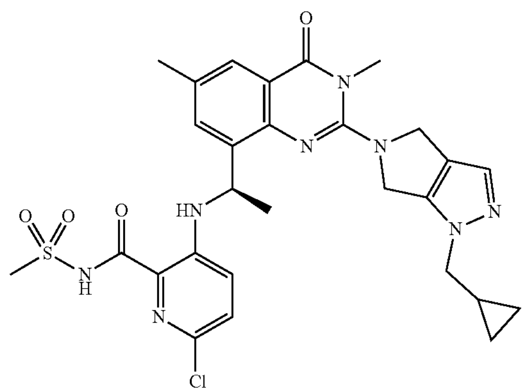 [SMILES: Cc1cc([C@@H](C)Nc2ccc(Cl)nc2C(=O)NS(C)(=O)=O)c2nc(N3Cc4cnn(CC5CC5)c4C3)n(C)c(=O)c2c1] | (R)-6-chloro-3-((1-(2-(1-(cyclopropylmethyl)-4,6-dihydropyrrolo[3,4-c]pyrazol-5(1H)-yl)-3,6-dimethyl-4-oxo-3,4-dihydroquinazolin-8-yl)ethyl)amino)-N-(methylsulfonyl)picolinamide | 2.39 min, 254 nm, MS (ES+)[b] $C_{28}H_{31}ClN_8O_4S$ requires: 610.1, found: 611.4 $[M + H]^+$ |
| 48 | 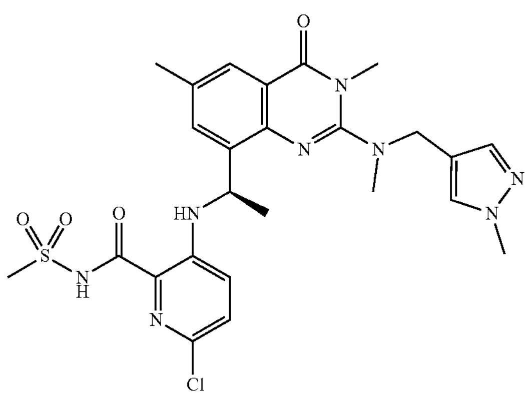 [SMILES: Cc1cc([C@@H](C)Nc2ccc(Cl)nc2C(=O)NS(C)(=O)=O)c2nc(N(C)Cc3cnn(C)c3)n(C)c(=O)c2c1] | (R)-6-chloro-3-((1-(3,6-dimethyl-2-(methyl((1-methyl-1H-pyrazol-4-yl)methyl)amino)-4-oxo-3,4-dihydroquinazolin-8-yl)ethyl)amino)-N-(methylsulfonyl)picolinamide | 2.23 min, 210 nm, MS (ES+)[b] $C_{25}H_{29}ClN_8O_4S$ requires: 572.1, found: 573.3 $[M + H]^+$ |
| 49 | 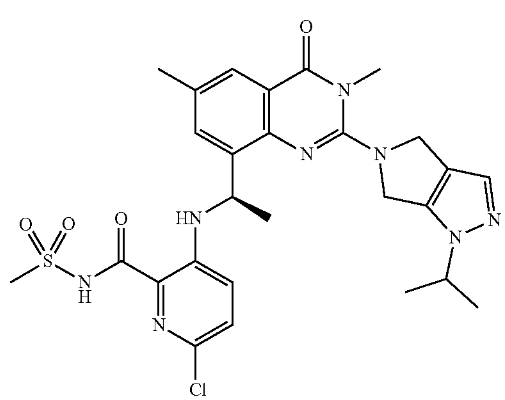 [SMILES: Cc1cc([C@@H](C)Nc2ccc(Cl)nc2C(=O)NS(C)(=O)=O)c2nc(N3Cc4cnn(C(C)C)c4C3)n(C)c(=O)c2c1] | (R)-6-chloro-3-((1-(2-(1-isopropyl-4,6-dihydropyrrolo[3,4-c]pyrazol-5(1H)-yl)-3,6-dimethyl-4-oxo-3,4-dihydroquinazolin-8-yl)ethyl)amino)-N-(methylsulfonyl)picolinamide | 2.37 min, 210 nm, MS (ES+)[b] $C_{27}H_{31}ClN_8O_4S$ requires: 598.1, found: 599.4 $[M + H]^+$ |

TABLE E4-continued compound list prepared according to Route A in Example 4

| Cpd. ID | Structure | Name | LCMS |
|---|---|---|---|
| 50 | 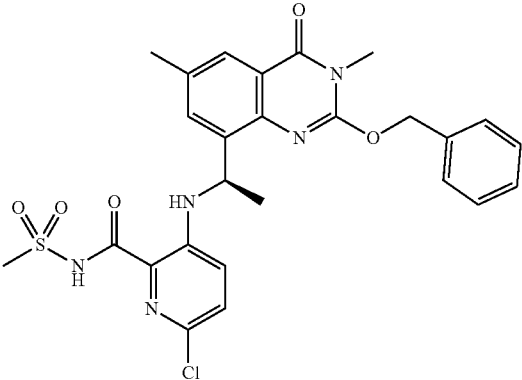 [SMILES: Cc1cc([C@@H](C)Nc2ccc(Cl)nc2C(=O)NS(C)(=O)=O)c2nc(OCc3ccccc3)n(C)c(=O)c2c1] | (R)-3-((1-(2-(benzyloxy)-3,6-dimethyl-4-oxo-3,4-dihydroquinazolin-8-yl)ethyl)amino)-6-chloro-N-(methylsulfonyl)picolinamide | 2.71 min, 210 nm, MS (ES+)[b] $C_{26}H_{26}ClN_5O_5S$ requires: 555.1, found: 556.3 $[M + H]^+$ |
| 51 | 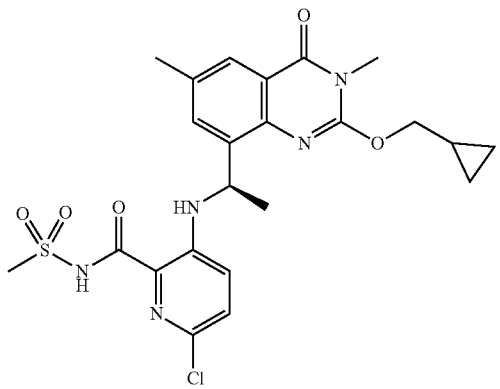 [SMILES: Cc1cc([C@@H](C)Nc2ccc(Cl)nc2C(=O)NS(C)(=O)=O)c2nc(OCC3CC3)n(C)c(=O)c2c1] | (R)-6-chloro-3-((1-(2-(cyclopropylmethoxy)-3,6-dimethyl-4-oxo-3,4-dihydroquinazolin-8-yl)ethyl)amino)-N-(methylsulfonyl)picolinamide | 2.66 min, 210 nm, MS (ES+)[b] $C_{23}H_{26}ClN_5O_5S$ requires: 519.1, found: 520.4 $[M + H]^+$ |
| 52 | 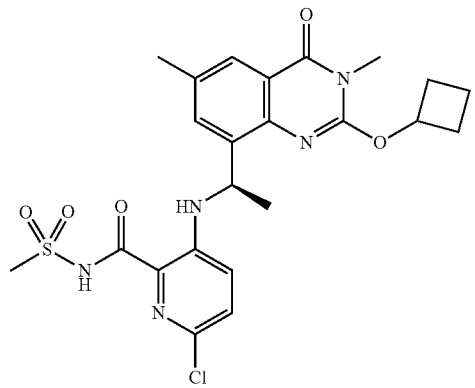 [SMILES: Cc1cc([C@@H](C)Nc2ccc(Cl)nc2C(=O)NS(C)(=O)=O)c2nc(OC3CCC3)n(C)c(=O)c2c1] | (R)-6-chloro-3-((1-(2-cyclobutoxy-3,6-dimethyl-4-oxo-3,4-dihydroquinazolin-8-yl)ethyl)amino)-N-(methylsulfonyl)picolinamide | 2.73 min, 254 nm, MS (ES+)[b] $C_{23}H_{26}ClN_5O_5S$ requires: 519.1, found: 520.4 $[M + H]^+$ |

TABLE E4-continued compound list prepared according to Route A in Example 4

| Cpd. ID | Structure | Name | LCMS |
|---|---|---|---|
| 53 | 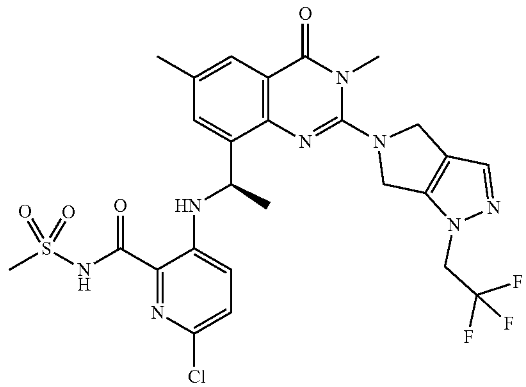 [SMILES: Cc1cc([C@@H](C)Nc2ccc(Cl)nc2C(=O)NS(C)(=O)=O)c2nc(N3Cc4cnn(CC(F)(F)F)c4C3)n(C)c(=O)c2c1] | (R)-6-chloro-3-((1-(3,6-dimethyl-4-oxo-2-(1-(2,2,2-trifluoroethyl)-4,6-dihydropyrrolo[3,4-c]pyrazol-5(1H)-yl)-3,4-dihydroquinazolin-8-yl)ethyl)amino)-N-(methylsulfonyl)picolinamide | 2.27 min, 254 nm, MS (ES+)[b] $C_{26}H_{26}ClF_3N_8O_4S$ requires: 638.1, found: 639.5 $[M + H]^+$ |
| 54 | 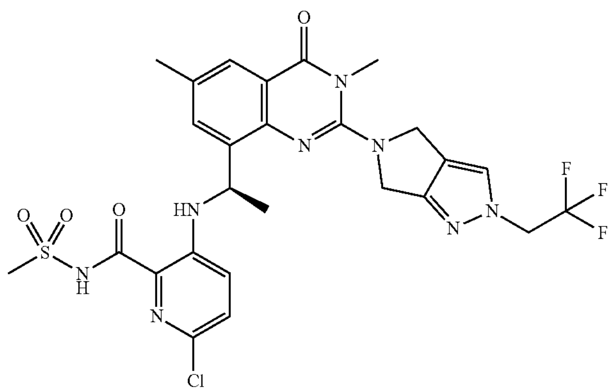 [SMILES: Cc1cc([C@@H](C)Nc2ccc(Cl)nc2C(=O)NS(C)(=O)=O)c2nc(N3Cc4cn(CC(F)(F)F)nc4C3)n(C)c(=O)c2c1] | (R)-6-chloro-3-((1-(3,6-dimethyl-4-oxo-2-(2-(2,2,2-trifluoroethyl)-2,6-dihydropyrrolo[3,4-c]pyrazol-5(4H)-yl)-3,4-dihydroquinazolin-8-yl)ethyl)amino)-N-(methylsulfonyl)picolinamide | 2.28 min, 254 nm, MS (ES+)[b] $C_{24}H_{29}ClN_6O_5S$ requires: 638.1, found: 639.5 $[M + H]^+$ |
| 55 | 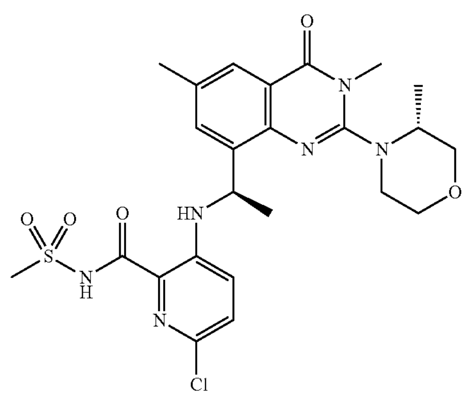 [SMILES: Cc1cc([C@@H](C)Nc2ccc(Cl)nc2C(=O)NS(C)(=O)=O)c2nc(N3CCOC[C@H]3C)n(C)c(=O)c2c1] | 6-chloro-3-(((R)-1-(3,6-dimethyl-2-((R)-3-methylmorpholino)-4-oxo-3,4-dihydroquinazolin-8-yl)ethyl)amino)-N-(methylsulfonyl)picolinamide | 2.39 min, 210 nm, MS (ES+)[b] $C_{26}H_{26}ClF_3N_8O_4S$ requires: 548.2, found: 549.5 $[M + H]^+$ |
| 56 | 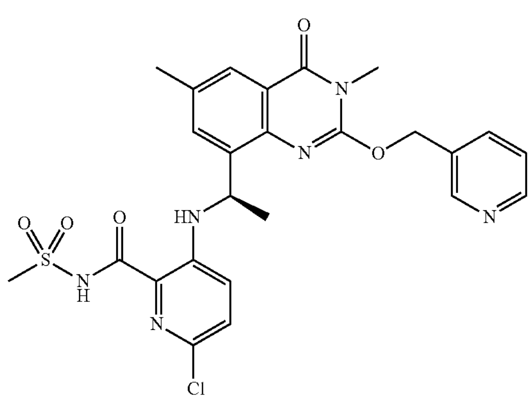 [SMILES: Cc1cc([C@@H](C)Nc2ccc(Cl)nc2C(=O)NS(C)(=O)=O)c2nc(OCc3cccnc3)n(C)c(=O)c2c1] | (R)-6-chloro-3-((1-(3,6-dimethyl-4-oxo-2-(pyridin-3-ylmethoxy)-3,4-dihydroquinazolin-8-yl)ethyl)amino)-N-(methylsulfonyl)picolinamide | 2.06 min, 210 nm, MS (ES+)[b] $C_{25}H_{25}ClN_6O_5S$ requires: 556.1, found: 557.6 $[M + H]^+$ |

TABLE E4-continued compound list prepared according to Route A in Example 4

| Cpd. ID | Structure | Name | LCMS |
|---|---|---|---|
| 57 | 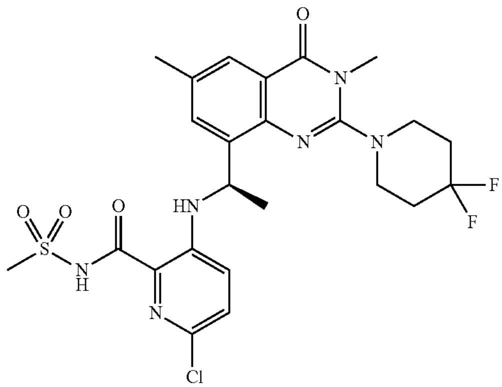 [SMILES: Cc1cc([C@@H](C)Nc2ccc(Cl)nc2C(=O)NS(C)(=O)=O)c2nc(N3CCC(F)(F)CC3)n(C)c(=O)c2c1] | (R)-6-chloro-3-((1-(2-(4,4-difluoropiperidin-1-yl)-3,6-dimethyl-4-oxo-3,4-dihydroquinazolin-8-yl)ethyl)amino)-N-(methylsulfonyl)picolinamide | 2.32 min, 210 nm, MS (ES+)[b] $C_{23}H_{26}ClF_2N_7O_4S$ requires: 569.1, found: 570.5 $[M + H]^+$ |
| 110 | 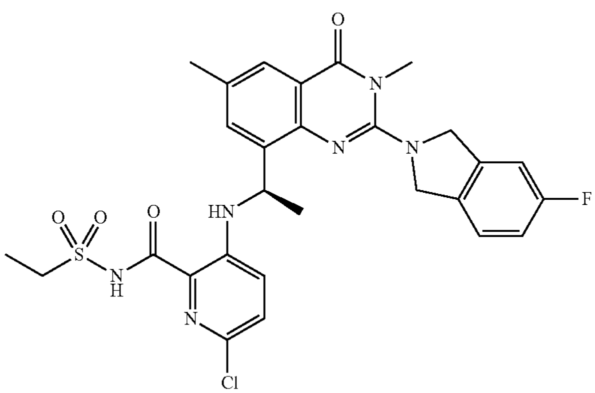 [SMILES: CCS(=O)(=O)NC(=O)c1nc(Cl)ccc1N[C@H](C)c1cc(C)cc2c(=O)n(C)c(N3Cc4ccc(F)cc4C3)nc12] | (R)-6-chloro-N-(ethylsulfonyl)-3-((1-(2-(5-fluoroisoindolin-2-yl)-3,6-dimethyl-4-oxo-3,4-dihydroquinazolin-8-yl)ethyl)amino)picolinamide | 2.71 min, 254 nm, MS (ES+)[b] $C_{28}H_{28}ClFN_6O_4S$, requires: 598.2, found: 599.2 $[M + H]^+$ |
| 146 | 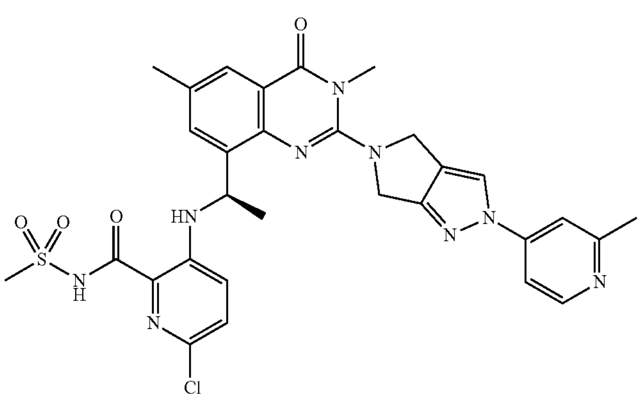 | (R)-6-chloro-3-((1-(3,6-dimethyl-2-(2-(2-methylpyridin-4-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.01 min, 210 nm, MS (ES+)[b] $C_{30}H_{30}ClN_9O_4S$, requires: 647.1, found: 648.2 $[M + H]^+$ |

TABLE E4-continued compound list prepared according to Route A in Example 4

| Cpd. ID | Structure | Name | LCMS |
|---|---|---|---|
| 147 | 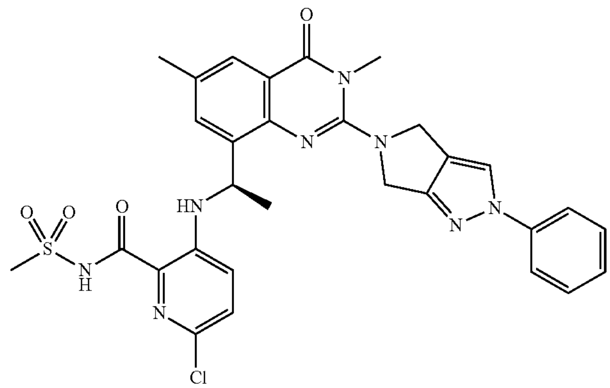 [SMILES: Cc1cc([C@@H](C)Nc2ccc(Cl)nc2C(=O)NS(C)(=O)=O)c2nc(N3Cc4cn(-c5ccccc5)nc4C3)n(C)c(=O)c2c1] | (R)-6-chloro-3-((1-(3,6-dimethyl-4-oxo-2-(2-phenyl-2,6-dihydropyrrolo[3,4-c]pyrazol-5(4H)-yl)-3,4-dihydroquinazolin-8-yl)ethyl)amino)-N-(methylsulfonyl)picolinamide | 2.66 min, 254 nm, MS (ES+)[b] $C_{30}H_{29}ClN_8O_4S$, requires: 632.2, found: 633.7 $[M + H]^+$ |
| 148 | 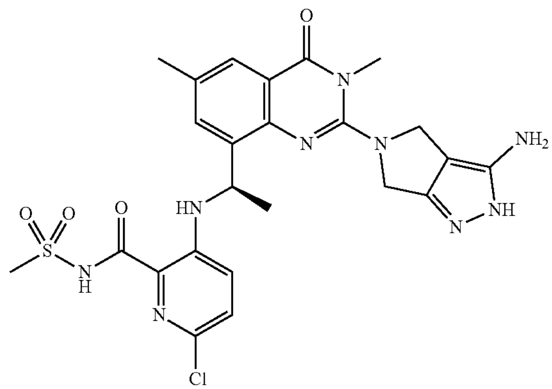 [SMILES: Cc1cc([C@@H](C)Nc2ccc(Cl)nc2C(=O)NS(C)(=O)=O)c2nc(N3Cc4n[nH]c(N)c4C3)n(C)c(=O)c2c1] | (R)-3-((1-(2-(3-amino-2,6-dihydropyrrolo[3,4-c]pyrazol-5(4H)-yl)-3,6-dimethyl-4-oxo-3,4-dihydroquinazolin-8-yl)ethyl)amino)-6-chloro-N-(methylsulfonyl)picolinamide | 1.91 min, 210 nm, MS (ES+)[b] $C_{24}H_{26}ClN_9O_4S$, requires: 571.2, found: 572.2 $[M + H]^+$ |
| 149 | 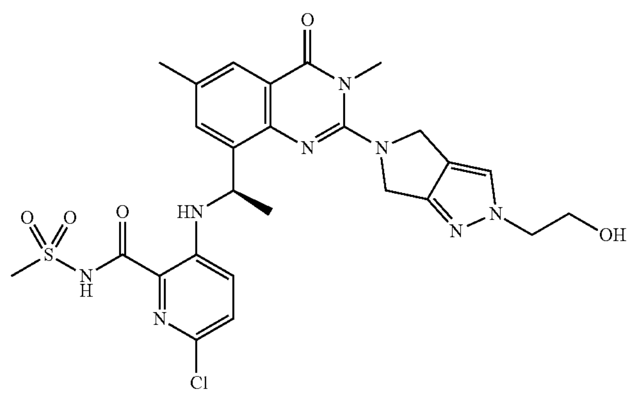 [SMILES: Cc1cc([C@@H](C)Nc2ccc(Cl)nc2C(=O)NS(C)(=O)=O)c2nc(N3Cc4cn(CCO)nc4C3)n(C)c(=O)c2c1] | (R)-6-chloro-3-((1-(2-(2-(2-hydroxyethyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 1.89 min, 210 nm, MS (ES+)[b] $C_{26}H_{29}ClN_8O_5S$, requires: 600.2, found: 601.2 $[M + H]^+$ |
| 163 | 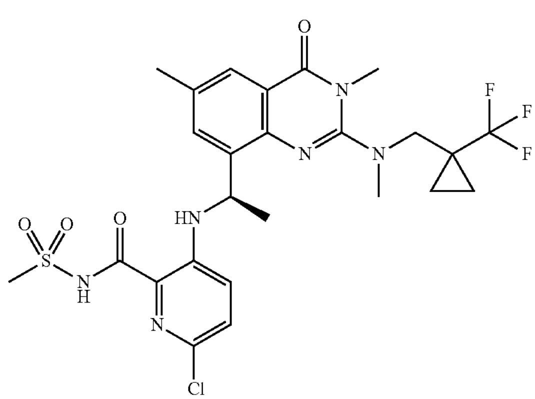 [SMILES: Cc1cc([C@@H](C)Nc2ccc(Cl)nc2C(=O)NS(C)(=O)=O)c2nc(N(C)CC3(C(F)(F)F)CC3)n(C)c(=O)c2c1] | (R)-6-chloro-3-((1-(3,6-dimethyl-2-(methyl((1-(trifluoromethyl)cyclopropyl)methyl)amino)-4-oxo-3,4-dihydroquinazolin-8-yl)ethyl)amino)-N-(methylsulfonyl)picolinamide | 2.69 min, 270 nm, MS (ES+)[b] $C_{25}H_{28}ClF_3N_6O_4S$ requires: 600.1, found: 601.5 $[M + H]^+$ |

TABLE E4-continued compound list prepared according to Route A in Example 4

| Cpd. ID | Structure | Name | LCMS |
|---|---|---|---|
| 164 | 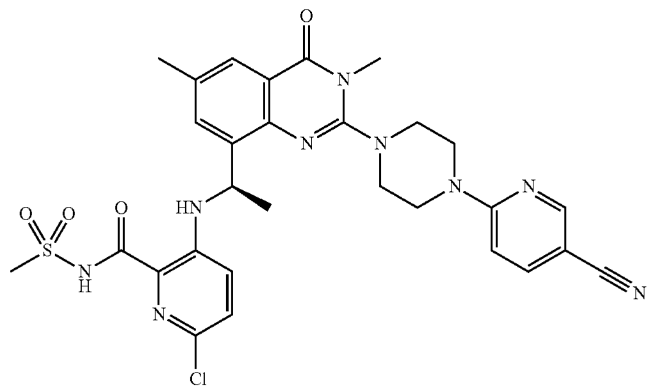 | (R)-6-chloro-3-((1-(2-(4-(5-cyanopyridin-2-yl)piperazin-1-yl)-3,6-dimethyl-4-oxo-3,4-dihydroquinazolin-8-yl)ethyl)amino)-N-(methylsulfonyl)picolinamide | 3.56 min, 254 nm, MS (ES+)$^c$ $C_{29}H_{30}ClN_9O_4S$, requires: 635.2, found: 636.2 [M + H]$^+$ |
| 165 | 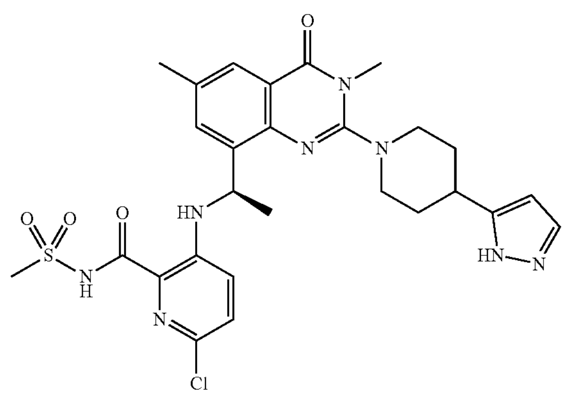 [SMILES: Cc1cc([C@@H](C)Nc2ccc(Cl)nc2C(=O)NS(C)(=O)=O)c2nc(N3CCC(c4ccn[nH]4)CC3)n(C)c(=O)c2c1] | (R)-3-((1-(2-(4-(1H-pyrazol-5-yl)piperidin-1-yl)-3,6-dimethyl-4-oxo-3,4-dihydroquinazolin-8-yl)ethyl)amino)-6-chloro-N-(methylsulfonyl)picolinamide | 3.14 min, 254 nm, MS (ES+)$^c$ $C_{27}H_{31}ClN_8O_4S$, requires: 598.2, found: 599.3 [M + H]$^+$ |
| 166 | 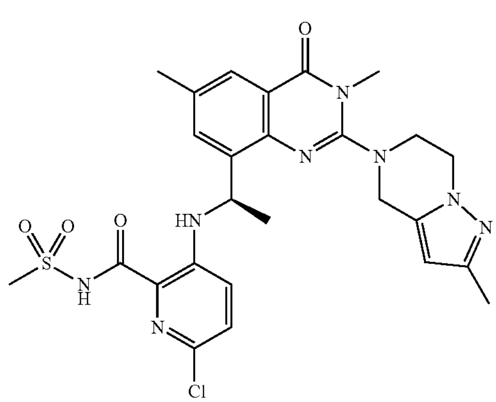 | (R)-6-chloro-3-((1-(3,6-dimethyl-2-(2-methyl-6,7-dihydropyrazolo[1,5-a]pyrazin-5(4H)-yl)-4-oxo-3,4-dihydroquinazolin-8-yl)ethyl)amino)-N-(methylsulfonyl)picolinamide | 3.10 min, 254 nm, MS (ES+)$^c$ $C_{26}H_{29}ClN_8O_4S$, requires: 584.2, found: 585.2 [M + H]$^+$ |

TABLE E4-continued compound list prepared according to Route A in Example 4

| Cpd. ID | Structure | Name | LCMS |
|---|---|---|---|
| 167 | 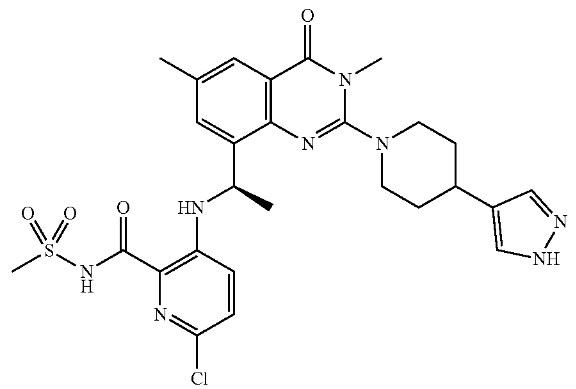 [SMILES: Cc1cc([C@@H](C)Nc2ccc(Cl)nc2C(=O)NS(C)(=O)=O)c2nc(N3CCC(c4cn[nH]c4)CC3)n(C)c(=O)c2c1] | (R)-3-((1-(2-(4-(1H-pyrazol-4-yl)piperidin-1-yl)-3,6-dimethyl-4-oxo-3,4-dihydroquinazolin-8-yl)ethyl)amino)-6-chloro-N-(methylsulfonyl)picolinamide | 2.02 min, 254 nm, MS (ES+)$^c$ $C_{27}H_{31}ClN_8O_4S$, requires: 598.2, found: 599.2 [M + H]$^+$ |
| 168 | 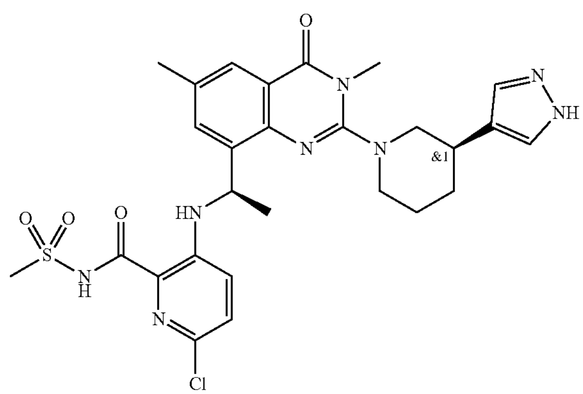 [SMILES: Cc1cc([C@@H](C)Nc2ccc(Cl)nc2C(=O)NS(C)(=O)=O)c2nc(N3CCC[C@H](c4cn[nH]c4)C3)n(C)c(=O)c2c1] | 3-(((R)-1-(2-((RS)-3-(1H-pyrazol-4-yl)piperidin-1-yl)-3,6-dimethyl-4-oxo-3,4-dihydroquinazolin-8-yl)ethyl)amino)-6-chloro-N-(methylsulfonyl)picolinamide | 2.16 min, 254 nm, MS (ES+)$^c$ $C_{27}H_{31}ClN_8O_4S$, requires: 598.1, found: 599.2 [M + H]$^+$ |
| 169 | 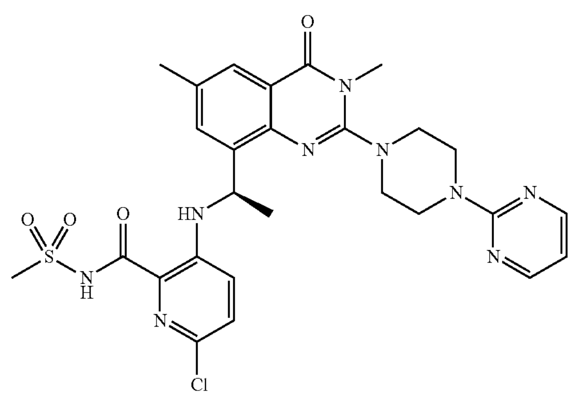 [SMILES: Cc1cc([C@@H](C)Nc2ccc(Cl)nc2C(=O)NS(C)(=O)=O)c2nc(N3CCN(c4ncccn4)CC3)n(C)c(=O)c2c1] | (R)-6-chloro-3-((1-(3,6-dimethyl-4-oxo-2-(4-(pyrimidin-2-yl)piperazin-1-yl)-3,4-dihydroquinazolin-8-yl)ethyl)amino)-N-(methylsulfonyl)picolinamide | 2.47 min, 254 nm, MS (ES+)$^b$ $C_{27}H_{30}ClN_9O_4S$, requires: 611.1, found: 612.2 [M + H]$^+$ |
| 170 | 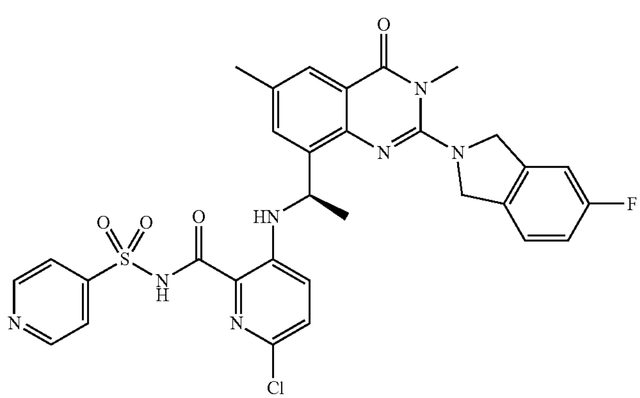 [SMILES: Cc1cc([C@@H](C)Nc2ccc(Cl)nc2C(=O)NS(=O)(=O)c2ccncc2)c2nc(N3Cc4ccc(F)cc4C3)n(C)c(=O)c2c1] | (R)-6-chloro-3-((1-(2-(5-fluoroisoindolin-2-yl)-3,6-dimethyl-4-oxo-3,4-dihydroquinazolin-8-yl)ethyl)amino)-N-(pyridin-4-ylsulfonyl)picolinamide | 2.65 min, 254 nm, MS (ES+)$^b$ $C_{31}H_{27}ClFN_7O_4S$, requires: 647.1, found: 648.1 [M + H]$^+$ |

TABLE E4-continued compound list prepared according to Route A in Example 4

| Cpd. ID | Structure | Name | LCMS |
|---|---|---|---|
| 171 | 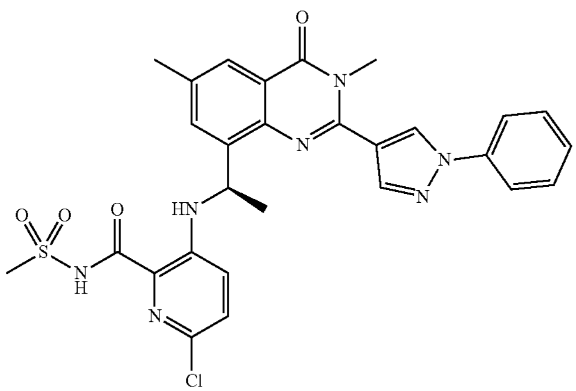 [SMILES: Cc1cc([C@@H](C)Nc2ccc(Cl)nc2C(=O)NS(C)(=O)=O)c2nc(-c3cnn(-c4ccccc4)c3)n(C)c(=O)c2c1] | (R)-6-chloro-3-((1-(3,6-dimethyl-4-oxo-2-(1-phenyl-1H-pyrazol-4-yl)-3,4-dihydroquinazolin-8-yl)ethyl)amino)-N-(methylsulfonyl)picolinamide | 2.56 min, 265 nm, MS (ES+)$^b$ $C_{28}H_{26}ClN_7O_4S$, requires: 591.1, found: 592.1 [M + H]$^+$ |
| 172 | 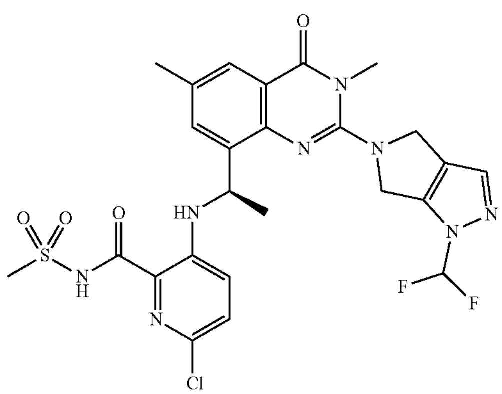 | (R)-6-chloro-3-((1-(2-(1-(difluoromethyl)-4,6-dihydropyrrolo[3,4-c]pyrazol-5(1H)-yl)-3,6-dimethyl-4-oxo-3,4-dihydroquinazolin-8-yl)ethyl)amino)-N-(methylsulfonyl)picolinamide | 2.38 min, 254 nm, MS (ES+)$^b$ $C_{25}H_{25}ClF_2N_8O_4S$, requires: 606.1, found: 607.1 [M + H]$^+$ |
| 173 | 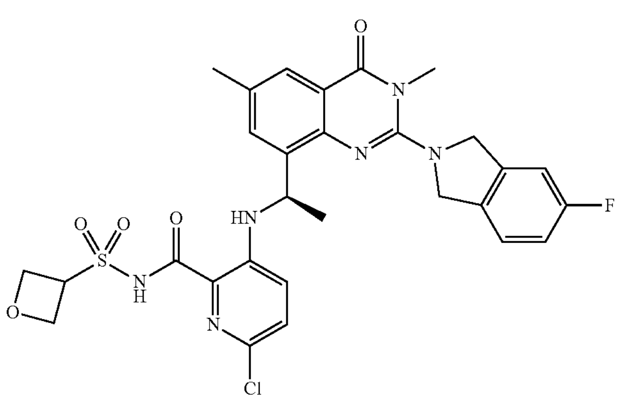 [SMILES: Cc1cc([C@@H](C)Nc2ccc(Cl)nc2C(=O)NS(=O)(=O)C2COC2)c2nc(N3Cc4ccc(F)cc4C3)n(C)c(=O)c2c1] | (R)-6-chloro-3-((1-(2-(5-fluoroisoindolin-2-yl)-3,6-dimethyl-4-oxo-3,4-dihydroquinazolin-8-yl)ethyl)amino)-N-(oxetan-3-ylsulfonyl)picolinamide | 2.57 min, 254 nm, MS (ES+)$^b$ $C_{29}H_{28}ClFN_6O_5S$, requires: 626.1, found: 627.2 [M + H]$^+$ |

TABLE E4-continued compound list prepared according to Route A in Example 4

| Cpd. ID | Structure | Name | LCMS |
|---|---|---|---|
| 174 | 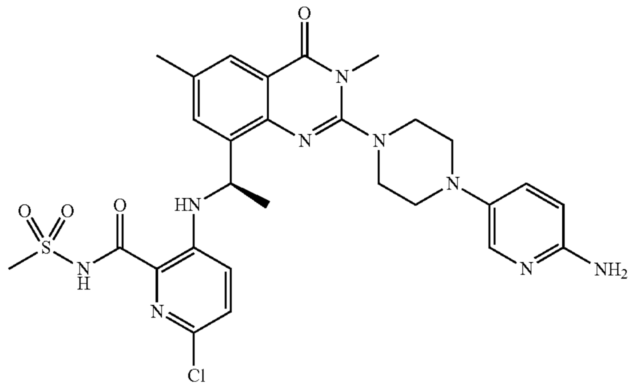 [SMILES: Cc1cc([C@@H](C)Nc2ccc(Cl)nc2C(=O)NS(C)(=O)=O)c2nc(N3CCN(c4ccc(N)nc4)CC3)n(C)c(=O)c2c1] | (R)-3-((1-(2-(4-(6-aminopyridin-3-yl)piperazin-1-yl)-3,6-dimethyl-4-oxo-3,4-dihydroquinazolin-8-yl)ethyl)amino)-6-chloro-N-(methylsulfonyl)picolinamide | 1.96 min, 265 nm, MS (ES+)[b] $C_{28}H_{32}ClN_9O_4S$, requires: 625.2, found: 626.2 [M + H]+ |
| 175 | 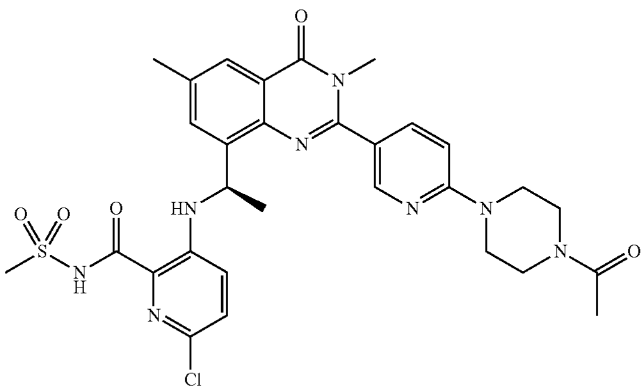 [SMILES: CC(=O)N1CCN(c2ccc(-c3nc4c([C@@H](C)Nc5ccc(Cl)nc5C(=O)NS(C)(=O)=O)cc(C)cc4c(=O)n3C)cn2)CC1] | (R)-3-((1-(2-(6-(4-acetylpiperazin-1-yl)pyridin-3-yl)-3,6-dimethyl-4-oxo-3,4-dihydroquinazolin-8-yl)ethyl)amino)-6-chloro-N-(methylsulfonyl)picolinamide | 2.12 min, 270 nm, MS (ES+)[b] $C_{30}H_{33}ClN_8O_5S$, requires: 652.2, found: 653.2 [M + H]+ |
| 176 | 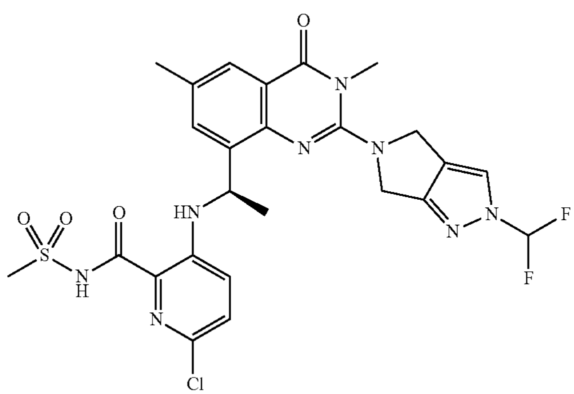 [SMILES: Cc1cc([C@@H](C)Nc2ccc(Cl)nc2C(=O)NS(C)(=O)=O)c2nc(N3Cc4cn(C(F)F)nc4C3)n(C)c(=O)c2c1] | (R)-6-chloro-3-((1-(2-(2-(difluoromethyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.39 min, 275 nm, MS (ES+)[b] $C_{25}H_{25}ClF_2N_8O_4S$, requires: 606.1, found: 607.2 [M + H]+ |
| 177 | 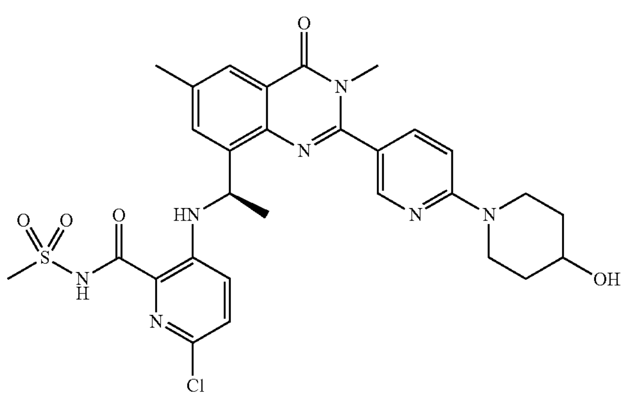 [SMILES: Cc1cc([C@@H](C)Nc2ccc(Cl)nc2C(=O)NS(C)(=O)=O)c2nc(-c3ccc(N4CCC(O)CC4)nc3)n(C)c(=O)c2c1] | (R)-6-chloro-3-((1-(2-(6-(4-hydroxypiperidin-1-yl)pyridin-3-yl)-3,6-dimethyl-4-oxo-3,4-dihydroquinazolin-8-yl)ethyl)amino)-N-(methylsulfonyl)picolinamide | 1.95 min, 265 nm, MS (ES+)[b] $C_{29}H_{32}ClN_7O_5S$, requires: 625.1, found: 626.2 [M + H]+ |

TABLE E4-continued compound list prepared according to Route A in Example 4

| Cpd. ID | Structure | Name | LCMS |
|---|---|---|---|
| 178 | 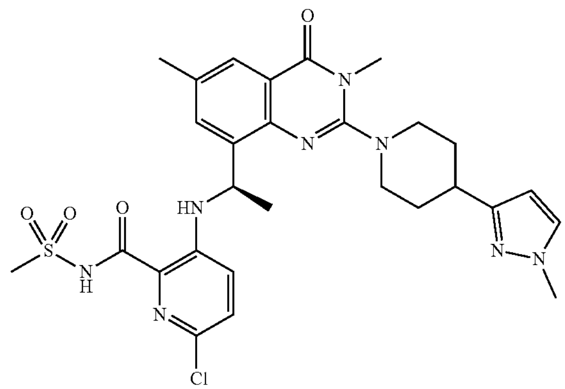 | (R)-6-chloro-3-((1-(3,6-dimethyl-2-(4-(1-methyl-1H-pyrazol-3-yl)piperidin-1-yl)-4-oxo-3,4-dihydroquinazolin-8-yl)ethyl)amino)-N-(methylsulfonyl)picolinamide | 2.41 min, 270 nm, MS (ES+)[b] $C_{28}H_{33}ClN_8O_4S$, requires: 612.2, found: 613.2 $[M + H]^+$ |
| 179 | 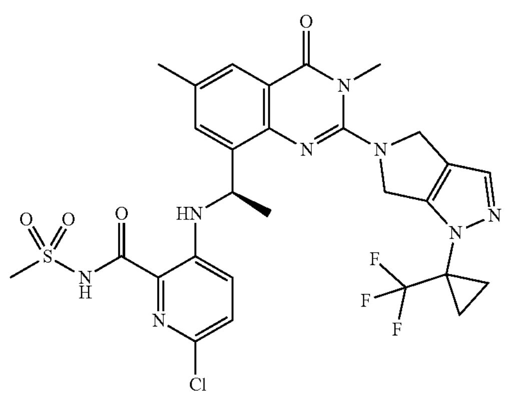 [SMILES: Cc1cc([C@@H](C)Nc2ccc(Cl)nc2C(=O)NS(C)(=O)=O)c2nc(N3Cc4cnn(C5(C(F)(F)F)CC5)c4C3)n(C)c(=O)c2c1] | (R)-6-chloro-3-((1-(3,6-dimethyl-4-oxo-2-(1-(1-(trifluoromethyl)cyclopropyl)-4,6-dihydropyrrolo[3,4-c]pyrazol-5(1H)-yl)-3,4-dihydroquinazolin-8-yl)ethyl)amino)-N-(methylsulfonyl)picolinamide | 2.43 min, 254 nm, MS (ES+)[b] $C_{28}H_{28}ClF_3N_8O_4S$, requires: 664.1, found: 665.1 $[M + H]^+$ |
| 180 | 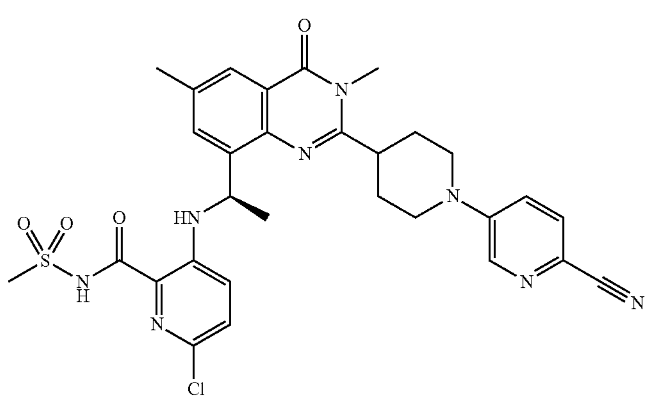 [SMILES: Cc1cc([C@@H](C)Nc2ccc(Cl)nc2C(=O)NS(C)(=O)=O)c2nc(C3CCN(c4ccc(C#N)nc4)CC3)n(C)c(=O)c2c1] | (R)-6-chloro-3-((1-(2-(1-(6-cyanopyridin-3-yl)piperidin-4-yl)-3,6-dimethyl-4-oxo-3,4-dihydroquinazolin-8-yl)ethyl)amino)-N-(methylsulfonyl)picolinamide | 2.38 min, 254 nm, MS (ES+)[b] $C_{30}H_{31}ClN_8O_4S$, requires: 634.1, found: 635.2 $[M + H]^+$ |

TABLE E4-continued compound list prepared according to Route A in Example 4

| Cpd. ID | Structure | Name | LCMS |
|---|---|---|---|
| 181 | 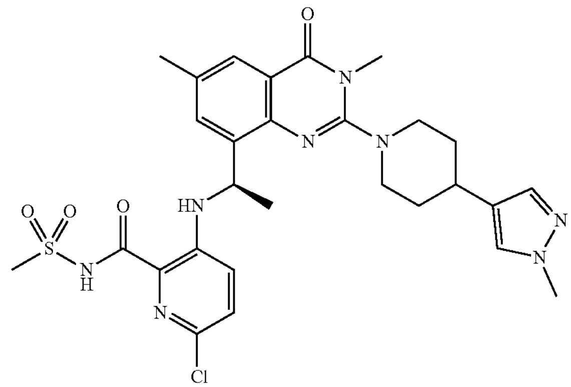 [SMILES: Cc1cc([C@@H](C)Nc2ccc(Cl)nc2C(=O)NS(C)(=O)=O)c2nc(N3CCC(c4cnn(C)c4)CC3)n(C)c(=O)c2c1] | (R)-6-chloro-3-((1-(3,6-dimethyl-2-(4-(1-methyl-1H-pyrazol-4-yl)piperidin-1-yl)-4-oxo-3,4-dihydroquinazolin-8-yl)ethyl)amino)-N-(methylsulfonyl)picolinamide | 2.39 min, 270 nm, MS (ES+)[b] $C_{28}H_{33}ClN_8O_4S$, requires: 612.2, found: 613.2 [M + H]+ |
| 182 | 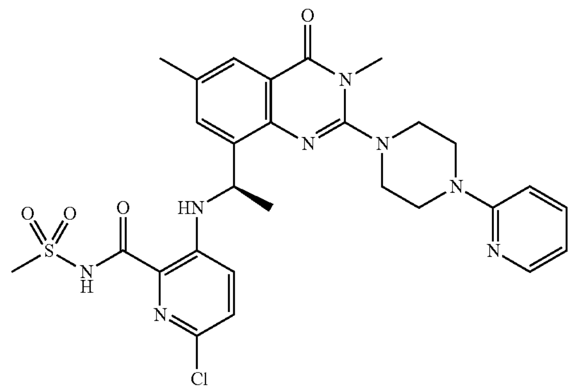 | (R)-6-chloro-3-((1-(3,6-dimethyl-4-oxo-2-(4-(pyridin-2-yl)piperazin-1-yl)-3,4-dihydroquinazolin-8-yl)ethyl)amino)-N-(methylsulfonyl)picolinamide | 2.05 min, 270 nm, MS (ES+)[b] $C_{28}H_{31}ClN_8O_4S$, requires: 610.1, found: 611.3 [M + H]+ |
| 183 | 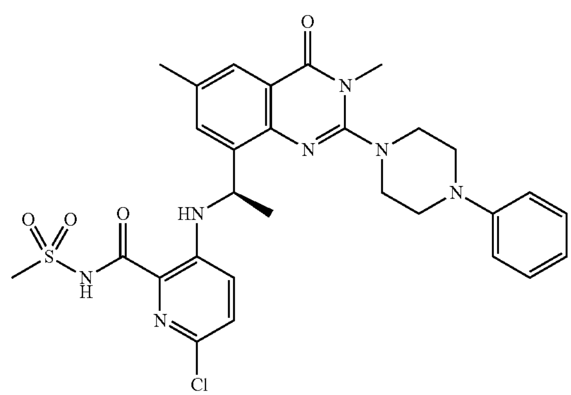 [SMILES: Cc1cc([C@@H](C)Nc2ccc(Cl)nc2C(=O)NS(C)(=O)=O)c2nc(N3CCN(c4ccccc4)CC3)n(C)c(=O)c2c1] | (R)-6-chloro-3-((1-(3,6-dimethyl-4-oxo-2-(4-phenylpiperazin-1-yl)-3,4-dihydroquinazolin-8-yl)ethyl)amino)-N-(methylsulfonyl)picolinamide | 2.09 min, 270 nm, MS (ES+)[b] $C_{29}H_{32}ClN_7O_4S$, requires: 609.1, found: 610.2 [M + H]+ |
| 184 | 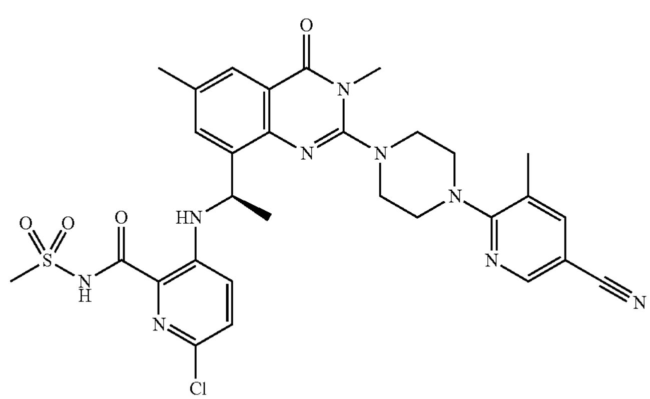 | (R)-6-chloro-3-((1-(2-(4-(5-cyano-3-methylpyridin-2-yl)piperazin-1-yl)-3,6-dimethyl-4-oxo-3,4-dihydroquinazolin-8-yl)ethyl)amino)-N-(methylsulfonyl)picolinamide | 2.20 min, 285 nm, MS (ES+)[b] $C_{30}H_{32}ClN_9O_4S$, requires: 649.2, found: 650.2 [M + H]+ |

TABLE E4-continued compound list prepared according to Route A in Example 4

| Cpd. ID | Structure | Name | LCMS |
|---|---|---|---|
| 185 | 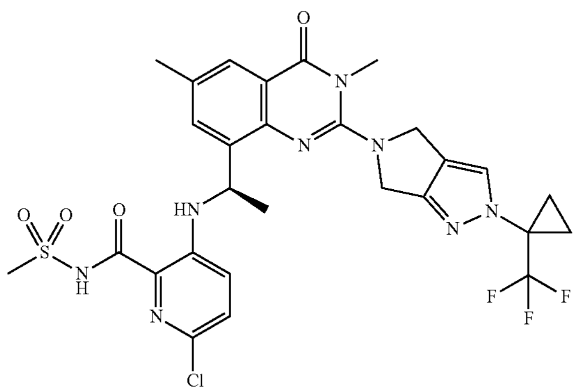 [SMILES: Cc1cc([C@@H](C)Nc2ccc(Cl)nc2C(=O)NS(C)(=O)=O)c2nc(N3Cc4cn(C5(C(F)(F)F)CC5)nc4C3)n(C)c(=O)c2c1] | (R)-6-chloro-3-((1-(3,6-dimethyl-4-oxo-2-(2-(1-(trifluoromethyl)cyclopropyl)-2,6-dihydropyrrolo[3,4-c]pyrazol-5(4H)-yl)-3,4-dihydroquinazolin-8-yl)ethyl)amino)-N-(methylsulfonyl)picolinamide | 2.43 min, 254 nm, MS (ES+)[b] $C_{28}H_{28}ClF_3N_8O_4S$, requires: 664.1, found: 665.1 [M + H]+ |
| 186 | 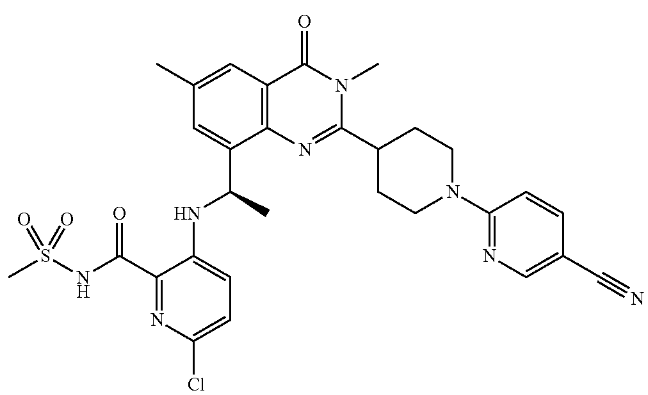 [SMILES: Cc1cc([C@@H](C)Nc2ccc(Cl)nc2C(=O)NS(C)(=O)=O)c2nc(C3CCN(c4ccc(C#N)cn4)CC3)n(C)c(=O)c2c1] | (R)-6-chloro-3-((1-(2-(1-(5-cyanopyridin-2-yl)piperidin-4-yl)-3,6-dimethyl-4-oxo-3,4-dihydroquinazolin-8-yl)ethyl)amino)-N-(methylsulfonyl)picolinamide | 2.48 min, 254 nm, MS (ES+)[b] $C_{30}H_{31}ClN_8O_4S$, requires: 634.1, found: 635.1 [M + H]+ |
| 187 | 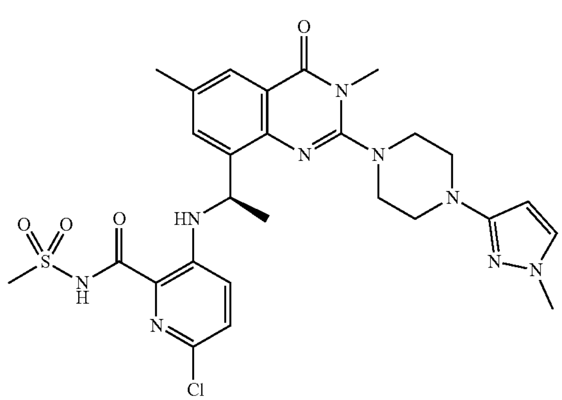 | (R)-6-chloro-3-((1-(3,6-dimethyl-2-(4-(1-methyl-1H-pyrazol-3-yl)piperazin-1-yl)-4-oxo-3,4-dihydroquinazolin-8-yl)ethyl)amino)-N-(methylsulfonyl)picolinamide | 2.31 min, 254 nm, MS (ES+)[b] $C_{27}H_{32}ClN_9O_4S$, requires: 613.2, found: 614.2 [M + H]+ |

TABLE E4-continued compound list prepared according to Route A in Example 4

| Cpd. ID | Structure | Name | LCMS |
|---|---|---|---|
| 188 | 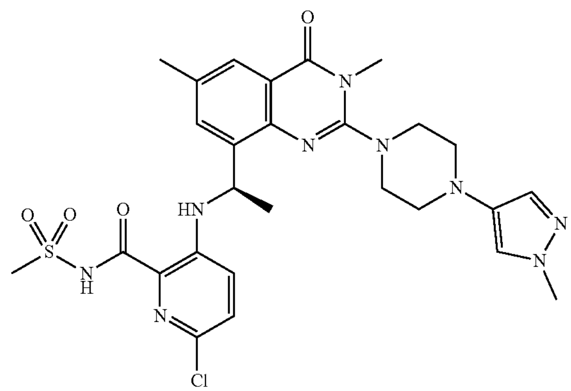 | (R)-6-chloro-3-((1-(3,6-dimethyl-2-(4-(1-methyl-1H-pyrazol-4-yl)piperazin-1-yl)-4-oxo-3,4-dihydroquinazolin-8-yl)ethyl)amino)-N-(methylsulfonyl)picolinamide | 2.19 min, 254 nm, MS (ES+)[b] $C_{27}H_{32}ClN_9O_4S$, requires: 613.2, found: 614.1 [M + H]+ |
| 189 | 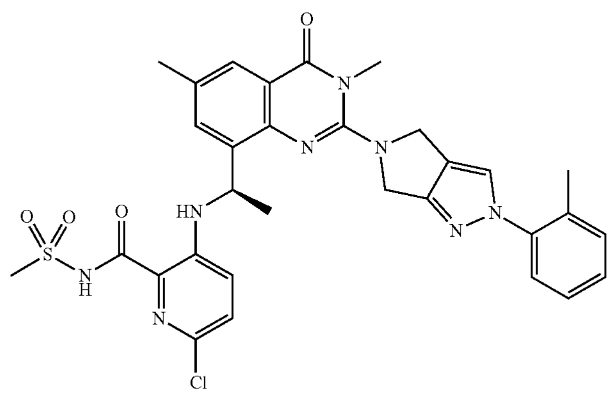 [SMILES: Cc1cc([C@@H](C)Nc2ccc(Cl)nc2C(=O)NS(C)(=O)=O)c2nc(N3Cc4cn(-c5ccccc5C)nc4C3)n(C)c(=O)c2c1] | (R)-6-chloro-3-((1-(3,6-dimethyl-4-oxo-2-(2-(o-tolyl)-2,6-dihydropyrrolo[3,4-c]pyrazol-5(4H)-yl)-3,4-dihydroquinazolin-8-yl)ethyl)amino)-N-(methylsulfonyl)picolinamide | 2.46 min, 254 nm, MS (ES+)[b] $C_{31}H_{31}ClN_8O_4S$, requires: 646.1, found: 647.2 [M + H]+ |
| 190 | 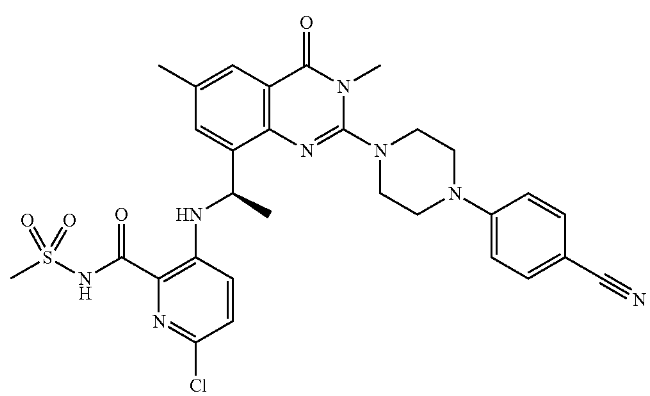 [SMILES: Cc1cc([C@@H](C)Nc2ccc(Cl)nc2C(=O)NS(C)(=O)=O)c2nc(N3CCN(c4ccc(C#N)cc4)CC3)n(C)c(=O)c2c1] | (R)-6-chloro-3-((1-(2-(4-(4-cyanophenyl)piperazin-1-yl)-3,6-dimethyl-4-oxo-3,4-dihydroquinazolin-8-yl)ethyl)amino)-N-(methylsulfonyl)picolinamide | 2.57 min, 254 nm, MS (ES+)[b] $C_{30}H_{31}ClN_8O_4S$, requires: 634.1, found: 635.2 [M + H]+ |
| 191 | 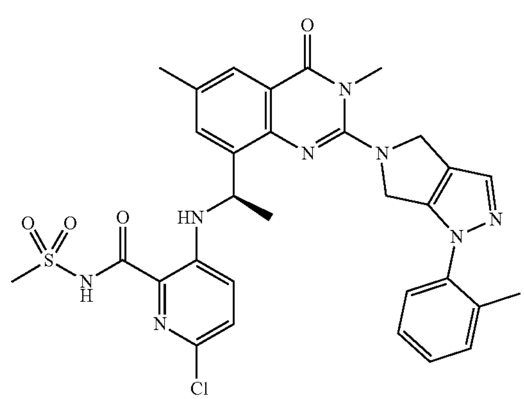 | (R)-6-chloro-3-((1-(3,6-dimethyl-4-oxo-2-(1-(o-tolyl)-4,6-dihydropyrrolo[3,4-c]pyrazol-5(1H)-yl)-3,4-dihydroquinazolin-8-yl)ethyl)amino)-N-(methylsulfonyl)picolinamide | 2.48 min, 254 nm, MS (ES+)[b] $C_{31}H_{31}ClN_8O_4S$, requires: 646.1, found: 647.2 [M + H]+ |

TABLE E4-continued compound list prepared according to Route A in Example 4

| Cpd. ID | Structure | Name | LCMS |
|---|---|---|---|
| 192 | 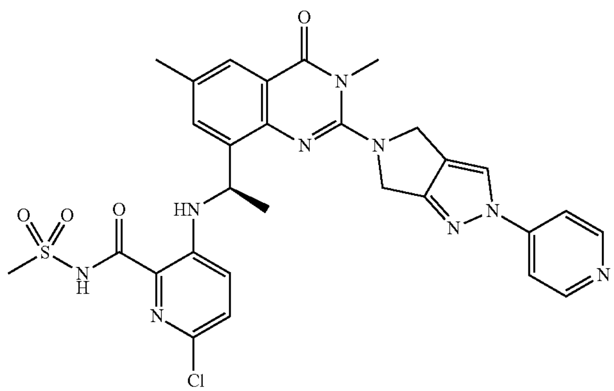 [SMILES: Cc1cc([C@@H](C)Nc2ccc(Cl)nc2C(=O)NS(C)(=O)=O)c2nc(N3Cc4cn(-c5ccncc5)nc4C3)n(C)c(=O)c2c1] | (R)-6-chloro-3-((1-(3,6-dimethyl-4-oxo-2-(2-(pyridin-4-yl)-2,6-dihydropyrrolo[3,4-c]pyrazol-5(4H)-yl)-3,4-dihydroquinazolin-8-yl)ethyl)amino)-N-(methylsulfonyl)picolinamide | 2.08 min, 254 nm, MS (ES+)$^b$ $C_{29}H_{28}ClN_9O_4S$, requires: 633.1, found: 634.1 [M + H]$^+$ |
| 193 | 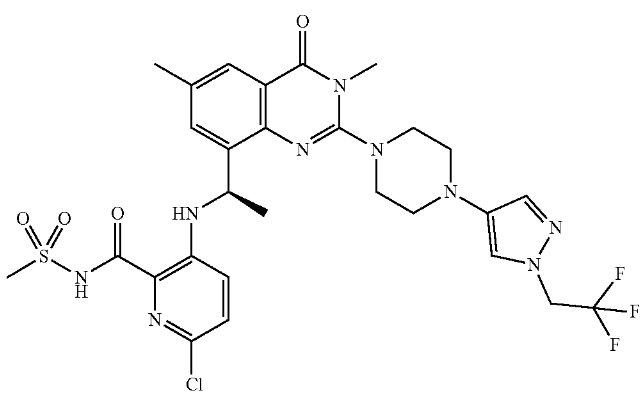 [SMILES: Cc1cc([C@@H](C)Nc2ccc(Cl)nc2C(=O)NS(C)(=O)=O)c2nc(N3CCN(c4cnn(CC(F)(F)F)c4)CC3)n(C)c(=O)c2c1] | (R)-6-chloro-3-((1-(3,6-dimethyl-4-oxo-2-(4-(1-(2,2,2-trifluoroethyl)-1H-pyrazol-4-yl)piperazin-1-yl)-3,4-dihydroquinazolin-8-yl)ethyl)amino)-N-(methylsulfonyl)picolinamide | 2.39 min, 210 nm, MS (ES+)$^b$ $C_{28}H_{31}ClF_3N_9O_4S$, requires: 681.1, found: 682.1 [M + H]$^+$ |
| 194 | 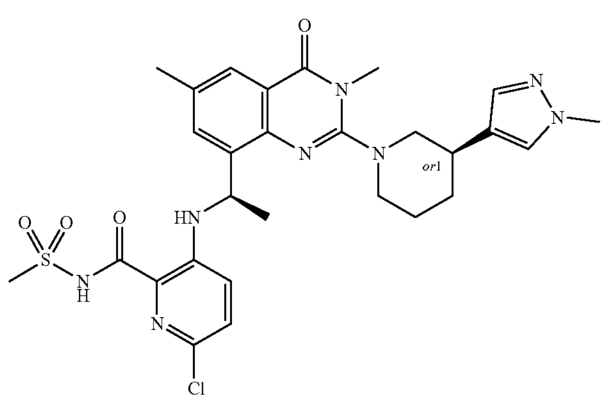 | 6-chloro-3-(((R)-1-(3,6-dimethyl-2-((R*)-3-(1-methyl-1H-pyrazol-4-yl)piperidin-1-yl)-4-oxo-3,4-dihydroquinazolin-8-yl)ethyl)amino)-N-(methylsulfonyl)picolinamide | 2.40 min, 254 nm, MS (ES+)$^b$ $C_{28}H_{33}ClN_8O_4S$, requires: 612.2, found: 613.2 [M + H]$^+$ |

TABLE E4-continued compound list prepared according to Route A in Example 4

| Cpd. ID | Structure | Name | LCMS |
|---|---|---|---|
| 195 | 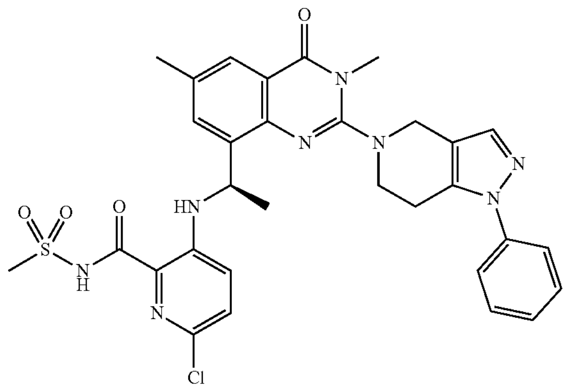 [SMILES: Cc1cc([C@@H](C)Nc2ccc(Cl)nc2C(=O)NS(C)(=O)=O)c2nc(N3CCc4c(cnn4-c4ccccc4)C3)n(C)c(=O)c2c1] | (R)-6-chloro-3-((1-(3,6-dimethyl-4-oxo-2-(1-phenyl-1,4,6,7-tetrahydro-5H-pyrazolo[4,3-c]pyridin-5-yl)-3,4-dihydroquinazolin-8-yl)ethyl)amino)-N-(methylsulfonyl)picolinamide | 2.54 min, 254 nm, MS (ES+)[b] $C_{31}H_{31}ClN_8O_4S$, requires: 646.1, found: 647.1 [M + H]$^+$ |
| 196 | 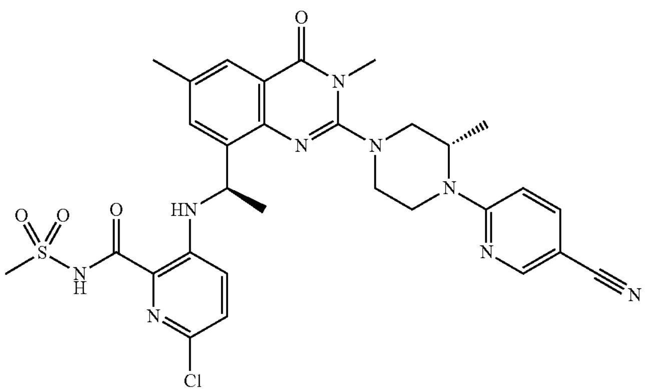 [SMILES: Cc1cc([C@@H](C)Nc2ccc(Cl)nc2C(=O)NS(C)(=O)=O)c2nc(N3CCN(c4ccc(C#N)cn4)[C@@H](C)C3)n(C)c(=O)c2c1] | 6-chloro-3-(((R)-1-(2-((S)-4-(5-cyanopyridin-2-yl)-3-methylpiperazin-1-yl)-3,6-dimethyl-4-oxo-3,4-dihydroquinazolin-8-yl)ethyl)amino)-N-(methylsulfonyl)picolinamide | 2.59 min, 254 nm, MS (ES+)[b] $C_{30}H_{32}ClN_9O_4S$, requires: 649.2, found: 650.1 [M + H]$^+$ |
| 197 | 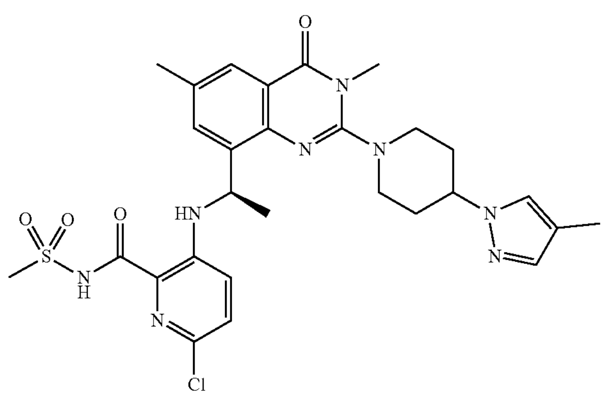 | (R)-6-chloro-3-((1-(3,6-dimethyl-2-(4-(4-methyl-1H-pyrazol-1-yl)piperidin-1-yl)-4-oxo-3,4-dihydroquinazolin-8-yl)ethyl)amino)-N-(methylsulfonyl)picolinamide | 2.49 min, 270 nm, MS (ES+)[b] $C_{28}H_{33}ClN_8O_4S$, requires: 612.2, found: 613.1 [M + H]$^+$ |
| 198 | 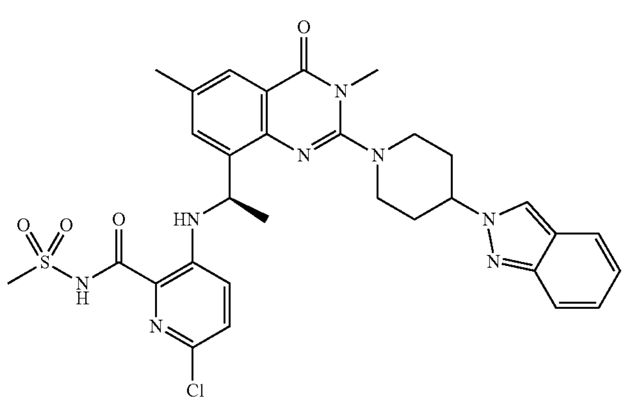 [SMILES: Cc1cc([C@@H](C)Nc2ccc(Cl)nc2C(=O)NS(C)(=O)=O)c2nc(N3CCC(n4cc5ccccc5n4)CC3)n(C)c(=O)c2c1] | (R)-3-((1-(2-(4-(2H-indazol-2-yl)piperidin-1-yl)-3,6-dimethyl-4-oxo-3,4-dihydroquinazolin-8-yl)ethyl)amino)-6-chloro-N-(methylsulfonyl)picolinamide | 2.58 min, 270 nm, MS (ES+)[b] $C_{31}H_{33}ClN_8O_4S$, requires: 648.2, found: 649.2 [M + H]$^+$ |

TABLE E4-continued compound list prepared according to Route A in Example 4

| Cpd. ID | Structure | Name | LCMS |
|---|---|---|---|
| 199 | 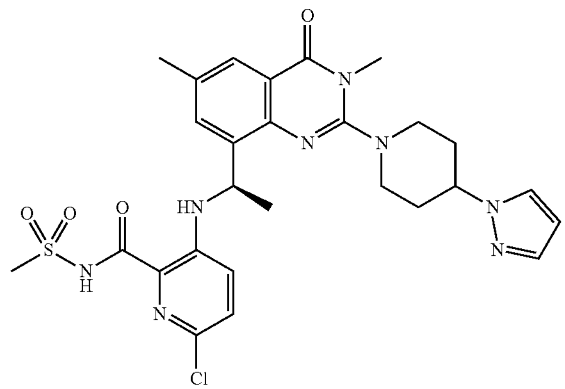 [SMILES: Cc1cc([C@@H](C)Nc2ccc(Cl)nc2C(=O)NS(C)(=O)=O)c2nc(N3CCC(n4cccn4)CC3)n(C)c(=O)c2c1] | (R)-3-((1-(2-(4-(1H-pyrazol-1-yl)piperidin-1-yl)-3,6-dimethyl-4-oxo-3,4-dihydroquinazolin-8-yl)ethyl)amino)-6-chloro-N-(methylsulfonyl)picolinamide | 2.41 min, 254 nm, MS (ES+)[b] $C_{27}H_{31}ClN_8O_4S$, requires: 598.1, found: 599.1 [M + H]+ |
| 200 | 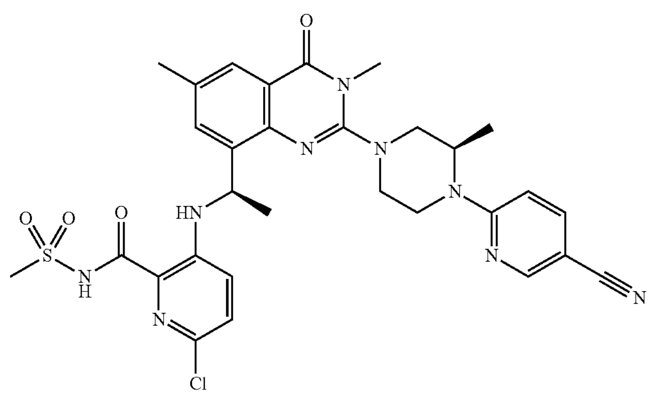 [SMILES: Cc1cc([C@@H](C)Nc2ccc(Cl)nc2C(=O)NS(C)(=O)=O)c2nc(N3CCN(c4ccc(C#N)cn4)[C@H](C)C3)n(C)c(=O)c2c1] | 6-chloro-3-(((R)-1-(2-((R)-4-(5-cyanopyridin-2-yl)-3-methylpiperazin-1-yl)-3,6-dimethyl-4-oxo-3,4-dihydroquinazolin-8-yl)ethyl)amino)-N-(methylsulfonyl)picolinamide | 2.60 min, 254 nm, MS (ES+)[b] $C_{30}H_{32}ClN_9O_4S$, requires: 649.2, found: 650.3 [M + H]+ |
| 201 | 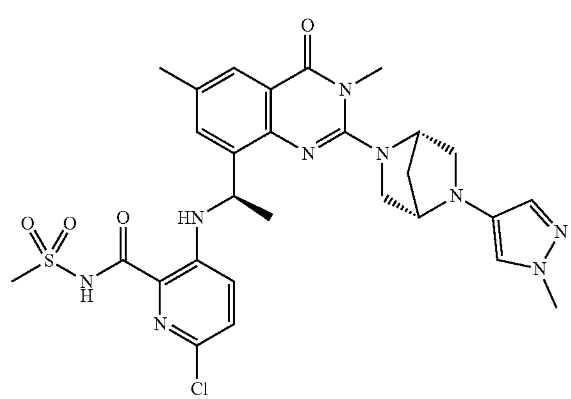 [SMILES: Cc1cc([C@@H](C)Nc2ccc(Cl)nc2C(=O)NS(C)(=O)=O)c2nc(N3C[C@@H]4C[C@H]3CN4c3cnn(C)c3)n(C)c(=O)c2c1] | 6-chloro-3-(((R)-1-(3,6-dimethyl-2-((1S,4S)-5-(1-methyl-1H-pyrazol-4-yl)-2,5-diazabicyclo[2.2.1]heptan-2-yl)-4-oxo-3,4-dihydroquinazolin-8-yl)ethyl)amino)-N-(methylsulfonyl)picolinamide | 2.18 min, 270 nm, MS (ES+)[b] $C_{28}H_{32}ClN_9O_4S$, requires: 625.2, found: 626.2 [M + H]+ |

TABLE E4-continued compound list prepared according to Route A in Example 4

| Cpd. ID | Structure | Name | LCMS |
|---|---|---|---|
| 202 | 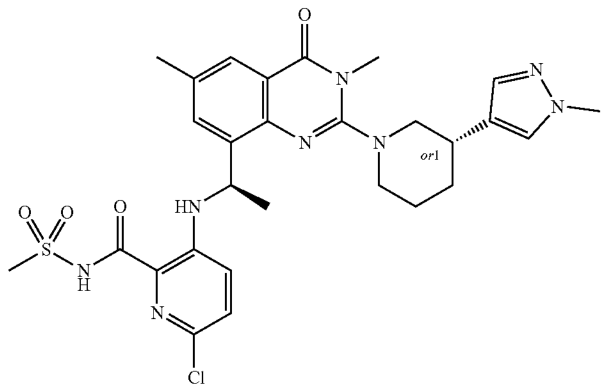 | 6-chloro-3-(((R)-1-(3,6-dimethyl-2-((R*)-3-(1-methyl-1H-pyrazol-4-yl)piperidin-1-yl)-4-oxo-3,4-dihydroquinazolin-8-yl)ethyl)amino)-N-(methylsulfonyl)picolinamide | 2.46 min, 254 nm, MS (ES+)[b] $C_{28}H_{33}ClN_8O_4S$, requires: 612.2, found: 613.2 $[M + H]^+$ |
| 203 | 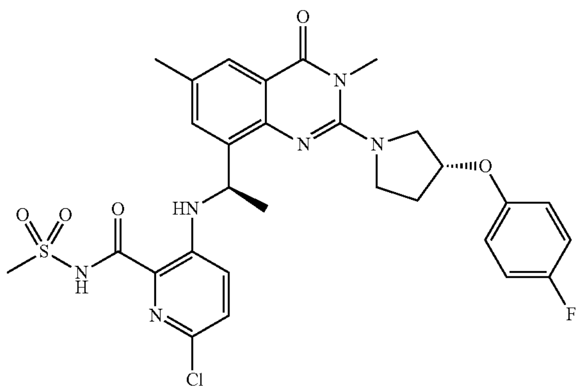 [SMILES: Cc1cc([C@@H](C)Nc2ccc(Cl)nc2C(=O)NS(C)(=O)=O)c2nc(N3CC[C@@H](Oc4ccc(F)cc4)C3)n(C)c(=O)c2c1] | 6-chloro-3-(((R)-1-(2-((R)-3-(4-fluorophenoxy)pyrrolidin-1-yl)-3,6-dimethyl-4-oxo-3,4-dihydroquinazolin-8-yl)ethyl)amino)-N-(methylsulfonyl)picolinamide | 5.05 min, 254 nm, MS (ES+)[c] $C_{29}H_{30}ClFN_6O_5S$, requires: 628.2, found: 629.1 $[M + H]^+$ |
| 204 | 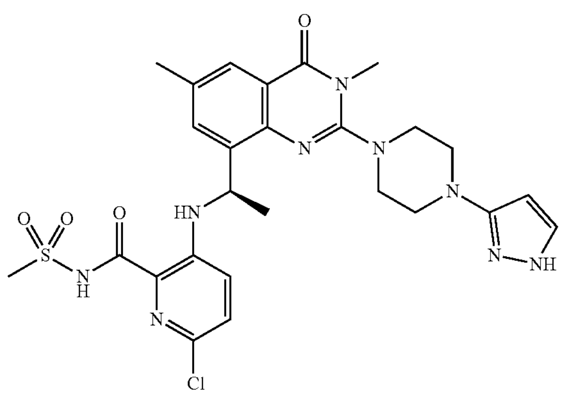 [SMILES: Cc1cc([C@@H](C)Nc2ccc(Cl)nc2C(=O)NS(C)(=O)=O)c2nc(N3CCN(c4cc[nH]n4)CC3)n(C)c(=O)c2c1] | (R)-3-((1-(2-(4-(1H-pyrazol-3-yl)piperazin-1-yl)-3,6-dimethyl-4-oxo-3,4-dihydroquinazolin-8-yl)ethyl)amino)-6-chloro-N-(methylsulfonyl)picolinamide | 2.08 min, 270 nm, MS (ES+)[b] $C_{26}H_{30}ClN_9O_4S$, requires: 599.1, found: 600.2 $[M + H]^+$ |
| 205 | 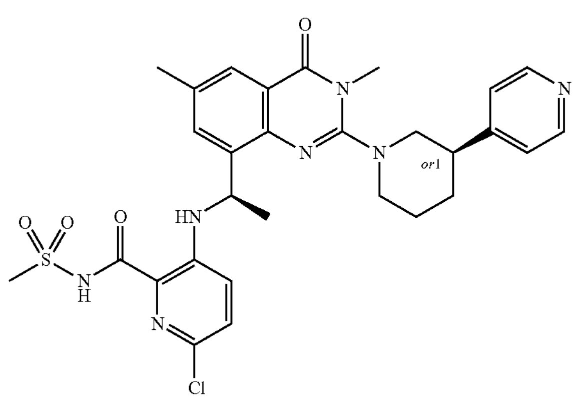 [SMILES: Cc1cc([C@@H](C)Nc2ccc(Cl)nc2C(=O)NS(C)(=O)=O)c2nc(N3CCC[C@H](c4ccncc4)C3)n(C)c(=O)c2c1] | 6-chloro-3-(((R)-1-(3,6-dimethyl-4-oxo-2-((R*)-3-(pyridin-4-yl)piperidin-1-yl)-3,4-dihydroquinazolin-8-yl)ethyl)amino)-N-(methylsulfonyl)picolinamide | 2.09 min, 270 nm, MS (ES+)[b] $C_{29}H_{32}ClN_7O_4S$, requires: 609.1, found: 610.2 $[M + H]^+$ |

TABLE E4-continued compound list prepared according to Route A in Example 4

| Cpd. ID | Structure | Name | LCMS |
|---|---|---|---|
| 206 | 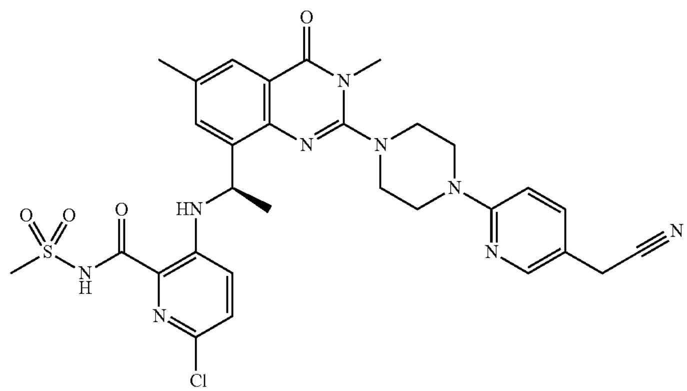 [SMILES: Cc1cc([C@@H](C)Nc2ccc(Cl)nc2C(=O)NS(C)(=O)=O)c2nc(N3CCN(c4ccc(CC#N)cn4)CC3)n(C)c(=O)c2c1] | (R)-6-chloro-3-((1-(2-(4-(5-(cyanomethyl)pyridin-2-yl)piperazin-1-yl)-3,6-dimethyl-4-oxo-3,4-dihydroquinazolin-8-yl)ethyl)amino)-N-(methylsulfonyl)picolinamide | 2.20 min, 285 nm, MS (ES+)[b] $C_{30}H_{32}ClN_9O_4S$, requires: 649.2, found: 650.2 $[M + H]^+$ |
| 207 | 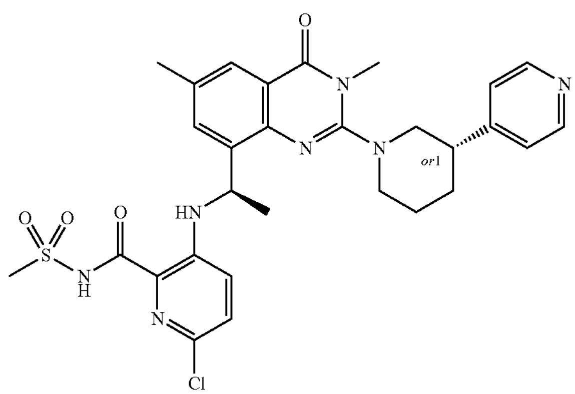 [SMILES: Cc1cc([C@@H](C)Nc2ccc(Cl)nc2C(=O)NS(C)(=O)=O)c2nc(N3CCC[C@@H](c4ccncc4)C3)n(C)c(=O)c2c1] | 6-chloro-3-(((R)-1-(3,6-dimethyl-4-oxo-2-((R*)-3-(pyridin-4-yl)piperidin-1-yl)-3,4-dihydroquinazolin-8-yl)ethyl)amino)-N-(methylsulfonyl)picolinamide | 2.09 min, 270 nm, MS (ES+)[b] $C_{29}H_{32}ClN_7O_4S$, requires: 609.1, found: 610.2 $[M + H]^+$ |
| 208 | 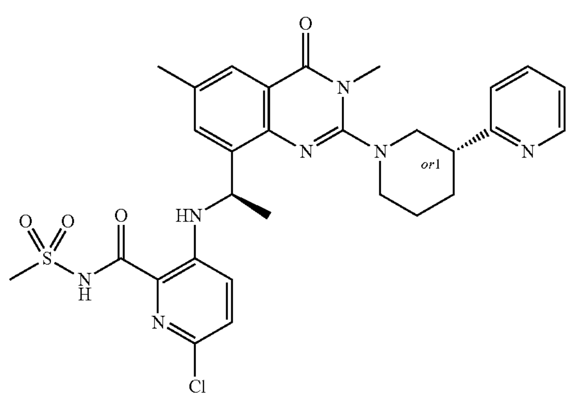 [SMILES: Cc1cc([C@@H](C)Nc2ccc(Cl)nc2C(=O)NS(C)(=O)=O)c2nc(N3CCC[C@@H](c4ccccn4)C3)n(C)c(=O)c2c1] | 6-chloro-3-(((R)-1-(3,6-dimethyl-4-oxo-2-((R*)-3-(pyridin-2-yl)piperidin-1-yl)-3,4-dihydroquinazolin-8-yl)ethyl)amino)-N-(methylsulfonyl)picolinamide | 2.24 min, 270 nm, MS (ES+)[b] $C_{29}H_{32}ClN_7O_4S$, requires: 609.2, found: 610.2 $[M + H]^+$ |

TABLE E4-continued compound list prepared according to Route A in Example 4

| Cpd. ID | Structure | Name | LCMS |
|---|---|---|---|
| 209 | 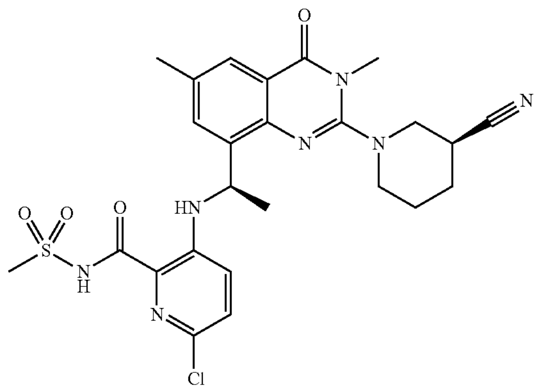 [SMILES: Cc1cc([C@@H](C)Nc2ccc(Cl)nc2C(=O)NS(C)(=O)=O)c2nc(N3CCC[C@H](C#N)C3)n(C)c(=O)c2c1] | 6-chloro-3-(((R)-1-(2-((S)-3-cyanopiperidin-1-yl)-3,6-dimethyl-4-oxo-3,4-dihydroquinazolin-8-yl)ethyl)amino)-N-(methylsulfonyl)picolinamide | 4.40 min, 254 nm, MS (ES+)$^c$ $C_{25}H_{28}ClN_7O_4S$, requires: 557.2, found: 558.1 $[M + H]^+$ |
| 210 | 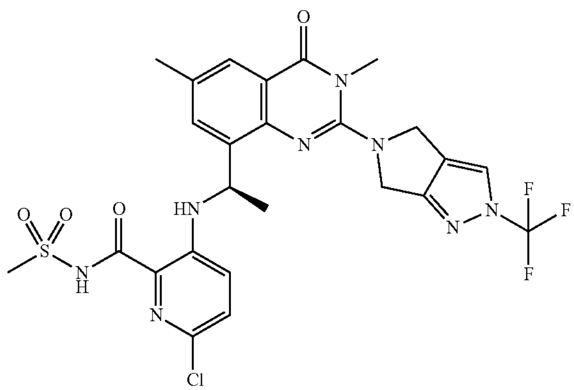 [SMILES: Cc1cc([C@@H](C)Nc2ccc(Cl)nc2C(=O)NS(C)(=O)=O)c2nc(N3Cc4cn(C(F)(F)F)nc4C3)n(C)c(=O)c2c1] | (R)-6-chloro-3-((1-(3,6-dimethyl-4-oxo-2-(2-(trifluoromethyl)-2,6-dihydropyrrolo[3,4-c]pyrazol-5(4H)-yl)-3,4-dihydroquinazolin-8-yl)ethyl)amino)-N-(methylsulfonyl)picolinamide | 2.37 min, 270 nm, MS (ES+)$^b$ $C_{25}H_{24}ClF_3N_8O_4S$, requires: 624.1, found: 625.1 $[M + H]^+$ |
| 211 | 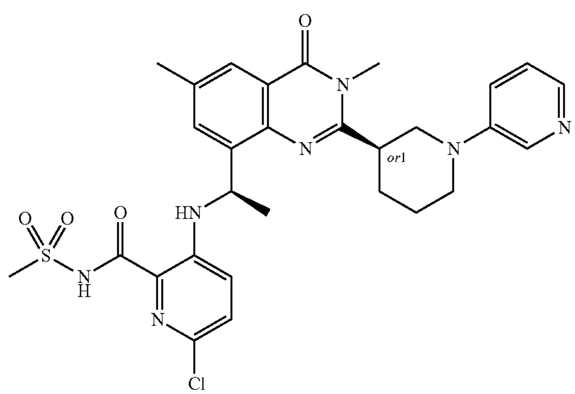 [SMILES: Cc1cc([C@@H](C)Nc2ccc(Cl)nc2C(=O)NS(C)(=O)=O)c2nc([C@@H]3CCCN(c4cccnc4)C3)n(C)c(=O)c2c1] | 6-chloro-3-(((R)-1-(3,6-dimethyl-4-oxo-2-((R*)-1-(pyridin-3-yl)piperidin-3-yl)-3,4-dihydroquinazolin-8-yl)ethyl)amino)-N-(methylsulfonyl)picolinamide | 2.04 min, 215 nm, MS (ES+)$^b$ $C_{29}H_{32}ClN_7O_4S$, requires: 609.1, found: 610.2 $[M + H]^+$ |
| 212 | 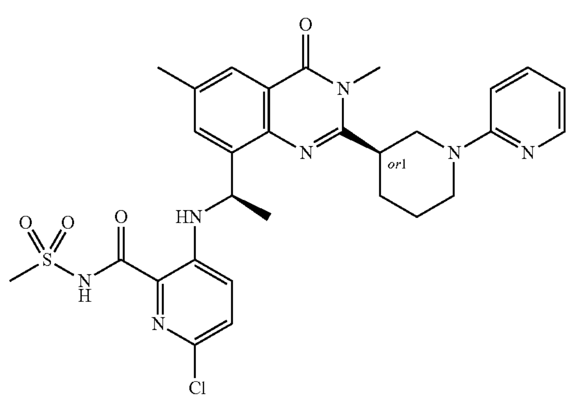 [SMILES: Cc1cc([C@@H](C)Nc2ccc(Cl)nc2C(=O)NS(C)(=O)=O)c2nc([C@@H]3CCCN(c4ccccn4)C3)n(C)c(=O)c2c1] | 6-chloro-3-(((R)-1-(3,6-dimethyl-4-oxo-2-((R*)-1-(pyridin-2-yl)piperidin-3-yl)-3,4-dihydroquinazolin-8-yl)ethyl)amino)-N-(methylsulfonyl)picolinamide | 2.04 min, 215 nm, MS (ES+)$^b$ $C_{29}H_{32}ClN_7O_4S$, requires: 609.1, found: 610.2 $[M + H]^+$ |

TABLE E4-continued compound list prepared according to Route A in Example 4

| Cpd. ID | Structure | Name | LCMS |
|---|---|---|---|
| 213 | 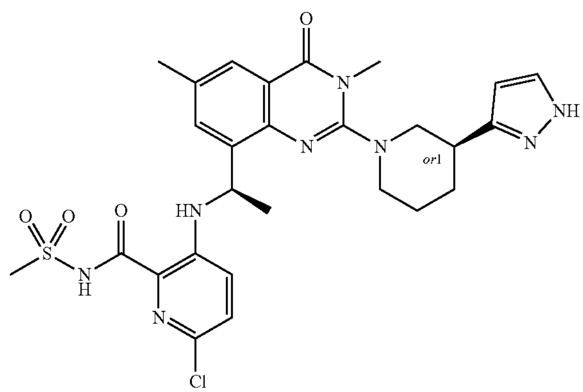 [SMILES: Cc1cc([C@@H](C)Nc2ccc(Cl)nc2C(=O)NS(C)(=O)=O)c2nc(N3CCC[C@H](c4cc[nH]n4)C3)n(C)c(=O)c2c1] | 3-(((R)-1-(2-((R*)-3-(1H-pyrazol-3-yl)piperidin-1-yl)-3,6-dimethyl-4-oxo-3,4-dihydroquinazolin-8-yl)ethyl)amino)-6-chloro-N-(methylsulfonyl)picolinamide | 2.30 min, 270 nm, MS (ES+)[b] $C_{27}H_{31}ClN_8O_4S$, requires: 598.1, found: 599.2 [M + H]+ |
| 214 | 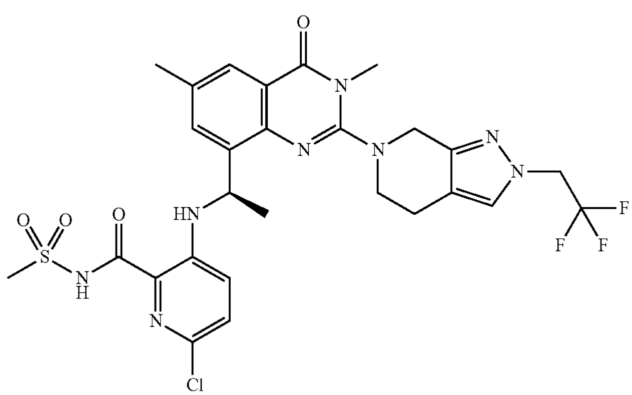 [SMILES: Cc1cc([C@@H](C)Nc2ccc(Cl)nc2C(=O)NS(C)(=O)=O)c2nc(N3CCc4cn(CC(F)(F)F)nc4C3)n(C)c(=O)c2c1] | (R)-6-chloro-3-((1-(3,6-dimethyl-4-oxo-2-(2-(2,2,2-trifluoroethyl)-2,4,5,7-tetrahydro-6H-pyrazolo[3,4-c]pyridin-6-yl)-3,4-dihydroquinazolin-8-yl)ethyl)amino)-N-(methylsulfonyl)picolinamide | 2.43 min, 254 nm, MS (ES+)[b] $C_{27}H_{28}ClF_3N_8O_4S$, requires: 652.1, found: 653.2 [M + H]+ |
| 215 | 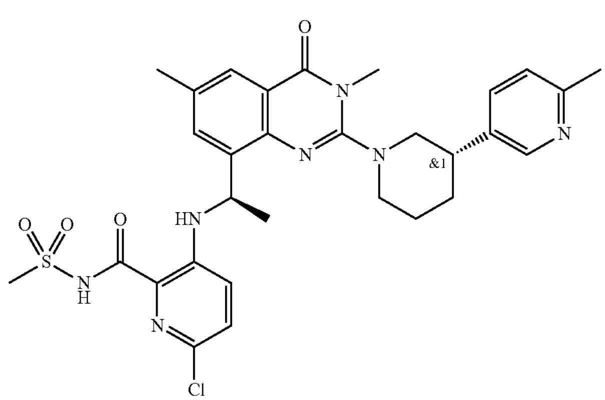 | 6-chloro-3-(((R)-1-(3,6-dimethyl-2-((RS)-3-(6-methylpyridin-3-yl)piperidin-1-yl)-4-oxo-3,4-dihydroquinazolin-8-yl)ethyl)amino)-N-(methylsulfonyl)picolinamide | 1.97 min, 270 nm, MS (ES+)[b] $C_{30}H_{34}ClN_7O_4S$, requires: 623.2, found: 624.3 [M + H]+ |

TABLE E4-continued compound list prepared according to Route A in Example 4

| Cpd. ID | Structure | Name | LCMS |
|---|---|---|---|
| 216 | 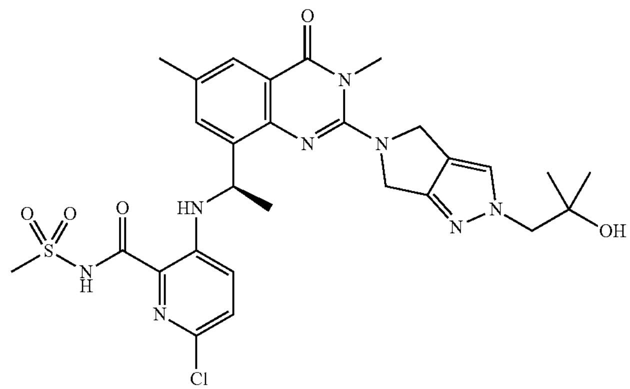 [SMILES: Cc1cc([C@@H](C)Nc2ccc(Cl)nc2C(=O)NS(C)(=O)=O)c2nc(N3Cc4cn(CC(C)(C)O)nc4C3)n(C)c(=O)c2c1] | (R)-6-chloro-3-((1-(2-(2-(2-hydroxy-2-methylpropyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.22 min, 254 nm, MS (ES+)[b] $C_{28}H_{33}ClN_8O_5S$, requires: 628.2, found: 629.2 $[M + H]^+$ |
| 217 | 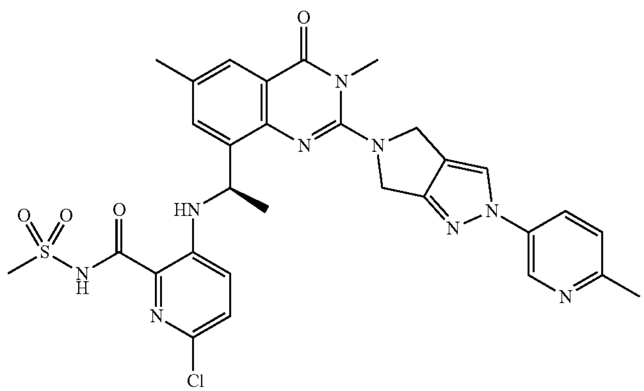 | (R)-6-chloro-3-((1-(3,6-dimethyl-2-(2-(6-methylpyridin-3-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.32 min, 270 nm, MS (ES+)[b] $C_{30}H_{30}ClN_9O_4S$, requires: 647.1, found: 648.4 $[M + H]^+$ |
| 218 | 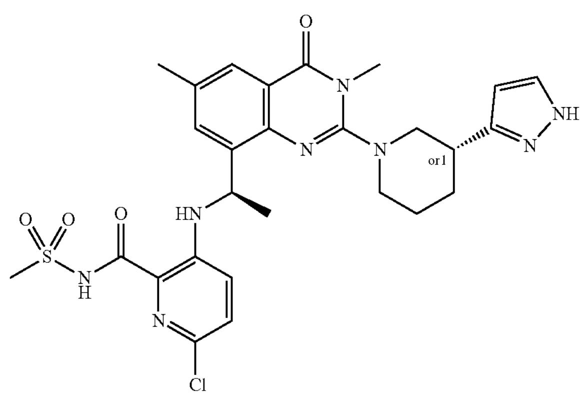 [SMILES: Cc1cc([C@@H](C)Nc2ccc(Cl)nc2C(=O)NS(C)(=O)=O)c2nc(N3CCC[C@@H](c4cc[nH]n4)C3)n(C)c(=O)c2c1] | 3-(((R)-1-(2-((R*)-3-(1H-pyrazol-3-yl)piperidin-1-yl)-3,6-dimethyl-4-oxo-3,4-dihydroquinazolin-8-yl)ethyl)amino)-6-chloro-N-(methylsulfonyl)picolinamide | 2.30 min, 270 nm, MS (ES+)[b] $C_{27}H_{31}ClN_8O_4S$, requires: 598.1, found: 599.2 $[M + H]^+$ |
| 219 | 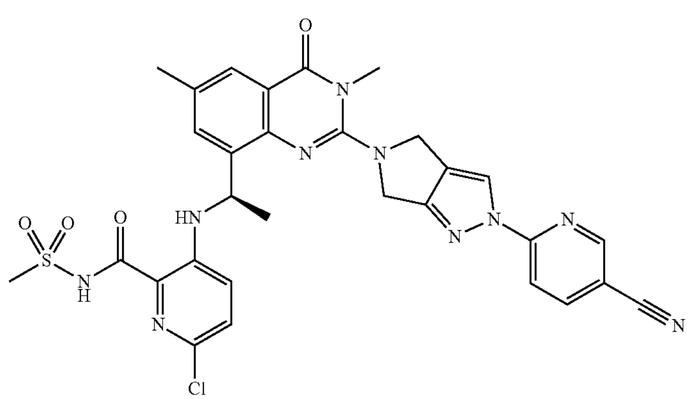 [SMILES: Cc1cc([C@@H](C)Nc2ccc(Cl)nc2C(=O)NS(C)(=O)=O)c2nc(N3Cc4cn(-c5ccc(C#N)cn5)nc4C3)n(C)c(=O)c2c1] | (R)-6-chloro-3-((1-(2-(2-(5-cyanopyridin-2-yl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.57 min, 210 nm, MS (ES+)b $C_{30}H_{27}ClN_{10}O_4S$, requires: 658.1, found: 659.1 $[M + H]+$ |

TABLE E4-continued compound list prepared according to Route A in Example 4

| Cpd. ID | Structure | Name | LCMS |
|---|---|---|---|
| 220 | 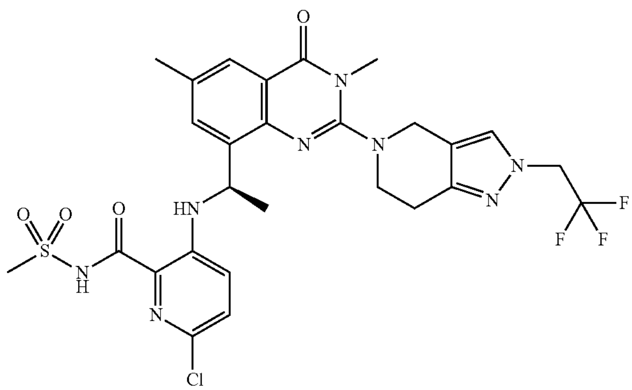 [SMILES: Cc1cc([C@@H](C)Nc2ccc(Cl)nc2C(=O)NS(C)(=O)=O)c2nc(N3CCc4nn(CC(F)(F)F)cc4C3)n(C)c(=O)c2c1] | (R)-6-chloro-3-((1-(3,6-dimethyl-4-oxo-2-(2-(2,2,2-trifluoroethyl)-2,4,6,7-tetrahydro-5H-pyrazolo[4,3-c]pyridin-5-yl)-3,4-dihydroquinazolin-8-yl)ethyl)amino)-N-(methylsulfonyl)picolinamide | 2.34 min, 270 nm, MS (ES+)[b] $C_{27}H_{28}ClF_3N_8O_4S$, requires: 652.1, found: 653.2 [M + H]+ |
| 221 | 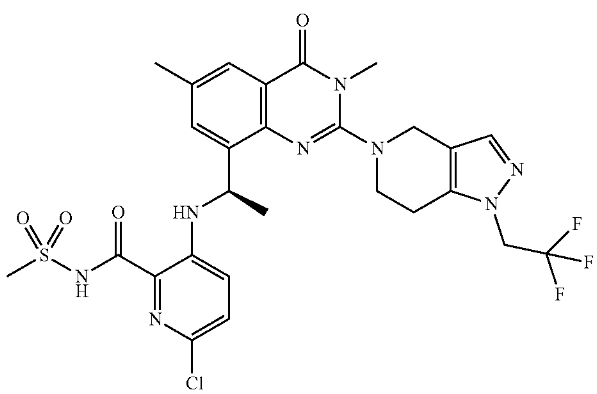 [SMILES: Cc1cc([C@@H](C)Nc2ccc(Cl)nc2C(=O)NS(C)(=O)=O)c2nc(N3CCc4c(cnn4CC(F)(F)F)C3)n(C)c(=O)c2c1] | (R)-6-chloro-3-((1-(3,6-dimethyl-4-oxo-2-(1-(2,2,2-trifluoroethyl)-1,4,6,7-tetrahydro-5H-pyrazolo[4,3-c]pyridin-5-yl)-3,4-dihydroquinazolin-8-yl)ethyl)amino)-N-(methylsulfonyl)picolinamide | 2.38 min, 270 nm, MS (ES+)[b] $C_{27}H_{28}ClF_3N_8O_4S$, requires: 652.1, found: 653.2 [M + H]+ |
| 222 | 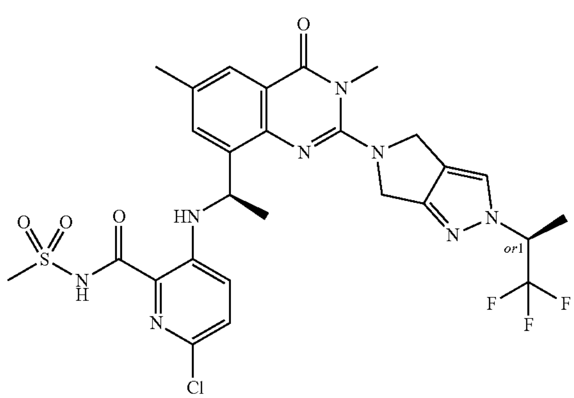 [SMILES: Cc1cc([C@@H](C)Nc2ccc(Cl)nc2C(=O)NS(C)(=O)=O)c2nc(N3Cc4cn([C@@H](C)C(F)(F)F)nc4C3)n(C)c(=O)c2c1] | 6-chloro-3-(((R)-1-(3,6-dimethyl-4-oxo-2-(2-((R*)-1,1,1-trifluoropropan-2-yl)-2,6-dihydropyrrolo[3,4-c]pyrazol-5(4H)-yl)-3,4-dihydroquinazolin-8-yl)ethyl)amino)-N-(methylsulfonyl)picolinamide | 2.36 min, 254 nm, MS (ES+)[b] $C_{27}H_{28}ClF_3N_8O_4S$, requires: 652.1, found: 653.2 [M + H]+ |

TABLE E4-continued compound list prepared according to Route A in Example 4

| Cpd. ID | Structure | Name | LCMS |
|---|---|---|---|
| 223 | 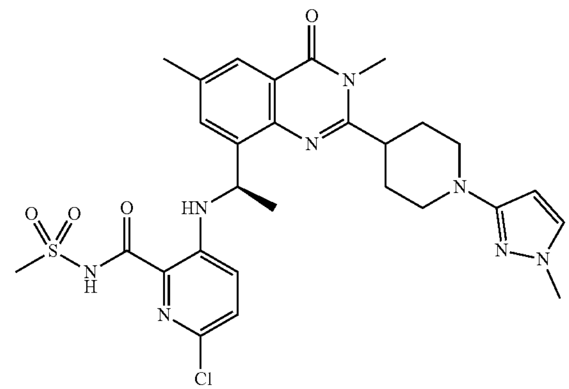 [SMILES: Cc1cc([C@@H](C)Nc2ccc(Cl)nc2C(=O)NS(C)(=O)=O)c2nc(C3CCN(c4ccn(C)n4)CC3)n(C)c(=O)c2c1] | (R)-6-chloro-3-((1-(3,6-dimethyl-2-(1-(1-methyl-1H-pyrazol-3-yl)piperidin-4-yl)-4-oxo-3,4-dihydroquinazolin-8-yl)ethyl)amino)-N-(methylsulfonyl)picolinamide | 2.26 min, 265 nm, MS (ES+)[b] $C_{28}H_{33}ClN_8O_4S$, requires: 612.2, found: 613.2 $[M + H]^+$ |
| 224 | 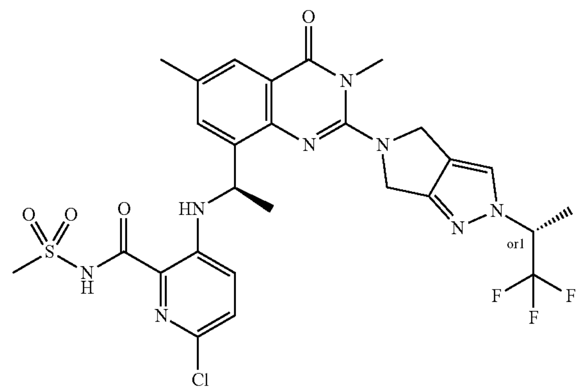 [SMILES: Cc1cc([C@@H](C)Nc2ccc(Cl)nc2C(=O)NS(C)(=O)=O)c2nc(N3Cc4cn([C@H](C)C(F)(F)F)nc4C3)n(C)c(=O)c2c1] | 6-chloro-3-(((R)-1-(3,6-dimethyl-4-oxo-2-(2-((R*)-1,1,1-trifluoropropan-2-yl)-2,6-dihydropyrrolo[3,4-c]pyrazol-5(4H)-yl)-3,4-dihydroquinazolin-8-yl)ethyl)amino)-N-(methylsulfonyl)picolinamide | 2.36 min, 254 nm, MS (ES+)[b] $C_{27}H_{28}ClF_3N_8O_4S$, requires: 652.1, found: 653.2 $[M + H]^+$ |
| 225 | 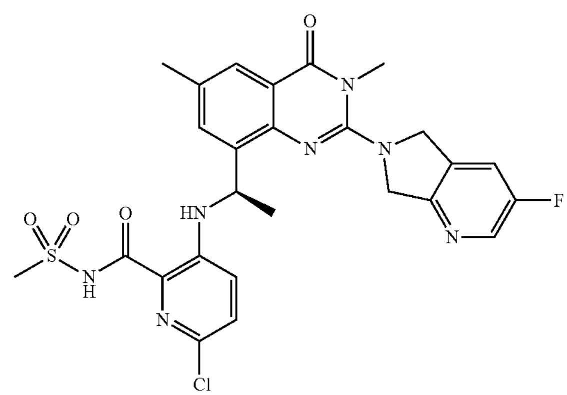 [SMILES: Cc1cc([C@@H](C)Nc2ccc(Cl)nc2C(=O)NS(C)(=O)=O)c2nc(N3Cc4cc(F)cnc4C3)n(C)c(=O)c2c1] | (R)-6-chloro-3-((1-(2-(3-fluoro-5,7-dihydro-6H-pyrrolo[3,4-b]pyridin-6-yl)-3,6-dimethyl-4-oxo-3,4-dihydroquinazolin-8-yl)ethyl)amino)-N-(methylsulfonyl)picolinamide | 3.43 min, 254 nm, MS (ES+)[c] $C_{26}H_{25}ClFN_7O_4S$, requires: 585.1, found: 586.2 $[M + H]^+$ |
| 226 | 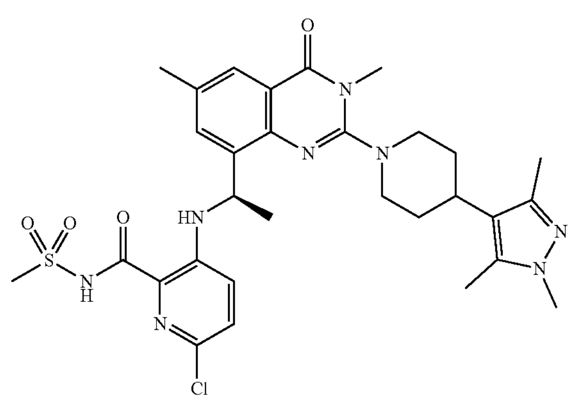 [SMILES: Cc1cc([C@@H](C)Nc2ccc(Cl)nc2C(=O)NS(C)(=O)=O)c2nc(N3CCC(c4c(C)nn(C)c4C)CC3)n(C)c(=O)c2c1] | (R)-6-chloro-3-((1-(3,6-dimethyl-4-oxo-2-(4-(1,3,5-trimethyl-1H-pyrazol-4-yl)piperidin-1-yl)-3,4-dihydroquinazolin-8-yl)ethyl)amino)-N-(methylsulfonyl)picolinamide | 2.44 min, 270 nm, MS (ES+)[b] $C_{30}H_{37}ClN_8O_4S$, requires: 640.2, found: 641.3 $[M + H]^+$ |

TABLE E4-continued compound list prepared according to Route A in Example 4

| Cpd. ID | Structure | Name | LCMS |
|---|---|---|---|
| 227 | 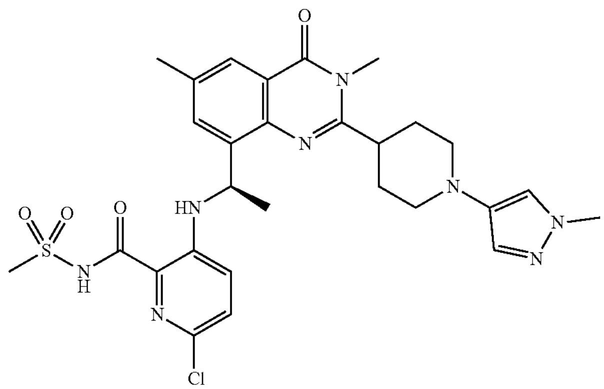 | (R)-6-chloro-3-((1-(3,6-dimethyl-2-(1-(1-methyl-1H-pyrazol-4-yl)piperidin-4-yl)-4-oxo-3,4-dihydroquinazolin-8-yl)ethyl)amino)-N-(methylsulfonyl) picolinamide | 2.09 min, 210 nm, MS (ES+)[b] $C_{28}H_{33}ClN_8O_4S$, requires: 612.2, found: 613.3 $[M + H]^+$ |
| 228 | 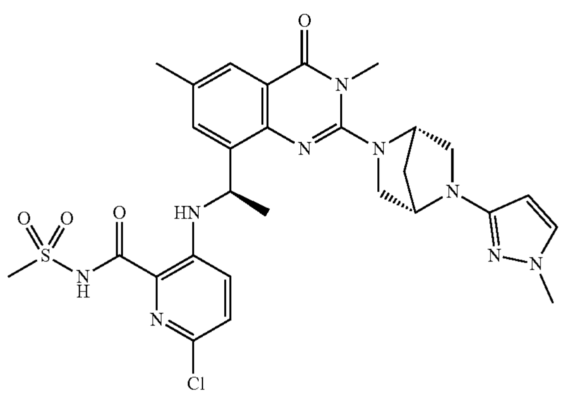 [SMILES: Cc1cc([C@@H](C)Nc2ccc(Cl)nc2C(=O)NS(C)(=O)=O)c2nc(N3C[C@@H]4C[C@H]3CN4c3ccn(C)n3)n(C)c(=O)c2c1] | 6-chloro-3-(((R)-1-(3,6-dimethyl-2-((1S,4S)-5-(1-methyl-1H-pyrazol-3-yl)-2,5-diazabicyclo[2.2.1]heptan-2-yl)-4-oxo-3,4-dihydroquinazolin-8-yl)ethyl)amino)-N-(methylsulfonyl) picolinamide | 2.06 min, 270 nm, MS (ES+)[b] $C_{28}H_{32}ClN_9O_4S$, requires: 625.2, found: 626.3 $[M + H]^+$ |
| 229 | 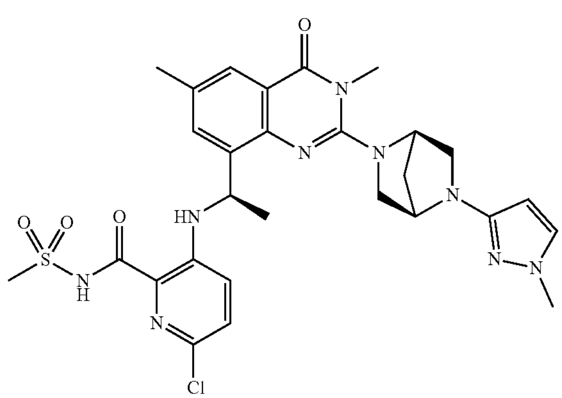 [SMILES: Cc1cc([C@@H](C)Nc2ccc(Cl)nc2C(=O)NS(C)(=O)=O)c2nc(N3C[C@H]4C[C@@H]3CN4c3ccn(C)n3)n(C)c(=O)c2c1] | 6-chloro-3-(((R)-1-(3,6-dimethyl-2-((1R,4R)-5-(1-methyl-1H-pyrazol-3-yl)-2,5-diazabicyclo[2.2.1]heptan-2-yl)-4-oxo-3,4-dihydroquinazolin-8-yl)ethyl)amino)-N-(methylsulfonyl) picolinamide | 2.23 min, 254 nm, MS (ES+)[b] $C_{28}H_{32}ClN_9O_4S$, requires: 625.2, found: 626.3 $[M + H]^+$ |

TABLE E4-continued compound list prepared according to Route A in Example 4

| Cpd. ID | Name | LCMS |
|---|---|---|
| 230 | (R)-6-chloro-3-((1-(2-(2-(2,2-difluoroethyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.23 min, 254 nm, MS (ES+)[b] $C_{26}H_{27}ClF_2N_8O_4S$, requires: 620.1, found: 621.2 $[M + H]^+$ |
| 231 | 6-chloro-3-(((R)-1-(3,6-dimethyl-4-oxo-2-((R*)-3-(1-(2,2,2-trifluoroethyl)-1H-pyrazol-4-yl)piperidin-1-yl)-3,4-dihydroquinazolin-8-yl)ethyl)amino)-N-(methylsulfonyl)picolinamide | 2.63 min, 210 nm, MS (ES+)[b] $C_{29}H_{32}ClF_3N_8O_4S$, requires: 680.1, found: 681.2 $[M + H]^+$ |
| 232 | (R)-6-chloro-3-((1-(2-(4-(3,5-dimethyl-1H-pyrazol-4-yl)piperidin-1-yl)-3,6-dimethyl-4-oxo-3,4-dihydroquinazolin-8-yl)ethyl)amino)-N-(methylsulfonyl)picolinamide | 2.16 min, 254 nm, MS (ES+)[b] $C_{29}H_{35}ClN_8O_4S$, requires: 626.2, found: 627.7 $[M + H]^+$ |
| 233 | 6-chloro-3-(((R)-1-(3,6-dimethyl-2-((1R,4R)-5-(1-methyl-1H-pyrazol-4-yl)-2,5-diazabicyclo[2.2.1]heptan-2-yl)-4-oxo-3,4-dihydroquinazolin-8-yl)ethyl)amino)-N-(methylsulfonyl)picolinamide | 2.08 min, 254 nm, MS (ES+)[b] $C_{28}H_{32}ClN_9O_4S$, requires: 625.2, found: 626.2 $[M + H]^+$ |

TABLE E4-continued compound list prepared according to Route A in Example 4

| Cpd. ID | Structure | Name | LCMS |
|---|---|---|---|
| 234 | 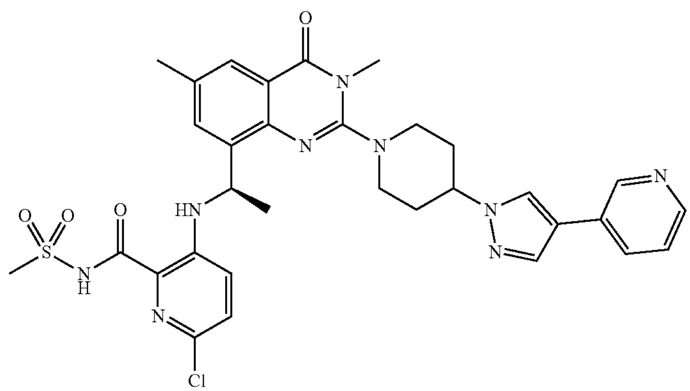 | (R)-6-chloro-3-((1-(3,6-dimethyl-4-oxo-2-(4-(4-(pyridin-3-yl)-1H-pyrazol-1-yl)piperidin-1-yl)-3,4-dihydroquinazolin-8-yl)ethyl)amino)-N-(methylsulfonyl)picolinamide | 3.66 min, 254 nm, MS (ES+)$^c$ C$_{32}$H$_{34}$ClN$_9$O$_4$S, requires: 675.2, found: 676.2 [M + H]$^+$ |
| 235 | 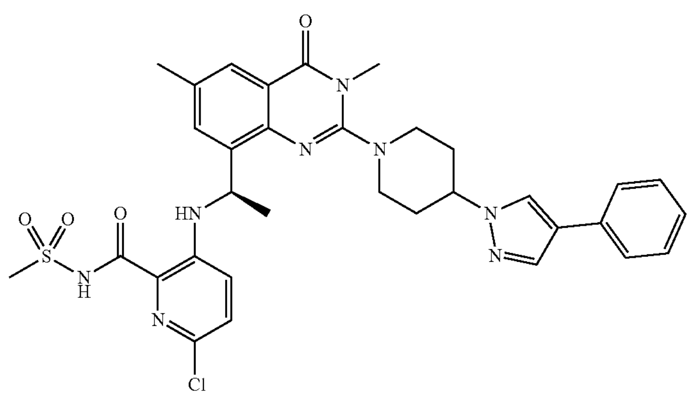 [SMILES: Cc1cc([C@@H](C)Nc2ccc(Cl)nc2C(=O)NS(C)(=O)=O)c2nc(N3CCC(n4cc(-c5ccccc5)cn4)CC3)n(C)c(=O)c2c1] | (R)-6-chloro-3-((1-(3,6-dimethyl-4-oxo-2-(4-(4-phenyl-1H-pyrazol-1-yl)piperidin-1-yl)-3,4-dihydroquinazolin-8-yl)ethyl)amino)-N-(methylsulfonyl)picolinamide | 3.86 min, 254 nm, MS (ES+)$^c$ C$_{33}$H$_{35}$ClN$_8$O$_4$S, requires: 674.2, found: 675.2 [M + H]$^+$ |
| 236 | 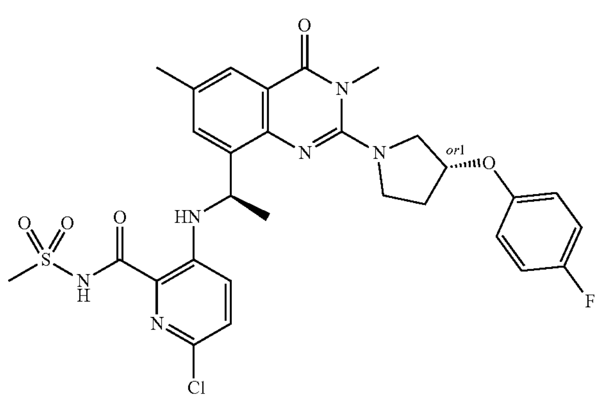 [SMILES: Cc1cc([C@@H](C)Nc2ccc(Cl)nc2C(=O)NS(C)(=O)=O)c2nc(N3CC[C@@H](Oc4ccc(F)cc4)C3)n(C)c(=O)c2c1] | 6-chloro-3-(((R)-1-(2-((R*)-3-(4-fluorophenoxy)pyrrolidin-1-yl)-3,6-dimethyl-4-oxo-3,4-dihydroquinazolin-8-yl)ethyl)amino)-N-(methylsulfonyl)picolinamide | 2.79 min, 254 nm, MS (ES+)$^b$ C$_{29}$H$_{30}$ClFN$_6$O$_5$S, requires: 628.1, found: 629.2 [M + H]$^+$ |

TABLE E4-continued compound list prepared according to Route A in Example 4

| Cpd. ID | Structure | Name | LCMS |
|---|---|---|---|
| 237 | 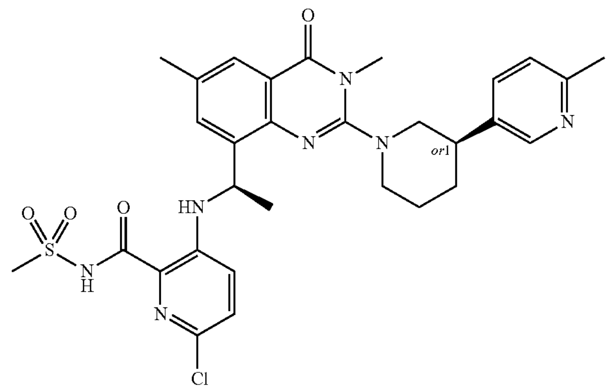 | 6-chloro-3-(((R)-1-(3,6-dimethyl-2-((R*)-3-(6-methylpyridin-3-yl)piperidin-1-yl)-4-oxo-3,4-dihydroquinazolin-8-yl)ethyl)amino)-N-(methylsulfonyl)picolinamide | 2.08 min, 210 nm, MS (ES+)[b] $C_{30}H_{34}ClN_7O_4S$, requires: 623.2, found: 624.2 $[M + H]^+$ |
| 238 | 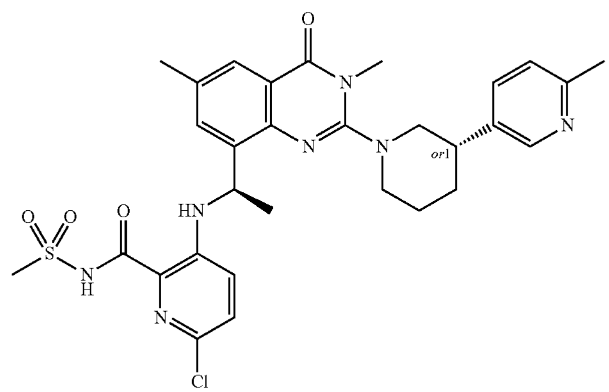 | 6-chloro-3-(((R)-1-(3,6-dimethyl-2-((R*)-3-(6-methylpyridin-3-yl)piperidin-1-yl)-4-oxo-3,4-dihydroquinazolin-8-yl)ethyl)amino)-N-(methylsulfonyl)picolinamide | 2.12 min, 270 nm, MS (ES+)[b] $C_{30}H_{34}ClN_7O_4S$, requires: 623.2, found: 624.2 $[M + H]^+$ |
| 239 | 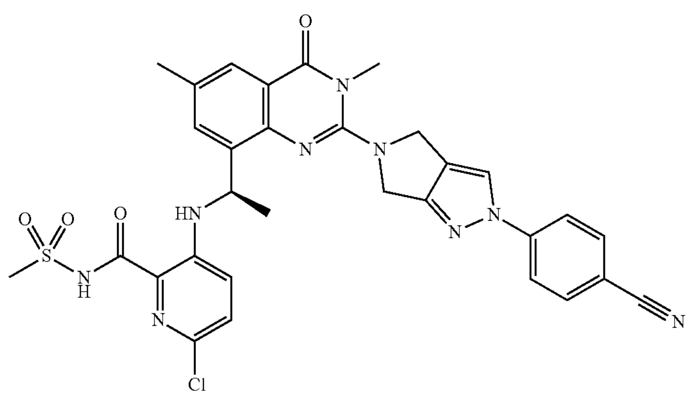 [SMILES: Cc1cc([C@@H](C)Nc2ccc(Cl)nc2C(=O)NS(C)(=O)=O)c2nc(N3Cc4cn(-c5ccc(C#N)cc5)nc4C3)n(C)c(=O)c2c1] | (R)-6-chloro-3-((1-(2-(2-(4-cyanophenyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.45 min, 220 nm, MS (ES+)[b] $C_{31}H_{28}ClN_9O_4S$, requires: 657.1, found: 658.2 $[M + H]^+$ |
| 240 | 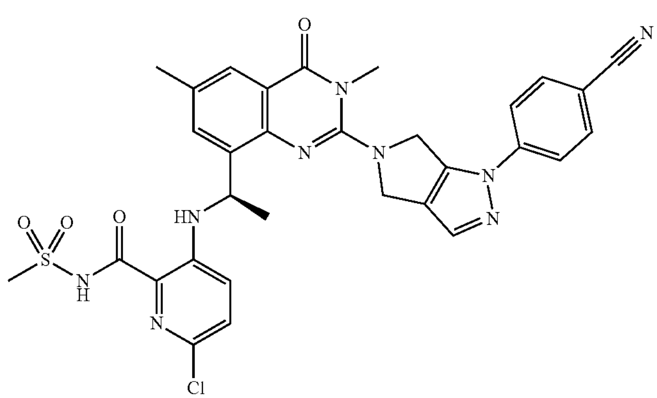 [SMILES: Cc1cc([C@@H](C)Nc2ccc(Cl)nc2C(=O)NS(C)(=O)=O)c2nc(N3Cc4cnn(-c5ccc(C#N)cc5)c4C3)n(C)c(=O)c2c1] | (R)-6-chloro-3-((1-(2-(1-(4-cyanophenyl)-4,6-dihydropyrrolo[3,4-c]pyrazol-5(1H)-yl)-3,6-dimethyl-4-oxo-3,4-dihydroquinazolin-8-yl)ethyl)amino)-N-(methylsulfonyl)picolinamide | 2.37 min, 254 nm MS (ES+)[b] $C_{31}H_{28}ClN_9O_4S$, requires: 657.1, found: 658.4 $[M + H]^+$ |

TABLE E4-continued compound list prepared according to Route A in Example 4

| Cpd. ID | Structure | Name | LCMS |
|---|---|---|---|
| 241 | 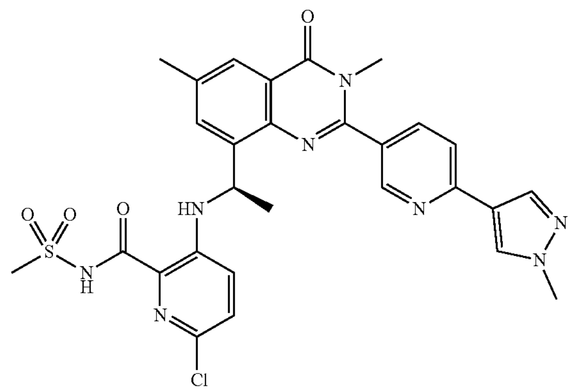 [SMILES: Cc1cc([C@@H](C)Nc2ccc(Cl)nc2C(=O)NS(C)(=O)=O)c2nc(-c3ccc(-c4cnn(C)c4)nc3)n(C)c(=O)c2c1] | (R)-6-chloro-3-((1-(3,6-dimethyl-2-(6-(1-methyl-1H-pyrazol-4-yl)pyridin-3-yl)-4-oxo-3,4-dihydroquinazolin-8-yl)ethyl)amino)-N-(methylsulfonyl)picolinamide | 2.19 min, 254 nm, MS (ES+)[b] $C_{28}H_{27}ClN_8O_4S$, requires: 606.1, found: 607.2 [M + H]+ |
| 242 | 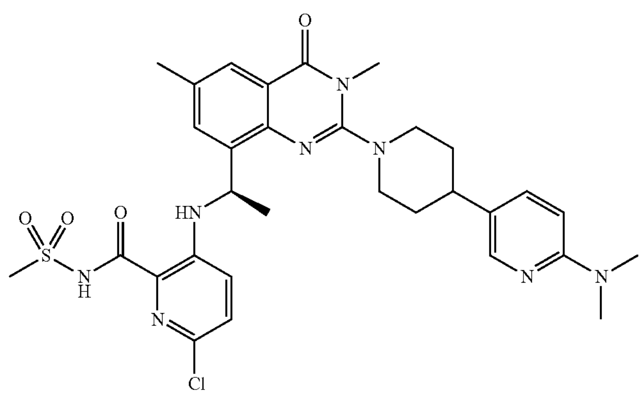 | (R)-6-chloro-3-((1-(2-(4-(6-(dimethylamino)pyridin-3-yl)piperidin-1-yl)-3,6-dimethyl-4-oxo-3,4-dihydroquinazolin-8-yl)ethyl)amino)-N-(methylsulfonyl)picolinamide | 2.11 min, 254 nm, MS (ES+)[b] $C_{31}H_{37}ClN_8O_4S$, requires: 652.2, found: 653.2 [M + H]+ |
| 243 | 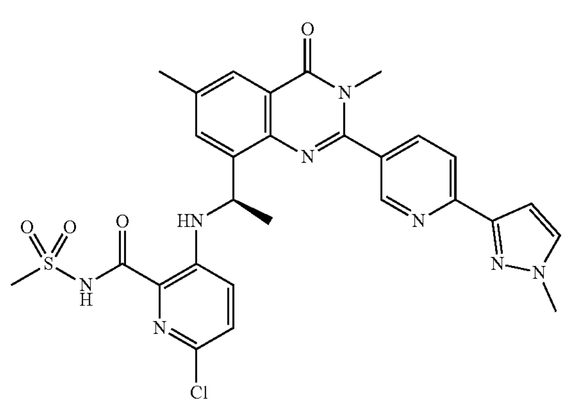 [SMILES: Cc1cc([C@@H](C)Nc2ccc(Cl)nc2C(=O)NS(C)(=O)=O)c2nc(-c3ccc(-c4ccn(C)n4)nc3)n(C)c(=O)c2c1] | (R)-6-chloro-3-((1-(3,6-dimethyl-2-(6-(1-methyl-1H-pyrazol-3-yl)pyridin-3-yl)-4-oxo-3,4-dihydroquinazolin-8-yl)ethyl)amino)-N-(methylsulfonyl)picolinamide | 2.26 min, 254 nm, MS (ES+)[b] $C_{28}H_{27}ClN_8O_4S$, requires: 606.1, found: 607.2 [M + H]+ |

TABLE E4-continued compound list prepared according to Route A in Example 4

| Cpd. ID | Structure | Name | LCMS |
|---|---|---|---|
| 244 | 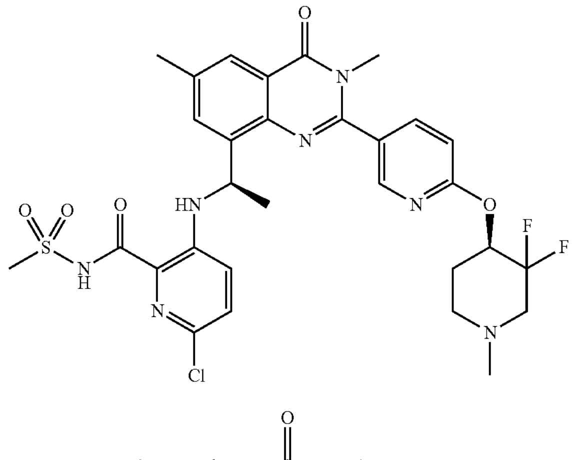 | 6-chloro-3-(((R)-1-(2-(6-(((R)-3,3-difluoro-1-methylpiperidin-4-yl)oxy)pyridin-3-yl)-3,6-dimethyl-4-oxo-3,4-dihydroquinazolin-8-yl)ethyl)amino)-N-(methylsulfonyl)picolinamide | 2.59 min, 254 nm, MS (ES+)$^c$ $C_{30}H_{32}ClF_2N_7O_5S$, requires: 675.2, found: 676.2 [M + H]$^+$ |
| 245 | 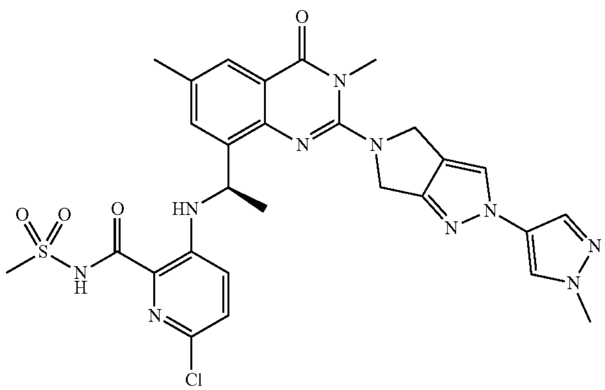 [SMILES: Cc1cc([C@@H](C)Nc2ccc(Cl)nc2C(=O)NS(C)(=O)=O)c2nc(N3Cc4cn(-c5cnn(C)c5)nc4C3)n(C)c(=O)c2c1] | (R)-6-chloro-3-((1-(3,6-dimethyl-2-(2-(1-methyl-1H-pyrazol-4-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.27 min, 254 nm, MS (ES+)$^b$ $C_{28}H_{29}ClN_{10}O_4S$, requires: 636.1, found: 637.1 [M + H]$^+$ |
| 246 | 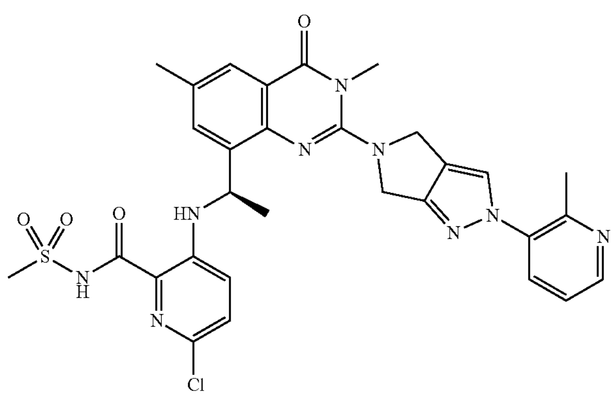 [SMILES: Cc1cc([C@@H](C)Nc2ccc(Cl)nc2C(=O)NS(C)(=O)=O)c2nc(N3Cc4cn(-c5cccnc5C)nc4C3)n(C)c(=O)c2c1] | (R)-6-chloro-3-((1-(3,6-dimethyl-2-(2-(2-methylpyridin-3-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.28 min, 254 nm, MS (ES+)$^b$ $C_{30}H_{30}ClN_9O_4S$, requires: 647.1, found: 648.2 [M + H]$^+$ |
| 247 | 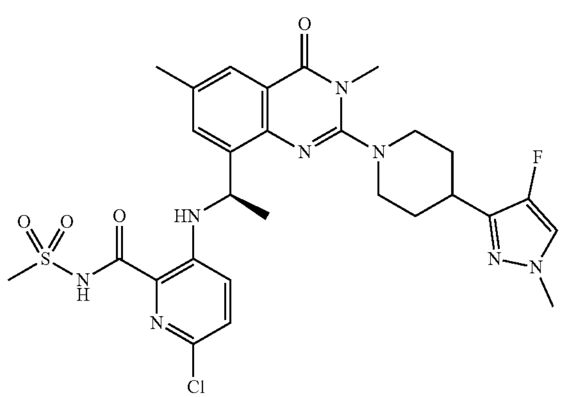 | (R)-6-chloro-3-((1-(2-(4-(4-fluoro-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.54 min, 210 nm, MS (ES+)$^b$ $C_{28}H_{32}ClFN_8O_4S$, requires: 630.1, found: 631.2 [M + H]$^+$ |

TABLE E4-continued compound list prepared according to Route A in Example 4

| Cpd. ID | Structure | Name | LCMS |
|---|---|---|---|
| 248 | 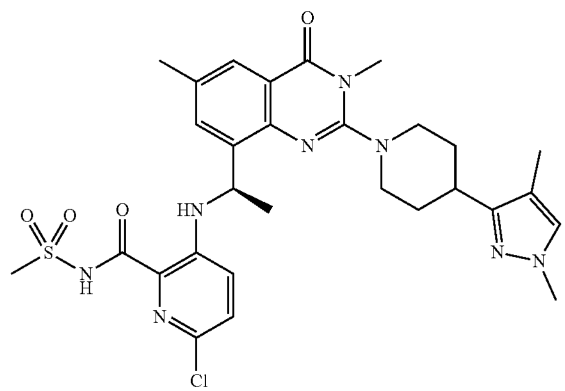 [SMILES: Cc1cc([C@@H](C)Nc2ccc(Cl)nc2C(=O)NS(C)(=O)=O)c2nc(N3CCC(c4nn(C)cc4C)CC3)n(C)c(=O)c2c1] | (R)-6-chloro-3-((1-(2-(4-(1,4-dimethyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.52 min, 254 nm, MS (ES+)[b] $C_{29}H_{35}ClN_8O_4S$, requires: 626.2, found: 627.2 [M + H]+ |
| 249 | 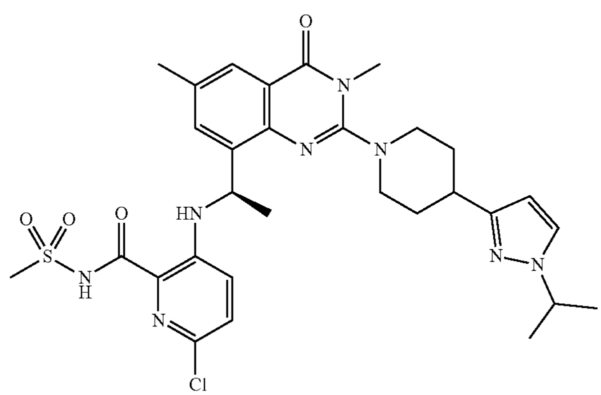 [SMILES: Cc1cc([C@@H](C)Nc2ccc(Cl)nc2C(=O)NS(C)(=O)=O)c2nc(N3CCC(c4ccn(C(C)C)n4)CC3)n(C)c(=O)c2c1] | (R)-6-chloro-3-((1-(2-(4-(1-isopropyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.64 min, 210 nm, MS (ES+)[b] $C_{30}H_{37}ClN_8O_4S$, requires: 640.2, found: 641.2 [M + H]+ |
| 250 | 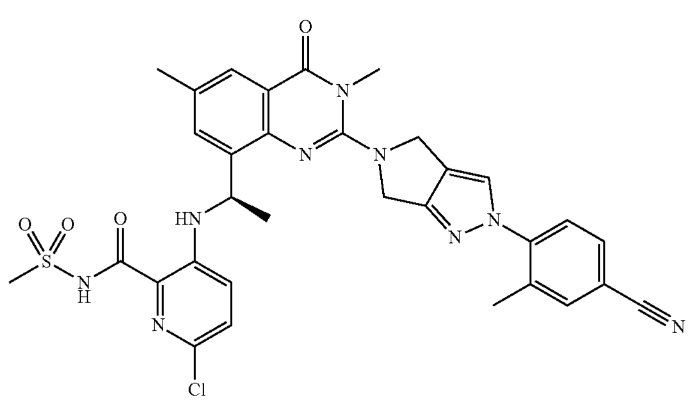 [SMILES: Cc1cc([C@@H](C)Nc2ccc(Cl)nc2C(=O)NS(C)(=O)=O)c2nc(N3Cc4cn(-c5ccc(C#N)cc5C)nc4C3)n(C)c(=O)c2c1] | (R)-6-chloro-3-((1-(2-(2-(4-cyano-2-methylphenyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.60 min, 210 nm, MS (ES+)[b] $C_{32}H_{30}ClN_9O_4S$, requires: 671.1, found: 672.2 [M + H]+ |

TABLE E4-continued compound list prepared according to Route A in Example 4

| Cpd. ID | Structure | Name | LCMS |
|---|---|---|---|
| 251 | 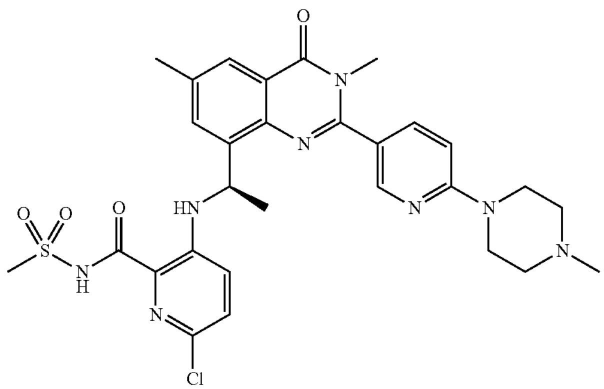 | (R)-6-chloro-3-((1-(3,6-dimethyl-2-(6-(4-methylpiperazin-1-321yridinedin-3-yl)-4-oxo-3,4-dihydroquinazolin-8-yl)ethyl)amino)-N-(methylsulfonyl)picolinamide | 1.94 min, 210 nm, MS (ES+)[b] $C_{29}H_{33}ClN_8O_4S$, requires: 624.2, found: 625.2 $[M + H]^+$ |
| 252 | 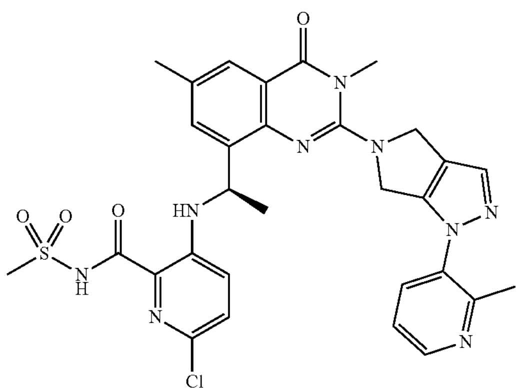 | (R)-6-chloro-3-((1-(3,6-dimethyl-2-(1-(2-methylpyridin-3-yl)-4,6-dihydropyrrolo[3,4-c]pyrazol-5(1H)-yl)-4-oxo-3,4-dihydroquinazolin-8-yl)ethyl)amino)-N-(methylsulfonyl)picolinamide | 2.27 min, 254 nm, MS (ES+)[b] $C_{30}H_{30}ClN_9O_4S$, requires: 647.1, found: 648.2 $[M + H]^+$ |
| 253 | 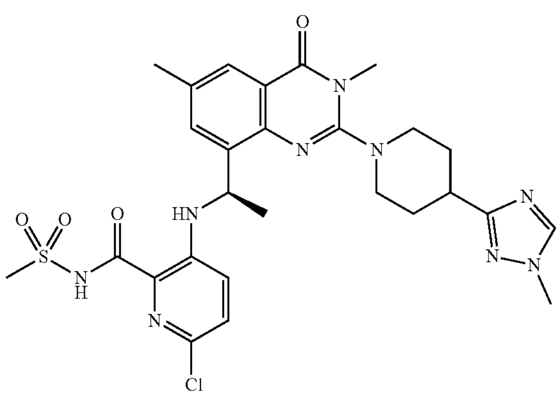 [SMILES: Cc1cc([C@@H](C)Nc2ccc(Cl)nc2C(=O)NS(C)(=O)=O)c2nc(N3CCC(c4ncn(C)n4)CC3)n(C)c(=O)c2c1] | (R)-6-chloro-3-((1-(3,6-dimethyl-2-(4-(1-methyl-1H-1,2,4-triazol-3-yl)piperidin-1-yl)-4-oxo-3,4-dihydroquinazolin-8-yl)ethyl)amino)-N-(methylsulfonyl)picolinamide | 2.19 min, 254 nm, MS (ES+)[b] $C_{27}H_{32}ClN_9O_4S$, requires: 613.2, found: 614.1 $[M + H]^+$ |
| 254 | 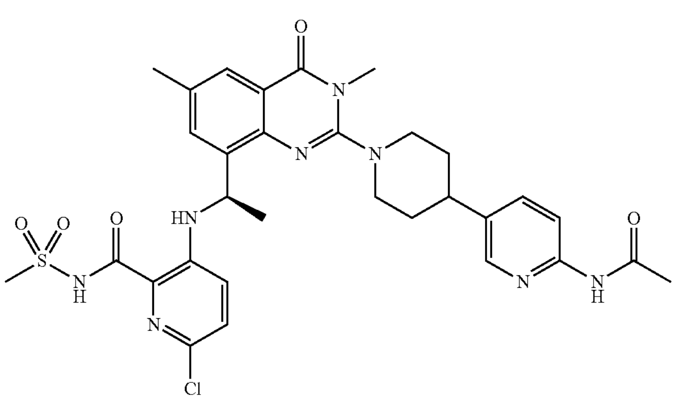 [SMILES: CC(=O)Nc1ccc(C2CCN(c3nc4c([C@@H](C)Nc5ccc(Cl)nc5C(=O)NS(C)(=O)=O)cc(C)cc4c(=O)n3C)CC2)cn1] | (R)-3-((1-(2-(4-(6-acetamidopyridin-3-yl)piperidin-1-yl)-3,6-dimethyl-4-oxo-3,4-dihydroquinazolin-8-yl)ethyl)amino)-6-chloro-N-(methylsulfonyl)picolinamide | 2.29 min, 254 nm, MS (ES+)[b] $C_{31}H_{35}ClN_8O_5S$, requires: 666.2, found: 667.2 $[M + H]^+$ |

TABLE E4-continued compound list prepared according to Route A in Example 4

| Cpd. ID | Structure | Name | LCMS |
|---|---|---|---|
| 255 | 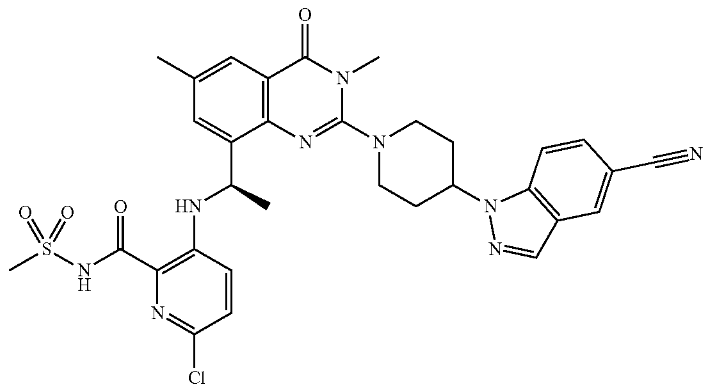 [SMILES: Cc1cc([C@@H](C)Nc2ccc(Cl)nc2C(=O)NS(C)(=O)=O)c2nc(N3CCC(n4ncc5cc(C#N)ccc54)CC3)n(C)c(=O)c2c1] | (R)-6-chloro-3-((1-(2-(4-(5-cyano-1H-indazol-1-yl)piperidin-1-yl)-3,6-dimethyl-4-oxo-3,4-dihydroquinazolin-8-yl)ethyl)amino)-N-(methylsulfonyl)picolinamide | 2.66 min, 254 nm, MS (ES+)[b] $C_{32}H_{32}ClN_9O_4S$, requires: 673.2, found: 674.2 [M + H]+ |
| 256 | 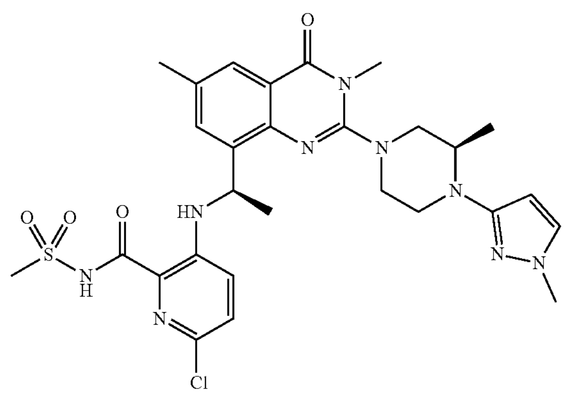 [SMILES: Cc1cc([C@@H](C)Nc2ccc(Cl)nc2C(=O)NS(C)(=O)=O)c2nc(N3CCN(c4ccn(C)n4)[C@H](C)C3)n(C)c(=O)c2c1] | 6-chloro-3-(((R)-1-(3,6-dimethyl-2-((R)-3-methyl-4-(1-methyl-1H-pyrazol-3-yl)piperazin-1-yl)-4-oxo-3,4-dihydroquinazolin-8-yl)ethyl)amino)-N-(methylsulfonyl)picolinamide | 2.39 min, 254 nm, MS (ES+)[b] $C_{28}H_{34}ClN_9O_4S$, requires: 627.2, found: 628.2 [M + H]+ |
| 257 | 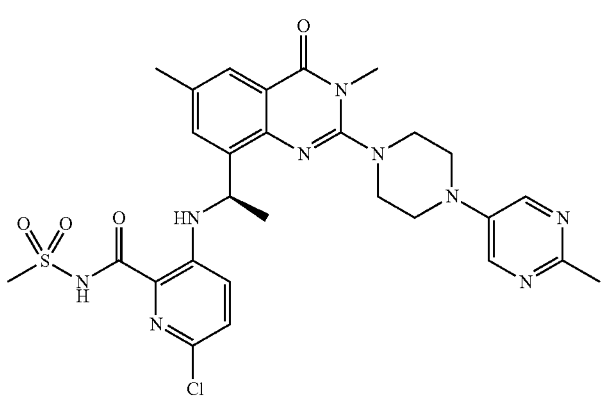 | (R)-6-chloro-3-((1-(3,6-dimethyl-2-(4-(2-methylpyrimidin-5-yl)piperazin-1-yl)-4-oxo-3,4-dihydroquinazolin-8-yl)ethyl)amino)-N-(methylsulfonyl)picolinamide | 2.13 min, 254 nm, MS (ES+)[b] $C_{28}H_{32}ClN_9O_4S$, requires: 625.2, found: 626.3 [M + H]+ |

TABLE E4-continued compound list prepared according to Route A in Example 4

| Cpd. ID | Structure | Name | LCMS |
|---|---|---|---|
| 258 | 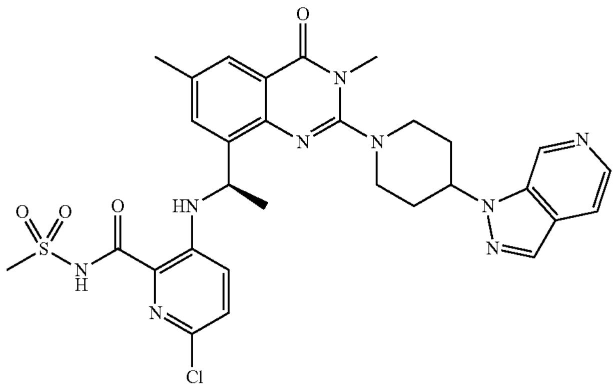 [SMILES: Cc1cc([C@@H](C)Nc2ccc(Cl)nc2C(=O)NS(C)(=O)=O)c2nc(N3CCC(n4ncc5ccncc54)CC3)n(C)c(=O)c2c1] | (R)-3-((1-(2-(4-(1H-pyrazolo[3,4-3]yridinedin-1-yl)piperidin-1-yl)-3,6-dimethyl-4-oxo-3,4-dihydroquinazolin-8-yl)ethyl)amino)-6-chloro-N-(methylsulfonyl)picolinamide | 3.46 min, 280 nm, MS (ES+)$^c$ C$_{30}$H$_{32}$ClN$_9$O$_4$S, requires: 649.2, found: 650.2 [M + H]$^+$ |
| 259 | 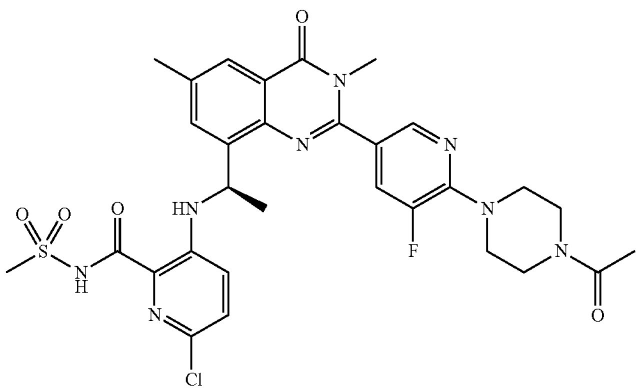 | (R)-3-((1-(2-(6-(4-acetylpiperazin-1-yl)-5-fluoropyridin-3-yl)-3,6-dimethyl-4-oxo-3,4-dihydroquinazolin-8-yl)ethyl)amino)-6-chloro-N-(methylsulfonyl)picolinamide | 2.11 min, 265 nm, MS (ES+)$^b$ C$_{30}$H$_{32}$ClFN$_8$O$_5$S, requires: 670.1, found: 671.2 [M + H]$^+$ |
| 260 | 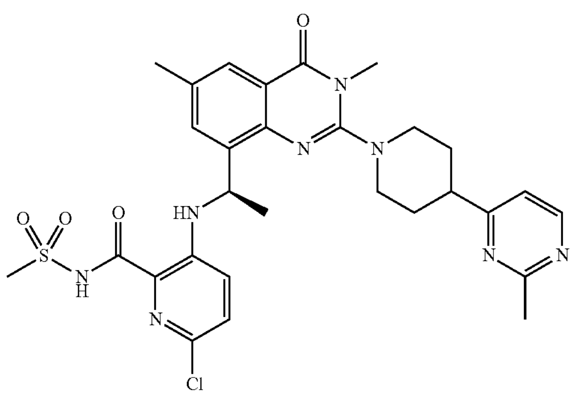 [SMILES: Cc1cc([C@@H](C)Nc2ccc(Cl)nc2C(=O)NS(C)(=O)=O)c2nc(N3CCC(c4ccnc(C)n4)CC3)n(C)c(=O)c2c1] | (R)-6-chloro-3-((1-(3,6-dimethyl-2-(4-(2-methylpyrimidin-4-yl)piperidin-1-yl)-4-oxo-3,4-dihydroquinazolin-8-yl)ethyl)amino)-N-(methylsulfonyl)picolinamide | 2.24 min, 210 nm, MS (ES+)$^b$ C$_{29}$H$_{33}$ClN$_8$O$_4$S, requires: 624.2, found: 625.3 [M + H]$^+$ |
| 261 | 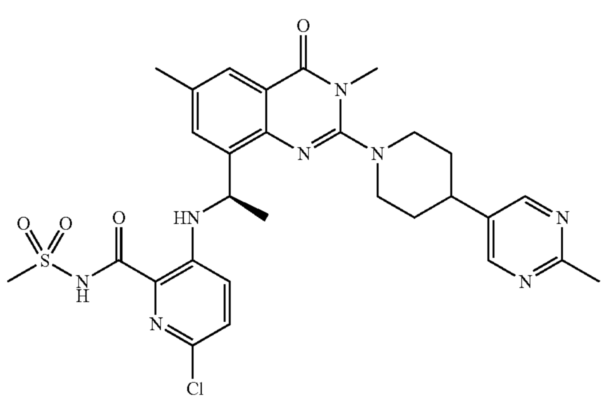 | (R)-6-chloro-3-((1-(3,6-dimethyl-2-(4-(2-methylpyrimidin-5-yl)piperidin-1-yl)-4-oxo-3,4-dihydroquinazolin-8-yl)ethyl)amino)-N-(methylsulfonyl)picolinamide | 2.17 min, 210 nm, MS (ES+)$^b$ C$_{29}$H$_{33}$ClN$_8$O$_4$S, requires: 624.2, found: 625.2 [M + H]$^+$ |

TABLE E4-continued compound list prepared according to Route A in Example 4

| Cpd. ID | Structure | Name | LCMS |
|---|---|---|---|
| 262 | 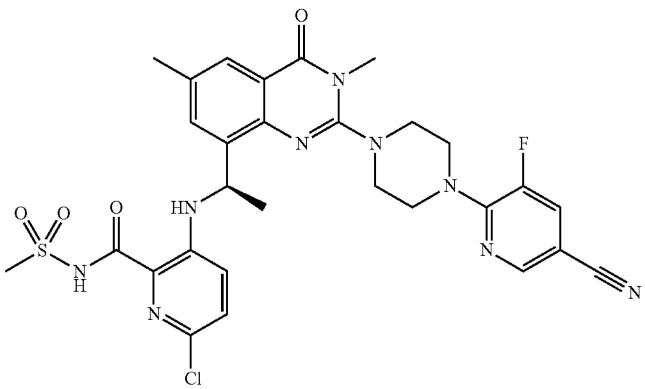 [SMILES: Cc1cc([C@@H](C)Nc2ccc(Cl)nc2C(=O)NS(C)(=O)=O)c2nc(N3CCN(c4ncc(C#N)cc4F)CC3)n(C)c(=O)c2c1] | (R)-6-chloro-3-((1-(2-(4-(5-cyano-3-fluoropyridin-2-yl)piperazin-1-yl)-3,6-dimethyl-4-oxo-3,4-dihydroquinazolin-8-yl)ethyl)amino)-N-(methylsulfonyl)picolinamide | 2.48 min, 254 nm, MS (ES+)[b] $C_{29}H_{29}ClFN_9O_4S$, requires: 653.1, found: 654.0 $[M + H]^+$ |
| 263 | 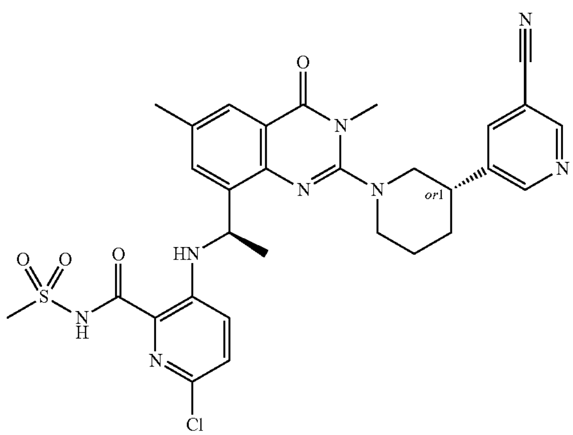 [SMILES: Cc1cc([C@@H](C)Nc2ccc(Cl)nc2C(=O)NS(C)(=O)=O)c2nc(N3CCC[C@@H](c4cncc(C#N)c4)C3)n(C)c(=O)c2c1] | 6-chloro-3-(((R)-1-(2-((R*)-3-(5-cyanopyridin-3-yl)piperidin-1-yl)-3,6-dimethyl-4-oxo-3,4-dihydroquinazolin-8-yl)ethyl)amino)-N-(methylsulfonyl)picolinamide | 2.50 min, 270 nm, MS (ES+)[b] $C_{30}H_{31}ClN_8O_4S$, requires: 634.1, found: 635.2 $[M + H]^+$ |
| 264 | 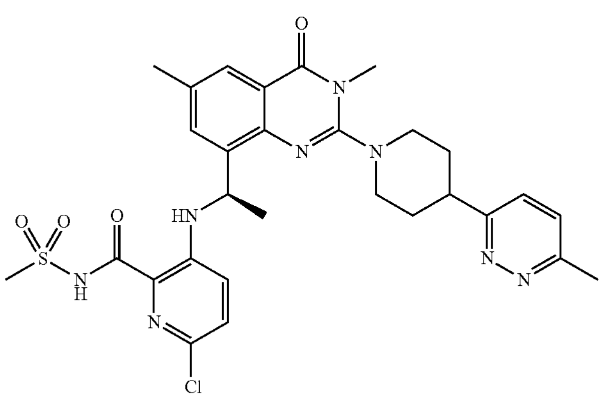 | (R)-6-chloro-3-((1-(3,6-dimethyl-2-(4-(6-methylpyridazin-3-yl)piperidin-1-yl)-4-oxo-3,4-dihydroquinazolin-8-yl)ethyl)amino)-N-(methylsulfonyl)picolinamide | 2.21 min, 210 nm, MS (ES+)[b] C29H33ClN8O4S, requires: 624.2, found: 625.2 $[M + H]^+$ |

TABLE E4-continued compound list prepared according to Route A in Example 4

| Cpd. ID | Structure | Name | LCMS |
|---|---|---|---|
| 265 | 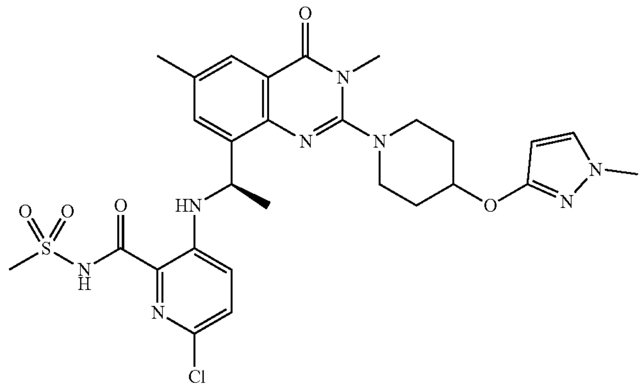 | (R)-6-chloro-3-((1-(3,6-dimethyl-2-(4-((1-methyl-1H-pyrazol-3-yl)oxy)piperidin-1-yl)-4-oxo-3,4-dihydroquinazolin-8-yl)ethyl)amino)-N-(methylsulfonyl)picolinamide | 2.42 min, 210 nm, MS (ES+)[b] $C_{28}H_{33}ClN_8O_5S$, requires: 628.2, found: 629.2 $[M + H]^+$ |
| 266 | 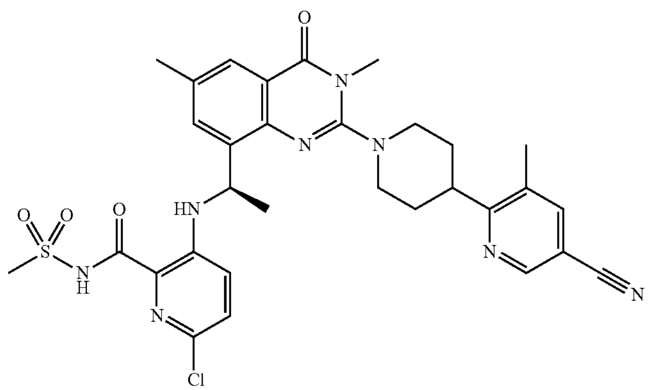 [SMILES: Cc1cc([C@@H](C)Nc2ccc(Cl)nc2C(=O)NS(C)(=O)=O)c2nc(N3CCC(c4ncc(C#N)cc4C)CC3)n(C)c(=O)c2c1] | (R)-6-chloro-3-((1-(2-(4-(5-cyano-3-methylpyridin-2-yl)piperidin-1-yl)-3,6-dimethyl-4-oxo-3,4-dihydroquinazolin-8-yl)ethyl)amino)-N-(methylsulfonyl)picolinamide | 2.67 min, 210 nm, MS (ES+)[b] $C_{31}H_{33}ClN_8O_4S$, requires: 647.4, found: 648.2 $[M + H]^+$ |
| 267 | 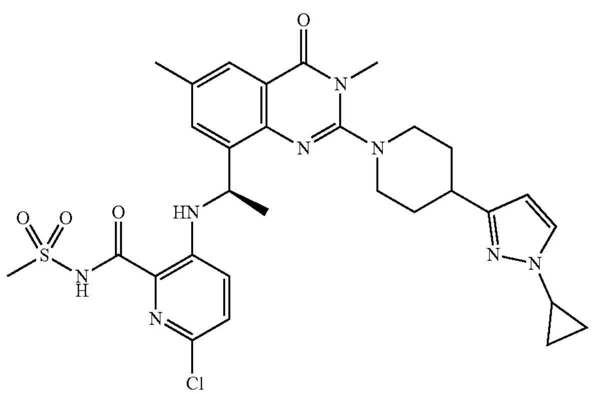 [SMILES: Cc1cc([C@@H](C)Nc2ccc(Cl)nc2C(=O)NS(C)(=O)=O)c2nc(N3CCC(c4ccn(C5CC5)n4)CC3)n(C)c(=O)c2c1] | (R)-6-chloro-3-((1-(2-(4-(1-cyclopropyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.46 min, 254 nm, MS (ES+)[b] $C_{30}H_{35}ClN_8O_4S$, requires: 638.2, found: 639.1 $[M + H]^+$ |
| 268 | 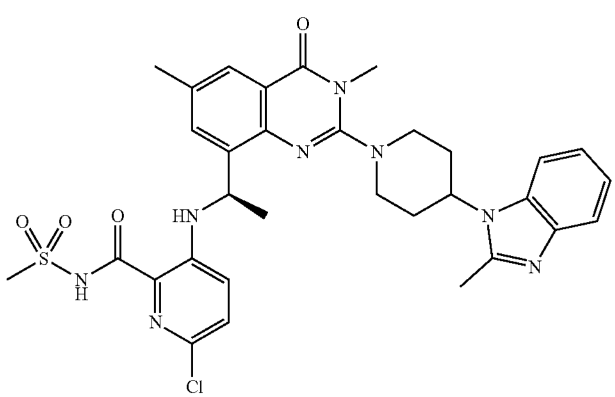 [SMILES: Cc1cc([C@@H](C)Nc2ccc(Cl)nc2C(=O)NS(C)(=O)=O)c2nc(N3CCC(n4c(C)nc5ccccc54)CC3)n(C)c(=O)c2c1] | (R)-6-chloro-3-((1-(3,6-dimethyl-2-(4-(2-methyl-1H-benzo[d]imidazol-1-yl)piperidin-1-yl)-4-oxo-3,4-dihydroquinazolin-8-yl)ethyl)amino)-N-(methylsulfonyl)picolinamide | 2.06 min, 270 nm, MS (ES+)[b] $C_{32}H_{35}ClN_8O_4S$, required: 662.2, found: 663.3 $[M + H]^+$ |

TABLE E4-continued compound list prepared according to Route A in Example 4

| Cpd. ID | Structure | Name | LCMS |
|---|---|---|---|
| 269 | 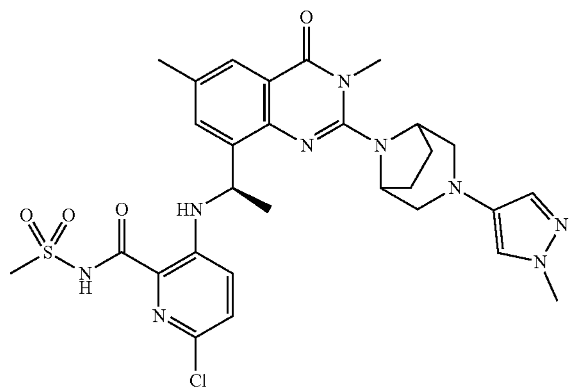 [SMILES: Cc1cc([C@@H](C)Nc2ccc(Cl)nc2C(=O)NS(C)(=O)=O)c2nc(N3C4CCC3CN(c3cnn(C)c3)C4)n(C)c(=O)c2c1] | 6-chloro-3-(((1R)-1-(3,6-dimethyl-2-(3-(1-methyl-1H-pyrazol-4-yl)-3,8-diazabicyclo[3.2.1]octan-8-yl)-4-oxo-3,4-dihydroquinazolin-8-yl)ethyl)amino)-N-(methylsulfonyl)picolinamide | 2.31 min, 254 nm, MS (ES+)[b] $C_{29}H_{34}ClN_9O_4S$, requires: 639.2, found: 640.3 $[M + H]^+$ |
| 270 | 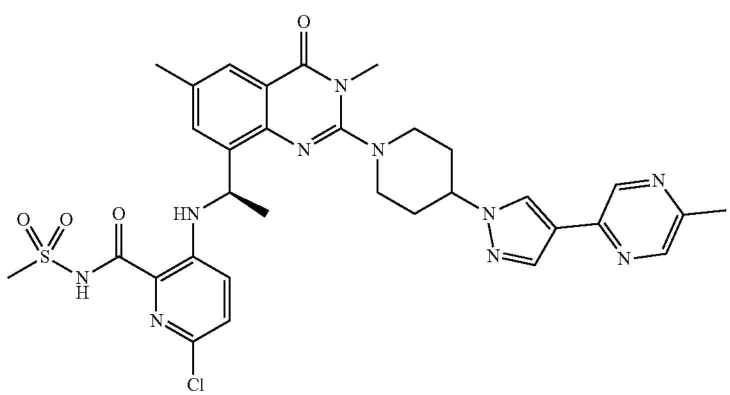 | (R)-6-chloro-3-((1-(3,6-dimethyl-2-(4-(4-(5-methylpyrazin-2-yl)-1H-pyrazol-1-yl)piperidin-1-yl)-4-oxo-3,4-dihydroquinazolin-8-yl)ethyl)amino)-N-(methylsulfonyl)picolinamide | 4.41 min, 254 nm, MS (ES+)[c] $C_{32}H_{35}ClN_{10}O_4S$, requires: 690.2, found: 691.2 $[M + H]^+$ |
| 271 | 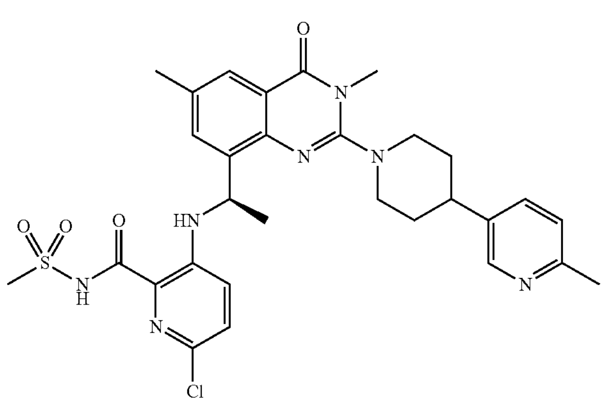 | (R)-6-chloro-3-((1-(3,6-dimethyl-2-(4-(6-methylpyridin-3-yl)piperidin-1-yl)-4-oxo-3,4-dihydroquinazolin-8-yl)ethyl)amino)-N-(methylsulfonyl)picolinamide | 3.41 min, 254 nm, MS (ES+)[c] $C_{30}H_{34}ClN_7O_4S$, requires: 623.2, found: 624.2 $[M + H]^+$ |

TABLE E4-continued compound list prepared according to Route A in Example 4

| Cpd. ID | Structure | Name | LCMS |
|---|---|---|---|
| 272 | 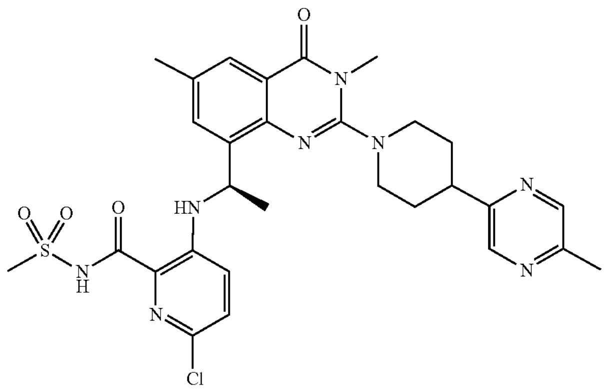 | (R)-6-chloro-3-((1-(3,6-dimethyl-2-(4-(5-methylpyrazin-2-yl)piperidin-1-yl)-4-oxo-3,4-dihydroquinazolin-8-yl)ethyl)amino)-N-(methylsulfonyl)picolinamide | 4.57 min, 280 nm, MS (ES+)$^c$ $C_{29}H_{33}ClN_8O_4S$, requires: 624.2, found: 625.2 $[M + H]^+$ |
| 273 | 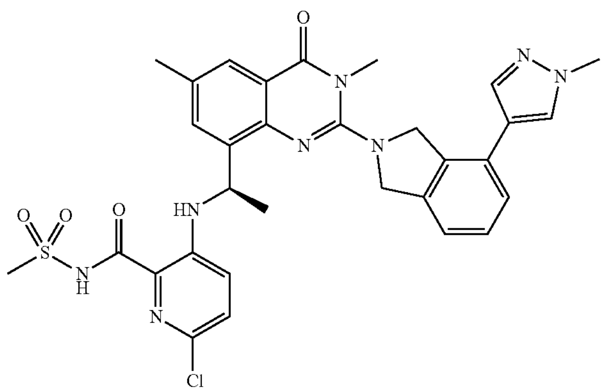 | (R)-6-chloro-3-((1-(3,6-dimethyl-2-(4-(1-methyl-1H-pyrazol-4-yl)isoindolin-2-yl)-4-oxo-3,4-dihydroquinazolin-8-yl)ethyl)amino)-N-(methylsulfonyl)picolinamide | 3.64 min, 254 nm, MS (ES+)$^c$ $C_{31}H_{31}ClN_8O_4S$, requires: 646.2, found: 647.2 $[M + H]^+$ |
| 274 | 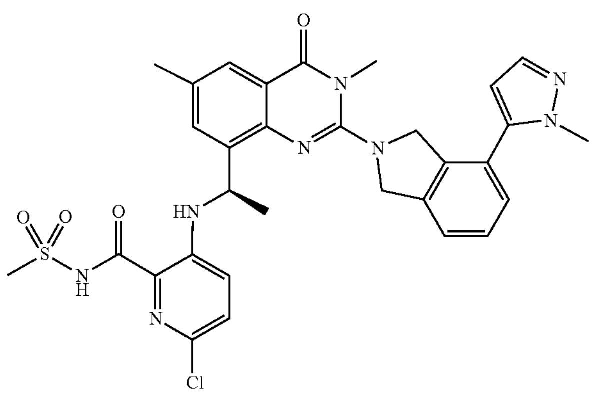 | (R)-6-chloro-3-((1-(3,6-dimethyl-2-(4-(1-methyl-1H-pyrazol-5-yl)isoindolin-2-yl)-4-oxo-3,4-dihydroquinazolin-8-yl)ethyl)amino)-N-(methylsulfonyl)picolinamide | 3.56 min, 254 nm, MS (ES+)$^c$ $C_{31}H_{31}ClN_8O_4S$, requires: 646.2, found: 647.2 $[M + H]^+$ |
| 275 | 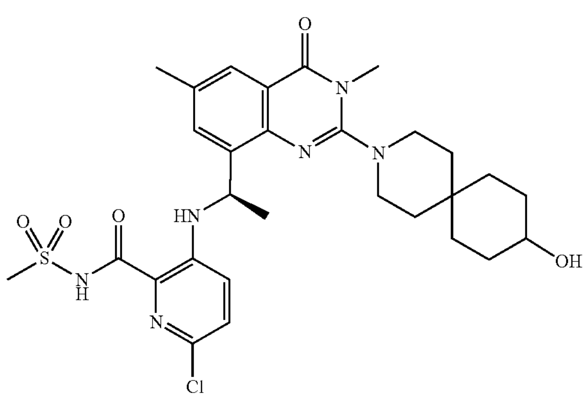 [SMILES: Cc1cc([C@@H](C)Nc2ccc(Cl)nc2C(=O)NS(C)(=O)=O)c2nc(N3CCC4(CCC(O)CC4)CC3)n(C)c(=O)c2c1] | (R)-6-chloro-3-((1-(2-(9-hydroxy-3-azaspiro[5.5]undecan-3-yl)-3,6-dimethyl-4-oxo-3,4-dihydroquinazolin-8-yl)ethyl)amino)-N-(methylsulfonyl)picolinamide | 3.47 min, 254 nm, MS (ES+)$^c$ $C_{29}H_{37}ClN_6O_5S$, requires: 616.2, found: 617.3 $[M + H]^+$ |

TABLE E4-continued compound list prepared according to Route A in Example 4

| Cpd. ID | Structure | Name | LCMS |
|---|---|---|---|
| 276 | 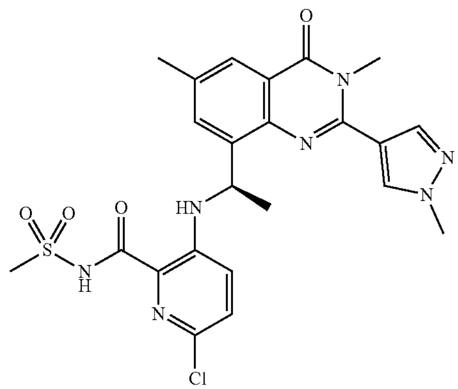 | (R)-6-chloro-3-((1-(2-(6,7-dihydroisoxazolo[4,5-c]pyridin-5(4H)-yl)-3,6-dimethyl-4-oxo-3,4-dihydroquinazolin-8-yl)ethyl)amino)-N-(methylsulfonyl)picolinamide | 3.29 min, 254 nm, MS (ES+)$^c$ $C_{25}H_{26}ClN_7O_5S$, requires: 571.1, found: 572.2 $[M + H]^+$ |
| 277 | 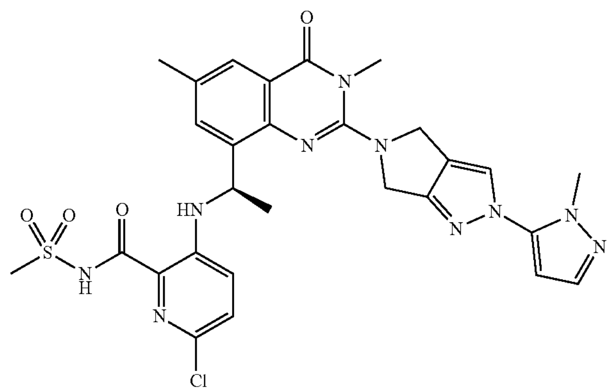 [SMILES: Cc1cc([C@@H](C)Nc2ccc(Cl)nc2C(=O)NS(C)(=O)=O)c2nc(N3Cc4cn(-c5ccnn5C)nc4C3)n(C)c(=O)c2c1] | (R)-6-chloro-3-((1-(3,6-dimethyl-2-(2-(1-methyl-1H-pyrazol-5-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.31 min, 220 nm, MS (ES+)$^b$ $C_{28}H_{29}ClN_{10}O_4S$, requires: 636.1, found: 637.2 $[M + H]^+$ |
| 278 | 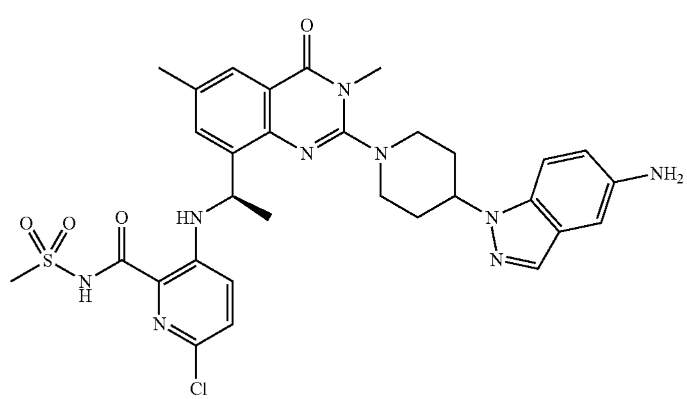 [SMILES: Cc1cc([C@@H](C)Nc2ccc(Cl)nc2C(=O)NS(C)(=O)=O)c2nc(N3CCC(n4ncc5cc(N)ccc54)CC3)n(C)c(=O)c2c1] | (R)-3-((1-(2-(4-(5-amino-1H-indazol-1-yl)piperidin-1-yl)-3,6-dimethyl-4-oxo-3,4-dihydroquinazolin-8-yl)ethyl)amino)-6-chloro-N-(methylsulfonyl)picolinamide | 2.02 min, 270 nm, MS (ES+)$^b$ $C_{31}H_{34}ClN_9O_4S$, requires: 663.2, found: 664.2 $[M + H]^+$ |

TABLE E4-continued compound list prepared according to Route A in Example 4

| Cpd. ID | Structure | Name | LCMS |
|---|---|---|---|
| 279 | 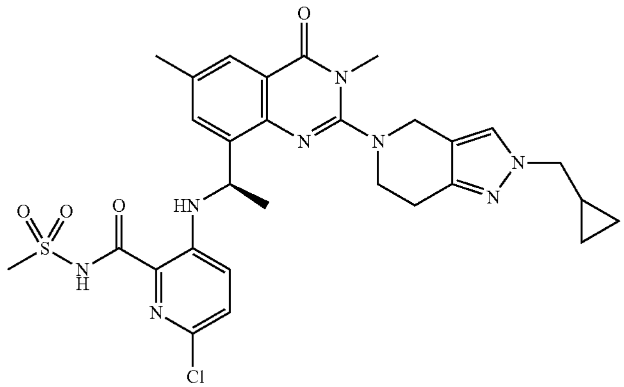 [SMILES: Cc1cc([C@@H](C)Nc2ccc(Cl)nc2C(=O)NS(C)(=O)=O)c2nc(N3CCc4nn(CC5CC5)cc4C3)n(C)c(=O)c2c1] | (R)-6-chloro-3-((1-(2-(2-(cyclopropylmethyl)-2,4,6,7-tetrahydro-5H-pyrazolo[4,3-c]pyridin-5-yl)-3,6-dimethyl-4-oxo-3,4-dihydroquinazolin-8-yl)ethyl)amino)-N-(methylsulfonyl)picolinamide | 2.44 min, 254 nm, MS (ES+)[b] $C_{29}H_{33}ClN_8O_4S$, requires: 624.2, found: 625.2 $[M+H]^+$ |
| 280 | 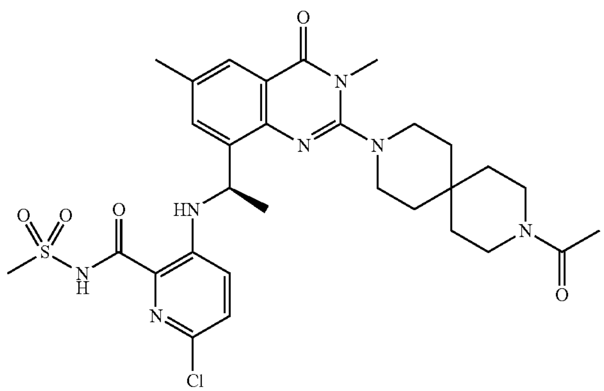 [SMILES: CC(=O)N1CCC2(CC1)CCN(c1nc3c([C@@H](C)Nc4ccc(Cl)nc4C(=O)NS(C)(=O)=O)cc(C)cc3c(=O)n1C)CC2] | (R)-3-((1-(2-(9-acetyl-3,9-diazaspiro[5.5]undecan-3-yl)-3,6-dimethyl-4-oxo-3,4-dihydroquinazolin-8-yl)ethyl)amino)-6-chloro-N-(methylsulfonyl)picolinamide | 3.30 min, 254 nm, MS (ES+)[c] $C_{30}H_{38}ClN_7O_5S$, requires: 643.2, found: 644.3 $[M+H]^+$ |
| 281 | 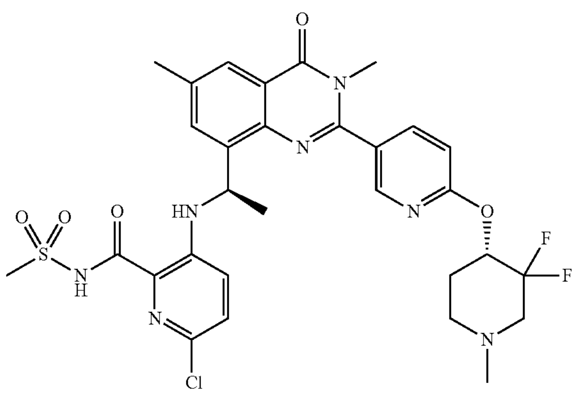 [SMILES: Cc1cc([C@@H](C)Nc2ccc(Cl)nc2C(=O)NS(C)(=O)=O)c2nc(-c3ccc(O[C@H]4CCN(C)CC4(F)F)nc3)n(C)c(=O)c2c1] | 6-chloro-3-(((R)-1-(2-(6-(((S)-3,3-difluoro-1-methylpiperidin-4-yl)oxy)pyridin-3-yl)-3,6-dimethyl-4-oxo-3,4-dihydroquinazolin-8-yl)ethyl)amino)-N-(methylsulfonyl)picolinamide | 2.58 min, 254 nm MS (ES+)[c] $C_{30}H_{32}ClF_2N_7O_5S$, requires: 675.2, found: 676.2 $[M+H]^+$ |
| 282 | 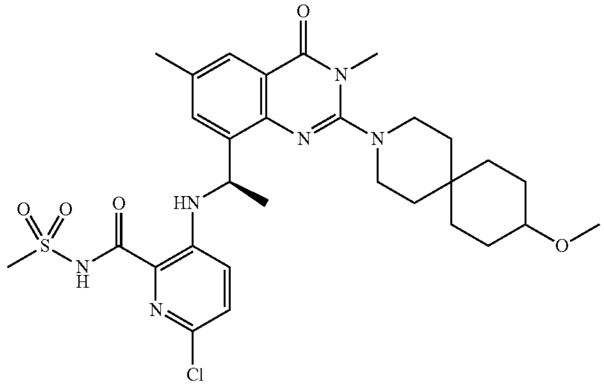 | (R)-6-chloro-3-((1-(2-(9-methoxy-3-azaspiro[5.5]undecan-3-yl)-3,6-dimethyl-4-oxo-3,4-dihydroquinazolin-8-yl)ethyl)amino)-N-(methylsulfonyl)picolinamide | 4.11 min, 254 nm, MS (ES+)[c] $C_{30}H_{39}ClN_6O_5S$, requires: 630.2, found: 631.3 $[M+H]^+$ |

TABLE E4-continued compound list prepared according to Route A in Example 4

| Cpd. ID | Structure | Name | LCMS |
|---|---|---|---|
| 283 | 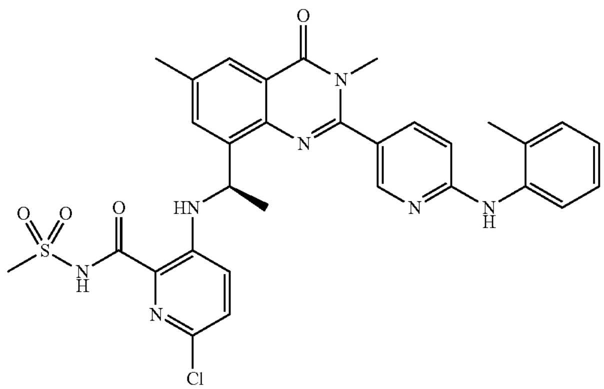 [SMILES: Cc1cc([C@@H](C)Nc2ccc(Cl)nc2C(=O)NS(C)(=O)=O)c2nc(-c3ccc(Nc4ccccc4C)nc3)n(C)c(=O)c2c1] | (R)-6-chloro-3-((1-(3,6-dimethyl-4-oxo-2-(6-(o-tolylamino)pyridin-3-yl)-3,4-dihydroquinazolin-8-yl)ethyl)amino)-N-(methylsulfonyl)picolinamide | 3.47 min, 254 nm, MS (ES+)$^c$ $C_{31}H_{30}ClN_7O_4S$, requires: 631.2, found: 632.2 $[M + H]^+$ |
| 284 | 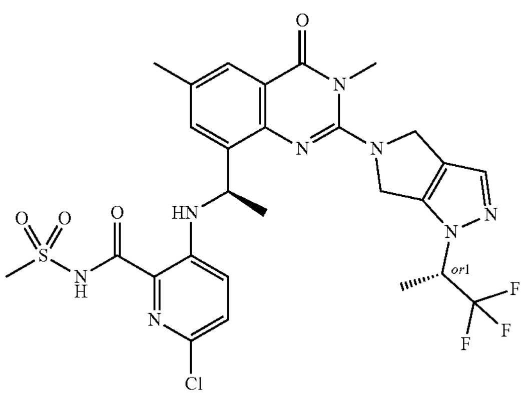 [SMILES: Cc1cc([C@@H](C)Nc2ccc(Cl)nc2C(=O)NS(C)(=O)=O)c2nc(N3Cc4cnn([C@@H](C)C(F)(F)F)c4C3)n(C)c(=O)c2c1] | 6-chloro-3-(((R)-1-(3,6-dimethyl-4-oxo-2-(1-((R*)-1,1,1-trifluoropropan-2-yl)-4,6-dihydropyrrolo[3,4-c]pyrazol-5(1H)-yl)-3,4-dihydroquinazolin-8-yl)ethyl)amino)-N-(methylsulfonyl)picolinamide | 2.48 min, 254 nm, MS (ES+)$^b$ $C_{27}H_{28}ClF_3N_8O_4S$, requires: 652.1, found: 653.1 $[M + H]^+$ |
| 285 | 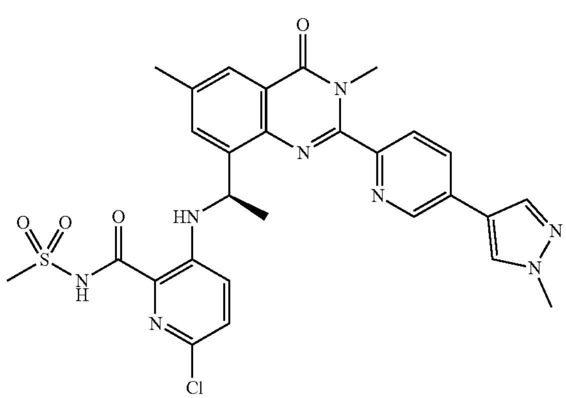 [SMILES: Cc1cc([C@@H](C)Nc2ccc(Cl)nc2C(=O)NS(C)(=O)=O)c2nc(-c3ccc(-c4cnn(C)c4)cn3)n(C)c(=O)c2c1] | (R)-6-chloro-3-((1-(3,6-dimethyl-2-(5-(1-methyl-1H-pyrazol-4-yl)pyridin-2-yl)-4-oxo-3,4-dihydroquinazolin-8-yl)ethyl)amino)-N-(methylsulfonyl)picolinamide | 2.24 min, 254 nm, MS (ES+)$^b$ $C_{28}H_{27}ClN_8O_4S$, requires: 606.1, found: 607.2 $[M + H]^+$ |

TABLE E4-continued compound list prepared according to Route A in Example 4

| Cpd. ID | Structure | Name | LCMS |
|---|---|---|---|
| 286 | 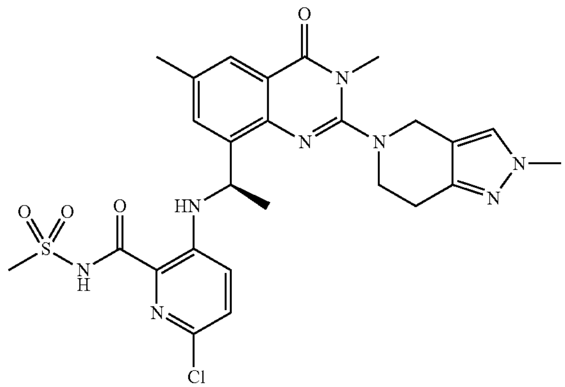 | (R)-6-chloro-3-((1-(3,6-dimethyl-2-(2-methyl-2,4,6,7-tetrahydro-5H-pyrazolo[4,3-c]pyridin-5-yl)-4-oxo-3,4-dihydroquinazolin-8-yl)ethyl)amino)-N-(methylsulfonyl)picolinamide | 2.19 min, 270 nm, MS (ES+)[b] $C_{26}H_{29}ClN_8O_4S$, requires: 584.1, found: 585.1 $[M+H]^+$ |
| 287 | 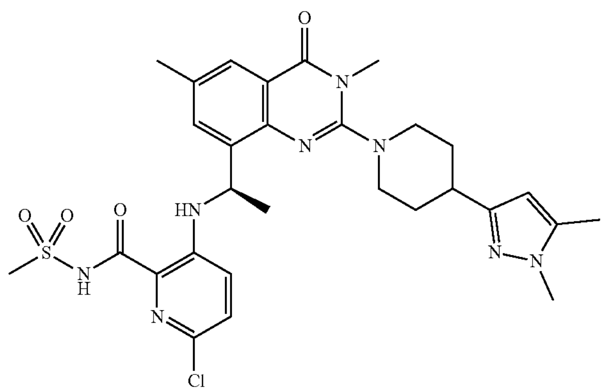 | (R)-6-chloro-3-((1-(2-(4-(1,5-dimethyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.44 min, 254 nm, MS (ES+)[b] $C_{29}H_{35}ClN_8O_4S$, requires: 626.2, found: 627.2 $[M+H]^+$ |
| 288 | 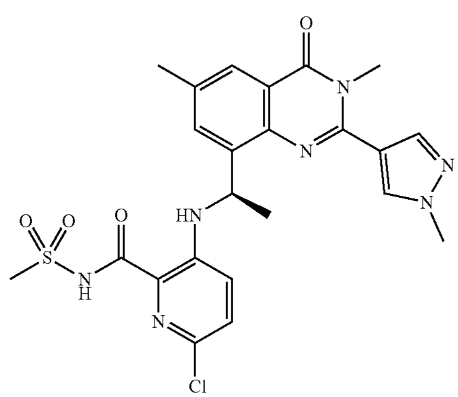 [SMILES: Cc1cc([C@@H](C)Nc2ccc(Cl)nc2C(=O)NS(C)(=O)=O)c2nc(-c3cnn(C)c3)n(C)c(=O)c2c1] | (R)-6-chloro-3-((1-(3,6-dimethyl-2-(1-methyl-1H-pyrazol-4-yl)-4-oxo-3,4-dihydroquinazolin-8-yl)ethyl)amino)-N-(methylsulfonyl)picolinamide | 2.17 min, 254 nm, MS (ES+)[b] $C_{23}H_{24}ClN_7O_4S$, requires: 529.1, found: 530.0 $[M+H]^+$ |
| 289 | 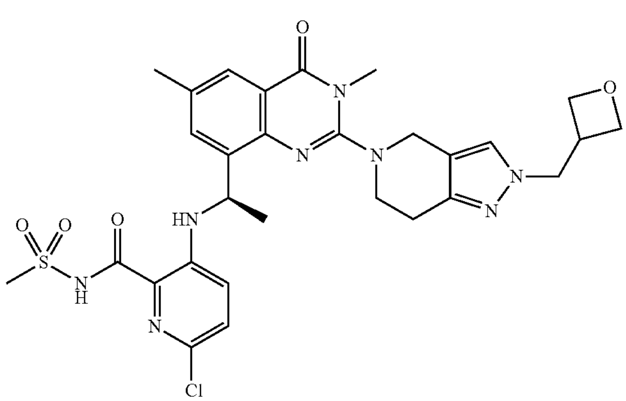 [SMILES: Cc1cc([C@@H](C)Nc2ccc(Cl)nc2C(=O)NS(C)(=O)=O)c2nc(N3CCc4nn(CC5COC5)cc4C3)n(C)c(=O)c2c1] | (R)-6-chloro-3-((1-(3,6-dimethyl-2-(2-(oxetan-3-ylmethyl)-2,4,6,7-tetrahydro-5H-pyrazolo[4,3-c]pyridin-5-yl)-4-oxo-3,4-dihydroquinazolin-8-yl)ethyl)amino)-N-(methylsulfonyl)picolinamide | 2.16 min, 254 nm, MS (ES+)[b] $C_{29}H_{33}ClN_8O_5S$, requires: 640.2, found: 641.2 $[M+H]^+$ |

TABLE E4-continued compound list prepared according to Route A in Example 4

| Cpd. ID | Structure | Name | LCMS |
|---|---|---|---|
| 290 | 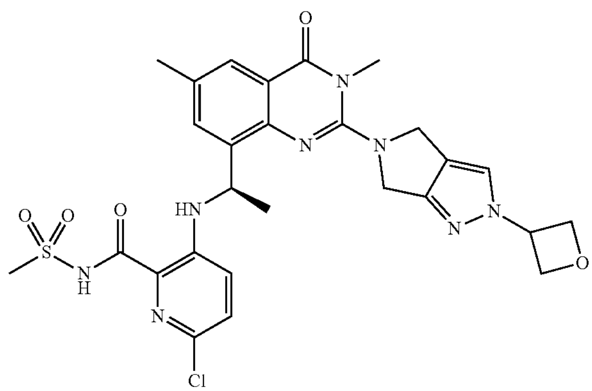 [SMILES: Cc1cc([C@@H](C)Nc2ccc(Cl)nc2C(=O)NS(C)(=O)=O)c2nc(N3Cc4cn(C5COC5)nc4C3)n(C)c(=O)c2c1] | (R)-6-chloro-3-((1-(3,6-dimethyl-2-(2-(oxetan-3-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.18 min, 270 nm, MS (ES+)$^b$ $C_{27}H_{29}ClN_8O_5S$, requires: 612.2, found: 613.2 [M + H]$^+$ |
| 291 | 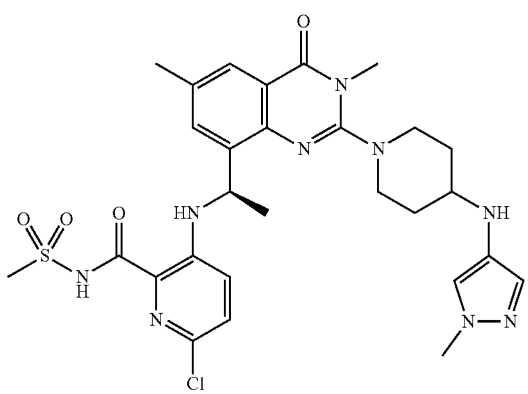 [SMILES: Cc1cc([C@@H](C)Nc2ccc(Cl)nc2C(=O)NS(C)(=O)=O)c2nc(N3CCC(Nc4cnn(C)c4)CC3)n(C)c(=O)c2c1] | (R)-6-chloro-3-((1-(3,6-dimethyl-2-(4-((1-methyl-1H-pyrazol-4-yl)amino)piperidin-1-yl)-4-oxo-3,4-dihydroquinazolin-8-yl)ethyl)amino)-N-(methylsulfonyl)picolinamide | 1.88 min, 270 nm, MS (ES+)$^b$ $C_{28}H_{34}ClN_9O_4S$, requires: 627.2, found: 628.2 [M + H]$^+$ |
| 292 | 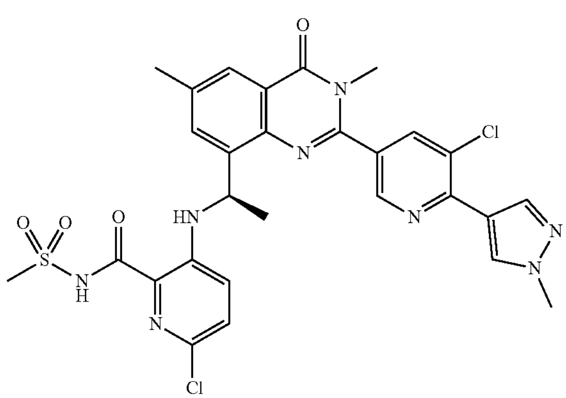 [SMILES: Cc1cc([C@@H](C)Nc2ccc(Cl)nc2C(=O)NS(C)(=O)=O)c2nc(-c3cnc(-c4cnn(C)c4)c(Cl)c3)n(C)c(=O)c2c1] | (R)-6-chloro-3-((1-(2-(5-chloro-6-(1-methyl-1H-pyrazol-4-yl)pyridin-3-yl)-3,6-dimethyl-4-oxo-3,4-dihydroquinazolin-8-yl)ethyl)amino)-N-(methylsulfonyl)picolinamide | 2.29 min, 220 nm, MS (ES+)$^b$ $C_{28}H_{26}Cl_2N_8O_4S$, requires: 640.1, found: 641.1 [M + H]$^+$ |

TABLE E4-continued compound list prepared according to Route A in Example 4

| Cpd. ID | Structure | Name | LCMS |
|---|---|---|---|
| 293 | 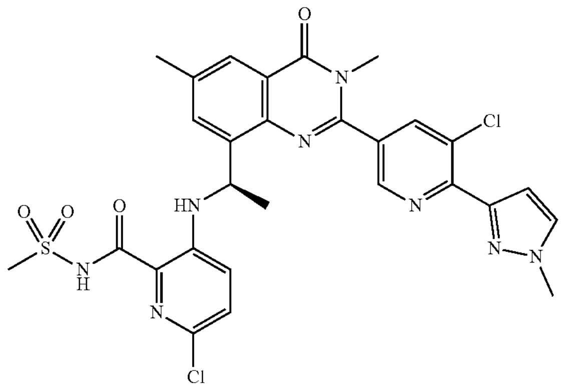 [SMILES: Cc1cc([C@@H](C)Nc2ccc(Cl)nc2C(=O)NS(C)(=O)=O)c2nc(-c3cnc(-c4ccn(C)n4)c(Cl)c3)n(C)c(=O)c2c1] | (R)-6-chloro-3-((1-(2-(5-chloro-6-(1-methyl-1H-pyrazol-3-yl)pyridin-3-yl)-3,6-dimethyl-4-oxo-3,4-dihydroquinazolin-8-yl)ethyl)amino)-N-(methylsulfonyl)picolinamide | 2.31 min, 254 nm, MS (ES+)[b] $C_{28}H_{26}Cl_2N_8O_4S$, requires: 640.1, found: 641.1 $[M + H]^+$ |
| 294 | 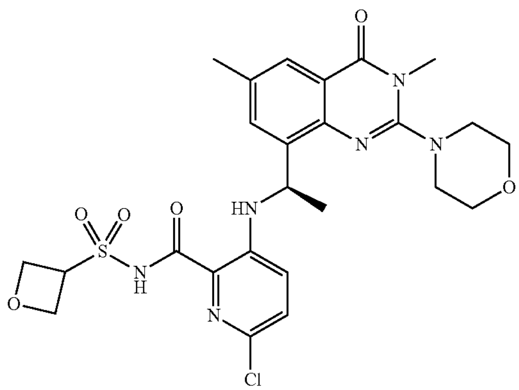 [SMILES: Cc1cc([C@@H](C)Nc2ccc(Cl)nc2C(=O)NS(=O)(=O)C2COC2)c2nc(N3CCOCC3)n(C)c(=O)c2c1] | (R)-6-chloro-3-((1-(3,6-dimethyl-2-morpholino-4-oxo-3,4-dihydroquinazolin-8-yl)ethyl)amino)-N-(oxetan-3-ylsulfonyl)picolinamide | 2.25 min, 270 nm, MS (ES+)[b] $C_{25}H_{29}ClN_6O_6S$, requires: 576.1, found: 577.1 $[M + H]^+$ |
| 295 | 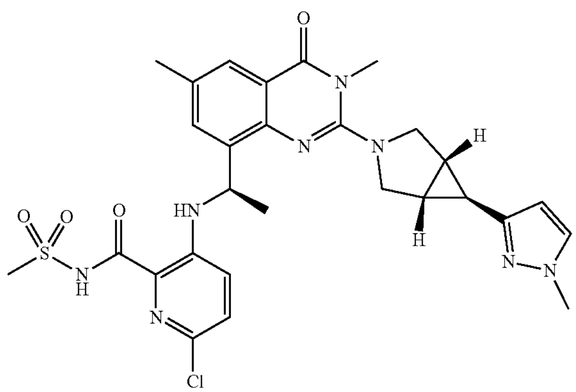 [SMILES: Cc1cc([C@@H](C)Nc2ccc(Cl)nc2C(=O)NS(C)(=O)=O)c2nc(N3C[C@@H]4[C@H](C3)[C@H]4c3ccn(C)n3)n(C)c(=O)c2c1] | 6-chloro-3-(((R)-1-(3,6-dimethyl-2-((1R,5S,6R)-6-(1-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 4.40 min, 254 nm, MS (ES+)[b] $C_{28}H_{31}ClN_8O_4S$, requires: 610.2, found: 611.2 $[M + H]^+$ |
| 296 | 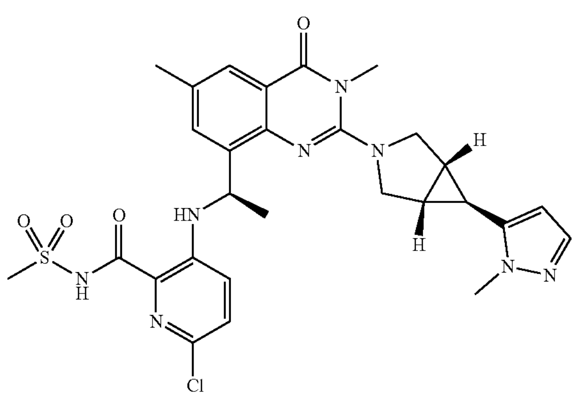 [SMILES: Cc1cc([C@@H](C)Nc2ccc(Cl)nc2C(=O)NS(C)(=O)=O)c2nc(N3C[C@@H]4[C@H](C3)[C@H]4c3ccnn3C)n(C)c(=O)c2c1] | 6-chloro-3-(((R)-1-(3,6-dimethyl-2-((1R,5S,6R)-6-(1-methyl-1H-pyrazol-5-yl)-3-azabicyclo[3.1.0]hexan-3-yl)-4-oxo-3,4-dihydroquinazolin-8-yl)ethyl)amino)-N-(methylsulfonyl)picolinamide | 4.31 min, 254 nm, MS (ES+)[c] $C_{28}H_{31}ClN_8O_4S$, requires: 610.2, found: 611.2 $[M + H]^+$ |

TABLE E4-continued compound list prepared according to Route A in Example 4

| Cpd. ID | Structure | Name | LCMS |
|---|---|---|---|
| 297 | 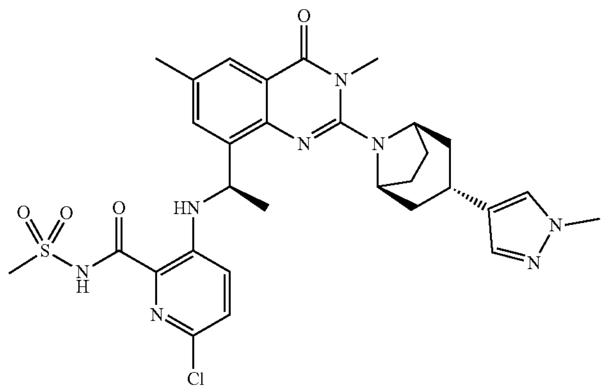 | 6-chloro-3-(((R)-1-(3,6-dimethyl-2-((1R,3R,5S)-3-(1-methyl-1H-pyrazol-4-yl)-8-azabicyclo[3.2.1]octan-8-yl)-4-oxo-3,4-dihydroquinazolin-8-yl)ethyl)amino)-N-(methylsulfonyl)picolinamide | 4.52 min, 254 nm, MS (ES+)$^c$ C$_{30}$H$_{35}$ClN$_8$O$_4$S, requires: 638.2, found: 639.3 [M + H]$^+$ |
| 298 | 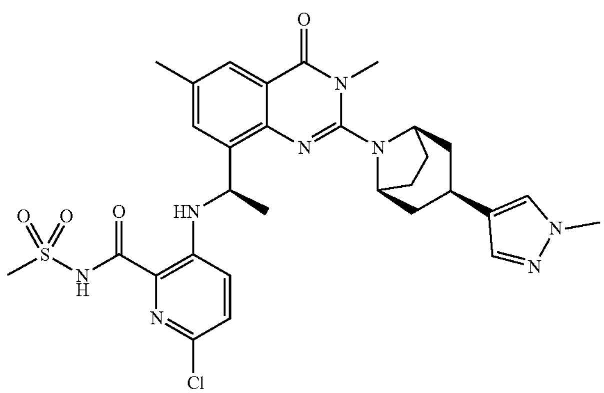 | 6-chloro-3-(((R)-1-(3,6-dimethyl-2-((1R,3S,5S)-3-(1-methyl-1H-pyrazol-4-yl)-8-azabicyclo[3.2.1]octan-8-yl)-4-oxo-3,4-dihydroquinazolin-8-yl)ethyl)amino)-N-(methylsulfonyl)picolinamide | 4.51 min, 254 nm, MS (ES+)$^c$ C$_{30}$H$_{35}$ClN$_8$O$_4$S, requires: 638.2, found: 639.3 [M + H]$^+$ |
| 299 | 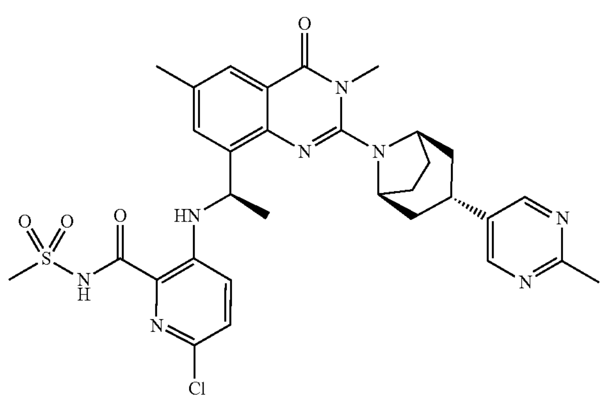 | 6-chloro-3-(((R)-1-(3,6-dimethyl-2-((1R,3R,5S)-3-(2-methylpyrimidin-5-yl)-8-azabicyclo[3.2.1]octan-8-yl)-4-oxo-3,4-dihydroquinazolin-8-yl)ethyl)amino)-N-(methylsulfonyl)picolinamide | 4.34 min, 254 nm, MS (ES+)$^c$ C$_{31}$H$_{35}$ClN$_8$O$_4$S, requires: 650.2, found: 651.3 [M + H]$^+$ |

TABLE E4-continued compound list prepared according to Route A in Example 4

| Cpd. ID | Structure | Name | LCMS |
|---|---|---|---|
| 300 | 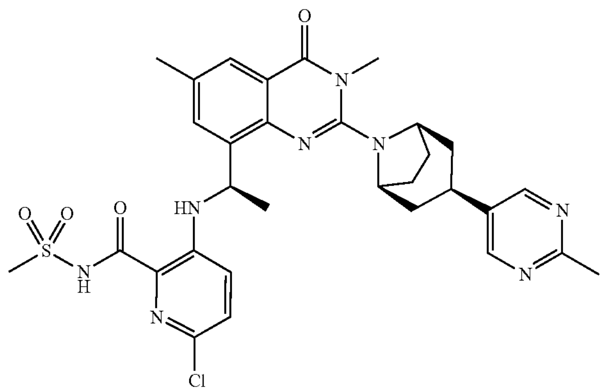 | 6-chloro-3-(((R)-1-(3,6-dimethyl-2-((1R,3S,5S)-3-(2-methylpyrimidin-5-yl)-8-azabicyclo[3.2.1]octan-8-yl)-4-oxo-3,4-dihydroquinazolin-8-yl)ethyl)amino)-N-(methylsulfonyl)picolinamide | 4.35 min, 254 nm, MS (ES+)$^c$ $C_{31}H_{35}ClN_8O_4S$, requires: 650.2, found: 651.2 $[M + H]^+$ |
| 301 | 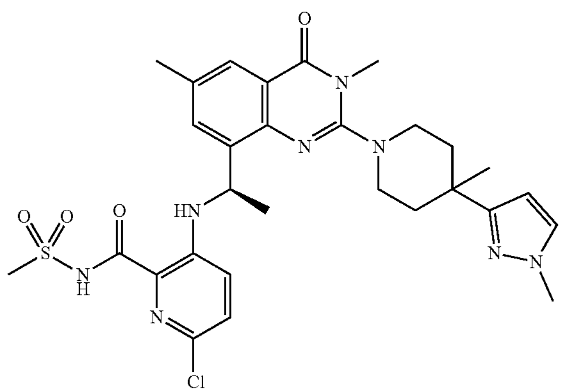 | (R)-6-chloro-3-((1-(3,6-dimethyl-2-(4-methyl-4-(1-methyl-1H-pyrazol-3-yl)piperidin-1-yl)-4-oxo-3,4-dihydroquinazolin-8-yl)ethyl)amino)-N-(methylsulfonyl)picolinamide | 2.41 min, 254 nm, MS (ES+)$^b$ $C_{29}H_{35}ClN_8O_4S$, requires: 626.2, found: 627.2 $[M + H]^+$ |
| 302 | 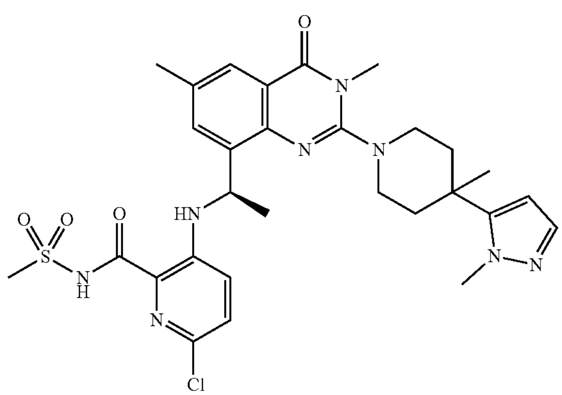 [SMILES: Cc1cc([C@@H](C)Nc2ccc(Cl)nc2C(=O)NS(C)(=O)=O)c2nc(N3CCC(C)(c4ccnn4C)CC3)n(C)c(=O)c2c1] | (R)-6-chloro-3-((1-(3,6-dimethyl-2-(4-methyl-4-(1-methyl-1H-pyrazol-5-yl)piperidin-1-yl)-4-oxo-3,4-dihydroquinazolin-8-yl)ethyl)amino)-N-(methylsulfonyl)picolinamide | 2.29 min, 254 nm, MS (ES+)$^b$ $C_{29}H_{35}ClN_8O_4S$, requires: 626.2, found: 627.2 $[M + H]^+$ |
| 303 | 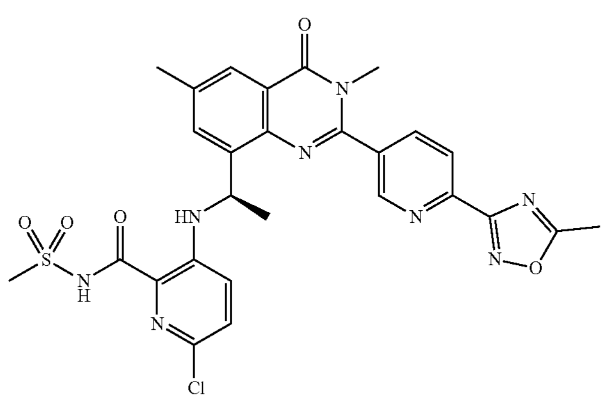 | (R)-6-chloro-3-((1-(3,6-dimethyl-2-(6-(5-methyl-1,2,4-oxadiazol-3-yl)pyridin-3-yl)-4-oxo-3,4-dihydroquinazolin-8-yl)ethyl)amino)-N-(methylsulfonyl)picolinamide | 2.14 min, 265 nm, MS (ES+)$^b$ $C_{27}H_{25}ClN_8O_5S$, requires: 608.1, found: 609.1 $[M + H]^+$ |

TABLE E4-continued compound list prepared according to Route A in Example 4

| Cpd. ID | Structure | Name | LCMS |
|---|---|---|---|
| 304 | 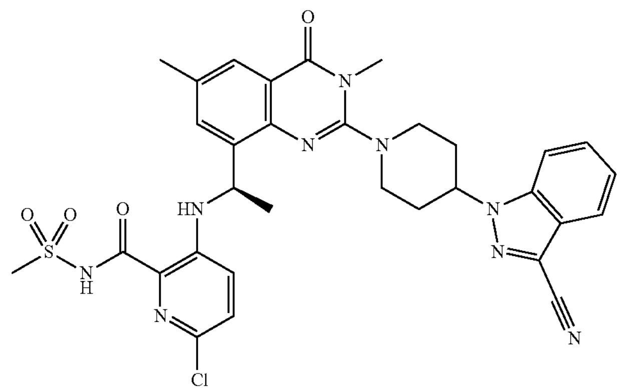 [SMILES: Cc1cc([C@@H](C)Nc2ccc(Cl)nc2C(=O)NS(C)(=O)=O)c2nc(N3CCC(n4nc(C#N)c5ccccc54)CC3)n(C)c(=O)c2c1] | (R)-6-chloro-3-((1-(2-(4-(3-cyano-1H-indazol-1-yl)piperidin-1-yl)-3,6-dimethyl-4-oxo-3,4-dihydroquinazolin-8-yl)ethyl)amino)-N-(methylsulfonyl)picolinamide | 2.73 min, 254 nm, MS (ES+)[b] $C_{32}H_{32}ClN_9O_4S$, requires: 673.2, found: 674.2 [M + H]$^+$ |
| 305 | 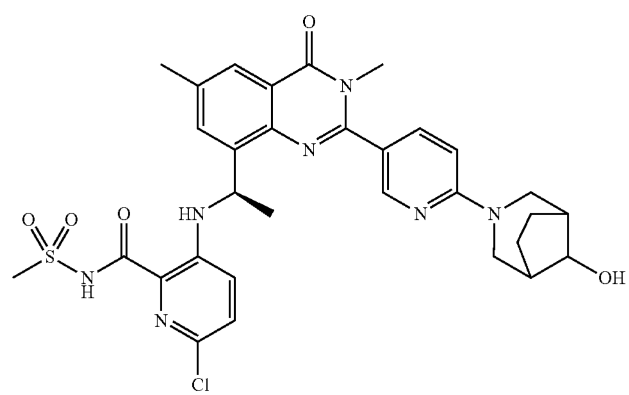 [SMILES: Cc1cc([C@@H](C)Nc2ccc(Cl)nc2C(=O)NS(C)(=O)=O)c2nc(-c3ccc(N4CC5CCC(C4)C5O)nc3)n(C)c(=O)c2c1] | 6-chloro-3-(((1R)-1-(2-(6-(8-hydroxy-3-azabicyclo[3.2.1]octan-3-yl)pyridin-3-yl)-3,6-dimethyl-4-oxo-3,4-dihydroquinazolin-8-yl)ethyl)amino)-N-(methylsulfonyl)picolinamide | 2.01 min, 254 nm, MS (ES+)[b] $C_{31}H_{34}ClN_7O_5S$, requires: 651.2, found: 652.2 [M + H]$^+$ |
| 306 | 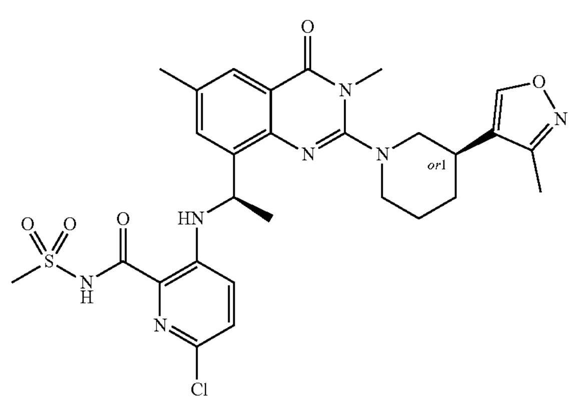 [SMILES: Cc1cc([C@@H](C)Nc2ccc(Cl)nc2C(=O)NS(C)(=O)=O)c2nc(N3CCC[C@H](c4conc4C)C3)n(C)c(=O)c2c1] | 6-chloro-3-(((R)-1-(3,6-dimethyl-2-((R*)-3-(3-methylisoxazol-4-yl)piperidin-1-yl)-4-oxo-3,4-dihydroquinazolin-8-yl)ethyl)amino)-N-(methylsulfonyl)picolinamide | 2.46 min, 215 nm, MS (ES+)[b] $C_{28}H_{32}ClN_7O_5S$, requires: 613.1, found: 614.2 [M + H]$^+$ |

TABLE E4-continued compound list prepared according to Route A in Example 4

| Cpd. ID | Structure | Name | LCMS |
|---|---|---|---|
| 307 | 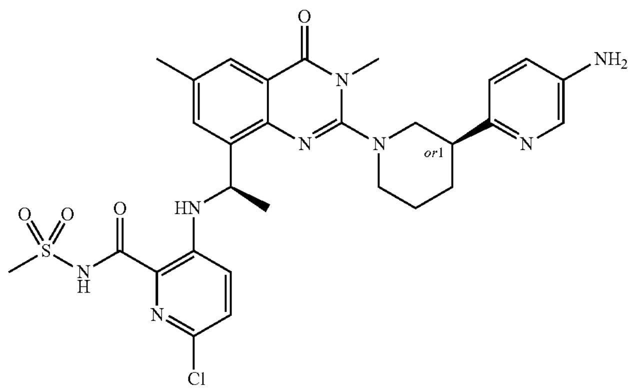 [SMILES: Cc1cc([C@@H](C)Nc2ccc(Cl)nc2C(=O)NS(C)(=O)=O)c2nc(N3CCC[C@H](c4ccc(N)cn4)C3)n(C)c(=O)c2c1] | 3-(((R)-1-(2-((R*)-3-(5-aminopyridin-2-yl)piperidin-1-yl)-3,6-dimethyl-4-oxo-3,4-dihydroquinazolin-8-yl)ethyl)amino)-6-chloro-N-(methylsulfonyl)picolinamide | 1.94 min, 254 nm, MS (ES+)[b] $C_{29}H_{33}ClN_8O_4S$, requires: 624.2, found: 625.2 [M + H]+ |
| 308 | 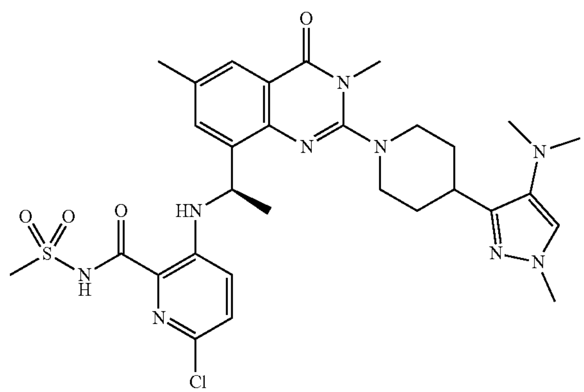 | (R)-6-chloro-3-((1-(2-(4-(4-(dimethylamino)-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 1.99 min, 270 nm, MS (ES+)[b] $C_{30}H_{38}ClN_9O_4S$, requires: 655.2, found: 656.2 [M + H]+ |
| 309 | 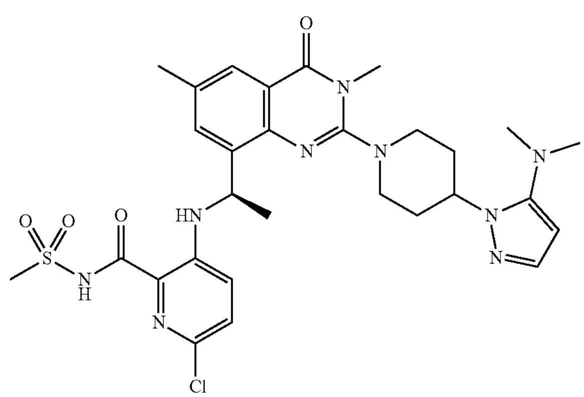 | (R)-6-chloro-3-((1-(2-(4-(5-(dimethylamino)-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.5 min, 254 nm, MS (ES+)[b] $C_{29}H_{36}ClN_9O_4S$, Requires: 641.2, found: 642.3 [M + H]+ |
| 310 | 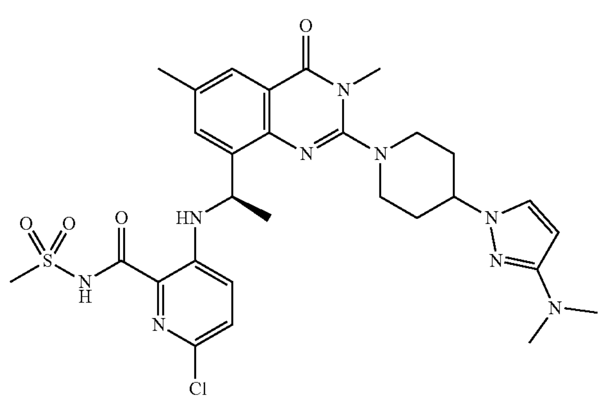 | (R)-6-chloro-3-((1-(2-(4-(3-(dimethylamino)-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.21 min, 210 nm, MS (ES+)[b] $C_{29}H_{36}ClN_9O_4S$, requires: 641.2, found: 642.2 [M + H]+ |

TABLE E4-continued compound list prepared according to Route A in Example 4

| Cpd. ID | Structure | Name | LCMS |
|---|---|---|---|
| 311 | 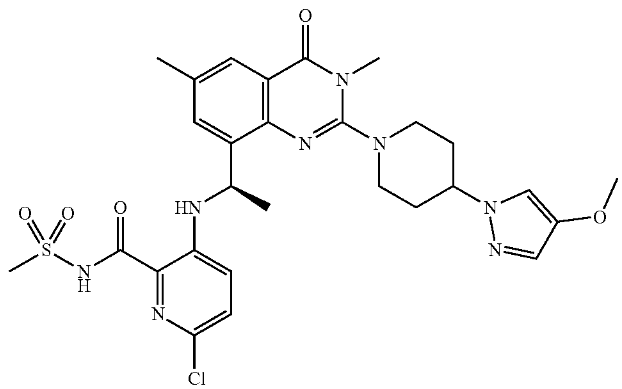 | (R)-6-chloro-3-((1-(2-(4-(4-methoxy-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.23 min, 270 nm, MS (ES+)[b] $C_{28}H_{33}ClN_8O_5S$, requires: 628.2, found: 629.3 [M + H]+ |
| 312 | 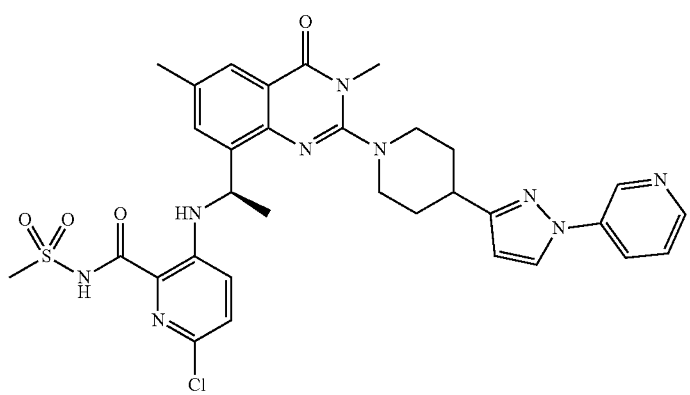 [SMILES: Cc1cc([C@@H](C)Nc2ccc(Cl)nc2C(=O)NS(C)(=O)=O)c2nc(N3CCC(c4ccn(-c5cccnc5)n4)CC3)n(C)c(=O)c2c1] | (R)-6-chloro-3-((1-(3,6-dimethyl-4-oxo-2-(4-(1-(pyridin-3-yl)-1H-pyrazol-3-yl)piperidin-1-yl)-3,4-dihydroquinazolin-8-yl)ethyl)amino)-N-(methylsulfonyl)picolinamide | 4.54 min, 280 nm, MS (ES+)[c] $C_{32}H_{34}ClN_9O_4S$, requires: 675.2, found: 676.2 [M + H]+ |
| 313 | 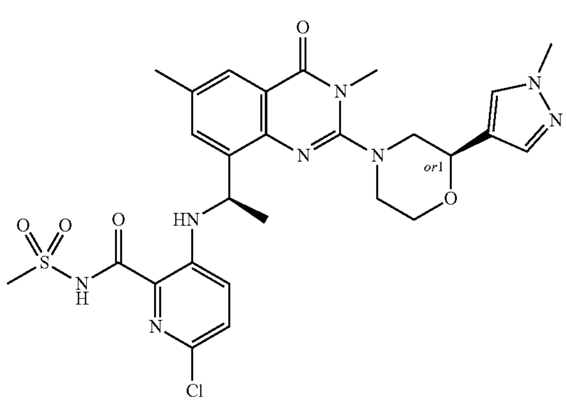 | 6-chloro-3-(((R)-1-(3,6-dimethyl-2-((R*)-2-(1-methyl-1H-pyrazol-4-yl)morpholino)-4-oxo-3,4-dihydroquinazolin-8-yl)ethyl)amino)-N-(methylsulfonyl)picolinamide | 2.18 min, 254 nm, MS (ES+)[b] $C_{27}H_{31}ClN_8O_5S$, requires: 614.2, found: 615.6 [M + H]+ |

TABLE E4-continued compound list prepared according to Route A in Example 4

| Cpd. ID | Structure | Name | LCMS |
|---|---|---|---|
| 314 | 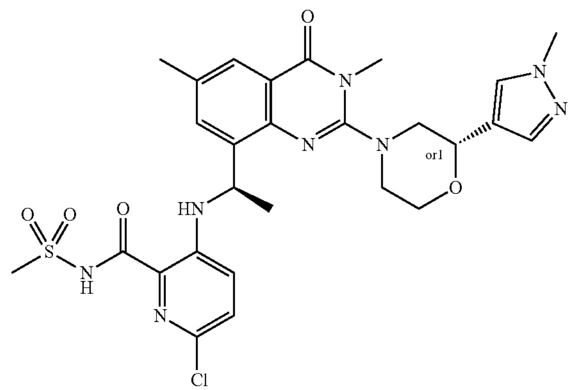 [SMILES: Cc1cc([C@@H](C)Nc2ccc(Cl)nc2C(=O)NS(C)(=O)=O)c2nc(N3CCO[C@@H](c4cnn(C)c4)C3)n(C)c(=O)c2c1] | 6-chloro-3-(((R)-1-(3,6-dimethyl-2-((R*)-2-(1-methyl-1H-pyrazol-4-yl)morpholino)-4-oxo-3,4-dihydroquinazolin-8-yl)ethyl)amino)-N-(methylsulfonyl)picolinamide | 2.18 min, 254 nm, MS (ES+)[b] $C_{27}H_{31}ClN_8O_5S$, requires: 614.1, found: 615.5 $[M + H]^+$ |
| 315 | 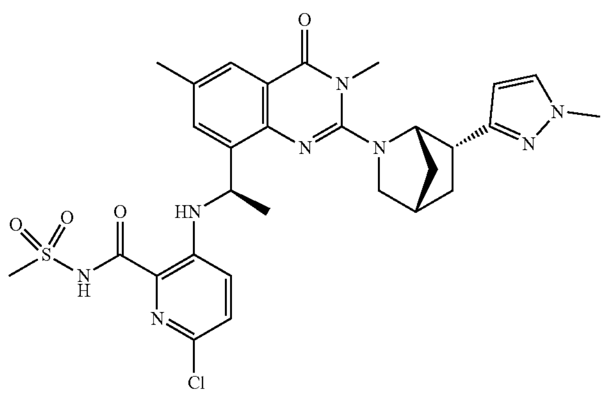 | 6-chloro-3-(((R)-1-(3,6-dimethyl-2-((1S,4S,6R)-6-(1-methyl-1H-pyrazol-3-yl)-2-azabicyclo[2.2.1]heptan-2-yl)-4-oxo-3,4-dihydroquinazolin-8-yl)ethyl)amino)-N-(methylsulfonyl)picolinamide | 2.36 min, 254 nm, MS (ES+)[b] $C_{29}H_{33}ClN_8O_4S$, requires: 624.2, found: 625.6 $[M + H]^+$ |
| 316 | 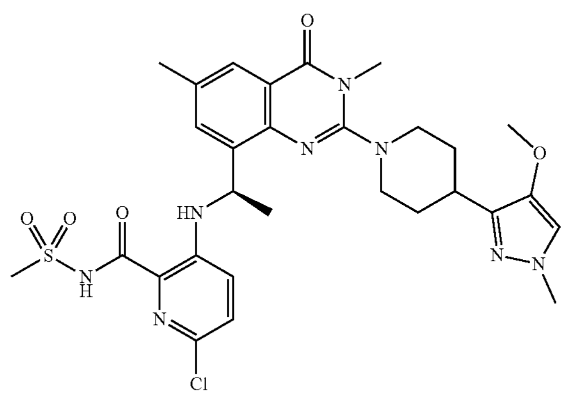 [SMILES: COc1cn(C)nc1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(2-(4-(4-methoxy-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.29 min, 270 nm, MS (ES+)[b] $C_{29}H_{35}ClN_8O_5S$, requires: 642.2, found: 643.3 $[M + H]^+$ |
| 317 | 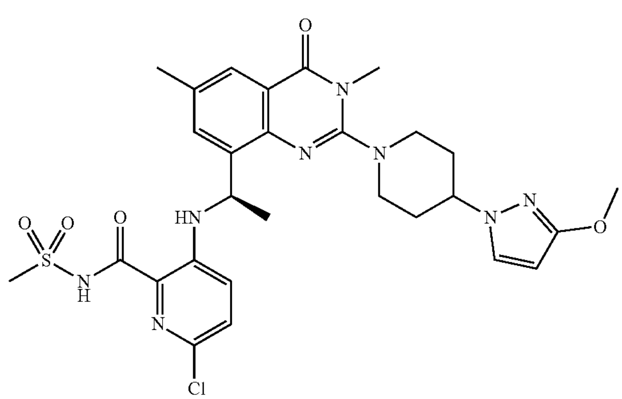 | (R)-6-chloro-3-((1-(2-(4-(3-methoxy-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.43 min, 254 nm, MS (ES+)[b] $C_{28}H_{33}ClN_8O_5S$, requires: 628.2, found: 629.6 $[M + H]^+$ |

TABLE E4-continued compound list prepared according to Route A in Example 4

| Cpd. ID | Structure | Name | LCMS |
|---|---|---|---|
| 318 | 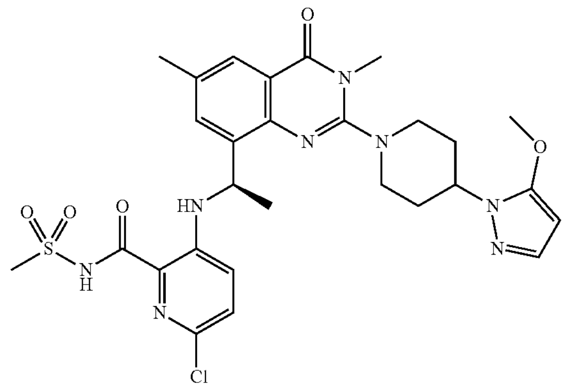 [SMILES: COc1ccnn1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(2-(4-(5-methoxy-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.46 min, 254 nm, MS (ES+)[b] $C_{28}H_{33}ClN_8O_5S$, requires: 628.2, found: 629.6 $[M + H]^+$ |
| 319 | 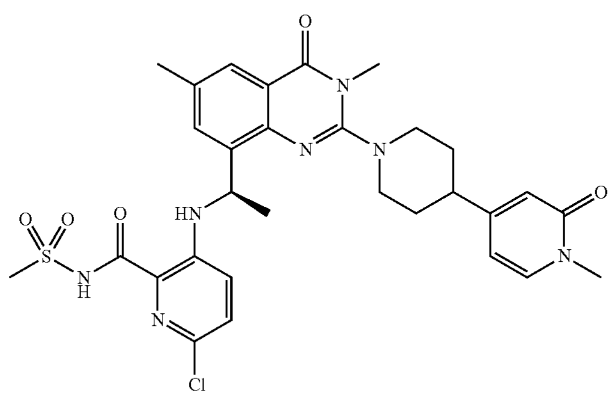 | (R)-6-chloro-3-((1-(3,6-dimethyl-2-(4-(1-methyl-2-oxo-1,2-dihydropyridin-4-yl)piperidin-1-yl)-4-oxo-3,4-dihydroquinazolin-8-yl)ethyl)amino)-N-(methylsulfonyl)picolinamide | 2.03 min, 210 nm, MS (ES+)[b] $C_{30}H_{34}ClN_7O_5S$, requires: 639.2, found: 640.2 $[M + H]^+$ |
| 320 | 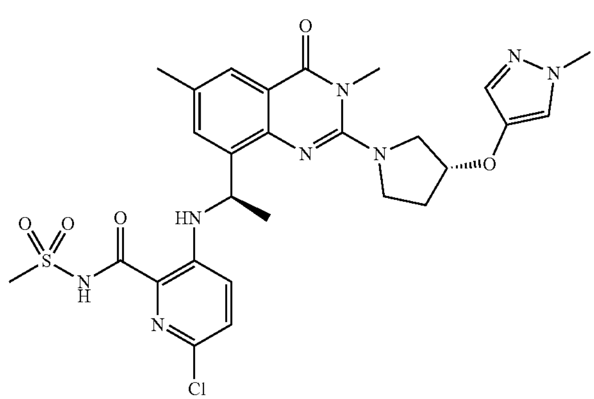 | 6-chloro-3-(((R)-1-(3,6-dimethyl-2-((R)-3-((1-methyl-1H-pyrazol-4-yl)oxy)pyrrolidin-1-yl)-4-oxo-3,4-dihydroquinazolin-8-yl)ethyl)amino)-N-(methylsulfonyl)picolinamide | 4.18 min, 254 nm, MS (ES+)[c] $C_{27}H_{31}ClN_8O_5S$, requires: 614.2, found: 615.2 $[M + H]^+$ |

TABLE E4-continued compound list prepared according to Route A in Example 4

| Cpd. ID | Structure | Name | LCMS |
|---|---|---|---|
| 321 | 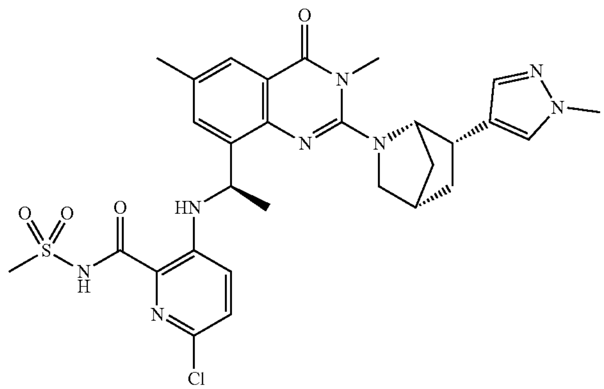 | 6-chloro-3-(((R)-1-(3,6-dimethyl-2-((1S,4S,6RS)-6-(1-methyl-1H-pyrazol-4-yl)-2-azabicyclo[2.2.1]heptan-2-yl)-4-oxo-3,4-dihydroquinazolin-8-yl)ethyl)amino)-N-(methylsulfonyl)picolinamide | 2.13 min, 254 nm, MS (ES+)$^b$ $C_{29}H_{33}ClN_8O_4S$, requires: 624.2, found: 625.2 [M + H]$^+$ |
| 322 | 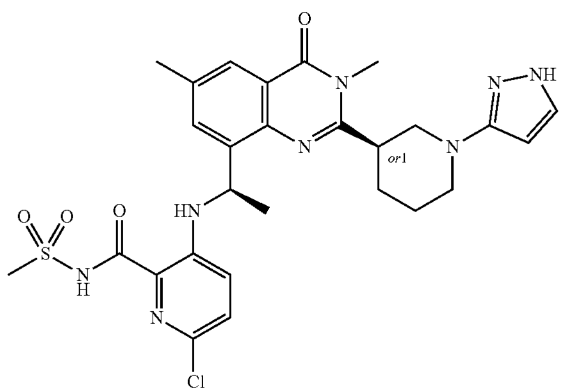 [SMILES: Cc1cc([C@@H](C)Nc2ccc(Cl)nc2C(=O)NS(C)(=O)=O)c2nc([C@@H]3CCCN(c4cc[nH]n4)C3)n(C)c(=O)c2c1] | 3-(((R)-1-(2-((R*)-1-(1H-pyrazol-3-yl)piperidin-3-yl)-3,6-dimethyl-4-oxo-3,4-dihydroquinazolin-8-yl)ethyl)amino)-6-chloro-N-(methylsulfonyl)picolinamide | 2.01 min, 254 nm, MS (ES+)$^b$ $C_{27}H_{31}ClN_8O_4S$, requires: 598.1, found: 599.2 [M + H]$^+$ |
| 323 | 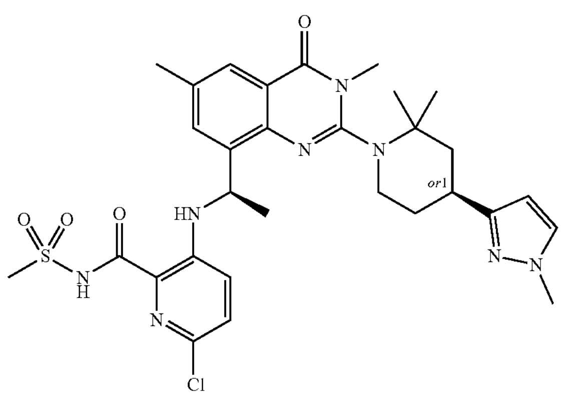 [SMILES: Cc1cc([C@@H](C)Nc2ccc(Cl)nc2C(=O)NS(C)(=O)=O)c2nc(N3CC[C@H](c4ccn(C)n4)CC3(C)C)n(C)c(=O)c2c1] | 6-chloro-3-(((R)-1-(2-((R*)-2,2-dimethyl-4-(1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.31 min, 254 nm, MS (ES+)$^b$ $C_{30}H_{37}ClN_8O_4S$, requires: 640.2, found: 641.3 [M + H]$^+$ |
| 324 | 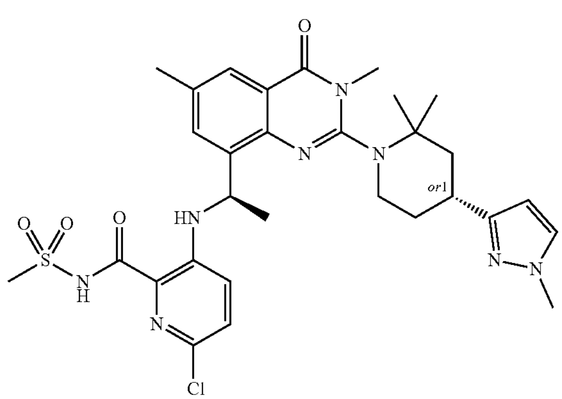 [SMILES: Cc1cc([C@@H](C)Nc2ccc(Cl)nc2C(=O)NS(C)(=O)=O)c2nc(N3CC[C@@H](c4ccn(C)n4)CC3(C)C)n(C)c(=O)c2c1] | 6-chloro-3-(((R)-1-(2-((R*)-2,2-dimethyl-4-(1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.30 min, 254 nm, MS (ES+)$^b$ $C_{30}H_{37}ClN_8O_4S$, requires: 640.2, found: 641.3 [M + H]$^+$ |

TABLE E4-continued compound list prepared according to Route A in Example 4

| Cpd. ID | Structure | Name | LCMS |
|---|---|---|---|
| 325 | 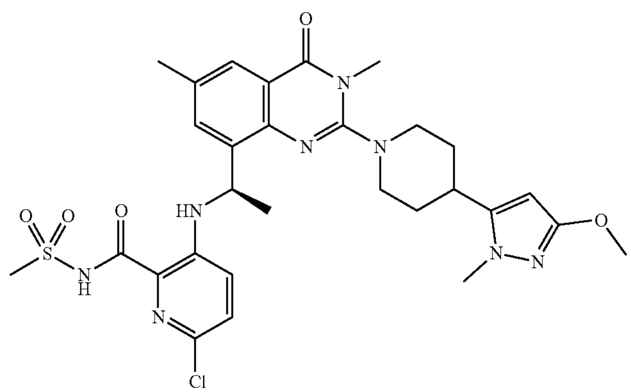 | (R)-6-chloro-3-((1-(2-(4-(3-methoxy-1-methyl-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.22 min, 254 nm, MS (ES+)[b] $C_{29}H_{35}ClN_8O_5S$, requires: 642.2, found: 643.2 [M + H]+ |
| 326 | 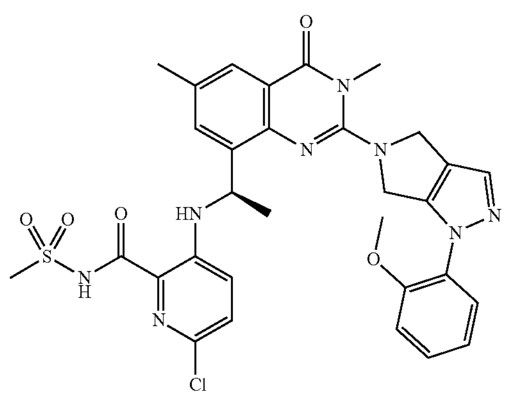 [SMILES: COc1ccccc1-n1ncc2c1CN(c1nc3c([C@@H](C)Nc4ccc(Cl)nc4C(=O)NS(C)(=O)=O)cc(C)cc3c(=O)n1C)C2] | (R)-6-chloro-3-((1-(2-(1-(2-methoxyphenyl)-4,6-dihydropyrrolo[3,4-c]pyrazol-5(1H)-yl)-3,6-dimethyl-4-oxo-3,4-dihydroquinazolin-8-yl)ethyl)amino)-N-(methylsulfonyl)picolinamide | 2.27 min, 254 nm, MS (ES+)[b] $C_{31}H_{31}ClN_8O_5S$, requires: 662.1, found: 663.2 [M + H]+ |
| 327 | 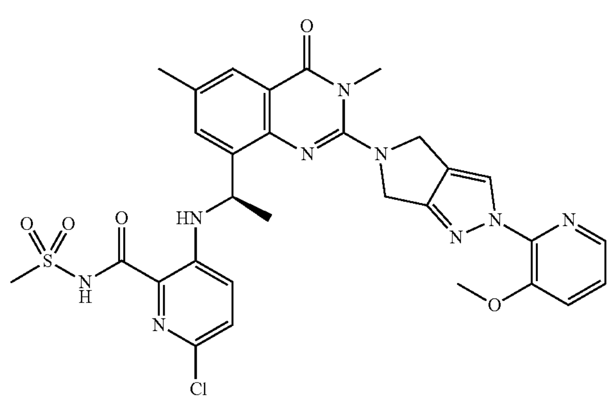 [SMILES: COc1cccnc1-n1cc2c(n1)CN(c1nc3c([C@@H](C)Nc4ccc(Cl)nc4C(=O)NS(C)(=O)=O)cc(C)cc3c(=O)n1C)C2] | (R)-6-chloro-3-((1-(2-(2-(3-methoxypyridin-2-yl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.28 min, 254 nm, MS (ES+)b $C_{30}H_{30}ClN_9O_5S$, requires: 663.1, found: 664.6 [M + H]+ |

TABLE E4-continued compound list prepared according to Route A in Example 4

| Cpd. ID | Structure | Name | LCMS |
|---|---|---|---|
| 328 | 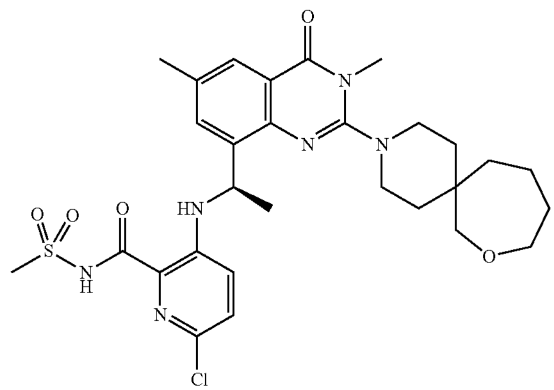 [SMILES: Cc1cc([C@@H](C)Nc2ccc(Cl)nc2C(=O)NS(C)(=O)=O)c2nc(N3CCC4(CCCCOC4)CC3)n(C)c(=O)c2c1] | (R)-6-chloro-3-((1-(3,6-dimethyl-4-oxo-2-(8-oxa-3-azaspiro[5.6]dodecan-3-yl)-3,4-dihydroquinazolin-8-yl)ethyl)amino)-N-(methylsulfonyl)picolinamide | 4.02 min, 254 nm, MS (ES+)$^c$ $C_{29}H_{37}ClN_6O_5S$, requires: 616.2, found: 617.3 [M + H]$^+$ |
| 329 | 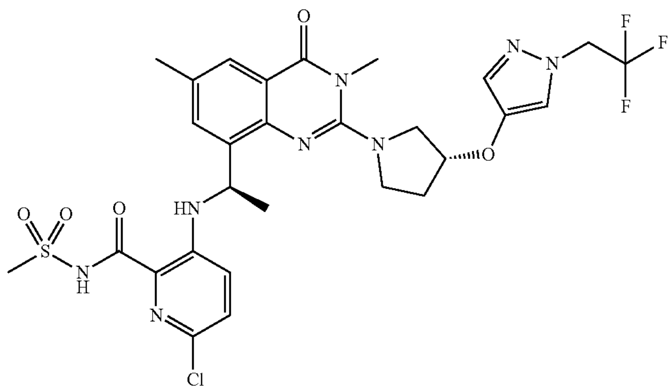 [SMILES: Cc1cc([C@@H](C)Nc2ccc(Cl)nc2C(=O)NS(C)(=O)=O)c2nc(N3CC[C@@H](Oc4cnn(CC(F)(F)F)c4)C3)n(C)c(=O)c2c1] | 6-chloro-3-(((R)-1-(3,6-dimethyl-4-oxo-2-((R)-3-((1-(2,2,2-trifluoroethyl)-1H-pyrazol-4-yl)oxy)pyrrolidin-1-yl)-3,4-dihydroquinazolin-8-yl)ethyl)amino)-N-(methylsulfonyl)picolinamide | 4.64 min, 254 nm, MS (ES+)$^c$ $C_{28}H_{30}ClF_3N_8O_5S$, requires: 682.2, found: 683.2 [M + H]$^+$ |
| 330 | 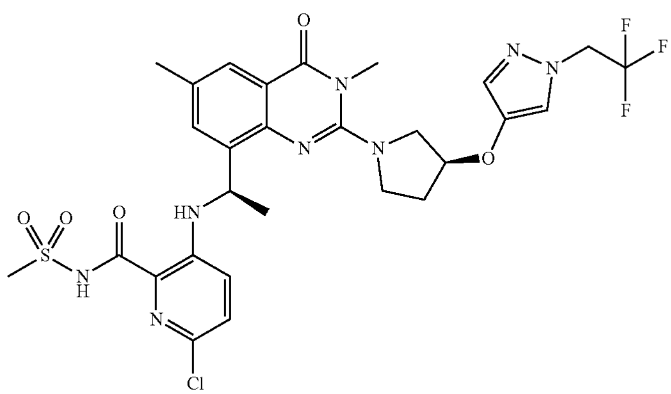 [SMILES: Cc1cc([C@@H](C)Nc2ccc(Cl)nc2C(=O)NS(C)(=O)=O)c2nc(N3CC[C@H](Oc4cnn(CC(F)(F)F)c4)C3)n(C)c(=O)c2c1] | 6-chloro-3-(((R)-1-(3,6-dimethyl-4-oxo-2-((S)-3-((1-(2,2,2-trifluoroethyl)-1H-pyrazol-4-yl)oxy)pyrrolidin-1-yl)-3,4-dihydroquinazolin-8-yl)ethyl)amino)-N-(methylsulfonyl)picolinamide | 4.64 min, 254 nm, MS (ES+)$^c$ $C_{28}H_{30}ClF_3N_8O_5S$, requires: 682.2, found: 683.2 [M + H]$^+$ |
| 331 | 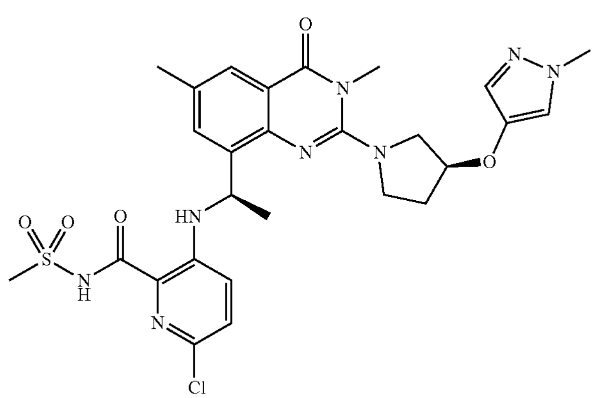 | 6-chloro-3-(((R)-1-(3,6-dimethyl-2-((S)-3-((1-methyl-1H-pyrazol-4-yl)oxy)pyrrolidin-1-yl)-4-oxo-3,4-dihydroquinazolin-8-yl)ethyl)amino)-N-(methylsulfonyl)picolinamide | 4.14 min, 280 nm, MS (ES+)$^c$ $C_{27}H_{31}ClN_8O_5S$, requires: 614.2, found: 615.2 [M + H]$^+$ |

TABLE E4-continued compound list prepared according to Route A in Example 4

| Cpd. ID | Structure | Name | LCMS |
|---|---|---|---|
| 332 | 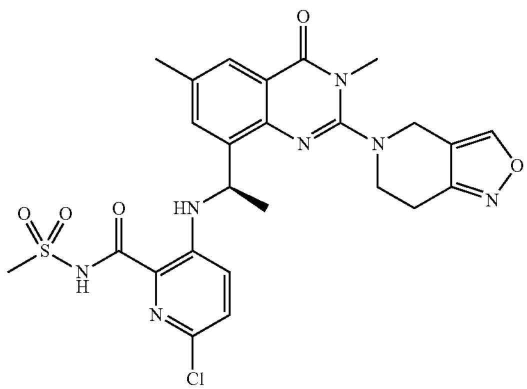 [SMILES: Cc1cc([C@@H](C)Nc2ccc(Cl)nc2C(=O)NS(C)(=O)=O)c2nc(N3CCc4nocc4C3)n(C)c(=O)c2c1] | (R)-6-chloro-3-((1-(2-(6,7-dihydroisoxazolo[4,3-c]pyridin-5(4H)-yl)-3,6-dimethyl-4-oxo-3,4-dihydroquinazolin-8-yl)ethyl)amino)-N-(methylsulfonyl)picolinamide | 3.26 min, 254 nm, MS (ES+)$^c$ $C_{25}H_{26}ClN_7O_5S$, requires: 571.1, found: 572.2 [M + H]$^+$ |
| 333 | 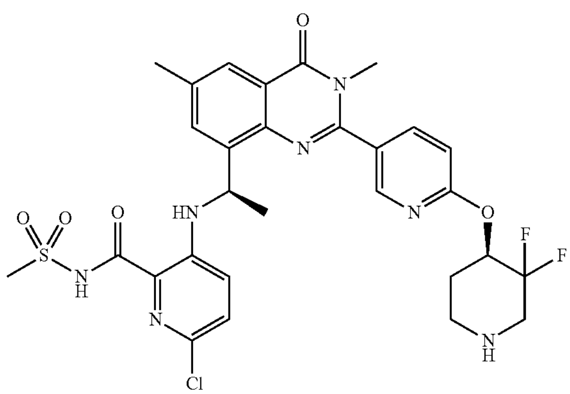 [SMILES: Cc1cc([C@@H](C)Nc2ccc(Cl)nc2C(=O)NS(C)(=O)=O)c2nc(-c3ccc(O[C@@H]4CCNCC4(F)F)nc3)n(C)c(=O)c2c1] | 6-chloro-3-(((R)-1-(2-(6-(((R)-3,3-difluoropiperidin-4-yl)oxy)pyridin-3-yl)-3,6-dimethyl-4-oxo-3,4-dihydroquinazolin-8-yl)ethyl)amino)-N-(methylsulfonyl)picolinamide | 2.58 min, 220 nm, MS (ES+)$^c$ $C_{29}H_{30}ClF_2N_7O_5S$, requires: 661.2, found: 662.2 [M + H]$^+$ |
| 334 | 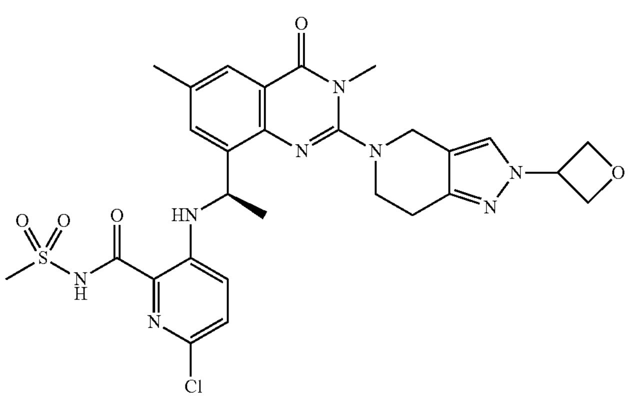 [SMILES: Cc1cc([C@@H](C)Nc2ccc(Cl)nc2C(=O)NS(C)(=O)=O)c2nc(N3CCc4nn(C5COC5)cc4C3)n(C)c(=O)c2c1] | (R)-6-chloro-3-((1-(3,6-dimethyl-2-(2-(oxetan-3-yl)-2,4,6,7-tetrahydro-5H-pyrazolo[4,3-c]pyridin-5-yl)-4-oxo-3,4-dihydroquinazolin-8-yl)ethyl)amino)-N-(methylsulfonyl)picolinamide | 2.25 min, 270 nm, MS (ES+)$^b$ $C_{28}H_{31}ClN_8O_5S$, requires: 626.2, found: 627.6 [M + H]$^+$ |

TABLE E4-continued compound list prepared according to Route A in Example 4

| Cpd. ID | Structure | Name | LCMS |
|---|---|---|---|
| 335 | 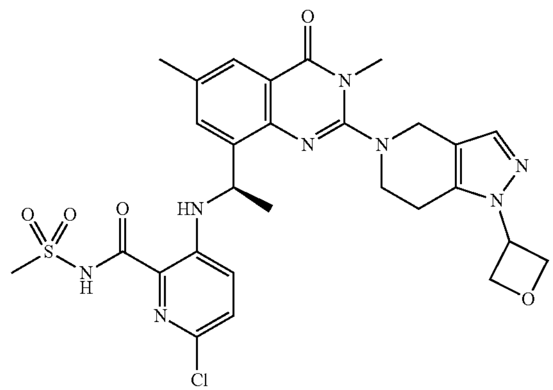 [SMILES: Cc1cc([C@@H](C)Nc2ccc(Cl)nc2C(=O)NS(C)(=O)=O)c2nc(N3CCc4c(cnn4C4COC4)C3)n(C)c(=O)c2c1] | (R)-6-chloro-3-((1-(3,6-dimethyl-2-(1-(oxetan-3-yl)-1,4,6,7-tetrahydro-5H-pyrazolo[4,3-c]pyridin-5-yl)-4-oxo-3,4-dihydroquinazolin-8-yl)ethyl)amino)-N-(methylsulfonyl)picolinamide | 2.25 min, 270 nm, MS (ES+)[b] C$_{28}$H$_{31}$ClN$_8$O$_5$S, requires: 626.2, found: 627.7 [M + H]$^+$ |
| 336 | 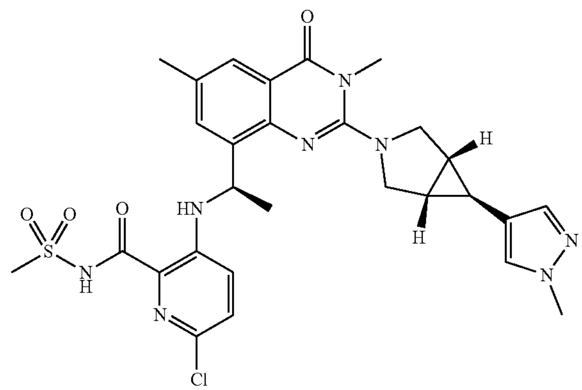 [SMILES: Cc1cc([C@@H](C)Nc2ccc(Cl)nc2C(=O)NS(C)(=O)=O)c2nc(N3C[C@@H]4[C@H](C3)[C@H]4c3cnn(C)c3)n(C)c(=O)c2c1] | 6-chloro-3-(((R)-1-(3,6-dimethyl-2-((1R,5S,6S)-6-(1-methyl-1H-pyrazol-4-yl)-3-azabicyclo[3.1.0]hexan-3-yl)-4-oxo-3,4-dihydroquinazolin-8-yl)ethyl)amino)-N-(methylsulfonyl)picolinamide | 2.26 min, 270 nm, MS (ES+)[b] C$_{28}$H$_{31}$ClN$_8$O$_4$S, requires: 610.1, found: 611.2 [M + H]$^+$ |
| 337 | 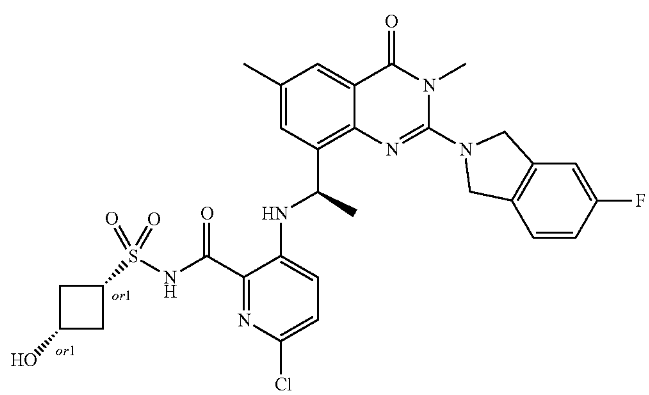 [SMILES: Cc1cc([C@@H](C)Nc2ccc(Cl)nc2C(=O)NS(=O)(=O)[C@H]2C[C@@H](O)C2)c2nc(N3Cc4ccc(F)cc4C3)n(C)c(=O)c2c1] | 6-chloro-3-(((R)-1-(2-(5-fluoroisoindolin-2-yl)-3,6-dimethyl-4-oxo-3,4-dihydroquinazolin-8-yl)ethyl)amino)-N-((((1S*,3S*)-3-hydroxycyclobutyl)sulfonyl)picolinamide | 2.41 min, 270 nm, MS (ES+)[b] C$_{30}$H$_{30}$ClFN$_6$O$_5$S, requires: 640.1, found: 641.2 [M + H]$^+$ |
| 338 | 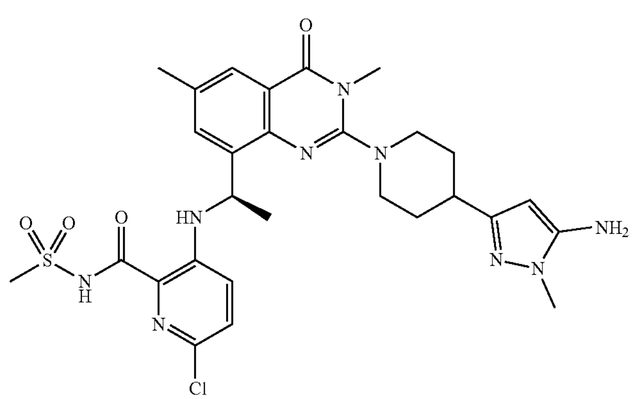 [SMILES: Cc1cc([C@@H](C)Nc2ccc(Cl)nc2C(=O)NS(C)(=O)=O)c2nc(N3CCC(c4cc(N)n(C)n4)CC3)n(C)c(=O)c2c1] | (R)-3-((1-(2-(4-(5-amino-1-methyl-1H-pyrazol-3-yl)piperidin-1-yl)-3,6-dimethyl-4-oxo-3,4-dihydroquinazolin-8-yl)ethyl)amino)-6-chloro-N-(methylsulfonyl)picolinamide | 1.91 min, 270 nm, MS (ES+)[b] C$_{28}$H$_{34}$ClN$_9$O$_4$S, requires: 627.2, found: 628.2 [M + H]$^+$ |

TABLE E4-continued compound list prepared according to Route A in Example 4

| Cpd. ID | Structure | Name | LCMS |
|---|---|---|---|
| 339 | 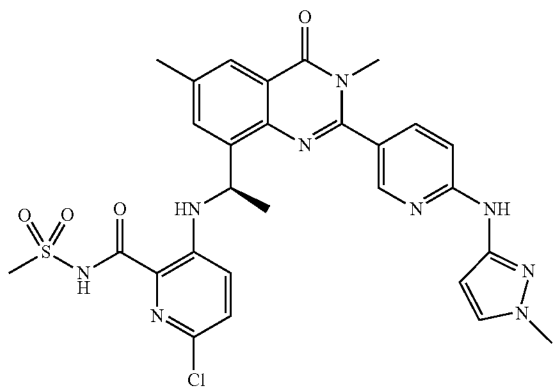 | (R)-6-chloro-3-((1-(3,6-dimethyl-2-(6-((1-methyl-1H-pyrazol-3-yl)amino)pyridin-3-yl)-4-oxo-3,4-dihydroquinazolin-8-yl)ethyl)amino)-N-(methylsulfonyl)picolinamide | 2.68 min, 254 nm, MS (ES+)$^c$ $C_{28}H_{28}ClN_9O_4S$, requires: 621.2, found: 622.3 [M + H]$^+$ |
| 340 | 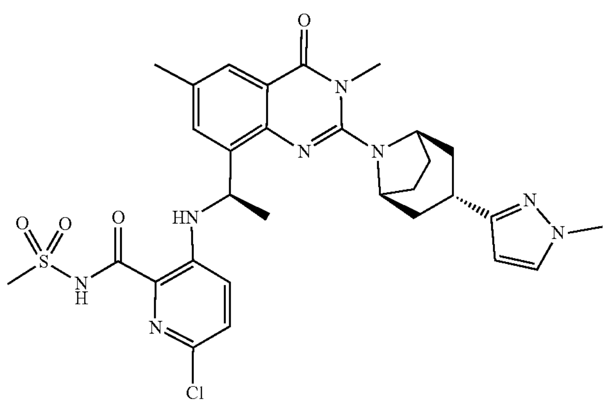 | 6-chloro-3-(((R)-1-(3,6-dimethyl-2-((1R,3R,5S)-3-(1-methyl-1H-pyrazol-3-yl)-8-azabicyclo[3.2.1]octan-8-yl)-4-oxo-3,4-dihydroquinazolin-8-yl)ethyl)amino)-N-(methylsulfonyl)picolinamide | 4.53 min, 254 nm, MS (ES+)$^c$ $C_{30}H_{35}ClN_8O_4S$, requires: 638.2, found: 639.3 [M + H]$^+$ |
| 341 | 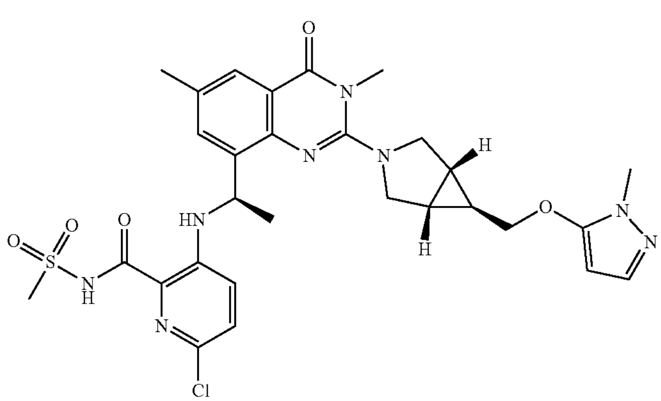 [SMILES: Cc1cc([C@@H](C)Nc2ccc(Cl)nc2C(=O)NS(C)(=O)=O)c2nc(N3C[C@@H]4[C@@H](COc5ccnn5C)[C@@H]4C3)n(C)c(=O)c2c1] | 6-chloro-3-(((R)-1-(3,6-dimethyl-2-((1R,5S,6R)-6-(((1-methyl-1H-pyrazol-5-yl)oxy)methyl)-3-azabicyclo[3.1.0]hexan-3-yl)-4-oxo-3,4-dihydroquinazolin-8-yl)ethyl)amino)-N-(methylsulfonyl)picolinamide | 2.32 min, 254 nm, MS (ES+)$^b$ $C_{29}H_{33}ClN_8O_5S$, requires: 640.2, found: 641.2 [M + H]$^+$ |

TABLE E4-continued compound list prepared according to Route A in Example 4

| Cpd. ID | Structure | Name | LCMS |
|---|---|---|---|
| 342 | 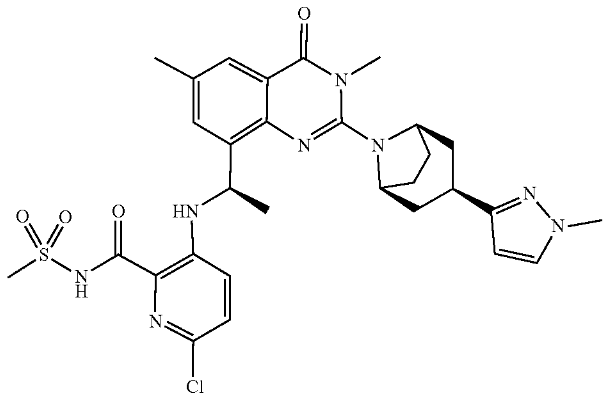 | 6-chloro-3-(((R)-1-(3,6-dimethyl-2-((1R,3S,5S)-3-(1-methyl-1H-pyrazol-3-yl)-8-azabicyclo[3.2.1]octan-8-yl)-4-oxo-3,4-dihydroquinazolin-8-yl)ethyl)amino)-N-(methylsulfonyl)picolinamide | 4.69 min, 254 nm, MS (ES+)$^c$ $C_{30}H_{35}ClN_8O_4S$, requires: 638.2, found: 639.3 [M + H]$^+$ |
| 343 | 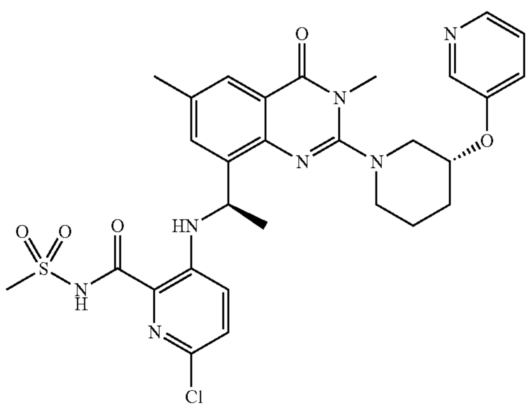 [SMILES: Cc1cc([C@@H](C)Nc2ccc(Cl)nc2C(=O)NS(C)(=O)=O)c2nc(N3CCC[C@@H](Oc4cccnc4)C3)n(C)c(=O)c2c1] | 6-chloro-3-(((R)-1-(3,6-dimethyl-4-oxo-2-((R)-3-(pyridin-3-yloxy)piperidin-1-yl)-3,4-dihydroquinazolin-8-yl)ethyl)amino)-N-(methylsulfonyl)picolinamide | 3.90 min, 254 nm, MS (ES+)$^c$ $C_{29}H_{32}ClN_7O_5S$, requires: 625.2, found: 626.3 [M + H]$^+$ |
| 344 | 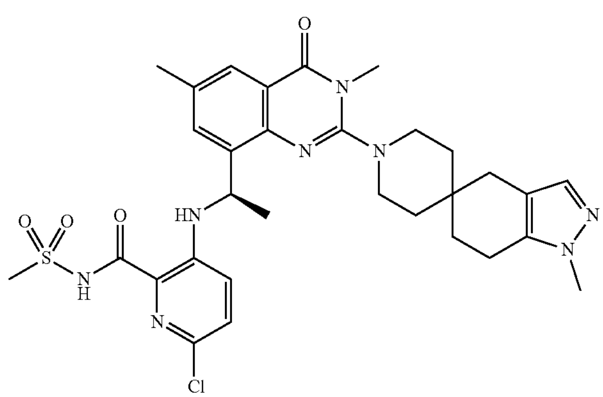 [SMILES: Cc1cc([C@@H](C)Nc2ccc(Cl)nc2C(=O)NS(C)(=O)=O)c2nc(N3CCC4(CCc5c(cnn5C)C4)CC3)n(C)c(=O)c2c1] | (R)-6-chloro-3-((1-(3,6-dimethyl-2-(1-methyl-1,4,6,7-tetrahydrospiro[indazole-5,4'-piperidin]-1'-yl)-4-oxo-3,4-dihydroquinazolin-8-yl)ethyl)amino)-N-(methylsulfonyl)picolinamide | 3.55 min, 254 nm, MS (ES+)$^c$ $C_{31}H_{37}ClN_8O_4S$, requires: 652.2, found: 653.3 [M + H]$^+$ |

TABLE E4-continued compound list prepared according to Route A in Example 4

| Cpd. ID | Structure | Name | LCMS |
|---|---|---|---|
| 345 | 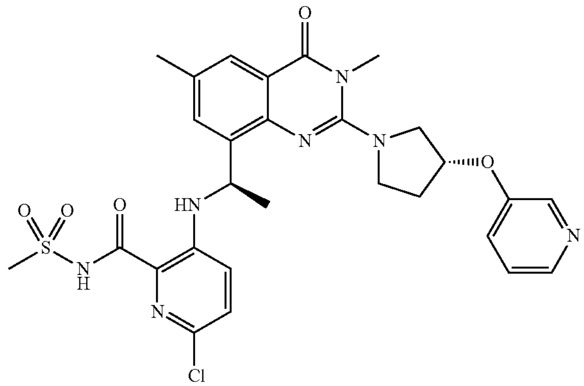 [SMILES: Cc1cc([C@@H](C)Nc2ccc(Cl)nc2C(=O)NS(C)(=O)=O)c2nc(N3CC[C@@H](Oc4cccnc4)C3)n(C)c(=O)c2c1] | 6-chloro-3-(((R)-1-(3,6-dimethyl-4-oxo-2-((R)-3-(pyridin-3-yloxy)pyrrolidin-1-yl)-3,4-dihydroquinazolin-8-yl)ethyl)amino)-N-(methylsulfonyl)picolinamide | 3.68 min, 254 nm, MS (ES+)$^c$ $C_{28}H_{30}ClN_7O_5S$, requires: 611.2, found: 612.2 [M + H]$^+$ |
| 346 | 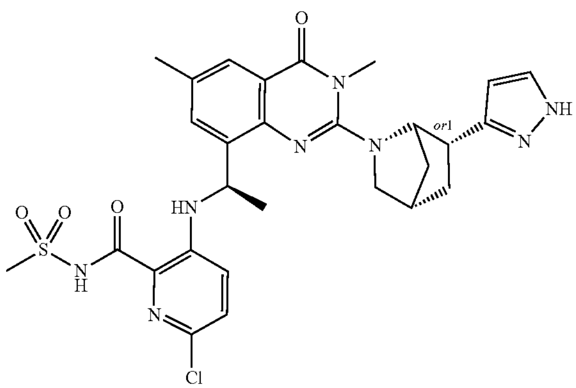 | 3-(((R)-1-(2-((1S,4S,6R*)-6-(1H-pyrazol-3-yl)-2-azabicyclo[2.2.1]heptan-2-yl)-3,6-dimethyl-4-oxo-3,4-dihydroquinazolin-8-yl)ethyl)amino)-6-chloro-N-(methylsulfonyl)picolinamide | 2.21 min, 254 nm, MS (ES+)$^b$ $C_{28}H_{31}ClN_8O_4S$, requires: 610.1, found: 611.2 [M + H]$^+$ |
| 347 | 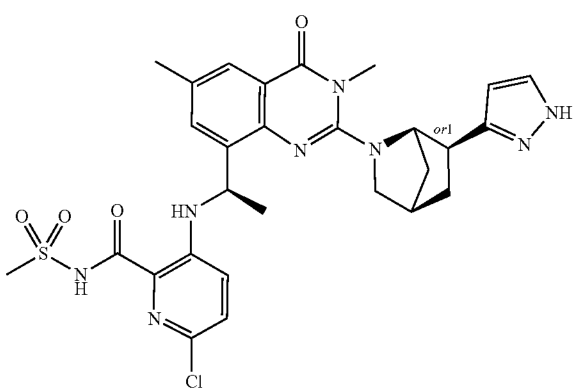 [SMILES: Cc1cc([C@@H](C)Nc2ccc(Cl)nc2C(=O)NS(C)(=O)=O)c2nc(N3C[C@@H]4C[C@H](c5cc[nH]n5)[C@H]3C4)n(C)c(=O)c2c1] | 3-(((R)-1-(2-((1R,4R,6R*)-6-(1H-pyrazol-3-yl)-2-azabicyclo[2.2.1]heptan-2-yl)-3,6-dimethyl-4-oxo-3,4-dihydroquinazolin-8-yl)ethyl)amino)-6-chloro-N-(methylsulfonyl)picolinamide | 2.30 min, 270 nm, MS (ES+)$_b$ $C_{28}H_{31}ClN_8O_4S$, requires: 610.1, found: 611.7 [M + H]$_+$ |
| 348 | 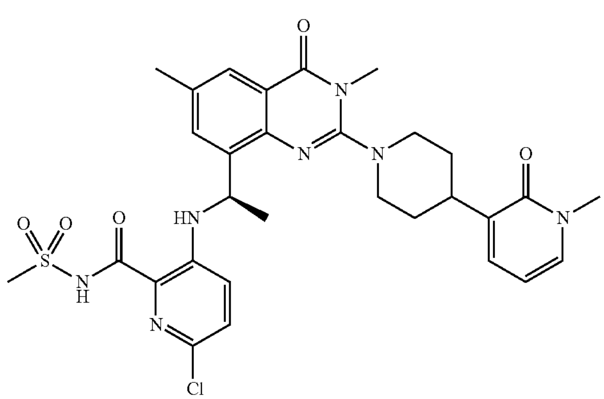 | (R)-6-chloro-3-((1-(3,6-dimethyl-2-(4-(1-methyl-2-oxo-1,2-dihydropyridin-3-yl)piperidin-1-yl)-4-oxo-3,4-dihydroquinazolin-8-yl)ethyl)amino)-N-(methylsulfonyl)picolinamide | 2.26 min, 270 nm, MS (ES+)$^b$ $C_{30}H_{34}ClN_7O_5S$, requires: 639.2, found: 640.2 [M + H]$^+$ |

TABLE E4-continued compound list prepared according to Route A in Example 4

| Cpd. ID | Structure | Name | LCMS |
|---|---|---|---|
| 349 | 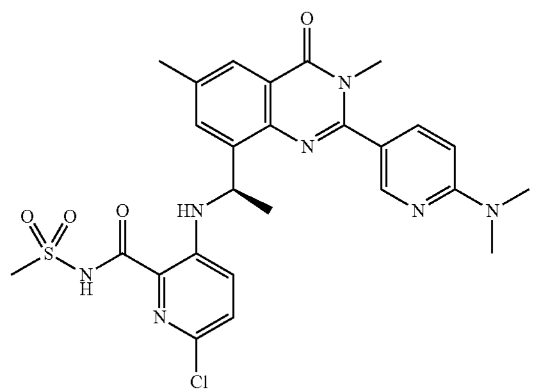 | (R)-6-chloro-3-((1-(2-(6-(dimethylamino)pyridin-3-yl)-3,6-dimethyl-4-oxo-3,4-dihydroquinazolin-8-yl)ethyl)amino)-N-(methylsulfonyl)picolinamide | 2.13 min, 220 nm, MS (ES+)[b] $C_{26}H_{28}ClN_7O_4S$, requires: 569.1, found: 570.6 [M + H]+ |
| 350 | 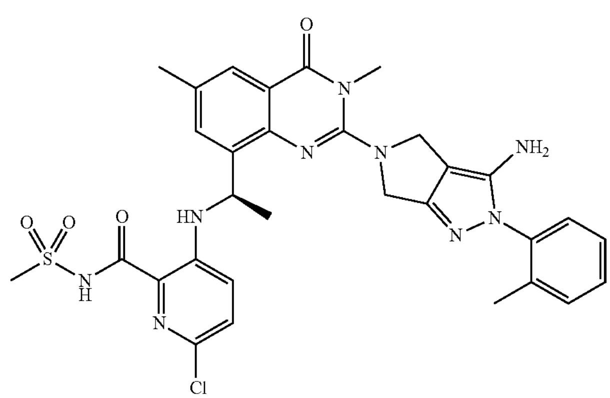 [SMILES: Cc1cc([C@@H](C)Nc2ccc(Cl)nc2C(=O)NS(C)(=O)=O)c2nc(N3Cc4nn(-c5ccccc5C)c(N)c4C3)n(C)c(=O)c2c1] | (R)-3-((1-(2-(3-amino-2-(o-tolyl)-2,6-dihydropyrrolo[3,4-c]pyrazol-5(4H)-yl)-3,6-dimethyl-4-oxo-3,4-dihydroquinazolin-8-yl)ethyl)amino)-6-chloro-N-(methylsulfonyl)picolinamide | 2.37 min, 254 nm, MS (ES+)[b] $C_{31}H_{32}ClN_9O_4S$, requires: 661.2, found: 662.8 [M + H]+ |
| 351 | 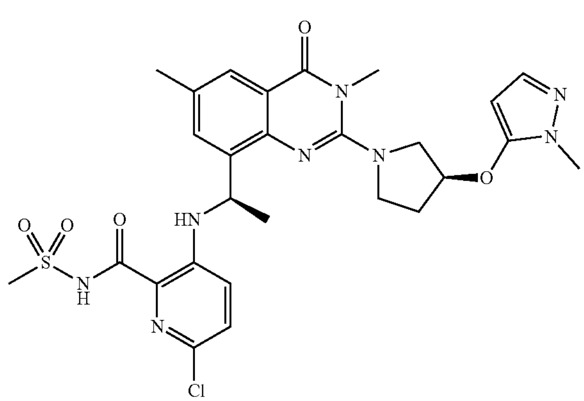 | 6-chloro-3-(((R)-1-(3,6-dimethyl-2-((S)-3-((1-methyl-1H-pyrazol-5-yl)oxy)pyrrolidin-1-yl)-4-oxo-3,4-dihydroquinazolin-8-yl)ethyl)amino)-N-(methylsulfonyl)picolinamide | 4.23 min, 254 nm, MS (ES+)[c] $C_{27}H_{31}ClN_8O_5S$, requires: 614.2, found: 615.2 [M + H]+ |

TABLE E4-continued compound list prepared according to Route A in Example 4

| Cpd. ID | Structure | Name | LCMS |
|---|---|---|---|
| 352 | 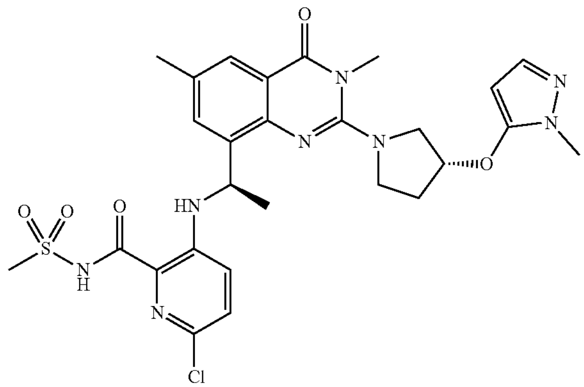 | 6-chloro-3-(((R)-1-(3,6-dimethyl-2-((R)-3-((1-methyl-1H-pyrazol-5-yl)oxy)pyrrolidin-1-yl)-4-oxo-3,4-dihydroquinazolin-8-yl)ethyl)amino)-N-(methylsulfonyl)picolinamide | 4.21 min, 280 nm, MS (ES+)$^c$ $C_{27}H_{31}ClN_8O_5S$, requires: 614.2, found: 615.2 [M + H]$^+$ |
| 353 | 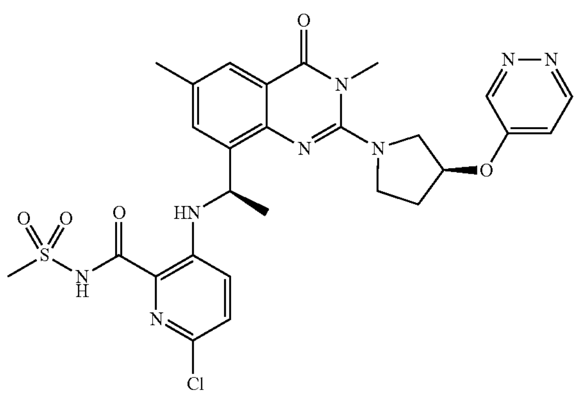 [SMILES: Cc1cc([C@@H](C)Nc2ccc(Cl)nc2C(=O)NS(C)(=O)=O)c2nc(N3CC[C@H](Oc4ccnnc4)C3)n(C)c(=O)c2c1] | 6-chloro-3-(((R)-1-(3,6-dimethyl-4-oxo-2-((S)-3-(pyridazin-4-yloxy)pyrrolidin-1-yl)-3,4-dihydroquinazolin-8-yl)ethyl)amino)-N-(methylsulfonyl)picolinamide | 3.70 min, 254 nm, MS (ES+)$^c$ $C_{27}H_{29}ClN_8O_5S$, requires: 612.2, found: 613.2 [M + H]$^+$ |
| 354 | 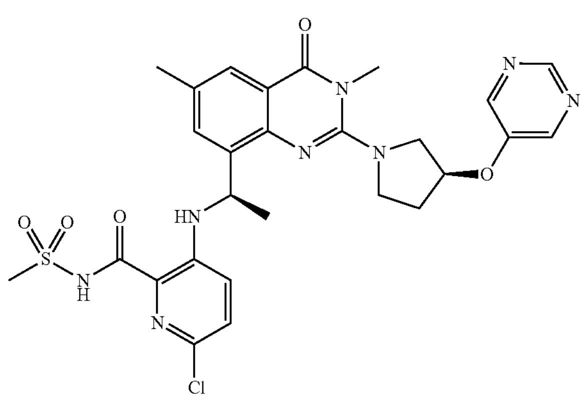 [SMILES: Cc1cc([C@@H](C)Nc2ccc(Cl)nc2C(=O)NS(C)(=O)=O)c2nc(N3CC[C@H](Oc4cncnc4)C3)n(C)c(=O)c2c1] | 6-chloro-3-(((R)-1-(3,6-dimethyl-4-oxo-2-((S)-3-(pyrimidin-5-yloxy)pyrrolidin-1-yl)-3,4-dihydroquinazolin-8-yl)ethyl)amino)-N-(methylsulfonyl)picolinamide | 4.09 min, 254 nm, MS (ES+)$^c$ $C_{27}H_{29}ClN_8O_5S$, requires: 612.2, found: 613.2 [M + H]$^+$ |

TABLE E4-continued compound list prepared according to Route A in Example 4

| Cpd. ID | Structure | Name | LCMS |
|---|---|---|---|
| 355 | 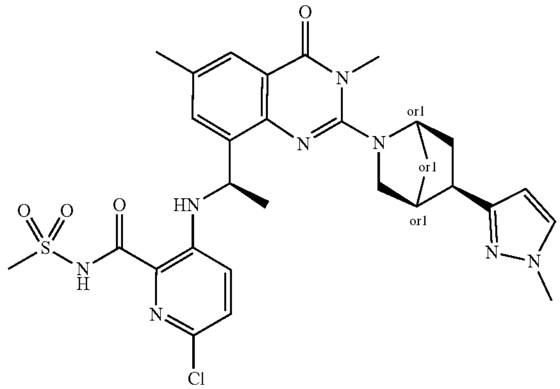 | 6-chloro-3-(((R)-1-(3,6-dimethyl-2-((1R*,4S*,5R*)-5-(1-methyl-1H-pyrazol-3-yl)-2-azabicyclo[2.2.1]heptan-2-yl)-4-oxo-3,4-dihydroquinazolin-8-yl)ethyl)amino)-N-(methylsulfonyl)picolinamide | 2.24 min, 254 nm, MS (ES+)[b] C29H33ClN8O4S, requires: 624.2, found: 625.2 [M + H]+ |
| 356 | 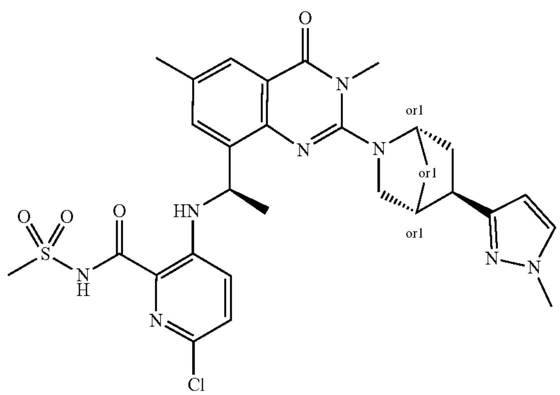 | 6-chloro-3-(((R)-1-(3,6-dimethyl-2-((1R*,4S*,5R*)-5-(1-methyl-1H-pyrazol-3-yl)-2-azabicyclo[2.2.1]heptan-2-yl)-4-oxo-3,4-dihydroquinazolin-8-yl)ethyl)amino)-N-(methylsulfonyl)picolinamide | 2.23 min, 254 nm, MS (ES+)[b] C29H33ClN8O4S, requires: 624.2, found: 625.2 [M + H]+ |
| 357 | 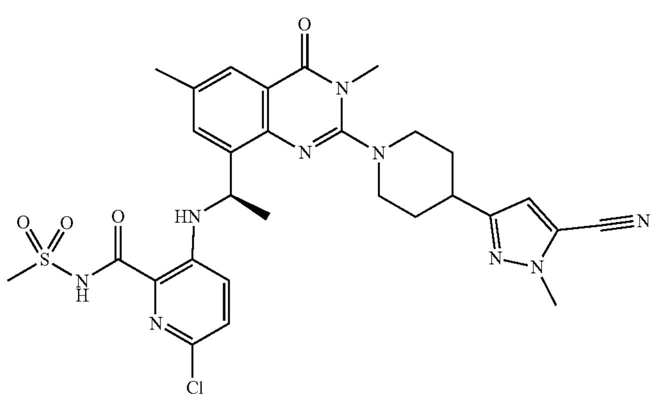 [SMILES: Cc1cc([C@@H](C)Nc2ccc(Cl)nc2C(=O)NS(C)(=O)=O)c2nc(N3CCC(c4cc(C#N)n(C)n4)CC3)n(C)c(=O)c2c1] | (R)-6-chloro-3-((1-(2-(4-(5-cyano-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.51 min, 270 nm, MS (ES+)[b] C29H32ClN9O4S, required: 637.2, found: 638.2 [M + H]+ |

TABLE E4-continued compound list prepared according to Route A in Example 4

| Cpd. ID | Structure | Name | LCMS |
|---|---|---|---|
| 358 | 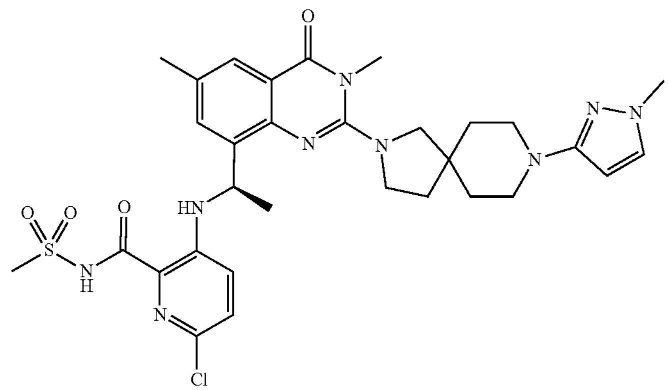 | (R)-6-chloro-3-((1-(3,6-dimethyl-2-(8-(1-methyl-1H-pyrazol-3-yl)-2,8-diazaspiro[4.5]decan-2-yl)-4-oxo-3,4-dihydroquinazolin-8-yl)ethyl)amino)-N-(methylsulfonyl)picolinamide | 2.25 min, 220 nm, MS (ES+)[b] $C_{31}H_{38}ClN_9O_4S$, requires: 667.2, found: 668.2 [M + H]+ |
| 359 | 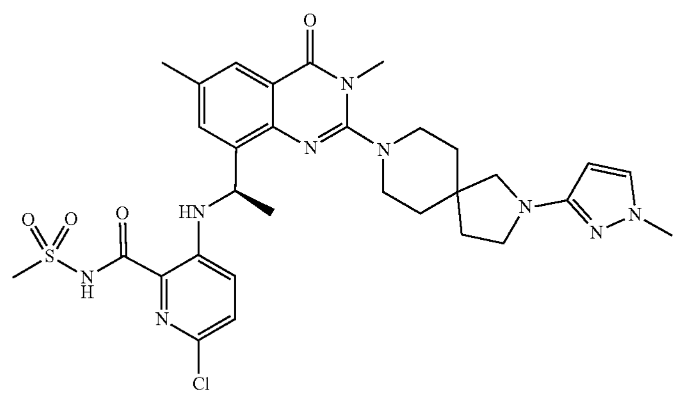 | (R)-6-chloro-3-((1-(3,6-dimethyl-2-(2-(1-methyl-1H-pyrazol-3-yl)-2,8-diazaspiro[4.5]decan-8-yl)-4-oxo-3,4-dihydroquinazolin-8-yl)ethyl)amino)-N-(methylsulfonyl)picolinamide | 2.27 min, 270 nm, MS (ES+)[b] $C_{31}H_{38}ClN_9O_4S$, requires: 667.2, found: 668.2 [M + H]+ |
| 360 | 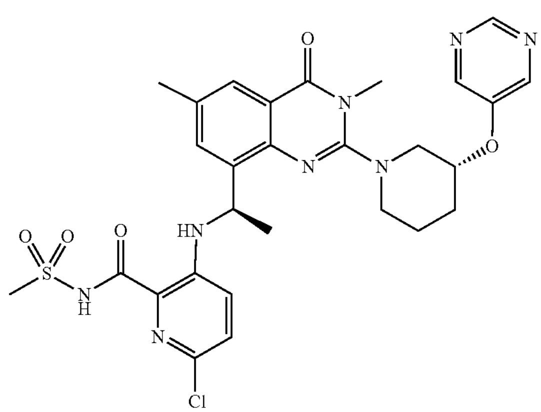 [SMILES: Cc1cc([C@@H](C)Nc2ccc(Cl)nc2C(=O)NS(C)(=O)=O)c2nc(N3CCC[C@@H](Oc4cncnc4)C3)n(C)c(=O)c2c1] | 6-chloro-3-(((R)-1-(3,6-dimethyl-4-oxo-2-((R)-3-(pyrimidin-5-yloxy)piperidin-1-yl)-3,4-dihydroquinazolin-8-yl)ethyl)amino)-N-(methylsulfonyl)picolinamide | 4.30 min, 254 nm, MS (ES+)[c] $C_{28}H_{31}ClN_8O_5S$, requires: 626.2, found: 627.2 [M + H]+ |

TABLE E4-continued compound list prepared according to Route A in Example 4

| Cpd. ID | Structure | Name | LCMS |
|---|---|---|---|
| 361 | 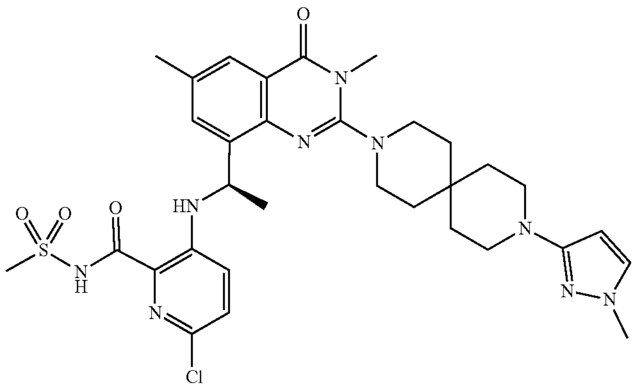 [SMILES: Cc1cc([C@@H](C)Nc2ccc(Cl)nc2C(=O)NS(C)(=O)=O)c2nc(N3CCC4(CCN(c5ccn(C)n5)CC4)CC3)n(C)c(=O)c2c1] | (R)-6-chloro-3-((1-(3,6-dimethyl-2-(9-(1-methyl-1H-pyrazol-3-yl)-3,9-diazaspiro[5.5]undecan-3-yl)-4-oxo-3,4-dihydroquinazolin-8-yl)ethyl)amino)-N-(methylsulfonyl)picolinamide | 2.36 min, 254 nm, MS (ES+)[b] $C_{32}H_{40}ClN_9O_4S$, requires: 681.2, found: 682.3 $[M + H]^+$ |
| 362 | 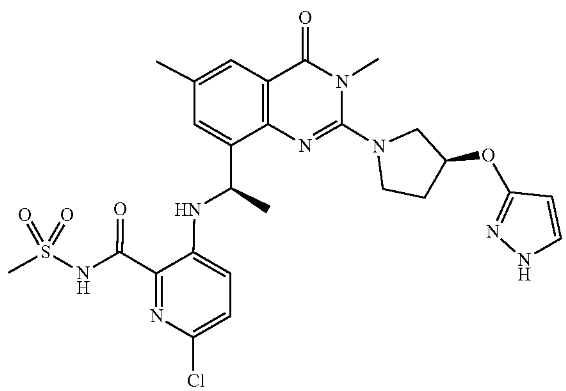 [SMILES: Cc1cc([C@@H](C)Nc2ccc(Cl)nc2C(=O)NS(C)(=O)=O)c2nc(N3CC[C@H](Oc4cc[nH]n4)C3)n(C)c(=O)c2c1] | 3-(((R)-1-(2-((S)-3-((1H-pyrazol-3-yl)oxy)pyrrolidin-1-yl)-3,6-dimethyl-4-oxo-3,4-dihydroquinazolin-8-yl)ethyl)amino)-6-chloro-N-(methylsulfonyl)picolinamide | 2.06 min, 254 nm, MS (ES+)[b] $C_{26}H_{29}ClN_8O_5S$, requires: 600.1, found: 601.1 $[M + H]^+$ |
| 363 | 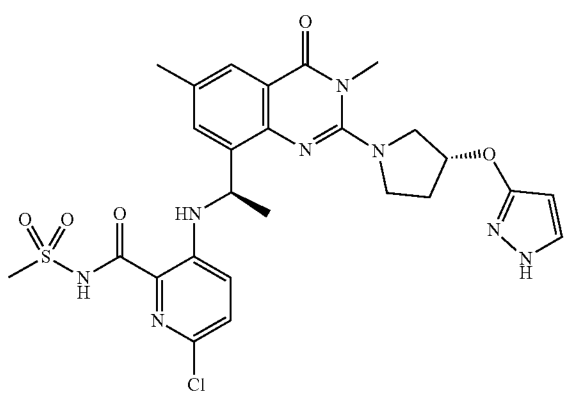 [SMILES: Cc1cc([C@@H](C)Nc2ccc(Cl)nc2C(=O)NS(C)(=O)=O)c2nc(N3CC[C@@H](Oc4cc[nH]n4)C3)n(C)c(=O)c2c1] | 3-(((R)-1-(2-((R)-3-((1H-pyrazol-3-yl)oxy)pyrrolidin-1-yl)-3,6-dimethyl-4-oxo-3,4-dihydroquinazolin-8-yl)ethyl)amino)-6-chloro-N-(methylsulfonyl)picolinamide | 2.06 min, 254 nm, MS (ES+)[b] $C_{26}H_{29}ClN_8O_5S$, requires: 600.1, found: 601.2 $[M + H]^+$ |
| 364 | 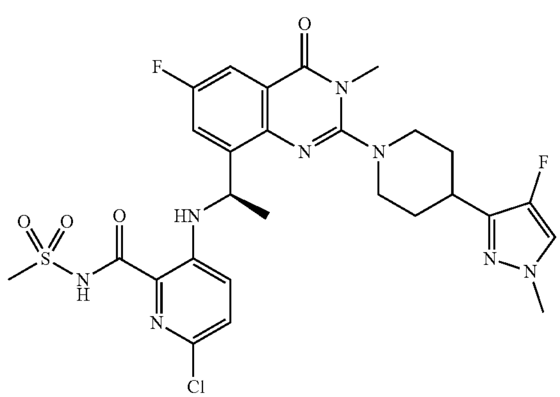 [SMILES: C[C@@H](Nc1ccc(Cl)nc1C(=O)NS(C)(=O)=O)c1cc(F)cc2c(=O)n(C)c(N3CCC(c4nn(C)cc4F)CC3)nc12] | (R)-6-chloro-3-((1-(6-fluoro-2-(4-(4-fluoro-1-methyl-1H-pyrazol-3-yl)piperidin-1-yl)-3-methyl-4-oxo-3,4-dihydroquinazolin-8-yl)ethyl)amino)-N-(methylsulfonyl)picolinamide | 2.54 min, 254 nm, MS (ES+)[b] $C_{27}H_{29}ClF_2N_8O_4S$, requires: 634.2, found: 636.0 $[M + H]^+$ |

TABLE E4-continued compound list prepared according to Route A in Example 4

| Cpd. ID | Structure | Name | LCMS |
|---|---|---|---|
| 365 | 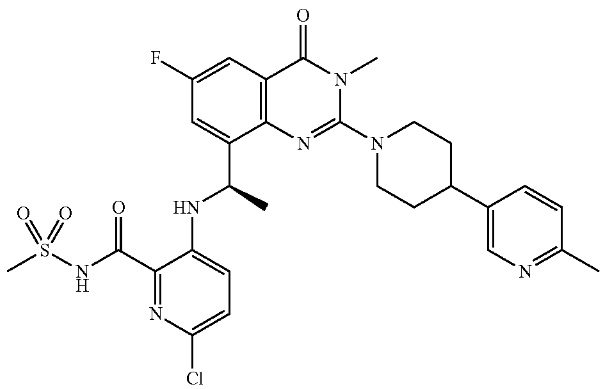 | (R)-6-chloro-3-((1-(6-fluoro-3-methyl-2-(4-(6-methylpyridin-3-yl)piperidin-1-yl)-4-oxo-3,4-dihydroquinazolin-8-yl)ethyl)amino)-N-(methylsulfonyl)picolinamide | 2.08 min, 254 nm, MS (ES+)[b] $C_{29}H_{31}ClFN_7O_4S$, requires: 627.1, found: 628.9 [M + H]+ |
| 366 | 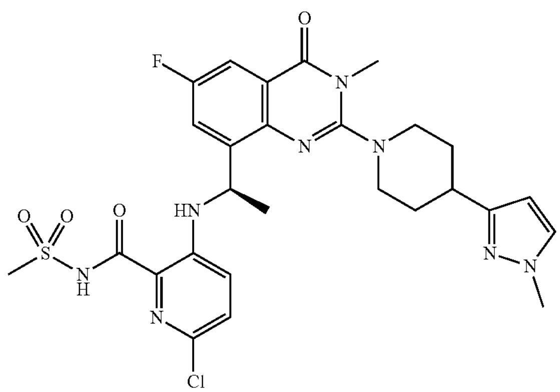 [SMILES: C[C@@H](Nc1ccc(Cl)nc1C(=O)NS(C)(=O)=O)c1cc(F)cc2c(=O)n(C)c(N3CCC(c4ccn(C)n4)CC3)nc12] | (R)-6-chloro-3-((1-(6-fluoro-3-methyl-2-(4-(1-methyl-1H-pyrazol-3-yl)piperidin-1-yl)-4-oxo-3,4-dihydroquinazolin-8-yl)ethyl)amino)-N-(methylsulfonyl)picolinamide | 2.44 min, 254 nm, MS (ES+)[b] $C_{27}H_{30}ClFN_8O_4S$, requires: 616.1, found: 617.9 [M + H]+ |
| 367 | 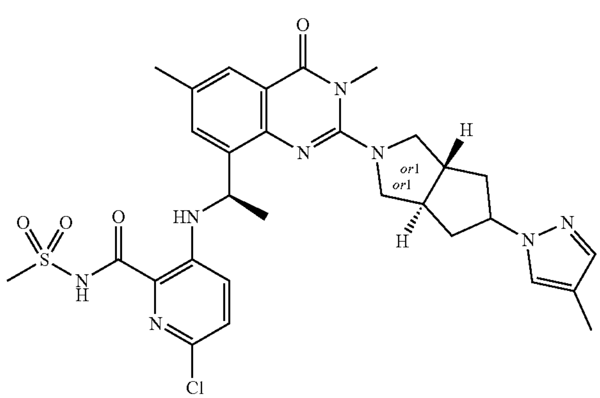 [SMILES: Cc1cc([C@@H](C)Nc2ccc(Cl)nc2C(=O)NS(C)(=O)=O)c2nc(N3C[C@@H]4CC(n5cc(C)cn5)C[C@H]4C3)n(C)c(=O)c2c1] | 6-chloro-3-(((R)-1-(3,6-dimethyl-2-((3aR*,6aR*)-5-(4-methyl-1H-pyrazol-1-yl)hexahydrocyclopenta[c]pyrrol-2(1H)-yl)-4-oxo-3,4-dihydroquinazolin-8-yl)ethyl)amino)-N-(methylsulfonyl)picolinamide | 3.69 min, 254 nm, MS (ES+)[c] $C_{30}H_{35}ClN_8O_4S$, requires: 638.2, found: 639.3 [M + H]+ |

TABLE E4-continued compound list prepared according to Route A in Example 4

| Cpd. ID | Structure | Name | LCMS |
|---|---|---|---|
| 368 | 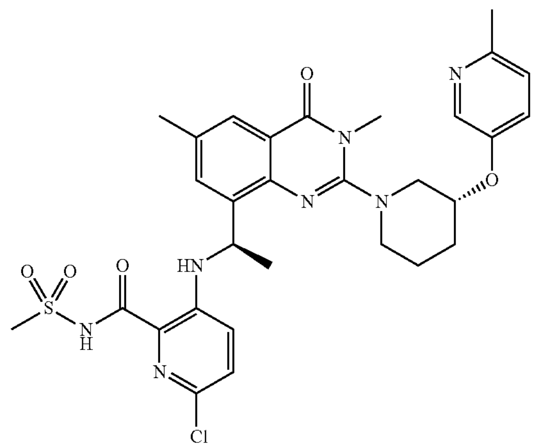 [SMILES: Cc1cc([C@@H](C)Nc2ccc(Cl)nc2C(=O)NS(C)(=O)=O)c2nc(N3CCC[C@@H](Oc4ccc(C)nc4)C3)n(C)c(=O)c2c1] | 6-chloro-3-(((R)-1-(3,6-dimethyl-2-((R)-3-((6-methylpyridin-3-yl)oxy)piperidin-1-yl)-4-oxo-3,4-dihydroquinazolin-8-yl)ethyl)amino)-N-(methylsulfonyl)picolinamide | 3.79 min, 254 nm, MS (ES+)$^c$ $C_{30}H_{34}ClN_7O_5S$, requires: 639.2, found: 640.3 $[M + H]^+$ |
| 369 | 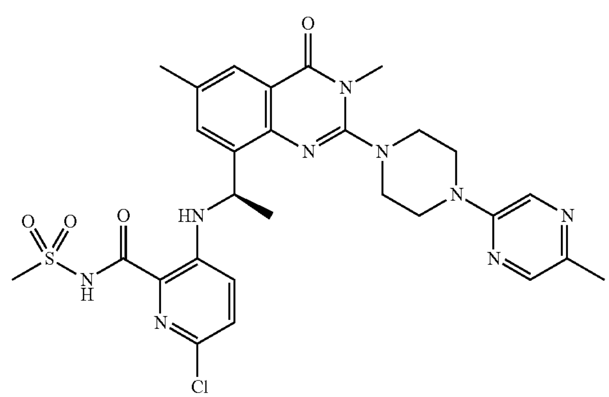 | (R)-6-chloro-3-((1-(3,6-dimethyl-2-(4-(5-methylpyrazin-2-yl)piperazin-1-yl)-4-oxo-3,4-dihydroquinazolin-8-yl)ethyl)amino)-N-(methylsulfonyl)picolinamide | 2.38 min, 254 nm, MS (ES+)$^b$ $C_{28}H_{32}ClN_9O_4S$, requires: 625.2, found: 626.2 $[M + H]^+$ |
| 370 | 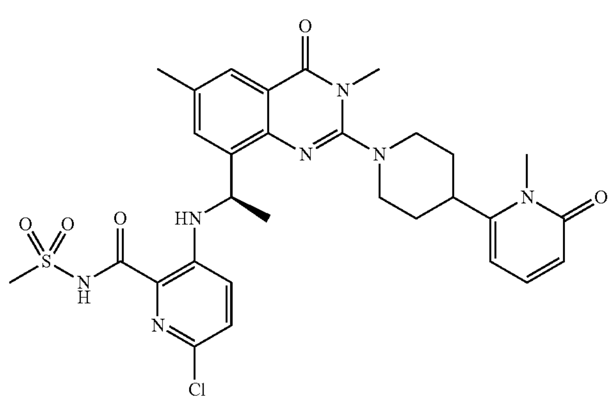 [SMILES: Cc1cc([C@@H](C)Nc2ccc(Cl)nc2C(=O)NS(C)(=O)=O)c2nc(N3CCC(c4cccc(=O)n4C)CC3)n(C)c(=O)c2c1] | (R)-6-chloro-3-((1-(3,6-dimethyl-2-(4-(1-methyl-6-oxo-1,6-dihydropyridin-2-yl)piperidin-1-yl)-4-oxo-3,4-dihydroquinazolin-8-yl)ethyl)amino)-N-(methylsulfonyl)picolinamide | 2.03 min, 210 nm, MS (ES+)$^b$ $C_{30}H_{34}ClN_7O_5S$, requires: 639.2, found: 640.2 $[M + H]^+$ |

TABLE E4-continued compound list prepared according to Route A in Example 4

| Cpd. ID | Structure | Name | LCMS |
|---|---|---|---|
| 371 | 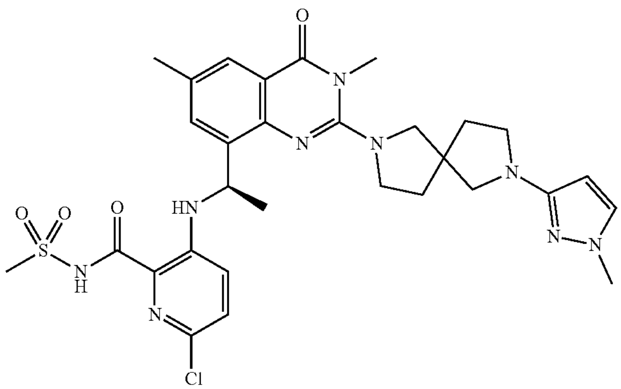 [SMILES: Cc1cc([C@@H](C)Nc2ccc(Cl)nc2C(=O)NS(C)(=O)=O)c2nc(N3CCC4(CCN(c5ccn(C)n5)C4)C3)n(C)c(=O)c2c1] | 6-chloro-3-(((1R)-1-(3,6-dimethyl-2-(7-(1-methyl-1H-pyrazol-3-yl)-2,7-diazaspiro[4.4]nonan-2-yl)-4-oxo-3,4-dihydroquinazolin-8-yl)ethyl)amino)-N-(methylsulfonyl) picolinamide | 2.51 min, 270 nm, MS (ES+)[b] $C_{30}H_{36}ClN_9O_4S$, requires: 653.2, found: 654.9 $[M + H]^+$ |
| 372 | 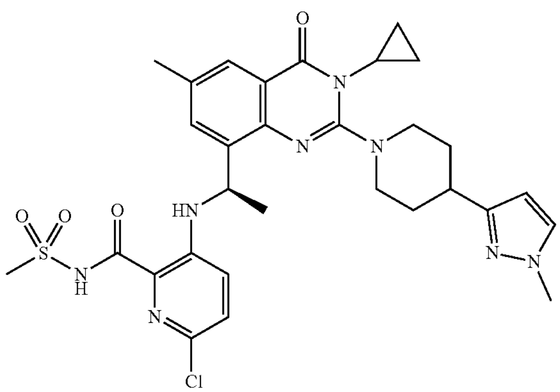 [SMILES: Cc1cc([C@@H](C)Nc2ccc(Cl)nc2C(=O)NS(C)(=O)=O)c2nc(N3CCC(c4ccn(C)n4)CC3)n(C3CC3)c(=O)c2c1] | (R)-6-chloro-3-((1-(3-cyclopropyl-6-methyl-2-(4-(1-methyl-1H-pyrazol-3-yl)piperidin-1-yl)-4-oxo-3,4-dihydroquinazolin-8-yl)ethyl)amino)-N-(methylsulfonyl) picolinamide | 2.37 min, 210 nm, MS (ES+)[b] $C_{30}H_{35}ClN_8O_4S$, requires: 638.2, found: 639.2 $[M + H]^+$ |
| 373 | 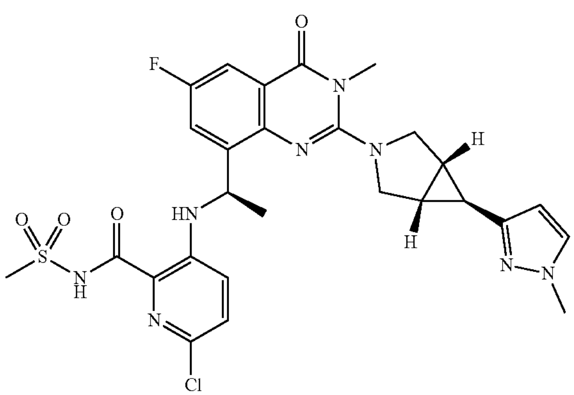 [SMILES: C[C@@H](Nc1ccc(Cl)nc1C(=O)NS(C)(=O)=O)c1cc(F)cc2c(=O)n(C)c(N3C[C@@H]4[C@H](C3)[C@H]4c3ccn(C)n3)nc12] | 6-chloro-3-(((R)-1-(6-fluoro-3-methyl-2-((1R,5S,6R)-6-(1-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl) picolinamide | 2.22 min, 265 nm, MS (ES+)[b] $C_{27}H_{28}ClFN_8O_4S$, requires: 614.1, found: 615.1 $[M + H]^+$ |
| 374 | 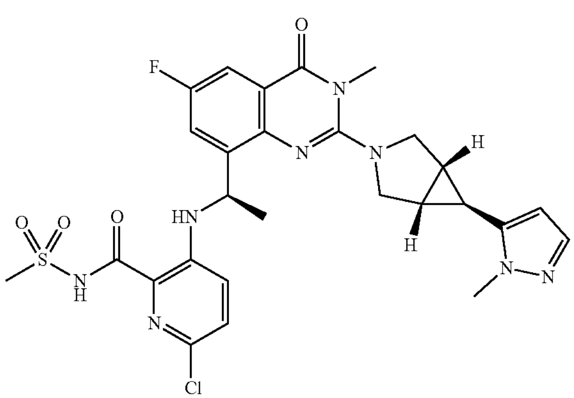 [SMILES: C[C@@H](Nc1ccc(Cl)nc1C(=O)NS(C)(=O)=O)c1cc(F)cc2c(=O)n(C)c(N3C[C@@H]4[C@H](C3)[C@H]4c3ccnn3C)nc12] | 6-chloro-3-(((R)-1-(6-fluoro-3-methyl-2-((1R,5S,6R)-6-(1-methyl-1H-pyrazol-5-yl)-3-azabicyclo[3.1.0]hexan-3-yl)-4-oxo-3,4-dihydroquinazolin-8-yl)ethyl)amino)-N-(methylsulfonyl) picolinamide | 2.17 min, 265 nm, MS (ES+)[b] $C_{27}H_{28}ClFN_8O_4S$, requires: 614.1, found: 615.1 $[M + H]^+$ |

TABLE E4-continued compound list prepared according to Route A in Example 4

| Cpd. ID | Structure | Name | LCMS |
|---|---|---|---|
| 375 | 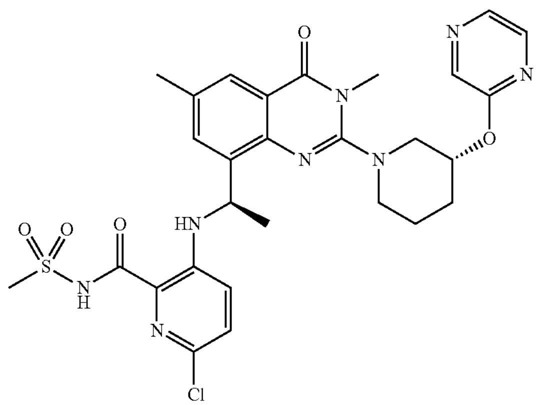 [SMILES: Cc1cc([C@@H](C)Nc2ccc(Cl)nc2C(=O)NS(C)(=O)=O)c2nc(N3CCC[C@@H](Oc4cnccn4)C3)n(C)c(=O)c2c1] | 6-chloro-3-(((R)-1-(3,6-dimethyl-4-oxo-2-((R)-3-(pyrazin-2-yloxy)piperidin-1-yl)-3,4-dihydroquinazolin-8-yl)ethyl)amino)-N-(methylsulfonyl)picolinamide | 4.74 min, 254 nm, MS (ES+)$^c$ $C_{28}H_{31}ClN_8O_5S$, requires: 626.2, found: 627.2 $[M + H]^+$ |
| 376 | 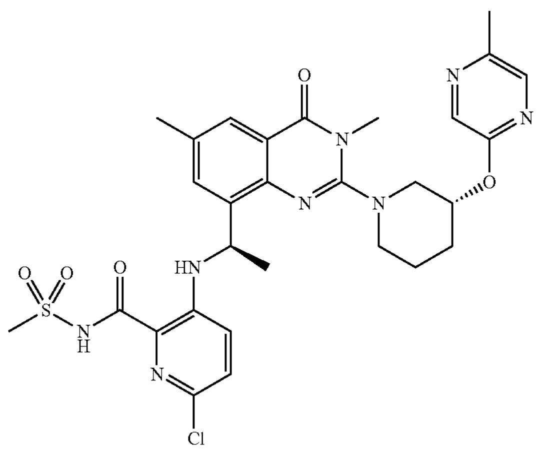 [SMILES: Cc1cc([C@@H](C)Nc2ccc(Cl)nc2C(=O)NS(C)(=O)=O)c2nc(N3CCC[C@@H](Oc4cnc(C)cn4)C3)n(C)c(=O)c2c1] | 6-chloro-3-(((R)-1-(3,6-dimethyl-2-((R)-3-((5-methylpyrazin-2-yl)oxy)piperidin-1-yl)-4-oxo-3,4-dihydroquinazolin-8-yl)ethyl)amino)-N-(methylsulfonyl)picolinamide | 3.85 min, 254 nm, MS (ES+)$^c$ $C_{29}H_{33}ClN_8O_5S$, requires: 640.2, found: 641.2 $[M + H]^+$ |
| 377 | 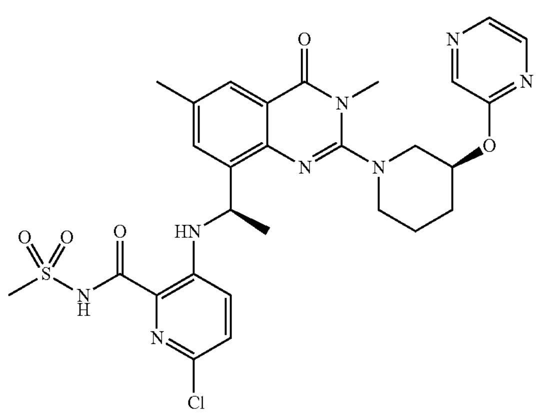 [SMILES: Cc1cc([C@@H](C)Nc2ccc(Cl)nc2C(=O)NS(C)(=O)=O)c2nc(N3CCC[C@H](Oc4cnccn4)C3)n(C)c(=O)c2c1] | 6-chloro-3-(((R)-1-(3,6-dimethyl-4-oxo-2-((S)-3-(pyrazin-2-yloxy)piperidin-1-yl)-3,4-dihydroquinazolin-8-yl)ethyl)amino)-N-(methylsulfonyl)picolinamide | 4.88 min, 254 nm, MS (ES+)$^c$ $C_{28}H_{31}ClN_8O_5S$, requires: 626.2, found: 627.2 $[M + H]^+$ |

TABLE E4-continued compound list prepared according to Route A in Example 4

| Cpd. ID | Structure | Name | LCMS |
|---|---|---|---|
| 378 | 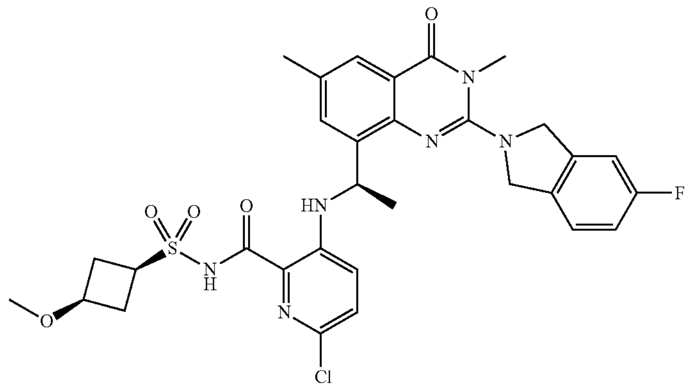 [SMILES: CO[C@H]1C[C@@H](S(=O)(=O)NC(=O)c2nc(Cl)ccc2N[C@H](C)c2cc(C)cc3c(=O)n(C)c(N4Cc5ccc(F)cc5C4)nc23)C1] | 6-chloro-3-(((R)-1-(2-(5-fluoroisoindolin-2-yl)-3,6-dimethyl-4-oxo-3,4-dihydroquinazolin-8-yl)ethyl)amino)-N-(((1s,3S)-3-methoxycyclobutyl)sulfonyl)picolinamide | 2.76 min, 215 nm, MS (ES+)[b] $C_{31}H_{32}ClFN_6O_5S$, requires: 654.1, found: 655.2 [M + H]+ |
| 379 | 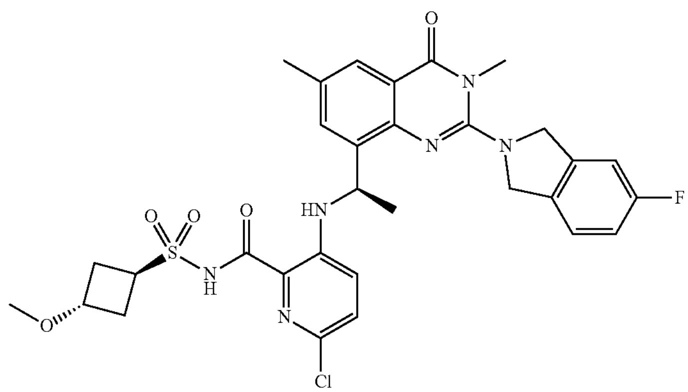 [SMILES: CO[C@H]1C[C@H](S(=O)(=O)NC(=O)c2nc(Cl)ccc2N[C@H](C)c2cc(C)cc3c(=O)n(C)c(N4Cc5ccc(F)cc5C4)nc23)C1] | 6-chloro-3-(((R)-1-(2-(5-fluoroisoindolin-2-yl)-3,6-dimethyl-4-oxo-3,4-dihydroquinazolin-8-yl)ethyl)amino)-N-(((1r,3R)-3-methoxycyclobutyl)sulfonyl)picolinamide | 2.76 min, 215 nm, MS (ES+)[b] $C_{31}H_{32}ClFN_6O_5S$, requires: 654.1, found: 655.2 [M + H]+ |
| 380 | 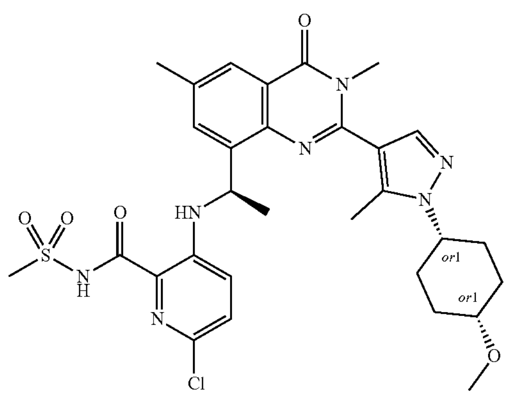 [SMILES: CO[C@H]1CC[C@@H](n2ncc(-c3nc4c([C@@H](C)Nc5ccc(Cl)nc5C(=O)NS(C)(=O)=O)cc(C)cc4c(=O)n3C)c2C)CC1] | 6-chloro-3-(((R)-1-(2-(1-((1S*,4S*)-4-methoxycyclohexyl)-5-methyl-1H-pyrazol-4-yl)-3,6-dimethyl-4-oxo-3,4-dihydroquinazolin-8-yl)ethyl)amino)-N-(methylsulfonyl)picolinamide | 2.55 min, 254 nm, MS (ES+)[b] $C_{30}H_{36}ClN_7O_5S$, requires: 641.2, found: 642.9 [M + H]+ |
| 381 | 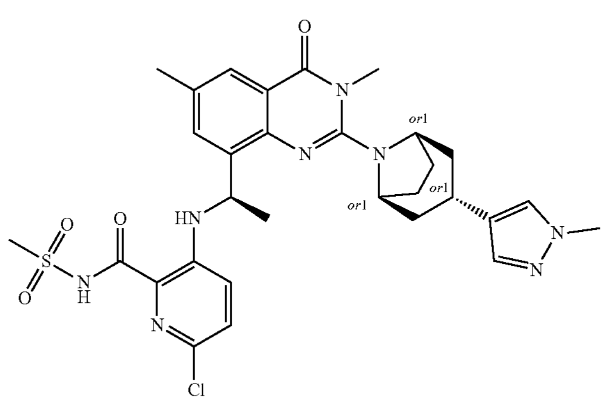 | 6-chloro-3-(((R)-1-(3,6-dimethyl-2-((1RS,3RS,5SR)-3-(1-methyl-1H-pyrazol-4-yl)-8-azabicyclo[3.2.1]octan-8-yl)-4-oxo-3,4-dihydroquinazolin-8-yl)ethyl)amino)-N-(methylsulfonyl)picolinamide | 2.40 min, 254 nm, MS (ES+)[b] $C_{30}H_{35}ClN_8O_4S$, requires: 638.2, found: 639.2 [M + H]+ |

TABLE E4-continued compound list prepared according to Route A in Example 4

| Cpd. ID | Structure | Name | LCMS |
|---|---|---|---|
| 382 | 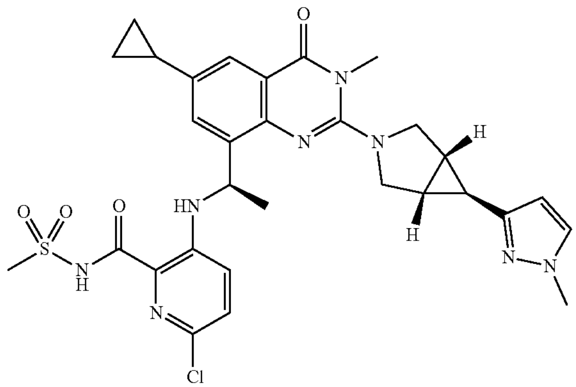 [SMILES: C[C@@H](Nc1ccc(Cl)nc1C(=O)NS(C)(=O)=O)c1cc(C2CC2)cc2c(=O)n(C)c(N3C[C@@H]4[C@H](C3)[C@H]4c3ccn(C)n3)nc12] | 6-chloro-3-(((R)-1-(6-cyclopropyl-3-methyl-2-((1R,5S,6R)-6-(1-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.43 min, 272 nm, MS (ES+)[b] $C_{30}H_{33}ClN_8O_4S$, requires: 636.2, found: 637.2 $[M + H]^+$ |
| 383 | 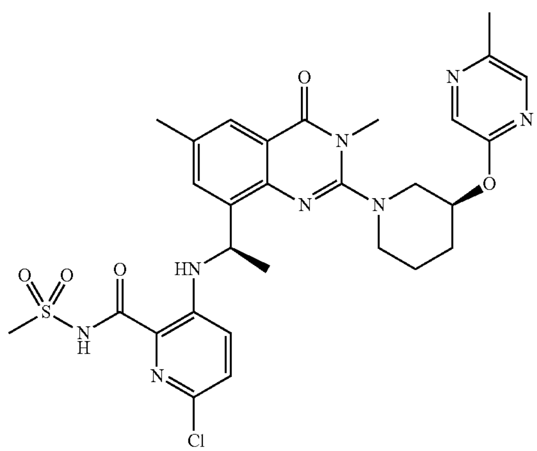 [SMILES: Cc1cc([C@@H](C)Nc2ccc(Cl)nc2C(=O)NS(C)(=O)=O)c2nc(N3CCC[C@H](Oc4cnc(C)cn4)C3)n(C)c(=O)c2c1] | 6-chloro-3-(((R)-1-(3,6-dimethyl-2-((S)-3-((5-methylpyrazin-2-yl)oxy)piperidin-1-yl)-4-oxo-3,4-dihydroquinazolin-8-yl)ethyl)amino)-N-(methylsulfonyl)picolinamide | 5.07 min, 254 nm, MS (ES+)[c] $C_{29}H_{33}ClN_8O_5S$, requires: 640.2, found: 641.2 $[M + H]^+$ |
| 384 | 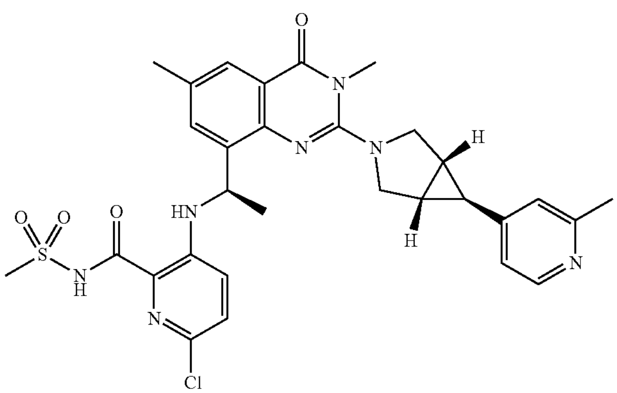 | 6-chloro-3-(((R)-1-(3,6-dimethyl-2-((1R,5S,6S)-6-(2-methylpyridin-4-yl)-3-azabicyclo[3.1.0]hexan-3-yl)-4-oxo-3,4-dihydroquinazolin-8-yl)ethyl)amino)-N-(methylsulfonyl)picolinamide | 2.02 min, 275 nm, MS (ES+)[b] $C_{30}H_{32}ClN_7O_4S$, requires: 621.1, found: 622.9 $[M + H]^+$ |

TABLE E4-continued compound list prepared according to Route A in Example 4

| Cpd. ID | Name | LCMS |
|---|---|---|
| 385 | 6-chloro-3-(((R)-1-(3,6-dimethyl-2-((1R,5S,6S)-6-(2-methylpyridin-3-yl)-3-azabicyclo[3.1.0]hexan-3-yl)-4-oxo-3,4-dihydroquinazolin-8-yl)ethyl)amino)-N-(methylsulfonyl)picolinamide | 2.02 min, 275 nm, MS (ES+)[b] C30H32ClN7O4S, requires: 621.1, found: 622.9 [M + H]+ |
| 386 | 6-chloro-3-(((R)-1-(6-cyclopropyl-3-methyl-2-((1R,5S,6S)-6-(1-methyl-1H-pyrazol-4-yl)-3-azabicyclo[3.1.0]hexan-3-yl)-4-oxo-3,4-dihydroquinazolin-8-yl)ethyl)amino)-N-(methylsulfonyl)picolinamide | 2.43 min, 272 nm, MS (ES+)[b] C30H33ClN8O4S, requires: 636.2, found: 637.2 [M + H]+ |
| 387 | 6-chloro-3-(((R)-1-(3,6-dimethyl-2-((1R,5S,6R)-6-(1-methyl-1H-1,2,3-triazol-4-yl)-3-azabicyclo[3.1.0]hexan-3-yl)-4-oxo-3,4-dihydroquinazolin-8-yl)ethyl)amino)-N-(methylsulfonyl)picolinamide | 2.17 min, 254 nm, MS (ES+)[b] C27H30ClN9O4S, requires: 611.1, found: 612.2 [M + H]+ |
| 388 | 6-chloro-3-(((R)-1-(6-fluoro-3-methyl-2-((S)-3-((1-methyl-1H-pyrazol-4-yl)oxy)pyrrolidin-1-yl)-4-oxo-3,4-dihydroquinazolin-8-yl)ethyl)amino)-N-(methylsulfonyl)picolinamide | 2.10 min, 269 nm, MS (ES+)[b] C26H28ClFN8O5S, requires: 618.1, found: 619.1 [M + H]+ |

TABLE E4-continued compound list prepared according to Route A in Example 4

| Cpd. ID | Structure | Name | LCMS |
|---|---|---|---|
| 389 | 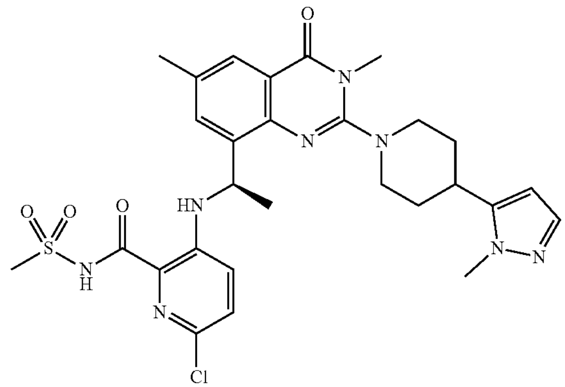 | (R)-6-chloro-3-((1-(3,6-dimethyl-2-(4-(1-methyl-1H-pyrazol-5-yl)piperidin-1-yl)-4-oxo-3,4-dihydroquinazolin-8-yl)ethyl)amino)-N-(methylsulfonyl)picolinamide | 2.23 min, 215 nm, MS (ES+)[b] C$_{28}$H$_{33}$ClN$_8$O$_4$S, requires: 612.2, found: 613.2 [M + H]$^+$ |
| 390 | 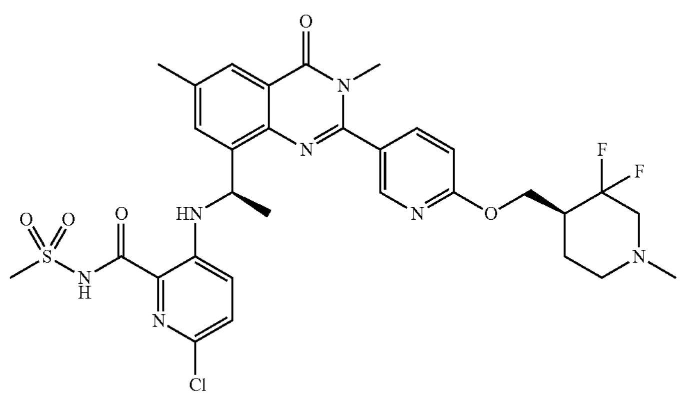 | 6-chloro-3-(((R)-1-(2-(6-(((S)-3,3-difluoro-1-methylpiperidin-4-yl)methoxy)pyridin-3-yl)-3,6-dimethyl-4-oxo-3,4-dihydroquinazolin-8-yl)ethyl)amino)-N-(methylsulfonyl)picolinamide | 2.59 min, 220 nm, MS (ES+)[c] C$_{31}$H$_{34}$ClF$_2$N$_7$O$_5$S, requires: 689.2, found: 690.2 [M + H]$^+$ |
| 391 | 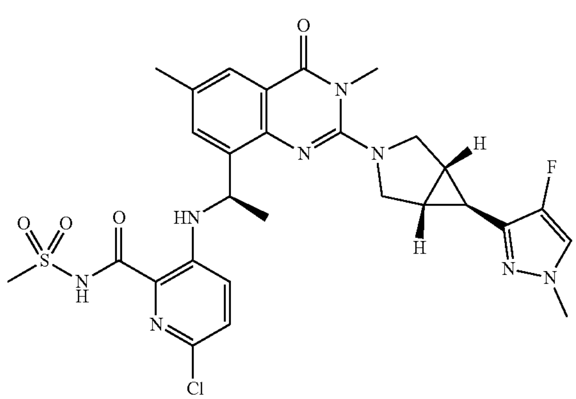 [SMILES: Cc1cc([C@@H](C)Nc2ccc(Cl)nc2C(=O)NS(C)(=O)=O)c2nc(N3C[C@@H]4[C@H](C3)[C@H]4c3nn(C)cc3F)n(C)c(=O)c2c1] | 6-chloro-3-(((R)-1-(2-((1R,5S,6R)-6-(4-fluoro-1-methyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 4.57 min, 254 nm, MS (ES+)[c] C$_{28}$H$_{30}$ClFN$_8$O$_4$S, requires: 628.2, found: 629.2 [M + H]$^+$ |

TABLE E4-continued compound list prepared according to Route A in Example 4

| Cpd. ID | Structure | Name | LCMS |
|---|---|---|---|
| 392 | 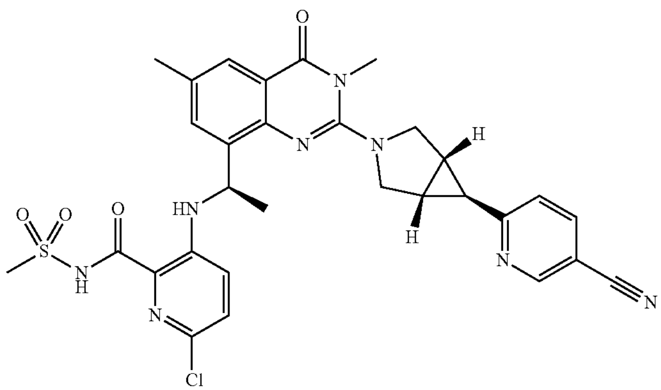 [SMILES: Cc1cc([C@@H](C)Nc2ccc(Cl)nc2C(=O)NS(C)(=O)=O)c2nc(N3C[C@@H]4[C@H](C3)[C@H]4c3ccc(C#N)cn3)n(C)c(=O)c2c1] | 6-chloro-3-(((R)-1-(2-((1R,5S,6R)-6-(5-cyanopyridin-2-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.37 min, 254 nm, MS (ES+)[b] $C_{30}H_{29}ClN_8O_4S$, requires: 632.1, found: 633.2 $[M + H]^+$ |
| 393 | 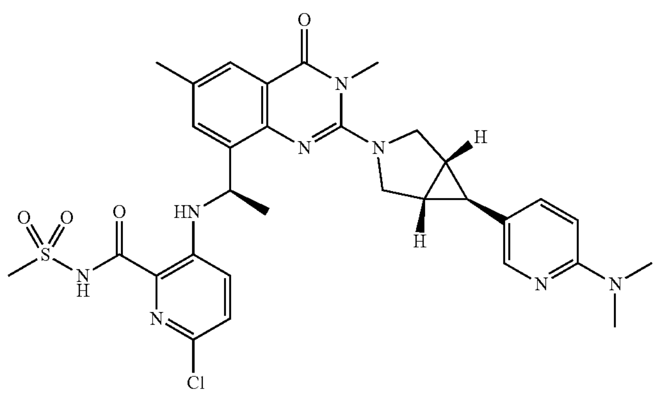 | 6-chloro-3-(((R)-1-(2-((1R,5S,6S)-6-(6-(dimethylamino)pyridin-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 1.94 min, 254 nm, MS (ES+)[b] $C_{31}H_{35}ClN_8O_4S$, requires: 650.2, found: 651.2 $[M + H]^+$ |
| 394 | 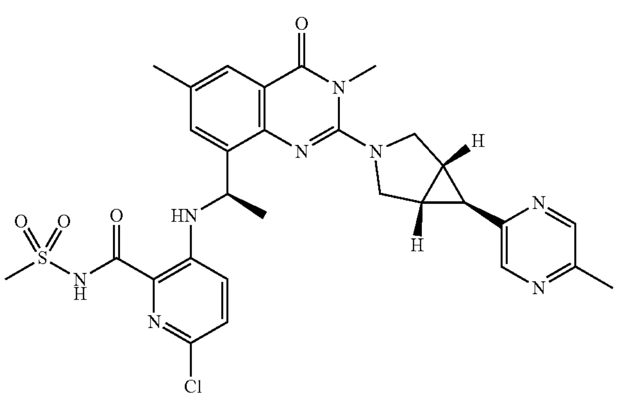 | 6-chloro-3-(((R)-1-(3,6-dimethyl-2-((1R,5S,6R)-6-(5-methylpyrazin-2-yl)-3-azabicyclo[3.1.0]hexan-3-yl)-4-oxo-3,4-dihydroquinazolin-8-yl)ethyl)amino)-N-(methylsulfonyl)picolinamide | 2.27 min, 254 nm, MS (ES+)[b] $C_{29}H_{31}ClN_8O_4S$, requires: 622.1, found: 623.2 $[M + H]^+$ |
| 395 | 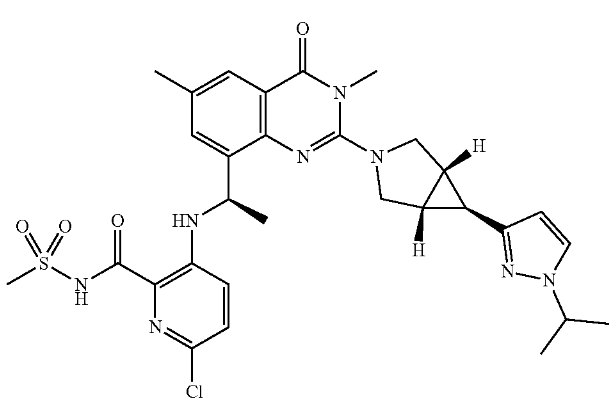 [SMILES: Cc1cc([C@@H](C)Nc2ccc(Cl)nc2C(=O)NS(C)(=O)=O)c2nc(N3C[C@@H]4[C@H](C3)[C@H]4c3ccn(C(C)C)n3)n(C)c(=O)c2c1] | 6-chloro-3-(((R)-1-(2-((1R,5S,6R)-6-(1-isopropyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.56 min, 254 nm, MS (ES+)[b] $C_{30}H_{35}ClN_8O_4S$, requires: 638.2, found: 639.3 $[M + H]^+$ |

TABLE E4-continued compound list prepared according to Route A in Example 4

| Cpd. ID | Structure | Name | LCMS |
|---|---|---|---|
| 396 | 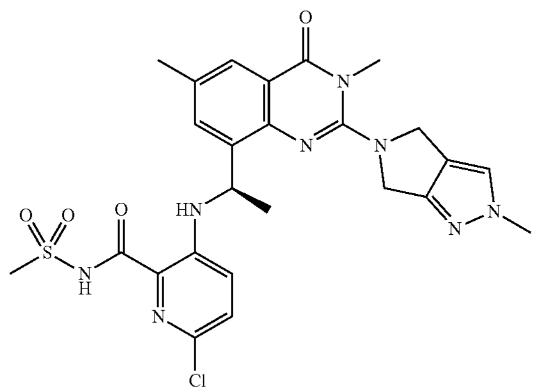 | (R)-6-chloro-3-((1-(3,6-dimethyl-2-(2-methyl-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.13 min, 271 nm, MS (ES+)[b] $C_{25}H_{27}ClN_8O_4S$, requires: 570.1, found: 571.1 $[M + H]^+$ |
| 397 | 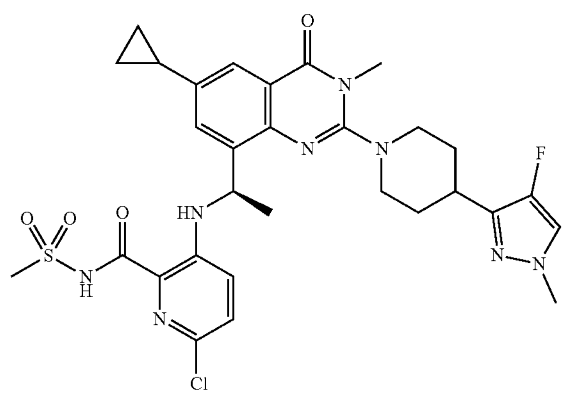 [SMILES: C[C@@H](Nc1ccc(Cl)nc1C(=O)NS(C)(=O)=O)c1cc(C2CC2)cc2c(=O)n(C)c(N3CCC(c4nn(C)cc4F)CC3)nc12] | (R)-6-chloro-3-((1-(6-cyclopropyl-2-(4-(4-fluoro-1-methyl-1H-pyrazol-3-yl)piperidin-1-yl)-3-methyl-4-oxo-3,4-dihydroquinazolin-8-yl)ethyl)amino)-N-(methylsulfonyl)picolinamide | 2.43 min, 254 nm, MS (ES+)[b] $C_{30}H_{34}ClFN_8O_4S$, requires: 656.2, found: 657.1 $[M + H]^+$ |
| 398 | 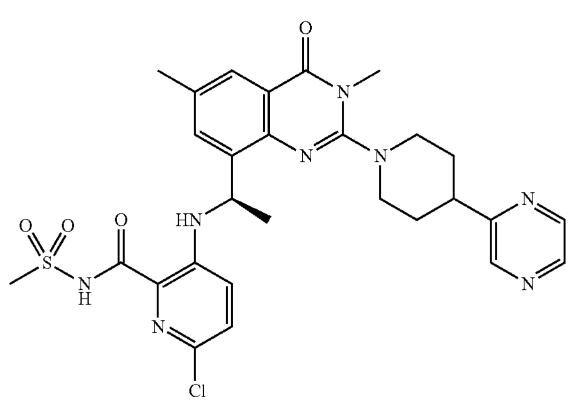 | (R)-6-chloro-3-((1-(3,6-dimethyl-4-oxo-2-(4-(pyrazin-2-yl)piperidin-1-yl)-3,4-dihydroquinazolin-8-yl)ethyl)amino)-N-(methylsulfonyl)picolinamide | 2.29 min, 270 nm, MS (ES+)[b] $C_{28}H_{31}ClN_8O_4S$, requires: 610.1, found: 611.2 $[M + H]^+$ |

TABLE E4-continued compound list prepared according to Route A in Example 4

| Cpd. ID | Structure | Name | LCMS |
|---|---|---|---|
| 399 | 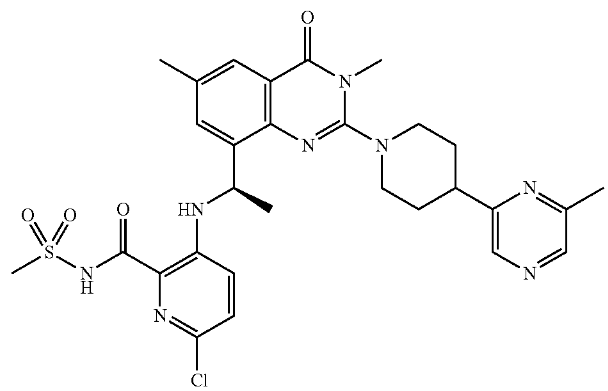 | (R)-6-chloro-3-((1-(3,6-dimethyl-2-(4-(6-methylpyrazin-2-yl)piperidin-1-yl)-4-oxo-3,4-dihydroquinazolin-8-yl)ethyl)amino)-N-(methylsulfonyl)picolinamide | 2.36 min, 254 nm, MS (ES+)[b] $C_{29}H_{33}ClN_8O_4S$, requires: 624.2, found: 625.2 [M + H]+ |
| 400 | 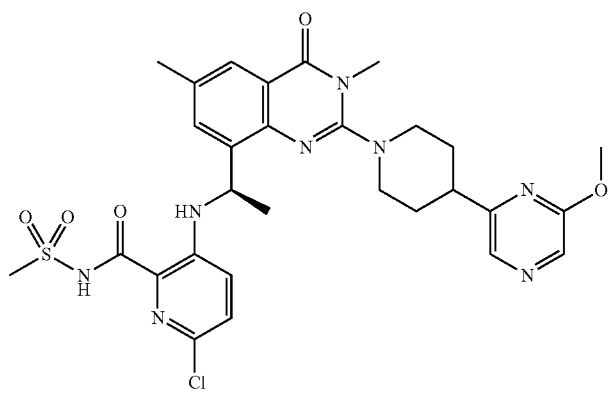 | (R)-6-chloro-3-((1-(2-(4-(6-methoxypyrazin-2-yl)piperidin-1-yl)-3,6-dimethyl-4-oxo-3,4-dihydroquinazolin-8-yl)ethyl)amino)-N-(methylsulfonyl)picolinamide | 2.47 min, 254 nm, MS (ES+)[b] $C_{29}H_{33}ClN_8O_5S$, requires: 640.2, found: 641.2 [M + H]+ |
| 401 | 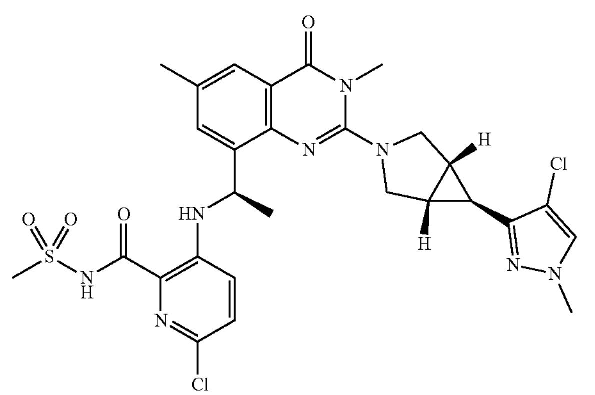 | 6-chloro-3-(((R)-1-(2-((1R,5S,6R)-6-(4-chloro-1-methyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 4.71 min, 254 nm, MS (ES+)[c] $C_{28}H_{30}Cl2N_8O_4S$, requires: 644.2, found: 645.2 [M + H]+ |
| 402 | 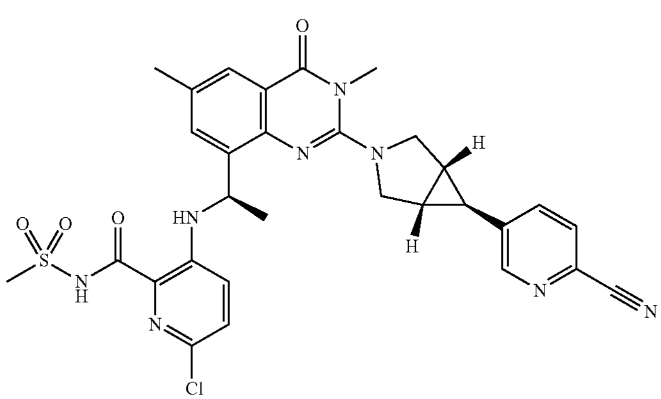 [SMILES: Cc1cc([C@@H](C)Nc2ccc(Cl)nc2C(=O)NS(C)(=O)=O)c2nc(N3C[C@@H]4[C@H](C3)[C@H]4c3ccc(C#N)nc3)n(C)c(=O)c2c1] | 6-chloro-3-(((R)-1-(2-((1R,5S,6S)-6-(6-cyanopyridin-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.37 min, 254 nm, MS (ES+)[b] $C_{30}H_{29}ClN_8O_4S$, requires: 632.1, found: 633.2 [M + H]+ |

TABLE E4-continued compound list prepared according to Route A in Example 4

| Cpd. ID | Structure | Name | LCMS |
|---|---|---|---|
| 403 | 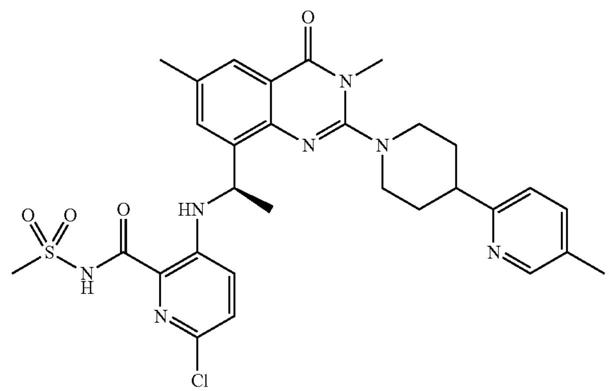 | (R)-6-chloro-3-((1-(3,6-dimethyl-2-(4-(5-methylpyridin-2-yl)piperidin-1-yl)-4-oxo-3,4-dihydroquinazolin-8-yl)ethyl)amino)-N-(methylsulfonyl)picolinamide | 2.06 min, 215 nm, MS (ES+)[b] $C_{30}H_{34}ClN_7O_4S$, requires: 623.2, found: 624.3 $[M + H]^+$ |
| 404 | 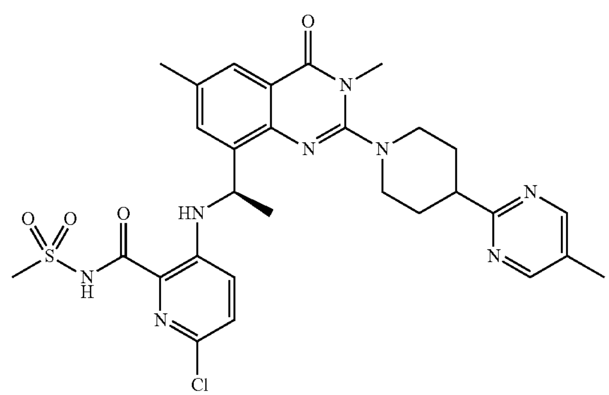 | (R)-6-chloro-3-((1-(3,6-dimethyl-2-(4-(5-methylpyrimidin-2-yl)piperidin-1-yl)-4-oxo-3,4-dihydroquinazolin-8-yl)ethyl)amino)-N-(methylsulfonyl)picolinamide | 2.05 min, 220 nm, MS (ES+)[b] $C_{29}H_{33}ClN_8O_4S$, requires: 624.2, found: 625.3 $[M + H]^+$ |
| 405 | 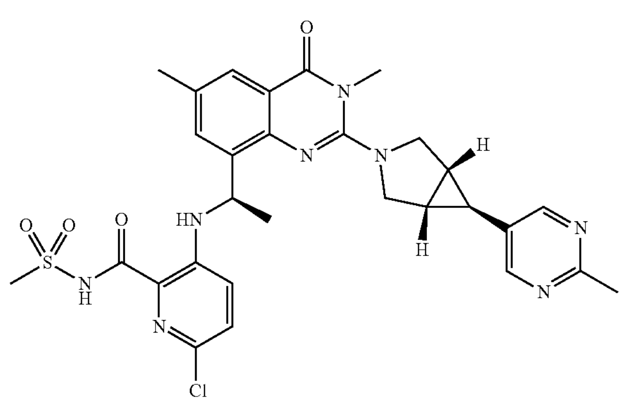 | 6-chloro-3-(((R)-1-(3,6-dimethyl-2-((1R,5S,6S)-6-(2-methylpyrimidin-5-yl)-3-azabicyclo[3.1.0]hexan-3-yl)-4-oxo-3,4-dihydroquinazolin-8-yl)ethyl)amino)-N-(methylsulfonyl)picolinamide | 2.22 min, 254 nm, MS (ES+)[b] $C_{29}H_{31}ClN_8O_4S$, requires: 622.1, found: 623.2 $[M + H]^+$ |

TABLE E4-continued compound list prepared according to Route A in Example 4

| Cpd. ID | Structure | Name | LCMS |
|---|---|---|---|
| 406 | 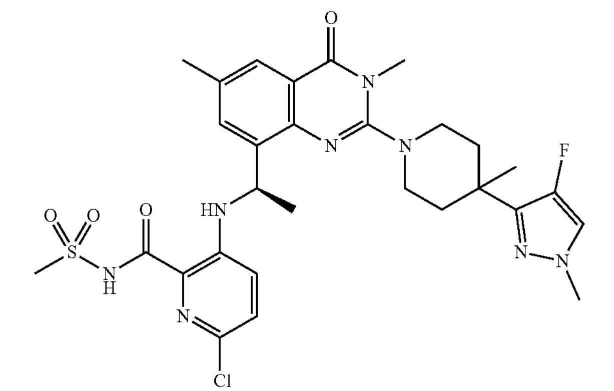 [SMILES: Cc1cc([C@@H](C)Nc2ccc(Cl)nc2C(=O)NS(C)(=O)=O)c2nc(N3CCC(C)(c4nn(C)cc4F)CC3)n(C)c(=O)c2c1] | (R)-6-chloro-3-((1-(2-(4-(4-fluoro-1-methyl-1H-pyrazol-3-yl)-4-methylpiperidin-1-yl)-3,6-dimethyl-4-oxo-3,4-dihydroquinazolin-8-yl)ethyl)amino)-N-(methylsulfonyl)picolinamide | 2.50 min, 254 nm, MS (ES+)[b] $C_{29}H_{34}ClFN_8O_4S$, requires: 644.2, found: 645.2 $[M + H]^+$ |
| 407 | 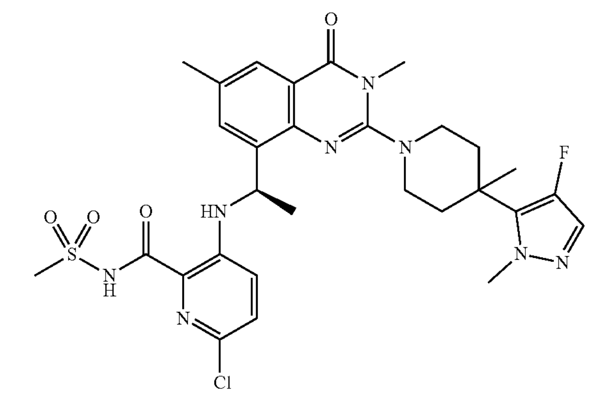 [SMILES: Cc1cc([C@@H](C)Nc2ccc(Cl)nc2C(=O)NS(C)(=O)=O)c2nc(N3CCC(C)(c4c(F)cnn4C)CC3)n(C)c(=O)c2c1] | (R)-6-chloro-3-((1-(2-(4-(4-fluoro-1-methyl-1H-pyrazol-5-yl)-4-methylpiperidin-1-yl)-3,6-dimethyl-4-oxo-3,4-dihydroquinazolin-8-yl)ethyl)amino)-N-(methylsulfonyl)picolinamide | 2.50 min, 254 nm, MS (ES+)[b] $C_{29}H_{34}ClFN_8O_4S$, requires: 644.2, found: 645.2 $[M + H]^+$ |
| 408 | 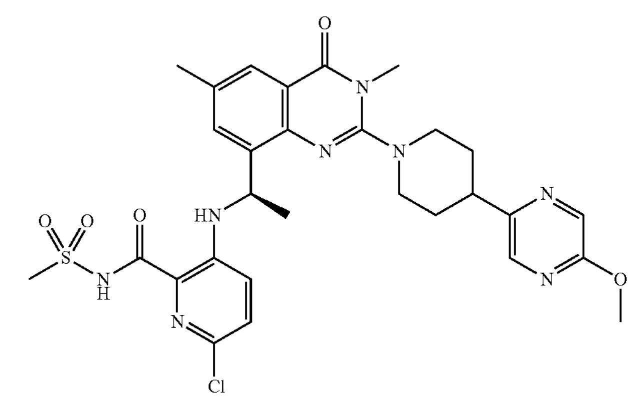 | (R)-6-chloro-3-((1-(2-(4-(5-methoxypyrazin-2-yl)piperidin-1-yl)-3,6-dimethyl-4-oxo-3,4-dihydroquinazolin-8-yl)ethyl)amino)-N-(methylsulfonyl)picolinamide | 2.63 min, 271 nm, MS (ES+)[b] $C_{29}H_{33}ClN_8O_5S$, requires: 640.2, found: 641.3 $[M + H]^+$ |
| 409 | 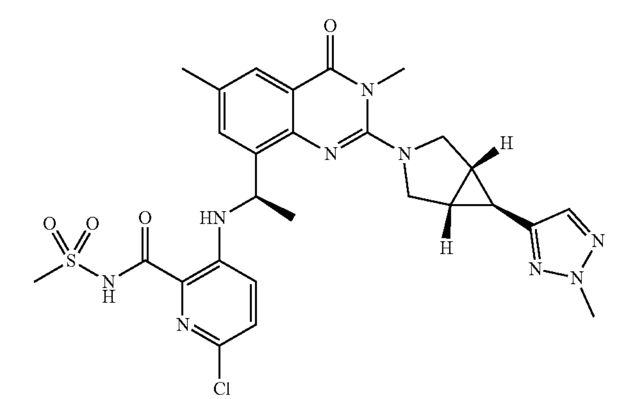 [SMILES: Cc1cc([C@@H](C)Nc2ccc(Cl)nc2C(=O)NS(C)(=O)=O)c2nc(N3C[C@@H]4[C@H](C3)[C@H]4c3cnn(C)n3)n(C)c(=O)c2c1] | 6-chloro-3-(((R)-1-(3,6-dimethyl-2-((1R,5S,6R)-6-(2-methyl-2H-1,2,3-triazol-4-yl)-3-azabicyclo[3.1.0]hexan-3-yl)-4-oxo-3,4-dihydroquinazolin-8-yl)ethyl)amino)-N-(methylsulfonyl)picolinamide | 2.36 min, 254 nm, MS (ES+)[b] $C_{27}H_{30}ClN_9O_4S$, requires: 611.1, found: 612.2 $[M + H]^+$ |

TABLE E4-continued compound list prepared according to Route A in Example 4

| Cpd. ID | Structure | Name | LCMS |
|---|---|---|---|
| 410 | 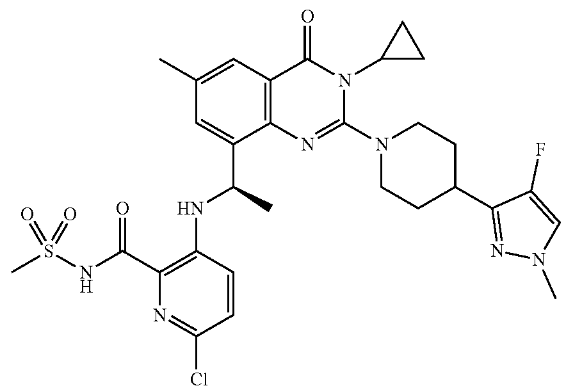 [SMILES: Cc1cc([C@@H](C)Nc2ccc(Cl)nc2C(=O)NS(C)(=O)=O)c2nc(N3CCC(c4nn(C)cc4F)CC3)n(C3CC3)c(=O)c2c1] | (R)-6-chloro-3-((1-(3-cyclopropyl-2-(4-(4-fluoro-1-methyl-1H-pyrazol-3-yl)piperidin-1-yl)-6-methyl-4-oxo-3,4-dihydroquinazolin-8-yl)ethyl)amino)-N-(methylsulfonyl)picolinamide | 2.49 min, 254 nm, MS (ES+)$^b$ C$_{30}$H$_{34}$ClFN$_8$O$_4$S, requires: 656.2, found: 657.2 [M + H]$^+$ |
| 411 | 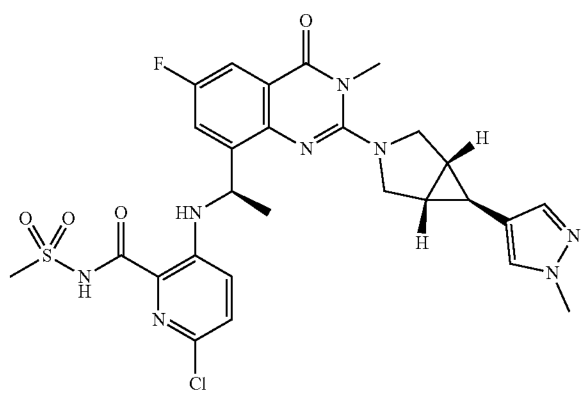 [SMILES: C[C@@H](Nc1ccc(Cl)nc1C(=O)NS(C)(=O)=O)c1cc(F)cc2c(=O)n(C)c(N3C[C@@H]4[C@H](C3)[C@H]4c3cnn(C)c3)nc12] | 6-chloro-3-(((R)-1-(6-fluoro-3-methyl-2-((1R,5S,6S)-6-(1-methyl-1H-pyrazol-4-yl)-3-azabicyclo[3.1.0]hexan-3-yl)-4-oxo-3,4-dihydroquinazolin-8-yl)ethyl)amino)-N-(methylsulfonyl)picolinamide | 2.27 min, 254 nm, MS (ES+)$^b$ C$_{27}$H$_{28}$ClFN$_8$O$_4$S, requires: 614.1, found: 615.2 [M + H]$^+$ |
| 412 | 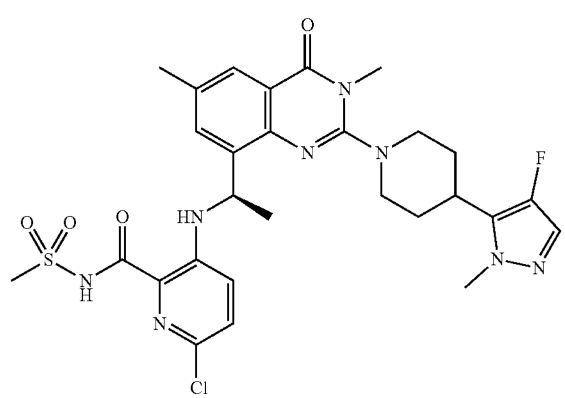 [SMILES: Cc1cc([C@@H](C)Nc2ccc(Cl)nc2C(=O)NS(C)(=O)=O)c2nc(N3CCC(c4c(F)cnn4C)CC3)n(C)c(=O)c2c1] | (R)-6-chloro-3-((1-(2-(4-(4-fluoro-1-methyl-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.46 min, 254 nm, MS (ES+)$^b$ C$_{28}$H$_{32}$ClFN$_8$O$_4$S, requires: 630.1, found: 631.2 [M + H]$^+$ |

TABLE E4-continued compound list prepared according to Route A in Example 4

| Cpd. ID | Name | LCMS |
|---|---|---|
| 413 | (R)-6-chloro-3-((1-(2-(4-(1-(difluoromethyl)-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.42 min, 254 nm, MS (ES+)[b] $C_{28}H_{31}ClF_2N_8O_4S$, requires: 648.1, found: 649.2 [M + H]+ |
| 414 | (R)-6-chloro-3-((1-(2-(4-(1-(difluoromethyl)-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.41 min, 254 nm, MS (ES+)[b] $C_{28}H_{31}ClF_2N_8O_4S$, requires: 648.1, found: 649.2 [M + H]+ |
| 415 | 6-chloro-3-(((R)-1-(2-((1R,5S,6R)-6-(1,4-dimethyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.32 min, 220 nm, MS (ES+)[b] $C_{29}H_{33}ClN_8O_4S$, requires: 624.2, found: 625.2 [M + H]+ |
| 416 | 6-chloro-3-(((R)-1-(3,6-dimethyl-2-((1R,5S,6S)-6-(3-methyl-1H-pyrazol-1-yl)-3-azabicyclo[3.1.0]hexan-3-yl)-4-oxo-3,4-dihydroquinazolin-8-yl)ethyl)amino)-N-(methylsulfonyl)picolinamide | 2.23 min, 270 nm, MS (ES+)[b] $C_{28}H_{31}ClN_8O_4S$, requires: 610.1, found: 611.1 [M + H]+ |

TABLE E4-continued compound list prepared according to Route A in Example 4

| Cpd. ID | Structure | Name | LCMS |
|---|---|---|---|
| 417 | 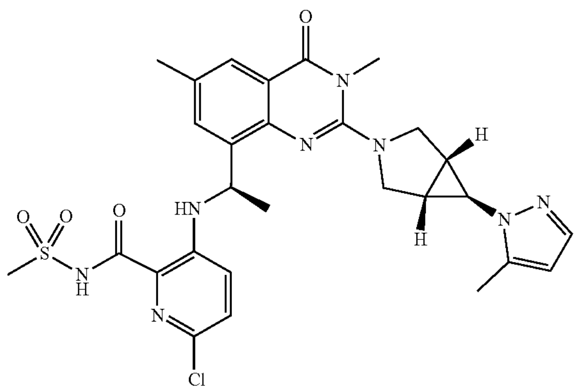 [SMILES: Cc1cc([C@@H](C)Nc2ccc(Cl)nc2C(=O)NS(C)(=O)=O)c2nc(N3C[C@@H]4[C@H](C3)[C@H]4n3nccc3C)n(C)c(=O)c2c1] | 6-chloro-3-(((R)-1-(3,6-dimethyl-2-((1R,5S,6S)-6-(5-methyl-1H-pyrazol-1-yl)-3-azabicyclo[3.1.0]hexan-3-yl)-4-oxo-3,4-dihydroquinazolin-8-yl)ethyl)amino)-N-(methylsulfonyl)picolinamide | 2.29 min, 270 nm, MS (ES+)$^b$ C$_{28}$H$_{31}$ClN$_8$O$_4$S, requires: 610.1, found: 611.2 [M + H]$^+$ |
| 418 | 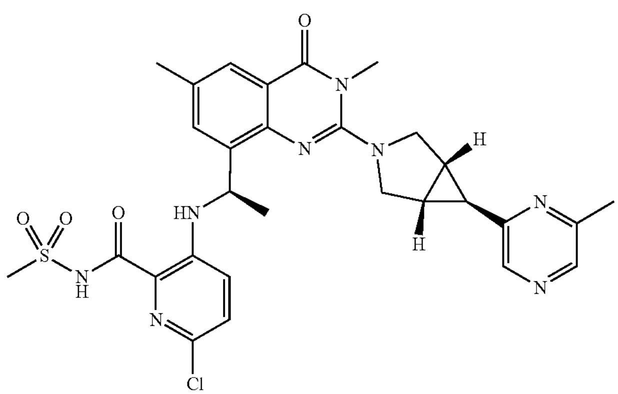 | 6-chloro-3-(((R)-1-(3,6-dimethyl-2-((1R,5S,6R)-6-(6-methylpyrazin-2-yl)-3-azabicyclo[3.1.0]hexan-3-yl)-4-oxo-3,4-dihydroquinazolin-8-yl)ethyl)amino)-N-(methylsulfonyl)picolinamide | 2.39 min, 275 nm, MS (ES+)$^b$ C$_{29}$H$_{31}$ClN$_8$O$_4$S, requires: 622.1, found: 623.2 [M + H]$^+$ |
| 419 | 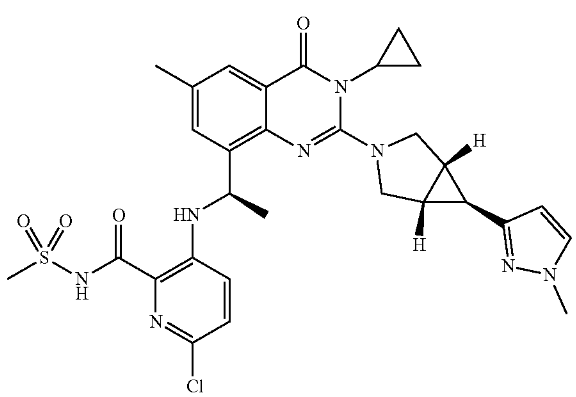 [SMILES: Cc1cc([C@@H](C)Nc2ccc(Cl)nc2C(=O)NS(C)(=O)=O)c2nc(N3C[C@@H]4[C@H](C3)[C@H]4c3ccn(C)n3)n(C3CC3)c(=O)c2c1] | 6-chloro-3-(((R)-1-(3-cyclopropyl-6-methyl-2-((1R,5S,6R)-6-(1-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.27 min, 210 nm, MS (ES+)$^b$ C$_{30}$H$_{33}$ClN$_8$O$_4$S, requires: 636.2, found: 637.2 [M + H]$^+$ |

TABLE E4-continued compound list prepared according to Route A in Example 4

| Cpd. ID | Structure | Name | LCMS |
|---|---|---|---|
| 420 | 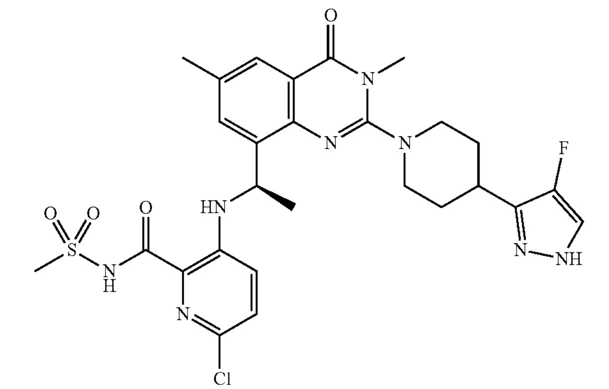 [SMILES: Cc1cc([C@@H](C)Nc2ccc(Cl)nc2C(=O)NS(C)(=O)=O)c2nc(N3CCC(c4n[nH]cc4F)CC3)n(C)c(=O)c2c1] | (R)-6-chloro-3-((1-(2-(4-(4-fluoro-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.22 min, 254 nm, MS (ES+)[b] $C_{27}H_{30}ClFN_8O_4S$, requires: 616.1, found: 617.2 $[M + H]^+$ |
| 421 | 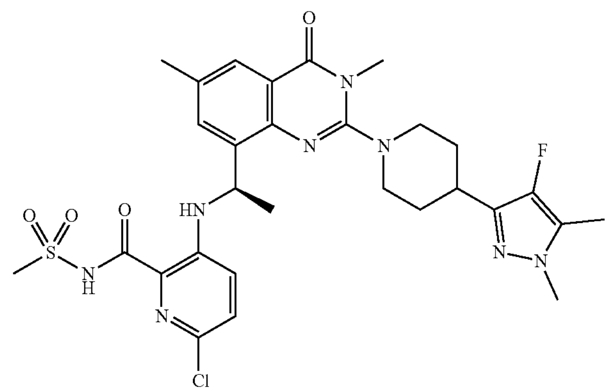 | (R)-6-chloro-3-((1-(2-(4-(4-fluoro-1,5-dimethyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.43 min, 254 nm, MS (ES+)[b] $C_{29}H_{34}ClFN_8O_4S$, requires: 644.2, found: 645.2 $[M + H]^+$ |
| 422 | 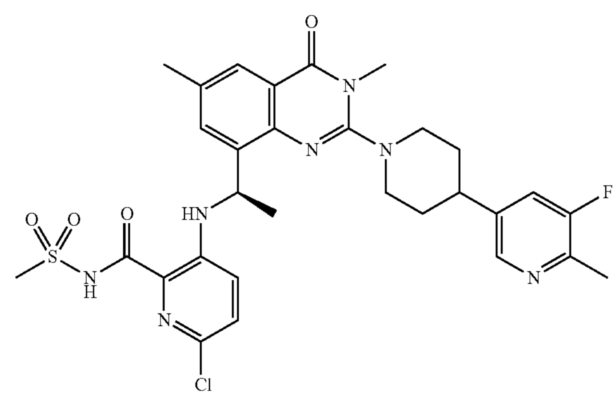 | (R)-6-chloro-3-((1-(2-(4-(5-fluoro-6-methylpyridin-3-yl)piperidin-1-yl)-3,6-dimethyl-4-oxo-3,4-dihydroquinazolin-8-yl)ethyl)amino)-N-(methylsulfonyl)picolinamide | 2.46 min, 220 nm, MS (ES+)[b] $C_{30}H_{33}ClFN_7O_4S$, requires: 641.2, found: 642.2 $[M + H]^+$ |
| 423 | 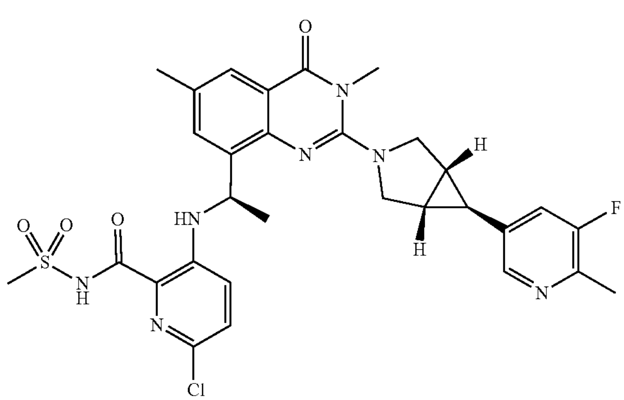 [SMILES: Cc1cc([C@@H](C)Nc2ccc(Cl)nc2C(=O)NS(C)(=O)=O)c2nc(N3C[C@@H]4[C@H](C3)[C@H]4c3cnc(C)c(F)c3)n(C)c(=O)c2c1] | 6-chloro-3-(((R)-1-(2-((1R,5S,6S)-6-(5-fluoro-6-methylpyridin-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.42 min, 272 nm, MS (ES+)[b] $C_{30}H_{31}ClFN_7O_4S$, requires: 639.1, found: 640.2 $[M + H]^+$ |

TABLE E4-continued compound list prepared according to Route A in Example 4

| Cpd. ID | Structure | Name | LCMS |
|---|---|---|---|
| 424 | 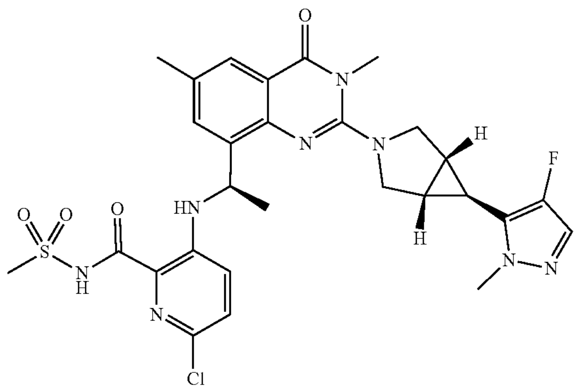 [SMILES: Cc1cc([C@@H](C)Nc2ccc(Cl)nc2C(=O)NS(C)(=O)=O)c2nc(N3C[C@@H]4[C@H](C3)[C@H]4c3c(F)cnn3C)n(C)c(=O)c2c1] | 6-chloro-3-(((R)-1-(2-(((1R,5S,6R)-6-(4-fluoro-1-methyl-1H-pyrazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 3.53 min, 254 nm, MS (ES+)$^c$ C$_{28}$H$_{30}$ClFN$_8$O$_4$S, requires: 628.2, found: 629.2 [M + H]$^+$ |
| 425 | 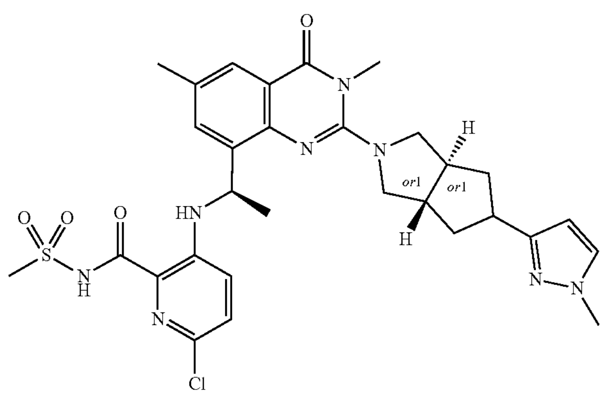 | 6-chloro-3-(((R)-1-(3,6-dimethyl-2-((3aS*,6aS*)-5-(1-methyl-1H-pyrazol-3-yl)hexahydrocyclopenta[c]pyrrol-2(1H)-yl)-4-oxo-3,4-dihydroquinazolin-8-yl)ethyl)amino)-N-(methylsulfonyl)picolinamide | 4.62 min, 254 nm, MS (ES+)$^c$ C$_{30}$H$_{35}$ClN$_8$O$_4$S, requires: 638.2, found: 639.2 [M + H]$^+$ |
| 426 | 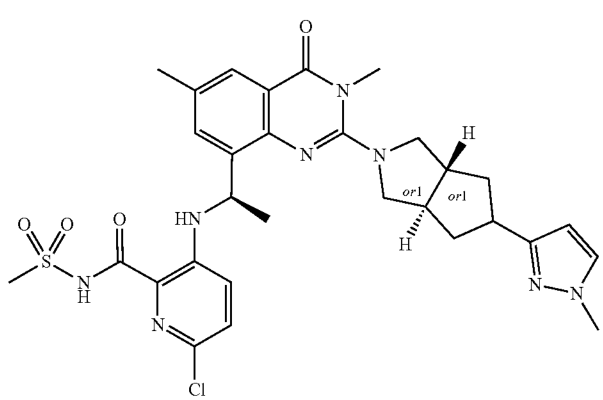 | 6-chloro-3-(((R)-1-(3,6-dimethyl-2-((3aR*,6aR*)-5-(1-methyl-1H-pyrazol-3-yl)hexahydrocyclopenta[c]pyrrol-2(1H)-yl)-4-oxo-3,4-dihydroquinazolin-8-yl)ethyl)amino)-N-(methylsulfonyl)picolinamide | 4.56 min, 254 nm, MS (ES+)$^c$ C$_{30}$H$_{35}$ClN$_8$O$_4$S, requires: 638.2, found: 639.2 [M + H]$^+$ |

TABLE E4-continued compound list prepared according to Route A in Example 4

| Cpd. ID | Structure | Name | LCMS |
|---|---|---|---|
| 427 | 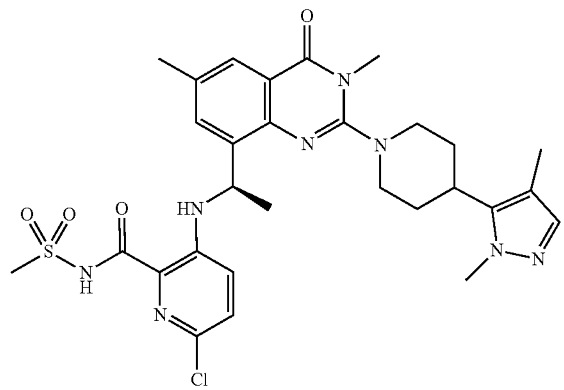 [SMILES: Cc1cc([C@@H](C)Nc2ccc(Cl)nc2C(=O)NS(C)(=O)=O)c2nc(N3CCC(c4c(C)cnn4C)CC3)n(C)c(=O)c2c1] | (R)-6-chloro-3-((1-(2-(4-(1,4-dimethyl-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.27 min, 210 nm, MS (ES+)[b] $C_{29}H_{35}ClN_8O_4S$, requires: 626.2, found: 627.2 $[M + H]^+$ |
| 428 | 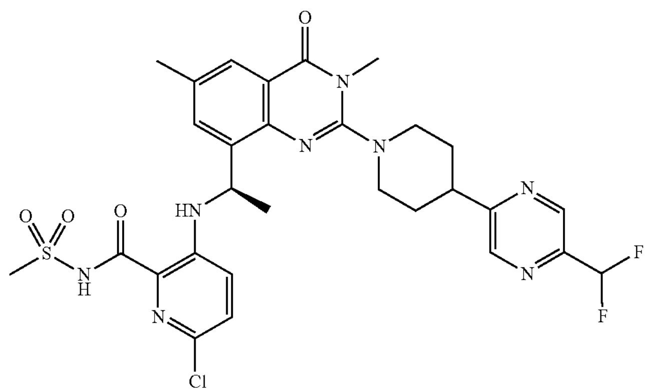 [SMILES: Cc1cc([C@@H](C)Nc2ccc(Cl)nc2C(=O)NS(C)(=O)=O)c2nc(N3CCC(c4cnc(C(F)F)cn4)CC3)n(C)c(=O)c2c1] | (R)-6-chloro-3-((1-(2-(4-(5-(difluoromethyl)pyrazin-2-yl)piperidin-1-yl)-3,6-dimethyl-4-oxo-3,4-dihydroquinazolin-8-yl)ethyl)amino)-N-(methylsulfonyl)picolinamide | 2.44 min, 270 nm, MS (ES+)[b] $C_{29}H_{31}ClF_2N_8O_4S$, requires: 660.1, found: 661.2 $[M + H]^+$ |
| 429 | 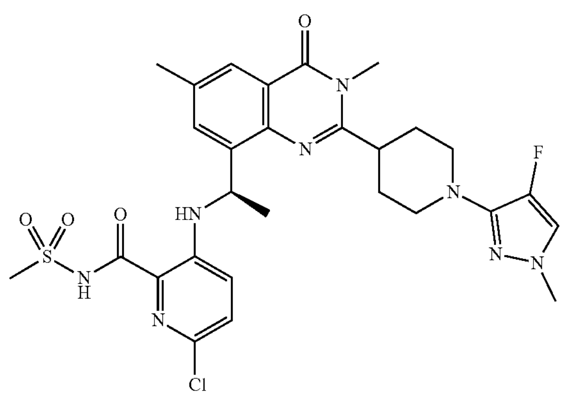 [SMILES: Cc1cc([C@@H](C)Nc2ccc(Cl)nc2C(=O)NS(C)(=O)=O)c2nc(C3CCN(c4nn(C)cc4F)CC3)n(C)c(=O)c2c1] | (R)-6-chloro-3-((1-(2-(1-(4-fluoro-1-methyl-1H-pyrazol-3-yl)piperidin-4-yl)-3,6-dimethyl-4-oxo-3,4-dihydroquinazolin-8-yl)ethyl)amino)-N-(methylsulfonyl)picolinamide | 2.30 min, 254 nm, MS (ES+)[b] $C_{28}H_{32}ClFN_8O_4S$, requires: 630.1, found: 631.2 $[M + H]^+$ |
| 430 | 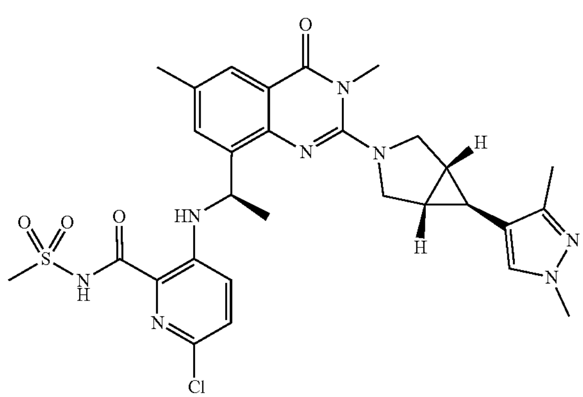 [SMILES: Cc1cc([C@@H](C)Nc2ccc(Cl)nc2C(=O)NS(C)(=O)=O)c2nc(N3C[C@@H]4[C@H](C3)[C@H]4c3cn(C)nc3C)n(C)c(=O)c2c1] | 6-chloro-3-(((R)-1-(2-((1R,5S,6S)-6-(1,3-dimethyl-1H-pyrazol-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.19 min, 254 nm, MS (ES+)[b] $C_{29}H_{33}ClN_8O_4S$, requires: 624.2, found: 625.2 $[M + H]^+$ |

TABLE E4-continued compound list prepared according to Route A in Example 4

| Cpd. ID | Structure | Name | LCMS |
|---|---|---|---|
| 431 | 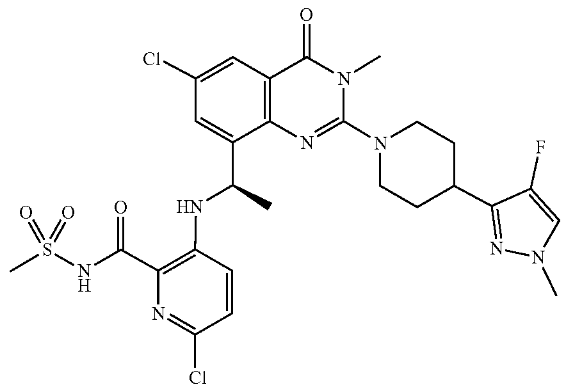 [SMILES: C[C@@H](Nc1ccc(Cl)nc1C(=O)NS(C)(=O)=O)c1cc(Cl)cc2c(=O)n(C)c(N3CCC(c4nn(C)cc4F)CC3)nc12] | (R)-6-chloro-3-((1-(6-chloro-2-(4-(4-fluoro-1-methyl-1H-pyrazol-3-yl)piperidin-1-yl)-3-methyl-4-oxo-3,4-dihydroquinazolin-8-yl)ethyl)amino)-N-(methylsulfonyl)picolinamide | 2.42 min, 254 nm, MS (ES+)[b] $C_{27}H_{29}Cl2FN_8O_4S$, requires: 650.1, found: 651.1 $[M + H]^+$ |
| 432 | 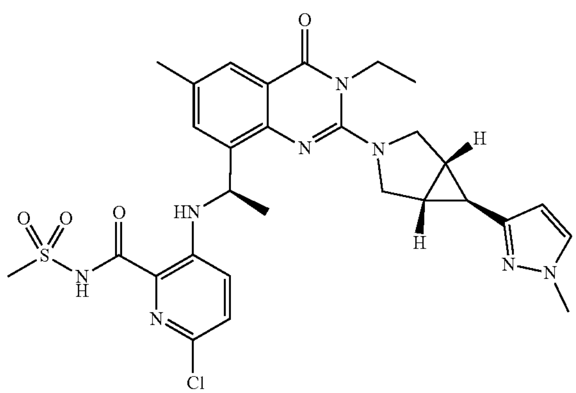 [SMILES: CCn1c(N2C[C@@H]3[C@H](C2)[C@H]3c2ccn(C)n2)nc2c([C@@H](C)Nc3ccc(Cl)nc3C(=O)NS(C)(=O)=O)cc(C)cc2c1=O] | 6-chloro-3-(((R)-1-(3-ethyl-6-methyl-2-((1R,5S,6R)-6-(1-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.51 min, 254 nm, MS (ES+)[b] $C_{29}H_{33}ClN_8O_4S$, requires: 624.2, found: 625.3 $[M + H]^+$ |
| 433 | 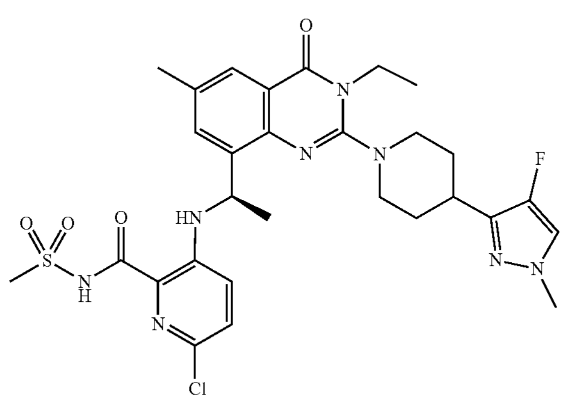 [SMILES: CCn1c(N2CCC(c3nn(C)cc3F)CC2)nc2c([C@@H](C)Nc3ccc(Cl)nc3C(=O)NS(C)(=O)=O)cc(C)cc2c1=O] | (R)-6-chloro-3-((1-(3-ethyl-2-(4-(4-fluoro-1-methyl-1H-pyrazol-3-yl)piperidin-1-yl)-6-methyl-4-oxo-3,4-dihydroquinazolin-8-yl)ethyl)amino)-N-(methylsulfonyl)picolinamide | 2.49 min, 254 nm, MS (ES+)[b] $C_{29}H_{34}ClFN_8O_4S$, requires: 644.2, found: 645.2 $[M + H]^+$ |

TABLE E4-continued compound list prepared according to Route A in Example 4

| Cpd. ID | Structure | Name | LCMS |
|---|---|---|---|
| 434 | 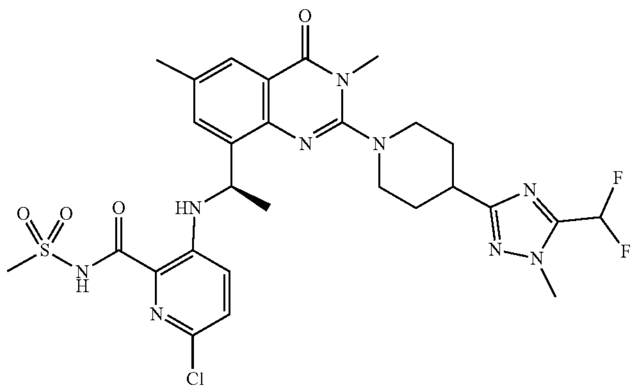 [SMILES: Cc1cc([C@@H](C)Nc2ccc(Cl)nc2C(=O)NS(C)(=O)=O)c2nc(N3CCC(c4nc(C(F)F)n(C)n4)CC3)n(C)c(=O)c2c1] | (R)-6-chloro-3-((1-(2-(4-(5-(difluoromethyl)-1-methyl-1H-1,2,4-triazol-3-yl)piperidin-1-yl)-3,6-dimethyl-4-oxo-3,4-dihydroquinazolin-8-yl)ethyl)amino)-N-(methylsulfonyl)picolinamide | 2.46 min, 270 nm, MS (ES+)[b] $C_{28}H_{32}ClF_2N_9O_4S$, requires: 663.2, found: 664.3 $[M + H]^+$ |
| 435 | 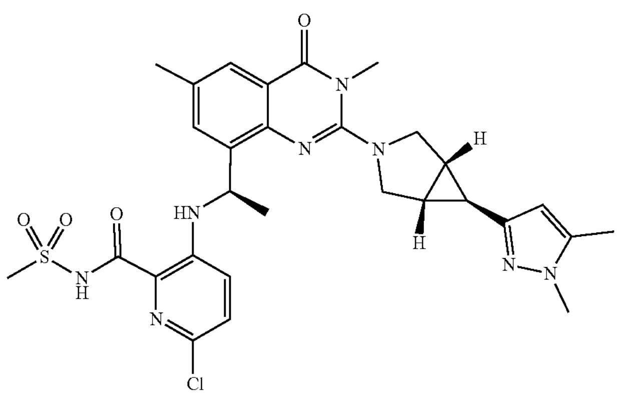 | 6-chloro-3-(((R)-1-(2-((1R,5S,6R)-6-(1,5-dimethyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.31 min, 210 nm, MS (ES+)[b] $C_{29}H_{33}ClN_8O_4S$, requires: 624.2, found: 625.2 $[M + H]^+$ |
| 436 | 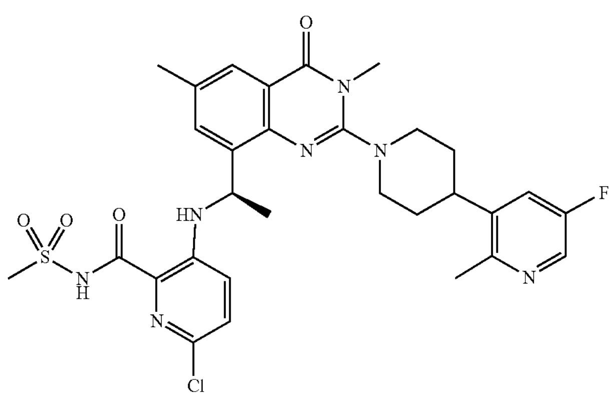 [SMILES: Cc1cc([C@@H](C)Nc2ccc(Cl)nc2C(=O)NS(C)(=O)=O)c2nc(N3CCC(c4cc(F)cnc4C)CC3)n(C)c(=O)c2c1] | (R)-6-chloro-3-((1-(2-(4-(5-fluoro-2-methylpyridin-3-yl)piperidin-1-yl)-3,6-dimethyl-4-oxo-3,4-dihydroquinazolin-8-yl)ethyl)amino)-N-(methylsulfonyl)picolinamide | 2.41 min, 254 nm, MS (ES+)[b] $C_{30}H_{33}ClFN_7O_4S$, requires: 641.2, found: 642.3 $[M + H]^+$ |
| 437 | 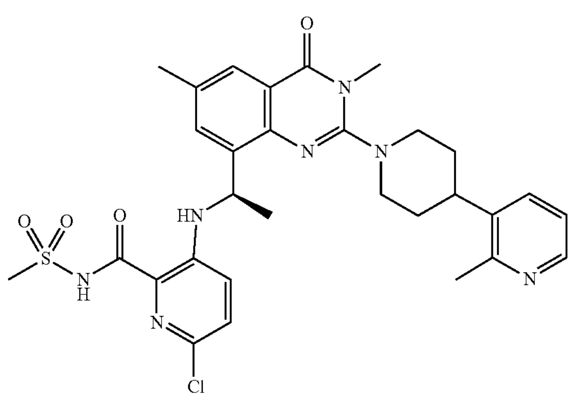 [SMILES: Cc1cc([C@@H](C)Nc2ccc(Cl)nc2C(=O)NS(C)(=O)=O)c2nc(N3CCC(c4cccnc4C)CC3)n(C)c(=O)c2c1] | (R)-6-chloro-3-((1-(3,6-dimethyl-2-(4-(2-methylpyridin-3-yl)piperidin-1-yl)-4-oxo-3,4-dihydroquinazolin-8-yl)ethyl)amino)-N-(methylsulfonyl)picolinamide | 1.91 min, 254 nm, MS (ES+)[b] $C_{30}H_{34}ClN_7O_4S$, requires: 623.2, found: 624.3 $[M + H]^+$ |

TABLE E4-continued compound list prepared according to Route A in Example 4

| Cpd. ID | Structure | Name | LCMS |
|---|---|---|---|
| 438 | 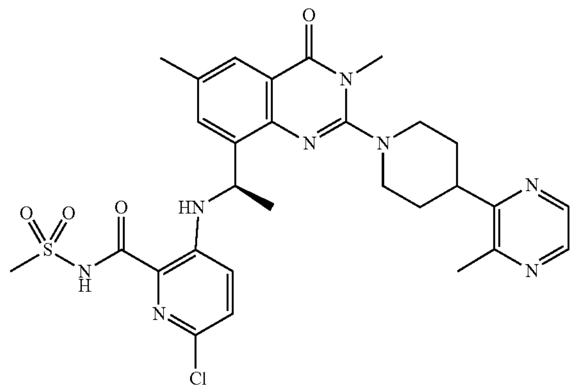 [SMILES: Cc1cc([C@@H](C)Nc2ccc(Cl)nc2C(=O)NS(C)(=O)=O)c2nc(N3CCC(c4nccnc4C)CC3)n(C)c(=O)c2c1] | (R)-6-chloro-3-((1-(3,6-dimethyl-2-(4-(3-methylpyrazin-2-yl)piperidin-1-yl)-4-oxo-3,4-dihydroquinazolin-8-yl)ethyl)amino)-N-(methylsulfonyl)picolinamide | 2.32 min, 254 nm, MS (ES+)[b] $C_{29}H_{33}ClN_8O_4S$, requires: 624.2, found: 625.2 $[M + H]^+$ |
| 439 | 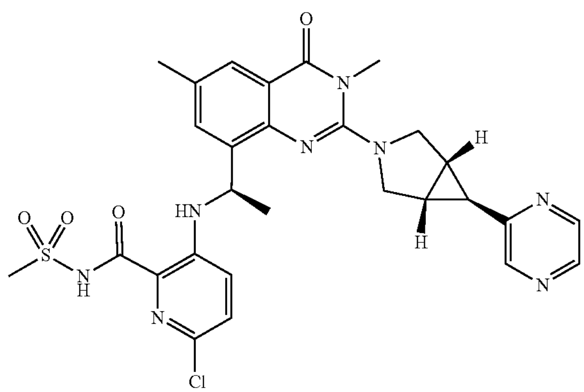 [SMILES: Cc1cc([C@@H](C)Nc2ccc(Cl)nc2C(=O)NS(C)(=O)=O)c2nc(N3C[C@@H]4[C@H](C3)[C@H]4c3cnccn3)n(C)c(=O)c2c1] | 6-chloro-3-(((R)-1-(3,6-dimethyl-4-oxo-2-(((1R,5S,6R)-6-(pyrazin-2-yl)-3-azabicyclo[3.1.0]hexan-3-yl)-3,4-dihydroquinazolin-8-yl)ethyl)amino)-N-(methylsulfonyl)picolinamide | 2.43 min, 215 nm, MS (ES+)[b] $C_{28}H_{29}ClN_8O_4S$, requires: 608.1, found: 609.2 $[M + H]^+$ |
| 440 | 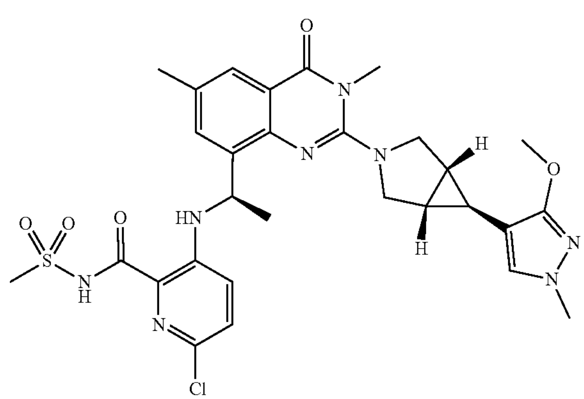 [SMILES: COc1nn(C)cc1[C@H]1[C@@H]2CN(c3nc4c([C@@H](C)Nc5ccc(Cl)nc5C(=O)NS(C)(=O)=O)cc(C)cc4c(=O)n3C)C[C@@H]21] | 6-chloro-3-(((R)-1-(2-(((1R,5S,6S)-6-(3-methoxy-1-methyl-1H-pyrazol-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.41 min, 215 nm, MS (ES+)[b] $C_{29}H_{33}ClN_8O_5S$, requires: 640.2, found: 641.3 $[M + H]^+$ |

TABLE E4-continued compound list prepared according to Route A in Example 4

| Cpd. ID | Structure | Name | LCMS |
|---|---|---|---|
| 441 | 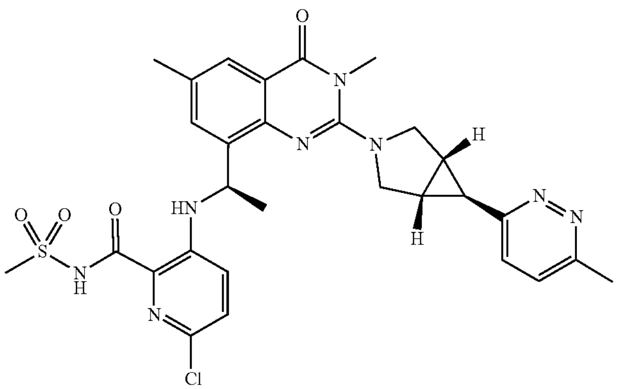 | 6-chloro-3-(((R)-1-(3,6-dimethyl-2-((1R,5S,6R)-6-(6-methylpyridazin-3-yl)-3-azabicyclo[3.1.0]hexan-3-yl)-4-oxo-3,4-dihydroquinazolin-8-yl)ethyl)amino)-N-(methylsulfonyl)picolinamide | 2.04 min, 270 nm MS (ES+)[b] $C_{29}H_{31}ClN_8O_4S$, requires: 622.1, found: 623.2 $[M + H]^+$ |
| 442 | 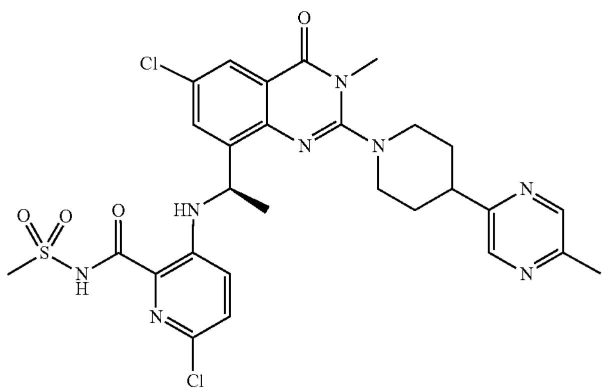 | (R)-6-chloro-3-((1-(6-chloro-3-methyl-2-(4-(5-methylpyrazin-2-yl)piperidin-1-yl)-4-oxo-3,4-dihydroquinazolin-8-yl)ethyl)amino)-N-(methylsulfonyl)picolinamide | 2.37 min, 254 nm, MS (ES+)[b] $C_{28}H_{30}Cl2N_8O_4S$, requires: 644.1, found: 645.2 $[M + H]^+$ |
| 443 | 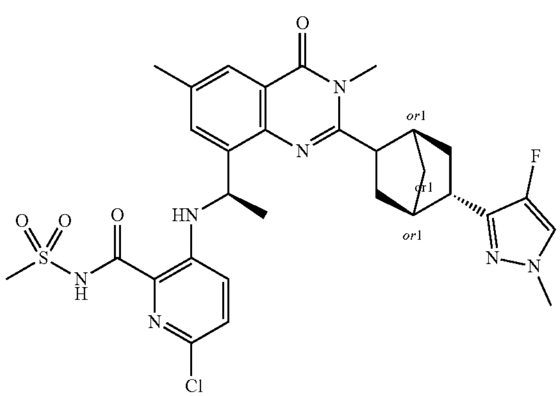 [SMILES: Cc1cc([C@@H](C)Nc2ccc(Cl)nc2C(=O)NS(C)(=O)=O)c2nc(C3C[C@H]4C[C@@H]3C[C@@H]4c3nn(C)cc3F)n(C)c(=O)c2c1] | 6-chloro-3-(((R)-1-(2-((1R*,4S*,5S*)-5-(4-fluoro-1-methyl-1H-pyrazol-3-yl)-2-azabicyclo[2.2.1]heptan-2-yl)-3,6-dimethyl-4-oxo-3,4-dihydroquinazolin-8-yl)ethyl)amino)-N-(methylsulfonyl)picolinamide | 2.37 min, 254 nm, MS (ES+)[b] $C_{29}H_{32}ClFN_8O_4S$, requires: 642.1, found: 643.2 $[M + H]^+$ |
| 444 | 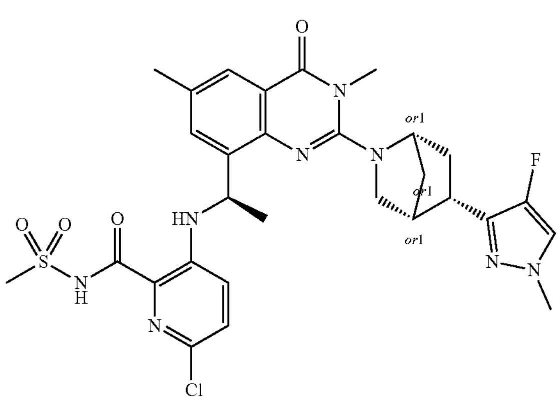 [SMILES: Cc1cc([C@@H](C)Nc2ccc(Cl)nc2C(=O)NS(C)(=O)=O)c2nc(N3C[C@@H]4C[C@H]3C[C@@H]4c3nn(C)cc3F)n(C)c(=O)c2c1] | 6-chloro-3-(((R)-1-(2-((1R*,4S*,5R*)-5-(4-fluoro-1-methyl-1H-pyrazol-3-yl)-2-azabicyclo[2.2.1]heptan-2-yl)-3,6-dimethyl-4-oxo-3,4-dihydroquinazolin-8-yl)ethyl)amino)-N-(methylsulfonyl)picolinamide | 2.37 min, 254 nm, MS (ES+)[b] $C_{29}H_{32}ClFN_8O_4S$, requires: 642.1, found: 643.2 $[M + H]^+$ |

TABLE E4-continued compound list prepared according to Route A in Example 4

| Cpd. ID | Structure | Name | LCMS |
|---|---|---|---|
| 445 | 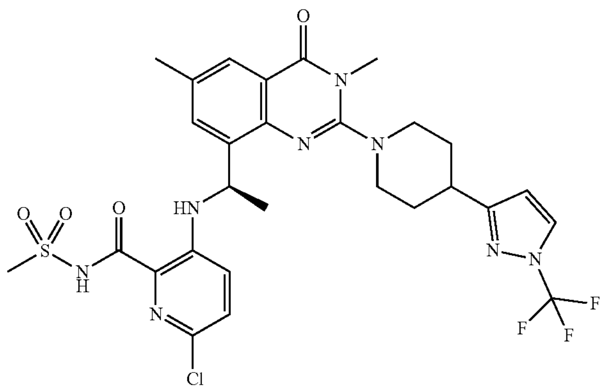 [SMILES: Cc1cc([C@@H](C)Nc2ccc(Cl)nc2C(=O)NS(C)(=O)=O)c2nc(N3CCC(c4ccn(C(F)(F)F)n4)CC3)n(C)c(=O)c2c1] | (R)-6-chloro-3-((1-(3,6-dimethyl-4-oxo-2-(4-(1-(trifluoromethyl)-1H-pyrazol-3-yl)piperidin-1-yl)-3,4-dihydroquinazolin-8-yl)ethyl)amino)-N-(methylsulfonyl)picolinamide | 2.51 min, 254 nm, MS (ES+)[b] $C_{28}H_{30}ClF_3N_8O_4S$, requires: 666.1, found: 667.2 [M + H]+ |
| 446 | 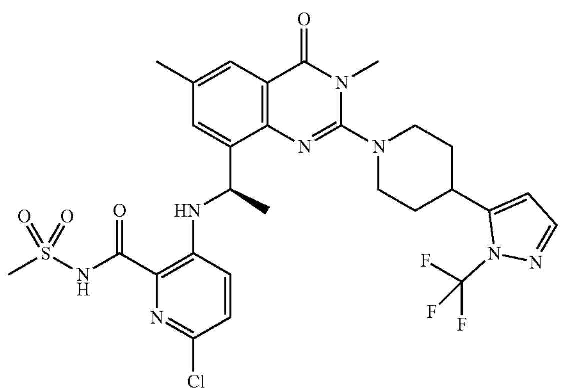 [SMILES: Cc1cc([C@@H](C)Nc2ccc(Cl)nc2C(=O)NS(C)(=O)=O)c2nc(N3CCC(c4ccnn4C(F)(F)F)CC3)n(C)c(=O)c2c1] | (R)-6-chloro-3-((1-(3,6-dimethyl-4-oxo-2-(4-(1-(trifluoromethyl)-1H-pyrazol-5-yl)piperidin-1-yl)-3,4-dihydroquinazolin-8-yl)ethyl)amino)-N-(methylsulfonyl)picolinamide | 2.51 min, 254 nm, MS (ES+)[b] $C_{28}H_{30}ClF_3N_8O_4S$, requires: 666.1, found: 667.2 [M + H]+ |
| 447 | 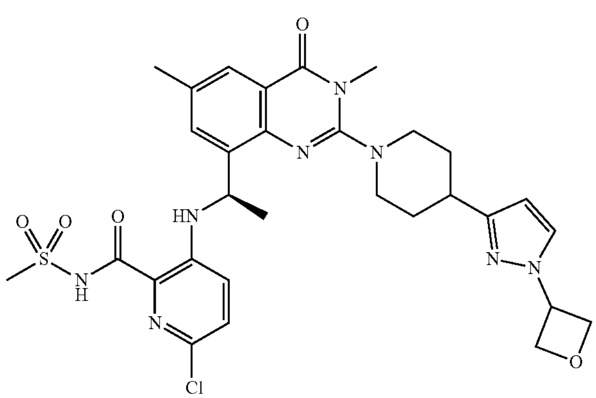 [SMILES: Cc1cc([C@@H](C)Nc2ccc(Cl)nc2C(=O)NS(C)(=O)=O)c2nc(N3CCC(c4ccn(C5COC5)n4)CC3)n(C)c(=O)c2c1] | (R)-6-chloro-3-((1-(3,6-dimethyl-2-(4-(1-(oxetan-3-yl)-1H-pyrazol-3-yl)piperidin-1-yl)-4-oxo-3,4-dihydroquinazolin-8-yl)ethyl)amino)-N-(methylsulfonyl)picolinamide | 2.23 min, 254 nm, MS (ES+)[b] $C_{30}H_{35}ClN_8O_5S$, requires: 654.2, found: 655.2 [M + H]+ |

TABLE E4-continued compound list prepared according to Route A in Example 4

| Cpd. ID | Structure | Name | LCMS |
|---|---|---|---|
| 448 | 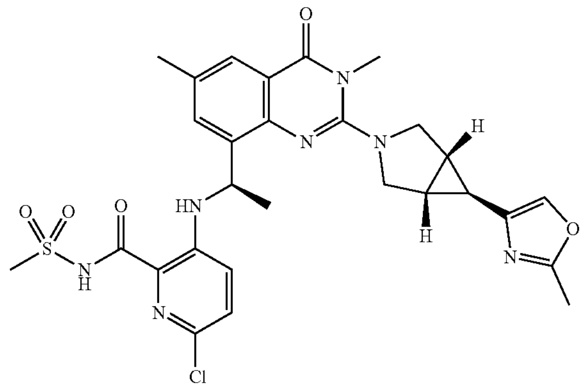 [SMILES: Cc1cc([C@@H](C)Nc2ccc(Cl)nc2C(=O)NS(C)(=O)=O)c2nc(N3C[C@@H]4[C@H](C3)[C@H]4c3coc(C)n3)n(C)c(=O)c2c1] | 6-chloro-3-(((R)-1-(3,6-dimethyl-2-((1R,5S,6R)-6-(2-methyloxazol-4-yl)-3-azabicyclo[3.1.0]hexan-3-yl)-4-oxo-3,4-dihydroquinazolin-8-yl)ethyl)amino)-N-(methylsulfonyl)picolinamide | 2.60 min, 254 nm, MS (ES+)[b] $C_{28}H_{30}ClN_7O_5S$, requires: 611.1, found: 612.1 $[M + H]^+$ |
| 449 | 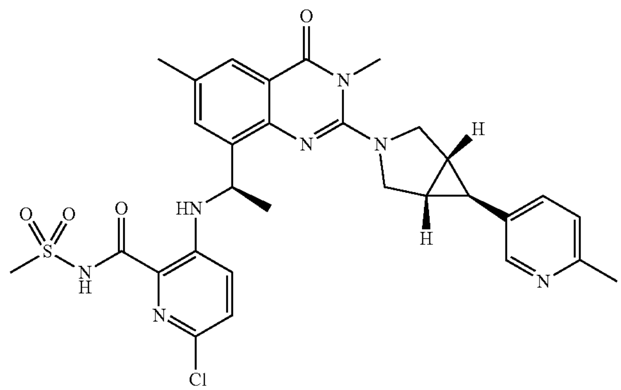 | 6-chloro-3-(((R)-1-(3,6-dimethyl-2-((1R,5S,6S)-6-(6-methylpyridin-3-yl)-3-azabicyclo[3.1.0]hexan-3-yl)-4-oxo-3,4-dihydroquinazolin-8-yl)ethyl)amino)-N-(methylsulfonyl)picolinamide | 1.99 min, 272 nm, MS (ES+)[b] $C_{30}H_{32}ClN_7O_4S$, requires: 621.1, found: 622.2 $[M + H]^+$ |
| 450 | 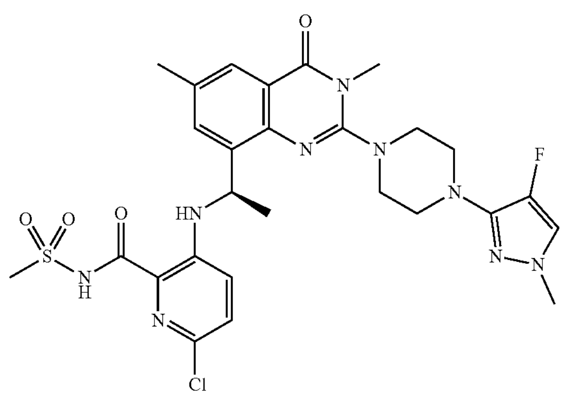 | (R)-6-chloro-3-((1-(2-(4-(4-fluoro-1-methyl-1H-pyrazol-3-yl)piperazin-1-yl)-3,6-dimethyl-4-oxo-3,4-dihydroquinazolin-8-yl)ethyl)amino)-N-(methylsulfonyl)picolinamide | 2.60 min, 254 nm, MS (ES+)[b] $C_{27}H_{31}ClFN_9O_4S$, requires: 631.1, found: 632.2 $[M + H]^+$ |
| 451 | 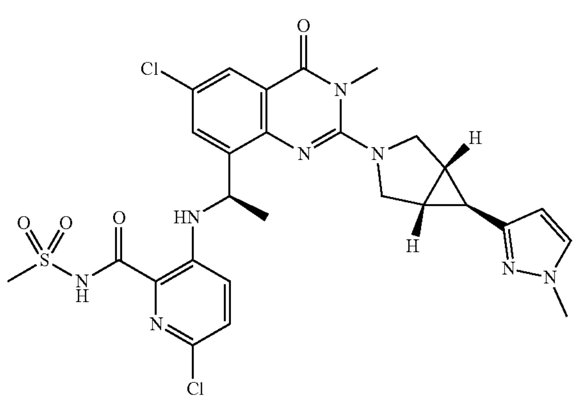 [SMILES: C[C@@H](Nc1ccc(Cl)nc1C(=O)NS(C)(=O)=O)c1cc(Cl)cc2c(=O)n(C)c(N3C[C@@H]4[C@H](C3)[C@H]4c3ccn(C)n3)nc12] | 6-chloro-3-(((R)-1-(6-chloro-3-methyl-2-((1R,5S,6R)-6-(1-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.51 min, 270 nm, MS (ES+)[b] $C_{27}H_{28}Cl2N_8O_4S$, requires: 630.1, found: 631.2 $[M + H]^+$ |

TABLE E4-continued compound list prepared according to Route A in Example 4

| Cpd. ID | Structure | Name | LCMS |
|---|---|---|---|
| 452 | 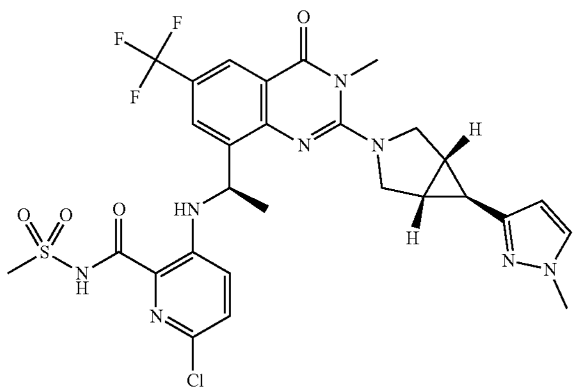 [SMILES: C[C@@H](Nc1ccc(Cl)nc1C(=O)NS(C)(=O)=O)c1cc(C(F)(F)F)cc2c(=O)n(C)c(N3C[C@@H]4[C@H](C3)[C@H]4c3ccn(C)n3)nc12] | 6-chloro-3-(((R)-1-(3-methyl-2-((1R,5S,6R)-6-(1-methyl-1H-pyrazol-3-yl)-3-azabicyclo[3.1.0]hexan-3-yl)-4-oxo-6-(trifluoromethyl)-3,4-dihydroquinazolin-8-yl)ethyl)amino)-N-(methylsulfonyl)picolinamide | 2.29 min, 268 nm, MS (ES+)[b] $C_{28}H_{28}ClF_3N_8O_4S$, requires: 664.1, found: 665.2 $[M + H]^+$ |
| 453 | 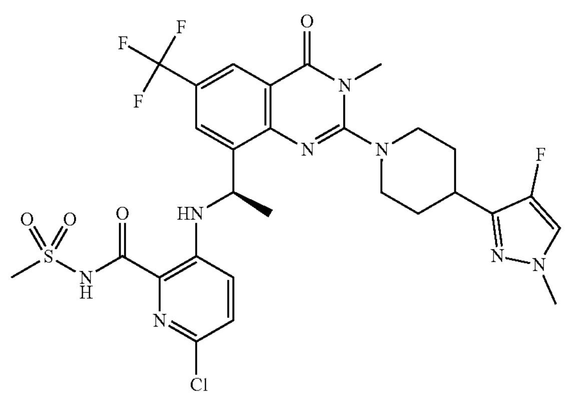 [SMILES: C[C@@H](Nc1ccc(Cl)nc1C(=O)NS(C)(=O)=O)c1cc(C(F)(F)F)cc2c(=O)n(C)c(N3CCC(c4nn(C)cc4F)CC3)nc12] | (R)-6-chloro-3-((1-(2-(4-(4-fluoro-1-methyl-1H-pyrazol-3-yl)piperidin-1-yl)-3-methyl-4-oxo-6-(trifluoromethyl)-3,4-dihydroquinazolin-8-yl)ethyl)amino)-N-(methylsulfonyl)picolinamide | 2.41 min, 268 nm, MS (ES+)[b] $C_{28}H_{29}ClF_4N_8O_4S$, requires: 684.1, found: 685.1 $[M + H]^+$ |
| 454 | 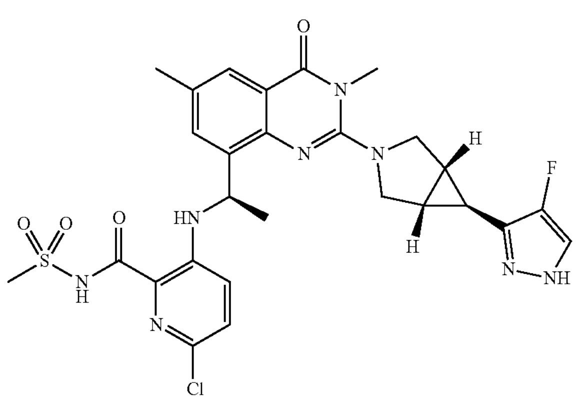 [SMILES: Cc1cc([C@@H](C)Nc2ccc(Cl)nc2C(=O)NS(C)(=O)=O)c2nc(N3C[C@@H]4[C@H](C3)[C@H]4c3n[nH]cc3F)n(C)c(=O)c2c1] | 6-chloro-3-(((R)-1-(2-((1R,5S,6R)-6-(4-fluoro-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.11 min, 270 nm, MS (ES+)[b] $C_{27}H_{28}ClFN_8O_4S$, requires: 614.1, found: 615.2 $[M + H]^+$ |

TABLE E4-continued compound list prepared according to Route A in Example 4

| Cpd. ID | Structure | Name | LCMS |
|---|---|---|---|
| 455 | 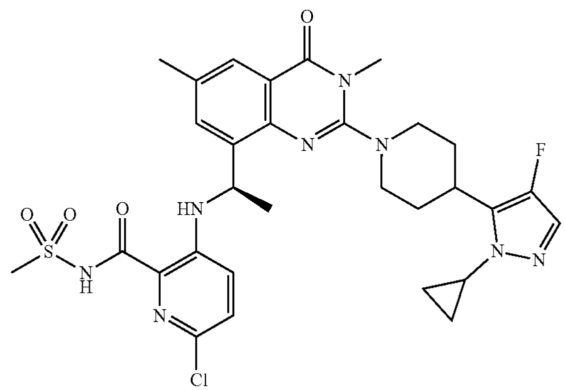 [SMILES: Cc1cc([C@@H](C)Nc2ccc(Cl)nc2C(=O)NS(C)(=O)=O)c2nc(N3CCC(c4c(F)cnn4C4CC4)CC3)n(C)c(=O)c2c1] | (R)-6-chloro-3-((1-(2-(4-(1-cyclopropyl-4-fluoro-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.45 min, 254 nm, MS (ES+)$^b$ $C_{30}H_{34}ClFN_8O_4S$, requires: 656.2, found: 657.2 [M + H]$^+$ |
| 456 | 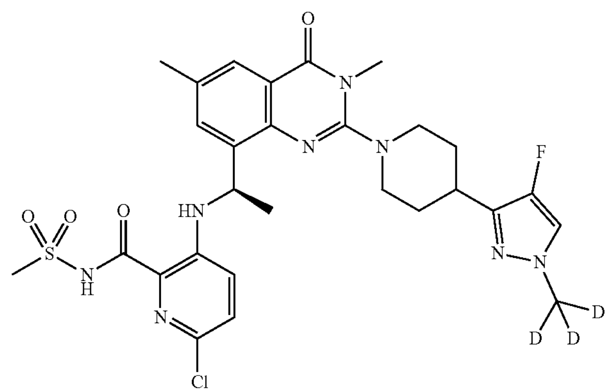 [SMILES: [2H]C([2H])([2H])n1cc(F)c(C2CCN(c3nc4c([C@@H](C)Nc5ccc(Cl)nc5C(=O)NS(C)(=O)=O)cc(C)cc4c(=O)n3C)CC2)n1] | (R)-6-chloro-3-((1-(2-(4-(4-fluoro-1-(methyl-d3)-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.33 min, 270 nm, MS (ES+)$^b$ $C_{28}H_{29}D_3ClFN_8O_4S$, requires: 633.2, found: 634.2 [M + H]$^+$ |
| 457 | 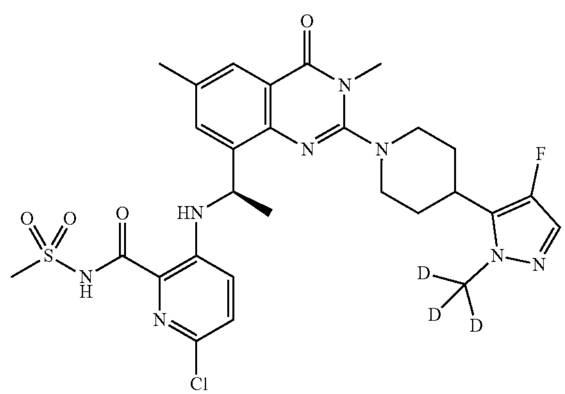 [SMILES: [2H]C([2H])([2H])n1ncc(F)c1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(2-(4-(4-fluoro-1-(methyl-d3)-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.33 min, 270 nm, MS (ES+)$^b$ $C_{28}H_{29}D_3ClFN_8O_4S$, requires: 633.2, found: 634.2 [M + H]$^+$ |
| 458 | 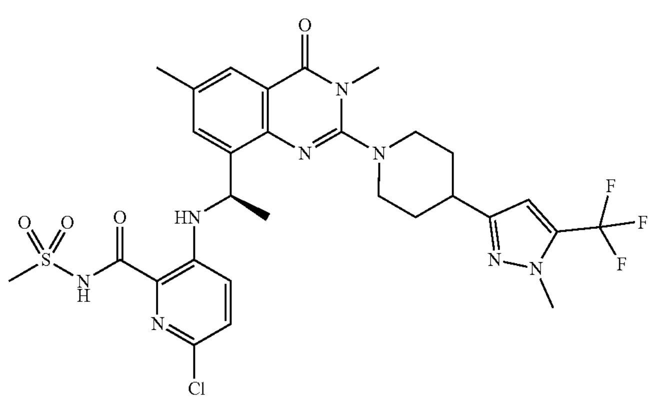 [SMILES: Cc1cc([C@@H](C)Nc2ccc(Cl)nc2C(=O)NS(C)(=O)=O)c2nc(N3CCC(c4cc(C(F)(F)F)n(C)n4)CC3)n(C)c(=O)c2c1] | (R)-6-chloro-3-((1-(3,6-dimethyl-2-(4-(1-methyl-5-(trifluoromethyl)-1H-1,2,4-triazol-3-yl)piperidin-1-yl)-4-oxo-3,4-dihydroquinazolin-8-yl)ethyl)amino)-N-(methylsulfonyl)picolinamide | 2.42 min, 254 nm, MS (ES+)$^b$ $C_{28}H_{31}ClF_3N_9O_4S$, requires: 681.1, found: 682.2 [M + H]$^+$ |

TABLE E4-continued compound list prepared according to Route A in Example 4

| Cpd. ID | Structure | Name | LCMS |
|---|---|---|---|
| 459 | 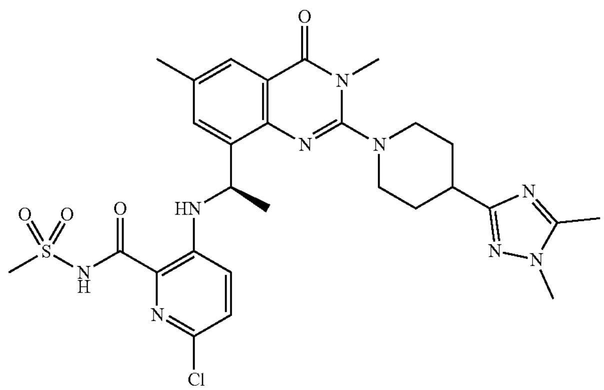 | (R)-6-chloro-3-((1-(2-(4-(1,5-dimethyl-1H-1,2,4-triazol-3-yl)piperidin-1-yl)-3,6-dimethyl-4-oxo-3,4-dihydroquinazolin-8-yl)ethyl)amino)-N-(methylsulfonyl)picolinamide | 1.97 min, 270 nm, MS (ES+)[b] $C_{28}H_{34}ClN_9O_4S$, requires: 627.2, found: 628.3 $[M + H]^+$ |
| 460 | 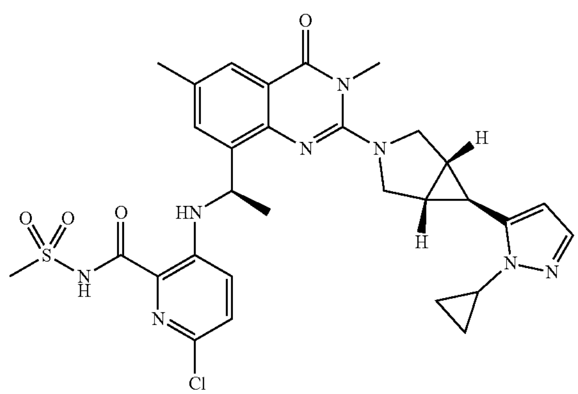 [SMILES: Cc1cc([C@@H](C)Nc2ccc(Cl)nc2C(=O)NS(C)(=O)=O)c2nc(N3C[C@@H]4[C@H](C3)[C@H]4c3ccnn3C3CC3)n(C)c(=O)c2c1] | 6-chloro-3-(((R)-1-(2-((1R,5S,6R)-6-(1-cyclopropyl-1H-pyrazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.29 min, 254 nm, MS (ES+)[b] $C_{30}H_{33}ClN_8O_4S$, requires: 636.2, found: 637.2 $[M + H]^+$ |
| 461 | 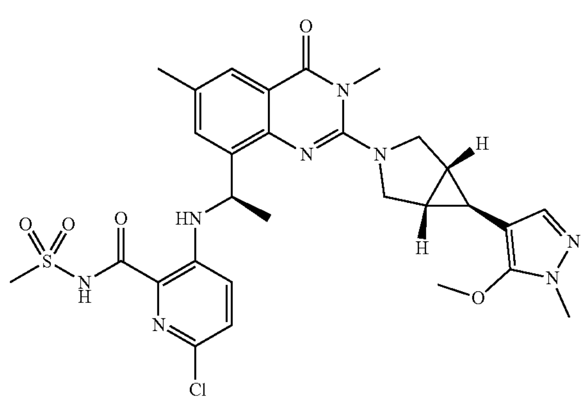 [SMILES: COc1c([C@H]2[C@@H]3CN(c4nc5c([C@@H](C)Nc6ccc(Cl)nc6C(=O)NS(C)(=O)=O)cc(C)cc5c(=O)n4C)C[C@@H]32)cnn1C] | 6-chloro-3-(((R)-1-(2-((1R,5S,6S)-6-(5-methoxy-1-methyl-1H-pyrazol-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.41 min, 215 nm, MS (ES+)[b] $C_{29}H_{33}ClN_8O_5S$, requires: 640.2, found: 641.3 $[M + H]^+$ |

TABLE E4-continued compound list prepared according to Route A in Example 4

| Cpd. ID | Structure | Name | LCMS |
|---|---|---|---|
| 462 | 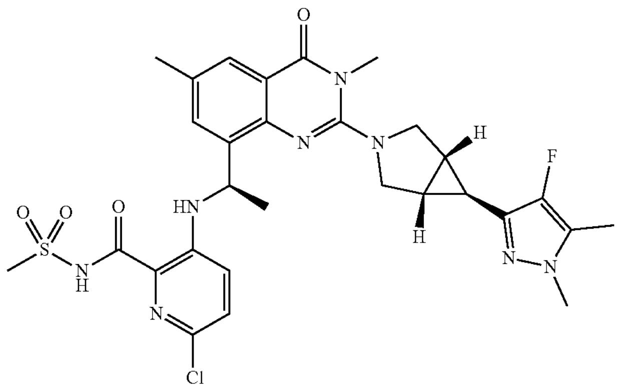 | 6-chloro-3-(((R)-1-(2-((1R,5S,6R)-6-(4-fluoro-1,5-dimethyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.34 min, 254 nm, MS (ES+)[b] $C_{29}H_{32}ClFN_8O_4S$, requires: 642.1, found: 643.2 $[M + H]^+$ |
| 463 | 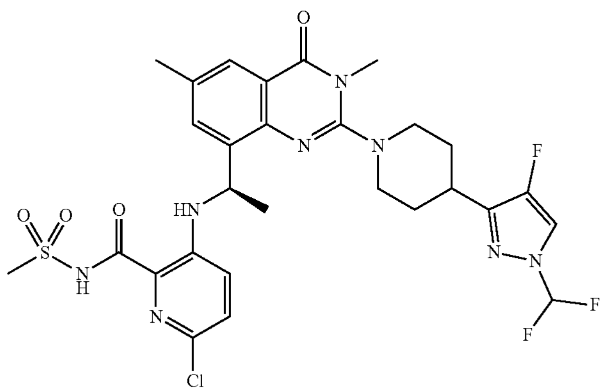 [SMILES: Cc1cc([C@@H](C)Nc2ccc(Cl)nc2C(=O)NS(C)(=O)=O)c2nc(N3CCC(c4nn(C(F)F)cc4F)CC3)n(C)c(=O)c2c1] | (R)-6-chloro-3-((1-(2-(4-(1-(difluoromethyl)-4-fluoro-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.54 min, 254 nm, MS (ES+)[b] $C_{28}H_{30}ClF_3N_8O_4S$, requires: 666.1, found: 667.1 $[M + H]^+$ |
| 464 | 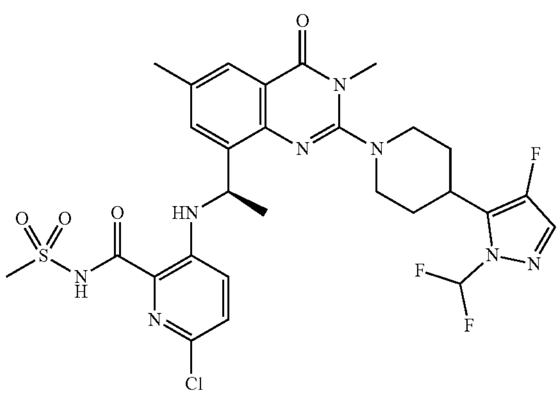 [SMILES: Cc1cc([C@@H](C)Nc2ccc(Cl)nc2C(=O)NS(C)(=O)=O)c2nc(N3CCC(c4c(F)cnn4C(F)F)CC3)n(C)c(=O)c2c1] | (R)-6-chloro-3-((1-(2-(4-(1-(difluoromethyl)-4-fluoro-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.54 min, 254 nm, MS (ES+)[b] $C_{28}H_{30}ClF_3N_8O_4S$, requires: 666.1, found: 667.1 $[M + H]^+$ |
| 465 | 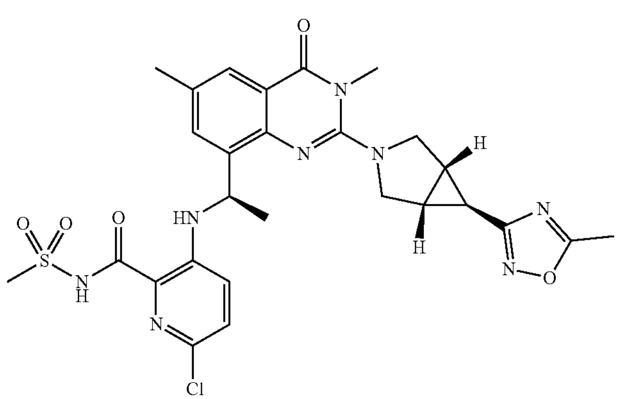 | 6-chloro-3-(((R)-1-(3,6-dimethyl-2-((1R,5S,6R)-6-(5-methyl-1,2,4-oxadiazol-3-yl)-3-azabicyclo[3.1.0]hexan-3-yl)-4-oxo-3,4-dihydroquinazolin-8-yl)ethyl)amino)-N-(methylsulfonyl)picolinamide | 2.36 min, 254 nm, MS (ES+)[b] $C_{27}H_{29}ClN_8O_5S$, requires: 612.1, found: 613.1 $[M + H]^+$ |

TABLE E4-continued compound list prepared according to Route A in Example 4

| Cpd. ID | Structure | Name | LCMS |
|---|---|---|---|
| 466 | 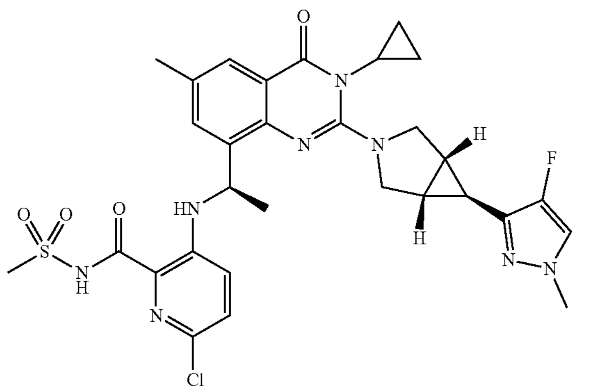 [SMILES: Cc1cc([C@@H](C)Nc2ccc(Cl)nc2C(=O)NS(C)(=O)=O)c2nc(N3C[C@@H]4[C@H](C3)[C@H]4c3nn(C)cc3F)n(C3CC3)c(=O)c2c1] | 6-chloro-3-(((R)-1-(3-cyclopropyl-2-((1R,5S,6R)-6-(4-fluoro-1-methyl-1H-pyrazol-3-yl)-3-azabicyclo[3.1.0]hexan-3-yl)-6-methyl-4-oxo-3,4-dihydroquinazolin-8-yl)ethyl)amino)-N-(methylsulfonyl) picolinamide | 2.42 min, 254 nm, MS (ES+)[b] $C_{30}H_{32}ClFN_8O_4S$, requires: 654.1, found: 655.2 $[M + H]^+$ |
| 467 | 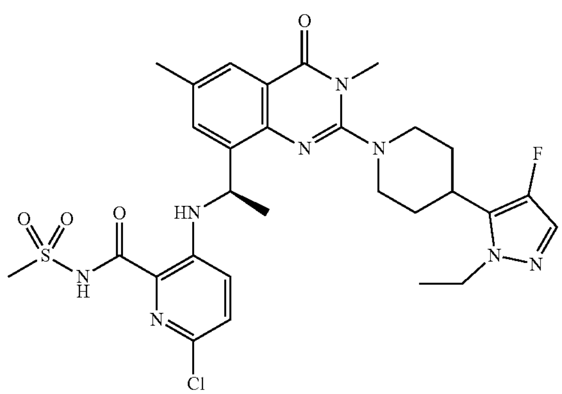 [SMILES: CCn1ncc(F)c1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(2-(4-(1-ethyl-4-fluoro-1H-pyrazol-5-yl)piperidin-1-yl)-3,6-dimethyl-4-oxo-3,4-dihydroquinazolin-8-yl)ethyl)amino)-N-(methylsulfonyl) picolinamide | 2.54 min, 254 nm, MS (ES+)[b] $C_{29}H_{34}ClFN_8O_4S$, requires: 644.2, found: 645.2 $[M + H]^+$ |
| 468 | 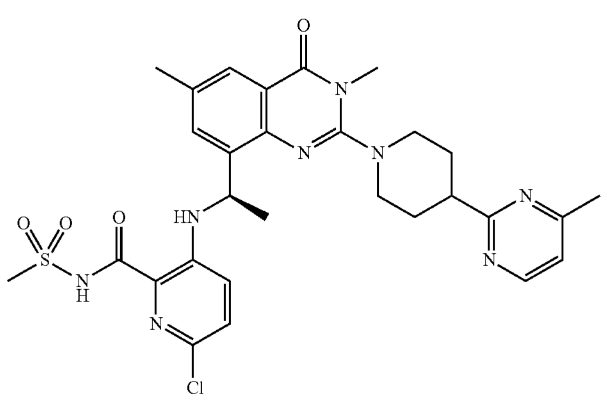 | (R)-6-chloro-3-((1-(3,6-dimethyl-2-(4-(4-methylpyrimidin-2-yl)piperidin-1-yl)-4-oxo-3,4-dihydroquinazolin-8-yl)ethyl)amino)-N-(methylsulfonyl) picolinamide | 2.39 min, 254 nm, MS (ES+)[b] $C_{29}H_{33}ClN_8O_4S$, requires: 624.2, found: 625.2 $[M + H]^+$ |

TABLE E4-continued compound list prepared according to Route A in Example 4

| Cpd. ID | Structure | Name | LCMS |
|---|---|---|---|
| 469 | 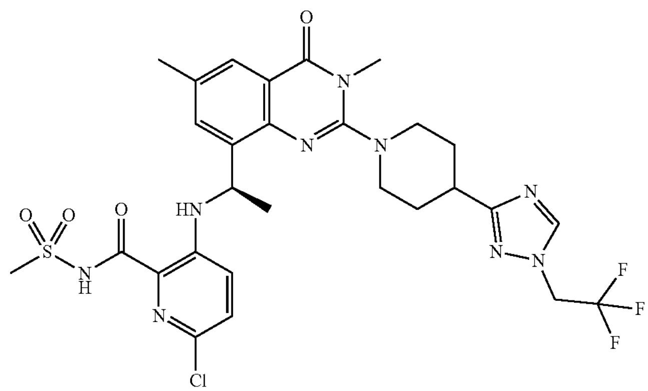 [SMILES: Cc1cc([C@@H](C)Nc2ccc(Cl)nc2C(=O)NS(C)(=O)=O)c2nc(N3CCC(c4ncn(CC(F)(F)F)n4)CC3)n(C)c(=O)c2c1] | (R)-6-chloro-3-((1-(3,6-dimethyl-4-oxo-2-(4-(1-(2,2,2-trifluoroethyl)-1H-1,2,4-triazol-3-yl)piperidin-1-yl)-3,4-dihydroquinazolin-8-yl)ethyl)amino)-N-(methylsulfonyl)picolinamide | 2.32 min, 254 nm, MS (ES+)[b] $C_{28}H_{31}ClF_3N_9O_4S$, requires: 681.1, found: 682.2 $[M + H]^+$ |
| 470 | 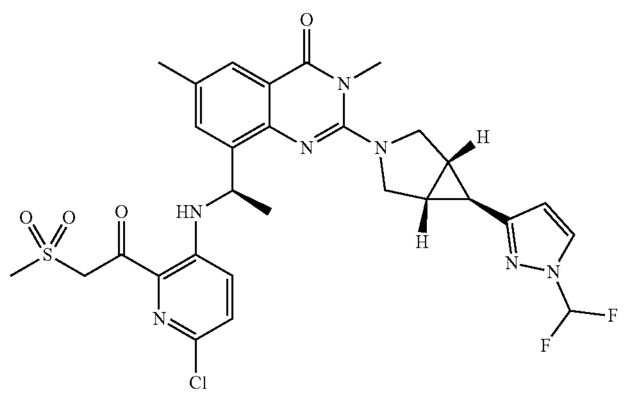 [SMILES: Cc1cc([C@@H](C)Nc2ccc(Cl)nc2C(=O)CS(C)(=O)=O)c2nc(N3C[C@@H]4[C@H](C3)[C@H]4c3ccn(C(F)F)n3)n(C)c(=O)c2c1] | 6-chloro-3-(((R)-1-(2-((1R,5S,6R)-6-(1-(difluoromethyl)-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.47 min, 254 nm, MS (ES+)[b] $C_{28}H_{29}ClF_2N_8O_4S$, requires: 646.2, found: 647.2 $[M + H]^+$ |
| 471 | 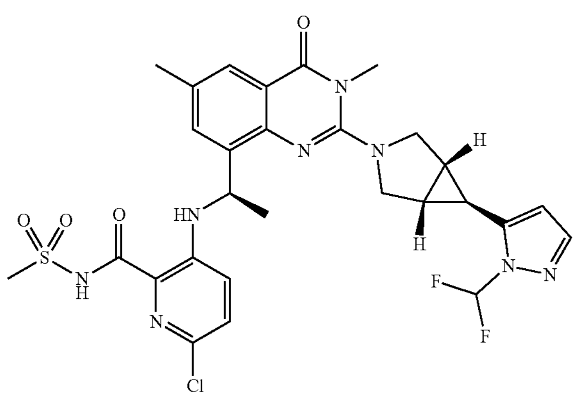 [SMILES: Cc1cc([C@@H](C)Nc2ccc(Cl)nc2C(=O)NS(C)(=O)=O)c2nc(N3C[C@@H]4[C@H](C3)[C@H]4c3ccnn3C(F)F)n(C)c(=O)c2c1] | 6-chloro-3-(((R)-1-(2-((1R,5S,6R)-6-(1-(difluoromethyl)-1H-pyrazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.41 min, 254 nm, MS (ES+)[b] $C_{28}H_{29}ClF_2N_8O_4S$, requires: 646.2, found: 647.2 $[M + H]^+$ |
| 472 | 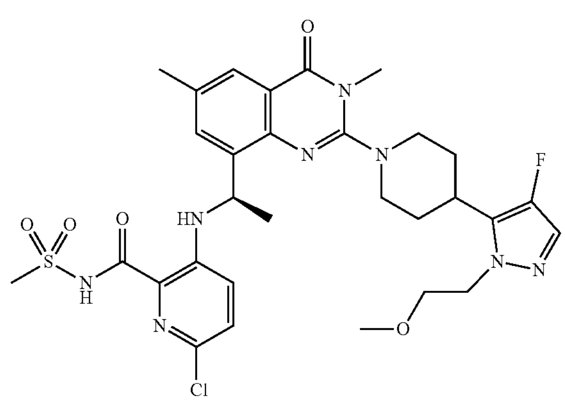 [SMILES: COCCn1ncc(F)c1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(2-(4-(4-fluoro-1-(2-methoxyethyl)-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.47 min, 254 nm, MS (ES+)[b] $C_{30}H_{36}ClFN_8O_5S$, requires: 674.2, found: 675.2 $[M + H]^+$ |

TABLE E4-continued compound list prepared according to Route A in Example 4

| Cpd. ID | Structure | Name | LCMS |
|---|---|---|---|
| 473 | 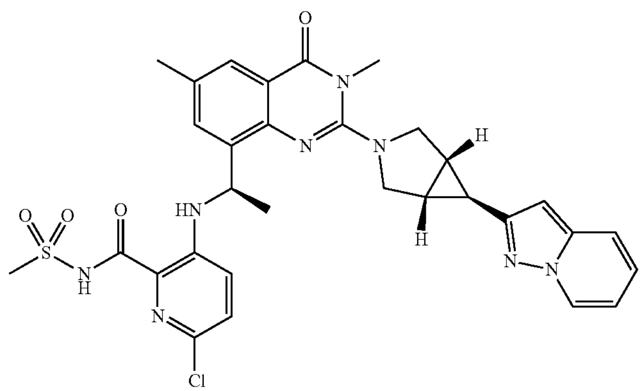 [SMILES: Cc1cc([C@@H](C)Nc2ccc(Cl)nc2C(=O)NS(C)(=O)=O)c2nc(N3C[C@@H]4[C@H](C3)[C@H]4c3cc4ccccn4n3)n(C)c(=O)c2c1] | 6-chloro-3-(((R)-1-(3,6-dimethyl-4-oxo-2-((1R,5S,6R)-6-(pyrazolo[1,5-a]pyridin-2-yl)-3-azabicyclo[3.1.0]hexan-3-yl)-3,4-dihydroquinazolin-8-yl)ethyl)amino)-N-(methylsulfonyl)picolinamide | 2.56 min, 254 nm, MS (ES+)$^b$ $C_{31}H_{31}ClN_8O_4S$, requires: 646.1, found: 647.3 [M + H]$^+$ |
| 474 | 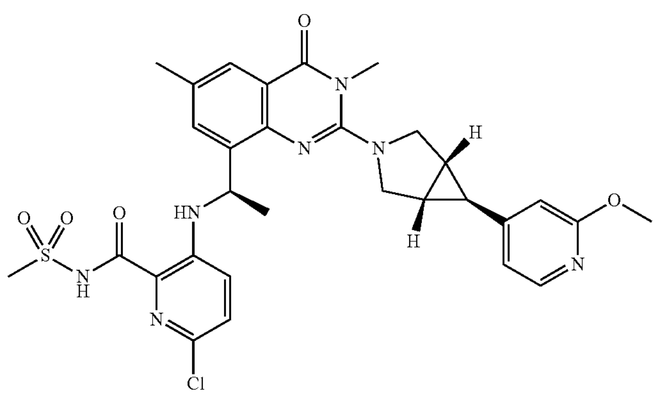 | 6-chloro-3-(((R)-1-(2-((1R,5S,6S)-6-(2-methoxypyridin-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.49 min, 254 nm, MS (ES+)$^b$ $C_{30}H_{32}ClN_7O_5S$, requires: 637.1, found: 638.2 [M + H]$^+$ |
| 475 | 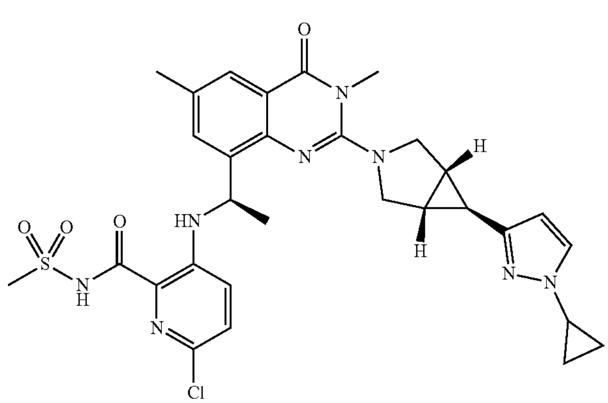 [SMILES: Cc1cc([C@@H](C)Nc2ccc(Cl)nc2C(=O)NS(C)(=O)=O)c2nc(N3C[C@@H]4[C@H](C3)[C@H]4c3ccn(C4CC4)n3)n(C)c(=O)c2c1] | 6-chloro-3-(((R)-1-(2-((1R,5S,6R)-6-(1-cyclopropyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.42 min, 254 nm, MS (ES+)$^b$ $C_{30}H_{33}ClN_8O_4S$, requires: 636.2, found: 637.2 [M + H]$^+$ |

TABLE E4-continued compound list prepared according to Route A in Example 4

| Cpd. ID | Structure | Name | LCMS |
|---|---|---|---|
| 476 | 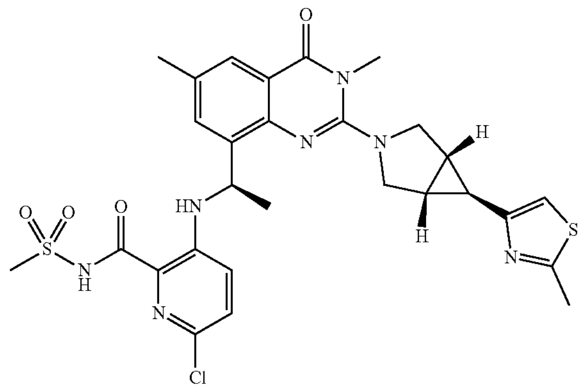 [SMILES: Cc1cc([C@@H](C)Nc2ccc(Cl)nc2C(=O)NS(C)(=O)=O)c2nc(N3C[C@@H]4[C@H](C3)[C@H]4c3csc(C)n3)n(C)c(=O)c2c1] | 6-chloro-3-(((R)-1-(3,6-dimethyl-2-((1R,5S,6R)-6-(2-methylthiazol-4-yl)-3-azabicyclo[3.1.0]hexan-3-yl)-4-oxo-3,4-dihydroquinazolin-8-yl)ethyl)amino)-N-(methylsulfonyl)picolinamide | 1.99 min, 254 nm, MS (ES+)[b] $C_{28}H_{30}ClN_7O_4S_2$, requires: 627.1, found: 628 [M + H]+ |
| 477 | 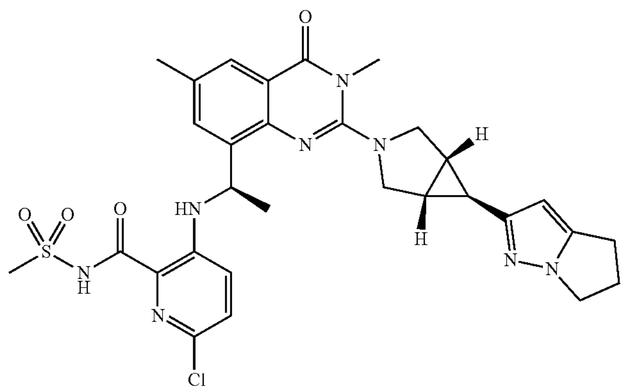 | 6-chloro-3-(((R)-1-(2-((1R,5S,6R)-6-(5,6-dihydro-4H-pyrrolo[1,2-b]pyrazol-2-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.39 min, 254 nm, MS (ES+)[b] $C_{30}H_{33}ClN_8O_4S$, requires: 636.2, found: 637.2 [M + H]+ |
| 478 | 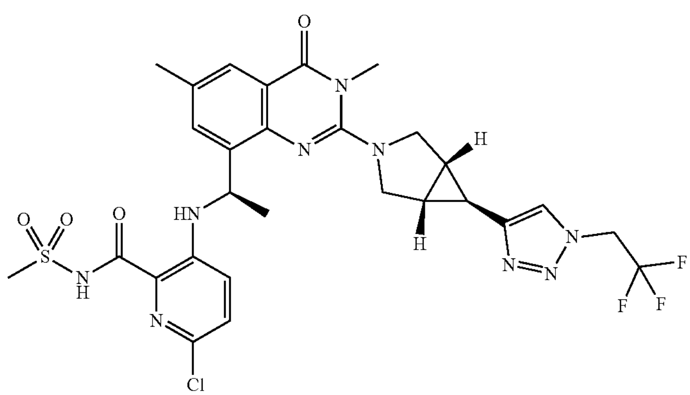 [SMILES: Cc1cc([C@@H](C)Nc2ccc(Cl)nc2C(=O)NS(C)(=O)=O)c2nc(N3C[C@@H]4[C@H](C3)[C@H]4c3cn(CC(F)(F)F)nn3)n(C)c(=O)c2c1] | 6-chloro-3-(((R)-1-(3,6-dimethyl-4-oxo-2-((1R,5S,6R)-6-(1-(2,2,2-trifluoroethyl)-1H-1,2,3-triazol-4-yl)-3-azabicyclo[3.1.0]hexan-3-yl)-3,4-dihydroquinazolin-8-yl)ethyl)amino)-N-(methylsulfonyl)picolinamide | 2.35 min, 254 nm, MS (ES+)[b] $C_{28}H_{29}ClF_3N_9O_4S$, requires: 679.1, found: 680.2 [M + H]+ |
| 479 | 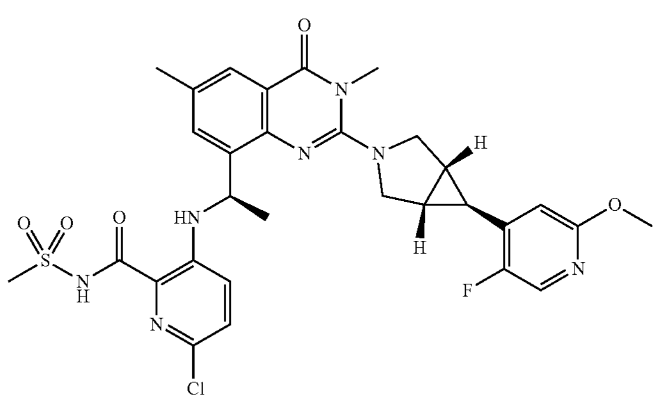 | 6-chloro-3-(((R)-1-(2-((1R,5S,6S)-6-(5-fluoro-2-methoxypyridin-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.62 min, 270 nm, MS (ES+)[b] $C_{30}H_{31}ClFN_7O_5S$, requires: 655.1, found: 656.2 [M + H]+ |

TABLE E4-continued compound list prepared according to Route A in Example 4

| Cpd. ID | Structure | Name | LCMS |
|---|---|---|---|
| 480 | 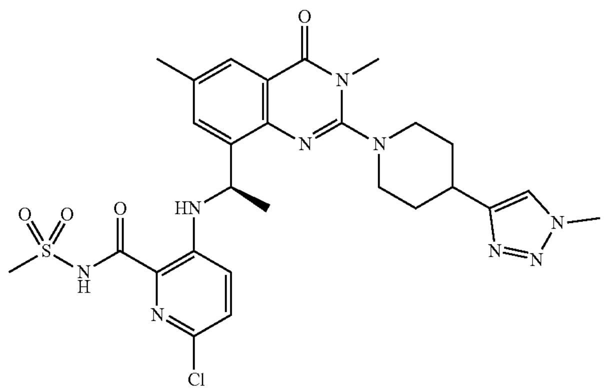 | (R)-6-chloro-3-((1-(3,6-dimethyl-2-(4-(1-methyl-1H-1,2,3-triazol-4-yl)piperidin-1-yl)-4-oxo-3,4-dihydroquinazolin-8-yl)ethyl)amino)-N-(methylsulfonyl)picolinamide | 2.23 min, 254 nm, MS (ES+)[b] $C_{27}H_{32}ClN_9O_4S$, requires: 613.2, found: 614.3 [M + H]+ |
| 481 | 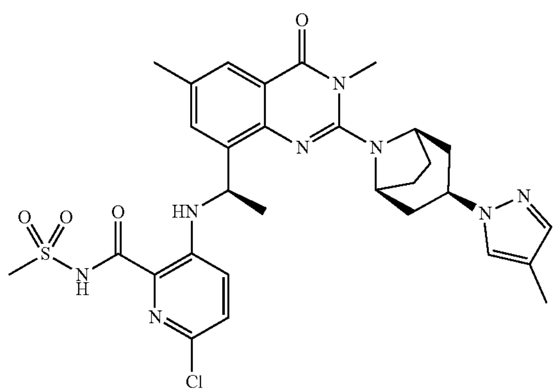 [SMILES: Cc1cc([C@@H](C)Nc2ccc(Cl)nc2C(=O)NS(C)(=O)=O)c2nc(N3[C@@H]4CC[C@H]3C[C@H](n3cc(C)cn3)C4)n(C)c(=O)c2c1] | 6-chloro-3-(((R)-1-(3,6-dimethyl-2-((1R,3S,5S)-3-(4-methyl-1H-pyrazol-1-yl)-8-azabicyclo[3.2.1]octan-8-yl)-4-oxo-3,4-dihydroquinazolin-8-yl)ethyl)amino)-N-(methylsulfonyl)picolinamide | 2.47 min, 254 nm, MS (ES+)[b] $C_{30}H_{35}ClN_8O_4S$, requires: 638.2, found: 639.2 [M + H]+ |
| 482 | 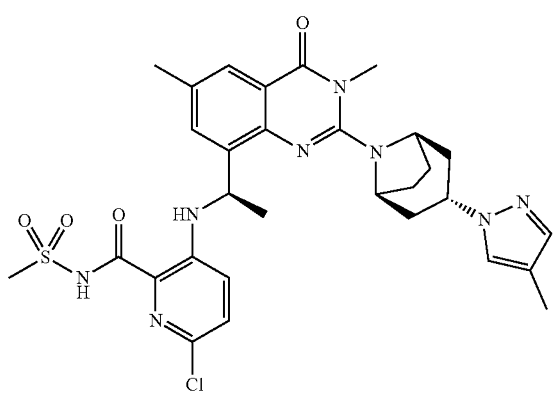 [SMILES: Cc1cc([C@@H](C)Nc2ccc(Cl)nc2C(=O)NS(C)(=O)=O)c2nc(N3[C@@H]4CC[C@H]3C[C@@H](n3cc(C)cn3)C4)n(C)c(=O)c2c1] | 6-chloro-3-(((R)-1-(3,6-dimethyl-2-((1R,3R,5S)-3-(4-methyl-1H-pyrazol-1-yl)-8-azabicyclo[3.2.1]octan-8-yl)-4-oxo-3,4-dihydroquinazolin-8-yl)ethyl)amino)-N-(methylsulfonyl)picolinamide | 2.55 min, 220 nm, MS (ES+)[b] $C_{30}H_{35}ClN_8O_4S$, requires: 638.2, found: 639.3 [M + H]+ |

TABLE E4-continued compound list prepared according to Route A in Example 4

| Cpd. ID | Structure | Name | LCMS |
|---|---|---|---|
| 483 | 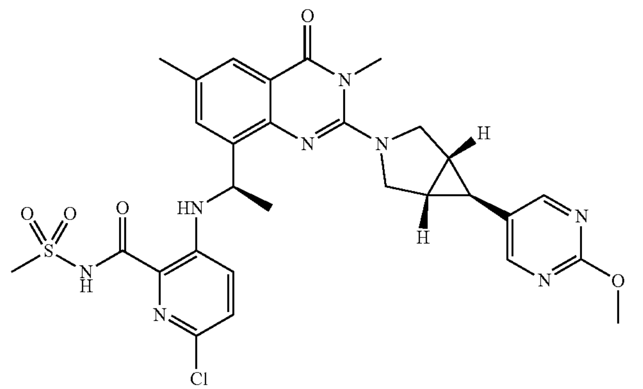 | 6-chloro-3-(((R)-1-(2-((1R,5S,6S)-6-(2-methoxypyrimidin-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.32 min, 254 nm, MS (ES+)[b] $C_{29}H_{31}ClN_8O_5S$, requires: 638.1, found: 639.2 $[M + H]^+$ |
| 484 | 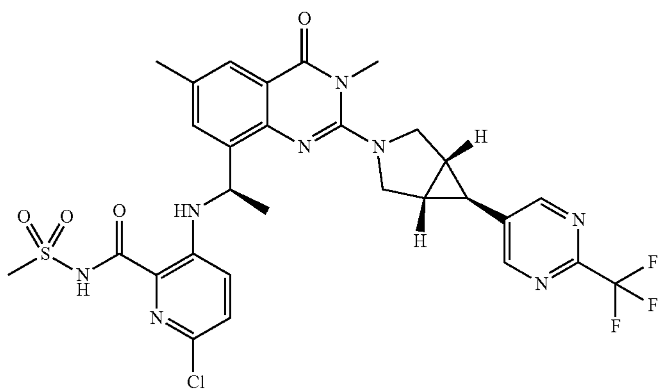 [SMILES: Cc1cc([C@@H](C)Nc2ccc(Cl)nc2C(=O)NS(C)(=O)=O)c2nc(N3C[C@@H]4[C@H](C3)[C@H]4c3cnc(C(F)(F)F)nc3)n(C)c(=O)c2c1] | 6-chloro-3-(((R)-1-(3,6-dimethyl-4-oxo-2-((1R,5S,6S)-6-(2-(trifluoromethyl)pyrimidin-5-yl)-3-azabicyclo[3.1.0]hexan-3-yl)-3,4-dihydroquinazolin-8-yl)ethyl)amino)-N-(methylsulfonyl)picolinamide | 2.51 min, 270 nm, MS (ES+)[b] $C_{29}H_{28}ClF_3N_8O_4S$, requires: 676.1, found: 677.1 $[M + H]^+$ |
| 485 | 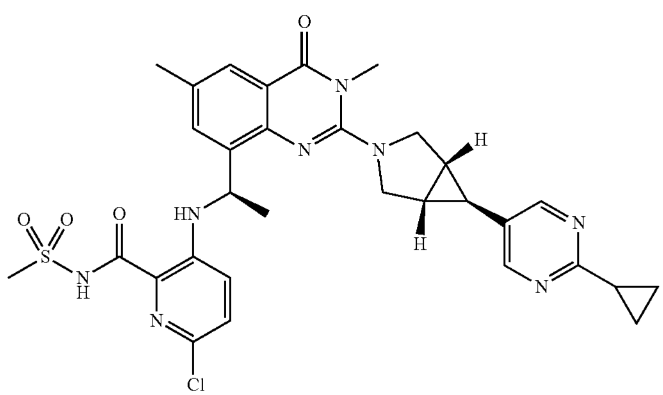 [SMILES: Cc1cc([C@@H](C)Nc2ccc(Cl)nc2C(=O)NS(C)(=O)=O)c2nc(N3C[C@@H]4[C@H](C3)[C@H]4c3cnc(C4CC4)nc3)n(C)c(=O)c2c1] | 6-chloro-3-(((R)-1-(2-((1R,5S,6S)-6-(2-cyclopropylpyrimidin-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.41 min, 270 nm, MS (ES+)[b] $C_{31}H_{33}ClN_8O_4S$, requires: 648.2, found: 649.2 $[M + H]^+$ |
| 486 | 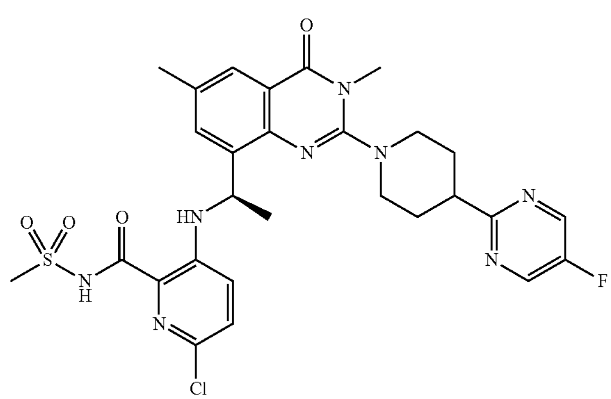 [SMILES: Cc1cc([C@@H](C)Nc2ccc(Cl)nc2C(=O)NS(C)(=O)=O)c2nc(N3CCC(c4ncc(F)cn4)CC3)n(C)c(=O)c2c1] | (R)-6-chloro-3-((1-(2-(4-(5-fluoropyrimidin-2-yl)piperidin-1-yl)-3,6-dimethyl-4-oxo-3,4-dihydroquinazolin-8-yl)ethyl)amino)-N-(methylsulfonyl)picolinamide | 2.47 min, 270 nm, MS (ES+)[b] $C_{28}H_{30}ClFN_8O_4S$, requires: 628.1, found: 629.2 $[M + H]^+$ |

TABLE E4-continued compound list prepared according to Route A in Example 4

| Cpd. ID | Structure | Name | LCMS |
|---|---|---|---|
| 487 | 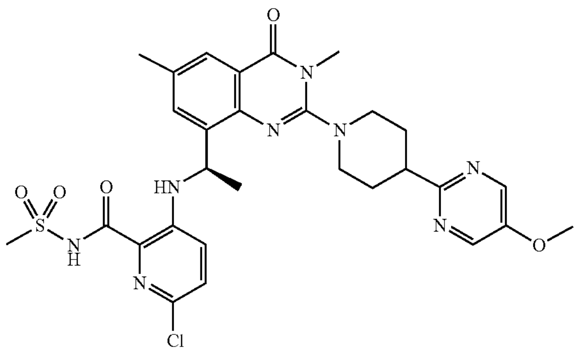 | (R)-6-chloro-3-((1-(2-(4-(5-methoxypyrimidin-2-yl)piperidin-1-yl)-3,6-dimethyl-4-oxo-3,4-dihydroquinazolin-8-yl)ethyl)amino)-N-(methylsulfonyl)picolinamide | 2.39 min, 254 nm, MS (ES+)[b] $C_{29}H_{33}ClN_8O_5S$, requires: 640.2, found: 641.2 $[M + H]^+$ |
| 488 | 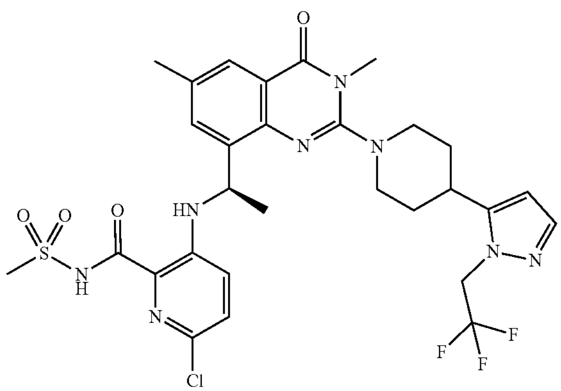 [SMILES: Cc1cc([C@@H](C)Nc2ccc(Cl)nc2C(=O)NS(C)(=O)=O)c2nc(N3CCC(c4ccnn4CC(F)(F)F)CC3)n(C)c(=O)c2c1] | (R)-6-chloro-3-((1-(3,6-dimethyl-4-oxo-2-(4-(1-(2,2,2-trifloroethyl)-1H-pyrazol-5-yl)piperidin-1-yl)-3,4-dihydroquinazolin-8-yl)ethyl)amino)-N-(methylsulfonyl)picolinamide | 2.60 min, 254 nm, MS (ES+)[b] $C_{29}H_{32}ClF_3N_8O_4S$, required: 680.1, found: 681.2 $[M + H]^+$ |
| 489 | 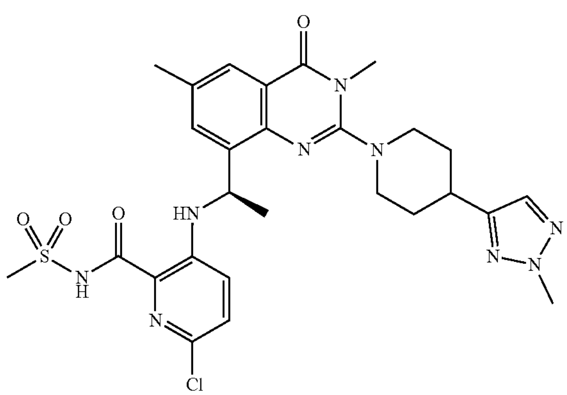 [SMILES: Cc1cc([C@@H](C)Nc2ccc(Cl)nc2C(=O)NS(C)(=O)=O)c2nc(N3CCC(c4cnn(C)n4)CC3)n(C)c(=O)c2c1] | (R)-6-chloro-3-((1-(3,6-dimethyl-2-(4-(2-methyl-2H-1,2,3-triazol-4-yl)piperidin-1-yl)-4-oxo-3,4-dihydroquinazolin-8-yl)ethyl)amino)-N-(methylsulfonyl)picolinamide | 2.340 min, 270 nm, MS (ES+)[b] $C_{27}H_{32}ClN_9O_4S$, requires: 613.2, found: 614.2 $[M + H]^+$ |
| 490 | 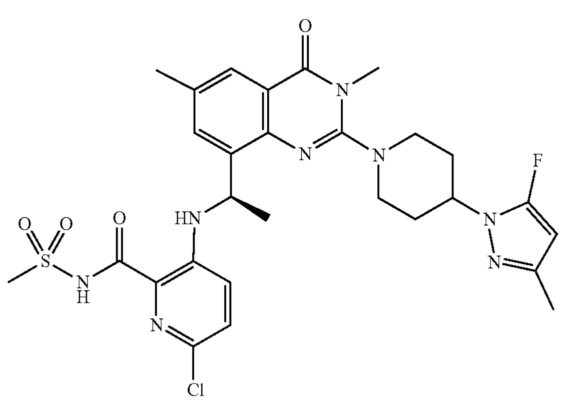 [SMILES: Cc1cc([C@@H](C)Nc2ccc(Cl)nc2C(=O)NS(C)(=O)=O)c2nc(N3CCC(n4nc(C)cc4F)CC3)n(C)c(=O)c2c1] | (R)-6-chloro-3-((1-(2-(4-(5-fluoro-3-methyl-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.56 min, 254 nm, MS (ES+)[b] $C_{28}H_{32}ClFN_8O_4S$, requires: 630.1, found: 631.2 $[M + H]^+$ |

TABLE E4-continued compound list prepared according to Route A in Example 4

| Cpd. ID | Structure | Name | LCMS |
|---|---|---|---|
| 491 | 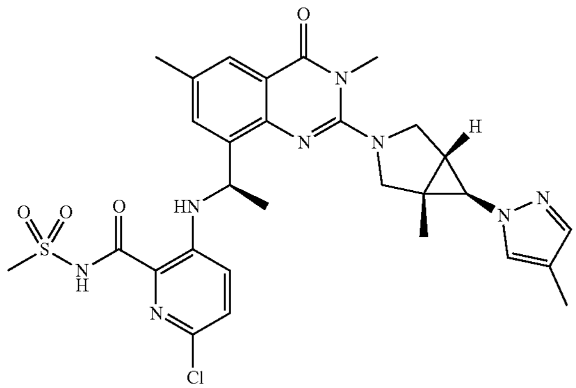 | 6-chloro-3-(((R)-1-(3,6-dimethyl-2-((1R,5S,6S)-6-(4-methyl-1H-pyrazol-1-yl)-3-azabicyclo[3.1.0]hexan-3-yl)-4-oxo-3,4-dihydroquinazolin-8-yl)ethyl)amino)-N-(methylsulfonyl)picolinamide | 2.42 min, 270 nm, MS (ES+)[b] $C_{28}H_{31}ClN_8O_4S$, requires: 610.2, found: 611.2 [M + H]+ |
| 492 | 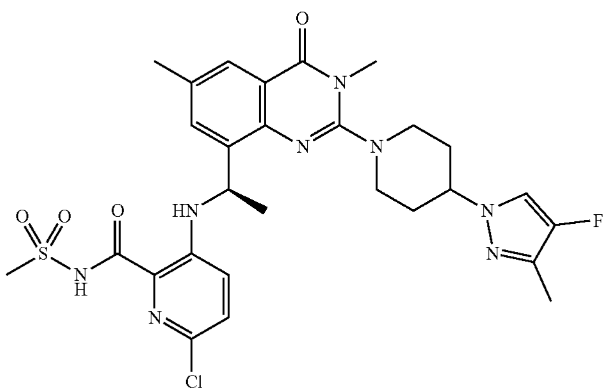 [SMILES: Cc1cc([C@@H](C)Nc2ccc(Cl)nc2C(=O)NS(C)(=O)=O)c2nc(N3CCC(n4cc(F)c(C)n4)CC3)n(C)c(=O)c2c1] | (R)-6-chloro-3-((1-(2-(4-(4-fluoro-3-methyl-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.50 min, 254 nm, MS (ES+)[b] $C_{28}H_{32}ClFN_8O_4S$, requires: 630.1, found: 631.2 [M + H]+ |
| 493 | 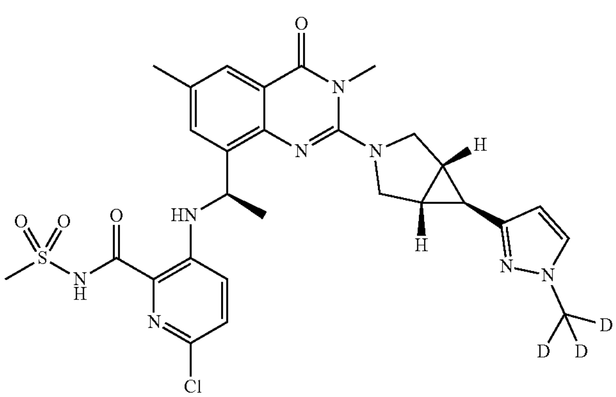 [SMILES: [2H]C([2H])([2H])n1ccc([C@H]2[C@@H]3CN(c4nc5c([C@@H](C)Nc6ccc(Cl)nc6C(=O)NS(C)(=O)=O)cc(C)cc5c(=O)n4C)C[C@@H]32)n1] | 6-chloro-3-(((R)-1-(3,6-dimethyl-2-((1R,5S,6R)-6-(1-(methyl-d3)-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.40 min, 220 nm, MS (ES+)[b] $C_{28}H_{28}D_3ClN_8O_4S$, requires: 613.2, found: 614.2 [M + H]+ |

TABLE E4-continued compound list prepared according to Route A in Example 4

| Cpd. ID | Structure | Name | LCMS |
|---|---|---|---|
| 494 | 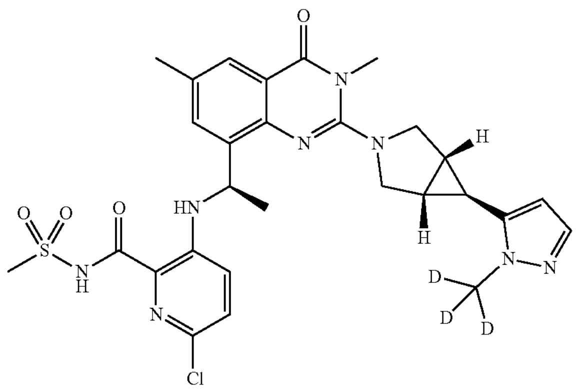 [SMILES: [2H]C([2H])([2H])n1nccc1[C@H]1[C@@H]2CN(c3nc4c([C@@H](C)Nc5ccc(Cl)nc5C(=O)NS(C)(=O)=O)cc(C)cc4c(=O)n3C)C[C@@H]21] | 6-chloro-3-(((R)-1-(3,6-dimethyl-2-((1R,5S,6R)-6-(1-(methyl-d3)-1H-pyrazol-5-yl)-3-azabicyclo[3.1.0]hexan-3-yl)-4-oxo-3,4-dihydroquinazolin-8-yl)ethyl)amino)-N-(methylsulfonyl) picolinamide | 2.26 min, 270 nm, MS (ES+)[b] $C_{28}H_{28}D_3ClN_8O_4S$, requires: 613.2, found: 614.2 $[M + H]^+$ |
| 495 | 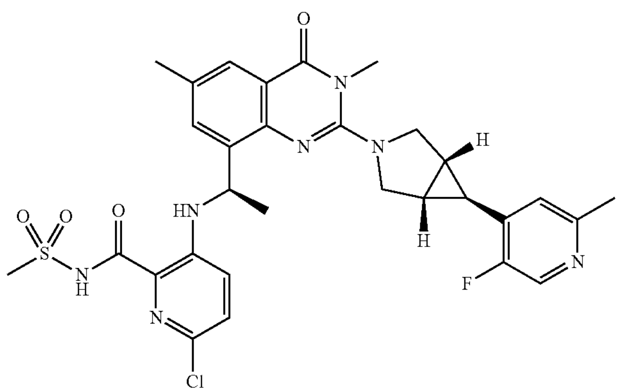 | 6-chloro-3-(((R)-1-(2-((1R,5S,6S)-6-(5-fluoro-2-methylpyridin-4-yl)-3-azabicyclo[3.1.0]hexan-3-yl)-3,6-dimethyl-4-oxo-3,4-dihydroquinazolin-8-yl)ethyl)amino)-N-(methylsulfonyl) picolinamide | 2.26 min, 254 nm, MS (ES+)[b] $C_{30}H_{31}ClFN_7O_4S$, requires: 639.1, found: 640.2 $[M + H]^+$ |
| 496 | 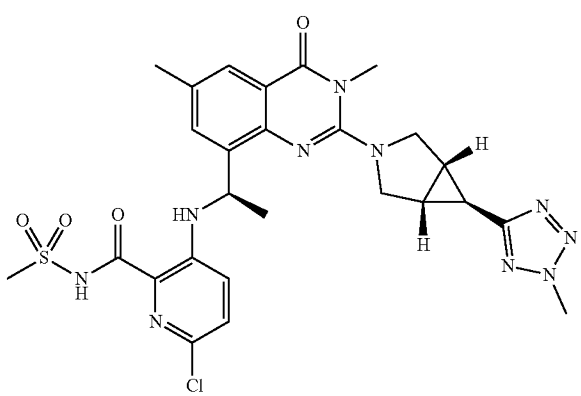 [SMILES: Cc1cc([C@@H](C)Nc2ccc(Cl)nc2C(=O)NS(C)(=O)=O)c2nc(N3C[C@@H]4[C@H](C3)[C@H]4c3nnn(C)n3)n(C)c(=O)c2c1] | 6-chloro-3-(((R)-1-(3,6-dimethyl-2-((1R,5S,6R)-6-(2-methyl-2H-tetrazol-5-yl)-3-azabicyclo[3.1.0]hexan-3-yl)-4-oxo-3,4-dihydroquinazolin-8-yl)ethyl)amino)-N-(methylsulfonyl) picolinamide | 2.30 min, 254 nm, MS (ES+)[b] $C_{26}H_{29}ClN_{10}O_4S$, requires: 612.1, found: 613.1 $[M + H]^+$ |
| 497 | 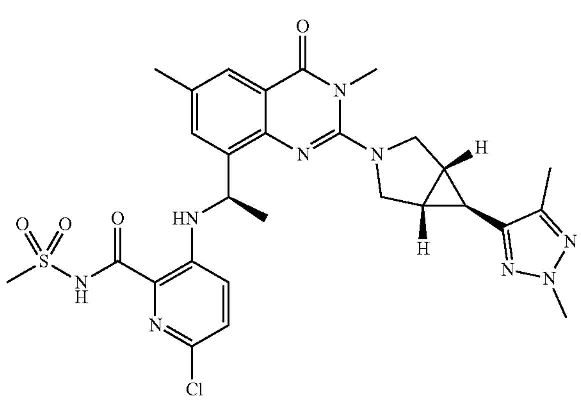 [SMILES: Cc1cc([C@@H](C)Nc2ccc(Cl)nc2C(=O)NS(C)(=O)=O)c2nc(N3C[C@@H]4[C@H](C3)[C@H]4c3nn(C)nc3C)n(C)c(=O)c2c1] | 6-chloro-3-(((R)-1-(2-((1R,5S,6R)-6-(2,5-dimethyl-2H-1,2,3-triazol-4-yl)-3-azabicyclo[3.1.0]hexan-3-yl)-3,6-dimethyl-4-oxo-3,4-dihydroquinazolin-8-yl)ethyl)amino)-N-(methylsulfonyl) picolinamide | 2.39 min, 254 nm, MS (ES+)[b] $C_{28}H_{32}ClN_9O_4S$, requires: 625.2, found: 626.2 $[M + H]^+$ |

TABLE E4-continued compound list prepared according to Route A in Example 4

| Cpd. ID | Structure | Name | LCMS |
|---|---|---|---|
| 498 | 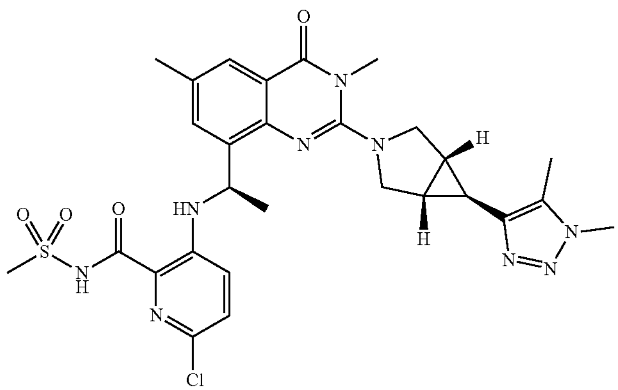 | 6-chloro-3-(((R)-1-(2-((1R,5S,6R)-6-(1,5-dimethyl-1H-1,2,3-triazol-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.17 min, 254 nm, MS (ES+)[b] $C_{28}H_{32}ClN_9O_4S$, requires: 625.2, found: 626.2 [M + H]+ |
| 499 | 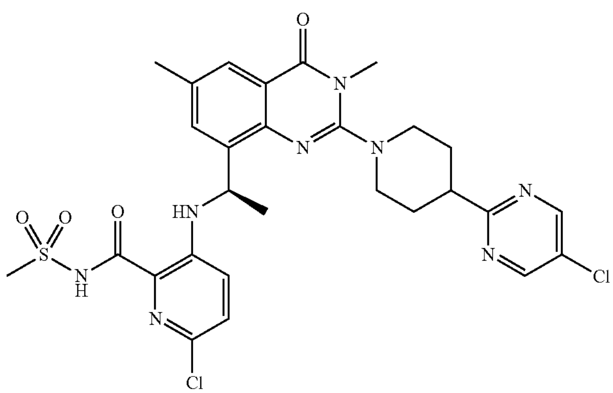 [SMILES: Cc1cc([C@@H](C)Nc2ccc(Cl)nc2C(=O)NS(C)(=O)=O)c2nc(N3CCC(c4ncc(Cl)cn4)CC3)n(C)c(=O)c2c1] | (R)-6-chloro-3-((1-(2-(4-(5-chloropyrimidin-2-yl)piperidin-1-yl)-3,6-dimethyl-4-oxo-3,4-dihydroquinazolin-8-yl)ethyl)amino)-N-(methylsulfonyl)picolinamide | 2.67 min, 270 nm, MS (ES+)[b] $C_{28}H_{30}Cl_2N_8O_4S$, requires: 644.2, found: 645.2 [M + H]+ |
| 500 | 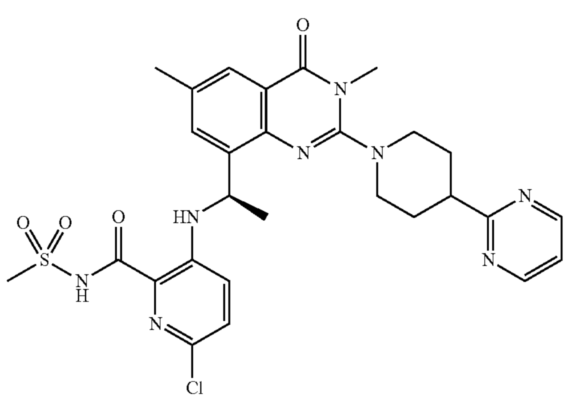 [SMILES: Cc1cc([C@@H](C)Nc2ccc(Cl)nc2C(=O)NS(C)(=O)=O)c2nc(N3CCC(c4ncccn4)CC3)n(C)c(=O)c2c1] | (R)-6-chloro-3-((1-(3,6-dimethyl-4-oxo-2-(4-(pyrimidin-2-yl)piperidin-1-yl)-3,4-dihydroquinazolin-8-yl)ethyl)amino)-N-(methylsulfonyl)picolinamide | 2.31 min, 215 nm, MS (ES+)[b] $C_{28}H_{31}ClN_8O_4S$, requires: 610.1, found: 611.2 [M + H]+ |

TABLE E4-continued compound list prepared according to Route A in Example 4

| Cpd. ID | Structure | Name | LCMS |
|---|---|---|---|
| 501 | 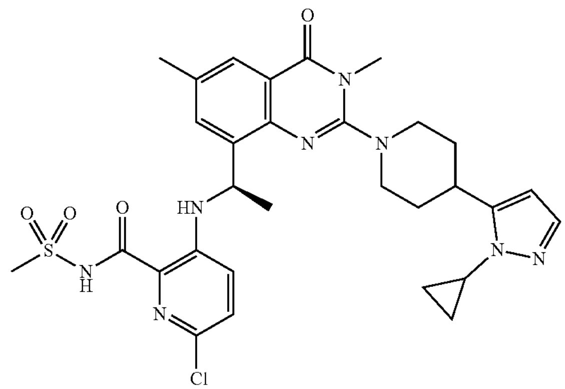 [SMILES: Cc1cc([C@@H](C)Nc2ccc(Cl)nc2C(=O)NS(C)(=O)=O)c2nc(N3CCC(c4ccnn4C4CC4)CC3)n(C)c(=O)c2c1] | (R)-6-chloro-3-((1-(2-(4-(1-cyclopropyl-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.44 min, 254 nm, MS (ES+)[b] $C_{30}H_{35}ClN_8O_4S$, requires: 638.2, found: 639.2 $[M + H]^+$ |
| 502 | 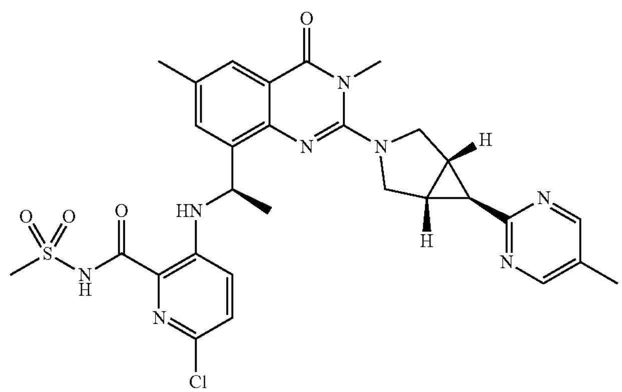 | 6-chloro-3-(((R)-1-(3,6-dimethyl-2-((1R,5S,6R)-6-(5-methylpyrimidin-2-yl)-3-azabicyclo[3.1.0]hexan-3-yl)-4-oxo-3,4-dihydroquinazolin-8-yl)ethyl)amino)-N-(methylsulfonyl)picolinamide | 2.56 min, 254 nm, MS (ES+)[b] $C_{29}H_{31}ClN_8O_4S$, requires: 622.1, found: 623.2 $[M + H]^+$ |
| 503 | 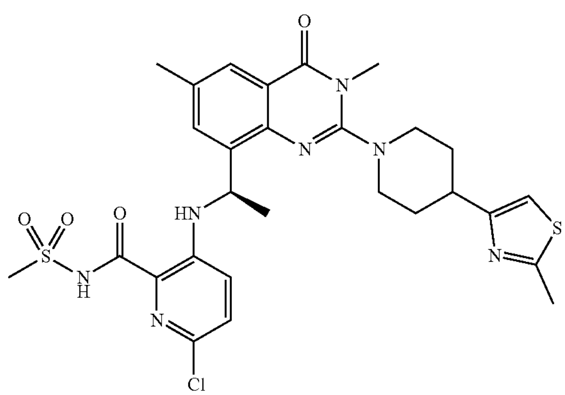 [SMILES: Cc1cc([C@@H](C)Nc2ccc(Cl)nc2C(=O)NS(C)(=O)=O)c2nc(N3CCC(c4csc(C)n4)CC3)n(C)c(=O)c2c1] | (R)-6-chloro-3-((1-(3,6-dimethyl-2-(4-(2-methylthiazol-4-yl)piperidin-1-yl)-4-oxo-3,4-dihydroquinazolin-8-yl)ethyl)amino)-N-(methylsulfonyl)picolinamide | 2.65 min, 254 nm, MS (ES+)[b] $C_{28}H_{32}ClN_7O_4S_2$, requires: 629.1, found: 630.2 $[M + H]^+$ |
| 504 | 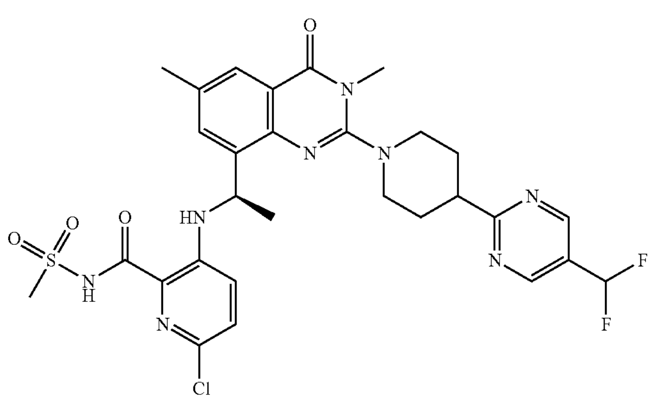 [SMILES: Cc1cc([C@@H](C)Nc2ccc(Cl)nc2C(=O)NS(C)(=O)=O)c2nc(N3CCC(c4ncc(C(F)F)cn4)CC3)n(C)c(=O)c2c1] | (R)-6-chloro-3-((1-(2-(4-(5-(difluoromethyl)pyrimidin-2-yl)piperidin-1-yl)-3,6-dimethyl-4-oxo-3,4-dihydroquinazolin-8-yl)ethyl)amino)-N-(methylsulfonyl)picolinamide | 2.43 min, 254 nm, MS (ES+)[c] $C_{29}H_{31}ClF_2N_8O_4S$, requires: 660.1, found: 661.2 $[M + H]^+$ |

TABLE E4-continued compound list prepared according to Route A in Example 4

| Cpd. ID | Structure | Name | LCMS |
|---|---|---|---|
| 505 | 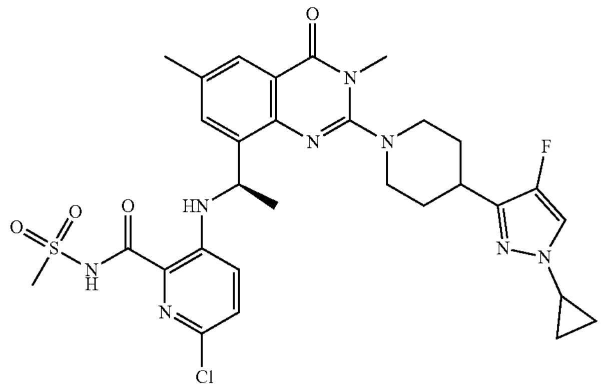 [SMILES: Cc1cc([C@@H](C)Nc2ccc(Cl)nc2C(=O)NS(C)(=O)=O)c2nc(N3CCC(c4nn(C5CC5)cc4F)CC3)n(C)c(=O)c2c1] | (R)-6-chloro-3-((1-(2-(4-(1-cyclopropyl-4-fluoro-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.64 min, 254 nm, MS (ES+)$^b$ $C_{30}H_{34}ClFN_8O_4S$, requires: 656.2, found: 657.2 [M + H]$^+$ |
| 506 | 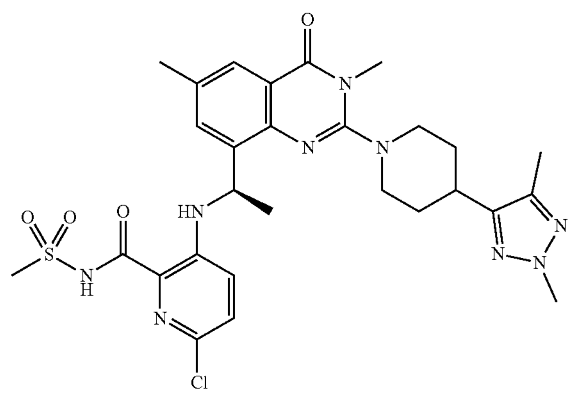 [SMILES: Cc1cc([C@@H](C)Nc2ccc(Cl)nc2C(=O)NS(C)(=O)=O)c2nc(N3CCC(c4nn(C)nc4C)CC3)n(C)c(=O)c2c1] | (R)-6-chloro-3-((1-(2-(4-(2,5-dimethyl-2H-1,2,3-triazol-4-yl)piperidin-1-yl)-3,6-dimethyl-4-oxo-3,4-dihydroquinazolin-8-yl)ethyl)amino)-N-(methylsulfonyl)picolinamide | 2.43 min, 254 nm, MS (ES+)$^b$ $C_{28}H_{34}ClN_9O_4S$, requires: 627.2, found: 628.2 [M + H]$^+$ |
| 507 | 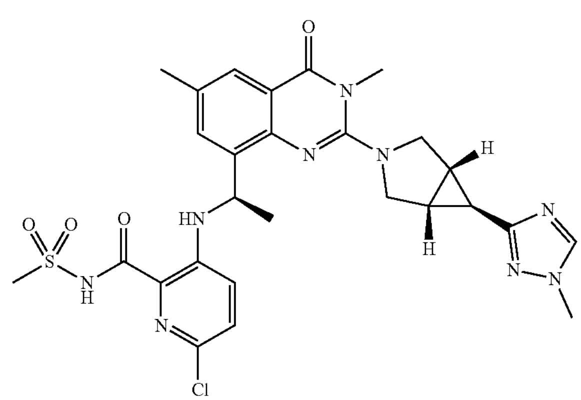 [SMILES: Cc1cc([C@@H](C)Nc2ccc(Cl)nc2C(=O)NS(C)(=O)=O)c2nc(N3C[C@@H]4[C@H](C3)[C@H]4c3ncn(C)n3)n(C)c(=O)c2c1] | 6-chloro-3-(((R)-1-(3,6-dimethyl-2-((1R,5S,6R)-6-(1-methyl-1H-1,2,4-triazol-3-yl)-3-azabicyclo[3.1.0]hexan-3-yl)-4-oxo-3,4-dihydroquinazolin-8-yl)ethyl)amino)-N-(methylsulfonyl)picolinamide | 2.22 min, 254 nm, MS (ES+)$^b$ $C_{27}H_{30}ClN_9O_4S$, requires: 611.1, found: 612.2 [M + H]$^+$ |

TABLE E4-continued compound list prepared according to Route A in Example 4

| Cpd. ID | Structure | Name | LCMS |
|---|---|---|---|
| 508 | 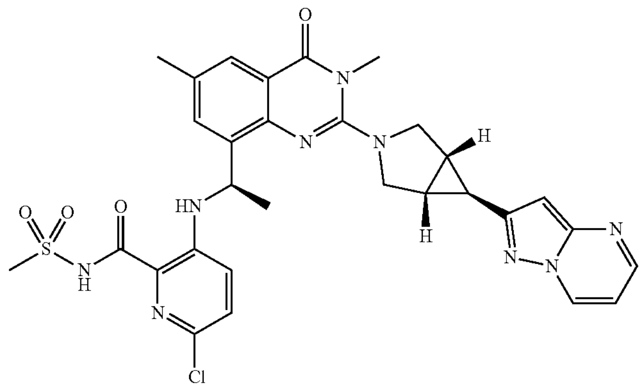 [SMILES: Cc1cc([C@@H](C)Nc2ccc(Cl)nc2C(=O)NS(C)(=O)=O)c2nc(N3C[C@@H]4[C@H](C3)[C@H]4c3cc4ncccn4n3)n(C)c(=O)c2c1] | 6-chloro-3-(((R)-1-(3,6-dimethyl-4-oxo-2-((1R,5S,6R)-6-(pyrazolo[1,5-a]pyrimidin-2-yl)-3-azabicyclo[3.1.0]hexan-3-yl)-3,4-dihydroquinazolin-8-yl)ethyl)amino)-N-(methylsulfonyl)picolinamide | 2.32 min, 254 nm, MS (ES+)[b] $C_{30}H_{30}ClN_9O_4S$, requires: 647.2, found: 648.2 $[M + H]^+$ |
| 509 | 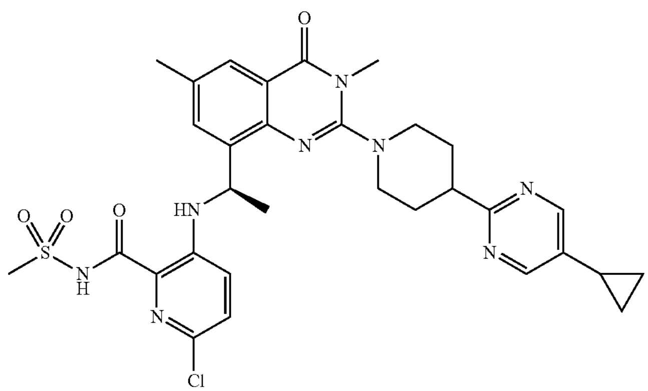 [SMILES: Cc1cc([C@@H](C)Nc2ccc(Cl)nc2C(=O)NS(C)(=O)=O)c2nc(N3CCC(c4ncc(C5CC5)cn4)CC3)n(C)c(=O)c2c1] | (R)-6-chloro-3-((1-(2-(4-(5-cyclopropylpyrimidin-2-yl)piperidin-1-yl)-3,6-dimethyl-4-oxo-3,4-dihydroquinazolin-8-yl)ethyl)amino)-N-(methylsulfonyl)picolinamide | 2.65 min, 254 nm, MS (ES+)[b] $C_{31}H_{35}ClN_8O_4S$, requires: 650.2, found: 651.3 $[M + H]^+$ |
| 510 | 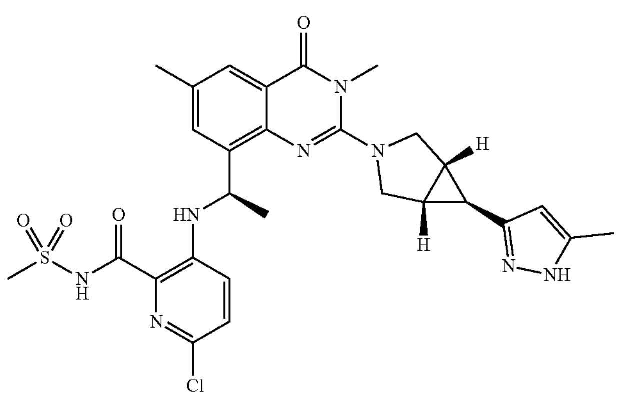 | 6-chloro-3-(((R)-1-(3,6-dimethyl-2-((1R,5S,6R)-6-(5-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.22 min, 254 nm, MS (ES+)[b] $C_{28}H_{31}ClN_8O_4S$, requires: 610.1, found: 611.2 $[M + H]^+$ |
| 511 | 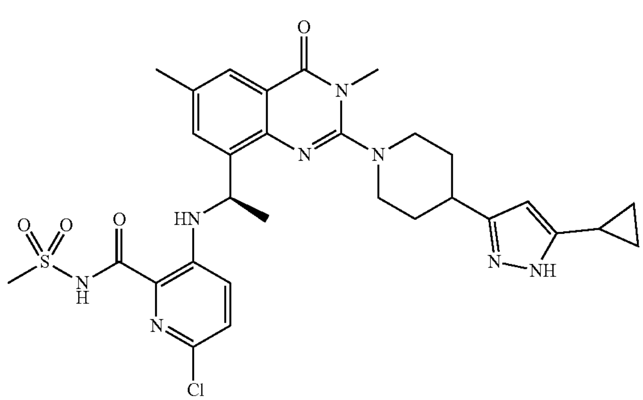 [SMILES: Cc1cc([C@@H](C)Nc2ccc(Cl)nc2C(=O)NS(C)(=O)=O)c2nc(N3CCC(c4cc(C5CC5)[nH]n4)CC3)n(C)c(=O)c2c1] | (R)-6-chloro-3-((1-(2-(4-(5-cyclopropyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.34 min, 254 nm, MS (ES+)[b] $C_{30}H_{35}ClN_8O_4S$, requires: 638.2, found: 639.2 $[M + H]^+$ |

TABLE E4-continued compound list prepared according to Route A in Example 4

| Cpd. ID | Structure | Name | LCMS |
|---|---|---|---|
| 512 | 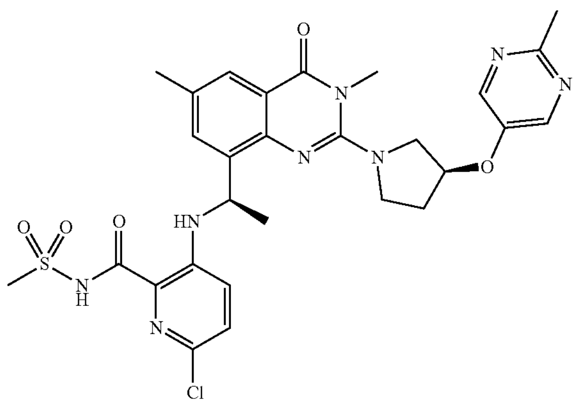 [SMILES: Cc1cc([C@@H](C)Nc2ccc(Cl)nc2C(=O)NS(C)(=O)=O)c2nc(N3CC[C@H](Oc4cnc(C)nc4)C3)n(C)c(=O)c2c1] | 6-chloro-3-(((R)-1-(3,6-dimethyl-2-((S)-3-((2-methylpyrimidin-5-yl)oxy)pyrrolidin-1-yl)-4-oxo-3,4-dihydroquinazolin-8-yl)ethyl)amino)-N-(methylsulfonyl)picolinamide | 2.18 min, 254 nm, MS (ES+)[b] $C_{28}H_{31}ClN_8O_5S$, requires: 626.1, found: 627.2 $[M + H]^+$ |
| 513 | 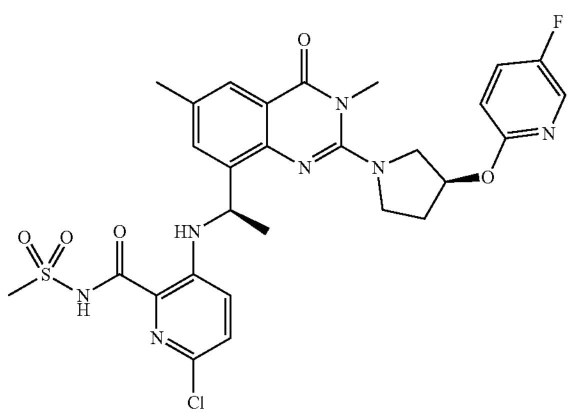 [SMILES: Cc1cc([C@@H](C)Nc2ccc(Cl)nc2C(=O)NS(C)(=O)=O)c2nc(N3CC[C@H](Oc4ccc(F)cn4)C3)n(C)c(=O)c2c1] | 6-chloro-3-(((R)-1-(2-((S)-3-((5-fluoropyridin-2-yl)oxy)pyrrolidin-1-yl)-3,6-dimethyl-4-oxo-3,4-dihydroquinazolin-8-yl)ethyl)amino)-N-(methylsulfonyl)picolinamide | 5.14 min, 254 nm, MS (ES+)[c] $C_{28}H_{29}ClFN_7O_5S$, requires: 629.2, found: 630.2 $[M + H]^+$ |
| 514 | 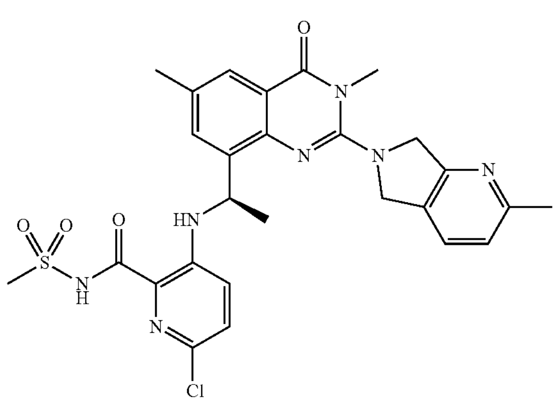 | (R)-6-chloro-3-((1-(3,6-dimethyl-2-(2-methyl-5,7-dihydro-6H-pyrrolo[3,4-b]pyridin-6-yl)-4-oxo-3,4-dihydroquinazolin-8-yl)ethyl)amino)-N-(methylsulfonyl)picolinamide | 4.10 min, 254 nm, MS (ES+)[c] $C_{27}H_{28}ClN_7O_4S$, requires: 581.2, found: 582.2 $[M + H]^+$ |

TABLE E4-continued compound list prepared according to Route A in Example 4

| Cpd. ID | Structure | Name | LCMS |
|---|---|---|---|
| 515 | 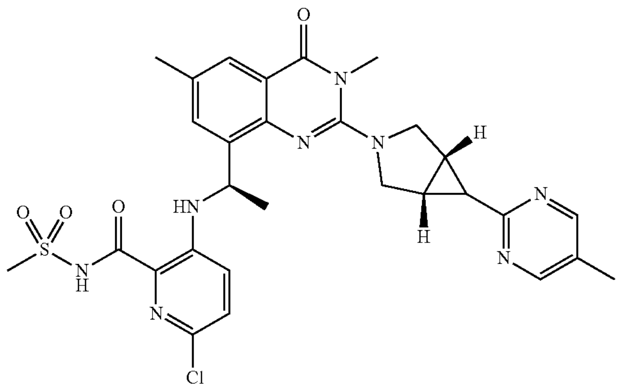 | 6-chloro-3-(((1R)-1-(3,6-dimethyl-2-((1R,5S)-6-(5-methylpyrimidin-2-yl)-3-azabicyclo[3.1.0]hexan-3-yl)-4-oxo-3,4-dihydroquinazolin-8-yl)ethyl)amino)-N-(methylsulfonyl)picolinamide | 3.60 min, 254 nm, MS (ES+)$^c$ $C_{29}H_{31}ClN_8O_4S$, requires: 622.2, found: 623.2 $[M + H]^+$ |
| 516 | 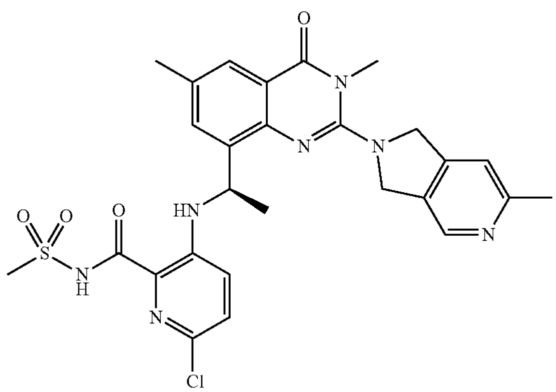 | (R)-6-chloro-3-((1-(3,6-dimethyl-2-(6-methyl-1,3-dihydro-2H-pyrrolo[3,4-c]pyridin-2-yl)-4-oxo-3,4-dihydroquinazolin-8-yl)ethyl)amino)-N-(methylsulfonyl)picolinamide | 3.13 min, 254 nm, MS (ES+)$^c$ $C_{27}H_{28}ClN_7O_4S$, requires: 581.2, found: 582.2 $[M + H]^+$ |
| 517 | 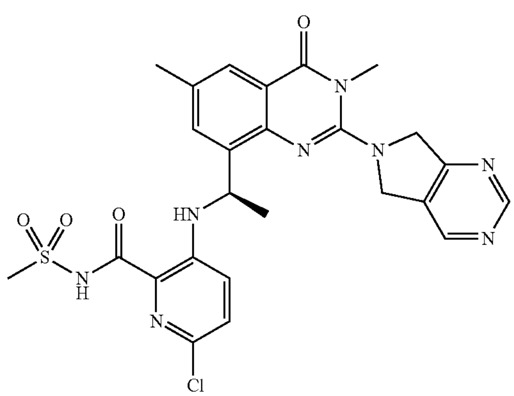 [SMILES: Cc1cc([C@@H](C)Nc2ccc(Cl)nc2C(=O)NS(C)(=O)=O)c2nc(N3Cc4cncnc4C3)n(C)c(=O)c2c1] | (R)-6-chloro-3-((1-(2-(5,7-dihydro-6H-pyrrolo[3,4-d]pyrimidin-6-yl)-3,6-dimethyl-4-oxo-3,4-dihydroquinazolin-8-yl)ethyl)amino)-N-(methylsulfonyl)picolinamide | 3.79 min, 254 nm, MS (ES+)$^c$ $C_{25}H_{25}ClN_8O_4S$, requires: 568.1, found: 569.1 $[M + H]^+$ |
| 518 | 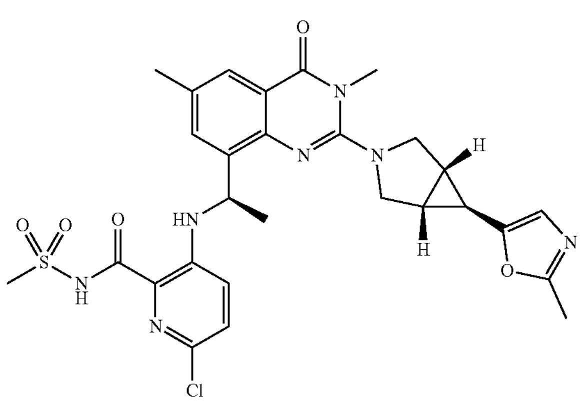 [SMILES: Cc1cc([C@@H](C)Nc2ccc(Cl)nc2C(=O)NS(C)(=O)=O)c2nc(N3C[C@@H]4[C@H](C3)[C@H]4c3cnc(C)o3)n(C)c(=O)c2c1] | 6-chloro-3-(((R)-1-(3,6-dimethyl-2-((1R,5S,6R)-6-(2-methyloxazol-5-yl)-3-azabicyclo[3.1.0]hexan-3-yl)-4-oxo-3,4-dihydroquinazolin-8-yl)ethyl)amino)-N-(methylsulfonyl)picolinamide | 2.49 min, 254 nm, MS (ES+)$^b$ $C_{28}H_{30}ClN_7O_5S$, requires: 611.1, found: 612.3 $[M + H]^+$ |

TABLE E4-continued compound list prepared according to Route A in Example 4

| Cpd. ID | Structure | Name | LCMS |
|---|---|---|---|
| 519 | 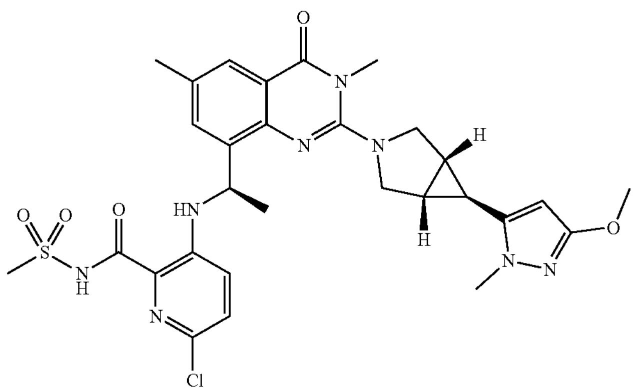 | 6-chloro-3-(((R)-1-(2-((1R,5S,6R)-6-(3-methoxy-1-methyl-1H-pyrazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.28 min, 254 nm, MS (ES+)[b] $C_{29}H_{33}ClN_8O_5S$, requires: 640.2, found: 641.2 [M + H]+ |
| 520 | 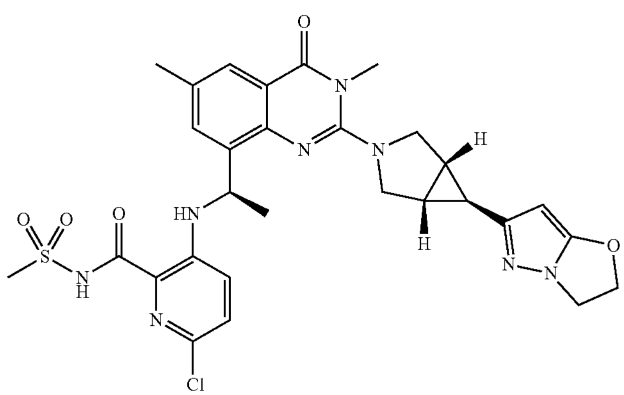 [SMILES: Cc1cc([C@@H](C)Nc2ccc(Cl)nc2C(=O)NS(C)(=O)=O)c2nc(N3C[C@@H]4[C@H](C3)[C@H]4c3cc4n(n3)CCO4)n(C)c(=O)c2c1] | 6-chloro-3-(((R)-1-(2-((1R,5S,6R)-6-(2,3-dihydropyrazolo[5,1-b]oxazol-6-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.21 min, 254 nm, MS (ES+)[b] $C_{29}H_{31}ClN_8O_5S$, requires: 638.1, found: 639.2 [M + H]+ |
| 521 | 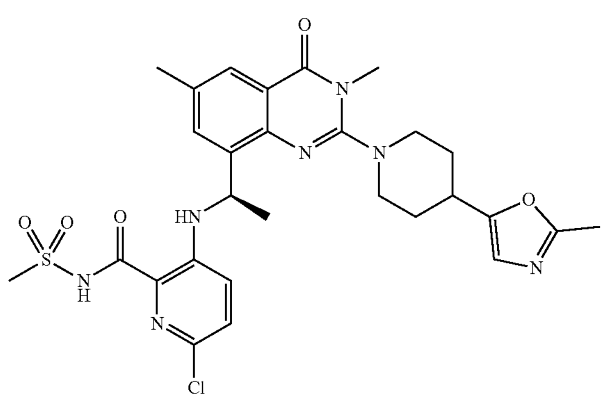 | (R)-6-chloro-3-((1-(3,6-dimethyl-2-(4-(2-methyloxazol-5-yl)piperidin-1-yl)-4-oxo-3,4-dihydroquinazolin-8-yl)ethyl)amino)-N-(methylsulfonyl)picolinamide | 2.40 min, 254 nm, MS (ES+)[b] $C_{28}H_{32}ClN_7O_5S$, requires: 613.1, found: 614.2 [M + H]+ |

TABLE E4-continued compound list prepared according to Route A in Example 4

| Cpd. ID | Structure | Name | LCMS |
|---|---|---|---|
| 522 | 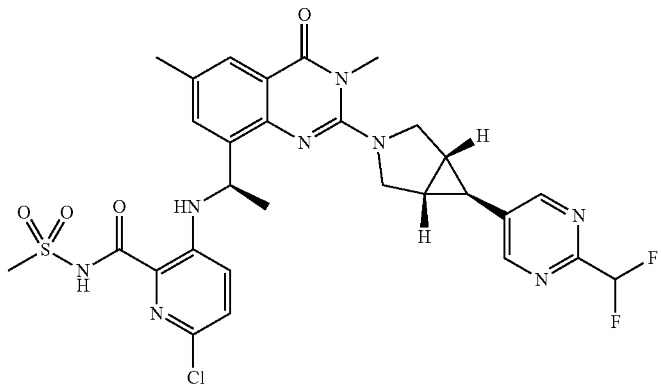 [SMILES: Cc1cc([C@@H](C)Nc2ccc(Cl)nc2C(=O)NS(C)(=O)=O)c2nc(N3C[C@@H]4[C@H](C3)[C@H]4c3cnc(C(F)F)nc3)n(C)c(=O)c2c1] | 6-chloro-3-(((R)-1-(2-((1R,5S,6S)-6-(2-(difluoromethyl)pyrimidin-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.47 min, 270 nm, MS (ES+)[b] C29H29ClF2N8O4S, requires: 658.1, found: 659.2 [M + H]+ |
| 523 | 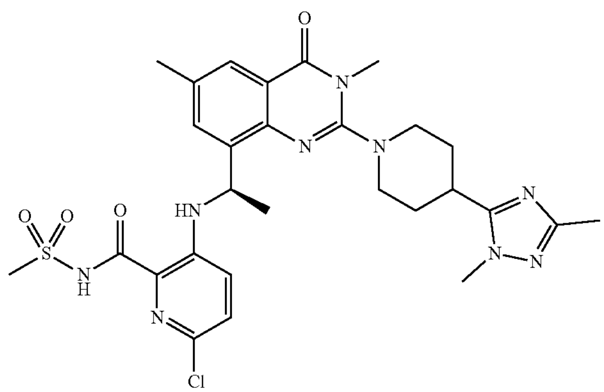 | (R)-6-chloro-3-((1-(2-(4-(1,3-dimethyl-1H-1,2,4-triazol-5-yl)piperidin-1-yl)-3,6-dimethyl-4-oxo-3,4-dihydroquinazolin-8-yl)ethyl)amino)-N-(methylsulfonyl)picolinamide | 2.11 min, 254 nm, MS (ES+)[b] C28H34ClN9O4S, requires: 627.2, found: 628.2 [M + H]+ |
| 524 | 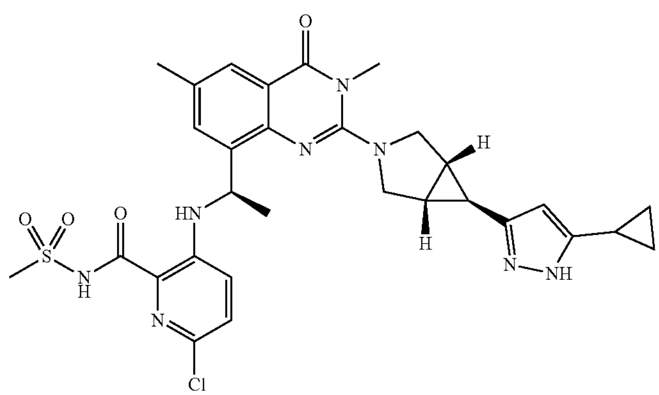 [SMILES: Cc1cc([C@@H](C)Nc2ccc(Cl)nc2C(=O)NS(C)(=O)=O)c2nc(N3C[C@@H]4[C@H](C3)[C@H]4c3cc(C4CC4)[nH]n3)n(C)c(=O)c2c1] | 6-chloro-3-(((R)-1-(2-((1R,5S,6R)-6-(5-cyclopropyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.30 min, 254 nm, MS (ES+)[b] C30H33ClN8O4S, requires: 636.2, found: 637.2 [M + H]+ |
| 525 | 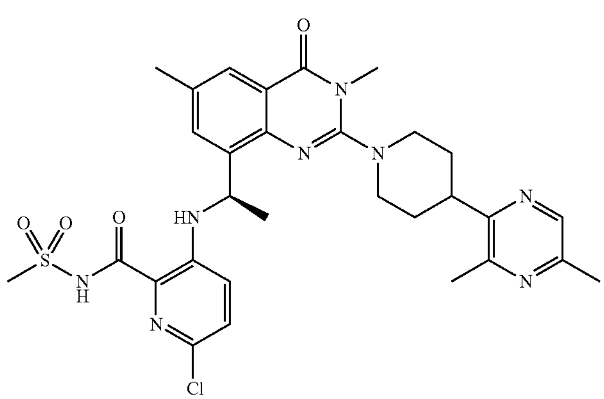 | (R)-6-chloro-3-((1-(2-(4-(3,5-dimethylpyrazin-2-yl)piperidin-1-yl)-3,6-dimethyl-4-oxo-3,4-dihydroquinazolin-8-yl)ethyl)amino)-N-(methylsulfonyl)picolinamide | 2.60 min, 254 nm, MS (ES+)[b] C30H35ClN8O4S, requires: 638.2, found: 639.3 [M + H]+ |

TABLE E4-continued compound list prepared according to Route A in Example 4

| Cpd. ID | Structure | Name | LCMS |
|---|---|---|---|
| 526 | 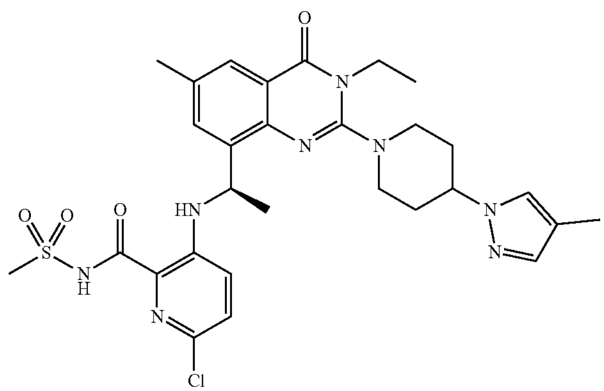 | (R)-6-chloro-3-((1-(3-ethyl-6-methyl-2-(4-(4-methyl-1H-pyrazol-1-yl)piperidin-1-yl)-4-oxo-3,4-dihydroquinazolin-8-yl)ethyl)amino)-N-(methylsulfonyl) picolinamide | 2.56 min, 254 nm, MS (ES+)[b] $C_{29}H_{35}ClN_8O_4S$, requires: 626.2, found: 627.2 [M + H]+ |
| 527 | 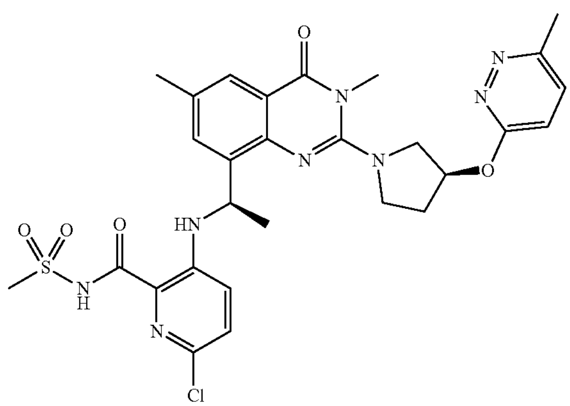 [SMILES: Cc1cc([C@@H](C)Nc2ccc(Cl)nc2C(=O)NS(C)(=O)=O)c2nc(N3CC[C@H](Oc4ccc(C)nn4)C3)n(C)c(=O)c2c1] | 6-chloro-3-(((R)-1-(3,6-dimethyl-2-((S)-3-((6-methylpyridazin-3-yl)oxy)pyrrolidin-1-yl)-4-oxo-3,4-dihydroquinazolin-8-yl)ethyl)amino)-N-(methylsulfonyl) picolinamide | 2.21 min, 254 nm, MS (ES+)[b] $C_{28}H_{31}ClN_8O_5S$, requires: 626.1, found: 627.2 [M + H]+ |
| 528 | 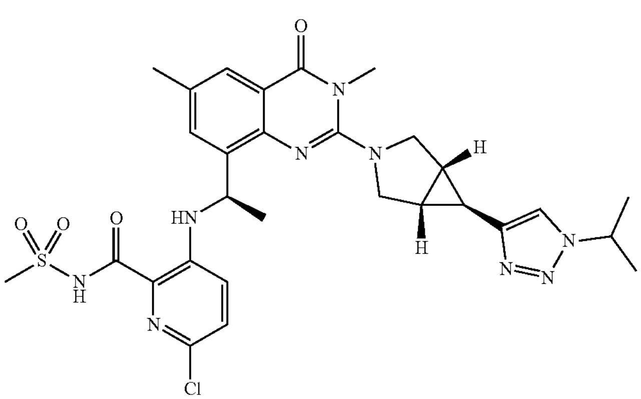 [SMILES: Cc1cc([C@@H](C)Nc2ccc(Cl)nc2C(=O)NS(C)(=O)=O)c2nc(N3C[C@@H]4[C@H](C3)[C@H]4c3cn(C(C)C)nn3)n(C)c(=O)c2c1] | 6-chloro-3-(((R)-1-(2-((1R,5S,6R)-6-(1-isopropyl-1H-1,2,3-triazol-4-yl)-3-azabicyclo[3.1.0]hexan-3-yl)-3,6-dimethyl-4-oxo-3,4-dihydroquinazolin-8-yl)ethyl)amino)-N-(methylsulfonyl) picolinamide | 2.24 min, 254 nm, MS (ES+)[b] $C_{29}H_{34}ClN_9O_4S$, requires: 639.2, found: 640.2 [M + H]+ |

TABLE E4-continued compound list prepared according to Route A in Example 4

| Cpd. ID | Structure | Name | LCMS |
|---|---|---|---|
| 529 | 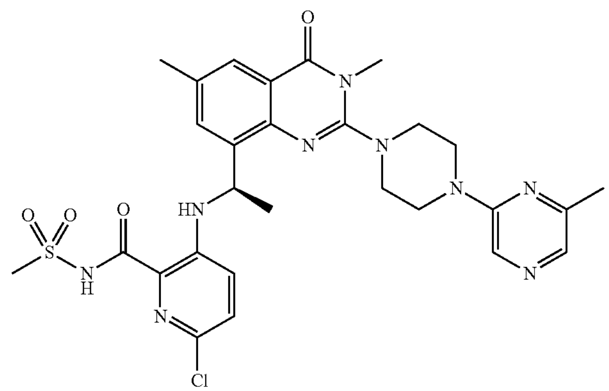 | (R)-6-chloro-3-((1-(3,6-dimethyl-2-(4-(6-methylpyrazin-2-yl)piperazin-1-yl)-4-oxo-3,4-dihydroquinazolin-8-yl)ethyl)amino)-N-(methylsulfonyl)picolinamide | 2.49 min, 215 nm, MS (ES+)[b] $C_{28}H_{32}ClN_9O_4S$, requires: 625.2, found: 626.3 $[M + H]^+$ |
| 530 | 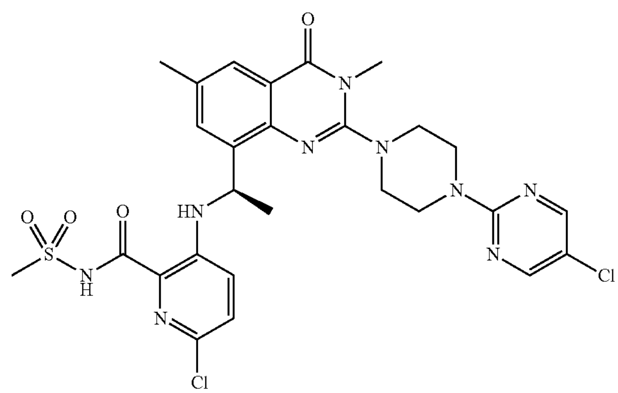 [SMILES: Cc1cc([C@@H](C)Nc2ccc(Cl)nc2C(=O)NS(C)(=O)=O)c2nc(N3CCN(c4ncc(Cl)cn4)CC3)n(C)c(=O)c2c1] | (R)-6-chloro-3-((1-(2-(4-(5-chloropyrimidin-2-yl)piperazin-1-yl)-3,6-dimethyl-4-oxo-3,4-dihydroquinazolin-8-yl)ethyl)amino)-N-(methylsulfonyl)picolinamide | 2.72 min, 254 nm, MS (ES+)[b] $C_{27}H_{29}Cl_2N_9O_4S$, requires: 645.1, found: 646.1 $[M + H]^+$ |
| 531 | 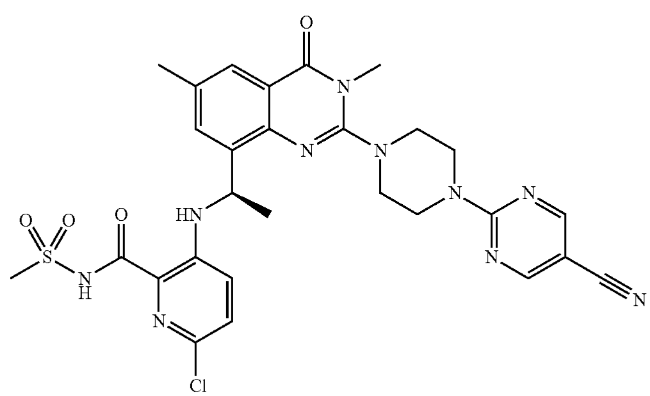 [SMILES: Cc1cc([C@@H](C)Nc2ccc(Cl)nc2C(=O)NS(C)(=O)=O)c2nc(N3CCN(c4ncc(C#N)cn4)CC3)n(C)c(=O)c2c1] | (R)-6-chloro-3-((1-(2-(4-(5-cyanopyrimidin-2-yl)piperazin-1-yl)-3,6-dimethyl-4-oxo-3,4-dihydroquinazolin-8-yl)ethyl)amino)-N-(methylsulfonyl)picolinamide | 2.37 min, 254 nm, MS (ES+)b $C_{28}H_{29}ClN_{10}O_4S$, requires: 636.1, found: 637.2 $[M + H]+$ |
| 532 | 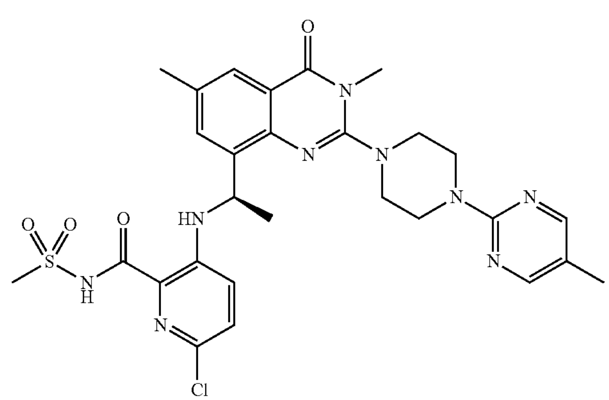 | (R)-6-chloro-3-((1-(3,6-dimethyl-2-(4-(5-methylpyrimidin-2-yl)piperazin-1-yl)-4-oxo-3,4-dihydroquinazolin-8-yl)ethyl)amino)-N-(methylsulfonyl)picolinamide | 2.49 min, 254 nm, MS (ES+)[b] $C_{28}H_{32}ClN_9O_4S$, requires: 625.2, found: 626.2 $[M + H]^+$ |

TABLE E4-continued compound list prepared according to Route A in Example 4

| Cpd. ID | Structure | Name | LCMS |
|---|---|---|---|
| 533 | 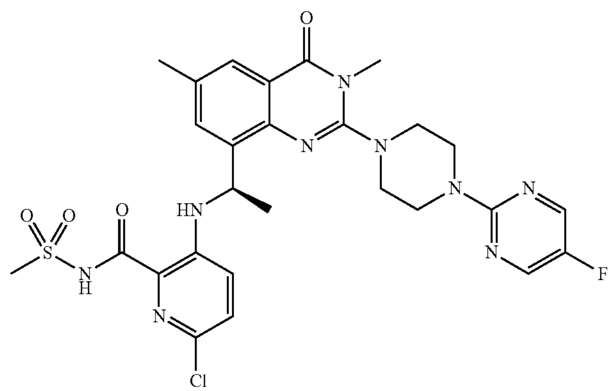 [SMILES: Cc1cc([C@@H](C)Nc2ccc(Cl)nc2C(=O)NS(C)(=O)=O)c2nc(N3CCN(c4ncc(F)cn4)CC3)n(C)c(=O)c2c1] | (R)-6-chloro-3-((1-(2-(4-(5-fluoropyrimidin-2-yl)piperazin-1-yl)-3,6-dimethyl-4-oxo-3,4-dihydroquinazolin-8-yl)ethyl)amino)-N-(methylsulfonyl)picolinamide | 2.49 min, 254 nm, MS (ES+)[b] $C_{27}H_{29}ClFN_9O_4S$, requires: 629.1, found: 630.2 [M + H]+ |
| 534 | 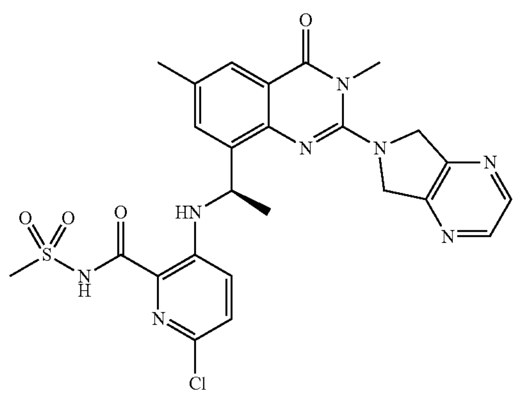 [SMILES: Cc1cc([C@@H](C)Nc2ccc(Cl)nc2C(=O)NS(C)(=O)=O)c2nc(N3Cc4nccnc4C3)n(C)c(=O)c2c1] | (R)-6-chloro-3-((1-(2-(5,7-dihydro-6H-pyrrolo[3,4-b]pyrazin-6-yl)-3,6-dimethyl-4-oxo-3,4-dihydroquinazolin-8-yl)ethyl)amino)-N-(methylsulfonyl)picolinamide | 4.01 min, 254 nm, MS (ES+)[c] $C_{25}H_{25}ClN_8O_4S$, requires: 568.1, found: 569.1 [M + H]+ |
| 535 | 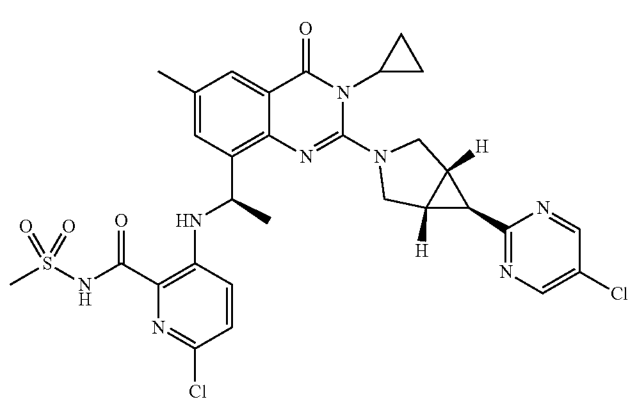 | 6-chloro-3-(((1R)-1-(2-((1R,5S)-6-(5-chloropyrimidin-2-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 3.88 min, 254 nm, MS (ES+)[c] $C_{28}H_{28}Cl_2N_8O_4S$, requires: 642.1, found: 643.2 [M + H]+ |

TABLE E4-continued compound list prepared according to Route A in Example 4

| Cpd. ID | Structure | Name | LCMS |
|---|---|---|---|
| 536 | 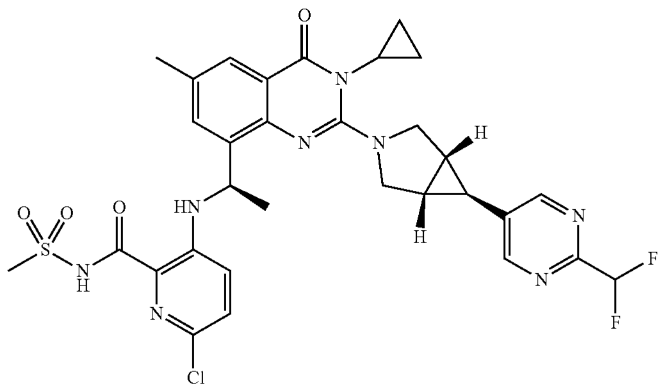 | 6-chloro-3-(((1R)-1-(2-((1R,5S)-6-(2-(difluoromethyl)pyrimidin-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 3.44 min, 254 nm, MS (ES+)$^c$ $C_{29}H_{29}ClF_2N_8O_4S$, requires: 658.2, found: 659.3 [M + H]$^+$ |
| 537 | 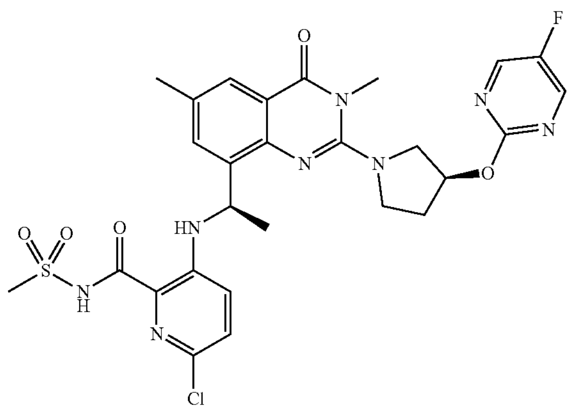 [SMILES: Cc1cc([C@@H](C)Nc2ccc(Cl)nc2C(=O)NS(C)(=O)=O)c2nc(N3CC[C@H](Oc4ncc(F)cn4)C3)n(C)c(=O)c2c1] | 6-chloro-3-(((R)-1-(2-((S)-3-((5-fluoropyrimidin-2-yl)oxy)pyrrolidin-1-yl)-3,6-dimethyl-4-oxo-3,4-dihydroquinazolin-8-yl)ethyl)amino)-N-(methylsulfonyl)picolinamide | 4.47 min, 254 nm, MS (ES+)$^c$ $C_{27}H_{28}ClFN_8O_5S$, requires: 630.2, found: 631.2 [M + H]$^+$ |
| 538 | 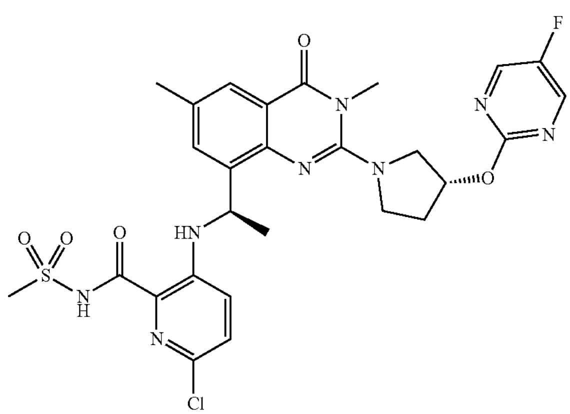 [SMILES: Cc1cc([C@@H](C)Nc2ccc(Cl)nc2C(=O)NS(C)(=O)=O)c2nc(N3CC[C@@H](Oc4ncc(F)cn4)C3)n(C)c(=O)c2c1] | 6-chloro-3-(((R)-1-(2-((R)-3-((5-fluoropyrimidin-2-yl)oxy)pyrrolidin-1-yl)-3,6-dimethyl-4-oxo-3,4-dihydroquinazolin-8-yl)ethyl)amino)-N-(methylsulfonyl)picolinamide | 4.59 min, 254 nm, MS (ES+)$^c$ $C_{27}H_{28}ClFN_8O_5S$, requires: 630.2, found: 631.2 [M + H]$^+$ |

TABLE E4-continued compound list prepared according to Route A in Example 4

| Cpd. ID | Structure | Name | LCMS |
|---|---|---|---|
| 539 | 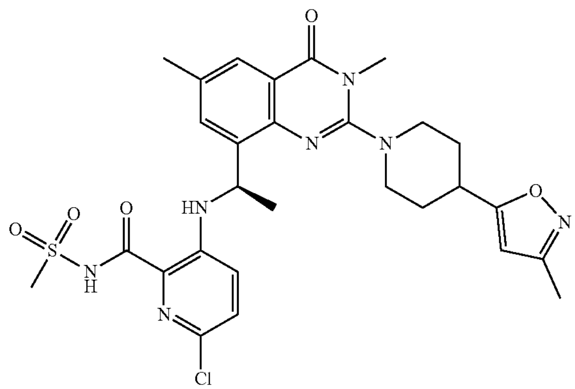 [SMILES: Cc1cc([C@@H](C)Nc2ccc(Cl)nc2C(=O)NS(C)(=O)=O)c2nc(N3CCC(c4cc(C)no4)CC3)n(C)c(=O)c2c1] | (R)-6-chloro-3-((1-(3,6-dimethyl-2-(4-(3-methylisoxazol-5-yl)piperidin-1-yl)-4-oxo-3,4-dihydroquinazolin-8-yl)ethyl)amino)-N-(methylsulfonyl)picolinamide | 3.59 min, 254 nm, MS (ES+)$^c$ $C_{28}H_{32}ClN_7O_5S$, requires: 613.2, found: 614.3 $[M + H]^+$ |
| 540 | 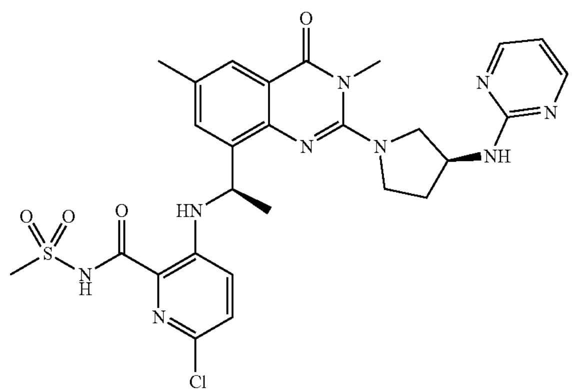 [SMILES: Cc1cc([C@@H](C)Nc2ccc(Cl)nc2C(=O)NS(C)(=O)=O)c2nc(N3CC[C@H](Nc4ncccn4)C3)n(C)c(=O)c2c1] | 6-chloro-3-(((R)-1-(3,6-dimethyl-4-oxo-2-((S)-3-(pyrimidin-2-ylamino)pyrrolidin-1-yl)-3,4-dihydroquinazolin-8-yl)ethyl)amino)-N-(methylsulfonyl)picolinamide | 4.05 min, 254 nm, MS (ES+)$^c$ $C_{27}H_{30}ClN_9O_4S$, requires: 611.2, found: 612.2 $[M + H]^+$ |
| 541 | 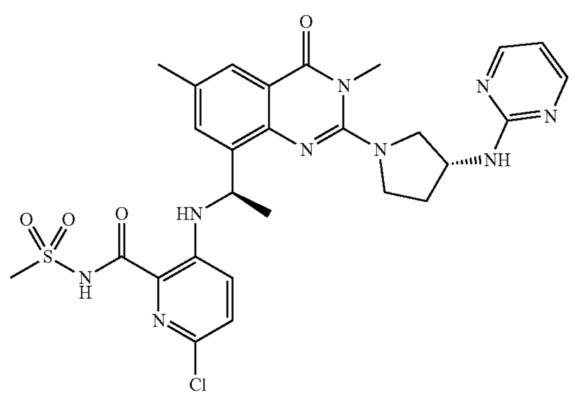 [SMILES: Cc1cc([C@@H](C)Nc2ccc(Cl)nc2C(=O)NS(C)(=O)=O)c2nc(N3CC[C@@H](Nc4ncccn4)C3)n(C)c(=O)c2c1] | 6-chloro-3-(((R)-1-(3,6-dimethyl-4-oxo-2-((R)-3-(pyrimidin-2-ylamino)pyrrolidin-1-yl)-3,4-dihydroquinazolin-8-yl)ethyl)amino)-N-(methylsulfonyl)picolinamide | 3.15 min, 254 nm, MS (ES+)$^c$ $C_{27}H_{30}ClN_9O_4S$, requires: 611.2, found: 612.2 $[M + H]^+$ |
| 542 | 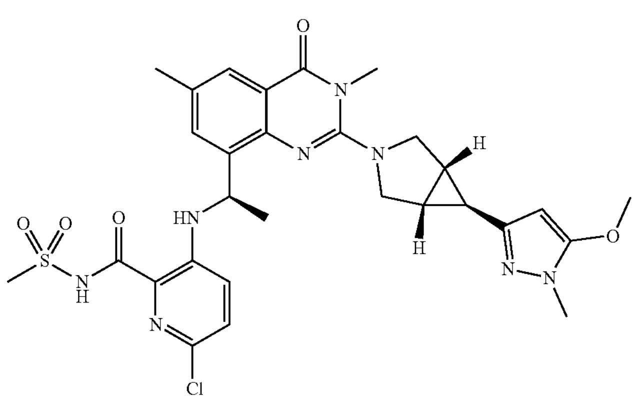 | 6-chloro-3-(((R)-1-(2-((1R,5S,6R)-6-(5-methoxy-1-methyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.28 min, 254 nm, MS (ES+)$^b$ $C_{29}H_{33}ClN_8O_5S$, requires: 640.2, found: 641.2 $[M + H]^+$ |

TABLE E4-continued compound list prepared according to Route A in Example 4

| Cpd. ID | Structure | Name | LCMS |
|---|---|---|---|
| 543 | 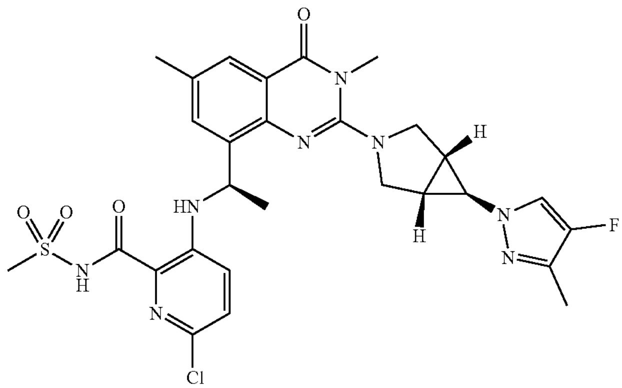 [SMILES: Cc1cc([C@@H](C)Nc2ccc(Cl)nc2C(=O)NS(C)(=O)=O)c2nc(N3C[C@@H]4[C@H](C3)[C@H]4n3cc(F)c(C)n3)n(C)c(=O)c2c1] | 6-chloro-3-(((R)-1-(2-((1R,5S,6S)-6-(4-fluoro-3-methyl-1H-pyrazol-1-yl)-3-azabicyclo[3.1.0]hexan-3-yl)-3,6-dimethyl-4-oxo-3,4-dihydroquinazolin-8-yl)ethyl)amino)-N-(methylsulfonyl) picolinamide | 2.37 min, 254 nm, MS (ES+)[b] $C_{28}H_{30}ClFN_8O_4S$, requires: 628.1, found: 629.2 $[M + H]^+$ |
| 544 | 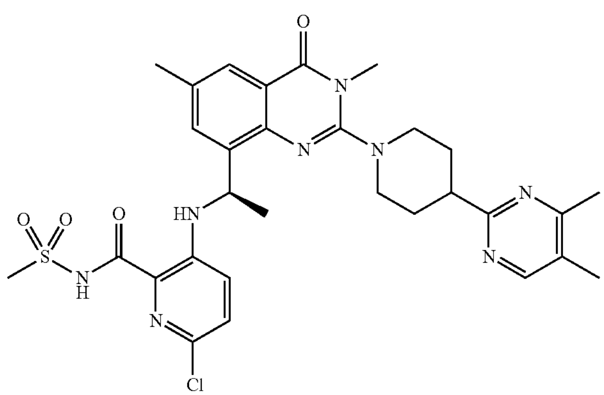 | (R)-6-chloro-3-((1-(2-(4-(4,5-dimethylpyrimidin-2-yl)piperidin-1-yl)-3,6-dimethyl-4-oxo-3,4-dihydroquinazolin-8-yl)ethyl)amino)-N-(methylsulfonyl) picolinamide | 2.43 min, 270 nm, MS (ES+)[b] $C_{30}H_{35}ClN_8O_4S$, requires: 638.2, found: 639.2 $[M + H]^+$ |
| 545 | 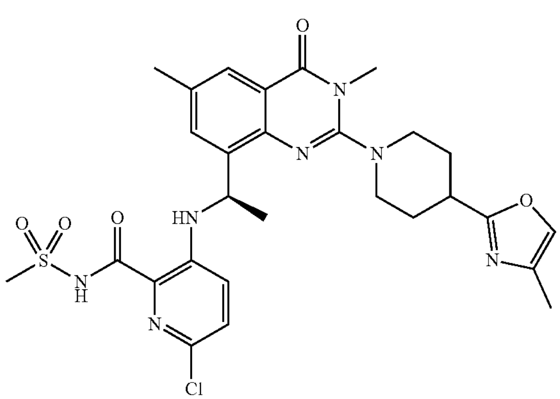 [SMILES: Cc1cc([C@@H](C)Nc2ccc(Cl)nc2C(=O)NS(C)(=O)=O)c2nc(N3CCC(c4nc(C)co4)CC3)n(C)c(=O)c2c1] | (R)-6-chloro-3-((1-(3,6-dimethyl-2-(4-(4-methyloxazol-2-yl)piperidin-1-yl)-4-oxo-3,4-dihydroquinazolin-8-yl)ethyl)amino)-N-(methylsulfonyl) picolinamide | 2.59 min, 254 nm, MS (ES+)[b] $C_{28}H_{32}ClN_7O_5S$, requires: 613.1, found: 614.3 $[M + H]^+$ |

TABLE E4-continued compound list prepared according to Route A in Example 4

| Cpd. ID | Name | LCMS |
|---|---|---|
| 546 | (R)-6-chloro-3-((1-(3-ethyl-6-methyl-2-(2-methyl-2,4,6,7-tetrahydro-5H-pyrazolo[4,3-c]pyridin-5-yl)-4-oxo-3,4-dihydroquinazolin-8-yl)ethyl)amino)-N-(methylsulfonyl)picolinamide | 2.22 min, 270 nm, MS (ES+)[b] $C_{27}H_{31}ClN_8O_4S$, requires: 598.2, found: 599.3 [M + H]+ |
| 547 | (R)-6-chloro-3-((1-(2-(4-(4-fluoro-5-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.33 min, 220 nm, MS (ES+)[b] $C_{28}H_{32}ClFN_8O_4S$, requires: 630.1, found: 631.3 [M + H]+ |
| 548 | 6-chloro-3-(((R)-1-(2-((1R,5S,6S)-6-(3-fluoro-2-methylpyridin-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.22 min, 270 nm, MS (ES+)[b] $C_{30}H_{31}ClFN_7O_4S$, requires: 639.1, found: 640.2 [M + H]+ |
| 549 | (R)-6-chloro-3-((1-(3,6-dimethyl-2-(4-(5-methyl-1H-1,2,4-triazol-1-yl)piperidin-1-yl)-4-oxo-3,4-dihydroquinazolin-8-yl)ethyl)amino)-N-(methylsulfonyl)picolinamide | 2.09 min, 254 nm, MS (ES+)[b] $C_{27}H_{32}ClN_9O_4S$, requires: 613.2, found: 614.2 [M + H]+ |

TABLE E4-continued compound list prepared according to Route A in Example 4

| Cpd. ID | Structure | Name | LCMS |
|---|---|---|---|
| 550 | 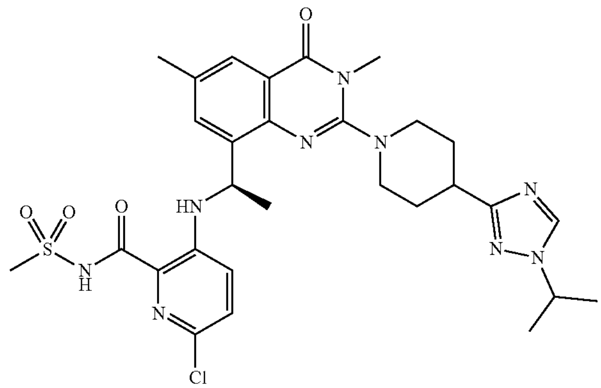 [SMILES: Cc1cc([C@@H](C)Nc2ccc(Cl)nc2C(=O)NS(C)(=O)=O)c2nc(N3CCC(c4ncn(C(C)C)n4)CC3)n(C)c(=O)c2c1] | (R)-6-chloro-3-((1-(2-(4-(1-isopropyl-1H-1,2,4-triazol-3-yl)piperidin-1-yl)-3,6-dimethyl-4-oxo-3,4-dihydroquinazolin-8-yl)ethyl)amino)-N-(methylsulfonyl)picolinamide | 2.19 min, 254 nm, MS (ES+)[b] $C_{29}H_{36}ClN_9O_4S$, requires: 641.2, found: 642.2 [M + H]+ |
| 551 | 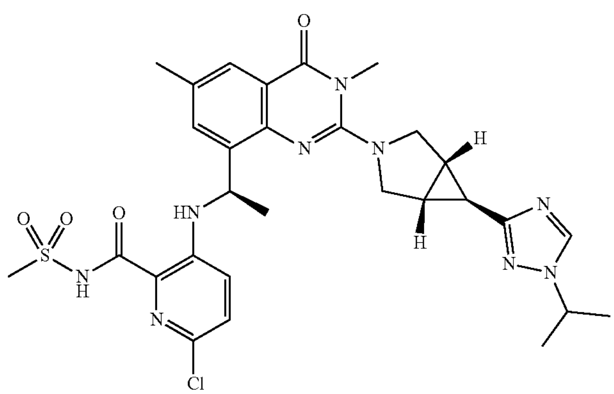 [SMILES: Cc1cc([C@@H](C)Nc2ccc(Cl)nc2C(=O)NS(C)(=O)=O)c2nc(N3C[C@@H]4[C@H](C3)[C@H]4c3ncn(C(C)C)n3)n(C)c(=O)c2c1] | 6-chloro-3-(((R)-1-(2-((1R,5S,6R)-6-(1-isopropyl-1H-1,2,4-triazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.23 min, 254 nm, MS (ES+)[b] $C_{29}H_{34}ClN_9O_4S$, requires: 639.2, found: 640.2 [M + H]+ |
| 552 | 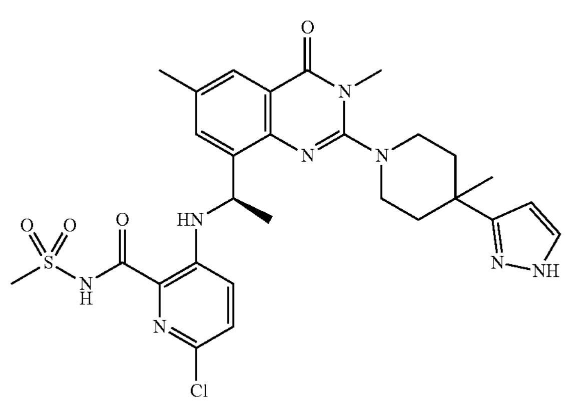 | (R)-6-chloro-3-((1-(3,6-dimethyl-2-(4-methyl-4-(1H-pyrazol-3-yl)piperidin-1-yl)-4-oxo-3,4-dihydroquinazolin-8-yl)ethyl)amino)-N-(methylsulfonyl)picolinamide | 2.43 min, 254 nm, MS (ES+)[b] $C_{28}H_{33}ClN_8O_4S$, requires: 612.2, found: 613.3 [M + H]+ |

TABLE E4-continued compound list prepared according to Route A in Example 4

| Cpd. ID | Structure | Name | LCMS |
|---|---|---|---|
| 553 | 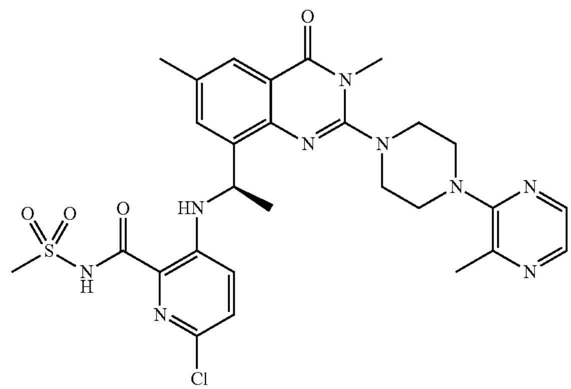 [SMILES: Cc1cc([C@@H](C)Nc2ccc(Cl)nc2C(=O)NS(C)(=O)=O)c2nc(N3CCN(c4nccnc4C)CC3)n(C)c(=O)c2c1] | (R)-6-chloro-3-((1-(3,6-dimethyl-2-(4-(3-methylpyrazin-2-yl)piperazin-1-yl)-4-oxo-3,4-dihydroquinazolin-8-yl)ethyl)amino)-N-(methylsulfonyl)picolinamide | 2.31 min, 254 nm, MS (ES+)[b] $C_{28}H_{32}ClN_9O_4S$, requires: 625.2, found: 626.2 [M + H]+ |
| 554 | 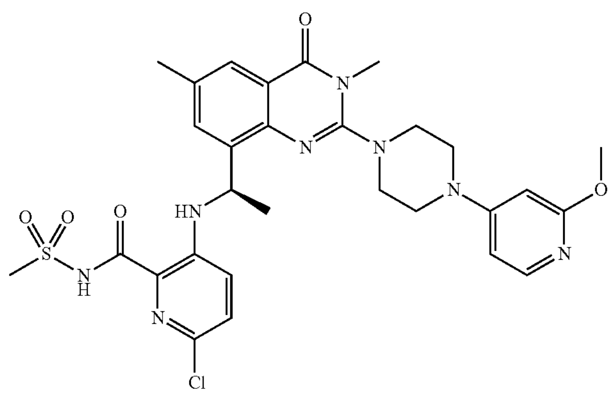 | (R)-6-chloro-3-((1-(2-(4-(2-methoxypyridin-4-yl)piperazin-1-yl)-3,6-dimethyl-4-oxo-3,4-dihydroquinazolin-8-yl)ethyl)amino)-N-(methylsulfonyl)picolinamide | 1.87 min, 254 nm, MS (ES+)[b] $C_{29}H_{33}ClN_8O_5S$, requires: 640.2, found: 641.2 [M + H]+ |
| 555 | 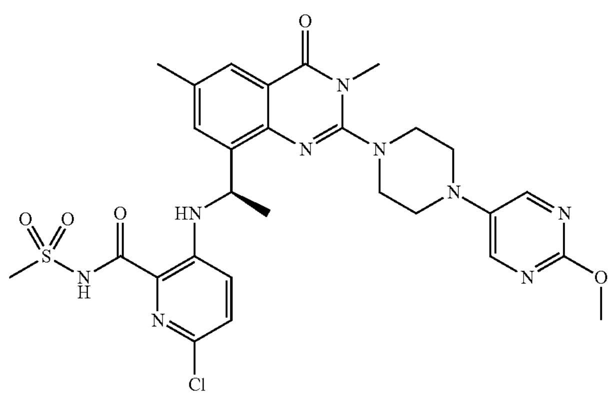 | (R)-6-chloro-3-((1-(2-(4-(2-methoxypyrimidin-5-yl)piperazin-1-yl)-3,6-dimethyl-4-oxo-3,4-dihydroquinazolin-8-yl)ethyl)amino)-N-(methylsulfonyl)picolinamide | 2.21 min, 220 nm, MS (ES+)[b] $C_{28}H_{32}ClN_9O_5S$, requires: 641.1, found: 642.2 [M + H]+ |
| 556 | 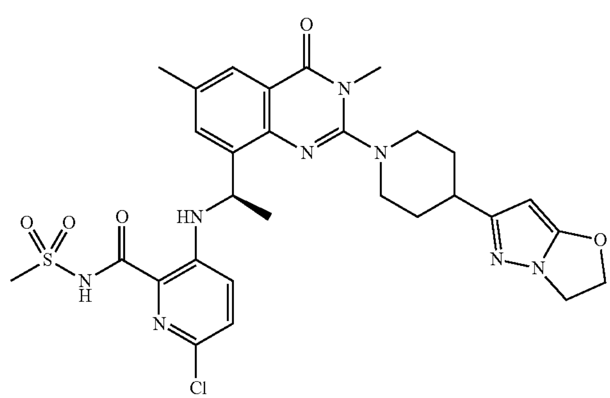 [SMILES: Cc1cc([C@@H](C)Nc2ccc(Cl)nc2C(=O)NS(C)(=O)=O)c2nc(N3CCC(c4cc5n(n4)CCO5)CC3)n(C)c(=O)c2c1] | (R)-6-chloro-3-((1-(2-(4-(2,3-dihydropyrazolo[5,1-b]oxazol-6-yl)piperidin-1-yl)-3,6-dimethyl-4-oxo-3,4-dihydroquinazolin-8-yl)ethyl)amino)-N-(methylsulfonyl)picolinamide | 2.38 min, 254 nm, MS (ES+)[b] $C_{29}H_{33}ClN_8O_5S$, requires: 640.2, found: 641.3 [M + H]+ |

TABLE E4-continued compound list prepared according to Route A in Example 4

| Cpd. ID | Structure | Name | LCMS |
|---|---|---|---|
| 557 | 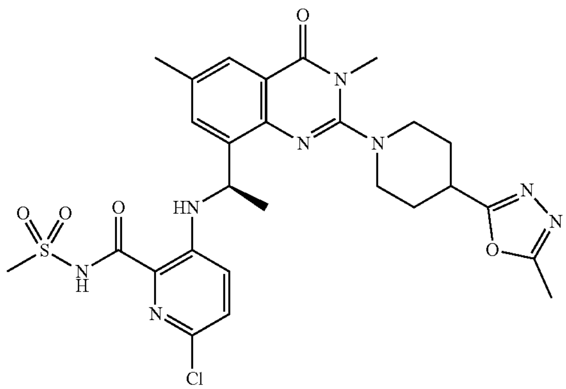 [SMILES: Cc1cc([C@@H](C)Nc2ccc(Cl)nc2C(=O)NS(C)(=O)=O)c2nc(N3CCC(c4nnc(C)o4)CC3)n(C)c(=O)c2c1] | (R)-6-chloro-3-((1-(3,6-dimethyl-2-(4-(5-methyl-1,3,4-oxadiazol-2-yl)piperidin-1-yl)-4-oxo-3,4-dihydroquinazolin-8-yl)ethyl)amino)-N-(methylsulfonyl)picolinamide | 2.34 min, 270 nm, MS (ES+)[b] $C_{27}H_{31}ClN_8O_5S$, requires: 614.1, found: 615.3 $[M + H]^+$ |
| 558 | 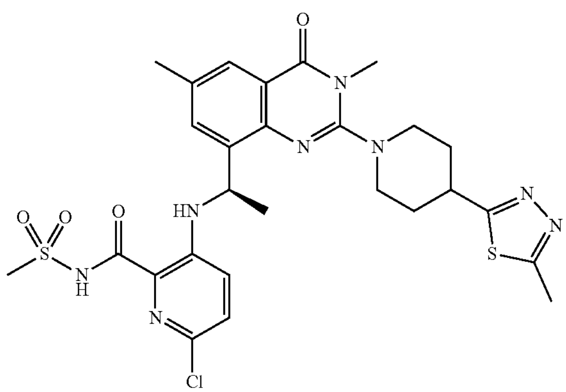 [SMILES: Cc1cc([C@@H](C)Nc2ccc(Cl)nc2C(=O)NS(C)(=O)=O)c2nc(N3CCC(c4nnc(C)s4)CC3)n(C)c(=O)c2c1] | (R)-6-chloro-3-((1-(3,6-dimethyl-2-(4-(5-methyl-1,3,4-thiadiazol-2-yl)piperidin-1-yl)-4-oxo-3,4-dihydroquinazolin-8-yl)ethyl)amino)-N-(methylsulfonyl)picolinamide | 2.21 min, 220 nm, MS (ES+)[b] $C_{27}H_{31}ClN_8O_4S_2$, requires: 630.1, found: 631.2 $[M + H]^+$ |
| 559 | 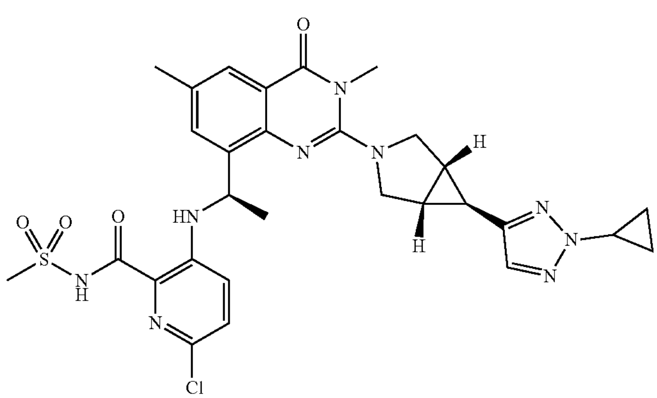 [SMILES: Cc1cc([C@@H](C)Nc2ccc(Cl)nc2C(=O)NS(C)(=O)=O)c2nc(N3C[C@@H]4[C@H](C3)[C@H]4c3cnn(C4CC4)n3)n(C)c(=O)c2c1] | 6-chloro-3-(((R)-1-(2-((1R,5S,6R)-6-(2-cyclopropyl-2H-1,2,3-triazol-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.46 min, 220 nm, MS (ES+)[b] $C_{29}H_{32}ClN_9O_4S$, requires: 637.2, found: 638.2 $[M + H]^+$ |

TABLE E4-continued compound list prepared according to Route A in Example 4

| Cpd. ID | Structure | Name | LCMS |
|---|---|---|---|
| 560 | 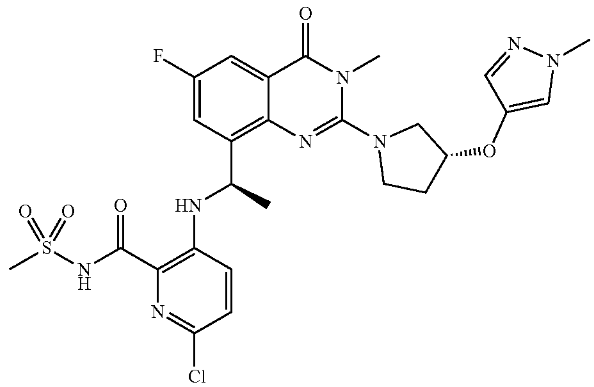 | 6-chloro-3-(((R)-1-(6-fluoro-3-methyl-2-((R)-3-((1-methyl-1H-pyrazol-4-yl)oxy)pyrrolidin-1-yl)-4-oxo-3,4-dihydroquinazolin-8-yl)ethyl)amino)-N-(methylsulfonyl) picolinamide | 2.08 min, 269 nm, MS (ES+)$^b$ $C_{26}H_{28}ClFN_8O_5S$, requires: 618.1, found: 619.1 $[M + H]^+$ |
| 561 | 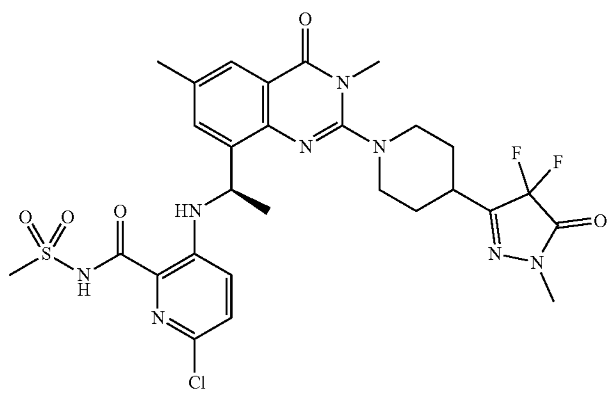 [SMILES: Cc1cc([C@@H](C)Nc2ccc(Cl)nc2C(=O)NS(C)(=O)=O)c2nc(N3CCC(C4=NN(C)C(=O)C4(F)F)CC3)n(C)c(=O)c2c1] | (R)-6-chloro-3-((1-(2-(4-(4,4-difluoro-1-methyl-5-oxo-4,5-dihydro-1H-pyrazol-3-yl)piperidin-1-yl)-3,6-dimethyl-4-oxo-3,4-dihydroquinazolin-8-yl)ethyl)amino)-N-(methylsulfonyl) picolinamide | 2.52 min, 254 nm, MS (ES+)$^b$ $C_{28}H_{31}ClF_2N_8O_5S$, requires: 664.1, found: 665.2 $[M + H]^+$ |
| 562 | 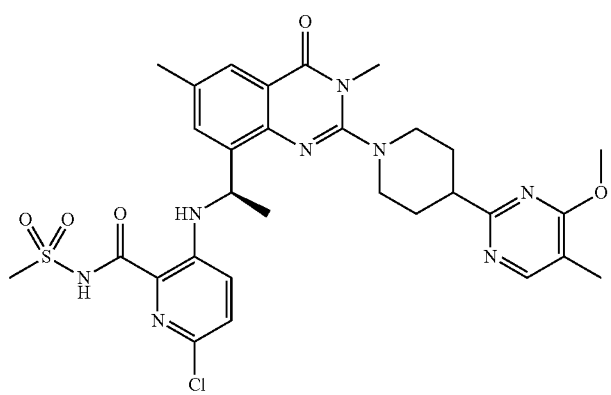 | (R)-6-chloro-3-((1-(2-(4-(4-methoxy-5-methylpyrimidin-2-yl)piperidin-1-yl)-3,6-dimethyl-4-oxo-3,4-dihydroquinazolin-8-yl)ethyl)amino)-N-(methylsulfonyl) picolinamide | 2.56 min, 270 nm, MS (ES+)$^b$ $C_{30}H_{35}ClN_8O_5S$, requires: 654.2, found: 655.2 $[M + H]^+$ |
| 563 | 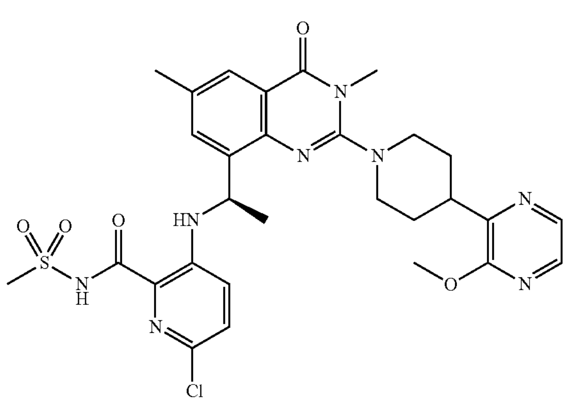 [SMILES: COc1nccnc1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(2-(4-(3-methoxypyrazin-2-yl)piperidin-1-yl)-3,6-dimethyl-4-oxo-3,4-dihydroquinazolin-8-yl)ethyl)amino)-N-(methylsulfonyl) picolinamide | 2.62 min, 270 nm, MS (ES+)$^b$ $C_{29}H_{33}ClN_8O_5S$, requires: 640.2, found: 641.2 $[M + H]^+$ |

TABLE E4-continued compound list prepared according to Route A in Example 4

| Cpd. ID | Structure | Name | LCMS |
|---|---|---|---|
| 564 | 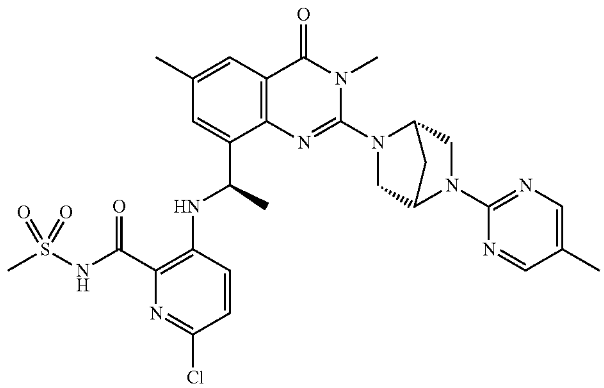 | 6-chloro-3-(((R)-1-(3,6-dimethyl-2-((1S,4S)-5-(5-methylpyrimidin-2-yl)-2,5-diazabicyclo[2.2.1]heptan-2-yl)-4-oxo-3,4-dihydroquinazolin-8-yl)ethyl)amino)-N-(methylsulfonyl)picolinamide | 2.27 min, 254 nm, MS (ES+)[b] $C_{29}H_{32}ClN_9O_4S$, requires: 637.2, found: 638.3 $[M + H]^+$ |
| 565 | 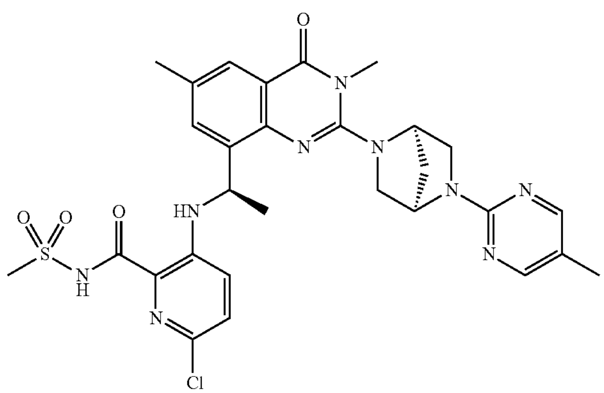 | 6-chloro-3-(((R)-1-(3,6-dimethyl-2-((1R,4R)-5-(5-methylpyrimidin-2-yl)-2,5-diazabicyclo[2.2.1]heptan-2-yl)-4-oxo-3,4-dihydroquinazolin-8-yl)ethyl)amino)-N-(methylsulfonyl)picolinamide | 2.31 min, 220 nm, MS (ES+)[b] $C_{29}H_{32}ClN_9O_4S$, requires: 637.2, found: 638.3 $[M + H]^+$ |
| 566 | 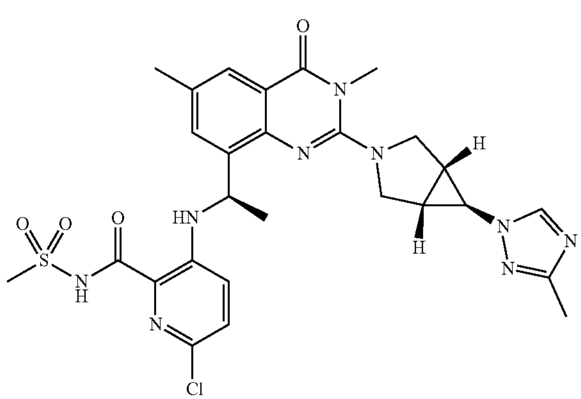 [SMILES: Cc1cc([C@@H](C)Nc2ccc(Cl)nc2C(=O)NS(C)(=O)=O)c2nc(N3C[C@@H]4[C@H](C3)[C@H]4n3cnc(C)n3)n(C)c(=O)c2c1] | 6-chloro-3-(((R)-1-(3,6-dimethyl-2-((1R,5S,6S)-6-(3-methyl-1H-1,2,4-triazol-1-yl)-3-azabicyclo[3.1.0]hexan-3-yl)-4-oxo-3,4-dihydroquinazolin-8-yl)ethyl)amino)-N-(methylsulfonyl)picolinamide | 2.15 min, 254 nm, MS (ES+)[b] $C_{27}H_{30}ClN_9O_4S$, requires: 611.1, found: 612.3 $[M + H]^+$ |

TABLE E4-continued compound list prepared according to Route A in Example 4

| Cpd. ID | Structure | Name | LCMS |
|---|---|---|---|
| 567 | 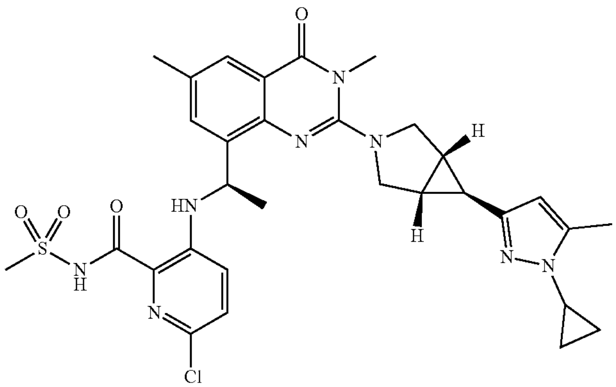 | 6-chloro-3-(((R)-1-(2-((1R,5S,6R)-6-(1-cyclopropyl-5-methyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.68 min, 270 nm, MS (ES+)[b] $C_{31}H_{35}ClN_8O_4S$, requires: 650.2, found: 651.4 [M + H]+ |
| 568 | 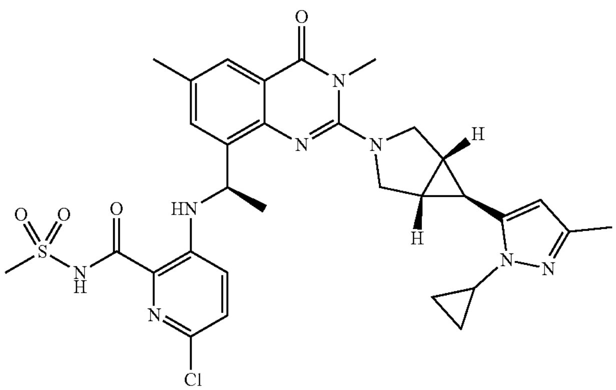 | 6-chloro-3-(((R)-1-(2-((1R,5S,6R)-6-(1-cyclopropyl-3-methyl-1H-pyrazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.39 min, 270 nm, MS (ES+)[b] $C_{31}H_{35}ClN_8O_4S$, requires: 650.2, found: 651.2 [M + H]+ |
| 569 | 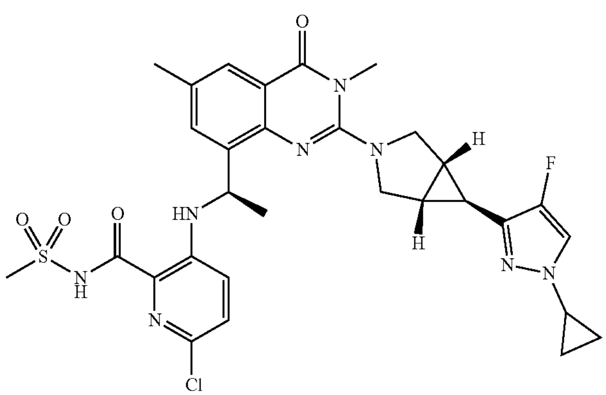 [SMILES: Cc1cc([C@@H](C)Nc2ccc(Cl)nc2C(=O)NS(C)(=O)=O)c2nc(N3C[C@@H]4[C@H](C3)[C@H]4c3nn(C4CC4)cc3F)n(C)c(=O)c2c1] | 6-chloro-3-(((R)-1-(2-((1R,5S,6R)-6-(1-cyclopropyl-4-fluoro-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.57 min, 254 nm, MS (ES+)[b] $C_{30}H_{32}ClFN_8O_4S$, requires: 654.2, found: 655.2 [M + H]+ |
| 570 | 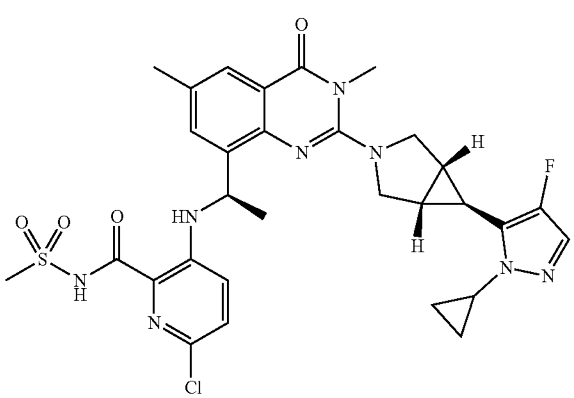 [SMILES: Cc1cc([C@@H](C)Nc2ccc(Cl)nc2C(=O)NS(C)(=O)=O)c2nc(N3C[C@@H]4[C@H](C3)[C@H]4c3c(F)cnn3C3CC3)n(C)c(=O)c2c1] | 6-chloro-3-(((R)-1-(2-((1R,5S,6R)-6-(1-cyclopropyl-4-fluoro-1H-pyrazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.53 min, 254 nm, MS (ES+)[b] $C_{30}H_{32}ClFN_8O_4S$, requires: 654.2, found: 655.2 [M + H]+ |

TABLE E4-continued compound list prepared according to Route A in Example 4

| Cpd. ID | Structure | Name | LCMS |
|---|---|---|---|
| 571 | 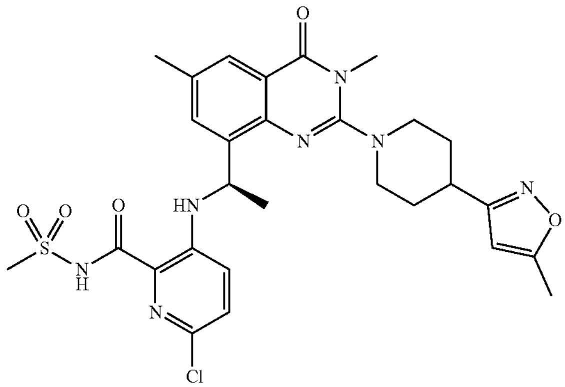 [SMILES: Cc1cc([C@@H](C)Nc2ccc(Cl)nc2C(=O)NS(C)(=O)=O)c2nc(N3CCC(c4cc(C)on4)CC3)n(C)c(=O)c2c1] | (R)-6-chloro-3-((1-(3,6-dimethyl-2-(4-(5-methylisoxazol-3-yl)piperidin-1-yl)-4-oxo-3,4-dihydroquinazolin-8-yl)ethyl)amino)-N-(methylsulfonyl)picolinamide | 1.97 min, 254 nm, MS (ES+)[b] $C_{28}H_{32}ClN_7O_5S$, requires: 613.1, found: 614.1 [M + H]+ |
| 572 | 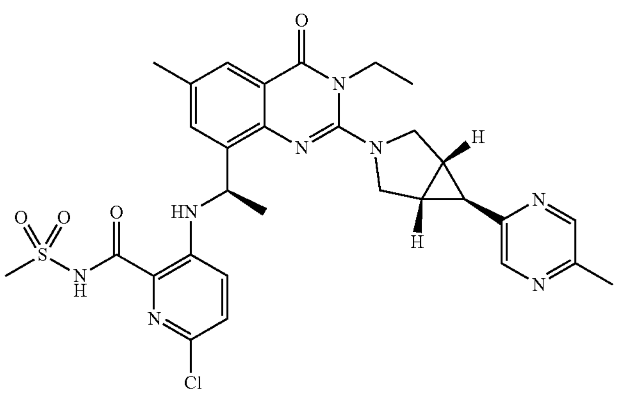 | 6-chloro-3-(((R)-1-(3-ethyl-6-methyl-2-((1R,5S,6R)-6-(5-methylpyrazin-2-yl)-3-azabicyclo[3.1.0]hexan-3-yl)-4-oxo-3,4-dihydroquinazolin-8-yl)ethyl)amino)-N-(methylsulfonyl)picolinamide | 2.57 min, 275 nm, MS (ES+)[b] $C_{30}H_{33}ClN_8O_4S$, requires: 636.2, found: 637.3 [M + H]+ |
| 573 | 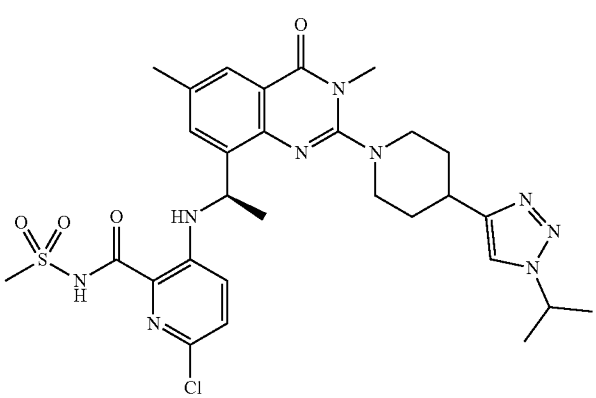 [SMILES: Cc1cc([C@@H](C)Nc2ccc(Cl)nc2C(=O)NS(C)(=O)=O)c2nc(N3CCC(c4cn(C(C)C)nn4)CC3)n(C)c(=O)c2c1] | (R)-6-chloro-3-((1-(2-(4-(1-isopropyl-1H-1,2,3-triazol-4-yl)piperidin-1-yl)-3,6-dimethyl-4-oxo-3,4-dihydroquinazolin-8-yl)ethyl)amino)-N-(methylsulfonyl)picolinamide | 2.29 min, 220 nm, MS (ES+)[b] $C_{29}H_{36}ClN_9O_4S$, requires: 641.2, found: 642.3 [M + H]+ |

TABLE E4-continued compound list prepared according to Route A in Example 4

| Cpd. ID | Structure | Name | LCMS |
|---|---|---|---|
| 574 | 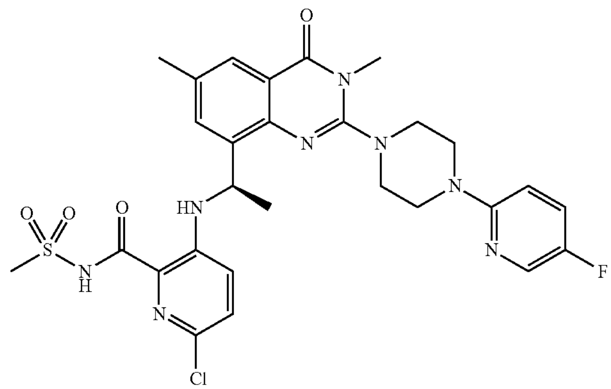 [SMILES: Cc1cc([C@@H](C)Nc2ccc(Cl)nc2C(=O)NS(C)(=O)=O)c2nc(N3CCN(c4ccc(F)cn4)CC3)n(C)c(=O)c2c1] | (R)-6-chloro-3-((1-(2-(4-(5-fluoropyridin-2-yl)piperazin-1-yl)-3,6-dimethyl-4-oxo-3,4-dihydroquinazolin-8-yl)ethyl)amino)-N-(methylsulfonyl)picolinamide | 2.56 min, 254 nm, MS (ES+)[b] $C_{28}H_{30}ClFN_8O_4S$, requires: 628.1, found: 629.2 [M + H]+ |
| 575 | 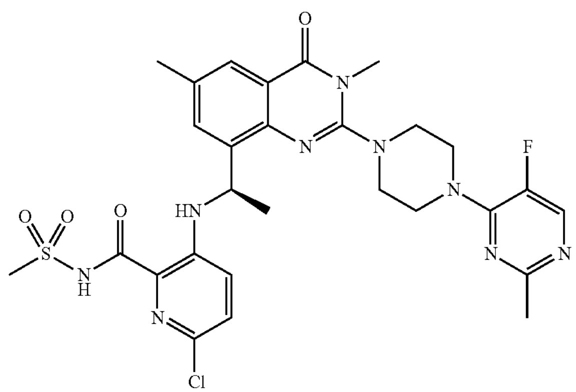 | (R)-6-chloro-3-((1-(2-(4-(5-fluoro-2-methylpyrimidin-4-yl)piperazin-1-yl)-3,6-dimethyl-4-oxo-3,4-dihydroquinazolin-8-yl)ethyl)amino)-N-(methylsulfonyl)picolinamide | 2.06 min, 220 nm, MS (ES+)[b] $C_{28}H_{31}ClFN_9O_4S$, requires: 643.1, found: 644.2 [M + H]+ |
| 576 | 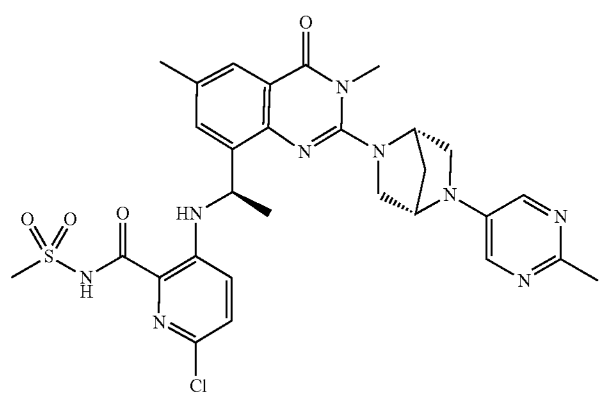 | 6-chloro-3-(((R)-1-(3,6-dimethyl-2-((1S,4S)-5-(2-methylpyrimidin-5-yl)-2,5-diazabicyclo[2.2.1]heptan-2-yl)-4-oxo-3,4-dihydroquinazolin-8-yl)ethyl)amino)-N-(methylsulfonyl)picolinamide | 2.00 min, 254 nm, MS (ES+)[b] $C_{29}H_{32}ClN_9O_4S$, requires: 637.2, found: 638.2 [M + H]+ |
| 577 | 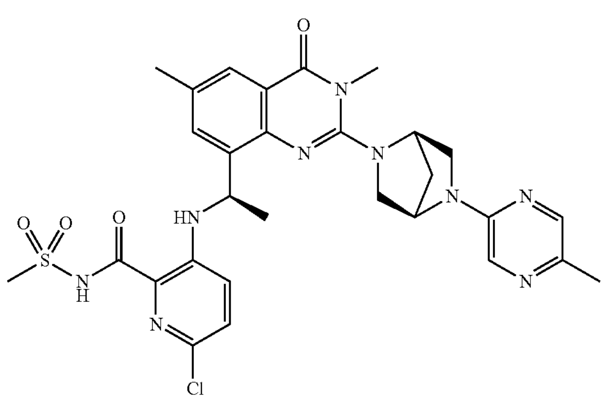 | 6-chloro-3-(((R)-1-(3,6-dimethyl-2-((1R,4R)-5-(5-methylpyrazin-2-yl)-2,5-diazabicyclo[2.2.1]heptan-2-yl)-4-oxo-3,4-dihydroquinazolin-8-yl)ethyl)amino)-N-(methylsulfonyl)picolinamide | 2.20 min, 254 nm, MS (ES+)[b] $C_{29}H_{32}ClN_9O_4S$, requires: 637.2, found: 638.2 [M + H]+ |

TABLE E4-continued compound list prepared according to Route A in Example 4

| Cpd. ID | Structure | Name | LCMS |
|---|---|---|---|
| 578 | 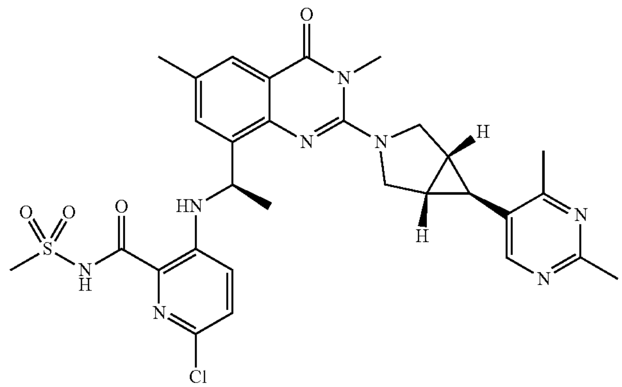 | 6-chloro-3-(((R)-1-(2-((1R,5S,6S)-6-(2,4-dimethylpyrimidin-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.18 min, 254 nm, MS (ES+)[b] C$_{30}$H$_{33}$ClN$_8$O$_4$S, requires: 636.2, found: 637.2 [M + H]$^+$ |
| 579 | 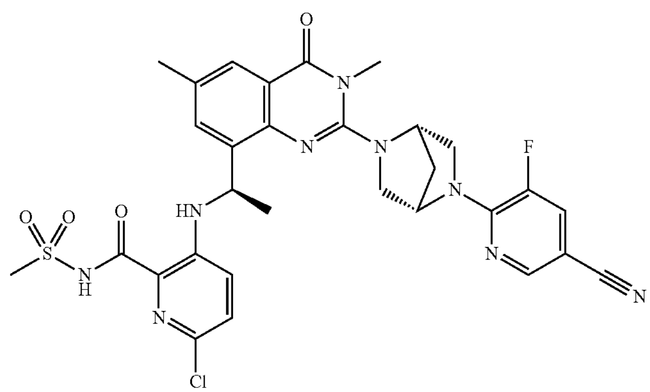 [SMILES: Cc1cc([C@@H](C)Nc2ccc(Cl)nc2C(=O)NS(C)(=O)=O)c2nc(N3C[C@@H]4C[C@H]3CN4c3ncc(C#N)cc3F)n(C)c(=O)c2c1] | 6-chloro-3-(((R)-1-(2-((1S,4S)-5-(5-cyano-3-fluoropyridin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.44 min, 220 nm, MS (ES+)[b] C$_{30}$H$_{29}$ClFN$_9$O$_4$S, requires: 665.1, found: 666.2 [M + H]$^+$ |
| 580 | 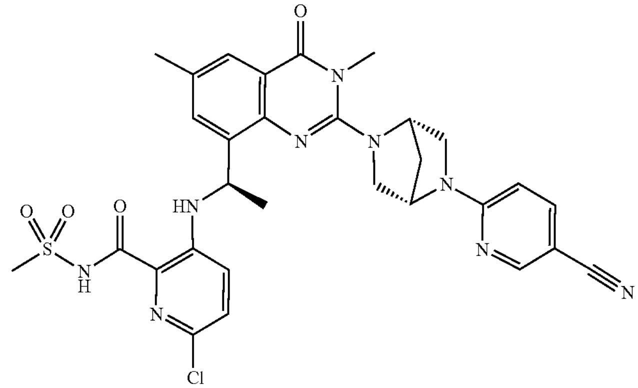 [SMILES: Cc1cc([C@@H](C)Nc2ccc(Cl)nc2C(=O)NS(C)(=O)=O)c2nc(N3C[C@@H]4C[C@H]3CN4c3ccc(C#N)cn3)n(C)c(=O)c2c1] | 6-chloro-3-(((R)-1-(2-((1S,4S)-5-(5-cyanopyridin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.33 min, 220 nm, MS (ES+)[b] C$_{30}$H$_{30}$ClN$_9$O$_4$S, requires: 647.1, found: 648.2 [M + H]$^+$ |

TABLE E4-continued compound list prepared according to Route A in Example 4

| Cpd. ID | Structure | Name | LCMS |
|---|---|---|---|
| 581 | 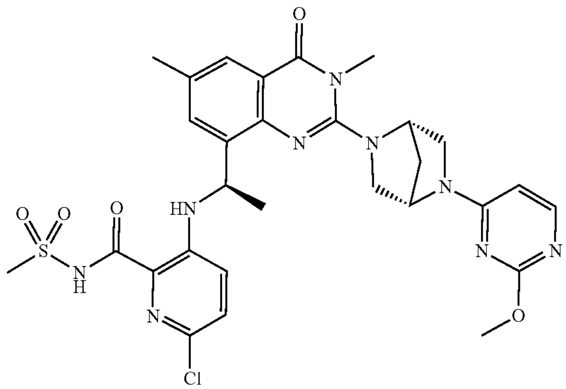 [SMILES: COc1nccc(N2C[C@@H]3C[C@H]2CN3c2nc3c([C@@H](C)Nc4ccc(Cl)nc4C(=O)NS(C)(=O)=O)cc(C)cc3c(=O)n2C)n1] | 6-chloro-3-(((R)-1-(2-((1S,4S)-5-(2-methoxypyrimidin-4-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 1.45 min, 254 nm, MS (ES+)[b] $C_{29}H_{32}ClN_9O_5S$, requires: 653.1, found: 654.1 [M + H]+ |
| 582 | 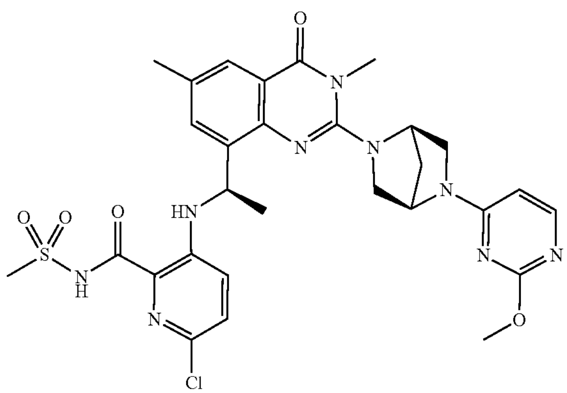 [SMILES: COc1nccc(N2C[C@H]3C[C@@H]2CN3c2nc3c([C@@H](C)Nc4ccc(Cl)nc4C(=O)NS(C)(=O)=O)cc(C)cc3c(=O)n2C)n1] | 6-chloro-3-(((R)-1-(2-((1R,4R)-5-(2-methoxypyrimidin-4-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 1.93 min, 254 nm, MS (ES+)[b] $C_{29}H_{32}ClN_9O_5S$, requires: 653.1, found: 654.2 [M + H]+ |
| 583 | 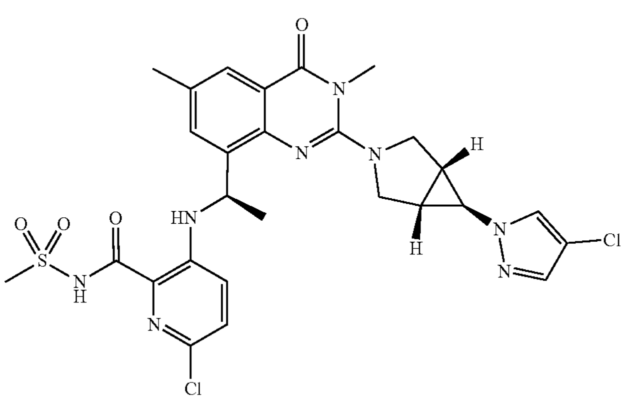 [SMILES: Cc1cc([C@@H](C)Nc2ccc(Cl)nc2C(=O)NS(C)(=O)=O)c2nc(N3C[C@@H]4[C@H](C3)[C@H]4n3cc(Cl)cn3)n(C)c(=O)c2c1] | 6-chloro-3-(((R)-1-(2-((1R,5S,6S)-6-(4-chloro-1H-pyrazol-1-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.37 min, 270 nm, MS (ES+)[b] $C_{27}H_{28}Cl_2N_8O_4S$, requires: 630.1, found: 631.1 [M + H]+ |

TABLE E4-continued compound list prepared according to Route A in Example 4

| Cpd. ID | Structure | Name | LCMS |
|---|---|---|---|
| 584 | 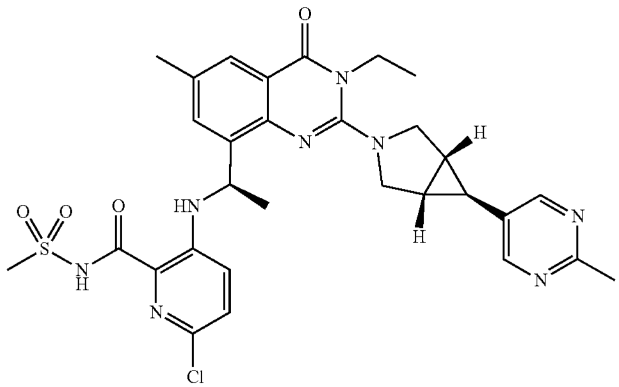 | 6-chloro-3-(((R)-1-(3-ethyl-6-methyl-2-((1R,5S,6S)-6-(2-methylpyrimidin-5-yl)-3-azabicyclo[3.1.0]hexan-3-yl)-4-oxo-3,4-dihydroquinazolin-8-yl)ethyl)amino)-N-(methylsulfonyl)picolinamide | 2.20 min, 254 nm, MS (ES+)[b] C$_{30}$H$_{33}$ClN$_8$O$_4$S, requires: 636.2, found: 637.2 [M + H]$^+$ |
| 585 | 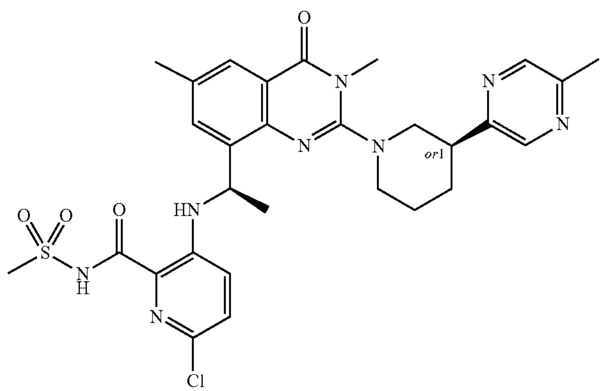 | 6-chloro-3-(((R)-1-(3,6-dimethyl-2-((R*)-3-(5-methylpyrazin-2-yl)piperidin-1-yl)-4-oxo-3,4-dihydroquinazolin-8-yl)ethyl)amino)-N-(methylsulfonyl)picolinamide | 2.40 min, 254 nm, MS (ES+)[b] C$_{29}$H$_{33}$ClN$_8$O$_4$S, requires: 624.2, found: 625.2 [M + H]$^+$ |
| 586 | 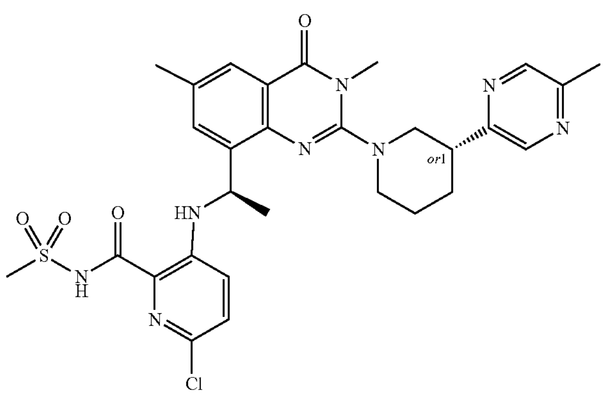 | 6-chloro-3-(((R)-1-(3,6-dimethyl-2-((R*)-3-(5-methylpyrazin-2-yl)piperidin-1-yl)-4-oxo-3,4-dihydroquinazolin-8-yl)ethyl)amino)-N-(methylsulfonyl)picolinamide | 2.42 min, 254 nm, MS (ES+)[b] C$_{29}$H$_{33}$ClN$_8$O$_4$S, requires: 624.2, found: 625.2 [M + H]$^+$ |
| 587 | 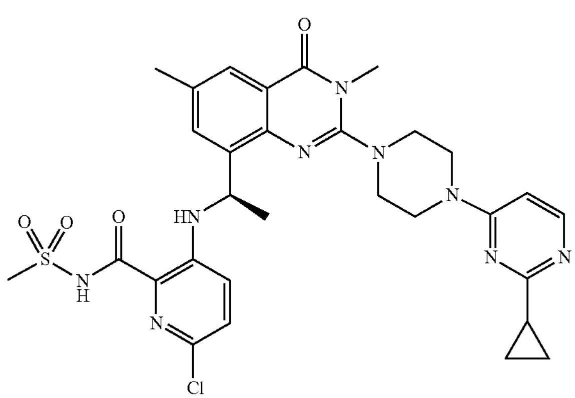 | 6-chloro-3-(((R)-1-(2-((R*)-3-(5-chloropyrimidin-2-yl)piperidin-1-yl)-3,6-dimethyl-4-oxo-3,4-dihydroquinazolin-8-yl)ethyl)amino)-N-(methylsulfonyl)picolinamide | 2.92 min, 270 nm, MS (ES+)[b] C$_{28}$H$_{30}$Cl$_2$N$_8$O$_4$S, requires: 644.1, found: 645.2 [M + H]$^+$ |

TABLE E4-continued compound list prepared according to Route A in Example 4

| Cpd. ID | Structure | Name | LCMS |
|---|---|---|---|
| 588 | 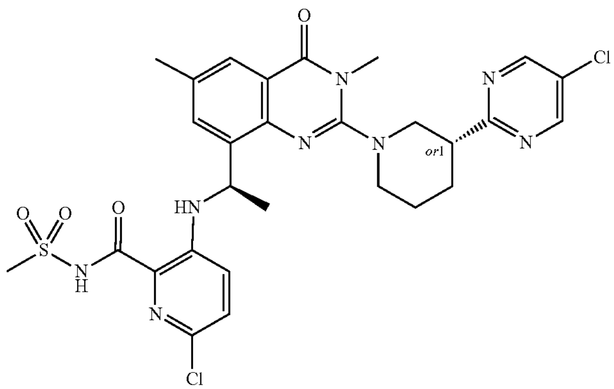 [SMILES: Cc1cc([C@@H](C)Nc2ccc(Cl)nc2C(=O)NS(C)(=O)=O)c2nc(N3CCC[C@@H](c4ncc(Cl)cn4)C3)n(C)c(=O)c2c1] | 6-chloro-3-(((R)-1-(2-((R*)-3-(5-chloropyrimidin-2-yl)piperidin-1-yl)-3,6-dimethyl-4-oxo-3,4-dihydroquinazolin-8-yl)ethyl)amino)-N-(methylsulfonyl)picolinamide | 2.67 min, 254 nm, MS (ES+)$^b$ C$_{28}$H$_{30}$Cl$_2$N$_8$O$_4$S, requires: 644.1, found: 645.1 [M + H]$^+$ |
| 589 | 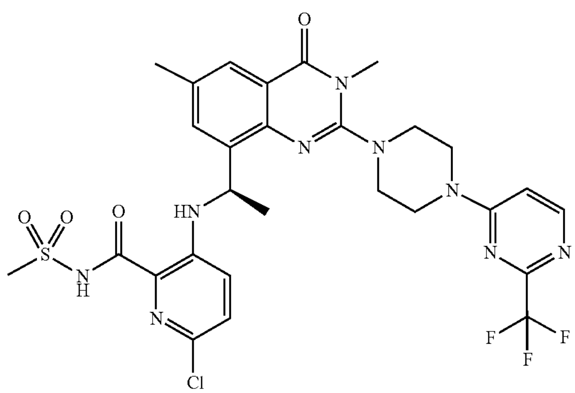 [SMILES: Cc1cc([C@@H](C)Nc2ccc(Cl)nc2C(=O)NS(C)(=O)=O)c2nc(N3CCN(c4ccnc(C(F)(F)F)n4)CC3)n(C)c(=O)c2c1] | (R)-6-chloro-3-((1-(3,6-dimethyl-4-oxo-2-(4-(2-(trifluoromethyl)pyrimidin-4-yl)piperazin-1-yl)-3,4-dihydroquinazolin-8-yl)ethyl)amino)-N-(methylsulfonyl)picolinamide | 2.57 min, 254 nm, MS (ES+)$^b$ C$_{28}$H$_{29}$ClF$_3$N$_9$O$_4$S, requires: 679.1, found: 680.3 [M + H]$^+$ |
| 590 | 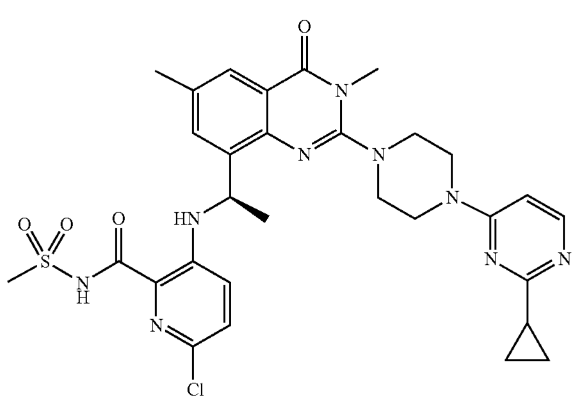 [SMILES: Cc1cc([C@@H](C)Nc2ccc(Cl)nc2C(=O)NS(C)(=O)=O)c2nc(N3CCN(c4ccnc(C5CC5)n4)CC3)n(C)c(=O)c2c1] | (R)-6-chloro-3-((1-(2-(4-(2-cyclopropylpyrimidin-4-yl)piperazin-1-yl)-3,6-dimethyl-4-oxo-3,4-dihydroquinazolin-8-yl)ethyl)amino)-N-(methylsulfonyl)picolinamide | 1.92 min, 215 nm, MS (ES+)$^b$ C$_{30}$H$_{34}$ClN$_9$O$_4$S, requires: 651.2, found: 652.2 [M + H]$^+$ |

TABLE E4-continued compound list prepared according to Route A in Example 4

| Cpd. ID | Structure | Name | LCMS |
|---|---|---|---|
| 591 | 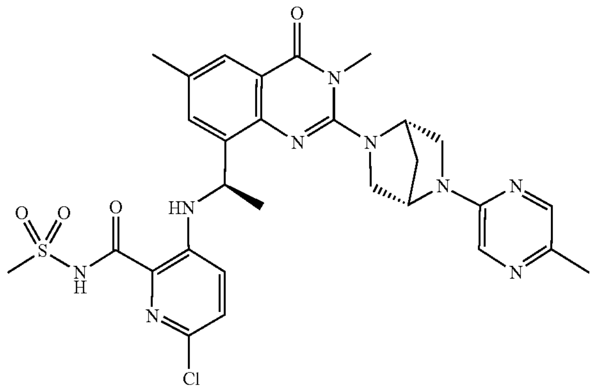 | 6-chloro-3-(((R)-1-(3,6-dimethyl-2-((1S,4S)-5-(5-methylpyrazin-2-yl)-2,5diazabicyclo[2.2.1]heptan-2-yl)-4-oxo-3,4-dihydroquinazolin-8-yl)ethyl)amino)-N-(methylsulfonyl)picolinamide | 2.22 min, 254 nm, MS (ES+)[b] $C_{29}H_{32}ClN_9O_4S$, requires: 637.2, found: 638.2 [M + H]+ |
| 592 | 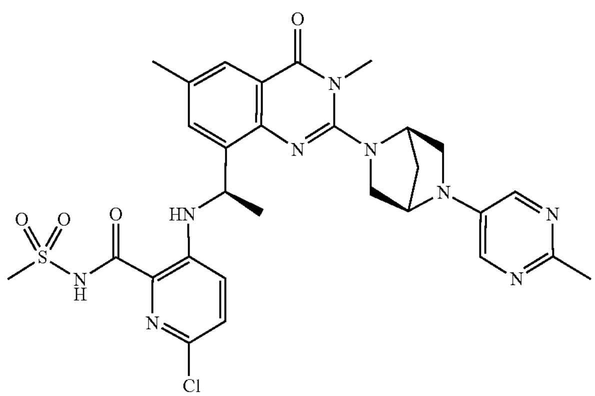 | 6-chloro-3-(((R)-1-(3,6-dimethyl-2-((1R,4R)-5-(2-methylpyrimidin-5-yl)-2,5-diazabicyclo[2.2.1]heptan-2-yl)-4-oxo-3,4-dihydroquinazolin-8-yl)ethyl)amino)-N-(methylsulfonyl)picolinamide | 2.01 min, 254 nm, MS (ES+)[b] $C_{29}H_{32}ClN_9O_4S$, requires: 637.2, found: 638.2 [M + H]+ |
| 593 | 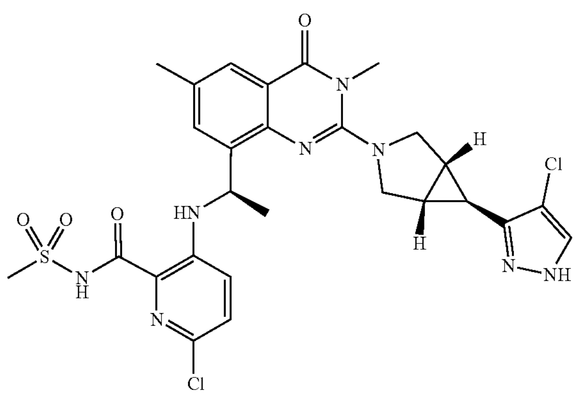 [SMILES: Cc1cc([C@@H](C)Nc2ccc(Cl)nc2C(=O)NS(C)(=O)=O)c2nc(N3C[C@@H]4[C@H](C3)[C@H]4c3n[nH]cc3Cl)n(C)c(=O)c2c1] | 6-chloro-3-(((R)-1-(2-((1R,5S,6R)-6-(4-chloro-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.20 min, 254 nm, MS (ES+)[b] $C_{27}H_{28}Cl_2N_8O_4S$, requires: 630.1, found: 631.1 [M + H]+ |

TABLE E4-continued compound list prepared according to Route A in Example 4

| Cpd. ID | Structure | Name | LCMS |
|---|---|---|---|
| 594 | 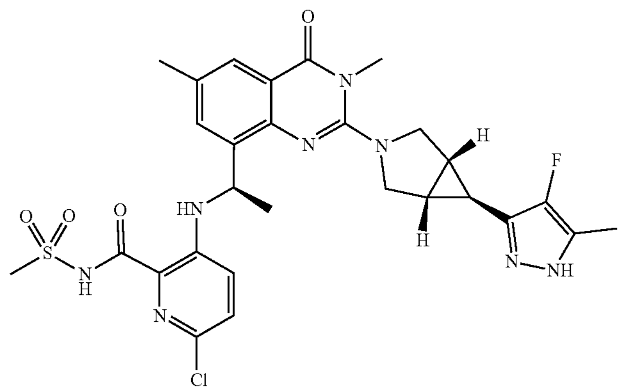 | 6-chloro-3-(((R)-1-(2-((1R,5S,6R)-6-(4-fluoro-5-methyl-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.21 min, 254 nm, MS (ES+)[b] $C_{28}H_{30}ClFN_8O_4S$, requires: 628.1, found: 629.2 $[M + H]^+$ |
| 595 | 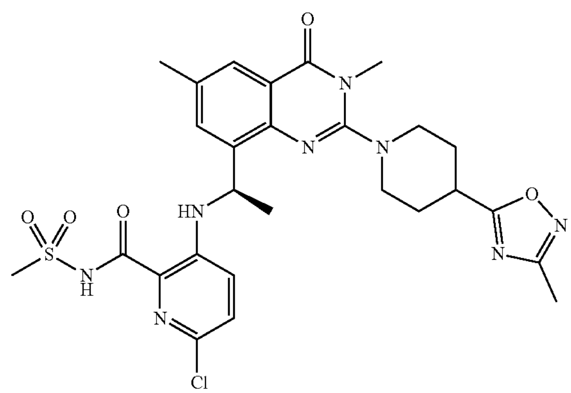 [SMILES: Cc1cc([C@@H](C)Nc2ccc(Cl)nc2C(=O)NS(C)(=O)=O)c2nc(N3CCC(c4nc(C)no4)CC3)n(C)c(=O)c2c1] | (R)-6-chloro-3-((1-(3,6-dimethyl-2-(4-(3-methyl-1,2,4-oxadiazol-5-yl)piperidin-1-yl)-4-oxo-3,4-dihydroquinazolin-8-yl)ethyl)amino)-N-(methylsulfonyl)picolinamide | 2.47 min, 215 nm, MS (ES+)[b] $C_{27}H_{31}ClN_8O_5S$, requires: 614.1, found: 615.3 $[M + H]^+$ |
| 596 | 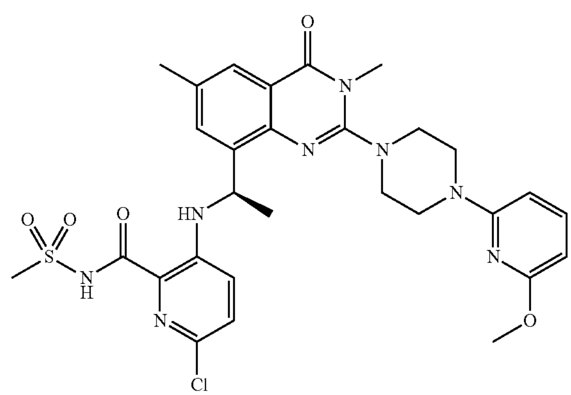 [SMILES: COc1cccc(N2CCN(c3nc4c([C@@H](C)Nc5ccc(Cl)nc5C(=O)NS(C)(=O)=O)cc(C)cc4c(=O)n3C)CC2)n1] | (R)-6-chloro-3-((1-(2-(4-(6-methoxypyridin-2-yl)piperazin-1-yl)-3,6-dimethyl-4-oxo-3,4-dihydroquinazolin-8-yl)ethyl)amino)-N-(methylsulfonyl)picolinamide | 2.72 min, 254 nm, MS (ES+)[b] $C_{29}H_{33}ClN_8O_5S$, requires: 640.2, found: 641.2 $[M + H]^+$ |
| 597 | 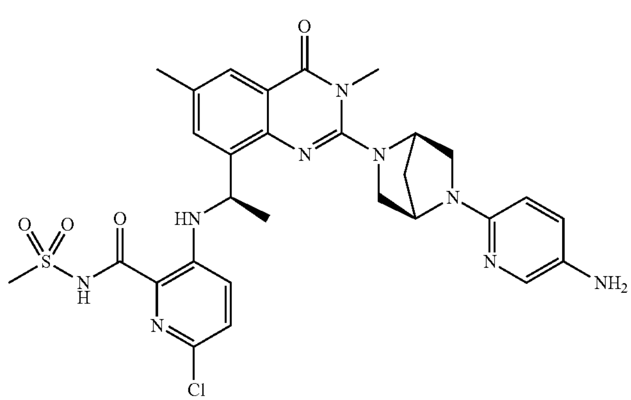 [SMILES: Cc1cc([C@@H](C)Nc2ccc(Cl)nc2C(=O)NS(C)(=O)=O)c2nc(N3C[C@H]4C[C@@H]3CN4c3ccc(N)cn3)n(C)c(=O)c2c1] | 3-(((R)-1-(2-((1R,4R)-5-(5-aminopyridin-2-yl)-2,5-diazabicyclo[2.2.1]heptan-2-yl)-3,6-dimethyl-4-oxo-3,4-dihydroquinazolin-8-yl)ethyl)amino)-6-chloro-N-(methylsulfonyl)picolinamide | 1.80 min, 254 nm, MS (ES+)[b] $C_{29}H_{32}ClN_9O_4S$, requires: 637.2, found: 638.2 $[M + H]^+$ |

TABLE E4-continued compound list prepared according to Route A in Example 4

| Cpd. ID | Structure | Name | LCMS |
|---|---|---|---|
| 598 | 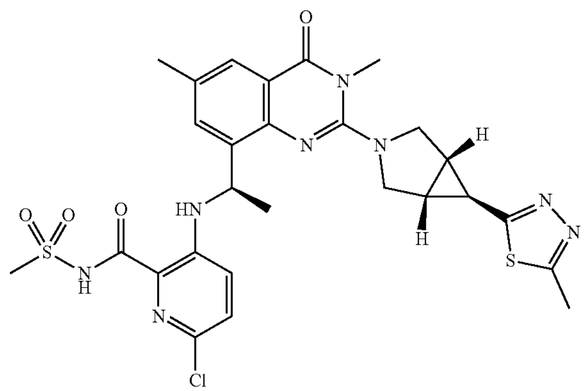 [SMILES: Cc1cc([C@@H](C)Nc2ccc(Cl)nc2C(=O)NS(C)(=O)=O)c2nc(N3C[C@@H]4[C@H](C3)[C@H]4c3nnc(C)s3)n(C)c(=O)c2c1] | 6-chloro-3-(((R)-1-(3,6-dimethyl-2-(((1R,5S,6R)-6-(5-methyl-1,3,4-thiadiazol-2-yl)-3-azabicyclo[3.1.0]hexan-3-yl)-4-oxo-3,4-dihydroquinazolin-8-yl)ethyl)amino)-N-(methylsulfonyl)picolinamide | 2.13 min, 270 nm, MS (ES+)[b] $C_{27}H_{29}ClN_8O_4S_2$ requires: 628.1, found: 629.2 [M + H]+ |
| 599 | 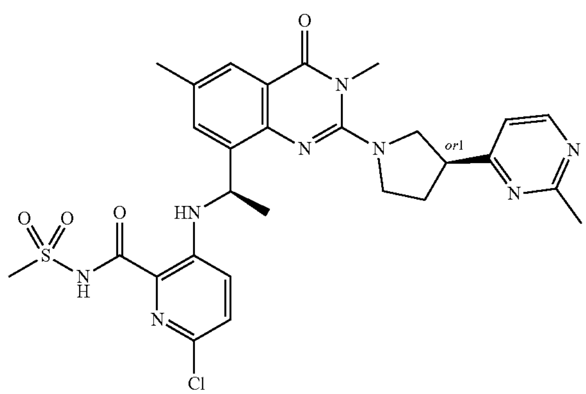 | 6-chloro-3-(((R)-1-(3,6-dimethyl-2-((R*)-3-(2-methylpyrimidin-4-yl)pyrrolidin-1-yl)-4-oxo-3,4-dihydroquinazolin-8-yl)ethyl)amino)-N-(methylsulfonyl)picolinamide | 2.59 min, 215 nm, MS (ES+)[b] $C_{28}H_{31}ClN_8O_4S$ requires: 610.1, found: 611.2 [M + H]+ |
| 600 | 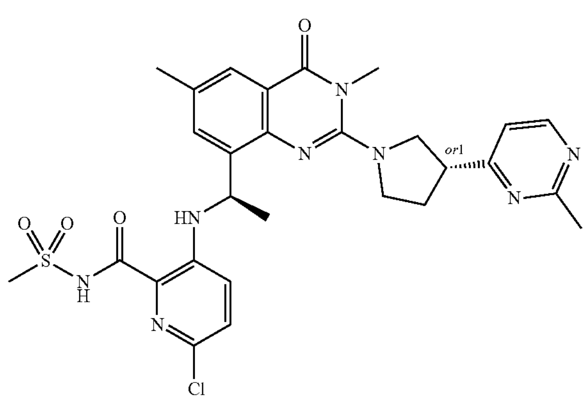 | 6-chloro-3-(((R)-1-(3,6-dimethyl-2-((R*)-3-(2-methylpyrimidin-4-yl)pyrrolidin-1-yl)-4-oxo-3,4-dihydroquinazolin-8-yl)ethyl)amino)-N-(methylsulfonyl)picolinamide | 2.59 min, 270 nm, MS (ES+)[b] $C_{28}H_{31}ClN_8O_4S$ requires: 610.1, found: 611.2 [M + H]+ |

TABLE E4-continued compound list prepared according to Route A in Example 4

| Cpd. ID | Structure | Name | LCMS |
|---|---|---|---|
| 601 | 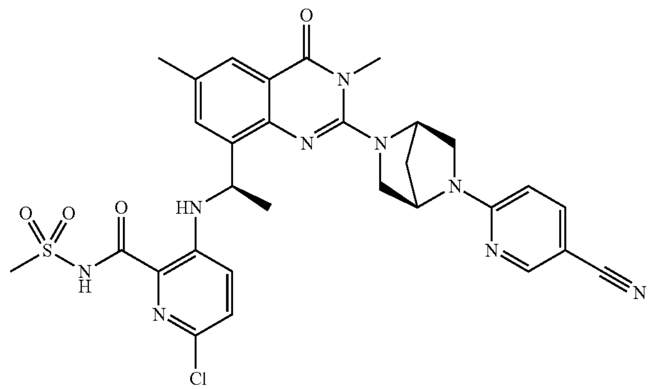 [SMILES: Cc1cc([C@@H](C)Nc2ccc(Cl)nc2C(=O)NS(C)(=O)=O)c2nc(N3C[C@H]4C[C@@H]3CN4c3ccc(C#N)cn3)n(C)c(=O)c2c1] | 6-chloro-3-(((R)-1-(2-((1R,4R)-5-(5-cyanopyridin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.38 min, 254 nm, MS (ES+)[b] $C_{30}H_{30}ClN_9O_4S$, requires: 647.1, found: 648.1 [M + H]+ |
| 602 | 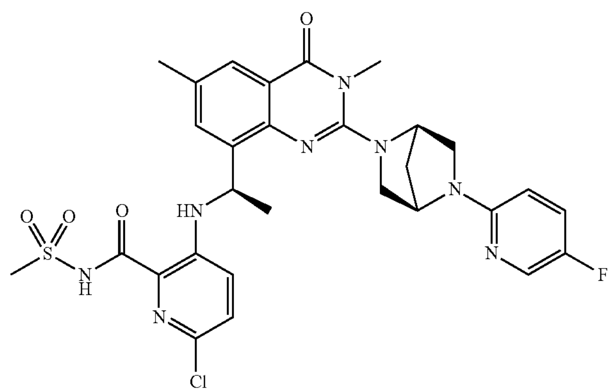 [SMILES: Cc1cc([C@@H](C)Nc2ccc(Cl)nc2C(=O)NS(C)(=O)=O)c2nc(N3C[C@H]4C[C@@H]3CN4c3ccc(F)cn3)n(C)c(=O)c2c1] | 6-chloro-3-(((R)-1-(2-((1R,4R)-5-(5-fluoropyridin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.29 min, 254 nm, MS (ES+)[b] $C_{29}H_{30}ClFN_8O_4S$, requires: 640.1, found: 641.2 [M + H]+ |
| 603 | 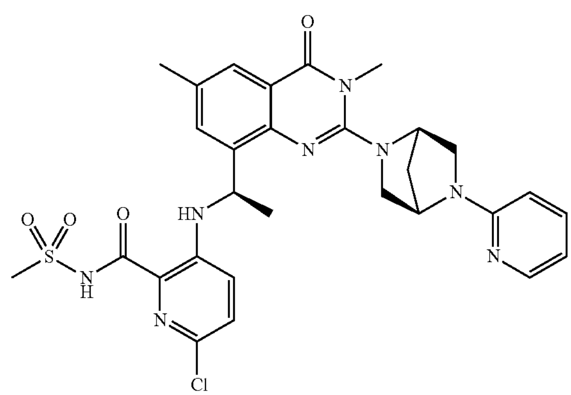 [SMILES: Cc1cc([C@@H](C)Nc2ccc(Cl)nc2C(=O)NS(C)(=O)=O)c2nc(N3C[C@H]4C[C@@H]3CN4c3ccccn3)n(C)c(=O)c2c1] | 6-chloro-3-(((R)-1-(3,6-dimethyl-4-oxo-2-((1R,4R)-5-(pyridin-2-yl)-2,5-diazabicyclo[2.2.1]heptan-2-yl)-3,4-dihydroquinazolin-8-yl)ethyl)amino)-N-(methylsulfonyl)picolinamide | 1.84 min, 254 nm, MS (ES+)[b] $C_{29}H_{31}ClN_8O_4S$, requires: 622.1, found: 623.2 [M + H]+ |
| 604 | 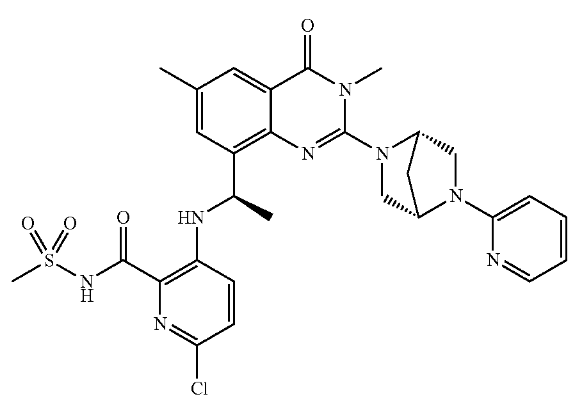 [SMILES: Cc1cc([C@@H](C)Nc2ccc(Cl)nc2C(=O)NS(C)(=O)=O)c2nc(N3C[C@@H]4C[C@H]3CN4c3ccccn3)n(C)c(=O)c2c1] | 6-chloro-3-(((R)-1-(3,6-dimethyl-4-oxo-2-((1S,4S)-5-(pyridin-2-yl)-2,5-diazabicyclo[2.2.1]heptan-2-yl)-3,4-dihydroquinazolin-8-yl)ethyl)amino)-N-(methylsulfonyl)picolinamide | 2.32 min, 254 nm, MS (ES+)[b] $C_{29}H_{31}ClN_8O_4S$, requires: 622.1, found: 623.2 [M + H]+ |

TABLE E4-continued compound list prepared according to Route A in Example 4

| Cpd. ID | Structure | Name | LCMS |
|---|---|---|---|
| 605 | 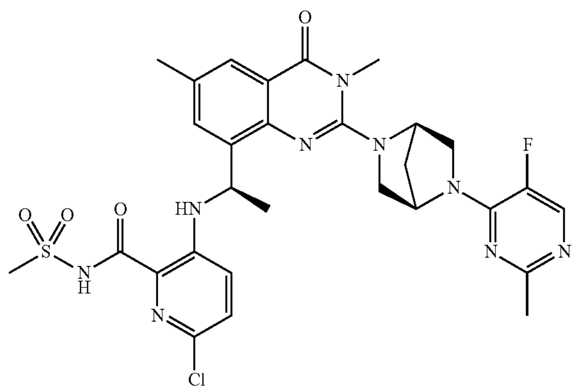 [SMILES: Cc1cc([C@@H](C)Nc2ccc(Cl)nc2C(=O)NS(C)(=O)=O)c2nc(N3C[C@H]4C[C@@H]3CN4c3nc(C)ncc3F)n(C)c(=O)c2c1] | 6-chloro-3-(((R)-1-(2-((1R,4R)-5-(5-fluoro-2-methylpyrimidin-4-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 1.96 min, 254 nm, MS (ES+)$^b$ C$_{29}$H$_{31}$ClFN$_9$O$_4$S, requires: 655.1, found: 656.2 [M + H]$^+$ |
| 606 | 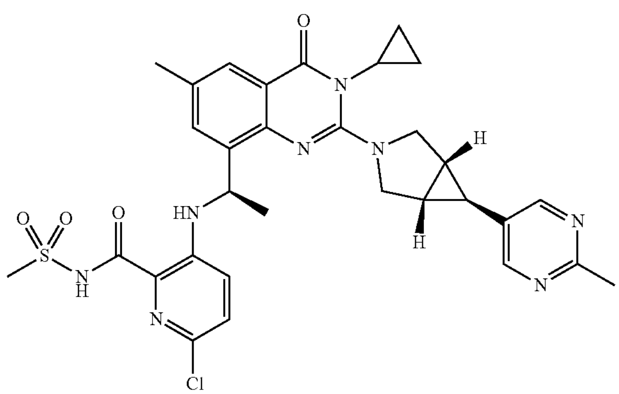 | 6-chloro-3-(((R)-1-(3-cyclopropyl-6-methyl-2-((1R,5S,6S)-6-(2-methylpyrimidin-5-yl)-3-azabicyclo[3.1.0]hexan-3-yl)-4-oxo-3,4-dihydroquinazolin-8-yl)ethyl)amino)-N-(methylsulfonyl)picolinamide | 2.10 min, 254 nm, MS (ES+)$^b$ C$_{31}$H$_{33}$ClN$_8$O$_4$S, requires: 648.2, found: 649.2 [M + H]$^+$ |
| 607 | 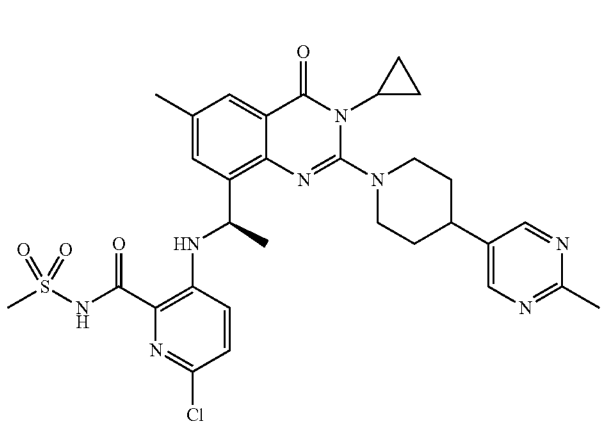 | (R)-6-chloro-3-((1-(3-cyclopropyl-6-methyl-2-(4-(2-methylpyrimidin-5-yl)piperidin-1-yl)-4-oxo-3,4-dihydroquinazolin-8-yl)ethyl)amino)-N-(methylsulfonyl)picolinamide | 2.34 min, 215 nm, MS (ES+)$^b$ C$_{31}$H$_{35}$ClN$_8$O$_4$S, requires: 650.2, found: 651.3 [M + H]$^+$ |

TABLE E4-continued compound list prepared according to Route A in Example 4

| Cpd. ID | Structure | Name | LCMS |
|---|---|---|---|
| 608 | 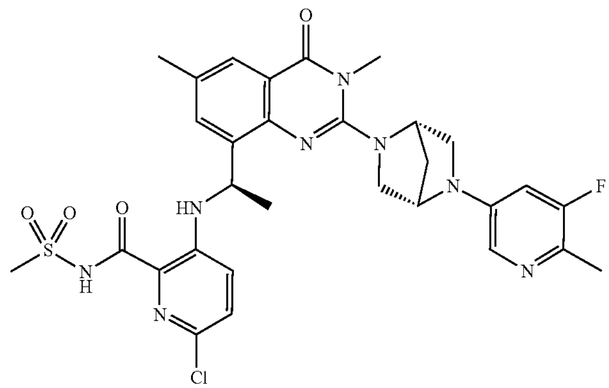 | 6-chloro-3-(((R)-1-(2-((1S,4S)-5-(5-fluoro-6-methylpyridin-3-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.06 min, 210 nm, MS (ES+)[b] $C_{30}H_{32}ClFN_8O_4S$, requires: 654.1, found: 655.2 [M + H]+ |
| 609 | 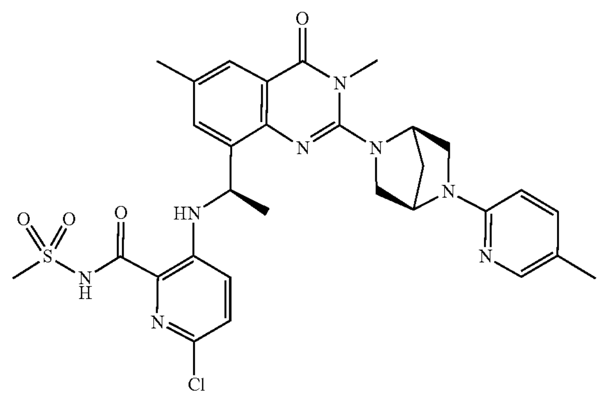 | 6-chloro-3-(((R)-1-(3,6-dimethyl-2-((1R,4R)-5-(5-methylpyridin-2-yl)-2,5-diazabicyclo[2.2.1]heptan-2-yl)-4-oxo-3,4-dihydroquinazolin-8-yl)ethyl)amino)-N-(methylsulfonyl)picolinamide | 2.13 min, 210 nm, MS (ES+)[b] $C_{30}H_{33}ClN_8O_4S$, requires: 636.2, found: 637.3 [M + H]+ |
| 610 | 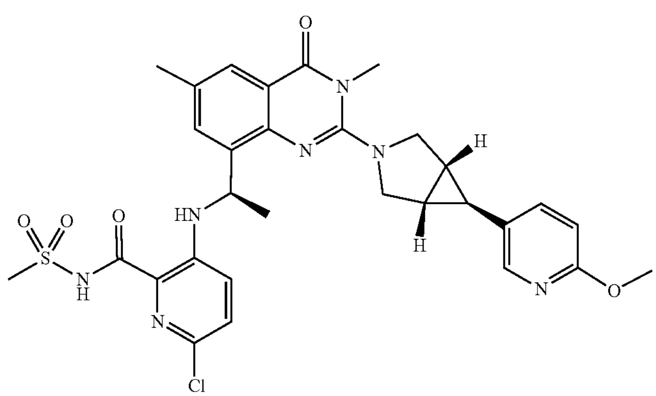 | 6-chloro-3-(((R)-1-(2-((1R,5S,6S)-6-(6-methoxypyridin-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 3.73 min, 254 nm, MS (ES+)[c] $C_{30}H_{32}ClN_7O_5S$ requires: 637.2, found: 638.2 [M + H]+ |
| 611 | 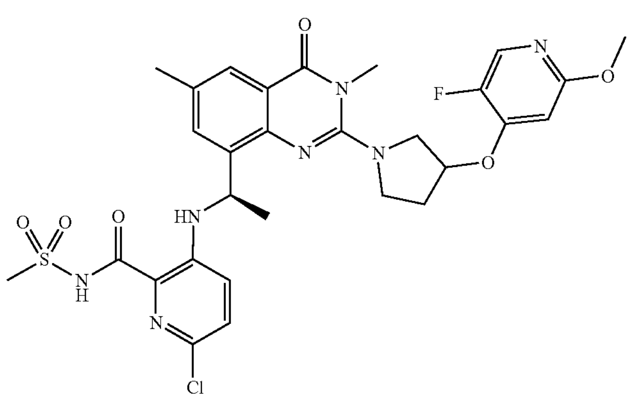 | 6-chloro-3-(((R)-1-(2-((S)-3-((5-fluoro-2-methoxypyridin-4-yl)oxy)pyrrolidin-1-yl)-3,6-dimethyl-4-oxo-3,4-dihydroquinazolin-8-yl)ethyl)amino)-N-(methylsulfonyl)picolinamide | 4.88 min, 254 nm, MS (ES+)[c] $C_{29}H_{31}ClFN_7O_6S$ requires: 659.2, found: 660.2 [M + H]+ |

TABLE E4-continued compound list prepared according to Route A in Example 4

| Cpd. ID | Structure | Name | LCMS |
|---|---|---|---|
| 612 | 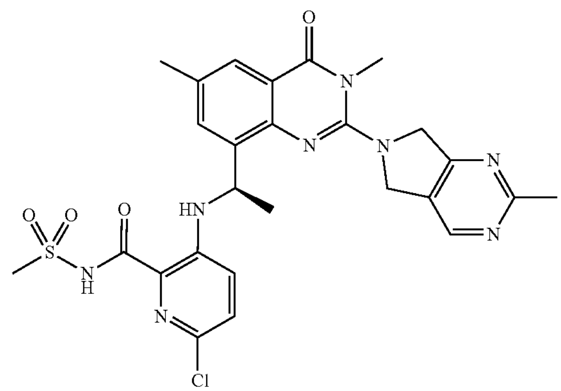 | (R)-6-chloro-3-((1-(3,6-dimethyl-2-(2-methyl-5,7-dihydro-6H-pyrrolo[3,4-d]pyrimidin-6-yl)-4-oxo-3,4-dihydroquinazolin-8-yl)ethyl)amino)-N-(methylsulfonyl)picolinamide | 3.86 min, 254 nm, MS (ES+)$^c$ $C_{26}H_{27}ClN_8O_4S$ requires: 582.2, found: 583.2 $[M+H]^+$ |
| 613 | 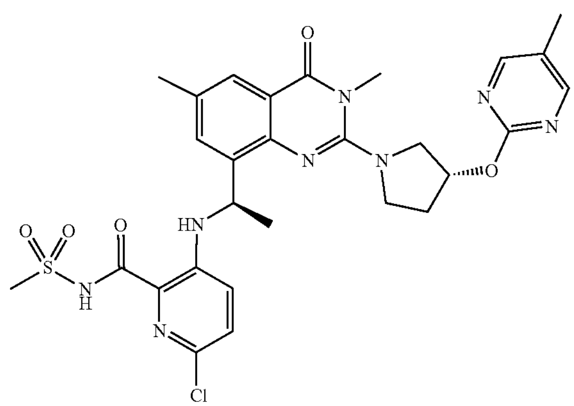 [SMILES: Cc1cnc(O[C@@H]2CCN(c3nc4c([C@@H](C)Nc5ccc(Cl)nc5C(=O)NS(C)(=O)=O)cc(C)cc4c(=O)n3C)C2)nc1] | 6-chloro-3-(((R)-1-(3,6-dimethyl-2-((R)-3-((5-methylpyrimidin-2-yl)oxy)pyrrolidin-1-yl)-4-oxo-3,4-dihydroquinazolin-8-yl)ethyl)amino)-N-(methylsulfonyl)picolinamide | 4.56 min, 254 nm, MS (ES+)$^c$ $C_{28}H_{31}ClN_8O_5S$ requires: 626.2, found: 627.3 $[M+H]^+$ |
| 614 | 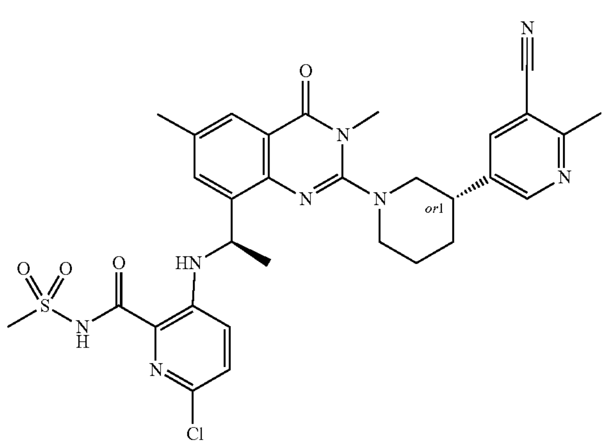 | 6-chloro-3-(((R)-1-(2-((R*)-3-(5-cyano-6-methylpyridin-3-yl)piperidin-1-yl)-3,6-dimethyl-4-oxo-3,4-dihydroquinazolin-8-yl)ethyl)amino)-N-(methylsulfonyl)picolinamide | 2.55 min, 254 nm, MS (ES+)$^b$ $C_{31}H_{33}ClN_8O_4S$ requires: 648.2, found: 649.4 $[M+H]^+$ |

TABLE E4-continued compound list prepared according to Route A in Example 4

| Cpd. ID | Structure | Name | LCMS |
|---|---|---|---|
| 615 | 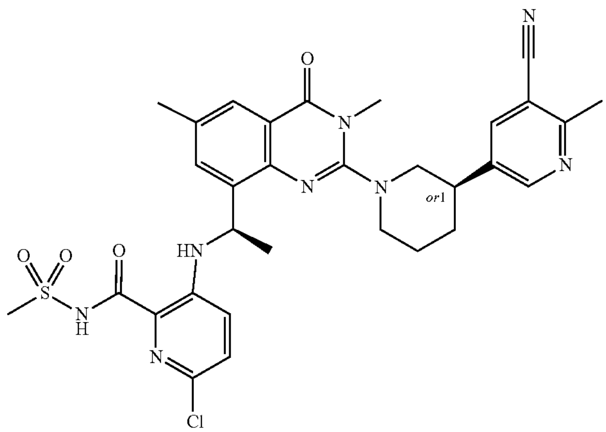 | 6-chloro-3-(((R)-1-(2-((R*)-3-(5-cyano-6-methylpyridin-3-yl)piperidin-1-yl)-3,6-dimethyl-4-oxo-3,4-dihydroquinazolin-8-yl)ethyl)amino)-N-(methylsulfonyl) picolinamide | 2.76 min, 270 nm, MS (ES+)[b] $C_{31}H_{33}ClN_8O_4S$ requires: 648.2, found: 649.2 [M + H]+ |
| 616 | 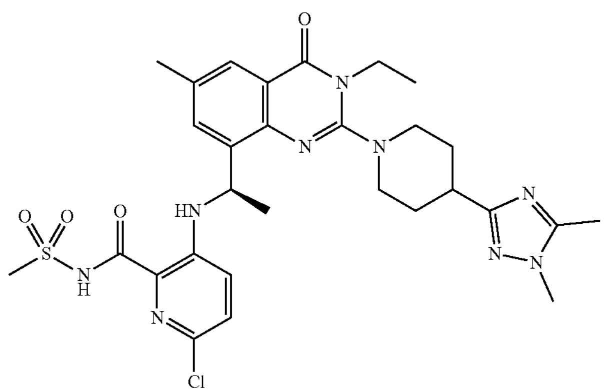 | (R)-6-chloro-3-((1-(2-(4-(1,5-dimethyl-1H-1,2,4-triazol-3-yl)piperidin-1-yl)-3-ethyl-6-methyl-4-oxo-3,4-dihydroquinazolin-8-yl)ethyl)amino)-N-(methylsulfonyl) picolinamide | 2.07 min, 254 nm, MS (ES+)[b] $C_{29}H_{36}ClN_9O_4S$ requires: 641.2, found: 642.2 [M + H]+ |
| 617 | 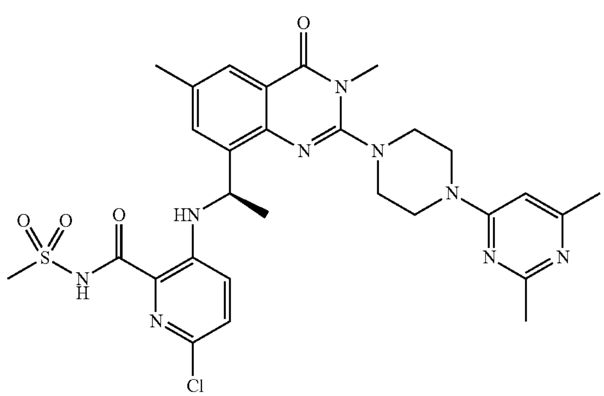 | (R)-6-chloro-3-((1-(2-(4-(2,6-dimethylpyrimidin-4-yl)piperazin-1-yl)-3,6-dimethyl-4-oxo-3,4-dihydroquinazolin-8-yl)ethyl)amino)-N-(methylsulfonyl) picolinamide | 1.86 min, 254 nm, MS (ES+)[b] $C_{29}H_{34}ClN_9O_4S$ requires: 639.2, found: 640.2 [M + H]+ |

TABLE E4-continued compound list prepared according to Route A in Example 4

| Cpd. ID | Structure | Name | LCMS |
|---|---|---|---|
| 618 | 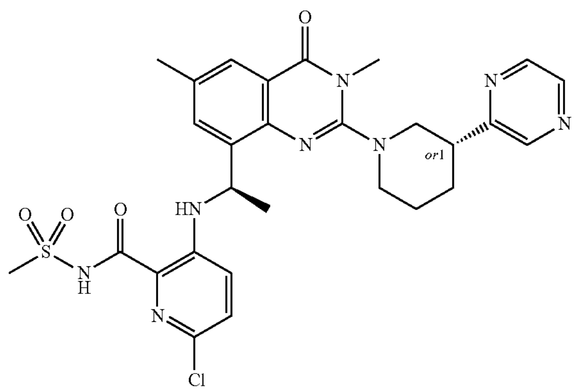 [SMILES: Cc1cc([C@@H](C)Nc2ccc(Cl)nc2C(=O)NS(C)(=O)=O)c2nc(N3CCC[C@@H](c4cnccn4)C3)n(C)c(=O)c2c1] | 6-chloro-3-(((R)-1-(3,6-dimethyl-4-oxo-2-((R*)-3-(pyrazin-2-yl)piperidin-1-yl)-3,4-dihydroquinazolin-8-yl)ethyl)amino)-N-(methylsulfonyl)picolinamide | 2.62 min, 210 nm, MS (ES+)[b] $C_{28}H_{31}ClN_8O_4S$ requires: 610.1, found: 611.2 [M + H]+ |
| 619 | 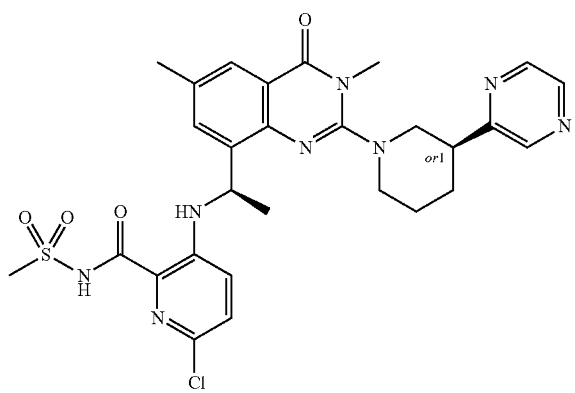 [SMILES: Cc1cc([C@@H](C)Nc2ccc(Cl)nc2C(=O)NS(C)(=O)=O)c2nc(N3CCC[C@H](c4cnccn4)C3)n(C)c(=O)c2c1] | 6-chloro-3-(((R)-1-(3,6-dimethyl-4-oxo-2-((R*)-3-(pyrazin-2-yl)piperidin-1-yl)-3,4-dihydroquinazolin-8-yl)ethyl)amino)-N-(methylsulfonyl)picolinamide | 2.63 min, 210 nm, MS (ES+)[b] $C_{28}H_{31}ClN_8O_4S$ requires: 610.1, found: 611.2 [M + H]+ |
| 620 | 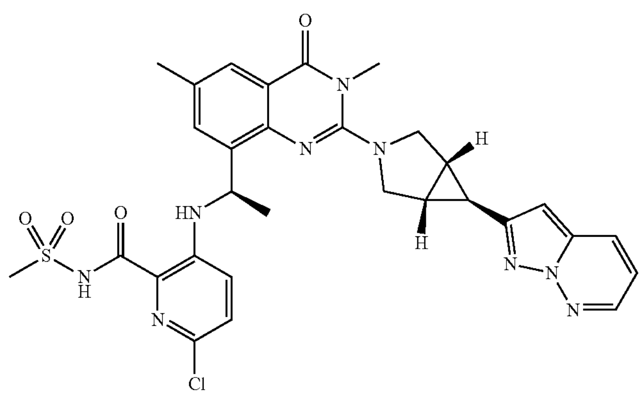 | 6-chloro-3-(((R)-1-(3,6-dimethyl-4-oxo-2-((1R,5S,6R)-6-(pyrazolo[1,5-b]pyridazin-2-yl)-3-azabicyclo[3.1.0]hexan-3-yl)-3,4-dihydroquinazolin-8-yl)ethyl)amino)-N-(methylsulfonyl)picolinamide | 2.42 min, 220 nm, MS (ES+)[b] $C_{30}H_{30}ClN_9O_4S$ requires: 647.1, found: 648.3 [M + H]+ |
| 621 | 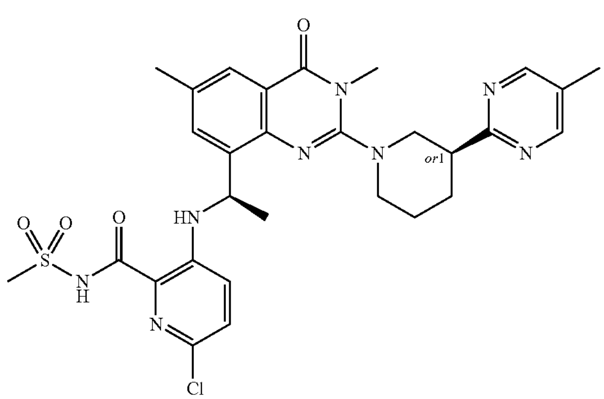 | 6-chloro-3-(((R)-1-(3,6-dimethyl-2-((R*)-3-(5-methylpyrimidin-2-yl)piperidin-1-yl)-4-oxo-3,4-dihydroquinazolin-8-yl)ethyl)amino)-N-(methylsulfonyl)picolinamide | 2.55 min, 254 nm, MS (ES+)[b] $C_{29}H_{33}ClN_8O_4S$ requires: 624.2, found: 625.3 [M + H]+ |

TABLE E4-continued compound list prepared according to Route A in Example 4

| Cpd. ID | Structure | Name | LCMS |
|---|---|---|---|
| 622 | 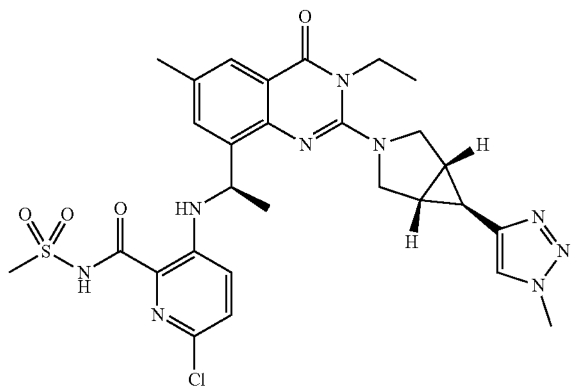 [SMILES: CCn1c(N2C[C@@H]3[C@H](C2)[C@H]3c2cn(C)nn2)nc2c([C@@H](C)Nc3ccc(Cl)nc3C(=O)NS(C)(=O)=O)cc(C)cc2c1=O] | 6-chloro-3-(((R)-1-(3-ethyl-6-methyl-2-((1R,5S,6R)-6-(1-methyl-1H-1,2,3-triazol-4-yl)-3-azabicyclo[3.1.0]hexan-3-yl)-4-oxo-3,4-dihydroquinazolin-8-yl)ethyl)amino)-N-(methylsulfonyl)picolinamide | 2.28 min, 220 nm, MS (ES+)[b] $C_{28}H_{32}ClN_9O_4S$ requires: 625.2, found: 626.3 [M + H]+ |
| 623 | 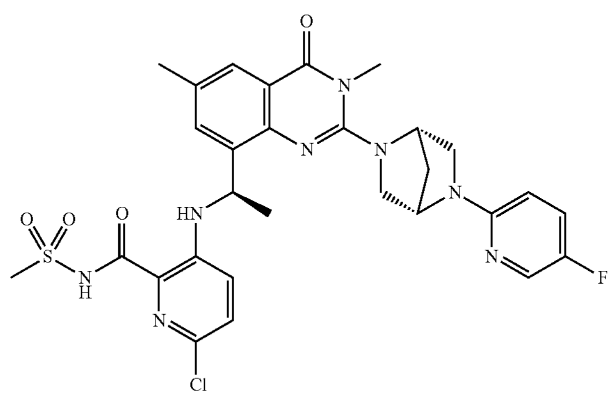 [SMILES: Cc1cc([C@@H](C)Nc2ccc(Cl)nc2C(=O)NS(C)(=O)=O)c2nc(N3C[C@@H]4C[C@H]3CN4c3ccc(F)cn3)n(C)c(=O)c2c1] | 6-chloro-3-(((R)-1-(2-((1S,4S)-5-(5-fluoropyridin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.36 min, 220 nm, MS (ES+)[b] $C_{29}H_{30}ClFN_8O_4S$ requires: 640.1, found: 641.2 [M + H]+ |
| 624 | 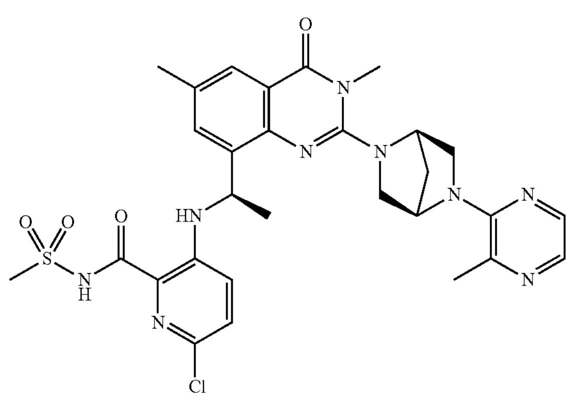 [SMILES: Cc1cc([C@@H](C)Nc2ccc(Cl)nc2C(=O)NS(C)(=O)=O)c2nc(N3C[C@H]4C[C@@H]3CN4c3nccnc3C)n(C)c(=O)c2c1] | 6-chloro-3-(((R)-1-(3,6-dimethyl-2-((1R,4R)-5-(3-methylpyrazin-2-yl)-2,5-diazabicyclo[2.2.1]heptan-2-yl)-4-oxo-3,4-dihydroquinazolin-8-yl)ethyl)amino)-N-(methylsulfonyl)picolinamide | 2.22 min, 254 nm, MS (ES+)[b] $C_{29}H_{32}ClN_9O_4S$ requires: 637.2, found: 638.3 [M + H]+ |

TABLE E4-continued compound list prepared according to Route A in Example 4

| Cpd. ID | Structure | Name | LCMS |
|---|---|---|---|
| 625 | 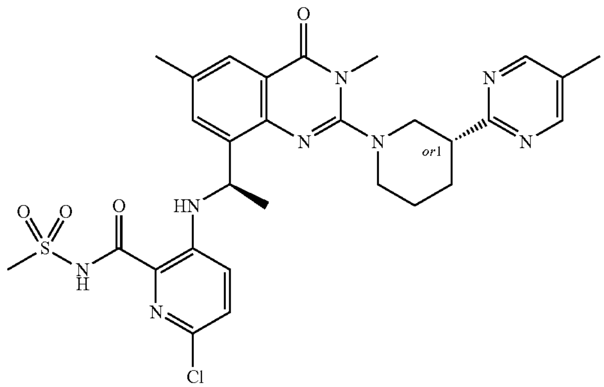 | 6-chloro-3-(((R)-1-(3,6-dimethyl-2-((R*)-3-(5-methylpyrimidin-2-yl)piperidin-1-yl)-4-oxo-3,4-dihydroquinazolin-8-yl)ethyl)amino)-N-(methylsulfonyl)picolinamide | 2.56 min, 254 nm, MS (ES+)[b] $C_{29}H_{33}ClN_8O_4S$ requires: 624.2, found: 625.3 [M + H]+ |
| 626 | 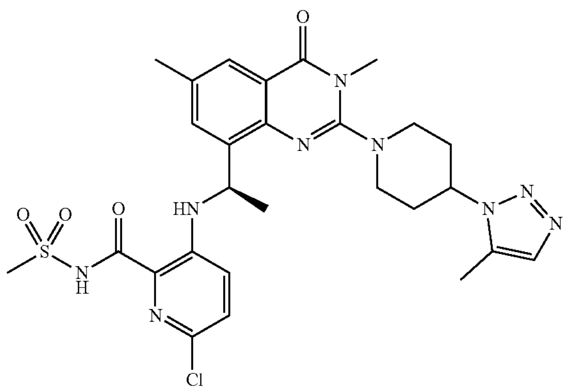 [SMILES: Cc1cc([C@@H](C)Nc2ccc(Cl)nc2C(=O)NS(C)(=O)=O)c2nc(N3CCC(n4nncc4C)CC3)n(C)c(=O)c2c1] | (R)-6-chloro-3-((1-(3,6-dimethyl-2-(4-(5-methyl-1H-1,2,3-triazol-1-yl)piperidin-1-yl)-4-oxo-3,4-dihydroquinazolin-8-yl)ethyl)amino)-N-(methylsulfonyl)picolinamide | 2.20 min, 254 nm, MS (ES+)[b] $C_{27}H_{32}ClN_9O_4S$ requires: 613.2, found: 614.2 [M + H]+ |
| 627 | 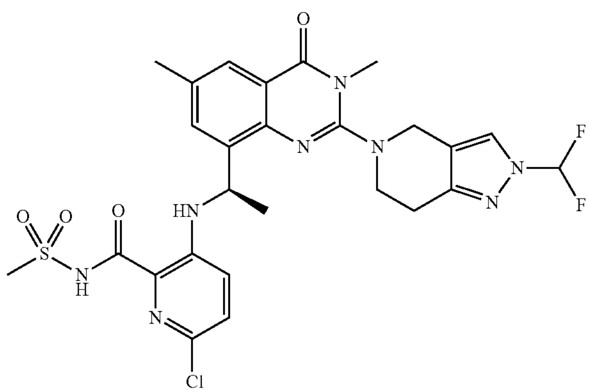 [SMILES: Cc1cc([C@@H](C)Nc2ccc(Cl)nc2C(=O)NS(C)(=O)=O)c2nc(N3CCc4nn(C(F)F)cc4C3)n(C)c(=O)c2c1] | (R)-6-chloro-3-((1-(2-(2-(difluoromethyl)-2,4,6,7-tetrahydro-5H-pyrazolo[4,3-c]pyridin-5-yl)-3,6-dimethyl-4-oxo-3,4-dihydroquinazolin-8-yl)ethyl)amino)-N-(methylsulfonyl)picolinamide | 2.33 min, 254 nm, MS (ES+)[b] $C_{26}H_{27}ClF_2N_8O_4S$ requires: 620.1, found: 621.2 [M + H]+ |
| 628 | 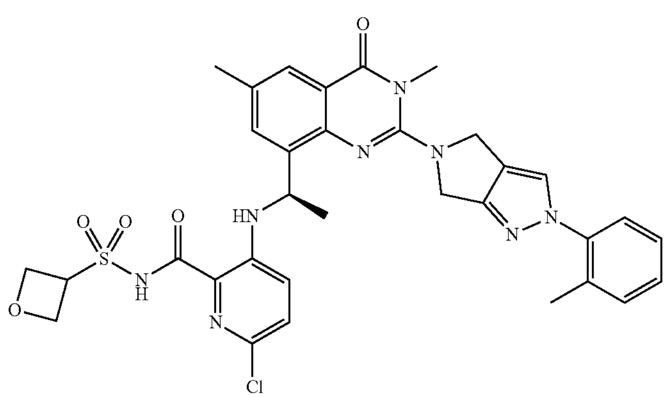 [SMILES: Cc1cc([C@@H](C)Nc2ccc(Cl)nc2C(=O)NS(=O)(=O)C2COC2)c2nc(N3Cc4cn(-c5ccccc5C)nc4C3)n(C)c(=O)c2c1] | (R)-6-chloro-3-((1-(3,6-dimethyl-4-oxo-2-(2-(o-tolyl)-2,6-dihydropyrrolo[3,4-c]pyrazol-5(4H)-yl)-3,4-dihydroquinazolin-8-yl)ethyl)amino)-N-(oxetan-3-ylsulfonyl)picolinamide | 2.65 min, 270 nm, MS (ES+)[b] $C_{33}H_{33}ClN_8O_5S$, requires: 688.2, found: 689.2 [M + H]+ |

TABLE E4-continued compound list prepared according to Route A in Example 4

| Cpd. ID | Structure | Name | LCMS |
|---|---|---|---|
| 629 | 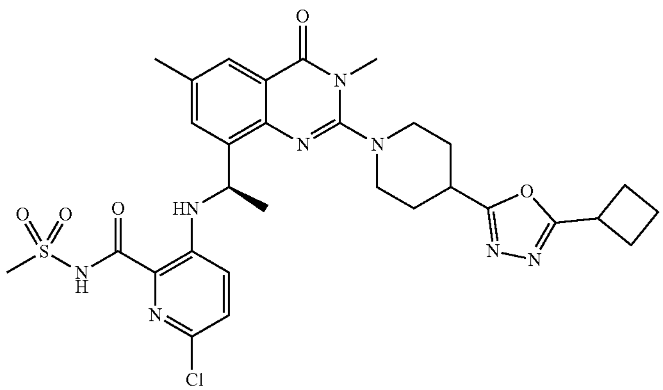 [SMILES: Cc1cc([C@@H](C)Nc2ccc(Cl)nc2C(=O)NS(C)(=O)=O)c2nc(N3CCC(c4nnc(C5CCC5)o4)CC3)n(C)c(=O)c2c1] | (R)-6-chloro-3-((1-(2-(4-(5-cyclobutyl-1,3,4-oxadiazol-2-yl)piperidin-1-yl)-3,6-dimethyl-4-oxo-3,4-dihydroquinazolin-8-yl)ethyl)amino)-N-(methylsulfonyl)picolinamide | 4.65 min, 280 nm, MS (ES+)$^c$ $C_{30}H_{35}ClN_8O_5S$, requires: 654.2, found: 655.2 $[M + H]^+$ |
| 630 | 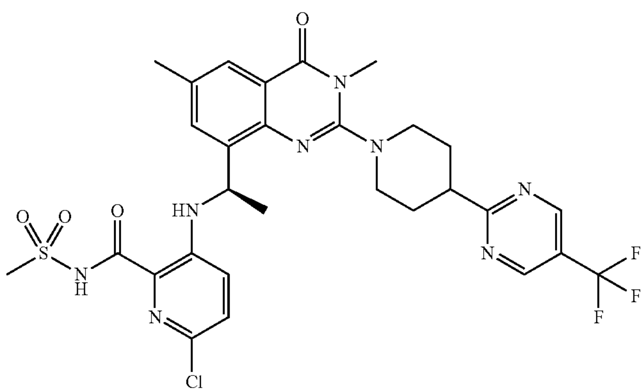 [SMILES: Cc1cc([C@@H](C)Nc2ccc(Cl)nc2C(=O)NS(C)(=O)=O)c2nc(N3CCC(c4ncc(C(F)(F)F)cn4)CC3)n(C)c(=O)c2c1] | (R)-6-chloro-3-((1-(3,6-dimethyl-4-oxo-2-(4-(5-(trifluoromethyl)pyrimidin-2-yl)piperidin-1-yl)-3,4-dihydroquinazolin-8-yl)ethyl)amino)-N-(methylsulfonyl)picolinamide | 2.69 min, 254 nm, MS (ES+)$^b$ $C_{29}H_{30}ClF_3N_8O_4S$, requires: 678.1, found: 679.1 $[M + H]^+$ |
| 631 | 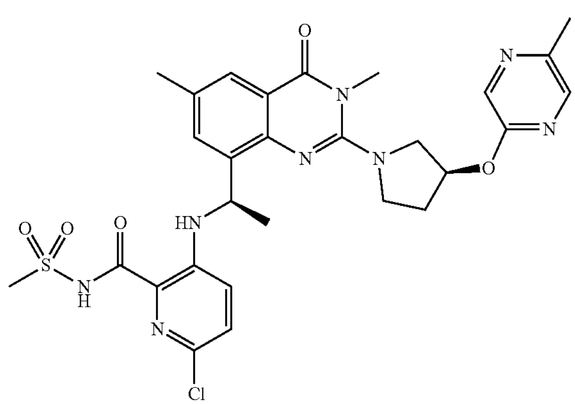 | 6-chloro-3-(((R)-1-(3,6-dimethyl-2-((S)-3-((5-methylpyrazin-2-yl)oxy)pyrrolidin-1-yl)-4-oxo-3,4-dihydroquinazolin-8-yl)ethyl)amino)-N-(methylsulfonyl)picolinamide | 3.59 min, 254 nm, MS (ES+)$^c$ $C_{28}H_{31}ClN_8O_5S$, requires: 626.2, found: 627.3 $[M + H]^+$ |

TABLE E4-continued compound list prepared according to Route A in Example 4

| Cpd. ID | Structure | Name | LCMS |
|---|---|---|---|
| 632 | 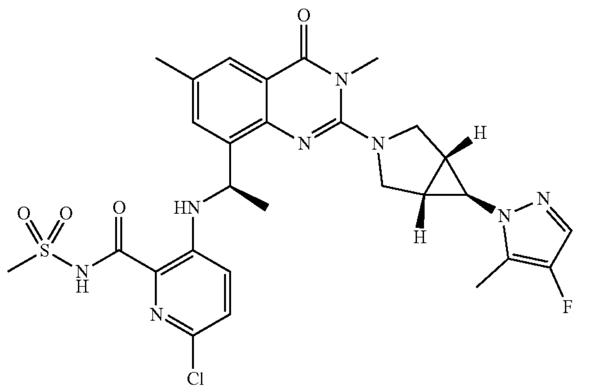 [SMILES: Cc1cc([C@@H](C)Nc2ccc(Cl)nc2C(=O)NS(C)(=O)=O)c2nc(N3C[C@@H]4[C@H](C3)[C@H]4n3ncc(F)c3C)n(C)c(=O)c2c1] | 6-chloro-3-(((R)-1-(2-((1R,5S,6S)-6-(4-fluoro-5-methyl-1H-pyrazol-1-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.36 min, 254 nm, MS (ES+)[b] $C_{28}H_{30}ClFN_8O_4S$, requires: 628.1, found: 629.2 $[M + H]^+$ |
| 633 | 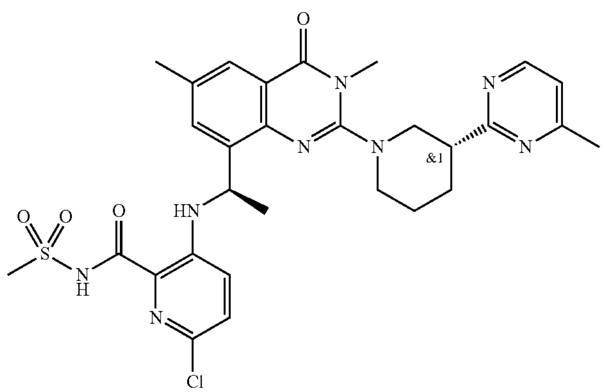 | 6-chloro-3-(((R)-1-(3,6-dimethyl-2-((RS)-3-(4-methylpyrimidin-2-yl)piperidin-1-yl)-4-oxo-3,4-dihydroquinazolin-8-yl)ethyl)amino)-N-(methylsulfonyl)picolinamide | 2.40 min, 254 nm, MS (ES+)[b] $C_{29}H_{33}ClN_8O_4S$, requires: 624.2, found: 625.2 $[M + H]^+$ |
| 634 | 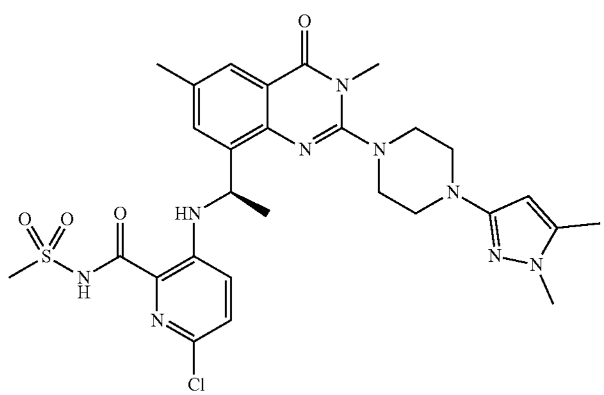 | (R)-6-chloro-3-((1-(2-(4-(1,5-dimethyl-1H-pyrazol-3-yl)piperazin-1-yl)-3,6-dimethyl-4-oxo-3,4-dihydroquinazolin-8-yl)ethyl)amino)-N-(methylsulfonyl)picolinamide | 2.13 min, 254 nm, MS (ES+)[b] $C_{28}H_{34}ClN_9O_4S$, requires: 627.2, found: 628.2 $[M + H]^+$ |
| 635 | 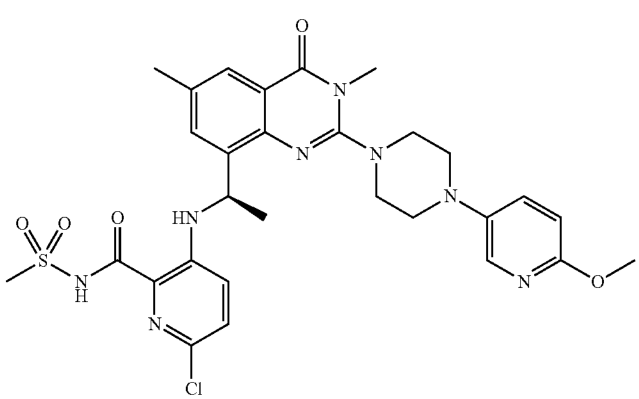 | (R)-6-chloro-3-((1-(2-(4-(6-methoxypyridin-3-yl)piperazin-1-yl)-3,6-dimethyl-4-oxo-3,4-dihydroquinazolin-8-yl)ethyl)amino)-N-(methylsulfonyl)picolinamide | 2.32 min, 210 nm, MS (ES+)[b] $C_{29}H_{33}ClN_8O_5S$, requires: 640.2, found: 641.2 $[M + H]^+$ |

TABLE E4-continued compound list prepared according to Route A in Example 4

| Cpd. ID | Structure | Name | LCMS |
|---|---|---|---|
| 636 | 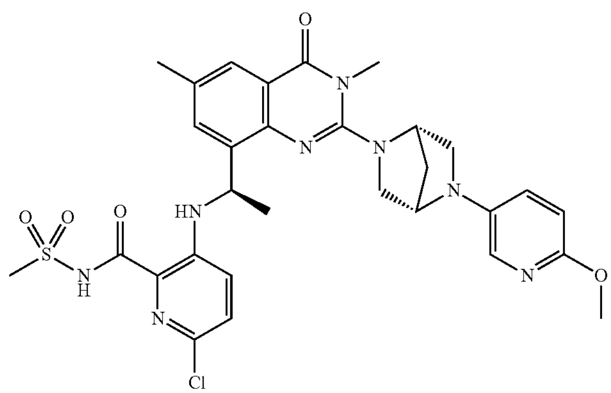 | 6-chloro-3-(((R)-1-(2-((1S,4S)-5-(6-methoxypyridin-3-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.37 min, 254 nm, MS (ES+)[b] $C_{30}H_{33}ClN_8O_5S$, requires: 652.2, found: 653.2 [M + H]+ |
| 637 | 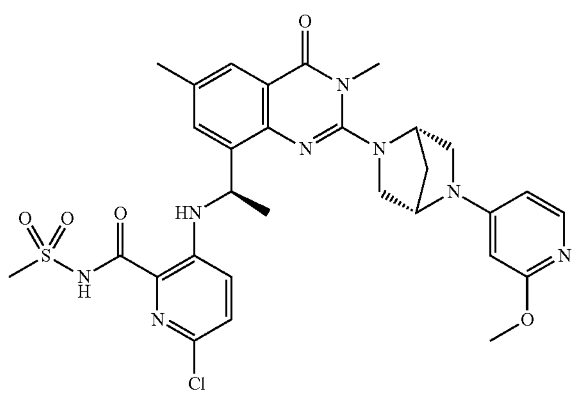 [SMILES: COc1cc(N2C[C@@H]3C[C@H]2CN3c2nc3c([C@@H](C)Nc4ccc(Cl)nc4C(=O)NS(C)(=O)=O)cc(C)cc3c(=O)n2C)ccn1] | 6-chloro-3-(((R)-1-(2-((1S,4S)-5-(2-methoxypyridin-4-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.1 min, 210 nm, MS (ES+)[b] $C_{30}H_{33}ClN_8O_5S$, requires: 652.2, found: 653.2 [M + H]+ |
| 638 | 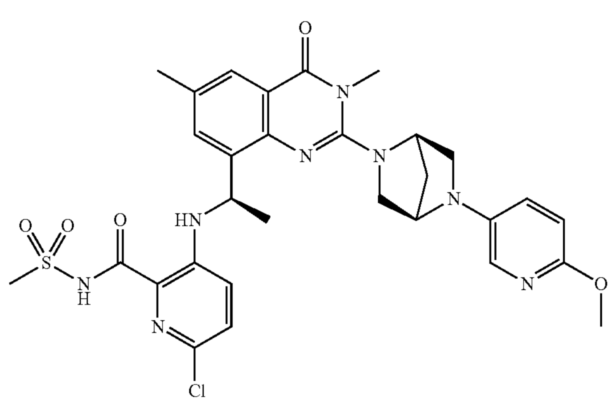 | 6-chloro-3-(((R)-1-(2-((1R,4R)-5-(6-methoxypyridin-3-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.39 min, 254 nm, MS (ES+)[b] $C_{30}H_{33}ClN_8O_5S$, requires: 652.2, found: 653.2 [M + H]+ |

TABLE E4-continued compound list prepared according to Route A in Example 4

| Cpd. ID | Structure | Name | LCMS |
|---|---|---|---|
| 639 | 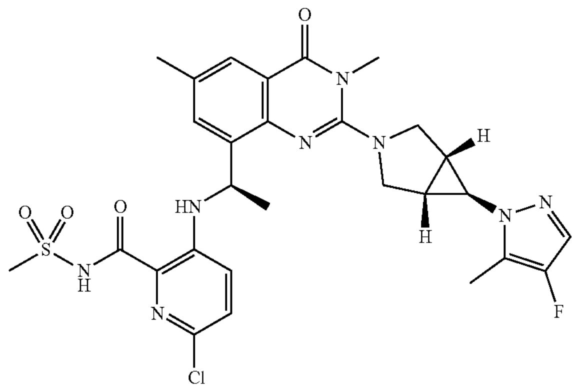 | 6-chloro-3-(((R)-1-(2-((1R,4R)-5-(2-methoxypyridin-4-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.11 min, 210 nm, MS (ES+)[b] $C_{30}H_{33}ClN_8O_5S$, requires: 652.2, found: 653.2 $[M + H]^+$ |
| 640 | 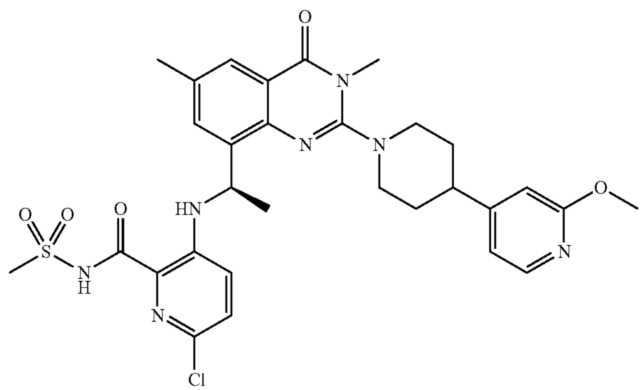 | (R)-6-chloro-3-((1-(2-(4-(2-methoxypyridin-4-yl)piperidin-1-yl)-3,6-dimethyl-4-oxo-3,4-dihydroquinazolin-8-yl)ethyl)amino)-N-(methylsulfonyl)picolinamide | 3.77 min, 254 nm, MS (ES+)[c] $C_{30}H_{34}ClN_7O_5S$, requires: 639.2, found: 640.2 $[M + H]^+$ |
| 641 | 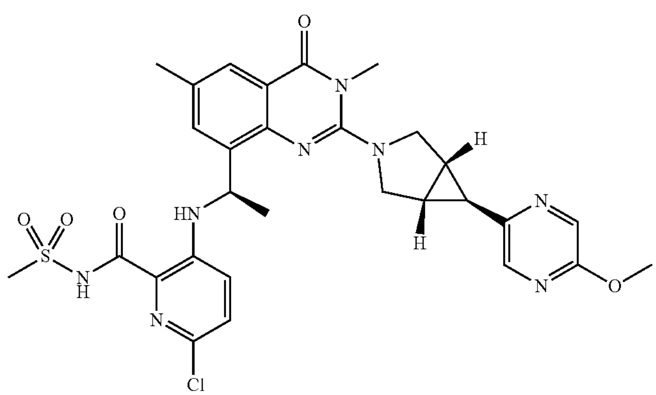 | 6-chloro-3-(((R)-1-(2-((1R,5S,6R)-6-(5-methoxypyrazin-2-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 3.77 min, 254 nm, MS (ES+)[c] $C_{29}H_{31}ClN_8O_5S$, requires: 638.2, found: 639.2 $[M + H]^+$ |
| 642 | 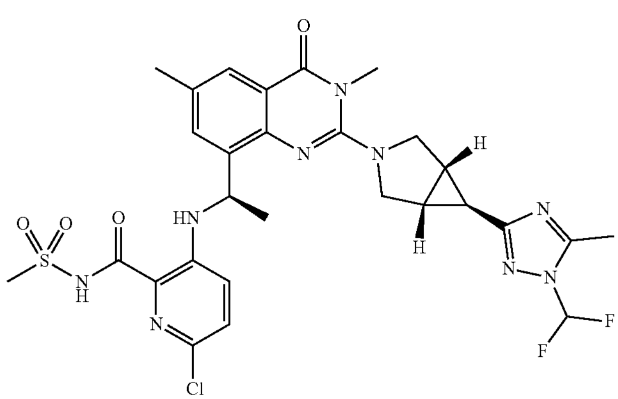 | 6-chloro-3-(((R)-1-(2-((1R,5S,6R)-6-(1-(difluoromethyl)-5-methyl-1H-1,2,4-triazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.35 min, 254 nm, MS (ES+)[b] $C_{28}H_{30}ClF_2N_9O_4S$, requires: 661.1, found: 662.3 $[M + H]^+$ |

TABLE E4-continued compound list prepared according to Route A in Example 4

| Cpd. ID | Structure | Name | LCMS |
|---|---|---|---|
| 643 | 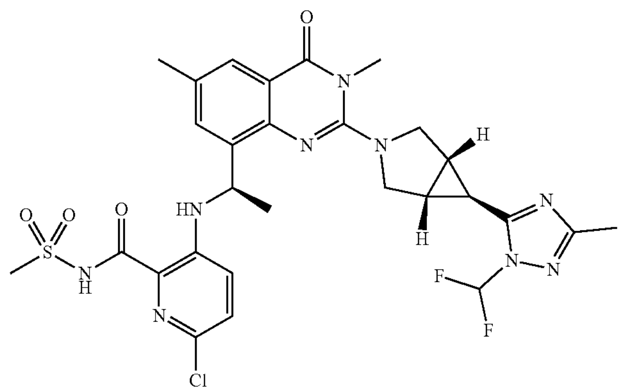 | 6-chloro-3-(((R)-1-(2-((1R,5S,6R)-6-(1-(difluoromethyl)-3-methyl-1H-1,2,4-triazol-5-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.31 min, 254 nm, MS (ES+)[b] $C_{28}H_{30}ClF_2N_9O_4S$, requires: 661.1, found: 662.3 [M + H]+ |
| 644 | 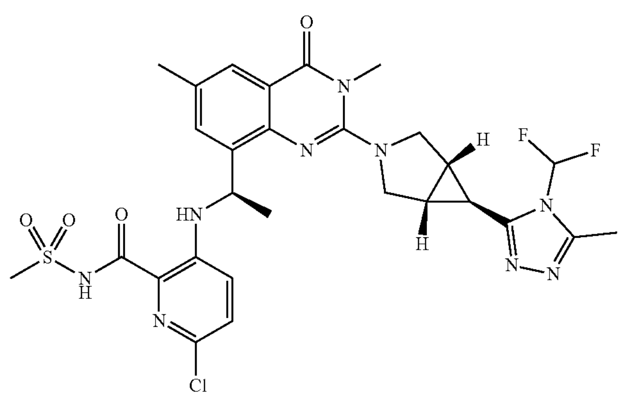 | 6-chloro-3-(((R)-1-(2-((1R,5S,6R)-6-(4-(difluoromethyl)-5-methyl-4H-1,2,4-triazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.11 min, 254 nm, MS (ES+)[b] $C_{28}H_{30}ClF_2N_9O_4S$, requires: 661.1, found: 662.3 [M + H]+ |
| 645 | 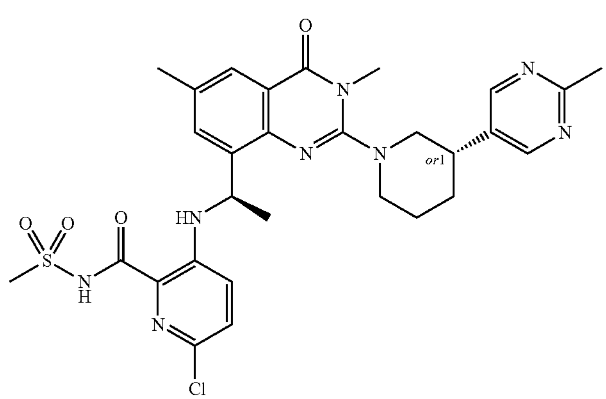 | 6-chloro-3-(((R)-1-(3,6-dimethyl-2-((R*)-3-(2-methylpyrimidin-5-yl)piperidin-1-yl)-4-oxo-3,4-dihydroquinazolin-8-yl)ethyl)amino)-N-(methylsulfonyl)picolinamide | 2.25 min, 254 nm, MS (ES+)[b] $C_{29}H_{33}ClN_8O_4S$, requires: 624.2, found: 625.3 [M + H]+ |

TABLE E4-continued compound list prepared according to Route A in Example 4

| Cpd. ID | Structure | Name | LCMS |
|---|---|---|---|
| 646 | 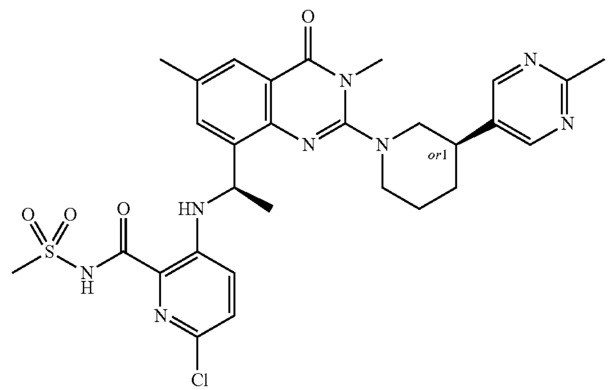 | 6-chloro-3-(((R)-1-(3,6-dimethyl-2-((R*)-3-(2-methylpyrimidin-5-yl)piperidin-1-yl)-4-oxo-3,4-dihydroquinazolin-8-yl)ethyl)amino)-N-(methylsulfonyl)picolinamide | 2.29 min, 254 nm, MS (ES+)[b] C$_{29}$H$_{33}$ClN$_8$O$_4$S, requires: 624.2, found: 625.3 [M + H]$^+$ |
| 647 | 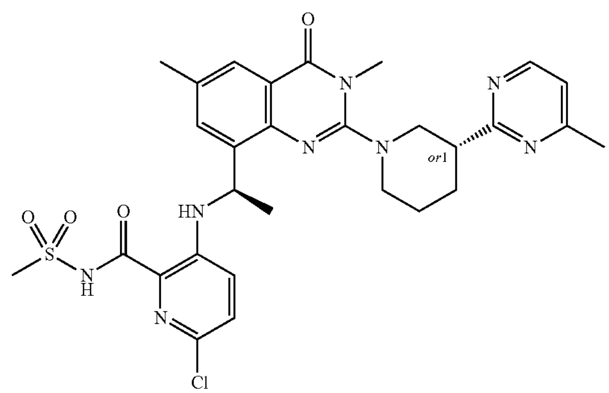 | 6-chloro-3-(((R)-1-(3,6-dimethyl-2-((R*)-3-(4-methylpyrimidin-2-yl)piperidin-1-yl)-4-oxo-3,4-dihydroquinazolin-8-yl)ethyl)amino)-N-(methylsulfonyl)picolinamide | 2.47 min, 254 nm, MS (ES+)[b] C$_{29}$H$_{33}$ClN$_8$O$_4$S, requires: 624.2, found: 625.3 [M + H]$^+$ |
| 648 | 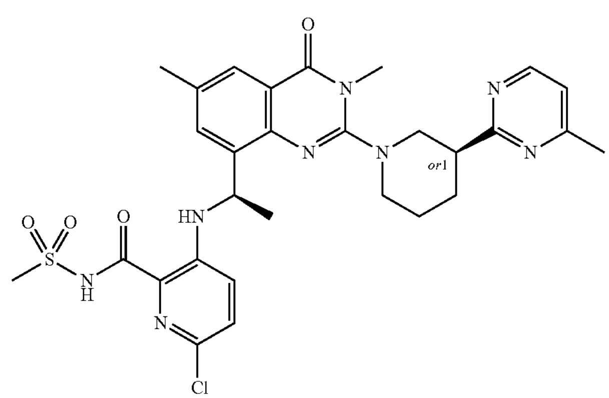 | 6-chloro-3-(((R)-1-(3,6-dimethyl-2-((R*)-3-(4-methylpyrimidin-2-yl)piperidin-1-yl)-4-oxo-3,4-dihydroquinazolin-8-yl)ethyl)amino)-N-(methylsulfonyl)picolinamide | 2.46 min, 254 nm, MS (ES+)[b] C$_{29}$H$_{33}$ClN$_8$O$_4$S, requires: 624.2, found: 625.3 [M + H]$^+$ |
| 649 | 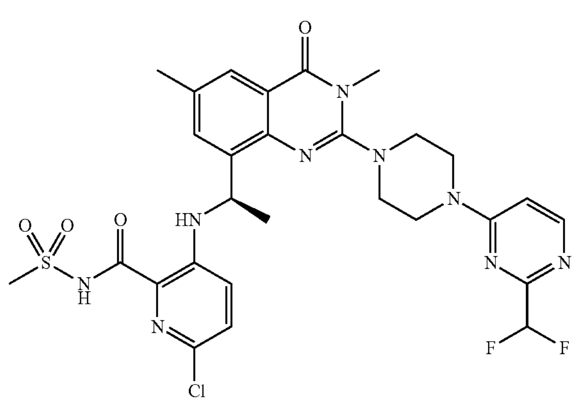 [SMILES: Cc1cc([C@@H](C)Nc2ccc(Cl)nc2C(=O)NS(C)(=O)=O)c2nc(N3CCN(c4ccnc(C(F)F)n4)CC3)n(C)c(=O)c2c1] | (R)-6-chloro-3-((1-(2-(4-(2-(difluoromethyl)pyrimidin-4-yl)piperazin-1-yl)-3,6-dimethyl-4-oxo-3,4-dihydroquinazolin-8-yl)ethyl)amino)-N-(methylsulfonyl)picolinamide | 2.34 min, 254 nm, MS (ES+)[b] C$_{28}$H$_{30}$ClF$_2$N$_9$O$_4$S, requires: 661.1, found: 662.3 [M + H]$^+$ |

TABLE E4-continued compound list prepared according to Route A in Example 4

| Cpd. ID | Structure | Name | LCMS |
|---|---|---|---|
| 650 | 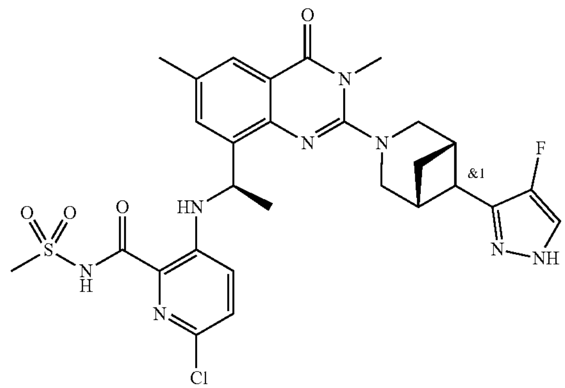 [SMILES: Cc1cc([C@@H](C)Nc2ccc(Cl)nc2C(=O)NS(C)(=O)=O)c2nc(N3C[C@H]4C[C@@H](C3)C4c3n[nH]cc3F)n(C)c(=O)c2c1] | 6-chloro-3-(((1R)-1-(2-((1R,5S)-6-(4-fluoro-1H-pyrazol-3-yl)-3-azabicyclo[3.1.1]heptan-3-yl)-3,6-dimethyl-4-oxo-3,4-dihydroquinazolin-8-yl)ethyl)amino)-N-(methylsulfonyl)picolinamide | 2.32 min, 254 nm, MS (ES+)[b] $C_{28}H_{30}ClFN_8O_4S$, requires: 628.1, found: 629.3 $[M + H]^+$ |
| 651 | 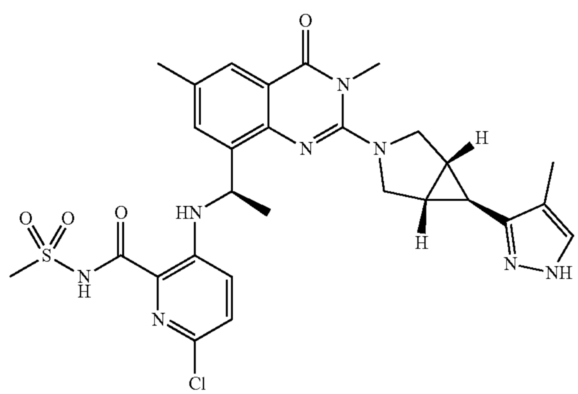 [SMILES: Cc1cc([C@@H](C)Nc2ccc(Cl)nc2C(=O)NS(C)(=O)=O)c2nc(N3C[C@@H]4[C@H](C3)[C@H]4c3n[nH]cc3C)n(C)c(=O)c2c1] | 6-chloro-3-(((R)-1-(3,6-dimethyl-2-((1R,5S,6R)-6-(4-methyl-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.22 min, 254 nm, MS (ES+)[b] $C_{28}H_{31}ClN_8O_4S$, requires: 610.1, found: 611.3 $[M + H]^+$ |
| 652 | 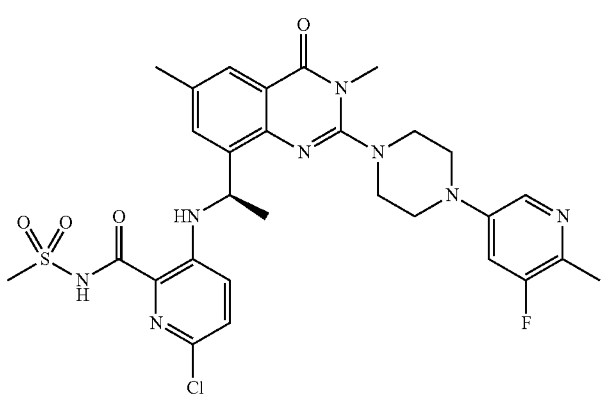 | (R)-6-chloro-3-((1-(2-(4-(5-fluoro-6-methylpyridin-3-yl)piperazin-1-yl)-3,6-dimethyl-4-oxo-3,4-dihydroquinazolin-8-yl)ethyl)amino)-N-(methylsulfonyl)picolinamide | 2.34 min, 254 nm, MS (ES+)[b] $C_{29}H_{32}ClFN_8O_4S$, requires: 642.1, found: 643.2 $[M + H]^+$ |

TABLE E4-continued compound list prepared according to Route A in Example 4

| Cpd. ID | Structure | Name | LCMS |
|---|---|---|---|
| 653 | 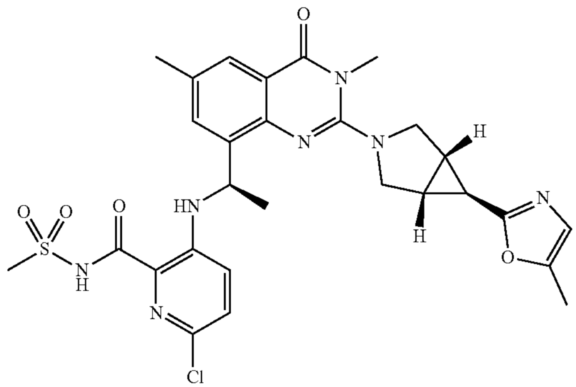 [SMILES: Cc1cc([C@@H](C)Nc2ccc(Cl)nc2C(=O)NS(C)(=O)=O)c2nc(N3C[C@@H]4[C@H](C3)[C@H]4c3ncc(C)o3)n(C)c(=O)c2c1] | 6-chloro-3-(((R)-1-(3,6-dimethyl-2-((1R,5S,6R)-6-(5-methyloxazol-2-yl)-3-azabicyclo[3.1.0]hexan-3-yl)-4-oxo-3,4-dihydroquinazolin-8-yl)ethyl)amino)-N-(methylsulfonyl)picolinamide | 2.39 min, 254 nm, MS (ES+)[b] $C_{28}H_{30}ClN_7O_5S$, requires: 611.1, found: 612.2 $[M + H]^+$ |
| 654 | 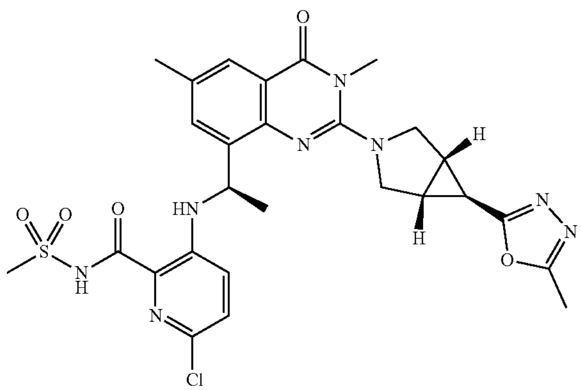 | 6-chloro-3-(((R)-1-(3,6-dimethyl-2-((1R,5S,6R)-6-(5-methyl-1,3,4-oxadiazol-2-yl)-3-azabicyclo[3.1.0]hexan-3-yl)-4-oxo-3,4-dihydroquinazolin-8-yl)ethyl)amino)-N-(methylsulfonyl)picolinamide | 2.17 min, 254 nm, MS (ES+)[b] $C_{27}H_{29}ClN_8O_5S$, requires: 612.1, found: 613.2 $[M + H]^+$ |
| 655 | 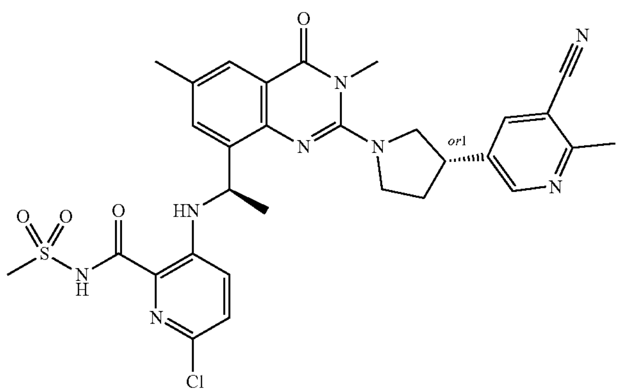 | 6-chloro-3-(((R)-1-(2-((R*)-3-(5-cyano-6-methylpyridin-3-yl)pyrrolidin-1-yl)-3,6-dimethyl-4-oxo-3,4-dihydroquinazolin-8-yl)ethyl)amino)-N-(methylsulfonyl)picolinamide | 2.37 min, 254 nm, MS (ES+)[b] $C_{30}H_{31}ClN_8O_4S$, requires: 634.1, found: 635.3 $[M + H]^+$ |
| 656 | 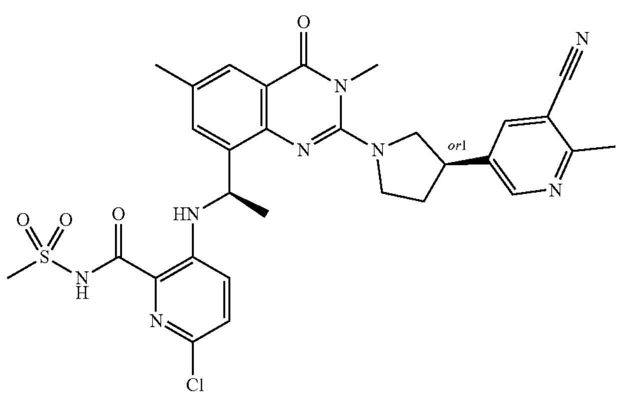 | 6-chloro-3-(((R)-1-(2-((R*)-3-(5-cyano-6-methylpyridin-3-yl)pyrrolidin-1-yl)-3,6-dimethyl-4-oxo-3,4-dihydroquinazolin-8-yl)ethyl)amino)-N-(methylsulfonyl)picolinamide | 2.4 min, 254 nm, MS (ES+)[b] $C_{30}H_{31}ClN_8O_4S$, requires: 634.1, found: 635.5 $[M + H]^+$ |

TABLE E4-continued compound list prepared according to Route A in Example 4

| Cpd. ID | Structure | Name | LCMS |
|---|---|---|---|
| 657 | 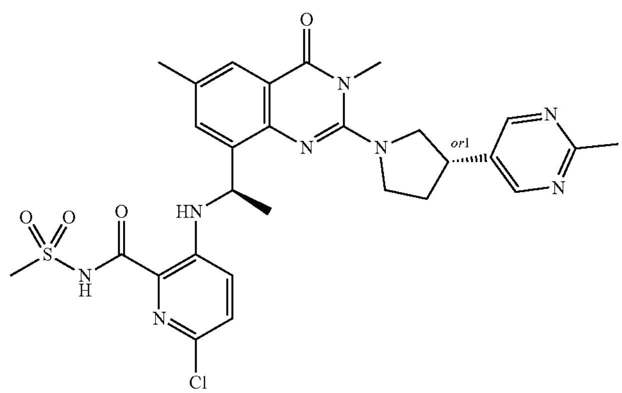 | 6-chloro-3-(((R)-1-(3,6-dimethyl-2-((R*)-3-(2-methylpyrimidin-5-yl)pyrrolidin-1-yl)-4-oxo-3,4-dihydroquinazolin-8-yl)ethyl)amino)-N-(methylsulfonyl)picolinamide | 2.18 min, 210 nm, MS (ES+)[b] $C_{28}H_{31}ClN_8O_4S$, requires: 610.1, found: 611.2 $[M+H]^+$ |
| 658 | 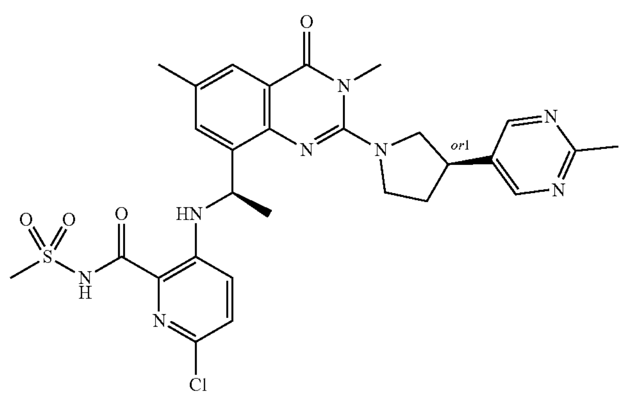 | 6-chloro-3-(((R)-1-(3,6-dimethyl-2-((R*)-3-(2-methylpyrimidin-5-yl)pyrrolidin-1-yl)-4-oxo-3,4-dihydroquinazolin-8-yl)ethyl)amino)-N-(methylsulfonyl)picolinamide | 2.16 min, 220 nm, MS (ES+)[b] $C_{28}H_{31}ClN_8O_4S$, requires: 610.1, found: 611.3 $[M+H]^+$ |
| 659 | 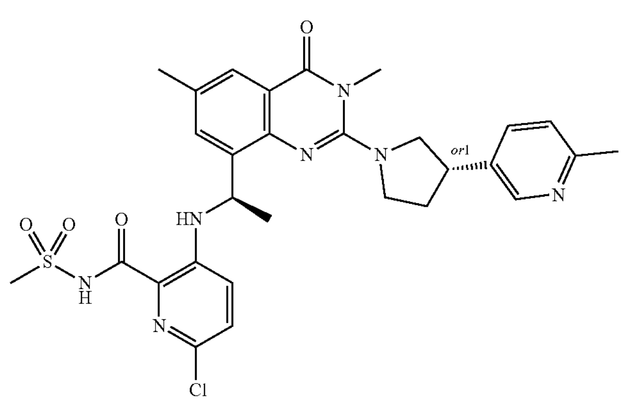 | 6-chloro-3-(((R)-1-(3,6-dimethyl-2-((R*)-3-(6-methylpyridin-3-yl)pyrrolidin-1-yl)-4-oxo-3,4-dihydroquinazolin-8-yl)ethyl)amino)-N-(methylsulfonyl)picolinamide | 1.94 min, 254 nm, MS (ES+)[b] $C_{29}H_{32}ClN_7O_4S$, requires: 609.1, found: 610.3 $[M+H]^+$ |

TABLE E4-continued compound list prepared according to Route A in Example 4

| Cpd. ID | Structure | Name | LCMS |
|---|---|---|---|
| 660 | 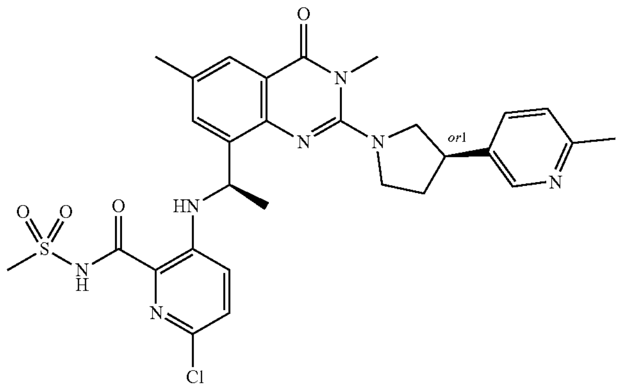 | 6-chloro-3-(((R)-1-(3,6-dimethyl-2-((R*)-3-(6-methylpyridin-3-yl)pyrrolidin-1-yl)-4-oxo-3,4-dihydroquinazolin-8-yl)ethyl)amino)-N-(methylsulfonyl)picolinamide | 1.94 min, 254 nm, MS (ES+)[b] $C_{29}H_{32}ClN_7O_4S$, requires: 609.1, found: 610.3 $[M + H]^+$ |
| 661 | 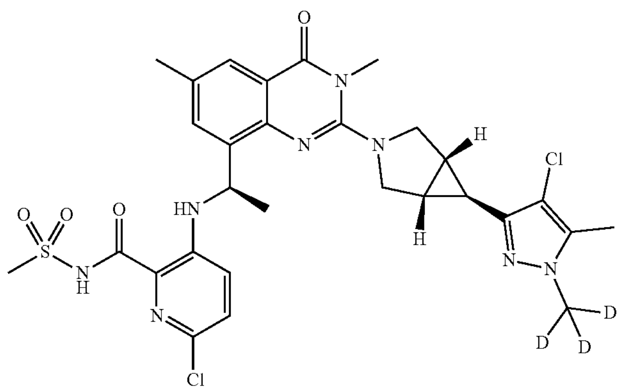 | 6-chloro-3-(((R)-1-(2-((1R,5S,6R)-6-(4-chloro-5-methyl-1-(methyl-d3)-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.54 min, 254 nm, MS (ES+)[b] $C_{29}H_{29}D_3Cl_2N_8O_4S$, requires: 661.1, found: 662.2 $[M + H]^+$ |
| 662 | 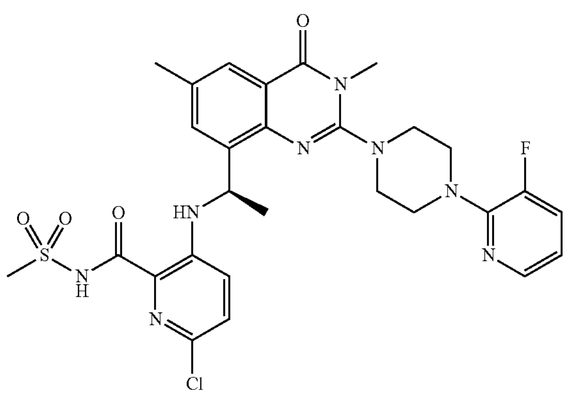 [SMILES: Cc1cc([C@@H](C)Nc2ccc(Cl)nc2C(=O)NS(C)(=O)=O)c2nc(N3CCN(c4ncccc4F)CC3)n(C)c(=O)c2c1] | (R)-6-chloro-3-((1-(2-(4-(3-fluoropyridin-2-yl)piperazin-1-yl)-3,6-dimethyl-4-oxo-3,4-dihydroquinazolin-8-yl)ethyl)amino)-N-(methylsulfonyl)picolinamide | 2.61 min, 254 nm, MS (ES+)[b] $C_{28}H_{30}ClFN_8O_4S$, requires: 628.1, found: 629.3 $[M + H]^+$ |
| 663 | 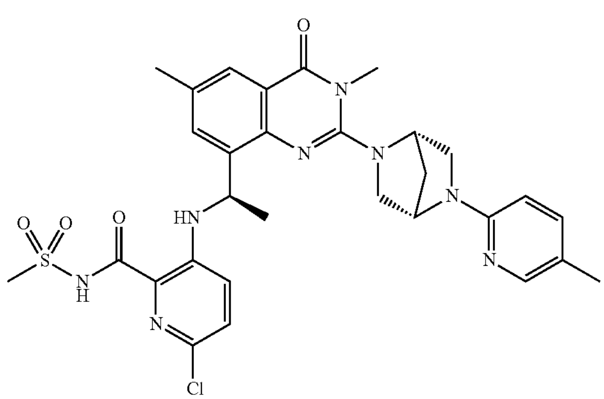 | 6-chloro-3-(((R)-1-(3,6-dimethyl-2-((1S,4S)-5-(5-methylpyridin-2-yl)-2,5-diazabicyclo[2.2.1]heptan-2-yl)-4-oxo-3,4-dihydroquinazolin-8-yl)ethyl)amino)-N-(methylsulfonyl)picolinamide | 1.92 min, 254 nm, MS (ES+)[b] $C_{30}H_{33}ClN_8O_4S$, requires: 636.2, found: 637.3 $[M + H]^+$ |

TABLE E4-continued compound list prepared according to Route A in Example 4

| Cpd. ID | Structure | Name | LCMS |
|---|---|---|---|
| 664 | 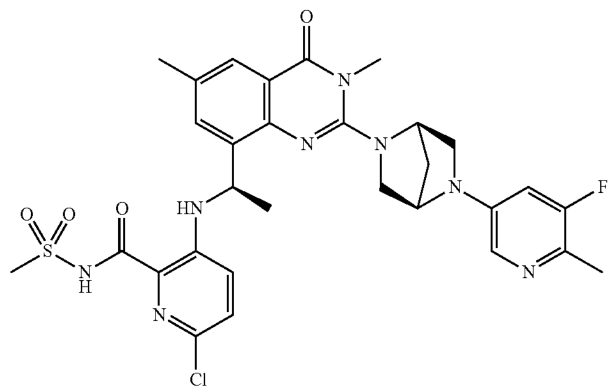 [SMILES: Cc1cc([C@@H](C)Nc2ccc(Cl)nc2C(=O)NS(C)(=O)=O)c2nc(N3C[C@H]4C[C@@H]3CN4c3cnc(C)c(F)c3)n(C)c(=O)c2c1] | 6-chloro-3-(((R)-1-(2-((1R,4R)-5-(5-fluoro-6-methylpyridin-3-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.17 min, 254 nm, MS (ES+)$^b$ $C_{30}H_{32}ClFN_8O_4S$, requires: 654.1, found: 655.3 $[M + H]^+$ |
| 665 | 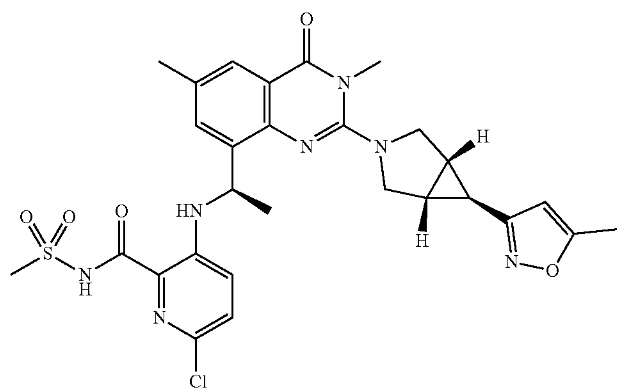 | 6-chloro-3-(((R)-1-(3,6-dimethyl-2-((1R,5S,6R)-6-(5-methylisoxazol-3-yl)-3-azabicyclo[3.1.0]hexan-3-yl)-4-oxo-3,4-dihydroquinazolin-8-yl)ethyl)amino)-N-(methylsulfonyl)picolinamide | 2.45 min, 254 nm, MS (ES+)$^b$ $C_{28}H_{30}ClN_7O_5S$, requires: 611.1, found: 612.3 $[M + H]^+$ |
| 666 | 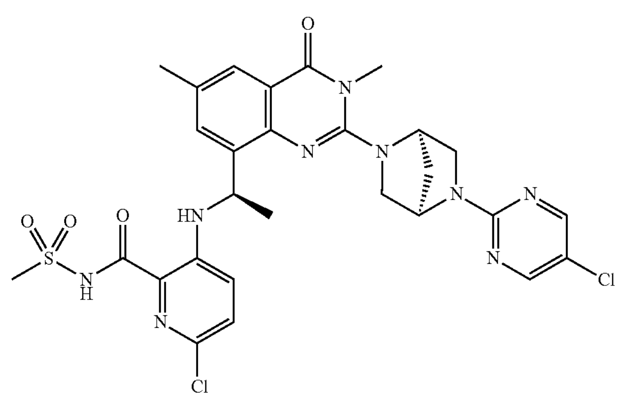 [SMILES: Cc1cc([C@@H](C)Nc2ccc(Cl)nc2C(=O)NS(C)(=O)=O)c2nc(N3C[C@H]4C[C@@H]3CN4c3ncc(Cl)cn3)n(C)c(=O)c2c1] | 6-chloro-3-(((R)-1-(2-((1R,4R)-5-(5-chloropyrimidin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.59 min, 254 nm, MS (ES+)$^b$ $C_{28}H_{29}Cl_2N_9O_4S$, requires: 657.1, found: 658.3 $[M + H]^+$ |

TABLE E4-continued compound list prepared according to Route A in Example 4

| Cpd. ID | Structure | Name | LCMS |
|---|---|---|---|
| 667 | 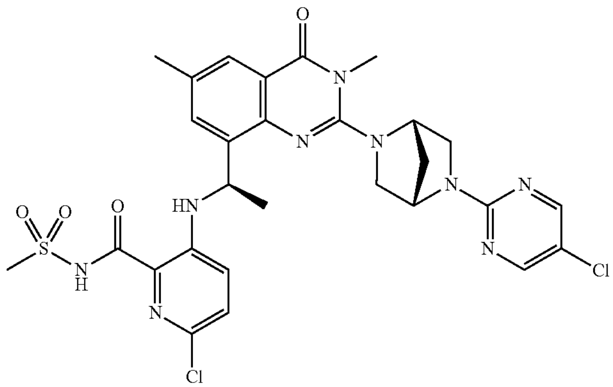 [SMILES: Cc1cc([C@@H](C)Nc2ccc(Cl)nc2C(=O)NS(C)(=O)=O)c2nc(N3C[C@@H]4C[C@H]3CN4c3ncc(Cl)cn3)n(C)c(=O)c2c1] | 6-chloro-3-(((R)-1-(2-((1S,4S)-5-(5-chloropyrimidin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.56 min, 254 nm, MS (ES+)[b] $C_{28}H_{29}Cl_2N_9O_4S$, requires: 657.1, found: 658.2 [M + H]+ |
| 668 | 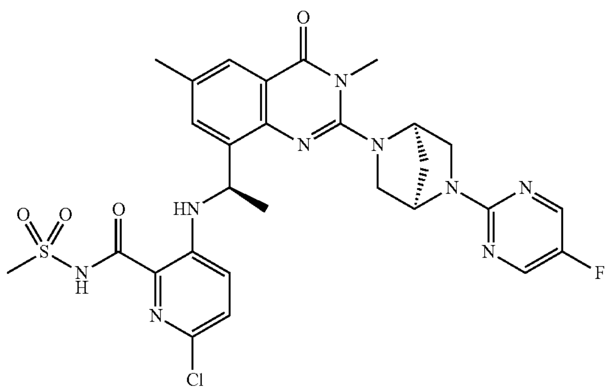 [SMILES: Cc1cc([C@@H](C)Nc2ccc(Cl)nc2C(=O)NS(C)(=O)=O)c2nc(N3C[C@H]4C[C@@H]3CN4c3ncc(F)cn3)n(C)c(=O)c2c1] | 6-chloro-3-(((R)-1-(2-((1R,4R)-5-(5-fluoropyrimidin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.45 min, 210 nm, MS (ES+)[b] $C_{28}H_{29}ClFN_9O_4S$, requires: 641.1, found: 642.3 [M + H]+ |
| 669 | 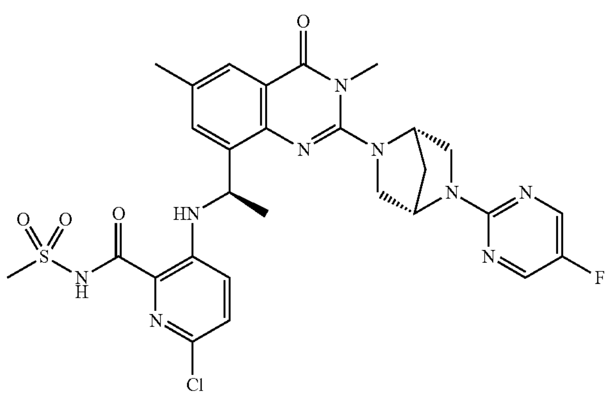 [SMILES: Cc1cc([C@@H](C)Nc2ccc(Cl)nc2C(=O)NS(C)(=O)=O)c2nc(N3C[C@@H]4C[C@H]3CN4c3ncc(F)cn3)n(C)c(=O)c2c1] | 6-chloro-3-(((R)-1-(2-((1S,4S)-5-(5-fluoropyrimidin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.41 min, 254 nm, MS (ES+)[b] $C_{28}H_{29}ClFN_9O_4S$, requires: 641.1, found: 642.3 [M + H]+ |
| 670 | 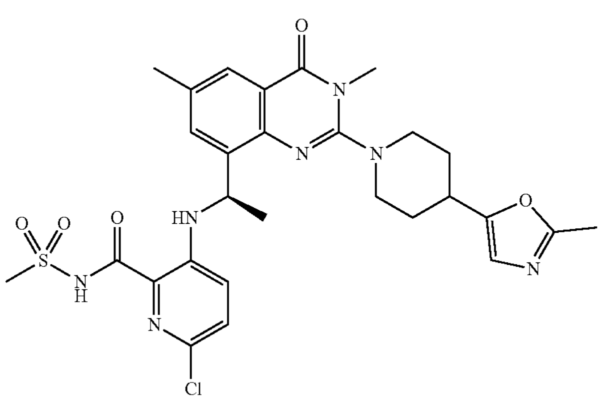 | (R)-6-chloro-3-((1-(3,6-dimethyl-2-(4-(2-methyloxazol-5-yl)piperidin-1-yl)-4-oxo-3,4-dihydroquinazolin-8-yl)ethyl)amino)-N-(methylsulfonyl)picolinamide | 2.36 min, 270 nm, MS (ES+)[b] $C_{28}H_{32}ClN_7O_5S$, requires: 613.1, found: 614.2 [M + H]+ |

TABLE E4-continued compound list prepared according to Route A in Example 4

| Cpd. ID | Structure | Name | LCMS |
|---|---|---|---|
| 671 | 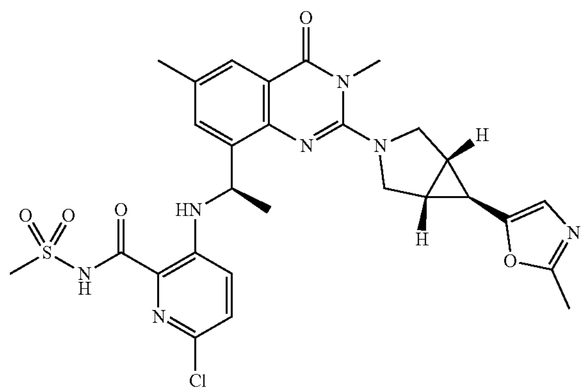 [SMILES: Cc1cc([C@@H](C)Nc2ccc(Cl)nc2C(=O)NS(C)(=O)=O)c2nc(N3C[C@@H]4[C@H](C3)[C@H]4c3cnc(C)o3)n(C)c(=O)c2c1] | 6-chloro-3-(((R)-1-(3,6-dimethyl-2-((1R,5S,6R)-6-(2-methyloxazol-5-yl)-3-azabicyclo[3.1.0]hexan-3-yl)-4-oxo-3,4-dihydroquinazolin-8-yl)ethyl)amino)-N-(methylsulfonyl)picolinamide | 2.37 min, 270 nm, MS (ES+)[b] $C_{28}H_{30}ClN_7O_5S$, requires: 611.1, found: 612.6 $[M + H]^+$ |
| 672 | 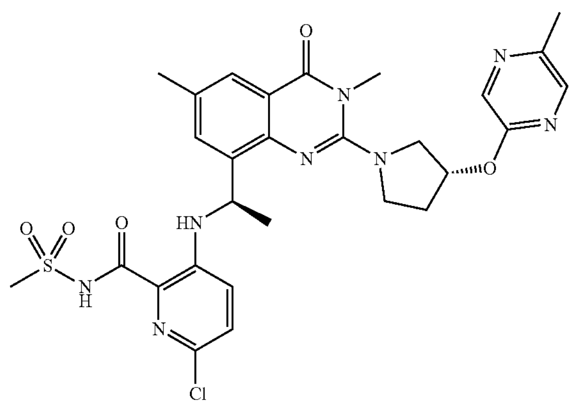 [SMILES: Cc1cc([C@@H](C)Nc2ccc(Cl)nc2C(=O)NS(C)(=O)=O)c2nc(N3CC[C@@H](Oc4cnc(C)cn4)C3)n(C)c(=O)c2c1] | 6-chloro-3-(((R)-1-(3,6-dimethyl-2-((R)-3-((5-methylpyrazin-2-yl)oxy)pyrrolidin-1-yl)-4-oxo-3,4-dihydroquinazolin-8-yl)ethyl)amino)-N-(methylsulfonyl)picolinamide | 4.58 min, 254 nm, MS (ES+)[c] $C_{28}H_{31}ClN_8O_5S$, requires: 626.2, found: 627.2 $[M + H]^+$ |
| 673 | 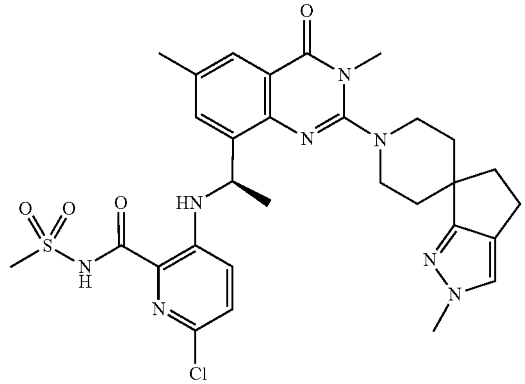 [SMILES: Cc1cc([C@@H](C)Nc2ccc(Cl)nc2C(=O)NS(C)(=O)=O)c2nc(N3CCC4(CCc5cn(C)nc54)CC3)n(C)c(=O)c2c1] | (R)-6-chloro-3-((1-(3,6-dimethyl-2-(2-methyl-4,5-dihydro-2H-spiro[cyclopenta[c]pyrazole-6,4'-piperidin]-1'-yl)-4-oxo-3,4-dihydroquinazolin-8-yl)ethyl)amino)-N-(methylsulfonyl)picolinamide | 3.77 min, 254 nm, MS (ES+)[c] $C_{30}H_{35}ClN_8O_4S$, requires: 638.2, found: 639.3 $[M + H]^+$ |

TABLE E4-continued compound list prepared according to Route A in Example 4

| Cpd. ID | Structure | Name | LCMS |
|---|---|---|---|
| 674 | 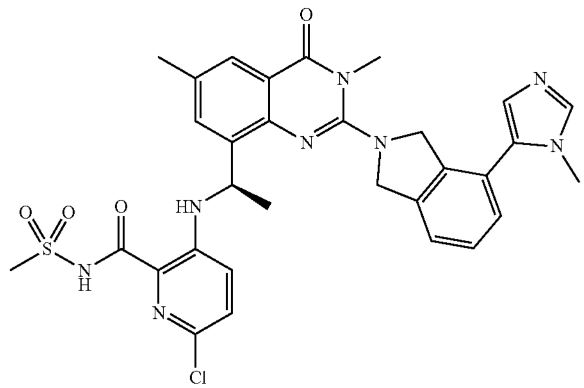 | (R)-6-chloro-3-((1-(3,6-dimethyl-2-(4-(1-methyl-1H-imidazol-5-yl)isoindolin-2-yl)-4-oxo-3,4-dihydroquinazolin-8-yl)ethyl)amino)-N-(methylsulfonyl)picolinamide | 3.69 min, 254 nm, MS (ES+)$^c$ $C_{31}H_{31}ClN_8O_4S$, requires: 646.2, found: 647.3 $[M + H]^+$ |
| 675 | 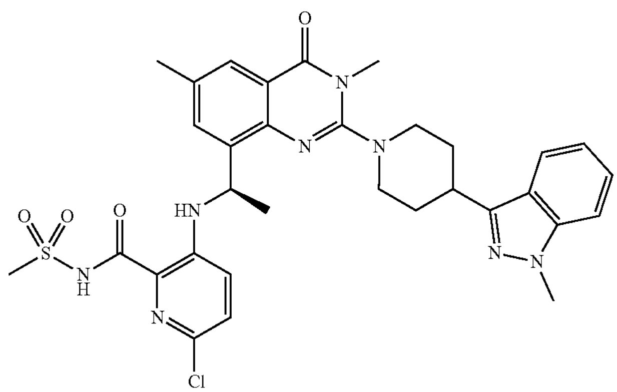 [SMILES: Cc1cc([C@@H](C)Nc2ccc(Cl)nc2C(=O)NS(C)(=O)=O)c2nc(N3CCC(c4nn(C)c5ccccc45)CC3)n(C)c(=O)c2c1] | (R)-6-chloro-3-((1-(3,6-dimethyl-2-(4-(1-methyl-1H-indazol-3-yl)piperidin-1-yl)-4-oxo-3,4-dihydroquinazolin-8-yl)ethyl)amino)-N-(methylsulfonyl)picolinamide | 4.01 min, 254 nm, MS (ES+)$^c$ $C_{32}H_{35}ClN_8O_4S$, requires: 662.2, found: 663.2 $[M + H]^+$ |
| 676 | 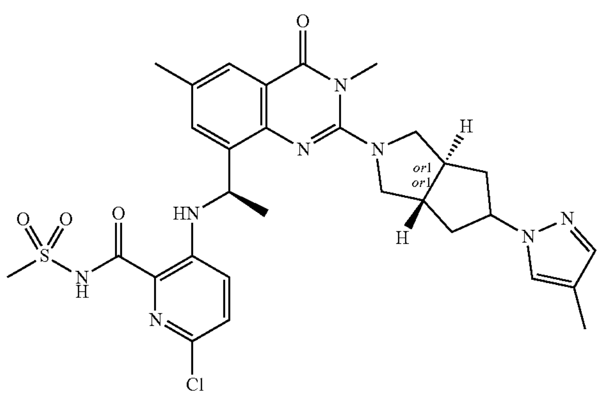 [SMILES: Cc1cc([C@@H](C)Nc2ccc(Cl)nc2C(=O)NS(C)(=O)=O)c2nc(N3C[C@H]4CC(n5cc(C)cn5)C[C@@H]4C3)n(C)c(=O)c2c1] | 6-chloro-3-(((R)-1-(3,6-dimethyl-2-((3aS*,6aS*)-5-(4-methyl-1H-pyrazol-1-yl)hexahydrocyclopenta[c]pyrrol-2(1H)-yl)-4-oxo-3,4-dihydroquinazolin-8-yl)ethyl)amino)-N-(methylsulfonyl)picolinamide | 3.65 min, 254 nm, MS (ES+)$^c$ $C_{30}H_{35}ClN_8O_4S$ requires: 638.2, found: 639.2 $[M + H]^+$ |
| 677 | 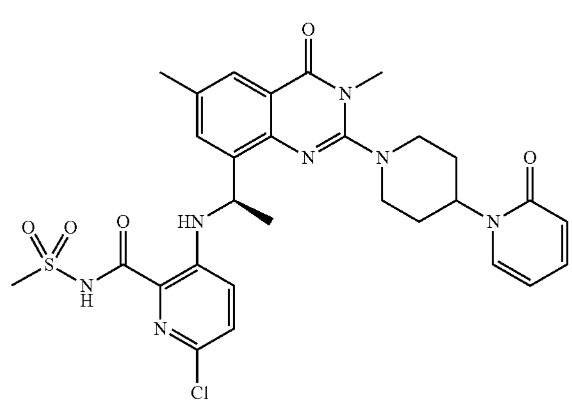 [SMILES: Cc1cc([C@@H](C)Nc2ccc(Cl)nc2C(=O)NS(C)(=O)=O)c2nc(N3CCC(n4ccccc4=O)CC3)n(C)c(=O)c2c1] | (R)-6-chloro-3-((1-(3,6-dimethyl-4-oxo-2-(4-(2-oxopyridin-1(2H)-yl)piperidin-1-yl)-3,4-dihydroquinazolin-8-yl)ethyl)amino)-N-(methylsulfonyl)picolinamide | 5.01 min, 254 nm, MS (ES+)$^c$ $C_{29}H_{32}ClN_7O_5S$, requires: 625.2, found: 626.2 $[M + H]^+$ |

TABLE E4-continued compound list prepared according to Route A in Example 4

| Cpd. ID | Structure | Name | LCMS |
|---|---|---|---|
| 678 | 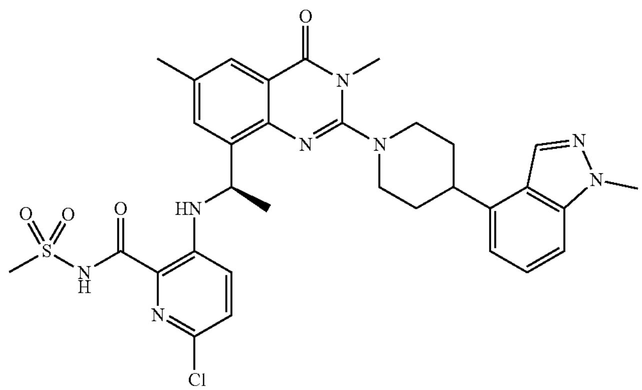 | (R)-6-chloro-3-((1-(3,6-dimethyl-2-(4-(1-methyl-1H-indazol-4-yl)piperidin-1-yl)-4-oxo-3,4-dihydroquinazolin-8-yl)ethyl)amino)-N-(methylsulfonyl)picolinamide | 5.07 min, 254 nm, MS (ES+)$^c$ $C_{32}H_{35}ClN_8O_4S$, requires: 662.2, found: 663.2 [M + H]$^+$ |
| 679 | 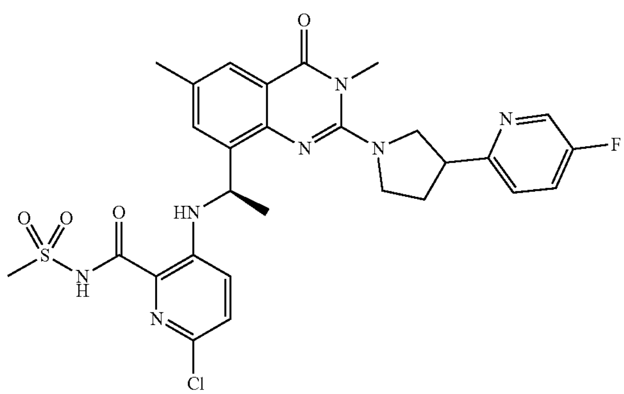 [SMILES: Cc1cc([C@@H](C)Nc2ccc(Cl)nc2C(=O)NS(C)(=O)=O)c2nc(N3CCC(c4ccc(F)cn4)C3)n(C)c(=O)c2c1] | 6-chloro-3-(((1R)-1-(2-(3-(5-fluoropyridin-2-yl)pyrrolidin-1-yl)-3,6-dimethyl-4-oxo-3,4-dihydroquinazolin-8-yl)ethyl)amino)-N-(methylsulfonyl)picolinamide | 4.80 min, 254 nm, MS (ES+)$^c$ $C_{28}H_{29}ClFN_7O_4S$, requires: 613.2, found: 614.2 [M + H]$^+$ |
| 680 | 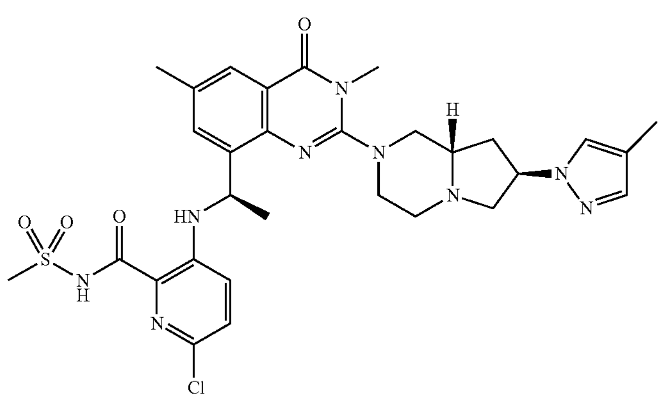 | 6-chloro-3-(((R)-1-(3,6-dimethyl-2-((7R,8aS)-7-(4-methyl-1H-pyrazol-1-yl)hexahydropyrrolo[1,2-a]pyrazin-2(1H)-yl)-4-oxo-3,4-dihydroquinazolin-8-yl)ethyl)amino)-N-(methylsulfonyl)picolinamide | 3.44 min, 254 nm, MS (ES+)$^c$ $C_{30}H_{36}ClN_9O_4S$, requires: 653.2, found: 654.2 [M + H]$^+$ |

TABLE E4-continued compound list prepared according to Route A in Example 4

| Cpd. ID | Structure | Name | LCMS |
|---|---|---|---|
| 681 | 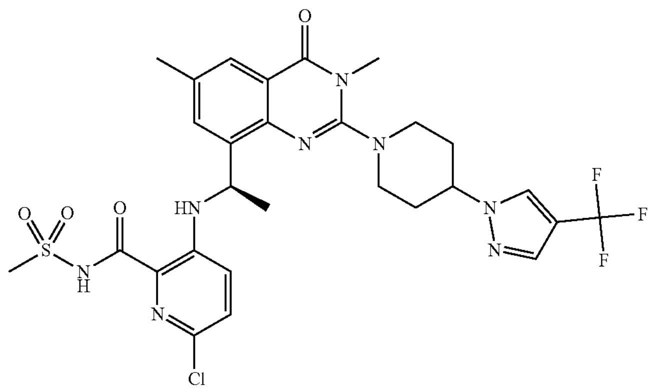 [SMILES: Cc1cc([C@@H](C)Nc2ccc(Cl)nc2C(=O)NS(C)(=O)=O)c2nc(N3CCC(n4cc(C(F)(F)F)cn4)CC3)n(C)c(=O)c2c1] | (R)-6-chloro-3-((1-(3,6-dimethyl-4-oxo-2-(4-(4-(trifluoromethyl)-1H-pyrazol-1-yl)piperidin-1-yl)-3,4-dihydroquinazolin-8-yl)ethyl)amino)-N-(methylsulfonyl)picolinamide | 4.97 min, 254 nm, MS (ES+)[c] $C_{28}H_{30}ClF_3N_8O_4S$, requires: 666.2, found: 667.2 $[M + H]^+$ |
| 682 | 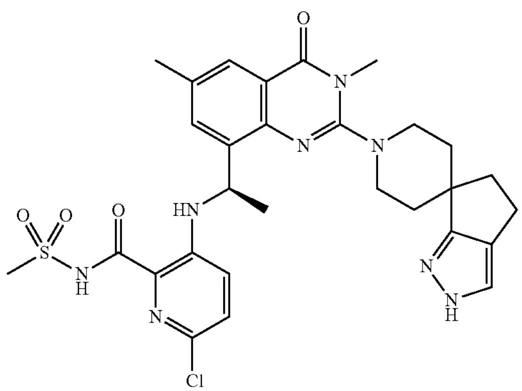 [SMILES: Cc1cc([C@@H](C)Nc2ccc(Cl)nc2C(=O)NS(C)(=O)=O)c2nc(N3CCC4(CCc5c[nH]nc54)CC3)n(C)c(=O)c2c1] | (R)-6-chloro-3-((1-(2-(4,5-dihydro-2H-spiro[cyclopenta[c]pyrazole-6,4'-piperidin]-1'-yl)-3,6-dimethyl-4-oxo-3,4-dihydroquinazolin-8-yl)ethyl)amino)-N-(methylsulfonyl)picolinamide | 4.46 min, 254 nm, MS (ES+)[c] $C_{29}H_{33}ClN_8O_4S$, requires: 624.2, found: 625.2 $[M + H]^+$ |
| 683 | 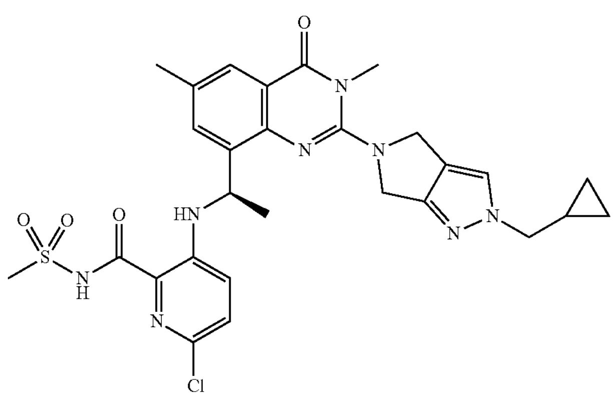 [SMILES: Cc1cc([C@@H](C)Nc2ccc(Cl)nc2C(=O)NS(C)(=O)=O)c2nc(N3Cc4cn(CC5CC5)nc4C3)n(C)c(=O)c2c1] | (R)-6-chloro-3-((1-(2-(2-(cyclopropylmethyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.52 min, 254 nm, MS (ES+)[b] $C_{28}H_{31}ClN_8O_4S$, requires: 610.2, found: 611.5 $[M + H]^+$ |
| 684 | 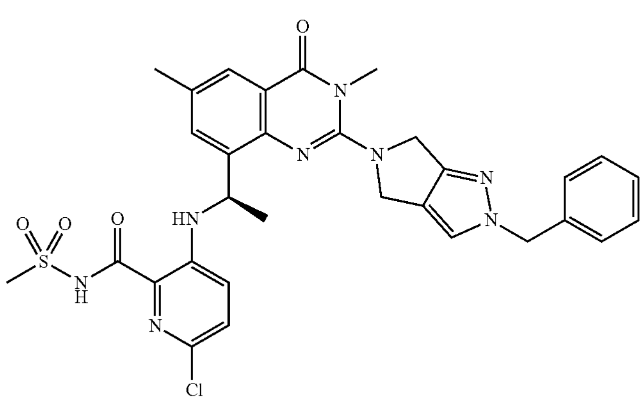 [SMILES: Cc1cc([C@@H](C)Nc2ccc(Cl)nc2C(=O)NS(C)(=O)=O)c2nc(N3Cc4cn(Cc5ccccc5)nc4C3)n(C)c(=O)c2c1] | (R)-3-((1-(2-(2-benzyl-2,6-dihydropyrrolo[3,4-c]pyrazol-5(4H)-yl)-3,6-dimethyl-4-oxo-3,4-dihydroquinazolin-8-yl)ethyl)amino)-6-chloro-N-(methylsulfonyl)picolinamide | 2.60 min, 210 nm, MS (ES+)[b] $C_{31}H_{31}ClN_8O_4S$, requires: 646.1, found: 647.1 $[M + H]^+$ |

TABLE E4-continued compound list prepared according to Route A in Example 4

| Cpd. ID | Structure | Name | LCMS |
|---|---|---|---|
| 685 | 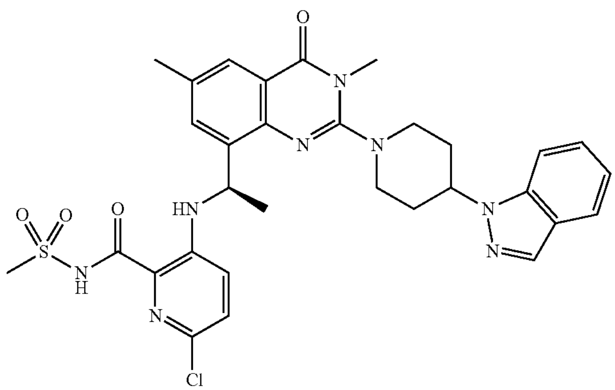 [SMILES: Cc1cc([C@@H](C)Nc2ccc(Cl)nc2C(=O)NS(C)(=O)=O)c2nc(N3CCC(n4ncc5ccccc54)CC3)n(C)c(=O)c2c1] | (R)-3-((1-(2-(4-(1H-indazol-1-yl)piperidin-1-yl)-3,6-dimethyl-4-oxo-3,4-dihydroquinazolin-8-yl)ethyl)amino)-6-chloro-N-(methylsulfonyl)picolinamide | 2.74 min, 210 nm, MS (ES+)[b] $C_{31}H_{33}ClN_8O_4S$, requires: 648.2, found: 649.1 $[M + H]^+$ |
| 686 | 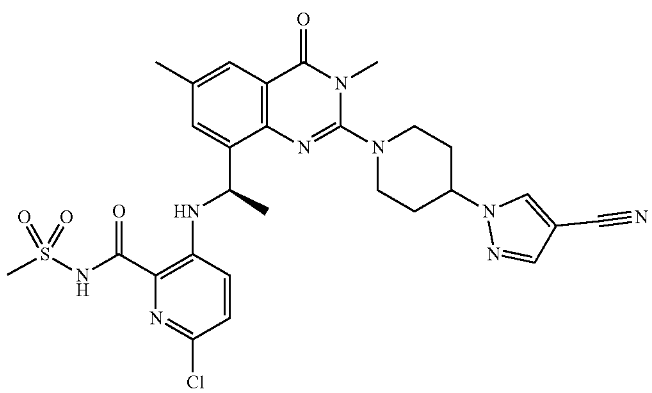 [SMILES: Cc1cc([C@@H](C)Nc2ccc(Cl)nc2C(=O)NS(C)(=O)=O)c2nc(N3CCC(n4cc(C#N)cn4)CC3)n(C)c(=O)c2c1] | (R)-6-chloro-3-((1-(2-(4-(4-cyano-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.44 min, 210 nm, MS (ES+)[b] $C_{28}H_{30}ClN_9O_4S$, requires: 623.2, found: 624.2 $[M + H]^+$ |
| 687 | 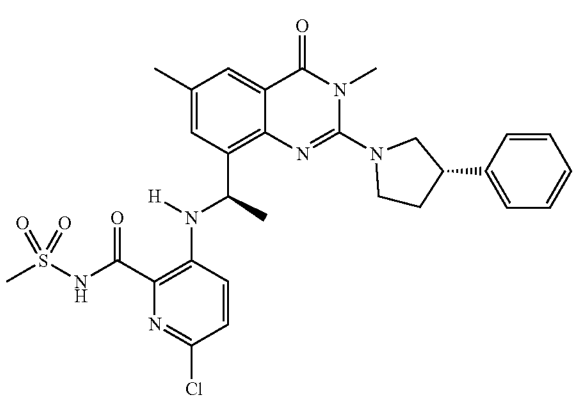 [SMILES: Cc1cc([C@@H](C)Nc2ccc(Cl)nc2C(=O)NS(C)(=O)=O)c2nc(N3CC[C@@H](c4ccccc4)C3)n(C)c(=O)c2c1] | 6-chloro-3-(((R)-1-(3,6-dimethyl-4-oxo-2-((S)-3-phenylpyrrolidin-1-yl)-3,4-dihydroquinazolin-8-yl)ethyl)amino)-N-(methylsulfonyl)picolinamide | 4.05 min, 254 nm, MS (ES+)[c] $C_{29}H_{31}ClN_6O_4S$, requires: 594.2, found: 595.1 $[M + H]^+$ |

TABLE E4-continued compound list prepared according to Route A in Example 4

| Cpd. ID | Structure | Name | LCMS |
|---|---|---|---|
| 688 | 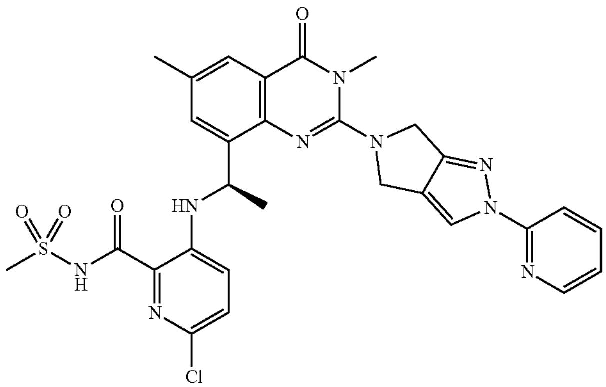 [SMILES: Cc1cc([C@@H](C)Nc2ccc(Cl)nc2C(=O)NS(C)(=O)=O)c2nc(N3Cc4cn(-c5ccccn5)nc4C3)n(C)c(=O)c2c1] | (R)-6-chloro-3-((1-(3,6-dimethyl-4-oxo-2-(2-(pyridin-2-yl)-2,6-dihydropyrrolo[3,4-c]pyrazol-5(4H)-yl)-3,4-dihydroquinazolin-8-yl)ethyl)amino)-N-(methylsulfonyl)picolinamide | 2.563 min, 285 nm, MS (ES+)[b] $C_{29}H_{28}ClN_9O_4S$, requires: 633.1, found: 634.2 [M + H]⁺ |
| 689 | 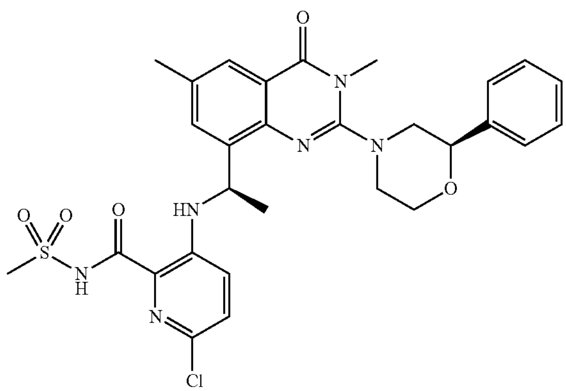 [SMILES: Cc1cc([C@@H](C)Nc2ccc(Cl)nc2C(=O)NS(C)(=O)=O)c2nc(N3CCO[C@H](c4ccccc4)C3)n(C)c(=O)c2c1] | 6-chloro-3-(((R)-1-(3,6-dimethyl-4-oxo-2-((R)-2-phenylmorpholino)-3,4-dihydroquinazolin-8-yl)ethyl)amino)-N-(methylsulfonyl)picolinamide | 3.71 min, 254 nm, MS (ES+)[c] $C_{29}H_{31}ClN_6O_5S$, requires: 610.2, found: 611.2 [M + H]⁺ |
| 690 | 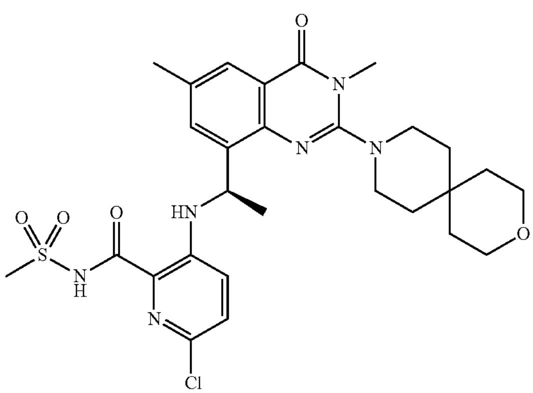 [SMILES: Cc1cc([C@@H](C)Nc2ccc(Cl)nc2C(=O)NS(C)(=O)=O)c2nc(N3CCC4(CCOCC4)CC3)n(C)c(=O)c2c1] | (R)-6-chloro-3-((1-(3,6-dimethyl-4-oxo-2-(3-oxa-9-azaspiro[5.5]undecan-9-yl)-3,4-dihydroquinazolin-8-yl)ethyl)amino)-N-(methylsulfonyl)picolinamide | 3.67 min, 254 nm, MS (ES+)[c] $C_{28}H_{35}ClN_6O_5S$, requires: 602.2, found: 603.2 [M + H]⁺ |
| 691 | 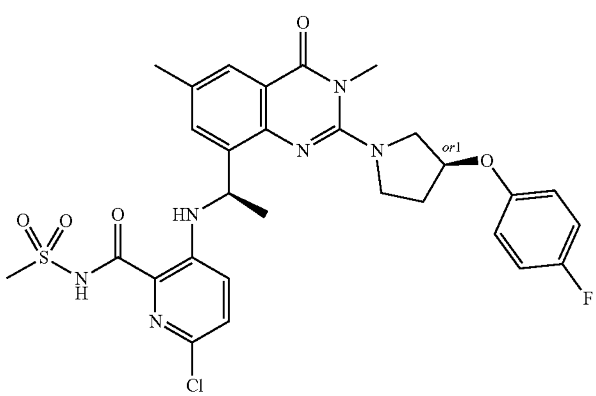 [SMILES: Cc1cc([C@@H](C)Nc2ccc(Cl)nc2C(=O)NS(C)(=O)=O)c2nc(N3CC[C@H](Oc4ccc(F)cc4)C3)n(C)c(=O)c2c1] | 6-chloro-3-(((R)-1-(2-((R*)-3-(4-fluorophenoxy)pyrrolidin-1-yl)-3,6-dimethyl-4-oxo-3,4-dihydroquinazolin-8-yl)ethyl)amino)-N-(methylsulfonyl)picolinamide | 2.83 min, 254 nm, MS (ES+)[b] $C_{29}H_{30}ClFN_6O_5S$, requires: 628.1, found: 629.2 [M + H]⁺ |

TABLE E4-continued compound list prepared according to Route A in Example 4

| Cpd. ID | Structure | Name | LCMS |
|---|---|---|---|
| 692 | 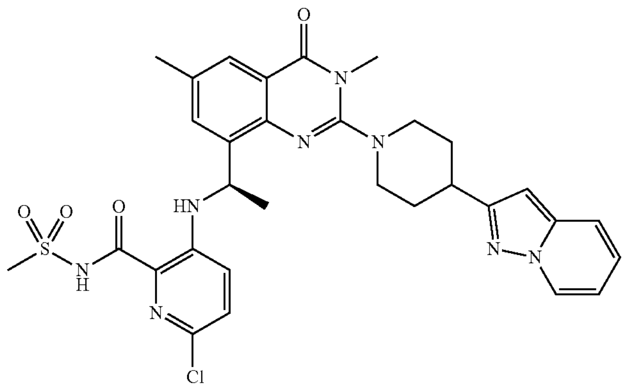 [SMILES: Cc1cc([C@@H](C)Nc2ccc(Cl)nc2C(=O)NS(C)(=O)=O)c2nc(N3CCC(c4cc5ccccn5n4)CC3)n(C)c(=O)c2c1] | (R)-6-chloro-3-((1-(3,6-dimethyl-4-oxo-2-(4-(pyrazolo[1,5-a]pyridin-2-yl)piperidin-1-yl)-3,4-dihydroquinazolin-8-yl)ethyl)amino)-N-(methylsulfonyl)picolinamide | 3.83 min, 254 nm, MS (ES+)$^c$ $C_{31}H_{33}ClN_8O_4S$, requires: 648.2, found: 649.2 [M + H]$^+$ |
| 693 | 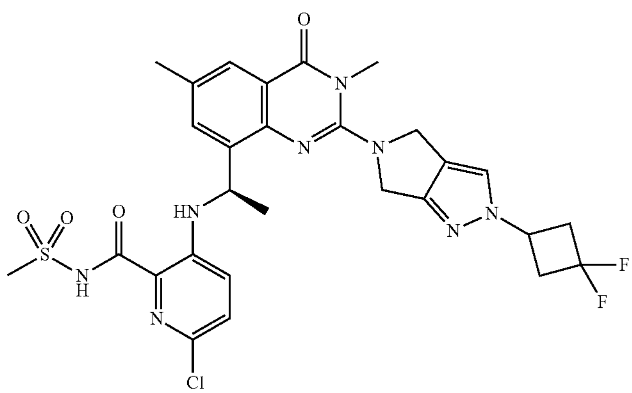 [SMILES: Cc1cc([C@@H](C)Nc2ccc(Cl)nc2C(=O)NS(C)(=O)=O)c2nc(N3Cc4cn(C5CC(F)(F)C5)nc4C3)n(C)c(=O)c2c1] | (R)-6-chloro-3-((1-(2-(2-(3,3-difluorocyclobutyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.32 min, 254 nm, MS (ES+)$^b$ $C_{28}H_{29}ClF_2N_8O_4S$, requires: 646.2, found: 647.3 [M + H]$^+$ |
| 694 | 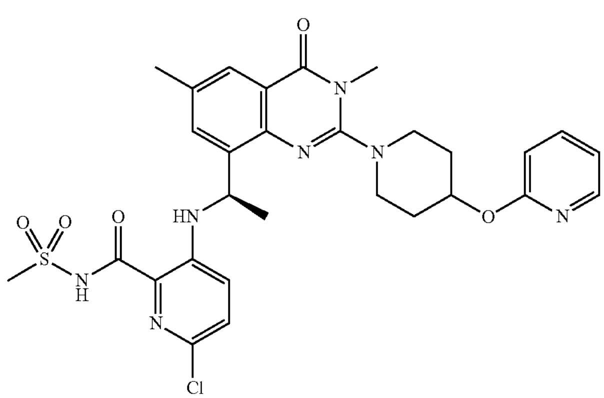 [SMILES: Cc1cc([C@@H](C)Nc2ccc(Cl)nc2C(=O)NS(C)(=O)=O)c2nc(N3CCC(Oc4ccccn4)CC3)n(C)c(=O)c2c1] | (R)-6-chloro-3-((1-(3,6-dimethyl-4-oxo-2-(4-(pyridin-2-yloxy)piperidin-1-yl)-3,4-dihydroquinazolin-8-yl)ethyl)amino)-N-(methylsulfonyl)picolinamide | 2.67 min, 210 nm, MS (ES+)$^b$ $C_{29}H_{32}ClN_7O_5S$, requires: 625.2, found: 626.3 [M + H]$^+$ |

TABLE E4-continued compound list prepared according to Route A in Example 4

| Cpd. ID | Structure | Name | LCMS |
|---|---|---|---|
| 695 | 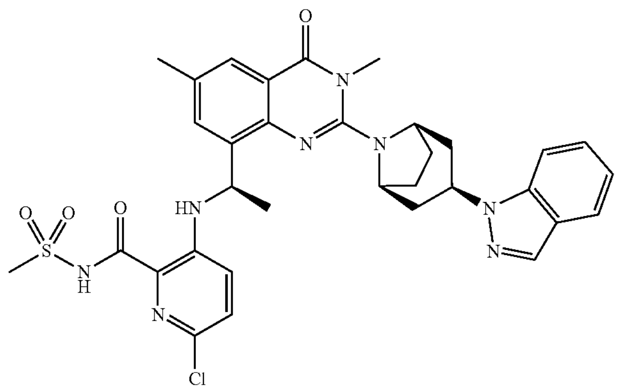 [SMILES: Cc1cc([C@@H](C)Nc2ccc(Cl)nc2C(=O)NS(C)(=O)=O)c2nc(N3[C@@H]4CC[C@H]3C[C@H](n3ncc5ccccc53)C4)n(C)c(=O)c2c1] | 3-(((R)-1-(2-((1R,3S,5S)-3-(1H-indazol-1-yl)-8-azabicyclo[3.2.1]octan-8-yl)-3,6-dimethyl-4-oxo-3,4-dihydroquinazolin-8-yl)ethyl)amino)-6-chloro-N-(methylsulfonyl)picolinamide | 4.16 min, 254 nm, MS (ES+)[c] $C_{33}H_{35}ClN_8O_4S$, requires: 674.2, found: 675.2 $[M + H]^+$ |
| 696 | 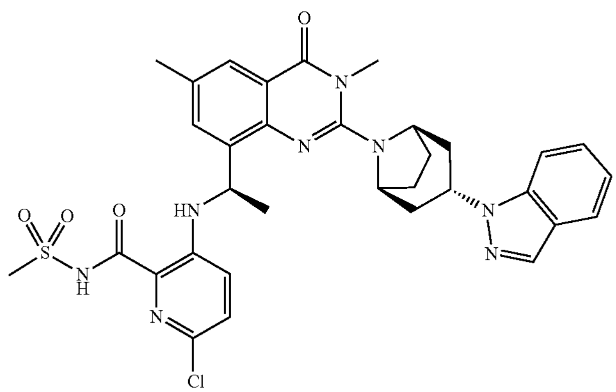 [SMILES: Cc1cc([C@@H](C)Nc2ccc(Cl)nc2C(=O)NS(C)(=O)=O)c2nc(N3[C@@H]4CC[C@H]3C[C@@H](n3ncc5ccccc53)C4)n(C)c(=O)c2c1] | 3-(((R)-1-(2-((1R,3R,5S)-3-(1H-indazol-1-yl)-8-azabicyclo[3.2.1]octan-8-yl)-3,6-dimethyl-4-oxo-3,4-dihydroquinazolin-8-yl)ethyl)amino)-6-chloro-N-(methylsulfonyl)picolinamide | 4.00 min, 254 nm, MS (ES+)[c] $C_{33}H_{35}ClN_8O_4S$, requires: 674.2, found: 675.2 $[M + H]^+$ |
| 697 | 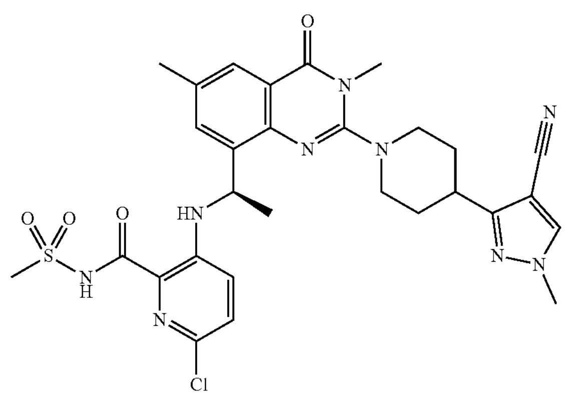 [SMILES: Cc1cc([C@@H](C)Nc2ccc(Cl)nc2C(=O)NS(C)(=O)=O)c2nc(N3CCC(c4nn(C)cc4C#N)CC3)n(C)c(=O)c2c1] | (R)-6-chloro-3-((1-(2-(4-(4-cyano-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.42 min, 254 nm, MS (ES+)[b] $C_{29}H_{32}ClN_9O_4S$, requires: 637.2, found: 638.2 $[M + H]^+$ |
| 698 | 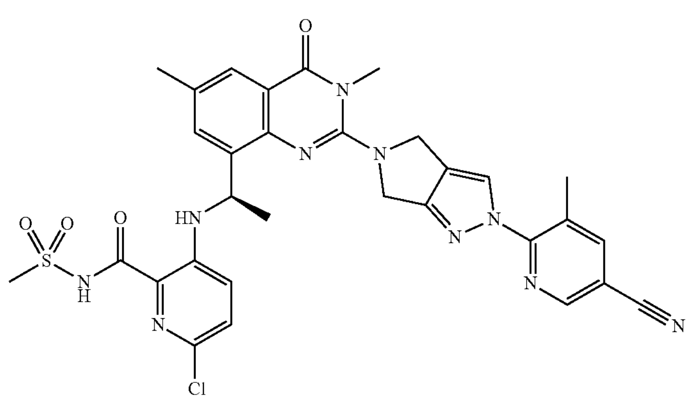 [SMILES: Cc1cc([C@@H](C)Nc2ccc(Cl)nc2C(=O)NS(C)(=O)=O)c2nc(N3Cc4cn(-c5ncc(C#N)cc5C)nc4C3)n(C)c(=O)c2c1] | (R)-6-chloro-3-((1-(2-(2-(5-cyano-3-methylpyridin-2-yl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.70 min, 254 nm, MS (ES+)[b] $C_{31}H_{29}ClN_{10}O_4S$, requires: 672.1, found: 673.3 $[M + H]^+$ |

TABLE E4-continued compound list prepared according to Route A in Example 4

| Cpd. ID | Structure | Name | LCMS |
|---|---|---|---|
| 699 | 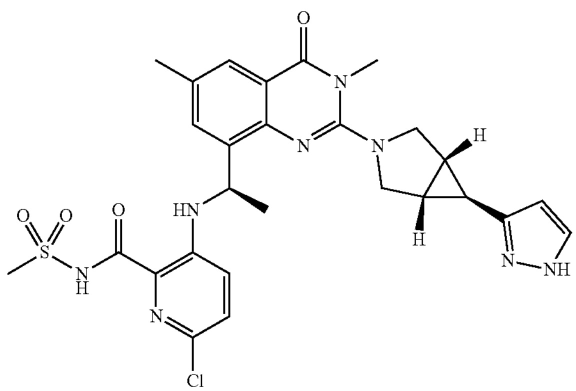 [SMILES: Cc1cc([C@@H](C)Nc2ccc(Cl)nc2C(=O)NS(C)(=O)=O)c2nc(N3C[C@@H]4[C@H](C3)[C@H]4c3cc[nH]n3)n(C)c(=O)c2c1] | 3-(((R)-1-(2-((1R,5S,6R)-6-(1H-pyrazol-3-yl)-3-azabicyclo[3.1.0]hexan-3-yl)-3,6-dimethyl-4-oxo-3,4-dihydroquinazolin-8-yl)ethyl)amino)-6-chloro-N-(methylsulfonyl)picolinamide | 3.15 min, 254 nm, MS (ES+)$^c$ C$_{27}$H$_{29}$ClN$_8$O$_4$S, requires: 596.2, found: 597.2 [M + H]$^+$ |
| 700 | 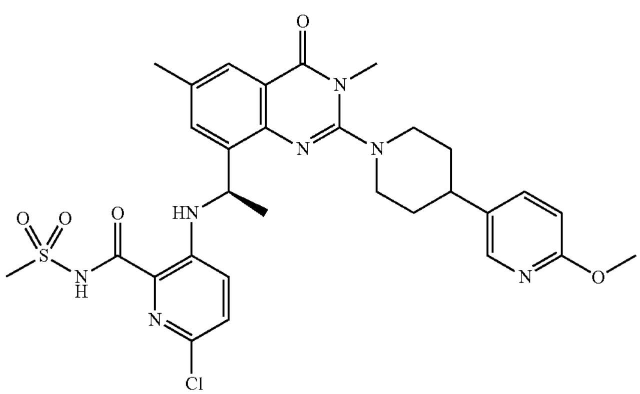 | (R)-6-chloro-3-((1-(2-(4-(6-methoxypyridin-3-yl)piperidin-1-yl)-3,6-dimethyl-4-oxo-3,4-dihydroquinazolin-8-yl)ethyl)amino)-N-(methylsulfonyl)picolinamide | 2.23 min, 234 nm, MS (ES+)$^b$ C$_{30}$H$_{34}$ClN$_7$O$_5$S, requires: 639.2, found: 640.5 [M + H]$^+$ |
| 701 | 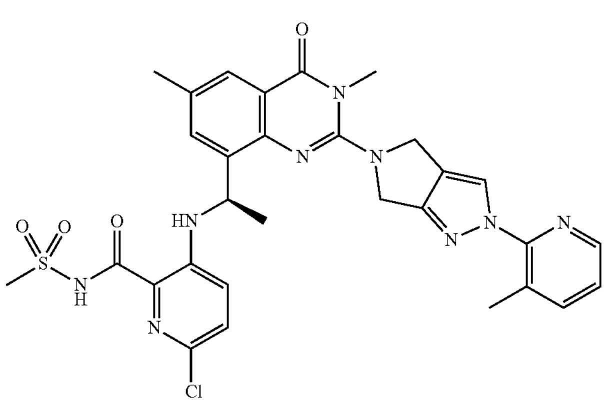 [SMILES: Cc1cc([C@@H](C)Nc2ccc(Cl)nc2C(=O)NS(C)(=O)=O)c2nc(N3Cc4cn(-c5ncccc5C)nc4C3)n(C)c(=O)c2c1] | (R)-6-chloro-3-((1-(3,6-dimethyl-2-(2-(3-methylpyridin-2-yl)-2,6-dihydropyrrolo[3,4-c]pyrazol-5(4H)-yl)-4-oxo-3,4-dihydroquinazolin-8-yl)ethyl)amino)-N-(methylsulfonyl)picolinamide | 2.52 min, 254 nm, MS (ES+)$^b$ C$_{30}$H$_{30}$ClN$_9$O$_4$S, requires: 647.1, found: 648.1 [M + H]$^+$ |

TABLE E4-continued compound list prepared according to Route A in Example 4

| Cpd. ID | Structure | Name | LCMS |
|---|---|---|---|
| 702 | 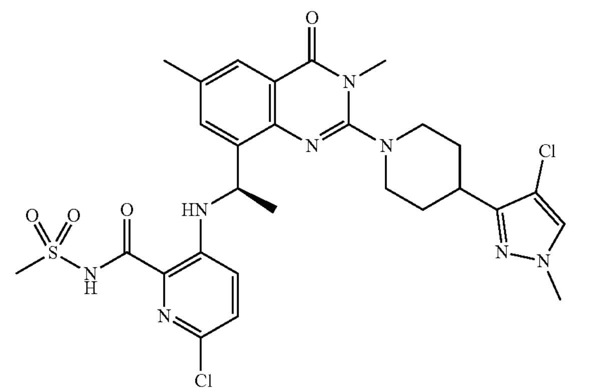 | (R)-6-chloro-3-((1-(2-(4-(4-chloro-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.55 min, 220 nm, MS (ES+)$^b$ $C_{28}H_{32}Cl_2N_8O_4S$, requires: 646.1, found: 647.1 [M + H]$^+$ |
| 703 | 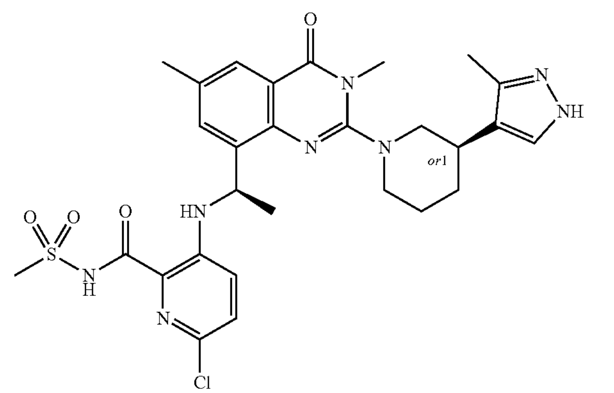 [SMILES: Cc1cc([C@@H](C)Nc2ccc(Cl)nc2C(=O)NS(C)(=O)=O)c2nc(N3CCC[C@H](c4c[nH]nc4C)C3)n(C)c(=O)c2c1] | 6-chloro-3-(((R)-1-(3,6-dimethyl-2-((R*)-3-(3-methyl-1H-pyrazol-4-yl)piperidin-1-yl)-4-oxo-3,4-dihydroquinazolin-8-yl)ethyl)amino)-N-(methylsulfonyl)picolinamide | 2.25 min, 254 nm, MS (ES+)$^b$ $C_{28}H_{33}ClN_8O_4S$, requires: 612.2, found: 613.2 [M + H]$^+$ |
| 704 | 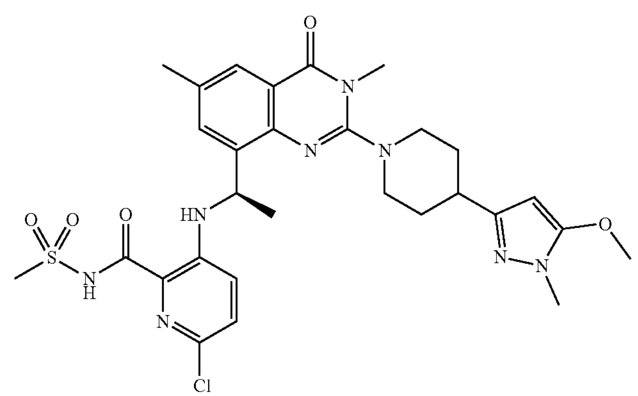 | (R)-6-chloro-3-((1-(2-(4-(5-methoxy-1-methyl-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.39 min, 254 nm, MS (ES+)$^b$ $C_{29}H_{35}ClN_8O_5S$, requires: 642.2, found: 643.2 [M + H]$^+$ |
| 705 | 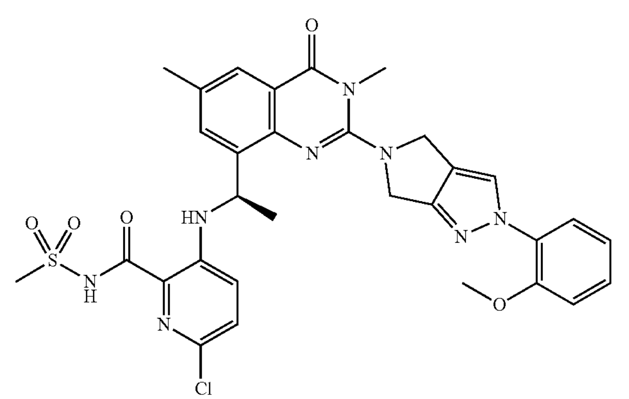 [SMILES: COc1ccccc1-n1cc2c(n1)CN(c1nc3c([C@@H](C)Nc4ccc(Cl)nc4C(=O)NS(C)(=O)=O)cc(C)cc3c(=O)n1C)C2] | (R)-6-chloro-3-((1-(2-(2-(2-methoxyphenyl)-2,6-dihydropyrrolo[3,4-c]pyrazol-5(4H)-yl)-3,6-dimethyl-4-oxo-3,4-dihydroquinazolin-8-yl)ethyl)amino)-N-(methylsulfonyl)picolinamide | 2.40 min, 254 nm, MS (ES+)$^b$ $C_{31}H_{31}ClN_8O_5S$, requires: 662.1, found: 663.2 [M + H]$^+$ |

TABLE E4-continued compound list prepared according to Route A in Example 4

| Cpd. ID | Structure | Name | LCMS |
|---|---|---|---|
| 706 | 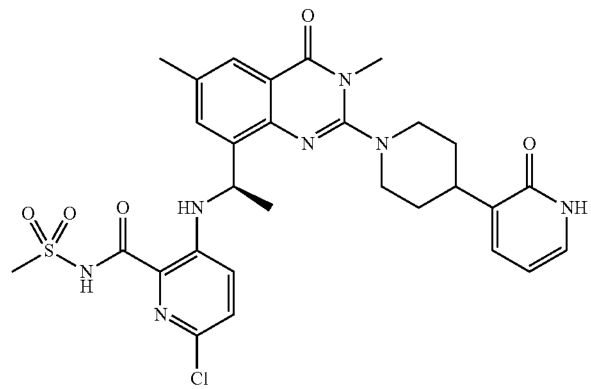 [SMILES: Cc1cc([C@@H](C)Nc2ccc(Cl)nc2C(=O)NS(C)(=O)=O)c2nc(N3CCC(c4ccc[nH]c4=O)CC3)n(C)c(=O)c2c1] | (R)-6-chloro-3-((1-(3,6-dimethyl-4-oxo-2-(4-(2-oxo-1,2-dihydropyridin-3-yl)piperidin-1-yl)-3,4-dihydroquinazolin-8-yl)ethyl)amino)-N-(methylsulfonyl)picolinamide | 2.15 min, 254 nm, MS (ES+)[b] $C_{29}H_{32}ClN_7O_5S$, requires: 625.1, found: 626.2 $[M + H]^+$ |
| 707 | 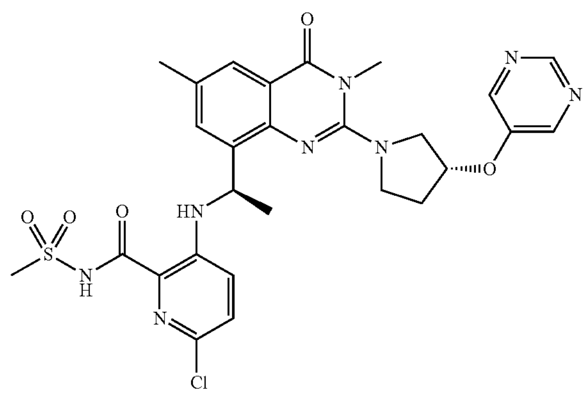 [SMILES: Cc1cc([C@@H](C)Nc2ccc(Cl)nc2C(=O)NS(C)(=O)=O)c2nc(N3CC[C@@H](Oc4cncnc4)C3)n(C)c(=O)c2c1] | 6-chloro-3-(((R)-1-(3,6-dimethyl-4-oxo-2-((R)-3-(pyrimidin-5-yloxy)pyrrolidin-1-yl)-3,4-dihydroquinazolin-8-yl)ethyl)amino)-N-(methylsulfonyl)picolinamide | 4.06 min, 254 nm, MS (ES+)[c] $C_{27}H_{29}ClN_8O_5S$, requires: 612.2, found: 613.2 $[M + H]^+$ |
| 708 | 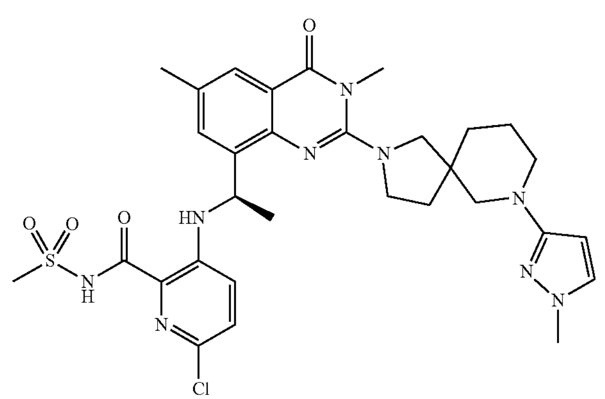 [SMILES: Cc1cc([C@@H](C)Nc2ccc(Cl)nc2C(=O)NS(C)(=O)=O)c2nc(N3CCC4(CCCN(c5ccn(C)n5)C4)C3)n(C)c(=O)c2c1] | 6-chloro-3-(((1R)-1-(3,6-dimethyl-2-(7-(1-methyl-1H-pyrazol-3-yl)-2,7-diazaspiro[4.5]decan-2-yl)-4-oxo-3,4-dihydroquinazolin-8-yl)ethyl)amino)-N-(methylsulfonyl)picolinamide | 2.41 min, 254 nm, MS (ES+)[b] $C_{31}H_{38}ClN_9O_4S$, requires: 667.2, found: 668.3 $[M + H]^+$ |

TABLE E4-continued compound list prepared according to Route A in Example 4

| Cpd. ID | Structure | Name | LCMS |
|---|---|---|---|
| 709 | 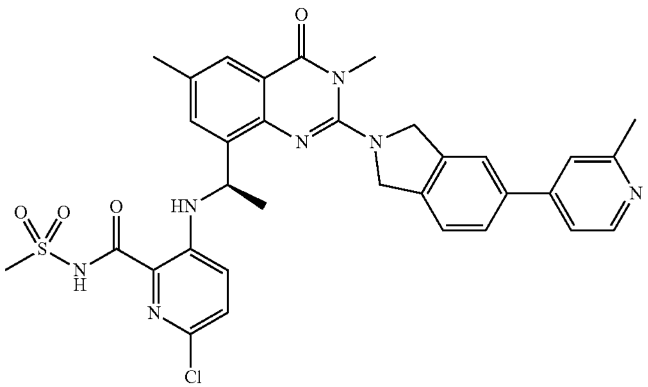 [SMILES: Cc1cc([C@@H](C)Nc2ccc(Cl)nc2C(=O)NS(C)(=O)=O)c2nc(N3Cc4ccc(-c5ccnc(C)c5)cc4C3)n(C)c(=O)c2c1] | (R)-6-chloro-3-((1-(3,6-dimethyl-2-(5-(2-methylpyridin-4-yl)isoindolin-2-yl)-4-oxo-3,4-dihydroquinazolin-8-yl)ethyl)amino)-N-(methylsulfonyl)picolinamide | 2.93 min, 254 nm, MS (ES+)$^c$ $C_{33}H_{32}ClN_7O_4S$, requires: 657.2, found: 658.2 [M + H]$^+$ |
| 710 | 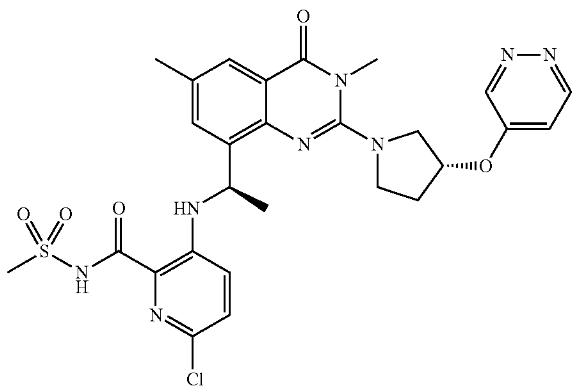 | 6-chloro-3-(((R)-1-(3,6-dimethyl-4-oxo-2-((R)-3-(pyridazin-4-yloxy)pyrrolidin-1-yl)-3,4-dihydroquinazolin-8-yl)ethyl)amino)-N-(methylsulfonyl)picolinamide | 3.64 min, 254 nm, MS (ES+)$^c$ $C_{27}H_{29}ClN_8O_5S$, requires: 612.2, found: 613.2 [M + H]$^+$ |
| 711 | 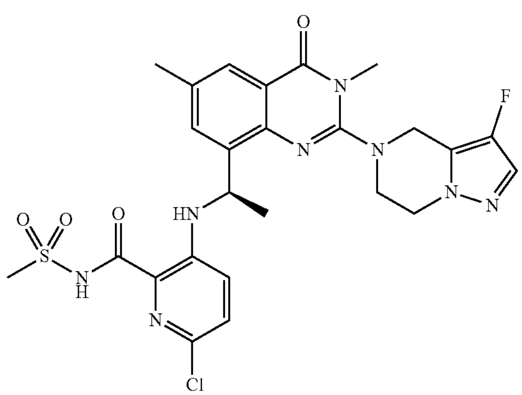 | (R)-6-chloro-3-((1-(2-(3-fluoro-6,7-dihydropyrazolo[1,5-a]pyrazin-5(4H)-yl)-3,6-dimethyl-4-oxo-3,4-dihydroquinazolin-8-yl)ethyl)amino)-N-(methylsulfonyl)picolinamide | 2.35 min, 270 nm, MS (ES+)$^b$ $C_{25}H_{26}ClFN_8O_4S$, requires: 588.1, found: 589.1 [M + H]$^+$ |
| 712 | 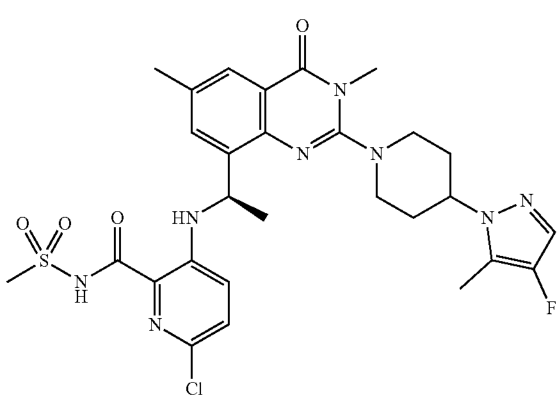 [SMILES: Cc1cc([C@@H](C)Nc2ccc(Cl)nc2C(=O)NS(C)(=O)=O)c2nc(N3CCC(n4ncc(F)c4C)CC3)n(C)c(=O)c2c1] | (R)-6-chloro-3-((1-(2-(4-(4-fluoro-5-methyl-1H-pyrazol-1-yl)piperidin-1-yl)-3,6-dimethyl-4-oxo-3,4-dihydroquinazolin-8-yl)ethyl)amino)-N-(methylsulfonyl)picolinamide | 2.56 min, 254 nm, MS (ES+)$^b$ $C_{28}H_{32}ClFN_8O_4S$, requires: 630.2, found: 631.2 [M + H]$^+$ |

TABLE E4-continued compound list prepared according to Route A in Example 4

| Cpd. ID | Structure | Name | LCMS |
|---|---|---|---|
| 713 | 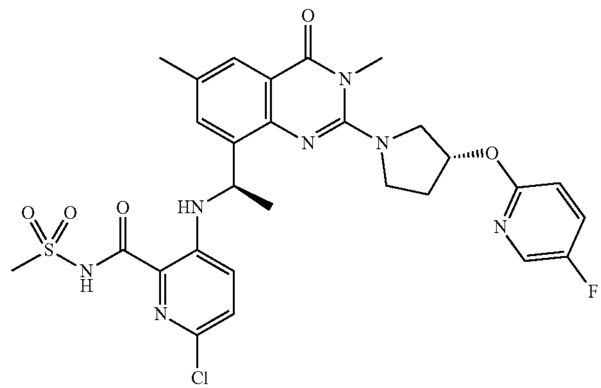 [SMILES: Cc1cc([C@@H](C)Nc2ccc(Cl)nc2C(=O)NS(C)(=O)=O)c2nc(N3CC[C@@H](Oc4ccc(F)cn4)C3)n(C)c(=O)c2c1] | 6-chloro-3-(((R)-1-(2-((R)-3-((5-fluoropyridin-2-yl)oxy)pyrrolidin-1-yl)-3,6-dimethyl-4-oxo-3,4-dihydroquinazolin-8-yl)ethyl)amino)-N-(methylsulfonyl)picolinamide | 5.15 min, 254 nm, MS (ES+)$^c$ $C_{28}H_{29}ClFN_7O_5S$, requires: 629.2, found: 630.2 $[M + H]^+$ |
| 714 | 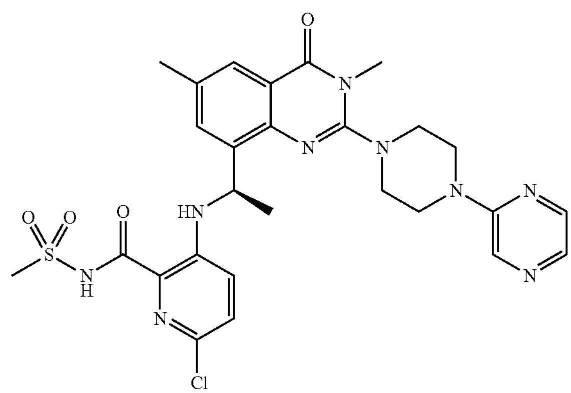 [SMILES: Cc1cc([C@@H](C)Nc2ccc(Cl)nc2C(=O)NS(C)(=O)=O)c2nc(N3CCN(c4cnccn4)CC3)n(C)c(=O)c2c1] | (R)-6-chloro-3-((1-(3,6-dimethyl-4-oxo-2-(4-(pyrazin-2-yl)piperazin-1-yl)-3,4-dihydroquinazolin-8-yl)ethyl)amino)-N-(methylsulfonyl)picolinamide | 2.37 min, 215 nm, MS (ES+)$^b$ $C_{27}H_{30}ClN_9O_4S$, requires: 611.1, found: 612.3 $[M + H]^+$ |
| 715 | 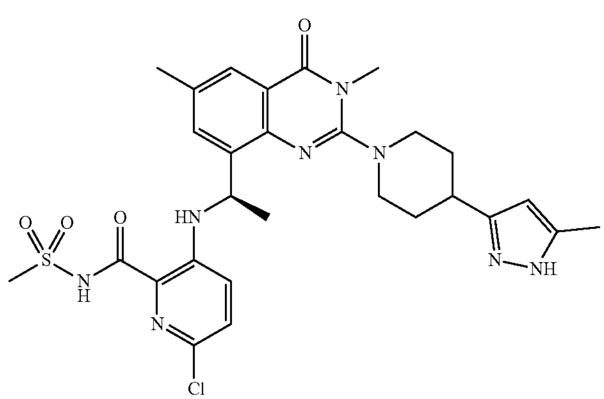 | (R)-6-chloro-3-((1-(3,6-dimethyl-2-(4-(5-methyl-1H-pyrazol-3-yl)piperidin-1-yl)-4-oxo-3,4-dihydroquinazolin-8-yl)ethyl)amino)-N-(methylsulfonyl)picolinamide | 2.23 min, 254 nm, MS (ES+)$^b$ $C_{28}H_{33}ClN_8O_4S$, requires: 612.2, found: 613.2 $[M + H]^+$ |

TABLE E4-continued compound list prepared according to Route A in Example 4

| Cpd. ID | Structure | Name | LCMS |
|---|---|---|---|
| 716 | 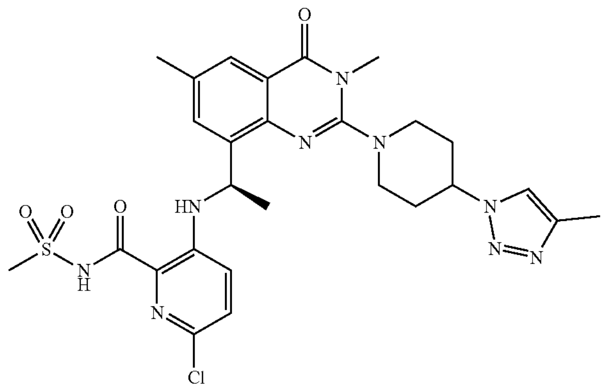 | (R)-6-chloro-3-((1-(3,6-dimethyl-2-(4-(4-methyl-1H-1,2,3-triazol-1-yl)piperidin-1-yl)-4-oxo-3,4-dihydroquinazolin-8-yl)ethyl)amino)-N-(methylsulfonyl)picolinamide | 2.19 min, 220 nm, MS (ES+)[b] $C_{27}H_{32}ClN_9O_4S$, requires: 613.2, found: 614.2 [M + H]+ |
| 717 | 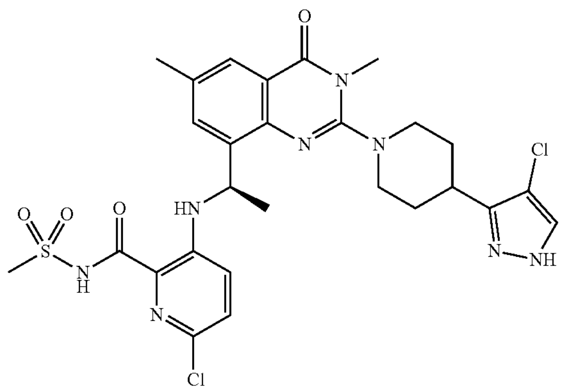 | (R)-6-chloro-3-((1-(2-(4-(4-chloro-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.40 min, 220 nm, MS (ES+)[b] $C_{27}H_{30}Cl_2N_8O_4S$, requires: 632.2, found: 633.2 [M + H]+ |
| 718 | 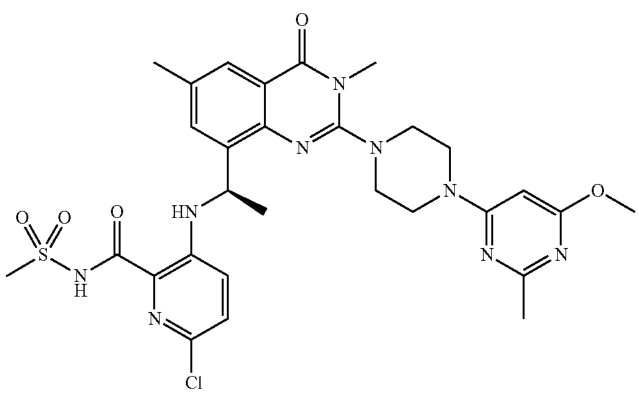 | (R)-6-chloro-3-((1-(2-(4-(6-methoxy-2-methylpyrimidin-4-yl)piperazin-1-yl)-3,6-dimethyl-4-oxo-3,4-dihydroquinazolin-8-yl)ethyl)amino)-N-(methylsulfonyl)picolinamide | 1.72 min, 220 nm, MS (ES+)[b] $C_{29}H_{34}ClN_9O_5S$, requires: 655.2, found: 656.2 [M + H]+ |
| 719 | 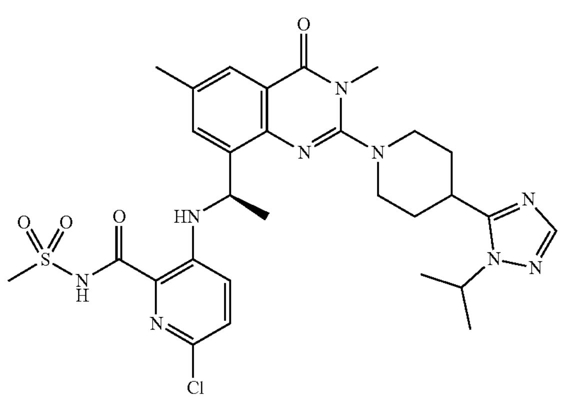 [SMILES: Cc1cc([C@@H](C)Nc2ccc(Cl)nc2C(=O)NS(C)(=O)=O)c2nc(N3CCC(c4ncnn4C(C)C)CC3)n(C)c(=O)c2c1] | (R)-6-chloro-3-((1-(2-(4-(1-isopropyl-1H-1,2,4-triazol-5-yl)piperidin-1-yl)-3,6-dimethyl-4-oxo-3,4-dihydroquinazolin-8-yl)ethyl)amino)-N-(methylsulfonyl)picolinamide | 2.20 min, 254 nm, MS (ES+)[b] $C_{29}H_{36}ClN_9O_4S$, requires: 641.2, found: 642.3 [M + H]+ |

TABLE E4-continued compound list prepared according to Route A in Example 4

| Cpd. ID | Structure | Name | LCMS |
|---|---|---|---|
| 720 | 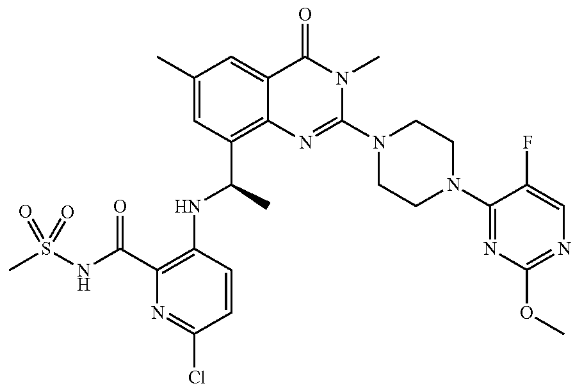 | (R)-6-chloro-3-((1-(2-(4-(5-fluoro-2-methoxypyrimidin-4-yl)piperazin-1-yl)-3,6-dimethyl-4-oxo-3,4-dihydroquinazolin-8-yl)ethyl)amino)-N-(methylsulfonyl)picolinamide | 2.45 min, 220 nm, MS (ES+)$^b$ $C_{28}H_{31}ClFN_9O_5S$, requires: 659.2, found: 660.3 [M + H]$^+$ |
| 721 | 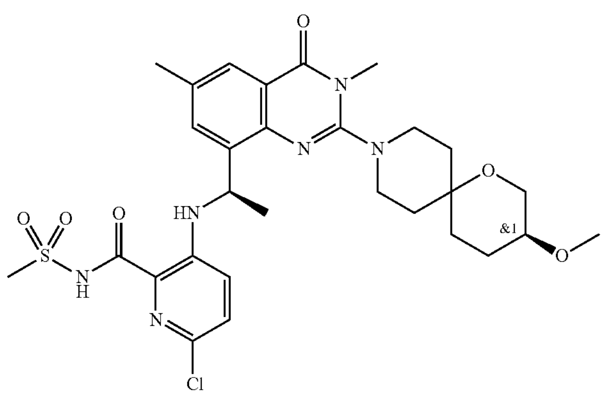 | 6-chloro-3-(((R)-1-(2-((RS)-3-methoxy-1-oxa-9-azaspiro[5.5]undecan-9-yl)-3,6-dimethyl-4-oxo-3,4-dihydroquinazolin-8-yl)ethyl)amino)-N-(methylsulfonyl)picolinamide | 3.58 min, 254 nm, MS (ES+)$^c$ $C_{29}H_{37}ClN_6O_6S$, requires: 632.2, found: 633.3 [M + H]$^+$ |
| 722 | 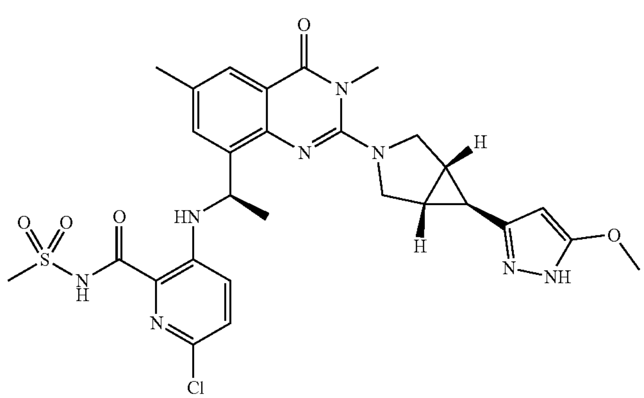 | 6-chloro-3-(((R)-1-(2-((1R,5S,6R)-6-(5-methoxy-1H-pyrazol-3-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 2.06 min, 210 nm, MS (ES+)$^b$ $C_{28}H_{31}ClN_8O_5S$, requires: 626.2, found: 627.2 [M + H]$^+$ |

TABLE E4-continued compound list prepared according to Route A in Example 4

| Cpd. ID | Structure | Name | LCMS |
|---|---|---|---|
| 723 | 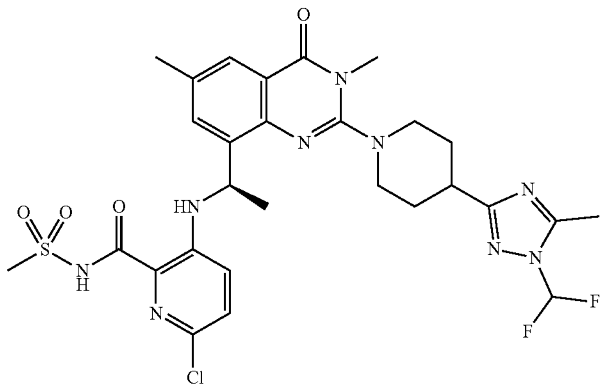 | (R)-6-chloro-3-((1-(2-(4-(1-(difluoromethyl)-5-methyl-1H-1,2,4-triazol-3-yl)piperidin-1-yl)-3,6-dimethyl-4-oxo-3,4-dihydroquinazolin-8-yl)ethyl)amino)-N-(methylsulfonyl)picolinamide | 2.25 min, 210 nm, MS (ES+)[b] $C_{28}H_{32}ClF_2N_9O_4S$, requires: 663.2, found: 664.2 $[M + H]^+$ |
| 724 | 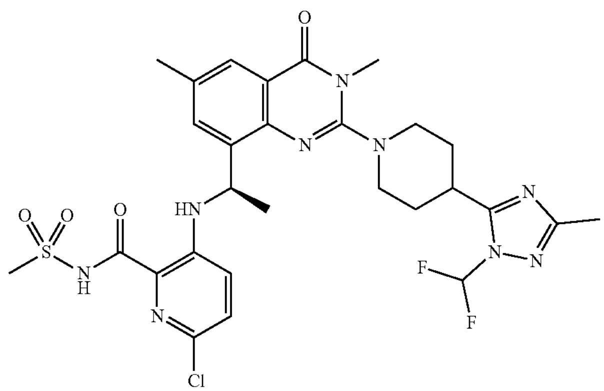 | (R)-6-chloro-3-((1-(2-(4-(1-(difluoromethyl)-3-methyl-1H-1,2,4-triazol-5-yl)piperidin-1-yl)-3,6-dimethyl-4-oxo-3,4-dihydroquinazolin-8-yl)ethyl)amino)-N-(methylsulfonyl)picolinamide | 2.46 min, 220 nm, MS (ES+)[b] $C_{28}H_{32}ClF_2N_9O_4S$, requires: 663.2, found: 664.4 $[M + H]^+$ |
| 725 | 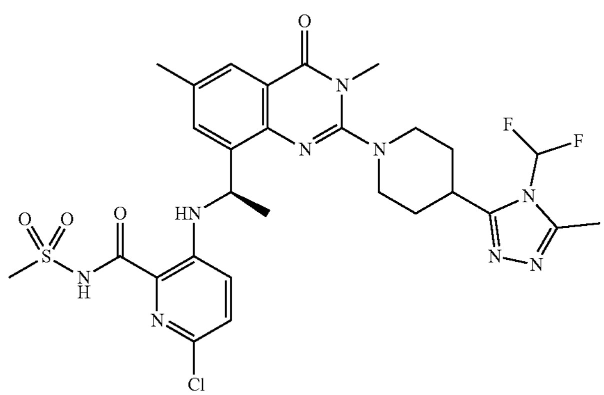 | (R)-6-chloro-3-((1-(2-(4-(4-(difluoromethyl)-5-methyl-4H-1,2,4-triazol-3-yl)piperidin-1-yl)-3,6-dimethyl-4-oxo-3,4-dihydroquinazolin-8-yl)ethyl)amino)-N-(methylsulfonyl)picolinamide | 2.06 min, 254 nm, MS (ES+)[b] $C_{28}H_{32}ClF_2N_9O_4S$, requires: 663.2, found: 664.2 $[M + H]^+$ |
| 726 | 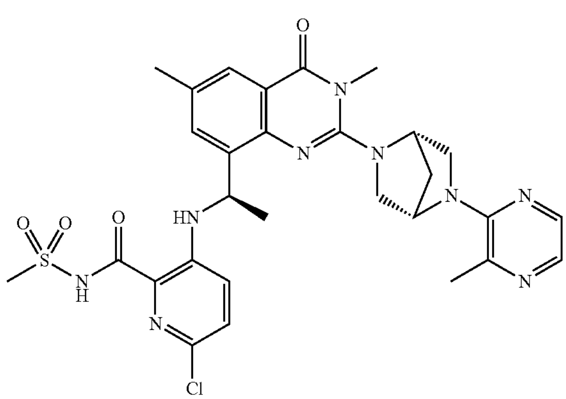 [SMILES: Cc1cc([C@@H](C)Nc2ccc(Cl)nc2C(=O)NS(C)(=O)=O)c2nc(N3C[C@@H]4C[C@H]3CN4c3nccnc3C)n(C)c(=O)c2c1] | 6-chloro-3-(((R)-1-(3,6-dimethyl-2-((1S,4S)-5-(3-methylpyrazin-2-yl)-2,5-diazabicyclo[2.2.1]heptan-2-yl)-4-oxo-3,4-dihydroquinazolin-8-yl)ethyl)amino)-N-(methylsulfonyl)picolinamide | 2.37 min, 265 nm, MS (ES+)[b] $C_{29}H_{32}ClN_9O_4S$, requires: 637.2, found: 638.2 $[M + H]^+$ |

TABLE E4-continued compound list prepared according to Route A in Example 4

| Cpd. ID | Structure | Name | LCMS |
|---|---|---|---|
| 727 | 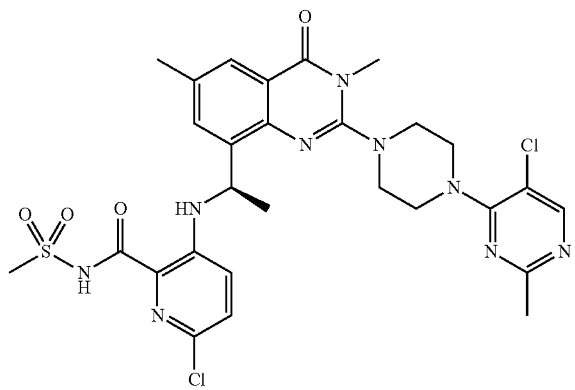 [SMILES: Cc1cc([C@@H](C)Nc2ccc(Cl)nc2C(=O)NS(C)(=O)=O)c2nc(N3CCN(c4nc(C)ncc4Cl)CC3)n(C)c(=O)c2c1] | (R)-6-chloro-3-((1-(2-(4-(5-chloro-2-methylpyrimidin-4-yl)piperazin-1-yl)-3,6-dimethyl-4-oxo-3,4-dihydroquinazolin-8-yl)ethyl)amino)-N-(methylsulfonyl)picolinamide | 2.34 min, 210 nm, MS (ES+)[b] $C_{28}H_{31}Cl_2N_9O_4S$, requires: 659.1, found: 660.2 $[M + H]^+$ |
| 728 | 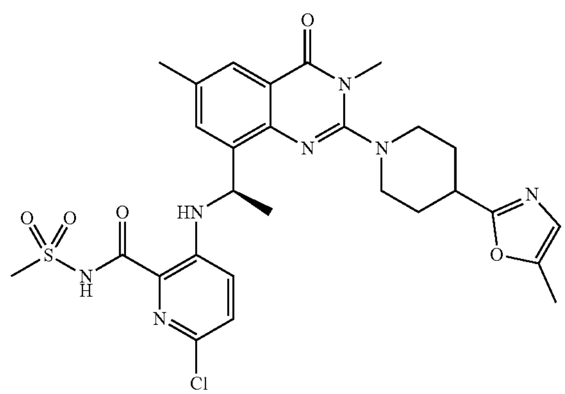 [SMILES: Cc1cc([C@@H](C)Nc2ccc(Cl)nc2C(=O)NS(C)(=O)=O)c2nc(N3CCC(c4ncc(C)o4)CC3)n(C)c(=O)c2c1] | (R)-6-chloro-3-((1-(3,6-dimethyl-2-(4-(5-methyloxazol-2-yl)piperidin-1-yl)-4-oxo-3,4-dihydroquinazolin-8-yl)ethyl)amino)-N-(methylsulfonyl)picolinamide | 2.34 min, 254 nm, MS (ES+)[b] $C_{28}H_{32}ClN_7O_5S$, requires: 613.1, found: 614.2 $[M + H]^+$ |
| 729 | 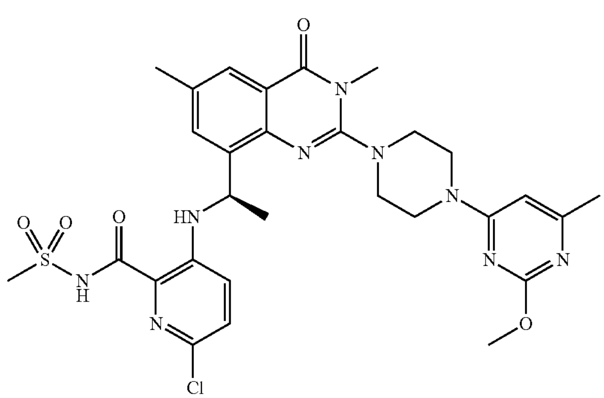 | (R)-6-chloro-3-((1-(2-(4-(2-methoxy-6-methylpyrimidin-4-yl)piperazin-1-yl)-3,6-dimethyl-4-oxo-3,4-dihydroquinazolin-8-yl)ethyl)amino)-N-(methylsulfonyl)picolinamide | 1.94 min, 254 nm, MS (ES+)[b] $C_{29}H_{34}ClN_9O_5S$, requires: 655.2, found: 656.2 $[M + H]^+$ |

TABLE E4-continued compound list prepared according to Route A in Example 4

| Cpd. ID | Structure | Name | LCMS |
|---|---|---|---|
| 730 | 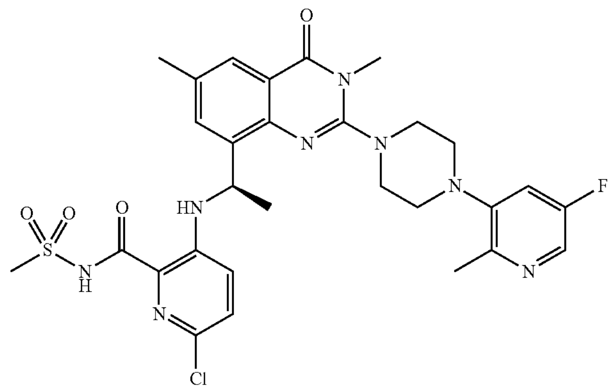 [SMILES: Cc1cc([C@@H](C)Nc2ccc(Cl)nc2C(=O)NS(C)(=O)=O)c2nc(N3CCN(c4cc(F)cnc4C)CC3)n(C)c(=O)c2c1] | (R)-6-chloro-3-((1-(2-(4-(5-fluoro-2-methylpyridin-3-yl)piperazin-1-yl)-3,6-dimethyl-4-oxo-3,4-dihydroquinazolin-8-yl)ethyl)amino)-N-(methylsulfonyl)picolinamide | 2.28 min, 254 nm, MS (ES+)[b] $C_{29}H_{32}ClFN_8O_4S$, requires 642.1, found: 643.2 [M + H]$^+$ |
| 731 | 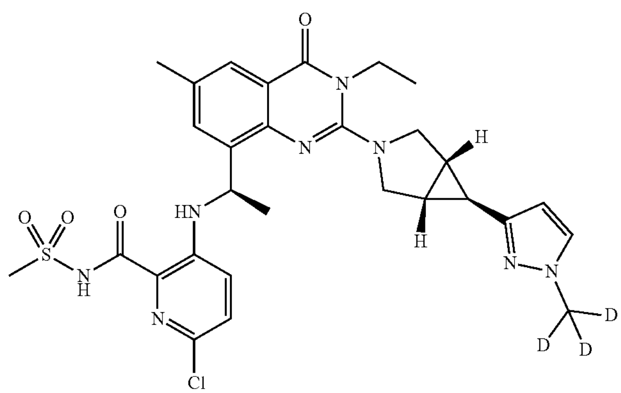 [SMILES: [2H]C([2H])([2H])n1ccc([C@H]2[C@@H]3CN(c4nc5c([C@@H](C)Nc6ccc(Cl)nc6C(=O)NS(C)(=O)=O)cc(C)cc5c(=O)n4CC)C[C@@H]32)n1] | 6-chloro-3-(((R)-1-(3-ethyl-6-methyl-2-((1R,5S,6R)-6-(1-(methyl-d3)-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.34 min, 254 nm, MS (ES+)[b] $C_{29}H_{30}D_3ClN_8O_4S$, requires: 627.2, found: 628.2 [M + H]$^+$ |
| 732 | 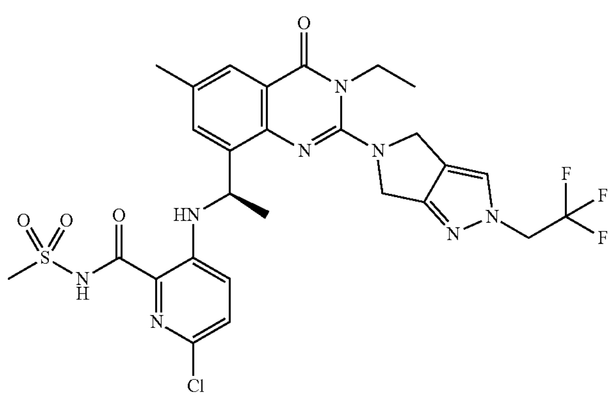 [SMILES: CCn1c(N2Cc3cn(CC(F)(F)F)nc3C2)nc2c([C@@H](C)Nc3ccc(Cl)nc3C(=O)NS(C)(=O)=O)cc(C)cc2c1=O] | (R)-6-chloro-3-((1-(3-ethyl-6-methyl-4-oxo-2-(2-(2,2,2-trifluoroethyl)-2,6-dihydropyrrolo[3,4-c]pyrazol-5(4H)-yl)-3,4-dihydroquinazolin-8-yl)ethyl)amino)-N-(methylsulfonyl)picolinamide | 2.46 min, 210 nm, MS (ES+)[b] $C_{27}H_{28}ClF_3N_8O_4S$, requires: 652.1, found: 653.2 [M + H]$^+$ |
| 733 | 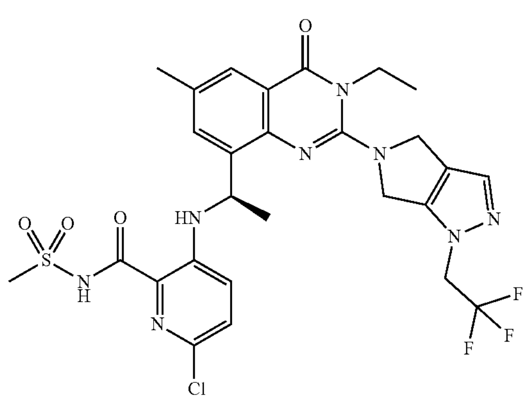 [SMILES: CCn1c(N2Cc3cnn(CC(F)(F)F)c3C2)nc2c([C@@H](C)Nc3ccc(Cl)nc3C(=O)NS(C)(=O)=O)cc(C)cc2c1=O] | (R)-6-chloro-3-((1-(3-ethyl-6-methyl-4-oxo-2-(1-(2,2,2-trifluoroethyl)-4,6-dihydropyrrolo[3,4-c]pyrazol-5(1H)-yl)-3,4-dihydroquinazolin-8-yl)ethyl)amino)-N-(methylsulfonyl)picolinamide | 2.38 min, 210 nm, MS (ES+)[b] $C_{27}H_{28}ClF_3N_8O_4S$, requires: 652.1, found: 653.2 [M + H]$^+$ |

TABLE E4-continued compound list prepared according to Route A in Example 4

| Cpd. ID | Structure | Name | LCMS |
|---|---|---|---|
| 734 | 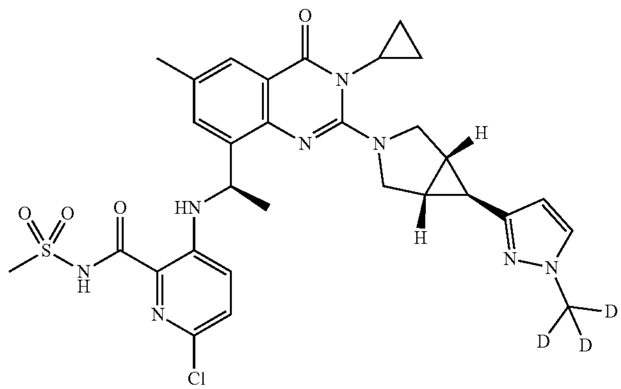 [SMILES: [2H]C([2H])([2H])n1ccc([C@H]2[C@@H]3CN(c4nc5c([C@@H](C)Nc6ccc(Cl)nc6C(=O)NS(C)(=O)=O)cc(C)cc5c(=O)n4C4CC4)C[C@@H]32)n1] | 6-chloro-3-(((R)-1-(3-cyclopropyl-6-methyl-2-((1R,5S,6R)-6-(1-(methyl-d3)-1H-pyrazol-3-yl)-3-azabicyclo[3.1.0]hexan-3-yl)-4-oxo-3,4-dihydroquinazolin-8-yl)ethyl)amino)-N-(methylsulfonyl)picolinamide | 2.21 min, 270 nm, MS (ES+)$^b$ $C_{30}H_{30}D_3ClN_8O_4S$, requires: 639.2, found: 640.2 [M + H]$^+$ |
| 735 | 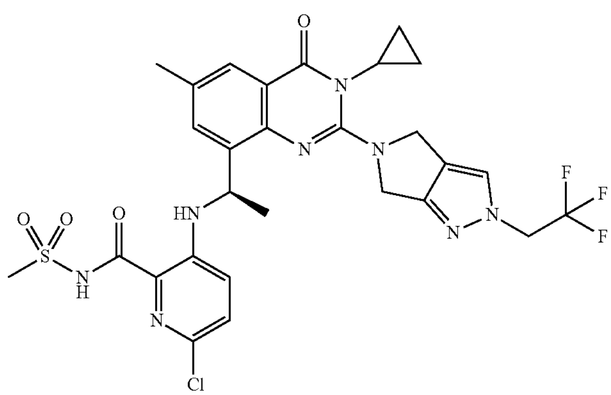 [SMILES: Cc1cc([C@@H](C)Nc2ccc(Cl)nc2C(=O)NS(C)(=O)=O)c2nc(N3Cc4cn(CC(F)(F)F)nc4C3)n(C3CC3)c(=O)c2c1] | (R)-6-chloro-3-((1-(3-cyclopropyl-6-methyl-4-oxo-2-(2-(2,2,2-trifluoroethyl)-2,6-dihydropyrrolo[3,4-c]pyrazol-5(4H)-yl)-3,4-dihydroquinazolin-8-yl)ethyl)amino)-N-(methylsulfonyl)picolinamide | 2.40 min, 270 nm, MS (ES+)$^b$ $C_{28}H_{28}ClF_3N_8O_4S$, requires: 664.2, found: 665.2 [M + H]$^+$ |
| 736 | 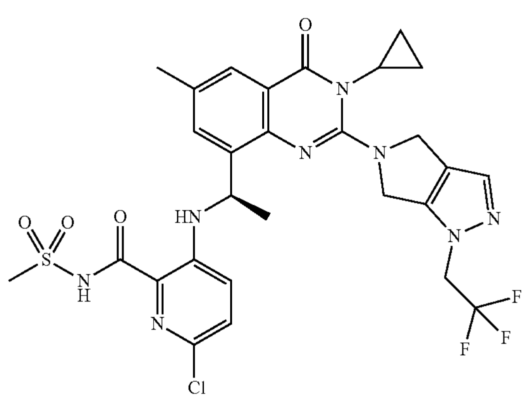 [SMILES: Cc1cc([C@@H](C)Nc2ccc(Cl)nc2C(=O)NS(C)(=O)=O)c2nc(N3Cc4cnn(CC(F)(F)F)c4C3)n(C3CC3)c(=O)c2c1] | (R)-6-chloro-3-((1-(3-cyclopropyl-6-methyl-4-oxo-2-(1-(2,2,2-trifluoroethyl)-4,6-dihydropyrrolo[3,4-c]pyrazol-5(1H)-yl)-3,4-dihydroquinazolin-8-yl)ethyl)amino)-N-(methylsulfonyl)picolinamide | 2.36 min, 210 nm, MS (ES+)$^b$ $C_{28}H_{28}ClF_3N_8O_4S$, requires: 664.2, found: 665.2 [M + H]$^+$ |

TABLE E4-continued compound list prepared according to Route A in Example 4

| Cpd. ID | Structure | Name | LCMS |
|---|---|---|---|
| 737 | 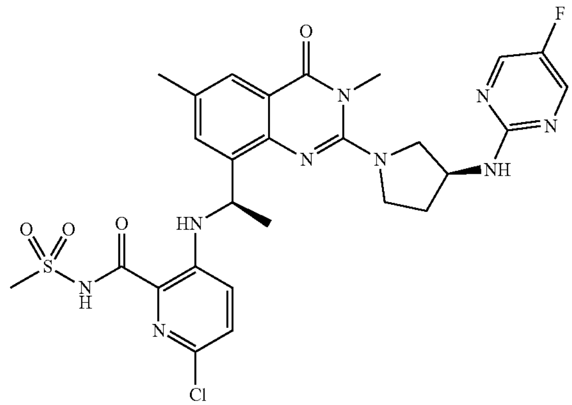 [SMILES: Cc1cc([C@@H](C)Nc2ccc(Cl)nc2C(=O)NS(C)(=O)=O)c2nc(N3CC[C@H](Nc4ncc(F)cn4)C3)n(C)c(=O)c2c1] | 6-chloro-3-(((R)-1-(2-((S)-3-((5-fluoropyrimidin-2-yl)amino)pyrrolidin-1-yl)-3,6-dimethyl-4-oxo-3,4-dihydroquinazolin-8-yl)ethyl)amino)-N-(methylsulfonyl)picolinamide | 4.51 min, 254 nm, MS (ES+)$^c$ C$_{27}$H$_{29}$ClFN$_9$O$_4$S, requires: 629.2, found: 630.2 [M + H]$^+$ |
| 738 | 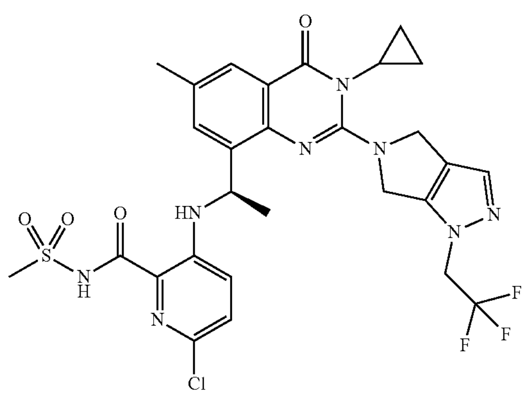 | 6-chloro-3-(((R)-1-(2-((S)-3-((5-chloropyrimidin-2-yl)amino)pyrrolidin-1-yl)-3,6-dimethyl-4-oxo-3,4-dihydroquinazolin-8-yl)ethyl)amino)-N-(methylsulfonyl)picolinamide | 4.80 min, 254 nm, MS (ES+)$^c$ C$_{27}$H$_{29}$Cl$_2$N$_9$O$_4$S, requires: 645.1, found: 646.2 [M + H]$^+$ |
| 739 | 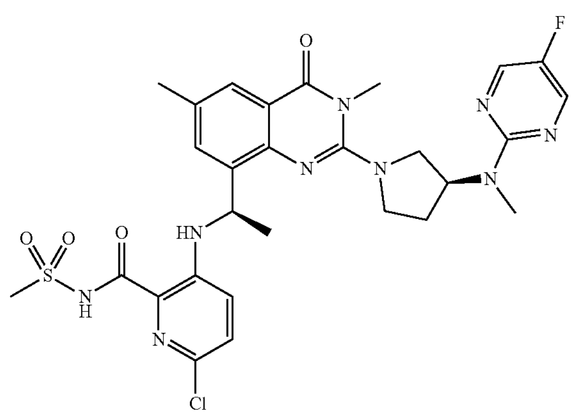 [SMILES: Cc1cc([C@@H](C)Nc2ccc(Cl)nc2C(=O)NS(C)(=O)=O)c2nc(N3CC[C@H](N(C)c4ncc(F)cn4)C3)n(C)c(=O)c2c1] | 6-chloro-3-(((R)-1-(2-((S)-3-((5-fluoropyrimidin-2-yl)(methyl)amino)pyrrolidin-1-yl)-3,6-dimethyl-4-oxo-3,4-dihydroquinazolin-8-yl)ethyl)amino)-N-(methylsulfonyl)picolinamide | 5.06 min, 254 nm, MS (ES+)$^c$ C$_{28}$H$_{31}$ClFN$_9$O$_4$S, requires: 643.2, found: 644.2 [M + H]$^+$ |

TABLE E4-continued compound list prepared according to Route A in Example 4

| Cpd. ID | Structure | Name | LCMS |
|---|---|---|---|
| 740 | 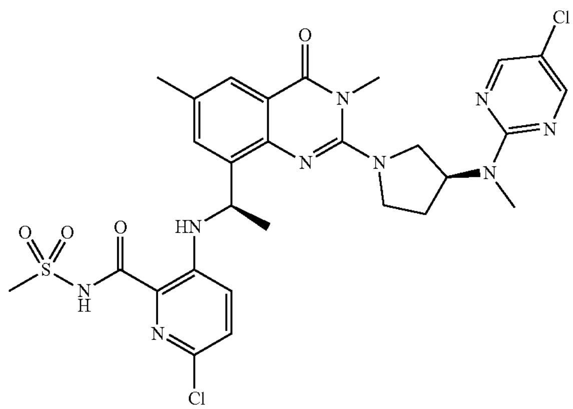 [SMILES: Cc1cc([C@@H](C)Nc2ccc(Cl)nc2C(=O)NS(C)(=O)=O)c2nc(N3CC[C@H](N(C)c4ncc(Cl)cn4)C3)n(C)c(=O)c2c1] | 6-chloro-3-(((R)-1-(2-((S)-3-((5-chloropyrimidin-2-yl)(methyl)amino)pyrrolidin-1-yl)-3,6-dimethyl-4-oxo-3,4-dihydroquinazolin-8-yl)ethyl)amino)-N-(methylsulfonyl)picolinamide | 5.40 min, 254 nm, MS (ES+)$^c$ $C_{28}H_{31}Cl_2N_9O_4S$ requires: 659.2, found: 660.3 [M + H]$^+$ |
| 741 | 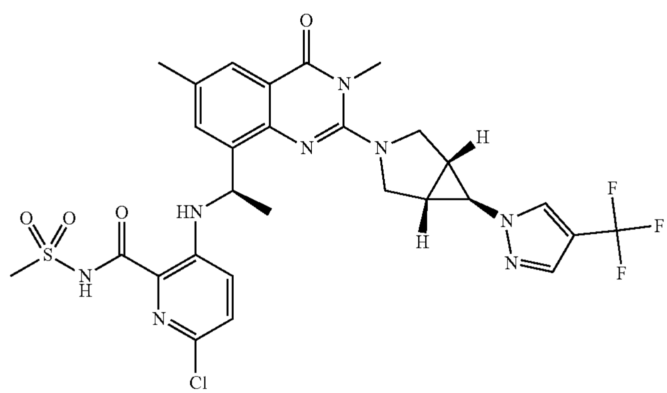 [SMILES: Cc1cc([C@@H](C)Nc2ccc(Cl)nc2C(=O)NS(C)(=O)=O)c2nc(N3C[C@@H]4[C@H](C3)[C@H]4n3cc(C(F)(F)F)cn3)n(C)c(=O)c2c1] | 6-chloro-3-(((R)-1-(3,6-dimethyl-4-oxo-2-((1R,5S,6S)-6-(4-(trifluoromethyl)-1H-pyrazol-1-yl)-3-azabicyclo[3.1.0]hexan-3-yl)-3,4-dihydroquinazolin-8-yl)ethyl)amino)-N-(methylsulfonyl)picolinamide | 2.55 min, 220 nm, MS (ES+)$^b$ $C_{28}H_{28}ClF_3N_8O_4S$ requires: 664.1, found: 665.2 [M + H]$^+$ |
| 742 | 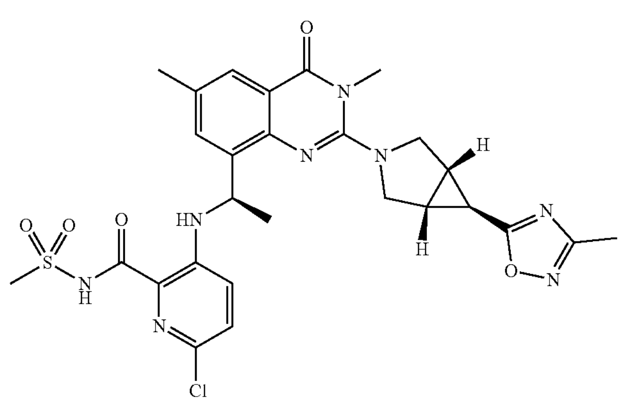 | 6-chloro-3-(((R)-1-(3,6-dimethyl-2-((1R,5S,6R)-6-(3-methyl-1,2,4-oxadiazol-5-yl)-3-azabicyclo[3.1.0]hexan-3-yl)-4-oxo-3,4-dihydroquinazolin-8-yl)ethyl)amino)-N-(methylsulfonyl)picolinamide | 2.34 min, 220 nm, MS (ES+)$^b$ $C_{27}H_{29}ClN_8O_5S$ requires: 612.1, found: 613.3 [M + H]$^+$ |

TABLE E4-continued compound list prepared according to Route A in Example 4

| Cpd. ID | Structure | Name | LCMS |
|---|---|---|---|
| 743 | 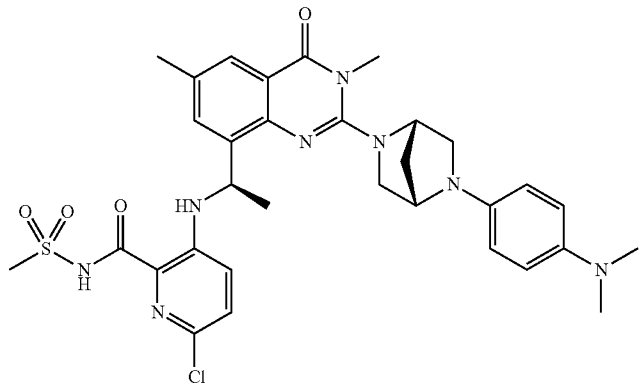 | 6-chloro-3-(((R)-1-(2-((1S,4R)-5-(4-(dimethylamino)phenyl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 1.92 min, 254 nm, MS (ES+)[b] $C_{32}H_{37}ClN_8O_4S$ requires: 665.2, found: 666.3 $[M + H]^+$ |
| 744 | 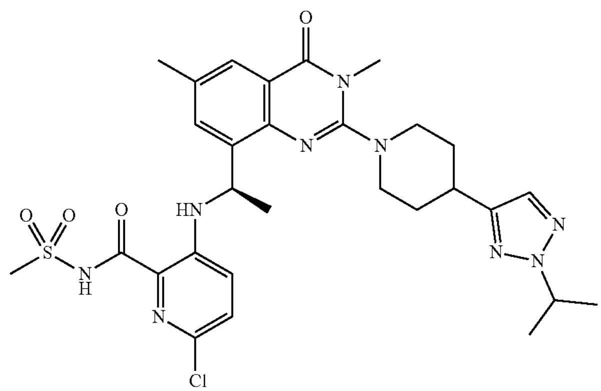 [SMILES: Cc1cc([C@@H](C)Nc2ccc(Cl)nc2C(=O)NS(C)(=O)=O)c2nc(N3CCC(c4cnn(C(C)C)n4)CC3)n(C)c(=O)c2c1] | (R)-6-chloro-3-((1-(2-(4-(2-isopropyl-2H-1,2,3-triazol-4-yl)piperidin-1-yl)-3,6-dimethyl-4-oxo-3,4-dihydroquinazolin-8-yl)ethyl)amino)-N-(methylsulfonyl)picolinamide | 2.64 min, 265 nm, MS (ES+)[b] $C_{29}H_{36}ClN_9O_4S$ requires: 641.2, found: 642.3 $[M + H]^+$ |
| 745 | 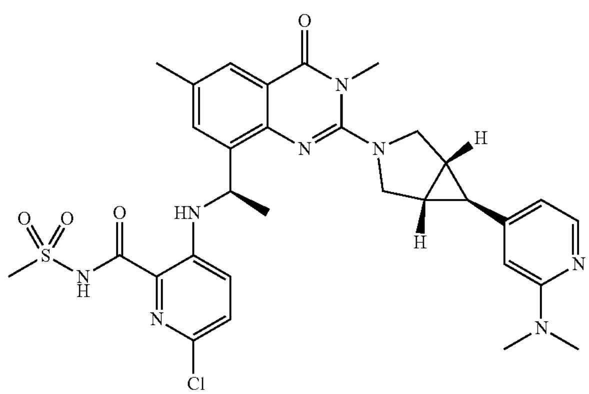 | 6-chloro-3-(((R)-1-(2-((1R,5S,6S)-6-(2-(dimethylamino)pyridin-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 1.99 min, 270 nm, MS (ES+)[b] $C_{31}H_{35}ClN_8O_4S$ requires: 650.2, found: 651.3 $[M + H]^+$ |
| 746 | 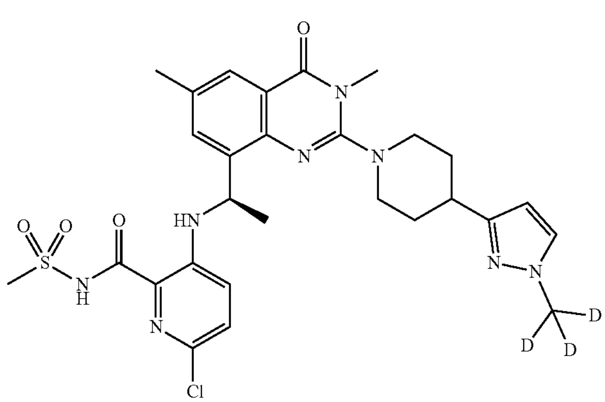 [SMILES: [2H]C([2H])([2H])n1ccc(C2CCN(c3nc4c([C@@H](C)Nc5ccc(Cl)nc5C(=O)NS(C)(=O)=O)cc(C)cc4c(=O)n3C)CC2)n1] | (R)-6-chloro-3-((1-(3,6-dimethyl-2-(4-(1-(methyl-d3)-1H-pyrazol-3-yl)piperidin-1-yl)-4-oxo-3,4-dihydroquinazolin-8-yl)ethyl)amino)-N-(methylsulfonyl)picolinamide | 2.35 min, 254 nm, MS (ES+)[b] $C_{28}H_{30}D_3ClN_8O_4S$ requires: 615.2, found: 616.3 $[M + H]^+$ |

TABLE E4-continued compound list prepared according to Route A in Example 4

| Cpd. ID | Structure | Name | LCMS |
|---|---|---|---|
| 747 | 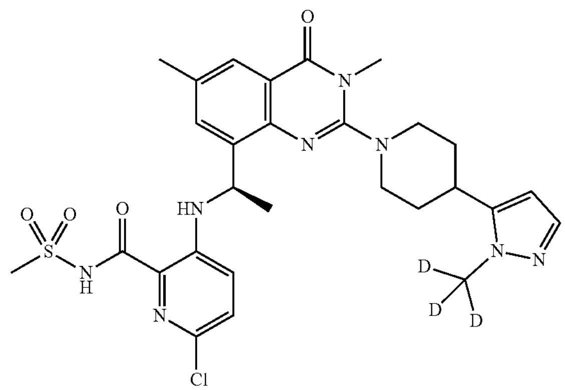 [SMILES: [2H]C([2H])([2H])n1nccc1C1CCN(c2nc3c([C@@H](C)Nc4ccc(Cl)nc4C(=O)NS(C)(=O)=O)cc(C)cc3c(=O)n2C)CC1] | (R)-6-chloro-3-((1-(3,6-dimethyl-2-(4-(1-(methyl-d3)-1H-pyrazol-5-yl)piperidin-1-yl)-4-oxo-3,4-dihydroquinazolin-8-yl)ethyl)amino)-N-(methylsulfonyl)picolinamide | 2.35 min, 254 nm, MS (ES+)[b] $C_{28}H_{30}D_3ClN_8O_4S$ requires: 615.2, found: 616.3 $[M + H]^+$ |
| 748 | 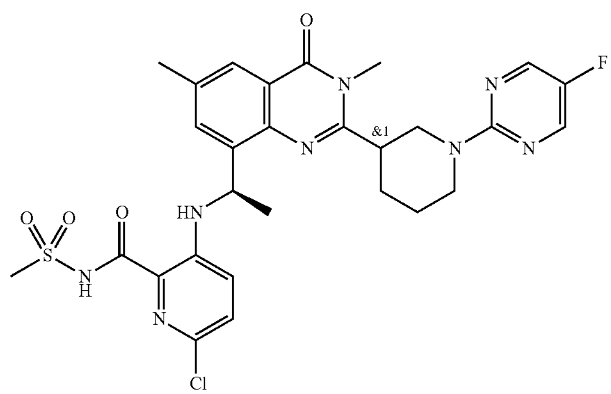 [SMILES: Cc1cc([C@@H](C)Nc2ccc(Cl)nc2C(=O)NS(C)(=O)=O)c2nc(C3CCCN(c4ncc(F)cn4)C3)n(C)c(=O)c2c1] | 6-chloro-3-(((1R)-1-(2-(1-(5-fluoropyrimidin-2-yl)piperidin-3-yl)-3,6-dimethyl-4-oxo-3,4-dihydroquinazolin-8-yl)ethyl)amino)-N-(methylsulfonyl)picolinamide | 2.66 min, 210 nm, MS (ES+)[b] $C_{28}H_{30}ClFN_8O_4S$ requires: 628.1, found: 629.2 $[M + H]^+$ |
| 749 | 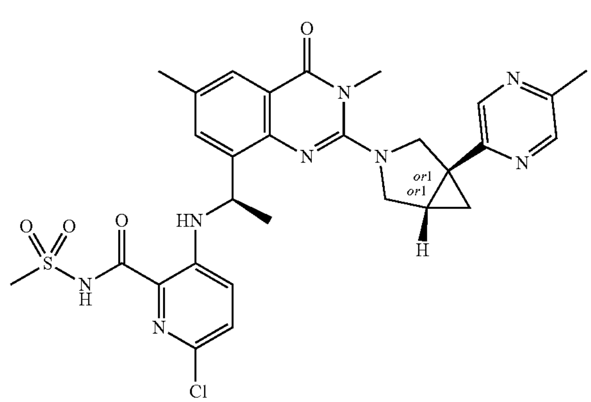 | 6-chloro-3-(((R)-1-(3,6-dimethyl-2-((1R*,5S*)-1-(5-methylpyrazin-2-yl)-3-azabicyclo[3.1.0]hexan-3-yl)-4-oxo-3,4-dihydroquinazolin-8-yl)ethyl)amino)-N-(methylsulfonyl)picolinamide | 2.43 min, 254 nm, MS (ES+)[b] $C_{29}H_{31}ClN_8O_4S$ requires: 622.1, found: 623.3 $[M + H]^+$ |

TABLE E4-continued compound list prepared according to Route A in Example 4

| Cpd. ID | Structure | Name | LCMS |
|---|---|---|---|
| 750 | 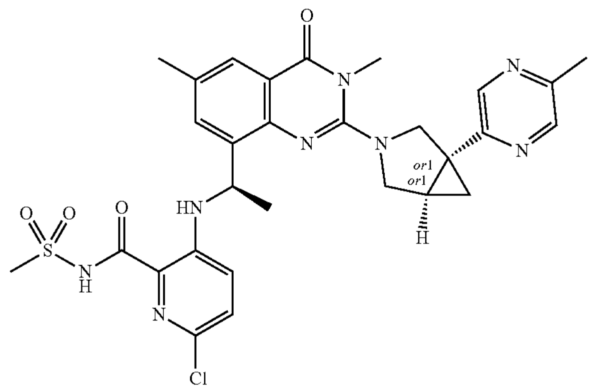 | 6-chloro-3-(((R)-1-(3,6-dimethyl-2-((1R*,5R*)-1-(5-methylpyrazin-2-yl)-3-azabicyclo[3.1.0]hexan-3-yl)-4-oxo-3,4-dihydroquinazolin-8-yl)ethyl)amino)-N-(methylsulfonyl)picolinamide | 2.44 min, 254 nm, MS (ES+)$^b$ C$_{29}$H$_{31}$ClN$_8$O$_4$S requires: 622.1, found: 623.3 [M + H]$^+$ |
| 751 | 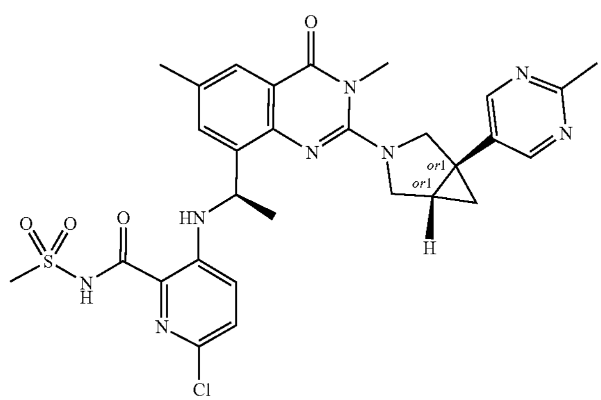 | 6-chloro-3-(((R)-1-(3,6-dimethyl-2-((1R*,5S*)-1-(2-methylpyrimidin-5-yl)-3-azabicyclo[3.1.0]hexan-3-yl)-4-oxo-3,4-dihydroquinazolin-8-yl)ethyl)amino)-N-(methylsulfonyl)picolinamide | 2.22 min, 220 nm, MS (ES+)$^b$ C$_{29}$H$_{31}$ClN$_8$O$_4$S requires: 622.1, found: 623.2 [M + H]$^+$ |
| 752 | 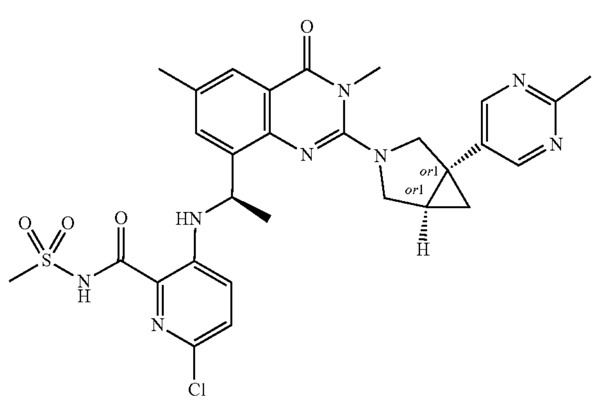 | 6-chloro-3-(((R)-1-(3,6-dimethyl-2-((1R*,5R*)-1-(2-methylpyrimidin-5-yl)-3-azabicyclo[3.1.0]hexan-3-yl)-4-oxo-3,4-dihydroquinazolin-8-yl)ethyl)amino)-N-(methylsulfonyl)picolinamide | 2.21 min, 220 nm, MS (ES+)$^b$ C$_{29}$H$_{31}$ClN$_8$O$_4$S requires: 622.1, found: 623.2 [M + H]$^+$ |

TABLE E4-continued compound list prepared according to Route A in Example 4

| Cpd. ID | Structure | Name | LCMS |
|---|---|---|---|
| 753 | 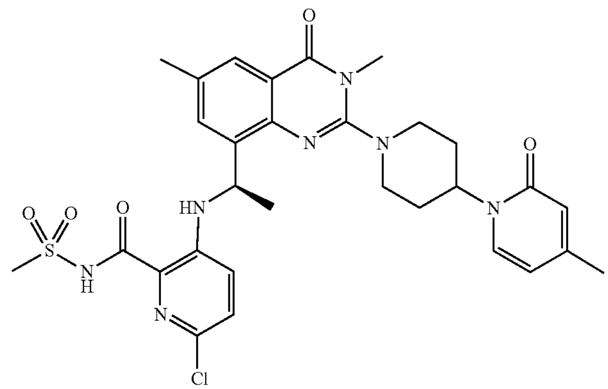 | (R)-6-chloro-3-((1-(3,6-dimethyl-2-(4-(4-methyl-2-oxopyridin-1(2H)-yl)piperidin-1-yl)-4-oxo-3,4-dihydroquinazolin-8-yl)ethyl)amino)-N-(methylsulfonyl)picolinamide | 2.20 min, 254 nm, MS (ES+)[b] $C_{30}H_{34}ClN_7O_5S$ requires: 639.2, found: 640.3 $[M + H]^+$ |
| 754 | 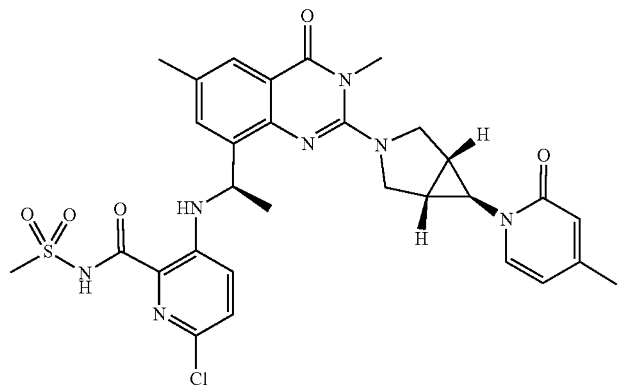 | 6-chloro-3-(((R)-1-(3,6-dimethyl-2-((1R,5S,6S)-6-(4-methyl-2-oxopyridin-1(2H)-yl)-3-azabicyclo[3.1.0]hexan-3-yl)-4-oxo-3,4-dihydroquinazolin-8-yl)ethyl)amino)-N-(methylsulfonyl)picolinamide | 2.15 min, 254 nm, MS (ES+)[b] $C_{30}H_{32}ClN_7O_5S$ requires: 637.1, found: 638.3 $[M + H]^+$ |
| 755 | 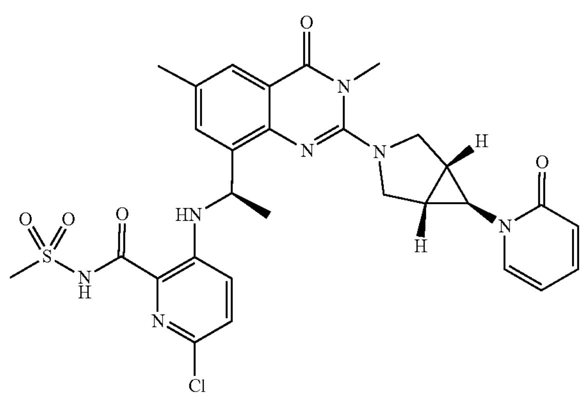 [SMILES: Cc1cc([C@@H](C)Nc2ccc(Cl)nc2C(=O)NS(C)(=O)=O)c2nc(N3C[C@@H]4[C@H](C3)[C@H]4n3ccccc3=O)n(C)c(=O)c2c1] | 6-chloro-3-(((R)-1-(3,6-dimethyl-4-oxo-2-((1R,5S,6S)-6-(2-oxopyridin-1(2H)-yl)-3-azabicyclo[3.1.0]hexan-3-yl)-3,4-dihydroquinazolin-8-yl)ethyl)amino)-N-(methylsulfonyl)picolinamide | 2.10 min, 210 nm, MS (ES+)[b] $C_{29}H_{30}ClN_7O_5S$ requires: 623.1, found: 624.2 $[M + H]^+$ |
| 756 | 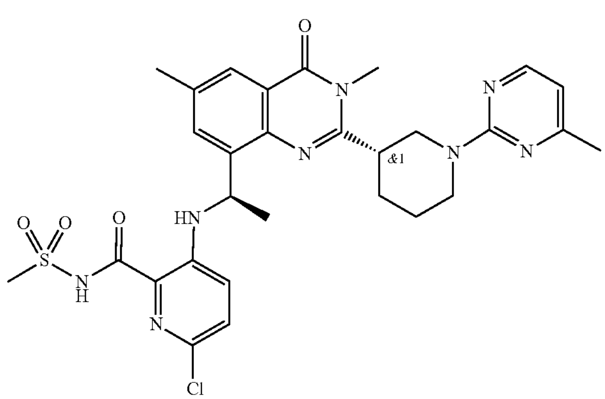 | 6-chloro-3-(((R)-1-(3,6-dimethyl-2-((RS)-1-(4-methylpyrimidin-2-yl)piperidin-3-yl)-4-oxo-3,4-dihydroquinazolin-8-yl)ethyl)amino)-N-(methylsulfonyl)picolinamide | 2.60 min, 265 nm, MS (ES+)[b] $C_{29}H_{33}ClN_8O_4S$ requires: 624.2, found: 625.3 $[M + H]^+$ |

TABLE E4-continued compound list prepared according to Route A in Example 4

| Cpd. ID | Structure | Name | LCMS |
|---|---|---|---|
| 757 | 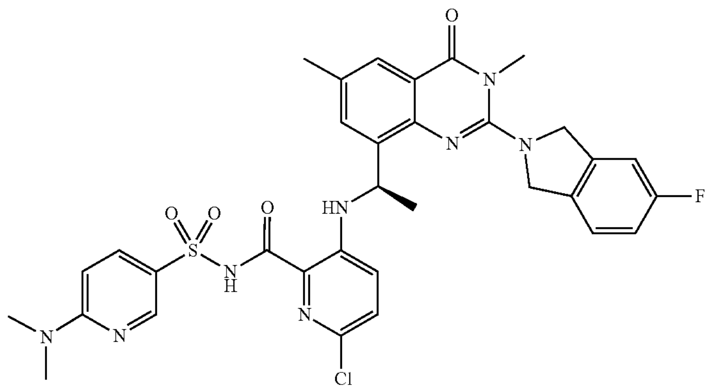 [SMILES: Cc1cc([C@@H](C)Nc2ccc(Cl)nc2C(=O)NS(=O)(=O)c2ccc(N(C)C)nc2)c2nc(N3Cc4ccc(F)cc4C3)n(C)c(=O)c2c1] | (R)-6-chloro-N-((6-(dimethylamino)pyridin-3-yl)sulfonyl)-3-((1-(2-(5-fluoroisoindolin-2-yl)-3,6-dimethyl-4-oxo-3,4-dihydroquinazolin-8-yl)ethyl)amino)picolinamide | 2.78 min, 210 nm, MS (ES+)[b] $C_{33}H_{32}ClFN_8O_4S$, requires: 690.2, found: 691.2 [M + H]+ |
| 758 | 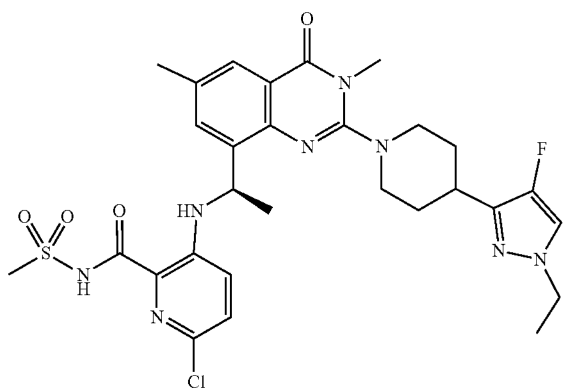 [SMILES: CCn1cc(F)c(C2CCN(c3nc4c([C@@H](C)Nc5ccc(Cl)nc5C(=O)NS(C)(=O)=O)cc(C)cc4c(=O)n3C)CC2)n1] | (R)-6-chloro-3-((1-(2-(4-(1-ethyl-4-fluoro-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.58 min, 254 nm, MS (ES+)[b] $C_{29}H_{34}ClFN_8O_4S$, requires: 644.2, found: 645.3 [M + H]+ |
| 759 | 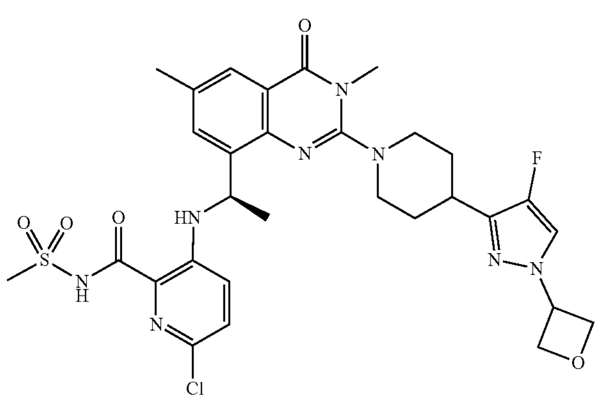 [SMILES: Cc1cc([C@@H](C)Nc2ccc(Cl)nc2C(=O)NS(C)(=O)=O)c2nc(N3CCC(c4nn(C5COC5)cc4F)CC3)n(C)c(=O)c2c1] | (R)-6-chloro-3-((1-(2-(4-(4-fluoro-1-(oxetan-3-yl)-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.43 min, 254 nm, MS (ES+)[b] $C_{30}H_{34}ClFN_8O_5S$, requires: 672.2, found: 673.2 [M + H]+ |

TABLE E4-continued compound list prepared according to Route A in Example 4

| Cpd. ID | Structure | Name | LCMS |
|---|---|---|---|
| 760 | 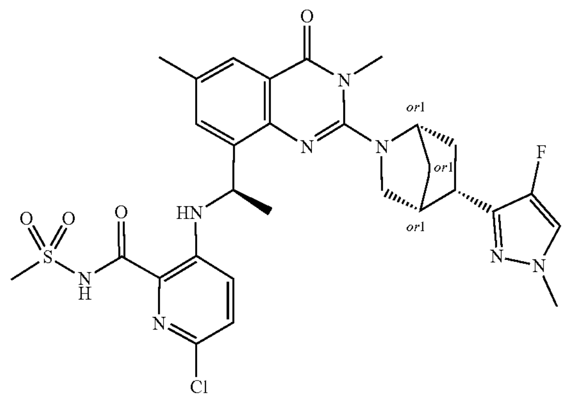 | 6-chloro-3-(((R)-1-(2-((1R*,4S*,5R*)-5-(4-fluoro-1-methyl-1H-pyrazol-3-yl)-2-azabicyclo[2.2.1]heptan-2-yl)-3,6-dimethyl-4-oxo-3,4-dihydroquinazolin-8-yl)ethyl)amino)-N-(methylsulfonyl)picolinamide | 2.47 min, 254 nm, MS (ES+)[b] $C_{29}H_{32}ClFN_8O_4S$, requires: 642.1, found: 643.2 [M + H]+ |
| 761 | 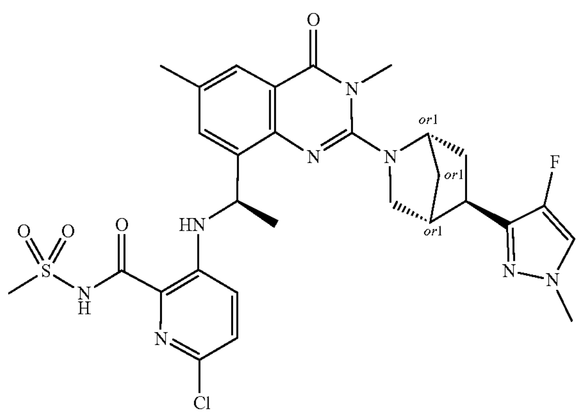 [SMILES: Cc1cc([C@@H](C)Nc2ccc(Cl)nc2C(=O)NS(C)(=O)=O)c2nc(N3C[C@@H]4C[C@H]3C[C@H]4c3nn(C)cc3F)n(C)c(=O)c2c1] | 6-chloro-3-(((R)-1-(2-((1R*,4S*,5S*)-5-(4-fluoro-1-methyl-1H-pyrazol-3-yl)-2-azabicyclo[2.2.1]heptan-2-yl)-3,6-dimethyl-4-oxo-3,4-dihydroquinazolin-8-yl)ethyl)amino)-N-(methylsulfonyl)picolinamide | 2.48 min, 254 nm, MS (ES+)[b] $C_{29}H_{32}ClFN_8O_4S$, requires: 642.1, found: 643.2 [M + H]+ |
| 762 | 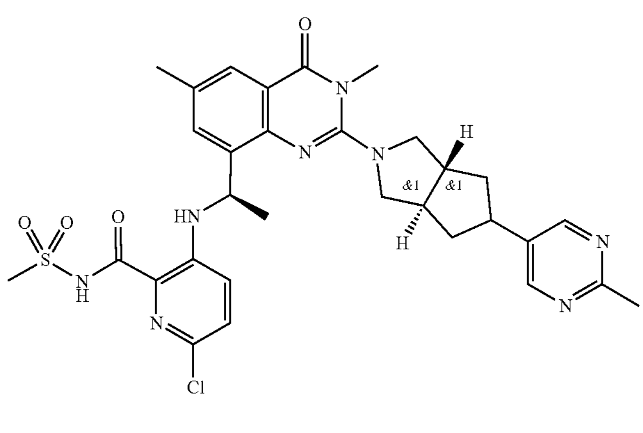 | 6-chloro-3-(((R)-1-(3,6-dimethyl-2-((3aRS,6aRS)-5-(2-methylpyrimidin-5-yl)hexahydrocyclopenta[c]pyrrol-2(1H)-yl)-4-oxo-3,4-dihydroquinazolin-8-yl)ethyl)amino)-N-(methylsulfonyl)picolinamide | 3.35 min, 254 nm, MS (ES+)[c] $C_{31}H_{35}ClN_8O_4S$, requires: 650.2, found: 651.3 [M + H]+ |

TABLE E4-continued compound list prepared according to Route A in Example 4

| Cpd. ID | Structure | Name | LCMS |
|---|---|---|---|
| 763 | 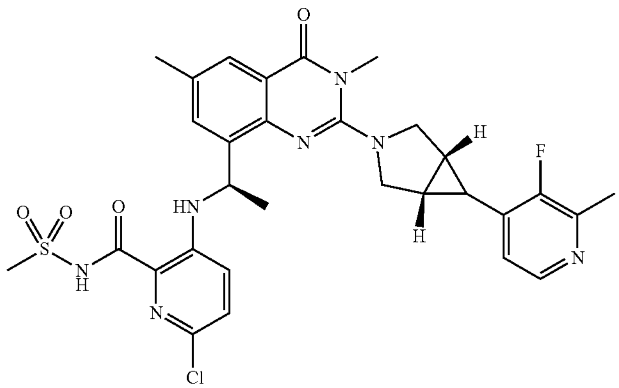 | 6-chloro-3-(((1R)-1-(2-((1R,5S)-6-(3-fluoro-2-methylpyridin-4-yl)-3-azabicyclo[3.1.0]hexan-3-yl)-3,6-dimethyl-4-oxo-3,4-dihydroquinazolin-8-yl)ethyl)amino)-N-(methylsulfonyl)picolinamide | 3.09 min, 254 nm, MS (ES+)$^c$ $C_{30}H_{31}ClFN_7O_4S$, requires: 639.2, found: 640.3 $[M + H]^+$ |
| 764 | 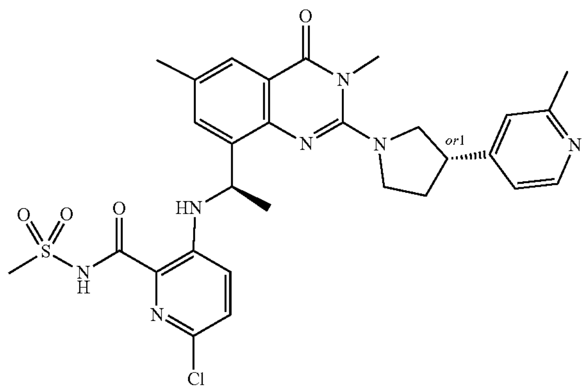 [SMILES: Cc1cc([C@@H](C)Nc2ccc(Cl)nc2C(=O)NS(C)(=O)=O)c2nc(N3CC[C@@H](c4ccnc(C)c4)C3)n(C)c(=O)c2c1] | 6-chloro-3-(((R)-1-(3,6-dimethyl-2-((R*)-3-(2-methylpyridin-4-yl)pyrrolidin-1-yl)-4-oxo-3,4-dihydroquinazolin-8-yl)ethyl)amino)-N-(methylsulfonyl)picolinamide | 1.91 min, 254 nm, MS (ES+)$^b$ $C_{29}H_{32}ClN_7O_4S$, requires: 609.1, found: 610.3 $[M + H]^+$ |
| 765 | 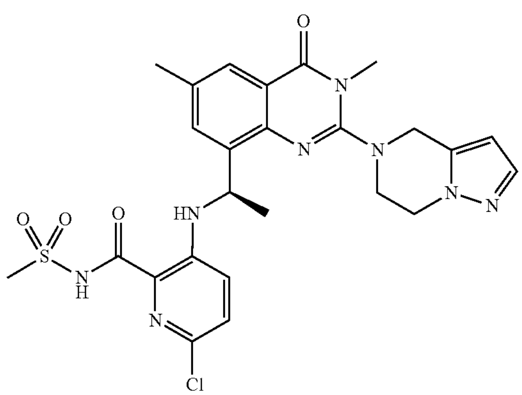 [SMILES: Cc1cc([C@@H](C)Nc2ccc(Cl)nc2C(=O)NS(C)(=O)=O)c2nc(N3CCn4nccc4C3)n(C)c(=O)c2c1] | (R)-6-chloro-3-((1-(2-(6,7-dihydropyrazolo[1,5-a]pyrazin-5(4H)-yl)-3,6-dimethyl-4-oxo-3,4-dihydroquinazolin-8-yl)ethyl)amino)-N-(methylsulfonyl)picolinamide | 2.17 min, 254 nm, MS (ES+)$^b$ $C_{25}H_{27}ClN_8O_4S$, requires: 570.1, found: 571.1 $[M + H]^+$ |
| 766 | 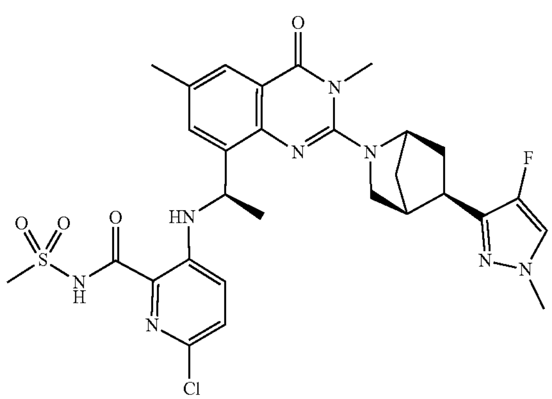 [SMILES: Cc1cc([C@@H](C)Nc2ccc(Cl)nc2C(=O)NS(C)(=O)=O)c2nc(N3C[C@H]4C[C@@H]3C[C@H]4c3nn(C)cc3F)n(C)c(=O)c2c1] | 6-chloro-3-(((R)-1-(2-((1R,4S,5R)-5-(4-fluoro-1-methyl-1H-pyrazol-3-yl)-2-azabicyclo[2.2.1]heptan-2-yl)-3,6-dimethyl-4-oxo-3,4-dihydroquinazolin-8-yl)ethyl)amino)-N-(methylsulfonyl)picolinamide | 2.53 min, 254 nm, MS (ES+)$^b$ $C_{29}H_{32}ClFN_8O_4S$, requires: 642.1, found: 643.2 $[M + H]^+$ |

TABLE E4-continued compound list prepared according to Route A in Example 4

| Cpd. ID | Structure | Name | LCMS |
|---|---|---|---|
| 767 | 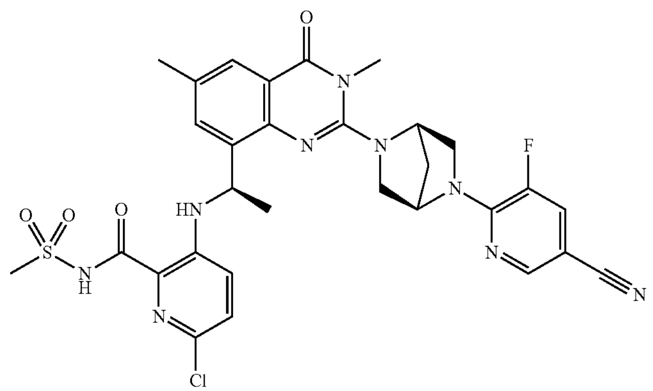 [SMILES: Cc1cc([C@@H](C)Nc2ccc(Cl)nc2C(=O)NS(C)(=O)=O)c2nc(N3C[C@H]4C[C@@H]3CN4c3ncc(C#N)cc3F)n(C)c(=O)c2c1] | 6-chloro-3-(((R)-1-(2-((1R,4R)-5-(5-cyano-3-fluoropyridin-2-yl)-2,5-diazabicyclo[2.2.1]heptan-2-yl)-3,6-dimethyl-4-oxo-3,4-dihydroquinazolin-8-yl)ethyl)amino)-N-(methylsulfonyl)picolinamide | 2.48 min, 220 nm, MS (ES+)[b] $C_{30}H_{29}ClFN_9O_4S$, requires: 665.2, found: 666.2 [M + H]+ |
| 768 | 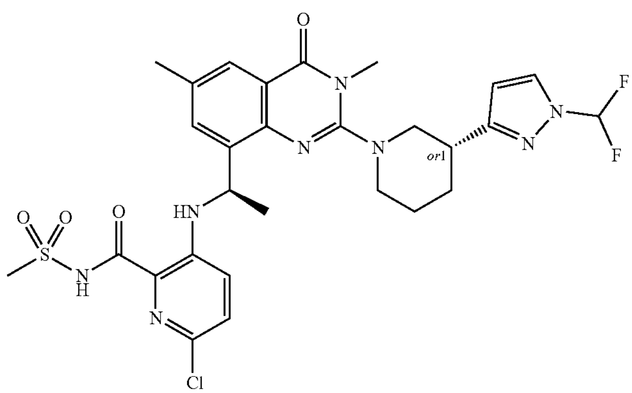 [SMILES: Cc1cc([C@@H](C)Nc2ccc(Cl)nc2C(=O)NS(C)(=O)=O)c2nc(N3CCC[C@@H](c4ccn(C(F)F)n4)C3)n(C)c(=O)c2c1] | 6-chloro-3-(((R)-1-(2-((R*)-3-(1-(difluoromethyl)-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.55 min, 210 nm, MS (ES+)[b] $C_{28}H_{31}ClF_2N_8O_4S$, requires: 648.1, found: 649.2 [M + H]+ |
| 769 | 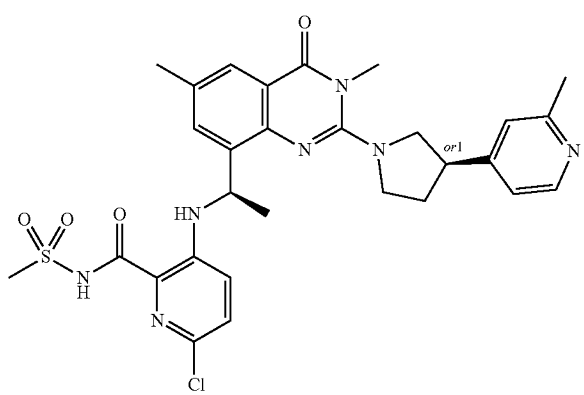 [SMILES: Cc1cc([C@@H](C)Nc2ccc(Cl)nc2C(=O)NS(C)(=O)=O)c2nc(N3CC[C@H](c4ccnc(C)c4)C3)n(C)c(=O)c2c1] | 6-chloro-3-(((R)-1-(3,6-dimethyl-2-((R*)-3-(2-methylpyridin-4-yl)pyrrolidin-1-yl)-4-oxo-3,4-dihydroquinazolin-8-yl)ethyl)amino)-N-(methylsulfonyl)picolinamide | 1.91 min, 254 nm, MS (ES+)[b] $C_{29}H_{32}ClN_7O_4S$, requires: 609.1, found: 610.3 [M + H]+ |

TABLE E4-continued compound list prepared according to Route A in Example 4

| Cpd. ID | Structure | Name | LCMS |
|---|---|---|---|
| 770 | 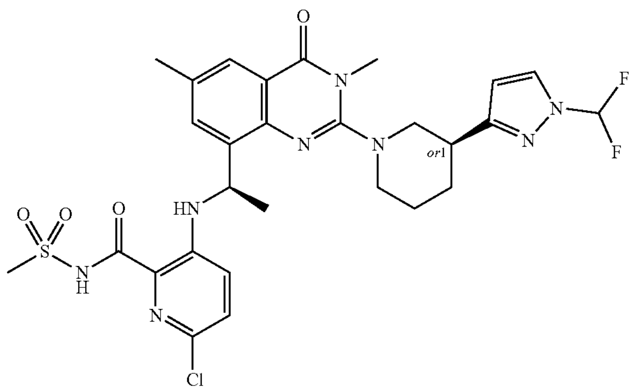 [SMILES: Cc1cc([C@@H](C)Nc2ccc(Cl)nc2C(=O)NS(C)(=O)=O)c2nc(N3CCC[C@H](c4ccn(C(F)F)n4)C3)n(C)c(=O)c2c1] | 6-chloro-3-(((R)-1-(2-((R*)-3-(1-(difluoromethyl)-1H-pyrazol-3-yl)piperidin-1-yl)-3,6-dimethyl-4-oxo-3,4-dihydroquinazolin-8-yl)ethyl)amino)-N-(methylsulfonyl)picolinamide | 2.53 min, 210 nm, MS (ES+)[b] $C_{28}H_{31}ClF_2N_8O_4S$, requires: 648.1, found: 649.2 [M + H]+ |
| 771 | 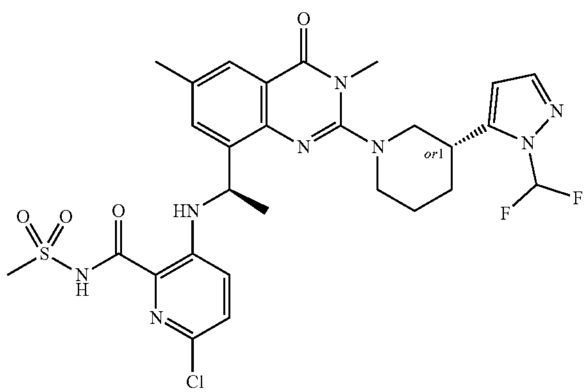 [SMILES: Cc1cc([C@@H](C)Nc2ccc(Cl)nc2C(=O)NS(C)(=O)=O)c2nc(N3CCC[C@@H](c4ccnn4C(F)F)C3)n(C)c(=O)c2c1] | 6-chloro-3-(((R)-1-(2-((R*)-3-(1-(difluoromethyl)-1H-pyrazol-5-yl)piperidin-1-yl)-3,6-dimethyl-4-oxo-3,4-dihydroquinazolin-8-yl)ethyl)amino)-N-(methylsulfonyl)picolinamide | 2.53 min, 210 nm, MS (ES+)[b] $C_{28}H_{31}ClF_2N_8O_4S$, requires: 648.1, found: 649.2 [M + H]+ |
| 772 | 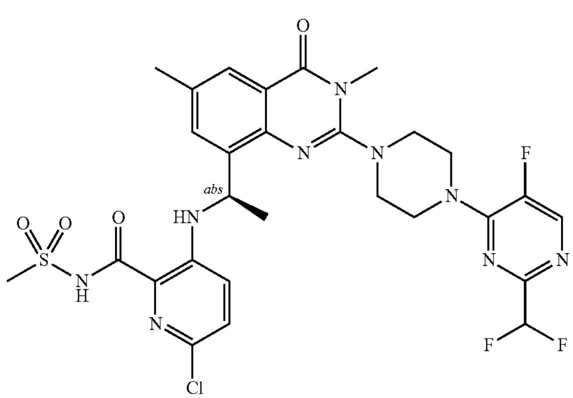 [SMILES: Cc1cc([C@@H](C)Nc2ccc(Cl)nc2C(=O)NS(C)(=O)=O)c2nc(N3CCN(c4nc(C(F)F)ncc4F)CC3)n(C)c(=O)c2c1] | (R)-6-chloro-3-((1-(2-(4-(2-(difluoromethyl)-5-fluoropyrimidin-4-yl)piperazin-1-yl)-3,6-dimethyl-4-oxo-3,4-dihydroquinazolin-8-yl)ethyl)amino)-N-(methylsulfonyl)picolinamide | 2.47 min, 254 nm, MS (ES+)[b] $C_{28}H_{29}ClF_3N_9O_4S$, requires: 679.1, found: 680.2 [M + H]+ |

[a]Observed utilizing LCMS Method A.
[b]Observed utilizing LCMS method B.
[c]Observed utilizing LCMS method C.

Example 5

Route B: Compound 1 (R)-6-chloro-3-((1-(2-(5-fluoroisoindolin-2-yl)-3,6-dimethyl-4-oxo-3,4-dihydroquinazolin-8-yl)ethyl)amino)-N-(methylsulfonyl)picolinamide

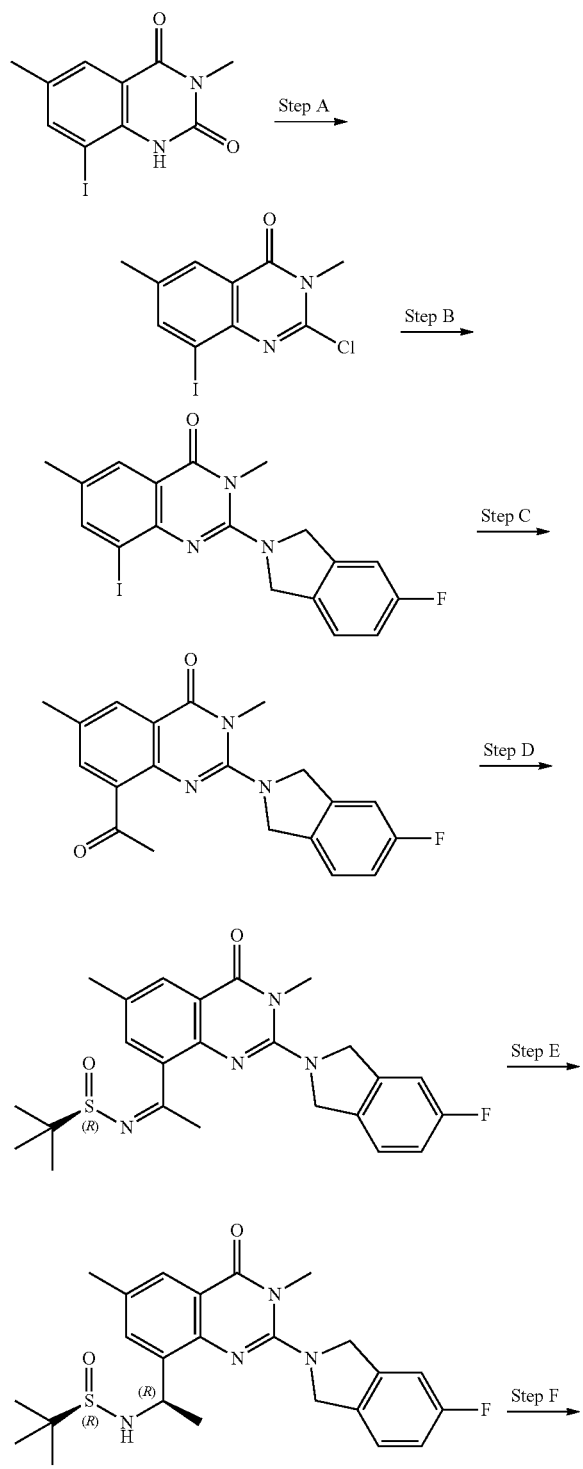

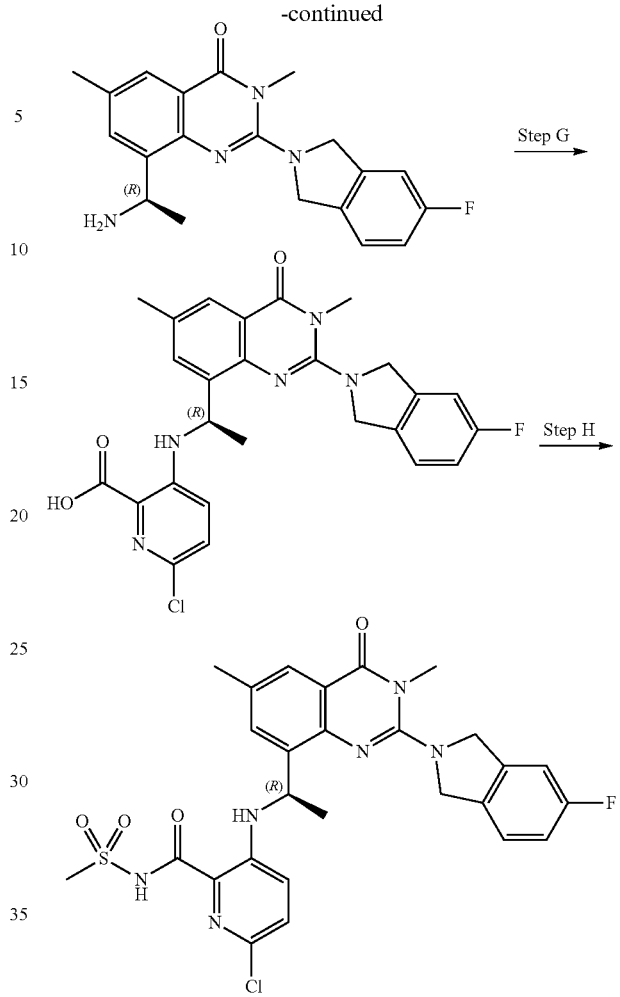

Step A: To a stirred solution of 8-iodo-3,6-dimethylquinazoline-2,4(1H,3H)-dione (350 g, 1.11 mol) in POCl$_3$ (3.11 L, 3.32 mol) was added DIPEA (386 g, 2.2 mol) at RT. The reaction mixture was heated at 100° C. for 24 h. After completion of the reaction as indicated by TLC (using 50% EtOAc: Hexane as a mobile phase), the resulting reaction mixture was cooled to room temperature and directly distilled under reduced pressure to afford the crude product. The liquid compound was poured into ice-cold water (1.00 L) to obtain a precipitate. The solid was filtered, washed with water, and dried under vacuum to afford 2-chloro-8-iodo-3,6-dimethylquinazolin-4(3H)-one as brown solid (320 g, 86%). LCMS MS (ES+) C$_{10}$H$_8$ClIN$_2$O requires: 333.9, found: 335.0 [M+H]$^+$. $^1$H NMR (DMSO-d$_6$, 400 MHz): δ 8.22 (d, J=1.6 Hz, 1H), 7.78 (dd, J=1.2, 2.0 Hz, 1H), 3.61 (s, 3H), 2.41 (s, 3H).

Step B: To a stirred solution of 2-chloro-8-iodo-3,6-dimethylquinazolin-4(3H)-one (320 g, 957 mmol) in DMSO (3.20 L) was added Et$_3$N (193 g, 1.91 mol) at RT. The reaction mixture was stirred for 10 min at which time 5-fluoroisoindoline (131 g, 957 mmol) was added. The resulting reaction mixture was stirred an additional 3 h at RT. After completion of the reaction as indicated by TLC (using 30% EtOAc: Hexane as a mobile phase), the resulting reaction mixture was poured into ice-cold water (1.00 L). The obtained solid was filtered, washed with cold water, and dried under vacuum to afford 2-(5-fluoroisoindolin-2-yl)-8- iodo-3,6-dimethylquinazolin-4(3H)-one as an off white solid (300 g, 72%). LCMS: MS (ES+) $C_{18}H_{15}FIN_3O$ requires: 435.0, found: 436.2 [M+H]$^+$. $^1$H NMR (DMSO-d$_6$, 400 MHz): δ 8.07 (d, J=2.0 Hz, 1H), 7.81 (dd, J=1.2, 2.0 Hz, 1H), 7.43-7.40 (m, 1H), 7.27 (dd, J=9.2, 2.4 Hz, 1H), 7.18-7.13 (m, 1H), 5.10-4.98 (m, 4H) 3.56 (s, 3H), 2.34 (s, 3H).

Step C: A solution of 2-(5-fluoroisoindolin-2-yl)-8-iodo-3,6-dimethylquinazolin-4(3H)-one (250 g, 575 mmol) in 1,4 Dioxane (2.50 mL) was prepared in 10 L glass three neck round bottom at room temperature. The reaction mixture was purged with N$_2$ gas for 15 minutes. After 15 min, tributyl (1-ethoxyvinyl) stannane (206 g, 575 mmol), and PdCl$_2$(PPh$_3$)$_2$ (40.0 g, 57.5 mmol) were added at same temperature. The reaction mixture was stirred at 120° C. for 16 h. After completion of the reaction as indicated by TLC (using 50% EtOAc: Hexane as a mobile phase), the reaction mixture was cooled to room temperature, 2N HCl (250 mL) was added, and the reaction mixture stirred at 50° C. for 30 min. After completion of the reaction as indicated by TLC (using 50% EtOAc in Hexane as a mobile phase), the reaction mixture was neutralized using aq. NaHCO$_3$ solution (1.50 L), filtered through a bed of celite, and washed with DCM (2.50 L). The filtrate was separated, and the organic layer dried over sodium sulfate before removal of volatiles under reduced pressure. The crude material was purified by trituration using 5% ethyl acetate in pentane to yield 8-acetyl-2-(5-fluoroisoindolin-2-yl)-3,6-dimethylquinazolin-4(3H)-one as a dark yellow solid (160 g, 79%). LCMS: MS (ES+) $C_{20}H_{18}FN_3O_2$ requires: 351.1, found: 352.6 [M+H]$^+$. $^1$H NMR (DMSO-d$_6$, 400 MHz): δ 8.00 (dd, J=2.0 Hz, 1H), 7.73-7.71 (m, 1H), 7.43-7.40 (m, 1H), 7.26 (dd, J=8.8, 2.0 Hz, 1H), 7.15 (dt, J=9.6, 2.8 Hz, 1H), 5.05-4.96 (m, 1H), 3.59 (s, 3H), 2.81 (s, 1H), 2.40 (s, 3H).

Step D: To a stirred solution of 8-acetyl-2-(5-fluoroisoindolin-2-yl)-3,6-dimethylquinazolin-4(3H)-one (100 g, 28.5 mmol) in Toluene (2.00 L) was added (R)-(+)-tert-Butylsulfinamide (86.2 g, 711 mmol) and Ti(O$^i$Pr)$_4$ (354 ml, 1.20 mol). A Dean-Stark apparatus was attached, and the resulting reaction mixture was stirred at 130° C. for 9 h. After completion of the reaction as indicated by TLC (using 50% EtOAc in Hexane as a mobile phase), the reaction mixture was cooled to room temperature. The reaction mixture was poured into water (500 mL), filtered through celite bed, and washed with DCM (1.00 L). The organic layer was separated, dried over sodium sulfate, and concentrated under reduced pressure to afford (R,Z)—N-(1-(2-(5-fluoroisoindolin-2-yl)-3,6-dimethyl-4-oxo-3,4-dihydroquinazolin-8-yl)ethylidene)-2-methylpropane-2-sulfinamide as a brown semi solid (142 g, Quantitative). LCMS: MS (ES+) $C_{24}H_{27}FN_4O_2S$ requires: 454.2, found: 455.3 [M+H]$^+$.

Step E: To a cooled −78° C. solution of (R,Z)—N-(1-(2-(5-fluoroisoindolin-2-yl)-3,6-dimethyl-4-oxo-3,4-dihydroquinazolin-8-yl)ethylidene)-2-methylpropane-2-sulfinamide (142 g, 312 mmol) in MeOH (1.42 L) and DCM (1.42 L) was added CeCl$_3$·7H$_2$O (105 g, 281 mmol) followed by portion wise addition of NaBH$_4$ (41.3 g, 1.09 mol). The reaction mixture was stirred at −78° C. for 6 h. After completion of the reaction as indicated by TLC (using 10% MeOH in DCM as a mobile phase), the reaction mixture was slowly poured into ice cold water (2.00 L), filtered through a bed of celite, and washed with DCM (6.00 L). The organic layer was separated, dried over sodium sulfate, and concentrated under reduced pressure. The crude material was purified by column chromatography (using neutral Al$_2$O$_3$ and 1% methanol in DCM as a mobile phase) to afford (R)—N—((R)-1-(2-(5-fluoroisoindolin-2-yl)-3,6-dimethyl-4-oxo-3,4-dihydroquinazolin-8-yl)ethyl)-2-methylpropane-2-sulfinamide as a yellow solid (26.0 g, 18% over two steps). LCMS: MS (ES+) $C_{24}H_{29}FN_4O_2S$ requires: 456.2, found: 457.3 [M+H]$^+$. $^1$H NMR (DMSO-d$_6$, 400 MHz): δ 7.71 (d, J=0.8 Hz, 1H), 7.62 (d, J=2.0 Hz, 1H), 7.41-7.38 (m, 1H), 7.24 (dd, J=8.8, 2.0 Hz, 1H), 7.12 (dt, J=9.2, 2.4 Hz, 1H), 5.74 (d, J=8.0 Hz, 1H), 5.13-5.10 (m, 1H), 5.04-4.90 (m, 4H), 3.56 (s, 3H), 2.37 (s, 3H), 1.46 (d, J=6.8 Hz, 3H), 1.10 (s, 9H).

Step F: To a cooled 0° C. solution of (R)—N—((R)-1-(2-(5-fluoroisoindolin-2-yl)-3,6-dimethyl-4-oxo-3,4-dihydroquinazolin-8-yl)ethyl)-2-methylpropane-2-sulfinamide (26.0 g, 56.9 mmol) in DCM (260 ml) was added 4M HCl in Dioxane (260 mL) dropwise. The cooling bath was removed, and the reaction mixture was stirred at room temperature for 16 h. After completion of the reaction as indicated by TLC (using 10% MeOH in DCM as a mobile phase), the reaction mixture was concentrated under reduced pressure. The crude residue was diluted with sat. NaHCO$_3$ solution and extracted with DCM. The organic layer was dried over sodium sulfate and concentrated under reduced pressure to afford (R)-8-(1-aminoethyl)-2-(5-fluoroisoindolin-2-yl)-3,6-dimethylquinazolin-4(3H)-one as a pale-yellow solid (9.50 g, 47%). LCMS: MS (ES+) $C_{20}H_{21}FN_4O$ requires: 352.2, found: 353.3 [M+H]$^+$. HPLC: 5.505 min, 96.44%, 254.0 nm. Chiral HPLC: 16.18 min, 95.69%, 236.0 nm. $^1$H NMR (DMSO-d$_6$, 400 MHz): δ 7.66 (s, 1H), 7.62 (s, 1H), 7.42-7.39 (m, 1H), 7.26 (d, J=9.2 Hz, 1H), 7.13 (dt, J=9.6, 2.4 Hz, 1H), 5.05-4.88 (m, 4H), 4.72-4.67 (m, 1H), 3.56 (s, 3H), 2.37 (s, 3H), 1.33 (d, J=6.4 Hz, 3H).

Step G: To a stirred solution of (R)-8-(1-aminoethyl)-2-(5-fluoroisoindolin-2-yl)-3,6-dimethylquinazolin-4(3H)-one (0.20 g, 0.56 mmol) and 6-Chloro-3-fluoropicolinic acid (0.08 g, 0.48 mmol) in DMSO (0.85 mL, 10 v) was added DIPEA (0.18 g, 0.14 mmol) at room temperature under nitrogen atmosphere. The resulting reaction mixture was stirred at 120° C. for 16 h. After completion of the reaction as indicated by TLC (using 5% MeOH:DCM as a mobile phase), the resulting reaction mixture was poured into water (10.0 mL) and extracted with EtOAc (3×10.0 mL). The combined organic layer was washed with brine solution, dried over Na$_2$SO$_4$, filtered, and concentrated under reduced pressure to afford crude product. The crude material was purified by flash column chromatography (C18 silica, 100% ACN) to afford (R)-6-chloro-3-((1-(2-(5-fluoroisoindolin-2-yl)-3,6-dimethyl-4-oxo-3,4-dihydroquinazolin-8-yl)ethyl)amino)picolinic acid as an off white solid (0.08 g, 33%). LCMS: MS (ES+) $C_{26}H_{23}ClFN_5O_3$ requires: 507.1, found: 508.3 [M+H]$^+$. $^1$H NMR (DMSO-d$_6$, 400 MHz): δ 12.99 (s, 1H), 8.46 (d, J=6.8 Hz, 1H), 7.72 (s, 1H), 7.46 (d, J=2.0 Hz, 1H), 7.42 (dd, J=8.4, 5.6 Hz, 1H), 7.31 (d, J=8.8 Hz, 1H), 7.26 (d, J=6.8 Hz, 1H), 7.18-7.13 (m, 1H), 7.06 (d, J=9.2 Hz, 1H), 5.43-5.39 (m, 1H), 5.10-4.96 (m, 4H), 3.59 (s, 3H), 2.32 (s, 3H), 1.61 (d, J=6.8 Hz, 3H).

Step H: To a stirred solution of (R)-6-chloro-3-((1-(2-(5-fluoroisoindolin-2-yl)-3,6-dimethyl-4-oxo-3,4-dihydroquinazolin-8-yl)ethyl)amino)picolinic acid (0.08 g, 0.15 mmol) in DCM (0.80 mL, 10 v) were added Methane sulfonamide (0.02 g, 0.18 mmol), EDC·HCl (0.06 g, 0.30 mmol) and DMAP (0.04 g, 0.34 mmol) at room temperature under nitrogen atmosphere. The resulting reaction mixture was stirred at room temperature for 12 h. After completion of the reaction as indicated by TLC (using 10% MeOH:DCM as a mobile phase), the resulting reaction mixture was directly concentrated under high vacuum to obtain crude product. The crude product was purified by flash column chromatography (C18 silica, 80% ACN in water) to afford (R)-6- chloro-3-((1-(2-(5-fluoroisoindolin-2-yl)-3,6-dimethyl-4-oxo-3,4-dihydroquinazolin-8-yl)ethyl)amino)-N-(methylsulfonyl)picolinamide as an off white solid (24.0 mg, 26%). LCMS: 2.739 min, 254.0 nm, MS (ES+) $C_{27}H_{26}ClFN_6O_4S$ requires: 584.1, found: 585.3 [M+H]+. HPLC: 5.38 min, 100%, 210.0 nm. Chiral HPLC: 12.706 min, 85.65%, 270.0 nm. $^1$H NMR (DMSO-d6, 400 MHz): δ 11.14 (s, 1H), 8.61 (br s, 1H), 7.73 (s, 1H), 7.52 (s, 1H), 7.43-7.39 (m, 2H), 7.26 (d, J=7.6 Hz, 1H), 7.16 (t, J=8.8 Hz, 2H), 5.41 (m, 1H), 5.11-5.03 (m, 2H), 5.03-4.95 (m, 2H), 3.59 (s, 3H), 3.35 (br s, 3H), 2.33 (s, 3H), 1.63 (d, J=6.0 Hz, 3H).

TABLE E5 compound list prepared according to Route B in Example 5

| Cpd. ID | Structure | Name | LCMS |
|---|---|---|---|
| 58 | 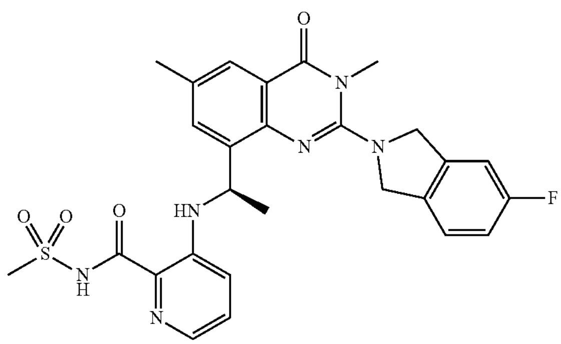 [SMILES: Cc1cc([C@@H](C)Nc2cccnc2C(=O)NS(C)(=O)=O)c2nc(N3Cc4ccc(F)cc4C3)n(C)c(=O)c2c1] | (R)-3-((1-(2-(5-fluoroisoindolin-2-yl)-3,6-dimethyl-4-oxo-3,4-dihydroquinazolin-8-yl)ethyl)amino)-N-(methylsulfonyl)picolinamide | 2.537 min, 254 nm, MS (ES+)$^a$ $C_{27}H_{27}FN_6O_4S$ requires: 550.2, found: 551.2 [M + H]+ |
| 59 | 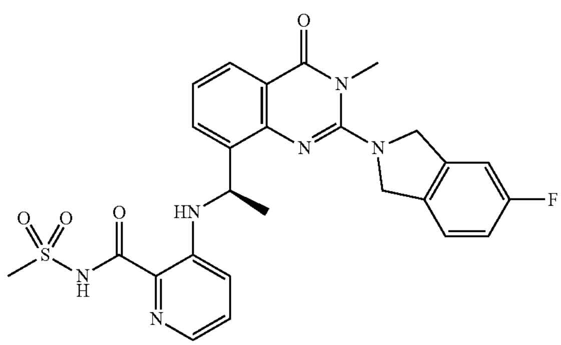 [SMILES: C[C@@H](Nc1cccnc1C(=O)NS(C)(=O)=O)c1cccc2c(=O)n(C)c(N3Cc4ccc(F)cc4C3)nc12] | (R)-3-((1-(2-(5-fluoroisoindolin-2-yl)-3-methyl-4-oxo-3,4-dihydroquinazolin-8-yl)ethyl)amino)-N-(methylsulfonyl)picolinamide | 2.42 min, 210 nm, MS (ES+)$^a$ $C_{26}H_{25}FN_6O_4S$ requires: 536.1, found: 537.3 [M + H]+ |
| 60 | 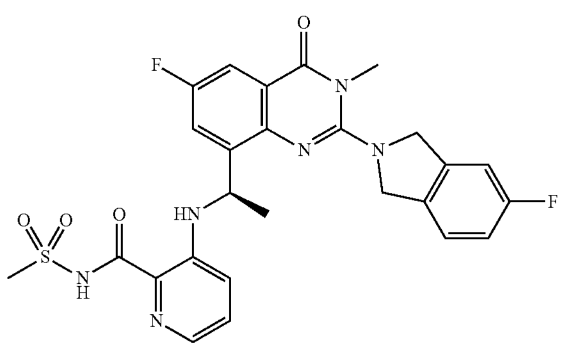 [SMILES: C[C@@H](Nc1cccnc1C(=O)NS(C)(=O)=O)c1cc(F)cc2c(=O)n(C)c(N3Cc4ccc(F)cc4C3)nc12] | (R)-3-((1-(6-fluoro-2-(5-fluoro-isoindolin-2-yl)-3-methyl-4-oxo-3,4-dihydroquinazolin-8-yl)ethyl)amino)-N-(methylsulfonyl)picolinamide | 2.43 min, 210 nm, MS (ES+)$^a$ $C_{26}H_{24}F_2N_6O_4S$ requires: 554.2, found: 555.4 [M + H]+ |
| 61 | 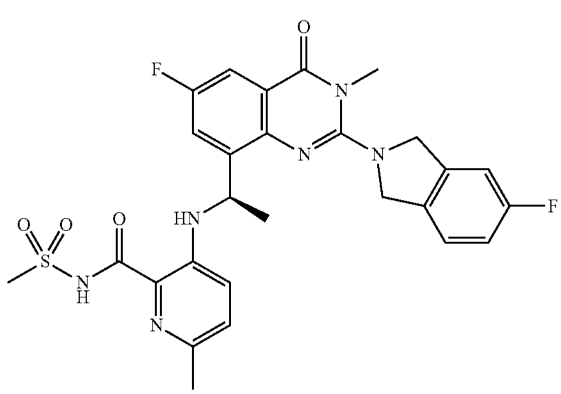 [SMILES: Cc1ccc(N[C@H](C)c2cc(F)cc3c(=O)n(C)c(N4Cc5ccc(F)cc5C4)nc23)c(C(=O)NS(C)(=O)=O)n1] | (R)-3-((1-(6-fluoro-2-(5-fluoroisoindolin-2-yl)-3-methyl-4-oxo-3,4-dihydroquinazolin-8-yl)ethyl)amino)-6-methyl-N-(methylsulfonyl)picolinamide | 2.503 min, 254 nm, MS (ES+)$^a$ $C_{27}H_{26}F_2N_6O_4S$ requires: 568.2, found: 569.3 [M + H]+ |

TABLE E5-continued compound list prepared according to Route B in Example 5

| Cpd. ID | Structure | Name | LCMS |
|---|---|---|---|
| 62 | 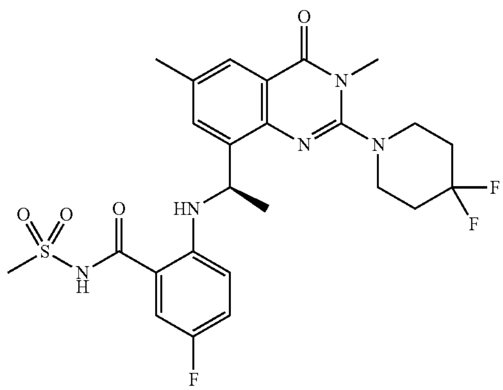 [SMILES: Cc1cc([C@@H](C)Nc2ccc(F)cc2C(=O)NS(C)(=O)=O)c2nc(N3CCC(F)(F)CC3)n(C)c(=O)c2c1] | (R)-2-((1-(2-(4,4-difluoropiperidin-1-yl)-3,6-dimethyl-4-oxo-3,4-dihydroquinazolin-8-yl)ethyl)amino)-5-fluoro-N-(methylsulfonyl)benzamide | 2.57 min, 254.0 nm, MS (ES+)$^a$ $C_{25}H_{28}F_3N_5O_4S$ requires: 551.1, found: 552.4 [M + H]$^+$. |
| 63 | 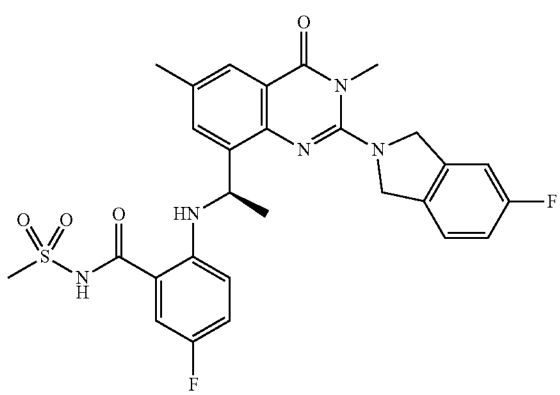 [SMILES: Cc1cc([C@@H](C)Nc2ccc(F)cc2C(=O)NS(C)(=O)=O)c2nc(N3Cc4ccc(F)cc4C3)n(C)c(=O)c2c1] | (R)-5-fluoro-2-((1-(2-(5-fluoroisoindolin-2-yl)-3,6-dimethyl-4-oxo-3,4-dihydroquinazolin-8-yl)ethyl)amino)-N-(methylsulfonyl)benzamide | 2.694 min, 254 nm, MS (ES+)$^a$ $C_{28}H_{27}F_2N_5O_4S$ requires: 567.61, found: 568.3 [M + H]$^+$ |
| 64 | 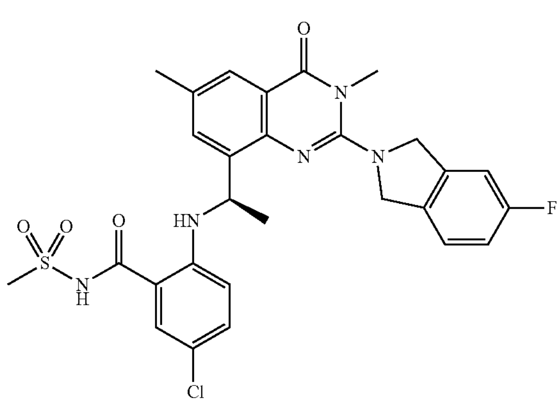 | (R)-5-chloro-2-((1-(2-(5-fluoroisoindolin-2-yl)-3,6-dimethyl-4-oxo-3,4-dihydroquinazolin-8-yl)ethyl)amino)-N-(methylsulfonyl)benzamide | 2.60 min, 254 nm, MS (ES+)$^a$ $C_{28}H_{27}ClFN_5O_4S$ requires: 583.2 found: 584.3 [M + H]$^+$ |

TABLE E5-continued compound list prepared according to Route B in Example 5

| Cpd. ID | Structure | Name | LCMS |
|---|---|---|---|
| 65 | 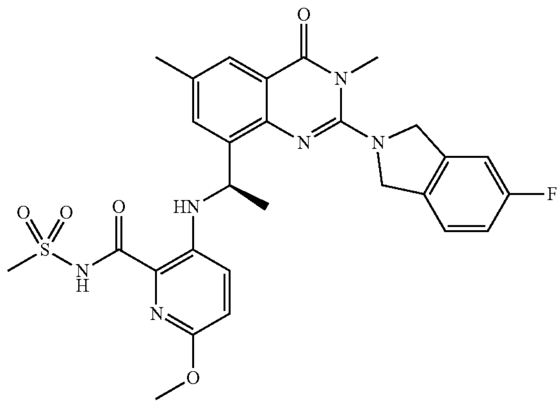 [SMILES: COc1ccc(N[C@H](C)c2cc(C)cc3c(=O)n(C)c(N4Cc5ccc(F)cc5C4)nc23)c(C(=O)NS(C)(=O)=O)n1] | (R)-3-((1-(2-(5-fluoroisoindolin-2-yl)-3,6-dimethyl-4-oxo-3,4-dihydroquinazolin-8-yl)ethyl)amino)-6-methoxy-N-(methylsulfonyl)picolinamide | 2.667 min, 254 nm, MS (ES+)$^a$ C$_{28}$H$_{29}$FN$_6$O$_5$S requires: 580.2, found: 581.6 [M + H]$^+$ |
| 66 | 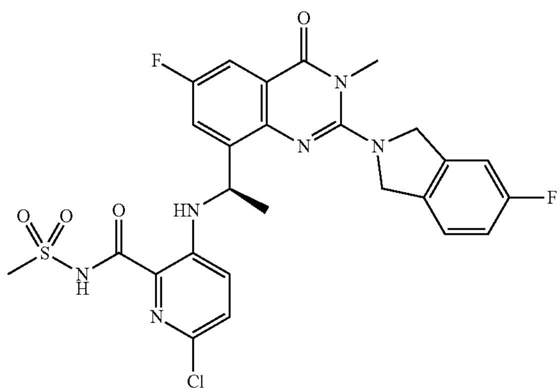 | (R)-6-chloro-3-((1-(6-fluoro-2-(5-fluoroisoindolin-2-yl)-3-methyl-4-oxo-3,4-dihydroquinazolin-8-yl)ethyl)amino)-N-(methylsulfonyl)picolinamide | 2.646 min, 210 nm, MS (ES+)$^a$ C$_{26}$H$_{23}$ClF$_2$N$_6$O$_4$S requires: 588.11, found: 588.8 [M + H]$^+$ |
| 67 | 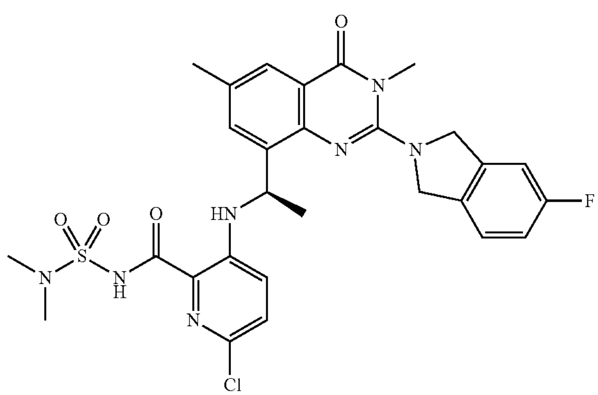 [SMILES: Cc1cc([C@@H](C)Nc2ccc(Cl)nc2C(=O)NS(=O)(=O)N(C)C)c2nc(N3Cc4ccc(F)cc4C3)n(C)c(=O)c2c1] | (R)-6-chloro-N-(N,N-dimethylsulfamoyl)-3-((1-(2-(5-fluoro-isoindolin-2-yl)-3,6-dimethyl-4-oxo-3,4-dihydroquinazolin-8-yl)ethyl)amino)picolinamide | 2.83 min, 220.0 nm, MS (ES+)$^b$ C$_{28}$H$_{29}$ClFN$_7$O$_4$S requires: 613.1, found: 614.2 [M + H]$^+$ |
| 68 | 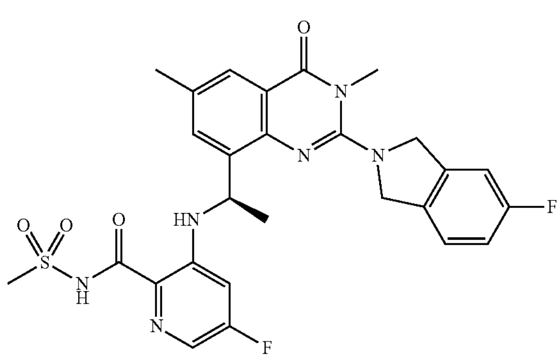 [SMILES: Cc1cc([C@@H](C)Nc2cc(F)cnc2C(=O)NS(C)(=O)=O)c2nc(N3Cc4ccc(F)cc4C3)n(C)c(=O)c2c1] | (R)-5-fluoro-3-((1-(2-(5-fluoro-isoindolin-2-yl)-3,6-dimethyl-4-oxo-3,4-dihydroquinazolin-8-yl)ethyl)amino)-N-(methylsulfonyl)picolinamide | 2.67 min, 254.0 nm, MS (ES+)$^b$ C$_{27}$H$_{26}$F$_2$N$_6$O$_4$S requires: 568.1, found: 569.0 [M + H]$^+$ |

TABLE E5-continued compound list prepared according to Route B in Example 5

| Cpd. ID | Structure | Name | LCMS |
|---|---|---|---|
| 69 | 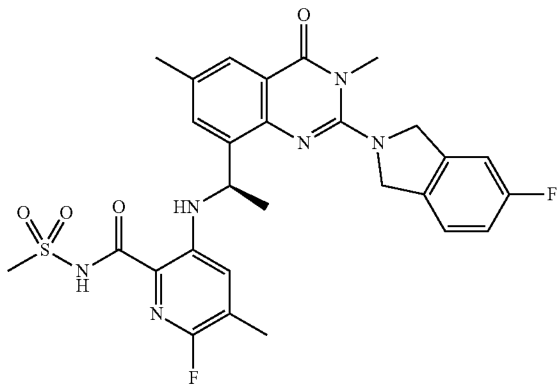 [SMILES: Cc1cc([C@@H](C)Nc2cc(C)c(F)nc2C(=O)NS(C)(=O)=O)c2nc(N3Cc4ccc(F)cc4C3)n(C)c(=O)c2c1] | (R)-6-fluoro-3-((1-(2-(5-fluoro-isoindolin-2-yl)-3,6-dimethyl-4-oxo-3,4-dihydroquinazolin-8-yl)ethyl)amino)-5-methyl-N-(methylsulfonyl)picolinamide | 2.63 min, 210.0 nm, MS (ES+)[b] $C_{28}H_{28}F_2N_6O_4S$ requires: 582.1, found: 583.4 [M + H]+ |
| 70 | 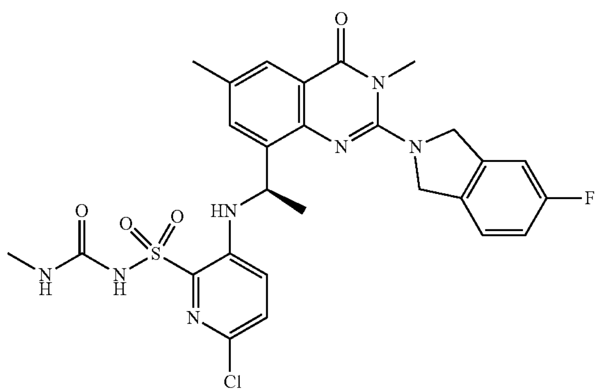 [SMILES: CNC(=O)NS(=O)(=O)c1nc(Cl)ccc1N[C@H](C)c1cc(C)cc2c(=O)n(C)c(N3Cc4ccc(F)cc4C3)nc12] | (R)-6-chloro-3-((1-(2-(5-fluoro-isoindolin-2-yl)-3,6-dimethyl-4-oxo-3,4-dihydroquinazolin-8-yl)ethyl)amino)-N-(methylcarbamoyl)pyridine-2-sulfonamide | 2.45 min, 265.0 nm, MS (ES+)[b] $C_{27}H_{27}ClFN_7O_4S$ requires: 599.1, found: 600.6 [M + H]+ |
| 71 | 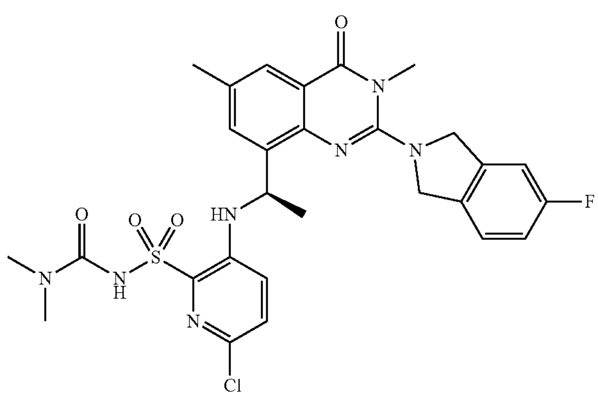 [SMILES: Cc1cc([C@@H](C)Nc2ccc(Cl)nc2S(=O)(=O)NC(=O)N(C)C)c2nc(N3Cc4ccc(F)cc4C3)n(C)c(=O)c2c1] | (R)-6-chloro-N-(dimethylcarbamoyl)-3-((1-(2-(5-fluoroisoindolin-2-yl)-3,6-dimethyl-4-oxo-3,4-dihydroquinazolin-8-yl)ethyl)amino)pyridine-2-sulfonamide | 2.53 min, MS (ES+)[b] $C_{28}H_{29}ClFN_7O_4S$ requires: 613.2, found: 614.4 [M + H]+ |
| 72 | 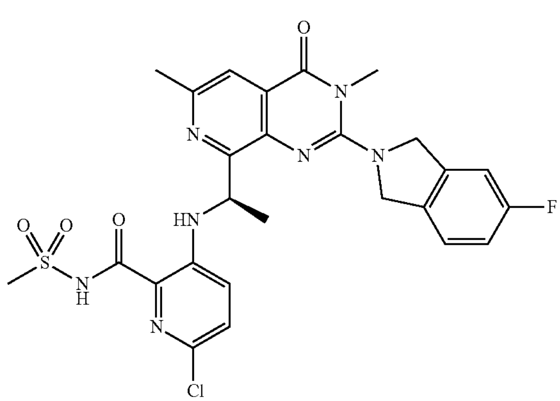 | (R)-6-chloro-3-((1-(2-(5-fluoroisoindolin-2-yl)-3,6-dimethyl-4-oxo-3,4-dihydro-pyrido[3,4-d]pyrimidin-8-yl)ethyl)amino)-N-(methylsulfonyl)picolinamide | 2.72 min, MS (ES+)[b] $C_{26}H_{25}ClFN_7O_4S$ requires: 585.1, found: 586.3 [M + H]+ |

TABLE E5-continued compound list prepared according to Route B in Example 5

| Cpd. ID | Structure | Name | LCMS |
|---|---|---|---|
| 73 | 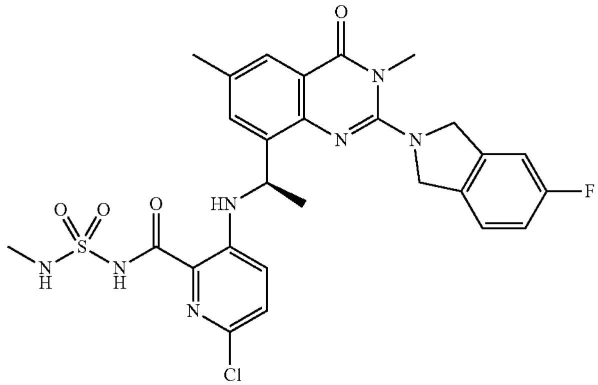 [SMILES: CNS(=O)(=O)NC(=O)c1nc(Cl)ccc1N[C@H](C)c1cc(C)cc2c(=O)n(C)c(N3Cc4ccc(F)cc4C3)nc12] | (R)-6-chloro-3-((1-(2-(5-fluoroisoindolin-2-yl)-3,6-dimethyl-4-oxo-3,4-dihydroquinazolin-8-yl)ethyl)amino)-N-(N-methylsulfamoyl)picolinamide | 2.606 min, MS (ES+)[b] $C_{27}H_{27}ClFN_7O_4S$ requires: 599.2, found: 600.6 [M+H]+ |
| 152 | 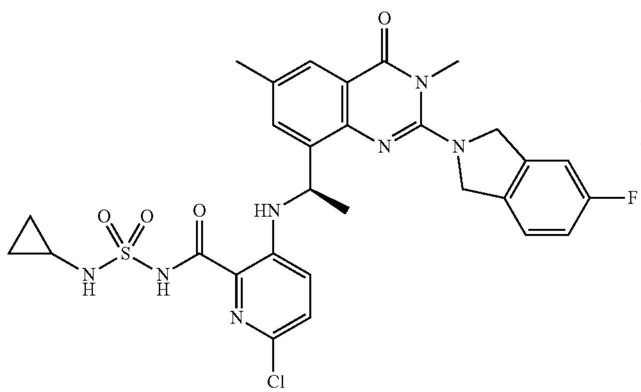 [SMILES: Cc1cc([C@@H](C)Nc2ccc(Cl)nc2C(=O)NS(=O)(=O)NC2CC2)c2nc(N3Cc4ccc(F)cc4C3)n(C)c(=O)c2c1] | (R)-6-chloro-N-(N-cyclopropylsulfamoyl)-3-((1-(2-(5-fluoroisoindolin-2-yl)-3,6-dimethyl-4-oxo-3,4-dihydroquinazolin-8-yl)ethyl)amino)picolinamide | 2.71 min, 210 nm, MS (ES+)[b] $C_{29}H_{29}ClFN_7O_4S$, requires: 626.2, found: 625.2 [M + H]+ |

[a]Observed utilizing LCMS Method A.
[b]Observed Utilizing LCMS Method B.

Example 6

Compound 74 (R)—N-((6-chloro-3-((1-(2-(5-fluoroisoindolin-2-yl)-3,6-dimethyl-4-oxo-3,4-dihydroquinazolin-8-yl)ethyl)amino)pyridin-2-yl)sulfonyl)acetamide

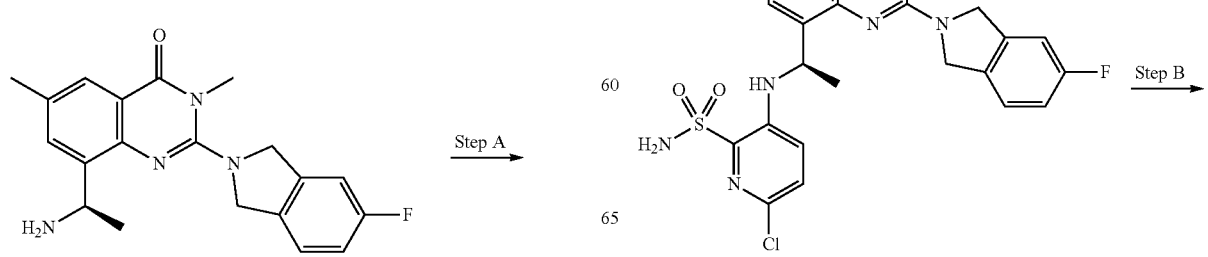

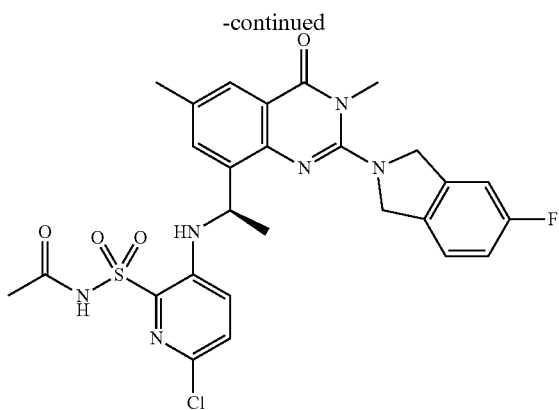

Step A: To a stirred solution of (R)-8-(1-aminoethyl)-2-(5-fluoroisoindolin-2-yl)-3,6-dimethylquinazolin-4(3H)-one (0.40 g, 1.13 mmol) and 6-chloro-3-fluoropyridine-2-sulfonamide (0.35 g, 1.70 mmol) in DMSO (4.00 mL), DIPEA (0.43 g, 3.40 mmol) was added and the resulting reaction mixture was stirred at 120° C. for 5 h. After completion of the reaction as indicated by TLC (using 50% EtOAc in Hexane as a mobile phase), the reaction mixture was poured into ice-water (50 mL) and the resulting precipitate was collected by vacuum filtration and dried over a vacuum. The crude material was purified by flash chromatography (silica gel, 230-400 mesh, 28% EtOAc/Hexane) to afford (R)-6-chloro-3-((1-(2-(5-fluoroisoindolin-2-yl)-3,6-dimethyl-4-oxo-3,4-dihydroquinazolin-8-yl)ethyl)amino)pyridine-2-sulfonamide as an off-white solid (0.21 g, 23%).

LCMS: MS (ES+) $C_{25}H_{24}ClFN_6O_3S$ requires: 542.1, found: 542.5 [M]$^+$. $^1$H NMR (DMSO-d$_6$, 400 MHz): δ 7.78-7.72 (m, 3H), 7.50 (d, J=2.0 Hz, 1H), 7.42-7.39 (m, 1H), 7.30 (d, J=8.8 Hz, 1H), 7.25 (dd, J=9.2, 2.4 Hz, 1H), 7.17-7.13 (m, 1H), 7.04 (d, J=9.2 Hz, 1H), 6.90 (d, J=6.8 Hz, 1H), 5.41-5.38 (m, 1H), 5.10-4.96 (m, 4H), 3.60 (s, 3H), 2.32 (s, 3H), 1.58 (d, J=6.4 Hz, 3H).

Step B: To a stirred solution of (R)-6-chloro-3-((1-(2-(5-fluoroisoindolin-2-yl)-3,6-dimethyl-4-oxo-3,4-dihydroquinazolin-8-yl)ethyl)amino)pyridine-2-sulfonamide (0.18 g, 0.33 mmol) in DCM (3 mL) was added Et$_3$N (0.050 g, 0.49 mmol) at 0° C. temperature. The reaction mixture was stirred at 0° C. for 5 min, followed by the dropwise addition of Acetic anhydride (0.05 g, 0.33 mmol). The resulting reaction mixture was stirred at RT for 3 h. After completion of the reaction as indicated by TLC (using 30% EtOAc in Hexane as a mobile phase), the reaction mixture was concentrated under a vacuum. The crude material was purified by reverse phase flash column chromatography (C18 silica, 72% ACN in water) to afford (R)—N-((6-chloro-3-((1-(2-(5-fluoroisoindolin-2-yl)-3,6-dimethyl-4-oxo-3,4-dihydroquinazolin-8-yl)ethyl)amino)456yridine-2-yl)sulfonyl)acetamide as an off-white solid (77.0 mg, 39%). LCMS: MS (ES+) $C_{27}H_{26}ClFN_6O_4S$ requires: 584.1, found: 584.5 [M+H]$^+$. HPLC: 9.77 min, 100%, 254.0 nm. CHIRAL HPLC: 100%, 1.98 min at 264.0 nm. NMR (400 MHz, DMSO) δ 12.49 (s, 1H), 7.72 (d, J=1.1 Hz, 1H), 7.65 (d, J=2.1 Hz, 1H), 7.40 (dd, J=8.4, 5.2 Hz, 1H), 7.34 (d, J=9.0 Hz, 1H), 7.24 (dd, J=9.0, 2.4 Hz, 1H), 7.21-7.09 (m, 2H), 7.03 (d, J=9.1 Hz, 1H), 5.46-5.35 (m, 1H), 5.13-4.93 (m, 4H), 3.60 (s, 3H), 2.32 (s, 3H), 1.99 (s, 3H), 1.59 (d, J=6.6 Hz, 3H).

TABLE E6 compound list prepared according to the procedure in Example 6

| Cpd. ID | Structure | Name | LCMS |
|---|---|---|---|
| 75 | 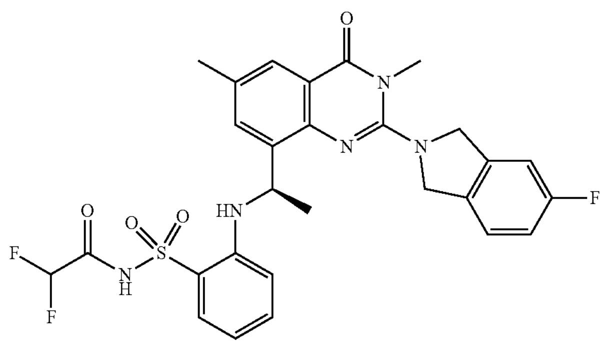 [SMILES: Cc1cc([C@@H](C)Nc2ccccc2S(=O)(=O)NC(=O)C(F)F)c2nc(N3Cc4ccc(F)cc4C3)n(C)c(=O)c2c1] | (R)-2,2-difluoro-N-((2-((1-(2-(5-fluoroisoindolin-2-yl)-3,6-dimethyl-4-oxo-3,4-dihydroquinazolin-8-yl)ethyl)amino)phenyl)sulfonyl)acetamide | 2.52 min, 254.0 nm, MS (ES+)$^a$ $C_{28}H_{26}F_3N_5O_4S$ requires: 585.17, found: 586.4 [M + H]$^+$ |
| 76 | 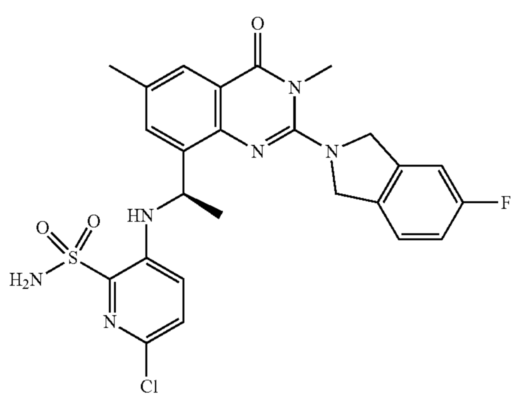 [SMILES: Cc1cc([C@@H](C)Nc2ccc(Cl)nc2S(N)(=O)=O)c2nc(N3Cc4ccc(F)cc4C3)n(C)c(=O)c2c1] | (R)-6-chloro-3-((1-(2-(5-fluoroisoindolin-2-yl)-3,6-dimethyl-4-oxo-3,4-dihydroquinazolin-8-yl)ethyl)amino)pyridine-2-sulfonamide | 2.36 min, 265.0 nm, MS (ES+)$^b$ $C_{25}H_{24}ClFN_6O_3S$ requires: 542.1, found: 543.3 [M + H]$^+$ |

TABLE E6-continued compound list prepared according to the procedure in Example 6

| Cpd. ID | Structure | Name | LCMS |
|---|---|---|---|
| 77 | 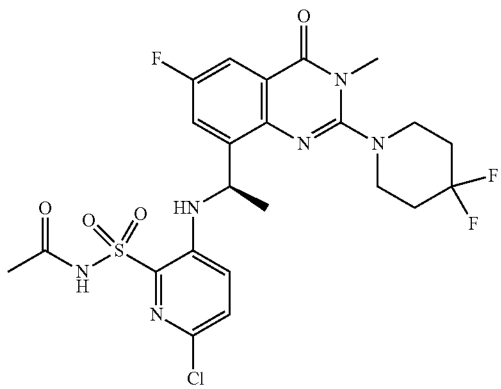 [SMILES: CC(=O)NS(=O)(=O)c1nc(Cl)ccc1N[C@H](C)c1cc(F)cc2c(=O)n(C)c(N3CCC(F)(F)CC3)nc12] | (R)-N-((6-chloro-3-((1-(2-(4,4-difluoropiperidin-1-yl)-6-fluoro-3-methyl-4-oxo-3,4-dihydroquinazolin-8-yl)ethyl)amino)pyridin-2-yl)sulfonyl)acetamide | 2.34 min, 210.0 nm, MS (ES+)[b] $C_{23}H_{24}ClF_3N_6O_4S$ requires: 572.1, found: 573.3 $[M + H]^+$ |
| 78 | 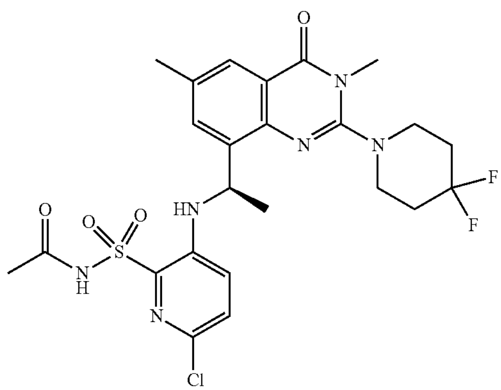 [SMILES: CC(=O)NS(=O)(=O)c1nc(Cl)ccc1N[C@H](C)c1cc(C)cc2c(=O)n(C)c(N3CCC(F)(F)CC3)nc12] | (R)-N-((6-chloro-3-((1-(2-(4,4-difluoropiperidin-1-yl)-3,6-dimethyl-4-oxo-3,4-dihydroquinazolin-8-yl)ethyl)amino)pyridin-2-yl)sulfonyl)acetamide | 2.271 min, 254.0 nm, MS (ES+)[b] $C_{24}H_{27}ClF_2N_6O_4S$ requires: 568.2, found: 569.8 $[M + H]^+$ |
| 79 | 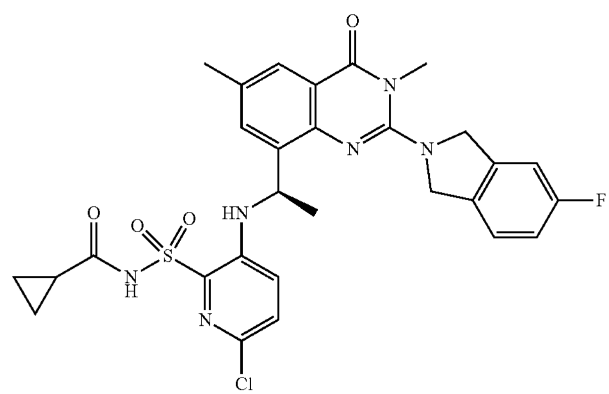 [SMILES: Cc1cc([C@@H](C)Nc2ccc(Cl)nc2S(=O)(=O)NC(=O)C2CC2)c2nc(N3Cc4ccc(F)cc4C3)n(C)c(=O)c2c1] | (R)-N-((6-chloro-3-((1-(2-(5-fluoroisoindolin-2-yl)-3,6-dimethyl-4-oxo-3,4-dihydroquinazolin-8-yl)ethyl)amino)pyridin-2-yl)sulfonyl)cyclopropanecarboxamide | 2.487 min, 254.0 nm, MS (ES+)[b] $C_{29}H_{28}ClFN_6O_4S$ requires: 610.2, found: 611.6 $[M + H]^+$ |
| 80 | 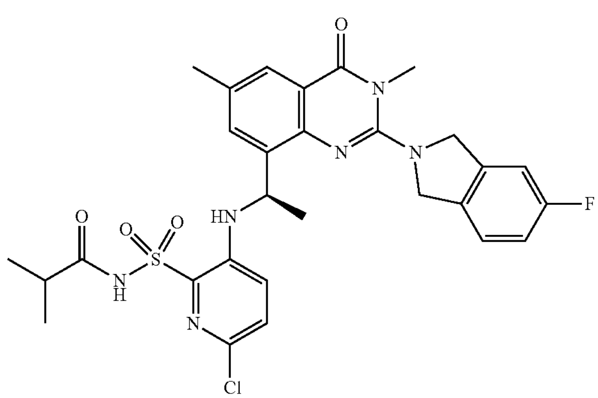 [SMILES: Cc1cc([C@@H](C)Nc2ccc(Cl)nc2S(=O)(=O)NC(=O)C(C)C)c2nc(N3Cc4ccc(F)cc4C3)n(C)c(=O)c2c1] | (R)-N-((6-chloro-3-((1-(2-(5-fluoroisoindolin-2-yl)-3,6-dimethyl-4-oxo-3,4-dihydroquinazolin-8-yl)ethyl)amino)pyridin-2-yl)sulfonyl)isobutyramide | 2.61 min, 210.0 nm, MS (ES+)[b] $C_{29}H_{30}ClFN_6O_4S$ requires: 612.2, found: 613.7 $[M + H]^+$ |

TABLE E6-continued compound list prepared according to the procedure in Example 6

| Cpd. ID | Structure | Name | LCMS |
|---|---|---|---|
| 81 | 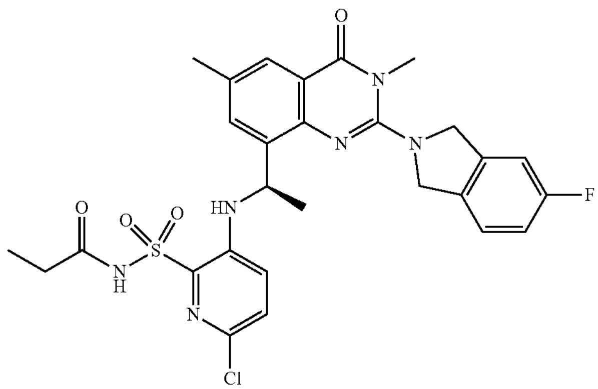 [SMILES: CCC(=O)NS(=O)(=O)c1nc(Cl)ccc1N[C@H](C)c1cc(C)cc2c(=O)n(C)c(N3Cc4ccc(F)cc4C3)nc12] | (R)-N-((6-chloro-3-((1-(2-(5-fluoroisoindolin-2-yl)-3,6-dimethyl-4-oxo-3,4-dihydroquinazolin-8-yl)ethyl)amino)pyridin-2-yl)sulfonyl)propionamide | 2.451 min, 210.0 nm, MS (ES+)[b] $C_{28}H_{28}ClFN_6O_4S$ requires: 598.2, found: 599.7 [M + H]+ |
| 131 | 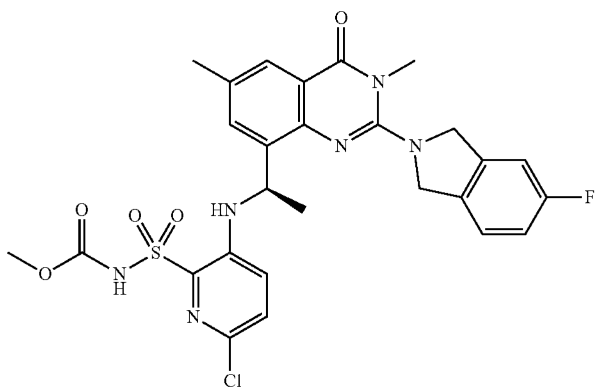 [SMILES: COC(=O)NS(=O)(=O)c1nc(Cl)ccc1N[C@H](C)c1cc(C)cc2c(=O)n(C)c(N3Cc4ccc(F)cc4C3)nc12] | methyl (R)-((6-chloro-3-((1-(2-(5-fluoroisoindolin-2-yl)-3,6-dimethyl-4-oxo-3,4-dihydroquinazolin-yl)ethyl)amino)pyridin-2-yl)sulfonyl) carbamate | 2.39 min, 210 nm, MS (ES+)[b] $C_{27}H_{26}ClFN_6O_5S$, requires: 601.5, found: 600.1 [M + H]+ |

[a] Observed utilizing LCMS Method A.
[b] Observed Utilizing LCMS Method B.

Example 7

Compound 82 (R)-6-chloro-3-((1-(2-(2,3-difluoro-phenyl)-3,6-dimethyl-4-oxo-3,4-dihydroquinazolin-8-yl)ethyl)amino)-N-(methylsulfonyl)picolinamide

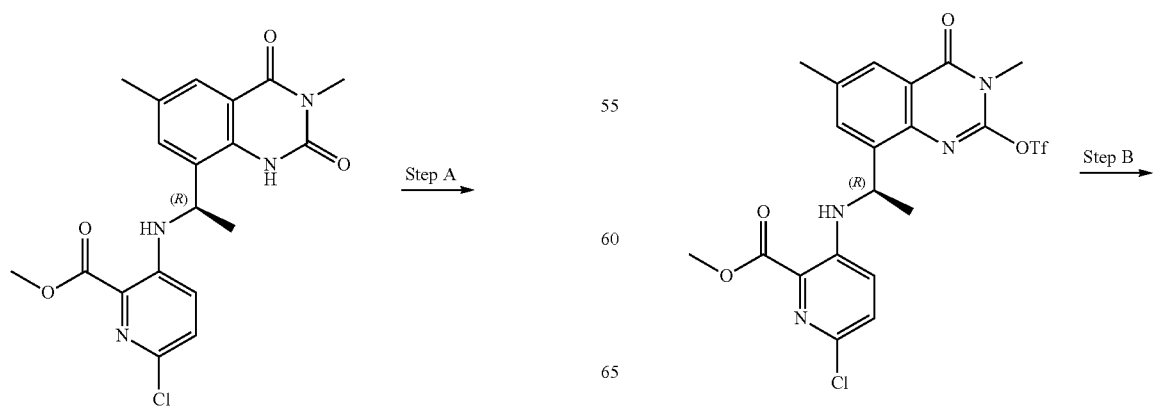

-continued

Step B

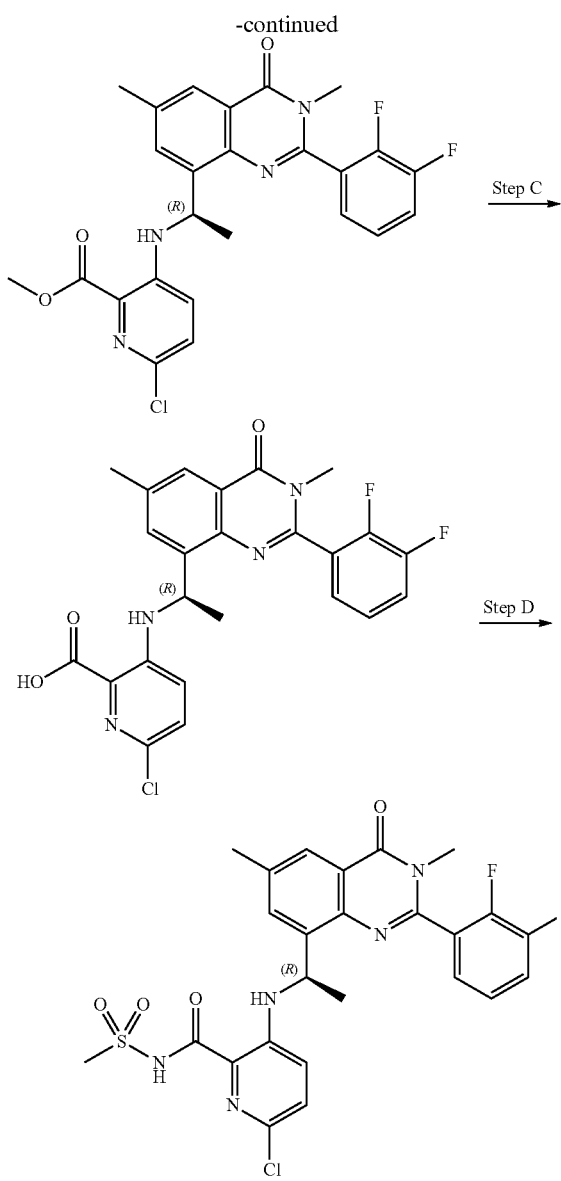

Step A: To a stirred solution of methyl (R)-6-chloro-3-((1-(3,6-dimethyl-2,4-dioxo-1,2,3,4-tetrahydroquinazolin-8-yl)ethyl)amino)picolinate (0.20 g, 0.49 mmol) in DCM (5.00 mL) was added pyridine (0.11 mL, 1.48 mmol) at 0° C. and reaction mixture was stirred for 15-20 min. To this reaction mixture, triflic anhydride (0.16 mL, 0.99 mmol) was added dropwise at 0° C. and the reaction was warmed to room temperature for 3 h. After completion of the reaction as indicated by TLC (using 50% EtOAc in Hexane as a mobile phase), the reaction mixture was concentrated under reduced pressure to afford crude. The crude was purified by flash chromatography (silica gel, 230-400 mesh, 15% EtOAc/Hexane) to afford methyl (R)-6-chloro-3-((1-(3,6-dimethyl-4-oxo-2-(((trifluoromethyl)sulfonyl)oxy)-3,4-dihydroquinazolin-8-yl)ethyl)amino)picolinate as an orange semi-solid (0.17 g, 64%). LCMS: MS (ES+) $C_{20}H_{18}ClF_3N_4O_6S$ requires: 534.1, found: 535.2 [M+H]⁺. ¹H NMR: (400 MHz, DMSO-d6): δ 8.20 (d, J=6.4 Hz, 1H), 7.88 (d, J=1.2 Hz, 1H), 7.69 (d, J=1.6 Hz, 1H), 7.30 (d, J=9.2 Hz, 1H), 6.87 (d, J=9.2 Hz, 1H), 5.27-5.23 (m, 1H), 3.89 (s, 3H), 3.51 (s, 3H), 2.40 (s, 3H), 1.58 (d, J=6.4 Hz, 3H).

Step B: To a stirred solution of methyl (R)-6-chloro-3-((1-(3,6-dimethyl-4-oxo-2-(((trifluoromethyl)sulfonyl)oxy)-3,4-dihydroquinazolin-8-yl)ethyl)amino)picolinate (0.10 g, 0.18 mmol) and 2,3-Difluorophenylboronic acid (0.02 g, 0.14 mmol) in Dioxane (3.00 mL) was added $Na_2CO_3$ (0.05 g, 0.56 mmol) in $H_2O$ (0.50 mL). The reaction mixture was purged with $N_2$ gas for 5 min followed by the addition of $PdCl_2$(dppf)·DCM (15.0 mg, 0.02 mmol). The reaction mixture was again purged with $N_2$ gas for 5 min and heated the reaction at 100° C. for 6 h. After completion of the reaction as indicated by TLC (using 50% EtOAc in Hexane as a mobile phase), the reaction mixture was poured onto ice-cold water (30 mL) and extracted with EtOAc (3×15 mL). The combined organic layer was dried over $Na_2SO_4$ and the solvent was removed in vacuo to afford crude. The crude was purified by flash chromatography (silica gel, 230-400 mesh, 15% EtOAc/Hexane) to afford methyl (R)-6-chloro-3-((1-(2-(2,3-difluorophenyl)-3,6-dimethyl-4-oxo-3,4-dihydroquinazolin-8-yl)ethyl)amino)picolinate as a light-brown solid (0.05 g, 54%). LCMS: MS (ES+) $C_{25}H_{21}ClF_2N_4O_3$ requires: 498.1, found: 499.2 [M+H]⁺. ¹H NMR: (DMSO-d6, 400 MHz): δ 8.35 (d, J=7.2 Hz, 1H), 7.94 (s, 1H), 7.72-7.70 (m, 2H), 7.60 (t, J=6.4 Hz, 1H), 7.48-7.46 (m, 1H), 7.31 (d, J=8.8 Hz, 1H), 7.12 (d, J=9.2 Hz, 1H), 5.39 (t, J=6.8 Hz, 1H), 3.81 (s, 3H), 3.37 (s, 3H), 2.43 (s, 3H), 1.59 (d, J=6.4 Hz, 3H).

Step C: To a stirred solution of methyl (R)-6-chloro-3-((1-(2-(2,3-difluorophenyl)-3,6-dimethyl-4-oxo-3,4-dihydroquinazolin-8-yl)ethyl)amino)picolinate (0.05 g, 0.10 mmol) in THF (2.00 mL) was added LiOH·H₂O (0.021 g, 0.50 mmol) in H₂O (0.5 mL) at room temperature. The reaction mixture was stirred at room temperature for 16 h. After completion of the reaction as indicated by TLC (using 5% MeOH in DCM as a mobile phase), the reaction mixture was concentrated under a vacuum to obtain the crude. The crude was diluted with water and acidified using 1N HCl to pH 5 and the resulting solid was collected by vacuum filtration. The solid was triturated using diethyl ether to afford (R)-6-chloro-3-((1-(2-(2,3-difluorophenyl)-3,6-dimethyl-4-oxo-3,4-dihydroquinazolin-8-yl)ethyl)amino)picolinic acid as an off-white solid (25.0 mg, 52%). LCMS: MS (ES+) $C_{24}H_{19}ClF_2N_4O_3$ requires: 484.1, found: 485.2 [M+H]⁺.

Step D: To a stirred solution of methanesulfonamide (0.004 g, 0.05 mmol) and DMAP (0.006 g, 0.05 mmol) in DCM (1.00 mL) was added (R)-6-chloro-3-((1-(2-(2,3-difluorophenyl)-3,6-dimethyl-4-oxo-3,4-dihydroquinazolin-8-yl)ethyl)amino)picolinic acid (0.025 g, 0.05 mmol) in one portion, followed by the addition of EDC·HCl (0.011 g, 0.06 mmol) in one portion at RT. The resulting reaction mixture was stirred at RT for 16 h. After completion of the reaction as indicated by TLC (using 10% MeOH in DCM as a mobile phase), the reaction mixture was concentrated under a vacuum to obtain the crude. Prep-HPLC purified the crude to afford (R)-6-chloro-3-((1-(2-(2,3-difluorophenyl)-3,6-dimethyl-4-oxo-3,4-dihydroquinazolin-8-yl)ethyl)amino)-N-(methylsulfonyl)picolinamide as a light-brown solid (0.07 g, 24%). PREP-HPLC: Column: Shim-Pack GIST C18 (250 mm×20 mm×5 μm). Mobile phase A: 0.05% Formic Acid in Water. Mobile phase B: Acetonitrile:Methanol (50:50). LCMS[a]: MS (ES+) $C_{25}H_{22}ClF_2N_5O_4S$ requires: 561.1, found: 562.2 [M+H]⁺. HPLC: 9.37 min, 99.15%, 210.0 nm. CHIRAL HPLC: 100%, 5.04 min at 270.0 nm. ¹H NMR: (DMSO-d6, 400 MHz): δ 11.10 (s, 1H), 8.73 (br s, 1H), 7.94 (s, 1H), 7.73-7.69 (m, 2H), 7.67-7.62 (m, 1H), 7.48-7.43 (m, 1H), 7.30 (br s, 1H), 7.09 (br s, 1H), 5.41 (t, J=6.0 Hz, 1H), 3.37 (s, 3H), 3.27 (br s, 3H), 2.43 (s, 3H), 1.58 (d, J=6.8 Hz, 3H).

TABLE E7 compound list prepared according to the procedure in Example 7

| Cpd. ID | Structure | Name | LCMSb |
|---|---|---|---|
| 83 | 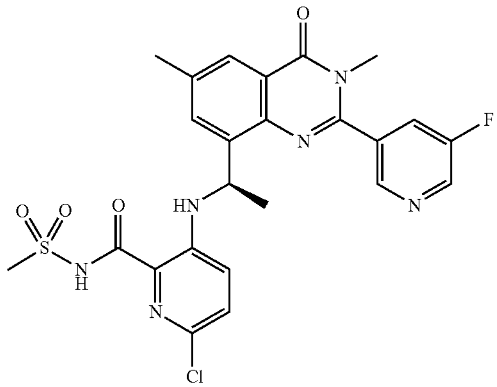 [SMILES: Cc1cc([C@@H](C)Nc2ccc(Cl)nc2C(=O)NS(C)(=O)=O)c2nc(-c3cncc(F)c3)n(C)c(=O)c2c1] | (R)-6-chloro-3-((1-(2-(5-fluoropyridin-3-yl)-3,6-dimethyl-4-oxo-3,4-dihydroquinazolin-8-yl)ethyl)amino)-N-(methylsulfonyl)picolinamide | 2.33 min, 254.0 nm, MS (ES+) $C_{24}H_{22}ClFN_6O_4S$ requires: 544.1, found: 544.6 $[M + H]^+$ |
| 84 | 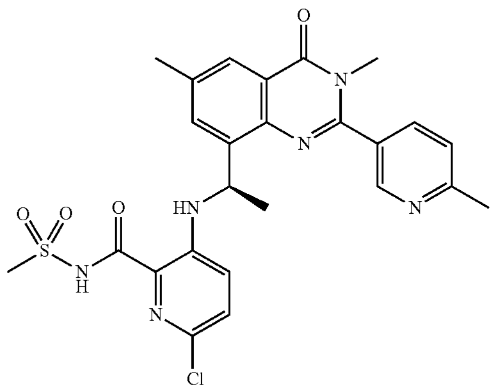 | (R)-6-chloro-3-((1-(3,6-dimethyl-2-(6-methylpyridin-3-yl)-4-oxo-3,4-dihydroquinazolin-8-yl)ethyl)amino)-N-(methylsulfonyl)picolinamide | 2.03 min, 230.0 nm, MS (ES+) $C_{25}H_{25}CN_6O_4S$ requires: 540.1, found: 541.3 $[M + H]^+$ |
| 85 | 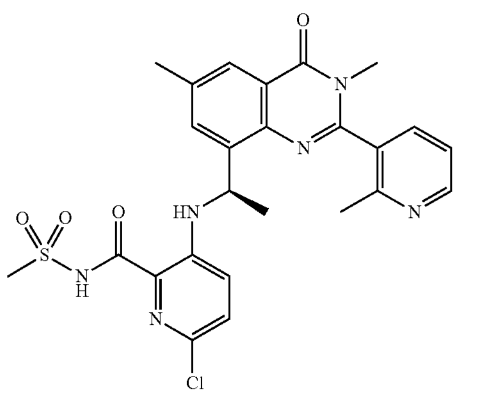 [SMILES: Cc1cc([C@@H](C)Nc2ccc(Cl)nc2C(=O)NS(C)(=O)=O)c2nc(-c3cccnc3C)n(C)c(=O)c2c1] | (R)-6-chloro-3-((1-(3,6-dimethyl-2-(2-methylpyridin-3-yl)-4-oxo-3,4-dihydroquinazolin-8-yl)ethyl)amino)-N-(methylsulfonyl)picolinamide | 1.99 min, 265.0 nm, MS (ES+) $C_{25}H_{25}ClN_6O_4S$ requires: 540.1, found: 541.3 $[M + H]^+$ |
| 86 | 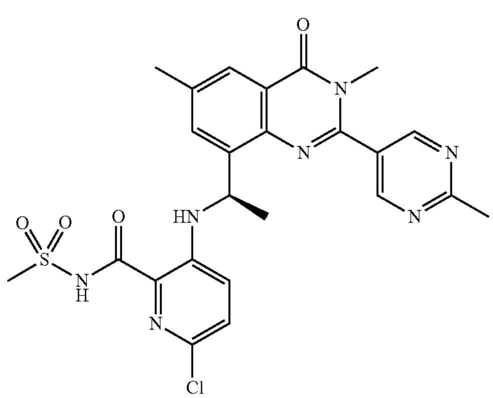 | (R)-6-chloro-3-((1-(3,6-dimethyl-2-(2-methylpyrimidin-5-yl)-4-oxo-3,4-dihydroquinazolin-8-yl)ethyl)amino)-N-(methylsulfonyl)picolinamide | 2.03 min, 265.0 nm, MS (ES+) $C_{24}H_{24}ClN_7O_4S$ requires: 541.1, found: 542.2 $[M + H]^+$ |

TABLE E7-continued compound list prepared according to the procedure in Example 7

| Cpd. ID | Structure | Name | LCMSb |
|---|---|---|---|
| 87 | 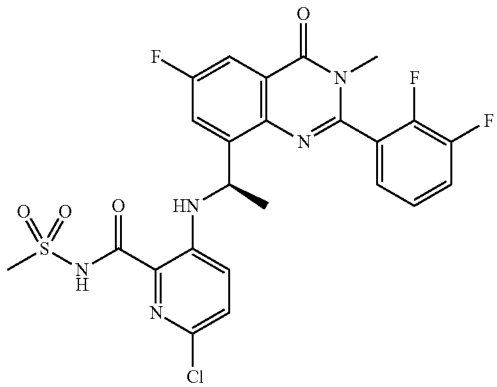 [SMILES: C[C@@H](Nc1ccc(Cl)nc1C(=O)NS(C)(=O)=O)c1cc(F)cc2c(=O)n(C)c(-c3cccc(F)c3F)nc12] | (R)-6-chloro-3-((1-(2-(2,3-difluorophenyl)-6-fluoro-3-methyl-4-oxo-3,4-dihydroquinazolin-8-yl)ethyl)amino)-N-(methylsulfonyl)picolinamide | 2.42 min, 254.0 nm, MS (ES+) $C_{24}H_{19}ClF_3N_5O_4S$ requires: 565.0, found: 566.1 $[M + H]^+$ |
| 88 | 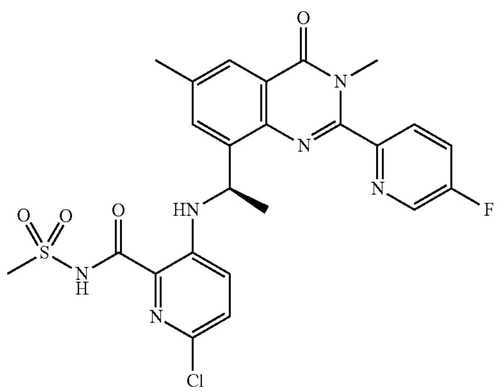 [SMILES: Cc1cc([C@@H](C)Nc2ccc(Cl)nc2C(=O)NS(C)(=O)=O)c2nc(-c3ccc(F)cn3)n(C)c(=O)c2c1] | (R)-6-chloro-3-((1-(2-(5-fluoropyridin-2-yl)-3,6-dimethyl-4-oxo-3,4-dihydroquinazolin-8-yl)ethyl)amino)-N-(methylsulfonyl)picolinamide | 2.32 min, 265.0 nm, MS (ES+) $C_{24}H_{22}ClFN_6O_4S$ requires: 544.1, found: 545.3 $[M + H]^+$ |
| 89 | 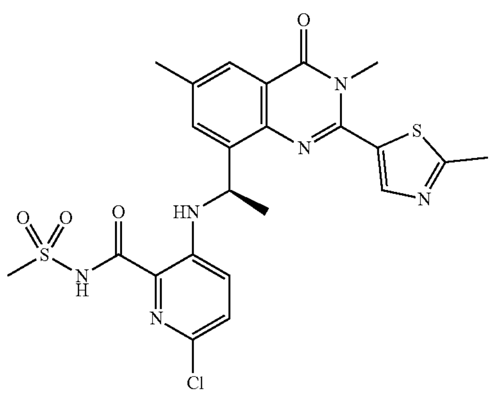 | (R)-6-chloro-3-((1-(3,6-dimethyl-2-(2-methylthiazol-5-yl)-4-oxo-3,4-dihydroquinazolin-8-yl)ethyl)amino)-N-(methylsulfonyl)picolinamide | 2.29 min, 254.0 nm, MS (ES+) $C_{23}H_{23}ClN_6O_4S_2$ requires: 546.0, found: 547.3 $[M + H]^+$ |
| 90 | 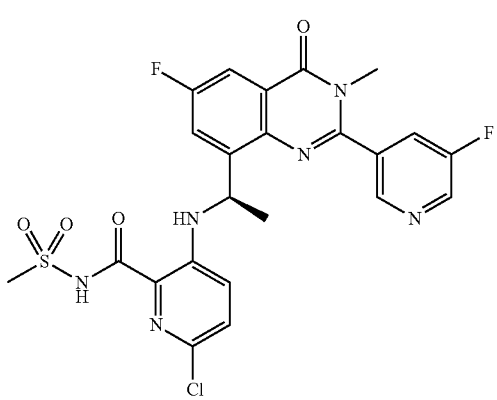 [SMILES: C[C@@H](Nc1ccc(Cl)nc1C(=O)NS(C)(=O)=O)c1cc(F)cc2c(=O)n(C)c(-c3cncc(F)c3)nc12] | (R)-6-chloro-3-((1-(6-fluoro-2-(5-fluoropyridin-3-yl)-3-methyl-4-oxo-3,4-dihydroquinazolin-8-yl)ethyl)amino)-N-(methylsulfonyl)picolinamide | 2.19 min, 254.0 nm, MS (ES+) $C_{23}H_{19}ClF_2N_6O_4S$ requires: 548.0, found: 549.2 $[M + H]^+$ |

TABLE E7-continued compound list prepared according to the procedure in Example 7

| Cpd. ID | Structure | Name | LCMSb |
|---|---|---|---|
| 91 | 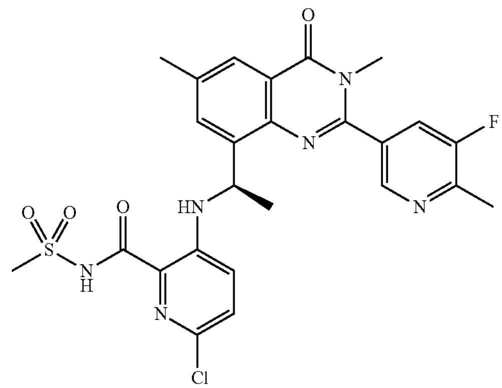 | (R)-6-chloro-3-((1-(2-(5-fluoro-6-methylpyridin-3-yl)-3,6-dimethyl-4-oxo-3,4-dihydroquinazolin-8-yl)ethyl)amino)-N-(methylsulfonyl)picolinamide | 2.231 min, 254.0 nm, MS (ES+) $C_{25}H_{24}ClFN_6O_4S$ requires: 558.1, found: 559.4 $[M + H]^+$ |
| 92 | 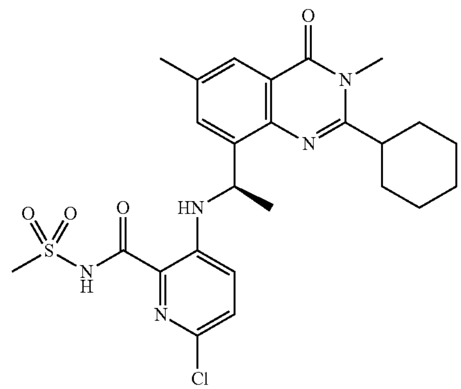 [SMILES: Cc1cc([C@@H](C)Nc2ccc(Cl)nc2C(=O)NS(C)(=O)=O)c2nc(C3CCCCC3)n(C)c(=O)c2c1] | (R)-6-chloro-3-((1-(2-cyclohexyl-3,6-dimethyl-4-oxo-3,4-dihydroquinazolin-8-yl)ethyl)amino)-N-(methylsulfonyl)picolinamide | 2.81 min, 210 nm, MS (ES+)[b] $C_{25}H_{30}ClN_5O_4S$ requires: 531.7, found: 532.5 $[M + H]^+$ |
| 773 | 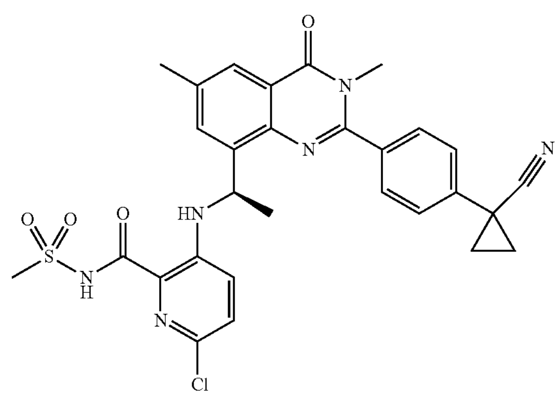 [SMILES: Cc1cc([C@@H](C)Nc2ccc(Cl)nc2C(=O)NS(C)(=O)=O)c2nc(-c3ccc(C4(C#N)CC4)cc3)n(C)c(=O)c2c1] | (R)-6-chloro-3-((1-(2-(4-(1-cyanocyclopropyl)phenyl)-3,6-dimethyl-4-oxo-3,4-dihydroquinazolin-8-yl)ethyl)amino)-N-(methylsulfonyl)picolinamide | 2.44 min, 254 nm, MS (ES+)[b] $C_{29}H_{27}ClN_6O_4S$, requires: 590.1, found: 591.1 $[M + H]^+$ |
| 774 | 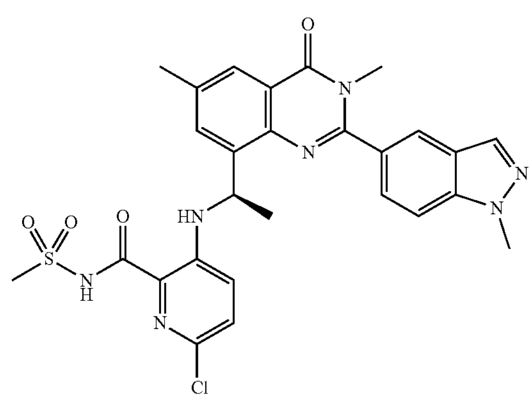 [SMILES: Cc1cc([C@@H](C)Nc2ccc(Cl)nc2C(=O)NS(C)(=O)=O)c2nc(-c3ccc4c(cnn4C)c3)n(C)c(=O)c2c1] | (R)-6-chloro-3-((1-(3,6-dimethyl-2-(1-methyl-1H-indazol-5-yl)-4-oxo-3,4-dihydroquinazolin-8-yl)ethyl)amino)-N-(methylsulfonyl)picolinamide | 2.22 min, 270 nm, MS (ES+)[b] $C_{27}H_{26}ClN_7O_4S$, requires: 579.1, found: 580.1 $[M + H]^+$ |

TABLE E7-continued compound list prepared according to the procedure in Example 7

| Cpd. ID | Structure | Name | LCMSb |
|---|---|---|---|
| 775 | 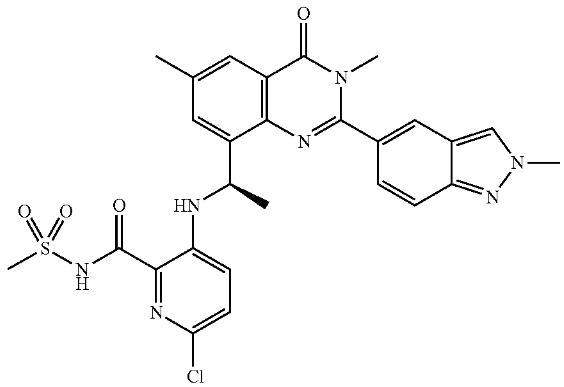 | (R)-6-chloro-3-((1-(3,6-dimethyl-2-(2-methyl-2H-indazol-5-yl)-4-oxo-3,4-dihydroquinazolin-8-yl)ethyl)amino)-N-(methylsulfonyl)picolinamide | 2.18 min, 254 nm, MS (ES+)[b] $C_{27}H_{26}ClN_7O_4S$, requires: 579.1, found: 580.1 [M + H]+ |
| 776 | 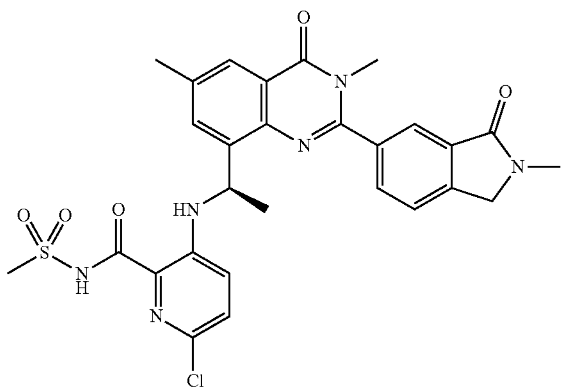 | (R)-6-chloro-3-((1-(3,6-dimethyl-2-(2-methyl-3-oxoisoindolin-5-yl)-4-oxo-3,4-dihydroquinazolin-8-yl)ethyl)amino)-N-(methylsulfonyl)picolinamide | 2.15 min, 210 nm, MS (ES+)[b] $C_{28}H_{27}ClN_6O_5S$, requires: 594.2, found: 595.2 [M + H]+ |
| 777 | 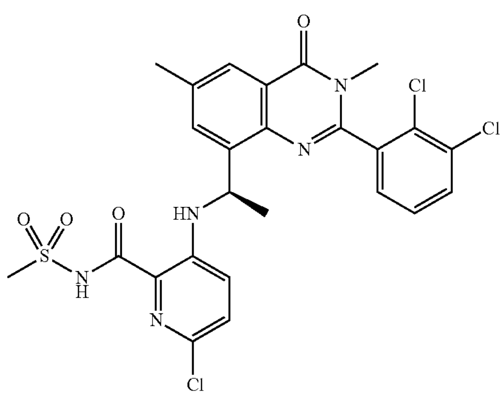 [SMILES: Cc1cc([C@@H](C)Nc2ccc(Cl)nc2C(=O)NS(C)(=O)=O)c2nc(-c3cccc(Cl)c3Cl)n(C)c(=O)c2c1] | (R)-6-chloro-3-((1-(2-(2,3-dichlorophenyl)-3,6-dimethyl-4-oxo-3,4-dihydroquinazolin-8-yl)ethyl)amino)-N-(methylsulfonyl)picolinamide | 2.67 min, 210 nm, MS (ES+)[b] $C_{25}H_{22}Cl_3N_5O_4S$, requires: 593.1, found: 594.0 [M + H]+ |
| 778 | 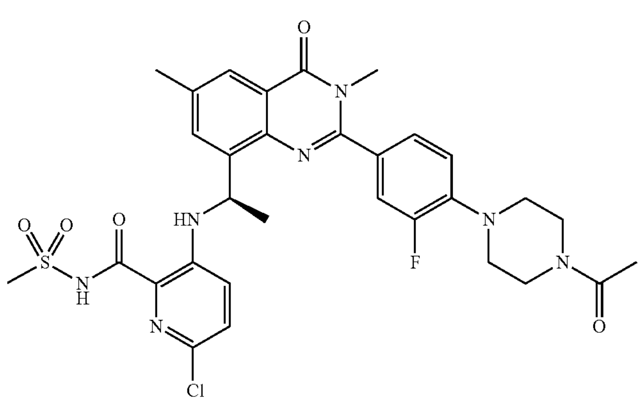 | (R)-3-((1-(2-(4-(4-acetylpiperazin-1-yl)-3-fluorophenyl)-3,6-dimethyl-4-oxo-3,4-dihydroquinazolin-8-yl)ethyl)amino)-6-chloro-N-(methylsulfonyl)picolinamide | 2.28 min, 270 nm, MS (ES+)[b] $C_{31}H_{33}ClFN_7O_5S$, requires: 669.1, found: 670.2 [M + H]+ |

TABLE E7-continued compound list prepared according to the procedure in Example 7

| Cpd. ID | Structure | Name | LCMSb |
|---|---|---|---|
| 779 | 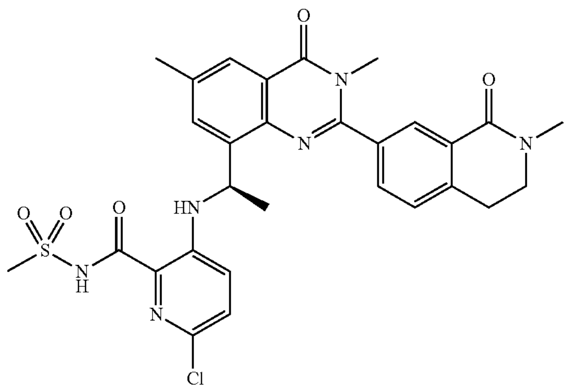 | (R)-6-chloro-3-((1-(3,6-dimethyl-2-(2-methyl-1-oxo-1,2,3,4-tetrahydroisoquinolin-7-yl)-4-oxo-3,4-dihydroquinazolin-8-yl)ethyl)amino)-N-(methylsulfonyl)picolinamide | 2.26 min, 254 nm, MS (ES+)[b] $C_{29}H_{29}ClN_6O_5S$, requires: 608.1, found: 609.2 [M + H]+ |
| 780 | 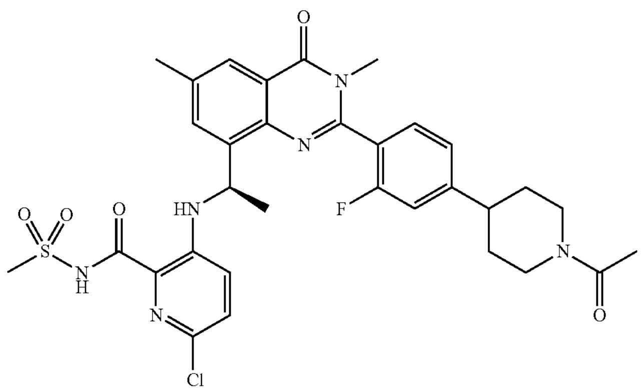 [SMILES: CC(=O)N1CCC(c2ccc(-c3nc4c([C@@H](C)Nc5ccc(Cl)nc5C(=O)NS(C)(=O)=O)cc(C)cc4c(=O)n3C)c(F)c2)CC1] | (R)-3-((1-(2-(4-(1-acetylpiperidin-4-yl)-2-fluorophenyl)-3,6-dimethyl-4-oxo-3,4-dihydroquinazolin-8-yl)ethyl)amino)-6-chloro-N-(methylsulfonyl)picolinamide | 2.33 min, 270 nm, MS (ES+)[b] $C_{32}H_{34}ClFN_6O_5S$, requires: 668.2, found: 669.2 [M + H]+ |
| 781 | 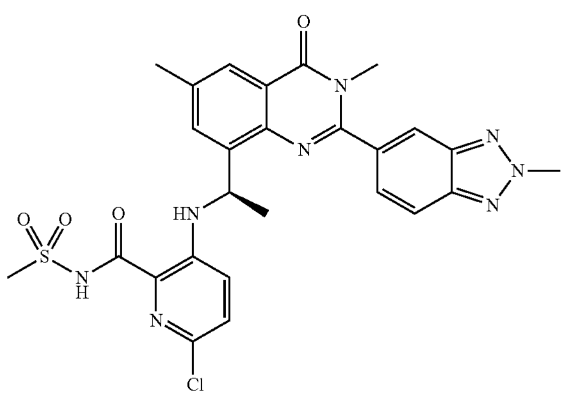 | (R)-6-chloro-3-((1-(3,6-dimethyl-2-(2-methyl-2H-benzo[d][1,2,3]triazol-5-yl)-4-oxo-3,4-dihydroquinazolin-8-yl)ethyl)amino)-N-(methylsulfonyl)picolinamide | 3.33 min, 254 nm, MS (ES+)[c] $C_{26}H_{25}ClN_8O_4S$, requires: 580.1, found: 581.1 [M + H]+ |
| 782 | 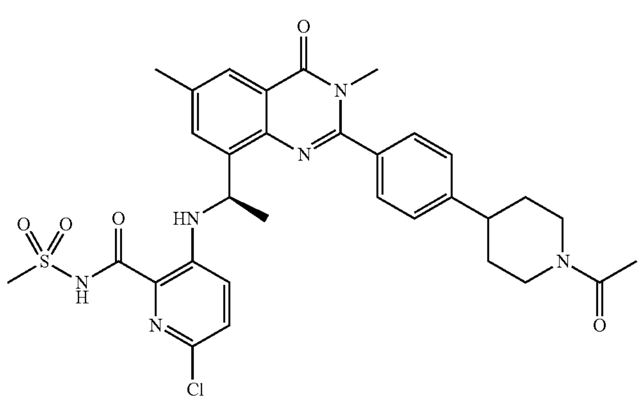 [SMILES: CC(=O)N1CCC(c2ccc(-c3nc4c([C@@H](C)Nc5ccc(Cl)nc5C(=O)NS(C)(=O)=O)cc(C)cc4c(=O)n3C)cc2)CC1] | (R)-3-((1-(2-(4-(1-acetylpiperidin-4-yl)phenyl)-3,6-dimethyl-4-oxo-3,4-dihydroquinazolin-8-yl)ethyl)amino)-6-chloro-N-(methylsulfonyl)picolinamide | 2.30 min, 270 nm, MS (ES+)[b] $C_{32}H_{35}ClN_6O_5S$, requires: 650.2, found: 651.2 [M + H]+ |

TABLE E7-continued compound list prepared according to the procedure in Example 7

| Cpd. ID | Structure | Name | LCMSb |
|---|---|---|---|
| 783 | 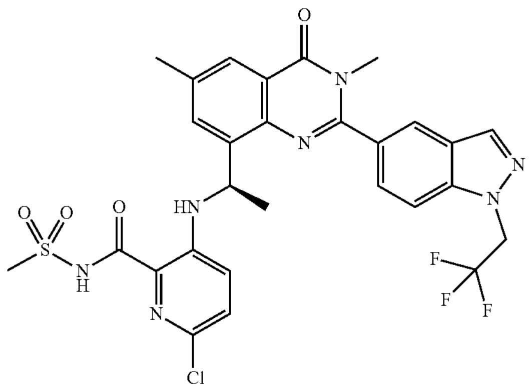 [SMILES: Cc1cc([C@@H](C)Nc2ccc(Cl)nc2C(=O)NS(C)(=O)=O)c2nc(-c3ccc4c(cnn4CC(F)(F)F)c3)n(C)c(=O)c2c1] | (R)-6-chloro-3-((1-(3,6-dimethyl-4-oxo-2-(1-(2,2,2-trifluoroethyl)-1H-indazol-5-yl)-3,4-dihydroquinazolin-8-yl)ethyl)amino)-N-(methylsulfonyl)picolinamide | 2.37 min, 254 nm, MS (ES+)$^b$ $C_{28}H_{25}ClF_3N_7O_4S$, requires: 647.1, found: 648.2 [M + H]$^+$ |
| 784 | 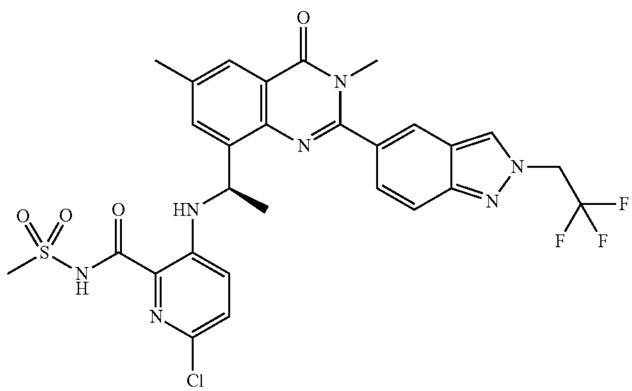 [SMILES: Cc1cc([C@@H](C)Nc2ccc(Cl)nc2C(=O)NS(C)(=O)=O)c2nc(-c3ccc4nn(CC(F)(F)F)cc4c3)n(C)c(=O)c2c1] | (R)-6-chloro-3-((1-(3,6-dimethyl-4-oxo-2-(2-(2,2,2-trifluoroethyl)-2H-indazol-5-yl)-3,4-dihydroquinazolin-8-yl)ethyl)amino)-N-(methylsulfonyl)picolinamide | 2.37 min, 254 nm, MS (ES+)$^b$ $C_{28}H_{25}ClF_3N_7O_4S$, requires: 647.1, found: 648.2 [M + H]$^+$ |
| 785 | 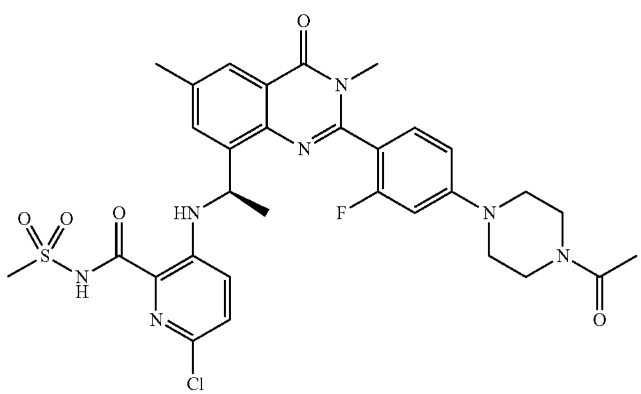 [SMILES: CC(=O)N1CCN(c2ccc(-c3nc4c([C@@H](C)Nc5ccc(Cl)nc5C(=O)NS(C)(=O)=O)cc(C)cc4c(=O)n3C)c(F)c2)CC1] | (R)-3-((1-(2-(4-(4-acetylpiperazin-1-yl)-2-fluorophenyl)-3,6-dimethyl-4-oxo-3,4-dihydroquinazolin-8-yl)ethyl)amino)-6-chloro-N-(methylsulfonyl)picolinamide | 2.33 min, 254 nm, MS (ES+)$^b$ $C_{31}H_{33}ClFN_7O_5S$, requires: 669.1, found: 670.2 [M + H]$^+$ |
| 786 | 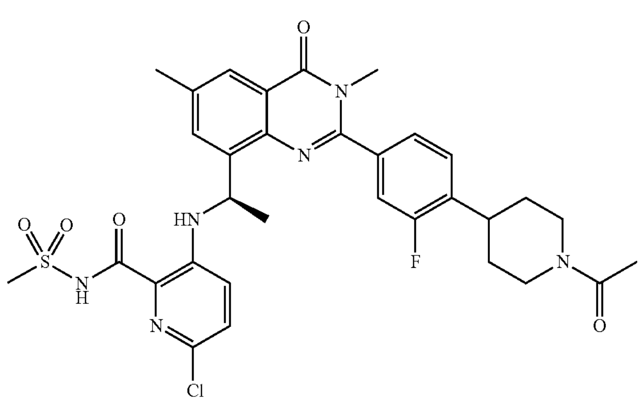 [SMILES: CC(=O)N1CCC(c2ccc(-c3nc4c([C@@H](C)Nc5ccc(Cl)nc5C(=O)NS(C)(=O)=O)cc(C)cc4c(=O)n3C)cc2F)CC1] | (R)-3-((1-(2-(4-(1-acetylpiperidin-4-yl)-3-fluorophenyl)-3,6-dimethyl-4-oxo-3,4-dihydroquinazolin-8-yl)ethyl)amino)-6-chloro-N-(methylsulfonyl)picolinamide | 2.34 min, 265 nm, MS (ES+)$^b$ $C_{32}H_{34}ClFN_6O_5S$, requires: 668.2, found 669.2 [M + H]$^+$ |

TABLE E7-continued compound list prepared according to the procedure in Example 7

| Cpd. ID | Structure | Name | LCMSb |
|---|---|---|---|
| 787 | 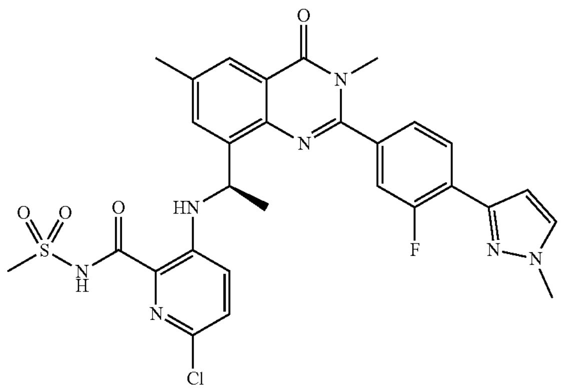 [SMILES: Cc1cc([C@@H](C)Nc2ccc(Cl)nc2C(=O)NS(C)(=O)=O)c2nc(-c3ccc(-c4ccn(C)n4)c(F)c3)n(C)c(=O)c2c1] | (R)-6-chloro-3-((1-(2-(3-fluoro-4-(1-methyl-1H-pyrazol-3-yl)phenyl)-3,6-dimethyl-4-oxo-3,4-dihydroquinazolin-8-yl)ethyl)amino)-N-(methylsulfonyl)picolinamide | 2.48 min, 254 nm, MS (ES+)[b] $C_{29}H_{27}ClFN_7O_4S$, requires: 623.1, found: 624.1 [M + H]+ |
| 788 | 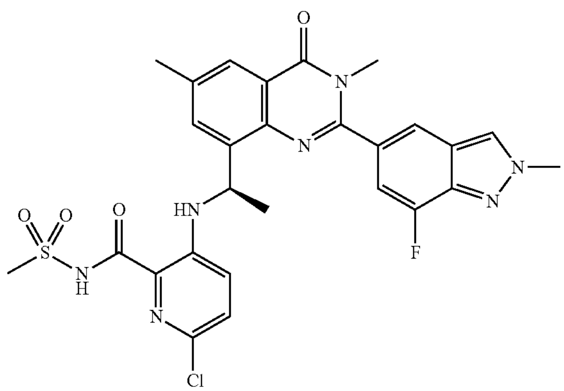 | (R)-6-chloro-3-((1-(2-(7-fluoro-2-methyl-2H-indazol-5-yl)-3,6-dimethyl-4-oxo-3,4-dihydroquinazolin-8-yl)ethyl)amino)-N-(methylsulfonyl)picolinamide | 2.32 min, 254 nm, MS (ES+)[b] $C_{27}H_{25}ClFN_7O_4S$, requires: 597.1, found: 598.1 [M + H]+ |
| 789 | 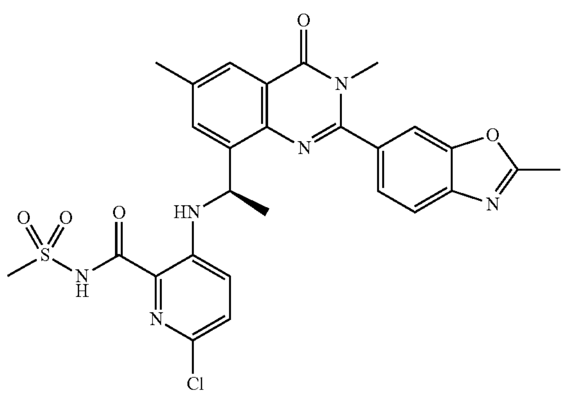 | (R)-6-chloro-3-((1-(3,6-dimethyl-2-(2-methylbenzo[d]oxazol-6-yl)-4-oxo-3,4-dihydroquinazolin-8-yl)ethyl)amino)-N-(methylsulfonyl)picolinamide | 2.38 min, 254 nm, MS (ES+)[b] $C_{27}H_{25}ClN_6O_5S$, requires: 580.1, found: 581.1 [M + H]+ |
| 790 | 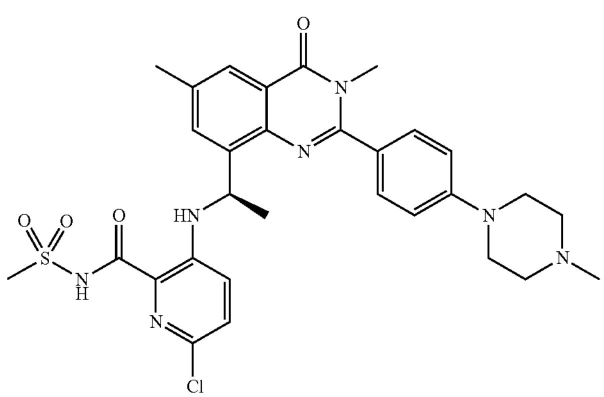 | (R)-6-chloro-3-((1-(3,6-dimethyl-2-(4-(4-methylpiperazin-1-yl)phenyl)-4-oxo-3,4-dihydroquinazolin-8-yl)ethyl)amino)-N-(methylsulfonyl)picolinamide | 1.98 min, 254 nm, MS (ES+)[b] $C_{30}H_{34}ClN_7O_4S$, requires: 623.2, found: 624.2 [M + H]+ |

TABLE E7-continued compound list prepared according to the procedure in Example 7

| Cpd. ID | Structure | Name | LCMSb |
|---|---|---|---|
| 791 | 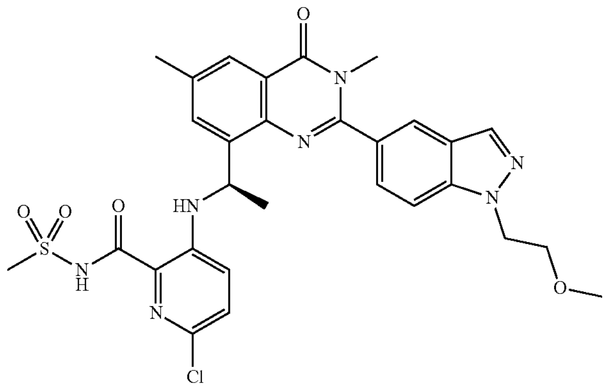 | (R)-6-chloro-3-((1-(2-(1-(2-methoxyethyl)-1H-indazol-5-yl)-3,6-dimethyl-4-oxo-3,4-dihydroquinazolin-8-yl)ethyl)amino)-N-(methylsulfonyl)picolinamide | 2.25 min, 254 nm, MS (ES+)[b] $C_{29}H_{30}ClN_7O_5S$, requires: 623.1, found: 624.1 [M + H]+ |
| 792 | 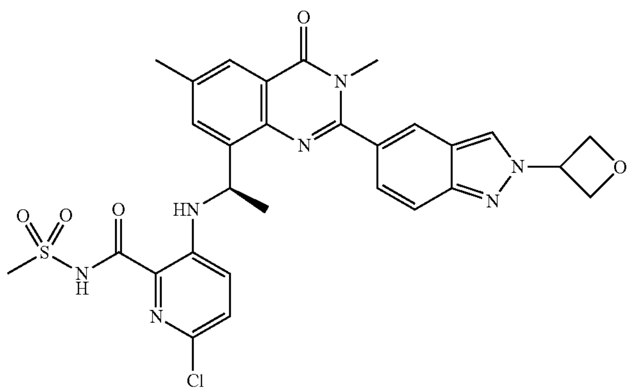 [SMILES: Cc1cc([C@@H](C)Nc2ccc(Cl)nc2C(=O)NS(C)(=O)=O)c2nc(-c3ccc4nn(C5COC5)cc4c3)n(C)c(=O)c2c1] | (R)-6-chloro-3-((1-(3,6-dimethyl-2-(2-(oxetan-3-yl)-2H-indazol-5-yl)-4-oxo-3,4-dihydroquinazolin-8-yl)ethyl)amino)-N-(methylsulfonyl)picolinamide | 2.14 min, 254 nm, MS (ES+)[b] $C_{29}H_{28}ClN_7O_5S$, requires: 621.1, found: 622.1 [M + H]+ |
| 793 | 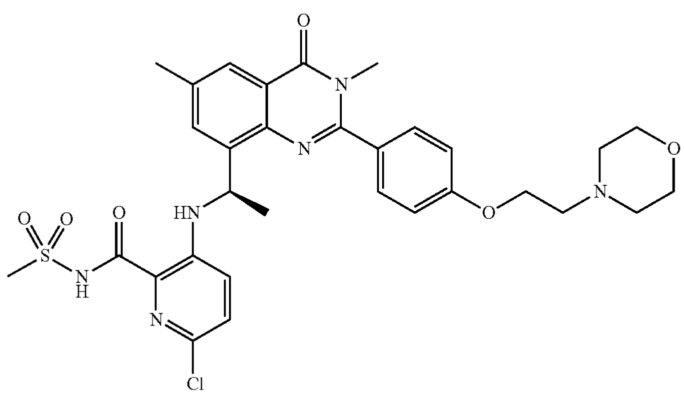 [SMILES: Cc1cc([C@@H](C)Nc2ccc(Cl)nc2C(=O)NS(C)(=O)=O)c2nc(-c3ccc(OCCN4CCOCC4)cc3)n(C)c(=O)c2c1] | (R)-6-chloro-3-((1-(3,6-dimethyl-2-(4-(2-morpholinoethoxy)phenyl)-4-oxo-3,4-dihydroquinazolin-8-yl)ethyl)amino)-N-(methylsulfonyl)picolinamide | 1.97 min, 265 nm, MS (ES+)[b] $C_{31}H_{35}ClN_6O_6S$, requires: 654.2, found: 655.2 [M + H]+ |
| 794 | 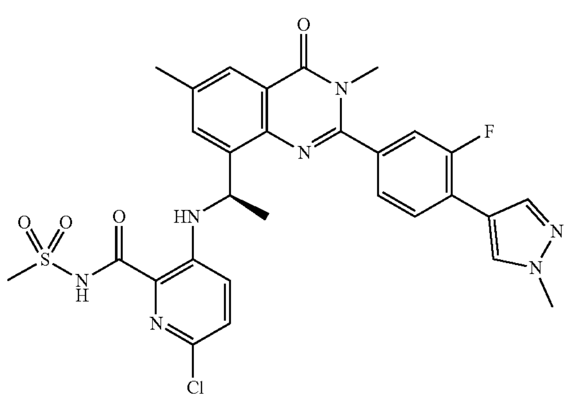 [SMILES: Cc1cc([C@@H](C)Nc2ccc(Cl)nc2C(=O)NS(C)(=O)=O)c2nc(-c3ccc(-c4cnn(C)c4)c(F)c3)n(C)c(=O)c2c1] | (R)-6-chloro-3-((1-(2-(3-fluoro-4-(1-methyl-1H-pyrazol-4-yl)phenyl)-3,6-dimethyl-4-oxo-3,4-dihydroquinazolin-8-yl)ethyl)amino)-N-(methylsulfonyl)picolinamide | 2.37 min, 265 nm, MS (ES+)[b] $C_{29}H_{27}ClFN_7O_4S$, requires: 623.1, found: 624.0 [M + H]+ |

TABLE E7-continued compound list prepared according to the procedure in Example 7

| Cpd. ID | Structure | Name | LCMSb |
|---|---|---|---|
| 795 | 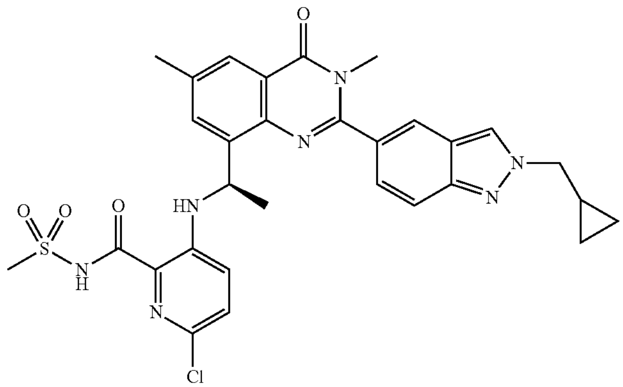 [SMILES: Cc1cc([C@@H](C)Nc2ccc(Cl)nc2C(=O)NS(C)(=O)=O)c2nc(-c3ccc4nn(CC5CC5)cc4c3)n(C)c(=O)c2c1] | (R)-6-chloro-3-((1-(2-(2-(cyclopropylmethyl)-2H-indazol-5-yl)-3,6-dimethyl-4-oxo-3,4-dihydroquinazolin-8-yl)ethyl)amino)-N-(methylsulfonyl)picolinamide | 2.33 min, 270 nm, MS (ES+)$^b$ $C_{30}H_{30}ClN_7O_4S$, requires: 619.1, found: 620.1 [M + H]$^+$ |
| 796 | 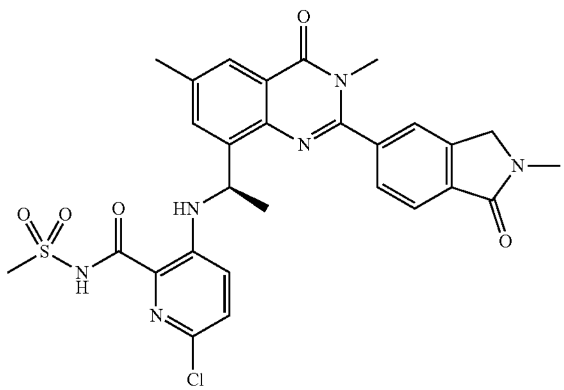 | (R)-6-chloro-3-((1-(3,6-dimethyl-2-(2-methyl-1-oxoisoindolin-5-yl)-4-oxo-3,4-dihydroquinazolin-8-yl)ethyl)amino)-N-(methylsulfonyl)picolinamide | 2.18 min, 254 nm, MS (ES+)$^b$ $C_{28}H_{27}ClN_6O_5S$, requires: 594.1, found: 595.1 [M + H]$^+$ |
| 797 | 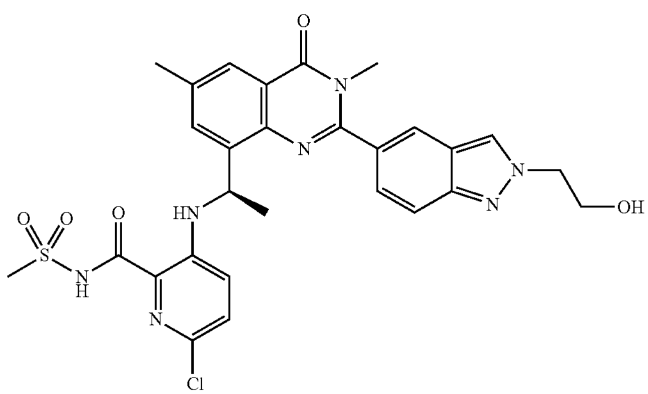 [SMILES: Cc1cc([C@@H](C)Nc2ccc(Cl)nc2C(=O)NS(C)(=O)=O)c2nc(-c3ccc4nn(CCO)cc4c3)n(C)c(=O)c2c1] | (R)-6-chloro-3-((1-(2-(2-(2-hydroxyethyl)-2H-indazol-5-yl)-3,6-dimethyl-4-oxo-3,4-dihydroquinazolin-8-yl)ethyl)amino)-N-(methylsulfonyl)picolinamide | 2.02 min, 270 nm MS (ES+)$^b$ $C_{28}H_{28}ClN_7O_5S$, requires: 609.1, found: 610.1 [M + H]$^+$ |
| 798 | 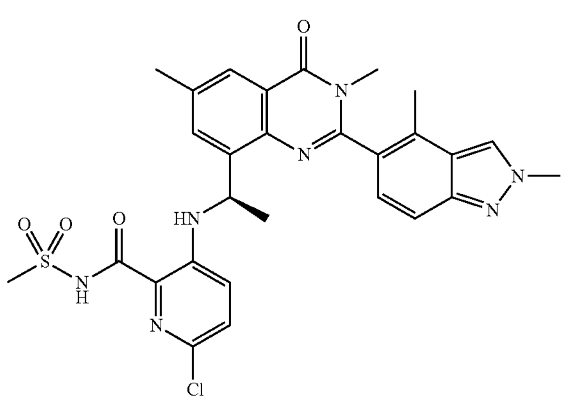 | (R)-6-chloro-3-((1-(2-(2,4-dimethyl-2H-indazol-5-yl)-3,6-dimethyl-4-oxo-3,4-dihydroquinazolin-8-yl)ethyl)amino)-N-(methylsulfonyl)picolinamide | 2.25 min, 270 nm, MS (ES+)$^b$ $C_{28}H_{28}ClN_7O_4S$, requires: 593.1, found: 594.2 [M + H]$^+$ |

TABLE E7-continued compound list prepared according to the procedure in Example 7

| Cpd. ID | Structure | Name | LCMS[b] |
|---|---|---|---|
| 799 | 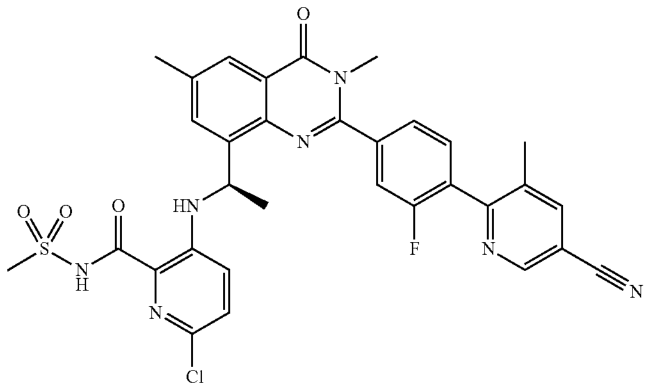 [SMILES: Cc1cc([C@@H](C)Nc2ccc(Cl)nc2C(=O)NS(C)(=O)=O)c2nc(-c3ccc(-c4ncc(C#N)cc4C)c(F)c3)n(C)c(=O)c2c1] | (R)-6-chloro-3-((1-(2-(4-(5-cyano-3-methylpyridin-2-yl)-3-fluorophenyl)-3,6-dimethyl-4-oxo-3,4-dihydroquinazolin-8-yl)ethyl)amino)-N-(methylsulfonyl)picolinamide | 2.52 min, 254 nm, MS (ES+)[b] $C_{32}H_{27}ClFN_7O_4S$, requires: 659.1, found: 660.2 [M + H]+ |
| 800 | 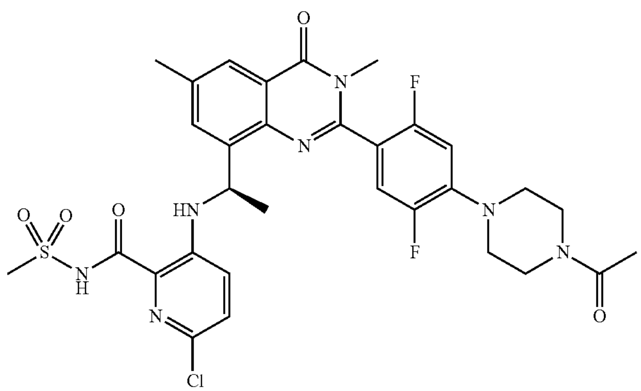 [SMILES: CC(=O)N1CCN(c2cc(F)c(-c3nc4c([C@@H](C)Nc5ccc(Cl)nc5C(=O)NS(C)(=O)=O)cc(C)cc4c(=O)n3C)cc2F)CC1] | (R)-3-((1-(2-(4-(4-acetylpiperazin-1-yl)-2,5-difluorophenyl)-3,6-dimethyl-4-oxo-3,4-dihydroquinazolin-8-yl)ethyl)amino)-6-chloro-N-(methylsulfonyl)picolinamide | 2.31 min, 295 nm, MS (ES+)[b] $C_{31}H_{32}ClF_2N_7O_5S$, requires: 687.1, found: 688.3 [M + H]+ |
| 801 | 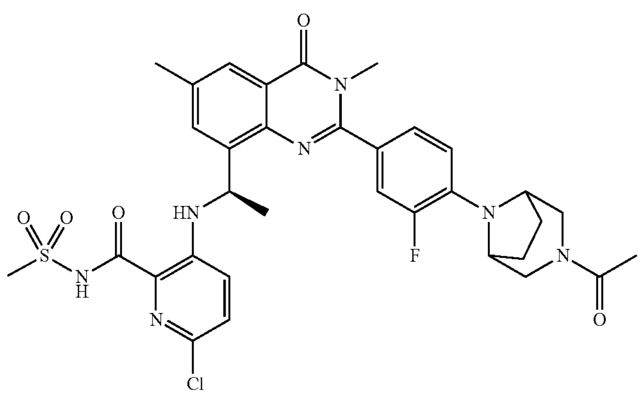 [SMILES: CC(=O)N1CC2CCC(C1)N2c1ccc(-c2nc3c([C@@H](C)Nc4ccc(Cl)nc4C(=O)NS(C)(=O)=O)cc(C)cc3c(=O)n2C)cc1F] | 3-(((1R)-1-(2-(4-(3-acetyl-3,8-diazabicyclo[3.2.1]octan-8-yl)-3-fluorophenyl)-3,6-dimethyl-4-oxo-3,4-dihydroquinazolin-8-yl)ethyl)amino)-6-chloro-N-(methylsulfonyl)picolinamide | 2.35 min, 220 nm, MS (ES+)[b] $C_{33}H_{35}ClFN_7O_5S$, requires: 695.2, found: 696.2 [M + H]+ |
| 802 | 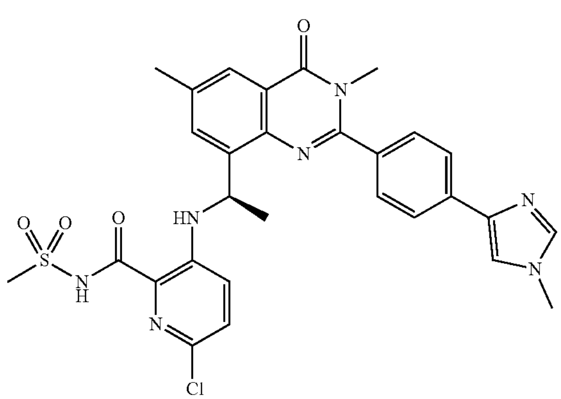 [SMILES: Cc1cc([C@@H](C)Nc2ccc(Cl)nc2C(=O)NS(C)(=O)=O)c2nc(-c3ccc(-c4cn(C)cn4)cc3)n(C)c(=O)c2c1] | (R)-6-chloro-3-((1-(3,6-dimethyl-2-(4-(1-methyl-1H-imidazol-4-yl)phenyl)-4-oxo-3,4-dihydroquinazolin-8-yl)ethyl)amino)-N-(methylsulfonyl)picolinamide | 1.92 min, 265 nm, MS (ES+)[b] $C_{29}H_{28}ClN_7O_4S$, requires: 6O5.1, found: 606.2 [M + H]+ |

TABLE E7-continued compound list prepared according to the procedure in Example 7

| Cpd. ID | Structure | Name | LCMSb |
|---|---|---|---|
| 803 | 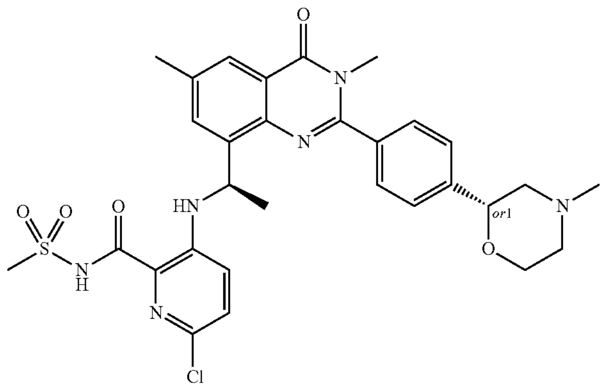 | 6-chloro-3-(((R)-1-(3,6-dimethyl-2-(4-((R*)-4-methylmorpholin-2-yl)phenyl)-4-oxo-3,4-dihydroquinazolin-8-yl)ethyl)amino)-N-(methylsulfonyl)picolinamide | 1.87 min, 254 nm, MS (ES+)[b] $C_{30}H_{33}ClN_6O_5S$, requires: 624.1, found: 625.2 [M + H]+ |
| 804 | 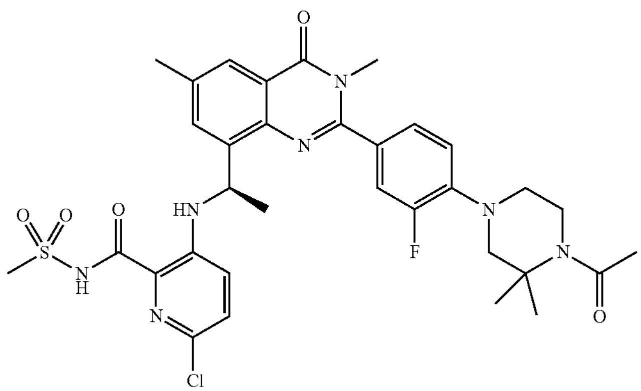 [SMILES: CC(=O)N1CCN(c2ccc(-c3nc4c([C@@H](C)Nc5ccc(Cl)nc5C(=O)NS(C)(=O)=O)cc(C)cc4c(=O)n3C)cc2F)CC1(C)C] | (R)-3-((1-(2-(4-(4-acetyl-3,3-dimethylpiperazin-1-yl)-3-fluorophenyl)-3,6-dimethyl-4-oxo-3,4-dihydroquinazolin-8-yl)ethyl)amino)-6-chloro-N-(methylsulfonyl)picolinamide | 2.24 min, 254 nm, MS (ES+)[b] $C_{33}H_{37}ClFN_7O_5S$, requires: 697.2, found: 698.2 [M + H]+ |
| 805 | 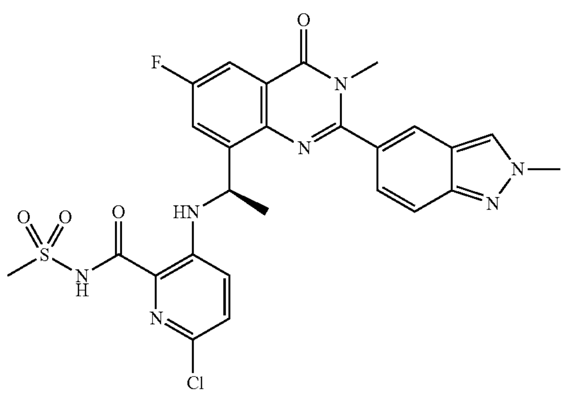 | (R)-6-chloro-3-((1-(6-fluoro-3-methyl-2-(2-methyl-2H-indazol-5-yl)-4-oxo-3,4-dihydroquinazolin-8-yl)ethyl)amino)-N-(methylsulfonyl)picolinamide | 2.30 min, 254 nm, MS (ES+)[b] $C_{26}H_{23}ClFN_7O_4S$, requires: 583.1, found: 584.6 [M + H]+ |
| 806 | 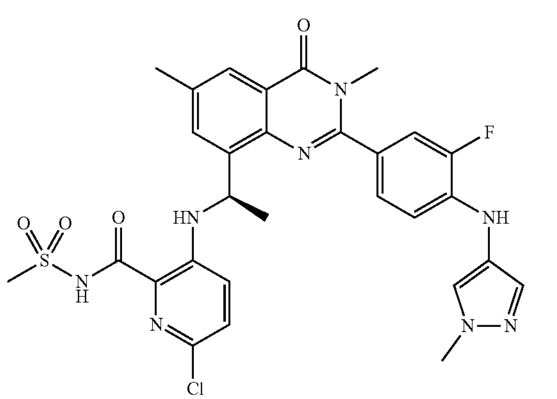 [SMILES: Cc1cc([C@@H](C)Nc2ccc(Cl)nc2C(=O)NS(C)(=O)=O)c2nc(-c3ccc(Nc4cnn(C)c4)c(F)c3)n(C)c(=O)c2c1] | (R)-6-chloro-3-((1-(2-(3-fluoro-4-((1-methyl-1H-pyrazol-4-yl)amino)phenyl)-3,6-dimethyl-4-oxo-3,4-dihydroquinazolin-8-yl)ethyl)amino)-N-(methylsulfonyl)picolinamide | 2.09 min, 210 nm, MS (ES+)[b] $C_{29}H_{28}ClFN_8O_4S$, requires: 638.1, found: 639.1 [M + H]+ |

TABLE E7-continued compound list prepared according to the procedure in Example 7

| Cpd. ID | Structure | Name | LCMSb |
|---|---|---|---|
| 807 | 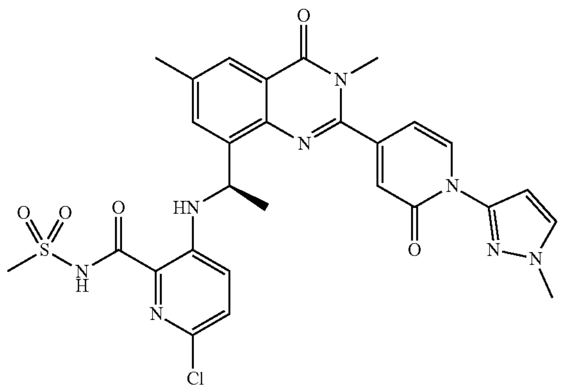 [SMILES: Cc1cc([C@@H](C)Nc2ccc(Cl)nc2C(=O)NS(C)(=O)=O)c2nc(-c3ccn(-c4ccn(C)n4)c(=O)c3)n(C)c(=O)c2c1] | (R)-6-chloro-3-((1-(3,6-dimethyl-2-(1-(1-methyl-1H-pyrazol-3-yl)-2-oxo-1,2-dihydropyridin-4-yl)-4-oxo-3,4-dihydroquinazolin-8-yl)ethyl)amino)-N-(methylsulfonyl)picolinamide | 2.08 min, 220 nm, MS (ES+)[b] $C_{28}H_{27}ClN_8O_5S$, requires: 622.1, found: 623.2 [M + H]+ |
| 808 | 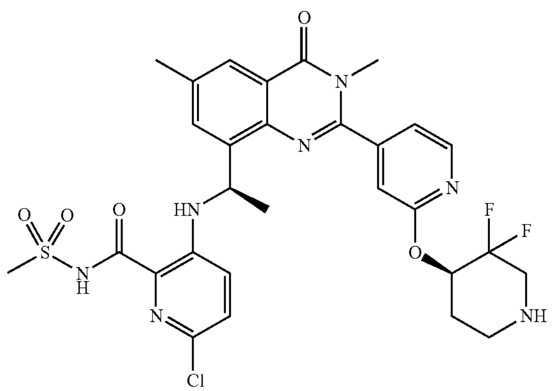 [SMILES: Cc1cc([C@@H](C)Nc2ccc(Cl)nc2C(=O)NS(C)(=O)=O)c2nc(-c3ccnc(O[C@@H]4CCNCC4(F)F)c3)n(C)c(=O)c2c1] | 6-chloro-3-(((R)-1-(2-(2-(((R)-3,3-difluoropiperidin-4-yl)oxy)pyridin-4-yl)-3,6-dimethyl-4-oxo-3,4-dihydroquinazolin-8-yl)ethyl)amino)-N-(methylsulfonyl)picolinamide | 1.88 min, 270 nm, MS (ES+)[b] $C_{29}H_{30}ClF_2N_7O_5S$, requires: 661.1, found: 662.1 [M + H]+ |
| 809 | 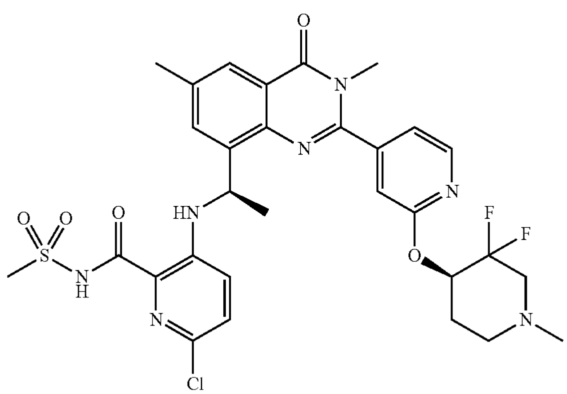 | 6-chloro-3-(((R)-1-(2-(2-(((R)-3,3-difluoro-1-methylpiperidin-4-yl)oxy)pyridin-4-yl)-3,6-dimethyl-4-oxo-3,4-dihydroquinazolin-8-yl)ethyl)amino)-N-(methylsulfonyl)picolinamide | 1.92 min, 254 nm, MS (ES+)[b] $C_{30}H_{32}ClF_2N_7O_5S$, requires: 675.1, found: 676.1 [M + H]+ |
| 810 | 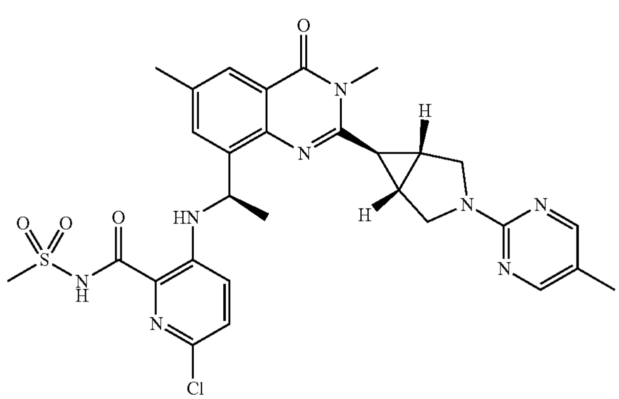 | 6-chloro-3-(((R)-1-(3,6-dimethyl-2-((1R,5S,6r)-3-(5-methylpyrimidin-2-yl)-3-azabicyclo[3.1.0]hexan-6-yl)-4-oxo-3,4-dihydroquinazolin-8-yl)ethyl)amino)-N-(methylsulfonyl)picolinamide | 2.31 min, 270 nm, MS (ES+)[b] $C_{29}H_{31}ClN_8O_4S$, requires: 622.2, found: 623.3 [M + H]+ |

TABLE E7-continued compound list prepared according to the procedure in Example 7

| Cpd. ID | Structure | Name | LCMSb |
|---|---|---|---|
| 811 | 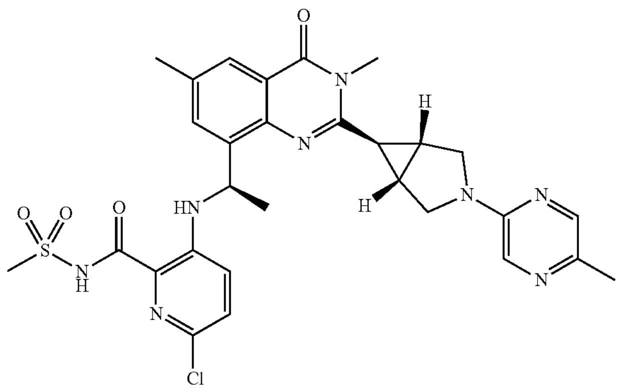 | 6-chloro-3-(((R)-1-(3,6-dimethyl-2-((1R,5S,6r)-3-(5-methylpyrazin-2-yl)-3-azabicyclo[3.1.0]hexan-6-yl)-4-oxo-3,4-dihydroquinazolin-8-yl)ethyl)amino)-N-(methylsulfonyl)picolinamide | 2.18 min, 254 nm, MS (ES+)[b] $C_{29}H_{31}ClN_8O_4S$, requires: 622.2, found: 623.3 [M + H]+ |
| 812 | 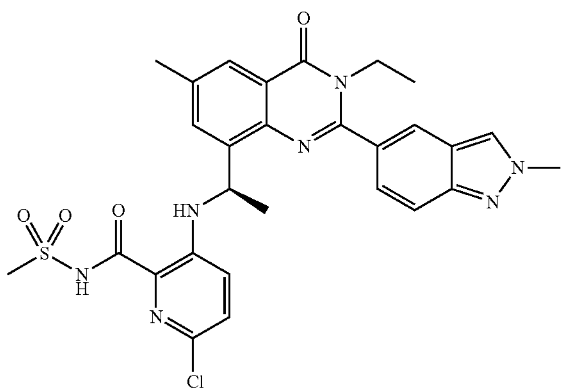 | (R)-6-chloro-3-((1-(3-ethyl-6-methyl-2-(2-methyl-2H-indazol-5-yl)-4-oxo-3,4-dihydroquinazolin-8-yl)ethyl)amino)-N-(methylsulfonyl)picolinamide | 2.15 min, 210 nm, MS (ES+)[b] $C_{28}H_{28}ClN_7O_4S$, requires: 593.2, found: 594.2 [M + H]+ |
| 813 | 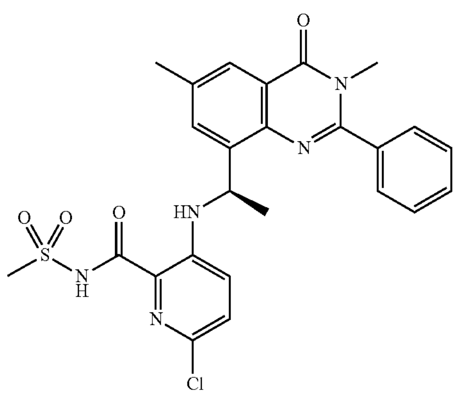 [SMILES: Cc1cc([C@@H](C)Nc2ccc(Cl)nc2C(=O)NS(C)(=O)=O)c2nc(-c3ccccc3)n(C)c(=O)c2c1] | (R)-6-chloro-3-((1-(3,6-dimethyl-4-oxo-2-phenyl-3,4-dihydroquinazolin-8-yl)ethyl)amino)-N-(methylsulfonyl)picolinamide | 2.52 min, 254 nm, MS (ES+)[b] $C_{25}H_{24}ClN_5O_4S$, requires: 525.1, found: 526.1 [M + H]+ |
| 814 | 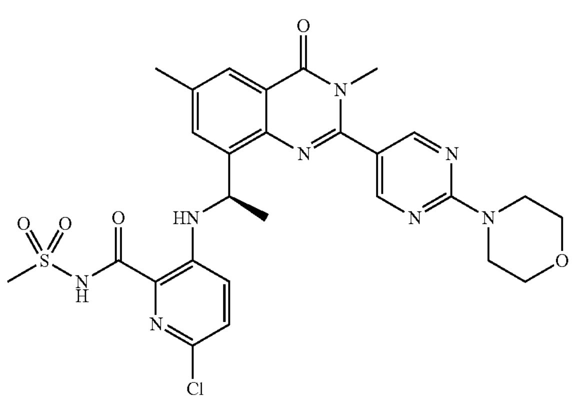 [SMILES: Cc1cc([C@@H](C)Nc2ccc(Cl)nc2C(=O)NS(C)(=O)=O)c2nc(-c3cnc(N4CCOCC4)nc3)n(C)c(=O)c2c1] | (R)-6-chloro-3-((1-(3,6-dimethyl-2-(2-morpholinopyrimidin-5-yl)-4-oxo-3,4-dihydroquinazolin-8-yl)ethyl)amino)-N-(methylsulfonyl)picolinamide | 3.33 min, 254 nm, MS (ES+)[c] $C_{27}H_{29}ClN_8O_5S$ requires: 612.2, found: 613.3 [M + H]+ |

TABLE E7-continued compound list prepared according to the procedure in Example 7

| Cpd. ID | Structure | Name | LCMSb |
|---|---|---|---|
| 815 | 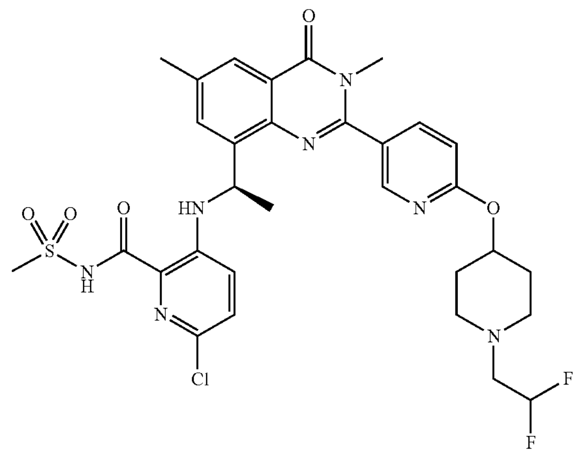 [SMILES: Cc1cc([C@@H](C)Nc2ccc(Cl)nc2C(=O)NS(C)(=O)=O)c2nc(-c3ccc(OC4CCN(CC(F)F)CC4)nc3)n(C)c(=O)c2c1] | (R)-6-chloro-3-((1-(2-(6-((1-(2,2-difluoroethyl)piperidin-4-yl)oxy)pyridin-3-yl)-3,6-dimethyl-4-oxo-3,4-dihydroquinazolin-8-yl)ethyl)amino)-N-(methylsulfonyl)picolinamide | 3.32 min, 254 nm, MS (ES+)[c] $C_{31}H_{34}ClF_2N_7O_5S$ requires: 689.2, found 690.2 [M + H]+ |
| 816 | 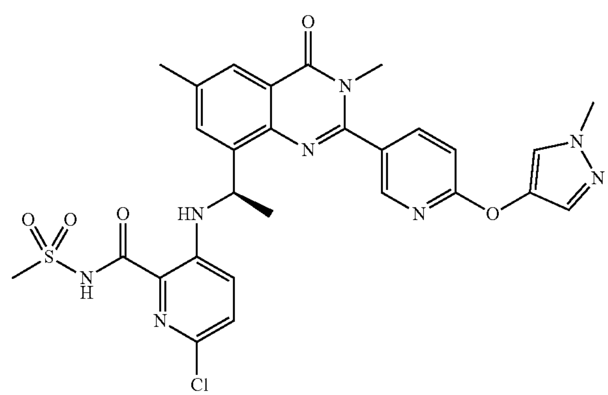 [SMILES: Cc1cc([C@@H](C)Nc2ccc(Cl)nc2C(=O)NS(C)(=O)=O)c2nc(-c3ccc(Oc4cnn(C)c4)nc3)n(C)c(=O)c2c1] | (R)-6-chloro-3-((1-(3,6-dimethyl-2-(6-((1-methyl-1H-pyrazol-4-yl)oxy)pyridin-3-yl)-4-oxo-3,4-dihydroquinazolin-8-yl)ethyl)amino)-N-(methylsulfonyl)picolinamide | 3.18 min, 220 nm, MS (ES+)[c] $C_{28}H_{27}ClN_8O_5S$, requires: 622.2, found: 623.2 [M + H]+ |
| 817 | 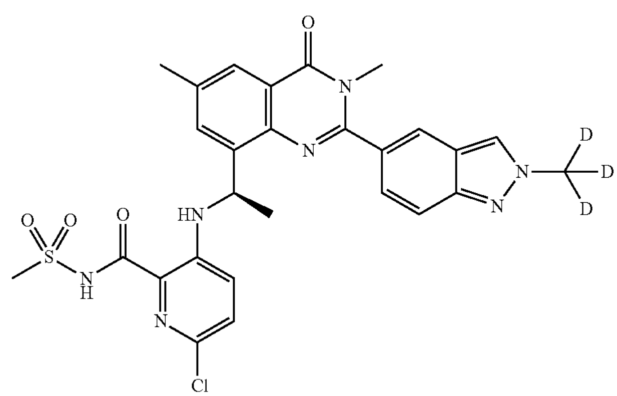 [SMILES: [2H]C([2H])([2H])n1cc2cc(-c3nc4c([C@@H](C)Nc5ccc(Cl)nc5C(=O)NS(C)(=O)=O)cc(C)cc4c(=O)n3C)ccc2n1] | (R)-6-chloro-3-((1-(3,6-dimethyl-2-(2-(methyl-d3)-2H-indazol-5-yl)-4-oxo-3,4-dihydroquinazolin-8-yl)ethyl)amino)-N-(methylsulfonyl)picolinamide | 2.26 min, 270 nm, MS (ES+)[b] $C_{27}H_{23}D_3ClN_7O_4S$, requires: 582.2, found: 583.4 [M + H]+ |

TABLE E7-continued compound list prepared according to the procedure in Example 7

| Cpd. ID | Structure | Name | LCMSb |
|---|---|---|---|
| 818 | 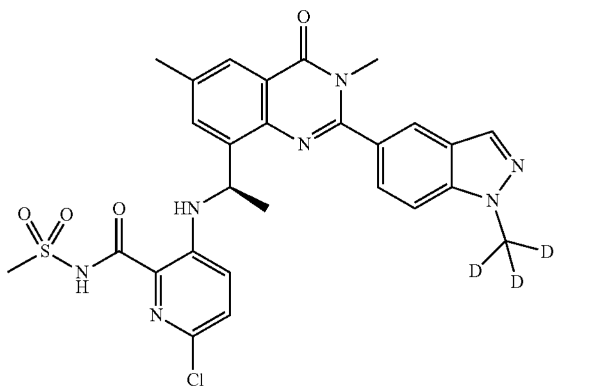 [SMILES: [2H]C([2H])([2H])n1ncc2cc(-c3nc4c([C@@H](C)Nc5ccc(Cl)nc5C(=O)NS(C)(=O)=O)cc(C)cc4c(=O)n3C)ccc21] | (R)-6-chloro-3-((1-(3,6-dimethyl-2-(1-(methyl-d3)-1H-indazol-5-yl)-4-oxo-3,4-dihydroquinazolin-8-yl)ethyl)amino)-N-(methylsulfonyl)picolinamide | 2.38 min, 220 nm, MS (ES+)[b] $C_{27}H_{23}D_3ClN_7O_4S$, requires: 582.2, found: 583.4 [M + H]+ |
| 819 | 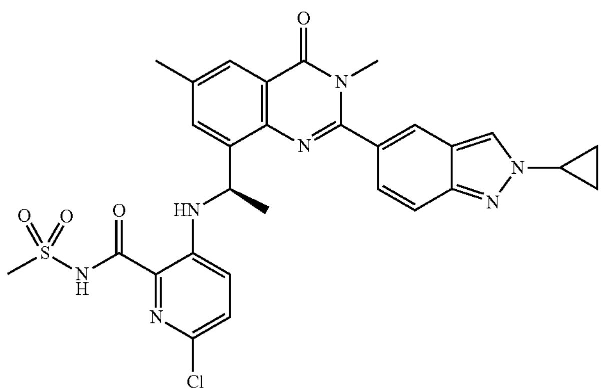 [SMILES: Cc1cc([C@@H](C)Nc2ccc(Cl)nc2C(=O)NS(C)(=O)=O)c2nc(-c3ccc4nn(C5CC5)cc4c3)n(C)c(=O)c2c1] | (R)-6-chloro-3-((1-(2-(2-cyclopropyl-2H-indazol-5-yl)-3,6-dimethyl-4-oxo-3,4-dihydroquinazolin-8-yl)ethyl)amino)-N-(methylsulfonyl)picolinamide | 2.41 min, 220 nm, MS (ES+)[b] $C_{29}H_{28}ClN_7O_4S$, requires: 605.2, found: 606.4 [M + H]+ |
| 820 | 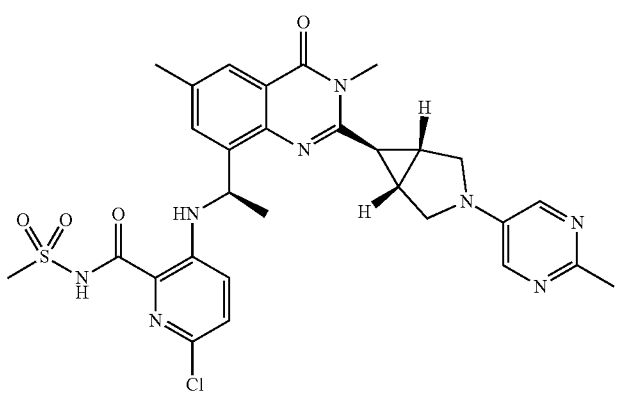 | 6-chloro-3-(((R)-1-(3,6-dimethyl-2-((1R,5S,6r)-3-(2-methylpyrimidin-5-yl)-3-azabicyclo[3.1.0]hexan-6-yl)-4-oxo-3,4-dihydroquinazolin-8-yl)ethyl)amino)-N-(methylsulfonyl)picolinamide | 2.13 min, 254 nm, MS (ES+)[b] $C_{29}H_{31}ClN_8O_4S$, requires: 622.1, found: 623.3 [M + H]+ |
| 821 | 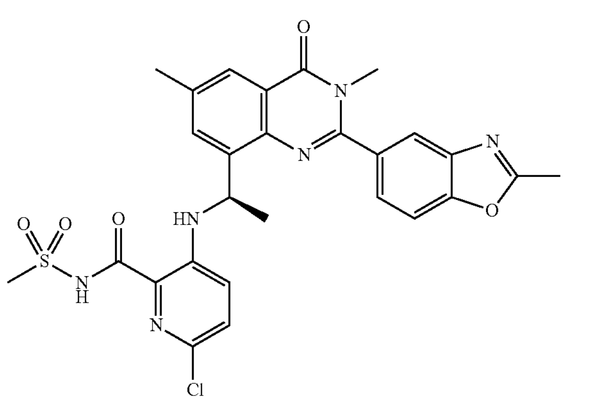 | (R)-6-chloro-3-((1-(3,6-dimethyl-2-(2-methylbenzo[d]oxazol-5-yl)-4-oxo-3,4-dihydroquinazolin-8-yl)ethyl)amino)-N-(methylsulfonyl)picolinamide | 2.32 min, 254 nm, MS (ES+)[b] $C_{27}H_{25}ClN_6O_5S$, requires: 580.1, found: 581.2 [M + H]+ |

TABLE E7-continued compound list prepared according to the procedure in Example 7

| Cpd. ID | Structure | Name | LCMSb |
|---|---|---|---|
| 822 | 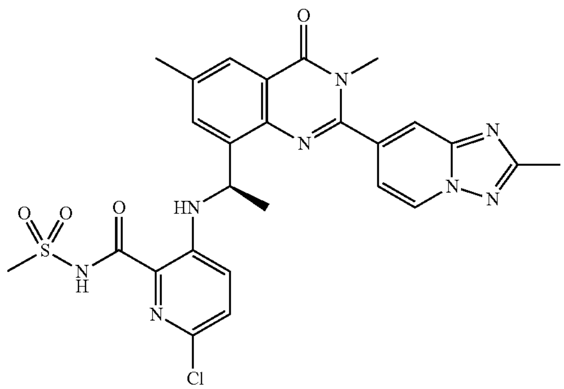 | (R)-6-chloro-3-((1-(3,6-dimethyl-2-(2-methyl-[1,2,4]triazolo[1,5-a]pyridin-7-yl)-4-oxo-3,4-dihydroquinazolin-8-yl)ethyl)amino)-N-(methylsulfonyl)picolinamide | 2.06 min, 254 nm, MS (ES+)[b] $C_{26}H_{25}ClN_8O_4S$, requires: 580.1, found: 581.2 [M + H]+ |
| 823 | 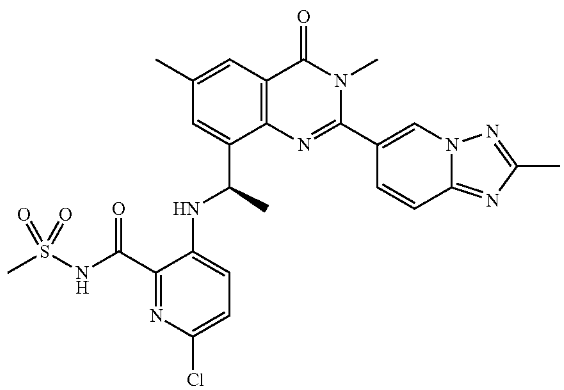 | (R)-6-chloro-3-((1-(3,6-dimethyl-2-(2-methyl-[1,2,4]triazolo[1,5-a]pyridin-6-yl)-4-oxo-3,4-dihydroquinazolin-8-yl)ethyl)amino)-N-(methylsulfonyl)picolinamide | 2.07 min, 254 nm, MS (ES+)[b] $C_{26}H_{25}ClN_8O_4S$, requires: 580.1, found: 581.2 [M + H]+ |
| 824 | 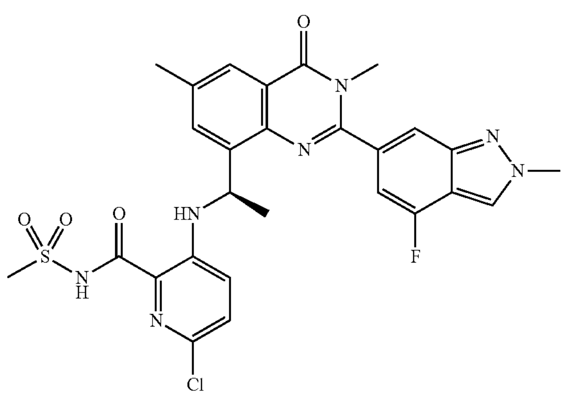 | (R)-6-chloro-3-((1-(2-(4-fluoro-2-methyl-2H-indazol-6-yl)-3,6-dimethyl-4-oxo-3,4-dihydroquinazolin-8-yl)ethyl)amino)-N-(methylsulfonyl)picolinamide | 2.28 min, 254 nm, MS (ES+)[b] $C_{27}H_{25}ClFN_7O_4S$, requires: 597.1, found: 598.2 [M + H]+ |
| 825 | 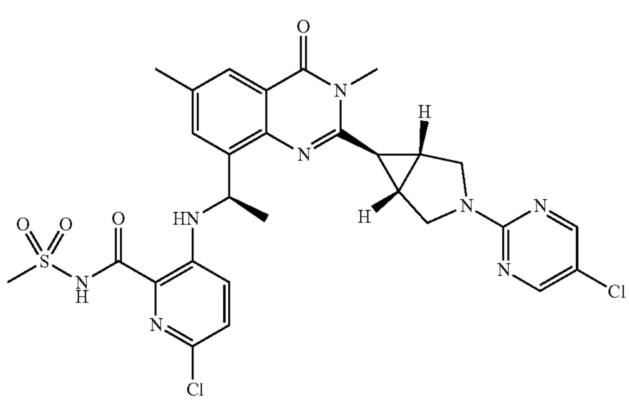 [SMILES: Cc1cc([C@@H](C)Nc2ccc(Cl)nc2C(=O)NS(C)(=O)=O)c2nc([C@H]3[C@@H]4CN(c5ncc(Cl)cn5)C[C@@H]43)n(C)c(=O)c2c1] | 6-chloro-3-(((R)-1-(2-((1R,5S,6r)-3-(5-chloropyrimidin-2-yl)-3-azabicyclo[3.1.0]hexan-6-yl)-3,6-dimethyl-4-oxo-3,4-dihydroquinazolin-8-yl)ethyl)amino)-N-(methylsulfonyl)picolinamide | 2.64 min, 254 nm, MS (ES+)[b] $C_{28}H_{28}Cl_2N_8O_4S$, requires: 642.1, found: 643.2 [M + H]+ |

TABLE E7-continued compound list prepared according to the procedure in Example 7

| Cpd. ID | Structure | Name | LCMSb |
|---|---|---|---|
| 826 | 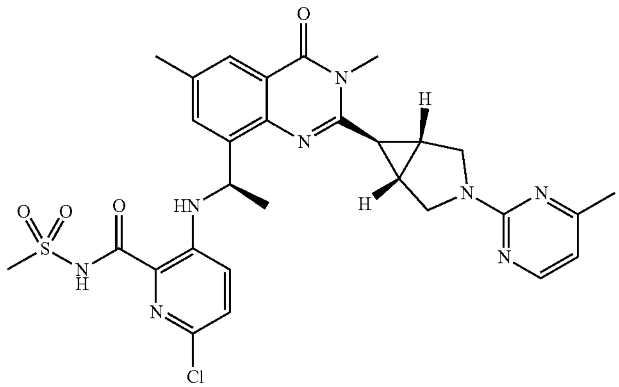 | 6-chloro-3-(((R)-1-(3,6-dimethyl-2-((1R,5S,6r)-3-(4-methylpyrimidin-2-yl)-3-azabicyclo[3.1.0]hexan-6-yl)-4-oxo-3,4-dihydroquinazolin-8-yl)ethyl)amino)-N-(methylsulfonyl)picolinamide | 2.31 min, 254 nm, MS (ES+)[b] $C_{29}H_{31}ClN_8O_4S$, requires: 622.1, found: 623.3 [M + H]+ |
| 827 | 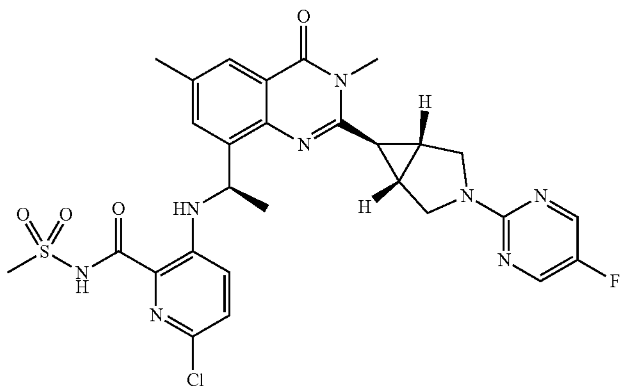 [SMILES: Cc1cc([C@@H](C)Nc2ccc(Cl)nc2C(=O)NS(C)(=O)=O)c2nc([C@H]3[C@@H]4CN(c5ncc(F)cn5)C[C@@H]43)n(C)c(=O)c2c1] | 6-chloro-3-(((R)-1-(2-((1R,5S,6r)-3-(5-fluoropyrimidin-2-yl)-3-azabicyclo[3.1.0]hexan-6-yl)-3,6-dimethyl-4-oxo-3,4-dihydroquinazolin-8-yl)ethyl)amino)-N-(methylsulfonyl)picolinamide | 2.48 min, 254 nm, MS (ES+)[b] $C_{28}H_{28}ClFN_8O_4S$, requires: 626.1, found: 627.3 [M + H]+ |
| 828 | 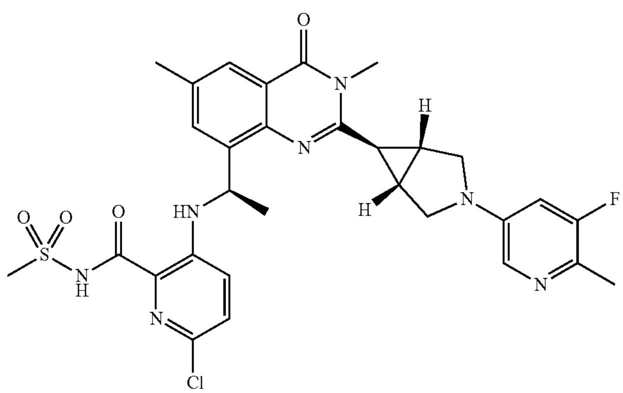 | 6-chloro-3-(((R)-1-(2-((1R,5S,6r)-3-(5-fluoro-6-methylpyridin-3-yl)-3-azabicyclo[3.1.0]hexan-6-yl)-3,6-dimethyl-4-oxo-3,4-dihydroquinazolin-8-yl)ethyl)amino)-N-(methylsulfonyl)picolinamide | 2.27 min, 254 nm, MS (ES+)[b] $C_{30}H_{31}ClFN_7O_4S$, requires: 639.1, found: 640.3 [M + H]+ |
| 829 | 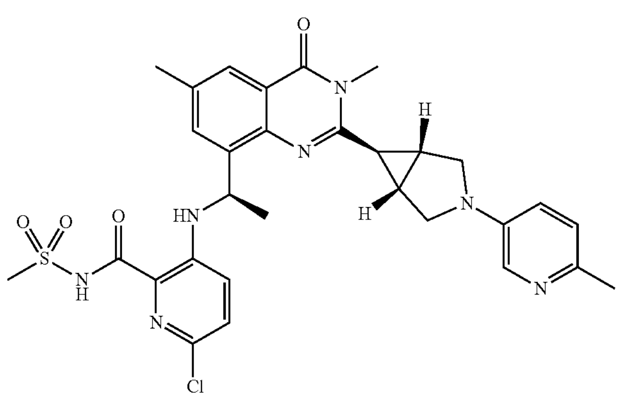 | 6-chloro-3-(((R)-1-(3,6-dimethyl-2-((1R,5S,6r)-3-(6-methylpyridin-3-yl)-3-azabicyclo[3.1.0]hexan-6-yl)-4-oxo-3,4-dihydroquinazolin-8-yl)ethyl)amino)-N-(methylsulfonyl)picolinamide | 1.96 min, 254 nm, MS (ES+)[b] $C_{30}H_{32}ClN_7O_4S$, requires: 621.1, found: 622.3 [M + H]+ |

TABLE E7-continued compound list prepared according to the procedure in Example 7

| Cpd. ID | Structure | Name | LCMSb |
|---|---|---|---|
| 830 | 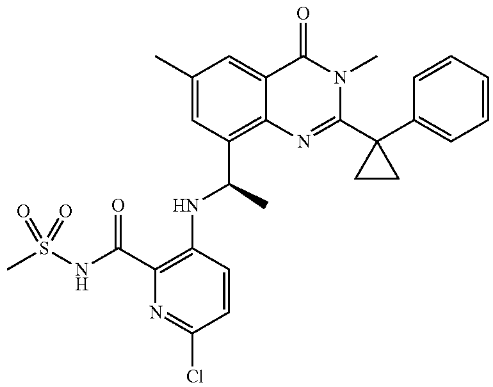 [SMILES: Cc1cc([C@@H](C)Nc2ccc(Cl)nc2C(=O)NS(C)(=O)=O)c2nc(C3(c4ccccc4)CC3)n(C)c(=O)c2c1] | (R)-6-chloro-3-((1-(3,6-dimethyl-4-oxo-2-(1-phenylcyclopropyl)-3,4-dihydroquinazolin-8-yl)ethyl)amino)-N-(methylsulfonyl)picolinamide | 3.91 min, 254 nm, MS (ES+)[c] $C_{28}H_{28}ClN_5O_4S$, requires: 565.2, found: 566.2 [M + H]+ |
| 831 | 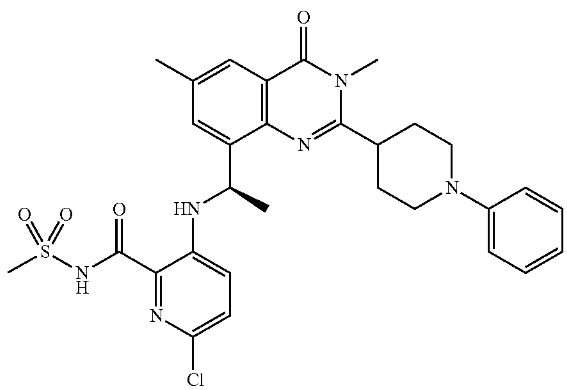 [SMILES: Cc1cc([C@@H](C)Nc2ccc(Cl)nc2C(=O)NS(C)(=O)=O)c2nc(C3CCN(c4ccccc4)CC3)n(C)c(=O)c2c1] | (R)-6-chloro-3-((1-(3,6-dimethyl-4-oxo-2-(1-phenylpiperidin-4-yl)-3,4-dihydroquinazolin-8-yl)ethyl)amino)-N-(methylsulfonyl)picolinamide | 2.56 min, 254 nm, MS (ES+)[b] $C_{30}H_{33}ClN_6O_4S$, requires: 608.2, found: 609.2 [M + H]+ |
| 832 | 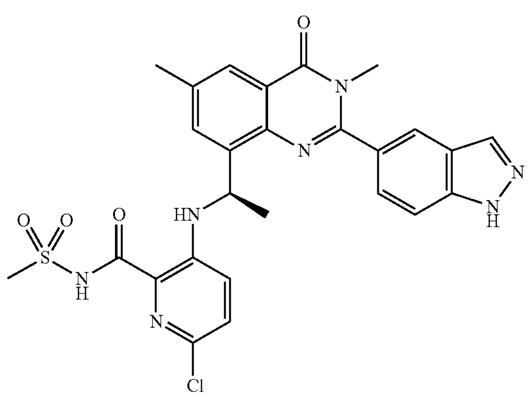 [SMILES: Cc1cc([C@@H](C)Nc2ccc(Cl)nc2C(=O)NS(C)(=O)=O)c2nc(-c3ccc4[nH]ncc4c3)n(C)c(=O)c2c1] | (R)-3-((1-(2-(1H-indazol-5-yl)-3,6-dimethyl-4-oxo-3,4-dihydroquinazolin-8-yl)ethyl)amino)-6-chloro-N-(methylsulfonyl)picolinamide | 2.21 min, 210 nm, MS (ES+)[b] $C_{26}H_{24}ClN_7O_4S$, requires: 565.1, found: 566.1 [M + H]+ |
| 833 | 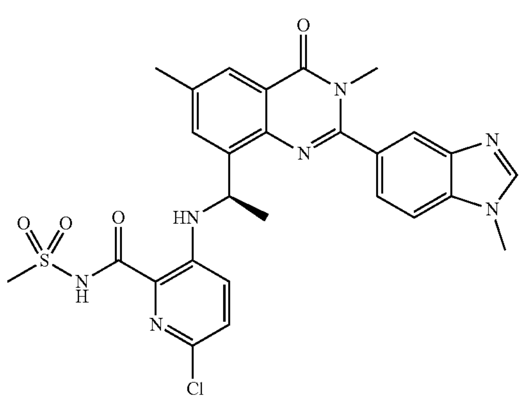 [SMILES: Cc1cc([C@@H](C)Nc2ccc(Cl)nc2C(=O)NS(C)(=O)=O)c2nc(-c3ccc4c(c3)ncn4C)n(C)c(=O)c2c1] | (R)-6-chloro-3-((1-(3,6-dimethyl-2-(1-methyl-1H-benzo[d]imidazol-5-yl)-4-oxo-3,4-dihydroquinazolin-8-yl)ethyl)amino)-N-(methylsulfonyl)picolinamide | 2.53 min, 254 nm, MS (ES+)[c] $C_{27}H_{26}ClN_7O_4S$, requires: 579.2, found: 580.3 [M + H]+ |

TABLE E7-continued compound list prepared according to the procedure in Example 7

| Cpd. ID | Structure | Name | LCMSb |
|---|---|---|---|
| 834 | 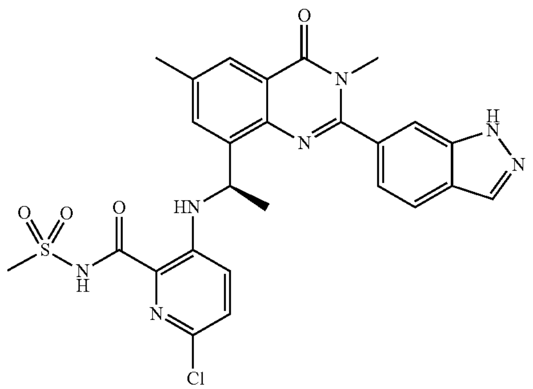 [SMILES: Cc1cc([C@@H](C)Nc2ccc(Cl)nc2C(=O)NS(C)(=O)=O)c2nc(-c3ccc4cn[nH]c4c3)n(C)c(=O)c2c1] | (R)-3-((1-(2-(1H-indazol-6-yl)-3,6-dimethyl-4-oxo-3,4-dihydroquinazolin-8-yl)ethyl)amino)-6-chloro-N-(methylsulfonyl)picolinamide | 2.27 min, 210 nm, MS (ES+)$^b$ $C_{26}H_{24}ClN_7O_4S$, requires: 565.1, found: 566.1 [M + H]$^+$ |
| 835 | 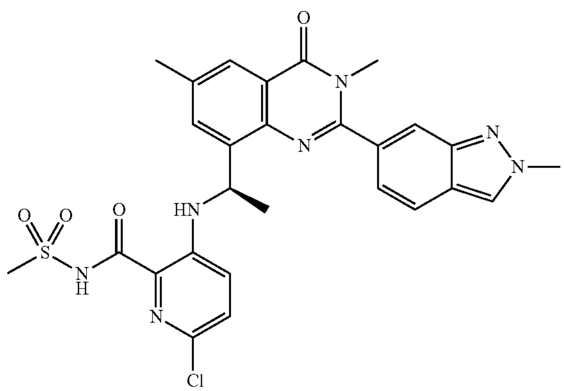 | (R)-6-chloro-3-((1-(3,6-dimethyl-2-(2-methyl-2H-indazol-6-yl)-4-oxo-3,4-dihydroquinazolin-8-yl)ethyl)amino)-N-(methylsulfonyl)picolinamide | 2.31 min, 254 nm, MS (ES+)$^b$ $C_{27}H_{26}ClN_7O_4S$, requires: 579.1, found: 580.1 [M + H]$^+$ |
| 836 | 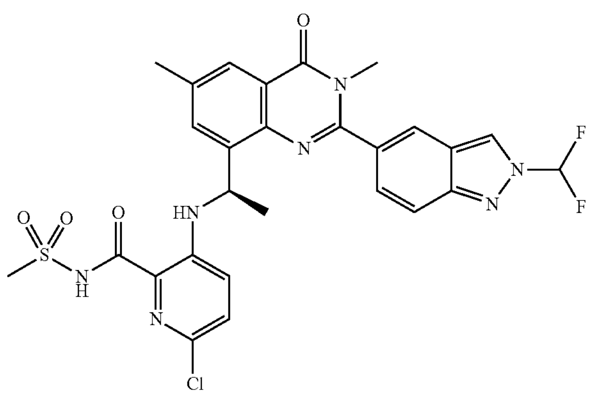 [SMILES: Cc1cc([C@@H](C)Nc2ccc(Cl)nc2C(=O)NS(C)(=O)=O)c2nc(-c3ccc4nn(C(F)F)cc4c3)n(C)c(=O)c2c1] | (R)-6-chloro-3-((1-(2-(2-(difluoromethyl)-2H-indazol-5-yl)-3,6-dimethyl-4-oxo-3,4-dihydroquinazolin-8-yl)ethyl)amino)-N-(methylsulfonyl)picolinamide | 2.36 min, 210 nm, MS (ES+)$^b$ $C_{27}H_{24}ClF_2N_7O_4S$, requires: 615.1, found: 616.1 [M + H]$^+$ |
| 837 | 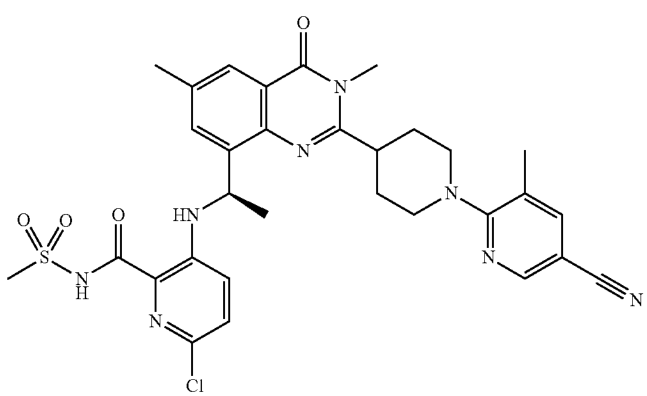 [SMILES: Cc1cc([C@@H](C)Nc2ccc(Cl)nc2C(=O)NS(C)(=O)=O)c2nc(C3CCN(c4ncc(C#N)cc4C)CC3)n(C)c(=O)c2c1] | (R)-6-chloro-3-((1-(2-(1-(5-cyano-3-methylpyridin-2-yl)piperidin-4-yl)-3,6-dimethyl-4-oxo-3,4-dihydroquinazolin-8-yl)ethyl)amino)-N-(methylsulfonyl)picolinamide | 2.46 min, 215 nm, MS (ES+)$^b$ $C_{31}H_{33}ClN_8O_4S$, requires: 648.2, found: 649.2 [M + H]$^+$ |

TABLE E7-continued compound list prepared according to the procedure in Example 7

| Cpd. ID | Structure | Name | LCMSb |
|---|---|---|---|
| 838 | 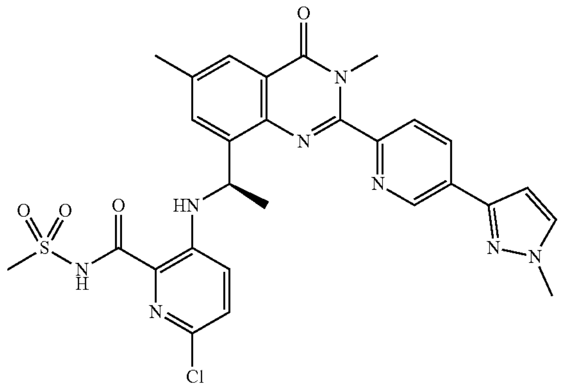 [SMILES: Cc1cc([C@@H](C)Nc2ccc(Cl)nc2C(=O)NS(C)(=O)=O)c2nc(-c3ccc(-c4ccn(C)n4)cn3)n(C)c(=O)c2c1] | (R)-6-chloro-3-((1-(3,6-dimethyl-2-(5-(1-methyl-1H-pyrazol-3-yl)pyridin-2-yl)-4-oxo-3,4-dihydroquinazolin-8-yl)ethyl)amino)-N-(methylsulfonyl)picolinamide | 2.33 min, 254 nm, MS (ES+)[b] $C_{28}H_{27}ClN_8O_4S$, requires: 606.1, found: 607.2 [M + H]+ |
| 839 | 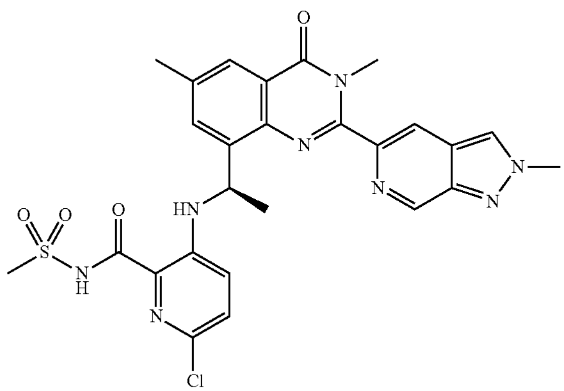 | (R)-6-chloro-3-((1-(3,6-dimethyl-2-(2-methyl-2H-pyrazolo[3,4-c]pyridin-5-yl)-4-oxo-3,4-dihydroquinazolin-8-yl)ethyl)amino)-N-(methylsulfonyl)picolinamide | 2.15 min, 254 nm, MS (ES+)[b] $C_{26}H_{25}ClN_8O_4S$, requires: 580.0, found: 581.2 [M + H]+ |
| 840 | 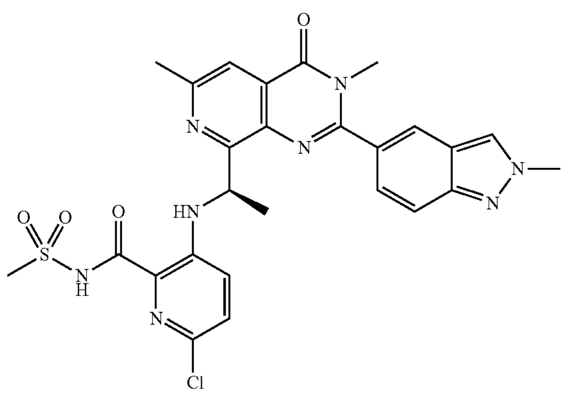 | (R)-6-chloro-3-((1-(3,6-dimethyl-2-(2-methyl-2H-indazol-5-yl)-4-oxo-3,4-dihydropyrido[3,4-d]pyrimidin-8-yl)ethyl)amino)-N-(methylsulfonyl)picolinamide | 2.04 min, 210 nm, MS (ES+)[b] $C_{26}H_{25}ClN_8O_4S$, requires: 580.1, found: 581.2 [M + H]+ |
| 841 | 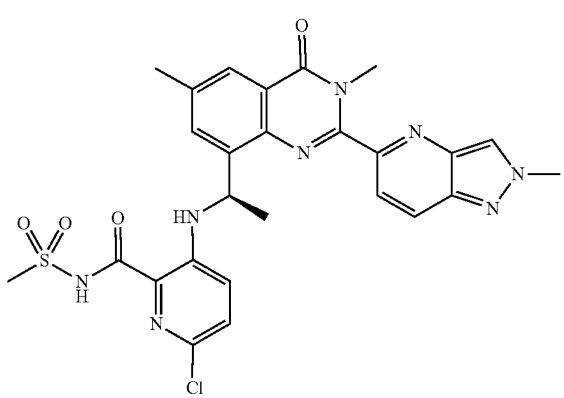 | (R)-6-chloro-3-((1-(3,6-dimethyl-2-(2-methyl-2H-pyrazolo[4,3-b]pyridin-5-yl)-4-oxo-3,4-dihydroquinazolin-8-yl)ethyl)amino)-N-(methylsulfonyl)picolinamide | 2.18 min, 215 nm, MS (ES+)[b] $C_{26}H_{25}ClN_8O_4S$, requires: 580.1, found: 581.2 [M + H]+ |

TABLE E7-continued compound list prepared according to the procedure in Example 7

| Cpd. ID | Structure | Name | LCMSb |
|---|---|---|---|
| 842 | 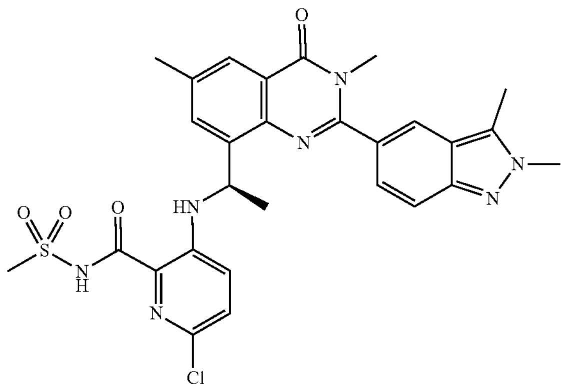 | (R)-6-chloro-3-((1-(2-(2,3-dimethyl-2H-indazol-5-yl)-3,6-dimethyl-4-oxo-3,4-dihydroquinazolin-8-yl)ethyl)amino)-N-(methylsulfonyl)picolinamide | 2.29 min, 254 nm, MS (ES+)[b] $C_{28}H_{28}ClN_7O_4S$, requires: 593.1, found: 594.2 [M + H]+ |
| 843 | 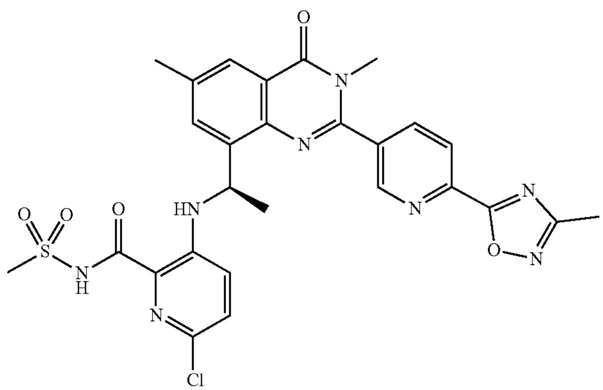 | (R)-6-chloro-3-((1-(3,6-dimethyl-2-(6-(3-methyl-1,2,4-oxadiazol-5-yl)pyridin-3-yl)-4-oxo-3,4-dihydroquinazolin-8-yl)ethyl)amino)-N-(methylsulfonyl)picolinamide | 2.30 min, 254 nm, MS (ES+)[b] $C_{27}H_{25}ClN_8O_5S$, requires: 608.1, found: 609.1 [M + H]+ |
| 844 | 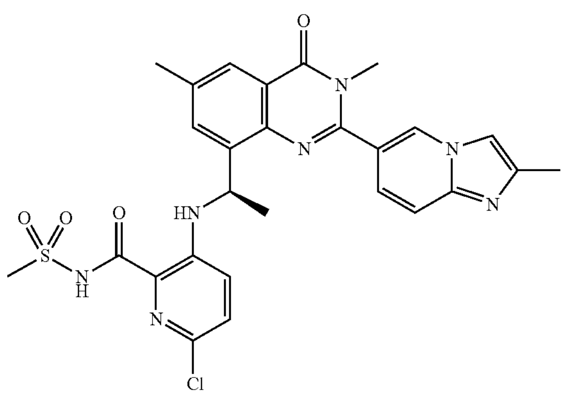 | (R)-6-chloro-3-((1-(3,6-dimethyl-2-(2-methylimidazo[1,2-a]pyridin-6-yl)-4-oxo-3,4-dihydroquinazolin-8-yl)ethyl)amino)-N-(methylsulfonyl)picolinamide | 1.81 min, 254 nm, MS (ES+)[b] $C_{27}H_{26}ClN_7O_4S$, requires: 579.2, found: 580.1 [M + H]+ |
| 845 | 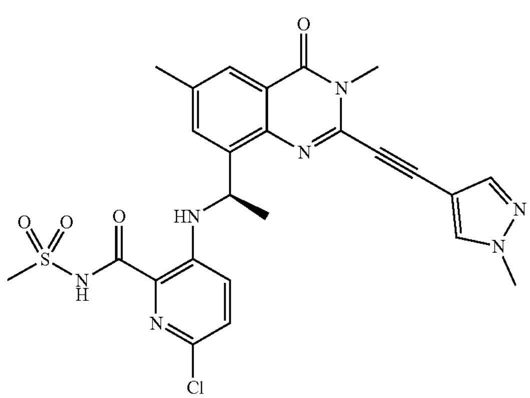 [SMILES: Cc1cc([C@@H](C)Nc2ccc(Cl)nc2C(=O)NS(C)(=O)=O)c2nc(C#Cc3cnn(C)c3)n(C)c(=O)c2c1] | (R)-6-chloro-3-((1-(3,6-dimethyl-2-((1-methyl-1H-pyrazol-4-yl)ethynyl)-4-oxo-3,4-dihydroquinazolin-8-yl)ethyl)amino)-N-(methylsulfonyl)picolinamide | 2.12 min, 220 nm, MS (ES+)[b] $C_{25}H_{24}ClN_7O_4S$, requires: 553.1, found: 554.1 [M + H]+ |

TABLE E7-continued compound list prepared according to the procedure in Example 7

| Cpd. ID | Structure | Name | LCMSb |
|---|---|---|---|
| 846 | 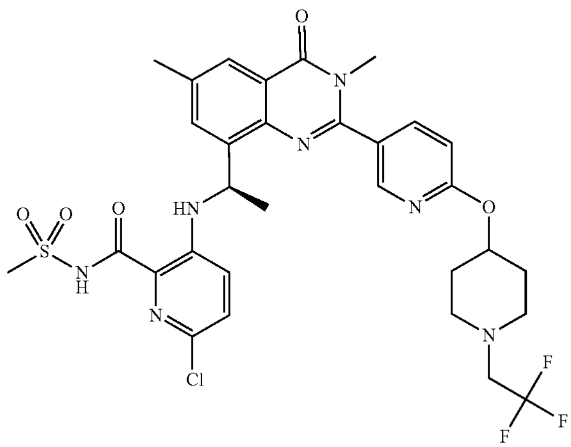 [SMILES: Cc1cc([C@@H](C)Nc2ccc(Cl)nc2C(=O)NS(C)(=O)=O)c2nc(-c3ccc(OC4CCN(CC(F)(F)F)CC4)nc3)n(C)c(=O)c2c1] | (R)-6-chloro-3-((1-(3,6-dimethyl-4-oxo-2-(6-((1-(2,2,2-trifluoroethyl)piperidin-4-yl)oxy)pyridin-3-yl)-3,4-dihydroquinazolin-8-yl)ethyl)amino)-N-(methylsulfonyl)picolinamide | 3.80 min, 254 nm, MS (ES+)$^c$ C$_{31}$H$_{33}$ClF$_3$N$_7$O$_5$S, requires: 707.2, found: 708.2 [M + H]$^+$ |
| 847 | 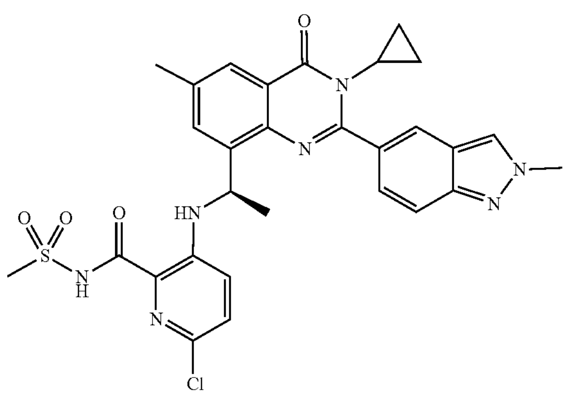 | (R)-6-chloro-3-((1-(3-cyclopropyl-6-methyl-2-(2-methyl-2H-indazol-5-yl)-4-oxo-3,4-dihydroquinazolin-8-yl)ethyl)amino)-N-(methylsulfonyl)picolinamide | 2.08 min, 254 nm, MS (ES+)$^b$ C$_{29}$H$_{28}$ClN$_7$O$_4$S, requires: 605.2, found: 606.2 [M + H]$^+$ |
| 848 | 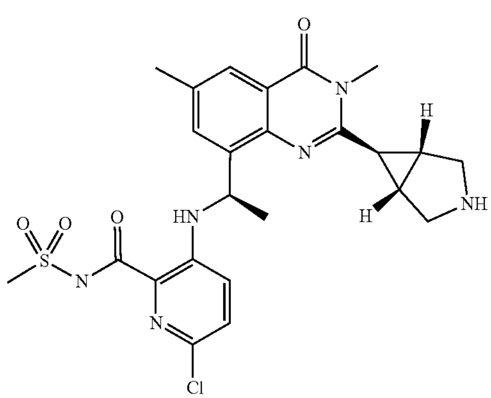 | 3-(((R)-1-(2-((1R,5S,6r)-3-azabicyclo[3.1.0]hexan-6-yl)-3,6-dimethyl-4-oxo-3,4-dihydroquinazolin-8-yl)ethyl)amino)-6-chloro-N-(methylsulfonyl)picolinamide | 1.75 min, 254 nm, MS (ES+)$^b$ C$_{24}$H$_{27}$ClN$_6$O$_4$S requires: 530.1, found: 531.2 [M + H]$^+$ |

TABLE E7-continued compound list prepared according to the procedure in Example 7

| Cpd. ID | Structure | Name | LCMS[b] |
|---|---|---|---|
| 849 | 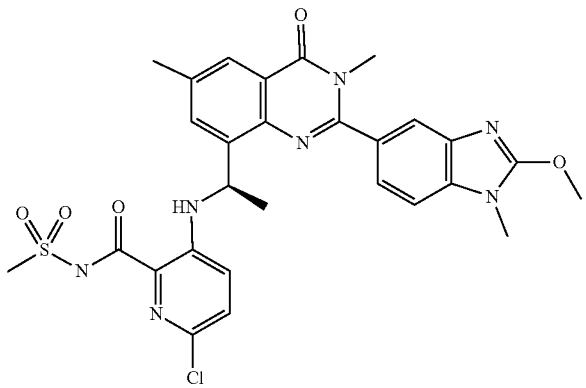 | (R)-6-chloro-3-((1-(2-(2-methoxy-1-methyl-1H-benzo[d]imidazol-5-yl)-3,6-dimethyl-4-oxo-3,4-dihydroquinazolin-8-yl)ethyl)amino)-N-(methylsulfonyl)picolinamide | 2.26 min, 254 nm, MS (ES+)[b] $C_{28}H_{28}ClN_7O_5S$ requires: 609.1, found: 610.2 [M + H]+ |
| 850 | 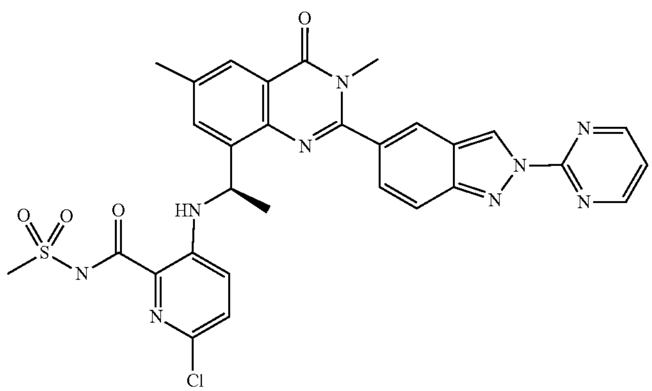 | (R)-6-chloro-3-((1-(3,6-dimethyl-4-oxo-2-(2-(pyrimidin-2-yl)-2H-indazol-5-yl)-3,4-dihydroquinazolin-8-yl)ethyl)amino)-N-(methylsulfonyl)picolinamide | 2.25 min, 254 nm, MS (ES+)[b] $C_{30}H_{26}ClN_9O_4S$ requires: 643.1, found: 644.2 [M + H]+ |
| 851 | 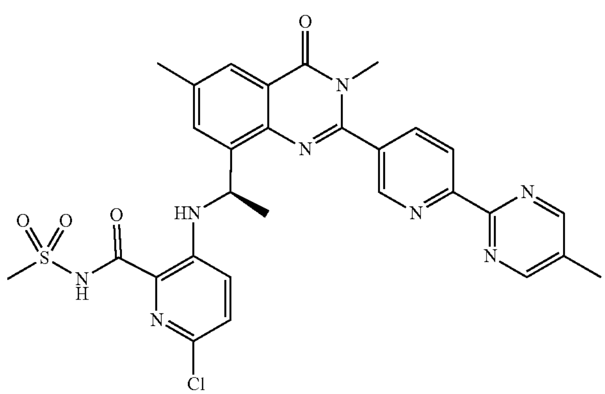 | (R)-6-chloro-3-((1-(3,6-dimethyl-2-(6-(5-methylpyrimidin-2-yl)pyridin-3-yl)-4-oxo-3,4-dihydroquinazolin-8-yl)ethyl)amino)-N-(methylsulfonyl)picolinamide | 2.15 min, 210 nm, MS (ES+)[b] $C_{29}H_{27}ClN_8O_4S$ requires: 618.2, found: 619.3 [M + H]+ |
| 852 | 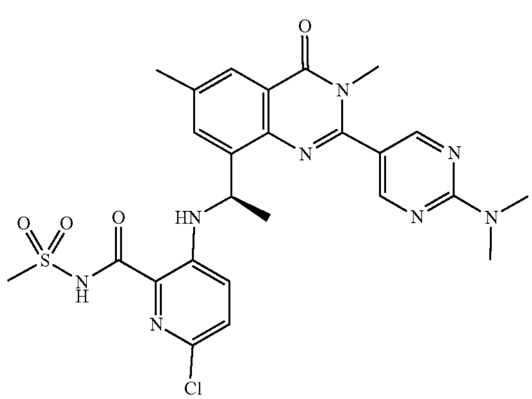 | (R)-6-chloro-3-((1-(2-(2-(dimethylamino)pyrimidin-5-yl)-3,6-dimethyl-4-oxo-3,4-dihydroquinazolin-8-yl)ethyl)amino)-N-(methylsulfonyl)picolinamide | 2.46 min, 315 nm, MS (ES+)[b] $C_{25}H_{27}ClN_8O_4S$ requires: 570.2, found: 571.5 [M + H]+ |

TABLE E7-continued compound list prepared according to the procedure in Example 7

| Cpd. ID | Structure | Name | LCMSb |
|---|---|---|---|
| 853 | 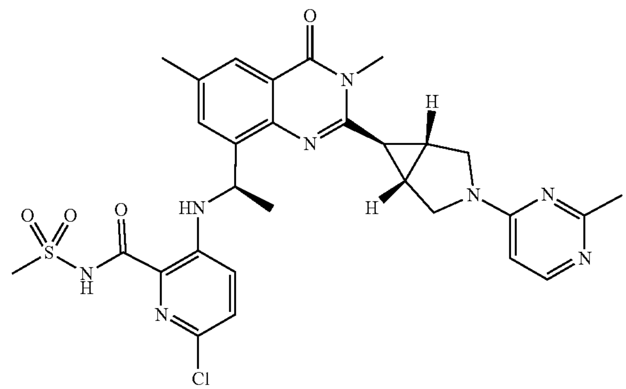 | 6-chloro-3-(((R)-1-(3,6-dimethyl-2-((1R,5S,6r)-3-(2-methylpyrimidin-4-yl)-3-azabicyclo[3.1.0]hexan-6-yl)-4-oxo-3,4-dihydroquinazolin-8-yl)ethyl)amino)-N-(methylsulfonyl)picolinamide | 1.94 min, 220 nm, MS (ES+)[b] $C_{29}H_{31}ClN_8O_4S$, requires: 622.2, found: 623.3 [M + H]+ |
| 854 | 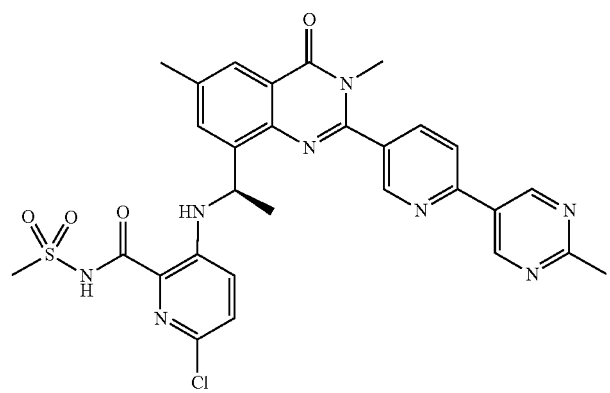 | (R)-6-chloro-3-((1-(3,6-dimethyl-2-(6-(2-methylpyrimidin-5-yl)pyridin-3-yl)-4-oxo-3,4-dihydroquinazolin-8-yl)ethyl)amino)-N-(methylsulfonyl)picolinamide | 2.17 min, 254 nm, MS (ES+)[b] $C_{29}H_{27}ClN_8O_4S$, requires: 618.2, found: 619.3 [M + H]+ |
| 855 | 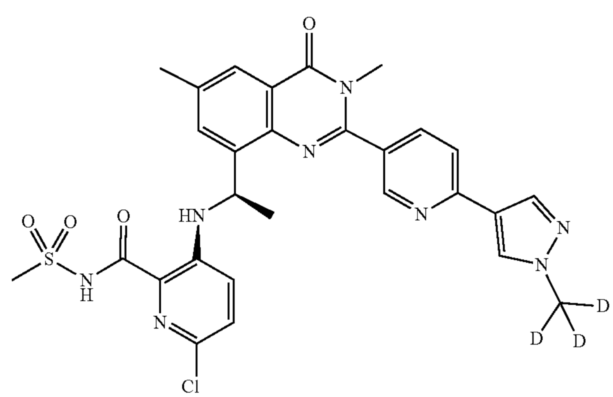 | (R)-6-chloro-3-((1-(3,6-dimethyl-2-(6-(1-(methyl-d3)-1H-pyrazol-4-yl)pyridin-3-yl)-4-oxo-3,4-dihydroquinazolin-8-yl)ethyl)amino)-N-(methylsulfonyl)picolinamide | 2.13 min, 220 nm, MS (ES+)[b] $C_{28}H_{24}D_3ClN_8O_4S$, requires: 609.2, found: 610.3 [M + H]+ |

TABLE E7-continued compound list prepared according to the procedure in Example 7

| Cpd. ID | Structure | Name | LCMSb |
|---|---|---|---|
| 856 | 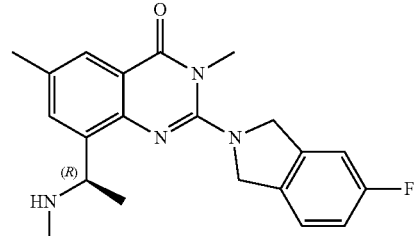 | (R)-6-chloro-3-((1-(2-(2-methoxypyrimidin-5-yl)-3,6-dimethyl-4-oxo-3,4-dihydroquinazolin-8-yl)ethyl)amino)-N-(methylsulfonyl)picolinamide | 2.19 min, 254 nm, MS (ES+)[b] $C_{24}H_{24}ClN_7O_5S$, requires: 557.1, found: 558.1 [M + H]+ |

[b]Observed Utilizing LCMS Method B.
[c]Observed utilizing LCMS method B.

Example 8

Compound 93 (R)-8-(1-((6-chloro-2-oxo-1,2-dihydropyridin-3-yl)amino)ethyl)-2-(5-fluoroisoindolin-2-yl)-3,6-dimethylquinazolin-4(3H)-one

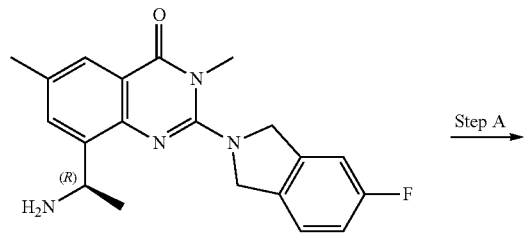

Step A →

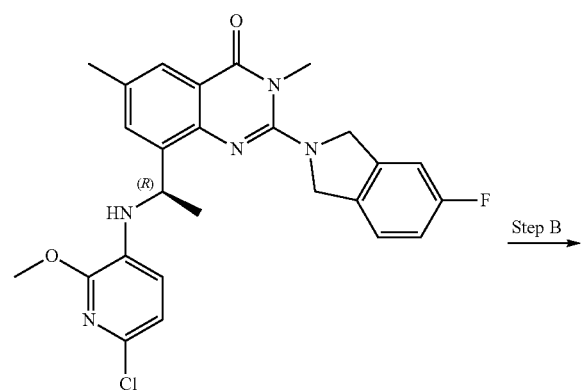

Step B →

-continued

Step A: To a stirred solution of (R)-8-(1-aminoethyl)-2-(5-fluoroisoindolin-2-yl)-3,6-dimethylquinazolin-4(3H)-one (1.00 g, 2.84 mmol) and 3-bromo-6-chloro-2-methoxypyridine (0.76 g, 3.40 mmol) in 1,4 Dioxane (100 mL) was added NaO<sup>t</sup>Bu (0.82 g, 8.52 mmol, 3.0 0 equiv). The reaction mixture was purged with $N_2$ gas for 15-20 min followed by the addition of $Pd_2(dba)_3$ (0.26 g, 0.28 mmol) and DavePhos (0.11 g, 0.28 mmol). The reaction mixture was stirred at 90° C. for 8 h. After completion of the reaction as indicated by TLC (using 60% EtOAc in Hexane as a mobile phase), the reaction mixture was diluted with water (30 mL) and extracted with EtOAc (3×30 mL). The combined organic layer was dried over $Na_2SO_4$ and the solvent was removed in vacuo to afford crude. The crude material was purified by flash column chromatography (silica gel, 230-400 mesh, 29% EtOAc/Hexane) to afford (R)-8-(1-((6-chloro-2-methoxypyridin-3-yl)amino)ethyl)-2-(5-fluoroisoindolin-2-yl)-3,6-dimethylquinazolin-4(3H)-one as a brown solid (1.10 g, 39%). LCMS: MS (ES+) $C_{26}H_{25}ClFN_5O_2$, requires: 493.2 found: 494.3 [M+H]+. $^1$H NMR (400 MHz, DMSO d$_6$): δ 7.68 (d, J=1.2 Hz, 1H), 7.52 (d, J=2.0 Hz, 1H), 7.43 (dd, J=8.4, 5.2 Hz, 1H), 7.28 (dd, J=9.0, 2.1 Hz, 1H), 7.22-7.10 (m, 1H), 6.68 (d, J=8.0 Hz, 1H), 6.59 (d, J=8.0 Hz, 1H), 5.98 (d, J=8.0 Hz, 1H), 5.25-5.12 (m 1H), 5.06-5.02 (m 4H), 3.83 (s, 3H), 3.59 (s, 3H), 2.31 (s, 3H), 1.54 (d, J=6.8 Hz, 3H).

Step B: To a stirred solution of (R)-8-(1-((6-chloro-2-methoxypyridin-3-yl) amino) ethyl)-2-(5-fluoroisoindolin-2-yl)-3,6-dimethylquinazolin-4(3H)-one (0.50 g, 1.01 mmol) at 0° C. in dry DCM (5.00 mL), and then BBr$_3$ (1.00 M in DCM) (2.50 mL, 2.53 mmol) was added dropwise at same temperature. The reaction mixture was stirred at RT for 48 h. After completion of the reaction as indicated by TLC (using 60% EtOAc in Hexane as a mobile phase), the reaction mixture was diluted with NaHCO$_3$ solution (30 mL) and extracted with DCM (3×50 mL). The combined organic layer was dried over Na$_2$SO$_4$ and the solvent was removed in vacuo to afford crude. The crude was purified by flash column chromatography (silica gel, 230-400 mesh, 53% EtOAc/Hexane) to afford (R)-8-(1-((6-chloro-2-oxo-1,2-dihydropyridin-3-yl)amino)ethyl)-2-(5-fluoroisoindolin-2-yl)-3,6-dimethylquinazolin-4(3H)-one as an off white solid (74.0 mg, 15%). LCMS: MS (ES+) C$_{25}$H$_{23}$ClFN$_5$O$_2$, requires: 479.15 found: 480.4 [M+H]$^+$. HPLC: 8.86 min, 97.04%, 254 nm. Chiral HPLC: 6.38 min, 100%, 235 nm. $^1$H NMR (400 MHz, DMSO d$_6$): δ 12.24 (s, 1H), 7.68 (d, J=1.2 Hz, 1H), 7.49 (d, J=1.2 Hz, 1H), 7.41 (dd, J=8.4, 4.8 Hz, 1H), 7.26 (dd, J=9.2, 2.0 Hz, 1H), 7.20-7.09 (m, 1H), 6.24 (br s, 2H), 5.86 (br s, 1H), 5.26-5.11 (m, 1H), 5.05-5.00 (m, 4H), 3.59 (s, 3H), 2.32 (s, 3H), 1.52 (d, J=6.8 Hz, 3H).

TABLE E8 compound list prepared according to the procedure in Example 8

| Cpd. ID | Structure | Name | LCMS |
|---|---|---|---|
| 94 | 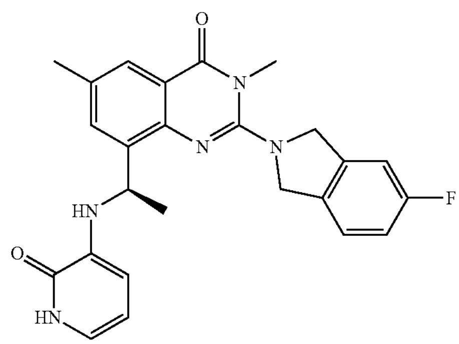 [SMILES: Cc1cc([C@@H](C)Nc2ccc[nH]c2=O)c2nc(N3Cc4ccc(F)cc4C3)n(C)c(=O)c2c1] | (R)-2-(5-fluoroisoindolin-2-yl)-3,6-dimethyl-8-(1-((2-oxo-1,2-dihydropyridin-3-yl)amino)ethyl)quinazolin-4(3H)-one | 2.21 min, 254 nm, MS (ES+)$^b$ C$_{25}$H$_{24}$FN$_5$O$_2$ requires: 445.1, found: 446.3 [M + H]$^+$ |
| 95 | 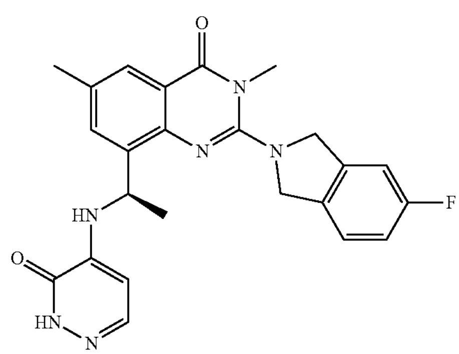 [SMILES: Cc1cc([C@@H](C)Nc2ccn[nH]c2=O)c2nc(N3Cc4ccc(F)cc4C3)n(C)c(=O)c2c1] | (R)-2-(5-fluoroisoindolin-2-yl)-3,6-dimethyl-8-(1-((3-oxo-2,3-dihydropyridazin-4-yl)amino)ethyl)quinazolin-4(3H)-one | 2.23 min, 254 nm, MS (ES+)$^a$ C$_{24}$H$_{23}$FN$_6$O$_2$ requires: 446.1, found: 447.2 [M + H]$^+$ |
| 96 | 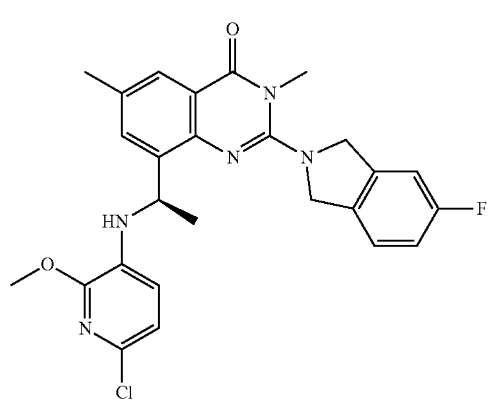 [SMILES: COc1nc(Cl)ccc1N[C@H](C)c1cc(C)cc2c(=O)n(C)c(N3Cc4ccc(F)cc4C3)nc12] | (R)-8-(1-((6-chloro-2-methoxypyridin-3-yl)amino)ethyl)-2-(5-fluoroisoindolin-2-yl)-3,6-dimethylquinazolin-4(3H)-one | 2.94 min, 254 nm, MS (ES+)$^a$ C$_{26}$H$_{25}$ClFN$_5$O$_2$, requires: 493.17 found: 494.3 [M + H]$^+$ |

TABLE E8-continued compound list prepared according to the procedure in Example 8

| Cpd. ID | Structure | Name | LCMS |
|---|---|---|---|
| 97 | 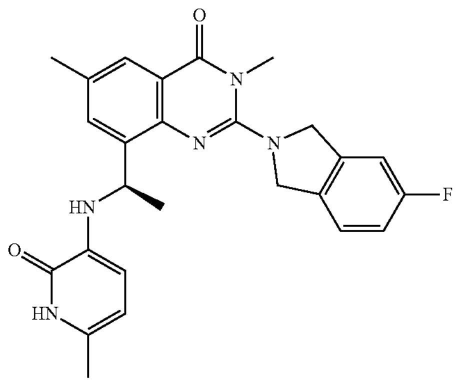 [SMILES: Cc1cc([C@@H](C)Nc2ccc(C)[nH]c2=O)c2nc(N3Cc4ccc(F)cc4C3)n(C)c(=O)c2c1] | (R)-2-(5-fluoroisoindolin-2-yl)-3,6-dimethyl-8-(1-((6-methyl-2-oxo-1,2-dihydropyridin-3-yl)amino)ethyl)quinazolin-4(3H)-one | 2.23 min, 254 nm, MS (ES+)$^a$ $C_{26}H_{26}FN_5O_2$ requires: 459.2, found: 460.3 [M + H]$^+$ |
| 98 | 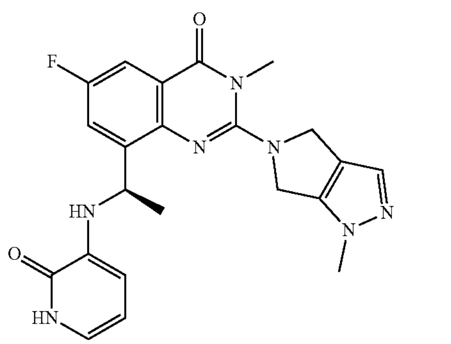 [SMILES: C[C@@H](Nc1ccc[nH]c1=O)c1cc(F)cc2c(=O)n(C)c(N3Cc4cnn(C)c4C3)nc12] | (R)-6-fluoro-3-methyl-2-(1-methyl-4,6-dihydropyrrolo[3,4-c]pyrazol-5(1H)-yl)-8-(1-((2-oxo-1,2-dihydropyridin-3-yl)amino)ethyl)quinazolin-4(3H)-one | 1.89 min, 254 nm, MS (ES+)$^a$ $C_{22}H_{22}FN_7O_2$ requires: 435.1, found: 436.3 [M + H]$^+$ |
| 99 | 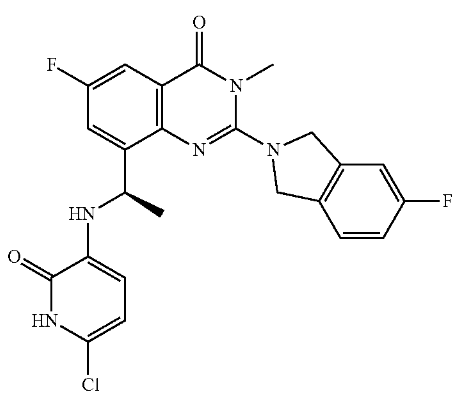 [SMILES: C[C@@H](Nc1ccc(Cl)[nH]c1=O)c1cc(F)cc2c(=O)n(C)c(N3Cc4ccc(F)cc4C3)nc12] | (R)-8-(1-((6-chloro-2-oxo-1,2-dihydropyridin-3-yl)amino)ethyl)-6-fluoro-2-(5-fluoroisoindolin-2-yl)-3-methylquinazolin-4(3H)-one | 2.39 min, 254 nm, MS (ES+)$^b$ $C_{24}H_{20}ClF_2N_5O_2$ requires: 483.1, found: 484.7 [M + H]$^+$ |
| 100 | 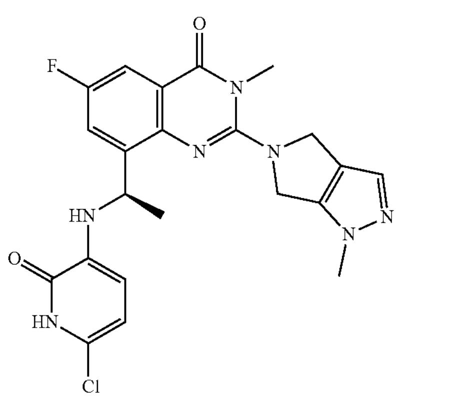 [SMILES: C[C@@H](Nc1ccc(Cl)[nH]c1=O)c1cc(F)cc2c(=O)n(C)c(N3Cc4cnn(C)c4C3)nc12] | (R)-8-(1-((6-chloro-2-oxo-1,2-dihydropyridin-3-yl)amino)ethyl)-6-fluoro-3-methyl-2-(1-methyl-4,6-dihydropyrrolo[3,4-c]pyrazol-5(1H)-yl)quinazolin-4(3H)-one | 1.88 min, 254 nm, MS (ES+)$^b$ $C_{22}H_{21}ClFN_7O_2$ requires: 469.1, found: 470.5 [M + H]$^+$ |

TABLE E8-continued compound list prepared according to the procedure in Example 8

| Cpd. ID | Structure | Name | LCMS |
|---|---|---|---|
| 101 | 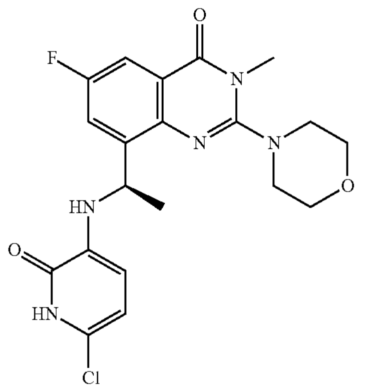 [SMILES: C[C@@H](Nc1ccc(Cl)[nH]c1=O)c1cc(F)cc2c(=O)n(C)c(N3CCOCC3)nc12] | (R)-8-(1-((6-chloro-2-oxo-1,2-dihydropyridin-3-yl)amino)ethyl)-6-fluoro-3-methyl-2-morpholinoquinazolin-4(3H)-one | 2.06 min, 210 nm, MS (ES+)[b] $C_{20}H_{21}ClFN_5O_3$ requires: 433.1, found: 435.1 [M + H]+ |

[a]Observed utilizing LCMS Method A.
[b]Observed Utilizing LCMS Method B.

Additionally, compounds herein may be synthesized in a racemic fashion and separated by chiral SFC purification to provide individual enantiomers. The procedures outlined below are representative:

Example 9

Compounds 102 and 103: 2,2-difluoro-N-((2-((1-(2-(5-fluoroisoindolin-2-yl)-3,6-dimethyl-4-oxo-3,4-dihydroquinazolin-8-yl)ethyl)amino)phenyl)sulfonyl)acetamide

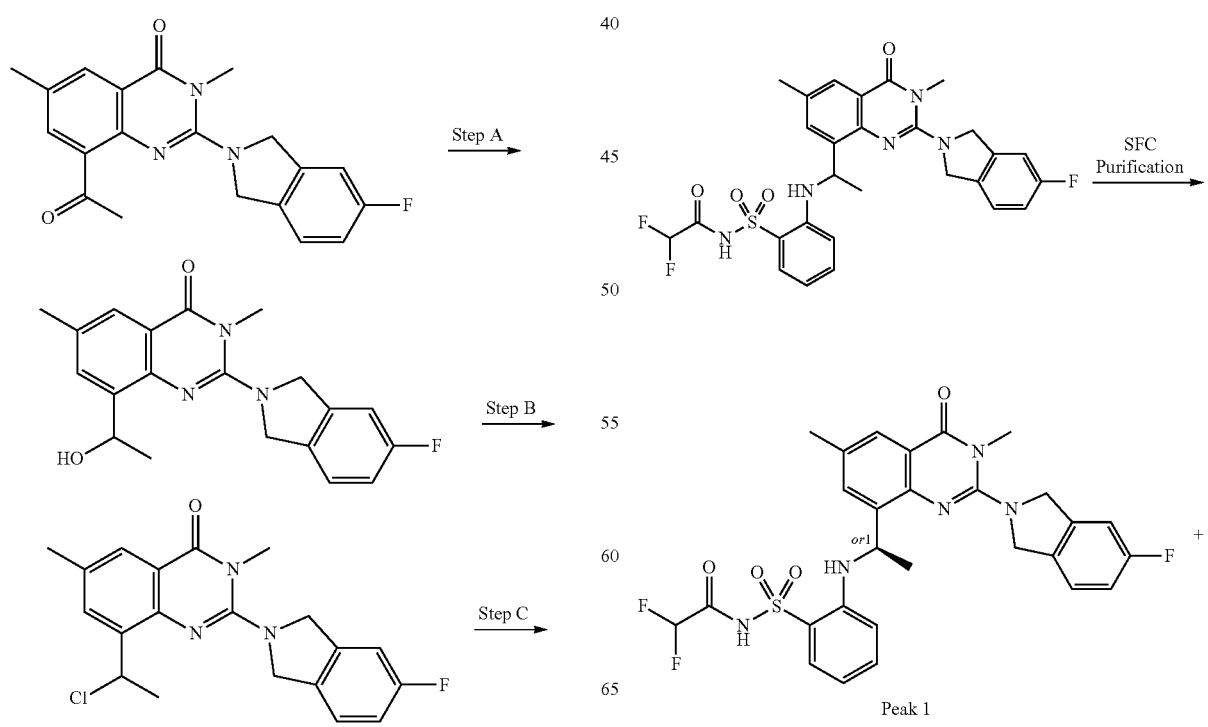

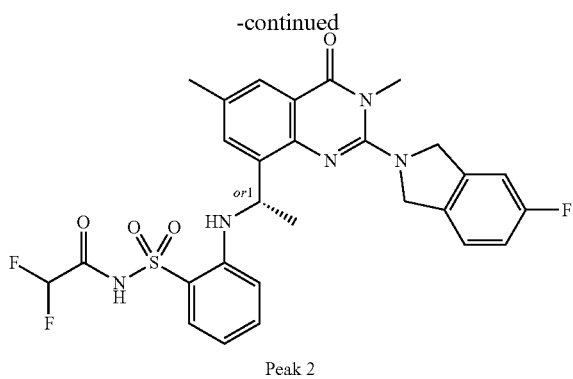

Peak 2

Step A: To a stirred solution of 8-acetyl-2-(5-fluoroisoindolin-2-yl)-3,6-dimethylquinazolin-4(3H)-one (25.0 g, 71.1 mmol) in MeOH (250 mL) and DCM (250 mL) was added NaBH$_4$ (6.72 g, 178 mmol) portion wise at 0° C. The reaction mixture was stirred at RT for 2 h. After completion of the reaction as indicated by TLC (using 50% EtOAc in Hexane as a mobile phase), the reaction mixture was slowly poured into ice cold water (500 mL) and extracted by DCM (3×500 mL). The organic layer was separated, dried over sodium sulfate, and concentrated under reduced pressure to afford 2,2-difluoro-N-((2-((1-(2-(5-fluoroisoindolin-2-yl)-3,6-dimethyl-4-oxo-3,4-dihydroquinazolin-8-yl)ethyl)amino)phenyl)sulfonyl)acetamide as off white solid (18.0 g, 72%). LCMS: MS (ES+) $C_{20}H_{20}FN_3O_2$ requires: 353.1, found: 354.6 [M+H]$^+$. $^1$H NMR (DMSO-d$_6$, 400 MHz): δ ppm, 7.69 (d, J=1.2 Hz, 1H), 7.64 (d, J=2.0 Hz, 1H), 7.41 (dd, J=8.4, 5.2 Hz, 1H), 7.26 (dd, J=8.8, 2.0 Hz, 1H), 7.14 (td, J=9.2, 2.4 Hz, 1H), 5.47-5.42 (m, 1H), 5.12 (d, J=4.4 Hz, 1H), 5.08-4.99 (m, 2H), 4.93-4.85 (m, 2H), 3.57 (s, 3H), 2.38 (s, 3H), 1.39 (d, J=6.4 Hz, 3H).

Step B: To a stirred solution of 2-(5-fluoroisoindolin-2-yl)-8-(1-hydroxyethyl)-3,6-dimethylquinazolin-4(3H)-one (5.00 g, 14.1 mmol) in DCM (100 mL) was added SOCl$_2$ (3.0 mL, 42.4 mmol) at 0° C. The reaction mixture was stirred at RT for 2 h. After completion of the reaction as indicated by TLC (using 30% EtOAc in Hexane as a mobile phase), the reaction mixture was directly concentrated under reduced pressure to afford crude. The crude material was purified by trituration by using n-pentane to afford 8-(1-chloroethyl)-2-(5-fluoroisoindolin-2-yl)-3,6-dimethylquinazolin-4(3H)-one as a pale brown solid. (5.01 g, 95%). LCMS: MS (ES+) $C_{21}H_{22}FN_3O_2$ requires: 367.1, found: 368.1 [M+MeOH]$^+$. HPLC: 10.07 min, 98.45%, 280.0 nm. $^1$H NMR (DMSO-d$_6$, 400 MHz): δ 7.79 (s, 1H), 7.76 (d, J=2.0 Hz, 1H), 7.42 (dd, J=8.4, 5.2 Hz, 1H), 7.27 (dd, J=9.2, 2.0 Hz, 1H), 7.15 (td, J=9.6, 2.4 Hz, 1H), 6.19 (q, J=7.2 Hz, 1H), 5.08-4.99 (m, 4H) 3.58 (s, 3H), 2.41 (s, 3H), 1.87 (d, J=6.8 Hz, 3H).

Step C: To a stirred solution of 8-(1-chloroethyl)-2-(5-fluoroisoindolin-2-yl)-3,6-dimethylquinazolin-4(3H)-one (1.50 g, 4.04 mmol) in Acetonitrile (15.0 mL). The 2-aminobenzenesulfonamide (1.04 g, 6.06 mmol), TBAI (746 mg, 2.02 mmol) and Cs$_2$CO$_3$ (3.94 g, 12.1 mmol) were added into reaction at room temperature. The reaction mixture was heated at 60° C. for 16 h. After completion of the reaction as indicated by TLC (using 50% EtOAc in Hexane as a mobile phase), the reaction mixture was diluted with water (2×50 mL) and extracted with EtOAc (3×50 mL). The combined organic layers were dried over Na$_2$SO$_4$, filtered, and concentrated under reduced pressure to afford crude product. The crude product was purified by flash column chromatography using (400-600 mesh silica, 35% EtOAc: Hexane) to afford 2-((1-(2-(5-fluoroisoindolin-2-yl)-3,6-dimethyl-4-oxo-3,4-dihydroquinazolin-8-yl)ethyl)amino)benzenesulfonamide as a yellow solid (1.00 g, 49%). LCMS: MS (ES+) $C_{26}H_{26}FN_5O_3S$ requires: 507.1, found: 508.3 [M+H]$^+$.

Step D: To a stirred solution of 2-((1-(2-(5-fluoroisoindolin-2-yl)-3,6-dimethyl-4-oxo-3,4-dihydroquinazolin-8-yl)ethyl) amino) benzenesulfonamide (0.30 g, 0.59 mmol) in DCM (6.00 mL) was added triethylamine (0.25 mL, 1.77 mmol) at 0° C. followed by difluoro acetic anhydride (68.0 μL, 0.59 mmol). The reaction mixture was stirred at RT for 3 h. After completion of the reaction as indicated by TLC (using 50% EtOAc in Hexane as a mobile phase), the reaction mixture was concentrated under reduced pressure to afford crude compound. The crude compound was purified by Prep-HPLC purification (Acetonitrile and 0.05% Formic acid in water) to afford 2,2-difluoro-N-((2-((1-(2-(5-fluoroisoindolin-2-yl)-3,6-dimethyl-4-oxo-3,4-dihydroquinazolin-8-yl)ethyl)amino)phenyl)sulfonyl)acetamide as an off-white solid (0.058 g, 17%). LCMS: MS (ES+) $C_{28}H_{26}F_3N_5O_4S$ requires: 585.1, found: 586.4 [M+H]$^+$. HPLC: 10.61 min, 96.18%, 210.0 nm. CHIRAL HPLC: 7.75 min and 8.37 min, 47.17% and 48.06%, 240.0 nm. $^1$H NMR: (400 MHz, DMSO-d6): δ 7.69-7.65 (m, 2H), 7.53 (s, 1H), 7.41 (dd, J=8.0, 5.2 Hz, 1H), 7.25 (d, J=8.0 Hz, 1H), 7.21-712 (m, 2H), 6.61 (t, J=7.6 Hz, 1H), 6.42 (d, J=8.4 Hz, 1H), 6.24 (t, J=53.2 Hz, 1H), 5.51-5.46 (m, 1H), 5.11-4.96 (m, 4H), 3.60 (s, 3H), 2.27 (s, 3H), 1.55 (d, J=6.4 Hz, 3H).

SFC Purification:

The resulting racemic mixture was subjected to chiral prep HPLC and isomers were separated in chiral SFC (Column: Chiral Pak IB N-5 (250 mm×10 mm×5 μm) Mobile phase: 0.1% TFA in HEPTANE_IPA (90:10) give Peak-1 and Peak-2.

Peak-1:2,2-difluoro-N-((2-((1-(2-(5-fluoroisoindolin-2-yl)-3,6-dimethyl-4-oxo-3,4-dihydroquinazolin-8-yl)ethyl) amino)phenyl)sulfonyl)acetamide Qt: 17.3 mg LCMS: MS (ES+) $C_{28}H_{26}F_3N_5O_4S$ requires: 585.1, found: 586.5 [M+H]$^+$. HPLC: 5.98 min, 95.06%, 210.0 nm. Chiral HPLC: 7.60 min, 95.17%, 288.0 nm. $^1$H NMR: (400 MHz, DMSO-d6): δ 7.70-7.69 (m, 1H), 7.65 (dd, J=6.4, 1.6 Hz, 1H), 7.52 (d, J=2.0 Hz, 1H), 7.41 (dd, J=5.2, 3.2 Hz, 1H), 7.25 (dd, J=5.2, 2.4 Hz, 1H), 7.21-7.12 (m, 2H), 6.60 (t, J=7.2 Hz, 1H), 6.40 (d, J=8.4 Hz, 1H), 6.21 (t, J=53.6 Hz, 1H), 5.48-5.45 (m, 1H), 5.11-4.96 (m, 4H), 3.61 (s, 3H), 2.27 (s, 3H), 1.55 (d, J=7.6 Hz, 3H).

Peak-2: 2,2-difluoro-N-((2-((1-(2-(5-fluoroisoindolin-2-yl)-3,6-dimethyl-4-oxo-3,4-dihydroquinazolin-8-yl)ethyl) amino)phenyl)sulfonyl)acetamide Qt: 16.4 g. LCMS: MS (ES+) $C_{28}H_{26}F_3N_5O_4S$ requires: 585.1, found: 586.4 [M+H]$^+$. HPLC: 5.96 min, 95.51%, 210.0 nm. Chiral HPLC: 7.98 min, 93.92%, 288.0 nm. $^1$H NMR: (400 MHz, DMSO-d6): δ 7.70-7.69 (m, 1H), 7.65 (dd, J=8.0, 1.6 Hz, 1H), 7.52 (d, J=2.0 Hz, 1H), 7.41 (dd, J=5.2, 3.2 Hz, 1H), 7.25 (dd, J=9.2, 2.0 Hz, 1H), 7.19-7.12 (m, 2H), 6.59 (t, J=7.2 Hz, 1H), 6.40 (d, J=8.4 Hz, 1H), 6.20 (t, J=53.6 Hz, 1H), 5.50-5.45 (m, 1H), 5.08-4.96 (m, 4H), 3.60 (s, 3H), 2.27 (s, 3H), 1.55 (d, J=6.4 Hz, 3H).

The compounds below were purified via chiral prep HPLC and isomers separated via chiral SFC (Column: CHIRALPAK IA 250×50 mm 5 μm), Mobile phase: 0.1% Ammonia IPA: Methanol (50:50) to give Peak-1 and Peak-2. These isomers were eluted at retention times 6.93 min (Peak-1) and 11.42 min (Peak-2).

TABLE E8 compound list prepared according to the procedure in Example 9

| Cpd. ID | Structure | Name | LCMS[a] |
|---|---|---|---|
| 104 (Peak 1) | 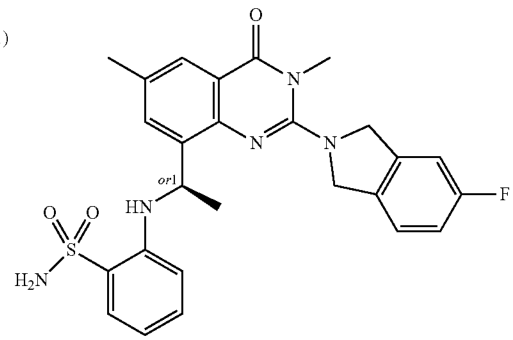 | 2-((1-(2-(5-fluoroisoindolin-2-yl)-3,6-dimethyl-4-oxo-3,4-dihydroquinazolin-8-yl)ethyl)amino)benzenesulfonamide | 2.77 min, 254 nm, MS (ES+) $C_{26}H_{26}FN_5O_3S$ requires: 507.6, found: 508.2 [M + H]+ |
| 105 (Peak 2) | 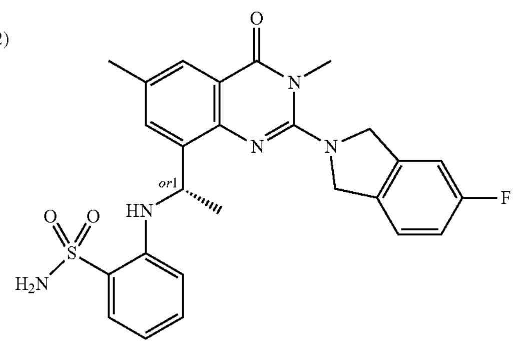 | 2-((1-(2-(5-fluoroisoindolin-2-yl)-3,6-dimethyl-4-oxo-3,4-dihydroquinazolin-8-yl)ethyl)amino)benzenesulfonamide | 2.77 min, 254 nm, MS (ES+) $C_{26}H_{26}FN_5O_3S$ requires: 507.6, found: 508.2 [M + H]+ |

[a]Observed utilizing LCMS Method A.

Example 10

Compounds 106 and 107: 4-((1-(2-(5-fluoroisoindolin-2-yl)-3,6-dimethyl-4-oxo-3,4-dihydroquinazolin-8-yl)ethyl)amino)-1-methyl-N-(methylsulfonyl)-1H-pyrazole-3-carboxamide

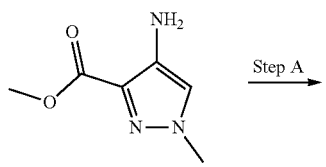

Step A →

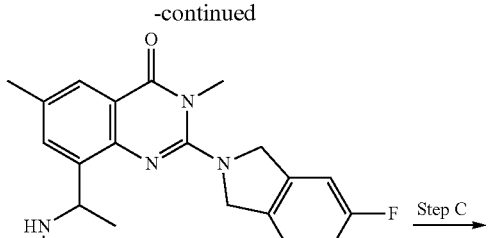

Step C →

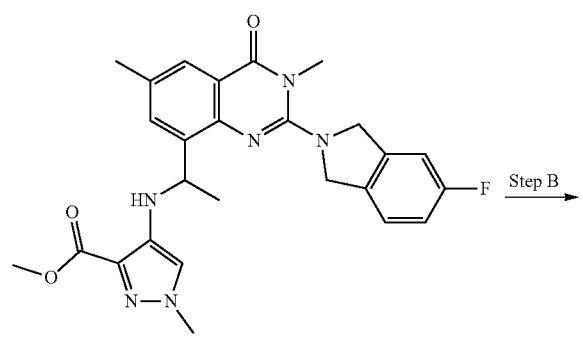

Step B →

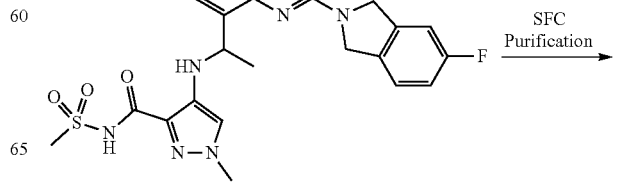

SFC Purification →

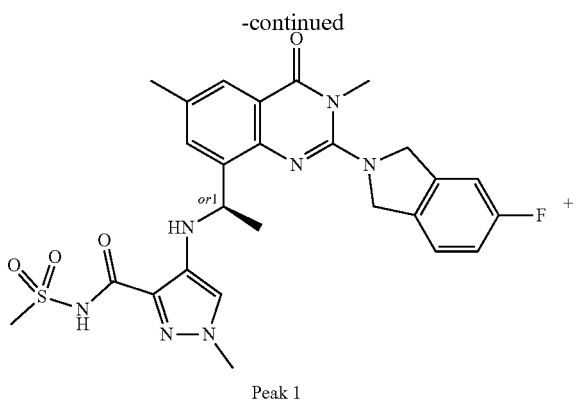

Peak 1

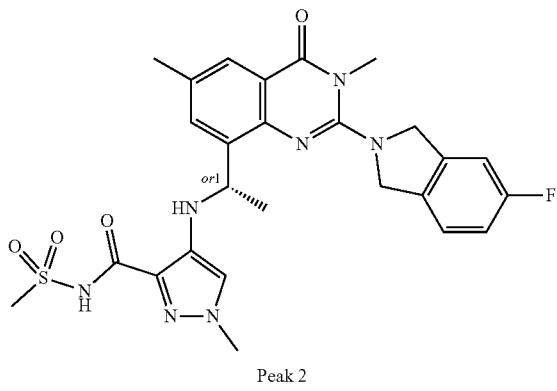

Peak 2

Step A: To a stirred solution of 8-(1-chloroethyl)-2-(5-fluoroisoindolin-2-yl)-3,6-dimethylquinazolin-4(3H)-one (0.40 g, 1.13 mmol) and methyl 4-amino-1-methyl-1H-pyrazole-3-carboxylate (0.17 g, 1.13 mmol) in acetonitrile (4.00 mL) was added tetra n-butyl ammonium iodide (0.83 g, 2.26 mmol) and stirred at 90° C. for 12 h. After completion of the reaction as indicated by TLC (using 60% EtOAc: Hex as a mobile phase), the resulting reaction mixture was diluted with water (30 mL) and extracted with ethyl acetate (3×30 mL). The combined organic layer was dried over $Na_2SO_4$ and concentrated under reduced pressure to afford crude product. The crude product was purified by flash column chromatography (100-200 silica, 80% EA in Hexane) to afford methyl 4-((1-(2-(5-fluoroisoindolin-2-yl)-3,6-dimethyl-4-oxo-3,4-dihydroquinazolin-8-yl)ethyl)amino)-1-methyl-1H-pyrazole-3-carboxylate (0.18 g, 32%). LCMS: MS (ES+) $C_{26}H_{27}FN_6O_3$, requires: 490.2, found: 491.4 $[M+H]^+$. $^1H$ NMR (400 MHz, DMSO $d_6$): δ 7.69 (s, 1H), 7.50 (s, 1H), 7.42 (dd, J=8.4, 5.6 Hz, 1H), 7.27 (d, J=7.6 Hz, 1H), 7.15 (t, J=8.8 Hz, 1H), 6.96 (s, 1H), 5.71 (br s, 1H), 5.10-4.97 (m, 4H), 4.85 (br s, 1H), 3.68 (s, 3H), 3.65 (s, 3H), 3.59 (s, 3H), 2.34 (s, 3H), 1.55 (d, J=6.8 Hz, 3H).

Step B: To a stirred solution of methyl 4-((1-(2-(5-fluoroisoindolin-2-yl)-3,6-dimethyl-4-oxo-3,4-dihydroquinazolin-8-yl) ethyl) amino)-1-methyl-1H-pyrazole-3-carboxylate (0.16 g, 0.32 mmol) in THF (1.60 mL) and MeOH (0.80 mL) was added 1N NaOH in $H_2O$ (0.8 mL) at room temperature. The reaction mixture was stirred at RT for 16 h. After completion of the reaction as indicated by TLC (60% EtOAc in Hexane as a mobile phase), the reaction mixture was concentrated under a vacuum to obtain the crude. The obtained crude was diluted with water, acidified using 2N HCl up to pH=5 and extracted with ethyl acetate (3×15 mL). The combined organic layers were dried over $Na_2SO_4$ and concentrated under reduced pressure to afford crude product. The obtained crude was purified by trituration using n-Pentane to afford 4-((1-(2-(5-fluoroisoindolin-2-yl)-3,6-dimethyl-4-oxo-3,4-dihydroquinazolin-8-yl)ethyl)amino)-1-methyl-1H-pyrazole-3-carboxylic acid as a brown solid (0.15 g, 97%). LCMS: MS (ES+) $C_{25}H_{25}FN_6O_3$, requires: 476.2, found: 477.3 $[M+H]^+$.

Step C: To a stirred solution of 4-((1-(2-(5-fluoroisoindolin-2-yl)-3,6-dimethyl-4-oxo-3,4-dihydroquinazolin-8-syl) ethyl)amino)-1-methyl-1H-pyrazole-3-carboxylic acid (0.30 g, 0.63 mmol) in DCM (3.00 mL) was added EDC·HCl (0.24 g, 1.26 mmol), methane sulfonamide (0.23 g, 2.52 mmol) and Dimethyl aminopyridine (38.0 mg, 0.31 mmol). The reaction mixture was stirred at RT for 16 h. After completion of the reaction as indicated by TLC (using 5% MeOH:DCM as a mobile phase), the resulting reaction mixture was diluted with water (20 mL) and extracted with dichloromethane (3×20 mL). The combined organic layers were dried over $Na_2SO_4$ and concentrated under reduced pressure to afford crude product. The crude product was purified by reverse phase flash column chromatography (C18 silica, 28% ACN in water) to afford 4-((1-(2-(5-fluoroisoindolin-2-yl)-3,6-dimethyl-4-oxo-3,4-dihydroquinazolin-8-yl)ethyl)amino)-1-methyl-N-(methylsulfonyl)-1H-pyrazole-3-carboxamide as an off-white solid (24.0 mg, 7%). LCMS$^a$: MS (ES+) $C_{26}H_{28}FN_7O_4S$, requires: 553.2, found: 554.4 $[M+H]^+$. HPLC: 96.20%, 8.160 min at 254 nm. CHIRAL HPLC: 46.48% and 49.29%, 5.49 and 5.71 min at 235 nm. $^1H$ NMR (400 MHz, DMSO $d_6$): δ 7.69 (s, 1H), 7.51 (d, J=1.6 Hz, 1H), 7.44-7.40 (m, 1H), 7.27 (d, J=8.4 Hz, 1H), 7.17 (t, J=7.2 Hz, 1H), 7.03 (s, 1H), 5.06-5.01 (m, 4H), 4.85-4.84 (m, 1H), 3.69 (s, 3H), 3.58 (s, 3H), 3.19 (s, 3H), 2.35 (s, 3H), 1.56 (d, J=6.4 Hz, 3H).

SFC Purification

The racemic mixture was subjected to chiral prep HPLC and isomers were separated in chiral SFC (Column: Chiralpak IB N-5 (250 mm×10 mm×5 µm), Mobile phase A: 0.1% $NH_3$ in heptane and Mobile phase B: 0.1% $NH_3$ in isopropanol) to give Peak 1 and Peak 2. These isomers were eluted at retention times 5.56 min (Peak 1) and 5.75 min (Peak 2).

Peak 1: 4-((1-(2-(5-fluoroisoindolin-2-yl)-3,6-dimethyl-4-oxo-3,4-dihydroquinazolin-8-yl)ethyl)amino)-1-methyl-N-(methylsulfonyl)-1H-pyrazole-3-carboxamide: Qt. 6.00 mg LCMS: 2.34 min, 210 nm, MS (ES+) $C_{26}H_{28}FN_7O_4S$ requires: 553.61, found: 554.3 $[M+H]^+$. HPLC: 8.87 min, 210 nm Chiral HPLC: 5.56 min, 95.67%, 235 nm. $^1H$ NMR (CD$_3$OD, 400 MHz): δ 7.79 (d, J=1.2 Hz, 1H), 7.55 (s, 1H), 7.40-7.37 (m, 1H), 7.16 (dd, J=8.8, 2.0 Hz, 1H), 7.07 (td, J=9.2, 2.4 Hz, 1H), 6.90 (s, 1H), 5.11-5.05 (m, 5H), 3.70 (s, 6H), 3.16 (s, 3H), 2.39 (s, 3H), 1.65 (d, J=6.8 Hz, 3H).

Peak 2: 4-((1-(2-(5-fluoroisoindolin-2-yl)-3,6-dimethyl-4-oxo-3,4-dihydroquinazolin-8-yl)ethyl)amino)-1-methyl-N-(methylsulfonyl)-1H-pyrazole-3-carboxamide: Qt. 6.00 mg LCMS: 2.34 min, 285 nm, MS (ES+)$C_{26}H_{28}FN_7O_4S$ requires: 553.61, found: 554.4 $[M+H]^+$. HPLC: 8.88 min, 210 nm Chiral HPLC: 5.75 min, 96.59%, 235 nm. $^1H$ NMR (CD$_3$OD, 400 MHz): δ ppm, 7.79 (d, J=0.8 Hz, 1H), 7.54 (d, J=1.6 Hz, 1H), 7.40-7.37 (m, 1H), 7.16 (dd, J=9.2, 2.0 Hz, 1H), 7.06 (td, J=9.2, 2.4 Hz, 1H), 6.90 (s, 1H), 5.15-4.99 (m, 5H), 3.71 (s, 3H), 3.70 (s, 3H), 3.17 (s, 3H), 2.39 (s, 3H), 1.65 (d, J=6.8 Hz, 3H).

TABLE E10 compound list prepared according to the procedure in Example 10

| Cpd. ID | Structure | Name | LCMS[a] |
|---|---|---|---|
| 108 (Peak 1) | 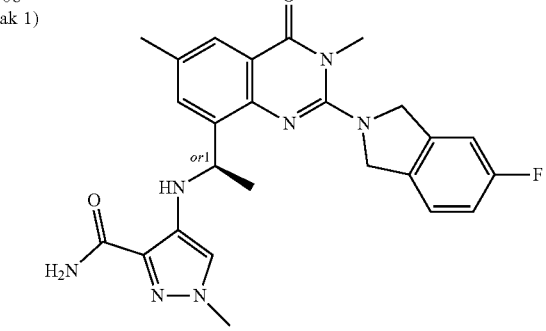 | 4-((1-(2-(5-fluoroisoindolin-2-yl)-3,6-dimethyl-4-oxo-3,4-dihydroquinazolin-8-yl)ethyl)amino)-1-methyl-1H-pyrazole-3-carboxamide | 2.09 min, 254 nm MS (ES+) $C_{25}H_{26}FN_7O_2$, requires: 475.2, found: 476.3 $[M + H]^+$ |

Example 11

Biological Assays

PI3K Wild Type Isoform and Mutant Enzyme Assays:

Activity against PI3Kα and PI3Kα H1047R enzymes were determined in biochemical assays using purified recombinant full-length proteins with the Transcreener ADP[2] TR-FRET Red Assay from Bellbrook Labs. (Catalogue number 3011-10K). Test compounds were dissolved in DMSO and were tested in 11 point 1:3 serial dilutions, typical final concentration range from 50,000 nM to 0.85 nM. Enzymes were pre-incubated with compounds for 2 hours at room temperature prior to initiating the reactions. Assays were initiated with a 2×ATP/PI(4,5)P2 diC8 substrate mixture. After 60 minutes at room temperature, the reactions were quenched with detection reagent and incubated for an additional 60 minutes at room temperature. The plates were read using a multimode reader and the emission ratio of 665 nm to 615 nm was determined. This ratio was converted to percent of control (POC). [1-(high control-sample signal)/(high control-low control)]*100. Wells without compound were used to determine high control values and wells without enzyme were used to determine low control values. The POC values were fit using a four-parameter logistic model and the value where the fit curve was equal to 50 POC was reported as the $IC_{50}$ using the Signals VitroVivo software package (PerkinElmer). Final assay conditions were: 40 mM HEPES pH 7.5, 20 mM NaCl, 25 mM $MgCl_2$, 0.01% Triton X-100. The enzyme source, catalogue number, final enzyme concentration, and final ATP and PI(4,5)P2 diC8 concentration can be found in the table E10 below.

TABLE E11 bioassay conditions

| Enzyme | PI3Kα | PI3Kα H1047R |
|---|---|---|
| Enzyme source | Sigma | Sigma |
| Enzyme Catalog # | 14-792M | 14-602M |
| Enzyme conc. | 5 nM | 5 nM |
| ATP conc. | 115 μM | 45 μM |
| 08:0 PI(4,5)P2 (Avanti) | 50 μM | 50 μM |

Homogenous Time-Resolved Fluorescence (HTRF) Phospho-AKT(S473) Cell Assay:

Compounds in the present disclosure were tested in a cell based HTRF phospho-AKT(S473) (CisBio/Revvity) assay in human breast cancer cell lines as a measurement of PIK3CA activity through measuring AKT, a downstream effector. The activity of mutant PI3Kα-H1047R and PI3Kα-Wild Type was measured in the T47D (PI3Kα-H1047R) and SKBR3 (PI3Kα-Wild Type) cell lines, respectively. T47D cells were plated at 20,000 cells per well in 50 μL in RPMI medium supplemented with 10% FBS and 0.2 units/mL insulin, in 384 well plates. SKBR3 cells were plated at 25,000 cells per well in 50 μL in McCoy's 5A medium supplemented with 10% FBS, in 384 well plates. Cells were plated using a Combi Multidrop reagent dispenser (ThermoFisher), and placed in 5% $CO_2$, 37° C. incubator overnight to adhere.

The next day, cells were treated with either compounds or vehicle (DMSO) in a 12-fold dose response curve of 1:3 dilutions, with 5 μM and 10 μM as the top concentrations for the T47D and SKBR3 cell lines, respectively. Compound treatment was facilitated via the D300e digital dispenser (Tecan), with a maximum DMSO concentration of 0.5%. Following compound addition, cell plates were incubated for 2 hours in 5% $CO_2$, 37° C. incubator. The SKBR3 cells were stimulated and treated with 70 ng/ml PDGF-BB ligand (ThermoFisher) for the remaining 15 minutes of the incubation. Following compound incubation, compound and media was aspirated from the cells and 25 μL of supplemented lysis buffer was added per well, and incubated for 45 minutes at room temperature, shaking at 600 rpm. Next, 16 μL of cell lysate was added to a 384 well low volume ProxyPlate (Perkin Elmer/Revvity) mixed with 4 μL of HTRF antibodies (1:1 Eu Cryptate+d2 Cryptate). HTRF supplemented lysis buffer and antibody reagents were used from the phosphor-AKT(S473) HTRF assay kit (CisBio/Revvity), following manufacturers protocol recommendations. Plates were sealed and incubated at 4° C. overnight.

The following day, plates were centrifuged for 1 minute at 1000 rpm, and read on a PHERAstar plate reader. $IC_{50}$ values were calculated using Spotfire software.

TABLE E12

PI3Kα Enzyme Assay Results
A < 100 nM ≤ B ≤ 250 nM ≤ C ≤ 500 nM ≤ D ≤ 1000 nM ≤ E

| Cpd. ID | PI3Kα H1047R IC$_{50}$ (nM) | PI3Kα WT IC$_{50}$ (nM) |
|---|---|---|
| 1 | D | E |
| 2 | E | E |
| 3 | C | E |
| 4 | C | E |
| 5 | D | E |
| 6 | E | E |
| 7 | E | E |
| 8 | C | E |
| 9 | D | E |
| 10 | C | E |
| 11 | C | E |
| 12 | C | E |
| 13 | D | E |
| 14 | C | E |
| 15 | C | E |
| 16 | C | E |
| 17 | E | E |
| 18 | E | E |
| 19 | E | E |
| 20 | E | E |
| 21 | C | E |
| 22 | E | E |
| 23 | A | E |
| 24 | C | E |
| 25 | E | E |
| 26 | D | E |
| 27 | D | E |
| 28 | D | E |
| 29 | C | E |
| 30 | B | E |
| 31 | B | E |
| 32 | C | D |
| 33 | C | E |
| 34 | D | E |
| 35 | E | E |
| 36 | E | E |
| 37 | C | E |
| 38 | D | E |
| 39 | D | E |
| 40 | E | E |
| 41 | D | E |
| 42 | D | E |
| 43 | E | E |
| 44 | B | E |
| 45 | B | D |
| 46 | E | E |
| 47 | A | D |
| 48 | B | E |
| 49 | B | E |
| 50 | C | E |
| 51 | A | E |
| 52 | B | E |
| 53 | B | E |
| 54 | B | E |
| 55 | D | E |
| 56 | E | E |
| 57 | E | E |
| 58 | E | E |
| 59 | E | E |
| 60 | E | E |
| 61 | E | E |
| 62 | A | E |
| 63 | E | E |
| 64 | E | E |
| 65 | E | E |
| 66 | B | A |
| 67 | E | E |
| 68 | E | E |
| 69 | E | E |
| 70 | C | E |
| 71 | E | E |
| 72 | B | E |
| 73 | C | E |
| 74 | B | E |
| 75 | E | E |
| 76 | A | E |
| 77 | E | E |
| 78 | D | E |
| 79 | B | E |
| 80 | B | E |
| 81 | A | E |
| 82 | E | E |
| 83 | E | E |
| 84 | E | E |
| 85 | E | E |
| 86 | E | E |
| 87 | E | E |
| 88 | E | E |
| 89 | B | D |
| 90 | E | E |
| 91 | C | E |
| 92 | A | E |
| 93 | E | E |
| 94 | E | E |
| 95 | E | E |
| 96 | E | E |
| 97 | E | E |
| 98 | E | E |
| 99 | B | E |
| 100 | A | E |
| 101 | B | E |
| 102 | E | E |
| 103 | E | E |
| 104 | E | E |
| 105 | E | E |
| 106 | E | E |
| 107 | E | E |
| 108 | E | E |

TABLE E13

PI3Kα Cell Assay Results
A < 250 nM ≤ B ≤ 500 nM ≤ C ≤ 1000 nM ≤ D ≤ 5000 nM ≤ E

| Cpd. ID | T47D IC$_{50}$ (nM) | SKBR3 IC$_{50}$ (nM) |
|---|---|---|
| 1 | A | D |
| 2 | D | E |
| 3 | A | D |
| 4 | A | D |
| 5 | A | D |
| 6 | D | E |
| 7 | D | E |
| 8 | B | D |
| 9 | B | D |
| 10 | D | E |
| 11 | B | E |
| 12 | B | D |
| 13 | B | D |
| 14 | B | D |
| 15 | B | D |
| 16 | B | D |
| 17 | D | E |
| 18 | D | E |
| 19 | C | E |
| 20 | C | D |
| 21 | A | D |
| 22 | D | E |
| 23 | C | D |
| 24 | B | D |
| 25 | B | D |

TABLE E13-continued

PI3Kα Cell Assay Results
A < 250 nM ≤ B ≤ 500 nM ≤ C ≤
1000 nM ≤ D ≤ 5000 nM ≤ E

| Cpd. ID | T47D IC$_{50}$ (nM) | SKBR3 IC$_{50}$ (nM) |
|---|---|---|
| 26 | A | D |
| 27 | A | D |
| 28 | A | D |
| 29 | B | D |
| 30 | A | D |
| 31 | B | D |
| 32 | B | D |
| 33 | B | D |
| 34 | B | D |
| 35 | D | E |
| 36 | B | D |
| 37 | A | C |
| 38 | B | D |
| 39 | A | D |
| 40 | B | D |
| 41 | B | D |
| 42 | B | D |
| 43 | B | D |
| 44 | A | D |
| 45 | A | D |
| 46 | C | D |
| 47 | A | D |
| 48 | A | D |
| 49 | A | D |
| 50 | D | D |
| 51 | A | C |
| 52 | C | D |
| 53 | A | D |
| 54 | A | D |
| 55 | A | D |
| 56 | B | D |
| 57 | C | D |
| 58 | B | D |
| 59 | D | E |
| 60 | D | D |
| 61 | D | E |
| 62 | D | D |
| 63 | D | D |
| 64 | D | D |
| 65 | C | D |
| 66 | B | D |
| 67 | C | E |
| 68 | D | E |
| 69 | D | E |
| 70 | D | E |
| 71 | D | E |
| 72 | B | D |
| 73 | A | D |
| 74 | B | E |
| 75 | D | E |
| 76 | B | D |
| 77 | D | E |
| 78 | B | D |
| 79 | B | E |
| 80 | C | E |
| 81 | B | E |
| 82 | C | D |
| 83 | B | D |
| 84 | B | D |
| 85 | D | E |
| 86 | C | D |
| 87 | D | E |
| 88 | B | D |
| 89 | A | D |
| 90 | D | D |
| 91 | A | D |
| 92 | A | D |
| 93 | A | E |
| 94 | D | E |
| 95 | D | D |
| 96 | D | E |
| 97 | C | E |
| 98 | D | E |
| 99 | C | E |
| 100 | A | E |
| 101 | D | E |
| 102 | D | E |
| 103 | D | E |
| 104 | B | E |
| 105 | D | E |
| 106 | D | E |
| 107 | D | E |
| 108 | D | E |
| 110 | B | D |
| 131 | C | E |
| 146 | A | D |
| 147 | B | E |
| 148 | D | E |
| 149 | B | D |
| 152 | B | E |
| 163 | B | D |
| 164 | A | D |
| 165 | A | D |
| 166 | A | D |
| 167 | A | D |
| 168 | A | D |
| 169 | A | D |
| 170 | A | E |
| 171 | A | D |
| 172 | A | D |
| 173 | A | D |
| 174 | A | D |
| 175 | A | D |
| 176 | A | D |
| 177 | A | D |
| 178 | A | D |
| 179 | A | D |
| 180 | A | D |
| 181 | A | D |
| 182 | A | D |
| 183 | A | D |
| 184 | A | D |
| 185 | A | D |
| 186 | A | D |
| 187 | A | D |
| 188 | A | D |
| 189 | B | E |
| 190 | A | D |
| 191 | A | E |
| 192 | A | D |
| 193 | A | D |
| 194 | A | D |
| 195 | A | D |
| 196 | A | D |
| 197 | A | D |
| 198 | A | D |
| 199 | A | D |
| 200 | A | D |
| 201 | A | D |
| 202 | A | D |
| 203 | A | D |
| 204 | A | D |
| 205 | A | D |
| 206 | A | D |
| 207 | A | D |
| 208 | B | E |
| 209 | A | D |
| 210 | A | D |
| 211 | A | D |
| 212 | A | D |
| 213 | A | D |
| 214 | A | D |
| 215 | A | D |
| 216 | A | D |
| 217 | A | D |
| 218 | A | D |

TABLE E13-continued

PI3Kα Cell Assay Results
A < 250 nM ≤ B ≤ 500 nM ≤ C ≤
1000 nM ≤ D ≤ 5000 nM ≤ E

| Cpd. ID | T47D IC$_{50}$ (nM) | SKBR3 IC$_{50}$ (nM) |
|---|---|---|
| 219 | A | D |
| 220 | A | D |
| 221 | A | D |
| 222 | A | D |
| 223 | A | D |
| 224 | A | D |
| 225 | A | D |
| 226 | A | D |
| 227 | A | D |
| 228 | A | D |
| 229 | A | D |
| 230 | A | D |
| 231 | A | D |
| 232 | A | D |
| 233 | A | D |
| 234 | A | D |
| 235 | B | E |
| 236 | B | D |
| 237 | A | D |
| 238 | A | D |
| 239 | A | D |
| 240 | A | D |
| 241 | A | D |
| 242 | A | D |
| 243 | A | D |
| 244 | A | D |
| 245 | A | D |
| 246 | A | D |
| 247 | A | D |
| 248 | A | D |
| 249 | A | D |
| 250 | A | D |
| 251 | A | D |
| 252 | A | D |
| 253 | B | D |
| 254 | A | D |
| 255 | A | D |
| 256 | A | D |
| 257 | A | D |
| 258 | A | D |
| 259 | A | D |
| 260 | A | D |
| 261 | A | D |
| 262 | A | D |
| 263 | A | D |
| 264 | A | D |
| 265 | A | D |
| 266 | A | D |
| 267 | A | D |
| 268 | A | E |
| 269 | A | D |
| 270 | A | E |
| 271 | A | D |
| 272 | A | D |
| 273 | A | E |
| 274 | A | D |
| 275 | A | E |
| 276 | A | D |
| 277 | A | D |
| 278 | A | D |
| 279 | A | D |
| 280 | A | D |
| 281 | A | D |
| 282 | A | E |
| 283 | A | E |
| 284 | A | D |
| 285 | A | D |
| 286 | A | D |
| 287 | A | D |
| 288 | A | D |
| 289 | A | E |
| 290 | A | D |
| 291 | A | D |
| 292 | A | D |
| 293 | B | D |
| 294 | A | D |
| 295 | A | D |
| 296 | B | D |
| 297 | B | E |
| 298 | A | E |
| 299 | A | D |
| 300 | A | E |
| 301 | A | E |
| 302 | A | D |
| 303 | B | D |
| 304 | B | E |
| 305 | A | E |
| 306 | A | D |
| 307 | A | E |
| 308 | A | E |
| 309 | B | E |
| 310 | A | D |
| 311 | A | D |
| 312 | A | D |
| 313 | B | D |
| 314 | A | E |
| 315 | A | E |
| 316 | B | D |
| 317 | B | D |
| 318 | A | D |
| 319 | A | D |
| 320 | A | D |
| 321 | B | D |
| 322 | A | D |
| 323 | B | E |
| 324 | A | E |
| 325 | A | D |
| 326 | A | D |
| 327 | B | D |
| 328 | B | E |
| 329 | A | D |
| 330 | A | D |
| 331 | A | D |
| 332 | A | D |
| 333 | A | D |
| 334 | A | D |
| 335 | A | D |
| 336 | A | D |
| 337 | A | D |
| 338 | A | D |
| 339 | A | D |
| 340 | B | E |
| 341 | A | D |
| 342 | A | D |
| 343 | B | E |
| 344 | A | E |
| 345 | A | D |
| 346 | B | E |
| 347 | B | E |
| 348 | A | E |
| 349 | A | D |
| 350 | A | E |
| 351 | A | D |
| 352 | A | D |
| 353 | B | D |
| 354 | A | D |
| 355 | A | D |
| 356 | A | D |
| 357 | A | D |
| 358 | A | D |
| 359 | B | E |
| 360 | B | E |
| 361 | B | E |
| 362 | A | D |
| 363 | A | D |
| 364 | B | D |

TABLE E13-continued

PI3Kα Cell Assay Results
A < 250 nM ≤ B ≤ 500 nM ≤ C ≤ 1000 nM ≤ D ≤ 5000 nM ≤ E

| Cpd. ID | T47D IC$_{50}$ (nM) | SKBR3 IC$_{50}$ (nM) |
|---|---|---|
| 365 | A | D |
| 366 | A | D |
| 367 | A | E |
| 368 | B | E |
| 369 | A | D |
| 370 | A | D |
| 371 | A | D |
| 372 | A | D |
| 373 | B | D |
| 374 | A | D |
| 375 | B | E |
| 376 | B | E |
| 377 | B | E |
| 378 | B | E |
| 379 | B | E |
| 380 | A | E |
| 381 | A | D |
| 382 | B | D |
| 383 | B | E |
| 384 | A | D |
| 385 | A | D |
| 386 | A | D |
| 387 | A | D |
| 388 | A | D |
| 389 | A | D |
| 390 | A | E |
| 391 | B | D |
| 392 | B | D |
| 393 | B | E |
| 394 | A | D |
| 395 | B | E |
| 396 | A | D |
| 397 | B | E |
| 398 | B | E |
| 399 | A | E |
| 400 | B | D |
| 401 | B | E |
| 402 | A | D |
| 403 | A | E |
| 404 | A | D |
| 405 | A | D |
| 406 | B | E |
| 407 | B | E |
| 408 | A | E |
| 409 | A | D |
| 410 | B | E |
| 411 | A | D |
| 412 | A | D |
| 413 | A | D |
| 414 | A | D |
| 415 | A | D |
| 416 | A | D |
| 417 | A | D |
| 418 | A | D |
| 419 | B | D |
| 420 | B | D |
| 421 | B | E |
| 422 | A | D |
| 423 | B | E |
| 424 | B | E |
| 425 | A | E |
| 426 | B | E |
| 427 | A | D |
| 428 | B | D |
| 429 | B | E |
| 430 | A | D |
| 431 | B | D |
| 432 | A | D |
| 433 | A | E |
| 434 | C | E |
| 435 | A | D |
| 436 | A | D |
| 437 | A | D |
| 438 | B | E |
| 439 | A | D |
| 440 | A | D |
| 441 | A | D |
| 442 | A | D |
| 443 | B | D |
| 444 | B | E |
| 445 | B | E |
| 446 | B | E |
| 447 | A | D |
| 448 | A | D |
| 449 | B | E |
| 450 | A | E |
| 451 | A | D |
| 452 | B | D |
| 453 | A | E |
| 454 | A | D |
| 455 | A | D |
| 456 | A | E |
| 457 | C | E |
| 458 | B | E |
| 459 | A | E |
| 460 | A | D |
| 461 | A | D |
| 462 | A | E |
| 463 | B | E |
| 464 | B | E |
| 465 | A | D |
| 466 | B | E |
| 467 | A | E |
| 468 | A | E |
| 469 | B | E |
| 470 | A | D |
| 471 | A | D |
| 472 | A | E |
| 473 | B | E |
| 474 | B | E |
| 475 | B | D |
| 476 | B | D |
| 477 | A | D |
| 478 | A | D |
| 479 | B | E |
| 480 | A | D |
| 481 | B | D |
| 482 | A | D |
| 483 | A | D |
| 484 | B | D |
| 485 | B | D |
| 486 | A | D |
| 487 | B | D |
| 488 | A | D |
| 489 | A | D |
| 490 | B | E |
| 491 | B | D |
| 492 | B | D |
| 493 | A | D |
| 494 | A | D |
| 495 | B | D |
| 496 | A | D |
| 497 | A | D |
| 498 | A | D |
| 499 | B | E |
| 500 | B | D |
| 501 | A | D |
| 502 | B | D |
| 503 | A | D |
| 504 | A | D |
| 505 | B | E |
| 506 | A | D |
| 507 | B | D |
| 508 | A | D |
| 509 | B | E |
| 510 | B | D |

TABLE E13-continued

PI3Kα Cell Assay Results
A < 250 nM ≤ B ≤ 500 nM ≤ C ≤
1000 nM ≤ D ≤ 5000 nM ≤ E

| Cpd. ID | T47D IC$_{50}$ (nM) | SKBR3 IC$_{50}$ (nM) |
|---|---|---|
| 511 | C | E |
| 512 | B | D |
| 513 | B | E |
| 514 | A | D |
| 515 | A | D |
| 516 | A | D |
| 517 | B | D |
| 518 | A | D |
| 519 | A | D |
| 520 | A | D |
| 521 | A | D |
| 522 | A | D |
| 523 | B | E |
| 524 | A | D |
| 525 | A | E |
| 526 | A | D |
| 527 | A | D |
| 528 | A | D |
| 529 | A | D |
| 530 | B | E |
| 531 | A | D |
| 532 | B | E |
| 533 | A | D |
| 534 | A | D |
| 535 | B | E |
| 536 | A | D |
| 537 | B | E |
| 538 | A | D |
| 539 | A | E |
| 540 | B | E |
| 541 | A | E |
| 542 | B | E |
| 543 | B | E |
| 544 | A | D |
| 545 | A | E |
| 546 | A | D |
| 547 | B | E |
| 548 | B | D |
| 549 | A | D |
| 550 | B | E |
| 551 | A | E |
| 552 | B | E |
| 553 | A | D |
| 554 | A | D |
| 555 | A | D |
| 556 | A | D |
| 557 | B | D |
| 558 | A | D |
| 559 | B | E |
| 560 | A | D |
| 561 | B | E |
| 562 | B | E |
| 563 | B | E |
| 564 | B | E |
| 565 | B | E |
| 566 | B | D |
| 567 | B | E |
| 568 | B | D |
| 569 | B | E |
| 570 | A | E |
| 571 | A | D |
| 572 | A | D |
| 573 | A | D |
| 574 | B | D |
| 575 | A | D |
| 576 | C | E |
| 577 | B | E |
| 578 | A | D |
| 579 | B | E |
| 580 | B | E |
| 581 | B | E |
| 582 | B | E |
| 583 | B | E |
| 584 | A | D |
| 585 | B | E |
| 586 | B | E |
| 587 | B | E |
| 588 | D | E |
| 589 | B | E |
| 590 | A | D |
| 591 | B | E |
| 592 | C | E |
| 593 | B | E |
| 594 | A | D |
| 595 | A | D |
| 596 | B | E |
| 597 | D | E |
| 598 | A | D |
| 599 | B | E |
| 600 | B | D |
| 601 | B | D |
| 602 | B | E |
| 603 | C | E |
| 604 | B | E |
| 605 | B | E |
| 606 | B | E |
| 607 | A | D |
| 608 | C | E |
| 609 | C | E |
| 610 | A | E |
| 611 | B | E |
| 612 | B | D |
| 613 | A | D |
| 614 | C | E |
| 615 | B | D |
| 616 | A | E |
| 617 | B | E |
| 618 | B | D |
| 619 | A | E |
| 620 | A | D |
| 621 | C | E |
| 622 | A | D |
| 623 | B | E |
| 624 | B | E |
| 625 | B | E |
| 626 | B | D |
| 627 | A | D |
| 628 | B | E |
| 629 | A | D |
| 630 | C | E |
| 631 | A | D |
| 632 | B | D |
| 633 | B | E |
| 634 | A | E |
| 635 | B | D |
| 636 | B | E |
| 637 | B | E |
| 638 | B | E |
| 639 | C | E |
| 640 | B | E |
| 641 | B | E |
| 642 | B | E |
| 643 | B | E |
| 644 | B | E |
| 645 | C | E |
| 646 | A | E |
| 647 | B | E |
| 648 | D | E |
| 649 | A | D |
| 650 | B | E |
| 651 | B | D |
| 652 | B | D |
| 653 | B | D |
| 654 | A | D |
| 655 | D | E |
| 656 | B | D |

TABLE E13-continued

PI3Kα Cell Assay Results
A < 250 nM ≤ B ≤ 500 nM ≤ C ≤ 1000 nM ≤ D ≤ 5000 nM ≤ E

| Cpd. ID | T47D IC$_{50}$ (nM) | SKBR3 IC$_{50}$ (nM) |
|---|---|---|
| 657 | B | E |
| 658 | C | E |
| 659 | A | D |
| 660 | B | E |
| 661 | B | E |
| 662 | B | E |
| 663 | C | F |
| 664 | C | E |
| 665 | A | D |
| 666 | B | E |
| 667 | C | E |
| 668 | B | E |
| 669 | B | E |
| 670 | A | D |
| 671 | A | D |
| 672 | A | D |
| 673 | B | E |
| 674 | B | E |
| 675 | B | E |
| 676 | B | E |
| 677 | B | E |
| 678 | B | E |
| 679 | B | D |
| 680 | B | E |
| 681 | B | E |
| 682 | B | E |
| 683 | B | D |
| 684 | A | D |
| 685 | B | E |
| 686 | A | B |
| 687 | B | E |
| 688 | B | E |
| 689 | A | D |
| 690 | A | D |
| 691 | B | E |
| 692 | A | D |
| 693 | A | D |
| 694 | B | E |
| 695 | B | E |
| 696 | C | E |
| 697 | B | D |
| 698 | B | D |
| 699 | B | D |
| 700 | B | E |
| 701 | B | E |
| 702 | B | E |
| 703 | B | E |
| 704 | B | E |
| 705 | B | E |
| 706 | C | E |
| 707 | B | D |
| 708 | B | E |
| 709 | B | E |
| 710 | D | E |
| 711 | B | D |
| 712 | A | D |
| 713 | B | D |
| 714 | A | D |
| 715 | A | D |
| 716 | A | D |
| 717 | B | E |
| 718 | B | E |
| 719 | B | E |
| 720 | A | D |
| 721 | B | E |
| 722 | B | D |
| 723 | B | D |
| 724 | B | D |
| 725 | B | D |
| 726 | B | D |
| 727 | B | D |
| 728 | B | D |
| 729 | B | D |
| 730 | B | D |
| 731 | A | D |
| 732 | A | D |
| 733 | C | D |
| 734 | B | D |
| 735 | B | D |
| 736 | C | E |
| 737 | B | E |
| 738 | B | E |
| 739 | B | E |
| 740 | B | E |
| 741 | C | E |
| 742 | B | D |
| 743 | D | E |
| 744 | B | E |
| 745 | B | E |
| 746 | A | E |
| 747 | A | D |
| 748 | C | E |
| 749 | B | E |
| 750 | B | E |
| 751 | B | E |
| 752 | C | E |
| 753 | A | D |
| 754 | A | E |
| 755 | B | D |
| 756 | C | E |
| 757 | B | E |
| 758 | B | E |
| 759 | B | E |
| 760 | B | E |
| 761 | B | D |
| 762 | B | E |
| 763 | B | D |
| 764 | A | D |
| 765 | B | D |
| 766 | B | E |
| 767 | B | E |
| 768 | B | E |
| 769 | A | D |
| 770 | B | E |
| 771 | B | E |
| 772 | A | E |
| 773 | A | D |
| 774 | A | C |
| 775 | A | D |
| 776 | B | D |
| 777 | C | E |
| 778 | A | D |
| 779 | A | D |
| 780 | A | D |
| 781 | A | D |
| 782 | A | D |
| 783 | A | D |
| 784 | A | D |
| 785 | A | D |
| 786 | A | D |
| 787 | A | D |
| 788 | A | D |
| 789 | A | D |
| 790 | A | E |
| 791 | A | D |
| 792 | A | D |
| 793 | A | E |
| 794 | A | D |
| 795 | A | D |
| 796 | A | D |
| 797 | A | D |
| 798 | A | D |
| 799 | B | E |
| 800 | A | D |
| 801 | A | E |
| 802 | A | D |

TABLE E13-continued

PI3Kα Cell Assay Results
A < 250 nM ≤ B ≤ 500 nM ≤ C ≤ 1000 nM ≤ D ≤ 5000 nM ≤ E

| Cpd. ID | T47D IC$_{50}$ (nM) | SKBR3 IC$_{50}$ (nM) |
|---|---|---|
| 803 | A | E |
| 804 | A | E |
| 805 | B | D |
| 806 | A | D |
| 807 | B | E |
| 808 | B | E |
| 809 | B | E |
| 810 | B | E |
| 811 | B | E |
| 812 | A | D |
| 813 | B | E |
| 814 | A | D |
| 815 | B | E |
| 816 | A | D |
| 817 | A | D |
| 818 | A | D |
| 819 | B | D |
| 820 | A | D |
| 821 | B | E |
| 822 | B | E |
| 823 | C | E |
| 824 | A | D |
| 825 | D | E |
| 826 | B | E |
| 827 | C | E |
| 828 | C | E |
| 829 | B | E |
| 830 | B | E |
| 831 | B | D |
| 832 | B | D |
| 833 | B | D |
| 834 | C | D |
| 835 | B | D |
| 836 | A | D |
| 837 | B | D |
| 838 | B | D |
| 839 | B | D |
| 840 | D | D |
| 841 | B | D |
| 842 | A | D |
| 843 | B | D |
| 844 | B | D |
| 845 | C | E |
| 846 | B | E |
| 847 | A | D |
| 848 | D | E |
| 849 | B | E |
| 850 | A | D |
| 851 | B | D |
| 852 | B | E |
| 853 | B | E |
| 854 | A | D |
| 855 | A | D |
| 856 | B | E |

TABLE E14

| PK Data Comparison of Compounds 1 & 1 acid derivative | | |
|---|---|---|
| Example | Compound 1 acid derivative | Compound 1 |
| PK-Mouse: IV Dose (mg/kg) | 3 | 3 |
| PK-Mouse: IV Cl (mL/min/kg) | 24.3 | 0.74 |
| PK-Mouse: IV-AUC$_{inf}$ (ng * h/mL) | 2066 | 67482 |
| PK-Mouse: PO Dose (mg/kg) | 30 | 30 |
| PK-Mouse: PO Vehicle | 20% Captisol (aq) | 20% Captisol (aq) |
| PK-Mouse: PO Vehicle appearance | Homogeneous opaque suspension | Cloudy suspension |
| PK-Mouse: PO Cmax (ng/mL) | 2493 | 35533 |
| PK-Mouse: PO AUC$_{inf}$ (ng * h/mL) | 8853 | 547826 |
| PK-Mouse: PO F (%) | 43 | 81 |
| PK-Mouse: PO observations | Fed | Fed |

What is claimed is:

1. A compound having the following structure of Formula (II):

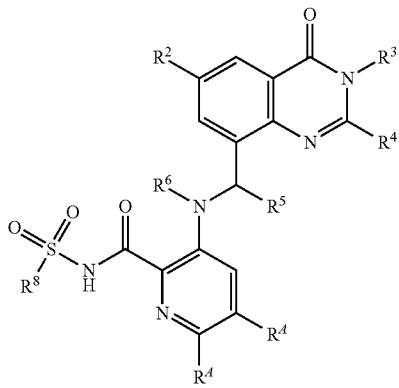

(II)

or a stereoisomer of the compound, tautomer of the compound, or a salt thereof, wherein:
- $R^2$ is $C_1$-$C_3$ alkyl;
- $R^3$ is $C_1$-$C_3$ alkyl;
- $R^5$ and $R^6$ are, each independently, hydrogen or $C_1$-$C_3$ alkyl;
- $R^4$ is 3-12 membered heterocyclyl or 5-10 membered heteroaryl, wherein the 3-12 membered heterocyclyl or 5-10 membered heteroaryl is optionally substituted with $C_1$-$C_6$ alkyl, $C_1$-$C_6$ haloalkyl, —O-phenyl, phenyl, or 5-10 membered heteroaryl, wherein the —O-phenyl, phenyl, or 5-10 membered heteroaryl is optionally substituted with 1, 2, 3, or 4 substituents each independently selected from the group consisting of $C_1$-$C_6$ alkyl, $C_1$-$C_6$ haloalkyl, $C_1$-$C_6$ alkoxy, halo, —CN, and $C_3$-$C_7$ cycloalkyl;
- $R^8$ is $C_1$-$C_4$ alkyl; and
- each $R^A$ is independently hydrogen or halo.

2. The compound of claim 1, wherein $R^2$ is —$CH_3$.

3. The compound of claim 1, wherein $R^3$ is —$CH_3$.

4. The compound of claim 1, wherein $R^5$ is —$CH_3$, and $R^6$ is hydrogen.

5. The compound of claim 1, wherein $R^8$ is —$CH_3$.

6. The compound of claim 1, wherein each $R^A$ is independently hydrogen or chloro.

7. The compound of claim 1, wherein $R^4$ is 3-12 membered heterocyclyl or 5-10 membered heteroaryl, wherein the 3-12 membered heterocyclyl or 5-10 membered heteroaryl is optionally substituted with $C_1$-$C_6$ alkyl, $C_1$-$C_6$ haloalkyl, or 5-10 membered heteroaryl optionally substituted with 1, 2, 3, or 4 substituents each independently selected from the group consisting of $C_1$-$C_6$ alkyl, $C_1$-$C_6$ haloalkyl, $C_1$-$C_6$ alkoxy, halo, —CN, and $C_3$-$C_7$ cycloalkyl.

8. The compound of claim 1, wherein $R^4$ is 6-9 membered heterocyclyl substituted with 5-9 membered heteroaryl or $C_1$-$C_3$ haloalkyl, wherein the 5-9 membered heteroaryl is optionally substituted with 1 or 2 substituents each independently selected from the group consisting of $C_1$-$C_3$ alkyl, $C_1$-$C_3$ haloalkyl, $C_1$-$C_3$ alkoxy, halo, —CN, and $C_3$-$C_6$ cycloalkyl.

9. The compound of claim 8, wherein the 6-9 membered heterocyclyl is piperazinyl, piperidine, 8-azabicyclo[3.2.1]octanyl, 2,5-diazabicyclo[2.2.1]heptanyl, 3-azabicyclo[3.1.0]hexanyl, 2,4,5,6-tetrahydropyrrolo[3,4-c]pyrazolyl, or 4,5,6,7-tetrahydro-2H-pyrazolo[4,3-c]pyridinyl.

10. The compound of claim 1, wherein R4 is a 3-12 membered heterocyclyl, which has one of the following structures:

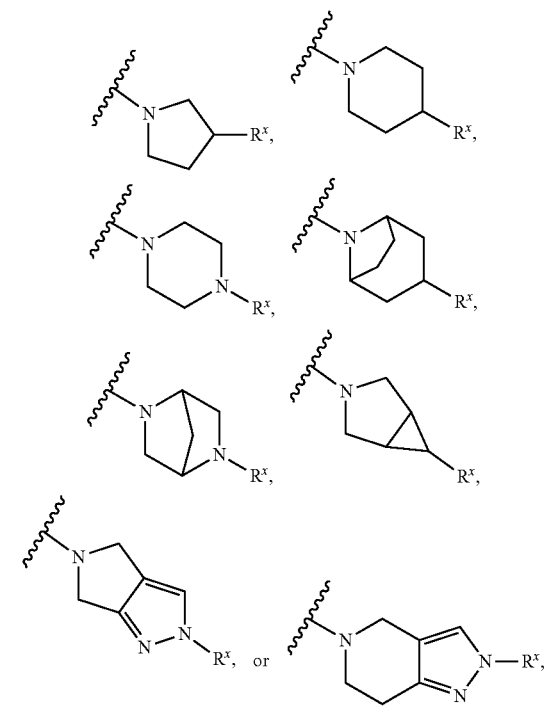

wherein $R^X$ is the $C_1$-$C_6$ alkyl, $C_1$-$C_6$ haloalkyl, —O-phenyl, phenyl, or 5-10 membered heteroaryl.

11. The compound of claim 8, wherein the 5-9 membered heteroaryl is pyrazolyl, pyridinyl, pyrimidinyl, pyrazinyl, pyrazolo[1,5-a]pyridinyl, or pyrazolo[1,5-b]pyridazinyl.

12. The compound of claim 8, wherein the 5-9 membered heteroaryl has one of the following structures:

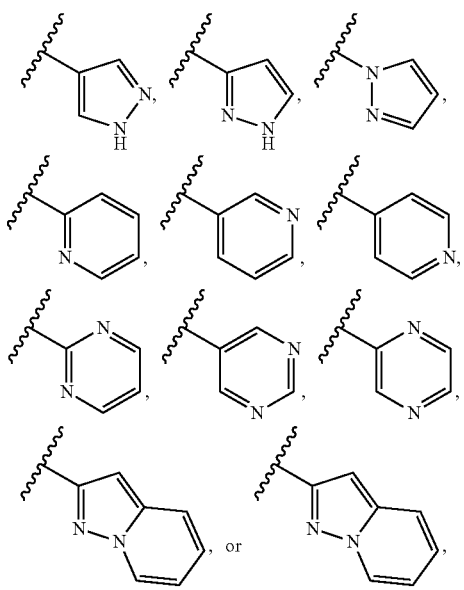

each optionally substituted with 1 or 2 substitutes each independently selected from the group consisting of —CH$_3$, —CHF$_2$, —CF$_3$, —CH$_2$CF$_3$, —OCH$_3$, —F, —CN, and cyclopropyl.

13. The compound of claim 1, wherein R$^4$ is 9 membered fused bicyclic heteroaryl optionally substituted with C$_1$-C$_3$ alkyl or C$_1$-C$_3$ haloalkyl.

14. The compound of claim 13, wherein R$^4$ is benzo[d]oxazolyl or indazolyl, each optionally substituted with C$_1$-C$_3$ alkyl or C$_1$-C$_3$ haloalkyl.

15. The compound of claim 14, wherein R$^4$ has one of the following structures:

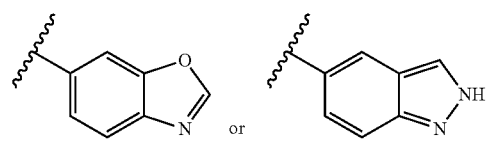

or each optionally substituted with C$_1$-C$_3$ alkyl or C$_1$-C$_3$ haloalkyl.

16. A compound, wherein the compound has one of the following structures:

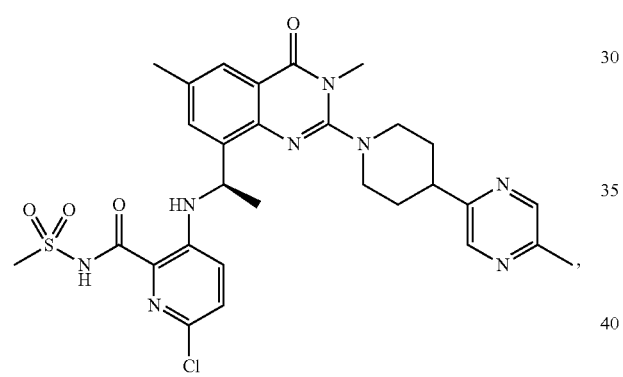

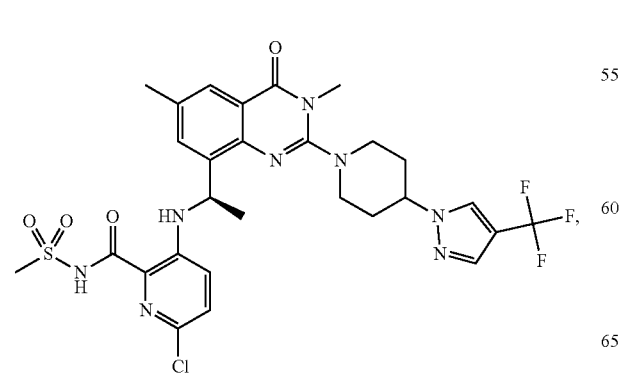

-continued

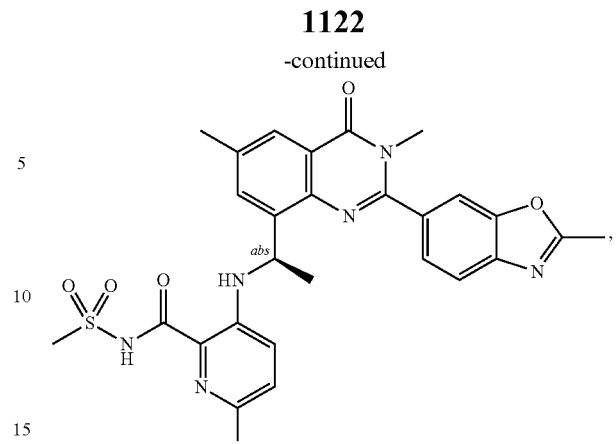

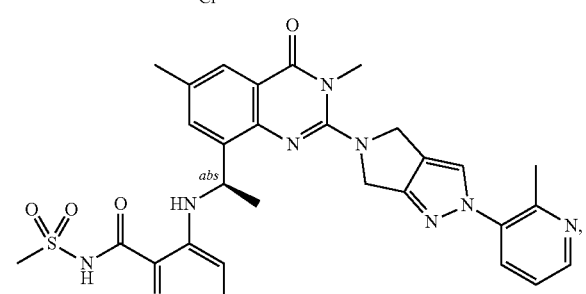

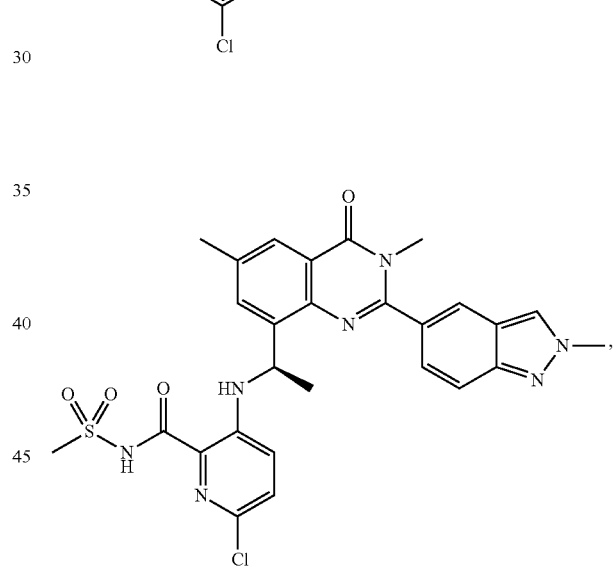

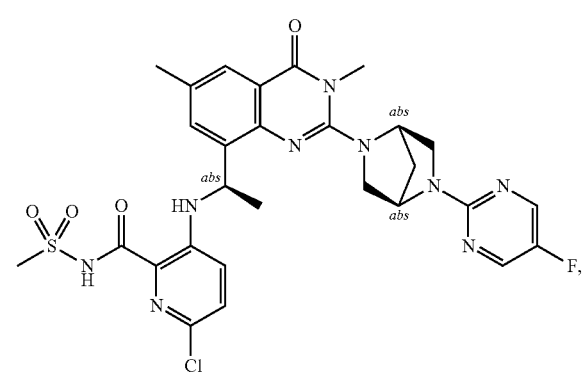

1123
-continued
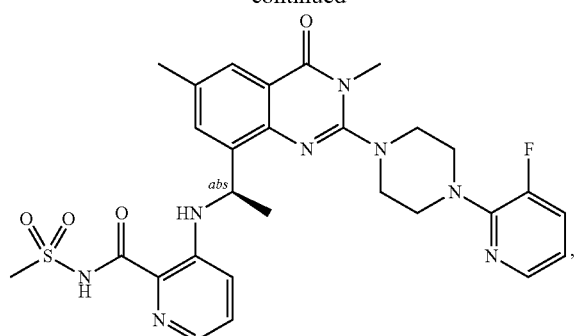
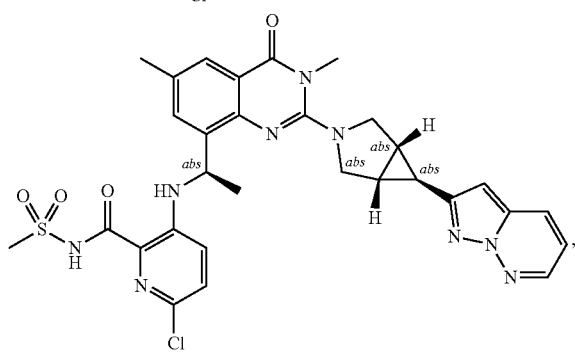
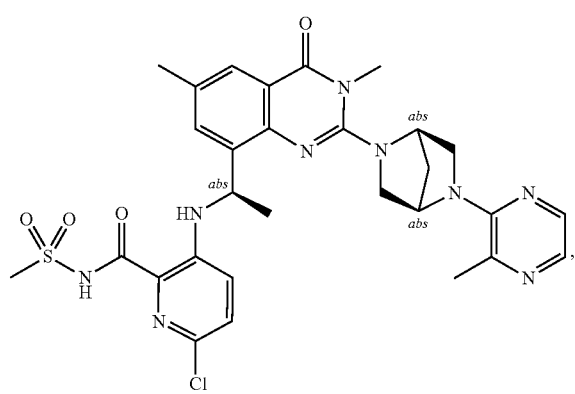
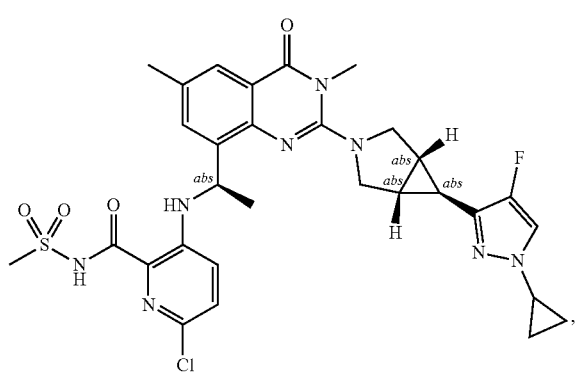
1124
-continued
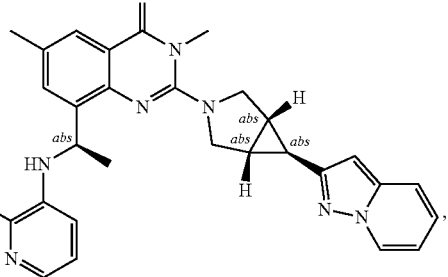
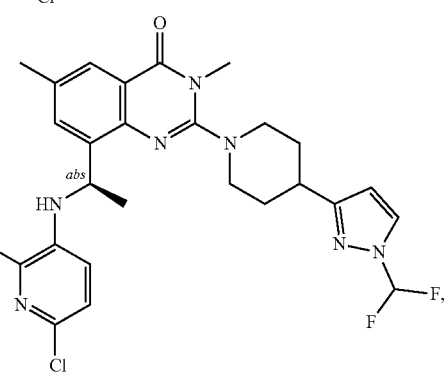
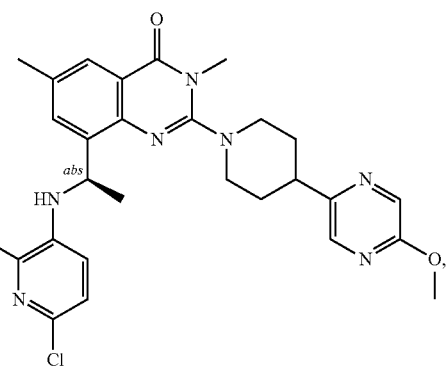
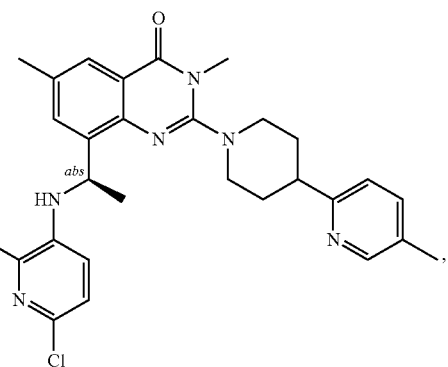

1125
-continued
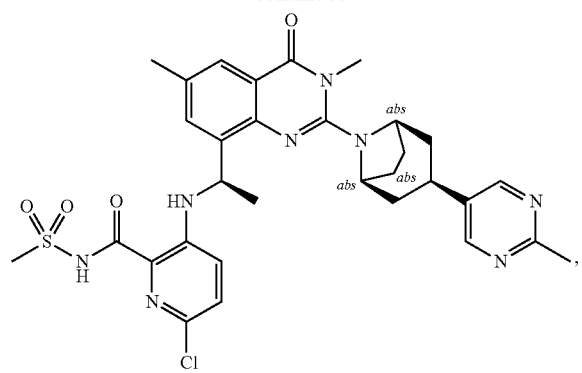
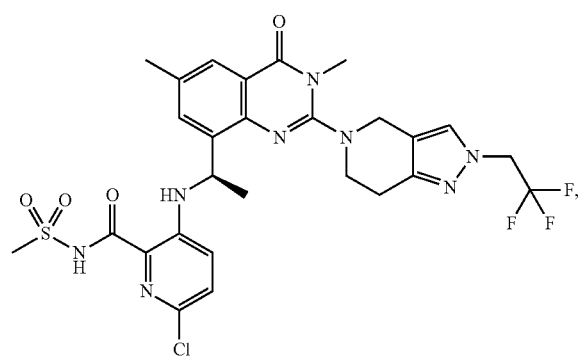
1126
-continued
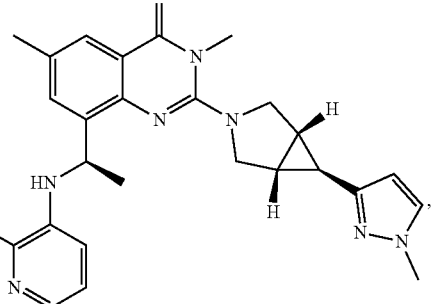
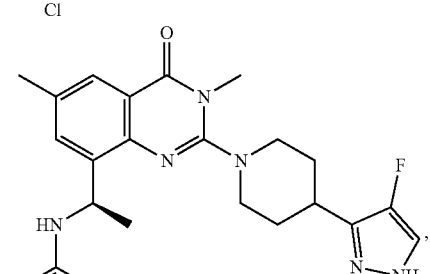
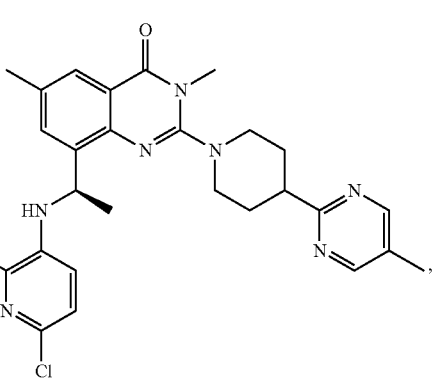
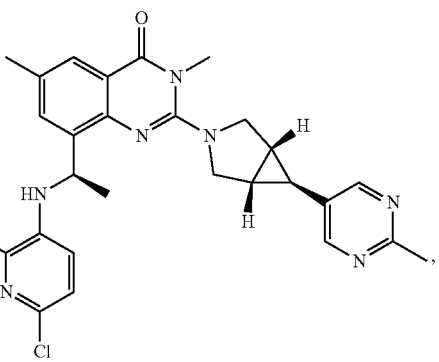

1127
-continued

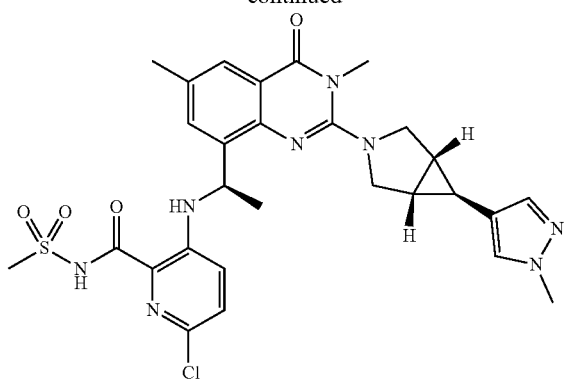

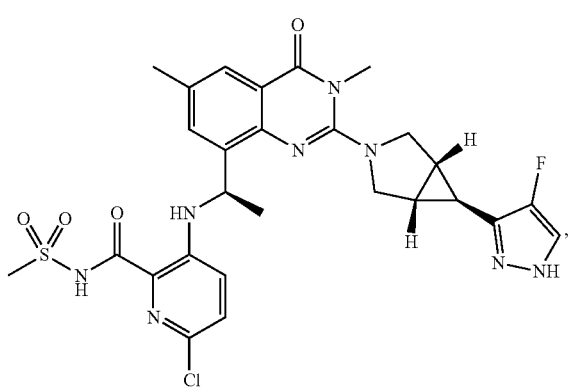

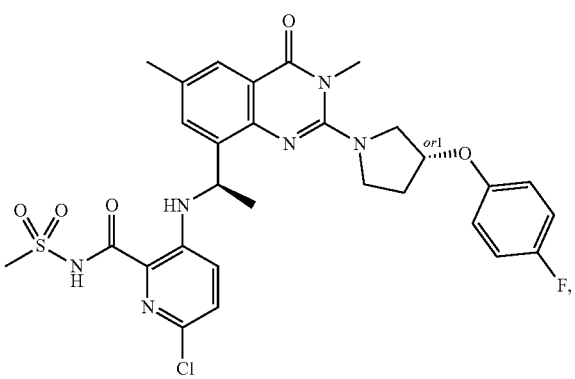

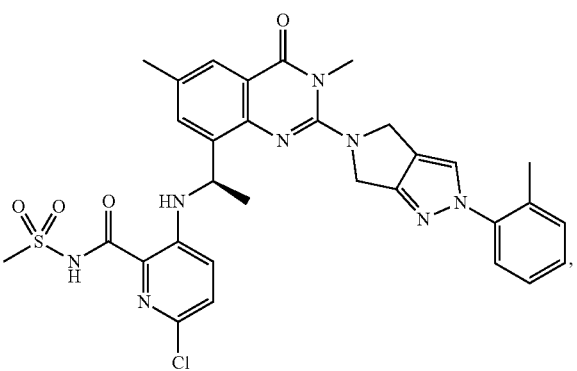

1128
-continued

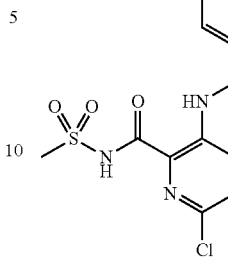

or a stereoisomer of the compound, tautomer of the compound, or a salt thereof.

17. A pharmaceutical composition comprising a compound of claim 1 and a pharmaceutically acceptable carrier.

18. The pharmaceutical composition of claim 17, further comprising an additional therapeutic agent.

19. A pharmaceutical composition comprising a compound of claim 16 and a pharmaceutically acceptable carrier.

20. The pharmaceutical composition of claim 19, further comprising an additional therapeutic agent.

21. The compound of claim 16, wherein the compound has the following structure:

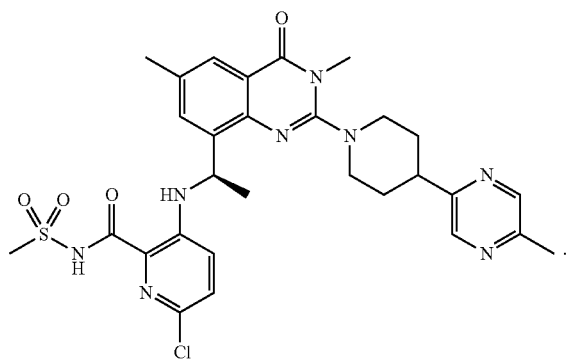

22. The compound of claim 16, wherein the compound has the following structure:

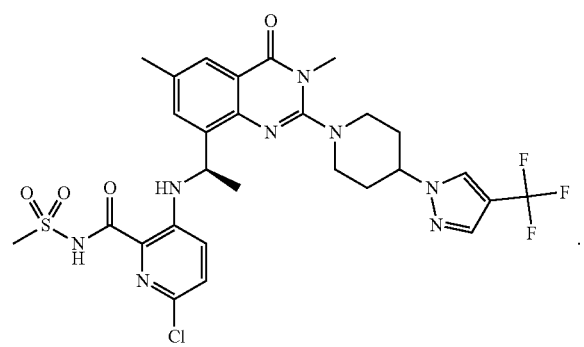 [SMILES: Cc1cc([C@@H](C)Nc2ccc(Cl)nc2C(=O)NS(C)(=O)=O)c2nc(N3CCC(n4cc(C(F)(F)F)cn4)CC3)n(C)c(=O)c2c1 ; "."]

23. The compound of claim 16, wherein the compound has the following structure:

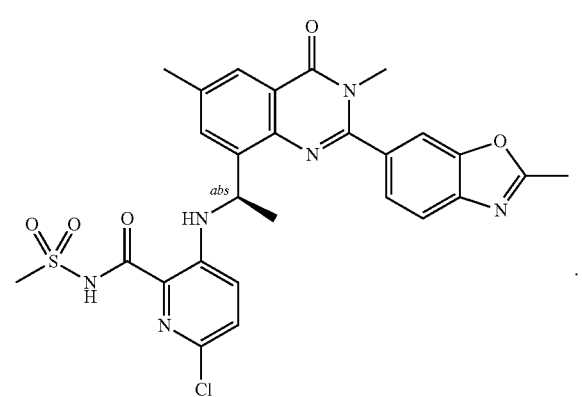

24. The compound of claim 16, wherein the compound has the following structure:

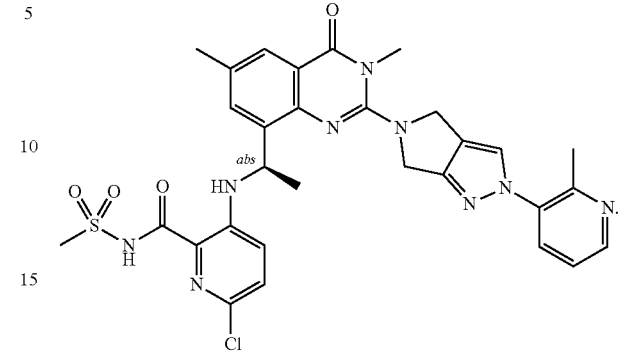

25. The compound of claim 16, wherein the compound has the following structure:

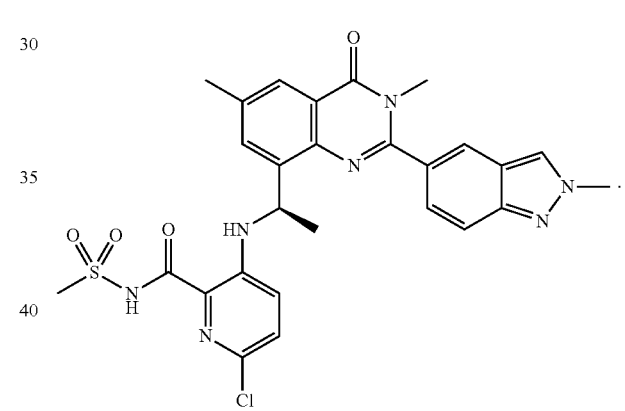

26. The compound of claim 16, wherein the compound has the following structure:

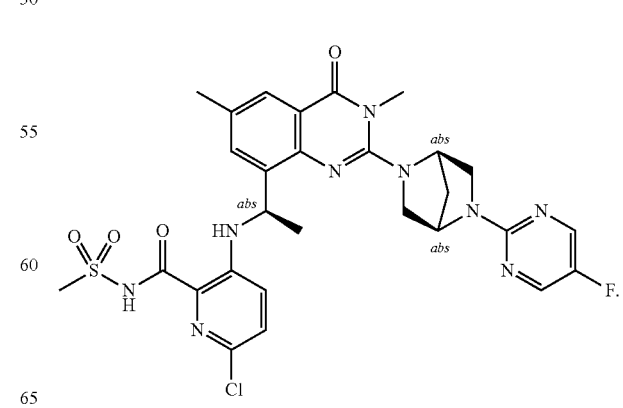

27. The compound of claim 16, wherein the compound has the following structure:
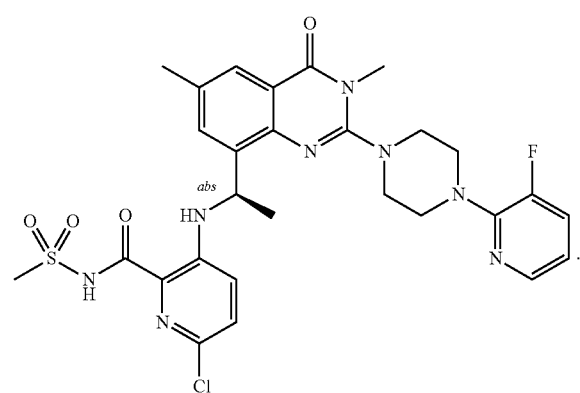 [SMILES: Cc1cc([C@@H](C)Nc2ccc(Cl)nc2C(=O)NS(C)(=O)=O)c2nc(N3CCN(c4ncccc4F)CC3)n(C)c(=O)c2c1 ; "."]
28. The compound of claim 16, wherein the compound has the following structure:
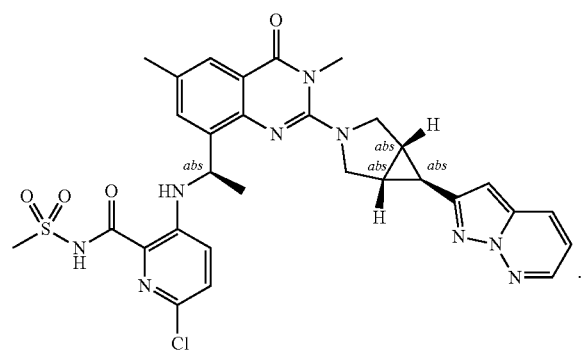 [SMILES: Cc1cc([C@@H](C)Nc2ccc(Cl)nc2C(=O)NS(C)(=O)=O)c2nc(N3C[C@@H]4[C@H](C3)[C@H]4c3cc4cccnn4n3)n(C)c(=O)c2c1 ; "."]
29. The compound of claim 16, wherein the compound has the following structure:
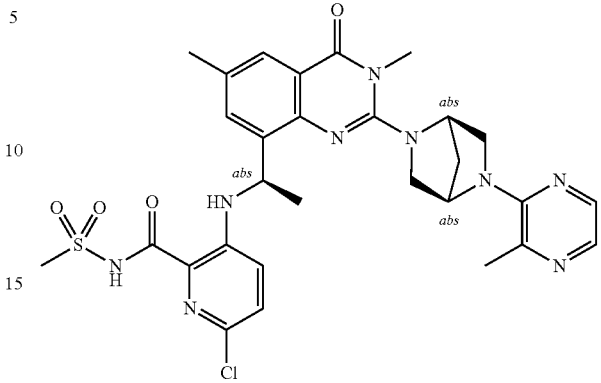
30. The compound of claim 16, wherein the compound has the following structure:
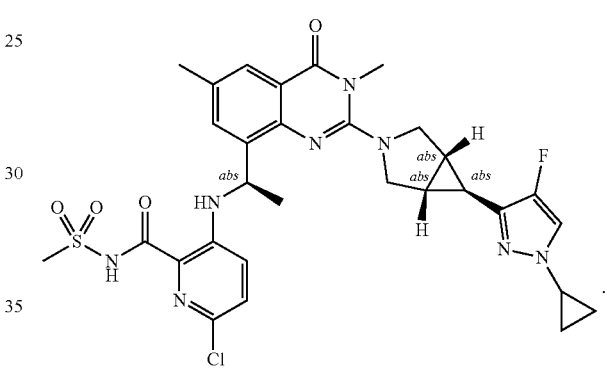
* * * * *